(12) United States Patent
Werner et al.

(10) Patent No.: US 11,524,938 B2
(45) Date of Patent: Dec. 13, 2022

(54) AROMATIC SULFONAMIDE DERIVATIVES

(71) Applicant: Bayer Pharma Aktiengesellschaft, Berlin (DE)

(72) Inventors: Stefan Werner, Berlin (DE); Stefanie Mesch, Wuppertal (DE); Arwed Cleve, Berlin (DE); Nico Bräuer, Falkensee (DE); Simon Anthony Herbert, Berlin (DE); Markus Koch, Berlin (DE); Henrik Dahllöf, Uppsala (SE); Maren Osmers, Dallgow-Döberitz (DE); Elizabeth Hardaker, Tooting (GB); Anton Lishchynskyi, Langen (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 147 days.

(21) Appl. No.: 17/067,434

(22) Filed: Oct. 9, 2020

(65) Prior Publication Data
US 2022/0324807 A1 Oct. 13, 2022

Related U.S. Application Data

(62) Division of application No. 16/098,767, filed as application No. PCT/EP2017/059882 on Apr. 26, 2017, now Pat. No. 10,844,016.

(30) Foreign Application Priority Data

May 3, 2016 (EP) .................................. 16167996

(51) Int. Cl.
*C07D 213/64* (2006.01)
*C07D 403/06* (2006.01)
(Continued)

(52) U.S. Cl.
CPC ............ *C07D 213/64* (2013.01); *A61P 29/00* (2018.01); *C07C 311/17* (2013.01); *C07C 311/40* (2013.01); *C07C 311/46* (2013.01); *C07C 323/62* (2013.01); *C07D 207/333* (2013.01); *C07D 207/416* (2013.01); *C07D 213/40* (2013.01); *C07D 213/60* (2013.01); *C07D 213/61* (2013.01); *C07D 213/65* (2013.01); *C07D 213/74* (2013.01); *C07D 213/85* (2013.01); *C07D 231/12* (2013.01); *C07D 231/14* (2013.01); *C07D 231/16* (2013.01); *C07D 231/18* (2013.01); *C07D 231/38* (2013.01); *C07D 231/56* (2013.01); *C07D 233/16* (2013.01); *C07D 233/61* (2013.01); *C07D 233/64* (2013.01); *C07D 233/68* (2013.01); *C07D 235/06* (2013.01); *C07D 235/08* (2013.01); *C07D 237/08* (2013.01); *C07D 239/26* (2013.01); *C07D 239/30* (2013.01); *C07D 239/34* (2013.01); *C07D 239/42* (2013.01); *C07D 249/06* (2013.01); *C07D 249/08* (2013.01); *C07D 249/10* (2013.01); *C07D 249/12* (2013.01); *C07D 249/14* (2013.01); *C07D 249/18* (2013.01); *C07D 249/20* (2013.01); *C07D 261/08* (2013.01); *C07D 263/32* (2013.01); *C07D 271/04* (2013.01); *C07D 271/06* (2013.01); *C07D 275/02* (2013.01); *C07D 277/26* (2013.01); *C07D 277/34* (2013.01); *C07D 277/56* (2013.01); *C07D 401/04* (2013.01);
(Continued)

(58) Field of Classification Search
CPC ................ C07D 401/04; C07D 401/12; C07D 403/04; C07D 403/06; C07D 405/04; C07D 405/06; C07D 231/12; C07D 471/04; A61P 29/00
See application file for complete search history.

(56) References Cited

U.S. PATENT DOCUMENTS 5,011,472 A 4/1991 Aebischer
10,844,016 B2 * 11/2020 Werner ................ C07D 271/04
(Continued)

FOREIGN PATENT DOCUMENTS

EP 2597088 A1 5/2013
WO 2011028741 A1 3/2011
(Continued)

OTHER PUBLICATIONS

Matsumura; Sci Rep. 2016; 6: 32461. doi: 10.1038/srep32461 (Year: 2016).*
Muller; Current Medicinal Chemistry, 2015, 22, 929-941. DOI: 10.2174/0929867322666141210155610 (Year: 2015).*
(Continued)

*Primary Examiner* — Daniel R Carcanague
(74) *Attorney, Agent, or Firm* — Morrison & Foerster LLP

(57) ABSTRACT

Substituted aromatic sulfonamides of formula (I)

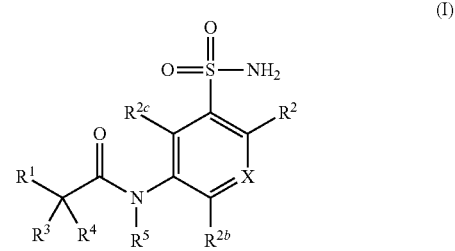

pharmaceutical compositions and combinations comprising said compounds and the use of said compounds for manufacturing a pharmaceutical composition for the treatment or prophylaxis of a disease.

9 Claims, 10 Drawing Sheets

(51) Int. Cl.
| | |
|---|---|
| C07D 231/14 | (2006.01) |
| C07D 231/16 | (2006.01) |
| C07D 231/18 | (2006.01) |
| C07D 233/61 | (2006.01) |
| C07D 233/64 | (2006.01) |
| C07D 233/68 | (2006.01) |
| C07D 401/04 | (2006.01) |
| C07D 403/04 | (2006.01) |
| C07D 405/06 | (2006.01) |
| C07D 239/34 | (2006.01) |
| C07D 249/06 | (2006.01) |
| C07D 249/08 | (2006.01) |
| C07D 249/14 | (2006.01) |
| C07D 471/04 | (2006.01) |
| C07D 261/08 | (2006.01) |
| C07D 271/06 | (2006.01) |
| C07C 311/46 | (2006.01) |
| C07F 5/02 | (2006.01) |
| C07D 207/416 | (2006.01) |
| C07D 231/56 | (2006.01) |
| C07D 213/85 | (2006.01) |
| C07D 277/56 | (2006.01) |
| C07D 249/20 | (2006.01) |
| C07D 213/60 | (2006.01) |
| C07C 311/17 | (2006.01) |
| C07D 213/61 | (2006.01) |
| C07D 239/30 | (2006.01) |
| C07D 239/42 | (2006.01) |
| C07D 249/10 | (2006.01) |
| C07D 213/65 | (2006.01) |
| C07D 249/12 | (2006.01) |
| C07D 233/16 | (2006.01) |
| C07C 323/62 | (2006.01) |
| C07D 237/08 | (2006.01) |
| C07D 213/40 | (2006.01) |
| C07D 239/26 | (2006.01) |
| C07D 235/06 | (2006.01) |
| C07C 311/40 | (2006.01) |
| C07D 213/74 | (2006.01) |
| C07D 405/04 | (2006.01) |
| C07D 271/04 | (2006.01) |
| C07D 277/26 | (2006.01) |
| C07D 249/18 | (2006.01) |
| C07D 277/34 | (2006.01) |
| C07D 275/02 | (2006.01) |
| C07D 263/32 | (2006.01) |
| C07D 231/38 | (2006.01) |
| C07D 207/333 | (2006.01) |
| A61P 29/00 | (2006.01) |
| C07D 235/08 | (2006.01) |
| C07D 401/12 | (2006.01) |
| C07D 231/12 | (2006.01) |

(52) U.S. Cl.
CPC ......... *C07D 401/12* (2013.01); *C07D 403/04* (2013.01); *C07D 403/06* (2013.01); *C07D 405/04* (2013.01); *C07D 405/06* (2013.01); *C07D 471/04* (2013.01); *C07F 5/025* (2013.01)

(56) References Cited

U.S. PATENT DOCUMENTS

| | | | |
|---|---|---|---|
| 2011/0281865 A1 | 11/2011 | Muthuppalaniappan | |
| 2017/0081294 A1* | 3/2017 | Sakuma | ............ C07D 401/12 |
| 2018/0338980 A1* | 11/2018 | Werner | ................ A61P 25/00 |
| 2021/0179577 A1* | 6/2021 | Hauff | ................ C07D 401/12 |

FOREIGN PATENT DOCUMENTS

| | | | | |
|---|---|---|---|---|
| WO | 2011120026 A1 | 9/2011 | | |
| WO | 2013105608 A1 | 7/2013 | | |
| WO | 2015005467 A1 | 1/2015 | | |
| WO | 2015005468 A1 | 1/2015 | | |
| WO | 2015088564 A1 | 6/2015 | | |
| WO | 2015088565 A1 | 6/2015 | | |
| WO | 2016198374 A1 | 12/2016 | | |
| WO | 2017191102 A1 | 11/2017 | | |
| WO | 2017192740 A2 | 11/2017 | | |
| WO | WO-2018104305 A1 * | 6/2018 | ........... | C07D 211/38 |
| WO | WO-2018104307 A1 * | 6/2018 | ........... | C07C 311/40 |
| WO | WO-2018210729 A1 * | 11/2018 | ........... | C07D 231/14 |

OTHER PUBLICATIONS

Ralevic; Current Medicinal Chemistry, 2015, 22, 851-865. DOI: 10.2174/0929867321666141215094050 (Year: 2015).*
Tsuda; Frontiers in Cellular Science 2013, 7, 191. doi: 10.3389/fncel.2013.00191 (Year: 2013).*
Werner; J. Med. Chem. 2019, 62, 24, 11194-11217. doi: 10.1021/acs.jmedchem.9b01304 (Year: 2019).*
Adams, A.M. et al. (2015). "Comparative Study of the Limitations and Challenges in Atom-Transfer C—H Oxidations," American Chemical Society, Org. Lett. 17:6066-6069.
Berge, S.M. et al. (Jan. 1977). "Pharmaceuticals Salts," J. Pharmaceutical Sciences 66:1-19.
Bernadou, J. et al. (2004). "Biomimetic Chemical Catalysts in the Oxidative Activation of Drugs," Adv. Synth. Catal. 346:171-184.
Bernstein, J. (2002). "Polymorphism in Molecular Crystals" Clarendon Press, Oxford, p. 115-118, 272.
Bo, X. et al. (2003). "Tissue distribution of P2X4 receptors studied with an ectodomain antibody," Cell Tissue Res 313: 159-165.
Bowen, C.A et al. (Presented Nov. 16, 2014 at Society for Neuroscience Annual Meeting). "Discovery and Characterization of Novel, Potent and Selective P2X4 Receptor Antagonists for the Treatment of Pain," Sunovion Pharmaceuticals Inc. 241.11:36.
Braga et al. (2005). "Making crystals from crystals: a green route to crystal enginering and polymorphism " J. Royal Soc. Chem. Commum. 3635-3645.
Brone, B. et al. (2007). "P2X currents in peritoneal macrophages of wild type and P2X4 -/- mice," Immunology Letters 113: 83-89.
Burnstock (1993). "Physiological and pathological roles of purines: An update" Drug Dev. Res. 28: 195-206.
Burnstock (2013). "Purinergic mechanisms and pain—An update" Eur. J. Pharmacol. 716:24-40.
Burnstock et al. (2011). "Purinergic signalling: From normal behaviour to pathological brain function" Prog. Neurobiol. 95:229-274.
Burnstock, G. et al. (2012). "Purinergic signaling in the airways," Pharmacological Reviews 64(4): 834-868.
Burnstock, G. et al. (Dec. 2014). "ATP-Gated P2X Receptors in Health and Disease," Frontiers in Cellular Neuroscience 7(227).
Calabresi, P. et al. (1996). Introduction of "Chemotherapy of Neoplastic Disease," Section X in The Pharmacological Basis of Therapeutics, 9th ed., McGraw-Hill: New York, pp. 1225-1230.
Cernak, T. et al. (2016). "The medicinal chemist's toolbox for late stage functionalization of drug-like molecules," Chem. Soc. Rev. 45:546-576.
Chen, M.S. et al. (Nov. 2, 2007). "A Predictably Selective Aliphatic C—H Oxidation Reaction for Complex Molecule Synthesis," Science 318:783-787.
Cross et al. (1976). "International Union of Pure and Applied Chemistry: Organic Chemistry Division Commission on Nomenclature of Organic Chemistry" Pure & Appl Chem. 45:11-30.

(56) References Cited

OTHER PUBLICATIONS

Davidovich et al., (2004). "Detection of polymorphism by Powder X-Ray Diffraction Interference by Preferred Orientation" Am. Pharm. Rev. 7(1): 10, 12, 14, 16, 100.
De Rivero Vaccari, J.P. et al. (2012). "P2X4 Receptors Influence Inflammasome Activation after Spinal Cord Injury," The Journal of Neruoscience, 32(9): 3058-3066.
Dean, J.A. (1995). "Analytical Chemistry Handbook" McGraw-Hill, Inc. Section 10, p. 10.24-10.26.
Greene, T.W. et al. (1999) "Protective Groups in Organic Synthesis," 3rd Edition, John Wiley & Sons, Inc. (Copy not attached).
Gruen, M. et al. (2014). "Use of dynamic weight bearing as a novel end-point for the assessment of abdominal pain in the LPS-induced peritonitis model in the rat," Journal of Neuroscience Methods 232: 118-124.
Guillory, J.K. (1999) "Chapter 5: Generation of Polymorphs, Hydrates, Solvates, and Amorphous Solids," in H.G. Brittain and M.Dekker eds., Polymorphism in Pharmaceutical Solids, pp. 183-226.
International Search Report dated Sep. 11, 2017, for PCT Application No. PCT/EP2017/059882, filed on Apr. 26, 2017, 5 pages.
Ivanisevic, I. et al. (2010). "Use of X-ray Powder Diffraction in the Pharmaceutical Industry" Pharm. Sci. Encycl.: Drub Discovery Development and Manufacturing, John Wiley & Sons, Inc. p. 1-42.
Jain, N.K et al. (1968). "Polymorphism in Pharmacy" Indian Drugs 23(6): 315-329.
Jordan, V.C. (Mar. 2003)."Tamoxifen: A most Unlikely Pioneering Medicine," Nature Reviews 2:205-213.
Kirk-Othmer Encyclopedia of Chemical Technology (2002) John Wiley & Sons, Inc., vol. 8, pp. 95-147.
Masood, M.A. et al. (2012). "Lead Diversification 2: Application to P38, gMTP and lead compounds," Bioorganic & Medicinal Chemistry Letters 22: 1255-1262.
Nema, S. et al. (1997). "Excipients and Their Use in Injectable Products," PDA J. Pharm. Sci. & Tech. 51(4):166-171.
Powell, M. et al. (1998). "Compendium of Excipients for Parenteral Formulations," PDA J. Pharm. Sci. & Tech. 52(5):238-311.
Robinson, I. et al. (2012). "Use of dynamic weight bearing as a novel end-point for the assessment of Freund's Complete Adjuvant induced hypersensitivity in mice," Neuroscience Letters 524: 107-110.
Seddon, K.R. et al. (2004). "Pseudopolymorph: A Polemic" Crystal Growth & Design 4(6): 1087.
Shul'Pina, L.S et al. (2015). "Oxidation of alkanes and benzene with hydrogen peroxide catalyzed by ferrocene in the presence of acids," Journal of Organometallic Chemistry 793: 217-231.
Strickley, R. et al. (1999). "Parenteral Formulations of Small Molecules Therapeutics Marketed in the United States (19991)—Part I," PDA J. Pharm. Sci. & Tech. 53(6):324-349.
Tetreault, P. et al. (2011). "Weight bearing evaluation in inflammatory, neuropathic and cancer chronic pain in freely moving rats," Physiology & Behavior 104: 495-502.
Trang, T. et al. (2012). "P2X4 purinoceptor signaling in chronic pain," Purinergic Signalling 8:621-628.
Tsuda, M. et al. (2009). "Behavioral phenotypes of mice lacking purinergic P2X4 receptors in acute and chronic pain assays," Molecular Pain 5:28.
Ulmann, L. et al. (2010). "P2X4 receptors mediate PGE2 release bytissue-resident macrophages and initiate inflammatory pain," The EMBO Journal 29(14): 2290-2300.
Ulmann, L. et al. (Oct. 29, 2008). "Up-Regulation of P2X4 Receptors in Spinal Microglia after Peripheral Nerve Injury Mediates BDNF Release and Neuropathic Pain," The Journal of Neuroscience 28(44): 11263-11268.
Vippagunta, S.R. et al. (2001). "Crystalline Solids," Advanced Drug Delivery Reviews 48:3-26.
Wang, J. et al. (2014). "Fluorine in Pharmaceutical Industry: Fluorine-Containing Drugs Introduced to the Market in the Last Decade (2001-2011 )," Chemical Reviews 114(4): 2432-2506.
Wang, L. et al. (2004). "P2 receptor mRNA expression profiles in human lymphocytes, monocytes and CD34+ stem and progenitor cells," BMC Immunology 5(16): 1-7.
Wender, P.A. et al. (2005). "Late-Stage Intermolecular CH Activation for Lead Diversification: A Highly Chemoselective Oxyfunctionalization of the C-9 Position of Potent Bryostatin Analogues," Organic Letters 7(1): 79-82.
Written Opinion of the International Search Authority dated Sep. 11, 2017, for PCT Application No. PCT/EP2017/059882, filed on Apr. 26, 2017, 9 pages.
Yu, L. et al. (1998). "Physical characterization of polymorphic drugs: an integrated characterization strategy," PSTT, 1(3): 118-127. 118-127.
Zhou, Y. et al. (2016). "Next Generation of Fluorine-Containing Pharmaceuticals, Compounds Currently in Phase 11-111 Clinical Trials of Major Pharmaceutical Companies: New Structural Trends and Therapeutic Areas," Chem. Rev. 116: 422-518.

* cited by examiner

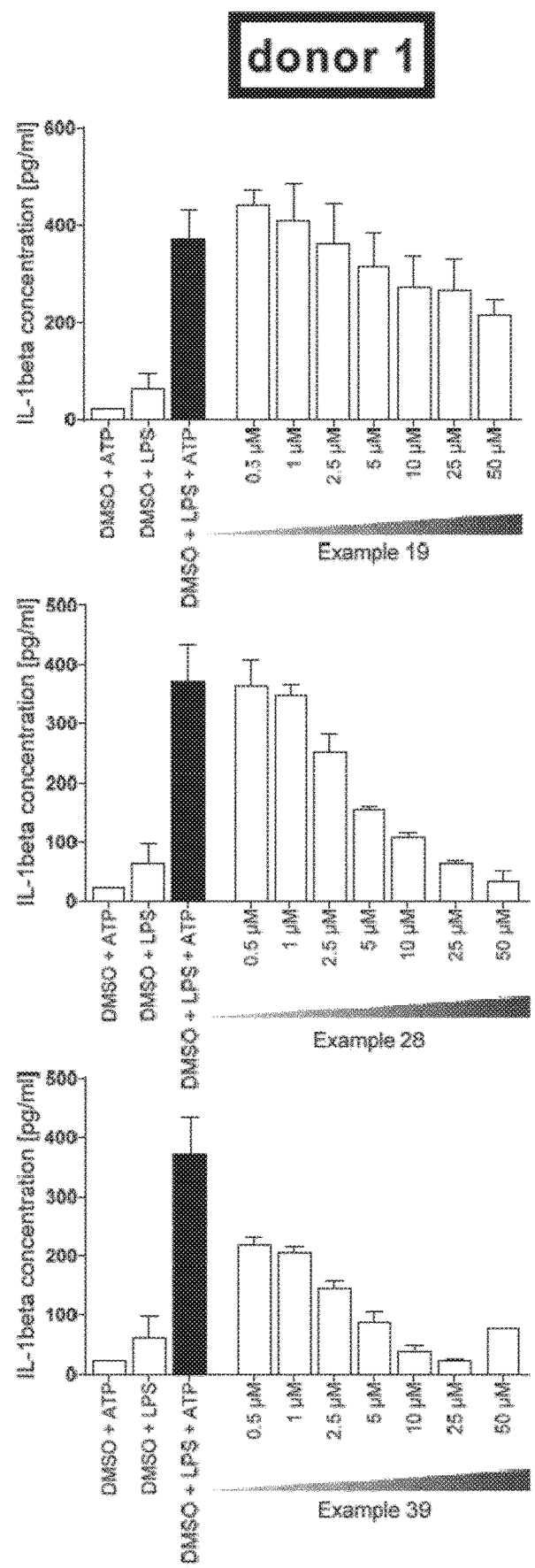
Fig. 2a(1)

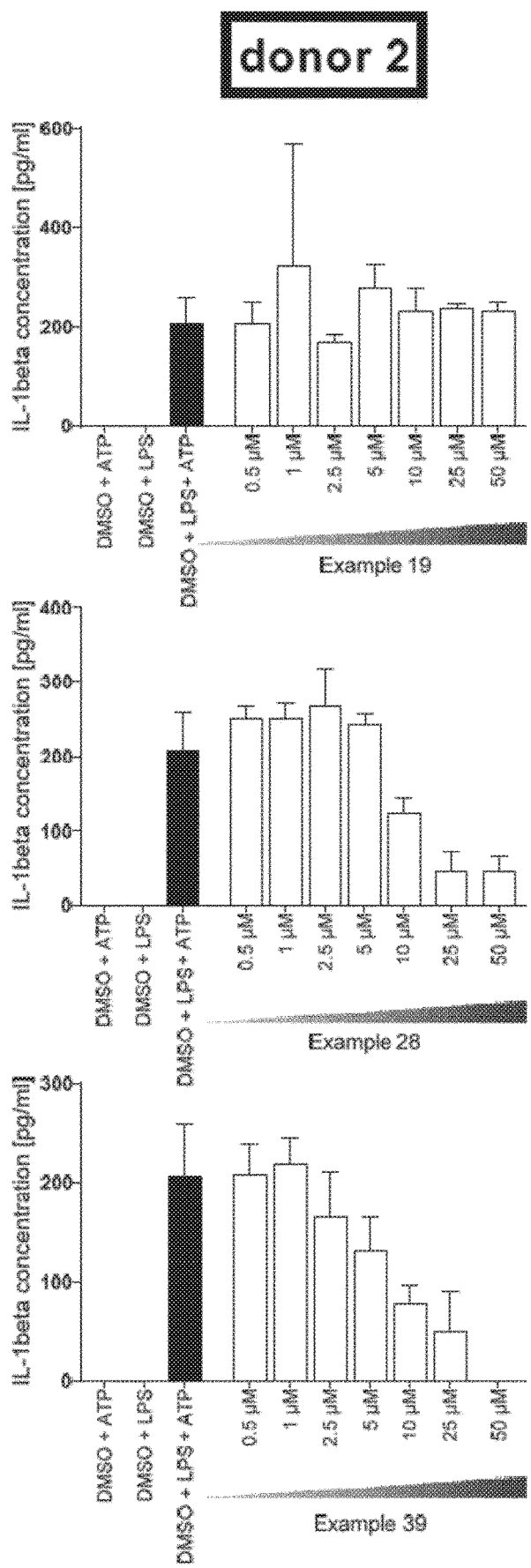
Fig. 2a(2)

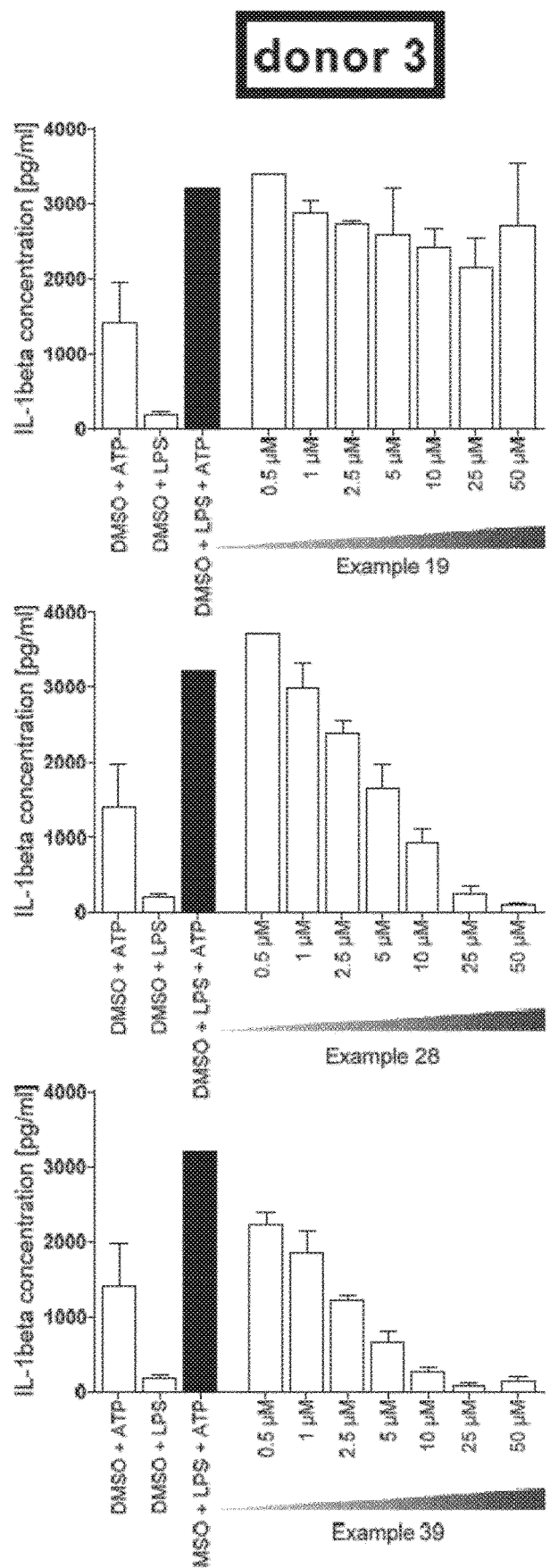
Fig. 2a(3)

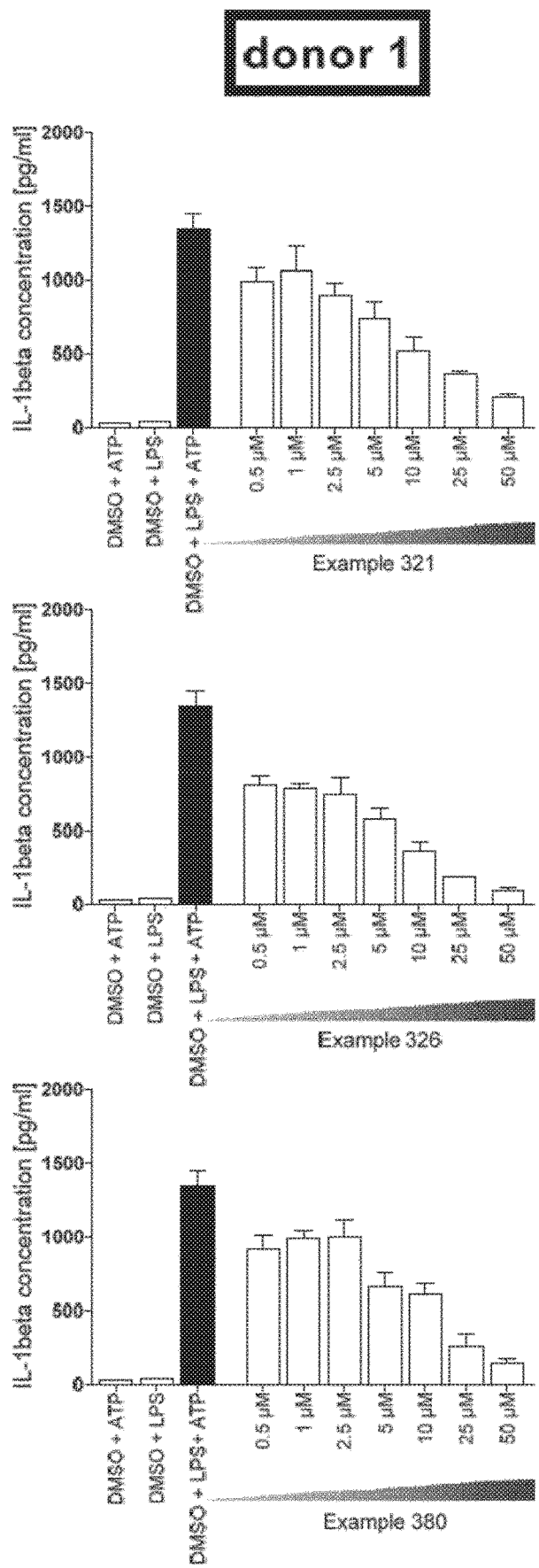
Fig. 2b(1)

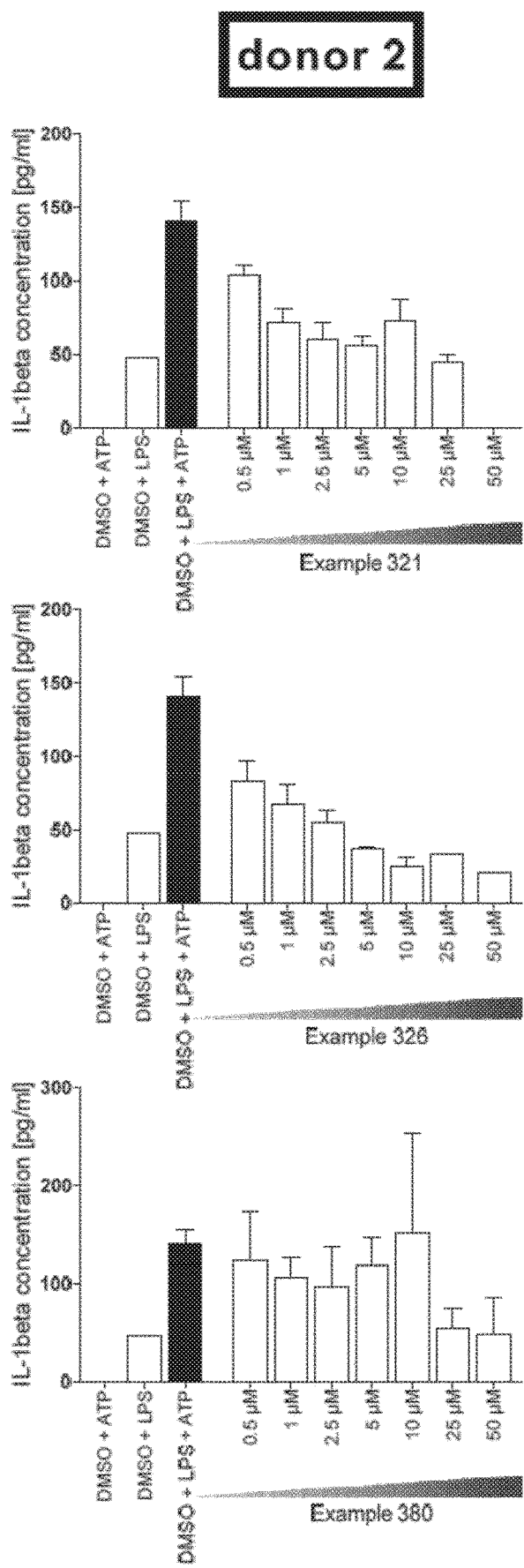
Fig. 2b(2)

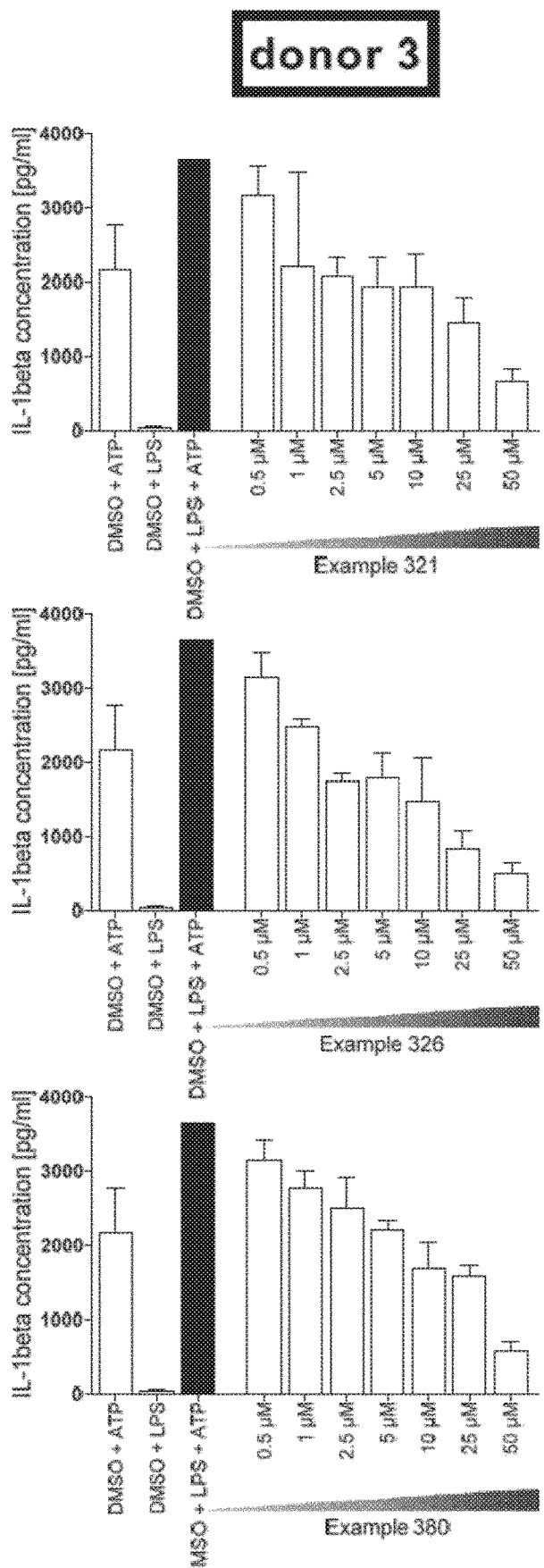
Fig. 2b(3)

AROMATIC SULFONAMIDE DERIVATIVES

CROSS REFERENCE TO RELATED APPLICATIONS

This application is a divisional application of U.S. patent application Ser. No. 16/098,767, which adopts the international filing date Apr. 26, 2017, now U.S. Pat. No. 10,844, 016, which is a national stage application under 35 U.S.C. § 371 of International Application No. PCT/EP2017/ 059882, filed internationally on Apr. 26, 2017, which claims the benefit of European Application No. 16167996.4, filed May 3, 2016.

FIELD OF APPLICATION OF THE INVENTION

The invention relates to substituted aromatic sulfonamides of formula (I) as described and defined herein, pharmaceutical compositions and combinations comprising said compounds and to the use of said compounds for manufacturing a pharmaceutical composition for the treatment or prophylaxis of a disease. The present invention, as described and defined herein, relates to pharmaceutical compositions and combinations comprising an active ingredient which is an antagonist or a negative allosteric modulator of P2X4. The use of such compounds for manufacturing a pharmaceutical composition for the treatment or prophylaxis of a disease, in particular in mammals, such as but not limited to diseases associated with pain, or for the treatment or prophylaxis of pain or neuronal damage and inflammation in the brain or spinal cord or arthritis or spondylitis syndromes (acute and chronic), inflammatory-induced pain, neuropathic pain, pelvic pain, cancer-associated pain, endometriosis-associated pain as well as endometriosis as such, cancer as such, multiple sclerosis as such, spinal cord or ischemic brain injury as such, as a sole agent or in combination with other active ingredients.

BACKGROUND OF THE INVENTION

Chronic inflammatory pain such as in, but not limited to, conditions of endometriosis and adenomyosis, arises as a consequence of inflammatory responses mounted by the immune system following tissue damage or local cell death and generally persists long after the initial injury has healed. Since a large percentage of patients with inflammatory diseases do not respond adequately to currently available anti-inflammatory treatments or analgesic drugs or suffer from intolerable side effects, investigation of alternative treatments for inflammatory conditions/disorders is warranted.

Adenosine triphosphate ATP is widely recognized as an important neurotransmitter implicated in various physiological and pathophysiological roles by acting through different subtypes of purinergic receptors (Burnstock 1993, Drug Dev Res 28:196-206; Burnstock 2011, Prog Neurobiol 95:229-274). To date, seven members of the P2X family have been cloned, comprising P2X1-7 (Burnstock 2013, Front Cell Neurosci 7:227). The P2X4 receptor is a ligand-gated ion channel that is expressed on a variety of cell types largely known to be involved in inflammatory/immune processes specifically including monocytes, macrophages, mast cells and microglia cells (Wang et al., 2004, BMC Immunol 5:16; Brone et al., 2007 Immunol Lett 113:83-89). Activation of P2X4 by extracellular ATP is known, amongst other things, to lead to release of pro-inflammatory cytokines and prostaglandins (PGE2) (Bo et al., 2003 Cell Tissue Res 313: 159-165; Ulmann et al., 2010, EMBO Journal 29:2290-2300; de Ribero Vaccari et al., 2012, J Neurosci 32:3058-3066). Numerous lines of evidence in the literature using animal models implicate P2X4 receptor in nociception and pain. Mice lacking the P2X4 receptor do not develop pain hypersensitivity in response to numerous inflammatory challenges such as complete Freunds Adjuvant, carrageenan or formalin (Ulmann et al., 2010, EMBO Journal 29:2290-2300). In addition, mice lacking the P2X4R do not develop mechanical allodynia after peripheral nerve injury, indicating an important role of P2X4 also in neuropathic pain conditions (Tsuda et al., 2009, Mol Pain 5:28; Ulmann et al., 2008, J Neurocsci 28:11263-11268).

Besides the prominent role of P2X4 in acute and chronic pain-related diseases (Trang and Salter, 2012, Purinergic Signalling 8:621-628; Burnstock, 2013 Eur J Pharmacol 716:24-40), P2X4 is considered as a critically important mediator of inflammatory diseases such as, respiratory diseases (e.g. asthma, COPD), lung diseases including fibrosis, cancer and atherosclerosis (Burnstock et al., 2012 Pharmacol Rev. 64:834-868).

EP 2 597 088 A1 describes P2X4 receptor antagonists and in particular a diazepine derivative of formula (III) or a pharmacologically acceptable salt thereof. Said document further disclosed the use of P2X4 receptor antagonist diazepine derivatives represented by the formula (I), (II), (III), or its pharmacologically acceptable salt, which shows P2X4 receptor antagonism, being effective as an agent for prevention or treatment of nociceptive, inflammatory, and neuropathic pain. In more detail, EP 2 597 088 A1 describes P2X4 receptor antagonists being effective as a preventive or therapeutic agent for pain caused by various cancers, diabetic neuritis, viral diseases such as herpes, and osteoarthritis. The preventive or therapeutic agent according to EP 2 597 088 A1 can also be used in combination with other agents such as opioid analgesic (e.g., morphine, fentanyl), sodium channel inhibitor (e.g., novocaine, lidocaine), or NSAIDs (e.g., aspirin, ibuprofen). The P2X4 receptor antagonist used for pain caused by cancers can be also used in combination with a carcinostatic such as a chemotherapic. Further P2X4 receptor antagonists and their use are disclosed in WO2013105608, WO2015005467 and WO2015005468.

"Discovery and characterization of novel, potent and selective P2X4 receptor antagonists for the treatment of pain" was presented at the Society for Neuroscience Annual Meeting 2014 (Carrie A Bowen et al.; poster N. 241.1) Said poster describes the methods to identify novel, potent and selective small-molecule antagonists that inhibit P2X4 across species, and how to evaluate selected compounds in experimental models of neuropatic and inflammatory pain. In particular a method for human, rat, mouse P2X4R Flipr-based screening, a human P2X4R electrophysiology assay, a suitable mouse neuropathy model and a mouse inflammation model were described.

WO2015/088564 and WO2015/088565 provide P2X4 receptor modulating compounds, methods of their synthesis, pharmaceutical compositions comprising the compounds, and methods of their use. Said P2X4 receptor modulating compounds are useful for the treatment, prevention, and/or management of various disorders, including but not limited to, chronic pain, neuropathy, inflammatory diseases and central nervous system disorders.

There is no reference in the state of the art about substituted aromatic sulfonamides of general formula (I) as described and defined herein and to the use of said compounds for manufacturing a pharmaceutical composition for the treatment or prophylaxis of a disease, particularly to the use of substituted aromatic sulfonamides of general formula (I) for the treatment or prophylaxis of diseases associated with pain, or for the treatment or prophylaxis of pain syndromes (acute and chronic), inflammatory-induced pain, neuropathic pain, pelvic pain, cancer-associated pain, endometriosis-associated pain as well as endometriosis as such, cancer as such, and proliferative diseases as such like endometriosis, as a sole agent or in combination with other active ingredients.

Therefore, the inhibitors of P2X4 of the current invention represent valuable compounds that should complement therapeutic options either as single agents or in combination with other drugs.

DESCRIPTION OF THE FIGURES

FIGS. 2a(1), 2a(2), and 2a(3) depict the results of ELISA assays to evaluate the effect of the compounds according to examples 19, 28 and 39 on the generation of IL-1β in human whole blood after ATP stimulation.

FIGS. 2b(1), 2b(2), and 2b(3) depict the results of ELISA assays to evaluate the effect of the compounds according to examples 321, 326, and 380 on the generation of IL-1β in human whole blood after ATP stimulation.

DESCRIPTION OF THE INVENTION

Figure 1:
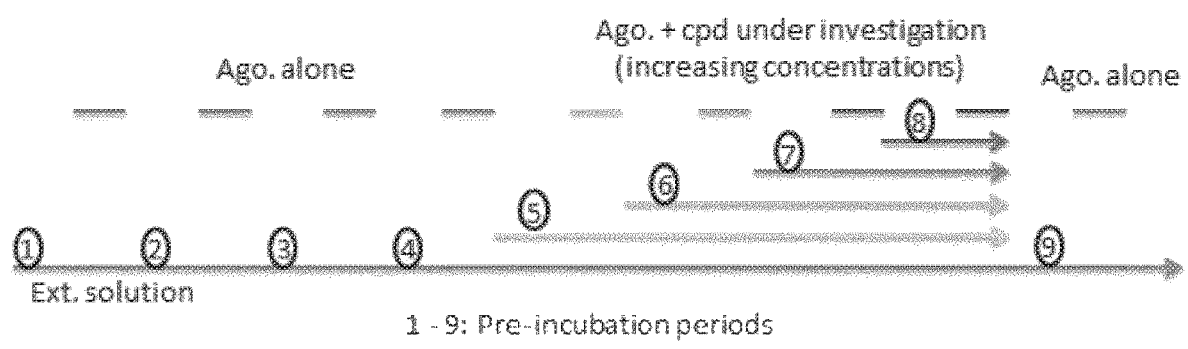
FIG. 1 depicts the application protocol for standard whole-cell voltage clamp experiments performed at room temperature using multihole technology.

The present invention relates to a compound of formula (I)

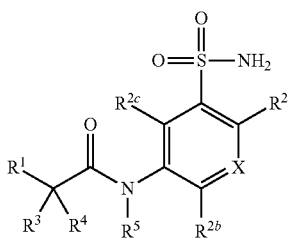

(I)

in which:
X represents C—$R^{2a}$ or N;
$R^1$ represents a group selected from:

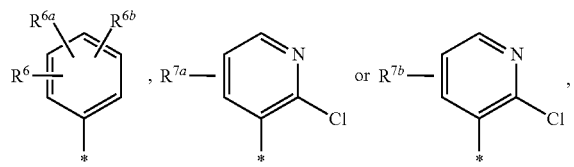

wherein * indicates the point of attachment of said group with the rest of the molecule;
$R^2$ represents phenyl or heteroaryl,
wherein said phenyl or heteroaryl groups are optionally substituted one to three times with $R^{11}$, being, independently from each other, the same or different, or substituted one time with $R^{11a}$ and optionally one to two times with $R^{11}$ being independently from each other, the same or different, or substituted with two adjacent substituents $R^{11}$ which together represent a methylendioxy group to form a 5-membered ring;
$R^{2a}$ represents hydrogen, cyano, nitro, halogen, $C_1$-$C_2$-alkyl or $C_1$-$C_2$-haloalkyl;
$R^{2b}$ represents hydrogen, halogen, $C_1$-$C_2$-alkyl or $C_1$-$C_2$-haloalkyl;
$R^{2c}$ represents hydrogen, halogen, $C_1$-$C_2$-alkyl or $C_1$-$C_2$-haloalkyl, wherein not less than one of $R^{2a}$, $R^{2b}$ and $R^{2c}$ represents hydrogen;
$R^3$ represents hydrogen or fluoro;
$R^4$ represents hydrogen, fluoro, methyl or OH;
$R^5$ represents hydrogen or $C_1$-$C_3$-alkyl;
$R^6$ represents halogen, cyano, nitro, OH, $C_1$-$C_4$-alkyl, $C_1$-$C_4$-haloalkyl, $C_1$-$C_4$-alkoxy, $C_1$-$C_4$-haloalkoxy or $F_3$CS—;
$R^{6a}$ and $R^{6b}$ are the same or different and represent, independently from each other, respectively
$R^{6a}$ hydrogen, halogen, hydroxy, nitro, cyano, $C_1$-$C_4$-alkyl, $C_3$-$C_6$-cycloalkyl, $C_1$-$C_4$-haloalkyl, $C_1$-$C_4$-alkoxy, $C_1$-$C_4$-haloalkoxy, HO—($C_2$-$C_4$-alkoxy)-, ($C_1$-$C_4$-alkoxy)-($C_2$-$C_4$-alkoxy)-, $R^9R^{10}$N—, $R^8$—C(O)—NH—, $R^8$—C(O)—, $R^8$—O—C(O)—, $R^9R^{10}$N—C(O)— or ($C_1$-$C_4$-alkyl)-$SO_2$—;
$R^{6b}$ hydrogen, halogen, hydroxy, nitro, cyano, $C_1$-$C_4$-alkyl, $C_3$-$C_6$-cycloalkyl, $C_1$-$C_4$-haloalkyl, $C_1$-$C_4$-haloalkoxy, HO—($C_2$-$C_4$-alkoxy)-, ($C_1$-$C_4$-alkoxy)-($C_2$-$C_4$-alkoxy)-, $R^9R^{10}$N—, $R^8$—C(O)—NH—, $R^8$—C(O)—, $R^8$—O—C(O)—, $R^9R^{10}$N—C(O)— or ($C_1$-$C_4$-alkyl)-$SO_2$—; or
$R^{6a}$ and $R^{6b}$ adjacent to each other together represent a group selected from —O—$CH_2$—$CH_2$—, —O—$CH_2$—O— or —O—$CH_2$—$CH_2$—O—;
$R^{7a}$ and $R^{7b}$ are the same or different and represent, independently from each other, hydrogen, hydroxy, halogen, $C_1$-$C_4$-alkyl or $C_1$-$C_4$-haloalkyl;
$R^8$ represents, independently from each respective occurrence, $C_1$-$C_6$-alkyl, $C_1$-$C_4$-alkoxy-$C_1$-$C_4$-alkyl, $C_3$-$C_6$-cycloalkyl or $C_1$-$C_4$-haloalkyl;
$R^9$ and $R^{10}$ are the same or different and represent, independently from each other, hydrogen, $C_1$-$C_4$-alkyl, $C_3$-$C_6$-cycloalkyl, $C_1$-$C_4$-haloalkyl or $(CH_3)_2$N—$C_1$-$C_4$-alkyl or
together with the nitrogen atom to which they are attached form a 4- to 6-membered nitrogen containing heterocyclic ring, said ring optionally containing one additional heteroatom selected from O, S, NH, $NR^a$ in which Ra represents a $C_1$-$C_6$-alkyl or $C_1$-$C_6$-haloalkyl group and being optionally substituted, one to three times, independently from each other, with halogen or $C_1$-$C_4$-alkyl;
$R^{11}$ represents, independently from each other, halogen, hydroxy, nitro, cyano, $C_1$-$C_4$-alkyl, $C_2$-$C_4$-alkenyl, $C_1$-$C_4$-haloalkyl, $C_1$-$C_6$-hydroxyalkyl, $C_1$-$C_4$-alkoxy, $C_1$-$C_4$-haloalkoxy, ($C_1$-$C_4$-alkoxy)-($C_1$-$C_4$-alkyl)-, ($C_1$-$C_4$-haloalkoxy)-($C_1$-$C_4$-alkyl)-, $R^9R^{10}$N—($C_1$-$C_4$-alkyl)-, $R^9R^{10}$N—, $R^8$—C(O)—NH—, $R^8$—C(O)—, $R^8$—O—C(O)—, $R^9R^{10}$N—C(O)—, ($C_1$-$C_4$-alkyl)-S— or ($C_1$-$C_4$-alkyl)-$SO_2$—;

$R^{11a}$ represents a group selected from $C_3$-$C_6$-cycloalkyl, morpholino,

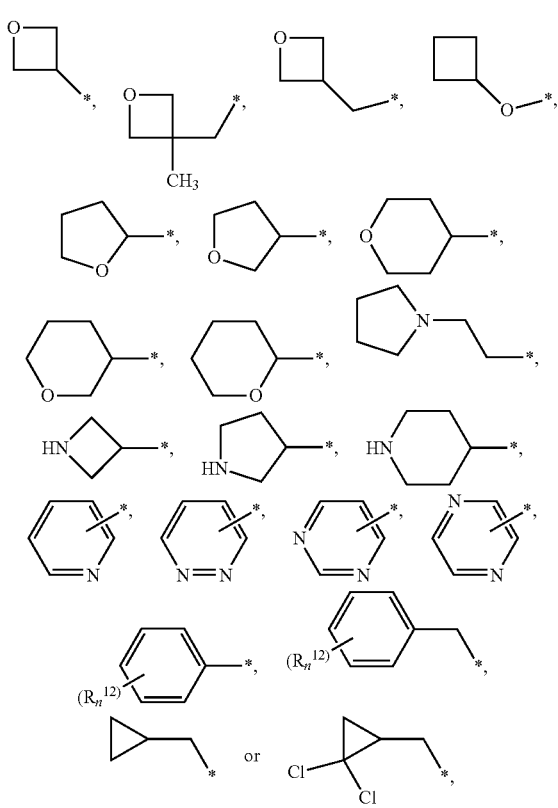

wherein * indicates the point of attachment of said group with the rest of the molecule;

$R^{12}$ represents, independently from each other, halogen, hydroxy, nitro, cyano, $C_1$-$C_4$-alkyl, $C_2$-$C_4$-alkenyl, $C_1$-$C_4$-haloalkyl, $C_1$-$C_4$-hydroxyalkyl, $C_1$-$C_4$-alkoxy, $C_1$-$C_4$-haloalkoxy, ($C_1$-$C_4$-alkoxy)-($C_2$-$C_4$-alkyl)-, ($C_1$-$C_4$-haloalkoxy)-($C_2$-$C_4$-alkyl)-, $R^9R^{10}$N—, $R^8$—C(O)—NH—, $R^8$—C(O)—, $R^8$—O—C(O)—, $R^9R^{10}$N—C(O)— or ($C_1$-$C_4$-alkyl)-SO$_2$—;

n represents 0, 1, 2 or 3;

or an N-oxide, a salt, a hydrate, a solvate, a tautomer or a stereoisomer of said compound, or a salt of said N-oxide, tautomer or stereoisomer.

In another embodiment the invention relates to a compound of formula (I), in which:

X represents C—$R^{2a}$ or N;

$R^1$ represents a group selected from:

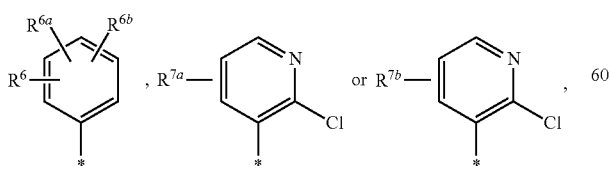

wherein * indicates the point of attachment of said group with the rest of the molecule;

$R^2$ represents a group selected from:

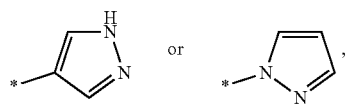 [SMILES: *c1cn[nH]c1 ; *n1cccn1]

wherein * indicates the point of attachment of said group with the rest of the molecule and said groups are optionally substituted one to two times with $R^{11}$, being, independently from each other, the same or different, or substituted one time with $R^{11a}$ and optionally one time with $R^{11}$ being independently from each other, the same or different;

$R^{2a}$ represents hydrogen, cyano, nitro, halogen, $C_1$-$C_2$-alkyl or $C_1$-$C_2$-haloalkyl;

$R^{2b}$ represents hydrogen, halogen, $C_1$-$C_2$-alkyl or $C_1$-$C_2$-haloalkyl;

$R^{2c}$ represents hydrogen, halogen, $C_1$-$C_2$-alkyl or $C_1$-$C_2$-haloalkyl, wherein not less than one of $R^{2a}$, $R^{2b}$ and $R^{2c}$ represents hydrogen;

$R^3$ represents hydrogen or fluoro;

$R^4$ represents hydrogen, fluoro, methyl or OH;

$R^5$ represents hydrogen or $C_1$-$C_3$-alkyl;

$R^6$ represents halogen, cyano, nitro, OH, $C_1$-$C_4$-alkyl, $C_1$-$C_4$-haloalkyl, $C_1$-$C_4$-alkoxy, $C_1$-$C_4$-haloalkoxy or F$_3$CS—;

$R^{6a}$ and $R^{6b}$ are the same or different and represent, independently from each other, respectively $R^{6a}$ hydrogen, halogen, hydroxy, nitro, cyano, $C_1$-$C_4$-alkyl, $C_3$-$C_6$-cycloalkyl, $C_1$-$C_4$-haloalkyl, $C_1$-$C_4$-alkoxy, $C_1$-$C_4$-haloalkoxy, HO—($C_2$-$C_4$-alkoxy)-, ($C_1$-$C_4$-alkoxy)-($C_2$-$C_4$-alkoxy)-, $R^9R^{10}$N—, $R^8$—C(O)—NH—, $R^8$—C(O)—, $R^8$—O—C(O)—, $R^9R^{10}$N—C(O)— or ($C_1$-$C_4$-alkyl)-SO$_2$—;

$R^{6b}$ hydrogen, halogen, hydroxy, nitro, cyano, $C_1$-$C_4$-alkyl, $C_3$-$C_6$-cycloalkyl, $C_1$-$C_4$-haloalkyl, $C_1$-$C_4$-haloalkoxy, HO—($C_2$-$C_4$-alkoxy)-, ($C_1$-$C_4$-alkoxy)-($C_2$-$C_4$-alkoxy)-, $R^9R^{10}$N—, $R^8$—C(O)—NH—, $R^8$—C(O)—, $R^8$—O—C(O)—, $R^9R^{10}$N—C(O)— or ($C_1$-$C_4$-alkyl)-SO$_2$—; or $R^{6a}$ and $R^{6b}$ adjacent to each other together represent a group selected from —O—CH$_2$—CH$_2$—, —O—CH$_2$—O— or —O—CH$_2$—CH$_2$—O—;

$R^{7a}$ and $R^{7b}$ are the same or different and represent, independently from each other, hydrogen, hydroxy, halogen, $C_1$-$C_4$-alkyl or $C_1$-$C_4$-haloalkyl;

$R^8$ represents, independently from each respective occurrence, $C_1$-$C_6$-alkyl, $C_1$-$C_4$-alkoxy-$C_1$-$C_4$-alkyl, $C_3$-$C_6$-cycloalkyl or $C_1$-$C_4$-haloalkyl;

$R^9$ and $R^{10}$ are the same or different and represent, independently from each other, hydrogen, $C_1$-$C_4$-alkyl, $C_3$-$C_6$-cycloalkyl, $C_1$-$C_4$-haloalkyl or (CH$_3$)$_2$N—$C_1$-$C_4$-alkyl or together with the nitrogen atom to which they are attached form a 4- to 6-membered nitrogen containing heterocyclic ring, said ring optionally containing one additional heteroatom selected from O, S, NH, NR$^a$ in which Ra represents a $C_1$-$C_6$-alkyl or $C_1$-$C_6$-haloalkyl group and being optionally substituted, one to three times, independently from each other, with halogen or $C_1$-$C_4$-alkyl;

$R^{11}$ represents, independently from each other, halogen, hydroxy, nitro, cyano, $C_1$-$C_4$-alkyl, $C_2$-$C_4$-alkenyl, $C_1$-$C_4$-haloalkyl, $C_1$-$C_6$-hydroxyalkyl, $C_1$-$C_4$-alkoxy, $C_1$-$C_4$-haloalkoxy, ($C_1$-$C_4$-alkoxy)-($C_1$-$C_4$-alkyl)-, ($C_1$-$C_4$-haloalkoxy)-($C_1$-$C_4$-alkyl)-, $R^9R^{10}$N—($C_1$-$C_4$- alkyl)-, $R^9R^{10}N-$, $R^8-C(O)-NH-$, $R^8-C(O)-$, $R^8-O-C(O)-$, $R^9R^{10}N-C(O)-$, $(C_1-C_4\text{-alkyl})-S-$ or $(C_1-C_4\text{-alkyl})-SO_2-$;

$R^{11a}$ represents a group selected from $C_3-C_6$-cycloalkyl, morpholino,

[structures shown]

wherein * indicates the point of attachment of said group with the rest of the molecule;

$R^{12}$ represents, independently from each other, halogen, hydroxy, nitro, cyano, $C_1-C_4$-alkyl, $C_2-C_4$-alkenyl, $C_1-C_4$-haloalkyl, $C_1-C_4$-hydroxyalkyl, $C_1-C_4$-alkoxy, $C_1-C_4$-haloalkoxy, $(C_1-C_4\text{-alkoxy})-(C_2-C_4\text{-alkyl})-$, $(C_1-C_4\text{-haloalkoxy})-(C_2-C_4\text{-alkyl})-$, $R^9R^{10}N-$, $R^8-C(O)-NH-$, $R^8-C(O)-$, $R^8-O-C(O)-$, $R^9R^{10}N-C(O)-$ or $(C_1-C_4\text{-alkyl})-SO_2-$;

n represents 0, 1, 2 or 3;

or an N-oxide, a salt, a hydrate, a solvate, a tautomer or a stereoisomer of said compound, or a salt of said N-oxide, tautomer or stereoisomer.

In a preferred embodiment the invention relates to a compound of formula (I), in which:

X represents $C-R^{2a}$ or N;

$R^1$ represents a group selected from:

[structures shown]

wherein * indicates the point of attachment of said group with the rest of the molecule;

$R^2$ represents

[structure shown]

wherein * indicates the point of attachment of said group with the rest of the molecule and said group is optionally substituted one to two times with $R^{11}$, being, independently from each other, the same or different, or substituted one time with $R^{11a}$ and optionally one time with $R^{11}$ being independently from each other, the same or different;

$R^{2a}$ represents hydrogen, fluoro, chloro or cyano;

$R^{2b}$ represents hydrogen, fluoro or chloro;

$R^{2c}$ represents hydrogen, fluoro or chloro;

wherein not less than one of $R^{2a}$, $R^{2b}$ and $R^{2c}$ represents hydrogen;

$R^3$ represents hydrogen or fluoro;

$R^4$ represents hydrogen, fluoro or OH;

$R^5$ represents hydrogen or methyl;

$R^6$ represents fluoro, chloro, bromo, cyano, nitro, OH, $C_1-C_3$-alkyl, difluoromethyl, trifluoromethyl, methoxy, ethoxy, difluoromethoxy or trifluoromethoxy;

$R^{6a}$ and $R^{6b}$ are the same or different and represent, independently from each other, respectively $R^{6a}$ hydrogen, fluoro, chloro, bromo, cyano, methyl, trifluoromethyl or methoxy;

$R^{6b}$ hydrogen or fluoro;

$R^{7a}$ and $R^{7b}$ represent hydrogen;

$R^{11}$ represents, independently from each other, cyano, $C_1-C_4$-alkyl, difluoromethyl, trifluoromethyl, difluoroethyl, $C_1-C_6$-hydroxyalkyl, $(C_1-C_3\text{-alkoxy})$-ethyl-, trifluoromethoxy-ethyl-, $F_2CH-CH_2-NH-CH_2-$, $H_3C-C(O)-$, $H_3C-CH_2-O-C(O)-$;

$R^{11a}$ represents a group selected from cyclopropyl,

[structures shown]

wherein * indicates the point of attachment of said group with the rest of the molecule;

or an N-oxide, a salt, a hydrate, a solvate, a tautomer or a stereoisomer of said compound, or a salt of said N-oxide, tautomer or stereoisomer.

In a preferred embodiment the invention relates to a compound of formula (I), in which:

X represents C—$R^{2a}$ or N;

$R^1$ represents a group selected from:

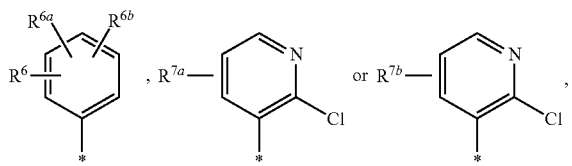

wherein * indicates the point of attachment of said group with the rest of the molecule;

$R^2$ represents

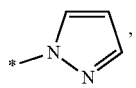

wherein * indicates the point of attachment of said group with the rest of the molecule and said groups are optionally substituted one to two times with $R^{11}$, being, independently from each other, the same or different, or substituted one time with $R^{11a}$ and optionally one time with $R^{11}$ being independently from each other, the same or different;

$R^{2a}$ represents hydrogen, fluoro, chloro or cyano;

$R^{2b}$ represents hydrogen, fluoro or chloro;

$R^{2c}$ represents hydrogen, fluoro or chloro;

wherein not less than one of $R^{2a}$, $R^{2b}$ and $R^{2c}$ represents hydrogen;

$R^3$ represents hydrogen or fluoro;

$R^4$ represents hydrogen, fluoro or methyl;

$R^5$ represents hydrogen or methyl;

$R^6$ represents fluoro, chloro, bromo, cyano, nitro, OH, $C_1$-$C_3$-alkyl, difluoromethyl, trifluoromethyl, methoxy, ethoxy, difluoromethoxy or trifluoromethoxy;

$R^{6a}$ and $R^{6b}$ are the same or different and represent, independently from each other, respectively $R^{6a}$ hydrogen, fluoro, chloro, bromo, cyano, methyl, trifluoromethyl or methoxy;

$R^{6b}$ hydrogen or fluoro;

$R^{7a}$ and $R^{7b}$ represent hydrogen;

$R^{11}$ represents, independently from each other, fluoro, chloro, bromo, cyano, methyl, difluoromethyl, trifluoromethyl, difluoroethyl, hydroxypropyl, $C_1$-$C_3$-alkoxy, methoxy-ethyl-, $F_2CH$—$CH_2$—NH—$CH_2$—, $F_2CH$—$CH_2$—NH—, $H_3C$—C(O)—, $H_3C$—$CH_2$—O—C(O)— or $H_3C$—S—;

$R^{11a}$ represents cyclopropyl; pyridyl or pyrazinyl, or an N-oxide, a salt, a hydrate, a solvate, a tautomer or a stereoisomer of said compound, or a salt of said N-oxide, tautomer or stereoisomer.

In a second aspect, the invention relates in particular to compounds of formula (Ia),

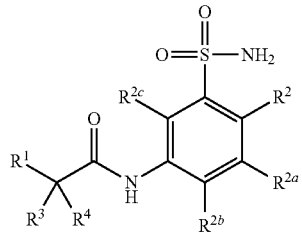

in which:

$R^1$ represents a group selected from:

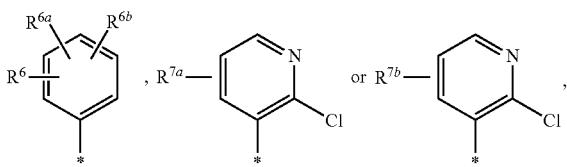

wherein * indicates the point of attachment of said group with the rest of the molecule;

$R^2$ represents phenyl or heteroaryl, wherein said phenyl or heteroaryl groups are optionally substituted one to three times with $R^{11}$, being, independently from each other, the same or different, or substituted one time with $R^{11a}$ and optionally one to two times with $R^{11}$ being independently from each other, the same or different, or substituted with two adjacent substituents $R^{11}$ which together represent a methylendioxy group to form a 5-membered ring;

$R^{2a}$ represents hydrogen, cyano, nitro, halogen, $C_1$-$C_2$-alkyl or $C_1$-$C_2$-haloalkyl; $R^{2b}$ represents hydrogen or halogen;

$R^{2c}$ represents hydrogen or halogen;

wherein not less than one of $R^{2a}$, $R^{2b}$ and $R^{2c}$ represents hydrogen;

$R^3$ represents hydrogen or fluoro;

$R^4$ represents hydrogen, fluoro, methyl or OH;

$R^6$ represents halogen, cyano, nitro, OH, $C_1$-$C_4$-alkyl, $C_1$-$C_4$-haloalkyl, $C_1$-$C_4$-alkoxy, $C_1$-$C_4$-haloalkoxy or $F_3CS$—;

$R^{6a}$ and $R^{6b}$ are the same or different and represent, independently from each other, respectively $R^{6a}$ hydrogen, halogen, hydroxy, nitro, cyano, $C_1$-$C_4$-alkyl, $C_3$-$C_6$-cycloalkyl, $C_1$-$C_4$-haloalkyl, $C_1$-$C_4$-alkoxy, $C_1$-$C_4$-haloalkoxy, HO—($C_2$-$C_4$-alkoxy)-, ($C_1$-$C_4$-alkoxy)-($C_2$-$C_4$-alkoxy)-, $R^9R^{10}N$—, $R^8$—C(O)—NH—, $R^8$—C(O)—, $R^8$—O—C(O)—, $R^9R^{10}N$—C(O)— or ($C_1$-$C_4$-alkyl)-$SO_2$—;

$R^{6b}$ hydrogen, halogen, hydroxy, nitro, cyano, $C_1$-$C_4$-alkyl, $C_3$-$C_6$-cycloalkyl, $C_1$-$C_4$-haloalkyl, $C_1$-$C_4$-haloalkoxy, HO—($C_2$-$C_4$-alkoxy)-, ($C_1$-$C_4$-alkoxy)-($C_2$-$C_4$-alkoxy)-, $R^9R^{10}N$—, $R^8$—C(O)—NH—, $R^8$—C(O)—, $R^8$—O—C(O)—, $R^9R^{10}N$—C(O)— or ($C_1$-$C_4$-alkyl)-$SO_2$—; or $R^{6a}$ and $R^{6b}$ adjacent to each other together represent a group selected from —O—$CH_2$—$CH_2$—, —O—$CH_2$—O— or —O—$CH_2$—$CH_2$—O—;

$R^{7a}$ and $R^{7b}$ are the same or different and represent, independently from each other, hydrogen, hydroxy, halogen, $C_1$-$C_4$-alkyl or $C_1$-$C_4$-haloalkyl;

R[8] represents, independently from each respective occurrence, $C_1$-$C_6$-alkyl, $C_1$-$C_4$-alkoxy-$C_1$-$C_4$-alkyl, $C_3$-$C_6$-cycloalkyl or $C_1$-$C_4$-haloalkyl;

R[9] and R[10] are the same or different and represent, independently from each other, hydrogen, $C_1$-$C_4$-alkyl, $C_3$-$C_6$-cycloalkyl, $C_1$-$C_4$-haloalkyl or $(CH_3)_2N$—$C_1$-$C_4$-alkyl or together with the nitrogen atom to which they are attached form a 4- to 6-membered nitrogen containing heterocyclic ring, said ring optionally containing one additional heteroatom selected from O, S, NH, NR$^a$ in which R$^a$ represents a $C_1$-$C_6$-alkyl or $C_1$-$C_6$-haloalkyl group and being optionally substituted, one to three times, independently from each other, with halogen or $C_1$-$C_4$-alkyl;

R[11] represents, independently from each other, halogen, hydroxy, nitro, cyano, $C_1$-$C_4$-alkyl, $C_2$-$C_4$-alkenyl, $C_1$-$C_4$-haloalkyl, $C_1$-$C_6$-hydroxyalkyl, $C_1$-$C_4$-alkoxy, $C_1$-$C_4$-haloalkoxy, ($C_1$-$C_4$-alkoxy)-($C_1$-$C_4$-alkyl)-, ($C_1$-$C_4$-haloalkoxy)-($C_1$-$C_4$-alkyl)-, R[9]R[10]N—($C_1$-$C_4$-alkyl)-, R[9]R[10]N—, R[8]—C(O)—NH—, R[8]—C(O)—, R[8]—O—C(O)—, R[9]R[10]N—C(O)—, ($C_1$-$C_4$-alkyl)-S— or ($C_1$-$C_4$-alkyl)-$SO_2$—;

R[11a] represents a group selected from $C_3$-$C_6$-cycloalkyl, morpholino,

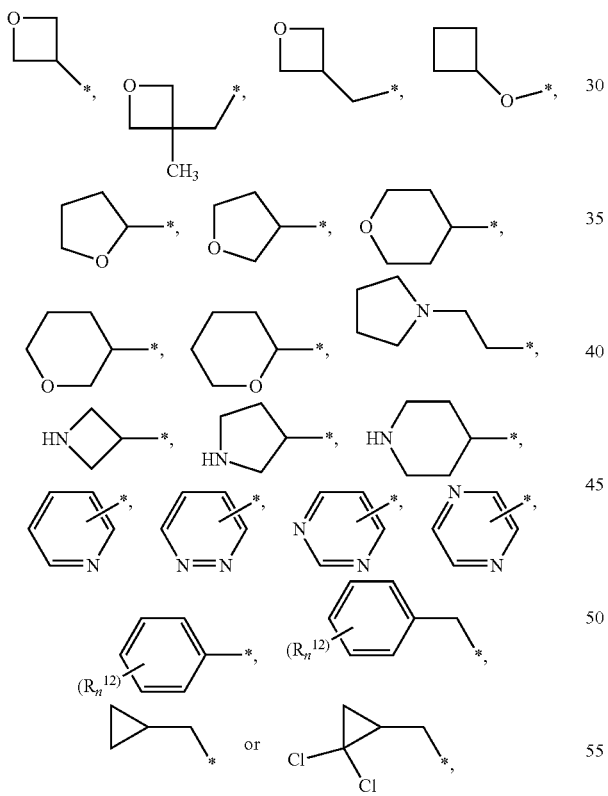

wherein * indicates the point of attachment of said group with the rest of the molecule;

R[12] represents, independently from each other, halogen, hydroxy, nitro, cyano, $C_1$-$C_4$-alkyl, $C_2$-$C_4$-alkenyl, $C_1$-$C_4$-haloalkyl, $C_1$-$C_4$-hydroxyalkyl, $C_1$-$C_4$-alkoxy, $C_1$-$C_4$-haloalkoxy, ($C_1$-$C_4$-alkoxy)-($C_2$-$C_4$-alkyl)-, ($C_1$-$C_4$-haloalkoxy)-($C_2$-$C_4$-alkyl)-, R[9]R[10]N—, R[8]—C(O)—NH—, R[8]—C(O)—, R[8]—O—C(O)—, R[9]R[10]N—C(O)— or ($C_1$-$C_4$-alkyl)-$SO_2$—;

n represents 0, 1, 2 or 3;

or an N-oxide, a salt, a hydrate, a solvate, a tautomer or a stereoisomer of said compound, or a salt of said N-oxide, tautomer or stereoisomer.

In a third aspect, the invention relates in particular to compounds of formula (Ia), supra, in which:

R[1] represents a group selected from:

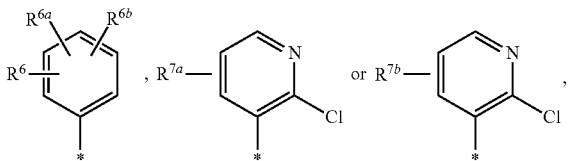

wherein * indicates the point of attachment of said group with the rest of the molecule;

R[2] represents phenyl or heteroaryl, wherein said phenyl or heteroaryl groups are optionally substituted one to three times with R[11], being, independently from each other, the same or different, or substituted one time with R[11a] and optionally one to two times with R[11] being independently from each other, the same or different;

R[2a] represents hydrogen, chloro or cyano;

R[2b] represents hydrogen or fluoro;

R[2c] represents hydrogen or fluoro;

wherein not less than one of R[2a], R[2b] and R[2c] represents hydrogen;

R[3] represents hydrogen or fluoro;

R[4] represents hydrogen, fluoro, methyl or OH;

R[6] represents halogen, cyano, nitro, OH, $C_1$-$C_4$-alkyl, $C_1$-$C_4$-haloalkyl, $C_1$-$C_4$-alkoxy, $C_1$-$C_4$-haloalkoxy or $F_3CS$—;

R[6a] and R[6b] are the same or different and represent, independently from each other, respectively R[6a] hydrogen, halogen, hydroxy, nitro, cyano, $C_1$-$C_4$-alkyl, $C_3$-$C_6$-cycloalkyl, $C_1$-$C_4$-haloalkyl, $C_1$-$C_4$-alkoxy, $C_1$-$C_4$-haloalkoxy, HO—($C_2$-$C_4$-alkoxy)-, ($C_1$-$C_4$-alkoxy)-($C_2$-$C_4$-alkoxy)-, R[9]R[10]N—, R[8]—C(O)—NH—, R[8]—C(O)—, R[8]—O—C(O)—, R[9]R[10]N—C(O)— or ($C_1$-$C_4$-alkyl)-$SO_2$—;

R[6b] hydrogen, halogen, hydroxy, nitro, cyano, $C_1$-$C_4$-alkyl, $C_3$-$C_6$-cycloalkyl, $C_1$-$C_4$-haloalkyl, $C_1$-$C_4$-haloalkoxy, HO—($C_2$-$C_4$-alkoxy)-, ($C_1$-$C_4$-alkoxy)-($C_2$-$C_4$-alkoxy)-, R[9]R[10]N—, R[8]—C(O)—NH—, R[8]—C(O)—, R[8]—O—C(O)—, R[9]R[10]N—C(O)— or ($C_1$-$C_4$-alkyl)-$SO_2$—;

R[8] represents, independently from each respective occurrence, $C_1$-$C_6$-alkyl;

R[9] and R[10] are the same or different and represent, independently from each other, hydrogen, $C_1$-$C_4$-alkyl, $C_3$-$C_6$-cycloalkyl, $C_1$-$C_4$-haloalkyl or $(CH_3)_2N$—$C_1$-$C_4$-alkyl or together with the nitrogen atom to which they are attached form a 4- to 6-membered nitrogen containing heterocyclic ring;

R[11] represents, independently from each other, halogen, hydroxy, cyano, $C_1$-$C_4$-alkyl, $C_1$-$C_4$-haloalkyl, C—$C_6$-hydroxyalkyl, $C_1$-$C_4$-alkoxy, $C_1$-$C_4$-haloalkoxy, ($C_1$-$C_4$-alkoxy)-($C_1$-$C_4$-alkyl)-, ($C_1$-$C_4$-haloalkoxy)-($C_1$-$C_4$-alkyl)-, R[9]R[10]N—($C_1$-$C_4$-alkyl)-, R[9]R[10]N—, $R^B$—C(O)—NH—, $R^8$—C(O)—, $R^8$—O—C(O)—, $R^9R^{10}$N—C(O)—, ($C_1$-$C_4$-alkyl)-S— or ($C_1$-$C_4$-alkyl)-$SO_2$—;

$R^{11a}$ represents a group selected from $C_3$-$C_6$-cycloalkyl, morpholino,

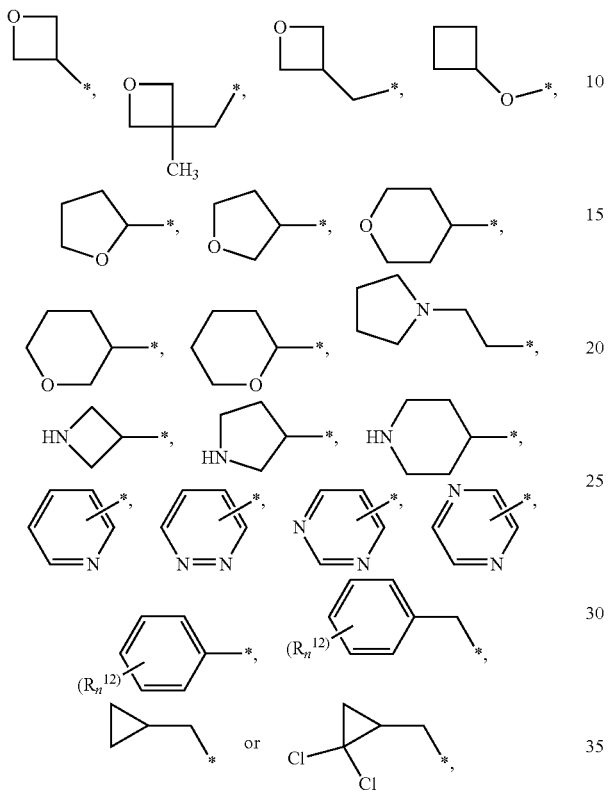

wherein * indicates the point of attachment of said group with the rest of the molecule;

$R^{12}$ represents, independently from each other, halogen, hydroxy, nitro, cyano, $C_1$-$C_4$-alkyl, $C_1$-$C_4$-haloalkyl, $C_1$-$C_4$-alkoxy, $C_1$-$C_4$-haloalkoxy;

n represents 0 or 1;

or an N-oxide, a salt, a hydrate, a solvate, a tautomer or a stereoisomer of said compound, or a salt of said N-oxide, tautomer or stereoisomer.

In a forth aspect, the invention relates in particular to compounds of formula (Ia), supra, in which:

$R^1$ represents

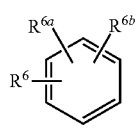

wherein * indicates the point of attachment of said group with the rest of the molecule;

$R^2$ represents phenyl or heteroaryl, wherein said phenyl or heteroaryl groups are optionally substituted one to three times with $R^{11}$, being, independently from each other, the same or different, or substituted one time with $R^{11a}$ and optionally one to two times with $R^{11}$ being independently from each other, the same or different;

$R^{2a}$ represents hydrogen, chloro or cyano;
$R^{2b}$ represents hydrogen or fluoro;
$R^{2c}$ represents hydrogen or fluoro;
  wherein not less than one of $R^{2a}$, $R^{2b}$ and $R^{2c}$ represents hydrogen;
$R^3$ represents hydrogen;
$R^4$ represents hydrogen;
$R^6$ represents halogen, OH, $C_1$-$C_4$-alkyl, $C_1$-$C_4$-haloalkyl, $C_1$-$C_4$-alkoxy or $C_1$-$C_4$-haloalkoxy;
$R^{6a}$ and $R^{6b}$ are the same or different and represent, independently from each other, respectively
$R^{6a}$ hydrogen, halogen, $C_1$-$C_4$-alkyl, $C_1$-$C_4$-haloalkyl or $C_1$-$C_4$-alkoxy;
$R^{6b}$ hydrogen or fluoro;
$R^8$ represents, independently from each respective occurrence, methyl or ethyl;
$R^9$ and $R^{10}$ are the same or different and represent, independently from each other, hydrogen, $C_1$-$C_4$-alkyl, $C_1$-$C_2$-haloalkyl or cyclopropyl or
  together with the nitrogen atom to which they are attached form a 5-membered nitrogen containing heterocyclic ring;
$R^{11}$ represents, independently from each other, halogen, cyano, $C_1$-$C_4$-alkyl, $C_1$-$C_4$-haloalkyl, $C_1$-$C_6$-hydroxyalkyl, $C_1$-$C_4$-alkoxy, $C_1$-$C_4$-haloalkoxy, ($C_1$-$C_3$-alkoxy)-ethyl-, methoxy-ethyl-, $R^9R^{10}$N—, $R^8$—C(O)—, $R^8$—O—C(O)— or $R^9R^{10}$N—C(O)—;
$R^{11a}$ represents a group selected from $C_3$-$C_5$-cycloalkyl,

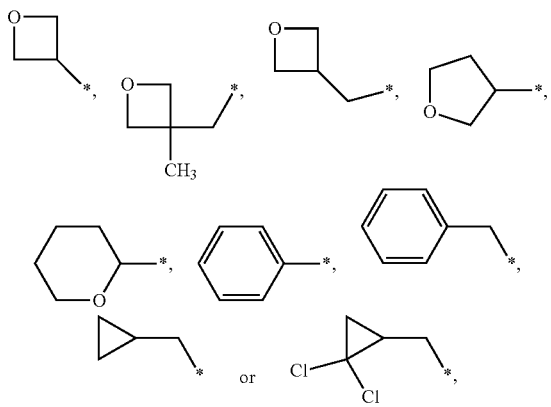

wherein * indicates the point of attachment of said group with the rest of the molecule;

or an N-oxide, a salt, a hydrate, a solvate, a tautomer or a stereoisomer of said compound, or a salt of said N-oxide, tautomer or stereoisomer.

In a fifth aspect, the invention relates in particular to compounds of formula (Ib)

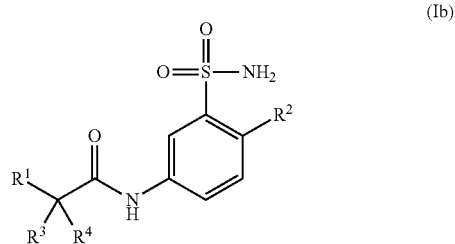

(Ib)

in which:

R¹ represents a group selected from:

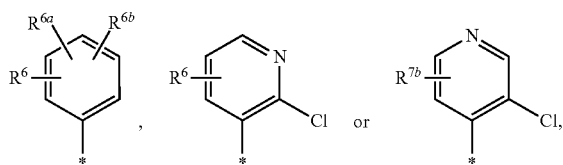

wherein * indicates the point of attachment of said group with the rest of the molecule;

R² represents phenyl or heteroaryl,
wherein said phenyl or heteroaryl groups are optionally substituted one to three times with $R^{11}$, being, independently from each other, the same or different, or substituted one time with $R^{11a}$ and optionally one to two times with $R^{11}$ being independently from each other, the same or different, or substituted with two adjacent substituents $R^{11}$ which together represent a methylendioxy group to form a 5-membered ring;

R³ represents hydrogen or fluoro;
R⁴ represents hydrogen, fluoro, methyl or OH;
R⁶ represents halogen, cyano, nitro, OH, $C_1$-$C_4$-alkyl, $C_1$-$C_4$-haloalkyl, $C_1$-$C_4$-alkoxy, $C_1$-$C_4$-haloalkoxy or $F_3CS$—;
$R^{6a}$ and $R^{6b}$ are the same or different and represent, independently from each other, respectively
$R^{6a}$ hydrogen, halogen, hydroxy, nitro, cyano, $C_1$-$C_4$-alkyl, $C_3$-$C_6$-cycloalkyl, $C_1$-$C_4$-haloalkyl, $C_1$-$C_4$-alkoxy, $C_1$-$C_4$-haloalkoxy, HO—($C_2$-$C_4$-alkoxy)-, ($C_1$-$C_4$-alkoxy)-($C_2$-$C_4$-alkoxy)-, $R^9R^{10}N$—, $R^8$—C(O)—NH—, $R^8$—C(O)—, $R^8$—O—C(O)—, $R^9R^{10}N$—C(O)— or ($C_1$-$C_4$-alkyl)-$SO_2$—;
$R^{6b}$ hydrogen, halogen, hydroxy, nitro, cyano, $C_1$-$C_4$-alkyl, $C_3$-$C_6$-cycloalkyl, $C_1$-$C_4$-haloalkyl, $C_1$-$C_4$-haloalkoxy, HO—($C_2$-$C_4$-alkoxy)-, ($C_1$-$C_4$-alkoxy)-($C_2$-$C_4$-alkoxy)-, $R^9R^{10}N$—, $R^8$—C(O)—NH—, $R^8$—C(O)—, $R^8$—O—C(O)—, $R^9R^{10}N$—C(O)— or ($C_1$-$C_4$-alkyl)-$SO_2$—; or
$R^{6a}$ and $R^{6b}$ adjacent to each other together represent a group selected from —O—$CH_2$—$CH_2$—, —O—$CH_2$—O— or —O—$CH_2$—$CH_2$—O—;
$R^{7a}$ and $R^{7b}$ are the same or different and represent, independently from each other, hydrogen, hydroxy, halogen, $C_1$-$C_4$-alkyl or $C_1$-$C_4$-haloalkyl;
R⁸ represents, independently from each respective occurrence, $C_1$-$C_6$-alkyl, $C_1$-$C_4$-alkoxy-$C_1$-$C_4$-alkyl, $C_3$-$C_6$-cycloalkyl or $C_1$-$C_4$-haloalkyl;
R⁹ and R¹⁰ are the same or different and represent, independently from each other, hydrogen, $C_1$-$C_4$-alkyl, $C_3$-$C_6$-cycloalkyl, $C_1$-$C_4$-haloalkyl or $(CH_3)_2N$—$C_1$-$C_4$-alkyl or
together with the nitrogen atom to which they are attached form a 4- to 6-membered nitrogen containing heterocyclic ring, said ring optionally containing one additional heteroatom selected from O, S, NH, $NR^a$ in which $R^a$ represents a $C_1$-$C_6$-alkyl or $C_1$-$C_6$-haloalkyl group and being optionally substituted, one to three times, independently from each other, with halogen or $C_1$-$C_4$-alkyl;
$R^{11}$ represents, independently from each other, halogen, hydroxy, nitro, cyano, $C_1$-$C_4$-alkyl, $C_2$-$C_4$-alkenyl, $C_1$-$C_4$-haloalkyl, $C_1$-$C_5$-hydroxyalkyl, $C_1$-$C_4$-alkoxy, $C_1$-$C_4$-haloalkoxy, ($C_1$-$C_4$-alkoxy)-($C_1$-$C_4$-alkyl)-, ($C_1$-$C_4$-haloalkoxy)-($C_1$-$C_4$-alkyl)-, $R^9R^{10}N$—($C_1$-$C_4$-alkyl)-, $R^9R^{10}N$—, $R^8$—C(O)—NH—, $R^8$—C(O)—, $R^8$—O—C(O)—, $R^9R^{10}N$—C(O)—, ($C_1$-$C_4$-alkyl)-S— or ($C_1$-$C_4$-alkyl)-$SO_2$—;
$R^{11a}$ represents a group selected from $C_3$-$C_6$-cycloalkyl, morpholino,

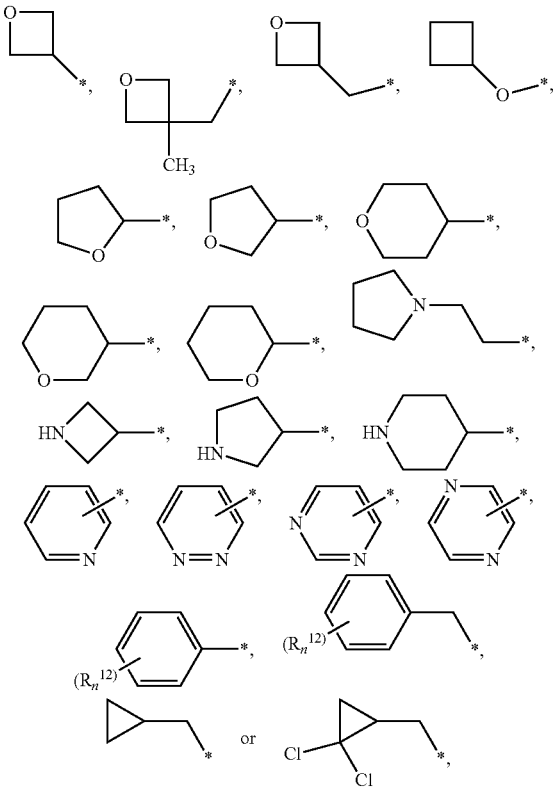

wherein * indicates the point of attachment of said group with the rest of the molecule;
$R^{12}$ represents, independently from each other, halogen, hydroxy, nitro, cyano, $C_1$-$C_4$-alkyl, $C_2$-$C_4$-alkenyl, $C_1$-$C_4$-haloalkyl, $C_1$-$C_4$-hydroxyalkyl, $C_1$-$C_4$-alkoxy, $C_1$-$C_4$-haloalkoxy, ($C_1$-$C_4$-alkoxy)-($C_2$-$C_4$-alkyl)-, ($C_1$-$C_4$-haloalkoxy)-($C_2$-$C_4$-alkyl)-, $R^9R^{10}N$—, $R^8$—C(O)—NH—, $R^8$—C(O)—, $R^8$—O—C(O)—, $R^9R^{10}N$—C(O)— or ($C_1$-$C_4$-alkyl)-$SO_2$—;
n represents 0, 1, 2 or 3;
or an N-oxide, a salt, a hydrate, a solvate, a tautomer or a stereoisomer of said compound, or a salt of said N-oxide, tautomer or stereoisomer.

In a sixth aspect, the invention relates in particular to compounds of formula (Ib), supra,
in which:
R¹ represents

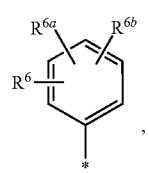

wherein * indicates the point of attachment of said group with the rest of the molecule;
$R^2$ represents heteroaryl,
wherein said heteroaryl groups are optionally substituted once with $R^{11}$;
$R^3$ represents hydrogen;
$R^4$ represents hydrogen;
$R^6$ represents halogen;
$R^{6a}$ and $R^{6b}$ represent hydrogen;
$R^{11}$ represents, independently from each other, halogen, cyano, $C_1$-$C_4$-alkyl or $C_1$-$C_4$-haloalkyl;
or an N-oxide, a salt, a hydrate, a solvate, a tautomer or a stereoisomer of said compound, or a salt of said N-oxide, tautomer or stereoisomer.

In particular the invention refers further to compounds of formula (I), (Ia) and (Ib) as described supra, wherein:
$R^1$ represents

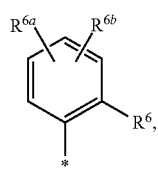

wherein * indicates the point of attachment of said group with the rest of the molecule;
$R^6$ represents halogen, cyano, nitro, OH, $C_1$-$C_4$-alkyl, $C_1$-$C_4$-haloalkyl, $C_1$-$C_4$-alkoxy or $C_1$-$C_4$-haloalkoxy;
$R^{6a}$ and $R^{6b}$ are the same or different and represent, independently from each other, respectively $R^{6a}$ hydrogen, halogen, hydroxy, nitro, cyano, $C_1$-$C_4$-alkyl, $C_3$-$C_6$-cycloalkyl, $C_1$-$C_4$-haloalkyl, $C_1$-$C_4$-alkoxy, $C_1$-$C_4$-haloalkoxy, HO—($C_2$-$C_4$-alkoxy)-, ($C_1$-$C_4$-alkoxy)-($C_2$-$C_4$-alkoxy)-, $R^9R^{10}N$—, $R^8$—C(O)—NH—, $R^8$—C(O)—, $R^8$—O—C(O)—, $R^9R^{10}N$—C(O)— or ($C_1$-$C_4$-alkyl)-$SO_2$—;

$R^{6b}$ hydrogen, halogen, hydroxy, nitro, cyano, $C_1$-$C_4$-alkyl, $C_3$-$C_6$-cycloalkyl, $C_1$-$C_4$-haloalkyl, $C_1$-$C_4$-haloalkoxy, HO—($C_2$-$C_4$-alkoxy)-, ($C_1$-$C_4$-alkoxy)-($C_2$-$C_4$-alkoxy)-, $R^9R^{10}N$—, $R^8$—C(O)—NH—, $R^8$—C(O)—, $R^8$—O—C(O)—, $R^9R^{10}N$—C(O)— or ($C_1$-$C_4$-alkyl)-$SO_2$—.

According to a further alternative the invention refers to compounds of formula (I), (Ia) and (Ib) as described supra, in which:
$R^1$ represents

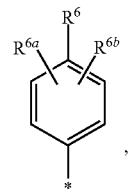

wherein * indicates the point of attachment of said group with the rest of the molecule;
$R^6$ represents halogen, cyano, nitro, OH, $C_1$-$C_4$-alkyl, $C_1$-$C_4$-haloalkyl, $C_1$-$C_4$-alkoxy or $C_1$-$C_4$-haloalkoxy;
$R^{6a}$ and $R^{6b}$ are the same or different and represent, independently from each other, respectively $R^{6a}$ hydrogen, halogen, hydroxy, nitro, cyano, $C_1$-$C_4$-alkyl, $C_3$-$C_6$-cycloalkyl, $C_1$-$C_4$-haloalkyl, $C_1$-$C_4$-alkoxy, $C_1$-$C_4$-haloalkoxy, HO—($C_2$-$C_4$-alkoxy)-, ($C_1$-$C_4$-alkoxy)-($C_2$-$C_4$-alkoxy)-, $R^9R^{10}N$—, $R^8$—C(O)—NH—, $R^8$—C(O)—, $R^8$—O—C(O)—, $R^9R^{10}N$—C(O)— or ($C_1$-$C_4$-alkyl)-$SO_2$—;

$R^{6b}$ hydrogen, halogen, hydroxy, nitro, cyano, $C_1$-$C_4$-alkyl, $C_3$-$C_6$-cycloalkyl, $C_1$-$C_4$-haloalkyl, $C_1$-$C_4$-haloalkoxy, HO—($C_2$-$C_4$-alkoxy)-, ($C_1$-$C_4$-alkoxy)-($C_2$-$C_4$-alkoxy)-, $R^9R^{10}N$—, $R^8$—C(O)—NH—, $R^8$—C(O)—, $R^8$—O—C(O)—, $R^9R^{10}N$—C(O)— or ($C_1$-$C_4$-alkyl)-$SO_2$—.

In particular the invention refers further to compounds of formula (I), (Ia) and (Ib) as described supra, wherein:
$R^1$ represents a group selected from:

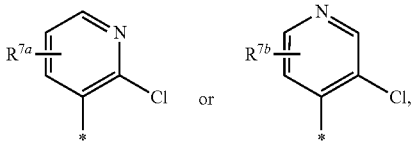

wherein * indicates the point of attachment of said group with the rest of the molecule;
$R^{7a}$ and $R^{7b}$ are the same or different and represent, independently from each other, hydrogen, hydroxy, fluoro, chloro, $C_1$-$C_4$-alkyl, difluoromethyl or trifluoromethyl.

In particular the invention refers further to compounds of formula (I), (Ia) and (Ib) as described supra, wherein:
$R^2$ represents phenyl,
wherein said phenyl group is optionally substituted one to three times with $R^{11}$, being, independently from each other, the same or different, or substituted one time with $R^{11a}$ and optionally one to two times with $R^{11}$ being independently from each other, the same or different, or substituted with two adjacent substituents $R^{11}$ which together represent a methylendioxy group to form a 5-membered ring.

In particular the invention refers further to compounds of formula (I), (Ia) and (Ib) as described supra, wherein:
$R^2$ represents 5-membered monocyclic heteroaryl,
wherein said heteroaryl groups are optionally substituted one to three times with $R^{11}$, being, independently from each other, the same or different, or substituted one time with $R^{11a}$ and optionally one to two times with $R^{11}$ being independently from each other, the same or different.

In particular the invention refers further to compounds of formula (I), (Ia) and (Ib) as described supra, wherein:
$R^2$ represents a group selected from:

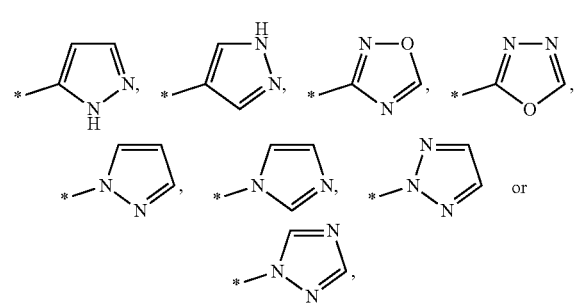

wherein * indicates the point of attachment of said group with the rest of the molecule and said groups are optionally substituted one to two times with $R^{11}$, being, independently from each other, the same or different, or substituted one time with $R^{11a}$ and optionally one time with $R^{11}$ being independently from each other, the same or different.

In particular the invention refers further to compounds of formula (I), (Ia) and (Ib) as described supra, wherein:
$R^2$ represents a group selected from:

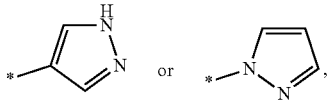 [SMILES: *c1cn[nH]c1 ; *n1cccn1]

wherein * indicates the point of attachment of said group with the rest of the molecule and said groups are optionally substituted one to two times with $R^{11}$, being, independently from each other, the same or different, or substituted one time with $R^{11a}$ and optionally one time with $R^{11}$ being independently from each other, the same or different.

In particular the invention refers further to compounds of formula (I), (Ia) and (Ib) as described supra, wherein:
$R^2$ represents

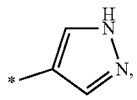

wherein * indicates the point of attachment of said group with the rest of the molecule and said group is optionally substituted one to two times with $R^{11}$, being, independently from each other, the same or different, or substituted one time with $R^{11a}$ and optionally one time with $R^{11}$ being independently from each other, the same or different.

In particular the invention refers further to compounds of formula (I), (Ia) and (Ib) as described supra, wherein:
$R^2$ represents

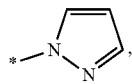

wherein * indicates the point of attachment of said group with the rest of the molecule and said group is optionally substituted one to two times with $R^{11}$, being, independently from each other, the same or different, or substituted one time with $R^{11a}$ and optionally one time with $R^{11}$ being independently from each other, the same or different.

In particular the invention refers further to compounds of formula (I), (Ia) and (Ib) as described supra, wherein:
$R^2$ represents 6-membered monocyclic heteroaryl,
wherein said heteroaryl groups are optionally substituted one to three times with $R^{11}$, being, independently from each other, the same or different, or substituted one time with $R^{11a}$ and optionally one to two times with $R^{11}$ being independently from each other, the same or different.

In particular the invention refers further to compounds of formula (I), (Ia) and (Ib) as described supra, wherein:
$R^2$ represents a group selected from:

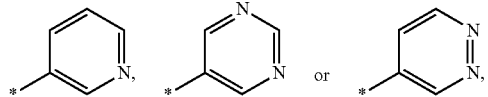

wherein said groups are optionally substituted one to three times with $R^{11}$, being, independently from each other, the same or different, or substituted one time with $R^{11a}$ and optionally one to two times with $R^{11}$ being independently from each other, the same or different.

In particular the invention refers further to compounds of formula (I), (Ia) and (Ib) as described supra, wherein:
$R^2$ represents [5,6]-annellated bicyclic heteroaryl,
wherein said heteroaryl groups are optionally substituted one to three times with $R^{11}$, being, independently from each other, the same or different, or substituted one time with $R^{11a}$ and optionally one to two times with $R^{11}$ being independently from each other, the same or different.

In particular the invention refers further to compounds of formula (I), (Ia) and (Ib) as described supra, wherein:
$R^2$ represents a group selected from:

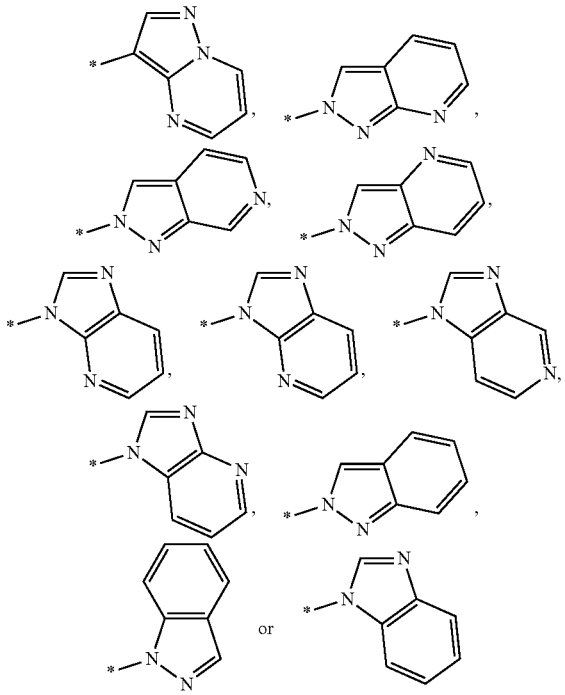

wherein * indicates the point of attachment of said group with the rest of the molecule.

According to a further aspect of the present invention compounds of formula (I), (Ia) and (Ib) as described supra are those in which:
$R^3$ represents hydrogen; and
$R^4$ represents hydrogen, methyl or OH.

According to a further aspect of the present invention compounds of formula (I), (Ia) and (Ib) as described supra are those in which:

$R^3$ represents hydrogen; and
$R^4$ represents hydrogen.

According to a further aspect of the present invention compounds of formula (I), (Ia) and (Ib) as described supra are those in which:
$R^3$ represents fluoro; and
$R^4$ represents fluoro.

According to a more particular aspect of the present invention compounds of formula (I), (Ia) and (Ib) as described supra are those in which:
$R^5$ represents hydrogen.

According to a further particular form of the invention the compounds of formula (Ia) and (Ib) are those in which:
$R^1$ represents

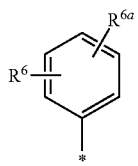

wherein * indicates the point of attachment of said group with the rest of the molecule and $R^6$, $R^{6a}$ represents independently from each other a fluorine, a chlorine or a hydrogen;
$R^2$ represents

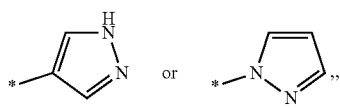

wherein * indicates the point of attachment of said group with the rest of the molecule and said group is optionally substituted one to two times with $R^{11}$, being, independently from each other, the same or different, or substituted one time with $R^{11a}$ and optionally one time with $R^{11}$ being independently from each other, the same or different;
$R^{2a}$, $R^{2b}$, and $R^{2c}$ represents a hydrogen.
$R^3$. $R^4$ $R^5$ represent a hydrogen.
$R^9$ and $R^{10}$ are the same or different and represent, independently from each other, hydrogen, $C_1$-$C_4$-alkyl, $C_1$-$C_2$-haloalkyl or cyclopropyl or
together with the nitrogen atom to which they are attached form a 5-membered nitrogen containing heterocyclic ring;
$R^{11}$ represents, independently from each other, halogen, cyano, $C_1$-$C_4$-alkyl, $C_1$-$C_4$-haloalkyl, $C_1$-$C_6$-hydroxy-alkyl, $C_1$-$C_4$-alkoxy, $C_1$-$C_4$-haloalkoxy, ($C_1$-$C_3$-alkoxy)-ethyl-, methoxy-ethyl-, $R^9R^{10}N$—, $R^8$—C(O)—, $R^8$—O—C(O)— or $R^9R^{10}N$—C(O)—;
$R^{11a}$ represents a group selected from $C_3$-$C_5$-cycloalkyl,

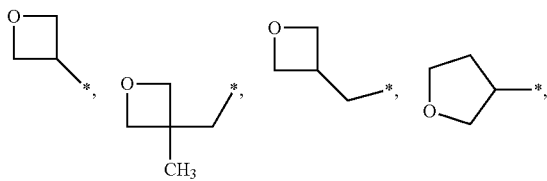

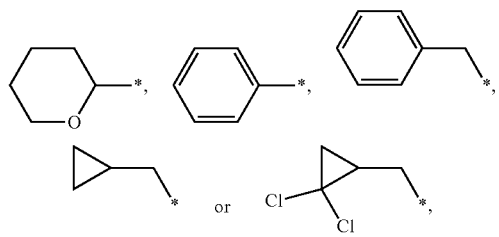

wherein * indicates the point of attachment of said group with the rest of the molecule;
or an N-oxide, a salt, a hydrate, a solvate, a tautomer or a stereoisomer of said compound, or a salt of said N-oxide, tautomer or stereoisomer.

According to a further particular form of the invention the compounds of formula (Ia) and (Ib) are those in which:
$R^1$ represents

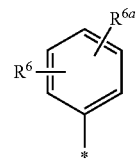

wherein * indicates the point of attachment of said group with the rest of the molecule and $R^6$, $R^{6a}$ represents independently from each other a fluorine, a chlorine or a hydrogen;
$R^2$ represents

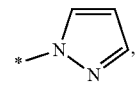 [SMILES: *n1cccn1]

wherein * indicates the point of attachment of said group with the rest of the molecule and said group is optionally substituted one to two times with $R^{11}$, being, independently from each other, the same or different, halogen, cyano, $C_1$-$C_4$-alkyl or $C_1$-$C_4$-haloalkyl;
$R^{2a}$, $R^{2b}$, and $R^{2c}$ represents a hydrogen.
$R^3$. $R^4$ $R^5$ represent a hydrogen.
$R^{6a}$ and $R^{6b}$ represent hydrogen;
$R^{11}$ represents, independently from each other, halogen, cyano, $C_1$-$C_4$-alkyl or $C_1$-$C_4$-haloalkyl;
or an N-oxide, a salt, a hydrate, a solvate, a tautomer or a stereoisomer of said compound, or a salt of said N-oxide, tautomer or stereoisomer.

One aspect of the invention are compounds of formula (I), (Ia), (Ib) as described in the examples, as characterized by their names in the title and their structures as well as the subcombinations of all residues specifically disclosed in the compounds of the examples.

Another aspect of the present invention are intermediates according to formulae 3a, 3b, 4a and 4b wherein $R^2$, $R^{2a}$, $R^{2b}$ and $R^{2c}$ are as defined in the description and claims of this invention.

In a particular embodiment of the present invention, in formulae 3a, 3b, 4a and 4b the group $R^2$, $R^{2a}$, $R^{2b}$ and $R^{2c}$ are defined as follows:

$R^2$ represents wherein * indicates the point of attachment of said group with the rest of the molecule and said group is optionally substituted one to two times with $R^{11}$, being, independently from each other, the same or different, or substituted one time with $R^{11a}$ and optionally one time with $R^{11}$ being independently from each other, the same or different;

$R^{2a}$, $R^{2b}$, and $R^{2c}$ represents a hydrogen.

Furthermore the present invention refers to intermediates according to formula 30 wherein $R^1$, $R^{2a}$, $R^{2b}$, $R^{2c}$, $R^3$ and $R^4$ are as defined in the description and claims of this invention, W represents an amino group which is optionally substituted with a protecting group (e.g., (dimethylamino)methylene or 2,4-dimethoxybenzyl) and V represents chloro or bromo.

In a particular a embodiment of the present invention, the groups of formula 30 are defined as follows:

$R^1$ represents wherein * indicates the point of attachment of said group with the rest of the molecule;

$R^6$ represents halogen, cyano, nitro, OH, $C_1$-$C_4$-alkyl, $C_1$-$C_4$-haloalkyl, $C_1$-$C_4$-alkoxy or $C_1$-$C_4$-haloalkoxy;

$R^{6a}$ and $R^{6b}$ are the same or different and represent, independently from each other, respectively $R^{6a}$ hydrogen, halogen, hydroxy, nitro, cyano, $C_1$-$C_4$-alkyl, $C_3$-$C_6$-cycloalkyl, $C_1$-$C_4$-haloalkyl, $C_1$-$C_4$-alkoxy, $C_1$-$C_4$-haloalkoxy, HO—($C_2$-$C_4$-alkoxy)-, ($C_1$-$C_4$-alkoxy)-($C_2$-$C_4$-alkoxy)-, $R^9R^{10}$N—, $R^6$—C(O)—NH—, $R^6$—C(O)—, $R^8$—O—C(O)—, $R^9R^{10}$N—C(O)— or ($C_1$-$C_4$-alkyl)-$SO_2$—;

$R^{6b}$ hydrogen, halogen, hydroxy, nitro, cyano, $C_1$-$C_4$-alkyl, $C_3$-$C_6$-cycloalkyl, $C_1$-$C_4$-haloalkyl, $C_1$-$C_4$-haloalkoxy, HO—($C_2$-$C_4$-alkoxy)-, ($C_1$-$C_4$-alkoxy)-($C_2$-$C_4$-alkoxy)-, $R^9R^{10}$N—, $R^8$—C(O)—NH—, $R^6$—C(O)—, $R^6$—O—C(O)—, $R^9R^{10}$N—C(O)— or ($C_1$-$C_4$-alkyl)-$SO_2$—.

$R^{2a}$, $R^{2b}$, and $R^{2c}$ represent a hydrogen.

$R^3$. $R^4$ $R^5$ represent a hydrogen.

Specific intermediates for the synthesis of compounds of formula (I), (Ia) and (Ib) according to present invention are:

1. 2-Chloro-N-(2,4-dimethoxybenzyl)-5-nitrobenzenesulfonamide
2. N-(2,4-Dimethoxybenzyl)-2-fluoro-5-nitrobenzenesulfonamide
3. N-(2,4-Dimethoxybenzyl)-5-nitro-2-[4-(trifluoromethyl)-1H-pyrazol-1-yl]benzenesulfonamide
4. 2-(4-Chloro-1H-pyrazol-1-yl)-N-(2,4-dimethoxybenzyl)-5-nitrobenzenesulfonamide
5. N-(2,4-Dimethoxybenzyl)-2-(4-fluoro-1H-pyrazol-1-yl)-5-nitrobenzenesulfonamide
6. 2-(4-Bromo-1H-pyrazol-1-yl)-N-(2,4-dimethoxybenzyl)-5-nitrobenzenesulfonamide
7. N-(2,4-Dimethoxybenzyl)-5-nitro-2-[3-(trifluoromethyl)-1H-1,2,4-triazol-1-yl]benzenesulfonamide
8. 2-[3-(Difluoromethyl)-1H-1,2,4-triazol-1-yl]-N-(2,4-dimethoxybenzyl)-5-nitrobenzenesulfonamide
9. 2-(4-Cyano-1H-pyrazol-1-yl)-N-(2,4-dimethoxybenzyl)-5-nitrobenzenesulfonamide
10. 5-Amino-N-(2,4-dimethoxybenzyl)-2-[4-(trifluoromethyl)-1H-pyrazol-1-yl]benzenesulfonamide
11. 5-Amino-2-(4-chloro-1H-pyrazol-1-yl)-N-(2,4-dimethoxybenzyl)benzenesulfonamide
12. 5-Amino-N-(2,4-dimethoxybenzyl)-2-(4-fluoro-1H-pyrazol-1-yl)benzenesulfonamide
13. 5-Amino-2-(4-bromo-1H-pyrazol-1-yl)-N-(2,4-dimethoxybenzyl)benzenesulfonamide
14. 5-Amino-N-(2,4-dimethoxybenzyl)-2-[3-(trifluoromethyl)-1H-1,2,4-triazol-1-yl]-benzenesulfonamide
15. 2-(2-Chlorophenyl)-N-{4-[3-(difluoromethyl)-1H-1,2,4-triazol-1-yl]-3-[(2,4-dimethoxy-benzyl)sulfamoyl]phenyl}acetamide
16. N-{4-[3-(Difluoromethyl)-1H-1,2,4-triazol-1-yl]-3-[(2,4-dimethoxybenzyl)sulfamoyl]-phenyl}-2-(2-fluorophenyl)acetamide
17. 2-Chloro-N-[(dimethylamino)methylene]-5-nitrobenzenesulfonamide
18. N-[(Dimethylamino)methylene]-5-nitro-2-[5-(trifluoromethyl)pyridin-3-yl]benzenesulfonamide
19. 5-Amino-N-[(dimethylamino)methylene]-2-[5-(trifluoromethyl)pyridin-3-yl]benzenesulfonamide
20. 2-[1-(Difluoromethyl)-1H-pyrazol-4-yl]-N-[(dimethylamino)methylene]-5-nitrobenzenesulfonamide
21. 5-Amino-2-[1-(difluoromethyl)-1H-pyrazol-4-yl]-N-[(dimethylamino)methylene]-benzenesulfonamide
22. 2-(2-Chlorophenyl)-N-(3-{[(dimethylamino)methylene]sulfamoyl}-4-[(trifluoro-methyl)-1H-pyrazol-1-yl]phenyl)acetamide
23. 2-(2-Chlorophenyl)-N-[3-{[(dimethylamino)methylene]sulfamoyl}-4-(4-fluoro-1H-pyrazol-1-yl)phenyl]acetamide
24. N-(2,4-Dimethoxybenzyl)-2-(4-methyl-1H-pyrazol-1-yl)-5-nitrobenzenesulfonamide
25. N-(2,4-Dimethoxybenzyl)-2-(3-methoxy-1H-1,2,4-triazol-1-yl)-5-nitrobenzenesulfonamide
26. 2-(4-Cyclopropyl-1H-imidazol-1-yl)-N-(2,4-dimethoxybenzyl)-5-nitrobenzenesulfonamide
27. N-(2,4-Dimethoxybenzyl)-2-(4-methyl-1H-imidazol-1-yl)-5-nitrobenzenesulfonamide
28. 2-(3-Cyclopropyl-1H-pyrazol-1-yl)-N-(2,4-dimethoxybenzyl)-5-nitrobenzenesulfonamide
29. N-(2,4-Dimethoxybenzyl)-5-nitro-2-(2H-pyrazolo[3,4-b]pyridin-2-yl)benzenesulfonamide
30. N-(2,4-Dimethoxybenzyl)-5-nitro-2-(2H-pyrazolo[3,4-c]pyridin-2-yl)benzenesulfonamide
31. N-(2,4-Dimethoxybenzyl)-5-nitro-2-(2H-pyrazolo[4,3-b]pyridin-2-yl)benzenesulfonamide
32. N-(2,4-Dimethoxybenzyl)-2-[4-(2-methoxyethyl)-1H-pyrazol-1-yl]-5-nitrobenzenesulfonamide
33. N-(2,4-Dimethoxybenzyl)-2-(3-fluoro-1H-pyrazol-1-yl)-5-nitrobenzenesulfonamide
35. 2-{4-[(2,2-Difluoroethyl)amino]-1H-pyrazol-1-yl}-N-(2,4-dimethoxybenzyl)-5-nitrobenzenesulfonamide
36. N-(2,4-Dimethoxybenzyl)-2-[4-(2-hydroxyethyl)-1H-pyrazol-1-yl]-5-nitrobenzenesulfonamide
37. N-(2,4-Dimethoxybenzyl)-5-nitro-2-[4-(2-oxoethyl)-1H-pyrazol-1-yl]benzenesulfonamide
38. 2-[4-(2,2-Difluoroethyl)-1H-pyrazol-1-yl]-N-(2,4-dimethoxybenzyl)-5-nitrobenzenesulfonamide
39. 2-(2-Chlorophenyl)-N-{4-[4-(2,2-difluoroethyl)-1H-pyrazol-1-yl]-3-[(2,4-dimethoxy-benzyl)sulfamoyl]phenyl}acetamide
42. 2-(4-{[(2,2-Difluoroethyl)amino]methyl}-1H-pyrazol-1-yl)-N-(2,4-dimethoxybenzyl)-5-nitrobenzenesulfonamide
43. tert-Butyl (2,2-difluoroethyl)[(1-{2-[(2,4-dimethoxybenzyl)sulfamoyl]-4-nitrophenyl}-1H-pyrazol-4-yl)methyl]carbamate
44. tert-Butyl {[1-(4-{[(2-chlorophenyl)acetyl]amino}-2-[(2,4-dimethoxybenzyl)-sulfamoyl]¬ ¬phenyl)-1H-pyrazol-4-yl]methyl}(2,2-difluoroethyl)carbamate
45. 2-(Benzylsulfanyl)-4-nitrobenzonitrile
46. 2-Cyano-N-(2,4-dimethoxybenzyl)-5-nitrobenzenesulfonamide
47. 2-[(2,4-Dimethoxybenzyl)sulfamoyl]-N'-hydroxy-4-nitrobenzenecarboximidamide
48. N-(2,4-Dimethoxybenzyl)-5-nitro-2-[5-(trifluoromethyl)-1,2,4-oxadiazol-3-yl]benzenesulfonamide
49. 2-(2-Chlorophenyl)-N-{3-[(2,4-dimethoxybenzyl)sulfamoyl]-4-[5-(trifluoromethyl)-1,2,4-oxadiazol-3-yl]phenyl}acetamide
50. 2-(2-Chlorophenyl)-N-{3-[(2,4-dimethoxybenzyl)sulfamoyl]-4-(4-methyl-1H-pyrazol-1-yl)phenyl}acetamide
51. 2-(2-Chlorophenyl)-N-{3-[(2,4-dimethoxybenzyl)sulfamoyl]-4-(3-methoxy-1H-1,2,4-triazol-1-yl)phenyl}acetamide
52. 2-(2-Chlorophenyl)-N-{4-(4-cyclopropyl-1H-imidazol-1-yl)-3-[(2,4-dimethoxy-benzyl)sulfamoyl]phenyl}acetamide
53. 2-(2-Chlorophenyl)-N-{3-[(2,4-dimethoxybenzyl)sulfamoyl]-4-(4-methyl-1H-imidazol-1-yl)phenyl}acetamide
54. 2-(2-Chlorophenyl)-N-{4-(3-cyclopropyl-1H-pyrazol-1-yl)-3-[(2,4-dimethoxy-benzyl)sulfamoyl]phenyl}acetamide
55. 2-(2-Chlorophenyl)-N-{3-[(2,4-dimethoxybenzyl)sulfamoyl]-4-(2H-pyrazolo[3,4-b]pyridin-2-yl)phenyl}acetamide
56. 2-(2-Chlorophenyl)-N-{3-[(2,4-dimethoxybenzyl)sulfamoyl]-4-(2H-pyrazolo[3,4-c]pyridin-2-yl)phenyl}acetamide
57. 2-(2-Chlorophenyl)-N-{3-[(2,4-dimethoxybenzyl)sulfamoyl]-4-(2H-pyrazolo[4,3-b]pyridin-2-yl)phenyl}acetamide
58. 2-(2-Chlorophenyl)-N-{3-[(2,4-dimethoxybenzyl)sulfamoyl]-4-[4-(2-methoxyethyl)-1H-pyrazol-1-yl]phenyl}acetamide
59. 2-(2-Chlorophenyl)-N-{3-[(2,4-dimethoxybenzyl)sulfamoyl]-4-(3-fluoro-1H-pyrazol-1-yl)phenyl}acetamide
60. 2-(2-Chlorophenyl)-N-(4-{4-[(2,2-difluoroethyl)amino]-1H-pyrazol-1-yl}-3-[(2,4-dimethoxybenzyl)sulfamoyl]phenyl)acetamide
61. N-{3-[(2,4-Dimethoxybenzyl)sulfamoyl]-4-(4-methyl-1H-pyrazol-1-yl)phenyl}-2-(2-fluorophenyl)acetamide 62 2-(2-Fluorophenyl)-N-{4-(4-cyclopropyl-1H-imidazol-1-yl)-3-[(2,4-dimethoxybenzyl)-sulfamoyl]phenyl}acetamide
63 N-{4-(3-Cyclopropyl-1H-pyrazol-1-yl)-3-[(2,4-dimethoxybenzyl)sulfamoyl]phenyl}-2-(2-fluorophenyl)acetamide
64 N-{3-[(2,4-Dimethoxybenzyl)sulfamoyl]-4-[4-(2-methoxyethyl)-1H-pyrazol-1-yl]-phenyl}-2-(2-fluorophenyl)acetamide
66 2-(Benzylsulfanyl)-4-nitrobenzohydrazide
67 2-(Benzylsulfanyl)-4-nitro-N'-(trifluoroacetyl)benzohydrazide
68 2-[2-(Benzylsulfanyl)-4-nitrophenyl]-5-(trifluoromethyl)-1,3,4-oxadiazole
69 N-(2,4-Dimethoxybenzyl)-5-nitro-2-[5-(trifluoromethyl)-1,3,4-oxadiazol-2-yl]benzenesulfonamide
70 2-(2-Chlorophenyl)-N-{3-[(2,4-dimethoxybenzyl)sulfamoyl]-4-[5-(trifluoromethyl)-1,3,4-oxadiazol-2-yl]phenyl}acetamide
71 N-{3-[(2,4-Dimethoxybenzyl)sulfamoyl]-4-[5-(trifluoromethyl)-1,3,4-oxadiazol-2-yl]phenyl}-2-(2-fluorophenyl)acetamide
72 2-Bromo-N-(2,4-dimethoxybenzyl)-5-nitrobenzenesulfonamide
73 5-Amino-2-bromo-N-(2,4-dimethoxybenzyl)benzenesulfonamide
74 N-{4-Bromo-3-[(2,4-dimethoxybenzyl)sulfamoyl]phenyl}-2-(2-chlorophenyl)acetamide
76 2-Bromo-N-[(dimethylamino)methylidene]-5-nitrobenzenesulfonamide
77 5-Amino-2-bromo-N-[(dimethylamino)methylidene]benzenesulfonamide
78 N-(4-Bromo-3-{[(dimethylamino)methylidene]sulfamoyl}phenyl)-2-(2-chlorophenyl)acetamide
79 N-(4-Bromo-3-{[(dimethylamino)methylidene]sulfamoyl}phenyl)-2-(2-fluorophenyl)acetamide
80 N-(4-Bromo-3-{[(dimethylamino)methylidene]sulfamoyl}phenyl)-2-(2-chloro-4-fluorophenyl)acetamide
81 2-(2-Chlorophenyl)-N-[3-{[(dimethylamino)methylidene]sulfamoyl}-4-(1H-pyrazol-4-yl)phenyl]acetamide
82 4-Amino-N-(2,4-dimethoxybenzyl)biphenyl-2-sulfonamide
83 5-Amino-2-(1-methyl-1H-pyrazol-4-yl)benzenesulfonamide
84 5-Amino-2-(1-cyclopropyl-1H-pyrazol-4-yl)-N-[(dimethylamino)methylidene]benzenesulfonamide
85 5-Amino-2-(1-tert-butyl-1H-pyrazol-4-yl)benzenesulfonamide
86 5-Amino-2-(1-methyl-1H-pyrazol-4-yl)benzenesulfonamide
87 5-Amino-N-[(dimethylamino)methylidene]-2-[1-(tetrahydro-2H-pyran-2-yl)-1H-pyrazol-4-yl]benzenesulfonamide
88 5-Amino-2-(1-cyclopentyl-1H-pyrazol-4-yl)benzenesulfonamide
89 5-Amino-2-[1-(2-methoxyethyl)-1H-pyrazol-4-yl]benzenesulfonamide
90 5-Amino-2-(1,3-dimethyl-1H-pyrazol-5-yl)benzenesulfonamide
91 5-Amino-2-[1-methyl-3-(trifluoromethyl)-1H-pyrazol-5-yl]benzenesulfonamide
92 5-Amino-N-[(dimethylamino)methylidene]-2-[5-(trifluoromethyl)pyridin-3-yl]-benzenesulfonamide
93 5-Amino-2-(1,3-dimethyl-1H-pyrazol-4-yl)benzenesulfonamide
94 5-Amino-2-[1-(difluoromethyl)-1H-pyrazol-4-yl]benzenesulfonamide
95 Tert-butyl 4-[4-(4-amino-2-sulfamoylphenyl)-1H-pyrazol-1-yl]piperidine-1-carboxylate
97 5-Bromo-2-chloro-N-[(dimethylamino)methylidene]pyridine-3-sulfonamide
98 2-Chloro-N-[(dimethylamino)methylidene]-5-[(diphenylmethylidene)amino]pyridine-3-sulfonamide
99 2-[1-(Difluoromethyl)-1H-pyrazol-4-yl]-N-[(dimethylamino)methylidene]-5-[(diphenyl-methylidene)amino]pyridine-3-sulfonamide
100 5-Amino-2-[1-(difluoromethyl)-1H-pyrazol-4-yl]-N-[(dimethylamino)methylidene]pyridine-3-sulfonamide
101 N-[(Dimethylamino)methylidene]-5-[(diphenylmethylidene)amino]-2-(1-methyl-1H-pyrazol-4-yl)pyridine-3-sulfonamide
102 5-Amino-N-[(dimethylamino)methylidene]-2-(1-methyl-1H-pyrazol-4-yl)pyridine-3-sulfonamide
103 N-[(Dimethylamino)methylidene]-5-[(diphenylmethylidene)amino]-5'-(trifluoromethyl)-2,3'-bipyridine-3-sulfonamide
104 5-Amino-N-[(dimethylamino)methylidene]-5'-(trifluoromethyl)-2,3'-bipyridine-3-sulfonamide
105 2-(2-Chlorophenyl)-N-[3-{[(dimethylamino)methylidene]sulfamoyl}-4-(4,4,5,5-tetramethyl-1,3,2-dioxaborolan-2-yl)phenyl]acetamide
106 5-Amino-2-(5-cyclopropyl-1,3,4-oxadiazol-2-yl)-N-[(dimethylamino)methylidene]-benzenesulfonamide
107 2-[4-(Difluoromethyl)-1H-pyrazol-1-yl]-N-[(dimethylamino)methylene]-5-nitrobenzenesulfonamide
108 5-Amino-2-(4-cyano-1H-pyrazol-1-yl)-N-[(dimethylamino)methylene]pyridine-3-sulfonamide
109 5-Amino-2-(4-chloro-1H-pyrazol-1-yl)-N-[(dimethylamino)methylene]pyridine-3-sulfonamide
110 5-Amino-2-(4-bromo-1H-pyrazol-1-yl)-N-[(dimethylamino)methylene]pyridine-3-sulfonamide
111 5-Amino-N-[(dimethylamino)methylene]-2-(4-fluoro-1H-pyrazol-1-yl)pyridine-3-sulfonamide
112 5-Amino-N-[(dimethylamino)methylidene]-2-[4-(trifluoromethyl)-1H-pyrazol-1-yl]-pyridine-3-sulfonamide
113 Methyl 1-(4-{[(2-chlorophenyl)acetyl]amino}-2-sulfamoylphenyl)-1H-pyrazole-4-carboxylate
114 N-(4-Bromo-3-sulfamoylphenyl)-2-(2-chlorophenyl)acetamide
115 N-(4-Bromo-3-{[(dimethylamino)methylene]sulfamoyl}phenyl)-2-(2-chlorophenyl)acetamide
116 N-[(Dimethylamino)methylene]-5-nitro-2-[4-(trifluoromethyl)-2H-1,2,3-triazol-2-yl]benzenesulfonamide
117 N-[(Dimethylamino)methylene]-5-nitro-2-[4-(trifluoromethyl)-1H-1,2,3-triazol-1-yl]benzenesulfonamide
118 2-(4-Cyano-1H-pyrazol-1-yl)-5-nitrobenzenesulfonamide
119 5-Amino-2-(4-cyano-1H-pyrazol-1-yl)benzenesulfonamide
120 Ethyl 1-{2-[(2,4-dimethoxybenzyl)sulfamoyl]-4-nitrophenyl}-1H-pyrazole-4-carboxylate
121 1-{2-[(2,4-Dimethoxybenzyl)sulfamoyl]-4-nitrophenyl}-1H-pyrazole-4-carboxylic acid
122 2-(Trimethylsilyl)ethyl (1-{2-[(2,4-dimethoxybenzyl)sulfamoyl]-4-nitrophenyl}-1H-pyrazol-4-yl)carbamate
123 2-(Trimethylsilyl)ethyl [1-(4-{[(2-chlorophenyl)acetyl]amino}-2-[(2,4-dimethoxybenzyl)sulfamoyl]phenyl)-1H-pyrazol-4-yl]carbamate
124 N-{4-(4-Amino-1H-pyrazol-1-yl)-3-[(2,4-dimethoxybenzyl)sulfamoyl]phenyl}-2-(2-chlorophenyl)acetamide 125 N-[1-(4-{[(2-Chlorophenyl)acetyl]amino}-2-[(2,4-dimethoxybenzyl)sulfamoyl]phenyl)-1H-pyrazol-4-yl]-2,2-difluoroacetamide
126 N-[1-(4-{[(2-Chlorophenyl)acetyl]amino}-2-[(2,4-dimethoxybenzyl)sulfamoyl]phenyl)-1H-pyrazol-4-yl]-3,3,3-trifluoropropanamide
127 (±)-N-[1-(4-{[(2-Chlorophenyl)acetyl]amino}-2-[(2,4-dimethoxybenzyl)sulfamoyl]phenyl)-1H-pyrazol-4-yl]-3,3,3-trifluoro-2-methylpropanamide
128 2-(2-Chlorophenyl)-N-(3-[(2,4-dimethoxybenzyl)sulfamoyl]-4-{4-(2,5-dimethyl-pyrrolidin-1-yl)-1H-pyrazol-1-yl}phenyl)acetamide (Mixture of stereoisomers)
129 N-(4-{4-[(2,2-Difluoroethyl)amino]-1H-pyrazol-1-yl}-3-[(2,4-dimethoxybenzyl)sulfamoyl]phenyl)-2-(2-fluorophenyl)acetamide
130 N-(2,2,2-Trifluoroethyl)-1H-pyrazol-4-amine
131 N-(2,4-Dimethoxybenzyl)-5-nitro-2-{4-[(2,2,2-trifluoroethyl)amino]-1H-pyrazol-1-yl}benzenesulfonamide
132 2-(2-Chlorophenyl)-N-(3-[(2,4-dimethoxybenzyl)sulfamoyl]-4-{4-[(2,2,2-trifluoroethyl)amino]-1H-pyrazol-1-yl}phenyl)acetamide
133 N-(2,4-Dimethoxybenzyl)-2-(4-isopropyl-1H-pyrazol-1-yl)-5-nitrobenzenesulfonamide
134 2-(2-Chlorophenyl)-N-{3-[(2,4-dimethoxybenzyl)sulfamoyl]-4-(4-isopropyl-1H-pyrazol-1-yl)phenyl}acetamide
135 N-{3-[(2,4-Dimethoxybenzyl)sulfamoyl]-4-(4-isopropyl-1H-pyrazol-1-yl)phenyl}-2-(2-fluorophenyl)acetamide
138 N-(2,4-Dimethoxybenzyl)-5-nitro-2-[4-(2,2,2-trifluoroethyl)-1H-pyrazol-1-yl]benzenesulfonamide
139 2-(2-Chlorophenyl)-N-{3-[(2,4-dimethoxybenzyl)sulfamoyl]-4-[4-(2,2,2-trifluoroethyl)-1H-pyrazol-1-yl]phenyl}acetamide
140 N-{3-[(2,4-Dimethoxybenzyl)sulfamoyl]-4-[4-(2,2,2-trifluoroethyl)-1H-pyrazol-1-yl]phenyl}-2-(2-fluorophenyl)acetamide
141 2-(5-Cyclopropyl-1,2,4-oxadiazol-3-yl)-N-(2,4-dimethoxybenzyl)-5-nitrobenzenesulfonamide
142 2-(2-Chlorophenyl)-N-{4-(5-cyclopropyl-1,2,4-oxadiazol-3-yl)-3-[(2,4-dimethoxybenzyl)sulfamoyl]phenyl}acetamide
143 5-[2-(Benzylsulfanyl)-4-nitrophenyl]-3-(trifluoromethyl)-1,2,4-oxadiazole
144 N-(2,4-Dimethoxybenzyl)-5-nitro-2-[3-(trifluoromethyl)-1,2,4-oxadiazol-5-yl]benzenesulfonamide
145 2-(2-Chlorophenyl)-N-{3-[(2,4-dimethoxybenzyl)sulfamoyl]-4-[3-(trifluoromethyl)-1,2,4-oxadiazol-5-yl]phenyl}acetamide
146 2-(Benzylsulfanyl)-N'-(difluoroacetyl)-4-nitrobenzohydrazide
147 2-[2-(Benzylsulfanyl)-4-nitrophenyl]-5-(difluoromethyl)-1,3,4-oxadiazole
148 2-[5-(Difluoromethyl)-1,3,4-oxadiazol-2-yl]-N-(2,4-dimethoxybenzyl)-5-nitrobenzenesulfonamide
149 2-(2-Chlorophenyl)-N-{4-[5-(difluoromethyl)-1,3,4-oxadiazol-2-yl]-3-[(2,4-dimethoxybenzyl)sulfamoyl]phenyl}acetamide
150 N-{4-[5-(Difluoromethyl)-1,3,4-oxadiazol-2-yl]-3-[(2,4-dimethoxybenzyl)sulfamoyl]phenyl}-2-(2-fluorophenyl)acetamide
151 5-[2-(Benzylsulfanyl)-4-nitrophenyl]-3-methyl-1,2,4-oxadiazole
152 N-(2,4-Dimethoxybenzyl)-2-(5-methyl-1,3,4-oxadiazol-2-yl)-5-nitrobenzenesulfonamide
153 2-(2-Chlorophenyl)-N-{3-[(2,4-dimethoxybenzyl)sulfamoyl]-4-(5-methyl-1,3,4-oxadiazol-2-yl)phenyl}acetamide
154 N-{3-[(2,4-Dimethoxybenzyl)sulfamoyl]-4-(5-methyl-1,3,4-oxadiazol-2-yl)phenyl}-2-(2-fluorophenyl)acetamide
155 N-{3-[(2,4-Dimethoxybenzyl)sulfamoyl]-4-(5-methyl-1,3,4-oxadiazol-2-yl)phenyl}-2-(4-methylphenyl)acetamide
156 tert-Butyl 3-(4-{[(2-chlorophenyl)acetyl]amino}-2-{[(dimethylamino)methylene]sulfamoyl}phenyl)-1H-pyrrole-1-carboxylate
157 2-(2-Chlorophenyl)-N-[3-{[(dimethylamino)methylene]sulfamoyl}-4-(1H-pyrrol-3-yl)phenyl]acetamide
158 2-(2-Chlorophenyl)-N-[3-{[(dimethylamino)methylene]sulfamoyl}-4-(1-methyl-1H-pyrrol-3-yl)phenyl]acetamide
159 2-(2-Chlorophenyl)-N-[4-(5-cyano-1-methyl-1H-pyrrol-2-yl)-3-{[(dimethylamino)methylene]sulfamoyl}phenyl]acetamide Another aspect of the invention relates to the use of any of the intermediates described herein for preparing a compound of formula (I) as defined herein or an N-oxide, a salt, a hydrate, a solvate, a tautomer or a stereoisomer of said compound, or a salt of said N-oxide, tautomer or stereoisomer.

Preferred intermediates are the Intermediate Examples as disclosed below.

A further aspect of the invention are compounds of formula (I), (Ia) and (Ib) which are present as their salts.

It is to be understood that the present invention relates to any sub-combination within any embodiment or aspect of the present invention of compounds of general formula (I), (Ia) and (Ib) supra.

More particularly still, the present invention covers compounds of general formula (I), (Ia) and (Ib) which are disclosed in the Example section of this text, infra.

In accordance with another aspect, the present invention covers methods of preparing compounds of the present invention, said methods comprising the steps as described in the Experimental Section herein.

Another embodiment of the invention are compounds according to the claims as disclosed in the Claims section wherein the definitions are limited according to the preferred or more preferred definitions as disclosed below or specifically disclosed residues of the exemplified compounds and subcombinations thereof.

Definitions

Constituents which are optionally substituted as stated herein, may be substituted, unless otherwise noted, one or more times, independently from one another at any possible position. When any variable occurs more than one time in any constituent, each definition is independent. For example, when $R^1$, $R^2$, $R^3$, $R^4$, $R^5$, $R^6$, $R^7$, $R^8$, $R^9$, $R^{10}$, $R^{11}$, $R^{12}$, X and/or Y occur more than one time in any compound of formula (I) each definition of $R^1$, $R^2$, $R^3$, $R^4$, $R^5$, $R^6$, $R^7$, $R^8$, $R^9$, $R^{10}$, $R^{11}$, $R^{12}$, X and Y is independent.

Should a constituent be composed of more than one part, e.g. $C_1$-$C_4$-alkoxy-$C_1$-$C_4$-alkyl-, the position of a possible substituent can be at any of these parts at any suitable position. A hyphen at the beginning of the constituent marks the point of attachment to the rest of the molecule. Should a ring be substituted the substituent could be at any suitable position of the ring, also on a ring nitrogen atom if suitable.

Furthermore, a constituent composed of more than one part and comprising several chemical residues, e.g. $C_1$-$C_4$-alkoxy-$C_1$-$C_4$-alkyl or phenyl-$C_1$-$C_4$-alkyl, should be read from left to right with the point of attachment to the rest of the molecule on the last part (in the example mentioned previously on the $C_1$-$C_4$-alkyl residue)

The term "comprising" when used in the specification includes "consisting of".

If it is referred to "as mentioned above" or "mentioned above" within the description it is referred to any of the disclosures made within the specification in any of the preceding pages.

"suitable" within the sense of the invention means chemically possible to be made by methods within the knowledge of a skilled person.

The terms as mentioned in the present text have preferably the following meanings:

The term "halogen", "halogen atom", "halo-" or "Hal-" is to be understood as meaning a fluorine, chlorine, bromine or iodine atom, preferably a fluorine or chlorine atom.

The term "$C_1$-$C_4$-alkyl" is to be understood as preferably meaning a linear or branched, saturated, monovalent hydrocarbon group having 1, 2, 3 or 4 carbon atoms, e.g. a methyl, ethyl, propyl, butyl, iso-propyl, iso-butyl, sec-butyl, tert-butyl group, particularly 1, 2 or 3 carbon atoms ("$C_1$-$C_3$-alkyl"), e.g. a methyl, ethyl, n-propyl- or iso-propyl group.

The term "$C_1$-$C_4$-haloalkyl" is to be understood as preferably meaning a linear or branched, saturated, monovalent hydrocarbon group in which the term "$C_1$-$C_4$-alkyl" is defined supra, and in which one or more hydrogen atoms is replaced by a halogen atom, in identically or differently, i.e. one halogen atom being independent from another. Particularly, said halogen atom is F. Said $C_1$-$C_4$-haloalkyl group is, for example, —$CF_3$, —$CHF_2$, —$CH_2F$, —$CF_2CF_3$, or —$CH_2CF_3$.

The term "$C_1$-$C_4$-alkoxy" is to be understood as preferably meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy or sec-butoxy group, or an isomer thereof.

The term "$C_1$-$C_4$-haloalkoxy" is to be understood as preferably meaning a linear or branched, saturated, monovalent $C_1$-$C_4$-alkoxy group, as defined supra, in which one or more of the hydrogen atoms is replaced, in identically or differently, by a halogen atom.

Particularly, said halogen atom is F. Said $C_1$-$C_4$-haloalkoxy group is, for example, —$OCF_3$, —$OCHF_2$, —$OCH_2F$, —$OCF_2CF_3$, or —$OCH_2CF_3$.

The term "$C_1$-$C_4$-hydroxyalkyl" is to be understood as meaning a linear or branched, saturated, monovalent hydrocarbon group in which the term "$C_1$-$C_4$-alkyl" is defined supra, and in which one or more hydrogen atoms is replaced by a hydroxy group, e.g. a hydroxymethyl, 1-hydroxyethyl, 2-hydroxyethyl, 1,2-dihydroxyethyl, 3-hydroxypropyl, 2-hydroxypropyl, 2,3-dihydroxypropyl, 1,3-dihydroxypropan-2-yl, 3-hydroxy-2-methyl-propyl, 2-hydroxy-2-methyl-propyl, 1-hydroxy-2-methyl-propyl group.

The term "$C_1$-$C_4$-alkoxy-$C_1$-$C_4$-alkyl" is to be understood as preferably meaning a linear or branched, saturated, monovalent alkyl group, as defined supra, in which one or more of the hydrogen atoms is replaced, in identically or differently, by a $C_1$-$C_4$-alkoxy group, as defined supra, e.g. methoxyalkyl, ethoxyalkyl, propyloxyalkyl, iso-propoxyalkyl, butoxyalkyl, iso-butoxyalkyl, tert-butoxyalkyl or sec-butoxyalkyl group, in which the term "$C_1$-$C_4$-alkyl" is defined supra, or an isomer thereof.

The term "$C_3$-$C_6$-cycloalkyl" is to be understood as meaning a saturated, monovalent, mono-, or bicyclic hydrocarbon ring which contains 3, 4, 5 or 6 carbon atoms ("$C_3$-$C_6$-cycloalkyl"). Said $C_3$-$C_6$-cycloalkyl group is for example, a monocyclic hydrocarbon ring, e.g. a cyclopropyl, cyclobutyl, cyclopentyl or cyclohexyl, or a bicyclic hydrocarbon ring.

The term "4- to 6-membered heterocycloalkyl" or "4- to 6-membered heterocyclic ring", is to be understood as meaning a saturated, monovalent, mono- or bicyclic hydrocarbon ring which contains 3, 4 or 5 carbon atoms, and one or more heteroatom-containing groups selected from C(=O), O, S, S(=O), S(=O)$_2$, NH, NR$^a$, in which R$^a$ represents a $C_1$-$C_6$-alkyl- or $C_1$-$C_6$-haloalkyl-group; it being possible for said heterocycloalkyl group to be attached to the rest of the molecule via any one of the carbon atoms or, if present, the nitrogen atom.

Particularly, said heterocycloalkyl can contain 4 or 5 carbon atoms, and one or more of the above-mentioned heteroatom-containing groups (a "5- to 6-membered heterocycloalkyl").

Particularly, without being limited thereto, said heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl, pyrrolinyl, or a 6-membered ring, such as tetrahydropyranyl, piperidinyl, morpholinyl, dithianyl, thiomorpholinyl, piperazinyl, or trithianyl, for example. Optionally, said heterocycloalkyl can be benzo fused.

The term "heteroaryl" is understood as preferably meaning a monovalent, monocyclic, bicyclic or tricyclic aromatic ring system having 5, 6, 7, 8, 9, 10, 11, 12, 13 or 14 ring atoms (a "5- to 14-membered heteroaryl" group), particularly 5, 6, 9 or 10 ring atoms, and which contains at least one heteroatom which may be identical or different, said heteroatom being such as oxygen, nitrogen or sulfur. In addition said ring system can be benzocondensed.

Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl, and benzo derivatives thereof, such as, for example, benzofuranyl, benzothienyl, benzoxazolyl, benzisoxazolyl, benzimidazolyl, benzotriazolyl, indazolyl, indolyl, isoindolyl; or pyridinyl, pyridazinyl, pyrimidinyl, pyrazinyl, triazinyl, and benzo derivatives thereof, such as, for example, quinolinyl, quinazolinyl, isoquinolinyl; or azocinyl, indolizinyl, purinyl, and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl or oxepinyl.

In general, and unless otherwise mentioned, the heteroarylic radical include all the possible isomeric forms thereof, e.g. the positional isomers thereof. Thus, for some illustrative non-restricting example, the term pyridyl includes pyridin-2-yl, pyridin-3-yl and pyridin-4-yl; or the term thienyl includes thien-2-yl and thien-3-yl. Preferably, the heteroaryl group is a pyridyl group.

As mentioned supra, said nitrogen atom-containing ring can be partially unsaturated, i.e. it can contain one or more double bonds, such as, without being limited thereto, a 2,5-dihydro-1H-pyrrolyl, 4H-[1,3,4]thiadiazinyl, 4,5-dihydrooxazolyl, or 4H-[1,4]thiazinyl ring, for example, or, it may be benzo-fused, such as, without being limited thereto, a dihydroisoquinolinyl ring, for example.

The term "$C_1$-$C_4$", as used throughout this text, e.g. in the context of the definition of "$C_1$-$C_4$-alkyl", "$C_1$-$C_4$-haloalkyl", "$C_1$-$C_4$-alkoxy", or "$C_1$-$C_4$-haloalkoxy" is to be understood as meaning an alkyl group having a finite number of carbon atoms of 1 to 4, i.e. 1, 2, 3 or 4 carbon atoms. It is to be understood further that said term "$C_1$-$C_4$" is to be interpreted as any sub-range comprised therein, e.g. $C_1$-$C_4$, $C_2$-$C_4$, $C_3$-$C_4$, $C_1$-$C_2$, $C_1$-$C_3$, particularly $C_1$-$C_2$, $C_1$-$C_3$, $C_1$-$C_4$, in the case of "$C_1$-$C_6$-haloalkyl" or "$C_1$-$C_4$-haloalkoxy" even more particularly $C_1$-$C_2$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_6$; particularly $C_3$-$C_6$.

The $R^9R^{10}N$—C(O)— group include, for example, —C(O)NH$_2$, —C(O)N(H)CH$_3$, —C(O)N(CH$_3$)$_2$, —C(O)N(H)CH$_2$CH$_3$, —C(O)N(CH$_3$)CH$_2$CH$_3$ or —C(O)N(CH$_2$CH$_3$)$_2$.

The $R^9R^{10}N$-group includes, for example, —NH$_2$, —N(H)CH$_3$, —N(CH$_3$)$_2$, —N(H)CH$_2$CH$_3$ and —N(CH$_3$)CH$_2$CH$_3$. In the case of $R^9R^{10}N$—, when $R^9$ and $R^{10}$ together with the nitrogen atom to which they are attached form a 4- to 6-membered nitrogen containing heterocyclic ring, said ring optionally containing one additional heteroatom selected from O, NH, NR$^a$ in which R$^a$ represents a $C_1$-$C_6$-alkyl- or $C_1$-$C_6$-haloalkyl- group, particularly a CH$_3$, or S and being optionally substituted, one to three times, independently from each other, with halogen or $C_1$-$C_4$-alkyl, particularly a CH$_3$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

Ring system substituent means a substituent attached to an aromatic or nonaromatic ring system which, for example, replaces an available hydrogen on the ring system.

As used herein, the term "one or more", e.g. in the definition of the substituents of the compounds of the general formulae of the present invention, is understood as meaning "one, two, three, four or five, particularly one, two, three or four, more particularly one, two or three, even more particularly one or two".

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as 2H (deuterium), $^3$H (tritium), 11C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{125}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of this invention may contain one or more asymmetric centre, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. R- or S-isomers, or E- or Z-isomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, namely:

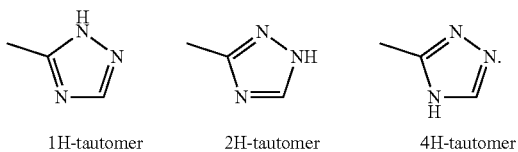

1H-tautomer    2H-tautomer    4H-tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible.

The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae such as "hydrochloride", "trifluoroacetate", "sodium salt", or "x HCl", "x CF3COOH", "x Na+", for example, are to be understood as not a stoichiometric specification, but solely as a salt form.

This applies analogously to cases in which synthesis intermediates or example compounds or salts thereof have been obtained, by the preparation and/or purification processes described, as solvates, such as hydrates with (if defined) unknown stoichiometric composition.

The salts include water-insoluble and, particularly, water-soluble salts.

Furthermore, derivatives of the compounds of formula (I) and the salts thereof which are converted into a compound of formula (I) or a salt thereof in a biological system (bioprecursors or pro-drugs) are covered by the invention. Said biological system is e.g. a mammalian organism, particularly a human subject. The bioprecursor is, for example, converted into the compound of formula (I) or a salt thereof by metabolic processes.

Furthermore, the present invention includes all possible crystalline forms, or polymorphs, of the compounds of the present invention, either as single polymorphs, or as a mixture of more than one polymorphs, in any ratio.

In the context of the properties of the compounds of the present invention the term "pharmacokinetic profile" means one single parameter or a combination thereof including permeability, bioavailability, exposure, and pharmacodynamic parameters such as duration, or magnitude of pharmacological effect, as measured in a suitable experiment. Compounds with improved pharmacokinetic profiles can, for example, be used in lower doses to achieve the same effect, may achieve a longer duration of action, or a may achieve a combination of both effects.

It has now been found, and this constitutes the basis of the present invention, that said compounds of the present invention have surprising and advantageous properties.

In particular, compounds according to the present invention have surprisingly been found to effectively be active as an antagonist or a negative allosteric modulator of P2X4.

An allosteric modulator is a substance which indirectly influences (modulates) the effects of an agonist or inverse agonist at a target protein, for example a receptor. Allosteric modulators bind to a site distinct from that of the orthosteric agonist binding site. Usually they induce a conformational change within the protein structure. A negative modulator (NAM) reduces the effects of the orthosteric ligand, but is inactive in the absence of the orthosteric ligand.

Commercial Utility and Medical Indications

As mentioned supra, the compounds of the present invention have surprisingly been found to effectively be active as an antagonist or a negative allosteric modulator of P2X4.

A compound according to the invention is used for the manufacture of a medicament.

A further aspect of the invention is the use of the compounds according to formula (I), (Ia) or (Ib) for the treatment or prophylaxis of a disease Furthermore, the invention relates to a compound of general formula (I) (Ia) or (Ib), or an N-oxide, a salt, a tautomer or a stereoisomer of said compound, or a salt of said N-oxide, tautomer or stereoisomer particularly a pharmaceutically acceptable salt thereof, or a mixture of same, as described and defined herein, for use in the treatment or prophylaxis of a disease.

The invention further relates to a method for using the compounds of general formula (I) (Ia) or (Ib) or an N-oxide, a salt, a tautomer or a stereoisomer of said compound, or a salt of said N-oxide, tautomer or stereoisomer to treat mammalian and human disorders and diseases, which include but are not limited to:

genitourinary, gastrointestinal, respiratory, proliferative and pain-related diseases, conditions and disorders;
gynecological diseases including primary and secondary dysmenorrhea, dyspareunia, vulvudynia, endometriosis and adenomyosis; endometriosis-associated pain; endometriosis-associated symptoms, wherein said symptoms are in particular abdominal pain, dysmenorrhea, dyspareunia, dysuria, dyschezia or pelvic hypersensitivity;
urinary tract disease states including those associated with bladder outlet obstruction; urinary incontinence conditions such as reduced bladder capacity, increased frequency of micturition, urge incontinence, stress incontinence, or bladder hyperreactivity; benign prostatic hypertrophy; prostatic hyperplasia; prostatitis; detrusor hyperreflexia; overactive urinary bladder and symptoms related to overactive urinary bladder wherein said symptoms are in particular increased urinary frequency, nocturia, urinary urgency or urge incontinence; pelvic hypersensitivity; urethritis; prostatitis; prostatodynia; cystitis, in particular interstitial cystitis; idiopathic bladder hypersensitivity; kidney disease as hyperprostaglandin E syndrome, classic Bartter syndrome;
cancer, cancer-related pain and cancer cachexia;
epilepsy, partial and generalized seizures;
respiratory disorders including asthma, chronic obstructive pulmonary disease, pulmonary fibrosis, interstitial pulmonary fibrosis, bronchospasm, chronic chough, refractory chronic cough, ideopahtic chronic cough;
gastrointestinal disorders including irritable bowel syndrome (IBS), inflammatory bowel disease (IBD), biliary colic and other biliary disorders, renal colic, diarrhea-dominant IBS; gastroesophageal reflux, gastrointestinal distension, Crohn's disease and the like;
fatty liver disorders, in particular NASH (Non-Alcoholic Steato-Hepatitis); fibrotic diseases including lung fibrosis, heart fibrosis, kidney fibrosis and fibrosis of other organs; metabolic syndrome including, for example, insulin resistance, hypertension, refractory hypertension, dyslipoproteinaemia and obesity, diabetes mellitus, in particular Diabetes type II, myocardial infarction; atherosclerosis; lipid disorders;
neurodegenerative disorders such as Alzheimer's disease, Multiple Sclerosis, Parkinson's disease, brain ischemia, traumatic brain injury, spinal cord injury;
pruritus.
heart disorders including ischemia reperfusion injury, cardiac ischemia, The present invention further relates to a method for using using the compounds of general formula (I) (Ia) or (Ib) or an N-oxide, a salt, a tautomer or a stereoisomer of said compound, or a salt of said N-oxide, tautomer or stereoisomer particularly a pharmaceutically acceptable salt thereof, or a mixture of same, to treat pain-associated mammalian disorders and diseases, which include but not limited to pain-associated diseases or disorders selected from the group consisting of hyperalgesia, allodynia, functional bowel disorders (such as irritable bowel syndrome), gout, arthritis (such as osteoarthritis, rheumatoid arthritis and ankylosing spondylitis), burning mouth syndrome, burns, migraine or cluster headaches, nerve injury, traumatic nerve injury, post-traumatic injuries (including fractures and sport injuries), neuritis, neuralgias, poisoning, ischemic injury, interstitial cystitis, cancer, trigeminal neuralgia, small fiber neuropathy, diabetic neuropathy, chronic arthritis and related neuralgias, HIV and HIV treatment-induced neuropathy, pruritus; impaired wound healing and disease of the skeleton like degeneration of the joints.

Furthermore, the present invention relates to a method for using using the compounds of general formula (I) (Ia) or (Ib) or an N-oxide, a salt, a tautomer or a stereoisomer of said compound, or a salt of said N-oxide, tautomer or stereoisomer particularly a pharmaceutically acceptable salt thereof, or a mixture of same, to treat mammalian and human disorders and diseases, which are associated with pain or pain syndromes that are in particular:

pain syndromes (including hyperalgesia, allodynia, acute and chronic inflammatory and neuropathic pain), preferably inflammatory pain, low back pain, surgical pain, visceral pain, dental pain, periodontitis, premenstrual pain, endometriosis-associated pain, pain associated with fibrotic diseases, central pain, pain due to burning mouth syndrome, pain due to burns, pain due to migraine, cluster headaches, pain due to nerve injury, pain due to neuritis, neuralgias, pain due to poisoning, pain due to ischemic injury, pain due to interstitial cystitis, cancer pain, pain due to viral, parasitic or bacterial infections, pain due to traumatic nerve-injury, pain due to post-traumatic injuries (including fractures and sport injuries), pain due to trigeminal neuralgia, pain associated with small fiber neuropathy, pain associated with diabetic neuropathy, postherpetic neuralgia, chronic lower back pain, neck pain phantom limb pain, pelvic pain syndrome, chronic pelvic pain, neuroma pain, complex regional pain syndrome, fibromyalgia, myofascial disorders, pain associated with gastrointestinal distension, chronic arthritic pain and related neuralgias, and pain associated with cancer, Morphine-resistant pain, pain associated with chemotherapy, HIV and HIV treatment-induced neuropathy; and pain associated with diseases or disorders selected from the group consisting of abdominal pain such as functional bowel disorders, irritable bowel syndrome, inflammatory bowel disease and selected from the group of arthritis (such as osteoarthritis, rheumatoid arthritis and ankylosing spondylitis).

Compounds of the invention are thus expected to be useful in the treatment of inflammation. The term "inflammation" is also understood to include any inflammatory disease, disorder or condition per se, any condition that has an inflammatory component associated with it, and/or any condition characterized by inflammation as a symptom, including, inter alia, acute, chronic, ulcerative, fibrotic, allergic and auto-immune diseases, infection by pathogens, immune reactions due to hypersensitivity, entering foreign bodies, physical injury, necrosis, endometriosis and other forms of inflammation known to those skilled in the art. The term thus also includes, for the purposes of this invention, inflammatory pain, pain generally and/or fever. The compounds of the present invention may also be useful in the treatment, viral infections (e.g. influenza, common cold, herpes zoster, hepatitis C and HIV), bacterial infections, fungal infections, surgical or dental procedures, malignancies (e.g. melanoma, breast cancer, colon cancer, lung cancer and prostate cancer), arthritis, osteoarthritis, juvenile arthritis, rheumatoid arthritis, juvenile onset rheumatoid arthritis, rheumatic fever, ankylosing spondylitis, Hodgkin's disease, systemic lupus erythematosus, vasculitis, pancreatitis, nephritis, bursitis, conjunctivitis, iritis, scleritis, uveitis, wound healing, dermatitis, eczema, stroke, diabetes mellitus, autoimmune diseases, allergic disorders, rhinitis, ulcers, mild to moderately active ulcerative colitis, familial adenomatous polyposis, coronary heart disease, sarcoidosis and any other disease with an inflammatory component.

Compounds of the invention are also expected to be useful in the treatment of conditions associated or causing bone loss in a subject. Conditions that may be mentioned in this regard include osteoporosis, osteoarthritis, Paget's disease and/or periodontal diseases.

Based on the P2X4 antagonising activity the compounds according to the invention are useful for the relief of pain, fever and inflammation of a variety of conditions including rheumatic fever, symptoms associated with influenza or other viral infections, common cold, lower back and neck pain, dysmenorrhea, headache, migraine (acute and prophylactic treatment), toothache, sprains and strains, myositis, neuralgia, synovitis, arthritis, including rheumatoid arthritis, juvenile rheumatoid arthritis, degenerative joint diseases (osteoarthritis), acute gout and ankylosing spondylitis, acute, subacute and chronic musculoskeletal pain syndromes such as bursitis, burns, injuries, and pain following surgical (post-operative pain) and dental procedures as well as the preemptive treatment of surgical pain. The pain may be mild pain, moderate pain, severe pain, musculoskeletal pain, complex regional pain syndrome, neuropathic pain, back pain such as acute visceral pain, neuropathies, acute trauma, chemotherapy-induced mononeuropathy pain states, polyneuropathy pain states (such as diabetic peripheral neuropathy and/or chemotherapy induced neuropathy), autonomic neuropathy pain states, pheripheral nervous system (PNS) lesion or central nervous system (CNS) lesion or disease related pain states, polyradiculopathies of cervical, lumbar or sciatica type, cauda equina syndrome, piriformis syndrome, paraplegia, quadriplegia, pain states related to various Polyneuritis conditions underlying various infections, chemical injuries, radiation exposure, underlying disease or deficiency conditions (such as beriberi, vitamin deficiencies, hypothyroidism, porphyria, cancer, HIV, autoimmune disease such as multiple sclerosis and spinal-cord injury, fibromyalgia, nerve injury, ischaemia, neurodegeneration, stroke, post stroke pain, inflammatory disorders, oesophagitis, gastroesophageal reflux disorder (GERD), irritable bowel syndrome, inflammatory bowel disease, overactive bladder, pelvic hypersensitivity, urinary incontinence, cystitis, stomach, duodenal ulcer, muscle pain, pain due to colicky and referred pain. Compounds of the present invention may also be useful for the treatment or prevention of hemophilic arthropathy and Parkinson's disease.

The invention relates also to a method for using the compounds of general formula (I) (Ia) or (Ib) or an N-oxide, a salt, a tautomer or a stereoisomer of said compound, or a salt of said N-oxide, tautomer or stereoisomer particularly a pharmaceutically acceptable salt thereof, or a mixture of same, to treat conditions treatable by inhibition of prostanoid-induced smooth muscle contraction by preventing the synthesis of contractile prostanoids and hence may be of relevance to use in treatment of dysmenorrhea premature labor and asthma.

The present invention relates to a method for the compounds of general formula (I) (Ia) or (Ib) or an N-oxide, a salt, a tautomer or a stereoisomer of said compound, or a salt of said N-oxide, tautomer or stereoisomer particularly a pharmaceutically acceptable salt thereof, or a mixture of same, to treat cancer and hyperproliferative disorders. Hyperproliferative disorders include, but are not limited to, for example: psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancers include, but are not limited to, invasive ductal carcinoma, invasive lobular carcinoma, and ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypothalmic glioma, cerebellar and cerebral astrocytoma, medulloblastoma, ependymoma, as well as neuroectodermal and pineal tumour.

Tumours of the male reproductive organs include, but are not limited to, prostate and testicular cancer.

Tumours of the female reproductive organs include, but are not limited to, endometrial, cervical, ovarian, vaginal, and vulvar cancer, as well as sarcoma of the uterus.

Tumours of the digestive tract include, but are not limited to, anal, colon, colorectal, oesophageal, gallbladder, gastric, pancreatic, rectal, small-intestine, and salivary gland cancers.

Tumours of the urinary tract include, but are not limited to, bladder, penile, kidney, and renal pelvis, ureter, urethral and human papillary renal cancers.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, squamous cell carcinoma, Kaposi's sarcoma, malignant melanoma, Merkel cell skin cancer, and non-melanoma skin cancer.

Head-and-neck cancers include, but are not limited to, laryngeal, hypopharyngeal, nasopharyngeal, oropharyngeal cancer, lip and oral cavity cancer and squamous cell.

Lymphomas include, but are not limited to, AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to, sarcoma of the soft tissue, osteosarcoma, malignant fibrous histiocytoma, lymphosarcoma, and rhabdomyosarcoma.

Leukemias include, but are not limited to, acute myeloid leukemia, acute lymphoblastic leukemia, chronic lymphocytic leukemia, chronic myelogenous leukemia, and hairy cell leukemia.

A preferred embodiment of the present invention relates to a method for using the compounds of general formula (I) (Ia) or (Ib) or an N-oxide, a salt, a tautomer or a stereoisomer of said compound, or a salt of said N-oxide, tautomer or stereoisomer particularly a pharmaceutically acceptable salt thereof, or a mixture of same, to treat a gynaecological disease, preferably dysmenorrhea, dyspareunia, vulvodynia or endometriosis, endometriosis-associated pain, or other endometriosis-associated symptoms, wherein said symptoms are in particular acute and chronic abdominal pain, dysmenorrhea, dyspareunia, dysuria, or dyschezia.

Another preferred embodiment of the present invention relates to a method for using the compounds of the present invention and compositions thereof, to treat a urinary tract disease, in particular overactive bladder or cystitis, preferably interstitial cystitis.

Another preferred embodiment of the present invention relates to a method for using the compounds of the present invention and compositions thereof, to treat a respiratory disorder, preferably cough, in particular chronic cough.

Another preferred embodiment of the present invention relates to a method for using the compounds of the present invention and compositions thereof, to treat a neurodegenerative disorders, preferably ischemic brain injury, spinal cord injury and Multiple Sclerosis.

Another preferred embodiment of the present invention relates to a method for using of general formula (I) (Ia) or (Ib) or an N-oxide, a salt, a tautomer or a stereoisomer of said compound, or a salt of said N-oxide, tautomer or stereoisomer particularly a pharmaceutically acceptable salt thereof, or a mixture of same, to treat arthritis, in particular rheumatoid arthritis and ankylosing spondylitis (Burnstock et al., 2012 Pharmacol Rev. 64:834-868).

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a gynaecological disease or a disease associated with undesired proliferation like endometriosis or cancer.

Preferably, the diseases treated with said method are gynaecological disorders, more preferably dysmenorrhea, dyspareunia or endometriosis, endometriosis-associated pain, or other endometriosis-associated symptoms, wherein said symptoms are in particular acute and chronic abdominal pain, dysmenorrhea, dyspareunia, dysuria, or dyschezia.

Further diseases, which can be treated with said method, are osteoarthritis, diabetic neuropathy, burning mouth syndrome, gastroesophageal reflux, migraine disorders, chronic cough, asthma, pruritus, irritable bowel disease, overactive urinary bladder, prostatic hyperplasia, interstitial cystitis.

Preferably, the method of treating the diseases mentioned above is not limited to the treatment of said disease but also includes the treatment of pain related to or associated with said diseases.

The compounds of the present invention can be used in particular in therapy and prevention, i.e. prophylaxis, of genitourinary, gastrointestinal, respiratory or pain-related disease, condition or disorder.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease.

Therefore, the present invention includes pharmaceutical compositions that are comprised of a pharmaceutically acceptable carrier or auxiliary and a pharmaceutically effective amount of a compound, or salt thereof, of the present invention.

Another aspect of the invention is a pharmaceutical composition comprising a pharmaceutically effective amount of a compound of formula (I) and a pharmaceutically acceptable auxiliary for the treatment of a disease mentioned supra, especially for the treatment of haematological tumours, solid tumours and/or metastases thereof.

A pharmaceutically acceptable carrier or auxiliary is preferably a carrier that is non-toxic and innocuous to a patient at concentrations consistent with effective activity of the active ingredient so that any side effects ascribable to the carrier do not vitiate the beneficial effects of the active ingredient. Carriers and auxiliaries are all kinds of additives assisting to the composition to be suitable for administration.

A pharmaceutically effective amount of compound is preferably that amount which produces a result or exerts the intended influence on the particular condition being treated.

The compounds of the present invention can be administered with pharmaceutically-acceptable carriers or auxiliaries well known in the art using any effective conventional dosage unit forms, including immediate, slow and timed release preparations, orally, parenterally, topically, nasally, ophthalmically, optically, sublingually, rectally, vaginally, subcutaneously, intra uterine and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing auxiliaries, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above.

Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate ; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for administration, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized.

Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)—Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC-CClF_2$ and $CClF_3$)

air displacement agents—examples include but are not limited to nitrogen and argon;

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate);

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection);

chelating agents (examples include but are not limited to edetate disodium and edetic acid);

colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate), flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas), plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, crosslinked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide); tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile i.v. solution: A 5 mg/ml solution of the desired compound of this invention can be made using sterile, injectable water, and the pH is adjusted if necessary. The solution is diluted for administration to 1-2 mg/ml with sterile 5% dextrose and is administered as an i.v. infusion over about 60 minutes.

Lyophilised powder for i.v. administration: A sterile preparation can be prepared with (i) 100-1000 mg of the desired compound of this invention as a lyophilised powder, (ii) 32-327 mg/ml sodium citrate, and (iii) 300-3000 mg Dextran 40. The formulation is reconstituted with sterile, injectable saline or dextrose 5% to a concentration of 10 to 20 mg/ml, which is further diluted with saline or dextrose 5% to 0.2-0.4 mg/ml, and is administered either IV bolus or by IV infusion over 15-60 minutes.

Intramuscular suspension: The following solution or suspension can be prepared, for intramuscular injection:

50 mg/ml of the desired, water-insoluble compound of this invention 5 mg/ml sodium carboxymethylcellulose 4 mg/ml TWEEN 80

9 mg/ml sodium chloride 9 mg/ml benzyl alcohol

Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Dose and Administration

Based upon standard laboratory techniques known to evaluate compounds useful for the treatment of disorders and/or disease, which are influenced by P2X4, by standard toxicity tests and by standard pharmacological assays for the determination of treatment of the conditions identified above in mammals, and by comparison of these results with the results of known medicaments that are used to treat these conditions. The effective dosage of the compounds of this invention can readily be determined for treatment of each desired indication. The amount of the active ingredient to be administered in the treatment of one of these conditions can vary widely according to such considerations as the particular compound and dosage unit employed the mode of administration, the period of treatment, the age and sex of the patient treated, and the nature and extent of the condition treated.

The total amount of the active ingredient to be administered will generally range from about 0.001 mg/kg to about 200 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. A preferred oral unit dosage for a administration of the compounds of the present invention includes but is not limited to 0.1 mg/kg to about 10 mg/kg body weight one to three times a day to once a week. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Combination Therapies

The term "combination" in the present invention is used as known to persons skilled in the art and may be present as a fixed combination, a non-fixed combination or kit of parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit of parts" in the present invention is used as known to persons skilled in the art and is defined as a combination wherein the said first active ingredient and the said second active ingredient are present in more than one unit. One example of a non-fixed combination or kit of parts is a combination wherein the said first active ingredient and the said second active ingredient are present separately. The components of the non-fixed combination or kit of parts may be administered separately, sequentially, simultaneously, concurrently or chronologically staggered.

The compounds of the present invention can be administered as the sole pharmaceutical agent or in combination with one or more other pharmaceutical agents where the combination causes no unacceptable adverse effects. The present invention relates also to such combinations.

Those combined pharmaceutical agents can be other agents having antiproliferative, antinociceptive and/or anti-inflammatory effects such as for example for the treatment of haematological tumours, solid tumours and/or metastases thereof and/or agents for the treatment of different pain syndromes and/or undesired side effects. The present invention relates also to such combinations.

Other anti-hyper-proliferative agents suitable for use with the composition of the invention include but are not limited to those compounds acknowledged to be used in the treatment of neoplastic diseases in Goodman and Gilman's The Pharmacological Basis of Therapeutics (Ninth Edition), editor Molinoff et al., publ. by McGraw-Hill, pages 1225-1287, (1996), which is hereby incorporated by reference, especially (chemotherapeutic) anti-cancer agents as defined supra.

For example, the compounds of the present invention can be combined with known hormonal therapeutic agents.

In particular, the compounds of the present invention can be administered in combination or as co-medication with hormonal contraceptives. Hormonal contraceptives can be administered via oral, subcutaneous, transdermal, intrauterine or intravaginal route, for example as Combined Oral Contraceptives (COCs) or Progestin-Only-Pills (POPs) or hormone-containing devices like implants, patches or intravaginal rings.

COCs include but are not limited to birth control pills or a birth control method that includes a combination of an estrogen (estradiol) and a progestogen (progestin). The estrogenic part is in most of the COCs ethinyl estradiol. Some COCs contain estradiol or estradiol valerate. Said COCs contain the progestins norethynodrel, norethindrone, norethindrone acetate, ethynodiol acetate, norgestrel, levonorgestrel, norgestimate, desogestrel, gestodene, drospirenone, dienogest, or nomegestrol acetate.

Birth control pills include for example but are not limited to Yasmin, Yaz, both containing ethinyl estradiol and drospirenone; Microgynon or Miranova containing levonorgestrel and ethinyl estradiol; Marvelon containing ethinyl estradiol and desogestrel; Valette containing ethinyl estradiol and dienogest; Belara and Enriqa containing ethinyl estradiol and chlormadinonacetate; Qlaira containing estradiol valerate and dienogest as active ingredients; and Zoely containing estradiol and normegestrol.

POPs are contraceptive pills that contain only synthetic progestogens (progestins) and do not contain estrogen. They are colloquially known as mini pills.

POPs include but are not limited to Cerazette containing desogestrel; Microlut containing levonorgestrel and Micronor containing norethindrone.

Other Progeston-Only forms are intrauterine devices (IUDs), for example Mirena containing levonorgestrel, or injectables, for example Depo-Provera containing medroxyprogesterone acetate, or implants, for example Implanon containing etonogestrel.

Other hormone-containing devices with contraceptive effect which are suitable for a combination with the compounds of the present invention are vaginal rings like Nuvaring containing ethinyl estradiol and etonogestrel, or transdermal systems like contraceptive patches, for example Ortho-Evra containing ethinyl estradiol and norelgestromin or Apleek (Lisvy) containing ethinyl estradiol and gestodene.

A preferred embodiment of the present invention is the administration of a compound of general formula (I) in combination with a COC or a POP or other Progestin-Only forms as well as vaginal rings or contraceptive patches as mentioned above.

Furthermore, the compounds of the present invention can be combined with therapeutic agents or active ingredients, that are already approved or that are still under development for the treatment and/or prophylaxis of diseases which are related to or mediated by P2X4.

For the treatment and/or prophylaxis of urinary tract diseases, the compounds of the present invention can be administered in combination or as co-medication with any substance that can be applied as therapeutic agent in the following indications:

Urinary tract disease states including those associated with bladder outlet obstruction; urinary incontinence conditions such as reduced bladder capacity, increased frequency of micturition, urge incontinence, stress incontinence, or bladder hyperreactivity; benign prostatic hypertrophy; prostatic hyperplasia; prostatitis; detrusor hyperreflexia; overactive urinary bladder and symptoms related to overactive urinary bladder wherein said symptoms are in particular increased urinary frequency, nocturia, urinary urgency or urge incontinence; pelvic hypersensitivity; urethritis; prostatitis; prostatodynia; cystitis, in particular interstitial cystitis; idiopathic bladder hypersensitivity; kidney disease as hyperprostaglandin E syndrome, classic Bartter syndrome For the treatment and/or prophylaxis of overactive bladder and symptoms related to overactive bladder, the compounds of the present invention can be administered in combination or as co-medication in addition to behavioral therapy like diet, lifestyle or bladder training with anticholinergics like oxybutynin, tolterodine, propiverine, solifenacin, darifenacin, trospium, fesoterdine; B-3 agonists like mirabegron; neurotoxins like onabutolinumtoxin A; or antidepressants like imipramine, duloxetine.

For the treatment and/or prophylaxis of interstitial cystitis, the compounds of the present invention can be administered in combination or as co-medication in addition to behavioral therapy like diet, lifestyle or bladder training with pentosans like elmiron; antidepressants like amitriptyline, imipramine; or antihistamines like loratadine.

For the treatment and/or prophylaxis of gynaecological diseases, the compounds of the present invention can be administered in combination or as co-medication with any substance that can be applied as therapeutic agent in the following indications:

dysmenorrhea, including primary and secondary; dyspareunia; endometriosis; endometriosis-associated pain; endometriosis-associated symptoms, wherein said symptoms are in particular acute and chronic abdominal pain, dysmenorrhea, dyspareunia, dysuria, or dyschezia.

For the treatment and/or prophylaxis of dysmenorrhea, including primary and secondary; dyspareunia; endometriosis and endometriosis-associated pain, the compounds of the present invention can be administered in in combination with ovulation inhibiting treatment, in particular COCs as mentioned above or contraceptive patches like Ortho-Evra or Apleek (Lisvy); or with progestogenes like dienogest (Visanne); or with GnRH analogous, in particular GnRH agonists and antagonists, for example leuprorelin, nafarelin, goserelin, cetrorelix, abarelix, ganirelix, degarelix; or with androgens: danazol.

For the treatment and/or prophylaxis of diseases, which are associated with pain, or pain syndromes, the compounds of the present invention can be administered in combination or as co-medication with any substance that can be applied as therapeutic agent in the following indications:

pain-associated diseases or disorders like hyperalgesia, allodynia, functional bowel disorders (such as irritable bowel syndrome) and arthritis (such as osteoarthritis, rheumatoid arthritis and ankylosing spondylitis), burning mouth syndrome, burns, migraine or cluster headache, nerve injury, traumatic nerve injury, post-traumatic injuries (including fractures and sport injuries), neuritis, neuralgia, poisoning, ischemic injury, interstitial cystitis, viral, trigeminal neuralgia, small fiber neuropathy, diabetic neuropathy, chronic arthritis and related neuralgias, HIV and HIV treatment-induced neuropathy.

The compounds of the present invention can be combined with other pharmacological agents and compounds that are intended to treat inflammatory diseases, inflammatory pain or general pain conditions.

In addition to well-known medicaments which are already approved and on the market, the compounds of the present invention can be administered in combination with inhibitors of the P2X purinoceptor family (e,g, P2X3 and P2X7), with inhibitors of IRAK4, with inhibitors of PTGES and with antagonists of the prostanoid EP4 receptor.

In particular, the compounds of the present invention can be administered in combination with pharmacological endometriosis agents, intended to treat inflammatory diseases, inflammatory pain or general pain conditions and/or interfering with endometriotic proliferation and endometriosis associated symptoms, namely with inhibitors of Aldo-keto-reductase 1C3 (AKR1C3) and with functional blocking antibodies of the prolactin receptor.

The compounds of the present invention can be combined with other pharmacological agents and compounds that are intended for the treatment, prevention or management of cancer.

In particular, the compounds of the present invention can be administered in combination with 131I-chTNT, abarelix, abiraterone, aclarubicin, ado-trastuzumab emtansine, afatinib, aflibercept, aldesleukin, alemtuzumab, Alendronic acid, alitretinoin, altretamine, amifostine, aminoglutethimide, Hexyl aminolevulinate, amrubicin, amsacrine, anastrozole, ancestim, anethole dithiolethione, angiotensin II, antithrombin Ill, aprepitant, arcitumomab, arglabin, arsenic trioxide, asparaginase, axitinib, azacitidine, basiliximab, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, cyclophosphamide, cyproterone, cytarabine, dacarbazine, dactinomycin, darbepoetin alfa, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin+estrone, dronabinol, eculizumab, edrecolomab, elliptinium acetate, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, lanreotide, lapatinib, lasocholine, lenalidomide, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxine mepesuccinate, omeprazole, ondansetron, oprelvekin, orgotein, orilotimod, oxaliplatin, oxycodone, oxymetholone, ozogamicine, p53 gene therapy, paclitaxel, palifermin, palladium-103 seed, palonosetron, pamidronic acid, panitumumab, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romiplostim, romurtide, roniciclib, samarium (153Sm) lexidronam, sargramostim, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Furthermore, the compounds of the present invention can be combined with active ingredients, which are well known for the treatment of cancer-related pain and chronic pain. Such combinations include, but are not limited to step II opioids like codeine phosphate, dextropropoxyphene, dihydro-codeine, Tramadol), step Ill opioids like morphine, fentanyl, buprenorphine, oxymorphone, oxycodone and hydromorphone; and other medications used for the treatment of cancer pain like steroids as Dexamethasone and methylprednisolone; bisphosphonates like Etidronate, Clodronate, Alendronate, Risedronate, and Zoledronate; tricyclic antidepressants like Amitriptyline, Clomipramine, Desipramine, Imipramine and Doxepin; class I antiarrhythmics like mexiletine and lidocaine; anticonvulsants like carbamazepine, Gabapentin, oxcarbazepine, phenytoin, pregabalin, topiramate, alprazolam, diazepam, flurazepam, pentobarbital and phenobarbital.

Methods of testing for a particular pharmacological or pharmaceutical property are well known to persons skilled in the art.

The example testing experiments described herein serve to illustrate the present invention and the invention is not limited to the examples given.

As will be appreciated by persons skilled in the art, the invention is not limited to the particular embodiments described herein, but covers all modifications of said embodiments that are within the spirit and scope of the invention as defined by the appended claims.

The following examples illustrate the invention in greater detail, without restricting it. Further compounds according to the invention, of which the preparation is not explicitly described, can be prepared in an analogous way.

The compounds, which are mentioned in the examples and the salts thereof represent preferred embodiments of the invention as well as a claim covering all subcombinations of the residues of the compound of formula (I) as disclosed by the specific examples.

The term "according to" within the experimental section is used in the sense that the procedure referred to is to be used "analogously to".

Synthesis of Compounds

The following schemes and general procedures illustrate general synthetic routes to the compounds of general formula (I), (Ia) and (Ib) of the invention and are not intended to be limiting. It is obvious to the person skilled in the art that the order of transformations as exemplified in schemes 1 to 5 can be modified in various ways. The order of transformations exemplified in schemes 1 to 5 is therefore not intended to be limiting. In addition, interconversion of substituents, for example of residues $R^1$, $R^2$, $R^{2a}$, $R^{2b}$, $R^{2c}$, $R^3$, $R^4$, $R^5$, $R^6$, $R^{6a}$, $R^{6b}$, $R^{7a}$, $R^{7b}$, $R^8$, $R^9$, $R^{10}$, $R^{11}$, $R^{11a}$, or $R^{12}$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts, Protective Groups in Organic Synthesis, 3rd edition, Wiley 1999).

All reagents used for the preparation of the compounds of the invention are commercially available, known in the literature or can be prepared as described.

ylamino)methylene. In case V corresponds to a leaving group LG (e.g. fluoride, chloride, tosyl) compounds 2 can be converted in a nucleophilic aromatic substitution reaction in a suitable solvent (e.g. acetonitrile) and in presence of a suitable base (e.g. potassium carbonate, cesium carbonate, . . . ) with a heteroaromatic system $R^2H$ that contains a nucleophilic nitrogen (e.g. pyrazole, imidazole, triazole, . . . ) to compounds 3 while forming a new C—N-bond. In case V corresponds to chloride or bromide, compounds 3 can be formed in a metal-catalyzed C—N coupling reaction with a nitrogen-containing heteroaromatic

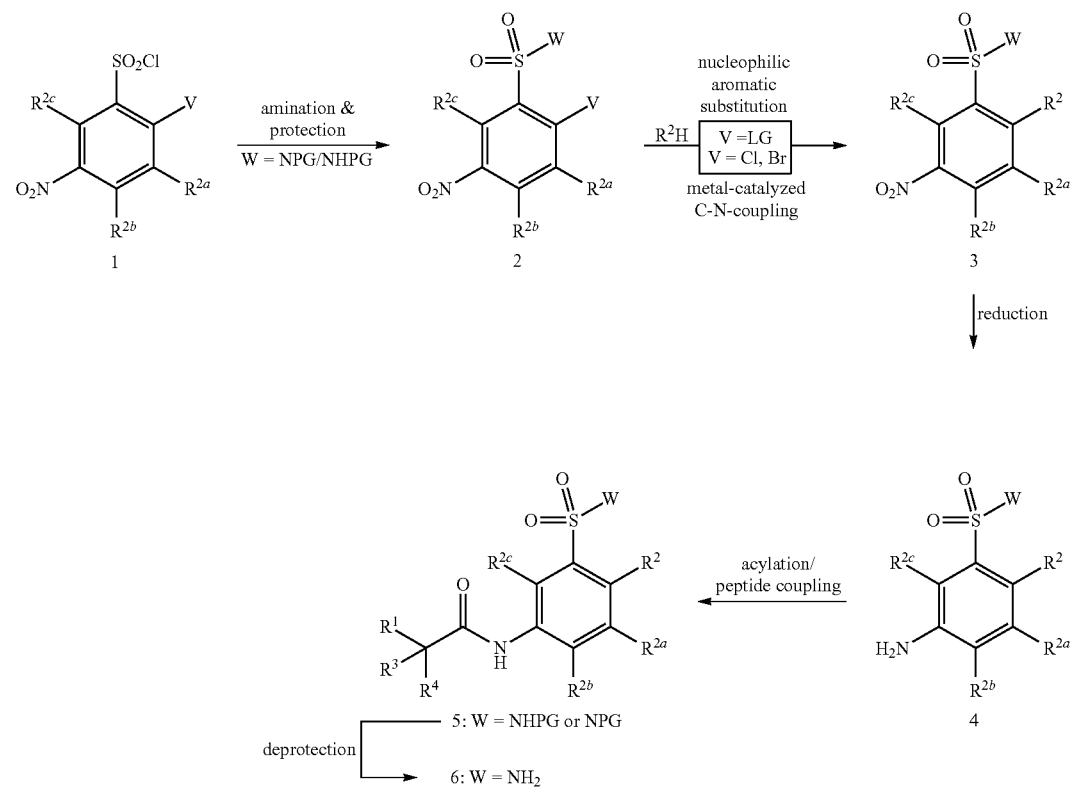

Scheme 1: General procedures for the preparation of compounds of general formula (and (Ia) corresponding to formula 6; $R^1$, $R^{2a}$, $R^{2b}$, $R^{2c}$, $R^3$, and $R^4$ are as defined in the description and claims of this invention; W corresponds to either an amine with hydrogen and/or a protecting group PG (e.g., (dimethylamino)methylene, 2,4-dimethoxybenzyl); V corresponds to LG, chloride or bromide; LG corresponds to a leaving group (e.g. chloride, fluoride, tosyl); $R^2$ is a heteroaromatic system with a nucleophilic nitrogen (e.g. pyrazole, imidazole, triazole) and undergoes a nucleophilic aromatic substitution at this nitrogen atom.

Compounds of general formula 6 can by synthesized as depicted in Scheme 1. The person skilled in the art will be able to convert sulfonyl chlorides 1 to the protected sulfonyl amides 2 and will be able to select a protecting group PG that is suitable for the following steps. Examples for suitable protecting groups PG are 2,4-dimethoxybenzyl or (dimethylamino)methylene.

system (e.g. 1,2,3-triazoles) and in the presence of a suitable catalytic system (e.g. tris(dibenzylideneacetone)dipalladium/di-tert-butyl(2',4',6'-triisopropyl-3,4,5,6-tetramethyl-[1,1'-biphenyl]-2-yl)phosphine/potassium phosphate/toluene). In the next step, nitro compounds 3 can be converted to the corresponding anilines 4 by reduction under hydrogenation conditions, in polar solvents such as ethanol, methanol, dioxane or tetrahydrofuran in the presence of for example Pd-, Pt-, Fe- or Sn-based catalysts. Anilines 4 can be converted to the corresponding amides 5 for example by reaction with acyl chlorides or by standard peptide bond formation using all known procedures, such as reaction of the corresponding carboxylic acid in the presence of a coupling reagent e.g. HATU. In the last step, amides 5 are deprotected to the desired sulfonamides 6. Deprotection conditions depend on the used protecting group (e.g. TFA/dichloromethane in case of 2,4-dimethoxybenzyl or aqueous ammonia/methanol in case of (dimethylamino)methylene).

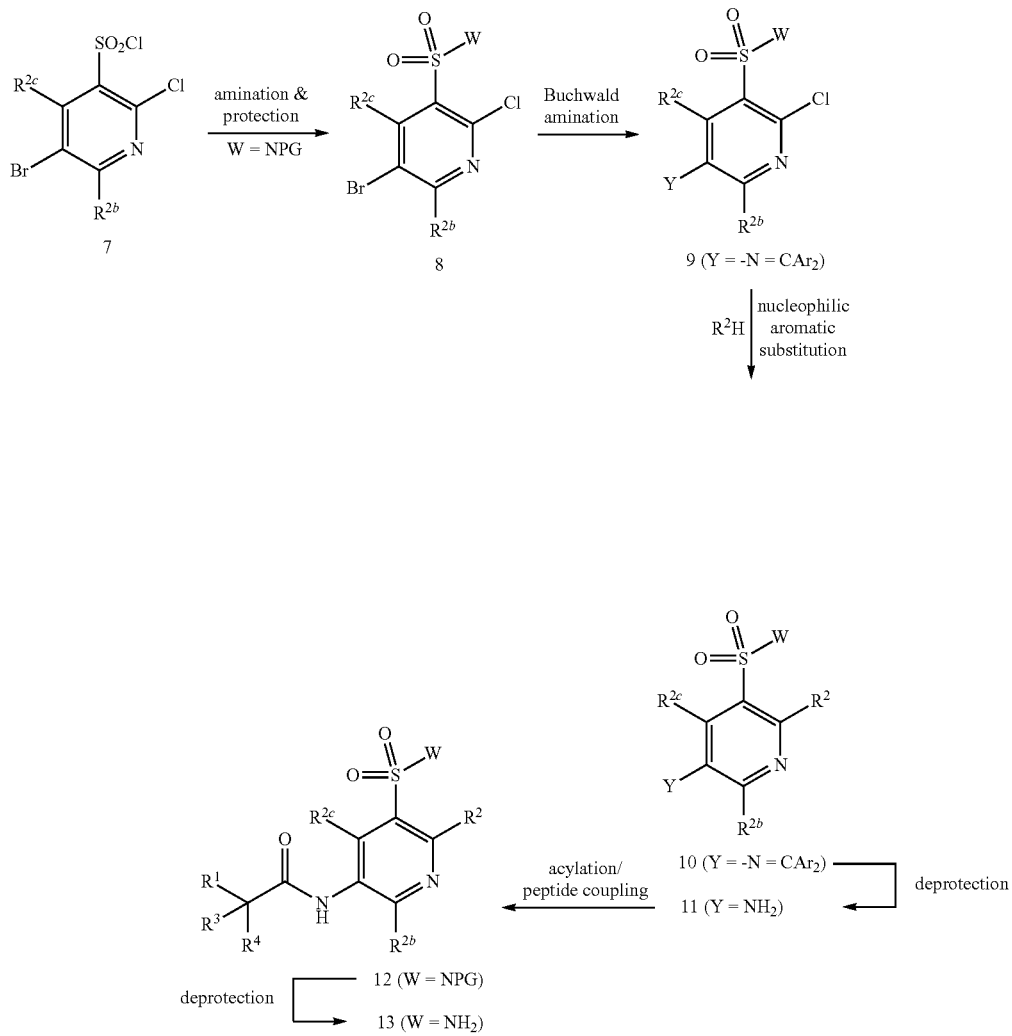

Scheme 2: General procedure for the preparation of compounds of general formula (I) and (Ib) corresponding to formula 13; $R^1$, $R^{2b}$, $R^{2c}$, $R^3$, and $R^4$ are as defined in the description and claims of this invention; W corresponds to either an amine with hydrogen and/or a protecting group PG (e.g. (dimethylamino)methylene); Ar is aryl; $R^2$ is a heteroaromatic system with a nucleophilic nitrogen (e.g. pyrazole, imidazole, triazole) and undergoes a nucleophilic aromatic substitution at this nitrogen atom.

Compounds of general formula 13 can by synthesized as depicted in Scheme 2. The person skilled in the art will be able to convert sulfonyl chlorides 7 to the protected sulfonyl amides 8 and will be able to select a protecting group PG that is suitable for the following steps. Example for a suitable protecting group PG is (dimethylamino)methylene (reaction of sulfonylchlorides 7 with ammonia, then reaction with 1,1-dimethoxy-N,N-dimethylmethanamine in DMF). Using protection and deprotection strategies, Buchwald amination of 8 in the presence of suitable catalysts (see for example WO2011120026A1) leads to intermediates 9. Nucleophilic aromatic substitution reaction in a suitable solvent (e.g. acetonitrile) and in presence of a suitable base (e.g. potassium carbonate, . . . ) with a heteroaromatic system $R^2H$ that contains a nucleophilic nitrogen (e.g. pyrazole, imidazole, triazole, . . . ) leads to pyridines 10. Deprotection of 10 (under acidic conditions in case Y═—N═CAr$_2$) is followed by conversion of the resulting anilines 11 to amides 12 for example by reaction with acyl chlorides or by standard peptide bond formation using all known procedures, such as reaction of the corresponding carboxylic acids in the presence of a coupling reagent e.g. HATU. In the last step, amide 12 is deprotected to the desired sulfonamides 13. Deprotection conditions depend on the used protecting group (e.g. aqueous ammonia/methanol in case of (dimethylamino)methylene).

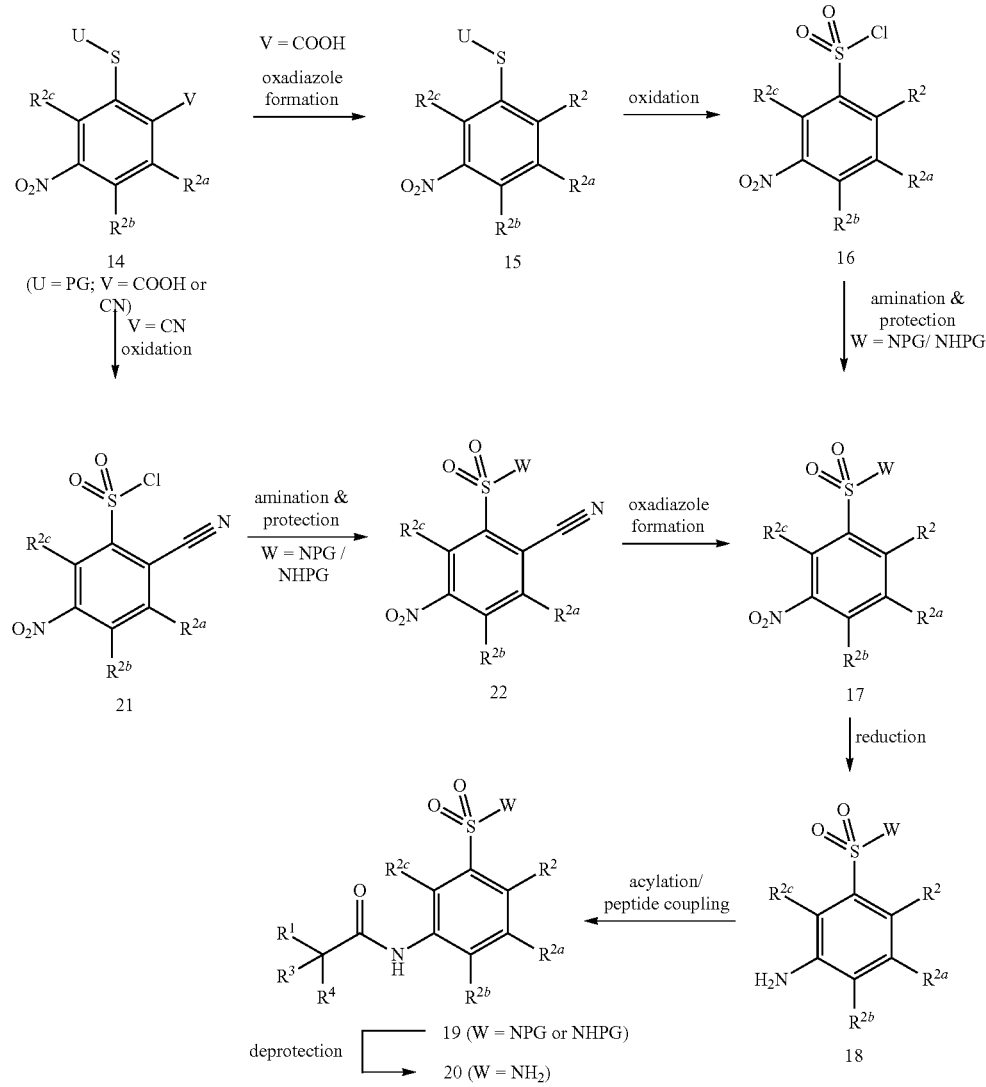

Scheme 3: General procedures for the preparation of compounds of general formula (I) and (Ia) corresponding to formula 20; $R^1$, $R^{2a}$, $R^{2b}$, $R^{2c}$, $R^3$ and $R^4$ are as defined in the description and claims of this invention, W corresponds to either an amine with hydrogen and/or a protecting group PG (e.g., (dimethylamino)methylene, 2,4-dimethoxybenzyl), $R^2$ corresponds to optionally substituted oxadiazolyl.

Compounds of general formula 20 can by synthesized as depicted in Scheme 3. Starting from the protected benzenethiols 14 (PG: e.g., benzyl, benzoyl) with V=COOH, 1,3,4-oxadiazol-2-yl- and 1,2,4-oxadiazol-5-yl-substituents can be prepared from the carboxy group by methods known to the person skilled in the art (see for example WO 2011/028741). Conversion of the protected benzenethiols 15 into benzenesulfonyl chlorides 16 can be achieved by oxidation in a protic solvent, e.g. with N-chlorosuccinimide in acetic acid or with chlorine gas in tetrachloromethane/water. The corresponding sulfonamides 17 can be obtained from intermediates 16 by reaction of ammonia or any amine in aprotic solvents such as dichloromethane and acetonitrile. Subsequent reduction under hydrogenation conditions, in polar solvents such as ethanol or tetrahydrofuran in the presence of for example Pd-, Pt-, Fe- or Sn-based catalysts yield the aniline derivatives with general formula 18. Subsequent acylation to the corresponding amides can be achieved for example by reaction with acyl chlorides or by standard peptide bond formation using all known procedures, such as reaction of the corresponding carboxylic acid in the presence of a coupling reagent e.g. HATU. For W equals a protected amino function subsequent deprotection with e.g. trifluoroacetic acid (TFA), results in compounds of general formula 20.

Alternatively, starting from intermediates 14 with V=CN, oxidation to benzenesulfonyl chlorides 21 can be performed in presence of the nitrile in a protic solvent, e.g. with N-chlorosuccinimide in acetic acid or with chlorine gas in tetrachloromethane/water. The corresponding sulfonamides 22 can be obtained from intermediates 21 by reaction of ammonia or any amine in aprotic solvents such as dichloromethane and acetonitrile. In a subsequent step, the nitrile group of intermediates 22 can be transformed into sulfonamides with 1,2,4-oxadiazol-2-yl-substituents 17 by methods known to the person skilled in the art (see for example WO 2011/028741).

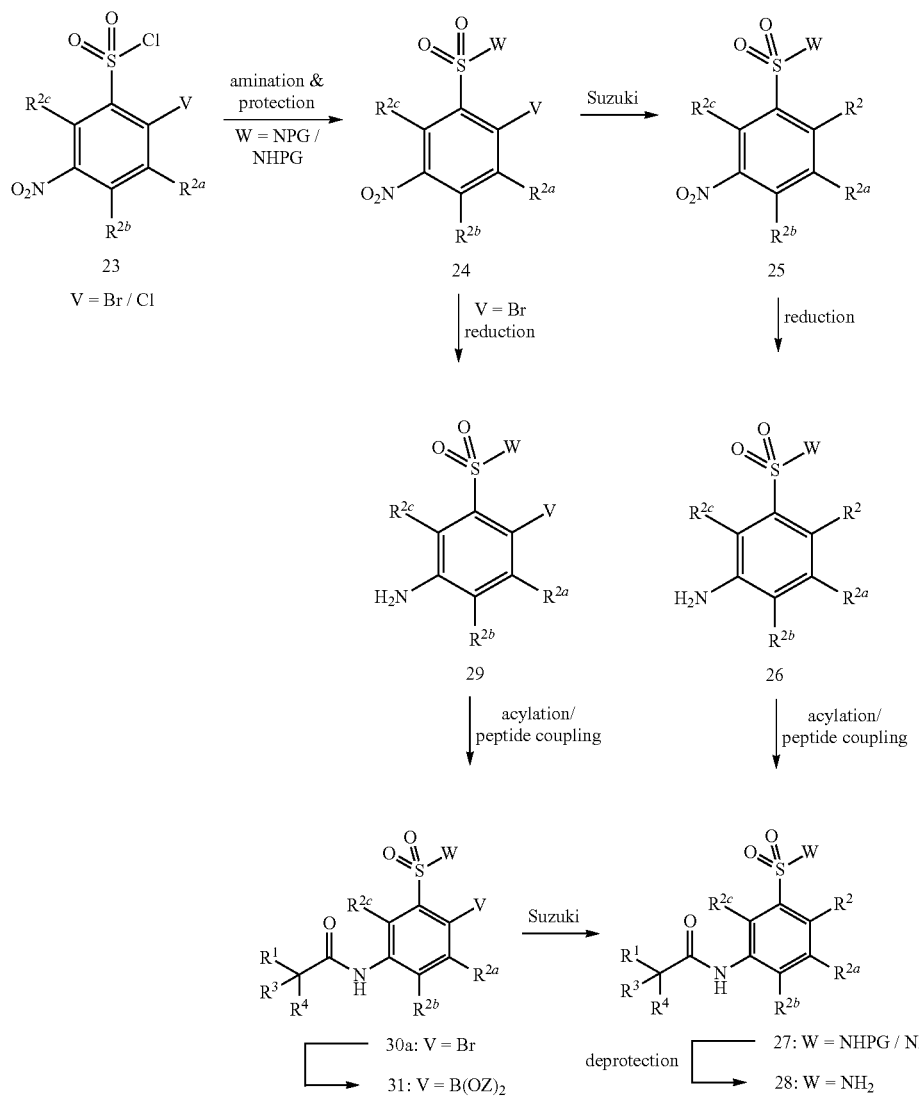

Scheme 4: General procedures for the preparation of compounds of general formula (I) and (Ia) corresponding to formula 28; $R^1$, $R^2$, $R^{2a}$, $R^{2b}$, $R^{2c}$, $R^3$ and $R^4$ are as defined in the description and claims of this invention, $B(OZ)_2$ corresponds to $B(OH)_2$ or $B(O_2C_6H_{12})$ or a mixture of both and W corresponds to either an amine with hydrogen and/or a protecting group PG (e.g., (dimethylamino)methylene, 2,4-dimethoxybenzyl).

Compounds of general formula 28 can by synthesized as depicted in Scheme 4. Starting from corresponding sulfonyl chlorides 23 (with V being either bromide or chloride) C-connected aryl and heteroaryl derivatives can be prepared via e.g. Suzuki cross-coupling reactions known to the person skilled in the art. Transformation of the protected sulfonamides 24 into aryl/heteroaryl compounds with general formula 25 can be achieved by reaction with the corresponding boronic acid (or ester or a mixture of both) under palladium catalysis in protic (e.g. isopropanol) or aprotic solvents. The corresponding amines 26 can be obtained from intermediates 25 by reduction under hydrogenation conditions, in polar solvents such as ethanol or tetrahydrofuran in the presence of for example Pd-, Pt-, Fe- or Sn-based catalysts. Subsequent acylation to the corresponding amides 27 can be achieved for example by reaction with acyl chlorides or by standard peptide bond formation using all known procedures, such as reaction of the corresponding carboxylic acid in the presence of a coupling reagent e.g. HATU. For W equals a protecting group subsequent deprotection with e.g. trifluoroacetic acid (TFA), results in compounds of general formula 28.

Alternatively, starting from intermediates 24 with V=Br, reduction under hydrogenation conditions, in polar solvents such as ethanol or tetrahydrofuran in the presence of for example Pt-, Fe- or Sn-based catalysts yields amines 29. The corresponding amides 30a can be obtained by reaction with acyl chlorides or by standard peptide bond formation using all known procedures. Subsequent arylation/heteroarylation using e.g. palladium catalyzed cross-couplings gives access to intermediates 27. Alternatively bromides 30a can be converted into the corresponding boronic acid/ester intermediates 31 ($B(OZ)_2=B(OH)_2$ or $B(O_2C_6H_{12})$) and further reacted using e.g. palladium catalysis known to the person skilled in the art to obtain intermediates 27 which after deprotection yield final products with general formula 28.

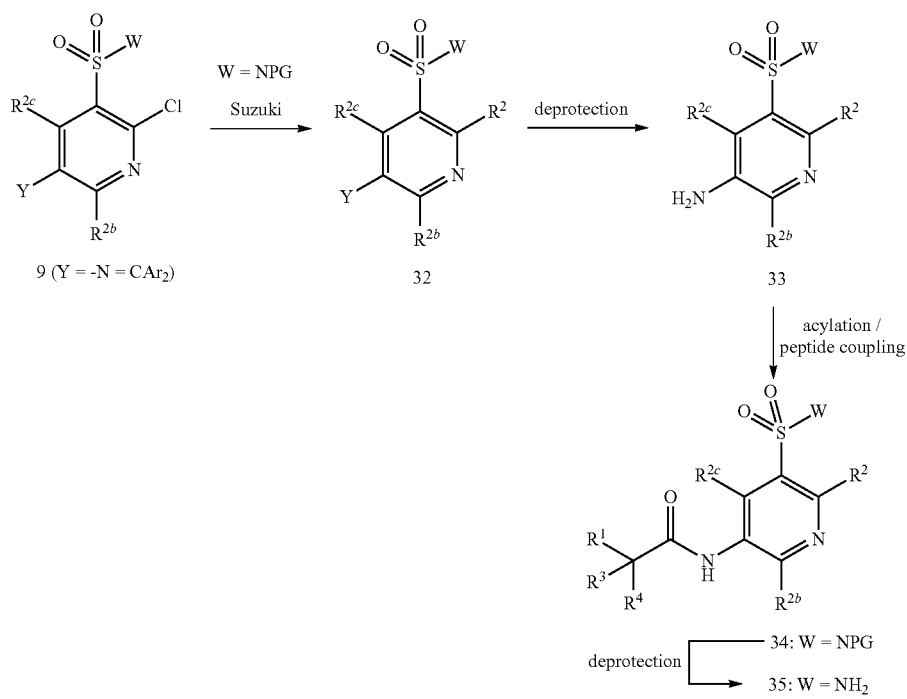

Scheme 5: General procedure for the preparation of compounds of general formula (I) and (Ib) corresponding to formula 35; $R^1$, $R^2$, $R^{2b}$, $R^{2c}$, $R^3$, $R^4$ are as defined in the description and claims of this invention, W corresponds to either amine with hydrogen and/or a protecting group PG (e.g., (dimethylamino)methylene, 2,4-dimethoxybenzyl); Ar is aryl.

Compounds of general formula 35 can by synthesized as depicted in Scheme 5. Starting from intermediate 9 C-coupled aryl and heteroaryl derivatives 32 can be prepared via e.g. palladium cross-couplings, e.g. Suzuki reactions, known to the person skilled in the art (see for example US 20110281865). Deprotection under e.g. acidic condition yields amines 33. Subsequent acylation to the corresponding amides can be achieved for example by reaction with acyl chlorides or by standard peptide bond formation using all known procedures, such as reaction of the corresponding carboxylic acid in the presence of a coupling reagent e.g. HATU. For W equals a protected amino function subsequent deprotection (with e.g. aqueous ammonia in case of (dimethylamino)methylene as protection group), results in compounds of general formula 35.

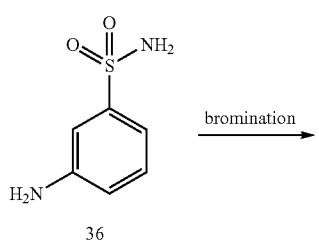

Scheme 6: General procedure for the preparation of compounds of formula 30a; $R^1$, $R^3$ and $R^4$ are as defined in the description and claims of this invention, $R^{2a}$, $R^{2b}$ and $R^{2c}$ are hydrogen, W corresponds to either an amine with hydrogen and/or a protecting group PG (e.g., (dimethylamino)methylene, 2,4-dimethoxybenzyl).

Compounds of general formula 30a can by synthesized as depicted in Scheme 6. Starting from the corresponding aniline 36, bromination (e.g. with NBS in DMF) leads to bromoaniline 37. Subsequent acylation to the corresponding amides 38 can be achieved for example by reaction with acyl chlorides or by standard peptide bond formation using all known procedures, such as reaction of the corresponding carboxylic acid in the presence of a coupling reagent e.g.

HATU. Subsequent protection of the sulfonamide moiety (e.g. with 1,1-dimethoxy-N,N-dimethylmethanamine in DMF) leads to protected amides 30a that then can be further transformed e.g. using Suzuki chemistry as described in Scheme 4.

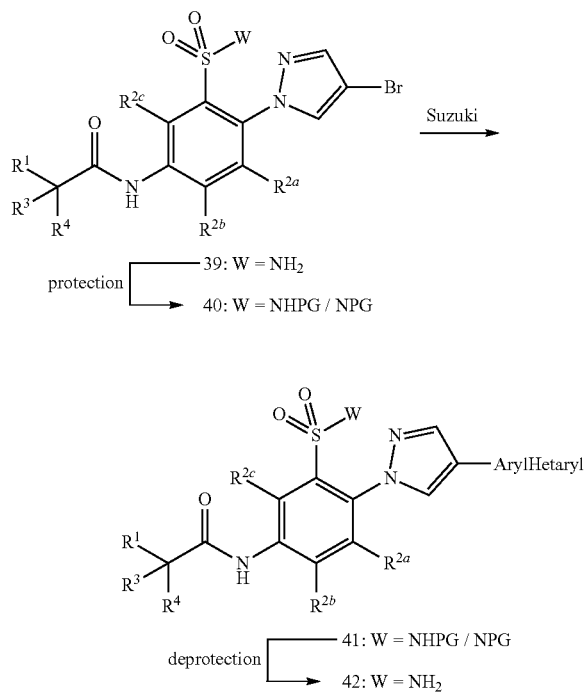

Scheme 7: General procedure for the preparation of compounds of general formula (I) and (Ia) corresponding to formula 42; $R^1$, $R^{2a}$, $R^{2b}$, $R^{2c}$, $R^3$ and $R^4$ are as defined in the description and claims of this invention, W corresponds to either an amine with hydrogen and/or a protecting group PG (e.g., (dimethylamino)methylene, 2,4-dimethoxybenzyl).

Compounds of general formula 42 can by synthesized as depicted in Scheme 7. After protection of the sulfonamide moiety of bromopyrazoles 39 (e.g. with a (dimethylamino) methylene group), these can be transformed e.g. via Suzuki cross-coupling reactions known to the person skilled in the art to compounds 41. For W equals a protecting group subsequent deprotection with e.g. aqueous ammonia in an alcohol (e.g. methanol, ethanol, propanol) results in compounds of general formula 42.

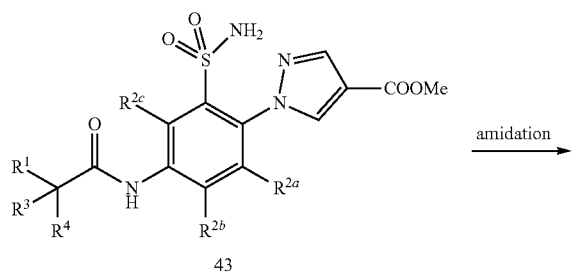

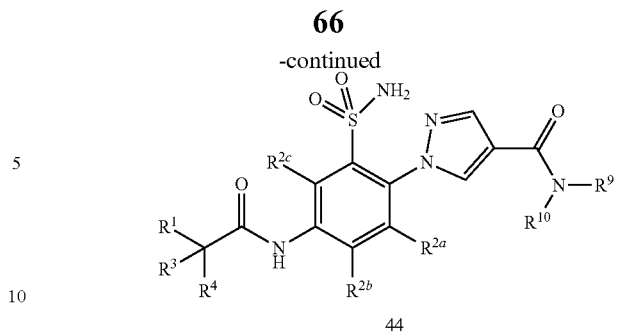

Scheme 8: General procedures for the preparation of compounds of general formula (I) and (Ia) corresponding to formula 44; $R^1$, $R^{2a}$, $R^{2b}$, $R^{2c}$, $R^3$, $R^4$, $R^9$ and $R^{10}$ are as defined in the description and claims of this invention.

Compounds of general formula 44 can by synthesized as depicted in Scheme 8. Carboxylic esters 43 can be transformed into the corresponding amides 44 either by direct transamidation (e.g. with a Lewis acid like bis(trimethylaluminum)-1,4-diazabicyclo[2.2.2]-octane (DABAL-Me₃) in THF) or by subsequent hydrolysis and amidation procedures known to the person skilled in the art.

In addition, example compounds can be further derivatized by late-stage functionalization chemistry (e.g. *Bioorg. Med. Chem. Lett.* 2012, 22, 1255-1262, *Chem. Soc. Rev.* 2016, 45(3), 546-476, *Chem. Rev.* 2016, 116(2), 422-518; *Chem Rev.* 2014, 114(4), 2432-2506), as known to a person skilled in the art. These can be for example fluorination, difluoromethylation, trifluoromethylation, cyanation, methoxylation, oxidation or alkylation reactions (for oxidation examples see *Org. Lett.* 2015, 17, 6066-6069, *Adv. Synth. Catal.* 2004, 346, 171-184, *Science* 2007, 318(5851), 783-7, *Org. Lett.*, 2005, 7(1), 79-82, *J. Organomet. Chem.*, 2015, 793, 217-231).

The compounds according to the invention are isolated and purified in a manner known per se, e.g. by distilling off the solvent in vacuo and recrystallizing the residue obtained from a suitable solvent or subjecting it to one of the customary purification methods, such as chromatography on a suitable support material. Furthermore, reverse phase preparative HPLC of compounds of the present invention which possess a sufficiently basic or acidic functionality, may result in the formation of a salt, such as, in the case of a compound of the present invention which is sufficiently basic, a trifluoroacetate or formate salt for example, or, in the case of a compound of the present invention which is sufficiently acidic, an ammonium salt for example. Salts of this type can either be transformed into its free base or free acid form, respectively, by various methods known to the person skilled in the art, or be used as salts in subsequent biological assays. Additionally, the drying process during the isolation of compounds of the present invention may not fully remove traces of cosolvents, especially such as formic acid or trifluoroacetic acid, to give solvates or inclusion complexes. The person skilled in the art will recognise which solvates or inclusion complexes are acceptable to be used in subsequent biological assays. It is to be understood that the specific form (e.g. salt, free base, solvate, inclusion complex) of a compound of the present invention as isolated as described herein is not necessarily the only form in which said compound can be applied to a biological assay in order to quantify the specific biological activity.

Salts of the compounds of formula (I), (Ia) and (Ib) according to the invention can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art. Especially preferred are hydrochlorides and the process used in the example section.

Pure diastereomers and pure enantiomers of the compounds and salts according to the invention can be obtained e.g. by asymmetric synthesis, by using chiral starting compounds in synthesis and by splitting up enantiomeric and diasteriomeric mixtures obtained in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated e.g. by forming diastereomers with a chiral auxilliary agent, resolving the diastereomers obtained and removing the chiral auxilliary agent. As chiral auxilliary agents, for example, chiral acids can be used to separate enantiomeric bases such as e.g. mandelic acid and chiral bases can be used to separate enantiomeric acids by formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxilliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

One preferred aspect of the invention is the process for the preparation of the compounds of general formula (I) (Ia) or (Ib) or an N-oxide, a salt, a tautomer or a stereoisomer of said compound, or a salt of said N-oxide, tautomer or stereoisomer according to the examples, as well as the intermediates used for their preparation.

Optionally, compounds of the formula (I), (Ia) and (Ib) can be converted into their salts, or, optionally, salts of the compounds of the formula (I), (Ia) and (Ib) can be converted into the free compounds. Corresponding processes are customary for the skilled person.

EXPERIMENTAL PART

Abbreviations

The following table lists the abbreviations used in this paragraph and in the Intermediate Examples and Examples section as far as they are not explained within the text body.

| Abbreviation | Meaning |
| --- | --- |
| AcOH | acetic acid (ethanoic acid) |
| aq. | aqueous |
| boc | t-butoxycarbonyl |
| br | broad |
| CI | chemical ionisation |
| d | doublet |
| DAD | diode array detector |
| DBU | 1,8-Diazabicyclo(5.4.0)undec-7-ene |
| DCM | dichloromethane |
| dd | double-doublet |
| DIPEA | diisopropylethylamine |
| DMF | N,N-dimethylformamide |
| DMSO | dimethyl sulfoxide |
| ELSD | Evaporative Light Scattering Detector |
| EtOAc | ethyl acetate |
| EtOH | ethanol |
| eq. | equivalent |
| ESI | electrospray (ES) ionisation |
| HATU | 1-[Bis(dimethylamino)methylene]-1H-1,2,3-triazolo[4,5-b]pyridinium 3-oxid hexafluorophosphate |
| HPLC | high performance liquid chromatography |
| LC-MS | liquid chromatography mass spectrometry |
| m | multiplet |
| MeCN | acetonitrile |
| MeOH | methanol |
| MS | mass spectrometry |
| MTBE | methyl tert-butylether |
| NMR | nuclear magnetic resonance spectroscopy: chemical shifts ($\delta$) are given in ppm. The chemical shifts were corrected by setting the DMSO signal to 2.50 ppm unless otherwise stated. |
| PDA | Photo Diode Array |
| PoraPak™; | a HPLC column obtainable from Waters |
| q | quartet |
| r.t. or rt | room temperature |
| Rt | retention time (as measured either with HPLC or UPLC) in minutes |
| s | singlet |
| SM | starting material |
| SQD | Single-Quadrupol-Detector |
| t | triplet |
| td | dublett of a triplet |
| dt | triplett of a dublet |
| TEA | triethylamine |
| THF | tetrahydrofuran |
| UPLC | ultra performance liquid chromatography |

Specific Experimental Descriptions

NMR peak forms in the following specific experimental descriptions are stated as they appear in the spectra, possible higher order effects have not been considered. Reactions employing microwave irradiation may be run with a Biotage Initator® microwave oven optionally equipped with a robotic unit. The reported reaction times employing microwave heating are intended to be understood as fixed reaction times after reaching the indicated reaction temperature. The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. from Separtis such as Isolute® Flash silica gel or Isolute® Flash NH$_2$ silica gel in combination with a Isolera® autopurifier (Biotage) and eluents such as gradients of e.g. hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia. In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc) of a compound of the present invention as isolated as described herein is not necessarily the only form in which said compound can be applied to a biological assay in order to quantify the specific biological activity.

The percentage yields reported in the following examples are based on the starting component that was used in the lowest molar amount. Most reaction conditions were not optimized for yield. Air and moisture sensitive liquids and solutions were transferred via syringe or cannula, and introduced into reaction vessels through rubber septa. Commercial grade reagents and solvents were used without further purification. The term "concentrated in vacuo" refers to use of a Buchi rotary evaporator at a minimum pressure of approximately 15 mm of Hg. All temperatures are reported uncorrected in degrees Celsius (° C.).

In order that this invention may be better understood, the following examples are set forth. These examples are for the purpose of illustration only, and are not to be construed as limiting the scope of the invention in any manner. All publications mentioned herein are incorporated by reference in their entirety.

Analytical LC-MS and UPLC-MS Conditions

LC-MS and UPLC-MS data given in the subsequent specific experimental descriptions refer (unless otherwise noted) to the following conditions:

Method A

Instrument: Waters Acquity UPLC-MS SingleQuad; Column: Acquity UPLC BEH C18 1.7 μm, 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm.

Method B

Instrument: Waters Acquity UPLC-MS SingleQuad; Column: Acquity UPLC BEH C18 1.7 μm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 ml/min; temperature: 60° C.; DAD scan: 210-400 nm.

Method C

Instrument: Waters Acquity UPLC-MS SingleQuad; Column: Acquity UPLC BEH C18 1.7 50×2.1 mm; eluent A: water+0.1 vol % formic acid (99%), eluent B: acetonitrile; gradient: 0-4.5 min 1-99% B, 4.5-5.0 min 99% B; flow 0.8 ml/min; temperature: 60° C.; DAD scan: 210-400 nm.

Method D

Instrument: Waters Acquity UPLC-MS SingleQuad; Column: Acquity UPLC BEH C18 1.7 μm, 50×2.1 mm; eluent A: water+0.2 vol % aqueous ammonia (32%), eluent B: acetonitrile; gradient: 0-4.5 min 5-95% B, 4.5-5.0 min 95% B; flow 0.8 ml/min; temperature: 50° C.; DAD scan: 210-400 nm.

Method E

Instrument: Waters Acquity UPLCMS SingleQuad; Column: Acquity UPLC BEH C18 1.7 μm, 50×2.1 mm; eluent A: water+0.1 vol % trifluoroacetic acid, eluent B: acetonitrile; gradient: 0-4.5 min 5-95% B, 4.5-5.0 min 95% B; flow 0.8 ml/min; temperature: 50° C.; DAD scan: 210-400 nm.

Method F (chiral HPLC)

Instrument: Agilent HPLC 1260; Column: Chiralpak IB 3μ 100×4.6 mm; eluent A: hexane+0.1% vol. diethylamine (99%), eluent B: ethanol; isocratic: 70% A+30% B; flow 1.0 mL/min; temperature: 25° C.; injection: 5 μl; DAD @ 254 nm.

Method G

Instrument: Agilent UHPLC 1290 SingleQuad; Column: Phenomenex Kinetex C18 1.7 50×2.1 mm; Eluent A: Water+0.1 vol % trifluoroacetic acid (99%), Eluent B: acetonitrile; gradient: 0-4.5 min 5-95% B, 4.5-5.0 min 95% B; flow 0.8 ml/min; temperature: 50° C.; DAD @ 254 nm.

Method H

Instrument: Agilent: 1260, Aurora SFC-Modul; Column: Luna Hilic 5 μm 100×4.6 mm; Eluent A: CO2, Eluent B: methanol+0.5 vol % ammonia (32%); isocratic: 20% B; flow 4.0 ml/min; temperature: 37.5° C.; BPR: 100 bar; MWD @ 254 nm.

Method I

Instrument: Waters Acquity UPLC-MS SingleQuad; Column: Acquity UPLC BEH C18 1.7 μm, 50×2.1 mm; eluent A: water+0.1 vol % formic acid (99%), eluent B: methanol; gradient: 0-1.6 min 1-99% B, 1.6-2.0 min 99% B; flow 0.8 ml/min; temperature: 60° C.; DAD scan: 210-400 nm.

Method J

Instrument: Waters Acquity UPLC-MS SingleQuad; Column: Acquity UPLC BEH C18 1.7 μm, 50×2.1 mm; eluent A: water+0.2 vol % aqueous ammonia (32%), eluent B: methanol; gradient: 0-1.6 min 1-99% B, 1.6-2.0 min 99% B; flow 0.8 ml/min; temperature: 60° C.; DAD scan: 210-400 nm.

Method K

Instrument: Agilent: 1260, Aurora SFC-Modul; Column: Chiralpak IA 5 μm 100×4.6 mm; Eluent A: $CO_2$, Eluent B: methanol+0.2 Vol-% diethylamine (99%); isocratic: 28% B; flow 4.0 ml/min; temperature: 37.5° C.; BPR: 100 bar; MWD @ 254 nm Method L Instrument: Agilent: 1260, Aurora SFC-Modul; Column: Chiralpak IA 5 μm 100×4.6 mm; Eluent A: $CO_2$, Eluent B: ethanol+0.2 Vol-% aqueous ammonia (32%); isocratic: 29% B; flow 4.0 ml/min; temperature: 37.5° C.; BPR: 100 bar; MWD @ 220 nm Method M Instrument: Agilent: 1260, Aurora SFC-Modul; Column: Chiralpak IA 5 μm 100×4.6 mm; Eluent A: $CO_2$, Eluent B: methanol+0.2 Vol-% diethylamine (99%); isocratic: 28% B; flow 4.0 ml/min; temperature: 37.5° C.; BPR: 100 bar; MWD @ 254 nm Method N Instrument: Agilent: 1260, Aurora SFC-Modul; Column: Chiralpak IA 5 μm 100×4.6 mm; Eluent A: $CO_2$, Eluent B: methanol; isocratic: 21% B; flow 4.0 ml/min; temperature: 37.5° C.; BPR: 100 bar; MWD @ 254 nm Method O Instrument: Agilent: 1260, Aurora SFC-Modul; Column: YMC Cellulose SC 3μ 100×4.6 mm; Eluent A: hexane+0.1 Vol-% diethylamine (99%), Eluent B: ethanol; isocratic: 10% B; flow 1.0 mL/min; temperature: 25° C.; DAD @ 254 nm Flash Column Chromatography Conditions "Purification by (flash) column chromatography" as stated in the subsequent specific experimental descriptions refers to the use of a Biotage Isolera purification system. For technical specifications see "Biotage product catalogue" on www.biotage.com.

General Experimental Procedures

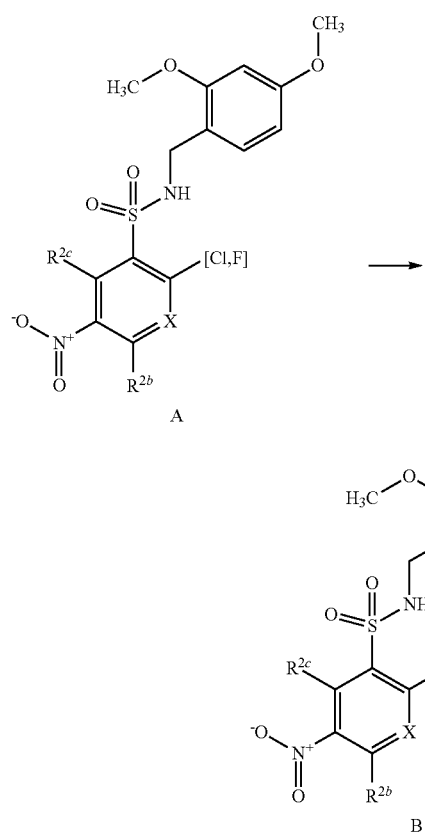

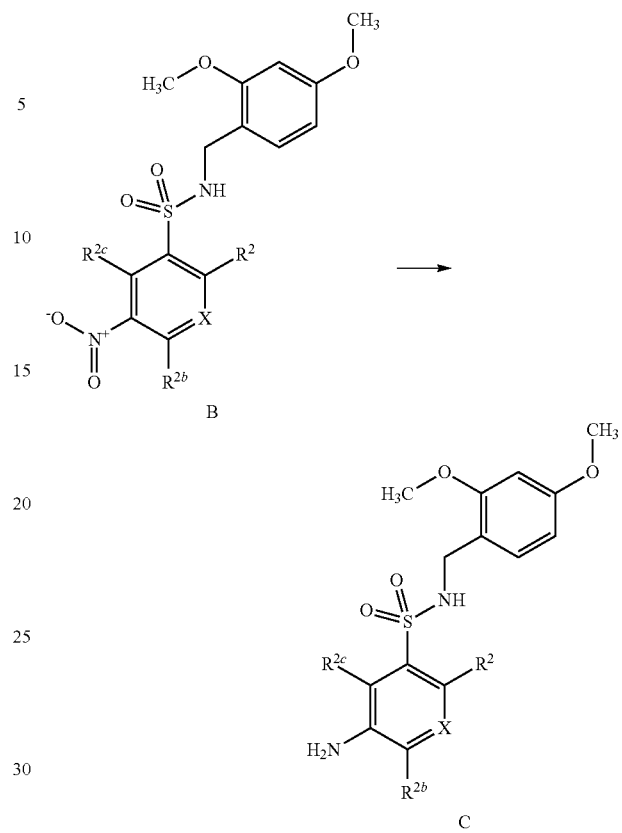

General Procedure GP1.1

Sulfonamide A (e.g. 1.29 mmol scale) was dissolved in acetonitrile (10 mL in case of 1.29 mmol scale) and cesium carbonate (1.0 eq) and the corresponding nucleophile (1.0 eq) were added. Stirring was continued at 110° C. until TLC showed consumption of starting material. The solvent was removed under reduced pressure, followed by addition of water and dichloromethane. Afterwards, the phases were separated, the organic phase was dried and it was concentrated in vacuo. The crude was either used without further purification or purified as indicated in the examples.

General Procedure GP1.2

Sulfonamide A (e.g. 1.29 mmol) was dissolved in acetonitrile (15 mL in case of 1.29 mmol scale) and finely powdered potassium carbonate (3.0 eq) and the corresponding azole (1.5 eq) were added. Stirring was continued at 100-110° C. until TLC showed consumption of starting material. The solvent was removed under reduced pressure, followed by addition of water and dichloromethane. Afterwards, the phases were separated, the organic phase was dried and it was concentrated in vacuo. The crude was either used without further purification or purified as indicated in the examples.

General Procedure GP2.1

Crude nitro compound B (e.g. 1.29 mmol) was dissolved in dioxane (15 mL in case of 1.29 mmol scale) and tin(II) chloride dihydrate (3.0 eq) was added and the reaction mixture was stirred for 2 h at 70° C. After cooling to room temperature the reaction mixture was filtered and concentrated in vacuo. The filtrate was either used without further purification or purified as indicated in the examples.

General Procedure GP2.2

Crude nitro compound B (e.g. 1.29 mmol) was dissolved in dioxane (15 mL in case of 1.29 mmol scale) and tin(II) chloride dihydrate (5.0 eq) was added and the reaction mixture was stirred for 2 h at 70° C. After cooling to room temperature the reaction mixture was filtered and concentrated in vacuo. The filtrate was either used without further purification or purified as indicated in the examples.

General Procedure GP2.3

Crude nitro compound B (e.g. 1.29 mmol) was dissolved in methanol (15 mL in case of 1.29 mmol scale) and Pd/C (10% loading, 50 mg) was added. The flask was evacuated three times and flushed with hydrogen (1 bar) and stirring was continued at room temperature. After completion of the reaction, the mixture was filtered and concentrated in vacuo. The crude was used without further purification.

General Procedure GP2.4

Crude nitro compound B (e.g. 1.29 mmol) was dissolved in methanol/dioxane (15 mL in case of 1.29 mmol scale) and Pd/C (10% loading, 50 mg) was added. The flask was evacuated three times and flushed with hydrogen (1 bar) and stirring was continued at room temperature. After completion of the reaction, the mixture was filtered and concentrated in vacuo. The crude was used without further purification.

General Procedure GP2.5

Crude nitro compound B (e.g. 1.29 mmol) was dissolved in methanol/dioxane (15 mL in case of 1.29 mmol scale) and Pt/C (10% loading, 50 mg) was added. The flask was evacuated three times and flushed with hydrogen (1 bar) and stirring was continued at room temperature. After completion of the reaction, the mixture was filtered and concentrated in vacuo. The crude was used without further purification.

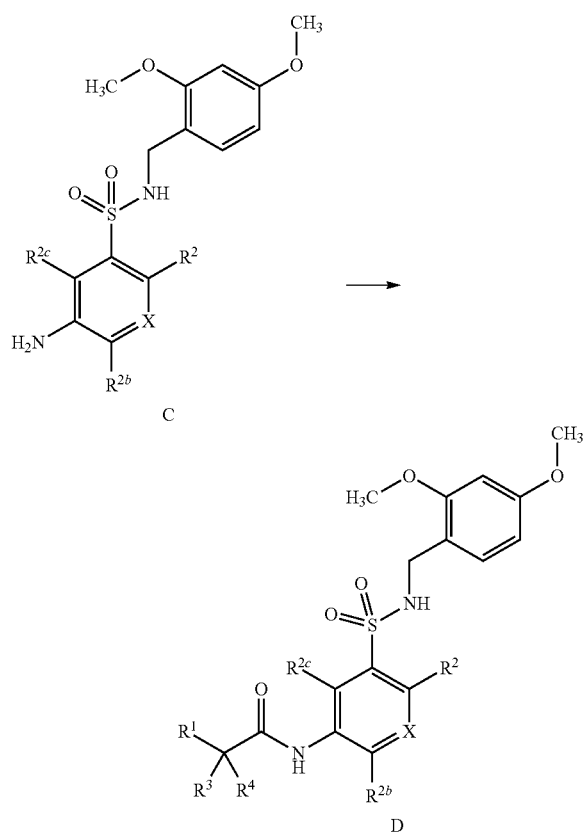

C

D

General Procedure GP3.1

Crude substituted aniline C (e.g. 1.29 mmol) was dissolved in dimethylformamide (6 mL in case of 1.29 mmol scale) followed by the addition of the corresponding acid (amount as indicated in examples), N,N-diisopropylethylamine (4.5 eq based on acid) and HATU (1.5 eq based on acid). The reaction mixture was either stirred overnight at room temperature or heated at 50° C. until TLC showed consumption of starting material. After cooling to room temperature the reaction mixture was concentrated in vacuo. Ethyl acetate and water were added, the organic phase was dried and concentrated in vacuo. The crude was used without further purification.

General Procedure GP3.2

Crude substituted aniline C (1.29 mmol) was dissolved in dimethylformamide (10 mL in case of 1.29 mmol scale) followed by the addition of the corresponding acid (amount as indicated in examples), N,N-diisopropylethylamine (2.7 eq based on acid) and HATU (1.0 eq based on acid). The reaction mixture was either stirred overnight at room temperature or heated at 50° C. until TLC showed consumption of starting material. After cooling to room temperature the reaction mixture was concentrated in vacuo. Ethyl acetate and water were added, the organic phase was dried and concentrated in vacuo. The crude was used without further purification.

General Procedure GP3.3

Crude substituted aniline C (1.29 mmol) was dissolved in dimethylformamide (10 mL in case of 1.29 mmol scale) followed by the addition of the corresponding acid (amount as indicated in examples), N,N-diisopropylethylamine (2.7 eq based on acid) and HATU (1.0 eq based on acid). The reaction mixture was either stirred overnight at room temperature or heated at 50° C. until TLC showed consumption of starting material. After cooling to room temperature the reaction mixture was concentrated in vacuo. Ethyl acetate and water were added, the organic phase was dried and concentrated in vacuo. The crude was used without further purification.

General Procedure GP3.4

Crude substituted aniline C (1.29 mmol) was dissolved in dimethylformamide (10 mL in case of 1.29 mmol scale) followed by the addition of the corresponding acid (amount as indicated in examples), N,N-diisopropylethylamine (2.0 eq based on acid) and HATU (1.0 eq based on acid). The reaction mixture was either stirred overnight at room temperature or heated at 50° C. until TLC showed consumption of starting material. After cooling to room temperature the reaction mixture was concentrated in vacuo. Ethyl acetate and water were added, the organic phase was dried and concentrated in vacuo. The crude was used without further purification.

General Procedure GP3.5

Crude substituted aniline C (1.29 mmol) was dissolved in dimethylformamide (10 mL in case of 1.29 mmol scale) followed by the addition of the corresponding acid (amount as indicated in examples), N,N-diisopropylethylamine (4.0 eq based on acid) and HATU (1.3 eq based on acid). The reaction mixture was either stirred overnight at room temperature or heated at 50° C. until TLC showed consumption of starting material. After cooling to room temperature the reaction mixture was concentrated in vacuo. Ethyl acetate and water were added, the organic phase was dried and concentrated in vacuo. The crude was used without further purification.

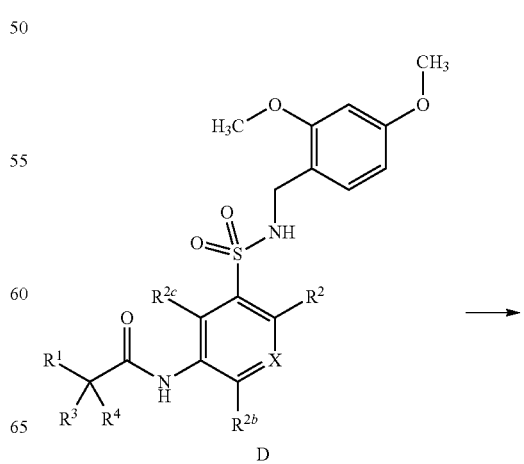

D

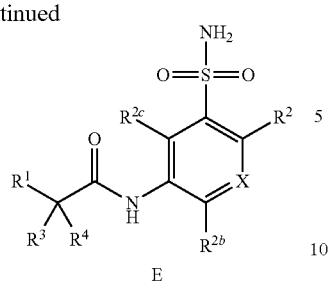

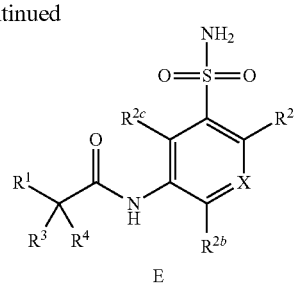

General Procedure GP4.1

Crude amide D (e.g. 1.29 mmol) was dissolved in dichloromethane (5-10 mL in case of 1.29 mmol scale), trifluoroacetic acid (50 eq) was added and the reaction mixture was stirred at room temperature until TLC showed consumption of starting material. The reaction mixture was concentrated in vacuo, ethyl acetate and water were added to the crude and the organic phase was dried and the solvent was removed under reduced pressure. The resulting residue was purified as indicated in the examples. Purification without aqueous extraction was also possible but made the HPLC purification more difficult.

General Procedure GP4.2

Crude amide D (e.g. 1.29 mmol) was dissolved in dichloromethane/trifluoroacetic acid 2/1 (6 mL in case of 1.29 mmol scale) and the reaction mixture was stirred at room temperature until TLC showed consumption of starting material. The reaction mixture was concentrated in vacuo, ethyl acetate and water were added to the crude and the organic phase was dried and the solvent was removed under reduced pressure. The resulting residue was purified as indicated in the examples. Purification without aqueous extraction was also possible but made the HPLC purification more difficult.

General Procedure GP4.3

Crude amide D (e.g. 1.29 mmol) was dissolved in dichloromethane/trifluoroacetic acid 1/1 (6 mL in case of 1.29 mmol scale) and the reaction mixture was stirred at room temperature until TLC showed consumption of starting material. The reaction mixture was concentrated in vacuo, ethyl acetate and water were added to the crude and the organic phase was dried and the solvent was removed under reduced pressure. The resulting residue was purified as indicated in the examples. Purification without aqueous extraction was also possible but made the HPLC purification more difficult.

General Procedure GP5.1

Solutions of substituted aniline C (0.20 mmol in 0.4 mL 1-methyl-2-pyrrolidon), the corresponding acid (0.40 mmol in 0.8 mL 1-methyl-2-pyrrolidon), HATU (0.40 mmol in 0.8 mL 1-methyl-2-pyrrolidon), N-methylmorpholine (0.80 mmol in 0.267 mL 1-methyl-2-pyrrolidon, containing 2.5% 4-dimethylaminopyridine) were added and shaken overnight. Then, it was concentrated in vacuo and the residue was redissolved in trifluoroacetic acid/dichloromethane 3/1 (2 mL, containing 5% water). The reaction mixture was again shaken overnight, followed by concentration in vacuo and purification by HPLC.

General Procedure GP5.2

Solutions of substituted aniline C (0.20 mmol in 0.8 mL 1,2-dichloroethane) and HATU (0.40 mmol in 0.8 mL 1,2-dichloroethane) were combined and the corresponding acid (0.40 mmol) and N,N-diisopropylethylamine (103 mg, 0.80 mmol) were added, followed by shaking overnight. Then, it was concentrated in vacuo and the residue was redissolved in trifluoroacetic acid (1 mL, containing 5% water). The reaction mixture was again shaken overnight, followed by concentration in vacuo and purification by HPLC.

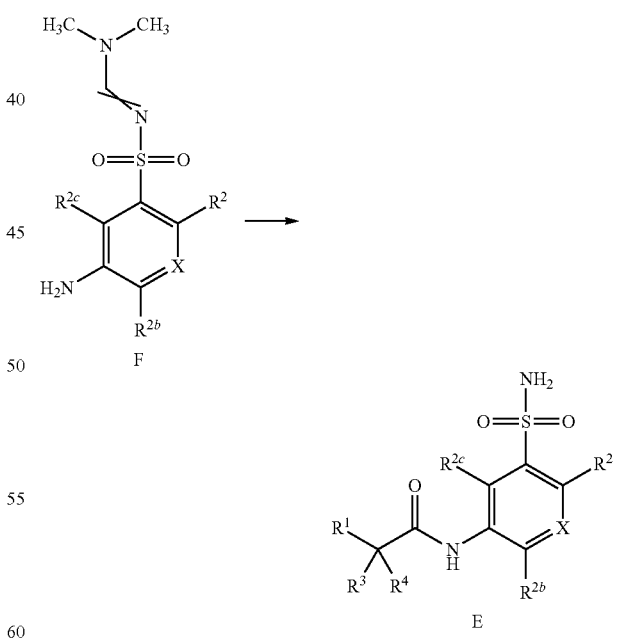

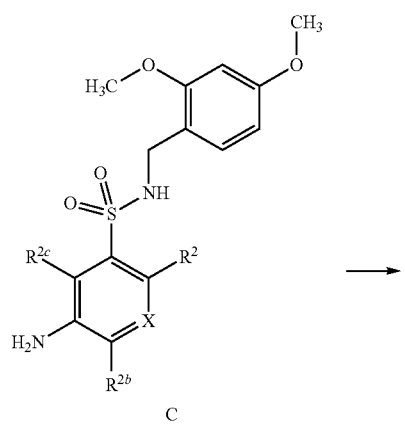

General Procedure GP6.1

Crude substituted aniline F (0.137 mmol) was dissolved in dimethylformamide (2 mL in case of 0.137 mmol scale) followed by the addition of the corresponding acid (amount as indicated in examples), N,N-diisopropylethylamine (2.7 eq based on acid) and HATU (1.0 eq based on acid). The reaction mixture was stirred overnight at room temperature followed by concentration in vacuo. Ethyl acetate and water were added, the organic phase was dried and concentrated in vacuo.

The crude was redissolved in methanol (1 mL), treated with concentrated aqueous ammonia (70 μL) and stirred overnight. The reaction mixture was concentrated in vacuo and purified as indicated in the examples.

General Procedure GP6.2

Crude substituted aniline F (amount as indicated in examples) in NMP (0.4 mL) was added to the corresponding acid (2 eq), followed by HATU (2 eq) in NMP (0.8 mL) and N-methylmorpholine (4 eq) in NMP (0.27 mL, containing 2.5% 4-dimethylaminopyridine). The reaction mixture was shaken overnight. Then, methanol (1 mL) and aqueous concentrated ammonia (2 mL) were added, followed by shaking at room temperature for 4 days. Purification by HPLC provided the desired compound E.

General Procedure GP6.3

Crude substituted aniline F (0.137 mmol) was dissolved in dimethylformamide (2 mL in case of 0.137 mmol scale) followed by the addition of the corresponding acid (amount as indicated in examples), N,N-diisopropylethylamine (2.0 eq based on acid) and HATU (1.0 eq based on acid). The reaction mixture was stirred overnight at room temperature followed by concentration in vacuo. Ethyl acetate and water were added, the organic phase was dried and concentrated in vacuo.

The crude was redissolved in methanol (2 mL), treated with concentrated aqueous ammonia (1 mL) and stirred overnight. The reaction mixture was concentrated in vacuo and purified as indicated in the examples.

General Procedure GP6.4

Crude substituted aniline F (0.137 mmol) was dissolved in dimethylformamide (2 mL in case of 0.137 mmol scale) followed by the addition of the corresponding acid (amount as indicated in examples), N,N-diisopropylethylamine (1.5 eq based on acid) and HATU (1.0 eq based on acid). The reaction mixture was stirred overnight at room temperature followed by concentration in vacuo. Dichloromethane and water were added, the organic phase was dried and concentrated in vacuo.

The crude was redissolved in methanol (2 mL), treated with concentrated aqueous ammonia (1 mL) and stirred overnight. The reaction mixture was concentrated in vacuo and purified as indicated in the examples.

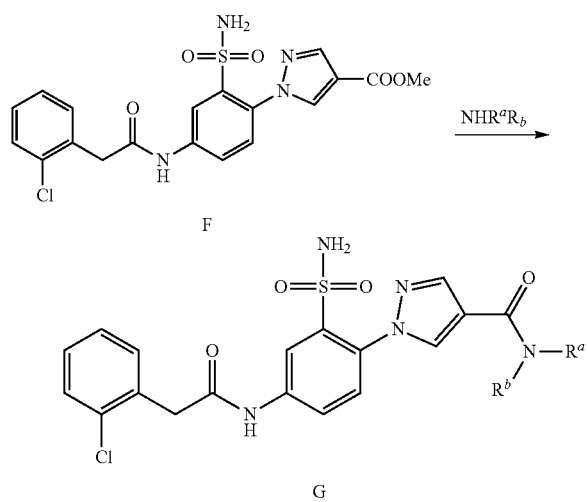

General Procedure GP7.1

Methyl 1-(4-{[(2-chlorophenyl)acetyl]amino}-2-sulfamoylphenyl)-1H-pyrazole-4-carboxylate (amount as indicated in examples) was dissolved in THF (2 mL in case of 0.22 mmol scale) and the vial was flushed with argon. The corresponding amine (2.5 eq) was added, followed by addition of bis(trimethylaluminum)-1,4-diazabicyclo[2.2.2]-octane (DABAL-Me$_3$, 3 eq). The reaction mixture was stirred overnight at room temperature, quenched with 1 M HCl and extracted with ethylacetate. The organic phases were washed with brine solution, dried over sodium sulfate, concentrated in vacuo and purified as indicated in the examples.

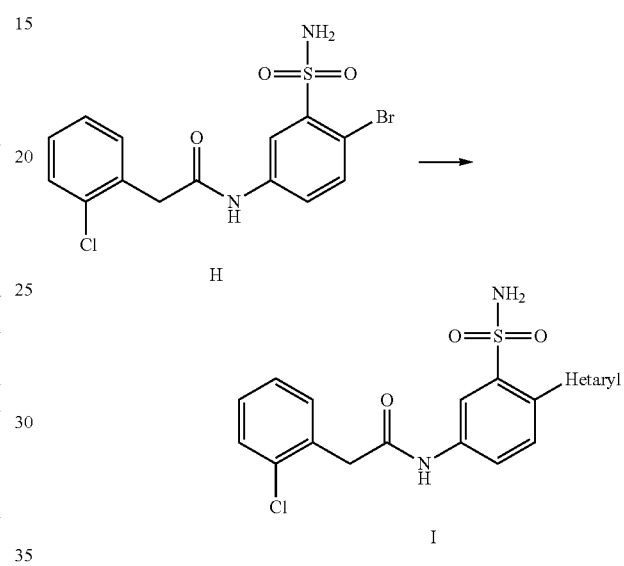

General Procedure GP8.1

N-(4-Bromo-3-{[(dimethylamino)methylene]sulfamoyl}phenyl)-2-(2-chlorophenyl)acetamide (amount as indicated in examples) was dissolved in methanol (1.5 mL in case of 0.33 mmol scale) and degassed with nitrogen. Bis(pinacolato)diboron (2.5 eq), mesylate[(di(1-adamantyl)-n-butylphosphine)-2-(2'-amino-1,1'-biphenyl)]palladium(II) (cataCXium® A Pd G3, 0.05 eq) and N,N-diisoproylethylamine (2.5 eq) were added and it was stirred for 1 hour at 50° C. The catalyst was removed by filtration and the filtrate was reduced in vacuo.

The crude was redissolved in n-propanol (1.5 mL in case of 0.33 mmol scale), followed by degassing with nitrogen. The corresponding hetarylbromide (2 eq), potassium fluoride (0.23 eq), bis(tri-tert-butylphosphine)palladium(0) (0.05 eq) and triphenylphosphine (0.05 eq) were added. It was again degassed with nitrogen and potassium phosphate (2.5 eq) was added, followed by irradiating for 1 hour at 100° C. in the microwave. The reaction mixture was concentrated in vacuo and extracted with water/dichloromethane. The organic phases were washed with brine solution, dried over sodium sulfate, concentrated in vacuo and purified as indicated in the examples.

General Procedure GP8.2

N-(4-Bromo-3-{[(dimethylamino)methylene]sulfamoyl}phenyl)-2-(2-chlorophenyl)acetamide (amount as indicated in examples) was dissolved in methanol (3 mL in case of 0.59 mmol scale) and degassed with nitrogen. Bis(pinacolato)diboron (2.5 eq), mesylate[(di(1-adamantyl)-n-butylphosphine)-2-(2'-amino-1,1'-biphenyl)]palladium(II) (cataCXium® A Pd G3, 0.05 eq) and N,N-diisoproylethylamine (2.5 eq) were added and it was stirred for 1 hour at 50° C. The catalyst was removed by filtration and the filtrate was reduced in vacuo.

The crude was redissolved in n-propanol (3 mL in case of 0.59 mmol scale), followed by degassing with nitrogen. The corresponding hetarylbromide (2 eq), potassium fluoride (0.23 eq), bis(tri-tert-butylphosphine)palladium(0) (0.05 eq) and triphenylphosphine (0.05 eq) were added. It was again degassed with nitrogen and potassium phosphate (2.5 eq) was added, followed by irradiating for 1 hour at 100° C. in the microwave.

Any precipitate was removed by filtration and the filtrate was concentrated in vacuo and redissolved in methanol (2 mL in case of 0.59 mmol scale). Aqueous ammonium hydroxide solution (33%, 2 mL) was added. It was stirred until UPLC-MS showed completion of deprotection. In most cases stirring overnight was sufficient, in certain cases longer stirring and addition of further aqueous ammonium hydroxide solution was necessary. The reaction mixture was then concentrated in vacuo and purified as indicated in the examples.

SYNTHESIS OF INTERMEDIATES

Intermediate 1

2-Chloro-N-(2,4-dimethoxybenzyl)-5-nitrobenzene-sulfonamide

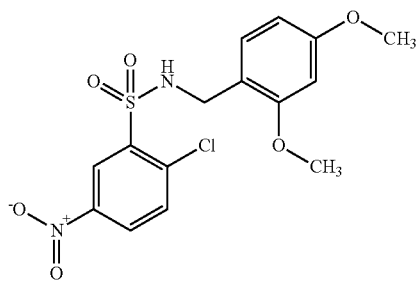

To a solution of 2-chloro-5-nitrobenzenesulfonylchloride (10.8 g, 42.2 mmol) in dichloromethane (108 mL) was added sodium bicarbonate (7.09 g, 84.4 mmol) and 1-(2,4-dimethoxyphenyl)methanamine (7.05 g, 42.2 mmol). The mixture was stirred overnight. The reaction mixture was concentrated in vacuo, followed by addition of water (75 mL) and ethyl acetate (75 mL). After stirring for 10 min the resulting precipitate was separated by filtration and it was dried at 40° C. overnight in vacuo to yield the title compound (14.1 g, 36.5 mmol, 86% yield).

LC-MS (Method A): Rt=1.17 min; MS (ESIneg): m/z=385 [M−H]⁻

$^1$H-NMR (400 MHz, DMSO-d6) δ [ppm]: 3.56 (s, 3H), 3.61 (s, 3H), 4.08 (s, 2H), 6.10 (d, 1H), 6.26 (dd, 1H), 7.04 (d, 1H), 7.79 (d, 1H), 8.19 (d, 1H), 8.28 (dd, 1H), 8.45 (s, 1H).

Intermediate 2

N-(2,4-Dimethoxybenzyl)-2-fluoro-5-nitrobenzene-sulfonamide

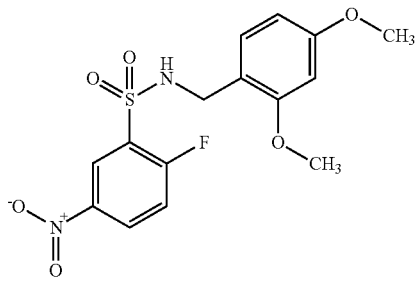

To a solution of 1-(2,4-dimethoxyphenyl)methanamine (0.669 g, 4.00 mmol) in dichloromethane (40 mL) was added under ice cooling N-ethyl-N-isopropylpropan-2-amine (1.29 g, 10.0 mmol). Over 25 min a solution of 2-fluoro-5-nitrobenzenesulfonyl chloride (0.958 g, 4.00 mmol) in dichloromethane (10 mL) was slowly added. Stirring was continued under ice cooling for 2 h, followed by stirring at room temperature overnight. It was washed with water, dried over sodium sulfate and concentrated in vacuo. Column chromatography on a Biotage Isolera system (silica gel, gradient n-hexane/ethyl acetate) gave the title compound (400 mg, 1.08 mmol, 27% yield, purity 70%).

LC-MS (Method A): Rt=1.12 min; MS (ESIneg): m/z=369 [M−H]⁻

Intermediate 3

N-(2,4-Dimethoxybenzyl)-5-nitro-2-[4-(trifluoromethyl)-1H-pyrazol-1-yl]benzenesulfonamide

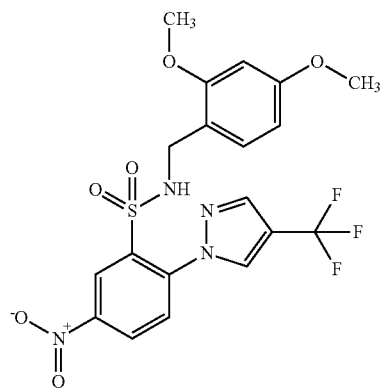

To a solution of 2-chloro-N-(2,4-dimethoxybenzyl)-5-nitrobenzenesulfonamide (5.69 g, 14.7 mmol) in acetonitrile (170 mL) were added 4-(trifluoromethyl)-1H-pyrazole (3.00 g, 22.1 mmol) and powdered potassium carbonate (6.09 g, 44.1 mmol) and it was stirred overnight at 100° C. The reaction mixture was concentrated in vacuo and the residue was extracted with dichloromethane and water. The organic phase was washed with brine and dried over sodium sulfate. Concentration under reduced pressure led to the crude title compound (7.50 g, quant., app. 95% purity) that was used without further purification in the next step.

LC-MS (Method B): Rt=1.31 min; MS (ESIpos): m/z=487 [M+H]$^+$ $^1$H-NMR (400 MHz, DMSO-d$_6$) δ [ppm]: 3.52 (s, 3H), 3.64 (s, 3H), 4.15 (d, 2H), 6.18 (d, 1H), 6.29 (dd, 1H), 7.08 (d, 1H), 7.93 (d, 1H), 8.03-8.09 (m, 1H), 8.25 (d, 1H), 8.39 (s, 1H), 8.49 (dd, 1H), 8.94 (s, 1H).

Intermediate 4

2-(4-Chloro-1H-pyrazol-1-yl)-N-(2,4-dimethoxybenzyl)-5-nitrobenzenesulfonamide

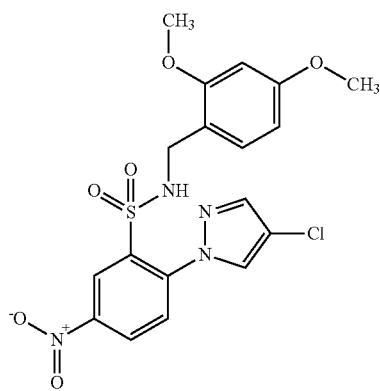

To a solution of 2-chloro-N-(2,4-dimethoxybenzyl)-5-nitrobenzenesulfonamide (5.03 g, 13.0 mmol) in acetonitrile (150 mL) were added 4-chloro-1H-pyrazole (2.00 g, 19.5 mmol) and powdered potassium carbonate (5.39 g, 39.0 mmol) and it was stirred overnight at 100° C. The reaction mixture was concentrated in vacuo and the residue was extracted with dichloromethane and water. The organic phase was washed with brine and dried. Concentration in vacuo led to the crude title compound (6.27 g, quant., app. 95% purity) that was used without further purification in the next step.

LC-MS (Method A): Rt=1.26 min; MS (ESIpos): m/z=453 [M+H]$^+$ $^1$H-NMR (400 MHz, DMSO-d$_6$) δ [ppm]: 3.48 (s, 3H), 3.62 (s, 3H), 4.15 (s, 2H), 6.14 (d, 1H), 6.27 (dd, 1H), 7.08 (d, 1H), 7.84 (d, 1H), 8.05 (s, 1H), 8.09 (d, 1H), 8.21 (d, 1H), 8.45 (dd, 1H), 8.57 (s, 1H).

Intermediate 5

N-(2,4-Dimethoxybenzyl)-2-(4-fluoro-1H-pyrazol-1-yl)-5-nitrobenzenesulfonamide

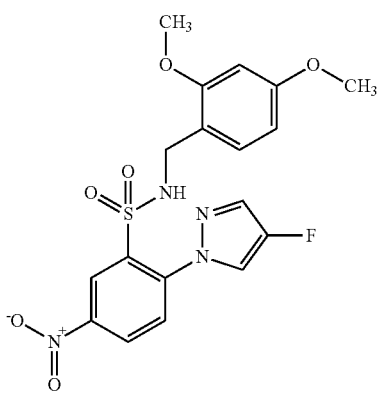

To a solution of 2-chloro-N-(2,4-dimethoxybenzyl)-5-nitrobenzenesulfonamide (5.00 g, 11.6 mmol) in acetonitrile (135 mL) were added 4-fluoro-1H-pyrazole (1.50 g, 17.4 mmol) and powdered potassium carbonate (4.82 g, 34.9 mmol) and it was stirred overnight at 100° C. The reaction mixture was concentrated in vacuo and the residue was extracted with dichloromethane and water. The organic phase was washed with brine and dried over sodium sulfate. Concentration in vacuo led to the crude title compound (5.54 g, quant., app. 85% purity) that was used without further purification in the next step.

LC-MS (Method A): Rt=1.23 min; MS (ESIpos): m/z=437 [M+H]$^+$ $^1$H-NMR (400 MHz, DMSO-d$_6$) δ [ppm]: 3.48 (s, 3H), 3.62 (s, 3H), 4.13 (s, 2H), 6.15 (d, 1H), 6.28 (dd, 1H), 7.09 (d, 1H), 7.81 (d, 1H), 8.00-8.10 (m, 2H), 8.23 (d, 1H), 8.43 (dd, 1H), 8.59 (s, 1H).

Intermediate 6

2-(4-Bromo-1H-pyrazol-1-yl)-N-(2,4-dimethoxybenzyl)-5-nitrobenzenesulfonamide

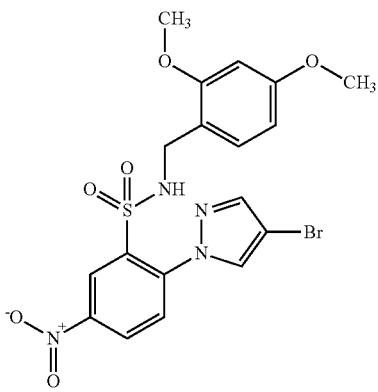

To a solution of 2-chloro-N-(2,4-dimethoxybenzyl)-5-nitrobenzenesulfonamide (1.75 g, 4.54 mmol) in acetonitrile (53 mL) were added 4-bromo-1H-pyrazole (1.00 g, 6.80 mmol) and powdered potassium carbonate (1.88 g, 13.6 mmol) and it was stirred overnight at 100° C. The reaction mixture was concentrated in vacuo and the residue was extracted with dichloromethane and water. The organic phase was washed with brine and dried over sodium sulfate. Concentration in vacuo led to the crude title compound (2.38 g, quant., app. 95% purity) that was used without further purification in the next step.

LC-MS (Method A): Rt=1.29 min; MS (ESIpos): m/z=497 [M+H]$^+$ $^1$H-NMR (400 MHz, DMSO-d$_6$) δ [ppm]: 3.48 (s, 3H), 3.62 (s, 3H), 4.13 (s, 2H), 6.15 (d, 1H), 6.28 (dd, 1H), 7.09 (d, 1H), 7.84 (d, 1H), 8.00-8.10 (m, 2H), 8.23 (s, 1H), 8.43 (dd, 1H), 8.65 (s, 1H).

Intermediate 7

N-(2,4-Dimethoxybenzyl)-5-nitro-2-[3-(trifluoromethyl)-1H-1,2,4-triazol-1-yl]benzenesulfonamide

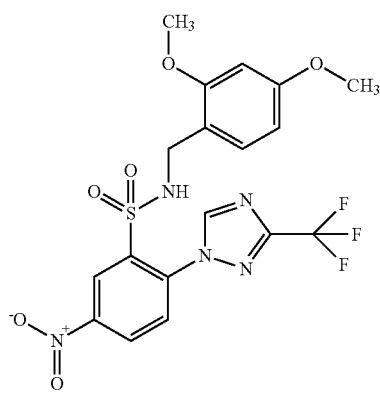

To a solution of 2-chloro-N-(2,4-dimethoxybenzyl)-5-nitrobenzenesulfonamide (2.00 g, 5.17 mmol) in acetonitrile (60 mL) were added 3-(trifluoromethyl)-1H-1,2,4-triazole (1.06 g, 7.76 mmol) and powdered potassium carbonate (2.14 g, 15.5 mmol) and it was stirred overnight at 100° C. The reaction mixture was concentrated in vacuo and the residue was extracted with dichloromethane and water. The organic phase was washed with brine and dried over sodium sulfate. Concentration in vacuo led to the crude title compound (2.33 g, 79% yield., app. 85% purity) that was used without further purification in the next step.

LC-MS (Method A): Rt=1.26 min; MS (ESIpos): m/z=488 [M+H]$^+$ $^1$H-NMR (400 MHz, DMSO-d$_6$) δ [ppm]: 3.59 (s, 3H), 3.66 (s, 3H), 4.06 (s, 2H), 6.26 (d, 1H), 6.31 (dd, 1H), 7.02 (d, 1H), 8.02 (d, 1H), 8.36 (s, 1H), 8.40 (d, 1H), 8.55 (dd, 1H), 9.21 (s, 1H).

Intermediate 8

2-[3-(Difluoromethyl)-1H-1,2,4-triazol-1-yl]-N-(2,4-dimethoxybenzyl)-5-nitrobenzenesulfonamide

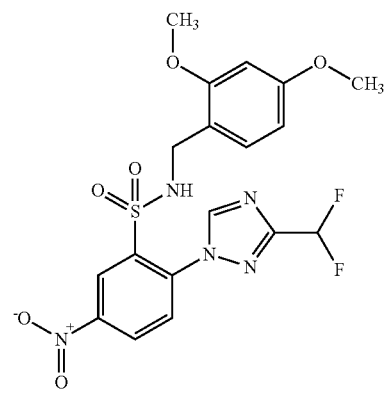

To a solution of 2-chloro-N-(2,4-dimethoxybenzyl)-5-nitrobenzenesulfonamide (550 mg, 1.42 mmol) in acetonitrile (15 mL) were added 3-(difluoromethyl)-1H-1,2,4-triazole (254 mg, 2.13 mmol) and powdered potassium carbonate (589 mg, 4.27 mmol) and it was irradiated for one hour at 120° C. in the microwave. The reaction mixture was concentrated in vacuo and the residue was extracted with dichloromethane and water. The aqueous phase was washed three times with dichloromethane. Then the combined organic phases were washed with brine and dried using a Whatman filter. Concentration under reduced pressure led to the title compound that was purified by flash chromatography (504 mg, 1.07 mmol, 76% yield, 95% purity).

LC-MS (Method A): Rt=1.12 min; MS (ESIpos): m/z=470 [M+H]$^+$ $^1$H-NMR (400 MHz, DMSO-d$_6$) δ [ppm]: 3.56 (s, 3H), 3.65 (s, 3H), 4.11 (s, 2H), 6.22 (d, 1H), 6.30 (dd, 1H), 7.05 (d, 1H), 7.31 (t, 1H), 7.98 (d, 1H), 8.17-8.25 (m, 1H), 8.32 (d, 1H), 8.52 (dd, 1H), 9.12 (s, 1H).

Intermediate 9

2-(4-Cyano-1H-pyrazol-1-yl)-N-(2,4-dimethoxybenzyl)-5-nitrobenzenesulfonamide

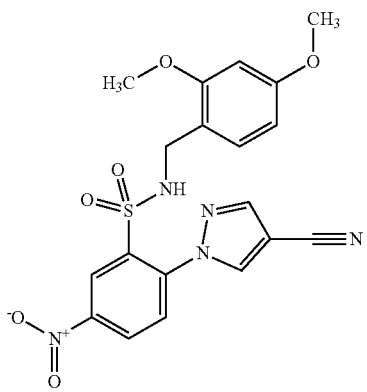

To a solution of 2-chloro-N-(2,4-dimethoxybenzyl)-5-nitrobenzenesulfonamide (15.0 g, 38.8 mmol) in acetonitrile (450 mL) were added 1H-pyrazole-4-carbonitrile (5.41 g, 93.1 mmol) and powdered potassium carbonate (16.1 g, 116 mmol) and it was stirred overnight at 100° C. The reaction mixture was concentrated in vacuo and the residue was extracted with ethyl acetate and water. Pure title compound precipitated and was filtered off (9.09 g 20.5 mmol, 53% yield, 97% purity), The organic phase was washed with brine and dried over sodium sulfate. Concentration in vacuo led to further crude title compound (9.11 g., app. 60% purity).

LC-MS (Method B): Rt=1.17 min; MS (ESIneg): m/z=442 [M−H]$^-$ $^1$H-NMR (400 MHz, DMSO-d$_6$) δ [ppm]: 3.53 (s, 3H), 3.64 (s, 3H), 4.08 (s, 2H), 6.20 (d, 1H), 6.29 (dd, 1H), 7.07 (d, 1H), 7.89 (d, 1H), 8.12 (br s, 1H), 8.30 (br s, 1H), 8.41-8.54 (m, 2H), 9.17 (br s, 1H).

Intermediate 10

5-Amino-N-(2,4-dimethoxybenzyl)-2-[4-(trifluoromethyl)-1H-pyrazol-1-yl]benzenesulfonamide

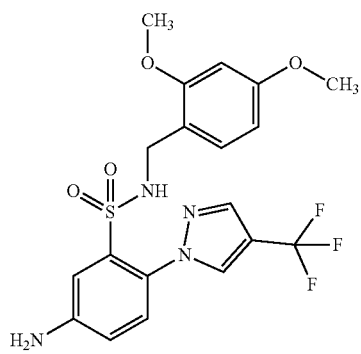 [SMILES: COc1ccc(CNS(=O)(=O)c2cc(N)ccc2-n2cc(C(F)(F)F)cn2)c(OC)c1]

Pd/C (10% loading, 750 mg) was added to a solution of N-(2,4-dimethoxybenzyl)-5-nitro-2-[4-(trifluoromethyl)-1H-pyrazol-1-yl]benzenesulfonamide (7.50 g, 14.7 mmol) in methanol (120 mL) and stirred under a hydrogen atmosphere for 4 h at room temperature. Some ethyl acetate was added to dissolve precipitated product, followed by filtration, washing and concentration in vacuo to give the crude title compound (6.50 g, quant., app. 95% purity) that was used without further purification in the next step.

LC-MS (Method A): Rt=1.20 min; MS (ESIpos): m/z=457 [M+H]$^+$ $^1$H-NMR (400 MHz, DMSO-d$_6$) δ [ppm]: 3.70 (s, 3H), 3.73 (s, 3H), 3.94 (d, 2H), 6.01 (s, 2H), 6.41-6.48 (m, 2H), 6.78 (dd, 1H), 7.09-7.14 (m, 2H), 7.18-7.27 (m, 2H), 8.12 (s, 1H), 8.56 (s, 1H).

Intermediate 11

5-Amino-2-(4-chloro-1H-pyrazol-1-yl)-N-(2,4-dimethoxybenzyl)benzenesulfonamide

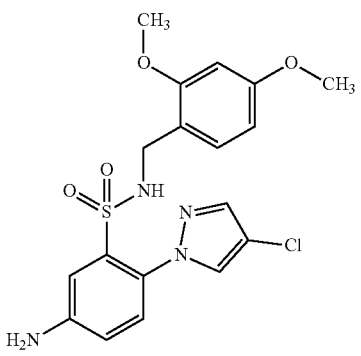

Pt/C (10% loading, 600 mg) was added to a solution of crude 2-(4-chloro-1H-pyrazol-1-yl)-N-(2,4-dimethoxybenzyl)-5-nitrobenzenesulfonamide (6.27 g, 13.9 mmol) in ethanol (100 mL) and stirred under a hydrogen atmosphere for 24 h at room temperature. The catalyst was filtered off, washed with ethyl acetate and the filtrate was concentrated in vacuo to give the crude title compound (5.99 g, quant., app. 90% purity) that was used without further purification in the next step.

LC-MS (Method A): Rt=1.23 min; MS (ESIpos): m/z=423 [M+H]$^+$ $^1$H-NMR (400 MHz, DMSO-d$_6$) δ [ppm]: 3.69 (s, 3H), 3.72 (s, 3H), 3.92 (d, 2H), 5.95 (s, 2H), 6.41-6.47 (m, 2H), 6.76 (dd, 1H), 7.08-7.12 (m, 2H), 7.15 (d, 1H), 7.19 (t, 1H), 7.78 (d, 1H), 8.15 (d, 1H).

Intermediate 12

5-Amino-N-(2,4-dimethoxybenzyl)-2-(4-fluoro-1H-pyrazol-1-yl)benzenesulfonamide

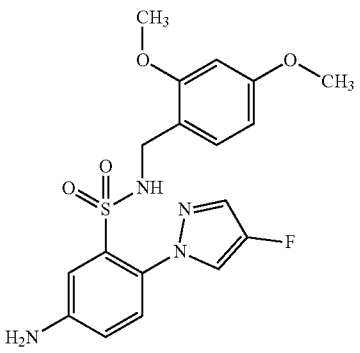

Pt/C (10% loading, 1.76 g) was added to a solution of crude N-(2,4-dimethoxybenzyl)-2-(4-fluoro-1H-pyrazol-1-yl)-5-nitrobenzenesulfonamide (5.50 g, 12.6 mmol) in a mixture of ethanol (125 mL) and dioxane (200 mL) and stirred under a hydrogen atmosphere for 8 h at room temperature. The catalyst was filtered off, washed with ethyl acetate and the filtrate was concentrated in vacuo to give the crude title compound (5.07 g, quant., app. 90% purity) that was used without further purification in the next step.

LC-MS (Method A): Rt=1.10 min

MS (ESIpos): m/z=407 [M+H]$^+$ $^1$H-NMR (400 MHz, DMSO-d$_6$) δ [ppm]: 3.69 (s, 3H), 3.72 (s, 3H), 3.92 (d, 2H), 5.93 (s, 2H), 6.42-6.47 (m, 2H), 6.78 (dd, 1H), 7.08-7.19 (m, 4H), 7.74 (dd, 1H), 8.07 (dd, 1H).

Intermediate 13

5-Amino-2-(4-bromo-1H-pyrazol-1-yl)-N-(2,4-dimethoxybenzyl)benzenesulfonamide

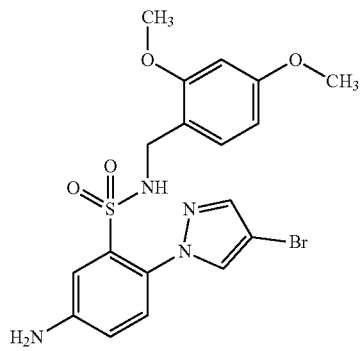 [SMILES: COc1ccc(CNS(=O)(=O)c2cc(N)ccc2-n2cc(F)cn2)c(OC)c1]

Pt/C (10% loading, 1.76 g) was added to a solution of crude 2-(4-bromo-1H-pyrazol-1-yl)-N-(2,4-dimethoxybenzyl)-5-nitrobenzenesulfonamide (5.60 g, 12.8 mmol) in ethanol (140 mL) and stirred under a hydrogen atmosphere for 14 h at room temperature. The catalyst was filtered off, washed with ethyl acetate and the filtrate was concentrated in vacuo to give the crude title compound (1.87 g, quant., app. 90% purity) that was used without further purification in the next step.

LC-MS (Method A): Rt=1.18 min; MS (ESIpos): m/z=467 (M+H)$^+$ $^1$H-NMR (400 MHz, DMSO-d$_6$) δ [ppm]: 3.69 (s, 3H), 3.72 (s, 3H), 3.92 (d, 2H), 5.95 (s, 2H), 6.39-6.48 (m, 2H), 6.77 (dd, 1H), 7.08-7.23 (m, 4H), 7.79 (d, 1H), 8.15 (d, 1H).

Intermediate 14

5-Amino-N-(2,4-dimethoxybenzyl)-2-[3-(trifluoromethyl)-1H-1,2,4-triazol-1-yl]-benzenesulfonamide

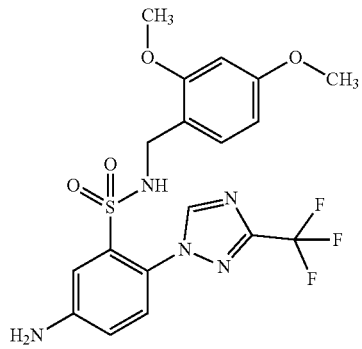 [SMILES: COc1ccc(CNS(=O)(=O)c2cc(N)ccc2-n2cnc(C(F)(F)F)n2)c(OC)c1]

Pd/C (10% loading, 170 mg) was added to a solution of crude N-(2,4-dimethoxybenzyl)-5-nitro-2-[3-(trifluoromethyl)-1H-1,2,4-triazol-1-yl]benzenesulfonamide (2.33 g, 4.78 mmol) in methanol (45 mL) and stirred under a hydrogen atmosphere overnight at room temperature.

The catalyst was filtered off, washed with ethyl acetate and the filtrate was concentrated in vacuo to give the crude title compound (2.04 g, quant., app. 95% purity) that was used without further purification in the next step.

LC-MS (Method A): Rt=1.13 min; MS (ESIpos): m/z=458 [M+H]$^+$ $^1$H-NMR (400 MHz, DMSO-d$_6$) δ [ppm]: 3.69 (s, 3H), 3.73 (s, 3H), 3.91 (s, 2H), 6.15 (s, 2H), 6.40-6.49 (m, 2H), 6.80 (dd, 1H), 7.09 (d, 1H), 7.14 (d, 1H), 7.28 (d, 1H), 7.56 (s, 1H), 8.91 (d, 1H).

Intermediate 15

2-(2-Chlorophenyl)-N-{4-[3-(difluoromethyl)-1H-1,2,4-triazol-1-yl]-3-[(2,4-dimethoxy-benzyl)sulfamoyl]phenyl}acetamide

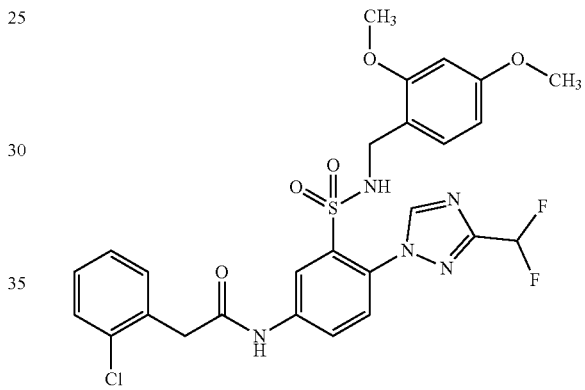

Pd/C (10% loading, 22 mg) was added to a solution of 2-[3-(difluoromethyl)-1H-1,2,4-triazol-1-yl]-N-(2,4-dimethoxybenzyl)-5-nitrobenzenesulfonamide (252 mg, 0.53 mmol) in methanol (3.5 mL) and tetrahydrofuran (1.5 mL) and stirred under a hydrogen atmosphere for 6 h at room temperature. The reaction mixture was filtered over Celite and concentrated in vacuo. The residue was redissolved in ethanol (5 mL), platinum/vanadium (55 mg, ½% on charcoal) was added and it was stirred for 3 h under a hydrogen atmosphere. The reaction mixture was filtered over Celite and concentrated in vacuo to give 213 mg crude 5-amino-2-[3-(difluoromethyl)-1H-1,2,4-triazol-1-yl]-N-(2,4-dimethoxy-benzyl)benzenesulfonamide that was used without further purification in the next step.

The crude material from the previous step (213 mg) was dissolved in dimethylformamide (5 mL) followed by the addition of (2-chlorophenyl)acetic acid (124 mg, 0.727 mmol), N,N-diisopropylethylamine (196 mg, 1.94 mmol) and HATU (276 mg, 0.727 mmol). The reaction mixture was stirred overnight at room temperature. It was then concentrated in vacuo and extracted with ethyl acetate and water. The aqueous phase was extracted three times with ethyl acetate. Then all organic phases were combined, washed with brine, dried using a Whatman filter and were concentrated in vacuo to give the title compound that was purified by preparative HPLC (112 mg, 0.189 mmol, 36% yield over 2 steps, 90% purity).

LC-MS (Method B): Rt=1.26 min; MS (ESIpos): m/z=592 [M+H]+

$^1$H-NMR (400 MHz, DMSO-d$_6$) δ [ppm] 3.63 (s, 3H), 3.68 (s, 3H), 3.92 (s, 2H), 3.99 (d, 2H), 6.33-6.39 (m, 2H), 7.06 (d, 1H), 7.21 (t, 1H), 7.30-7.38 (m, 2H), 7.44-7.51 (m, 2H), 7.60 (d, 1H), 7.68 (t, 1H), 7.95 (dd, 1H), 8.20 (d, 1H), 8.92 (s, 1H), 10.79 (s, 1H).

Intermediate 16

N-{4-[3-(Difluoromethyl)-1H-1,2,4-triazol-1-yl]-3-[(2,4-dimethoxybenzyl)sulfamoyl]-phenyl}-2-(2-fluorophenyl)acetamide

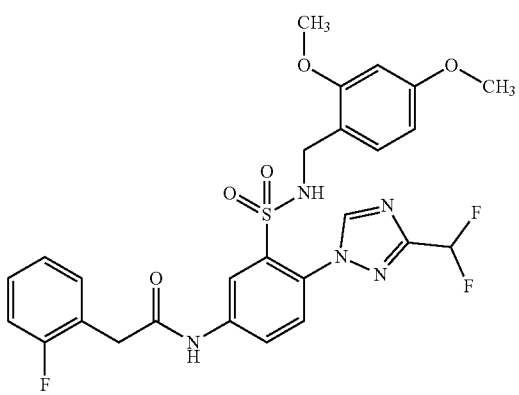 [SMILES: COc1ccc(CNS(=O)(=O)c2cc(NC(=O)Cc3ccccc3F)ccc2-n2cnc(C(F)F)n2)c(OC)c1]

Pd/C (10% loading, 22 mg) was added to a solution of 2-[3-(difluoromethyl)-1H-1,2,4-triazol-1-yl]-N-(2,4-dimethoxybenzyl)-5-nitrobenzenesulfonamide (252 mg, 0.53 mmol) in methanol (3.5 mL) and tetrahydrofuran (1.5 mL) and stirred under a hydrogen atmosphere for 6 h at room temperature. The reaction mixture was filtered over Celite and concentrated in vacuo. The residue was redissolved in ethanol (5 mL), platinum/vanadium (55 mg, ½% on charcoal) was added and it was stirred for 3 h under a hydrogen atmosphere. The reaction mixture was filtered over Celite and concentrated in vacuo to give 213 mg crude 5-amino-2-[3-(difluoromethyl)-1H-1,2,4-triazol-1-yl]-N-(2,4-dimethoxy-benzyl)benzenesulfonamide that was used without further purification in the next step.

The crude material from the previous step (213 mg) was dissolved in dimethylformamide (5 mL) followed by the addition of (2-fluorophenyl)acetic acid (112 mg, 0.727 mmol), N,N-diisopropylethylamine (196 mg, 1.94 mmol) and HATU (276 mg, 0.727 mmol). The reaction mixture was stirred overnight at room temperature. It was then concentrated in vacuo and extracted with ethyl acetate and water. The aqueous phase was extracted three times with ethyl acetate. Then all organic phases were combined, washed with brine, dried using a Whatman filter and were concentrated in vacuo to give the title compound that was purified by preparative HPLC (94 mg, 0.163 mmol, 31% yield over 2 steps, 90% purity).

LC-MS (Method B): Rt=1.21 min, MS (ESIpos): m/z=576 [M+H]+

$^1$H-NMR (400 MHz, DMSO-d$_6$) δ [ppm] 3.62 (s, 3H), 3.67 (s, 3H), 3.82 (s, 2H), 3.99 (d, 2H), 6.33-6.37 (m, 2H), 7.07 (d, 1H), 7.17-7.24 (m, 2H), 7.21 (t, 1H), 7.31-7.38 (m, 1H), 7.40-7.46 (m, 1H), 7.60 (d, 1H), 7.67 (t, 1H), 7.94 (dd, 1H), 8.18 (d, 1H), 8.92 (s, 1H), 10.76 (s, 1H).

Intermediate 17

2-Chloro-N-[(dimethylamino)methylene]-5-nitrobenzenesulfonamide

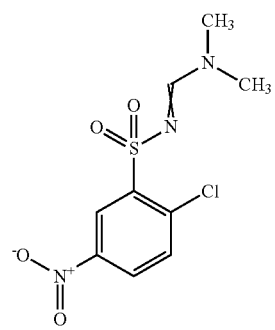

1,1-Dimethoxy-N,N-dimethylmethanamine (3.02 g, 25.4 mmol) was added to a solution of 2-chloro-5-nitrobenzenesulfonamide (3.00 g, 12.7 mmol) in N,N-dimethylformamide (43 mL) and was stirred at room temperature for 2 days. The reaction mixture was concentrated in vacuo and the residue was extracted with dichloromethane/water. The organic phase was washed with brine and dried. Concentration in vacuo gave the crude title compound (4.18 g, quant., app. 90% purity) that was used without further purification in the next step.

LC-MS (Method A): Rt=0.86 min; MS (ESIpos): m/z=292 [M+H]+

$^1$H-NMR (400 MHz, DMSO-d$_6$) δ [ppm] 2.94-2.96 (m, 3H), 3.20 (s, 3H), 7.91 (d, 1H), 8.31-8.33 (m, 1H), 8.39 (dd, 1H), 8.69 (d, 1H).

Intermediate 18

N-[(Dimethylamino)methylene]-5-nitro-2-[5-(trifluoromethyl)pyridin-3-yl]benzenesulfonamide

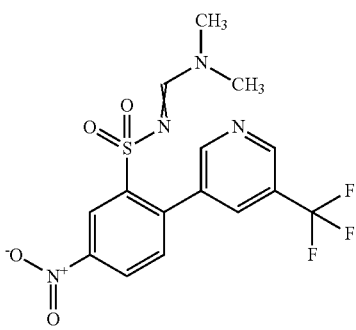

2-Chloro-N-[(dimethylamino)methylene]-5-nitrobenzenesulfonamide (1.10 g, 3.77 mmol) was dissolved in degassed n-propanol (33 mL) and treated with [5-(trifluoromethyl)pyridin-3-yl]boronic acid (1.08 g, 5.68 mmol), bis(triphenylphosphine)palladium(II) dichloride (132 mg, 0.189 mmol) and triphenylphosphine (49.5 mg, 0.189 mmol). Aqueous degassed 2M potassium carbonate solution (5.65 mL) was added, the vial was sealed and stirred for 16 hours at 100° C. After cooling to room temperature water was added and it was extracted three times with ethyl acetate followed by concentration in vacuo.

The partly deprotected target molecule was reprotected as previously described by stirring at room temperature with 1,1-dimethoxy-N,N-dimethylmethanamine in NDMF. The reaction mixture was concentrated in vacuo and the residue was purified by preparative HPLC (Chromatorex C-18 10 μm, 125×30 mm, acetonitrile/water+0.1% aqueous ammonia (32%)) to give the title compound (174 mg, 0.432 mmol, 11% yield, 95% purity).

LC-MS (Method B): Rt=1.08 min; MS (ESIpos): m/z=403 [M+H]$^+$ $^1$H-NMR (400 MHz, DMSO-d$_6$) δ [ppm] 2.76 (s, 3H), 2.99 (s, 3H), 7.76 (s, 1H), 7.81 (d, 1H), 8.33-8.36 (m, 1H), 8.52 (dd, 1H), 8.76 (d, 1H), 8.88 (d, 1H), 9.09 (dd, 1H).

Intermediate 19

5-Amino-N-[(dimethylamino)methylene]-2-[5-(trifluoromethyl)pyridin-3-yl]benzenesulfonamide

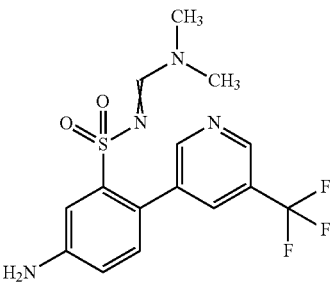 [SMILES: CN(C)C=NS(=O)(=O)c1cc(N)ccc1-c1cncc(C(F)(F)F)c1]

Pd/C (10% loading, 21 mg) was added to a solution of N-[(dimethylamino)methylene]-5-nitro-2-[5-(trifluoromethyl)pyridin-3-yl]benzenesulfonamide (174 mg, 0.39 mmol) in a mixture of methanol (10 mL) and dioxane (10 mL) and stirred under a hydrogen atmosphere overnight at room temperature. The catalyst was filtered off, washed with ethyl acetate and the filtrate was concentrated in vacuo to give the title compound (140 mg, quant., 95% purity) that was used without further purification in the next step.

LC-MS (Method A): Rt=0.90 min; MS (ESIpos): m/z=373 [M+H]$^+$

Intermediate 20

2-[1-(Difluoromethyl)-1H-pyrazol-4-yl]-N-[(dimethylamino)methylene]-5-nitrobenzenesulfonamide

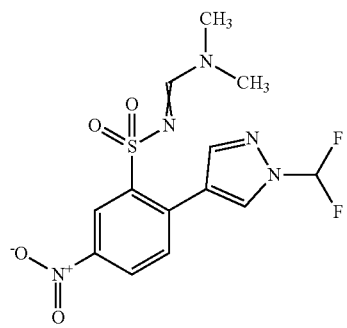

2-Chloro-N-[(dimethylamino)methylene]-5-nitrobenzenesulfonamide (1.00 g, 3.43 mmol) was dissolved in degassed n-propanol (30 mL) and treated with 1-(difluoromethyl)-4-(4,4,5,5-tetramethyl-1,3,2-dioxaborolan-2-yl)-1H-pyrazole (1.25 g, 5.14 mmol), bis(triphenylphosphine)palladium(II) dichloride (121 mg, 0.171 mmol) and triphenylphosphine (45.0 mg, 0.171 mmol). Aqueous degassed 2M potassium carbonate solution (5.14 mL) was added, the vial was sealed and stirred for 16 hours at 100° C. After cooling to room temperature water was added and it was extracted three times with ethyl acetate followed by concentration in vacuo.

The residue was redissolved in a mixture of methanol (25 mL) and n-propanol (25 mL) and concentrated aqueous ammonia (50 mL) was added to completely deprotect the target molecule for easier purification. The reaction mixture was extracted with dichloromethane and ethyl acetate. The organic phases were dried, followed by concentration in vacuo and purification by preparative HPLC (Chromatorex C-18 10 μm, 125×30 mm, acetonitrile/water+0.1% aqueous ammonia (32%)) to give 2-[1-(difluoromethyl)-1H-pyrazol-4-yl]-5-nitrobenzenesulfonamide (383 mg).

Next, the deprotected target molecule was reprotected as previously described by stirring at room temperature with 1,1-dimethoxy-N,N-dimethylmethanamine in DMF. Concentration in vacuo gave the title compound (418 mg) that was used without further purification in the next step.

LC-MS (Method B): Rt=0.98 min; MS (ESIpos): m/z=374 [M+H]$^+$ $^1$H-NMR (400 MHz, DMSO-d$_6$) δ [ppm] 2.76 (d, 3H), 3.02 (s, 3H), 7.85 (d, 1H), 7.91-7.93 (m, 2H), 7.95 (t, 1H), 8.19-8.21 (m, 1H), 8.43 (dd, 1H), 8.72 (d, 1H), 8.77 (d, 1H).

Intermediate 21

5-Amino-2-[1-(difluoromethyl)-1H-pyrazol-4-yl]-N-[(dimethylamino)methylene]-benzenesulfonamide

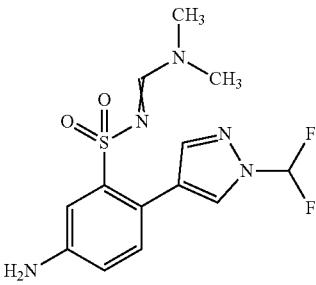 [SMILES: CN(C)C=NS(=O)(=O)c1cc(N)ccc1-c1cnn(C(F)F)c1]

Pd/C (10% loading, 54 mg) was added to a solution of 2-[1-(difluoromethyl)-1H-pyrazol-4-yl]-N-[(dimethylamino)methylene]-5-nitrobenzenesulfonamide (418 mg, 1.01 mmol) in a mixture of methanol (10 mL) and dioxane (10 mL) and stirred under a hydrogen atmosphere overnight at room temperature. The catalyst was filtered off, washed with ethyl acetate and the filtrate was concentrated in vacuo to give the crude title compound (370 mg, quant., 90% purity) that was used without further purification in the next step.

LC-MS (Method A): Rt=0.74 min; MS (ESIpos): m/z=344 [M+H]$^+$

Intermediate 22

2-(2-Chlorophenyl)-N-(3-{[(dimethylamino)methylene]sulfamoyl}-4-[4-(trifluoro-methyl)-1H-pyrazol-1-yl]phenyl)acetamide

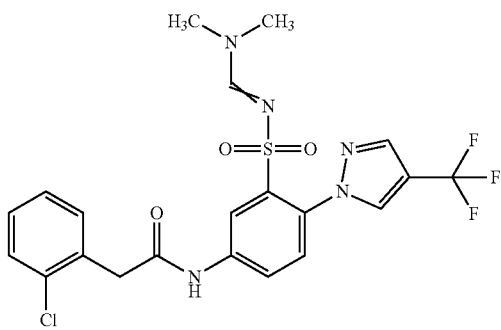 [SMILES: CN(C)C=NS(=O)(=O)c1cc(NC(=O)Cc2ccccc2Cl)ccc1-n1cc(C(F)(F)F)cn1]

2-(2-Chlorophenyl)-N-{3-sulfamoyl-4-[4-(trifluoromethyl)-1H-pyrazol-1-yl]phenyl}acetamide (2.00 g, 3.92 mmol) was dissolved in dimethylformamide (13.3 mL) and treated with dimethylformamide dimethyl acetate (935 mg, 7.85 mmol) followed by stirring at room temperature over the weekend. The reaction mixture was reduced in vacuo and extracted with dichloromethane and water. The desired compound already partly precipitated. The organic phase was dried, concentrated in vacuo and further purified by stirring as suspension in n-propanol followed by filtration. All precipitated fractions were combined to give the title compound of sufficient purity for the next steps (1.33 g, 2.59 mmol, 66% yield, 95% purity).

LC-MS (Method B): Rt=1.19 min; MS (ESIpos): m/z=514 [M+H]$^+$

Major E/Z-Isomer $^1$H-NMR (400 MHz, DMSO-d$_6$) δ [ppm] 2.77 (s, 3H), 3.01 (s, 3H), 3.91 (s, 2H), 7.30-7.36 (m, 2H), 7.43-7.52 (m, 3H), 7.58 (s, 1H), 7.97 (dd, 1H), 8.14 (s, 1H), 8.38 (d, 1H), 8.62-8.64 (m, 1H), 10.80 (s, 1H).

Intermediate 23

2-(2-Chlorophenyl)-N-[3-{[(dimethylamino)methylene]sulfamoyl}-4-(4-fluoro-1H-pyrazol-1-yl)phenyl]acetamide

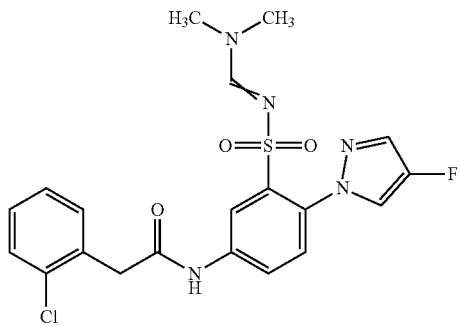 [SMILES: CN(C)C=NS(=O)(=O)c1cc(NC(=O)Cc2ccccc2Cl)ccc1-n1cc(F)cn1]

2-(2-Chlorophenyl)-N-[4-(4-fluoro-1H-pyrazol-1-yl)-3-sulfamoylphenyl]acetamide (125 mg, 0.31 mmol) was dissolved in dimethylformamide (1 mL) and treated with dimethylformamide dimethyl acetate (72.9 mg, 0.61 mmol) followed by stirring at room temperature over the weekend. The reaction mixture was reduced in vacuo and extracted with dichloromethane and water. The organic phase was washed with brine and was dried over sodium sulfate and concentrated in vacuo to give the title compound of sufficient purity for the next steps (167 mg, quant).

LC-MS (Method A): Rt=1.06 min; MS (ESIpos): m/z=464 [M+H]$^+$

Intermediate 24

N-(2,4-Dimethoxybenzyl)-2-(4-methyl-1H-pyrazol-1-yl)-5-nitrobenzenesulfonamide

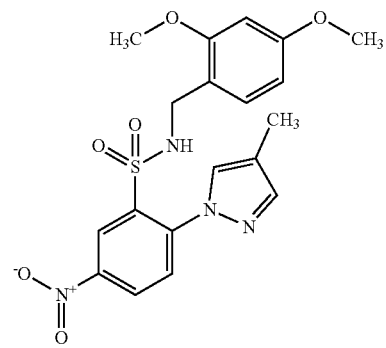

To a solution of 2-chloro-N-(2,4-dimethoxybenzyl)-5-nitrobenzenesulfonamide (800 mg, 2.07 mmol) in acetonitrile (16 mL) were added 4-methyl-1H-pyrazole (260 μl, 3.1 mmol, CAS-RN 7554-65-5) and powdered potassium carbonate (857 mg, 6.20 mmol) and it was irradiated for 2 h at 140° C. in the microwave. After addition of further 4-methyl-1H-pyrazole (347 μl, 4.1 mmol) the mixture again was irradiated for 2 h at 140° C. in the microwave. The reaction mixture was concentrated in vacuo and the residue was extracted with dichloromethane and water. The aqueous phase was washed three times with dichloromethane. Then the combined organic phases were washed with brine and dried using a Whatman filter. Concentration under reduced pressure led to the title compound that was purified by flash chromatography (718 mg, 64% yield, 80% purity).

LC-MS (Method B): Rt=1.30 min; MS (ESIpos): m/z=433 [M+H]$^+$ $^1$H-NMR (400 MHz, DMSO-d$_6$) δ [ppm]: 2.13 (s, 3H), 3.41 (s, 3H), 3.60 (s, 3H), 4.17 (d, 2H), 6.09 (d, 1H), 6.26 (dd, 1H), 7.09 (d, 1H), 7.77 (d, 1H), 7.81 (s, 1H), 8.11 (s, 1H), 8.17 (d, 1H), 8.28 (t, 1H), 8.40 (dd, 1H).

Intermediate 25

N-(2,4-Dimethoxybenzyl)-2-(3-methoxy-1H-1,2,4-triazol-1-yl)-5-nitrobenzenesulfonamide

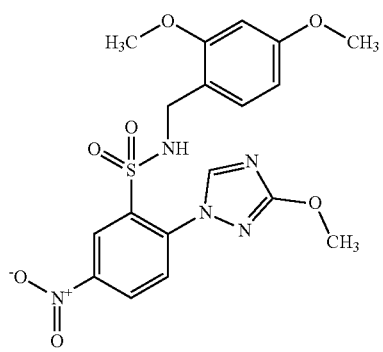

To a solution of 2-chloro-N-(2,4-dimethoxybenzyl)-5-nitrobenzenesulfonamide (700 mg, 1.81 mmol) in acetonitrile (19 mL) were added 3-methoxy-4H-1,2,4-triazole (269 mg, 2.71 mmol) and powdered potassium carbonate (750 mg, 5.43 mmol) and the mixture was irradiated for 1 h at 120° C. in the microwave. The reaction mixture was filtered and concentrated in vacuo, and the residue was extracted with dichloromethane and water. The aqueous phase was washed three times with dichloromethane. Then the combined organic phases were washed with brine and dried using a Whatman filter. Concentration under reduced pressure led to the title compound that was purified by flash chromatography (293 mg, 31% yield, 85% purity).

LC-MS (Method A): Rt=1.08 min; MS (ESIpos): m/z=450 [M+H]$^+$ $^1$H-NMR (400 MHz, DMSO-d$_6$) δ [ppm]: 3.30 (s, 3H), 3.51 (s, 3H), 3.62 (s, 3H), 4.12 (d, 2H), 6.16 (d, 1H), 6.27 (dd, 1H), 7.09 (d, 1H), 7.83 (t, 1H), 7.85 (d, 1H), 8.18 (d, 1H), 8.35 (s, 1H), 8.43 (dd, 1H).

Intermediate 26

2-(4-Cyclopropyl-1H-imidazol-1-yl)-N-(2,4-dimethoxybenzyl)-5-nitrobenzenesulfonamide

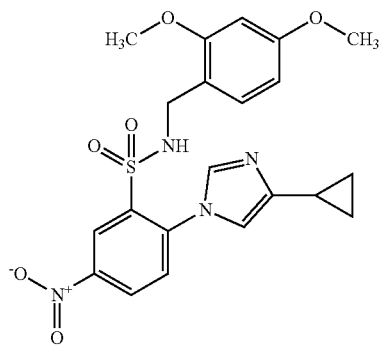

To a solution of 2-chloro-N-(2,4-dimethoxybenzyl)-5-nitrobenzenesulfonamide (700 mg, 1.81 mmol) in acetonitrile (14 mL) were added 5-cyclopropyl-1H-imidazole (294 mg, 2.71 mmol, CAS-RN 89830-98-8) and powdered potassium carbonate (750 mg, 5.43 mmol) and the mixture was irradiated for 1 h at 120° C. in the microwave. 4-Cyclopropyl-1H-imidazole (196 mg, 1.81 mmol) was added, and microwave irradiation was continued for 2 h at 140° C. The reaction mixture was filtered and concentrated in vacuo, and the residue was extracted with dichloromethane and water. The aqueous phase was washed three times with dichloromethane. Then the combined organic phases were washed with brine and dried using a Whatman filter. Concentration under reduced pressure led to the title compound that was purified by flash chromatography (309 mg, 22% yield, 60% purity).

LC-MS (Method A): Rt=1.06 min; MS (ESIpos): m/z=459 [M+H]$^+$ $^1$H-NMR (400 MHz, DMSO-d$_6$) δ [ppm]: 0.71 (m, 2H), 0.82 (m, 2H), 1.87 (m, 1H), 3.61 (s, 3H), 3.68 (s, 3H), 4.01 (d, 2H), 6.33 (d, 1H), 6.36 (dd, 1H), 7.02 (d, 1H), 7.17 (s, 1H), 7.67 (d, 1H), 7.74 (s, 1H), 8.41 (dd, 1H), 8.43 (d, 1H), 8.49 (t, 1H).

Intermediate 27

N-(2,4-Dimethoxybenzyl)-2-(4-methyl-1H-imidazol-1-yl)-5-nitrobenzenesulfonamide

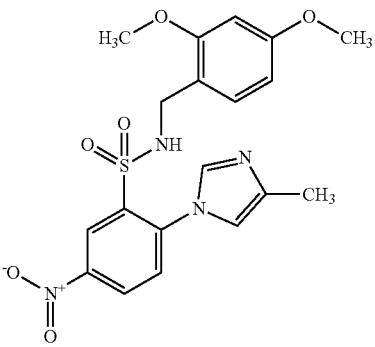

To a solution of 2-chloro-N-(2,4-dimethoxybenzyl)-5-nitrobenzenesulfonamide (700 mg, 1.81 mmol) in acetonitrile (14 mL) were added 5-methyl-1H-imidazole (223 mg, 2.71 mmol, CAS-RN 822-36-6) and powdered potassium carbonate (750 mg, 5.43 mmol) and the mixture was irradiated for 2 h at 110° C. in the microwave. 4-Methyl-1H-imidazole (223 mg, 2.71 mmol) was added, and microwave irradiation was continued for 2 h at 110° C. The reaction mixture was filtered and concentrated in vacuo, and the residue was extracted with dichloromethane and water. The aqueous phase was washed three times with dichloromethane. Then the combined organic phases were washed with brine and dried using a Whatman filter. Concentration under reduced pressure led to the title compound that was purified by flash chromatography (252 mg, 29% yield, 90% purity).

LC-MS (Method B): Rt=1.03 min; MS (ESIpos): m/z=433 [M+H]$^+$ $^1$H-NMR (400 MHz, DMSO-d$_6$) δ [ppm]: 2.18 (s, 3H), 3.60 (s, 3H), 3.68 (s, 3H), 4.01 (d, 2H), 6.33 (d, 1H), 6.34 (dd, 1H), 7.00 (d, 1H), 7.12 (s, 1H), 7.66 (d, 1H), 7.75 (s, 1H), 8.41 (dd, 1H), 8.43 (d, 1H), 8.46 (t, 1H).

Intermediate 28

2-(3-Cyclopropyl-1H-pyrazol-1-yl)-N-(2,4-dimethoxybenzyl)-5-nitrobenzenesulfonamide

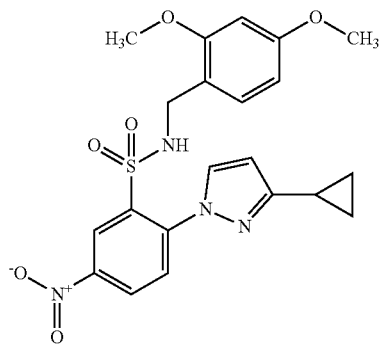

To a solution of 2-chloro-N-(2,4-dimethoxybenzyl)-5-nitrobenzenesulfonamide (700 mg, 1.81 mmol) in acetonitrile (14 mL) were added 3-cyclopropyl-1H-pyrazole (240 μl, 2.71 mmol, CAS-RN 100114-57-6) and powdered potassium carbonate (750 mg, 5.43 mmol) and the mixture was irradiated for 1 h at 120° C. in the microwave. 5-Cyclopropyl-1H-pyrazole (240 μl, 2.71 mmol) was added, and microwave irradiation was continued for 2 h at 140° C. The reaction mixture was filtered and concentrated in vacuo, and the residue was extracted with dichloromethane and water. The aqueous phase was washed three times with dichloromethane. Then the combined organic phases were washed with brine and dried using a Whatman filter. Concentration under reduced pressure led to the title compound that was purified by flash chromatography (187 mg, 21% yield, 95% purity).

LC-MS (Method B): Rt=1.34 min, MS (ESIpos): m/z=459 [M+H]$^+$ $^1$H-NMR (400 MHz, DMSO-d$_6$) δ [ppm]: 0.76 (m, 2H), 1.00 (m, 2H), 2.03 (m, 1H), 3.40 (s, 3H), 3.60 (s, 3H), 4.17 (s, 2H), 6.11 (d, 1H), 6.28 (dd, 1H), 6.42 (d, 1H), 7.09 (d, 1H), 7.78 (d, 1H), 8.18 (d, 1H), 8.21 (d, 1H), 8.37 (t, 1H), 8.39 (dd, 1H).

Intermediate 29

N-(2,4-Dimethoxybenzyl)-5-nitro-2-(2H-pyrazolo[3,4-b]pyridin-2-yl)benzenesulfonamide

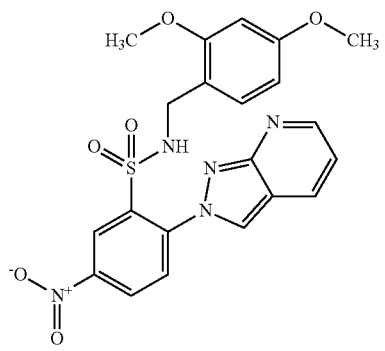

To a solution of 2-chloro-N-(2,4-dimethoxybenzyl)-5-nitrobenzenesulfonamide (700 mg, 1.81 mmol) in acetonitrile (18 mL) were added 1H-pyrazolo[3,4-b]pyridine (307 mg, 2.58 mmol, CAS-RN 271-73-8) and powdered potassium carbonate (750 mg, 5.43 mmol) and the mixture was irradiated for 2 h at 120° C. in the microwave. The reaction mixture was filtered and concentrated in vacuo, and the residue was extracted with dichloromethane and water. The aqueous phase was washed three times with dichloromethane. Then the combined organic phases were washed with brine and dried using a Whatman filter. Concentration under reduced pressure led to the title compound that was purified by flash chromatography (428 mg, 37% yield, 70% purity).

LC-MS (Method B): Rt=1.24 min; MS (ESIpos): m/z=470 [M+H]$^+$ $^1$H-NMR (400 MHz, DMSO-d$_6$) δ [ppm]: 3.51 (s, 3H), 3.62 (s, 3H), 4.20 (d, 2H), 6.15 (d, 1H), 6.29 (dd, 1H), 7.13 (d, 1H), 7.45 (dd, 1H), 7.98 (t, 1H), 8.14 (d, 1H), 8.24 (dd, 1H), 8.46 (dd, 1H), 8.52 (d, 1H), 8.63 (dd, 1H), 8.65 (s, 1H).

Intermediate 30

N-(2,4-Dimethoxybenzyl)-5-nitro-2-(2H-pyrazolo[3,4-c]pyridin-2-yl)benzenesulfonamide

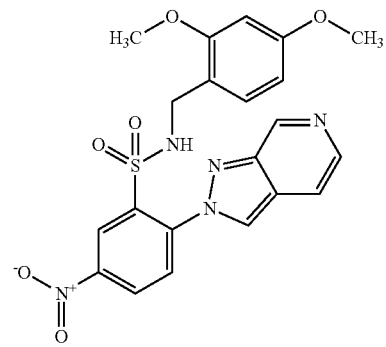

To a solution of 2-chloro-N-(2,4-dimethoxybenzyl)-5-nitrobenzenesulfonamide (700 mg, 1.81 mmol) in acetonitrile (18 mL) were added 1H-pyrazolo[3,4-c]pyridine (307 mg, 2.58 mmol, CAS-RN 271-47-6) and powdered potassium carbonate (750 mg, 5.43 mmol) and the mixture was irradiated for 2 h at 120° C. in the microwave. The reaction mixture was filtered and concentrated in vacuo, and the residue was extracted with dichloromethane and water. The aqueous phase was washed three times with dichloromethane. Then the combined organic phases were washed with brine and dried using a Whatman filter. Concentration under reduced pressure led to the title compound that was purified by flash chromatography (610 mg, 72% yield, 95% purity).

LC-MS (Method B): Rt=1.15 min, MS (ESIpos): m/z=470 [M+H]$^+$ $^1$H-NMR (400 MHz, DMSO-d$_6$) δ [ppm]: 3.55 (s, 3H), 3.64 (s, 3H), 4.15 (d, 2H), 6.19 (d, 1H), 6.29 (dd, 1H), 7.07 (d, 1H), 7.96 (dd, 1H), 7.99 (t, 1H), 8.10 (d, 1H), 8.33 (d, 1H), 8.45 (d, 1H), 8.50 (dd, 1H), 8.71 (d, 1H), 9.00 (s, 1H).

Intermediate 31

N-(2,4-Dimethoxybenzyl)-5-nitro-2-(2H-pyrazolo[4,3-b]pyridin-2-yl)benzenesulfonamide

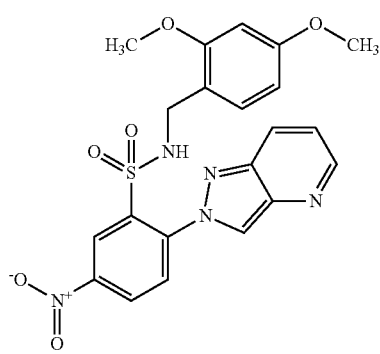

To a solution of 2-chloro-N-(2,4-dimethoxybenzyl)-5-nitrobenzenesulfonamide (700 mg, 1.81 mmol) in acetonitrile (18 mL) were added 1H-pyrazolo[4,3-b]pyridine (307 mg, 2.58 mmol, CAS-RN 272-52-6) and powdered potassium carbonate (750 mg, 5.43 mmol) and the mixture was irradiated for 2 h at 120° C. in the microwave. The reaction mixture was filtered and concentrated in vacuo, and the residue was extracted with dichloromethane and water. The aqueous phase was washed three times with dichloromethane. Then the combined organic phases were washed with brine and dried using a Whatman filter. Concentration under reduced pressure led to the title compound that was purified by flash chromatography (270 mg, 20% yield, 60% purity).

LC-MS (Method B): Rt=1.16 min; MS (ESIpos): m/z=470 [M+H]$^+$ $^1$H-NMR (400 MHz, DMSO-d$_6$) δ [ppm]: 3.55 (s, 3H), 3.63 (s, 3H), 4.16 (d, 2H), 6.18 (d, 1H), 6.29 (dd, 1H), 7.08 (d, 1H), 7.54 (dd, 1H), 7.99 (d, 1H), 8.00 (t, 1H), 8.01 (dd, 1H), 8.32 (d, 1H), 8.49 (dd, 1H), 8.71 (dd, 1H), 8.80 (s, 1H).

Intermediate 32

N-(2,4-Dimethoxybenzyl)-2-[4-(2-methoxyethyl)-1H-pyrazol-1-yl]-5-nitrobenzenesulfonamide

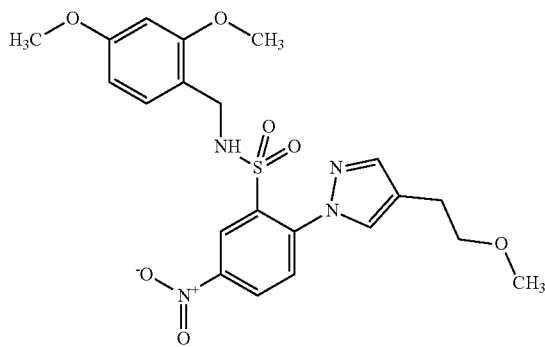

To a solution of 2-chloro-N-(2,4-dimethoxybenzyl)-5-nitrobenzenesulfonamide (1.41 g, 3.65 mmol) in acetonitrile (16 mL) were added 4-(2-methoxyethyl)-1H-pyrazole (260 μl, 3.1 mmol, CAS-RN 1696383-18-12) and powdered potassium carbonate (1.51 g, 10.9 mmol) and it was irradiated for 2 h at 140° C. in the microwave. The reaction mixture was filtered, concentrated in vacuo, and the residue was purified by HPLC (300 mg, 15% yield, 85% purity).

LC-MS (Method B): Rt=1.26 min; MS (ESIpos): m/z=477 [M+H]$^+$ $^1$H-NMR (400 MHz, DMSO-d$_6$) δ [ppm]: 2.75 (t, 2H), 3.29 (s, 3H), 3.43 (s, 3H), 3.55 (t, 2H), 3.60 (s, 3H), 4.16 (d, 2H), 6.11 (d, 1H), 6.26 (dd, 1H), 7.09 (d, 1H), 7.78 (d, 1H), 7.85 (s, 1H), 8.17 (s, 1H), 8.19 (d, 1H), 8.26 (t, 1H), 8.40 (dd, 1H).

Intermediate 33

N-(2,4-Dimethoxybenzyl)-2-(3-fluoro-1H-pyrazol-1-yl)-5-nitrobenzenesulfonamide

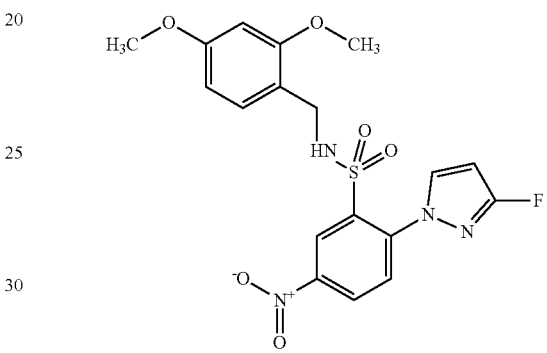

To a solution of 2-chloro-N-(2,4-dimethoxybenzyl)-5-nitrobenzenesulfonamide (700 mg, 1.81 mmol) in acetonitrile (19 mL) were added 3-fluoro-1H-pyrazole (234 mg, 2.71 mmol, CAS-RN 14521-81-4) and powdered potassium carbonate (750 mg, 5.43 mmol) and the mixture was irradiated for 2 h at 120° C. in the microwave. 3-Fluoro-1H-pyrazole (234 mg, 2.71 mmol) was added, and microwave irradiation was continued for 2 h at 120° C. The reaction mixture was filtered and concentrated in vacuo, and the residue was extracted with dichloromethane and water. The aqueous phase was washed three times with dichloromethane. Then the combined organic phases were washed with brine and dried using a Whatman filter. Concentration under reduced pressure led to the title compound that was purified by flash chromatography (567 mg, 61% yield, 85% purity).

LC-MS (Method B): Rt=1.25 min; MS (ESIpos): m/z=437 [M+H]$^+$ $^1$H-NMR (400 MHz, DMSO-d$_6$) δ [ppm]: 3.52 (s, 3H), 3.63 (s, 3H), 4.14 (s, 2H), 6.19 (d, 1H), 6.28 (dd, 1H), 6.46 (dd, 1H), 7.06 (d, 1H), 7.82 (d, 1H), 8.04 (s, 1H), 8.23 (dd, 1H), 8.26 (d, 1H), 8.44 (dd, 1H).

Intermediate 34

N-(2,2-Difluoroethyl)-1H-pyrazol-4-amine

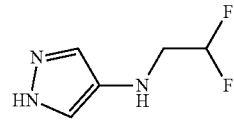

To a solution of 1H-pyrazol-4-amine (300 mg, 95% purity, 3.43 mmol) in acetonitrile (17 mL) were added 2,2-difluoroethyl trifluoromethanesulfonate (690 µl, 5.1 mmol, CAS-RN 74427-22-8), powdered potassium carbonate (1.06 g, 7.65 mmol), and triethylamine (720 µL, 5.1 mmol). The mixture was heated to 120° C. overnight. For work-up, it was filtered, and the solid was rinsed with ethyl acetate. Concentration of the filtrate in vacuo followed by flash chromatography led to the title compound (505 mg, 90% yield, 90% purity).

LC-MS (Method B): Rt=0.43 min

MS (ESIpos): m/z=148 (M+H)+

1H-NMR (400 MHz, DMSO-d6) δ [ppm]: 3.23 (tdd, 2H), 4.72 (t, 1H), 6.05 (tt, 1H), 7.12 (s, 2H), 12.10 (s, 1H).

Intermediate 35

2-{4-[(2,2-Difluoroethyl)amino]-1H-pyrazol-1-yl}-N-(2,4-dimethoxybenzyl)-5-nitrobenzenesulfonamide

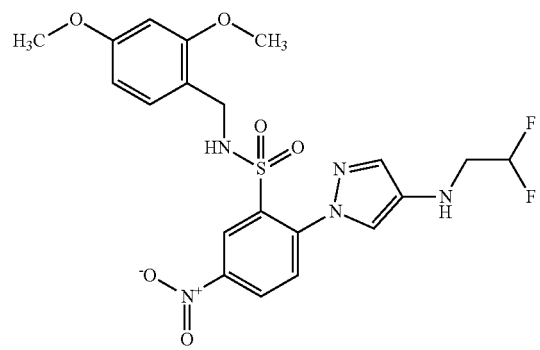

To a solution of 2-chloro-N-(2,4-dimethoxybenzyl)-5-nitrobenzenesulfonamide (623 mg, 1.53 mmol) in acetonitrile (16 mL) were added N-(2,2-difluoroethyl)-1H-pyrazol-4-amine (500 mg, 3.06 mmol) and powdered potassium carbonate (634 mg, 4.59 mmol) and it was irradiated for 12 h at 120° C. in the microwave. The reaction mixture was filtered, concentrated in vacuo, and the residue was purified by flash chromatography (280 mg, 31% yield, 85% purity).

LC-MS (Method A): Rt=1.23 min; MS (ESIpos): m/z=498 [M+H]+

1H-NMR (400 MHz, DMSO-d6) δ [ppm]: 3.38 (m, 2H), 3.38 (s, 3H), 3.59 (s, 3H), 4.16 (d, 2H), 5.49 (t, 1H), 6.08 (d, 1H), 6.15 (tt, 1H), 6.25 (dd, 1H), 7.08 (d, 1H), 7.65 (s, 1H), 7.73 (d, 1H), 7.80 (s, 1H), 8.17 (d, 1H), 8.24 (t, 1H), 8.38 (dd, 1H).

Intermediate 36

N-(2,4-Dimethoxybenzyl)-2-[4-(2-hydroxyethyl)-1H-pyrazol-1-yl]-5-nitrobenzenesulfonamide

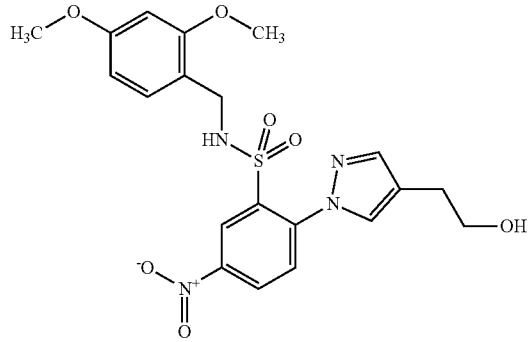

To a solution of 2-chloro-N-(2,4-dimethoxybenzyl)-5-nitrobenzenesulfonamide (661 mg, 1.71 mmol) in acetonitrile (13 mL) were added 2-(1H-pyrazol-4-yl)ethanol (383 mg, 3.42 mmol, CAS-RN 180207-57-2) and powdered potassium carbonate (944 mg, 6.83 mmol), and the mixture was irradiated for 2 h at 140° C. in the microwave. The reaction mixture was diluted with water and extracted with ethyl acetate. The combined organic phases were washed with brine and dried using a Whatman filter. Concentration under reduced pressure led to the title compound that was purified by flash chromatography (285 mg, 34% yield, 95% purity).

LC-MS (Method B): Rt=1.08 min; MS (ESIpos): m/z=463 (M+H)+

1H-NMR (400 MHz, DMSO-d6) δ [ppm]: 2.66 (t, 2H), 3.42 (s, 3H), 3.60 (s, 3H), 3.62 (td, 2H), 4.17 (d, 2H), 4.75 (t, 1H), 6.11 (d, 1H), 6.26 (dd, 1H), 7.09 (d, 1H), 7.78 (d, 1H), 7.85 (s, 1H), 8.15 (s, 1H), 8.19 (d, 1H), 8.28 (t, 1H), 8.40 (dd, 1H).

Intermediate 37

N-(2,4-Dimethoxybenzyl)-5-nitro-2-[4-(2-oxoethyl)-1H-pyrazol-1-yl]benzenesulfonamide

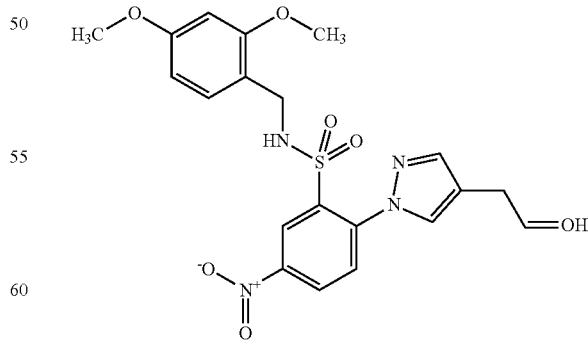

To a solution of N-(2,4-dimethoxybenzyl)-2-[4-(2-hydroxyethyl)-1H-pyrazol-1-yl]-5-nitrobenzenesulfonamide (279 mg, 573 µmol, 95% purity) in dichloromethane (19 mL), 1,1,1-tris(acetyloxy)-1λ5,2-benziodoxol-3(1H)-one (486 mg, 1.15 mmol) was added, and the mixture was stirred for 2 h at room temperature. The reaction mixture was diluted with aqueous sodium thiosulfate solution (10%) and saturated aqueous sodium hydrogen carbonate solution (1:1), and extracted with dichloromethane. The combined organic phases were washed with brine and dried using a Whatman filter. Concentration under reduced pressure led to the crude title compound that was used without further purification (440 mg, 33% yield, 20% purity).

LC-MS (Method B): Rt=1.11 min; MS (ESIpos): m/z=461 (M+H)$^+$ $^1$H-NMR (400 MHz, DMSO-d$_6$) δ [ppm]: 3.44 (s, 3H), 3.61 (s, 3H), 3.77 (t, 2H), 4.17 (d, 2H), 6.12 (d, 1H), 6.27 (dd, 1H), 7.09 (d, 1H), 7.80 (d, 1H), 7.90 (s, 1H), 8.20 (d, 1H), 8.23 (t, 1H), 8.26 (s, 1H), 8.42 (dd, 1H), 9.71 (t, 1H).

Intermediate 38

2-[4-(2,2-Difluoroethyl)-1H-pyrazol-1-yl]-N-(2,4-dimethoxybenzyl)-5-nitrobenzenesulfonamide

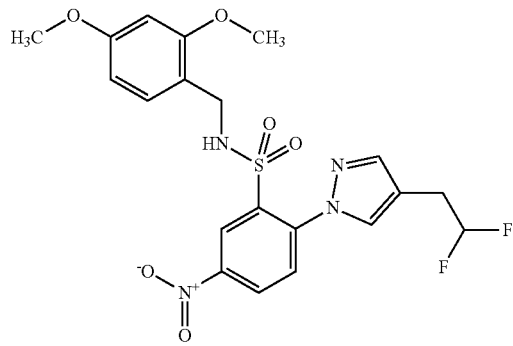

To a solution of crude N-(2,4-dimethoxybenzyl)-5-nitro-2-[4-(2-oxoethyl)-1H-pyrazol-1-yl]benzenesulfonamide (440 mg, 191 μmol, 20% purity) in tetrahydrofuran (500 μL), 2-methoxy-N-(2-methoxyethyl)-N-(trifluoro-λ$^4$-sulfanyl)ethanamine (210 mL, 2.7 M in toluene, 570 μmol) was added, and the mixture was stirred at room temperature overnight. The reaction mixture was diluted with ethyl acetate, and washed with saturated aqueous sodium hydrogen carbonate solution and with brine. The organic phase was dried using a Whatman filter and evaporated in vacuo. Purification by flash chromatography yielded the title compound (56 mg, 43% yield, 70% purity).

LC-MS (Method B): Rt=1.26 min; MS (ESIpos): m/z=483 (M+H)$^+$ $^1$H-NMR (400 MHz, DMSO-d$_6$) δ [ppm]: 3.16 (td, 2H), 3.44 (s, 3H), 3.61 (s, 3H), 4.16 (d, 2H), 6.12 (d, 1H), 6.26 (tt, 1H), 6.26 (dd, 1H), 7.09 (d, 1H), 7.79 (d, 1H), 7.89 (s, 1H), 8.20 (d, 1H), 8.20 (t, 1H), 8.26 (s, 1H), 8.42 (dd, 1H).

Intermediate 39

2-(2-Chlorophenyl)-N-{4-[4-(2,2-difluoroethyl)-1H-pyrazol-1-yl]-3-[(2,4-dimethoxy-benzyl)sulfamoyl]phenyl}acetamide

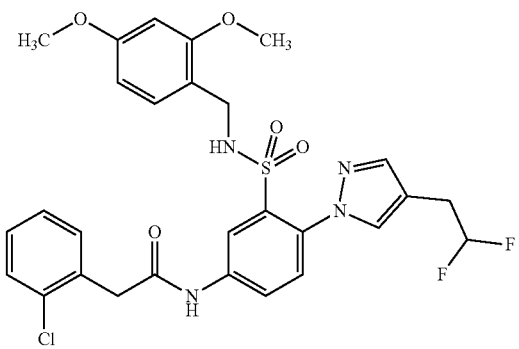 [SMILES: COc1ccc(CNS(=O)(=O)c2cc(NC(=O)Cc3ccccc3Cl)ccc2-n2cc(CC(F)F)cn2)c(OC)c1]

Tin(II) chloride dihydrate (530 mg, 2.35 mmol) was added to a solution of 2-[4-(2,2-difluoroethyl)-1H-pyrazol-1-yl]-N-(2,4-dimethoxybenzyl)-5-nitrobenzenesulfonamide (227 mg, 469 μmol) in dioxane (6 mL), followed by stirring for 6 h at 70° C. The reaction mixture was concentrated in vacuo. Water was added to the residue and the mixture was extracted three times with ethyl acetate. The combined organic phase was filtered over Celite, washed with brine, dried using sodium sulfate, and concentrated in vacuo to give 245 mg crude 5-amino-2-[4-(2,2-difluoroethyl)-1H-pyrazol-1-yl]-N-(2,4-dimethoxybenzyl)-benzenesulfonamide that was used without further purification in the next step.

The crude material from the previous step (217 mg) was dissolved in DMF (6 mL) followed by the addition of (2-chlorophenyl)acetic acid (84 mg, 492 μmol), N,N-diisopropylethylamine (230 μL, 1.3 mmol) and HATU (187 mg, 492 μmol). The reaction mixture was stirred for 3.5 h at room temperature. Saturated aqueous sodium hydrogen carbonate solution was added and the mixture was extracted three times with ethyl acetate. Then all organic phases were combined, washed with brine, dried over a Whatman filter and concentrated in vacuo to give the title compound that was used without further purification (336 mg, 40% purity, 47% yield over 2 steps).

LC-MS (Method A): Rt=1.34 min; MS (ESIpos): m/z=605 (M+H)$^+$

Intermediate 40

2,2-Difluoro-N-(1H-pyrazol-4-ylmethyl)ethanamine

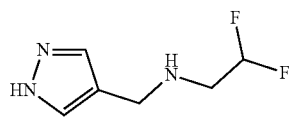 [SMILES: FC(F)CNCc1cn[nH]c1]

To a solution of 1-(1H-pyrazol-4-yl)methanamine dihydrochloride (500 mg, 2.94 mmol) in acetonitrile (30 mL) were added 2,2-difluoroethyl trifluoromethanesulfonate (590 μL, 4.4 mmol, CAS-RN 74427-22-8), powdered potassium carbonate (1.02 g, 7.35 mmol), and triethylamine (1.2 mL, 8.8 mmol). The mixture was heated to 100° C. for 4 h and to 70° C. overnight. For work-up, it was filtered, and the solid was rinsed with dichloromethane. Concentration of the filtrate in vacuo followed by extraction of the residue with dichloromethane and evaporation of the organic phase led to the title compound (482 mg, 86% yield, 85% purity).

LC-MS (Method B): Rt=0.49 min; MS (ESIpos): m/z=162 (M+H)$^+$ $^1$H-NMR (400 MHz, DMSO-d$_6$) δ [ppm]: 2.82 (td, 2H), 3.61 (s, 2H), 5.98 (tt, 1H), 7.50 (s, 2H).

Intermediate 41 tert-Butyl (2,2-difluoroethyl)(1H-pyrazol-4-ylmethyl)carbamate

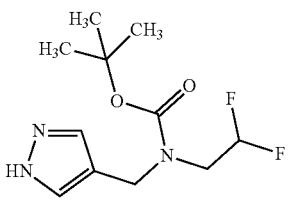 [SMILES: CC(C)(C)OC(=O)N(Cc1cn[nH]c1)CC(F)F]

To a solution of 2,2-difluoro-N-(1H-pyrazol-4-ylmethyl)ethanamine (370 mg, 2.30 mmol) in dichloromethane (23 mL), di-tert-butyl dicarbonate (551 mg, 2.53 mmol) was added, and the mixture was stirred for 90 min at room temperature. The reaction mixture was diluted with saturated aqueous sodium hydrogen carbonate solution, and extracted with dichloromethane. The combined organic phases were concentrated under reduced pressure yielding the crude title compound that was used without further purification (302 mg, 45% yield, 90% purity).

LC-MS (Method B): Rt=0.95 min; MS (ESIpos): m/z=262 (M+H)$^+$ $^1$H-NMR (400 MHz, DMSO-d$_6$) δ [ppm]: 2.82 (td, 2H), 3.62 (s, 2H), 5.99 (tt, 1H), 7.74 (s, 2H), 8.12 (s, 2H).

Intermediate 42

2-(4-{[(2,2-Difluoroethyl)amino]methyl}-1H-pyrazol-1-yl)-N-(2,4-dimethoxybenzyl)-5-nitrobenzenesulfonamide

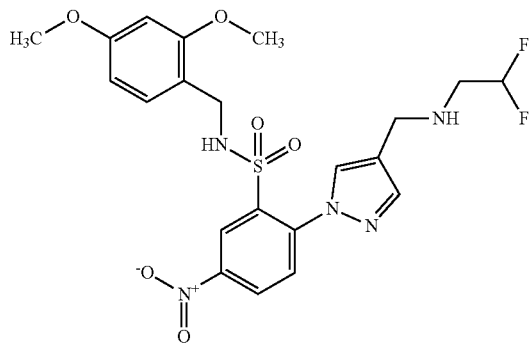

To a solution of 2-chloro-N-(2,4-dimethoxybenzyl)-5-nitrobenzenesulfonamide (200 mg, 517 µmol) in acetonitrile (10 mL) were added tert-butyl (2,2-difluoroethyl)(1H-pyrazol-4-ylmethyl)carbamate (300 mg, 90% purity, 1.03 mmol) and powdered potassium carbonate (286 mg, 2.07 mmol), and the mixture was irradiated for 4 h at 120° C. in the microwave. The reaction mixture was diluted with water and extracted with ethyl acetate. The combined organic phases were washed with brine and dried using a Whatman filter. Concentration under reduced pressure led to the title compound that was purified by flash chromatography (84 mg, 22% yield, 70% purity).

LC-MS (Method B): Rt=1.21 min: MS (ESIpos): m/z=512 (M+H)$^+$ $^1$H-NMR (400 MHz, DMSO-d$_6$) δ [ppm]: 2.89 (td, 2H), 3.44 (s, 3H), 3.61 (s, 3H), 3.71 (s, 2H), 4.16 (d, 2H), 6.02 (tt, 1H), 6.12 (d, 1H), 6.27 (dd, 1H), 7.09 (d, 1H), 7.80 (d, 1H), 7.90 (s, 1H), 8.19 (d, 1H), 8.21 (s, 1H), 8.26 (t, 1H), 8.41 (dd, 1H).

Intermediate 43 tert-Butyl (2,2-difluoroethyl)[(1-{2-[(2,4-dimethoxybenzyl)sulfamoyl]-4-nitrophenyl}-1H-pyrazol-4-yl)methyl]carbamate

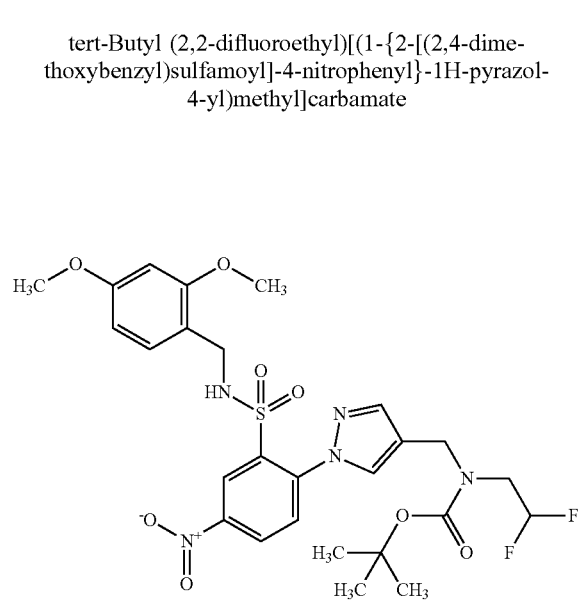

To a solution of 2-(4-{[(2,2-difluoroethyl)amino]methyl}-1H-pyrazol-1-yl)-N-(2,4-dimethoxy-benzyl)-5-nitrobenzenesulfonamide (370 mg, 723 µmol) in dichloromethane (7 mL), di-tert-butyl dicarbonate (174 mg, 796 µmol) and 4-(dimethylamino)pyridine (4.4 mg, 36 µmol) were added, and the mixture was stirred overnight at room temperature. Another portion of di-tert-butyl dicarbonate (174 mg, 796 µmol) and 4-(dimethylamino)pyridine (4.4 mg, 36 µmol) were added, and stirring was continued for 3 h. The reaction mixture was diluted with saturated aqueous sodium hydrogen carbonate solution, and extracted with dichloromethane. The combined organic phases were concentrated under reduced pressure yielding the crude title compound that was used without further purification (150 mg, 17% yield, 50% purity).

LC-MS (Method B): Rt=1.42 min

MS (ESIpos): m/z=612 (M+H)$^+$

Intermediate 44 tert-Butyl {[1-(4-{[(2-chlorophenyl)acetyl]amino}-2-[(2,4-dimethoxybenzyl)sulfamoyl]phenyl)-1H-pyrazol-4-yl]methyl}(2,2-difluoroethyl)carbamate

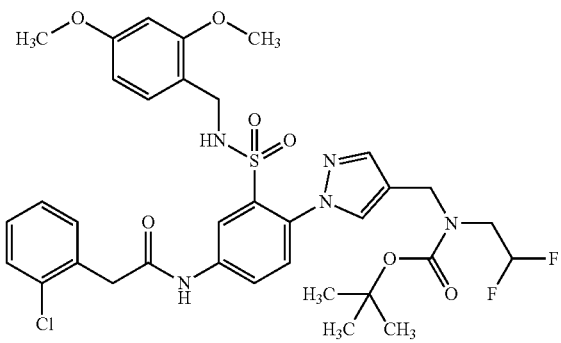 [SMILES: COc1ccc(CNS(=O)(=O)c2cc(NC(=O)Cc3ccccc3Cl)ccc2-n2cc(CN(CC(F)F)C(=O)OC(C)(C)C)cn2)c(OC)c1]

Tin(II) chloride dihydrate (277 mg, 1.23 mmol) was added to a solution of tert-butyl (2,2-difluoroethyl)[(1-{2-[(2,4-dimethoxybenzyl)sulfamoyl]-4-nitrophenyl}-1H-pyrazol-4-yl)-methyl]carbamate (150 mg, 123 μmol, 50% purity) in dioxane (3 mL), followed by stirring for 4 h at 70° C. The reaction mixture was concentrated in vacuo. Water was added to the residue and the mixture was extracted three times with ethyl acetate. The combined organic phase was filtered over Celite, washed with brine, dried using sodium sulfate, and concentrated in vacuo to give 74 mg crude tert-butyl [(1-{4-amino-2-[(2,4-dimethoxybenzyl)sulfamoyl]phenyl}-1H-pyrazol-4-yl)methyl](2,2-difluoroethyl)carbamate that was used without further purification in the next step.

The crude material from the previous step (74 mg) was dissolved in DMF (2.5 mL) followed by the addition of (2-chlorophenyl)acetic acid (33 mg, 191 μmol), N,N-diisopropylethylamine (89 μL, 510 μmol) and HATU (72.6 mg, 191 μmol). The reaction mixture was stirred for 3 h at room temperature. Saturated aqueous sodium hydrogen carbonate solution was added and the mixture was extracted three times with ethyl acetate. Then all organic phases were combined, washed with brine, dried over a Whatman filter and concentrated in vacuo to give the title compound that was used without further purification (76 mg, 50% purity, 42% yield over 2 steps).

LC-MS (Method A): Rt=1.36 min; MS (ESIpos): m/z=734 (M+H)+

Intermediate 45

2-(Benzylsulfanyl)-4-nitrobenzonitrile

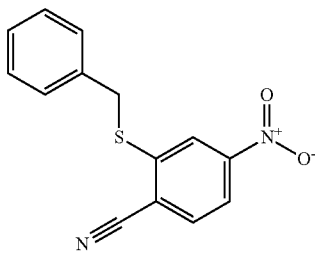 [SMILES: N#Cc1ccc([N+](=O)[O-])cc1SCc1ccccc1]

To a solution of 2-bromo-4-nitrobenzonitrile (400 mg, 1.76 mmol) in dioxane (34 mL), phenylmethanethiol (197 μL, 1.67 mmol), (9,9-dimethyl-9H-xanthene-4,5-diyl)bis(diphenyl-phosphane) (51 mg, 88 μmol), tris(dibenzylideneacetone)dipalladium(0) chloroform adduct (91 mg, 88 μmol), and N,N-diisopropylethylamine (614 μL, 3.5 mmol) were added, and the mixture was stirred for 3 h at 100° C. The reaction mixture was concentrated in vacuo, and taken up in water and ethyl acetate. The aqueous phase was extracted with ethyl acetate. The combined organic phases were dried over a Whatman filter, and concentrated under reduced pressure yielding the crude title compound that was purified by flash chromatography (457 mg, 91% yield, 95% purity).

¹H-NMR (400 MHz, DMSO-d₆) δ [ppm]: 4.58 (s, 2H), 7.28 (dd, 1H), 7.35 (dd, 2H), 7.44 (d, 2H), 8.10 (dd, 1H), 8.12 (d, 1H), 8.30 (d, 1H).

Intermediate 46

2-Cyano-N-(2,4-dimethoxybenzyl)-5-nitrobenzenesulfonamide

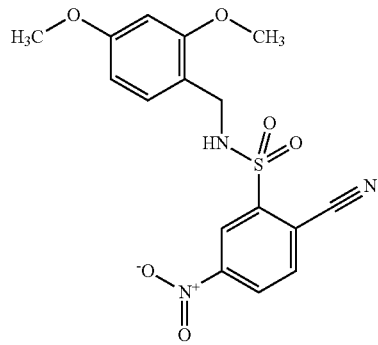

2-(Benzylsulfanyl)-4-nitrobenzonitrile (450 mg, 1.55 mmol, 95% purity) was stirred with N-chlorosuccimide (634 mg, 4.75 mmol) in acetic acid (15 mL) at room temperature for 3 h. The reaction mixture was concentrated in vacuo to give 390 mg crude 2-cyano-5-nitrobenzenesulfonyl chloride that was used without further purification in the next step.

The crude material from the previous step (390 mg) was dissolved in dichloromethane (7.7 mL) followed by the addition of 1-(2,4-dimethoxyphenyl)methanamine (291 mg, 1.74 mmol), and sodium hydrogen carbonate (531 mg, 6.33 mmol) at 0° C. The reaction mixture was stirred for 1 h at 0° C. and for 1 h at room temperature. The reaction mixture was concentrated in vacuo, and taken up in water and ethyl acetate. The aqueous phase was extracted with ethyl acetate. The combined organic phases were washed with brine, dried over a Whatman filter, and concentrated under reduced pressure yielding the crude title compound that was purified by flash chromatography (118 mg, 12% yield, 60% purity).

LC-MS (Method B): Rt=1.05 min; MS (ESIpos): m/z=378 (M+H)+

¹H-NMR (400 MHz, DMSO-d₆) δ [ppm]: 3.56 (s, 3H), 3.62 (s, 3H), 4.11 (d, 2H), 6.11 (d, 1H), 6.26 (dd, 1H), 7.02 (d, 1H), 8.20 (d, 1H), 8.26 (d, 1H), 8.43 (dd, 1H), 8.76 (t, 1H).

Intermediate 47

2-[(2,4-Dimethoxybenzyl)sulfamoyl]-N-hydroxy-4-nitrobenzenecarboximidamide

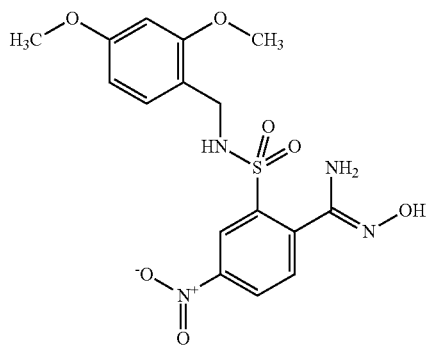

Hydroxyammonium chloride (258 mg, 3.71 mmol) was dissolved in DMSO (5 mL). Potassium tert-butylate (416 mg, 3.71 mmol) was added in small portions at 10° C., followed by stirring for 1 h. Then, a solution of 2-cyano-N-(2,4-dimethoxybenzyl)-5-nitrobenzenesulfonamide (140 mg, 371 µmol) in DMSO (3 mL) was added, and the mixture was stirred overnight at room temperature. The reaction mixture was poured onto ice water. The precipitate was filtered and dried in vacuo to yield the title compound (126 mg, 74% yield, 90% purity).

LC-MS (Method B): Rt=0.99 min; MS (ESIneg): m/z=409 (M−H)−

$^1$H-NMR (400 MHz, DMSO-$d_6$) δ [ppm]: 3.47 (s, 3H), 3.60 (s, 3H), 4.07 (d, 2H), 6.08 (d, 1H), 6.23 (s, 2H), 6.25 (dd, 1H), 7.06 (d, 1H), 7.79 (d, 1H), 7.89 (t, 1H), 8.03 (d, 1H), 8.33 (dd, 1H), 10.02 (s, 1H).

Intermediate 48

N-(2,4-Dimethoxybenzyl)-5-nitro-2-[5-(trifluoromethyl)-1,2,4-oxadiazol-3-yl]benzenesulfonamide

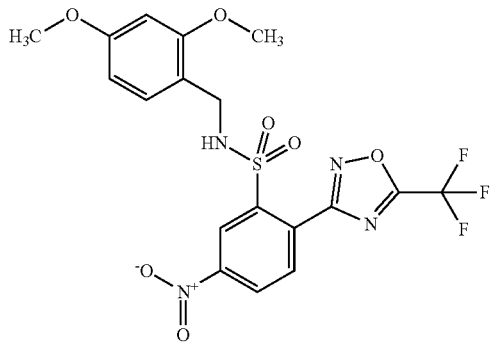

2-[(2,4-Dimethoxybenzyl)sulfamoyl]-N-hydroxy-4-nitrobenzenecarboximidamide (125 mg, 305 µmol) was stirred with trifluoroacetic anhydride (47 µL, 340 µmol) in tetrahydrofuran (2.5 mL) at reflux for 2 h and at room temperature overnight. Another trifluoroacetic anhydride (43 µL, 300 µmol) was added and the reaction was heated to reflux for 90 min. The reaction mixture was taken up in water and extracted with ethyl acetate. The organic phase was washed with brine, dried over a Whatman filter, and concentrated under reduced pressure yielding the crude title compound that was purified by flash chromatography (87 mg, 56% yield, 95% purity).

LC-MS (Method A): Rt=1.36 min; MS (ESIneg): m/z=487 (M−H)−

$^1$H-NMR (400 MHz, DMSO-$d_6$) δ [ppm]: 3.54 (s, 3H), 3.64 (s, 3H), 4.07 (d, 2H), 6.22 (d, 1H), 6.27 (dd, 1H), 7.01 (d, 1H), 7.99 (d, 1H), 8.13 (t, 1H), 8.41 (d, 1H), 8.52 (dd, 1H).

Intermediate 49

2-(2-Chlorophenyl)-N-{3-[(2,4-dimethoxybenzyl)sulfamoyl]-4-[5-(trifluoromethyl)-1,2,4-oxadiazol-3-yl]phenyl}acetamide

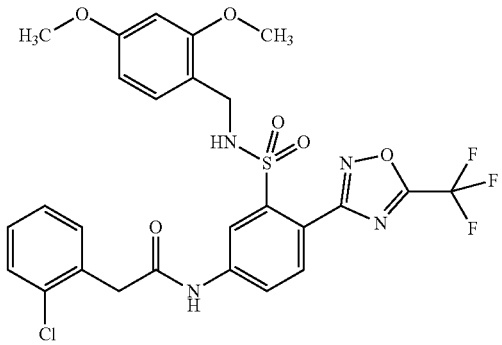 [SMILES: COc1ccc(CNS(=O)(=O)c2cc(NC(=O)Cc3ccccc3Cl)ccc2-c2noc(C(F)(F)F)n2)c(OC)c1]

Tin(II) chloride dihydrate (196 mg, 870 µmol) was added to a solution of N-(2,4-dimethoxy-benzyl)-5-nitro-2-[5-(trifluoromethyl)-1,2,4-oxadiazol-3-yl]benzenesulfonamide (85.0 mg, 174 µmol) in dioxane (2.2 mL), followed by stirring for 4 h at 70° C. and overnight at room temperature. The reaction mixture was concentrated in vacuo. Water was added to the residue and the mixture was extracted three times with ethyl acetate. The combined organic phase was filtered over Celite, dried over a Whatman filter, and concentrated in vacuo to give 74 mg crude 5-amino-N-(2,4-dimethoxybenzyl)-2-[5-(trifluoromethyl)-1,2,4-oxadiazol-3-yl]benzenesulfonamide that was used without further purification in the next step.

The crude material from the previous step (70 mg) was dissolved in DMF (3 mL) followed by the addition of (2-chlorophenyl)acetic acid (31.3 mg, 183 µmol), N,N-diisopropylethylamine (110 µL, 610 µmol) and HATU (69.7 mg, 183 µmol). The reaction mixture was stirred overnight at room temperature. Saturated aqueous sodium hydrogen carbonate solution was added and the mixture was extracted three times with ethyl acetate. Then all organic phases were combined, washed with brine, dried over a Whatman filter and concentrated in vacuo to give the title compound that was used without further purification (112 mg, 40% purity, 8% yield over 2 steps).

LC-MS (Method A): Rt=1.36 min; MS (ESIneg): m/z=609 (M−H)−

Intermediate 50

2-(2-Chlorophenyl)-N-{3-[(2,4-dimethoxybenzyl)sulfamoyl]-4-(4-methyl-1H-pyrazol-1-yl)phenyl}acetamide

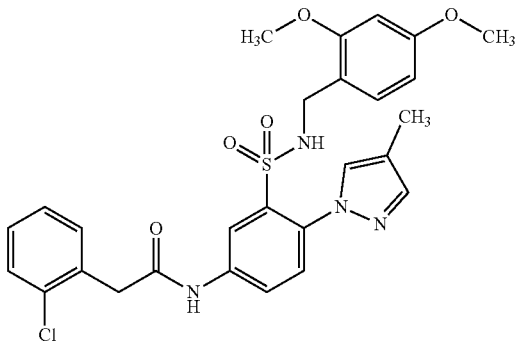 [SMILES: COc1ccc(CNS(=O)(=O)c2cc(NC(=O)Cc3ccccc3Cl)ccc2-n2cc(C)cn2)c(OC)c1]

Platinum/vanadium (130 mg, ½% on charcoal) was added to a solution of N-(2,4-dimeth-oxybenzyl)-2-(4-methyl-1H-pyrazol-1-yl)-5-nitrobenzenesulfonamide (540 mg, 80% purity, 1.00 mmol) in ethanol (12 mL) and stirred under a hydrogen atmosphere for three days at room temperature. The reaction mixture was filtered over Celite and concentrated in vacuo to give 520 mg crude 5-amino-N-(2,4-dimethoxybenzyl)-2-(4-methyl-1H-pyrazol-1-yl)benzenesulfonamide that was used without further purification in the next step.

The crude material from the previous step (520 mg) was dissolved in DMF (13 mL) followed by the addition of (2-chlorophenyl)acetic acid (331 mg, 1.94 mmol), DMF (900 µL, 5.2 mmol) and HATU (737 mg, 1.94 mmol). The reaction mixture was stirred for 72 h at room temperature. Water was added and the mixture was extracted three times with ethyl acetate. Then all organic phases were combined, washed with brine, dried over a Whatman filter and concentrated in vacuo to give the title compound that was purified by preparative HPLC (176 mg, 60% purity, 19% yield over 2 steps).

LC-MS (Method B): Rt=1.34 min; MS (ESIpos): m/z=555 [M+H]$^+$ $^1$H-NMR (400 MHz, DMSO-d$_6$) δ [ppm] 2.09 (s, 3H), 3.59 (s, 3H), 3.66 (s, 3H), 3.79 (s, 2H), 4.01 (d, 2H), 6.33 (d, 1H), 6.34 (dd, 1H), 7.07 (d, 1H), 7.15 (m, 2H), 7.33 (m, 2H), 7.44 (d, 1H), 7.60 (s, 1H), 7.77 (t, 1H), 7.83 (s, 1H), 7.93 (dd, 1H), 8.06 (d, 1H), 10.63 (s, 1H).

Intermediate 51

2-(2-Chlorophenyl)-N-{3-[(2,4-dimethoxybenzyl)sulfamoyl]-4-(3-methoxy-1H-1,2,4-triazol-1-yl)phenyl}acetamide

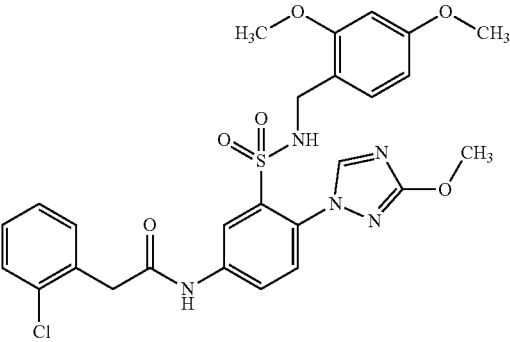 [SMILES: COc1ccc(CNS(=O)(=O)c2cc(NC(=O)Cc3ccccc3Cl)ccc2-n2cnc(OC)n2)c(OC)c1]

Platinum/vanadium (71 mg, ½% on charcoal) was added to a solution of N-(2,4-dimeth-oxybenzyl)-2-(3-methoxy-1H-1,2,4-triazol-1-yl)-5-nitrobenzenesulfonamide (290 mg, 85% purity, 0.55 mmol) in ethanol (6 mL) and stirred under a hydrogen atmosphere for two days at room temperature. The reaction mixture was filtered over Celite and concentrated in vacuo to give 520 mg crude 5-amino-N-(2,4-dimethoxybenzyl)-2-(3-methoxy-1H-1,2,4-triazol-1-yl)benzenesulfonamide that was used without further purification in the next step. The crude material from the previous step (200 mg) was dissolved in DMF (5 mL) followed by the addition of (2-chlorophenyl)acetic acid (331 mg, 1.94 mmol), N,N-diisopropylethylamine (332 µL, 1.9 mmol) and HATU (272 mg, 0.72 mmol). The reaction mixture was stirred for 24 h at room temperature. Water was added and the mixture was extracted three times with ethyl acetate. Then all organic phases were combined, washed with brine, dried over a Whatman filter and concentrated in vacuo to give the title compound that was purified by preparative HPLC (17 mg, 60% purity, 3% yield over 2 steps).

LC-MS (Method B): Rt=1.16 min; MS (ESIpos): m/z=572 [M+H]$^+$

Intermediate 52

2-(2-Chlorophenyl)-N-{4-(4-cyclopropyl-1H-imidazol-1-yl)-3-[(2,4-dimethoxy-benzyl)sulfamoyl]phenyl}acetamide

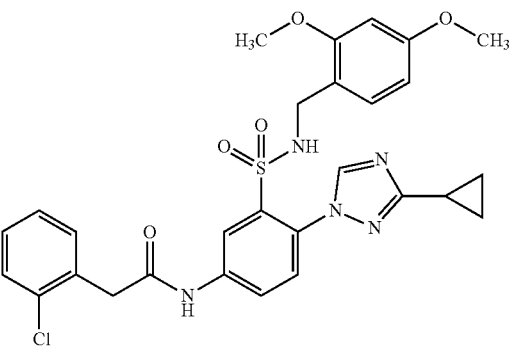

Tin(II) chloride dihydrate (244 mg, 1.08 mmol) was added to a solution of 2-(4-cyclopropyl-1H-imidazol-1-yl)-N-(2,4-dimethoxybenzyl)-5-nitrobenzenesulfonamide (99.0 mg, 216 µmol) in dioxane (5 mL) and stirred for 2 h at 70° C. The reaction mixture was concentrated in vacuo. Water was added to the residue and the mixture was extracted three times with ethyl acetate. The combined organic phase was filtered over Celite, washed with brine, dried using a Whatman filter, and concentrated in vacuo to give 140 mg crude 5-amino-2-(4-cyclopropyl-1H-imidazol-1-yl)-N-(2,4-dimethoxybenzyl)benzenesulfonamide that was used without further purification in the next step.

The crude material from the previous step (140 mg) was dissolved in DMF (3.4 mL) followed by the addition of (2-chlorophenyl)acetic acid (83.6 mg, 490 µmol), N,N-diisopropylethylamine (230 µL, 1.3 mmol) and HATU (186 mg, 490 µmol). The reaction mixture was stirred overnight at 60° C. Water was added and the mixture was extracted three times with ethyl acetate. Then all organic phases were combined, washed with brine, dried over a Whatman filter and concentrated in vacuo to give the title compound that was used without further purification (35 mg, 52% purity, 15% yield over 2 steps).

LC-MS (Method B): Rt=1.25 min; MS (ESIpos): m/z=581 [M+H]$^+$

Intermediate 53

2-(2-Chlorophenyl)-N-{3-[(2,4-dimethoxybenzyl)sulfamoyl]-4-(4-methyl-1H-imidazol-1-yl)phenyl}acetamide

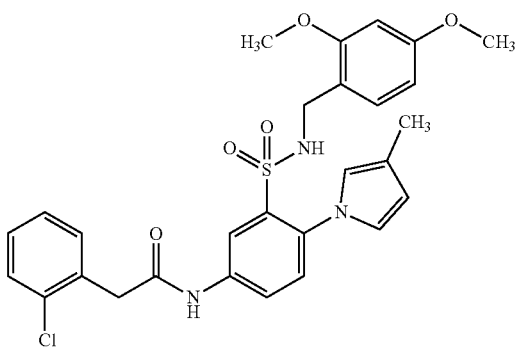 [SMILES: COc1ccc(CNS(=O)(=O)c2cc(NC(=O)Cc3ccccc3Cl)ccc2-n2ccc(C)c2)c(OC)c1]

Tin(II) chloride dihydrate (784 mg, 1.08 mmol) was added to a solution of N-(2,4-dimeth-oxybenzyl)-2-(4-methyl-1H-imidazol-1-yl)-5-nitrobenzenesulfonamide (300 mg, 695 µmol) in dioxane (16 mL) and stirred for 2.5 h at 70° C. The reaction mixture was concentrated in vacuo. Water was added to the residue and the mixture was extracted three times with ethyl acetate. The combined organic phases were filtered over Celite, washed with brine, dried using a Whatman filter, and concentrated in vacuo to give 243 mg crude 5-amino-N-(2,4-dimethoxybenzyl)-2-(4-methyl-1H-imidazol-1-yl)benzenesulfonamide that was used without further purification in the next step.

The crude material from the previous step (243 mg) was dissolved in DMF (6.2 mL) followed by the addition of (2-chlorophenyl)acetic acid (154 mg, 904 µmol), N,N-diisopropylethylamine (420 µL, 2.4 mmol) and HATU (344 mg, 904 µmol). The reaction mixture was stirred overnight at 60° C. Water was added and the mixture was extracted three times with ethyl acetate. Then all organic phases were combined, washed with brine, dried over a Whatman filter and concentrated in vacuo to give the title compound that was purified by HPLC (69 mg, 85% purity, 15% yield over 2 steps).

LC-MS (Method B): Rt=1.19 min, MS (ESIpos): m/z=555 [M+H]$^+$ $^1$H-NMR (400 MHz, DMSO-d$_6$) δ [ppm] 2.13 (s, 3H), 3.64 (s, 3H), 3.71 (s, 3H), 3.89 (d, 2H), 3.90 (s, 2H), 6.42 (dd, 1H), 6.44 (d, 1H), 6.88 (d, 1H), 7.04 (d, 1H), 7.32 (m, 2H), 7.33 (d, 1H), 7.45 (m, 2H), 7.51 (d, 1H), 7.71 (t, 1H), 7.88 (dd, 1H), 8.26 (d, 1H), 10.73 (s, 1H).

Intermediate 54

2-(2-Chlorophenyl)-N-{4-(3-cyclopropyl-1H-pyrazol-1-yl)-3-[(2,4-dimethoxy-benzyl)sulfamoyl]phenyl}acetamide

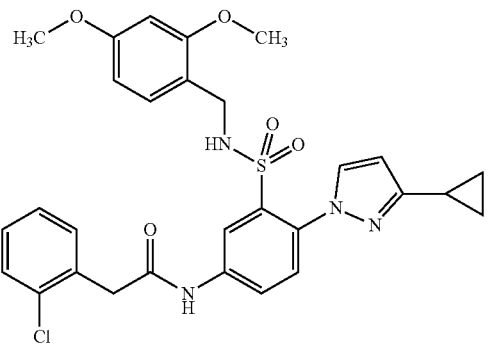 [SMILES: COc1ccc(CNS(=O)(=O)c2cc(NC(=O)Cc3ccccc3Cl)ccc2-n2ccc(C3CC3)n2)c(OC)c1]

Tin(II) chloride dihydrate (437 mg, 1.94 mmol) was added to a solution of 2-(3-cyclopropyl-1H-pyrazol-1-yl)-N-(2,4-dimethoxybenzyl)-5-nitrobenzenesulfonamide (187 mg, 387 µmol) in dioxane (9 mL) and stirred for 4.5 h at 70° C. The reaction mixture was concentrated in vacuo. Water was added to the residue and the mixture was extracted three times with ethyl acetate. The combined organic phases were filtered over Celite, washed with brine, dried using a Whatman filter, and concentrated in vacuo to give 170 mg crude 5-amino-2-(3-cyclopropyl-1H-pyrazol-1-yl)-N-(2,4-dimethoxybenzyl)benzenesulfonamide that was used without further purification in the next step.

The crude material from the previous step (170 mg) was dissolved in DMF (3.3 mL) followed by the addition of (2-chlorophenyl)acetic acid (81 mg, 475 µmol), N,N-diisopropylethylamine (220 µL, 1.3 mmol) and HATU (180 mg, 475 µmol). The reaction mixture was stirred overnight at 60° C. Water was added and the mixture was extracted three times with ethyl acetate. Then all organic phases were combined, washed with brine, dried over a Whatman filter and concentrated in vacuo to give the title compound that was used without further purification (306 mg, 60% purity, 82% yield over 2 steps).

LC-MS (Method B): Rt=1.39 min; MS (ESIpos): m/z=581 [M+H]$^+$ $^1$H-NMR (400 MHz, DMSO-d$_6$) δ [ppm] 0.61 (m, 2H), 0.87 (m, 2H), 1.89 (m, 1H), 3.57 (s, 3H), 3.68 (s, 3H), 3.90 (s, 2H), 4.00 (d, 2H), 6.24 (d, 1H), 6.36 (d, 1H), 6.37 (dd, 1H), 7.08 (d, 1H), 7.33 (m, 2H), 7.45 (d, 1H), 7.46 (m, 2H), 7.83 (t, 1H), 7.91 (d, 1H), 7.94 (dd, 1H), 8.10 (d, 1H), 10.66 (s, 1H).

Intermediate 55

2-(2-Chlorophenyl)-N-{3-[(2,4-dimethoxybenzyl)sulfamoyl]-4-(2H-pyrazolo[3,4-b]pyridin-2-yl)phenyl}acetamide

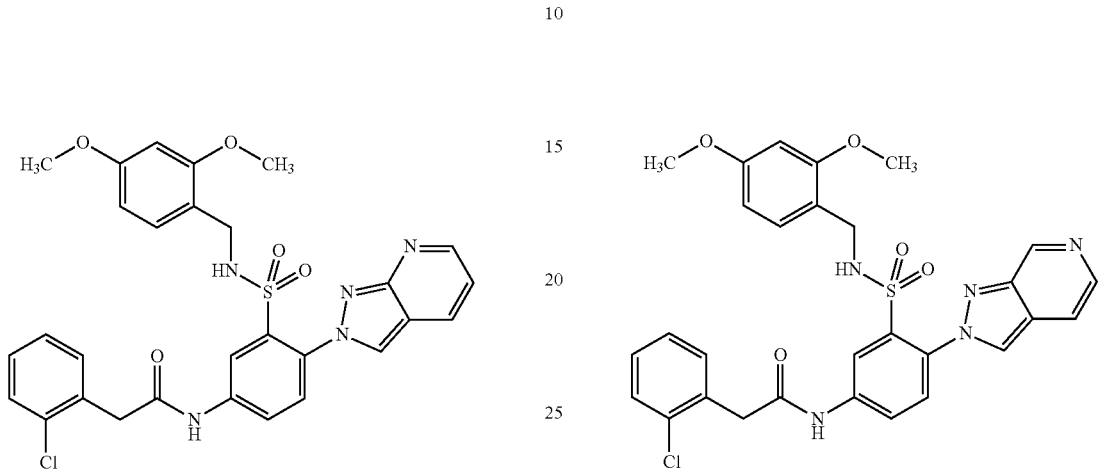

Tin(II) chloride dihydrate (721 mg, 3.19 mmol) was added to a solution of N-(2,4-dimeth-oxybenzyl)-5-nitro-2-(2H-pyrazolo[3,4-b]pyridin-2-yl)benzenesulfonamide (428 mg, 70% purity, 639 μmol) in dioxane (15 mL) and stirred for 4 h at 70° C. The reaction mixture was concentrated in vacuo. Water was added to the residue and the mixture was extracted three times with ethyl acetate. The combined organic phases were filtered over Celite, washed with brine, dried using a Whatman filter, and concentrated in vacuo to give 339 mg crude 5-amino-N-(2,4-dimethoxybenzyl)-2-(2H-pyrazolo[3,4-b]pyridin-2-yl)benzenesulfonamide that was used without further purification in the next step.

The crude material from the previous step (339 mg) was dissolved in DMF (6.4 mL) followed by the addition of (2-chlorophenyl)acetic acid (158 mg, 925 μmol), N,N-diisopropylethylamine (430 μL, 2.5 mmol) and HATU (352 mg, 925 μmol). The reaction mixture was stirred for 5 h at 100° C. Water was added and the mixture was extracted three times with ethyl acetate. Then all organic phases were combined, washed with brine, dried over a Whatman filter and concentrated in vacuo to give the title compound that was used without further purification (751 mg, 45% purity, 89% yield over 2 steps).

LC-MS (Method B): Rt=1.30 min; MS (ESIpos): m/z=592 [M+H]$^+$ $^1$H-NMR (400 MHz, DMSO-d$_6$) δ [ppm] 3.68 (s, 3H), 3.69 (s, 3H), 3.93 (s, 2H), 4.03 (d, 2H), 6.37 (dd, 1H), 6.40 (d, 1H), 7.10 (d, 1H), 7.34 (m, 3H), 7.38 (t, 1H), 7.48 (m, 2H), 7.63 (d, 1H), 7.99 (dd, 1H), 8.22 (d, 1H), 8.37 (dd, 1H), 8.47 (s, 1H), 8.52 (dd, 1H), 10.74 (s, 1H).

Intermediate 56

2-(2-Chlorophenyl)-N-{3-[(2,4-dimethoxybenzyl)sulfamoyl]-4-(2H-pyrazolo[3,4-c]pyridin-2-yl)phenyl}acetamide Tin(II) chloride dihydrate (1.39 g, 6.17 mmol) was added to a solution of N-(2,4-dimeth-oxybenzyl)-5-nitro-2-(2H-pyrazolo[3,4-c]pyridin-2-yl)benzenesulfonamide (610 mg, 1.23 mmol) in dioxane (28 mL) and stirred for 4 h at 70° C. The reaction mixture was concentrated in vacuo. Water was added to the residue and the mixture was extracted three times with ethyl acetate. The combined organic phases were filtered over Celite, washed with brine, dried using a Whatman filter, and concentrated in vacuo to give 498 mg crude 5-amino-N-(2,4-dimethoxybenzyl)-2-(2H-pyrazolo[3,4-c]pyridin-2-yl)benzenesulfonamide that was used without further purification in the next step.

The crude material from the previous step (498 mg) was dissolved in DMF (9.9 mL) followed by the addition of (2-chlorophenyl)acetic acid (246 mg, 1.44 mmol), N,N-diisopropylethylamine (670 μL, 3.8 mmol) and HATU (549 mg, 1.44 mmol). The reaction mixture was stirred overnight at 60° C. Water was added and the mixture was extracted three times with ethyl acetate. Then all organic phases were combined, washed with brine, dried over a Whatman filter and concentrated in vacuo to give the title compound that was used without further purification (1.09 g, 50% purity, 75% yield over 2 steps).

LC-MS (Method B): Rt=1.26 min; MS (ESIpos): m/z=592 [M+H]$^+$ $^1$H-NMR (400 MHz, DMSO-d$_6$) δ [ppm] 3.67 (s, 3H), 3.69 (s, 3H), 3.94 (s, 2H), 4.00 (d, 2H), 6.36 (dd, 1H), 6.38 (d, 1H), 7.08 (d, 1H), 7.35 (m, 2H), 7.40 (t, 1H), 7.48 (m, 2H), 7.68 (d, 1H), 7.87 (dd, 1H), 8.01 (dd, 1H), 8.25 (d, 1H), 8.35 (d, 1H), 8.53 (s, 1H), 8.80 (s, 1H), 10.79 (s, 1H).

Intermediate 57

2-(2-Chlorophenyl)-N-{3-[(2,4-dimethoxybenzyl)sulfamoyl]-4-(2H-pyrazolo[4,3-b]pyridin-2-yl)phenyl}acetamide

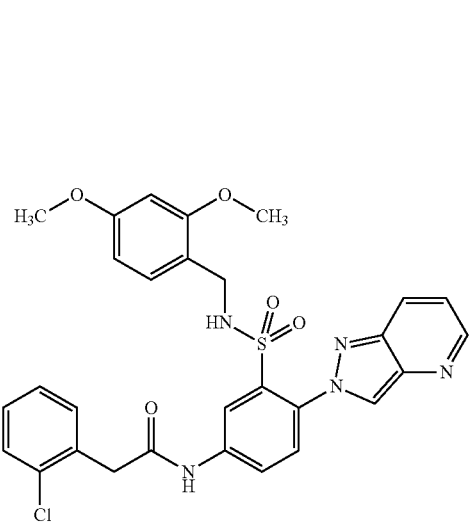 [SMILES: COc1ccc(CNS(=O)(=O)c2cc(NC(=O)Cc3ccccc3Cl)ccc2-n2cc3ncccc3n2)c(OC)c1]

Tin(II) chloride dihydrate (389 mg, 1.72 mmol) was added to a solution of N-(2,4-dimeth-oxybenzyl)-5-nitro-2-(2H-pyrazolo[4,3-b]pyridin-2-yl)benzenesulfonamide (270 mg, 60% purity, 345 μmol) in dioxane (8 mL) and stirred for 195 min at 70° C. The reaction mixture was concentrated in vacuo. Water was added to the residue and the mixture was extracted three times with ethyl acetate. The combined organic phases were filtered over Celite, washed with brine, dried using a Whatman filter, and concentrated in vacuo to give 214 mg crude 5-amino-N-(2,4-dimethoxybenzyl)-2-(2H-pyrazolo[4,3-b]pyridin-2-yl)benzenesulfonamide that was used without further purification in the next step.

The crude material from the previous step (214 mg) was dissolved in DMF (3 mL) followed by the addition of (2-chlorophenyl)acetic acid (75 mg, 437 μmol), N,N-diisopropylethylamine (25 μL, 150 μmol) and HATU (166 mg, 437 μmol). The reaction mixture was stirred overnight at 80° C. Water was added and the mixture was extracted three times with ethyl acetate. Then all organic phases were combined, washed with brine, dried over a Whatman filter and concentrated in vacuo to give the title compound that was used without further purification (405 mg, 25% purity, 50% yield over 2 steps).

LC-MS (Method B): Rt=1.25 min; MS (ESIneg): m/z=590 [M−H]⁻

Intermediate 58

2-(2-Chlorophenyl)-N-{3-[(2,4-dimethoxybenzyl)sulfamoyl]-4-[4-(2-methoxyethyl)-1H-pyrazol-1-yl]phenyl}acetamide

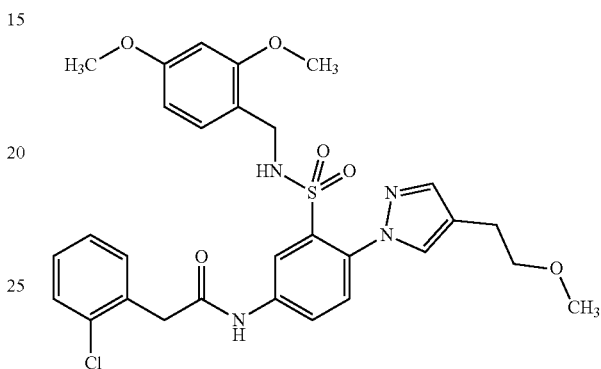

Tin(II) chloride dihydrate (389 mg, 1.72 mmol) was added to a solution of N-(2,4-dimeth-oxybenzyl)-2-[4-(2-methoxyethyl)-1H-pyrazol-1-yl]-5-nitrobenzenesulfonamide (928 mg, 80% purity, 1.56 mmol) in dioxane (20 mL) and stirred for 4 h at 70° C. The reaction mixture was concentrated in vacuo. Water was added to the residue and the mixture was extracted three times with ethyl acetate. The combined organic phases were filtered over Celite, washed with brine, dried using sodium sulfate, and concentrated in vacuo to give 578 mg crude 5-amino-N-(2,4-dimethoxybenzyl)-2-[4-(2-methoxyethyl)-1H-pyrazol-1-yl]benzenesulfonamide that was used without further purification in the next step.

The crude material from the previous step (255 mg) was dissolved in DMF (6 mL) followed by the addition of (2-chlorophenyl)acetic acid (195 mg, 1.14 mmol), N,N-diisopropylethylamine (400 μL, 2.3 mmol) and HATU (434 mg, 1.14 mmol). The reaction mixture was stirred for 2 days at room temperature. Saturated aqueous sodium hydrogen carbonate solution was added and the mixture was extracted three times with ethyl acetate. Then all organic phases were combined, washed with brine, dried over a Whatman filter and concentrated in vacuo to give the title compound that was used without further purification (556 mg, 50% purity, 30% yield over 2 steps).

LC-MS (Method A): Rt=1.32 min; MS (ESIpos): m/z=599 [M+H]⁺

Intermediate 59

2-(2-Chlorophenyl)-N-{3-[(2,4-dimethoxybenzyl)sulfamoyl]-4-(3-fluoro-1H-pyrazol-1-yl)phenyl}acetamide

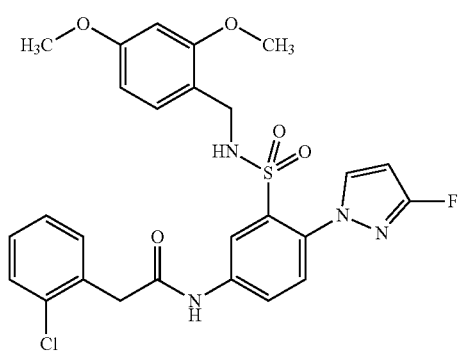 [SMILES: COc1ccc(CNS(=O)(=O)c2cc(NC(=O)Cc3ccccc3Cl)ccc2-n2ccc(F)n2)c(OC)c1]

Tin(II) chloride dihydrate (1.21 g, 5.36 mmol) was added to a solution of N-(2,4-dimethoxy-benzyl)-2-(3-fluoro-1H-pyrazol-1-yl)-5-nitrobenzenesulfonamide (550 mg, 85% purity, 1.07 mmol) in dioxane (25 mL) and stirred for 3 h at 70° C. The reaction mixture was concentrated in vacuo. Water was added to the residue and the mixture was extracted three times with ethyl acetate. The combined organic phases were filtered over Celite, washed with brine, dried using a Whatman filter, and concentrated in vacuo to give 1.0 g crude 5-amino-N-(2,4-dimethoxybenzyl)-2-(3-fluoro-1H-pyrazol-1-yl)benzenesulfonamide that was used without further purification in the next step.

The crude material from the previous step (1.0 g) was dissolved in DMF (7.6 mL) followed by the addition of (2-chlorophenyl)acetic acid (189 mg, 1.11 mmol), N,N-diisopropylethylamine (64 µL, 370 µmol) and HATU (421 mg, 1.11 mmol). The reaction mixture was stirred overnight at 60° C. Water was added and the mixture was extracted three times with ethyl acetate. Then all organic phases were combined, washed with brine, dried over a Whatman filter and concentrated in vacuo to give the title compound that was used without further purification (847 mg, 40% purity, 57% yield over 2 steps).

LC-MS (Method B): Rt=1.34 min; MS (ESIpos): m/z=559 [M+H]$^+$

Intermediate 60

2-(2-Chlorophenyl)-N-(4-{4-[(2,2-difluoroethyl)amino]-1H-pyrazol-1-yl}-3-[(2,4-dimethoxybenzyl)sulfamoyl]phenyl)acetamide

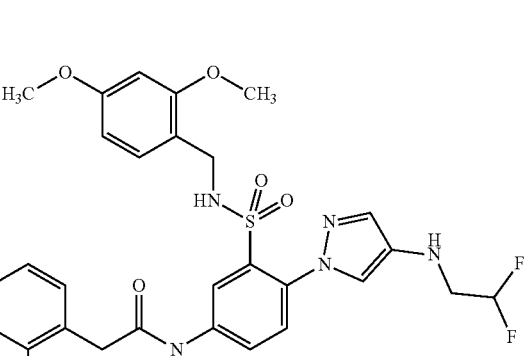

Tin(II) chloride dihydrate (318 mg, 1.41 mmol) was added to a solution of 2-{4-[(2,2-difluoroethyl)amino]-1H-pyrazol-1-yl}-N-(2,4-dimethoxybenzyl)-5-nitrobenzenesulfonamide (140 mg, 281 µmol) in dioxane (3.6 mL) and stirred for 4 h at 70° C. The reaction mixture was concentrated in vacuo. Water was added to the residue and the mixture was extracted three times with ethyl acetate. The combined organic phases were filtered over Celite, washed with brine, dried using a Whatman filter, and concentrated in vacuo to give 114 mg crude 5-amino-2-{4-[(2,2-difluoroethyl)amino]-1H-pyrazol-1-yl}-N-(2,4-dimethoxy-benzyl)benzenesulfonamide that was used without further purification in the next step.

The crude material from the previous step (107 mg) was dissolved in DMF (4.5 mL) followed by the addition of (2-chlorophenyl)acetic acid (48 mg, 282 µmol), N,N-diisopropylethylamine (160 µL, 940 µmol) and HATU (107 mg, 282 µmol). The reaction mixture was stirred overnight at room temperature. Water was added and the mixture was extracted three times with ethyl acetate. Then all organic phases were combined, washed with brine, dried over a Whatman filter and concentrated in vacuo to give the title compound that was used without further purification (196 mg, 30% purity, 34% yield over 2 steps).

LC-MS (Method B): Rt=1.27 min; MS (ESIpos): m/z=620 [M+H]$^+$

Intermediate 61

N-{3-[(2,4-Dimethoxybenzyl)sulfamoyl]-4-(4-methyl-1H-pyrazol-1-yl)phenyl}-2-(2-fluorophenyl)acetamide

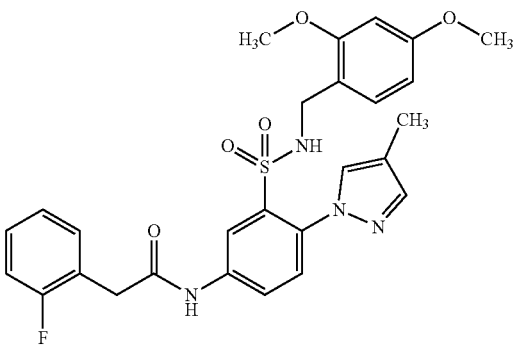 [SMILES: COc1ccc(CNS(=O)(=O)c2cc(NC(=O)Cc3ccccc3F)ccc2-n2cc(C)cn2)c(OC)c1]

Tin(II) chloride dihydrate (1.49 g, 6.61 mmol) was added to a solution of N-(2,4-dimeth-oxybenzyl)-2-(4-methyl-1H-pyrazol-1-yl)-5-nitrobenzenesulfonamide (715 mg, 80% purity, 1.32 mmol) in dioxane (17 mL) and stirred for 4.5 h at 70° C. The reaction mixture was concentrated in vacuo. Water was added to the residue and the mixture was extracted three times with ethyl acetate. The combined organic phases were filtered over Celite, washed with brine, dried using a Whatman filter, and concentrated in vacuo to give 440 mg crude 5-amino-N-(2,4-dimethoxybenzyl)-2-(4-methyl-1H-pyrazol-1-yl)benzenesul-fonamide that was used without further purification in the next step.

The crude material from the previous step (435 mg) was dissolved in DMF (8 mL) followed by the addition of (2-fluorophenyl)acetic acid (187 mg, 1.22 mmol), N,N-diisopropylethylamine (565 µL, 3.2 mmol) and HATU (462 mg, 1.22 mmol). The reaction mixture was stirred overnight at 60° C. Water was added and the mixture was extracted three times with ethyl acetate. Then all organic phases were combined, washed with brine, dried over a Whatman filter and concentrated in vacuo to give the title compound that was used without further purification (634 mg, 65% purity, 58% yield over 2 steps).

LC-MS (Method B): Rt=1.31 min; MS (ESIpos): m/z=539 [M+H]$^+$ $^1$H-NMR (400 MHz, DMSO-d$_6$) δ [ppm] 2.09 (s, 3H), 3.60 (s, 3H), 3.67 (s, 3H), 3.90 (s, 2H), 4.00 (d, 2H), 6.34 (dd, 1H), 6.35 (d, 1H), 7.06 (d, 1H), 7.33 (m, 2H), 7.44 (d, 1H), 7.46 (m, 2H), 7.60 (s, 1H), 7.76 (t, 1H), 7.83 (s, 1H), 7.93 (dd, 1H), 8.08 (d, 1H), 10.65 (s, 1H).

Intermediate 62

2-(2-Fluorophenyl)-N-{4-(4-cyclopropyl-1H-imidazol-1-yl)-3-[(2,4-dimethoxybenzyl)-sulfamoyl]phenyl}acetamide

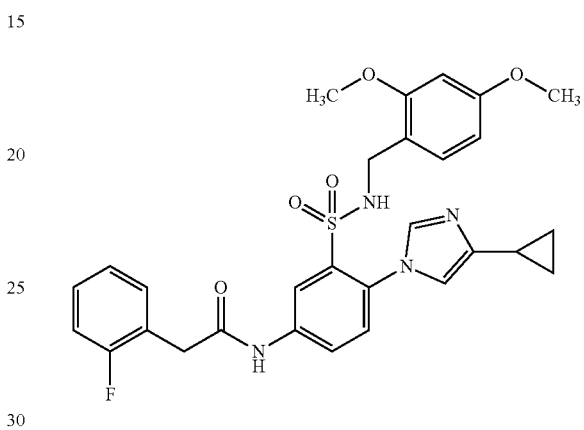

Tin(II) chloride dihydrate (650 mg, 2.88 mmol) was added to a solution of 2-(4-cyclopropyl-1H-imidazol-1-yl)-N-(2,4-dimethoxybenzyl)-5-nitrobenzenesulfonamide (440.0 mg, 60% purity, 576 µmol) in dioxane (13 mL) and stirred for 4 h at 70° C. The reaction mixture was concentrated in vacuo. Water was added to the residue and the mixture was extracted three times with ethyl acetate. The combined organic phases were filtered over Celite, washed with brine, dried using a Whatman filter, and concentrated in vacuo to give 252 mg crude 5-amino-2-(4-cyclopropyl-1H-imidazol-1-yl)-N-(2,4-dimethoxybenzyl)benzenesulfonamide that was used without further purification in the next step.

The crude material from the previous step (250 mg) was dissolved in DMF (1.2 mL) followed by the addition of (2-fluorophenyl)acetic acid (27.0 mg, 175 µmol), N,N-diisopropylethylamine (81 µL, 470 µmol) and HATU (67 mg, 175 µmol). The reaction mixture was stirred overnight at 60° C. and for another 2.5 h at 100° C. Water was added and the mixture was extracted three times with ethyl acetate. Then all organic phases were combined, washed with brine, dried over a Whatman filter and concentrated in vacuo to give the title compound that was used without further purification (50 mg, 50% purity, 8% yield over 2 steps).

LC-MS (Method B): Rt=1.21 min; MS (ESIpos): m/z=565 [M+H]$^+$

Intermediate 63

N-{4-(3-Cyclopropyl-1H-pyrazol-1-yl)-3-[(2,4-dimethoxybenzyl)sulfamoyl]phenyl}-2-(2-fluorophenyl)acetamide

Intermediate 64

N-{3-[(2,4-Dimethoxybenzyl)sulfamoyl]-4-[4-(2-methoxyethyl)-1H-pyrazol-1-yl]-phenyl}-2-(2-fluorophenyl)acetamide

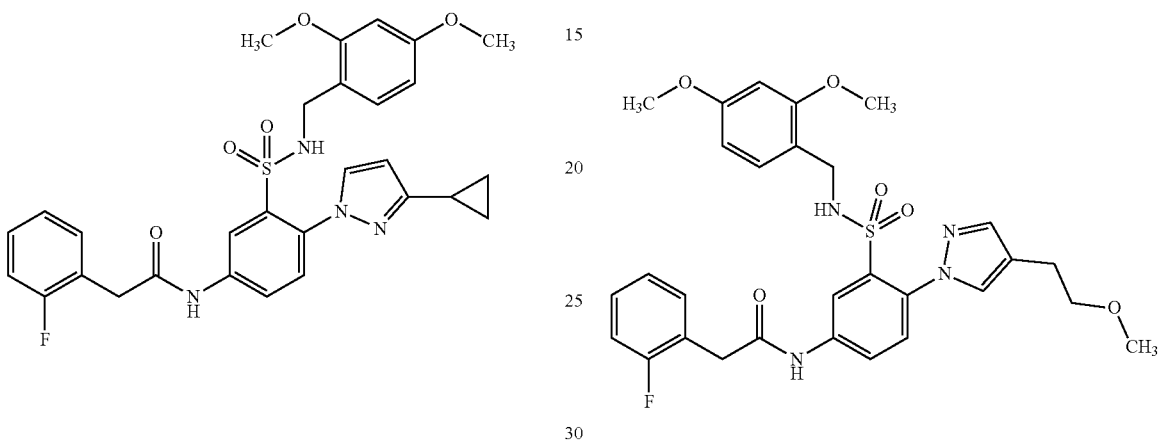

Tin(II) chloride dihydrate (783 mg, 3.47 mmol) was added to a solution of 2-(3-cyclopropyl-1H-pyrazol-1-yl)-N-(2,4-dimethoxybenzyl)-5-nitrobenzenesulfonamide (530 mg, 60% purity, 694 μmol) in dioxane (16 mL) and stirred for 4 h at 70° C. The reaction mixture was concentrated in vacuo. Water was added to the residue and the mixture was extracted three times with ethyl acetate. The combined organic phases were filtered over Celite, washed with brine, dried using a Whatman filter, and concentrated in vacuo to give 315 mg crude 5-amino-2-(3-cyclopropyl-1H-pyrazol-1-yl)-N-(2,4-dimethoxybenzyl)benzenesulfonamide that was used without further purification in the next step.

The crude material from the previous step (315 mg) was dissolved in DMF (5.7 mL) followed by the addition of (2-fluorophenyl)acetic acid (127 mg, 827 μmol), N,N-diisopropylethylamine (380 μL, 2.2 mmol) and HATU (314 mg, 827 μmol). The reaction mixture was stirred overnight at 60° C. Water was added and the mixture was extracted three times with ethyl acetate. Then all organic phases were combined, washed with brine, dried over a Whatman filter and concentrated in vacuo to give the title compound that was used without further purification (507 mg, 50% purity, 65% yield over 2 steps).

LC-MS (Method B): Rt=1.36 min; MS (ESIpos): m/z=565 [M+H]$^+$ $^1$H-NMR (400 MHz, DMSO-d$_6$) δ [ppm] 0.61 (m, 2H), 0.87 (m, 2H), 1.89 (m, 1H), 3.56 (s, 3H), 3.67 (s, 3H), 3.79 (s, 2H), 4.00 (d, 2H), 6.24 (d, 1H), 6.35 (d, 1H), 6.36 (dd, 1H), 7.07 (d, 1H), 7.33 (m, 2H), 7.42 (m, 2H), 7.44 (d, 1H), 7.84 (t, 1H), 7.91 (d, 1H), 7.95 (dd, 1H), 8.07 (d, 1H), 10.64 (s, 1H).

Tin(II) chloride dihydrate (389 mg, 1.72 mmol) was added to a solution of N-(2,4-dimeth-oxybenzyl)-2-[4-(2-methoxyethyl)-1H-pyrazol-1-yl]-5-nitrobenzenesulfonamide (928 mg, 80% purity, 1.56 mmol) in dioxane (20 mL) and stirred for 4 h at 70° C. The reaction mixture was concentrated in vacuo. Water was added to the residue and the mixture was extracted three times with ethyl acetate. The combined organic phases were filtered over Celite, washed with brine, dried using sodium sulfate, and concentrated in vacuo to give 578 mg crude 5-amino-N-(2,4-dimethoxybenzyl)-2-[4-(2-methoxyethyl)-1H-pyrazol-1-yl]benzenesulfonamide that was used without further purification in the next step.

The crude material from the previous step (255 mg) was dissolved in DMF (6 mL) followed by the addition of (2-fluorophenyl)acetic acid (176 mg, 1.14 mmol), N,N-diisopropylethylamine (400 μL, 2.3 mmol) and HATU (434 mg, 1.14 mmol). The reaction mixture was stirred for 2 days at room temperature. Saturated aqueous sodium hydrogen carbonate solution was added and the mixture was extracted three times with ethyl acetate. Then all organic phases were combined, washed with brine, dried over a Whatman filter and concentrated in vacuo to give the title compound that was used without further purification (503 mg, 50% purity, 28% yield over 2 steps).

LC-MS (Method A): Rt=1.29 min; MS (ESIpos): m/z=583 [M+H]$^+$

Intermediate 65

2-(Benzylsulfanyl)-4-nitrobenzoic acid

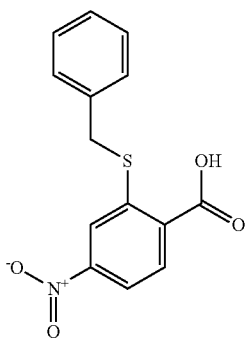

To a solution of 2-bromo-4-nitrobenzoic acid (5.00 g, 20.3 mmol) in dioxane (500 mL), phenylmethanethiol (2.4 mL, 20.3 mmol), (9,9-dimethyl-9H-xanthene-4,5-diyl)bis(diphenyl-phosphane) (588 mg, 1.02 mmol), tris(dibenzylideneacetone)dipalladium(0) chloroform adduct (1.05 g, 1.02 μmol), and N,N-diisopropylethylamine (7.1 mL, 41 mmol) were added, and the mixture was stirred for 2 h at 100° C. The reaction mixture was concentrated in vacuo, and purified by flash chromatography to yield the title compound (6.2 g, 96% yield, 85% purity).

LC-MS (Method A): Rt=1.14 min; MS (ESIneg): m/z=288 (M–H)–

$^1$H-NMR (400 MHz, DMSO-$d_6$) δ [ppm]: 4.37 (s, 2H), 7.28 (dd, 1H), 7.36 (dd, 2H), 7.47 (d, 2H), 7.99 (dd, 1H), 8.08 (d, 1H), 8.20 (d, 1H).

Intermediate 66

2-(Benzylsulfanyl)-4-nitrobenzohydrazide

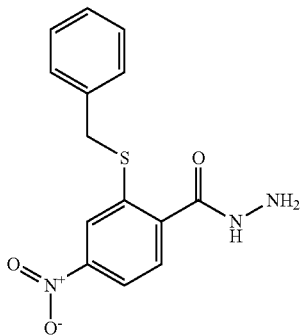 [SMILES: NNC(=O)c1ccc([N+](=O)[O-])cc1SCc1ccccc1]

To a slurry of 2-(benzylsulfanyl)-4-nitrobenzoic acid (8.41 g, 29.1 mmol) in tetrahydrofuran (220 mL), N,N'-dicyclohexylcarbodiimide (6.6 g, 32 mmol), 1-hydroxypyrrolidine-2,5-dione (3.68 g, 32 mmol), and N,N-diisopropylethylamine (5.6 mL, 32 mmol) were added, and the mixture was stirred for 1 h at room temperature. Then, hydrazine hydrate (1:1) (1.6 mL, 32 mmol) was added, and stirring at room temperature was continued for 21 h. Water was added to the reaction mixture, and it was extracted with ethyl acetate. The combined organic phases were washed with brine, dried over a Whatman filter, and concentrated under reduced pressure yielding the crude title compound that was purified by flash chromatography (3.71 g, 36% yield, 85% purity).

LC-MS (Method B): Rt=0.95 min; MS (ESIpos): m/z=304 (M+H)+

$^1$H-NMR (400 MHz, DMSO-$d_6$) δ [ppm]: 4.36 (s, 2H), 4.56 (s, 2H), 7.26 (dd, 1H), 7.33 (dd, 2H), 7.41 (d, 2H), 7.56 (d, 1H), 8.01 (dd, 1H), 8.14 (d, 1H), 9.78 (s, 1H).

Intermediate 67

2-(Benzylsulfanyl)-4-nitro-N'-(trifluoroacetyl)benzohydrazide

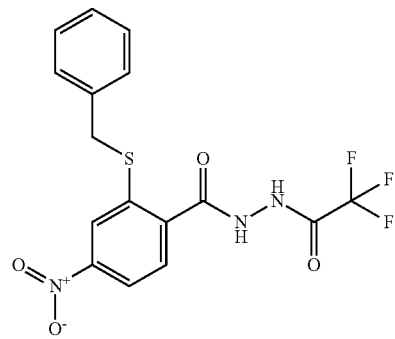 [SMILES: O=C(NNC(=O)C(F)(F)F)c1ccc([N+](=O)[O-])cc1SCc1ccccc1]

To a slurry of 2-(benzylsulfanyl)-4-nitrobenzohydrazide (3.70 g, 85% purity, 10.4 mmol) in acetonitrile (86 mL), N,N-diisopropylethylamine (2.2 mL, 12 mmol), and trifluoroacetic anhydride (1.6 ml, 11 mmol) were added at –50° C. The mixture was allowed to warm to room temperature and stirred for 17 h. The reaction was poured into aqueous sodium hydroxide solution (5%). The mixture was extracted with ethyl acetate. The combined organic phases were washed with brine, dried over a Whatman filter, and concentrated under reduced pressure yielding the crude title compound that was purified by flash chromatography (4.35 g, 84% yield, 80% purity).

LC-MS (Method A): Rt=1.13 min; MS (ESIneg): m/z=398 (M–H)–

$^1$H-NMR (400 MHz, DMSO-$d_6$) δ [ppm]: 4.38 (s, 2H), 7.25 (dd, 1H), 7.33 (dd, 2H), 7.42 (d, 2H), 7.66 (d, 1H), 8.03 (dd, 1H), 8.16 (d, 1H).

Intermediate 68

2-[2-(Benzylsulfanyl)-4-nitrophenyl]-5-(trifluoromethyl)-1,3,4-oxadiazole

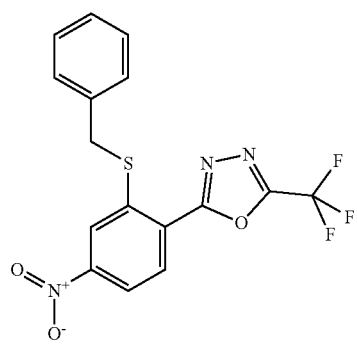 [SMILES: O=[N+]([O-])c1ccc(-c2nnc(C(F)(F)F)o2)c(SCc2ccccc2)c1]

A solution of 2-(benzylsulfanyl)-4-nitro-N-(trifluoroacetyl)benzohydrazide (4.34 g, 80% purity, 8.69 mmol) and 3,3,3-triethyl-1-(methoxycarbonyl)diazathian-3-ium-1-ide 2,2-dioxide (8.29 g, 34.8 mmol) in tetrahydrofuran (150 mL) was irradiated for 30 min at 150° C. in the microwave. Water was added to the reaction mixture, and it was extracted with ethyl acetate. The combined organic phases were washed with brine, dried over a Whatman filter, and concentrated under reduced pressure yielding the crude title compound that was purified by flash chromatography (3.28 g, 94% yield, 95% purity).

LC-MS (Method A): Rt=1.43 min; MS (ESIpos): m/z=382 (M+H)+

$^1$H-NMR (400 MHz, DMSO-$d_6$) δ [ppm]: 4.55 (s, 2H), 7.29 (dd, 1H), 7.35 (dd, 2H), 7.47 (d, 2H), 8.16 (dd, 1H), 8.22 (d, 1H), 8.38 (d, 1H).

Intermediate 69

N-(2,4-Dimethoxybenzyl)-5-nitro-2-[5-(trifluoromethyl)-1,3,4-oxadiazol-2-yl]benzenesulfonamide

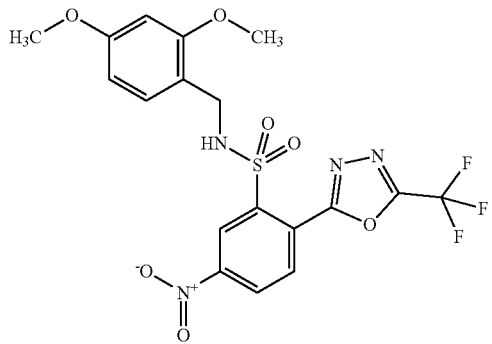

2-[2-(Benzylsulfanyl)-4-nitrophenyl]-5-(trifluoromethyl)-1,3,4-oxadiazole (3.60 g, 95% purity, 8.97 mmol) was stirred with N-chlorosuccimide (3.59 g, 26.9 mmol) in acetic acid (80 mL) at room temperature for 6 h. The reaction mixture was concentrated in vacuo to give 9.14 g crude 5-nitro-2-[5-(trifluoromethyl)-1,3,4-oxadiazol-2-yl]benzenesulfonyl chloride that was used without further purification in the next step.

Crude material from the previous step (3.21 g) was dissolved in dichloromethane (42 mL) followed by the addition of sodium hydrogen carbonate (1.51 g, 17.9 mmol), and slow addition of 1-(2,4-dimethoxyphenyl)methanamine (1.31 mL, 9 mmol) at room temperature. The reaction mixture was stirred for 17 h at room temperature. Water was added to the reaction mixture, and it was extracted with dichloromethane. The combined organic phases were washed with brine, dried over a Whatman filter, and concentrated under reduced pressure yielding the crude title compound that was purified by flash chromatography (582 mg, 13% yield, 95% purity).

LC-MS (Method A): Rt=1.31 min; MS (ESIneg): m/z=487 (M−H)−

$^1$H-NMR (400 MHz, DMSO-$d_6$) δ [ppm]: 3.56 (s, 3H), 3.65 (s, 3H), 4.06 (d, 2H), 6.22 (d, 1H), 6.26 (dd, 1H), 6.97 (d, 1H), 8.14 (d, 1H), 8.43 (d, 1H), 8.51 (t, 1H), 8.55 (dd, 1H).

Intermediate 70

2-(2-Chlorophenyl)-N-{3-[(2,4-dimethoxybenzyl)sulfamoyl]-4-[5-(trifluoromethyl)-1,3,4-oxadiazol-2-yl]phenyl}acetamide

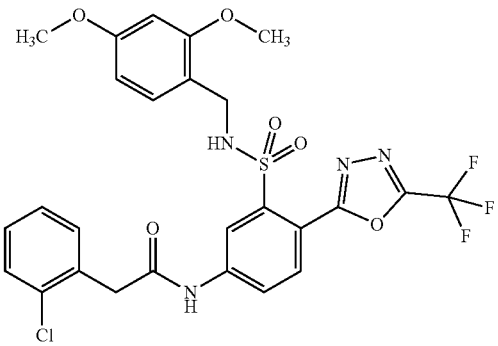 [SMILES: COc1ccc(CNS(=O)(=O)c2cc(NC(=O)Cc3ccccc3Cl)ccc2-c2nnc(C(F)(F)F)o2)c(OC)c1]

Tin(II) chloride dihydrate (1.02 g, 4.51 mmol) was added to a solution of N-(2,4-dimethoxy-benzyl)-5-nitro-2-[5-(trifluoromethyl)-1,3,4-oxadiazol-2-yl]benzenesulfonamide (464 mg, 95% purity, 903 μmol) in dioxane (12 mL), followed by stirring for 7 h at 70° C. and overnight at room temperature. The reaction mixture was concentrated in vacuo. Water was added to the residue and the mixture was extracted three times with ethyl acetate. The combined organic phases were filtered over Celite, dried over a Whatman filter, and concentrated in vacuo to give 485 mg crude 5-amino-N-(2,4-dimethoxybenzyl)-2-[5-(trifluoromethyl)-1,3,4-oxadiazol-2-yl]benzenesulfonamide that was used without further purification in the next step.

Crude material from the previous step (207 mg) was dissolved in DMF (9 mL) followed by the addition of (2-chlorophenyl)acetic acid (154 mg, 902 μmol), N,N-diisopropylethylamine (310 μL, 1.8 mmol) and HATU (343 mg, 902 μmol). The reaction mixture was stirred for 5 h at room temperature. Saturated aqueous sodium hydrogen carbonate solution was added and the mixture was extracted three times with ethyl acetate. Then all organic phases were combined, washed with brine, dried over a Whatman filter and concentrated in vacuo to give the title compound that was used without further purification (369 mg, 40% purity, 10% yield over 2 steps).

LC-MS (Method A): Rt=0.81 min; MS (ESIneg): m/z=609 (M−H)−

Intermediate 71

N-{3-[(2,4-Dimethoxybenzyl)sulfamoyl]-4-[5-(trifluoromethyl)-1,3,4-oxadiazol-2-yl]phenyl}-2-(2-fluorophenyl)acetamide

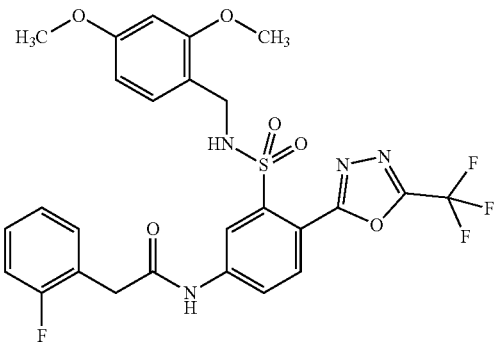 [SMILES: COc1ccc(CNS(=O)(=O)c2cc(NC(=O)Cc3ccccc3F)ccc2-c2nnc(C(F)(F)F)o2)c(OC)c1]

Tin(II) chloride dihydrate (1.02 g, 4.51 mmol) was added to a solution of N-(2,4-dimethoxybenzyl)-5-nitro-2-[5-(trifluoromethyl)-1,3,4-oxadiazol-2-yl]benzenesulfonamide (464 mg, 95% purity, 903 µmol) in dioxane (12 mL), followed by stirring for 7 h at 70° C. and overnight at room temperature. The reaction mixture was concentrated in vacuo. Water was added to the residue and the mixture was extracted three times with ethyl acetate. The combined organic phases were filtered over Celite, dried over a Whatman filter, and concentrated in vacuo to give 485 mg crude 5-amino-N-(2,4-dimethoxybenzyl)-2-[5-(trifluoromethyl)-1,3,4-oxadiazol-2-yl]benzenesulfonamide that was used without further purification in the next step.

Crude material from the previous step (207 mg) was dissolved in DMF (9 mL) followed by the addition of (2-fluorophenyl)acetic acid (139 mg, 902 µmol), N,N-diisopropylethylamine (310 µL, 1.8 mmol) and HATU (343 mg, 902 µmol). The reaction mixture was stirred for 5 h at room temperature. Saturated aqueous sodium hydrogen carbonate solution was added and the mixture was extracted three times with ethyl acetate. Then all organic phases were combined, washed with brine, dried over a Whatman filter and concentrated in vacuo to give the title compound that was used without further purification (403 mg, 40% purity, 16% yield over 2 steps).

LC-MS (Method A): Rt=0.77 min; MS (ESIneg): m/z=593 (M−H)−

Intermediate 72

2-Bromo-N-(2,4-dimethoxybenzyl)-5-nitrobenzenesulfonamide

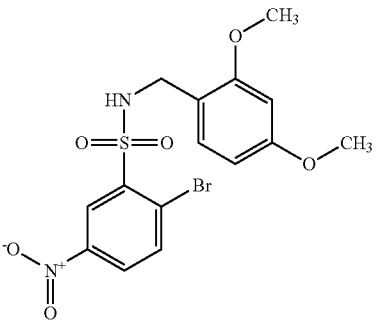

2-Bromo-5-nitrobenzenesulfonyl chloride (5.00 g, 16.6 mmol) was dissolved in dichloromethane (48 ml) and sodium bicarbonate (2.80 g, 33.3 mmol) was added, followed by the slow addition of 1-(2,4-dimethoxyphenyl)methanamine (2.7 ml, 18 mmol). The reaction was stirred for 30 minutes at room temperature. Dichloromethane and water were added. The phases were separated and the organic phase was washed with brine. The combined organic phases were dried over Whatman filter and the solvent was removed under reduced pressure. The crude was crystallized from diethyl ether (5.57 g, 78% yield).

LC-MS (Method B): Rt=1.16 min; MS (ESIneg): m/z=429 [M−H]−

Intermediate 73

5-Amino-2-bromo-N-(2,4-dimethoxybenzyl)benzenesulfonamide

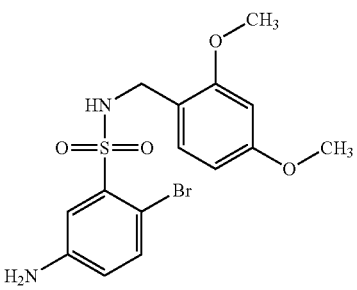 [SMILES: COc1ccc(CNS(=O)(=O)c2cc(N)ccc2Br)c(OC)c1]

Ammonium chloride (3.52 g, 65.7 mmol) and iron powder (3.67 g, 65.7 mmol) were suspended in water (150 ml). Then a solution of 2-bromo-N-(2,4-dimethoxybenzyl)-5-nitrobenzenesulfonamide (5.67 g, 13.1 mmol) in THF/methanol (1/1; 150 ml) was added and the reaction was heated at 80° C. for 2 h. Afterwards the mixture was filtered over Celite, the solvent was removed under reduced pressure. The crude was partitioned in ethyl acetate and water. The phases were separated and the aqueous phase was extracted with ethyl acetate. The combined organic phases were dried over Whatman filter and the solvent was removed under reduced pressure. The crude was used in the next step without further purification (5.10 g, 96% purity, 97% yield)

LC-MS (Method A): Rt=1.05 min; MS (ESIneg): m/z=399 [M−H]−

Intermediate 74

N-{4-Bromo-3-[(2,4-dimethoxybenzyl)sulfamoyl]phenyl}-2-(2-chlorophenyl)acetamide

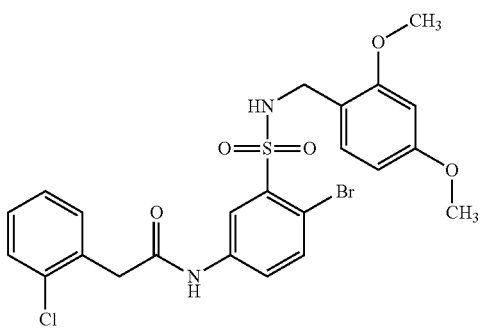 [SMILES: COc1ccc(CNS(=O)(=O)c2cc(NC(=O)Cc3ccccc3Cl)ccc2Br)c(OC)c1]

5-Amino-2-bromo-N-(2,4-dimethoxybenzyl)benzenesulfonamide (5.00 g, 12.5 mmol) was dissolved in DMF (100 ml) and (2-chlorophenyl)acetic acid (2.55 g, 15.0 mmol) was added followed by the addition of N,N-diisopropylethylamine (11 ml, 62 mmol) and HATU (6.16 g, 16.2 mmol). The reaction was stirred at 50° C. for 16 h. The solvent was removed under reduced pressure and ethyl acetate and water were added. The phases were separated and the aqueous phase was extracted with ethyl acetate. The combined organic phases were dried over Whatman filter and the solvent was removed under reduced pressure. The crude was purified by chromatography on silica gel (Biotage, ethyl acetate/hexane) to yield the title compound (5.70 g, 94% purity, 83% yield)

LC-MS (Method A): Rt=1.29 min; MS (ESIneg): m/z=551 [M−H]−

Intermediate 75

2-Bromo-5-nitrobenzenesulfonamide

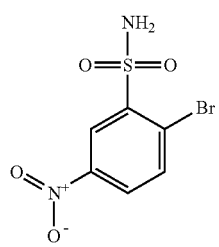

2-Bromo-5-nitrobenzenesulfonyl chloride (20.0 g, 66.6 mmol) was dissolved in 1,4-dioxane (100 ml) and cooled to 0° C. Aqueous ammonia (400 ml, 0.50 M, 200 mmol) was slowly added and stirring was continued at room temperature until completion of the reaction. The solvent was removed under reduced pressure and dichloromethane was added. The organic phase was washed with water three times. The suspension was filtered (solid is product), and the organic phase was washed with brine. The combined organic phases were dried over sodium sulfate and the solvent was removed under reduced pressure. The crude was recrystallized from diethyl ether to yield 16.4 g (93% purity, 88% yield).

LC-MS (Method B): Rt=0.45 min; MS (ESIpos): m/z=281 [M+H]+

Intermediate 76

2-Bromo-N-[(dimethylamino)methylidene]-5-nitrobenzenesulfonamide

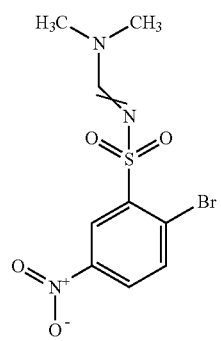

2-Bromo-5-nitrobenzenesulfonamide (16.4 g, 58.3 mmol) was dissolved in DMF (200 ml) at room temperature and 1,1-dimethoxy-N,N-dimethylmethanamine (15 ml, 120 mmol) was added. Stirring was continued until completion of the reaction. The solvent was removed under reduced pressure and the crude partitioned between dichloromethane and brine. The organic phase was dried over Whatman filter and the solvent was removed under reduced pressure. The crude was used in the next step without further purification (19.2 g, 78% purity, 98% yield).

LC-MS (Method A): Rt=0.92 min; MS (ESIpos): m/z=336 [M+H]+

Intermediate 77

5-Amino-2-bromo-N-[(dimethylamino)methylidene]benzenesulfonamide

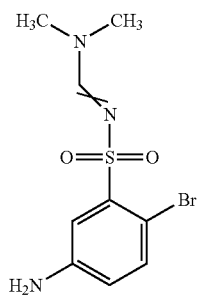 [SMILES: CN(C)CNS(=O)(=O)c1cc(N)ccc1Br]

2-Bromo-N-[(dimethylamino)methylidene]-5-nitrobenzenesulfonamide (12.7 g, 37.8 mmol) was dissolved in methanol (170 ml) and the flask was flushed with nitrogen. Platinum on charcoal (5% loading, 1.61 g, 8.26 mmol) was added and the flask was evacuated and subsequently flushed with hydrogen (1 bar). Stirring was continued at room temperature until completion of the reaction. The reaction mixture was filtered over Celite and the solvent was removed under reduced pressure. The crude was used without further purification in the next step (5.5 g, 76% purity, 59% yield).

LC-MS (Method A): Rt=0.75 min; MS (ESIpos): m/z=306 [M+H]⁺

Intermediate 78

N-(4-Bromo-3-{[(dimethylamino)methylidene]sulfamoyl}phenyl)-2-(2-chlorophenyl)acetamide

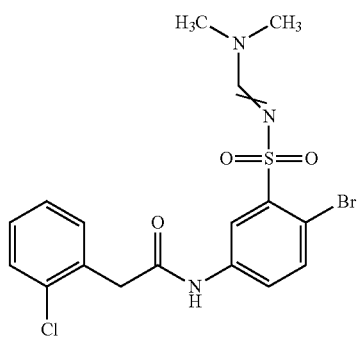 [SMILES: CN(C)CNS(=O)(=O)c1cc(NC(=O)Cc2ccccc2Cl)ccc1Br]

5-Amino-2-bromo-N-[(dimethylamino)methylidene]benzenesulfonamide (4.85 g, 15.8 mmol) was dissolved in DMF (100 ml) and (2-chlorophenyl)acetic acid (3.24 g, 19.0 mmol) was added followed by the addition of N,N-diisopropylethylamine (13 ml, 79 mmol) and HATU (9.64 g, 25.3 mmol). The reaction mixture was stirred for 3 h at 50° C. The solvent was removed under reduced pressure and ethyl acetate and water were added. The phases were separated and the aqueous phase was extracted with ethyl acetate. The combined organic phases were dried over Whatman filter and the solvent was removed under reduced pressure. The crude was suspended in dichloromethane and filtered, the solvent was removed and the crude was used without further purification in the next step (15.7 g).

LC-MS (Method B): Rt=1.08 min; MS (ESIpos): m/z=458 [M+H]⁺

This intermediate can also be used as the HCl salt.

Intermediate 79

N-(4-Bromo-3-{(dimethylamino)methylidene]sulfamoyl}phenyl)-2-(2-fluorophenyl)acetamide

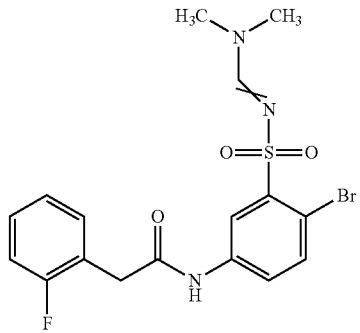

5-Amino-2-bromo-N-[(dimethylamino)methylidene]benzenesulfonamide (1.00 g, 3.27 mmol) was dissolved in DMF (21 ml) and (2-fluorophenyl)acetic acid (604 mg, 3.92 mmol) was added followed by the addition of N,N-diisopropylethylamine (2.7 ml, 16 mmol) and HATU (1.99 g, 5.23 mmol). The reaction was stirred at 50° C. for 16 h. The solvent was removed under reduced pressure and ethyl acetate and water were added. The phases were separated and the aqueous phase was extracted with ethyl acetate. The combined organic phases were dried over Whatman filter and the solvent was removed under reduced pressure. The crude was suspended in tert-butyl methyl ether/hexane (1/1), filtered and the solvent was removed under reduced pressure. The crude was used in the next step without further purification (1.17 g, 85% purity, 81% yield).

LC-MS (Method B): Rt=1.05 min; MS (ESIpos): m/z=442 [M+H]⁺

Intermediate 80

N-(4-Bromo-3-{[(dimethylamino)methylidene]sulfamoyl}phenyl)-2-(2-chloro-4-fluorophenyl)acetamide

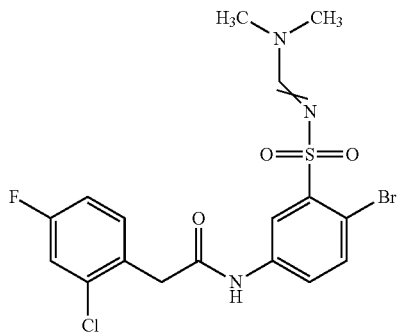 [SMILES: CN(C)CNS(=O)(=O)c1cc(NC(=O)Cc2ccc(F)cc2Cl)ccc1Br]

5-Amino-2-bromo-N-[(dimethylamino)methylidene]benzenesulfonamide (1.00 g, 3.27 mmol) was dissolved in DMF (21 ml) and (2-chloro-4-fluorophenyl)acetic acid (739 mg, 3.92 mmol) was added followed by the addition of N,N-diisopropylethylamine (2.7 ml, 16 mmol) and HATU (1.99 g, 5.23 mmol). The reaction was stirred at 50° C. for 16 h. The solvent was removed under reduced pressure and water and ethyl acetate were added. The phases were separated and the aqueous phase was extracted with ethyl acetate. The combined organic phases were dried over Whatman filter and the solvent was removed under reduced pressure. The crude was triturated in dichloromethane and diethyl ether and filtered. The solid was used in the next step without further purification (1.10 g, 82% purity, 71% yield).

LC-MS (Method A): Rt=1.12 min; MS (ESIneg): m/z=474 [M−H]⁻

Intermediate 81

2-(2-Chlorophenyl)-N-[3-{[(dimethylamino)methylidene]sulfamoyl}-4-(1H-pyrazol-4-yl)phenyl]acetamide

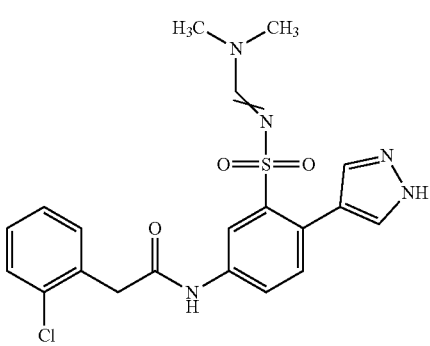 [SMILES: CN(C)CNS(=O)(=O)c1cc(NC(=O)Cc2ccccc2Cl)ccc1-c1cn[nH]c1]

2-(2-Chlorophenyl)-N-(3-{[(dimethylamino)methylidene]sulfamoyl}-4-[1-(tetrahydro-2H-pyran-2-yl)-1H-pyrazol-4-yl]phenyl)acetamide (1.30 g, 2.45 mmol) was dissolved in dichloromethane (20 ml) and trifluoroacetic acid (4.7 ml, 61 mmol) was added and stirring was continued at room temperature until completion of the reaction. The solvent was removed under reduced pressure and the crude was co-distilled with toluene and used without further purification in the next step.

LC-MS (Method A): Rt=0.93 min; MS (ESIpos): m/z=446 [M+H]$^+$

Intermediate 82

4-Amino-N-(2,4-dimethoxybenzyl)biphenyl-2-sulfonamide

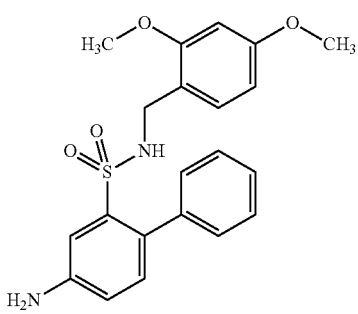 [SMILES: COc1ccc(CNS(=O)(=O)c2cc(N)ccc2-c2ccccc2)c(OC)c1]

2-Chloro-N-(2,4-dimethoxybenzyl)-5-nitrobenzenesulfonamide (300 mg, 776 μmol) and phenylboronic acid (113 mg, 931 μmol) were dissolved in DMF (10 ml) and [1,1'-Bis(diphenylphosphino)ferrocene]dichloropalladium(II) (1:1) (CAS 95464-05-4) (127 mg, 155 μmol) and aqueous potassium carbonate (1.2 ml, 1.0 M, 1.2 mmol) were added. The reaction was heated at 120° C. for 1 h in the microwave. Afterwards water and ethyl acetate were added and the phases were separated. The aqueous phase was extracted with ethyl acetate three times. The combined organic layers were dried over Whatman filter and the solvent was removed under reduced pressure. The crude was purified by chromatography on silica gel (Biotage, hexane/ethyl acetate) to yield 260 mg (99% purity, 78% yield).

LC-MS (Method A): Rt=1.33 min; MS (ESIpos): m/z=429 [M+H]$^+$

N-(2,4-dimethoxybenzyl)-4-nitrobiphenyl-2-sulfonamide (260 mg, 607 μmol) was dissolved in THF (15 ml) and the flask was flushed with nitrogen. Palladium on charcoal (10% loading, 6.46 mg, 60.7 μmol) was added and the flask was evacuated and subsequently flushed with hydrogen (1 bar). Stirring was continued at room temperature until completion of the reaction. The reaction mixture was filtered over Celite and the solvent was removed under reduced pressure. The crude was used without further purification in the next step (270 mg).

LC-MS (Method A): Rt=1.20 min; MS (ESIpos): m/z=399 [M+H]$^+$

Intermediate 83

5-Amino-2-(1-methyl-1H-pyrazol-4-yl)benzenesulfonamide

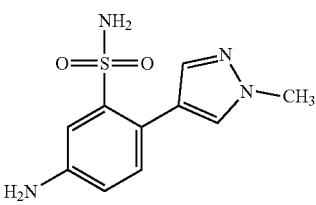 [SMILES: Cn1cc(-c2ccc(N)cc2S(N)(=O)=O)cn1]

2-Bromo-5-nitrobenzenesulfonamide (800 mg, 2.85 mmol) and 1-methyl-4-(4,4,5,5-tetramethyl-1,3,2-dioxaborolan-2-yl)-1H-pyrazole (1.18 g, 5.69 mmol) were dissolved in n-propanol (38 ml) and bis(triphenylphosphine)palladium(II) dichloride (CAS 13965-03-2) (100 mg, 142 μmol), triphenylphosphine (37.3 mg, 142 μmol) and aq. potassium carbonate (4.3 ml, 2.0 M, 8.5 mmol) were added. The reaction was purged with argon for 5 minutes and subsequently heated at 120° C. for 1 h in the microwave (4 bar/40 W). Afterwards the mixture was filtered over Celite, the solvent was removed under reduced pressure and the crude was co-distilled with methanol and used without further purification in the next step.

2-(1-Methyl-1H-pyrazol-4-yl)-5-nitrobenzenesulfonamide (800 mg, 2.83 mmol) was dissolved in THF (78 ml) and the flask was flushed with nitrogen. Palladium on charcoal (10% loading, 308 mg, 2.89 mmol) was added and the flask was evacuated and subsequently flushed with hydrogen (1 bar). Stirring was continued at room temperature until completion of the reaction. The reaction mixture was filtered over Celite and the solvent was removed under reduced pressure. The crude was co-distilled with THF and used without further purification in the next step (1.6 g).

LC-MS (Method B): Rt=0.50 min; MS (ESIpos): m/z=253 [M+H]$^+$

137

Intermediate 84

5-Amino-2-(1-cyclopropyl-1H-pyrazol-4-yl)-N-[(dimethylamino)methylidene]benzenesulfonamide

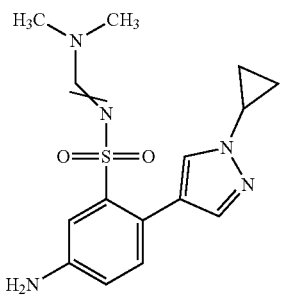 [SMILES: CN(C)CNS(=O)(=O)c1cc(N)ccc1-c1cnn(C2CC2)c1]

2-Chloro-5-nitrobenzenesulfonamide (674 mg, 2.85 mmol) and 1-cyclopropyl-4-(4,4,5,5-tetramethyl-1,3,2-dioxaborolan-2-yl)-1H-pyrazole (1.00 g, 4.27 mmol) were dissolved in n-propanol (34 ml) and bis(triphenylphosphine)palladium(II) dichloride (CAS 13965-03-2) (100 mg, 142 μmol) and triphenylphosphine (37.3 mg, 142 μmol) were added. The reaction was purged with argon for 5 minutes and aq. potassium carbonate (5.7 ml, 1.0 M, 5.7 mmol) was added. The reaction was heated at 100° C. for 3 h. Afterwards the mixture was filtered over Celite and the solvent was removed under reduced pressure. Ethyl acetate and water were added. The phases were separated and the aqueous phase was extracted with ethyl acetate. The combined organic phases were dried over Whatman filter and the solvent was removed under reduced pressure. The crude was used in the next step without further purification.

2-(1-Cyclopropyl-1H-pyrazol-4-yl)-5-nitrobenzenesulfonamide (1.17 g, 3.79 mmol) and 1,1-dimethoxy-N,N-dimethylmethanamine (1.0 ml, 7.6 mmol) were dissolved in DMF (25 ml) and the reaction was stirred at room temperature until completion of the reaction. The solvent was removed under reduced pressure and the crude was used without further purification in the next step.

2-(1-Cyclopropyl-1H-pyrazol-4-yl)-N-[(dimethylamino)methylidene]-5-nitrobenzenesulfonamide (1.84 g, 5.06 mmol) was dissolved in THF (30 ml) and the flask was flushed with nitrogen. Palladium on charcoal (10% loading, 53.9 g, 506 μmol) was added and the flask was evacuated and subsequently flushed with hydrogen (1 bar). Stirring was continued at room temperature until completion of the reaction. The reaction mixture was filtered over Celite and the solvent was removed under reduced pressure. The crude was used without further purification in the next step (1.3 g, 53% purity, 75% yield over 3 steps).

LC-MS (Method A): Rt=0.70 min; MS (ESIpos): m/z=334 [M+H]$^+$

138

Intermediate 85

5-Amino-2-(1-tert-butyl-1H-pyrazol-4-yl)benzenesulfonamide

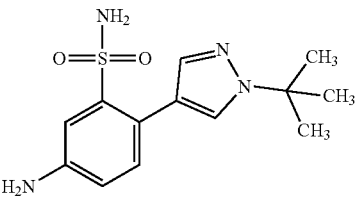 [SMILES: CC(C)(C)n1cc(-c2ccc(N)cc2S(N)(=O)=O)cn1]

2-Chloro-N-[(dimethylamino)methylidene]-5-nitrobenzenesulfonamide (200 mg, 686 μmol) and 1-tert-butyl-4-(4,4,5,5-tetramethyl-1,3,2-dioxaborolan-2-yl)-1H-pyrazole (206 mg, 823 μmol) were dissolved in n-propanol (9.2 ml) and bis(triphenylphosphine)palladium(II) dichloride (CAS 13965-03-2) (24.1 mg, 34.3 μmol), triphenylphosphine (8.99 mg, 34.3 μmol) and aq. potassium carbonate (860 μl, 2.0 M, 1.7 mmol) were added. The reaction was purged with argon for 5 minutes and heated at 80° C. for 16 h. Afterwards the mixture was filtered over Celite, the solvent was removed under reduced pressure and the crude was co-distilled with THF and used without further purification in the next step.

2-(1-tert-Butyl-1H-pyrazol-4-yl)-5-nitrobenzenesulfonamide (250 mg, 771 μmol) was dissolved in methanol (50 ml) and the flask was flushed with nitrogen. Palladium on charcoal (10% loading, 83.6 mg, 786 μmol) was added and the flask was evacuated and subsequently flushed with hydrogen (1 bar). Stirring was continued at room temperature until completion of the reaction. The reaction mixture was filtered over Celite and the solvent was removed under reduced pressure. The crude was used without further purification in the next step (230 mg).

LC-MS (Method A): Rt=0.80 min; MS (ESIpos): m/z=295 [M+H]$^+$

Intermediate 86

5-Amino-2-(1-methyl-1H-pyrazol-4-yl)benzenesulfonamide

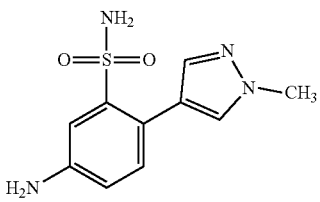 [SMILES: Cn1cc(-c2ccc(N)cc2S(N)(=O)=O)cn1]

2-(1-Methyl-1H-pyrazol-4-yl)-5-nitrobenzenesulfonamide (800 mg, 2.83 mmol) was dissolved in methanol (100 ml) and the flask was flushed with nitrogen. Palladium on charcoal (10% loading, 308 mg, 2.89 mmol) was added and the flask was evacuated and subsequently flushed with hydrogen (1 bar). Stirring was continued until completion of the reaction. The reaction mixture was filtered over Celite and the solvent was removed under reduced pressure. The crude was co-distilled with THF and used without further purification in the next step (1.59 g).

LC-MS (Method B): Rt=0.50 min; MS (ESIpos): m/z=253 [M+H]+

Intermediate 87

5-Amino-N-[(dimethylamino)methylidene]-2-[1-(tetrahydro-2H-pyran-2-yl)-1H-pyrazol-4-yl]benzenesulfonamide

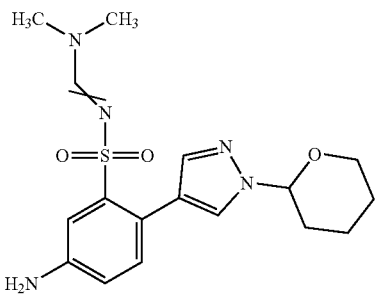 [SMILES: CN(C)CNS(=O)(=O)c1cc(N)ccc1-c1cnn(C2CCCCO2)c1]

2-Bromo-N-[(dimethylamino)methylidene]-5-nitrobenzenesulfonamide (2.0 g, 6.86 mmol) and 1-(tetrahydro-2H-pyran-2-yl)-4-(4,4,5,5-tetramethyl-1,3,2-dioxaborolan-2-yl)-1H-pyrazole (3.81 g mg, 13.7 mmol) were dissolved in n-propanol (92 ml) and bis(triphenylphosphine)palladium (II) dichloride (CAS 13965-03-2) (241 mg, 342 µmol), triphenylphosphine (90 mg, 340 µmol) and aq. potassium carbonate (8.6 ml, 2.0 M, 17 mmol) were added. The solution was purged with argon for 5 minutes and the reaction was heated at 80° C. for 16 h. Afterwards the mixture was filtered over Celite, the solvent was removed under reduced pressure and the crude was co-distilled with THE and used without further purification in the next step.

5-Nitro-2-[1-(tetrahydro-2H-pyran-2-yl)-1H-pyrazol-4-yl]benzenesulfonamide (3.00 g, 8.51 mmol) and 1,1-dimethoxy-N,N-dimethylmethanamine (2.3 ml, 17 mmol) were dissolved in DMF (29 ml) and stirred for 24 h at room temperature. The solvent was removed under reduced pressure and dichloromethane and brine were added. The phases were separated and the organic phase was washed with water. The combined organic phases were dried over Whatman filter and the solvent was removed under reduced pressure. The crude was used in the next step without further purification.

N-[(Dimethylamino)methylidene]-5-nitro-2-[1-(tetrahydro-2H-pyran-2-yl)-1H-pyrazol-4-yl]benzenesulfonamide (3.50 g, 8.59 mmol) was dissolved in methanol (860 ml) and the flask was flushed with nitrogen. Palladium on charcoal (10% loading, 932 mg, 8.76 mmol) was added and the flask was evacuated and subsequently flushed with hydrogen (1 bar). Stirring was continued at room temperature. After 1 h the flask was evacuated three times and flushed with hydrogen. Stirring was continued for 3 h. The reaction mixture was filtered over Celite and the solvent was removed under reduced pressure. The crude was used without further purification in the next step (3.4 g).

LC-MS (Method A): Rt=0.88 min; MS (ESIpos): m/z=378 [M+H]+

Intermediate 88

5-Amino-2-(1-cyclopentyl-1H-pyrazol-4-yl)benzenesulfonamide

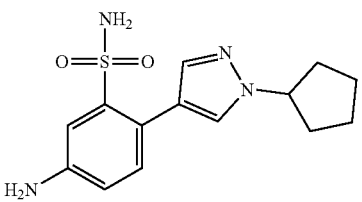 [SMILES: Nc1ccc(-c2cnn(C3CCCC3)c2)c(S(N)(=O)=O)c1]

2-Chloro-N-[(dimethylamino)methylidene]-5-nitrobenzenesulfonamide (550 mg, 1.89 mmol) and 1-cyclopentyl-4-(4,4,5,5-tetramethyl-1,3,2-dioxaborolan-2-yl)-1H-pyrazole (989 mg, 3.77 mmol) were dissolved in n-propanol (25 ml) and bis(triphenylphosphine)palladium(II) dichloride (CAS 13965-03-2) (66.4 mg, 94.3 µmol), triphenylphosphine (24.7 mg, 94.3 µmol) and aq. potassium carbonate (2.4 ml, 2.0 M, 4.7 mmol) were added. The solution was purged with argon for 5 minutes and the reaction was heated at 80° C. for 16 h. Afterwards the mixture was filtered over Celite, the solvent was removed under reduced pressure and the crude was co-distilled with THE and used without further purification in the next step.

2-(1-Cyclopentyl-1H-pyrazol-4-yl)-5-nitrobenzenesulfonamide (640 mg, 1.90 mmol) was dissolved in methanol (50 ml) and the flask was flushed with nitrogen. Palladium on charcoal (10% loading, 206 mg, 1.94 mmol) was added and the flask was evacuated and subsequently flushed with hydrogen (1 bar). Stirring was continued at room temperature for 4 h. The reaction mixture was filtered over Celite and the solvent was removed under reduced pressure. The crude was used without further purification in the next step (590 mg).

LC-MS (Method A): Rt=0.87 min; MS (ESIpos): m/z=307 [M+H]+

Intermediate 89

5-Amino-2-[1-(2-methoxyethyl)-1H-pyrazol-4-yl]benzenesulfonamide

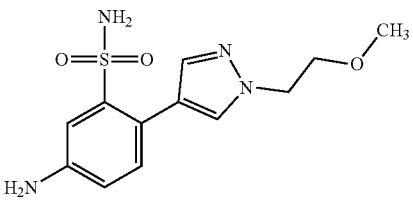 [SMILES: COCCn1cc(-c2ccc(N)cc2S(N)(=O)=O)cn1]

2-Chloro-N-[(dimethylamino)methylidene]-5-nitrobenzenesulfonamide (550 mg, 1.89 mmol) and 1-(2-methoxyethyl)-4-(4,4,5,5-tetramethyl-1,3,2-dioxaborolan-2-yl)-1H-pyrazole (951 mg, 3.77 mmol) were dissolved in n-propanol (25 ml) and bis(triphenylphosphine)palladium(II) dichloride (CAS 13965-03-2) (66.4 mg, 94.3 µmol), triphenylphosphine (24.7 mg, 94.3 µmol) and aq. potassium carbonate (2.4 ml, 2.0 M, 4.7 mmol) were added. The reaction was heated at 80° C. for 16 h. The reaction was filtered over Celite and the solvent was removed under reduced pressure. The crude was co-distilled with THF and used without further purification in the next step.

2-[1-(2-Methoxyethyl)-1H-pyrazol-4-yl]-5-nitrobenzenesulfonamide (620 mg, 1.90 mmol) was dissolved in methanol (50 ml) and the flask was purged with nitrogen. Afterwards, palladium on charcoal (10% loading, 206 mg, 1.94 mmol) was added and the flask was evacuated and refilled with hydrogen (1 bar). The reaction was stirred at room temperature until completion of the reaction. The mixture was filtered over Celite, the solvent was removed under reduced pressure and the crude was used without further purification in the next step (580 mg).

LC-MS (Method A): Rt=0.59 min; MS (ESIpos): m/z=297 [M+H]$^+$

Intermediate 90

5-Amino-2-(1,3-dimethyl-1H-pyrazol-5-yl)benzenesulfonamide

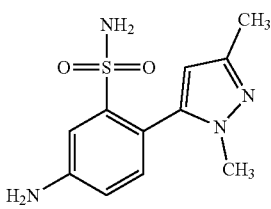 [SMILES: Cc1cc(-c2ccc(N)cc2S(N)(=O)=O)n(C)n1]

2-Bromo-N-[(dimethylamino)methylidene]-5-nitrobenzenesulfonamide (400 mg, 1.19 mmol) and (1,3-dimethyl-1H-pyrazol-5-yl)boronic acid (333 mg, 2.38 mmol) were dissolved in n-propanol (110 ml) and bis(triphenylphosphine)palladium(II) dichloride (CAS 13965-03-2) (41.9 mg, 59.5 µmol), triphenylphosphine (21.6 mg, 59.5 µmol) and aq. potassium carbonate (1.8 ml, 2.0 M, 3.6 mmol) were added. The solution was purged with argon for 5 minutes and the reaction was heated at 120° C. for 1 h in the microwave (4 bar/40 W). Afterwards the mixture was filtered over Celite, the solvent was removed under reduced pressure and the crude was co-distilled with methanol and used without further purification in the next step.

2-(1,3-Dimethyl-1H-pyrazol-5-yl)-5-nitrobenzenesulfonamide (450 mg, 1.52 mmol) was dissolved in methanol (33 ml) and the flask was flushed with nitrogen. Palladium on charcoal (10% loading, 165 mg, 1.55 mmol) was added and the flask was evacuated and subsequently flushed with hydrogen (1 bar). Stirring was continued at room temperature for 4 h. The reaction mixture was filtered over Celite and the solvent was removed under reduced pressure. The crude was co-distilled with THF and used without further purification in the next step (435 mg).

LC-MS (Method B): Rt=0.56 min; MS (ESIpos): m/z=267 [M+H]$^+$

Intermediate 91

5-Amino-2-[1-methyl-3-(trifluoromethyl)-1H-pyrazol-5-yl]benzenesulfonamide

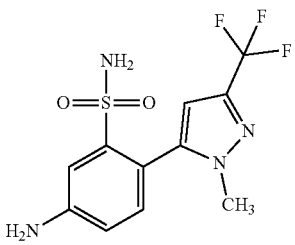 [SMILES: Cn1nc(C(F)(F)F)cc1-c1ccc(N)cc1S(N)(=O)=O]

2-Chloro-N-[(dimethylamino)methylidene]-5-nitrobenzenesulfonamide (550 mg, 1.89 mmol) and 1-methyl-5-(4,4,5,5-tetramethyl-1,3,2-dioxaborolan-2-yl)-3-(trifluoromethyl)-1H-pyrazole (1.04 g, 3.77 mmol) were dissolved in n-propanol (25 ml) and bis(triphenylphosphine)palladium (II) dichloride (CAS 13965-03-2) (66.4 mg, 94.3 µmol), triphenylphosphine (24.7 mg, 94.3 µmol) and aq. potassium carbonate (2.4 ml, 2.0 M, 4.7 mmol) were added. The solution was purged with argon for 5 minutes and the reaction was heated at 80° C. for 16 h. Afterwards the mixture was filtered over Celite, the solvent was removed under reduced pressure and the crude was co-distilled with THF and used without further purification in the next step.

2-[1-Methyl-3-(trifluoromethyl)-1H-pyrazol-5-yl]-5-nitrobenzenesulfonamide (660 mg, 1.88 mmol) was dissolved in methanol (190 ml) and the flask was flushed with nitrogen. Platinum on charcoal (5% loading, 375 mg, 1.92 mmol) was added and the flask was evacuated and subsequently flushed with hydrogen (1 bar). Stirring was continued at room temperature for 18 h. The reaction mixture was filtered over Celite and the solvent was removed under reduced pressure. The crude was used without further purification in the next step (600 mg).

LC-MS (Method A): Rt=0.86 min; MS (ESIpos): m/z=321 [M+H]$^+$

Intermediate 92

5-Amino-N-[(dimethylamino)methylidene]-2-[5-(trifluoromethyl)pyridin-3-yl]-benzenesulfonamide

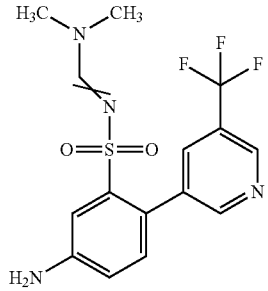 [SMILES: CN(C)CNS(=O)(=O)c1cc(N)ccc1-c1cncc(C(F)(F)F)c1]

5-Amino-2-bromo-N-[(dimethylamino)methylidene]benzenesulfonamide (300 mg, 980 µmol) and [5-(trifluoromethyl)pyridin-3-yl]boronic acid (374 mg, 1.96 mmol) were dissolved in DMF (27 ml) and triphenylphosphine (12.8 mg, 49.0 µmol) and potassium fluoride (14.2 mg, 245 µmol) were added. The solution was purged with argon for 5 minutes and bis(triphenylphosphine)palladium(II) dichloride (CAS 13965-03-2) (34.5 mg, 49.0 µmol) followed by aq. potassium phosphate solution (730 µl, 2.0 M, 1.5 mmol) were added. The reaction was heated at 100° C. for 1 h in the microwave. Afterwards the mixture was filtered over Celite, the solvent was removed under reduced pressure and the crude was used without further purification in the next step (365 mg).

LC-MS (Method B): Rt=0.91 min; MS (ESIpos): m/z=373 [M+H]$^+$

Intermediate 93

5-Amino-2-(1,3-dimethyl-1H-pyrazol-4-yl)benzenesulfonamide

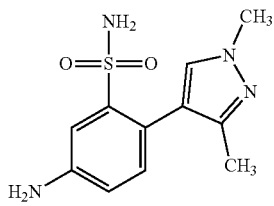 [SMILES: Cc1nn(C)cc1-c1ccc(N)cc1S(N)(=O)=O]

2-Chloro-N-[(dimethylamino)methylidene]-5-nitrobenzenesulfonamide (550 mg, 1.89 mmol) and 1,3-dimethyl-4-(4,4,5,5-tetramethyl-1,3,2-dioxaborolan-2-yl)-1H-pyrazole (837 mg, 3.77 mmol) were dissolved in n-propanol (25 ml) and bis(triphenylphosphine)palladium(II) dichloride (CAS 13965-03-2) (66.4 mg, 94.3 µmol), triphenylphosphine (24.7 mg, 94.3 µmol) and aq. potassium carbonate (2.4 ml, 2.0 M, 4.7 mmol) were added. The reaction was heated at 80° C. for 16 h. Afterwards the mixture was filtered over Celite, the solvent was removed under reduced pressure. The crude was co-distilled with THF and used without further purification in the next step.

2-(1,3-Dimethyl-1H-pyrazol-4-yl)-5-nitrobenzenesulfonamide (560 mg, 1.89 mmol) was dissolved in methanol (50 ml) and the flask was flushed with nitrogen. Palladium on charcoal (10% loading, 205 mg, 1.93 mmol) was added and the flask was evacuated and subsequently flushed with hydrogen (1 bar). Stirring was continued at room temperature for 16 h. The reaction mixture was filtered over Celite and the solvent was removed under reduced pressure. The crude was used without further purification in the next step (500 mg).

LC-MS (Method A): Rt=0.63 min; MS (ESIpos): m/z=267 [M+H]$^+$

Intermediate 94

5-Amino-2-[1-(difluoromethyl)-1H-pyrazol-4-yl]benzenesulfonamide

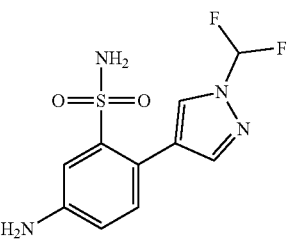 [SMILES: Nc1ccc(-c2cnn(C(F)F)c2)c(S(N)(=O)=O)c1]

2-Bromo-N-[(dimethylamino)methylidene]-5-nitrobenzenesulfonamide (800 mg, 2.3 mmol) and 1-(difluoromethyl)-4-(4,4,5,5-tetramethyl-1,3,2-dioxaborolan-2-yl)-1H-pyrazole (700 mg, 2.87 mmol) were dissolved in n-propanol (15 ml) and bis(triphenyl-phosphine)palladium(II) dichloride (CAS 13965-03-2) (84 mg, 119 µmol) and triphenylphosphine (31 mg, 119 µmol) were added. The solution was purged with argon for 5 minutes and aq. potassium carbonate (3.6 ml, 2.0 M, 7.2 mmol) was added. The reaction was heated at 100° C. for 16 h. Water and ethyl acetate were added. The phases were separated and the aqueous phase was extracted with ethyl acetate. The combined organic phases were dried over Whatman filter and the solvent was removed under reduced pressure. The crude was used in the next step without further purification. 2-[1-(Difluoromethyl)-1H-pyrazol-4-yl]-N-[(dimethylamino)methylidene]-5-nitrobenzenesulfonamide (2.16 g, 5.79 mmol) was dissolved in tetrahydrofurane (50 ml) and platinum on charcoal (5% loading, 307 mg, 1.57 mmol) was added. The flask was evacuated three times and flushed with hydrogen (1 bar). The reaction was stirred for 4 h at room temperature. According to UPLC-MS the reaction was not complete and same amounts of platinum on charcoal were added and the reaction was stirred under hydrogen atmosphere for further 16 h. Afterwards, the mixture was filtered over Celite and the solvent was removed under reduced pressure. The crude was taken to the next step without further purification. 5-Amino-2-[1-(difluoromethyl)-1H-pyrazol-4-yl]-N-[(dimethylamino)methylidene]benzenesulfonamide (670 mg, 1.95 mmol) was dissolved in methanol (25 ml) and treated with 25% aqueous ammonia solution (25 ml) at room temperature until completion of the reaction. The solvent was removed under reduced pressure and the crude was purified by chromatography on silica gel (Biotage, gradient dichloromethane/ethyl acetate) and subsequent HPLC purification ((Waters XBrigde C18 5µ 100×30 mm, acetonitrile/water+0.1% formic acid) to yield 53 mg (99% purity, 9% yield over 3 steps). The reactions were repeated and the crude was used for the next steps using this intermediate.

LC-MS (Method B): Rt=0.58 min; MS (ESIpos): m/z=289 [M+H]$^+$

Intermediate 95 tert-Butyl 4-[4-(4-amino-2-sulfamoylphenyl)-1H-pyrazol-1-yl]piperidine-1-carboxylate

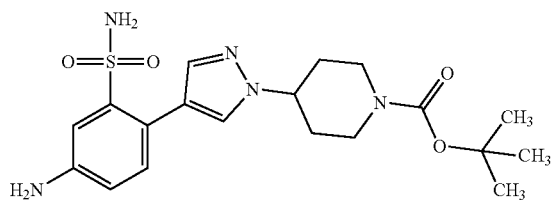 [SMILES: CC(C)(C)OC(=O)N1CCC(n2cc(-c3ccc(N)cc3S(N)(=O)=O)cn2)CC1]

2-Chloro-N-[(dimethylamino)methylidene]-5-nitrobenzenesulfonamide (250 mg, 857 µmol) and tert-butyl 4-[4-(4,4,5,5-tetramethyl-1,3,2-dioxaborolan-2-yl)-1H-pyrazol-1-yl]piperidine-1-carboxylate (485 mg, 1.29 mmol) were dissolved in n-propanol (12 ml) and bis(triphenylphosphine)palladium(II) dichloride (CAS 13965-03-2) (30.2 mg, 42.9 µmol), triphenylphosphine (11.2 mg, 42.9 µmol) and aq. potassium carbonate (1.1 ml, 2.0 M, 2.1 mmol) were added. The solution was purged with argon for 5 minutes and the reaction was heated at 80° C. for 16 h. Afterwards the mixture was filtered over Celite, the solvent was removed under reduced pressure and the crude was co-distilled with THF and used without further purification in the next step.

tert-Butyl 4-[4-(4-nitro-2-sulfamoylphenyl)-1H-pyrazol-1-yl]piperidine-1-carboxylate (400 20 mg, 886 µmol) was dissolved in tetrahydrofurane (89 ml) and the flask was flushed with nitrogen. Palladium on charcoal (10% loading, 96.1 mg, 904 µmol) was added and the flask was evacuated and subsequently flushed with hydrogen (1 bar). Stirring was continued at room temperature for 4 h. The reaction mixture was filtered over Celite and the solvent was removed under reduced pressure. The crude was used without further purification in the next step (380 mg).

LC-MS (Method A): Rt=0.98 min; MS (ESIpos): m/z=422 [M+H]$^+$

Intermediate 96

1-(Oxetan-2-ylmethyl)-4-(4,4,5,5-tetramethyl-1,3,2-dioxaborolan-2-yl)-1H-pyrazole

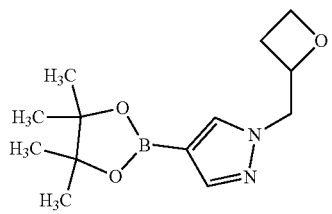

4-(4,4,5,5-Tetramethyl-1,3,2-dioxaborolan-2-yl)-1H-pyrazole (500 mg, 2.58 mmol) was dissolved in DMF (20.0 ml) and 2-(bromomethyl)oxetane (778 mg, 5.15 mmol) and cesium carbonate (1.68 g, 5.15 mmol) were added. The reaction was heated for 1 h at 100° C. in the microwave (0 bar/18 W). The suspension was filtered and the solvent was removed under reduced pressure. The reagent was used without further purification in the next step (770 mg).

LC-MS (Method B): Rt=0.83 min; MS (ESIpos): m/z=266 [M+H]$^+$

Intermediate 97

5-Bromo-2-chloro-N-[(dimethylamino)methylidene]pyridine-3-sulfonamide

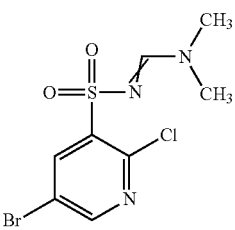 [SMILES: CN(C)CNS(=O)(=O)c1cc(Br)cnc1Cl]

5-Bromo-2-chloropyridine-3-sulfonamide (3.86 g, 14.2 mmol) and 1,1-dimethoxy-N,N-dimethylmethanamine (3.8 ml, 28 mmol) were dissolved in DMF (40 ml) and stirred for 2 h at room temperature. The solvent was removed under reduced pressure and dichloromethane and brine were added. The phases were separated and the organic phase was washed with water. The combined organic phases were dried over Whatman filter and the solvent was removed under reduced pressure. The crude was used in the next step without further purification (5.12 g).

LC-MS (Method B): Rt=0.89 min; MS (ESIpos): m/z=326 [M+H]$^+$

Intermediate 98

2-Chloro-N-[(dimethylamino)methylidene]-5-[(diphenylmethylidene)amino]pyridine-3-sulfonamide

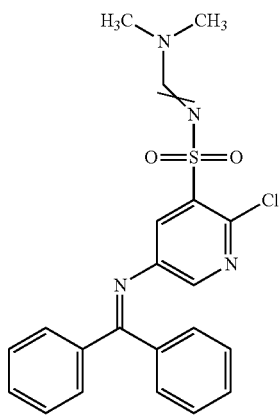 [SMILES: CN(C)CNS(=O)(=O)c1cc(N=C(c2ccccc2)c2ccccc2)cnc1Cl]

5-Bromo-2-chloro-N-[(dimethylamino)methylidene]pyridine-3-sulfonamide (5.00 g, 15.3 mmol), 1,1-diphenylmethanimine (3.9 ml, 23 mmol), XantPhos (886 mg, 1.53 mmol) and palladium(II) acetate (172 mg, 765 µmol) were dissolved in dioxane (150 ml). The solution was purged with argon for 5 minutes and cesium carbonate (15.0 g, 45.9 mmol) was added.

The reaction was heated at 100° C. for 1 h, Afterwards, the solvent was removed under reduced pressure and water and ethyl acetate were added. The phases were separated and the aqueous phase was extracted with ethyl acetate. The combined organic phases were dried over Whatman filter and the solvent was removed under reduced pressure. Half of the crude was used without further purification and 3 g were purified by chromatography on ammonia coated silica gel (Biotage, hexane/ethyl acetate) to yield 1.00 g (78% purity, 15% yield based on total amount of starting material)

LC-MS (Method B): Rt=1.26 min; MS (ESIpos): m/z=427 [M+H]$^+$

Intermediate 99

2-[1-(Difluoromethyl)-1H-pyrazol-4-yl]-N-[(dimethylamino)methylidene]-5-[(diphenyl-methylidene)amino]pyridine-3-sulfonamide

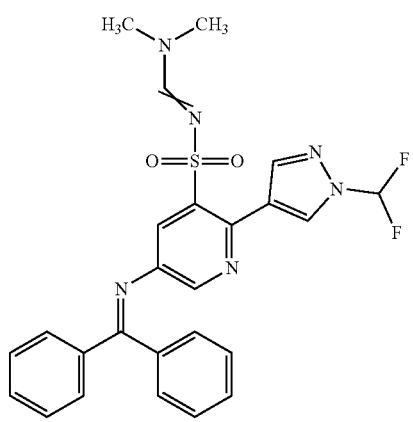 [SMILES: CN(C)CNS(=O)(=O)c1cc(N=C(c2ccccc2)c2ccccc2)cnc1-c1cnn(C(F)F)c1]

2-Chloro-N-[(dimethylamino)methylidene]-5-[(diphenylmethylidene)amino]pyridine-3-sulfonamide (1.50 g, 3.51 mmol, crude) and 1-(difluoromethyl)-4-(4,4,5,5-tetramethyl-1,3,2-dioxaborolan-2-yl)-1H-pyrazole (1.71 g, 7.03 mmol) were dissolved in n-propanol (30 ml)/DMF (15 ml) and bis(triphenylphosphine)palladium(II) dichloride (CAS 13965-03-2) (371 mg, 527 µmol), triphenylphosphine (225 mg, 0.85 mmol), potassium fluoride (408 mg, 7.03 mmol) and aq. potassium phosphate solution (1.8 ml, 2.0 M, 3.5 mmol) were added. The solution was purged with argon for 5 minutes and the reaction was heated at 100° C. for 1 h in the microwave (1 bar/30 W). The solvent was removed under reduced pressure and water and ethyl acetate were added. The phases were separated and the aqueous phase was extracted with ethyl acetate. The combined organic phases were dried over Whatman filter and the solvent was removed under reduced pressure. The crude was purified by chromatography on ammonia coated silica gel (Biotage, hexane/ethyl acetate)(1.54 g, 65% purity, 86% yield).

LC-MS (Method B): Rt=1.26 min; MS (ESIpos): m/z=509 [M+H]$^+$

Intermediate 100

5-Amino-2-[1-(difluoromethyl)-1H-pyrazol-4-yl]-N-[(dimethylamino)methylidene]pyridine-3-sulfonamide

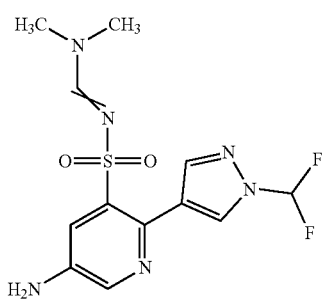 [SMILES: CN(C)CNS(=O)(=O)c1cc(N)cnc1-c1cnn(C(F)F)c1]

2-[1-(Difluoromethyl)-1H-pyrazol-4-yl]-N-[(dimethylamino)methylidene]-5-[(diphenylmethylidene)amino]pyridine-3-sulfonamide (1.54 g, 3.03 mmol) was dissolved in dioxane (15 ml) and aq. HCl (2.0 ml, 3.0 M, 6.1 mmol) was added. The reaction was stirred for 1 h at room temperature. The solvent was removed under reduced pressure and the crude was used without further purification in the next step (2.45 g).

LC-MS (Method B): Rt=0.66 min; MS (ESIpos): m/z=345 [M+H]$^+$

Intermediate 101

N-[(Dimethylamino)methylidene]-5-[(diphenylmethylidene)amino]-2-(1-methyl-1H-pyrazol-4-yl)pyridine-3-sulfonamide

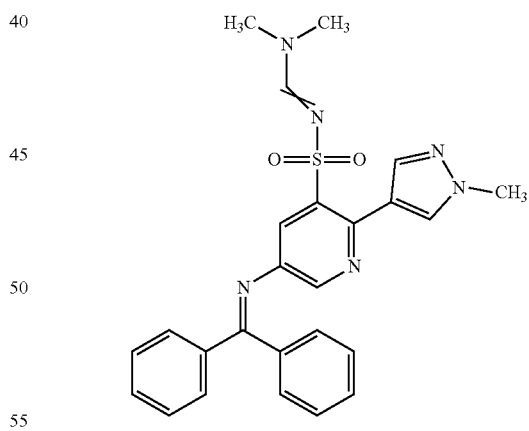

DMF was dried over molecular sieves and purged with argon. Then 2-chloro-N-[(dimethylamino)methylidene]-5-[(diphenylmethylidene)amino]pyridine-3-sulfonamide (350 mg, 820 µmol), 1-methyl-4-(4,4,5,5-tetramethyl-1,3,2-dioxaborolan-2-yl)-1H-pyrazole (341 mg, 1.64 mmol) and potassium fluoride (143 mg, 2.46 mmol) were dissolved in dry and degassed DMF (15 ml) and the solution was purged again with argon for 5 minutes followed by addition of bis(tri-tert-butylphosphine)palladium(0) (CAS 53199-31-8) (251 mg, 492 µmol). The reaction was heated for 18 h at 100° C. The solvent was removed under reduced pressure and ethyl acetate and water were added. The phases were separated and the aqueous phase was extracted with ethyl acetate. The combined organic phases were dried over Whatman filter and the solvent was removed under reduced pressure. The crude was used in the next step without further purification (450 mg).

LC-MS (Method A): Rt=1.16 min; MS (ESIpos): m/z=473 [M+H]$^+$

Intermediate 102

5-Amino-N-[(dimethylamino)methylidene]-2-(1-methyl-1H-pyrazol-4-yl)pyridine-3-sulfonamide

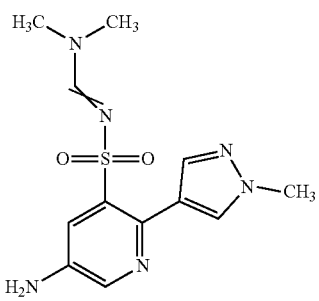 [SMILES: CN(C)CNS(=O)(=O)c1cc(N)cnc1-c1cnn(C)c1]

N-[(Dimethylamino)methylidene]-5-[(diphenylmethylidene)amino]-2-(1-methyl-1H-pyrazol-4-yl)pyridine-3-sulfonamide (430 mg, 910 µmol) was dissolved in dioxane (16.0 ml) and aqueous HCl (610 µl, 3.0 M, 1.8 mmol) was added and the reaction was stirred for 1 h at room temperature. The solvent was removed under reduced pressure and the crude was used without further purification in the next step (500 mg).

LC-MS (Method B): Rt=0.52 min; MS (ESIpos): m/z=309 [M+H]$^+$

Intermediate 103

N-[(Dimethylamino)methylidene]-5-[(diphenylmethylidene)amino]-5'-(trifluoromethyl)-2,3'-bipyridine-3-sulfonamide

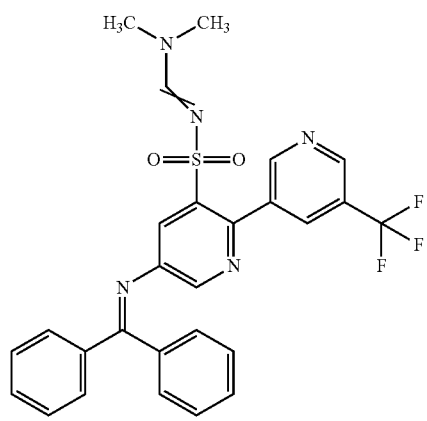 [SMILES: CN(C)CNS(=O)(=O)c1cc(N=C(c2ccccc2)c2ccccc2)cnc1-c1cncc(C(F)(F)F)c1]

2-Chloro-N-[(dimethylamino)methylidene]-5-[(diphenylmethylidene)amino]pyridine-3-sulfonamide (150 mg, 351 µmol) and [5-(trifluoromethyl)pyridin-3-yl]boronic acid (80.5 mg, 422 µmol) were dissolved in n-propanol (10 ml) and bis(triphenylphosphine)palladium(II) dichloride (CAS 13965-03-2) (12.4 mg, 17.6 µmol), triphenylphosphine (4.61 mg, 17.6 µmol) and aq. potassium carbonate (1.1 ml, 1.0 M, 1.1 mmol) were added. The reaction was heated at 100° C. for 1 h. The solvent was removed under reduced pressure and the crude partitioned between ethyl acetate and water. The phases were separated and the aqueous phase was washed with ethyl acetate. The combined organic phases were dried over Whatman filter and the solvent was removed under reduced pressure. The crude was dissolved in DMF (10 ml) and 1,1-dimethoxy-N,N-dimethylmethanamine (140 µl, 1.1 mmol) was added. The reaction was stirred at room temperature for 2 h. The solvent was removed under reduced pressure and the crude was used without further purification in the next step (260 mg).

LC-MS (Method B): Rt=1.33 min; MS (ESIpos): m/z=538 [M+H]$^+$

Intermediate 104

5-Amino-N-[(dimethylamino)methylidene]-5'-(trifluoromethyl)-2,3'-bipyridine-3-sulfonamide

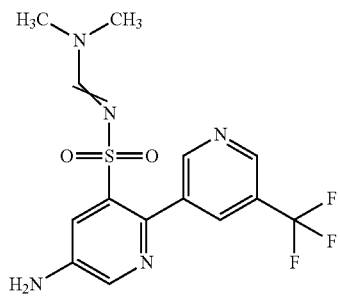 [SMILES: CN(C)CNS(=O)(=O)c1cc(N)cnc1-c1cncc(C(F)(F)F)c1]

N-[(Dimethylamino)methylidene]-5-[(diphenylmethylidene)amino]-5'-(trifluoromethyl)-2,3'-bipyridine-3-sulfonamide (230 mg, 428 µmol) was dissolved in dioxane (20 ml) and aq. HCl (290 µl, 3.0 M, 860 µmol) was added and stirring was continued at room temperature for 2 h. Afterwards, the solvent was removed under reduced pressure and the crude was used without further purification in the next step (250 mg).

LC-MS (Method B): Rt=0.81 min; MS (ESIpos): m/z=374 [M+H]$^+$

Intermediate 105

2-(2-Chlorophenyl)-N-[3-{[(dimethylamino)methylidene]sulfamoyl}-4-(4,4,5,5-tetramethyl-1,3,2-dioxaborolan-2-yl)phenyl]acetamide

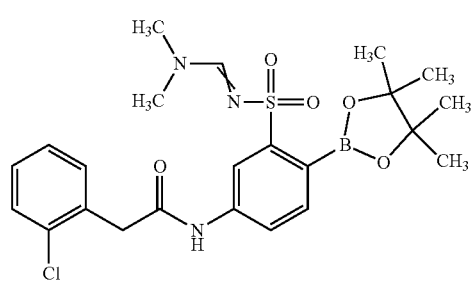 [SMILES: CN(C)CNS(=O)(=O)c1cc(NC(=O)Cc2ccccc2Cl)ccc1B1OC(C)(C)C(C)(C)O1]

N-(4-Bromo-3-{[(dimethylamino)methylidene]sulfamoyl}phenyl)-2-(2-chlorophenyl)-acetamide (250 mg, 545 µmol), 4,4,4',4',5,5,5',5'-octamethyl-2,2'-bi-1,3,2-dioxaborolane (346 mg, 1.4 mmol) and CataXCium A Pre Cat (20.0 mg, 27.2 µmol) were dissolved in methanol (10 ml) and N,N-diisopropylethylamine (237 µl, 1.4 mmol) was added under argon atmosphere. The reaction was stirred for 2 h at 50° C. The solution was used as it is in the next step.

Reaction was performed multiple times on that scale only.

LC-MS (Method B): Rt=1.23 min; MS (ESIpos): m/z=506 [M+H]⁺

Intermediate 106

5-Amino-2-(5-cyclopropyl-1,3,4-oxadiazol-2-yl)-N-[(dimethylamino)methylidene]-benzenesulfonamide

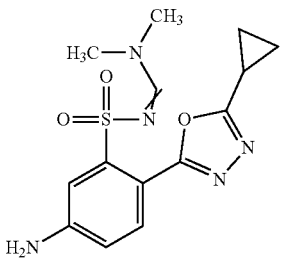 [SMILES: CN(C)CNS(=O)(=O)c1cc(N)ccc1-c1nnc(C2CC2)o1]

2-Bromo-4-nitrobenzoic acid (1.50 g, 6.10 mmol) was dissolved in DMF (50 ml) and cyclopropanecarbohydrazide (671 mg, 6.71 mmol), HATU (2.78 g, 7.32 mmol) and N,N-diisopropylethylamine (5.3 ml, 30 mmol) were added. The reaction was stirred at room temperature for 2 h. Afterwards, the solvent was removed under reduced pressure and the crude partitioned between ethyl acetate and water. The phases were separated and the aqueous phase was extracted three times with water. The combined organic phases were dried over Whatman filter and the solvent was removed under reduced pressure. The crude was used in the next step without further purification (7.9 g). 2-Bromo-N'-(cyclopropylcarbonyl)-4-nitrobenzohydrazide (7.87 g, 24.0 mmol) was dissolved in DMF (100 ml) and N,N-diisopropylethylamine (8.4 ml, 48 mmol) and 4-methylbenzenesulfonyl chloride (4.57 g, 24.0 mmol) were added successively. The reaction was stirred at room temperature for 2 h. Same amount of reagent was added and stirring was continued for 2 h. Afterwards, the solvent was removed under reduced pressure and the crude was dissolved in ethyl acetate. After washing with water, the aqueous phase was extracted three times with ethyl acetate and the combined organic layers were dried over Whatman filter. The crude was purified on silica gel (Biotage, hexane/ethyl acetate) to yield 1.35 g (85% purity, 18% yield over 2 steps).

LC-MS (Method B): Rt=1.16 min; MS (ESIpos): m/z=310 [M+H]⁺ 2-(2-Bromo-4-nitrophenyl)-5-cyclopropyl-1,3,4-oxadiazole (1.00 g, 3.22 mmol) was dissolved in 1,4-dioxane (75 ml) and XantPhos (93.3 mg, 161 µmol), dipalladium-tris(dibenzylideneacetone)chloroform complex (CAS 52522-40-4) (167 mg, 161 µmol) and N,N-diisopropylethylamine (1.1 ml, 6.4 mmol) were added. The reaction was heated to 100° C. and a solution of phenylmethanethiol (360 µl, 3.1 mmol) in 1,4-dioxane (1 ml) was added. Stirring was continued for 1 h at 100° C. Afterwards, the solvent was removed under reduced pressure and the crude was partitioned between ethyl acetate and water. The phases were separated and the aqueous phase was extracted three times with ethyl acetate. The combined organic phases were dried over Whatman filter and the solvent was removed under reduced pressure. The crude was used in the next step without further purification (1.42 g).

2-[2-(Benzylsulfanyl)-4-nitrophenyl]-5-cyclopropyl-1,3,4-oxadiazole (1.42 g, 4.02 mmol) was dissolved in acetic acid (40 ml) and N-chlorosuccinimide (1.61 g, 12.1 mmol) was added and the reaction was stirred for 3 h at room temperature. The solvent was removed under reduced pressure and the crude was used without further purification in the next step (1.96 g).

2-(5-Cyclopropyl-1,3,4-oxadiazol-2-yl)-5-nitrobenzenesulfonyl chloride (1.96 g, 5.94 mmol) was added to a solution of ammonia in 1,4-dioxane (0.5 M, 300 ml) and stirring was continued for 16 h at room temperature. The solvent was removed under reduced pressure and the crude was redissolved in 1,4-dioxane (100 ml) and treated with concentrated ammonia solution until completion of the reaction. The solvent was removed under reduced pressure. The crude was suspended in 1,4-dioxane and the suspension as filtered. The filtrate was concentrated and pure product was obtained after HPLC purification (three times, Chromatorex C-18 10 µm, 125×30 mm, acetonitrile/water+0.2% aqueous ammonia (32%)) to yield 3.6 g (194%, 43% purity).

LC-MS (Method A): Rt=0.88 min; MS (ESIpos): m/z=311 [M+H]⁺

2-(5-Cyclopropyl-1,3,4-oxadiazol-2-yl)-5-nitrobenzenesulfonamide (3.60 g, 11.6 mmol) was dissolved in DMF (40 ml) and 1,1-dimethoxy-N,N-dimethylmethanamine (3.1 ml, 23 mmol) was added. The reaction was stirred at room temperature until completion of the reaction. The solvent was removed under reduced pressure and ethyl acetate and water were added. The phases were separated and the aqueous phase was extracted with ethyl acetate. The combined organic phases were dried over Whatman filter and the solvent was removed under reduced pressure. The pure compound was obtained after chromatography on silica gel (Biotage, hexane/ethyl acetate) (0.4 g, 99% purity, 9% yield).

LC-MS (Method B): Rt=0.91 min; MS (ESIpos): m/z=366 [M+H]⁺

2-(5-Cyclopropyl-1,3,4-oxadiazol-2-yl)-N-[(dimethylamino)methylidene]-5-nitrobenzenesulfonamide (400 mg, 1.09 mmol) was dissolved in THF (200 ml) and platinum on charcoal (5% loading, 214 mg, 109 µmol) was added. The flask was evacuated and subsequently flushed with hydrogen (1 bar). Stirring was continued for 4 h at room temperature. LC-MS indicated uncomplete reaction. The mixture was filtered over Celite and the solvent was removed under reduced pressure. The crude was dissolved in ethanol (200 ml) and palladium on charcoal (10% loading, 214 mg, 109 µmol) was added. The flask was evacuated and then flushed with hydrogen (1 bar) and the reaction was stirred for 3 h. Afterwards more catalyst (214 mg, 109 µmol) was added and stirring was continued for further 3 h. The mixture was filtered over Celite and the solvent was removed under reduced pressure. The crude was used in the next step without further purification (260 mg, 85% purity, 70% yield).

LC-MS (Method A): Rt=0.71 min; MS (ESIpos): m/z=336 [M+H]⁺

Intermediate 107

2-[4-(Difluoromethyl)-1H-pyrazol-1-yl]-N-[(dimethylamino)methylene]-5-nitrobenzenesulfonamide

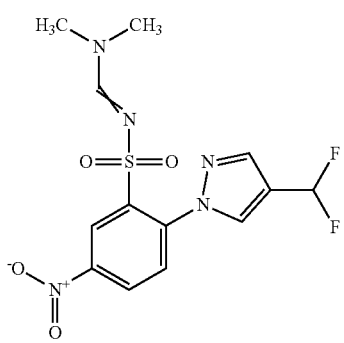

2-Chloro-N-[(dimethylamino)methylene]-5-nitrobenzenesulfonamide (2.02 g, 6.94 mmol) and 1-(1H-pyrazol-4-yl)ethanone (1.00 g, 10.4 mmol) were dissolved in acetonitrile, powdered potassium carbonate (2.88 g, 20.8 mmol) was added and the reaction mixture was stirred at 100° C. overnight. Then, it was concentrated in vacuo and was extracted with dichloromethane/water. The organic phase was washed again with brine, followed by drying over sodium sulfate and concentration in vacuo.

As the protection group was partly lost, it was redissolved in DMF (6.6 mL) and 1,1-dimethoxy-N,N-dimethylmethanamine (0.882 g, 7.4 mmol) was added. It was stirred overnight, concentrated in vacuo and extracted with dichloromethane/water. The organic phase was washed again with brine, followed by drying over sodium sulfate and concentration in vacuo to provide 1.3 g of crude N-[(dimethylamino)methylene]-2-(3-formyl-1H-pyrazol-1-yl)-5-nitrobenzenesulfonamide.

Bis(2-methoxyethyl)aminosulfur trifluoride (DeoxoFluor®; 3.09 mL of 2.7 M toluene solution, 8.34 mmol) was added to the crude material from the previous step (1.03 g, 2.94 mmol) and the reaction mixture was stirred for 5 hours at 80° C. Ethylacetate and 2M aqueous potassium carbonate solution were added for extraction. The organic phase was dried over sodium sulfate and concentrated in vacuo. Purification by (flash) column chromatography on a Biotage system led to the title compound (600 mg, 1.61 mmol, 24% yield over 3 steps, 90% purity).

LC-MS (Method A): Rt=0.96 min; MS (ESIpos): m/z=374 [M+H]$^+$

Intermediate 108

5-Amino-2-(4-cyano-1H-pyrazol-1-yl)-N-[(dimethylamino)methylene]pyridine-3-sulfonamide

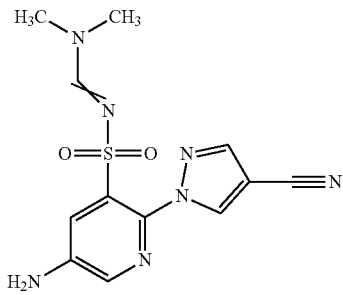 [SMILES: CN(C)CNS(=O)(=O)c1cc(N)cnc1-n1cc(C#N)cn1]

2-Chloro-N-[(dimethylamino)methylene]-5-[(diphenylmethylene)amino]pyridine-3-sulfonamide (480 mg, 1.12 mmol) was dissolved in DMSO (14 mL). 1H-Pyrazole-4-carbonitrile (209 mg, 2.25 mmol), potassium iodide (187 mg, 1.12 mmol) and potassium phosphate (358 mg, 1.69 mmol) were added and the reaction mixture was stirred overnight at 100° C. Afterwards it was concentrated in vacuo, extracted with dichloromethane/water and the organic phase was washed with brine and dried over sodium sulfate followed by concentration in vacuo.

Due to partial deprotection, the material was redissolved in DMF (2 mL) and stirred overnight with 1,1-dimethoxy-N,N-dimethylmethanamine (0.4 mL). Afterwards it was concentrated in vacuo, extracted with dichloromethane/water and the organic phase was washed with brine and dried over sodium sulfate followed by concentration in vacuo.

LC-MS (Method A): Rt=1.22 min, MS (ESIpos): m/z=484 [M+H]$^+$

The compound from the previous step was dissolved in dioxane (2.5 mL) and 2M HCl in dioxane (1.18 mL, 2.36 mmol) was added, followed by stirring overnight. It was concentrated in vacuo and extracted with ethyl acetate/water. The organic phase was washed with brine, dried over sodium sulfate and concentrated in vacuo to yield the crude title compound (110 mg) that was used without further purification in the next steps.

LC-MS (Method A): Rt=0.58 min, MS (ESIpos): m/z=320 [M+H]$^+$

Intermediate 109

5-Amino-2-(4-chloro-1H-pyrazol-1-yl)-N-[(dimethylamino)methylene]pyridine-3-sulfonamide

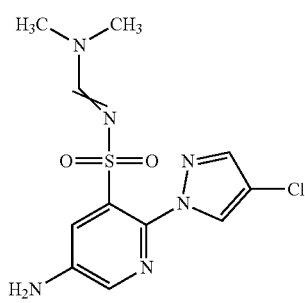 [SMILES: CN(C)CNS(=O)(=O)c1cc(N)cnc1-n1cc(Cl)cn1]

2-Chloro-N-[(dimethylamino)methylene]-5-[(diphenylmethylene)amino]pyridine-3-sulfonamide (1.00 g, 2.34 mmol) was dissolved in DMSO (18 mL). 4-Chloro-1H-pyrazole (480 mg, 4.69 mmol), potassium iodide (389 mg, 2.34 mmol) and potassium phosphate (746 mg, 3.51 mmol) were added and the reaction mixture was stirred overnight at 100° C. Afterwards it was concentrated in vacuo, extracted with dichloromethane/water and the organic phase was washed with brine and dried over sodium sulfate followed by concentration in vacuo.

Due to partial deprotection, the material was redissolved in DMF (2 mL) and stirred overnight with 1,1-dimethoxy-N,N-dimethylmethanamine (0.5 mL). Stirring overnight resulted in a precipitate that was removed by filtration (229 mg pure 2-(4-chloro-1H-pyrazol-1-yl)-N-[(dimethylamino)methylene]-5-[(diphenylmethylene)amino]pyridine-3-sulfonamide). The filtrate was concentrated in vacuo, extracted with dichloromethane/water and the organic phase was washed with brine and dried over sodium sulfate followed by concentration in vacuo to give crude 2-(4-chloro-1H-pyrazol-1-yl)-N-[(dimethylamino)methylene]-5-[(diphenylmethylene)amino]pyridine-3-sulfonamide (549 mg).

LC-MS (Method A): Rt=1.31 min, MS (ESIpos): m/z=493 [M+H]$^+$ $^1$H-NMR (400 MHz, DMSO-d$_6$) δ [ppm] 2.80 (s, 3H), 3.09 (s, 3H), 7.27-7.33 (m, 2H), 7.38-7.44 (m, 3H), 7.49-7.56 (m, 2H), 7.58-7.64 (m, 1H), 7.67 (s, 1H), 7.69-7.76 (m, 2H), 7.79-7.83 (m, 2H), 8.17 (d, 1H), 8.32 (d, 1H).

The pure material (229 mg) from the previous step was dissolved in dioxane (2.0 mL) and 2M HCl in dioxane (1.00 mL, 2.00 mmol) was added, followed by stirring overnight. It was concentrated in vacuo and extracted with ethyl acetate/water. The organic phase was washed with brine, dried over sodium sulfate and concentrated in vacuo to yield the crude title compound (200 mg) that was used without further purification in the next steps.

LC-MS (Method A): Rt=0.71 min, MS (ESIpos): m/z=329 [M+H]$^+$

Intermediate 110

5-Amino-2-(4-bromo-1H-pyrazol-1-yl)-N-[(dimethylamino)methylene]pyridine-3-sulfonamide

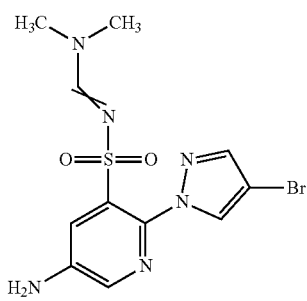 [SMILES: CN(C)CNS(=O)(=O)c1cc(N)cnc1-n1cc(Br)cn1]

2-Chloro-N-[(dimethylamino)methylene]-5-[(diphenylmethylene)amino]pyridine-3-sulfonamide (1.00 g, 2.34 mmol) was dissolved in DMSO (18 mL). 4-Bromo-1H-pyrazole (689 mg, 4.69 mmol), potassium iodide (389 mg, 2.34 mmol) and potassium phosphate (746 mg, 3.51 mmol) were added and the reaction mixture was stirred overnight at 100° C. Afterwards it was concentrated in vacuo, extracted with dichloromethane/water and the organic phase was washed with brine and dried over sodium sulfate followed by concentration in vacuo.

Due to partial deprotection, the material was redissolved in DMF (2 mL) and stirred overnight with 1,1-dimethoxy-N,N-dimethylmethanamine (0.5 mL). Stirring overnight resulted in a precipitate that was removed by filtration (213 mg pure 2-(4-bromo-1H-pyrazol-1-yl)-N-[(dimethylamino)methylene]-5-[(diphenylmethylene)amino]pyridine-3-sulfonamide). The filtrate was concentrated in vacuo, extracted with dichloromethane/water and the organic phase was washed with brine and dried over sodium sulfate followed by concentration in vacuo to give crude 2-(4-bromo-1H-pyrazol-1-yl)-N-[(dimethylamino)-methylene]-5-[(diphenylmethylene)amino]pyridine-3-sulfonamide (758 mg).

LC-MS (Method A): Rt=1.32 min, MS (ESIpos): m/z=537/539 [M+H]$^+$ $^1$H-NMR (400 MHz, DMSO-d$_6$) δ [ppm] 2.79 (s, 3H), 3.09 (s, 3H), 7.27-7.33 (m, 2H), 7.38-7.45 (m, 3H), 7.49-7.56 (m, 2H), 7.58-7.67 (m, 2H), 7.73 (d, 2H), 7.79-7.83 (m, 2H), 8.16 (d, 1H), 8.31 (d, 1H).

The pure material (213 mg) from the previous step was dissolved in dioxane (2.0 mL) and 2M HCl in dioxane (1.00 mL, 2.00 mmol) was added, followed by stirring overnight. It was concentrated in vacuo and extracted with ethyl acetate/water. The organic phase was washed with brine, dried over sodium sulfate and concentrated in vacuo to yield the crude title compound (168 mg) that was used without further purification in the next steps.

LC-MS (Method A): Rt=0.73 min, MS (ESIpos): m/z=373/375 [M+H]$^+$

Intermediate 111

5-Amino-N-[(dimethylamino)methylene]-2-(4-fluoro-1H-pyrazol-1-yl)pyridine-3-sulfonamide

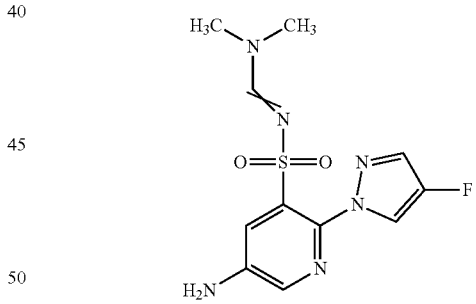

2-Chloro-N-[(dimethylamino)methylene]-5-[(diphenylmethylene)amino]pyridine-3-sulfonamide (1.00 g, 2.34 mmol) was dissolved in DMSO (18 mL). 4-Fluoro-1H-pyrazole (403 mg, 4.69 mmol), potassium iodide (389 mg, 2.34 mmol) and potassium phosphate (746 mg, 3.51 mmol) were added and the reaction mixture was stirred overnight at 100° C. Afterwards it was concentrated in vacuo, extracted with dichloromethane/water and the organic phase was washed with brine and dried over sodium sulfate followed by concentration in vacuo.

Due to partial deprotection, the material was redissolved in dimethylformamide (2 mL) and stirred overnight with 1,1-dimethoxy-N,N-dimethylmethanamine (0.5 mL). The reaction mixture was concentrated in vacuo, extracted with dichloromethane/water and the organic phase was washed with brine and dried over sodium sulfate followed by concentration in vacuo to give crude N-[(dimethylamino)methylene]-5-[(diphenylmethylene)amino]-2-(4-fluoro-1H-pyrazol-1-yl)pyridine-3-sulfonamide (723 mg).

LC-MS (Method A): Rt=1.25 min, MS (ESIpos): m/z=477 [M+H]+

Crude material (723 mg) from the previous step was dissolved in dioxane (4.0 mL) and 2M HCl in dioxane (3.00 mL, 6.00 mmol) was added, followed by stirring overnight. It was concentrated in vacuo and extracted with ethyl acetate/water. The organic phase was washed with brine, dried over sodium sulfate and concentrated in vacuo to yield crude title compound (455 mg) that was used without further purification in the next steps.

LC-MS (Method A): Rt=0.62 min, MS (ESIpos): m/z=313 [M+H]+

Intermediate 112

5-Amino-N-[(dimethylamino)methylidene]-2-[4-(trifluoromethyl)-1H-pyrazol-1-yl]-pyridine-3-sulfonamide

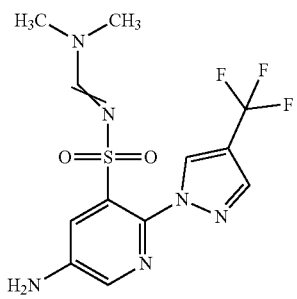 [SMILES: CN(C)CNS(=O)(=O)c1cc(N)cnc1-n1cc(C(F)(F)F)cn1]

The reaction was carried out on a three times 1 g scale. 2-Chloro-N-[(dimethylamino)methylidene]-5-[(diphenylmethylidene)amino]pyridine-3-sulfonamide (3.00 g, 7.03 mmol) and 4-(trifluoromethyl)-1H-pyrazole (1.43 g, 10.5 mmol) were dissolved in DMSO (110 ml, 1.6 mol) and potassium iodide (583 mg, 3.51 mmol) and potassium phosphate (2.24 g, 10.5 mmol) were added. The reaction was heated for 5 h in the microwave at 100° C. Afterwards, the solid was filtered off and to the filtrate ethyl acetate and water were added. The organic phase was washed with brine and dried over sodium sulfate. The solvent was removed under reduced pressure and the crude was purified by chromatography on silica gel (Biotage, ethyl acetate/hexane) to yield 15.7 g (424% yield).

LC-MS (Method A): Rt=1.40 min; MS (ESIpos): m/z=472 [M+H]+

5-[(Diphenylmethylidene)amino]-2-[4-(trifluoromethyl)-1H-pyrazol-1-yl]pyridine-3-sulfonamide (3.50 g, 7.42 mmol) was dissolved in 1,4-dioxane (100 ml) and HCl (4.9 ml, 3.0 M, 15 mmol) was added. The reaction was stirred at room temperature for 2 h. The solvent was removed under reduced pressure and the crude was partitioned between ethyl acetate and water. Afterwards, the organic phase was dried over Whatman filter and the solvent was removed under reduced pressure. The crude was dissolved in acetonitrile and water and lyophilized over night.

LC-MS (Method B): Rt=0.56 min, MS (ESIpos): m/z=307 [M+H]+

Intermediate 113

Methyl 1-(4-{[(2-chlorophenyl)acetyl]amino}-2-sulfamoylphenyl)-1H-pyrazole-4-carboxylate

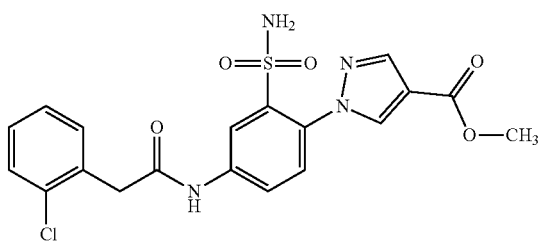 [SMILES: COC(=O)c1cnn(-c2ccc(NC(=O)Cc3ccccc3Cl)cc2S(N)(=O)=O)c1]

According to general procedures GP1.2, GP2.3, GP3.3 and GP4.1, 2-chloro-N-(2,4-dimethoxybenzyl)-5-nitrobenzenesulfonamide (2.04 g, 5.29 mmol), methyl 1H-pyrazole-4-carboxylate (1.00 g, 7.93 mmol) and (2-chlorophenyl)acetic acid (10.5 g, 6.16 mmol) were converted without purification of intermediates to the title compound and were purified at the end by crystallization from hexane/ethyl acetate (2/1) (1.10 g, 2.45 mmol, 46% yield over 4 steps, 90% purity).

LC-MS (Method A): Rt=1.01 min; MS (ESIpos): m/z=449 [M+H]+

Intermediate 114

N-(4-Bromo-3-sulfamoylphenyl)-2-(2-chlorophenyl)acetamide

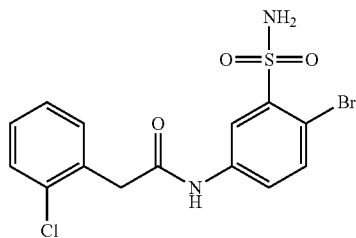 [SMILES: NS(=O)(=O)c1cc(NC(=O)Cc2ccccc2Cl)ccc1Br]

3-Aminobenzenesulfonamide (70.0 g, 406 mmol) was dissolved in dimethylformamide (540 mL) and cooled to 0° C. A solution of N-bromosuccinimide (76.0 g, 427 mmol) in dimethylformamide (300 mL) was added over 1.5 hours. It was allowed to warm up to room temperature within 1 hour and stirring at room temperature was continued for 2 hours. The reaction mixture was concentrated in vacuo, extracted with ethyl acetate (500 mL) and washed several times with water (250 mL) and brine solution (300 mL). The aqueous phases were reextracted twice with ethyl acetate and all organic phases were combined, dried over sodium sulfate and concentrated in vacuo to yield 141 g of crude 5-amino-2-bromobenzenesulfonamide.

LC-MS (Method A): Rt=0.56 min; MS (ESIpos): m/z=251/253 [M+H]+

1H-NMR (400 MHz, DMSO-$d_6$) δ [ppm]: 5.71 (s, 2H), 6.60 (dd, 1H), 7.25-7.24 (br s, 2H), 7.27 (d, 1H), 7.34 (d, 1H).

Part of the crude 5-amino-2-bromobenzenesulfonamide from the previous step (54.3 g) and (2-chlorophenyl)acetic acid (38.8 g, 0.23 mmol) were suspended in dimethylformamide (1000 mL) and cooled to 0° C. N,N-Diisopropylethylamine (83.9 g, 0.65 mmol) and 1-[bis(dimethylamino)methylene]-1H-1,2,3-triazolo[4,5-b]pyridinium 3-oxide hexafluorophosphate (HATU, 90.5 g, 0.24 mmol) were added slowly while keeping the temperature below 10° C. It was allowed to warm up to room temperature overnight. The reaction mixture was concentrated in vacuo, extracted with ethyl acetate (1250 mL), washed with 1M sodium hydroxide solution (500 mL) and twice with water (500 mL). The organic phase was dried over sodium sulfate and concentrated in vacuo. This crude product (66 g) was suspended in dichloromethane (350 mL) and shaken in an ultrasonic bath, resulting in a white precipitate of the title compound that was filtered off and dried in a drying oven (25.0 g, 61.9 mmol, 40% over 2 steps, 96% purity).

LC-MS (Method A): Rt=1.00 min; MS (ESIpos): m/z=403/405 [M+H]+

$^1$H-NMR (400 MHz, DMSO-d$_6$) δ [ppm]: 3.86 (s, 2H), 7.28-7.35 (m, 2H), 7.40-7.48 (m, 2H), 7.57 (s, 2H), 7.70-7.78 (m, 2H), 8.34-8.38 (m, 1H), 10.65 (s, 1H).

Intermediate 115

N-(4-Bromo-3-{[(dimethylamino)methylene]sulfamoyl}phenyl)-2-(2-chlorophenyl)acetamide

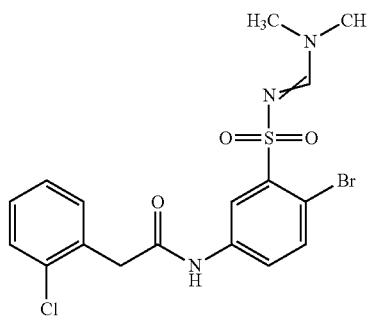

N-(4-Bromo-3-sulfamoylphenyl)-2-(2-chlorophenyl)acetamide (25.0 g, 61.9 mmol) was dissolved in dimethylformamide (320 mL) and 1,1-dimethoxy-N,N-dimethylmethanamine (14.6 g, 119 mmol) was added. It was stirred at room temperature for 3 hours, followed by concentration in vacuo and extraction with ethyl acetate (80 mL). Under these conditions the title compound went into solution and recrystallized upon ice cooling. This precipitate was filtered off and washed with a small amount of ethyl acetate to yield the pure title compound (25.8 g, 56.2 mmol, 97% purity, 91% yield).

LC-MS (Method B): Rt=1.09 min; MS (ESIpos): m/z=458/460 [M+H]+

$^1$H-NMR (400 MHz, DMSO-d$_6$) δ [ppm]: 2.93 (s, 3H), 3.19 (s, 3H), 3.86 (s, 2H), 7.28-7.35 (m, 2H), 7.40-7.48 (m, 2H), 7.68 (d, 1H), 7.74 (dd, 1H), 8.27 (s, 1H), 8.37 (d, 1H), 10.63 (s, 1H).

Intermediate 116 and Intermediate 117

Tris(dibenzylideneacetone)dipalladium(0) (409 mg, 0.45 mmol) and 2-di-tert-butylphosphino-3,4,5,6-tetramethyl-2',4',6'-triisopropyl-1,1'-biphenyl (Tetramethyl di-tBuXPhos, 215 mg, 0.45 mmol) were dissolved in -toluene (12 mL) and evacuated and flushed with argon three times. The mixture was heated to 120° C. (resulting in a brownish color) and 2-bromo-N-[(dimethylamino)methylene]-5-nitrobenzenesulfonamide (3.00 g, 8.92 mmol) and 4-(trifluoromethyl)-1H-1,2,3-triazole (2.08 g, 15.2 mmol) were added, followed by addition of potassium phosphate (3.79 g, 17.9 mmol) and stirring at 20° C. overnight. After cooling to room temperature, the reaction mixture was extracted with ethylacetate and washed with brine solution. The organic phase was dried over sodium sulfate and concentrated in vacuo. To reprotect the target compound, the crude was redissolved in dimethylformide (9 mL) and 1,1-dimethoxy-N,N-dimethylmethanamine (1.5 mL) was added. It was stirred at room temperature overnight and extracted with dichloromethane/water. The organic phase was washed with brine solution, dried over sodium sulfate and concentrated in vacuo. Chromatography over a Biotage Isolera system allowed to purify and separate the two title compounds.

Intermediate 116

N-[(Dimethylamino)methylene]-5-nitro-2-[4-(trifluoromethyl)-2H-1,2,3-triazol-2-yl]benzenesulfonamide

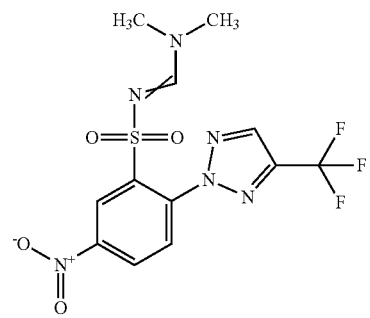

193 mg, 0.492 mmol, 6% yield, 90% purity

LC-MS (Method A): Rt=1.06 min; MS (ESIpos): m/z=393 [M+H]+

$^1$H-NMR (400 MHz, DMSO-d$_6$) δ [ppm]: 2.87 (s, 3H), 3.14 (s, 3H), 7.92 (s, 1H), 8.07 (d, 1H), 8.62 (dd, 1H), 8.79 (d, 1H), 8.87 (s, 1H).

Intermediate 117

N-[(Dimethylamino)methylene]-5-nitro-2-[4-(trifluoromethyl)-1H-1,2,3-triazol-1-yl]benzenesulfonamide

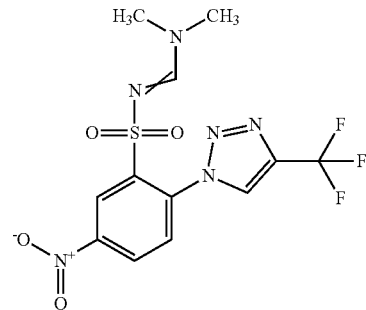

180 mg, 0.459 mmol, 5% yield, 90% purity

LC-MS (Method A): Rt=1.04 min; MS (ESIpos): m/z=393 [M+H]+

$^1$H-NMR (400 MHz, DMSO-d$_6$) δ [ppm]: 2.80 (d, 3H), 3.08 (s, 3H), 7.88 (s, 1H), 8.11 (d, 1H), 8.65 (dd, 1H), 8.77 (d, 1H), 9.35 (d, 1H).

Intermediate 118

2-(4-Cyano-1H-pyrazol-1-yl)-5-nitrobenzenesulfonamide

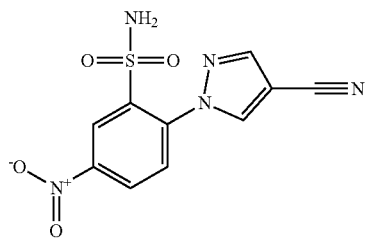

2-Chloro-5-nitrobenzenesulfonamide (250 mg, 1.06 mmol) was dissolved in acetonitrile (10 mL), followed by addition of 1H-pyrazole-4-carbonitrile (148 mg, 1.59 mmol) and finely powdered potassium carbonate (438 mg, 3.17 mmol). The reaction mixture was stirred overnight at 100° C. After cooling to room temperature dichloromethane and water were added and the organic phase was washed with brine solution, dried over sodium sulfate and concentrated in vacuo. Purification by preparative HPLC (Chromatorex C-18 10 μm, 125×30 mm, acetonitrile/water+0.1% formic acid) gave the title compound (128 mg, 0.436 mmol, 41% yield, 70% purity).

LC-MS (Method A): Rt=0.78 min; MS (ESIpos): m/z=294 [M+H]+

$^1$H-NMR (400 MHz, DMSO-d$_6$) δ [ppm]: 7.94 (br d, 2H), 7.98 (d, 1H), 8.42 (d, 1H), 8.61 (dd, 1H), 8.83 (d, 1H), 9.04 (d, 1H).

Intermediate 119

5-Amino-2-(4-cyano-1H-pyrazol-1-yl)benzenesulfonamide

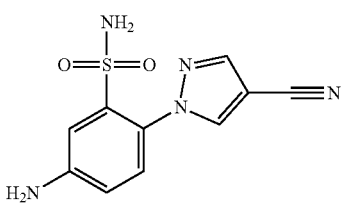 [SMILES: N#Cc1cnn(-c2ccc(N)cc2S(N)(=O)=O)c1]

2-(4-Cyano-1H-pyrazol-1-yl)-5-nitrobenzenesulfonamide (128 mg, 0.44 mmol) was dissolved in methanol (17 mL) and dioxane (3 mL). The flask was evacuated and flushed with nitrogen, followed by the addition of palladium on carbon (13 mg, 10% loading). It was again evacuated and now flushed with hydrogen, followed by stirring under a hydrogen atmosphere for 5 h at room temperature. The hydrogen was removed, the catalyst filtered off and the filtrate was concentrated in vacuo. It was redissolved in dichloromethane and again concentrated in vacuo to give the title compound (81 mg, 0.308 mmol, 70% yield, 79% purity).

LC-MS (Method B): Rt=0.46 min; MS (ESIpos): m/z=264 [M+H]+

$^1$H-NMR (400 MHz, DMSO-d$_6$) δ [ppm]: 6.06 (s, 2H), 6.77 (dd, 1H), 7.17-7.23 (m, 4H), 8.23 (d, 1H), 8.71 (d, 1H).

Intermediate 120

Ethyl 1-{2-[(2,4-dimethoxybenzyl)sulfamoyl]-4-nitrophenyl}-1H-pyrazole-4-carboxylate

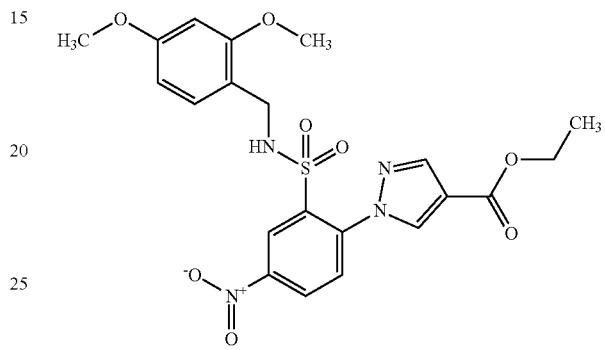

To a solution of 2-chloro-N-(2,4-dimethoxybenzyl)-5-nitrobenzenesulfonamide (5 g, 12.9 mmol) in acetonitrile (250 mL) were added ethyl 1H-pyrazole-4-carboxylate (2.72 g, 19.4 mmol, CAS-RN 37622-90-5) and powdered potassium carbonate (5.36 g, 38.8 mmol) and it was heated for 19 h to 90° C. The reaction mixture was diluted with water and extracted with ethyl acetate. The combined organic phases were washed with brine and dried using a Whatman filter. Concentration under reduced pressure led to the title compound that was used without further purification (7.8 g, 98% yield, 80% purity).

LC-MS (Method A): Rt=1.27 min; MS (ESIpos): m/z=491 [M+H]+

$^1$H-NMR (400 MHz, DMSO-d$_6$) δ [ppm]: 1.30 (t, 3H), 3.51 (s, 3H), 3.63 (s, 3H), 4.14 (s, 2H), 4.29 (q, 2H), 6.17 (d, 1H), 6.28 (dd, 1H), 7.07 (d, 1H), 7.91 (d, 1H), 8.05 (br s, 1H), 8.24 (d, 1H), 8.29 (s, 1H), 8.46 (dd, 1H), 8.84 (s, 1H).

Intermediate 121

1-{2-[(2,4-Dimethoxybenzyl)sulfamoyl]-4-nitrophenyl}-1H-pyrazole-4-carboxylic acid

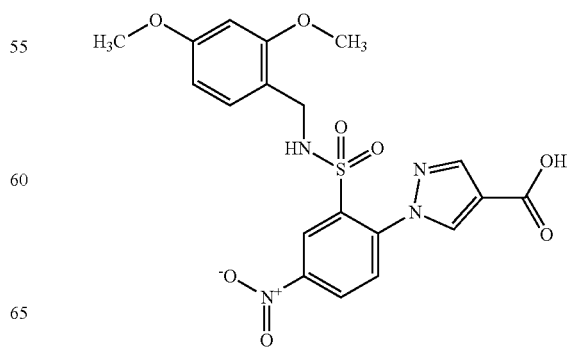

To a solution of ethyl 1-{2-[(2,4-dimethoxybenzyl)sulfamoyl]-4-nitrophenyl}-1H-pyrazole-4-carboxylate (7.8 g, 12.9 mmol, 80% purity) in tetrahydrofuran (129 mL) was added a solution of lithium hydroxide (1.55 g, 64.6 mmol) in water (11.6 mL) and it was stirred for 18 h at room temperature. The solvent was evaporated and the crude was suspended in water (15 mL), and acidified to a pH of 5 using aq. HCl (55 mL, 1.0 M). The slurry was stirred for 30 min, and filtered. The precipitate was dried at 50° C. in vacuo (5.7 g, 91% yield, 95% purity).

LC-MS (Method A): Rt=1.08 min; MS (ESIpos): m/z=463 [M+H]$^+$ $^1$H-NMR (400 MHz, DMSO-d$_6$) δ [ppm]: 3.50 (s, 3H), 3.62 (s, 3H), 4.14 (d, 2H), 6.16 (d, 1H), 6.28 (dd, 1H), 7.07 (d, 1H), 7.90 (d, 1H), 8.12 (t, 1H), 8.22 (d, 1H), 8.24 (s, 1H), 8.45 (dd, 1H), 8.76 (s, 1H), 12.82 (br s, 1H).

Intermediate 122

2-(Trimethylsilyl)ethyl (1-{2-[(2,4-dimethoxybenzyl)sulfamoyl]-4-nitrophenyl}-1H-pyrazol-4-yl)carbamate

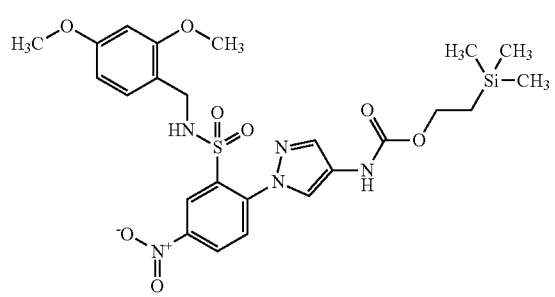

To a solution of 1-{2-[(2,4-dimethoxybenzyl)sulfamoyl]-4-nitrophenyl}-1H-pyrazole-4-carboxylic acid (5.7 g, 11.7 mmol, 95% purity) and triethylamine (2.45 mL, 17.6 mmol) in dioxane (59 mL) was added diphenyl phosphorazidate (6.45 g, 23.4 mmol), and the solution was heated to 50° C. for 75 min. Then, 2-(trimethylsilyl)ethanol (8.39 mL, 58.5 mmol) was added, and the mixture was stirred at 100° C. for 3 h. The reaction mixture was diluted with ethyl acetate, and washed with saturated aqueous sodium hydrogen carbonate solution and with brine. The organic phase was dried using a Whatman filter and evaporated in vacuo. Purification by flash chromatography yielded the title compound (6.5 g, 86% yield, 89% purity).

LC-MS (Method A): Rt=1.46 min; MS (ESIpos): m/z=578 [M+H]$^+$ $^1$H-NMR (400 MHz, DMSO-d$_6$) δ [ppm]: 0.07 (s, 9H), 1.03 (m, 2H), 3.46 (s, 3H), 3.63 (s, 3H), 4.18 (d, 2H), 4.21 (m, 2H), 6.14 (d, 1H), 6.29 (dd, 1H), 7.10 (d, 1H), 7.81 (d, 1H), 7.88 (s, 1H), 8.17 (t, 1H), 8.20 (d, 1H), 8.21 (s, 1H), 8.40 (dd, 1H), 9.74 (s, 1H).

Intermediate 123

2-(Trimethylsilyl)ethyl [1-(4-{[(2-chlorophenyl)acetyl]amino}-2-[(2,4-dimethoxybenzyl)sulfamoyl]phenyl)-1H-pyrazol-4-yl]carbamate

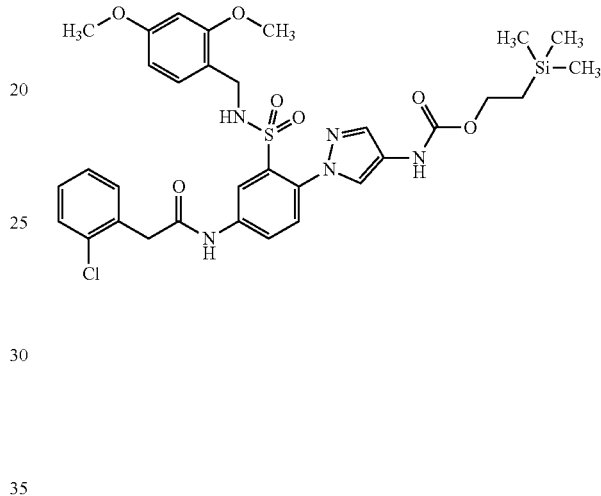

Tin(II) chloride dihydrate (11.1 g, 50.3 mmol) was added to a solution of 2-(trimethylsilyl)ethyl (1-{2-[(2,4-dimethoxybenzyl)sulfamoyl]-4-nitrophenyl}-1H-pyrazol-4-yl)carbamate (6.5 g, 89% purity, 10.1 mmol) in dioxane (129 mL), followed by stirring for 4 h at 70° C. and overnight at room temperature. The reaction mixture was concentrated in vacuo. Water was added to the residue and the mixture was neutralized with 5% aqueous sodium hydroxide solution, then extracted three times with ethyl acetate. The combined organic phases were filtered over Celite, dried over a Whatman filter, and concentrated in vacuo to give 5.5 g crude 2-(trimethylsilyl)ethyl (1-{4-amino-2-[(2,4-dimethoxybenzyl)sulfamoyl]phenyl}-1H-pyrazol-4-yl)carbamate that was used without further purification in the next step.

Crude material from the previous step (5.5 g) was dissolved in DMF (154 mL) followed by the addition of (2-chlorophenyl)acetic acid (2.74 g, 16.1 mmol), N,N-diisopropylethylamine (5.6 mL, 32.1 mmol) and HATU (6.11 g, 16.1 mmol). The reaction mixture was stirred for 17 h at room temperature. Saturated aqueous sodium hydrogen carbonate solution was added and the mixture was extracted three times with ethyl acetate. Then all organic phases were combined, washed with brine, dried over a Whatman filter and concentrated in vacuo to give the title compound that was used without further purification (10.55 g, 50% purity, 75% yield over 2 steps).

LC-MS (Method B): Rt=1.49 min; MS (ESIpos): m/z=700 [M+H]$^+$

Intermediate 124

N-{4-(4-Amino-1H-pyrazol-1-yl)-3-[(2,4-dimethoxybenzyl)sulfamoyl]phenyl}-2-(2-chlorophenyl)acetamide

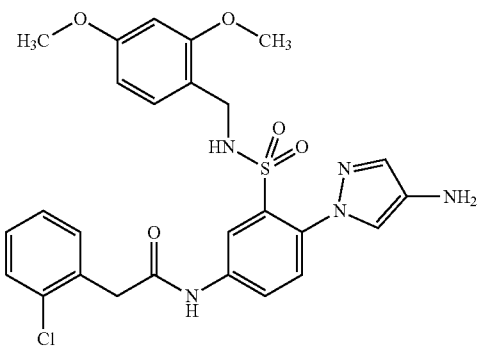 [SMILES: COc1ccc(CNS(=O)(=O)c2cc(NC(=O)Cc3ccccc3Cl)ccc2-n2cc(N)cn2)c(OC)c1]

To a solution of 2-(trimethylsilyl)ethyl [1-(4-{[(2-chlorophenyl)acetyl]amino}-2-[(2,4-dimethoxybenzyl)sulfamoyl]phenyl)-1H-pyrazol-4-yl]carbamate (10.55 g, 7.53 mmol) in tetrahydrofuran (4 mL), a 1 M solution of tetrabutylammonium fluoride in tetrahydrofuran (15.1 mL, 15.1 mmol) was added, and the mixture was heated for 2.5 h to 50° C. Additional 1 M solution of tetrabutylammonium fluoride in tetrahydrofuran (3.77 mL, 3.77 mmol) was added, and heating to 50° C. was continued for 3 h. The reaction mixture was diluted with water and extracted with ethyl acetate. The combined organic phases were washed with brine and dried using a Whatman filter. Concentration under reduced pressure led to the title compound that was purified by flash chromatography (2.9 g, 55% yield, 80% purity).

LC-MS (Method B): Rt=1.18 min; MS (ESIpos): m/z=556 [M+H]$^+$ $^1$H-NMR (400 MHz, DMSO-d$_6$) δ [ppm]: 3.56 (s, 3H), 3.63 (s, 3H), 3.84 (s, 2H), 3.95 (d, 2H), 4.13 (s, 2H), 6.30 (dd, 1H), 6.31 (d, 1H), 7.02 (d, 1H), 7.24 (s, 1H), 7.28 (s, 1H), 7.30 (m, 2H), 7.36 (d, 1H), 7.42 (m, 2H), 7.77 (t, 1H), 7.87 (dd, 1H), 8.02 (d, 1H), 10.57 (s, 1H).

Intermediate 125

N-[1-(4-{[(2-Chlorophenyl)acetyl]amino}-2-[(2,4-dimethoxybenzyl)sulfamoyl]phenyl)-1H-pyrazol-4-yl]-2,2-difluoroacetamide

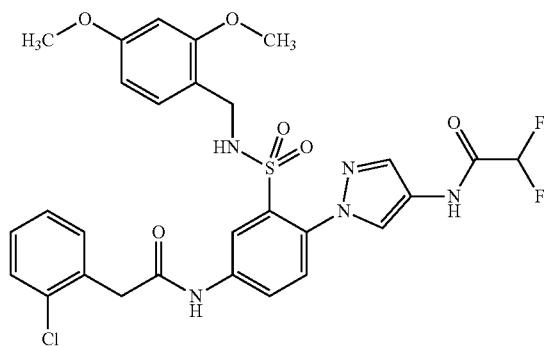 [SMILES: COc1ccc(CNS(=O)(=O)c2cc(NC(=O)Cc3ccccc3Cl)ccc2-n2cc(NC(=O)C(F)F)cn2)c(OC)c1]

N-{4-(4-Amino-1H-pyrazol-1-yl)-3-[(2,4-dimethoxybenzyl)sulfamoyl]phenyl}-2-(2-chloro-phenyl)acetamide (200 mg, 360 μmol) was dissolved in DMF (6.9 mL), and difluoroacetic acid (45.4 μL, 719 μmol), N,N-diisopropylethylamine (251 μL, 1.44 mmol) and HATU (274 mg, 719 μmol) were added. The reaction mixture was stirred overnight at room temperature. Saturated aqueous sodium hydrogen carbonate solution was added and the mixture was extracted three times with ethyl acetate. Then all organic phases were combined, washed with brine, dried over a Whatman filter and concentrated in vacuo to give the crude title compound (251 mg) that was used without further purification.

LC-MS (Method B): Rt=1.24 min; MS (ESIpos): m/z=634 [M+H]$^+$

Intermediate 126

N-[1-(4-{[(2-Chlorophenyl)acetyl]amino}-2-[(2,4-dimethoxybenzyl)sulfamoyl]phenyl)-1H-pyrazol-4-yl]-3,3,3-trifluoropropanamide

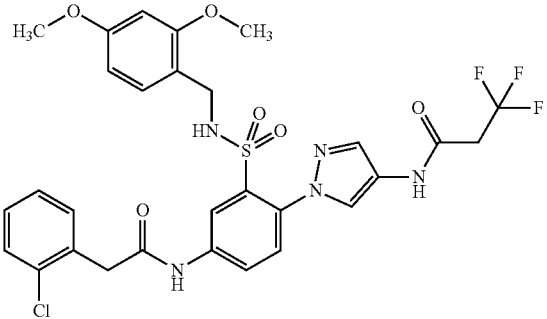 [SMILES: COc1ccc(CNS(=O)(=O)c2cc(NC(=O)Cc3ccccc3Cl)ccc2-n2cc(NC(=O)CC(F)(F)F)cn2)c(OC)c1]

A mixture of N-{4-(4-amino-1H-pyrazol-1-yl)-3-[(2,4-dimethoxybenzyl)sulfamoyl]phenyl}-2-(2-chlorophenyl)acetamide (200 mg, 288 μmol, 80% purity), N,N-diisopropylethylamine (150 μL, 863 μmol), and 3,3,3-trifluoropropanoyl chloride (35.6 μL, 345 μmol) in THF (400 μL) was stirred vigorously at room temperature for 7 days. Saturated aqueous sodium hydrogen carbonate solution was added and the mixture was extracted three times with dichloromethane. Then all organic phases were combined, washed with brine, dried over a Whatman filter and concentrated in vacuo to give the crude title compound (285 mg) that was used without further purification.

LC-MS (Method B): Rt=1.27 min; MS (ESIpos): m/z=666 [M+H]$^+$

Intermediate 127

(±)-N-[1-(4-{[(2-Chlorophenyl)acetyl]amino}-2-[(2,4-dimethoxybenzyl)sulfamoyl]phenyl)-1H-pyrazol-4-yl]-3,3,3-trifluoro-2-methylpropanamide

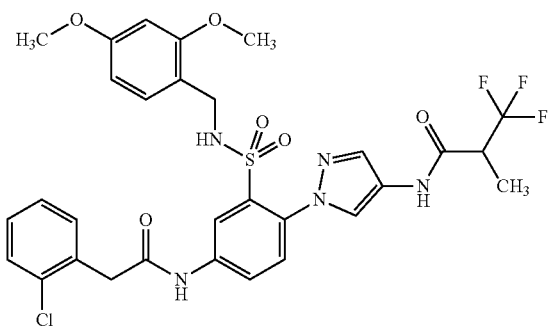 [SMILES: COc1ccc(CNS(=O)(=O)c2cc(NC(=O)Cc3ccccc3Cl)ccc2-n2cc(NC(=O)C(C)C(F)(F)F)cn2)c(OC)c1]

A mixture of N-{4-(4-amino-1H-pyrazol-1-yl)-3-[(2,4-dimethoxybenzyl)sulfamoyl]phenyl}-2-(2-chlorophenyl)acetamide (216 mg, 350 µmol, 90% purity), N,N-diisopropylethylamine (305 µL, 1.75 mmol), and (±)-3,3,3-trifluoro-2-methylpropanoyl chloride (112 mg, 700 µmol) was combined at 0° C. and stirred at room temperature overnight. Saturated aqueous sodium hydrogen carbonate solution was added and the mixture was extracted three times with dichloromethane. Then all organic phases were combined, washed with brine, dried over a Whatman filter and concentrated in vacuo to give the crude title compound (327 mg) that was used without further purification.

LC-MS (Method A): Rt=1.31 min; MS (ESIpos): m/z=680 [M+H]$^+$

Intermediate 128

2-(2-Chlorophenyl)-N-(3-[(2,4-dimethoxybenzyl)sulfamoyl]-4-{4-(2,5-dimethyl-pyrrolidin-1-yl)-1H-pyrazol-1-yl}phenyl)acetamide (Mixture of stereoisomers)

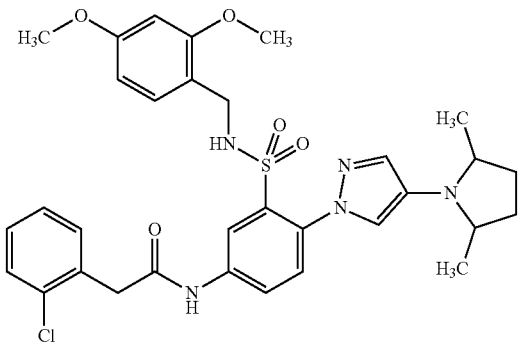 [SMILES: COc1ccc(CNS(=O)(=O)c2cc(NC(=O)Cc3ccccc3Cl)ccc2-n2cc(N3C(C)CCC3C)cn2)c(OC)c1]

To a solution of N-{4-(4-amino-1H-pyrazol-1-yl)-3-[(2,4-dimethoxybenzyl)sulfamoyl]phenyl}-2-(2-chlorophenyl)acetamide (400 mg, 575 µmol, 80% purity) in acetonitrile (10 mL) were added 2,5-dibromohexane (107 µL, 691 µmol, CAS-RN 24774-58-1) and powdered potassium carbonate (191 mg, 1.38 mmol), and the mixture was stirred for 6 days at 90° C. The reaction mixture was diluted with water and extracted with ethyl acetate. The combined organic phases were washed with brine and dried using a Whatman filter. Concentration under reduced pressure led to the crude title compound (531 mg) as a mixture of stereoisomers that was used without further purification.

LC-MS (Method A): Rt=1.29 min and 1.36 min; MS (ESIpos): m/z=638 [M+H]$^+$ each.

Intermediate 129

N-(4-{4-[(2,2-Difluoroethyl)amino]-1H-pyrazol-1-yl}-3-[(2,4-dimethoxybenzyl)sulfamoyl]phenyl)-2-(2-fluorophenyl)acetamide

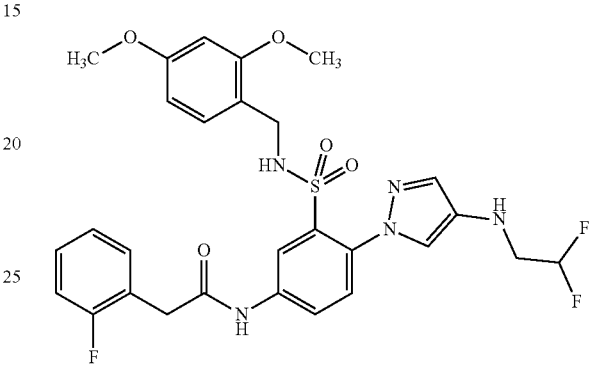

Tin(II) chloride dihydrate (621 mg, 2.75 mmol) was added to a solution of 2-{4-[(2,2-difluoroethyl)amino]-1H-pyrazol-1-yl}-N-(2,4-dimethoxybenzyl)-5-nitrobenzenesulfonamide (274 mg, 551 µmol) in dioxane (7.1 mL) and stirred for 4 h at 70° C. The reaction mixture was concentrated in vacuo. Water was added to the residue and the mixture was extracted three times with ethyl acetate. The combined organic phases were filtered over Celite, washed with brine, dried using a Whatman filter, and concentrated in vacuo to give 114 mg crude 5-amino-2-{4-[(2,2-difluoroethyl)amino]-1H-pyrazol-1-yl}-N-(2,4-dimethoxy-benzyl)benzenesulfonamide that was used without further purification in the next step.

The crude material from the previous step (230 mg) was dissolved in DMF (10 mL) followed by the addition of (2-fluorophenyl)acetic acid (114 mg, 738 µmol), N,N-diisopropylethylamine (343 µL, 1.97 mmol) and HATU (281 mg, 738 µmol). The reaction mixture was stirred overnight at room temperature. Water was added and the mixture was extracted three times with ethyl acetate. Then all organic phases were combined, washed with brine, dried over a Whatman filter and concentrated in vacuo to give the title compound that was used without further purification (426 mg, 60% purity, 77% yield over 2 steps).

LC-MS (Method B): Rt=1.25 min; MS (ESIpos): m/z=604 [M+H]$^+$

Intermediate 130

N-(2,2,2-Trifluoroethyl)-1H-pyrazol-4-amine

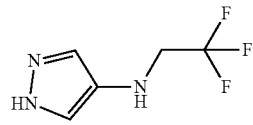

To a solution of 1H-pyrazol-4-amine (300 mg, 95% purity, 3.43 mmol) in acetonitrile (17 mL) were added 2,2,2-trifluoroethyl trifluoromethanesulfonate (741 µl, 5.1 mmol, CAS-RN 6226-25-1), powdered potassium carbonate (1.06 g, 7.65 mmol), and triethylamine (720 µL, 5.1 mmol). The mixture was heated to 900C for 4 h and stirred at room temperature overnight. For work-up, it was filtered, and the solid was rinsed with ethyl acetate. Concentration of the filtrate in vacuo followed by flash chromatography led to the title compound (435 mg, 73% yield, 95% purity).

LC-MS (Method A): Rt=0.61 min; MS (ESIpos): m/z=166 (M+H)⁺

¹H-NMR (400 MHz, DMSO-d₆) δ [ppm]: 3.62 (qd, 2H), 5.06 (t, 1H), 7.13 (s, 2H), 12.12 (s, 1H).

Intermediate 131

N-(2,4-Dimethoxybenzyl)-5-nitro-2-{4-[(2,2,2-trifluoroethyl)amino]-1H-pyrazol-1-yl}benzenesulfonamide

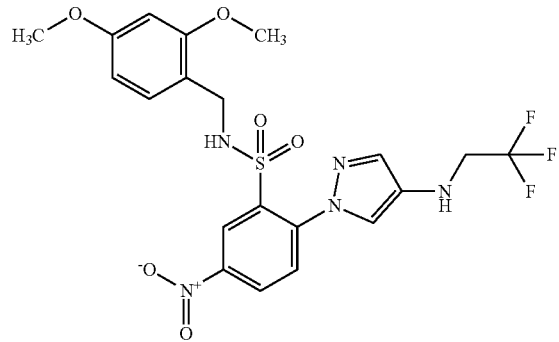

To a solution of 2-chloro-N-(2,4-dimethoxybenzyl)-5-nitrobenzenesulfonamide (371 mg, 911 µmol) in acetonitrile (9.6 mL) were added N-(2,2,2-trifluoroethyl)-1H-pyrazol-4-amine (430 mg, 1.82 mmol) and powdered potassium carbonate (377 mg, 2.73 mmol) and it was irradiated for 12 h at 120° C. in the microwave. The reaction mixture was filtered, concentrated in vacuo, and the residue was purified by flash chromatography (345 mg, 55% yield, 75% purity).

LC-MS (Method B): Rt=1.28 min; MS (ESIpos): m/z=516 [M+H]⁺

¹H-NMR (400 MHz, DMSO-d₆) δ [ppm]: 3.38 (s, 3H), 3.59 (s, 3H), 3.81 (qd, 2H), 4.16 (d, 2H), 5.80 (t, 1H), 6.08 (d, 1H), 6.25 (dd, 1H), 7.08 (d, 1H), 7.67 (s, 1H), 7.70 (d, 1H), 7.83 (s, 1H), 8.16 (d, 1H), 8.22 (t, 1H), 8.38 (dd, 1H).

Intermediate 132

2-(2-Chlorophenyl)-N-(3-[(2,4-dimethoxybenzyl)sulfamoyl]-4-{4-[(2,2,2-trifluoroethyl)amino]-1H-pyrazol-1-yl}phenyl)acetamide Tin(II) chloride dihydrate (558 mg, 2.47 mmol) was added to a solution of N-(2,4-dimethoxybenzyl)-5-nitro-2-{4-[(2,2,2-trifluoroethyl)amino]-1H-pyrazol-1-yl}benzenesulfonamide (340 mg, 495 µmol, 75% purity) in dioxane (6.3 mL) and stirred for 4 h at 70° C. The reaction mixture was concentrated in vacuo. Water was added to the residue and the mixture was extracted three times with ethyl acetate. The combined organic phases were filtered over Celite, washed with brine, dried using a Whatman filter, and concentrated in vacuo to give 320 mg crude 5-amino-N-(2,4-dimethoxybenzyl)-2-{4-[(2,2,2-trifluoroethyl)amino]-1H-pyrazol-1-yl}benzenesulfonamide that was used without further purification in the next step.

The crude material from the previous step (315 mg) was dissolved in DMF (8.2 mL) followed by the addition of (2-chlorophenyl)acetic acid (116 mg, 681 µmol), N,N-diisopropylethylamine (316 µL, 1.82 mmol) and HATU (259 mg, 681 µmol). The reaction mixture was stirred overnight at room temperature. Water was added and the mixture was extracted three times with ethyl acetate. Then all organic phases were combined, washed with brine, dried over a Whatman filter and concentrated in vacuo to give the title compound that was used without further purification (528 mg, 55% purity, 92% yield over 2 steps).

LC-MS (Method B): Rt=1.33 min; MS (ESIpos): m/z=638 [M+H]⁺

Intermediate 133

N-(2,4-Dimethoxybenzyl)-2-(4-isopropyl-1H-pyrazol-1-yl)-5-nitrobenzenesulfonamide

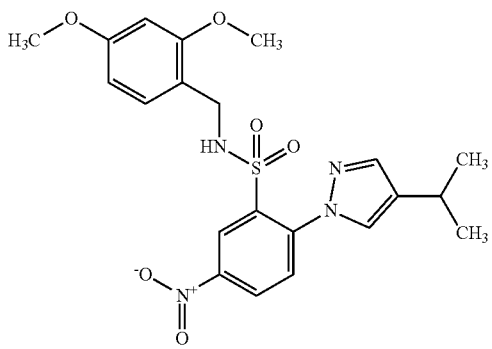

To a solution of 2-chloro-N-(2,4-dimethoxybenzyl)-5-nitrobenzenesulfonamide (1.0 g, 2.59 mmol) in acetonitrile (13 mL) were added 4-isopropyl-1H-pyrazole hydrochloride (568 mg, 3.88 mmol, CAS-RN 1390654-61-1) and powdered potassium carbonate (1.43 g, 10.3 mmol). The mixture was irradiated overnight at 120° C. and another night at 130° C. in the microwave. The reaction mixture was filtered, concentrated in vacuo, and the residue was purified by flash chromatography (646 mg, 49% yield, 90% purity).

LC-MS (Method B): Rt=1.37 min; MS (ESIpos): m/z=461 [M+H]$^+$ $^1$H-NMR (400 MHz, DMSO-d$_6$) δ [ppm]: 1.24 (d, 6H), 2.89 (sept, 1H), 3.42 (s, 3H), 3.60 (s, 3H), 4.16 (d, 2H), 6.11 (d, 1H), 6.26 (dd, 1H), 7.09 (d, 1H), 7.81 (d, 1H), 7.89 (s, 1H), 8.16 (s, 1H), 8.20 (d, 1H), 8.28 (t, 1H), 8.40 (dd, 1H).

Intermediate 134

2-(2-Chlorophenyl)-N-{3-[(2,4-dimethoxybenzyl)sulfamoyl]-4-(4-isopropyl-1H-pyrazol-1-yl)phenyl}acetamide

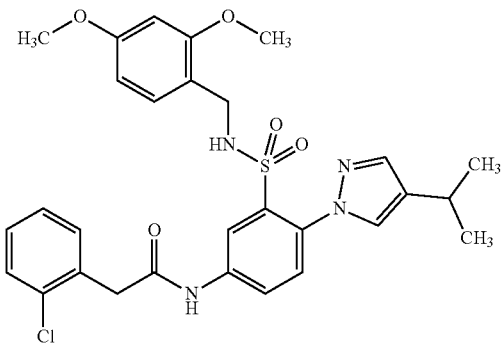 [SMILES: COc1ccc(CNS(=O)(=O)c2cc(NC(=O)Cc3ccccc3Cl)ccc2-n2cc(C(C)C)cn2)c(OC)c1]

Tin(II) chloride dihydrate (1.42 g, 6.29 mmol) was added to a solution of N-(2,4-dimethoxybenzyl)-2-(4-isopropyl-1H-pyrazol-1-yl)-5-nitrobenzenesulfonamide (644 mg, 1.26 mmol, 90% purity) in dioxane (16 mL) and stirred for 4 h at 70° C. The reaction mixture was concentrated in vacuo. Water was added to the residue and the mixture was extracted three times with ethyl acetate. The combined organic phases were filtered over Celite, washed with brine, dried using a Whatman filter, and concentrated in vacuo to give 443 mg crude 5-amino-N-(2,4-dimethoxybenzyl)-2-(4-isopropyl-1H-pyrazol-1-yl)benzenesulfonamide that was used without further purification in the next step.

Crude material from the previous step (220 mg) was dissolved in DMF (5 mL) followed by the addition of (2-chlorophenyl)acetic acid (124 mg, 728 μmol), N,N-diisopropylethylamine (338 μL, 1.94 mmol) and HATU (277 mg, 728 μmol). The reaction mixture was stirred overnight at room temperature. Saturated aqueous sodium hydrogen carbonate solution was added and the mixture was extracted three times with ethyl acetate. Then all organic phases were combined, washed with brine, dried over a Whatman filter and concentrated in vacuo to give the title compound that was used without further purification (410 mg, 65% purity, 73% yield over 2 steps).

LC-MS (Method A): Rt=1.43 min; MS (ESIpos): m/z=583 [M+H]$^+$

Intermediate 135

N-{3-[(2,4-Dimethoxybenzyl)sulfamoyl]-4-(4-isopropyl-1H-pyrazol-1-yl)phenyl}-2-(2-fluorophenyl)acetamide

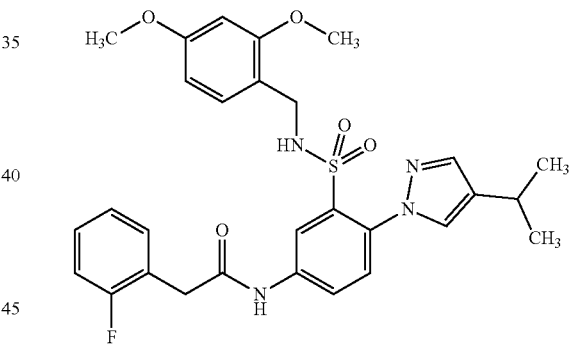

Crude 5-amino-N-(2,4-dimethoxybenzyl)-2-(4-isopropyl-1H-pyrazol-1-yl)benzenesulfonamide (220 mg) was dissolved in DMF (5 mL) followed by the addition of (2-fluorophenyl)acetic acid (112 mg, 728 μmol), N,N-diisopropylethylamine (338 μL, 1.94 mmol) and HATU (277 mg, 728 μmol). The reaction mixture was stirred overnight at room temperature. Saturated aqueous sodium hydrogen carbonate solution was added and the mixture was extracted three times with ethyl acetate. Then all organic phases were combined, washed with brine, dried over a Whatman filter and concentrated in vacuo to give the title compound that was used without further purification (407 mg, 65% purity, 74% yield over 2 steps).

LC-MS (Method A): Rt=1.40 min; MS (ESIpos): m/z=567 [M+H]$^+$

Intermediate 136

2-[(Dimethylamino)methylene]-4,4,4-trifluoro-N,N-dimethylbutan-1-iminium hexafluorophosphate

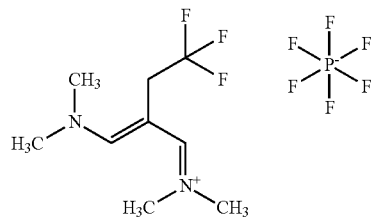

To a solution of 4,4,4-trifluorobutanoic acid (5.0 g, 35.2 mmol, CAS-RN 406-93-9) in DMF (17.5 mL), at 50° C. phosphoric trichloride (3.28 mL, 35.2 mmol) was added dropwise. After stirring for 2 h at 70° C., the solution was cooled to room temperature. This reaction mixture and 5N NaOH (12.7 mL, 63.3 mmol) were added concurrently over 30 min to a mixture of 55% hexafluorophosphoric acid (6.1 mL, 38.0 mol) and 5N NaOH (14.1 mL) in water (46 mL) maintaining the temperature at <10° C. The mixture was stirred for 1 h at 0° C. and filtered off. The yellow solid was washed with water. then dried in vacuo at <40° C. to give the title compound (545 mg, 4% yield, 95% purity).

LC-MS (Method A): Rt=0.56 min; MS (ESIpos): m/z=209 [M+H]$^+$ $^1$H-NMR (400 MHz, DMSO-d$_6$) δ [ppm]: 3.30 (s, 12H), 3.62 (q, 2H), 7.72 (s, 2H).

Intermediate 137

4-(2,2,2-Trifluoroethyl)-1H-pyrazole

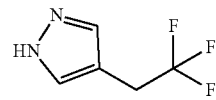

Hydrazine monohydrate (82 mg, 1.69 mmol) was added dropwise to a stirred solution of 2-[(dimethylamino)methylene]-4,4,4-trifluoro-N,N-dimethylbutan-1-iminium hexafluorophosphate (543 mg, 1.53 mmol) in methanol (7.5 mL). The resulting solution was refluxed for 90 min, and cooled to room temperature. Concentrated hydrochloric acid (378 μL) was added and heating at reflux was continued for 2 h. The solvent was evaporated in vacuo and the residue was taken up in water and adjusted to pH 10 with 2M NaOH (3 mL). The product was extracted with dichloromethane. The combined extracts were dried over a Whatman filter and concentrated in vacuo to give the title compound (226 mg, 88% yield, 90% purity) that was used without further purification.

LC-MS (Method B): Rt=0.71 min; MS (ESIpos): m/z=151 [M+H]$^+$ $^1$H-NMR (400 MHz, DMSO-d$_6$) δ [ppm]: 3.48 (q, 2H), 7.44 (s, 1H), 7.72 (s, 1H), 12.85 (s, 1H).

Intermediate 138

N-(2,4-Dimethoxybenzyl)-5-nitro-2-[4-(2,2,2-trifluoroethyl)-1H-pyrazol-1-yl]benzenesulfonamide

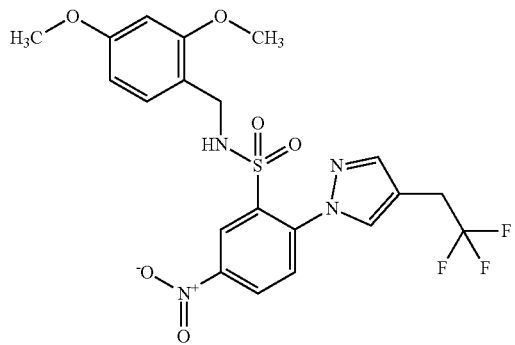

To a solution of 2-chloro-N-(2,4-dimethoxybenzyl)-5-nitrobenzenesulfonamide (417 mg, 1.08 mmol) in acetonitrile (17 mL) were added 4-(2,2,2-trifluoroethyl)-1H-pyrazole (270 mg, 1.62 mmol, 90% purity) and powdered potassium carbonate (447 mg, 3.24 mmol). The mixture was irradiated for 195 min at 120° C. in the microwave. The reaction mixture was diluted with water and extracted with ethyl acetate. The combined organic phases were washed with brine and dried using a Whatman filter. Concentration under reduced pressure led to the title compound that was purified by flash chromatography (185 mg, 29% yield, 85% purity).

LC-MS (Method B): Rt=1.33 min; MS (ESIpos): m/z=501 [M+H]$^+$ $^1$H-NMR (400 MHz, DMSO-d$_6$) δ [ppm]: 3.46 (s, 3H), 3.61 (s, 3H), 3.65 (q, 1H), 4.16 (d, 2H), 6.14 (d, 1H), 6.27 (dd, 1H), 7.09 (d, 1H), 7.81 (d, 1H), 7.94 (s, 1H), 8.16 (t, 1H), 8.21 (d, 1H), 8.34 (s, 1H), 8.42 (dd, 1H).

Intermediate 139

2-(2-Chlorophenyl)-N-{3-[(2,4-dimethoxybenzyl)sulfamoyl]-4-[4-(2,2,2-trifluoroethyl)-1H-pyrazol-1-yl]phenyl}acetamide

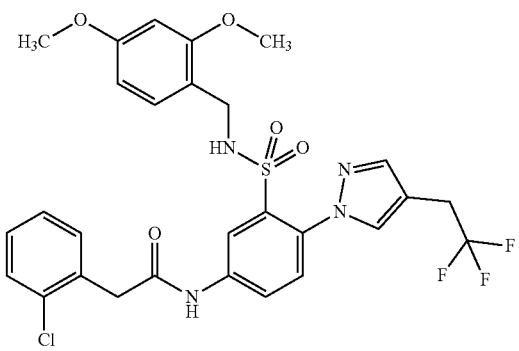 [SMILES: COc1ccc(CNS(=O)(=O)c2cc(NC(=O)Cc3ccccc3Cl)ccc2-n2cc(CC(F)(F)F)cn2)c(OC)c1]

Tin(II) chloride dihydrate (344 mg, 1.53 mmol) was added to a solution of N-(2,4-dimeth-oxybenzyl)-5-nitro-2-[4-(2,2,2-trifluoroethyl)-1H-pyrazol-1-yl]benzenesulfonamide (180 mg, 306 μmol, 85% purity) in dioxane (3.9 mL)

and stirred for 4 h at 70° C. The reaction mixture was concentrated in vacuo. Water was added to the residue and the mixture was extracted three times with ethyl acetate. The combined organic phases were filtered over Celite, washed with brine, dried using a Whatman filter, and concentrated in vacuo to give 196 mg crude 5-amino-N-(2,4-dimethoxybenzyl)-2-[4-(2,2,2-trifluoroethyl)-1H-pyrazol-1-yl]benzenesulfonamide that was used without further purification in the next step.

Crude material from the previous step (145 mg) was dissolved in DMF (6 mL) followed by the addition of (2-chlorophenyl)acetic acid (63 mg, 371 µmol), N,N-diisopropylethylamine (215 µL, 1.24 mmol) and HATU (141 mg, 371 µmol). The reaction mixture was stirred at room temperature for 2 days. Saturated aqueous sodium hydrogen carbonate solution was added and the mixture was extracted three times with ethyl acetate. Then all organic phases were combined, washed with brine, dried over a Whatman filter and concentrated in vacuo to give the title compound that was used without further purification (220 mg, 85% purity, 98% yield over 2 steps).

LC-MS (Method A): Rt=1.37 min; MS (ESIpos): m/z=623 [M+H]$^+$

Intermediate 140

N-{3-[(2,4-Dimethoxybenzyl)sulfamoyl]-4-[4-(2,2,2-trifluoroethyl)-1H-pyrazol-1-yl]phenyl}-2-(2-fluorophenyl)acetamide

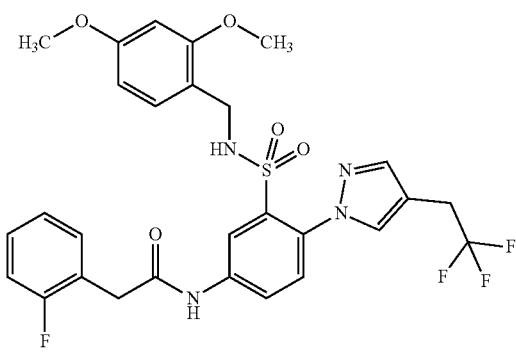 [SMILES: COc1ccc(CNS(=O)(=O)c2cc(NC(=O)Cc3ccccc3F)ccc2-n2cc(CC(F)(F)F)cn2)c(OC)c1]

Crude 5-amino-N-(2,4-dimethoxybenzyl)-2-[4-(2,2,2-trifluoroethyl)-1H-pyrazol-1-yl]benzenesulfonamide (89 mg) was dissolved in DMF (4 mL) followed by the addition of (2-fluorophenyl)acetic acid (117 mg, 760 µmol), N,N-diisopropylethylamine (165 µL, 950 µmol) and HATU (217 mg, 570 µmol). The reaction mixture was stirred for 3 days at room temperature. Saturated aqueous sodium hydrogen carbonate solution was added and the mixture was extracted three times with ethyl acetate. Then all organic phases were combined, washed with brine, dried over a Whatman filter and concentrated in vacuo to give the title compound that was used without further purification (136 mg, 85% purity, 98% yield over 2 steps).

LC-MS (Method A): Rt=1.36 min; MS (ESIpos): m/z=607 [M+H]$^+$

Intermediate 141

2-(5-Cyclopropyl-1,2,4-oxadiazol-3-yl)-N-(2,4-dimethoxybenzyl)-5-nitrobenzenesulfonamide

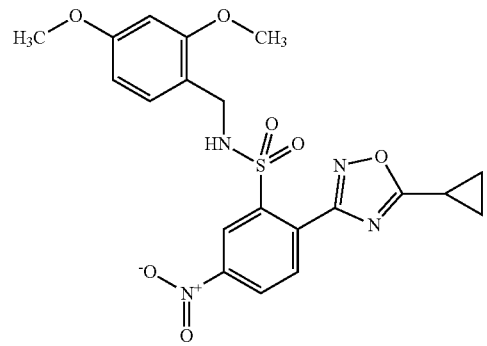

2-[(2,4-Dimethoxybenzyl)sulfamoyl]-N'-hydroxy-4-nitrobenzenecarboximidamide (84 mg, 205 µmol) was stirred with cyclopropanecarboxylic anhydride (51 µL, 450 µmol) in toluene (4.2 mL) at reflux overnight. Another cyclopropanecarboxylic anhydride (27 µL, 225 µmol) was added and the reaction was heated to reflux for 3 h. The reaction mixture was taken up in water and extracted with ethyl acetate. The organic phase was washed with brine, dried over a Whatman filter, and concentrated under reduced pressure yielding the crude title compound that was purified by flash chromatography (60 mg, 48% yield, 75% purity).

LC-MS (Method B): Rt=1.32 min; MS (ESIneg): m/z=459 (M−H)−

$^1$H-NMR (400 MHz, DMSO-d$_6$) δ [ppm]: 1.19 (m, 2H), 1.38 (m, 2H), 2.53 (m, 1H), 3.42 (s, 3H), 3.60 (s, 3H), 4.16 (d, 2H), 6.07 (d, 1H), 6.25 (dd, 1H), 7.06 (d, 1H), 7.75 (t, 1H), 7.98 (d, 1H), 8.18 (d, 1H), 8.43 (dd, 1H).

Intermediate 142

2-(2-Chlorophenyl)-N-{4-(5-cyclopropyl-1,2,4-oxadiazol-3-yl)-3-[(2,4-dimethoxybenzyl)sulfamoyl]phenyl}acetamide

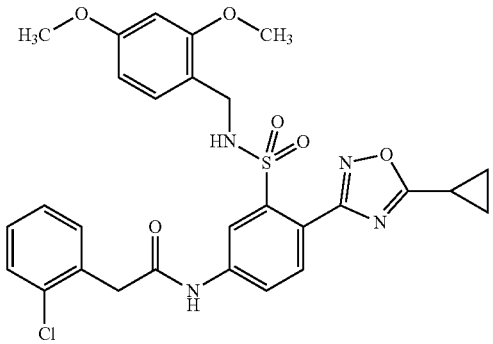 [SMILES: COc1ccc(CNS(=O)(=O)c2cc(NC(=O)Cc3ccccc3Cl)ccc2-c2noc(C3CC3)n2)c(OC)c1]

Tin(II) chloride dihydrate (252 mg, 1.12 mmol) was added to a solution of 2-(5-cyclopropyl-1,2,4-oxadiazol-3-yl)-N-(2,4-dimethoxybenzyl)-5-nitrobenzenesulfonamide (103 mg, 224 µmol) in dioxane (2.9 mL), followed by stirring for 4 h at 70° C. and overnight at room temperature.

The reaction mixture was concentrated in vacuo. Ethyl acetate was added to the residue and the mixture was extracted with brine. The organic phase was filtered over Celite, dried over a Whatman filter, and concentrated in vacuo to give 118 mg crude 5-amino-2-(5-cyclopropyl-1,2,4-oxadiazol-3-yl)-N-(2,4-dimethoxybenzyl)benzenesulfonamide that was used without further purification in the next step.

The crude material from the previous step (118 mg) was dissolved in DMF (4.4 mL) followed by the addition of (2-chlorophenyl)acetic acid (76.4 mg, 448 µmol), N,N-diisopropylethylamine (156 µL, 896 µmol) and HATU (170 mg, 448 µmol). The reaction mixture was stirred overnight at room temperature. Saturated aqueous sodium hydrogen carbonate solution was added and the mixture was extracted with ethyl acetate. Then the organic phase was washed with brine, dried over a Whatman filter and concentrated in vacuo to give the title compound that was used without further purification (135 mg, 95% purity, 98% yield over 2 steps).

LC-MS (Method A): Rt=1.35 min; MS (ESIpos): m/z=583 [M+H]+

Intermediate 143

5-[2-(Benzylsulfanyl)-4-nitrophenyl]-3-(trifluoromethyl)-1,2,4-oxadiazole

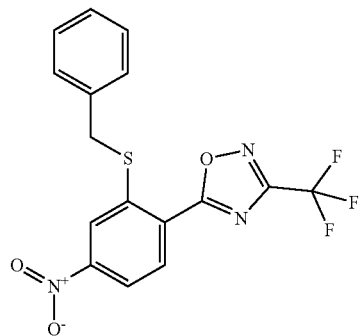 [SMILES: O=[N+]([O-])c1ccc(-c2nc(C(F)(F)F)no2)c(SCc2ccccc2)c1]

To a suspension of 2-(benzylsulfanyl)-4-nitrobenzoic acid (715 mg, 2.35 mmol, 95% purity) in toluene (7.4 mL) thionyl chloride (343 µL, 4.70 mmol) was added. The mixture was heated to 70° C. for 210 min. The solvent was removed under reduced pressure, the residue was co-distilled with toluene and then dissolved in THF (10 mL). 2,2,2-Trifluoro-N-hydroxyethanimidamide (341 mg, 2.53 mmol, CAS-RN 4314-35-6) and N,N-diisopropylethylamine (1.20 mL, 6.90 mmol) were added, and the mixture was stirred at room temperature overnight and at reflux for 2 h. Water was added to the reaction mixture, and it was extracted with ethyl acetate. The combined organic phases were washed with brine, dried over a Whatman filter, and concentrated under reduced pressure yielding the crude title compound that was purified by flash chromatography (640 mg, 69% yield, 95% purity).

LC-MS (Method B): Rt=1.51 min; MS (ESIpos): m/z=382 (M+H)+

$^1$H-NMR (400 MHz, DMSO-$d_6$) δ [ppm]: 4.57 (s, 2H), 7.29 (dd, 1H), 7.35 (dd, 2H), 7.47 (d, 2H), 8.16 (dd, 1H), 8.38 (d, 1H), 8.38 (d, 1H).

Intermediate 144

N-(2,4-Dimethoxybenzyl)-5-nitro-2-[3-(trifluoromethyl)-1,2,4-oxadiazol-5-yl]benzenesulfonamide

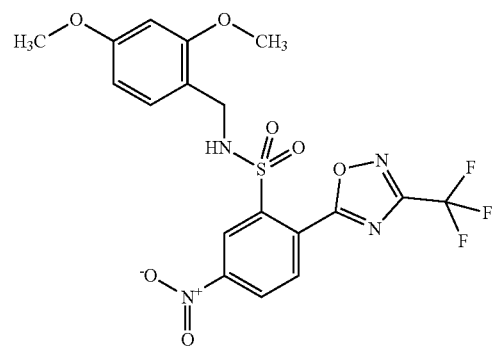

5-[2-(Benzylsulfanyl)-4-nitrophenyl]-3-(trifluoromethyl)-1,2,4-oxadiazole (636 mg, 1.58 mmol, 95% purity) was stirred with N-chlorosuccimide (952 mg, 7.13 mmol) in acetic acid (15 mL) at room temperature for 5 h. The reaction mixture was concentrated in vacuo to give 565 mg crude 5-nitro-2-[3-(trifluoromethyl)-1,2,4-oxadiazol-3-yl]benzenesulfonyl chloride that was used without further purification in the next step.

Crude material from the previous step (565 mg) was dissolved in dichloromethane (8 mL) followed by the addition of sodium hydrogen carbonate (531 mg, 6.32 mmol), and slow addition of 1-(2,4-dimethoxyphenyl)methanamine (291 µL, 1.74 mmol) at room temperature. The reaction mixture was stirred overnight at room temperature. Water was added to the reaction mixture, and it was extracted with dichloromethane. The combined organic phases were washed with brine, dried over a Whatman filter, and concentrated under reduced pressure yielding the crude title compound that was purified by flash chromatography (153 mg, 16% yield, 80% purity).

LC-MS (Method A): Rt=1.36 min; MS (ESIneg): m/z=487 (M–H)–

$^1$H-NMR (400 MHz, DMSO-$d_6$) δ [ppm]: 3.57 (s, 3H), 3.65 (s, 3H), 4.06 (d, 2H), 6.24 (d, 1H), 6.26 (dd, 1H), 6.97 (d, 1H), 8.18 (d, 1H), 8.44 (d, 1H), 8.55 (dd, 1H), 8.56 (t, 1H).

Intermediate 145

2-(2-Chlorophenyl)-N-{3-[(2,4-dimethoxybenzyl)sulfamoyl]-4-[3-(trifluoromethyl)-1,2,4-oxadiazol-5-yl]phenyl}acetamide

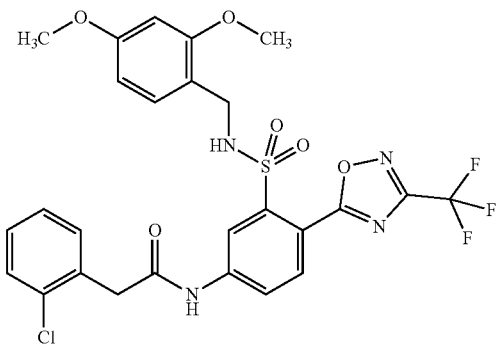 [SMILES: COc1ccc(CNS(=O)(=O)c2cc(NC(=O)Cc3ccccc3Cl)ccc2-c2nc(C(F)(F)F)no2)c(OC)c1]

Tin(II) chloride dihydrate (425 mg, 1.88 mmol) was added to a solution of N-(2,4-dimeth-oxybenzyl)-5-nitro-2-[3-(trifluoromethyl)-1,2,4-oxadiazol-5-yl]benzenesulfonamide (230 mg, 80% purity, 377 μmol) in dioxane (4.8 mL), followed by stirring for 5 h at 70° C. and overnight at room temperature. The reaction mixture was concentrated in vacuo. Water was added to the residue and the mixture was extracted three times with ethyl acetate. The combined organic phases were filtered over Celite, dried over a Whatman filter, and concentrated in vacuo to give 217 mg crude 5-amino-N-(2,4-dimethoxybenzyl)-2-[3-(trifluoromethyl)-1,2,4-oxadiazol-5-yl]benzenesulfonamide that was used without further purification in the next step.

Crude material from the previous step (216 mg) was dissolved in DMF (8 mL) followed by the addition of (2-chlorophenyl)acetic acid (129 mg, 754 μmol), N,N-diisopropylethylamine (263 μL, 1.51 mmol) and HATU (287 mg, 754 μmol). The reaction mixture was stirred overnight at room temperature. Saturated aqueous sodium hydrogen carbonate solution was added and the mixture was extracted three times with ethyl acetate. Then all organic phases were combined, washed with brine, dried over a Whatman filter and concentrated in vacuo to give the title compound that was used without further purification (355 mg, 65% purity, 98% yield over 2 steps).

LC-MS (Method B): Rt=1.43 min; MS (ESIneg): m/z=609 (M–H)–

Intermediate 146

2-(Benzylsulfanyl)-N'-(difluoroacetyl)-4-nitrobenzohydrazide

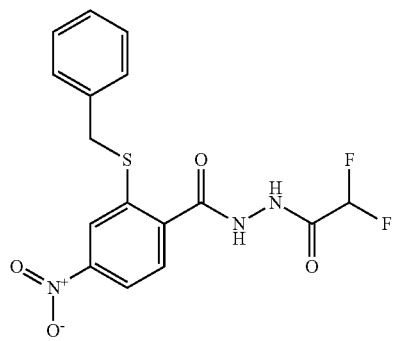 [SMILES: O=C(NNC(=O)C(F)F)c1ccc([N+](=O)[O-])cc1SCc1ccccc1]

To a slurry of 2-(benzylsulfanyl)-4-nitrobenzohydrazide (2.64 g, 95% purity, 8.27 mmol) in acetonitrile (100 mL), N,N-diisopropylethylamine (1.73 mL, 9.92 mmol), and difluoroacetic anhydride (1.13 ml, 9.10 mmol) were added at –50° C. The mixture was allowed to warm to room temperature and stirred for 5 h. The reaction was poured into aqueous sodium hydroxide solution (5%). The mixture was extracted with ethyl acetate. The combined organic phases were washed with brine, dried over a Whatman filter, and concentrated under reduced pressure yielding the crude title compound that was used without purification (3.57 g, 91% yield, 80% purity).

LC-MS (Method A): Rt=1.08 min; MS (ESIneg): m/z=380 (M–H)–

$^1$H-NMR (400 MHz, DMSO-$d_6$) δ [ppm]: 4.32 (s, 2H), 5.97 (t, 1H), 7.25 (dd, 1H), 7.32 (dd, 2H), 7.43 (d, 2H), 7.69 (d, 1H), 7.96 (dd, 1H), 8.11 (d, 1H).

Intermediate 147

2-[2-(Benzylsulfanyl)-4-nitrophenyl]-5-(difluoromethyl)-1,3,4-oxadiazole

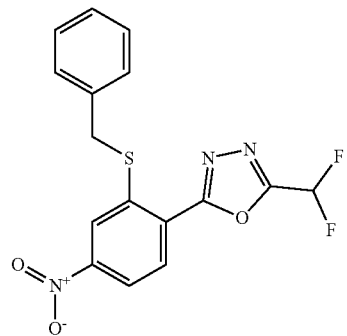 [SMILES: O=[N+]([O-])c1ccc(-c2nnc(C(F)F)o2)c(SCc2ccccc2)c1]

A solution of 2-(benzylsulfanyl)-N'-(difluoroacetyl)-4-nitrobenzohydrazide (3.57 g, 80% purity, 7.49 mmol) and 3,3,3-triethyl-1-(methoxycarbonyl)diazathian-3-ium-1-ide 2,2-dioxide (7.38 g, 31.0 mmol) in tetrahydrofuran (90 mL) was irradiated for 30 min at 150° C. in the microwave. Water was added to the reaction mixture, and it was extracted with ethyl acetate. The combined organic phases were washed with brine, dried over a Whatman filter, and concentrated under reduced pressure yielding the crude title compound that was purified by flash chromatography (2.18 g, 76% yield, 95% purity).

LC-MS (Method A): Rt=1.33 min; MS (ESIpos): m/z=364 (M+H)⁺

¹H-NMR (400 MHz, DMSO-d₆) δ [ppm]: 4.54 (s, 2H), 7.29 (dd, 1H), 7.35 (dd, 2H), 7.47 (d, 2H), 7.59 (t, 1H), 8.15 (dd, 1H), 8.20 (d, 1H), 8.36 (d, 1H).

Intermediate 148

2-[5-(Difluoromethyl)-1,3,4-oxadiazol-2-yl]-N-(2,4-dimethoxybenzyl)-5-nitrobenzenesulfonamide

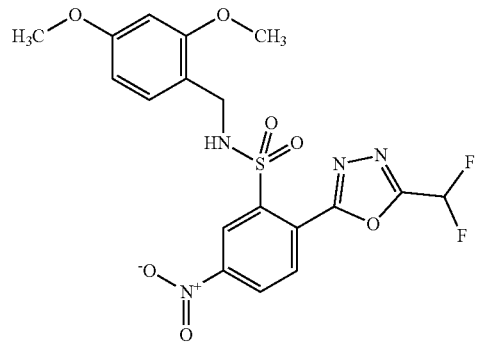

2-[2-(Benzylsulfanyl)-4-nitrophenyl]-5-(difluoromethyl)-1,3,4-oxadiazole (1.23 g, 95% purity, 2.93 mmol) was stirred with N-chlorosuccimide (1.76 g, 13.2 mmol) in acetic acid (29 mL) at room temperature for 16 h. The reaction mixture was concentrated in vacuo to give 3 g crude 2-[5-(difluoromethyl)-1,3,4-oxadiazol-2-yl]-5-nitrobenzenesulfonyl chloride that was used without further purification in the next step.

Crude material from the previous step (3 g) was dissolved in dichloromethane (13.5 mL) followed by the addition of sodium hydrogen carbonate (983 mg, 17.7 mmol), and slow addition of 1-(2,4-dimethoxyphenyl)methanamine (484 µL, 3.22 mmol) at 0° C. The reaction mixture was stirred for 3 h at 0° C. and for 22 h at room temperature. Water was added to the reaction mixture, and it was extracted with dichloromethane. The combined organic phases were washed with brine, dried over a Whatman filter, and concentrated under reduced pressure yielding the crude title compound that was purified by flash chromatography (242 mg, 16% yield, 90% purity).

LC-MS (Method B): Rt=1.21 min; MS (ESIpos): m/z=488 (M+H+NH₃)*

¹H-NMR (400 MHz, DMSO-d₆) δ [ppm]: 3.53 (s, 3H), 3.64 (s, 3H), 4.09 (d, 2H), 6.19 (d, 1H), 6.26 (dd, 1H), 6.99 (d, 1H), 7.64 (t, 1H), 8.14 (d, 1H), 8.33 (t, 1H), 8.39 (d, 1H), 8.52 (dd, 1H).

Intermediate 149

2-(2-Chlorophenyl)-N-{4-[5-(difluoromethyl)-1,3,4-oxadiazol-2-yl]-3-[(2,4-dimethoxybenzyl)sulfamoyl]phenyl}acetamide

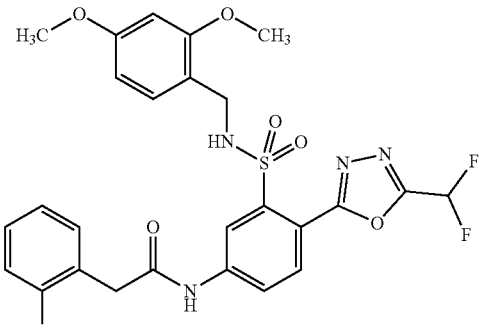

Tin(II) chloride dihydrate (1.12 g, 4.95 mmol) was added to a solution of 2-[5-(difluoromethyl)-1,3,4-oxadiazol-2-yl]-N-(2,4-dimethoxybenzyl)-5-nitrobenzenesulfonamide (466 mg, 990 µmol) in dioxane (12.7 mL), followed by stirring for 4.5 h at 70° C. The reaction mixture was concentrated in vacuo. Water was added to the residue and the mixture was extracted three times with ethyl acetate. The combined organic phases were filtered over Celite, dried over a Whatman filter, and concentrated in vacuo to give 489 mg crude 5-amino-2-[5-(difluoromethyl)-1,3,4-oxadiazol-2-yl]-N-(2,4-dimethoxybenzyl)benzenesulfonamide that was used without further purification.

Crude material from the previous step (218 mg) was dissolved in DMF (5.1 mL) followed by the addition of (2-chlorophenyl)acetic acid (127 mg, 742 µmol), N,N-diisopropylethylamine (345 µL, 1.98 mmol) and HATU (282 mg, 742 µmol). The reaction mixture was stirred for 23 h at room temperature. Saturated aqueous sodium hydrogen carbonate solution was added and the mixture was extracted three times with ethyl acetate. Then all organic phases were combined, washed with brine, dried over a Whatman filter and concentrated in vacuo to give the title compound that was used without further purification (499 mg, 60% purity, 23% yield over 2 steps).

LC-MS (Method B): Rt=0.83 min; MS (ESIpos): m/z=593 (M+H)⁺

Intermediate 150

N-{4-[5-(Difluoromethyl)-1,3,4-oxadiazol-2-yl]-3-[(2,4-dimethoxybenzyl)sulfamoyl]phenyl}-2-(2-fluorophenyl)acetamide

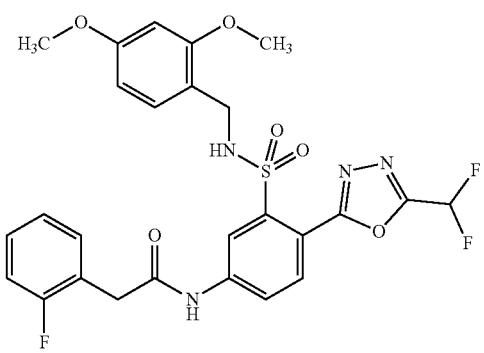 [SMILES: COc1ccc(CNS(=O)(=O)c2cc(NC(=O)Cc3ccccc3F)ccc2-c2nnc(C(F)F)o2)c(OC)c1]

Crude 5-amino-2-[5-(difluoromethyl)-1,3,4-oxadiazol-2-yl]-N-(2,4-dimethoxybenzyl)benzenesulfonamide (218 mg) was dissolved in DMF (5 mL) followed by the addition of (2-fluorophenyl)acetic acid (92 mg, 594 μmol), N,N-diisopropylethylamine (207 μL, 1.19 mmol) and HATU (226 mg, 594 μmol). The reaction mixture was stirred overnight at room temperature. Saturated aqueous sodium hydrogen carbonate solution was added and the mixture was extracted three times with ethyl acetate. Then all organic phases were combined, washed with brine, dried over a Whatman filter and concentrated in vacuo to give the title compound that was used without further purification (466 mg, 37% purity, 60% yield over 2 steps).

LC-MS (Method B): Rt=0.80 min; MS (ESIpos): m/z=577 [M+H]$^+$

Intermediate 151

5-[2-(Benzylsulfanyl)-4-nitrophenyl]-3-methyl-1,2,4-oxadiazole

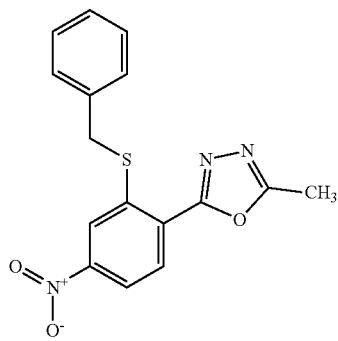 [SMILES: Cc1nnc(-c2ccc([N+](=O)[O-])cc2SCc2ccccc2)o1]

To a suspension of 2-(benzylsulfanyl)-4-nitrobenzoic acid (1.94 g, 6.69 mmol) in toluene (20 mL) thionyl chloride (3.42 mL, 46.8 mmol) was added. The mixture was heated to 70° C. for 150 min. The solvent was removed under reduced pressure, the residue was co-distilled with toluene and then dissolved in THF (77 mL). This solution was added dropwise over 30 min to a solution of acetohydrazide (991 mg, 13.4 mmol) and N,N-diisopropylethylamine (1.28 mL, 7.36 mmol) in THF (11 mL), and the mixture was stirred at room temperature at reflux for 75 min. Water was added to the reaction mixture, and it was extracted with ethyl acetate. The combined organic phases were washed with brine, dried over a Whatman filter, and concentrated under reduced pressure to yield 2.44 g of crude N'-acetyl-2-(benzylsulfanyl)-4-nitrobenzohydrazide.

A solution of the crude hydrazide (2.43 g) and 3,3,3-triethyl-1-(methoxycarbonyl)diazathian-3-ium-1-ide 2,2-dioxide (7.55 g, 31.7 mmol) in tetrahydrofuran (75 mL) was irradiated for 30 min at 150° C. in the microwave. Water was added to the reaction mixture, and it was extracted with ethyl acetate. The combined organic phases were washed with brine, dried over a Whatman filter, and concentrated under reduced pressure yielding the crude title compound that was purified by flash chromatography (2.08 g, 86% yield, 90% purity).

LC-MS (Method A): Rt=1.25 min; MS (ESIpos): m/z=328 (M+H)$^+$ $^1$H-NMR (400 MHz, DMSO-d$_6$) δ [ppm]: 2.61 (s, 3H), 4.50 (s, 2H), 7.28 (dd, 1H), 7.35 (dd, 2H), 7.47 (d, 2H), 8.11 (d, 1H), 8.13 (dd, 1H), 8.32 (d, 1H).

Intermediate 152

N-(2,4-Dimethoxybenzyl)-2-(5-methyl-1,3,4-oxadiazol-2-yl)-5-nitrobenzenesulfonamide

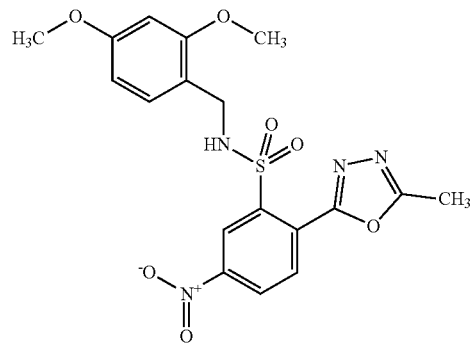

2-[2-(Benzylsulfanyl)-4-nitrophenyl]-5-methyl-1,3,4-oxadiazole (1.81 g, 5.51 mmol) was stirred with N-chlorosuccimide (3.32 g, 24.8 mmol) in acetic acid (55 mL) at room temperature for 210 min. The reaction mixture was concentrated in vacuo to give 7.34 g crude 2-(5-methyl-1,3,4-oxadiazol-2-yl)-5-nitrobenzenesulfonyl chloride that was used without further purification in the next step.

Crude material from the previous step (7.34 g) was dissolved in dichloromethane (61 mL) followed by the addition of sodium hydrogen carbonate (1.85 g, 22.1 mmol), and slow addition of 1-(2,4-dimethoxyphenyl)methanamine (911 μL, 6.07 mmol) at 0° C. The reaction mixture was stirred for 18 h at room temperature. Water was added to the reaction mixture, and it was extracted with dichloromethane. The combined organic phases were washed with brine, dried over a Whatman filter, and concentrated under reduced pressure yielding the crude title compound that was purified by flash chromatography (462 mg, 17% yield, 90% purity).

LC-MS (Method A): Rt=1.13 min; MS (ESIpos): m/z=435 (M+H)+

¹H-NMR (400 MHz, DMSO-d₆) δ [ppm]: 2.65 (s, 3H), 3.44 (s, 3H), 3.61 (s, 3H), 4.14 (d, 2H), 6.11 (d, 1H), 6.24 (dd, 1H), 7.01 (d, 1H), 8.08 (d, 1H), 8.16 (t, 1H), 8.28 (d, 1H), 8.48 (dd, 1H).

Intermediate 153

2-(2-Chlorophenyl)-N-{3-[(2,4-dimethoxybenzyl)sulfamoyl]-4-(5-methyl-1,3,4-oxadiazol-2-yl)phenyl}acetamide

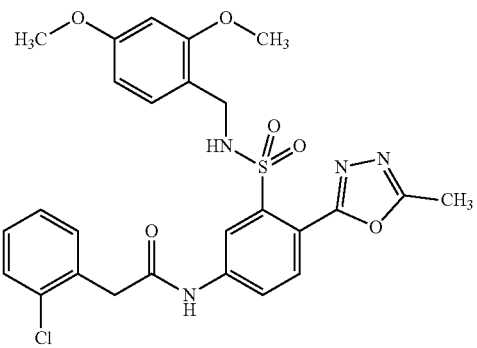 [SMILES: COc1ccc(CNS(=O)(=O)c2cc(NC(=O)Cc3ccccc3Cl)ccc2-c2nnc(C)o2)c(OC)c1]

Tin(II) chloride dihydrate (1.07 g, 4.75 mmol) was added to a solution of N-(2,4-dimethoxy-benzyl)-2-(5-methyl-1,3,4-oxadiazol-2-yl)-5-nitrobenzenesulfonamide (459 mg, 951 μmol, 90% purity) in dioxane (12.1 mL), followed by stirring for 4 h at 70° C. The reaction mixture was concentrated in vacuo. Water was added to the residue and the mixture was extracted three times with ethyl acetate. The combined organic phases were filtered over Celite, dried over a Whatman filter, and concentrated in vacuo to give 459 mg crude 5-amino-2-(5-methyl-1,3,4-oxadiazol-2-yl)-N-(2,4-dimethoxybenzyl)benzenesulfonamide that was used without further purification.

Crude material from the previous step (127 mg) was dissolved in DMF (3.2 mL) followed by the addition of (2-chlorophenyl)acetic acid (80.1 mg, 470 μmol), N,N-diisopropylethylamine (218 μL, 1.25 mmol) and HATU (179 mg, 470 μmol). The reaction mixture was stirred for 17 h at room temperature. Saturated aqueous sodium hydrogen carbonate solution was added and the mixture was extracted three times with ethyl acetate. Then all organic phases were combined, washed with brine, dried over a Whatman filter and concentrated in vacuo to give the title compound that was used without further purification (260 mg, 60% purity, 88% yield over 2 steps).

LC-MS (Method B): Rt=1.23 min; MS (ESIpos): m/z=557 (M+H)⁺

Intermediate 154

N-{3-[(2,4-Dimethoxybenzyl)sulfamoyl]-4-(5-methyl-1,3,4-oxadiazol-2-yl)phenyl}-2-(2-fluorophenyl)acetamide

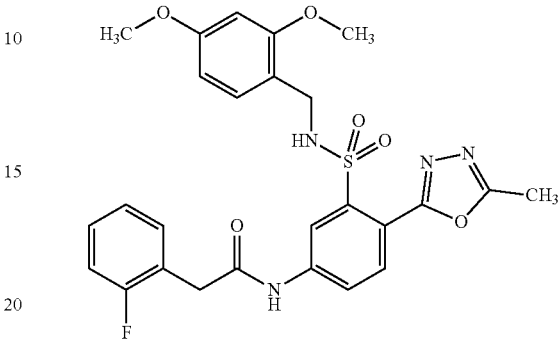

Crude 5-amino-2-(5-methyl-1,3,4-oxadiazol-2-yl)-N-(2,4-dimethoxybenzyl)benzenesulfonamide (229 mg) was dissolved in DMF (5 mL) followed by the addition of (2-fluorophenyl)acetic acid (147 mg, 951 μmol), N,N-diisopropylethylamine (331 μL, 1.90 mmol) and HATU (362 mg, 951 μmol). The reaction mixture was stirred overnight at room temperature. Saturated aqueous sodium hydrogen carbonate solution was added and the mixture was extracted three times with ethyl acetate. Then all organic phases were combined, washed with brine, dried over a Whatman filter and concentrated in vacuo to give the title compound that was used without further purification (427 mg, 60% purity, 88% yield over 2 steps).

LC-MS (Method A): Rt=1.17 min; MS (ESIpos): m/z=541 [M+H]⁺

Intermediate 155

N-{3-[(2,4-Dimethoxybenzyl)sulfamoyl]-4-(5-methyl-1,3,4-oxadiazol-2-yl)phenyl}-2-(4-methylphenyl)acetamide

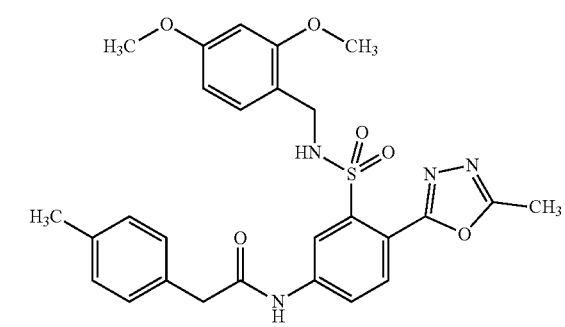

Crude 5-amino-2-(5-methyl-1,3,4-oxadiazol-2-yl)-N-(2,4-dimethoxybenzyl)benzenesulfonamide (229 mg) was dissolved in DMF (5 mL) followed by the addition of (4-methylphenyl)acetic acid (143 mg, 952 μmol), N,N-diisopropylethylamine (332 μL, 1.90 mmol) and HATU (362 mg, 952 μmol). The reaction mixture was stirred overnight at room temperature. Saturated aqueous sodium hydrogen carbonate solution was added and the mixture was extracted three times with ethyl acetate. Then all organic phases were combined, washed with brine, dried over a Whatman filter and concentrated in vacuo to give the title compound that was used without further purification (351 mg, 72% purity, 88% yield over 2 steps).

LC-MS (Method A): Rt=1.25 min; MS (ESIpos): m/z=537 [M+H]$^+$

Intermediate 156 tert-Butyl 3-(4-{[(2-chlorophenyl)acetyl]amino}-2-{[(dimethylamino)methylene]sulfamoyl}phenyl)-1H-pyrrole-1-carboxylate

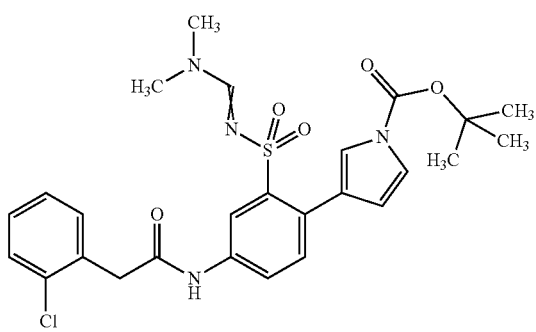 [SMILES: CN(C)C=NS(=O)(=O)c1cc(NC(=O)Cc2ccccc2Cl)ccc1-c1ccn(C(=O)OC(C)(C)C)c1]

N-(4-Bromo-3-{[(dimethylamino)methylidene]sulfamoyl}phenyl)-2-(2-chlorophenyl)acetamide (500 mg, 1.09 mmol), tert-butyl 3-(4,4,5,5-tetramethyl-1,3,2-dioxaborolan-2-yl)-1H-pyrrole-1-carboxylate (479 mg, 1.64 mmol) and potassium fluoride (139 mg, 2.4 mmol) were dissolved in dry and degassed DMF (11 ml) and the solution was purged again with argon for 5 minutes followed by addition of bis(tri-tert-butylphosphine)palladium(0) (CAS 53199-31-8) (28 mg, 54 µmol). The reaction was heated for 3 h at 100° C. Saturated aqueous sodium hydrogen carbonate solution was added to the reaction mixture, and it was extracted with ethyl acetate. The combined organic phases were washed with brine, dried over a Whatman filter, and concentrated under reduced pressure yielding the crude title compound that was purified by flash chromatography (470 mg, 75% yield, 95% purity).

LC-MS (Method A): Rt=1.30 min; MS (ESIpos): m/z=545 (M+H)$^+$ $^1$H-NMR (400 MHz, DMSO-d$_6$) δ [ppm]: 1.57 (s, 9H), 2.74 (s, 3H), 2.92 (s, 3H), 3.87 (s, 2H), 6.41 (dd, 1H), 7.26 (dd, 1H), 7.31 (d, 1H), 7.32 (m, 2H), 7.37 (dd, 1H), 7.45 (m, 2H), 7.58 (s, 1H), 7.84 (dd, 1H), 8.29 (d, 1H), 10.57 (s, 1H).

Intermediate 157

2-(2-Chlorophenyl)-N-[3-{[(dimethylamino)methylene]sulfamoyl}-4-(1H-pyrrol-3-yl)phenyl]acetamide

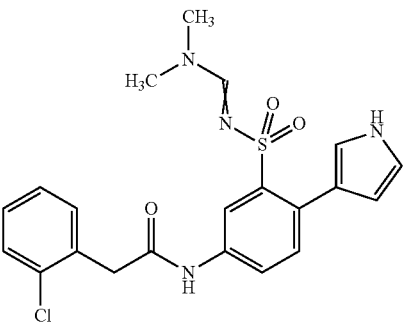 [SMILES: CN(C)C=NS(=O)(=O)c1cc(NC(=O)Cc2ccccc2Cl)ccc1-c1cc[nH]c1]

tert-Butyl 3-(4-{[(2-chlorophenyl)acetyl]amino}-2-{[(dimethylamino)methylene]sulfamoyl}-phenyl)-1H-pyrrole-1-carboxylate (350 mg, 610 µmol, 95% purity) was dissolved in dichloromethane (6 mL) and treated with trifluoroacetic acid (1.18 mL, 15.3 mmol) followed by stirring at room temperature for 5 h. The mixture was concentrated in vacuo and purified by HPLC to give the title compound (60 mg, 18% yield, 80% purity).

LC-MS (Method A): Rt=1.01 min; MS (ESIpos): m/z=445 (M+H)$^+$ $^1$H-NMR (400 MHz, DMSO-d$_6$) δ [ppm]: 2.66 (s, 3H), 2.84 (s, 3H), 3.86 (s, 2H), 6.16 (dd, 1H), 6.76 (dd, 1H), 6.88 (dd, 1H), 7.22 (d, 1H), 7.25 (s, 1H), 7.32 (m, 2H), 7.44 (m, 2H), 7.79 (dd, 1H), 8.25 (d, 1H), 10.49 (s, 1H), 10.91 (s, 1H).

Intermediate 158

2-(2-Chlorophenyl)-N-[3-{[(dimethylamino)methylene]sulfamoyl}-4-(1-methyl-1H-pyrrol-3-yl)phenyl]acetamide

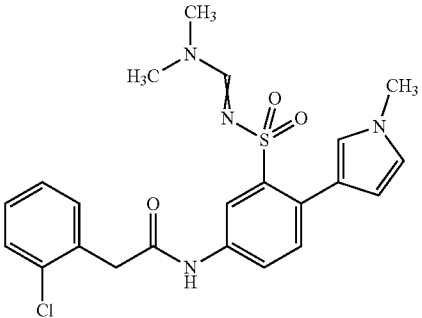 [SMILES: CN(C)C=NS(=O)(=O)c1cc(NC(=O)Cc2ccccc2Cl)ccc1-c1ccn(C)c1]

N-(4-Bromo-3-{[(dimethylamino)methylidene]sulfamoyl}phenyl)-2-(2-chlorophenyl)acetamide (200 mg, 436 µmol), 1-methyl-3-(4,4,5,5-tetramethyl-1,3,2-dioxaborolan-2-yl)-1H-pyrrole (181 mg, 872 µmol, CAS-RN 953040-54-5) and potassium fluoride (76 mg, 1.3 mmol) were dissolved in dry and degassed DMF (4.4 ml) and the solution was purged again with argon for 5 minutes followed by addition of bis(tri-tert-butylphosphine)palladium(0) (11 mg, 22 µmol, CAS-RN 53199-31-8). The reaction was heated for 4 h at 100° C.

Saturated aqueous sodium hydrogen carbonate solution was added to the reaction mixture, and it was extracted with ethyl acetate. The combined organic phases were washed with brine, dried over a Whatman filter, and concentrated under reduced pressure yielding the crude title compound that was purified by flash chromatography (107 mg, 51% yield, 95% purity).

LC-MS (Method A): Rt=1.07 min; MS (ESIpos): m/z=459 (M+H)$^+$ $^1$H-NMR (400 MHz, DMSO-d$_6$) δ [ppm]: 2.67 (s, 3H), 2.89 (s, 3H), 3.67 (s, 3H), 3.86 (s, 2H), 6.09 (dd, 1H), 6.70 (dd, 1H), 6.84 (dd, 1H), 7.20 (d, 1H), 7.32 (m, 2H), 7.40 (s, 1H), 7.44 (m, 2H), 7.79 (dd, 1H), 8.25 (d, 1H), 10.49 (s, 1H).

Intermediate 159

2-(2-Chlorophenyl)-N-[4-(5-cyano-1-methyl-1H-pyrrol-2-yl)-3-{[(dimethylamino)methylene]sulfamoyl}phenyl]acetamide

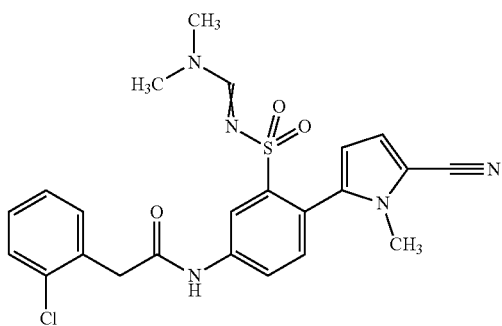 [SMILES: CN(C)C=NS(=O)(=O)c1cc(NC(=O)Cc2ccccc2Cl)ccc1-c1ccc(C#N)n1C]

N-(4-Bromo-3-{[(dimethylamino)methylidene]sulfamoyl}phenyl)-2-(2-chlorophenyl)acetamide (250 mg, 545 μmol), (5-cyano-1-methyl-1H-pyrrol-2-yl)boronic acid (163 mg, 1.09 mmol, CAS-RN 860617-71-6) and potassium fluoride (95 mg, 1.64 mmol) were dissolved in dry and degassed DMF (5.5 ml) and the solution was purged again with argon for 5 minutes followed by addition of bis(tri-tert-butylphosphine)palladium(0) (14 mg, 27 μmol, CAS-RN 53199-31-8). The reaction was heated for 3 h at 100° C. Saturated aqueous sodium hydrogen carbonate solution was added to the reaction mixture, and it was extracted with ethyl acetate. The product precipitated from both phases, was filtered off and dried under reduced pressure yielding the title compound in sufficient purity (100 mg, 35% yield, 94% purity).

LC-MS (Method A): Rt=1.13 min; MS (ESIpos): m/z=484 (M+H)$^+$ $^1$H-NMR (400 MHz, DMSO-d$_6$) δ [ppm]: 2.82 (s, 3H), 2.98 (s, 3H), 3.35 (s, 3H), 3.90 (s, 2H), 6.12 (d, 1H), 7.01 (d, 1H), 7.24 (s, 1H), 7.33 (m, 2H), 7.34 (d, 1H), 7.45 (m, 2H), 7.93 (dd, 1H), 8.37 (d, 1H), 10.73 (s, 1H).

SYNTHESIS OF EXAMPLES

Example 1

2-(2-Chlorophenyl)-N-[4-(2-oxopyridin-1(2H)-yl)-3-sulfamoylphenyl]acetamide

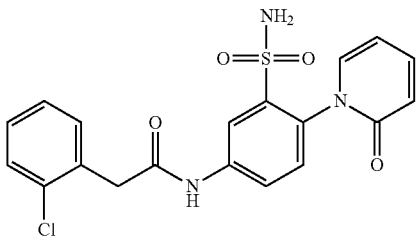 [SMILES: NS(=O)(=O)c1cc(NC(=O)Cc2ccccc2Cl)ccc1-n1ccccc1=O]

According to general procedures GP1.1, GP2.2, GP3.1 and GP4.1, 2-chloro-N-(2,4-dimethoxybenzyl)-5-nitrobenzenesulfonamide (500 mg, 1.29 mmol), pyridin-2-ol (123 mg, 1.29 mmol) and (2-chlorophenyl)acetic acid (240 mg, 1.41 mmol) were converted without purification of intermediates to the title compound and were purified at the end by preparative HPLC (Waters XBridge C18 5μ 100×30 mm, acetonitrile/water+0.1% formic acid) followed by another by preparative HPLC (Waters XBridge C18 5μ 100×30 mm, acetonitrile/water+0.2% aqueous ammonia (32%)) (9.3 mg, 0.0222 mmol, 1% yield over 4 steps, 98% purity). The 0-connected regioisomer was also isolated.

LC-MS (Method B): Rt=0.74 min; MS (ESIpos): m/z=418 [M+H]$^+$ $^1$H-NMR (400 MHz, DMSO-d$_6$) δ [ppm]: 3.89 (s, 2H), 6.32 (td, 1H), 6.47 (d, 1H), 7.18 (s, 2H), 7.28-7.34 (m, 2H), 7.37 (d, 1H), 7.42-7.47 (m, 2H), 7.48-7.56 (m, 2H), 7.92 (dd, 1H), 8.34 (d, 1H), 10.74 (s, 1H).

Example 2

N-[4-(4-Chloro-2-oxopyridin-1(2H)-yl)-3-sulfamoylphenyl]-2-(2-chlorophenyl)-acetamide

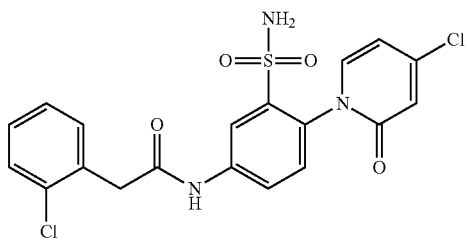 [SMILES: NS(=O)(=O)c1cc(NC(=O)Cc2ccccc2Cl)ccc1-n1ccc(Cl)cc1=O]

According to general procedures GP1.1, GP2.1, GP3.1 and GP4.1, 2-chloro-N-(2,4-dimethoxybenzyl)-5-nitrobenzenesulfonamide (1.50 g, 3.88 mmol), 4-chloropyridin-2-ol (502 mg, 3.88 mmol) and (2-chlorophenyl)acetic acid (634 mg, 3.72 mmol) were converted without purification of intermediates to the title compound and were purified at the end by preparative HPLC (Waters XBridge C18 5μ 100×30 mm, acetonitrile/water+0.2% aqueous ammonia (32%))) followed by a second preparative HPLC (Phenomenex Kinetex C18 5μ 100×30 mm, acetonitrile/water+0.1% trifluoroacetic acid) (7.3 mg, 0.0161 mmol, 1% yield over 4 steps, 97% purity). The 0-connected regioisomer was also isolated.

LC-MS (Method C): Rt=1.91 min; MS (ESIpos): m/z=452 [M+H]+

¹H-NMR (500 MHz, DMSO-d₆) δ [ppm]: 3.90 (s, 2H), 6.43 (dd, 1H), 6.63 (d, 1H), 7.26-7.36 (m, 4H), 7.40 (d, 1H), 7.43-7.48 (m, 2H), 7.58 (d, 1H), 7.91 (dd, 1H), 8.36 (d, 1H), 10.76 (s, 1H).

Example 3

2-(2-Chlorophenyl)-N-[4-(3,5-dichloro-2-oxopyridin-1(2H)-yl)-3-sulfamoylphenyl]-acetamide

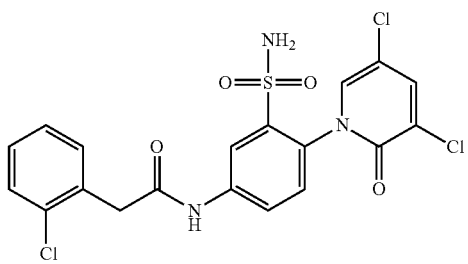 [SMILES: NS(=O)(=O)c1cc(NC(=O)Cc2ccccc2Cl)ccc1-n1cc(Cl)cc(Cl)c1=O]

According to general procedures GP1.1, GP2.1, GP3.1 and GP4.1, 2-chloro-N-(2,4-dimethoxybenzyl)-5-nitrobenzenesulfonamide (3.00 g, 7.76 mmol), 3,5-dichloropyridin-2-ol (1.27 g, 7.76 mmol) and (2-chlorophenyl)acetic acid (879 mg, 5.16 mmol) were converted without purification of intermediates to the title compound and were purified at the end by preparative HPLC (Phenomenex Kinetex C18 5μ 100×30 mm, acetonitrile/water+0.1% trifluoroacetic acid) followed by crystallization from methanol (13 mg, 0.0267 mmol, 1% yield over 4 steps, 99% purity).

LC-MS (Method C): Rt=2.14 min; MS (ESIpos): m/z=486 [M+H]+

¹H-NMR (500 MHz, DMSO-d₆) δ [ppm]: 3.90 (s, 2H), 7.29-7.36 (m, 2H), 7.38 (s, 2H), 7.43-7.49 (m, 3H), 7.83 (d, 1H), 7.90 (dd, 1H), 8.04 (d, 1H), 8.36 (d, 1H), 10.77 (s, 1H).

Example 4

N-[4-(3-Chloro-2-oxopyridin-1(2H)-yl)-3-sulfamoylphenyl]-2-(2-chlorophenyl)-acetamide

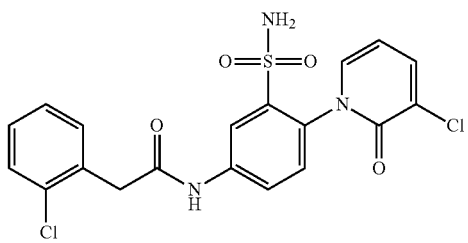 [SMILES: NS(=O)(=O)c1cc(NC(=O)Cc2ccccc2Cl)ccc1-n1cccc(Cl)c1=O]

According to general procedures GP1.1, GP2.1, GP3.1 and GP4.1, 2-chloro-N-(2,4-dimethoxybenzyl)-5-nitrobenzenesulfonamide (1.50 g, 3.88 mmol), 3-chloropyridin-2-ol (502 mg, 3.88 mmol) and (2-chlorophenyl)acetic acid (646 mg, 3.78 mmol) were converted without purification of intermediates to the title compound and were purified at the end by preparative HPLC (YMC Triart C18 5μ 100×30 mm, acetonitrile/water+0.1% formic acid) followed by crystallization from methanol (21.8 mg, 0.0482 mmol, 1% yield over 4 steps, 98% purity). The 0-connected regioisomer was also isolated.

LC-MS (Method C): Rt=1.83 min; MS (ESIpos): m/z=452 [M+H]+

¹H-NMR (500 MHz, DMSO-d₆) δ [ppm]: 3.91 (s, 2H), 6.33 (t, 1H), 7.25-7.36 (m, 4H), 7.41-7.47 (m, 3H), 7.53 (dd, 1H), 7.83 (dd, 1H), 7.92 (dd, 1H), 8.37 (d, 1H), 10.77 (s, 1H).

Examples 5 and 6

According to general procedures GP1.2, GP2.3, GP3.2 and GP4.2, 2-chloro-N-(2,4-dimethoxybenzyl)-5-nitrobenzenesulfonamide (500 mg, 1.29 mmol), 5-methyl-1H-1,2,4-triazole (161 mg, 1.94 mmol) and (2-chlorophenyl)acetic acid (202 mg, 1.18 mmol) were converted without purification of intermediates to 2-(2-chlorophenyl)-N-[4-(3-methyl-1H-1,2,4-triazol-1-yl)-3-sulfamoylphenyl]acetamide and 2-(2-chlorophenyl)-N-[4-(5-methyl-1H-1,2,4-triazol-1-yl)-3-sulfamoylphenyl]acetamide. The two regioisomers were purified and separated at the end by preparative HPLC (Waters XBridge C18 5μ 100×30 mm, acetonitrile/water+0.2% aqueous ammonia (32%)) followed by another preparative HPLC (Waters XBridge C18 5μ 100×30 mm, acetonitrile/water+0.1% formic acid).

Example 5

2-(2-Chlorophenyl)-N-[4-(3-methyl-1H-1,2,4-triazol-1-yl)-3-sulfamoylphenyl]-acetamide

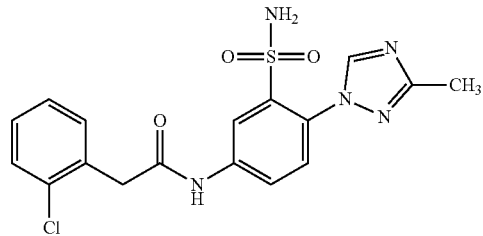 [SMILES: Cc1ncn(-c2ccc(NC(=O)Cc3ccccc3Cl)cc2S(N)(=O)=O)n1]

37 mg, 0.0912 mmol, 7% yield over 4 steps, 98% purity
LC-MS (Method A): Rt=0.89 min; LC-MS (Method F): Rt=3.37 min; MS (ESIpos): m/z=406 [M+H]+

¹H-NMR (400 MHz, DMSO-d₆) δ [ppm]: 2.36 (s, 3H), 3.92 (s, 2H), 7.30-7.37 (m, 2H), 7.42-7.52 (m, 4H), 7.56 (d, 1H), 7.96 (dd, 1H), 8.39 (d, 1H), 8.66 (s, 1H), 10.83 (s, 1H).

Example 6

2-(2-Chlorophenyl)-N-[4-(5-methyl-1H-1,2,4-triazol-1-yl)-3-sulfamoylphenyl]-acetamide

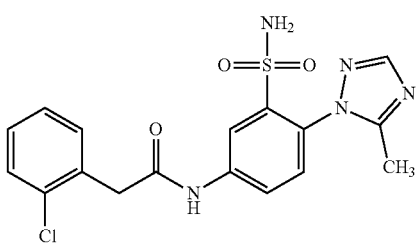 [SMILES: Cc1ncnn1-c1ccc(NC(=O)Cc2ccccc2Cl)cc1S(N)(=O)=O]

8 mg, 0.0197 mmol, 2% yield over 4 steps, 97% purity

LC-MS (Method A): Rt=0.89 min; LC-MS (Method F): Rt=1.68 min; MS (ESIpos): m/z=452 [M+H]+

¹H-NMR (400 MHz, DMSO-d₆) δ [ppm]: 2.22 (s, 3H), 3.93 (s, 2H), 7.25 (s, 2H), 7.31-7.38 (m, 2H), 7.43-7.50 (m, 2H), 7.57 (d, 1H), 7.98 (dd, 1H), 8.03 (s, 1H), 8.41 (d, 1H), 10.87 (s, 1H).

Example 7

2-(2-Chlorophenyl)-N-{3-sulfamoyl-4-[3-(trifluoromethyl)-1H-1,2,4-triazol-1-yl]-phenyl}acetamide

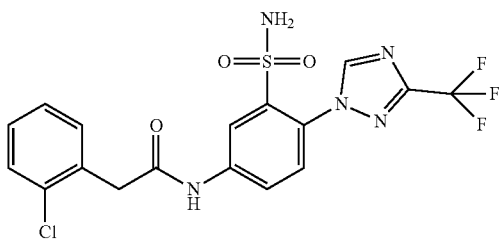 [SMILES: NS(=O)(=O)c1cc(NC(=O)Cc2ccccc2Cl)ccc1-n1cnc(C(F)(F)F)n1]

According to general procedures GP1.2, GP2.3, GP3.2 and GP4.2, 2-chloro-N-(2,4-dimethoxybenzyl)-5-nitrobenzenesulfonamide (500 mg, 1.29 mmol), 5-(trifluoromethyl)-1H-1,2,4-triazole (266 mg, 1.94 mmol) and (2-chlorophenyl)acetic acid (175 mg, 1.02 mmol) were converted without purification of intermediates to the title compound and were purified at the end by preparative HPLC (Chromatorex C-18 10 μm, 125×30 mm, acetonitrile/water+0.1% aqueous ammonia (32%)) (35 mg, 0.0761 mmol, 6% yield over 4 steps, 98% purity).

LC-MS (Method B): Rt=0.79 min; MS (ESIpos): m/z=460 [M+H]+

¹H-NMR (600 MHz, DMSO-d₆) δ [ppm]: 3.93 (s, 2H), 7.30-7.36 (m, 2H), 7.43-7.46 (m, 2H), 7.54 (s, 2H), 7.66 (d, 1H), 7.96 (dd, 1H), 8.45 (d, 1H), 9.03 (s, 1H), 10.87 (s, 1H).

Example 8

2-(2-Chlorophenyl)-N-{4-[5-methyl-3-(trifluoromethyl)-1H-1,2,4-triazol-1-yl]-3-sulfamoylphenyl}acetamide

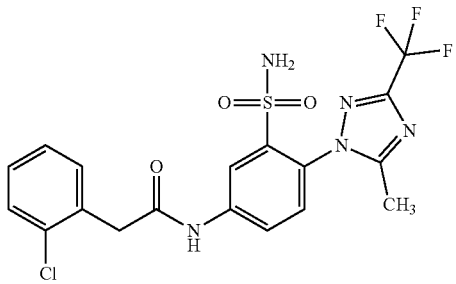 [SMILES: Cc1nc(C(F)(F)F)nn1-c1ccc(NC(=O)Cc2ccccc2Cl)cc1S(N)(=O)=O]

According to general procedures GP1.2, GP2.3, GP3.2 and GP4.2, 2-chloro-N-(2,4-dimethoxybenzyl)-5-nitrobenzenesulfonamide (500 mg, 1.29 mmol), 3-methyl-5-(trifluoromethyl)-1H-1,2,4-triazole (293 mg, 1.94 mmol) and (2-chlorophenyl)acetic acid (203 mg, 1.19 mmol) were converted without purification of intermediates to the title compound and were purified at the end by preparative HPLC (YMC Triart C18 5μ 100×30 mm, acetonitrile/water+0.1% formic acid) (49.4 mg, 0.104 mmol, 8% yield over 4 steps, 98% purity).

LC-MS (Method A): Rt=1.08 min; MS (ESIpos): m/z=474 [M+H]+

¹H-NMR (400 MHz, DMSO-d₆) δ [ppm]: 2.29 (s, 3H), 3.93 (s, 2H), 7.30-7.37 (m, 2H), 7.44-7.50 (m, 2H), 7.61 (s, 2H), 7.65 (d, 1H), 7.95 (dd, 1H), 8.46 (d, 1H), 10.91 (s, 1H).

Example 9

2-(2-Chlorophenyl)-N-[4-(1H-imidazol-1-yl)-3-sulfamoylphenyl]acetamide

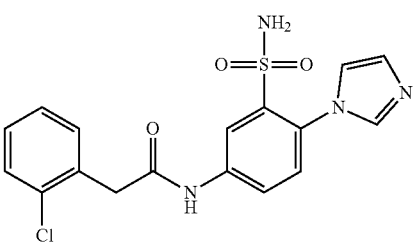 [SMILES: NS(=O)(=O)c1cc(NC(=O)Cc2ccccc2Cl)ccc1-n1ccnc1]

According to general procedures GP1.2, GP2.3, GP3.2 and GP4.2, 2-chloro-N-(2,4-dimethoxybenzyl)-5-nitrobenzenesulfonamide (500 mg, 1.29 mmol), 1H-imidazole (132 mg, 1.94 mmol) and (2-chlorophenyl)acetic acid (203 mg, 1.19 mmol) were converted without purification of intermediates to the title compound and were purified at the end by preparative HPLC (Waters XBridge C18 5μ 100×30 mm, acetonitrile/water+0.2% aqueous ammonia (32%)) (6 mg, 0.0154 mmol, 1% yield over 4 steps, 99% purity).

LC-MS (Method B): Rt=0.68 min; MS (ESIpos): m/z=391 [M+H]+

¹H-NMR (400 MHz, DMSO-d₆) δ [ppm]: 3.91 (s, 2H), 7.02 (t, 1H), 7.30-7.37 (m, 3H), 7.40 (d, 1H), 7.43-7.49 (m, 2H), 7.52 (s, 2H), 7.75 (t, 1H), 7.89 (dd, 1H), 8.40 (d, 1H), 10.78 (s, 1H).

Example 10

2-(2-Chlorophenyl)-N-{3-sulfamoyl-4-[4-(trifluoromethyl)-1H-imidazol-1-yl]phenyl}-acetamide

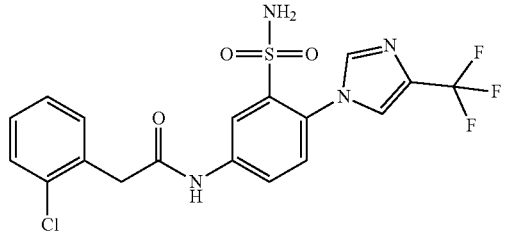 [SMILES: NS(=O)(=O)c1cc(NC(=O)Cc2ccccc2Cl)ccc1-n1cnc(C(F)(F)F)c1]

According to general procedures GP1.2, GP2.3, GP3.2 and GP4.2, 2-chloro-N-(2,4-dimethoxybenzyl)-5-nitrobenzenesulfonamide (500 mg, 1.29 mmol), 4-(trifluoromethyl)-1H-imidazole (264 mg, 1.94 mmol) and (2-chlorophenyl) acetic acid (199 mg, 1.17 mmol) were converted without purification of intermediates the title compound and were purified at the end by preparative HPLC (Chromatorex C-18 10 µm, 125×30 mm, acetonitrile/water+0.1% aqueous ammonia (32%)) followed by another preparative HPLC (Waters XBridge C18 5µ 100×30 mm, acetonitrile/water+0.1% formic acid) (11 mg, 0.0240 mmol, 2% yield over 4 steps, 99% purity).

LC-MS (Method A): Rt=1.05 min; MS (ESIpos): m/z=459 [M+H]$^+$ $^1$H-NMR (400 MHz, DMSO-d$_6$) δ [ppm] 3.92 (s, 2H), 7.30-7.37 (m, 2H), 7.43-7.49 (m, 2H), 7.51 (d, 1H), 7.72 (s, 2H), 7.90 (dd, 1H), 7.95 (s, 1H), 7.97-7.99 (m, 1H), 8.42 (d, 1H), 10.83 (s, 1H).

Example 11

2-(2-Chlorophenyl)-N-{3-sulfamoyl-4-[3-(trifluoromethyl)-1H-pyrazol-1-yl]phenyl}-acetamide

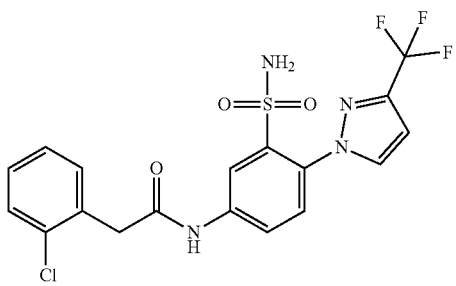 [SMILES: NS(=O)(=O)c1cc(NC(=O)Cc2ccccc2Cl)ccc1-n1ccc(C(F)(F)F)n1]

According to general procedures GP1.2, GP2.4, GP3.2 and GP4.2, 2-chloro-N-(2,4-dimethoxybenzyl)-5-nitrobenzenesulfonamide (500 mg, 1.29 mmol), 3-(trifluoromethyl)-1H-pyrazole (264 mg, 1.94 mmol) and (2-chlorophenyl)acetic acid (243 mg, 1.42 mmol) were converted without purification of intermediates to the title compound and were purified at the end by preparative HPLC (Waters XBridge C18 5µ 100×30 mm, acetonitrile/water+0.1% formic acid) followed by another preparative HPLC (Waters XBridge C18 5µ 100×30 mm, acetonitrile/water+0.2% aqueous ammonia (32%)) (6.7 mg, 0.0146 mmol, 1% yield over 4 steps, 98% purity).

LC-MS (Method B): Rt=1.05 min; MS (ESIpos): m/z=459 [M+H]$^+$ $^1$H-NMR (400 MHz, DMSO-d$_6$) δ [ppm] 3.92 (s, 2H), 6.98 (d, 1H), 7.29-7.36 (m, 2H), 7.40-7.52 (m, 4H), 7.61 (d, 1H), 7.98 (dd, 1H), 8.26-8.30 (m, 1H), 8.42 (d, 1H), 10.85 (s, 1H).

Example 12

2-(2-Chlorophenyl)-N-{4-[3-(difluoromethyl)-1H-pyrazol-1-yl]-3-sulfamoyl-phenyl}acetamide

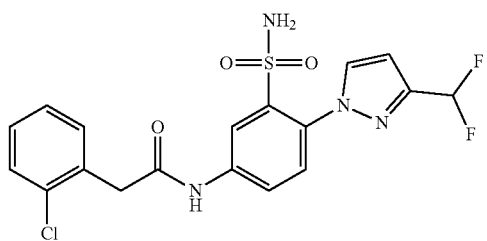 [SMILES: NS(=O)(=O)c1cc(NC(=O)Cc2ccccc2Cl)ccc1-n1ccc(C(F)F)n1]

According to general procedures GP1.2, GP2.3, GP3.3 and GP4.1, N-(2,4-dimethoxybenzyl)-2-fluoro-5-nitrobenzenesulfonamide (250 mg, 0.68 mmol), 3-(difluoromethyl)-1H-pyrazole (120 mg, 1.01 mmol) and (2-chlorophenyl) acetic acid (102 mg, 0.60 mmol) were converted without purification of intermediates to the title compound and were purified at the end twice by preparative HPLC (Chromatorex C-18 10 µm, 125×30 mm, acetonitrile/water+0.1% aqueous ammonia (32%)) (4 mg, 0.00907 mmol, 1% yield over 4 steps, 80% purity).

LC-MS (Method B): Rt=0.95 min; MS (ESIpos): m/z=441 [M+H]$^+$ $^1$H-NMR (400 MHz, DMSO-d$_6$) δ [ppm] 3.92 (s, 2H), 6.75-6.78 (m, 1H), 7.18 (t, 1H), 7.31-7.36 (m, 2H), 7.38 (m, 2H), 7.43-7.49 (m, 2H), 7.58 (d, 1H), 7.98 (dd, 1H), 8.20 (d, 1H), 8.40 (d, 1H), 10.82 (s, 1H).

Example 13

2-(2-Chlorophenyl)-N-{4-[5-cyclopropyl-3-(difluoromethyl)-1H-pyrazol-1-yl]-3-sulfamoylphenyl}acetamide

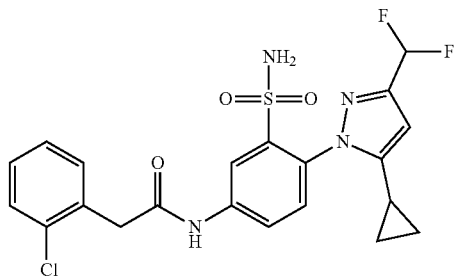 [SMILES: NS(=O)(=O)c1cc(NC(=O)Cc2ccccc2Cl)ccc1-n1nc(C(F)F)cc1C1CC1]

According to general procedures GP1.2, GP2.3, GP3.3 and GP4.2, N-(2,4-dimethoxybenzyl)-2-fluoro-5-nitrobenzenesulfonamide (350 mg, 0.95 mmol), 5-cyclopropyl-3-(difluoromethyl)-1H-pyrazole (224 mg, 1.42 mmol) and (2-chlorophenyl)acetic acid (202 mg, 1.18 mmol) were converted without purification of intermediates to the title compound and were purified at the end purified by preparative HPLC (Waters XBridge C18 5µ 100×30 mm, acetonitrile/water+0.2% aqueous ammonia (32%)) followed by another preparative HPLC (Waters XBridge C18 5µ 100×30 mm, acetonitrile/water+0.1% formic acid) (12.7 mg, 0.0264 mmol, 3% yield over 4 steps, 90% purity).

LC-MS (Method A): Rt=1.19 min; MS (ESIpos): m/z=481 [M+H]$^+$ $^1$H-NMR (400 MHz, DMSO-d$_6$) δ [ppm] 0.70-0.75 (m, 2H), 0.76-0.84 (m, 2H), 1.52-1.60 (m, 1H), 3.92 (s, 2H), 6.37 (s, 1H), 7.06 (t, 1H), 7.12 (s, 2H), 7.31-7.37 (m, 2H), 7.43-7.50 (m, 2H), 7.63 (d, 1H), 8.00 (dd, 1H), 8.41 (d, 1H), 10.84 (s, 1H).

Example 14

2-(2-Chlorophenyl)-N-{4-[4-methyl-3-(trifluoromethyl)-1H-pyrazol-1-yl]-3-sulfamoylphenyl}acetamide

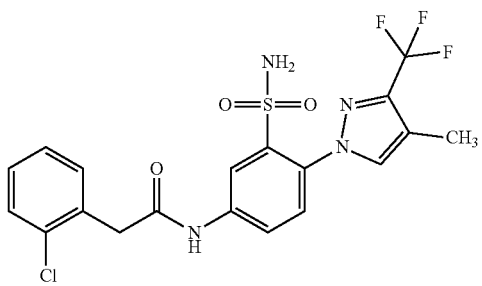 [SMILES: Cc1cn(-c2ccc(NC(=O)Cc3ccccc3Cl)cc2S(N)(=O)=O)nc1C(F)(F)F]

According to general procedures GP1.2, GP2.4, GP3.2 and GP4.2, 2-chloro-N-(2,4-dimethoxybenzyl)-5-nitrobenzenesulfonamide (500 mg, 1.29 mmol), 4-methyl-3-(trifluoromethyl)-1H-pyrazole (291 mg, 1.94 mmol) and (2-chlorophenyl)acetic acid (255 mg, 1.50 mmol) were converted without purification of intermediates to the title compound and were purified at the end twice by preparative HPLC (Waters XBridge C18 5μ 100×30 mm, acetonitrile/water+0.2% aqueous ammonia (32%)) followed by another preparative HPLC (Chromatorex C-18 10 μm, 125×30 mm, acetonitrile/water+0.1% formic acid) (43 mg, 0.0909 mmol, 7% yield over 4 steps, 97% purity).

LC-MS (Method B): Rt=1.18 min; MS (ESIpos): m/z=473 [M+H]$^+$ $^1$H-NMR (400 MHz, DMSO-d$_6$) δ [ppm] 2.19 (s, 3H), 3.92 (s, 2H), 7.30-7.37 (m, 2H), 7.41 (s, 2H), 7.43-7.49 (m, 2H), 7.58 (d, 1H), 7.98 (dd, 1H), 8.10 (s, 1H), 8.40 (d, 1H), 10.83 (s, 1H).

Example 15

2-(2-Chlorophenyl)-N-{4-[5-methyl-3-(trifluoromethyl)-1H-pyrazol-1-yl]-3-sulfamoylphenyl}acetamide

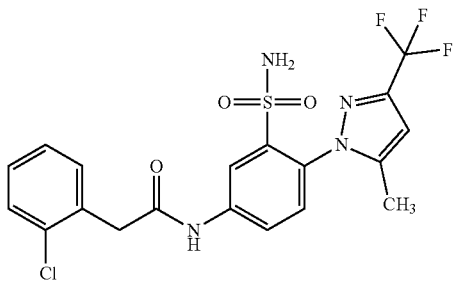 [SMILES: Cc1cc(C(F)(F)F)nn1-c1ccc(NC(=O)Cc2ccccc2Cl)cc1S(N)(=O)=O]

According to general procedures GP1.2, GP2.4, GP3.2 and GP4.2, 2-chloro-N-(2,4-dimethoxybenzyl)-5-nitrobenzenesulfonamide (500 mg, 1.29 mmol), 5-methyl-3-(trifluoromethyl)-1H-pyrazole (291 mg, 1.94 mmol) and (2-chlorophenyl)acetic acid (268 mg, 1.57 mmol) were converted without purification of intermediates to the title compound and were purified at the end twice by preparative HPLC (Waters XBridge C18 5μ 100×30 mm, acetonitrile/water+0.2% aqueous ammonia (32%)) (36.5 mg, 0.0772 mmol, 6% yield over 4 steps, 98% purity).

LC-MS (Method B): Rt=1.13 min; MS (ESIpos): m/z=473 [M+H]$^+$ $^1$H-NMR (400 MHz, DMSO-d$_6$) δ [ppm] 2.12 (s, 3H), 3.92 (s, 2H), 6.73 (s, 1H), 7.24 (s, 2H), 7.31-7.36 (m, 2H), 7.44-7.49 (m, 2H), 7.57 (d, 1H), 7.97 (dd, 1H), 8.42 (d, 1H), 10.88 (s, 1H).

Example 16

2-(2-Chlorophenyl)-N-[3-sulfamoyl-4-(1H-1,2,4-triazol-1-yl)phenyl]acetamide

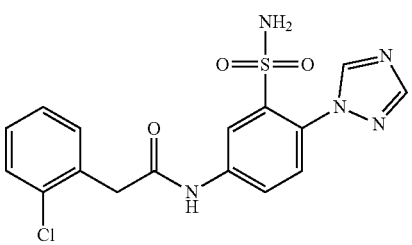 [SMILES: NS(=O)(=O)c1cc(NC(=O)Cc2ccccc2Cl)ccc1-n1cncn1]

According to general procedures GP1.2, GP2.3, GP3.4 and GP4.2, 2-chloro-N-(2,4-dimethoxybenzyl)-5-nitrobenzenesulfonamide (500 mg, 1.29 mmol), 1H-1,2,4-triazole (134 mg, 1.94 mmol) and (2-chlorophenyl)acetic acid (303 mg, 1.77 mmol) were converted without purification of intermediates to the title compound and were purified at the end by preparative HPLC (Waters XBridge C18 5μ 100×30 mm, acetonitrile/water+0.2% aqueous ammonia (32%)) (27 mg, 0.0689 mmol, 5% yield over 4 steps, 97% purity).

LC-MS (Method B): Rt=0.68 min; MS (ESIpos): m/z=392 [M+H]$^+$ $^1$H-NMR (400 MHz, DMSO-d$_6$) δ [ppm] 3.92 (s, 2H), 7.30-7.37 (m, 2H), 7.43-7.50 (m, 4H), 7.59 (d, 1H), 7.98 (dd, 1H), 8.23 (s, 1H), 8.42 (d, 1H), 8.82 (s, 1H), 10.85 (s, 1H).

Example 17

2-(2-Chlorophenyl)-N-{4-[3-(difluoromethyl)-1H-1,2,4-triazol-1-yl]-3-sulfamoyl-phenyl}acetamide

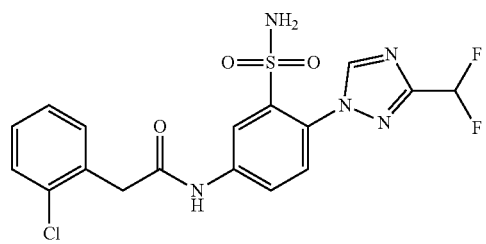 [SMILES: NS(=O)(=O)c1cc(NC(=O)Cc2ccccc2Cl)ccc1-n1cnc(C(F)F)n1]

2-(2-Chlorophenyl)-N-{4-[3-(difluoromethyl)-1H-1,2,4-triazol-1-yl]-3-[(2,4-dimethoxybenzyl)sulfamoyl]phenyl}acetamide (112 mg, 0.189 mmol) was dissolved in dichloromethane (5 mL) and treated with trifluoroacetic acid (129 mg, 1.14 mmol) followed by stirring at room temperature overnight and for one hour at 55° C. It was concentrated in vacuo and extracted with dichloromethane and sodium bicarbonate solution. The aqueous phase was reextracted twice with dichloromethane and twice with 1-butanol. The combined organic phases were washed with brine, dried over a Whatman filter and concentrated in vacuo. Purification by HPLC gave the title compound (5 mg, 0.0113 mmol, 6%, 95% purity).

LC-MS (Method B): Rt=0.79 min; MS (ESIpos): m/z=442 [M+H]$^+$ $^1$H-NMR (400 MHz, DMSO-d$_6$) δ [ppm] 3.93 (s, 2H), 7.21 (t, 1H), 7.30-7.37 (m, 2H), 7.43-7.49 (m, 2H), 7.55 (s, 2H), 7.64 (d, 1H), 7.97 (dd, 1H), 8.44 (d, 1H), 8.95 (s, 1H), 10.90 (s, 1H).

Example 18

N-{4-[3-(Difluoromethyl)-1H-1,2,4-triazol-1-yl]-3-sulfamoylphenyl}-2-(2-fluoro-phenyl)acetamide

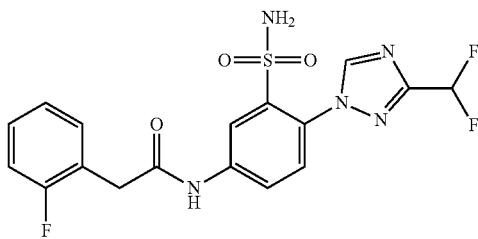

N-{4-[3-(Difluoromethyl)-1H-1,2,4-triazol-1-yl]-3-[(2,4-dimethoxybenzyl)sulfamoyl]phenyl}-2-(2-fluorophenyl)acetamide (94 mg, 0.163 mmol) was dissolved in dichloromethane (5 mL) and treated with trifluoroacetic acid (112 mg, 0.979 mmol) followed by stirring at room temperature overnight and for one hour at 55° C. It was concentrated in vacuo and extracted with dichloromethane and sodium bicarbonate solution. The aqueous phase was reextracted twice with dichloromethane and twice with 1-butanol. The combined organic phases were washed with brine, dried over a Whatman filter and concentrated in vacuo.

Purification by HPLC gave the title compound (2 mg, 0.00470 mmol, 3%, 98% purity).

LC-MS (Method B): Rt=0.70 min; MS (ESIpos): m/z=426 [M+H]$^+$ $^1$H-NMR (400 MHz, DMSO-d$_6$) δ [ppm] 3.82 (s, 2H), 7.07-7.37 (m, 4H), 7.39-7.44 (m, 1H), 7.55 (s, 2H), 7.64 (d, 1H), 7.96 (dd, 1H), 8.43 (d, 1H), 8.95 (s, 1H), 10.86 (s, 1H).

Example 19

2-(2-Chlorophenyl)-N-{3-sulfamoyl-4-[4-(trifluoromethyl)-1H-pyrazol-1-yl]phenyl}acetamide

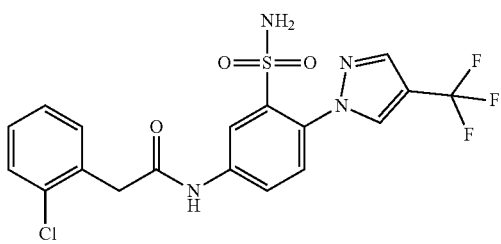 [SMILES: NS(=O)(=O)c1cc(NC(=O)Cc2ccccc2Cl)ccc1-n1cc(C(F)(F)F)cn1]

5-Amino-N-(2,4-dimethoxybenzyl)-2-[4-(trifluoromethyl)-1H-pyrazol-1-yl]benzenesulfonamide (22.3 g, 48.9 mmol) was dissolved in DMF (460 mL) followed by the addition of (2-chlorophenyl)acetic acid (12.5 g, 73.3 mmol), N,N-diisopropylethylamine (25.3 g, 195 mmol) and HATU (27.9 g, 73.3 mmol). The reaction mixture was stirred overnight at room temperature. It was then concentrated in vacuo and extracted with dichloromethane and water. The organic phase was washed with sodium bicarbonate solution, brine and ammonium chloride solution, dried over sodium sulfate and concentrated again in vacuo. The protected product precipitated already partly during washing with ammonium chloride and was removed prior to drying with sodium sulfate.

Both, the residue and the precipitate were dissolved in dichloromethane (150 mL) and treated with trifluoroacetic acid (75 mL), followed by stirring overnight at room temperature.

Again, the product already partly precipitated and was removed. The remaining solution was concentrated in vacuo and extracted with dichloromethane and water. The organic phase was washed with bicarbonate solution and brine, dried over sodium sulfate and was finally concentrated in vacuo. During the aqueous workup, the product partly precipitated again. The combined precipitate fractions plus the concentrated fraction from the organic phase were combined and purified by crystallization from refluxing ethyl acetate to give the title compound (12.3 g, 26.8 mmol, 55% yield over 2 steps, 98% purity).

LC-MS (Method B): Rt=1.06 min; MS (ESIpos): m/z=459 [M+H]$^+$ $^1$H-NMR (400 MHz, DMSO-d$_6$) δ [ppm] 3.92 (s, 2H), 7.30-7.37 (m, 2H), 7.42-7.48 (m, 4H), 7.60 (d, 1H), 7.98 (dd, 1H), 8.18 (s, 1H), 8.39 (d, 1H), 8.74 (s, 1H), 10.83 (s, 1H).

Example 20

2-(2-Fluorophenyl)-N-{3-sulfamoyl-4-[4-(trifluoromethyl)-1H-pyrazol-1-yl]phenyl}-acetamide

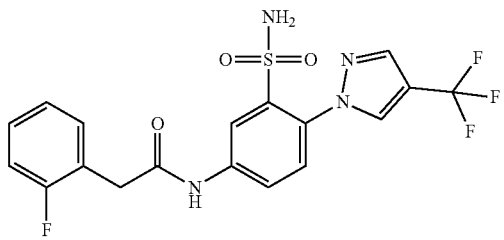 [SMILES: NS(=O)(=O)c1cc(NC(=O)Cc2ccccc2F)ccc1-n1cc(C(F)(F)F)cn1]

5-Amino-N-(2,4-dimethoxybenzyl)-2-[4-(trifluoromethyl)-1H-pyrazol-1-yl]benzenesulfonamide (350 mg, 0.767 mmol) was dissolved in DMF (15 mL) followed by the addition of (2-fluorophenyl)acetic acid (130 mg, 0.843 mmol), N,N-diisopropylethylamine (496 mg, 3.83 mmol) and HATU (466 mg, 1.23 mmol). The reaction mixture was stirred overnight at room temperature. It was then concentrated in vacuo and extracted with dichloromethane and water. The organic phase was washed with brine, dried over sodium sulfate and concentrated again in vacuo.

The residue was dissolved in dichloromethane (10 mL) and treated with trifluoroacetic acid (4.37 g, 38.3 mmol), followed by stirring overnight at room temperature. It was concentrated in vacuo and purified by preparative HPLC (Chromatorex C-18 10 μm, 125×30 mm, acetonitrile/water+ 0.1% formic acid) %)) to give the title compound (60.5 mg, 0.137 mmol, 18% yield over 2 steps, 98% purity).

LC-MS (Method A): Rt=1.10 min; MS (ESIpos): m/z=443 [M+H]+

¹H-NMR (400 MHz, DMSO-d₆) δ [ppm] 3.82 (s, 2H), 7.17-7.23 (m, 2H), 7.31-7.49 (m, 4H), 7.60 (d, 1H), 7.98 (dd, 1H), 8.18 (s, 1H), 8.39 (d, 1H), 8.74 (s, 1H), 10.82 (s, 1H).

Example 21

2-[2-(Difluoromethyl)phenyl]-N-{3-sulfamoyl-4-[4-(trifluoromethyl)-1H-pyrazol-1-yl]phenyl}acetamide

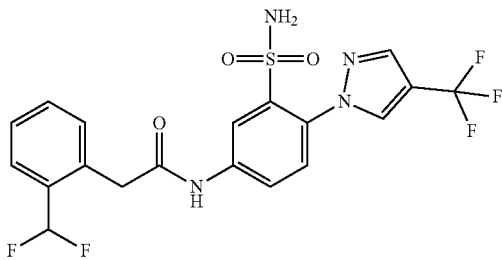 [SMILES: NS(=O)(=O)c1cc(NC(=O)Cc2ccccc2C(F)F)ccc1-n1cc(C(F)(F)F)cn1]

5-Amino-N-(2,4-dimethoxybenzyl)-2-[4-(trifluoromethyl)-1H-pyrazol-1-yl]benzenesulfonamide (350 mg, 0.767 mmol) was dissolved in DMF (15 mL) followed by the addition of [2-(difluoromethyl)phenyl]acetic acid (157 mg, 0.843 mmol), N,N-diisopropylethylamine (496 mg, 3.83 mmol) and HATU (466 mg, 1.23 mmol). The reaction mixture was stirred overnight at room temperature. It was then concentrated in vacuo and extracted with dichloromethane and water. The organic phase was washed with brine, dried over sodium sulfate and concentrated again in vacuo.

The residue was dissolved in dichloromethane (10 mL) and treated with trifluoroacetic acid 4.37 g, 38.3 mmol), followed by stirring overnight at room temperature. It was concentrated in vacuo and purified by preparative HPLC (Chromatorex C-18 10 μm, 125×30 mm, acetonitrile/water+ 0.1% formic acid) %)) to give the title compound (65 mg, 0.137 mmol, 18% yield over 2 steps, 95% purity).

LC-MS (Method A): Rt=1.14 min; MS (ESIpos): m/z=475 [M+H]+

¹H-NMR (400 MHz, DMSO-d₆) δ [ppm] 3.95 (s, 2H), 7.24 (t, 1H), 7.41-7.48 (m, 4H), 7.51-7.56 (m, 1H), 7.58-7.63 (m, 2H), 7.97 (dd, 1H), 8.18 (s, 1H), 8.38 (d, 1H), 8.74 (s, 1H), 10.81 (s, 1H).

Example 22

N-{3-Sulfamoyl-4-[4-(trifluoromethyl)-1H-pyrazol-1-yl]phenyl}-2-[2-(trifluoromethyl)-phenyl]acetamide

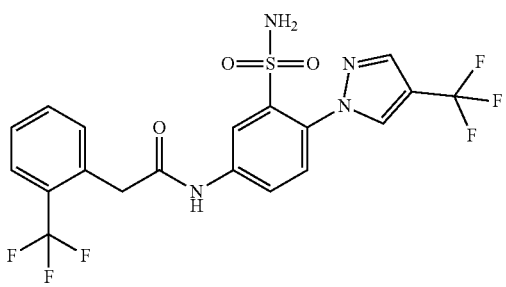 [SMILES: NS(=O)(=O)c1cc(NC(=O)Cc2ccccc2C(F)(F)F)ccc1-n1cc(C(F)(F)F)cn1]

5-Amino-N-(2,4-dimethoxybenzyl)-2-[4-(trifluoromethyl)-1H-pyrazol-1-yl]benzenesulfonamide (350 mg, 0.767 mmol) was dissolved in DMF (15 mL) followed by the addition of [2-(trifluoromethyl)phenyl]acetic acid (172 mg, 0.843 mmol), N,N-diisopropylethylamine (496 mg, 3.83 mmol) and HATU (466 mg, 1.23 mmol). The reaction mixture was stirred overnight at room temperature. It was then concentrated in vacuo and extracted with dichloromethane and water. The organic phase was washed with brine, dried over sodium sulfate and concentrated again in vacuo.

The residue was dissolved in dichloromethane (10 mL) and treated with trifluoroacetic acid 4.37 g, 38.3 mmol), followed by stirring overnight at room temperature. It was concentrated in vacuo and purified by preparative HPLC (Chromatorex C-18 10 μm, 125×30 mm, acetonitrile/water+ 0.1% formic acid) to give the title compound (48 mg, 0.0975 mmol, 13% yield over 2 steps, 95% purity).

LC-MS (Method A): Rt=1.18 min; MS (ESIpos): m/z=493 [M+H]+

¹H-NMR (400 MHz, DMSO-d₆) δ [ppm] 4.01 (s, 2H), 7.43 (s, 2H), 7.49-7.63 (m, 3H), 7.65-7.76 (m, 2H), 7.96 (dd, 1H), 8.18 (s, 1H), 8.38 (d, 1H), 8.74 (s, 1H), 10.82 (s, 1H).

Example 23 N-[4-(3-tert-Butyl-1H-1,2,4-triazol-1-yl)-3-sulfamoylphenyl]-2-(2-chlorophenyl)-acetamide

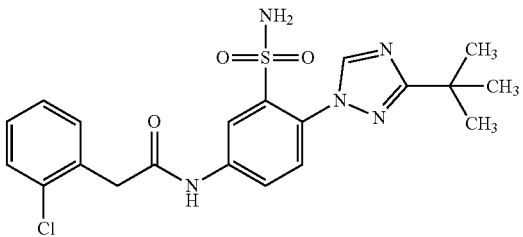 [SMILES: CC(C)(C)c1ncn(-c2ccc(NC(=O)Cc3ccccc3Cl)cc2S(N)(=O)=O)n1]

According to general procedures GP1.2, GP2.4, GP3.4 and GP4.2, 2-chloro-N-(2,4-dimethoxybenzyl)-5-nitrobenzenesulfonamide (500 mg, 1.29 mmol), 3-tert-butyl-1H-1, 2,4-triazole (242 mg, 1.94 mmol) and (2-chlorophenyl) acetic acid (296 mg, 1.74 mmol) were converted without purification of intermediates to the title compound and were purified at the end by preparative HPLC (Waters XBridge C18 5μ 100×30 mm, acetonitrile/water+0.2% aqueous ammonia (32%)) (96 mg, 0.214 mmol, 17% yield over 4 steps, 97% purity).

LC-MS (Method B): Rt=0.92 min; MS (ESIpos): m/z=448 [M+H]+

¹H-NMR (400 MHz, DMSO-d₆) δ [ppm]: 1.34 (s, 9H), 3.92 (s, 2H), 7.30-7.37 (m, 2H), 7.43-7.50 (m, 4H), 7.63 (d, 1H), 7.99 (dd, 1H), 8.40 (d, 1H), 8.71 (s, 1H), 10.83 (s, 1H).

Example 24

2-(2-Chlorophenyl)-N-[4-(3-chloro-1H-1,2,4-triazol-1-yl)-3-sulfamoylphenyl]-acetamide

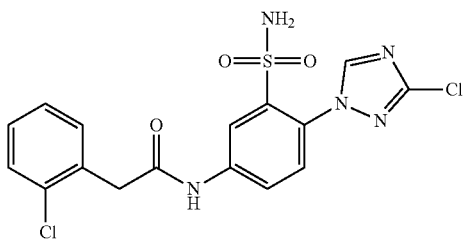

According to general procedures GP1.2, GP2.1, GP3.4 and GP4.2, 2-chloro-N-(2,4-dimethoxybenzyl)-5-nitrobenzenesulfonamide (500 mg, 1.29 mmol), 3-chloro-1H-1,2,4-triazole (201 mg, 1.94 mmol) and (2-chlorophenyl)acetic acid (203 mg, 1.19 mmol) were converted without purification of intermediates to the title compound and were purified at the end by preparative HPLC (Waters XBridge C18 5μ 100×30 mm, acetonitrile/water+0.2% aqueous ammonia (32%)) (9 mg, 0.0211 mmol, 2% yield over 4 steps, 97% purity).

LC-MS (Method B): Rt=0.70 min; MS (ESIpos): m/z=426 [M+H]$^+$ $^1$H-NMR (600 MHz, DMSO-d$_6$) δ [ppm]: 3.92 (s, 2H), 7.31-7.35 (m, 2H), 7.43-7.49 (m, 2H), 7.60 (s, 2H), 7.62 (d, 1H), 7.95 (dd, 1H), 8.42 (d, 1H), 8.81 (s, 1H), 10.87 (s, 1H).

Example 25

2-(2-Chlorophenyl)-N-[4-(4-chloro-1H-pyrazol-1-yl)-3-sulfamoylphenyl]acetamide

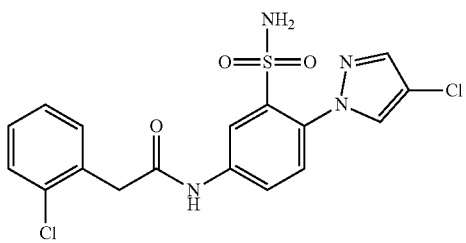

According to general procedures GP1.2, GP2.1, GP3.4 and GP4.2, 2-chloro-N-(2,4-dimethoxybenzyl)-5-nitrobenzenesulfonamide (500 mg, 1.29 mmol), 4-chloro-1H-pyrazole (199 mg, 1.94 mmol) and (2-chlorophenyl)acetic acid (313 mg, 1.83 mmol) were converted without purification of intermediates to the title compound and were purified at the end by preparative HPLC (Waters XBridge C18 5μ 100×30 mm, acetonitrile/water+0.2% aqueous ammonia (32%)) (55 mg, 0.129 mmol, 10% yield over 4 steps, 99% purity).

LC-MS (Method B): Rt=0.95 min; MS (ESIpos): m/z=425 [M+H]$^+$ $^1$H-NMR (500 MHz, DMSO-d$_6$) δ [ppm]: 3.91 (s, 2H), 7.31-7.37 (m, 2H), 7.41 (s, 2H), 7.44-7.49 (m, 2H), 7.55 (d, 1H), 7.87 (s, 1H), 7.97 (dd, 1H), 8.35 (d, 1H), 8.38 (d, 1H), 10.81 (s, 1H).

Example 26

2-(2-Chlorophenyl)-N-[4-(4-fluoro-1H-pyrazol-1-yl)-3-sulfamoylphenyl]acetamide

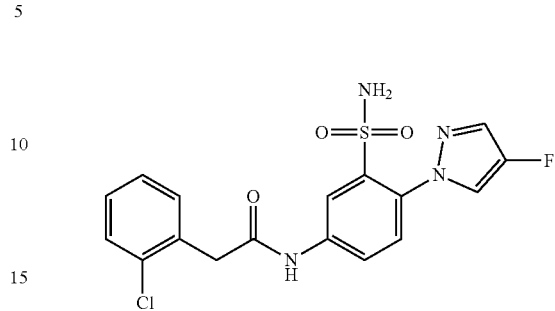

According to general procedures GP1.2, GP2.1, GP3.4 and GP4.2, 2-chloro-N-(2,4-dimethoxybenzyl)-5-nitrobenzenesulfonamide (500 mg, 1.29 mmol), 4-fluoro-1H-pyrazole (167 mg, 1.94 mmol) and (2-chlorophenyl)acetic acid (151 mg, 1.89 mmol) were converted without purification of intermediates to the title compound and were purified at the end by preparative HPLC (Waters XBridge C18 5μ 100×30 mm, acetonitrile/water+0.2% aqueous ammonia (32%)) (43 mg, 0.105 mmol, 8% yield over 4 steps, 97% purity).

LC-MS (Method B): Rt=0.88 min; MS (ESIpos): m/z=409 [M+H]$^+$ $^1$H-NMR (500 MHz, DMSO-d$_6$) δ [ppm]: 3.91 (s, 2H), 7.30-7.37 (m, 2H), 7.39 (s, 2H), 7.43-7.50 (m, 2H), 7.53 (d, 1H), 7.84 (d, 1H), 7.97 (dd, 1H), 8.26 (d, 1H), 8.37 (d, 1H), 10.79 (s, 1H).

Example 27

2-(2-Chlorophenyl)-N-[4-(4-isopropoxy-1H-pyrazol-1-yl)-3-sulfamoylphenyl]-acetamide

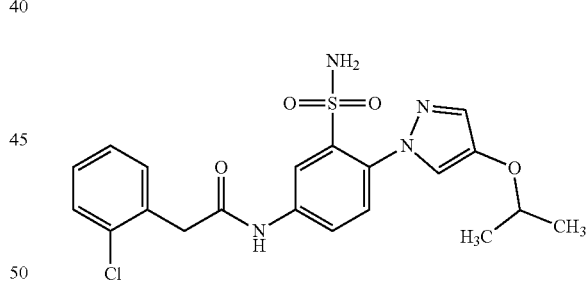

According to general procedures GP1.2, GP2.2, GP3.5 and GP4.1, 2-chloro-N-(2,4-dimethoxybenzyl)-5-nitrobenzenesulfonamide (400 mg, 1.03 mmol), 4-isopropoxy-1H-pyrazole (196 mg, 1.55 mmol) and (2-chlorophenyl)acetic acid (264 mg, 1.55 mmol) were converted without purification of intermediates to the title compound and were purified at the end by preparative HPLC (Waters XBridge C18 5μ 100×30 mm, acetonitrile/water+0.1% formic acid) (16 mg, 0.0356 mmol, 3% yield over 4 steps, 95% purity).

LC-MS (Method A): Rt=1.13 min; MS (ESIpos): m/z=449 [M+H]$^+$ $^1$H-NMR (400 MHz, DMSO-d$_6$) δ [ppm]: 1.27 (d, 6H), 3.89 (s, 2H), 4.25-4.32 (m, 1H), 7.29-7.36 (m, 2H), 7.38-7.48 (m, 4H), 7.52 (d, 1H), 7.56 (d, 1H), 7.86 (d, 1H), 7.96 (dd, 1H), 8.33 (d, 1H), 10.74 (s, 1H).

Example 28

N-[4-(4-Bromo-1H-pyrazol-1-yl)-3-sulfamoylphenyl]-2-(2-chlorophenyl)acetamide

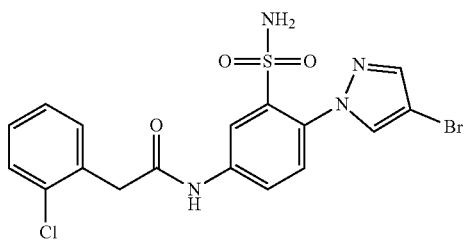 [SMILES: NS(=O)(=O)c1cc(NC(=O)Cc2ccccc2Cl)ccc1-n1cc(Br)cn1]

According to general procedures GP1.2, GP2.2, GP3.5 and GP4.1, 2-chloro-N-(2,4-dimethoxybenzyl)-5-nitrobenzenesulfonamide (400 mg, 1.03 mmol), 4-bromo-1H-pyrazole (228 mg, 1.55 mmol) and (2-chlorophenyl)acetic acid (264 mg, 1.55 mmol) were converted without purification of intermediates to the title compound and were purified at the end by preparative HPLC (Waters XBridge C18 5μ 100×30 mm, acetonitrile/water+0.1% formic acid) (27 mg, 0.0575 mmol, 6% yield over 4 steps, 95% purity).

LC-MS (Method A): Rt=1.10 min; MS (ESIpos): m/z=469/471 [M+H]$^+$ $^1$H-NMR (400 MHz, DMSO-d$_6$) δ [ppm]: 3.90 (s, 2H), 7.29-7.36 (m, 2H), 7.41 (s, 2H), 7.42-7.48 (m, 2H), 7.54 (d, 1H), 7.87 (d, 1H), 7.96 (dd, 1H), 8.34 (d, 1H), 8.37 (d, 1H), 10.80 (s, 1H).

Example 29

2-(2-Chlorophenyl)-N-[4-(3-isobutyl-1H-1,2,4-triazol-1-yl)-3-sulfamoylphenyl]-acetamide

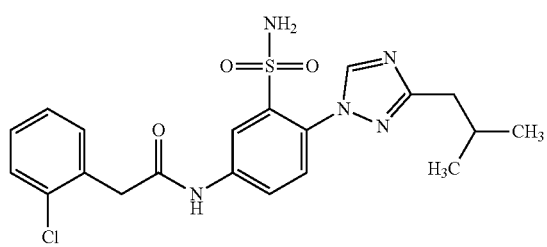 [SMILES: CC(C)Cc1ncn(-c2ccc(NC(=O)Cc3ccccc3Cl)cc2S(N)(=O)=O)n1]

According to general procedures GP1.2, GP2.2, GP3.3 and GP4.1, 2-chloro-N-(2,4-dimethoxybenzyl)-5-nitrobenzenesulfonamide (500 mg, 1.29 mmol), 4-isobutyl-1H-pyrazole (243 mg, 1.94 mmol) and (2-chlorophenyl)acetic acid (330 mg, 1.94 mmol) were converted without purification of intermediates to the title compound and were purified at the end by preparative HPLC (Chromatorex C-18 10 μm, 125×30 mm, acetonitrile/water+0.1% aqueous ammonia (32%)) (27 mg, 0.0603 mmol, 5% yield over 4 steps, 98% purity).

LC-MS (Method B): Rt=0.93 min; MS (ESIpos): m/z=448 [M+H]$^+$ $^1$H-NMR (400 MHz, DMSO-d$_6$) δ [ppm]: 0.93 (d, 6H), 1.99-2.11 (m, 1H), 2.57 (d, 2H), 3.91 (s, 2H), 7.27-7.37 (m, 2H), 7.37-7.49 (m, 4H), 7.58 (d, 1H), 7.97 (dd, 1H), 8.39 (d, 1H), 8.68 (s, 1H), 10.82 (s, 1H).

Example 30

2-(2-Chlorophenyl)-N-{4-[4-(methylsulfanyl)-1H-pyrazol-1-yl]-3-sulfamoylphenyl}-acetamide

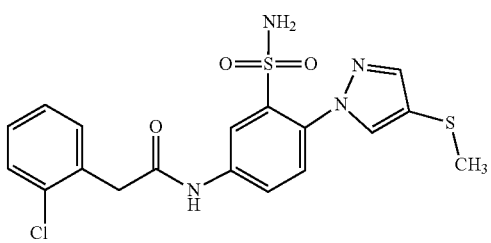 [SMILES: CSc1cnn(-c2ccc(NC(=O)Cc3ccccc3Cl)cc2S(N)(=O)=O)c1]

According to general procedures GP1.2, GP2.2, GP3.5 and GP4.1, 2-chloro-N-(2,4-dimethoxybenzyl)-5-nitrobenzenesulfonamide (400 mg, 1.03 mmol), 4-(methylsulfanyl)-1H-pyrazole (177 mg, 1.55 mmol) and (2-chlorophenyl)acetic acid (264 mg, 1.55 mmol) were converted without purification of intermediates to the title compound and were purified at the end by preparative HPLC (Waters XBridge C18 5μ 100×30 mm, acetonitrile/water+0.1% formic acid) (31 mg, 0.0709 mmol, 7% yield over 4 steps, 95% purity).

LC-MS (Method A): Rt=1.09 min; MS (ESIpos): m/z=437 [M+H]$^+$ $^1$H-NMR (400 MHz, DMSO-d$_6$) δ [ppm]: 2.40 (s, 3H), 3.90 (s, 2H), 7.29-7.36 (m, 2H), 7.39-7.49 (m, 4H), 7.54 (d, 1H), 7.81 (d, 1H), 7.97 (dd, 1H), 8.17 (d, 1H), 8.36 (d, 1H), 10.78 (s, 1H).

Example 31

2-(2-Chlorophenyl)-N-[4-(4-methoxy-1H-pyrazol-1-yl)-3-sulfamoylphenyl]acetamide

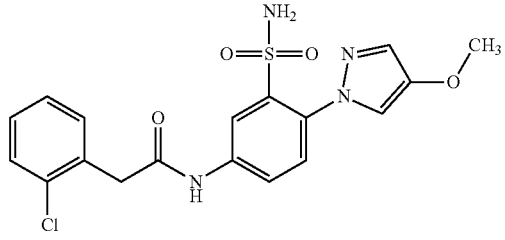 [SMILES: COc1cnn(-c2ccc(NC(=O)Cc3ccccc3Cl)cc2S(N)(=O)=O)c1]

According to general procedures GP1.2, GP2.4, GP3.4 and GP4.2, 2-chloro-N-(2,4-dimethoxybenzyl)-5-nitrobenzenesulfonamide (500 mg, 1.29 mmol), 4-methoxy-1H-pyrazole (190 mg, 1.94 mmol) and (2-chlorophenyl)acetic acid (304 mg, 1.78 mmol) were converted without purification of intermediates to the title compound and were purified at the end by preparative HPLC (Waters XBridge C18 5μ 100×30 mm, acetonitrile/water+0.2% aqueous ammonia (32%)) (83 mg, 0.0197 mmol, 15% yield over 4 steps, 98% purity).

LC-MS (Method B): Rt=0.90 min; MS (ESIpos): m/z=421 [M+H]$^+$ $^1$H-NMR (400 MHz, DMSO-d$_6$) δ [ppm]: 3.75 (s, 3H), 3.90 (s, 2H), 7.29-7.36 (m, 2H), 7.40-7.48 (m, 4H), 7.51 (d, 1H), 7.59 (d, 1H), 7.89 (d, 1H), 7.97 (dd, 1H), 8.34 (d, 1H), 10.74 (s, 1H).

Example 32

N-[4-(1H-Benzimidazol-1-yl)-3-sulfamoylphenyl]-2-(2-chlorophenyl)acetamide

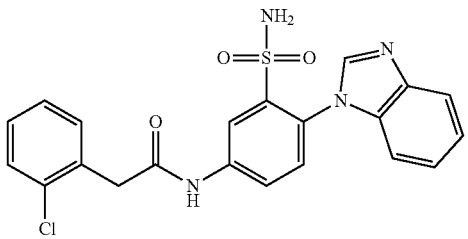 [SMILES: NS(=O)(=O)c1cc(NC(=O)Cc2ccccc2Cl)ccc1-n1cnc2ccccc21]

According to general procedures GP1.2, GP2.4, GP3.4 and GP4.2, 2-chloro-N-(2,4-dimethoxybenzyl)-5-nitrobenzenesulfonamide (500 mg, 1.29 mmol), 1H-benzimidazole (229 mg, 1.94 mmol) and (2-chlorophenyl)acetic acid (322 mg, 1.89 mmol) were converted without purification of intermediates to the title compound and were purified at the end by preparative HPLC (Waters XBridge C18 5μ 100×30 mm, acetonitrile/water+0.2% aqueous ammonia (32%)) (83 mg, 0.0197 mmol, 15% yield over 4 steps, 98% purity).

LC-MS (Method B): Rt=0.83 min; MS (ESIpos): m/z=441 [M+H]$^+$ $^1$H-NMR (400 MHz, DMSO-d$_6$) δ [ppm]: 3.94 (s, 2H), 7.07-7.12 (m, 1H), 7.20-7.28 (m, 2H), 7.30-7.37 (m, 2H), 7.44-7.52 (m, 3H), 7.58 (s, 2H), 7.69-7.74 (m, 1H), 7.95 (dd, 1H), 8.22 (s, 1H), 8.50 (d, 1H), 10.85 (s, 1H).

Example 33

N-[4-(4-Chloro-1H-imidazol-1-yl)-3-sulfamoylphenyl]-2-(2-chlorophenyl)acetamide

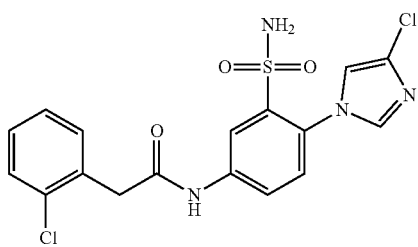 [SMILES: NS(=O)(=O)c1cc(NC(=O)Cc2ccccc2Cl)ccc1-n1cnc(Cl)c1]

According to general procedures GP1.2, GP2.1, GP3.4 and GP4.2, 2-chloro-N-(2,4-dimethoxybenzyl)-5-nitrobenzenesulfonamide (500 mg, 1.29 mmol), 4-chloro-1H-imidazole (199 mg, 1.94 mmol) and (2-chlorophenyl)acetic acid (255 mg, 1.50 mmol) were converted without purification of intermediates to the title compound and were purified at the end by preparative HPLC (Waters XBridge C18 5μ 100×30 mm, acetonitrile/water+0.2% aqueous ammonia (32%)) followed by another preparative HPLC (Waters XBridge C18 5μ 100×30 mm, methanol/water+0.1% formic acid) (23 mg, 0.0541 mmol, 4% yield over 4 steps, 96% purity).

LC-MS (Method B): Rt=0.75 min; MS (ESIpos): m/z=425 [M+H]$^+$ $^1$H-NMR (400 MHz, DMSO-d$_6$) δ [ppm]: 3.90 (s, 2H), 7.29-7.36 (m, 2H), 7.40-7.48 (m, 4H), 7.65 (s, 2H), 7.72 (d, 1H), 7.87 (dd, 1H), 8.39 (d, 1H), 10.80 (s, 1H).

Example 34

2-(2-Chlorophenyl)-N-{4-[3-(dimethylamino)-1H-1,2,4-triazol-1-yl]-3-sulfamoyl-phenyl}acetamide

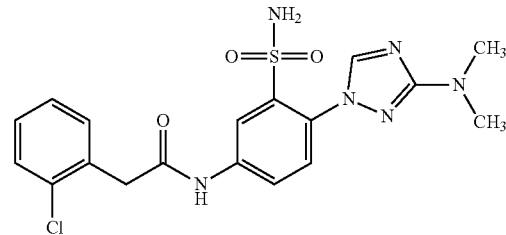 [SMILES: CN(C)c1ncn(-c2ccc(NC(=O)Cc3ccccc3Cl)cc2S(N)(=O)=O)n1]

According to general procedures GP1.2, GP2.4, GP3.4 and GP4.2, 2-chloro-N-(2,4-dimethoxybenzyl)-5-nitrobenzenesulfonamide (500 mg, 1.29 mmol), N,N-dimethyl-1H-1,2,4-triazol-3-amine (217 mg, 1.94 mmol) and (2-chlorophenyl)acetic acid (310 mg, 1.82 mmol) were converted without purification of intermediates to the title compound and were purified at the end by preparative HPLC (Waters XBridge C18 5μ 100×30 mm, acetonitrile/water+0.2% aqueous ammonia (32%)) followed by another preparative HPLC (Waters XBridge C18 5μ 100×30 mm, methanol/water+0.1% formic acid) (45 mg, 0.103 mmol, 8% yield over 4 steps, 99% purity).

LC-MS (Method B): Rt=0.80 min; MS (ESIpos): m/z=435 [M+H]$^+$ $^1$H-NMR (400 MHz, DMSO-d$_6$) δ [ppm]: 2.93 (s, 6H), 3.90 (s, 2H), 7.29-7.36 (m, 2H), 7.42-7.49 (m, 2H), 7.56 (d, 1H), 7.59 (s, 2H), 7.96 (dd, 1H), 8.37 (d, 1H), 8.45 (s, 1H), 10.79 (s, 1H).

Example 35

2-(2-Chlorophenyl)-N-[4-(3-ethyl-1H-1,2,4-triazol-1-yl)-3-sulfamoylphenyl]acetamide

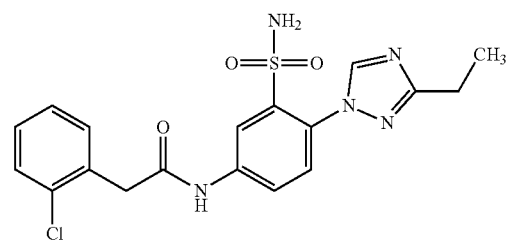 [SMILES: CCc1ncn(-c2ccc(NC(=O)Cc3ccccc3Cl)cc2S(N)(=O)=O)n1]

According to general procedures GP1.2, GP2.4, GP3.4 and GP4.2, 2-chloro-N-(2,4-dimethoxybenzyl)-5-nitrobenzenesulfonamide (500 mg, 1.29 mmol), 3-ethyl-1H-1,2,4-triazole (188 mg, 1.94 mmol) and (2-chlorophenyl)acetic acid (286 mg, 1.67 mmol) were converted without purification of intermediates to the title compound and were purified at the end by preparative HPLC (Waters XBridge C18 5μ 100×30 mm, acetonitrile/water+0.2% aqueous ammonia (32%)) followed by another preparative HPLC (Waters XBridge C18 5μ 100×30 mm, methanol/water+0.1% formic acid) (20 mg, 0.0476 mmol, 4% yield over 4 steps, 97% purity).

LC-MS (Method B): Rt=0.75 min; MS (ESIpos): m/z=420 [M+H]⁺

¹H-NMR (400 MHz, DMSO-d₆) δ [ppm]: 1.25 (t, 3H), 2.73 (q, 2H), 3.91 (s, 2H), 7.29-7.36 (m, 2H), 7.42-7.50 (m, 4H), 7.58 (d, 1H), 7.97 (dd, 1H), 8.39 (d, 1H), 8.68 (s, 1H), 10.82 (s, 1H).

Example 36 and Example 37

According to general procedures GP1.2, GP2.4, GP3.4 and GP4.2, 2-chloro-N-(2,4-dimethoxybenzyl)-5-nitrobenzenesulfonamide (500 mg, 1.29 mmol), 3-cyclopropyl-1H-1,2,4-triazole (212 mg, 1.94 mmol) and (2-chlorophenyl)acetic acid (310 mg, 1.82 mmol) were converted without purification of intermediates to (2-chlorophenyl)-N-[4-(3-cyclopropyl-1H-1,2,4-triazol-1-yl)-3-sulfamoylphenyl]acetamide and 2-(2-chlorophenyl)-N-[4-(5-cyclopropyl-1H-1,2,4-triazol-1-yl)-3-sulfamoylphenyl]acetamide. The two regioisomers were purified and separated at the end by preparative HPLC (Waters XBridge C18 5μ 100×30 mm, acetonitrile/water+0.2% aqueous ammonia (32%)) followed by another preparative HPLC (YMC Triart C18 5μ 100×30 mm, acetonitrile/water+0.1% formic acid).

Example 36

(2-Chlorophenyl)-N-[4-(3-cyclopropyl-1H-1,2,4-triazol-1-yl)-3-sulfamoylphenyl]-acetamide

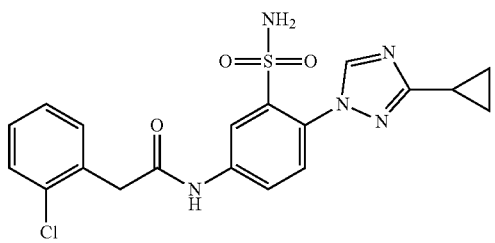 [SMILES: NS(=O)(=O)c1cc(NC(=O)Cc2ccccc2Cl)ccc1-n1cnc(C2CC2)n1]

83.4 mg, 0.124 mmol, 10% yield over 4 steps, 98% purity
LC-MS (Method E): Rt=1.86 min; MS (ESIpos): m/z=432 [M+H]⁺

¹H-NMR (400 MHz, DMSO-d₆) δ [ppm]: 0.83-0.88 (m, 2H), 0.94-1.01 (m, 2H), 2.06-2.13 (m, 1H), 3.91 (s, 2H), 7.29-7.36 (m, 2H), 7.41-7.53 (m, 4H), 7.57 (d, 1H), 7.95 (dd, 1H), 8.39 (d, 1H), 8.61 (s, 1H), 10.82 (s, 1H).

Example 37

2-(2-Chlorophenyl)-N-[4-(5-cyclopropyl-1H-1,2,4-triazol-1-yl)-3-sulfamoyl-phenyl]acetamide

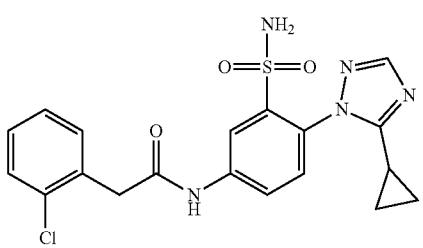 [SMILES: NS(=O)(=O)c1cc(NC(=O)Cc2ccccc2Cl)ccc1-n1ncnc1C1CC1]

12.6 mg, 0.0292 mmol, 2% yield over 4 steps, 98% purity
LC-MS (Method E): Rt=1.82 min; MS (ESIpos): m/z=432 [M+H]⁺

¹H-NMR (400 MHz, DMSO-d₆) δ [ppm]: 0.92 (s, 4H), 1.63-1.71 (m, 1H), 3.92 (s, 2H), 7.22 (s, 2H), 7.30-7.37 (m, 2H), 7.43-7.49 (m, 2H), 7.61 (d, 1H), 7.98 (s, 1H), 8.00 (dd, 1H), 8.42 (d, 1H), 10.86 (s, 1H).

Example 38

2-(2-Chlorophenyl)-N-{4-[3-(methoxymethyl)-1H-1,2,4-triazol-1-yl]-3-sulfamoyl-phenyl}acetamide

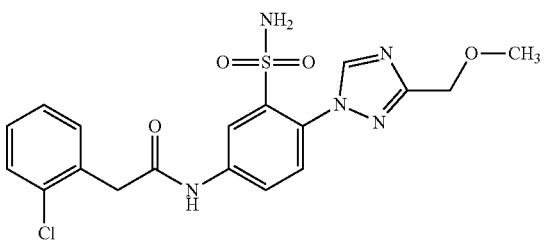 [SMILES: COCc1ncn(-c2ccc(NC(=O)Cc3ccccc3Cl)cc2S(N)(=O)=O)n1]

According to general procedures GP1.2, GP2.4, GP3.4 and GP4.2, 2-chloro-N-(2,4-dimethoxybenzyl)-5-nitrobenzenesulfonamide (500 mg, 1.29 mmol), 3-(methoxymethyl)-1H-1,2,4-triazole (219 mg, 1.94 mmol) and (2-chlorophenyl)acetic acid (306 mg, 1.80 mmol) were converted without purification of intermediates to the title compound and were purified at the end by preparative HPLC (Waters XBridge C18 5μ 100×30 mm, acetonitrile/water+0.2% aqueous ammonia (32%)) (14.5 mg, 0.0333 mmol, 3% yield over 4 steps, 98% purity).

LC-MS (Method B): Rt=0.67 min; MS (ESIpos): m/z=436 [M+H]⁺

¹H-NMR (400 MHz, DMSO-d₆) δ [ppm]: 3.31 (s, 3H), 3.92 (s, 2H), 4.50 (s, 2H), 7.29-7.37 (m, 2H), 7.43-7.49 (m, 4H), 7.60 (d, 1H), 7.97 (dd, 1H), 8.41 (d, 1H), 8.78 (s, 1H), 10.84 (s, 1H).

Example 39

2-(2-Chlorophenyl)-N-[4-(4-cyano-1H-pyrazol-1-yl)-3-sulfamoylphenyl]acetamide

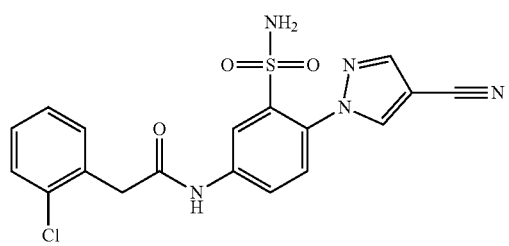

Method 1: Pd/C (10% loading, 350 mg) was added to a solution of 2-(4-cyano-1H-pyrazol-1-yl)-N-(2,4-dimethoxybenzyl)-5-nitrobenzenesulfonamide (9.09 g, 20.5 mmol) in a mixture of methanol (120 mL) and tetrahydrofuran (250 mL) and stirred at room temperature for 3 h under a flow of hydrogen. The catalyst was removed by filtration, followed by washing with tetrahydrofuran and concentration of the filtrate in vacuo. It was extracted with ethyl acetate/water.

Sodium carbonate solution was added and it was stirred overnight. The resulting precipitate was removed by filtration and discarded. The organic phase was separated, dried over sodium sulfate and concentrated in vacuo to give crude 5-amino-2-(4-cyano-1H-pyrazol-1-yl)-N-(2,4-dimethoxybenzyl)benzenesulfonamide (6.37 g) that was used without further purification in the next step.

LC-MS (Method B): Rt=1.06 min; MS (ESIpos): m/z=414 [M+H]$^+$ $^1$H-NMR (400 MHz, DMSO-d$_6$) δ [ppm]: 3.69 (s, 3H), 3.72 (s, 3H), 3.92 (br d, 2H), 6.04 (s, 2H), 6.40-6.48 (m, 2H), 6.78 (dd, 1H), 7.08-7.14 (m, 2H), 7.19 (d, 1H), 7.27 (br t, 1H), 8.25 (s, 1H), 8.70 (s, 1H).

The crude material from the previous step (6.37 g) was dissolved in DMF (87 mL) followed by the addition of (2-chlorophenyl)acetic acid (3.94 g, 23.1 mmol), N,N-diisopropylethylamine (5.97 g, 46.2 mmol) and HATU (8.78 g, 23.1 mmol). The reaction mixture was stirred over the weekend at room temperature. It was then concentrated in vacuo and extracted with ethyl acetate and water. The organic phase was washed with ammonium chloride, sodium bicarbonate solution and brine, dried over sodium sulfate and concentrated again in vacuo to yield crude 2-(2-chlorophenyl)-N-{4-(4-cyano-1H-pyrazol-1-yl)-3-[(2,4-dimethoxybenzyl)-sulfamoyl]phenyl}acetamide (9.77 g) that was used without further purification in the next step.

LC-MS (Method B): Rt=1.27 min; MS (ESIpos): m/z=566 [M+H]$^+$

The crude material from the previous step (9.77 g) was dissolved in a mixture of dichloromethane (30 mL) and trifluoroacetic acid (15 mL) and was stirred at room temperature overnight. It was concentrated in vacuo, dissolved in dichloromethane and concentrated in vacuo again to remove remaining trifluoroacetic acid. It was then stirred in a mixture of dichloromethane/water over the weekend. The resulting precipitate was removed by filtration and provided pure title compound (5.40 g, 13.0 mmol, 63% yield over 3 steps, 97% purity). Purity could be further improved by recrystallization form ethyl acetate/hexanes.

LC-MS (Method B): Rt=0.84 min, MS (ESIpos): m/z=416 [M+H]$^+$ $^1$H-NMR (400 MHz, DMSO-d$_6$) δ [ppm]: 3.91 (s, 2H), 7.29-7.36 (m, 2H), 7.42-7.49 (m, 4H), 7.58 (d, 1H), 7.97 (dd, 1H), 8.31 (d, 1H), 8.39 (d, 1H), 8.86 (d, 1H), 10.84 (br s, 1H).

Method 2: 5-Amino-2-(4-cyano-1H-pyrazol-1-yl)benzenesulfonamide (81 mg, 0.31 mmol) was dissolved in dimethylformamide (1 mL), followed by the addition of N,N-diisopropylethylamine (119 mg, 0.92 mmol), (2-chlorophenyl)acetic acid (63 mg, 0.37 mmol) and HATU (1-[bis(dimethylamino)methylene]-1H-1,2,3-triazolo[4,5-b]pyridinium 3-oxid hexafluorophosphate, 140 mg, 0.37 mmol). The reaction mixture was stirred overnight at room temperature. Then it was concentrated in vacuo, ethyl acetate and water were added and the organic phase was washed with brine, dried over sodium sulfate and was concentrated in vacuo. Purification by preparative HPLC (Chromatorex C-18 10 μm, 125×30 mm, acetonitrile/water+0.1% aqueous ammonia (32%)) gave the title compound (33 mg, 0.0794 mmol, 26% yield, 50% purity).

Example 40

N-[4-(4-tert-Butyl-1H-imidazol-1-yl)-3-sulfamoylphenyl]-2-(2-chlorophenyl)acetamide

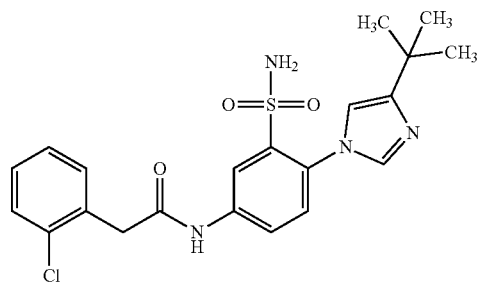 [SMILES: CC(C)(C)c1cn(-c2ccc(NC(=O)Cc3ccccc3Cl)cc2S(N)(=O)=O)cn1]

According to general procedures GP1.2 (but 4.5 eq 4-tert-butyl-1H-imidazole and 9 eq base, 2d 100° C.), GP2.4, GP3.4 and GP4.2, 2-chloro-N-(2,4-dimethoxybenzyl)-5-nitrobenzenesulfonamide (500 mg, 1.29 mmol), 4-tert-butyl-1H-imidazole (723 mg, 5.82 mmol) and (2-chlorophenyl)acetic acid (333 mg, 1.95 mmol) were converted without purification of intermediates to the title compound and were purified at the end by preparative HPLC (Waters XBridge C18 5μ 100×30 mm, acetonitrile/water+0.2% aqueous ammonia (32%)) followed by another preparative HPLC (YMC Trait C18 5μ 100×30 mm, acetonitrile/water+0.2% aqueous ammonia (32%)) (25 mg, 0.0559 mmol, 4% yield over 4 steps, 97% purity).

LC-MS (Method B): Rt=0.91 min; MS (ESIpos): m/z=447 [M+H]$^+$ $^1$H-NMR (400 MHz, DMSO-d$_6$) δ [ppm]: 1.24 (s, 9H), 3.90 (s, 2H), 6.99 (d, 1H), 7.28-7.36 (m, 2H), 7.36-7.49 (m, 5H), 7.63 (d, 1H), 7.87 (dd, 1H), 8.38 (d, 1H), 10.75 (s, 1H).

Example 41

2-(2-Chlorophenyl)-N-[4-(3-cyano-1H-1,2,4-triazol-1-yl)-3-sulfamoylphenyl]acetamide

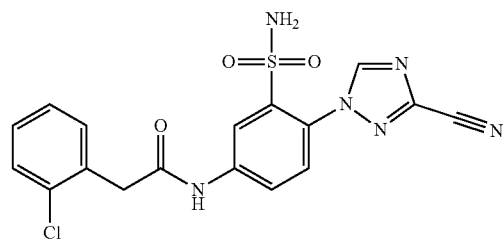 [SMILES: N#Cc1ncn(-c2ccc(NC(=O)Cc3ccccc3Cl)cc2S(N)(=O)=O)n1]

According to general procedures GP1.2, GP2.2, GP3.5 and GP4.1, 2-chloro-N-(2,4-dimethoxybenzyl)-5-nitrobenzenesulfonamide (400 mg, 1.03 mmol), 1H-1,2,4-triazole-3-carbonitrile (145 mg, 1.55 mmol) and (2-chlorophenyl)acetic acid (264 mg, 1.55 mmol) were converted without purification of intermediates to the title compound and were purified at the end by preparative HPLC (Waters XBridge C18 5μ 100×30 mm, acetonitrile/water+0.1% aqueous ammonia (32%)) followed by another preparative HPLC (YMC Trait C18 5μ 100×30 mm, acetonitrile/water+0.1% formic acid) (3.8 mg, 0.00912 mmol, 1% yield over 4 steps, 95% purity).

LC-MS (Method A): Rt=0.98 min; MS (ESIpos): m/z=417 [M+H]+

¹H-NMR (400 MHz, DMSO-d₆) δ [ppm]: 3.93 (s, 2H), 7.28-7.38 (m, 2H), 7.41-7.51 (m, 2H), 7.60-7.69 (m, 3H), 7.92-8.02 (m, 1H), 8.43 (s, 1H), 9.12 (s, 1H), 10.90 (s, 1H).

Example 42

N-[4-(4-Bromo-1H-imidazol-1-yl)-3-sulfamoylphenyl]-2-(2-chlorophenyl)acetamide

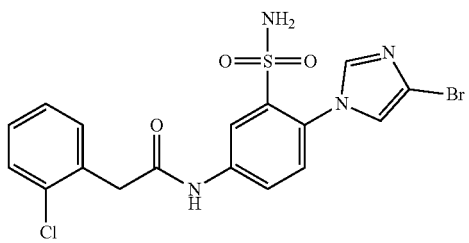 [SMILES: NS(=O)(=O)c1cc(NC(=O)Cc2ccccc2Cl)ccc1-n1cnc(Br)c1]

According to general procedures GP1.2, GP2.2, GP3.3 and GP4.1, 2-chloro-N-(2,4-dimethoxybenzyl)-5-nitrobenzenesulfonamide (500 mg, 1.29 mmol), 4-bromo-1H-imidazole (285 mg, 1.94 mmol) and (2-chlorophenyl)acetic acid (330 mg, 1.94 mmol) were converted without purification of intermediates to the title compound and were purified at the end by preparative HPLC (Waters XBridge C18 5μ 100×30 mm, acetonitrile/water+0.1% formic acid) followed by another preparative HPLC (Waters XBridge C18 5μ 100×30 mm, methanol/water+0.1% formic acid) (20 mg, 0.0426 mmol, 3% yield over 4 steps, 98% purity).

LC-MS (Method A): Rt=0.97 min; MS (ESIpos): m/z=469/471 [M+H]+

¹H-NMR (400 MHz, DMSO-d6) δ[ppm]: 3.91 (s, 2H), 7.29-7.35 (m, 2H), 7.41-7.48 (m, 4H), 7.65 (s, 2H), 7.73 (d, 1H), 7.89 (dd, 1H), 8.40 (d, 1H), 10.80 (s, 1H).

Example 43 and Example 44

According to general procedures GP1.2, GP2.2, GP3.3 and GP4.1, 2-chloro-N-(2,4-dimethoxybenzyl)-5-nitrobenzenesulfonamide (500 mg, 1.29 mmol), 3H-imidazo[4,5-b]pyridine (231 mg, 1.94 mmol) and (2-chlorophenyl)acetic acid (330 mg, 1.94 mmol) were converted without purification of intermediates to 2-(2-chlorophenyl)-N-[4-(3H-imidazo[4,5-b]pyridin-3-yl)-3-sulfamoylphenyl]acetamide and 2-(2-chlorophenyl)-N-[4-(1H-imidazo[4,5-b]pyridin-1-yl)-3-sulfamoylphenyl]acetamide. The two regioisomers were purified and separated at the end by preparative HPLC (YMC Triart C18 5μ 100×30 mm, acetonitrile/water+0.1% formic acid).

Example 43

2-(2-Chlorophenyl)-N-[4-(3H-imidazo[4,5-b]pyridin-3-yl)-3-sulfamoylphenyl]-acetamide

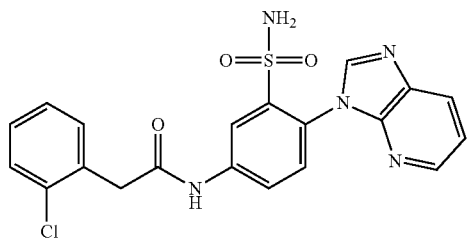 [SMILES: NS(=O)(=O)c1cc(NC(=O)Cc2ccccc2Cl)ccc1-n1cnc2cccnc21]

1 mg, 0.00226 mmol, 1% yield over 4 steps, 98% purity
LC-MS (Method G): Rt=1.52 min; MS (ESIpos): m/z=442 [M+H]+

¹H-NMR (600 MHz, DMSO-d6) δ[ppm]: 3.93 (s, 2H), 7.26 (dd, 1H), 7.31-7.37 (m, 2H), 7.44-7.49 (m, 2H), 7.53-7.56 (m, 2H), 7.61 (s, 2H), 7.96 (dd, 1H), 8.46 (dd, 1H), 8.47 (d, 1H), 8.49 (d, 1H), 10.87 (s, 1H).

Example 44

2-(2-Chlorophenyl)-N-[4-(1H-imidazo[4,5-b]pyridin-1-yl)-3-sulfamoylphenyl]-acetamide

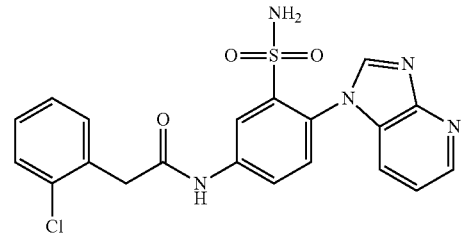 [SMILES: NS(=O)(=O)c1cc(NC(=O)Cc2ccccc2Cl)ccc1-n1cnc2ncccc21]

5 mg, 0.0113 mmol, 1% yield over 4 steps, 95% purity
LC-MS (Method G): Rt=1.61 min; MS (ESIpos): m/z=442 (M+H)+

¹H-NMR (600 MHz, DMSO-d6) δ[ppm]: 3.94 (s, 2H), 7.31-7.37 (m, 3H), 7.45-7.49 (m, 2H), 7.52-7.57 (m, 3H), 7.95 (dd, 1H), 8.16 (dd, 1H), 8.29 (dd, 1H), 8.46 (s, 1H), 8.48 (d, 1H), 10.84 (s, 1H).

Example 45 and Example 46

According to general procedures GP1.2, GP2.2, GP3.5 and GP4.1, 2-chloro-N-(2,4-dimethoxybenzyl)-5-nitrobenzenesulfonamide (500 mg, 1.29 mmol), 3H-imidazo[4,5-c]pyridine (231 mg, 1.94 mmol) and (2-chlorophenyl)acetic acid (330 mg, 1.94 mmol) were converted without purification of intermediates to 2-(2-chlorophenyl)-N-[4-(1H-imidazo[4,5-c]pyridin-1-yl)-3-sulfamoylphenyl]acetamide and 2-(2-chlorophenyl)-N-[4-(3H-imidazo[4,5-c]pyridin-3-yl)-3-sulfamoylphenyl]acetamide. The two regioisomers were purified and separated at the end by preparative HPLC (Phenomenex Kinetex C18 5μ 100×30 mm, acetonitrile/water+0.1% formic acid) followed by another by preparative HPLC (Luna Hilic 5μ 250×30 mm, C02/methanol+0.5% ammonia (32%)).

Example 45

2-(2-Chlorophenyl)-N-[4-(1H-imidazo[4,5-c]pyridin-1-yl)-3-sulfamoylphenyl]-acetamide

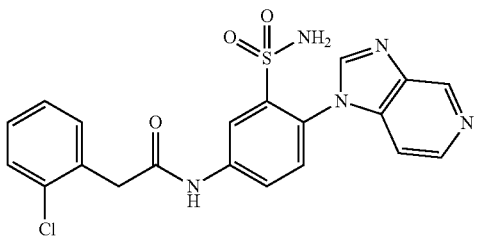 [SMILES: NS(=O)(=O)c1cc(NC(=O)Cc2ccccc2Cl)ccc1-n1cnc2cnccc21]

5 mg, 0.0113 mmol, 1% yield over 4 steps, 95% purity
LC-MS (Method H): Rt=2.75 min; MS (ESIpos): m/z=442 [M+H]$^+$
$^1$H-NMR (400 MHz, DMSO-d6) δ[ppm]: 3.94 (s, 2H), 7.28 (d, 1H), 7.31-7.38 (m, 2H), 7.43-7.50 (m, 2H), 7.58 (d, 1H), 7.61-7.68 (m, 2H), 7.97 (dd, 1H), 8.37-8.43 (m, 1H), 8.47-8.54 (m, 2H), 9.15 (s, 1H), 10.90 (s, 1H).

Example 46

2-(2-Chlorophenyl)-N-[4-(3H-imidazo[4,5-c]pyridin-3-yl)-3-sulfamoylphenyl]-acetamide

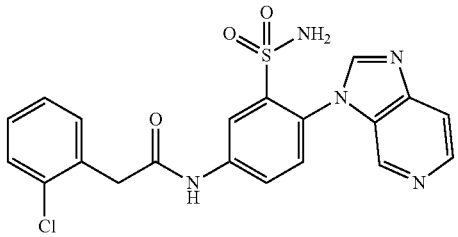 [SMILES: NS(=O)(=O)c1cc(NC(=O)Cc2ccccc2Cl)ccc1-n1cnc2ccncc21]

5 mg, 0.0113 mmol, 1% yield over 4 steps, 85% purity
LC-MS (Method H): Rt=3.34 min; MS (ESIpos): m/z=442 [M+H]$^+$
$^1$H-NMR (600 MHz, DMSO-d6) δ[ppm]: 3.94 (s, 2H), 7.27-7.39 (m, 2H), 7.42-7.50 (m, 2H), 7.67 (d, 1H), 7.73-7.82 (m, 3H), 7.94 (dd, 1H), 7.98-8.03 (m, 1H), 8.42-8.48 (m, 2H), 8.95 (s, 1H), 10.91 (s, 1H).

Example 47

2-(2-Chlorophenyl)-N-[4-(2,4-dimethyl-1H-imidazol-1-yl)-3-sulfamoylphenyl]-acetamide

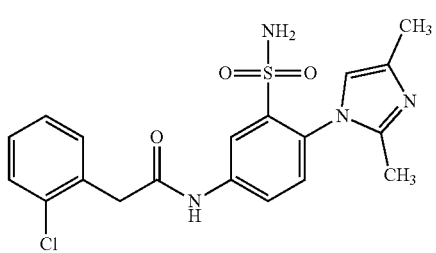 [SMILES: Cc1cn(-c2ccc(NC(=O)Cc3ccccc3Cl)cc2S(N)(=O)=O)c(C)n1]

According to general procedures GP1.2, GP2.4, GP3.4 and GP4.2, 2-chloro-N-(2,4-dimethoxybenzyl)-5-nitrobenzenesulfonamide (500 mg, 1.29 mmol), 2,4-dimethyl-1H-imidazole (207 mg, 1.94 mmol) and (2-chlorophenyl)acetic acid (262 mg, 1.53 mmol) were converted without purification of intermediates to the title compound and were purified at the end by preparative HPLC (Waters XBridge C18 5μ 100×30 mm, acetonitrile/water+0.2% aqueous ammonia (32%)) followed by another preparative HPLC (Waters YMC Triart C18 5μ 100×30 mm, acetonitrile/water+0.1% formic acid) (1 mg, 0.00239 mmol, 1% yield over 4 steps, 95% purity).
LC-MS (Method A): Rt=0.76 min; MS (ESIpos): m/z=419 [M+H]$^+$
$^1$H-NMR (400 MHz, DMSO-d6) δ[ppm]: 1.97 (s, 3H), 2.07 (s, 3H), 3.90 (s, 2H), 6.74 (s, 1H), 7.26-7.38 (m, 5H), 7.41-7.49 (m, 2H), 7.87 (dd, 1H), 8.37 (d, 1H), 10.77 (s, 1H).

Example 48

2-(2-Fluorophenyl)-N-[4-(4-fluoro-1H-pyrazol-1-yl)-3-sulfamoylphenyl]acetamide

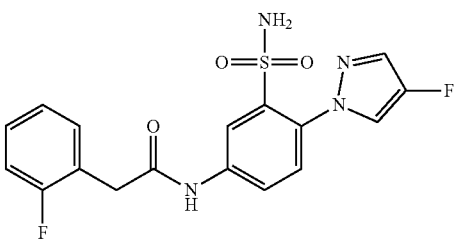 [SMILES: NS(=O)(=O)c1cc(NC(=O)Cc2ccccc2F)ccc1-n1cc(F)cn1]

According to general procedures GP1.2, GP2.1, GP3.3 and GP4.1, 2-chloro-N-(2,4-dimethoxybenzyl)-5-nitrobenzenesulfonamide (450 mg, 1.17 mmol), 4-fluoro-1H-pyrazole (150 mg, 1.75 mmol) and (2-fluorophenyl)acetic acid (284 mg, 1.85 mmol) were converted without purification of intermediates to the title compound and were purified at the end by preparative HPLC (Waters XBridge C18 5μ 100×30 mm, acetonitrile/water+0.1% formic acid) (38 mg, 0.0969 mmol, 8% yield over 4 steps, 93% purity).
LC-MS (Method A): Rt=0.97 min; MS (ESIpos): m/z=393 [M+H]$^+$
$^1$H-NMR (400 MHz, DMSO-d$_6$) δ [ppm]: 3.80 (s, 2H), 7.15-7.22 (m, 2H), 7.29-7.44 (m, 4H), 7.52 (d, 1H), 7.83 (dd, 1H), 7.96 (dd, 1H), 8.26 (dd, 1H), 8.36 (d, 1H), 10.76 (s, 1H).

Example 49

N-[4-(4-Chloro-1H-pyrazol-1-yl)-3-sulfamoylphenyl]-2-[2-(difluoromethyl)-phenyl]acetamide

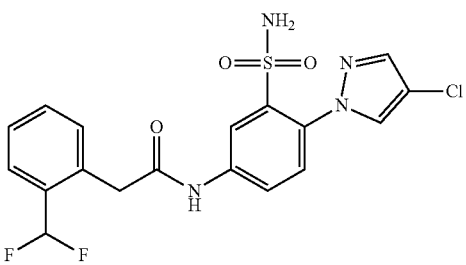 [SMILES: NS(=O)(=O)c1cc(NC(=O)Cc2ccccc2C(F)F)ccc1-n1cc(Cl)cn1]

According to general procedures GP1.2, GP2.1, GP3.3 and GP4.1, 2-chloro-N-(2,4-dimethoxybenzyl)-5-nitrobenzenesulfonamide (500 mg, 1.29 mmol), 4-chloro-1H-pyrazole (199 mg, 1.94 mmol) and [2-(difluoromethyl)phenyl] acetic acid (330 mg, 1.77 mmol) were converted without purification of intermediates the title compound and were purified at the end by preparative HPLC (Waters XBridge C18 5µ 100×30 mm, acetonitrile/water+0.1% formic acid) (29 mg, 0.0659 mmol, 5% yield over 4 steps, 90% purity).

LC-MS (Method A): Rt=1.09 min; MS (ESIpos): m/z=441 [M+H]⁺

¹H-NMR (400 MHz, DMSO-d₆) δ [ppm]: 3.94 (s, 2H), 7.23 (t, 1H), 7.38-7.46 (m, 4H), 7.49-7.62 (m, 3H), 7.86 (d, 1H), 7.95 (dd, 1H), 8.34 (d, 1H), 8.35 (d, 1H), 10.77 (s, 1H).

Example 50

N-[4-(4-Chloro-1H-pyrazol-1-yl)-3-sulfamoylphenyl]-2-(2-fluorophenyl)acetamide

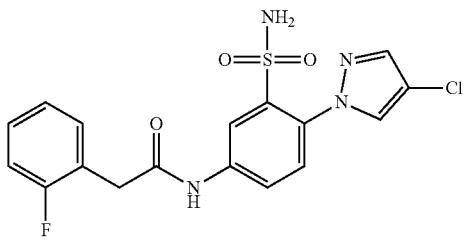 [SMILES: NS(=O)(=O)c1cc(NC(=O)Cc2ccccc2F)ccc1-n1cc(Cl)cn1]

According to general procedures GP1.2, GP2.1, GP3.3 and GP4.1, 2-chloro-N-(2,4-dimethoxybenzyl)-5-nitrobenzenesulfonamide (500 mg, 1.29 mmol), 4-chloro-1H-pyrazole (199 mg, 1.94 mmol) and (2-fluorophenyl)acetic acid (273 mg, 1.77 mmol) were converted without purification of intermediates to the title compound and were purified at the end by preparative HPLC (Waters XBridge C18 5µ 100×30 mm, acetonitrile/water+0.1% formic acid) (25 mg, 0.0659 mmol, 5% yield over 4 steps, 90% purity).

LC-MS (Method A): Rt=1.04 min; MS (ESIpos): m/z=409 [M+H]⁺

¹H-NMR (400 MHz, DMSO-d₆) δ [ppm]: 3.80 (s, 2H), 7.16-7.23 (m, 2H), 7.30-7.44 (m, 4H), 7.54 (d, 1H), 7.86 (d, 1H), 7.96 (dd, 1H), 8.34 (d, 1H), 8.36 (d, 1H), 10.78 (s, 1H).

Example 51

2-[2-(Difluoromethyl)phenyl]-N-[4-(4-fluoro-1H-pyrazol-1-yl)-3-sulfamoyl-phenyl]acetamide

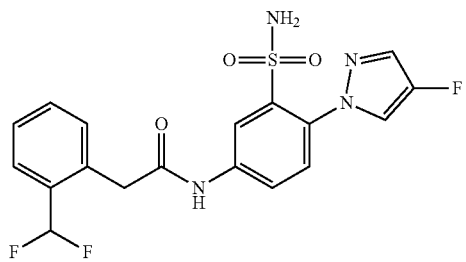 [SMILES: NS(=O)(=O)c1cc(NC(=O)Cc2ccccc2C(F)F)ccc1-n1cc(F)cn1]

According to general procedures GP1.2, GP2.1, GP3.3 and GP4.1, 2-chloro-N-(2,4-dimethoxybenzyl)-5-nitrobenzenesulfonamide (450 mg, 1.17 mmol), 4-fluoro-1H-pyrazole (150 mg, 1.75 mmol) and [2-(difluoromethyl)phenyl] acetic acid (343 mg, 1.85 mmol) were converted without purification of intermediates to the title compound and were purified at the end by preparative HPLC (Waters XBridge C18 5µ 100×30 mm, acetonitrile/water+0.1% formic acid) (24 mg, 0.566 mmol, 5% yield over 4 steps, 90% purity).

LC-MS (Method A): Rt=1.02 min; MS (ESIpos): m/z=425 [M+H]⁺

¹H-NMR (400 MHz, DMSO-d₆) δ [ppm]: 3.94 (s, 2H), 7.23 (t, 1H), 7.38 (s, 2H), 7.42-7.46 (m, 2H), 7.50-7.55 (m, 2H), 7.58-7.63 (m, 1H), 7.83 (dd, 1H), 7.95 (dd, 1H), 8.26 (dd, 1H), 8.35 (d, 1H), 10.76 (s, 1H).

Example 52

N-[4-(4-Cyano-1H-pyrazol-1-yl)-3-sulfamoylphenyl]-2-(2-fluorophenyl)acetamide

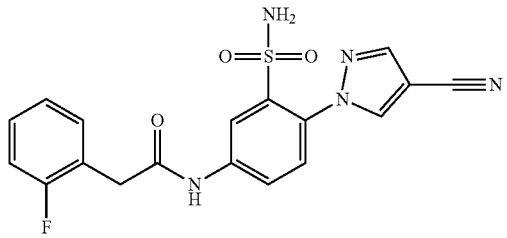

According to general procedures GP1.2, GP2.4, GP3.4 and GP4.2, 2-chloro-N-(2,4-dimethoxybenzyl)-5-nitrobenzenesulfonamide (1.00 g, 2.59 mmol), 1H-pyrazole-4-carbonitrile (361 mg, 3.88 mmol) and (2-fluorophenyl)acetic acid (226 mg, 1.47 mmol) were converted without purification of intermediates to the title compound and were purified at the end by preparative HPLC (Chromatorex C-18 10 µm, 125×30 mm, acetonitrile/water+0.1% aqueous ammonia (32%)) followed by another preparative HPLC (YMC Triart C-18 µm, 100×30 mm, acetonitrile/water+ 0.1% aqueous ammonia (32%)) (44 mg, 0.110 mmol, 4% yield over 4 steps, 98% purity).

LC-MS (Method B): Rt=0.73 min; MS (ESIpos): m/z=400 [M+H]⁺

¹H-NMR (400 MHz, DMSO-d₆) δ [ppm]: 3.81 (s, 2H), 7.16-7.23 (m, 2H), 7.30-7.50 (m, 4H), 7.58 (d, 1H), 7.96 (dd, 1H), 8.31 (d, 1H), 8.39 (d, 1H), 8.86 (d, 1H), 10.82 (s, 1H).

Example 53

2-(2-Methoxyphenyl)-N-{3-sulfamoyl-4-[3-(trifluoromethyl)-1H-1,2,4-triazol-1-yl]-phenyl}acetamide

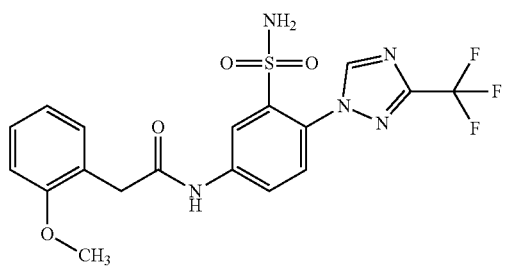 [SMILES: COc1ccccc1CC(=O)Nc1ccc(-n2cnc(C(F)(F)F)n2)c(S(N)(=O)=O)c1]

According to general procedure GP5.1, 5-amino-N-(2,4-dimethoxybenzyl)-2-[3-(trifluoromethyl)-1H-1,2,4-triazol-1-yl]benzenesulfonamide (0.20 mmol) and (2-methoxyphenyl)acetic acid (0.40 mmol) were converted to the title compound (3.4 mg, 0.00747 mmol, 4% yield, 100% purity).

LC-MS (Method A): Rt=1.07 min; MS (ESIpos): m/z=456 [M+H]$^+$

Example 54

2-(2-Fluorophenyl)-N-{3-sulfamoyl-4-[3-(trifluoromethyl)-1H-1,2,4-triazol-1-yl]phenyl}acetamide

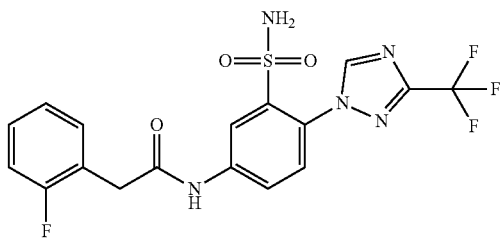 [SMILES: NS(=O)(=O)c1cc(NC(=O)Cc2ccccc2F)ccc1-n1cnc(C(F)(F)F)n1]

According to general procedure GP5.1, 5-amino-N-(2,4-dimethoxybenzyl)-2-[3-(trifluoromethyl)-1H-1,2,4-triazol-1-yl]benzenesulfonamide (0.20 mmol) and (2-fluorophenyl)acetic acid (0.40 mmol) were converted the title compound (12.7 mg, 0.0286 mmol, 14% yield, 100% purity).

LC-MS (Method A): Rt=1.07 min; MS (ESIpos): m/z=444 [M+H]$^+$

Example 55

2-(3-Fluorophenyl)-N-{3-sulfamoyl-4-[3-(trifluoromethyl)-1H-1,2,4-triazol-1-yl]-phenyl}acetamide

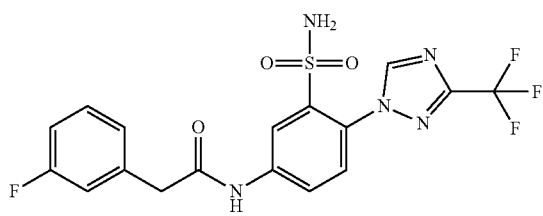 [SMILES: NS(=O)(=O)c1cc(NC(=O)Cc2cccc(F)c2)ccc1-n1cnc(C(F)(F)F)n1]

According to general procedure GP5.1, 5-amino-N-(2,4-dimethoxybenzyl)-2-[3-(trifluoromethyl)-1H-1,2,4-triazol-1-yl]benzenesulfonamide (0.20 mmol) and (3-fluorophenyl)acetic acid (0.40 mmol) were converted to the title compound (11.6 mg, 0.0262 mmol, 13% yield, 100% purity).

LC-MS (Method A): Rt=1.08 min; MS (ESIpos): m/z=444 [M+H]$^+$

Example 56

2-(2-Chloro-4-fluorophenyl)-N-{3-sulfamoyl-4-[3-(trifluoromethyl)-1H-1,2,4-triazol-1-yl]phenyl}acetamide

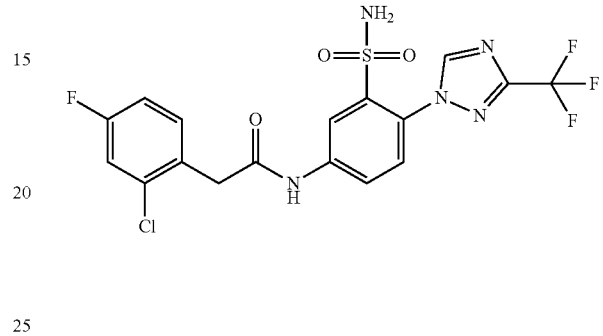

According to general procedure GP5.1, 5-amino-N-(2,4-dimethoxybenzyl)-2-[3-(trifluoromethyl)-1H-1,2,4-triazol-1-yl]benzenesulfonamide (0.20 mmol) and (2-chloro-4-fluorophenyl)acetic acid (0.40 mmol) were converted to the title compound (13.8 mg, 0.0289 mmol, 14% yield, 100% purity).

LC-MS (Method A): Rt=1.13 min; MS (ESIpos): m/z=478 [M+H]$^+$

Example 57

2-[2-(Difluoromethoxy)phenyl]-N-{3-sulfamoyl-4-[3-(trifluoromethyl)-1H-1,2,4-triazol-1-yl]phenyl}acetamide

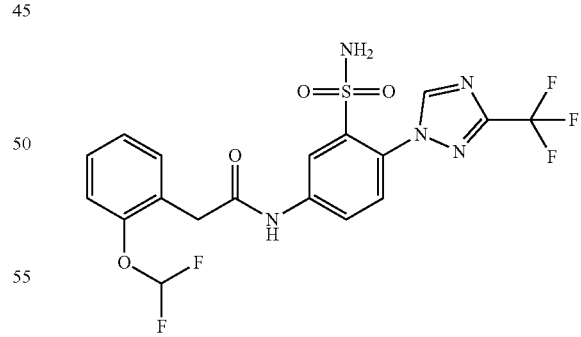

According to general procedure GP5.1, 5-amino-N-(2,4-dimethoxybenzyl)-2-[3-(trifluoromethyl)-1H-1,2,4-triazol-1-yl]benzenesulfonamide (0.20 mmol) and [2-(difluoromethoxy)phenyl]acetic acid (0.40 mmol) were converted the title compound (3.4 mg, 0.00692 mmol, 3% yield, 100% purity).

LC-MS (Method A): Rt=1.12 min; MS (ESIpos): m/z=492 [M+H]$^+$

Example 58

2-(2-Chloro-5-fluorophenyl)-N-{3-sulfamoyl-4-[3-(trifluoromethyl)-1H-1,2,4-triazol-1-yl]phenyl}acetamide

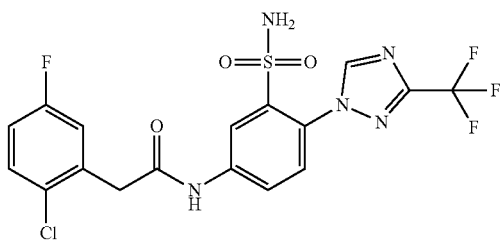 [SMILES: NS(=O)(=O)c1cc(NC(=O)Cc2cc(F)ccc2Cl)ccc1-n1cnc(C(F)(F)F)n1]

According to general procedure GP5.1, 5-amino-N-(2,4-dimethoxybenzyl)-2-[3-(trifluoromethyl)-1H-1,2,4-triazol-1-yl]benzenesulfonamide (0.20 mmol) and (2-chloro-5-fluorophenyl)acetic acid (0.40 mmol) were converted to the title compound (5.2 mg, 0.0109 mmol, 5% yield, 100% purity).

LC-MS (Method A): Rt=1.13 min; MS (ESIpos): m/z=478 [M+H]$^+$

Example 59

2-(3-Chloropyridin-4-yl)-N-{3-sulfamoyl-4-[3-(trifluoromethyl)-1H-1,2,4-triazol-1-yl]phenyl}acetamide

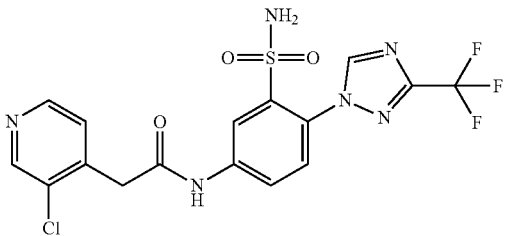

According to general procedure GP5.1, 5-amino-N-(2,4-dimethoxybenzyl)-2-[3-(trifluoromethyl)-1H-1,2,4-triazol-1-yl]benzenesulfonamide (0.20 mmol) and (3-chloropyridin-4-yl)acetic acid (0.40 mmol) were converted to the title compound (8.0 mg, 0.0174 mmol, 9% yield, 82% purity).

LC-MS (Method A): Rt=0.92 min; MS (ESIpos): m/z=461 [M+H]$^+$

Example 60

2-[4-(Difluoromethyl)phenyl]-N-{3-sulfamoyl-4-[3-(trifluoromethyl)-1H-1,2,4-triazol-1-yl]phenyl}acetamide

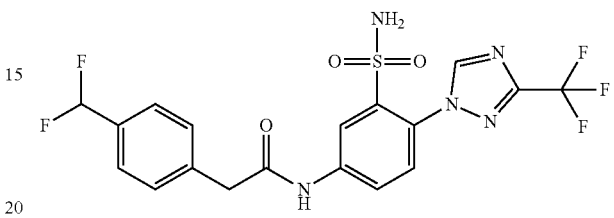

According to general procedure GP5.1, 5-amino-N-(2,4-dimethoxybenzyl)-2-[3-(trifluoromethyl)-1H-1,2,4-triazol-1-yl]benzenesulfonamide (0.20 mmol) and [4-(difluoromethyl)phenyl]acetic acid (0.40 mmol) were converted to the title compound (11.4 15 mg, 0.0240 mmol, 12% yield, 100% purity).

LC-MS (Method A): Rt=1.10 min; MS (ESIpos): m/z=476 [M+H]$^+$

Example 61

2-(2-Chlorophenyl)-2,2-difluoro-N-{3-sulfamoyl-4-[3-(trifluoromethyl)-1H-1,2,4-triazol-1-yl]phenyl}acetamide

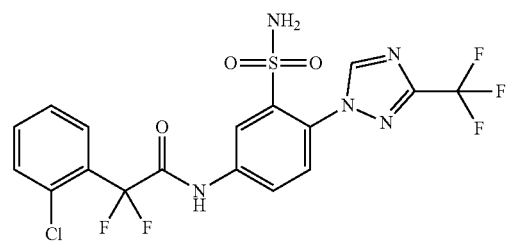 [SMILES: NS(=O)(=O)c1cc(NC(=O)C(F)(F)c2ccccc2Cl)ccc1-n1cnc(C(F)(F)F)n1]

According to general procedure GP5.1, 5-amino-N-(2,4-dimethoxybenzyl)-2-[3-(trifluoromethyl)-1H-1,2,4-triazol-1-yl]benzenesulfonamide (0.20 mmol) and (2-chlorophenyl)(difluoro)acetic acid (0.40 mmol) were converted the title compound (16.2 mg, 0.0327 mmol, 16% yield, 100% purity).

LC-MS (Method A): Rt=1.17 min; MS (ESIpos): m/z=496 (M+H)$^+$

Example 62

N-[4-(4-Bromo-1H-pyrazol-1-yl)-3-sulfamoylphenyl]-2-(2-chlorophenyl)-2,2-difluoroacetamide

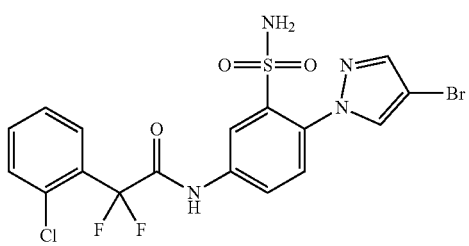 [SMILES: NS(=O)(=O)c1cc(NC(=O)C(F)(F)c2ccccc2Cl)ccc1-n1cc(Br)cn1]

According to general procedure GP5.1, 5-amino-2-(4-bromo-1H-pyrazol-1-yl)-N-(2,4-dimethoxybenzyl)benzenesulfonamide (0.20 mmol) and (2-chlorophenyl)(difluoro)acetic acid (0.40 mmol) were converted to the title compound (5.8 mg, 0.0115 mmol, 6% yield, 100% purity).

LC-MS (Method A): Rt=1.21 min; MS (ESIpos): m/z=505 $[M+H]^+$

Example 63

N-[4-(4-Bromo-1H-pyrazol-1-yl)-3-sulfamoylphenyl]-2-(2-fluorophenyl)acetamide

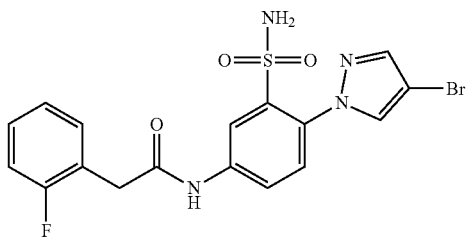 [SMILES: NS(=O)(=O)c1cc(NC(=O)Cc2ccccc2F)ccc1-n1cc(Br)cn1]

According to general procedure GP5.1, 5-amino-2-(4-bromo-1H-pyrazol-1-yl)-N-(2,4-dimethoxybenzyl)benzenesulfonamide (0.20 mmol) and (2-fluorophenyl)acetic acid (0.40 mmol) were converted to the title compound (9.6 mg, 0.0212 mmol, 11% yield, 100% purity).

LC-MS (Method A): Rt=1.10 min; MS (ESIpos): m/z=453 $[M+H]^+$

Example 64

N-[4-(4-Bromo-1H-pyrazol-1-yl)-3-sulfamoylphenyl]-2-[2-(trifluoromethyl)-phenyl]acetamide

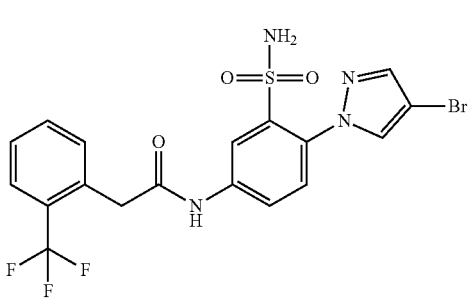 [SMILES: NS(=O)(=O)c1cc(NC(=O)Cc2ccccc2C(F)(F)F)ccc1-n1cc(Br)cn1]

According to general procedure GP5.1, 5-amino-2-(4-bromo-1H-pyrazol-1-yl)-N-(2,4-dimethoxybenzyl)benzenesulfonamide (0.20 mmol) and [2-(trifluoromethyl)phenyl]acetic acid (0.40 mmol) were converted to the title compound (23.4 mg, 0.0465 mmol, 23% yield, 100% purity).

LC-MS (Method A): Rt=1.19 min; MS (ESIpos): m/z=503 $[M+H]^+$

Example 65

N-[4-(4-Bromo-1H-pyrazol-1-yl)-3-sulfamoylphenyl]-2-(3-fluorophenyl)acetamide

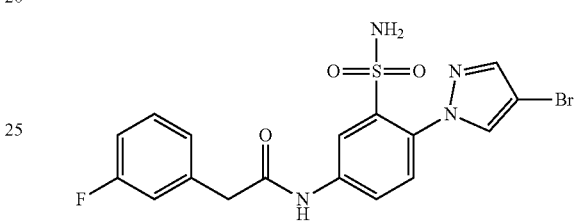

According to general procedure GP5.1, 5-amino-2-(4-bromo-1H-pyrazol-1-yl)-N-(2,4-dimethoxybenzyl)benzenesulfonamide (0.20 mmol) and (3-fluorophenyl)acetic acid (0.40 mmol) were converted to the title compound (12.3 mg, 0.0271 mmol, 14% yield, 100% purity).

LC-MS (Method A): Rt=1.12 min; MS (ESIpos): m/z=453 $[M+H]^+$

Example 66

N-[4-(4-Bromo-1H-pyrazol-1-yl)-3-sulfamoylphenyl]-2-(2-methylphenyl)acetamide

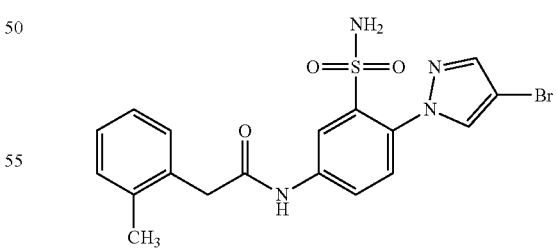

According to general procedure GP5.1, 5-amino-2-(4-bromo-1H-pyrazol-1-yl)-N-(2,4-dimethoxybenzyl)benzenesulfonamide (0.20 mmol) and (2-methylphenyl)acetic acid (0.40 mmol) were converted to the title compound (25.9 mg, 0.0576 mmol, 29% yield, 100% purity).

LC-MS (Method A): Rt=1.15 min; MS (ESIpos): m/z=449 $[M+H]^+$

Example 67

N-[4-(4-Bromo-1H-pyrazol-1-yl)-3-sulfamoylphenyl]-2-(2-chloropyridin-3-yl)-acetamide

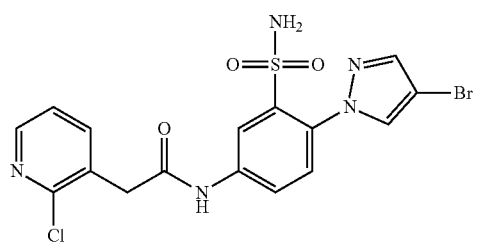 [SMILES: NS(=O)(=O)c1cc(NC(=O)Cc2cccnc2Cl)ccc1-n1cc(Br)cn1]

According to general procedure GP5.1, 5-amino-2-(4-bromo-1H-pyrazol-1-yl)-N-(2,4-dimethoxybenzyl)benzenesulfonamide (0.20 mmol) and (2-chloropyridin-3-yl)acetic acid (0.40 mmol) were converted to the title compound (13.4 mg, 0.0285 mmol, 14% yield, 79% purity).

LC-MS (Method A): Rt=0.98 min; MS (ESIpos): m/z=470 [M+H]$^+$

Example 68

N-[4-(4-Bromo-1H-pyrazol-1-yl)-3-sulfamoylphenyl]-2-(2-chloro-4-fluorophenyl)-acetamide

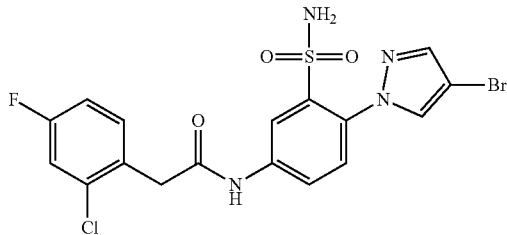 [SMILES: NS(=O)(=O)c1cc(NC(=O)Cc2ccc(F)cc2Cl)ccc1-n1cc(Br)cn1]

According to general procedure GP5.1, 5-amino-2-(4-bromo-1H-pyrazol-1-yl)-N-(2,4-dimethoxybenzyl)benzenesulfonamide (0.20 mmol) and (2-chloro-4-fluorophenyl)acetic acid (0.40 mmol) were converted to the title compound (3.0 mg, 0.00615 mmol, 3% yield, 100% purity).

LC-MS (Method A): Rt=1.17 min; MS (ESIpos): m/z=487 [M+H]$^+$

Example 69

N-[4-(4-Bromo-1H-pyrazol-1-yl)-3-sulfamoylphenyl]-2-[2-(difluoromethoxy)-phenyl]acetamide

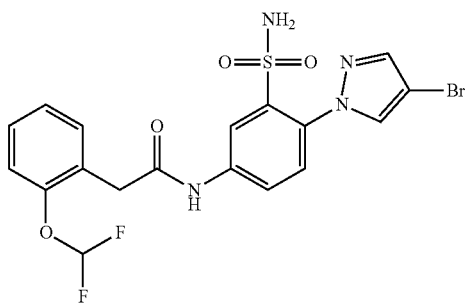 [SMILES: NS(=O)(=O)c1cc(NC(=O)Cc2ccccc2OC(F)F)ccc1-n1cc(Br)cn1]

According to general procedure GP5.1, 5-amino-2-(4-bromo-1H-pyrazol-1-yl)-N-(2,4-dimethoxybenzyl)benzenesulfonamide (0.20 mmol) and [2-(difluoromethoxy)phenyl]acetic acid (0.40 mmol) were converted to the title compound (21.5 mg, 0.0429 mmol, 21% yield, 100% purity).

LC-MS (Method A): Rt=1.15 min; MS (ESIpos): m/z=501 [M+H]$^+$

Example 70

N-[4-(4-Bromo-1H-pyrazol-1-yl)-3-sulfamoylphenyl]-2-[2-(trifluoromethoxy)-phenyl]acetamide

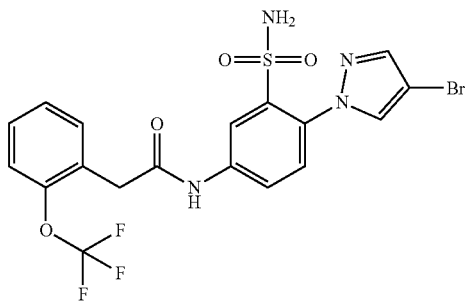 [SMILES: NS(=O)(=O)c1cc(NC(=O)Cc2ccccc2OC(F)(F)F)ccc1-n1cc(Br)cn1]

According to general procedure GP5.1, 5-amino-2-(4-bromo-1H-pyrazol-1-yl)-N-(2,4-dimethoxybenzyl)benzenesulfonamide (0.20 mmol) and [2-(trifluoromethoxy)phenyl]acetic acid (0.40 mmol) were converted to the title compound (16.8 mg, 0.0324 mmol, 16% yield, 100% purity).

LC-MS (Method A): Rt=1.22 min; MS (ESIpos): m/z=519 [M+H]$^+$

Example 71

N-[4-(4-Bromo-1H-pyrazol-1-yl)-3-sulfamoylphenyl]-2-(2-chloro-4,5-difluorophenyl)-acetamide

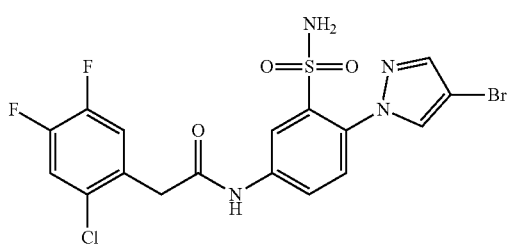 [SMILES: NS(=O)(=O)c1cc(NC(=O)Cc2cc(F)c(F)cc2Cl)ccc1-n1cc(Br)cn1]

According to general procedure GP5.1, 5-amino-2-(4-bromo-1H-pyrazol-1-yl)-N-(2,4-dimethoxybenzyl)benzenesulfonamide (0.20 mmol) and (2-chloro-4,5-difluorophenyl)acetic acid (0.40 mmol) were converted to the title compound (4.6 mg, 0.00910 mmol, 5% yield, 100% purity).

LC-MS (Method A): Rt=1.20 min; MS (ESIpos): m/z=505 [M+H]$^+$

Example 72

N-[4-(4-Bromo-1H-pyrazol-1-yl)-3-sulfamoylphenyl]-2-(3-chloropyridin-4-yl)acetamide

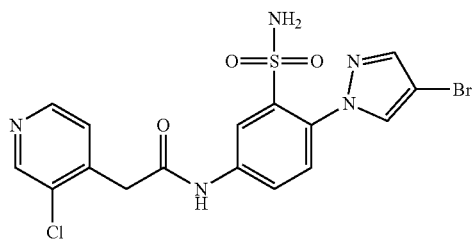 [SMILES: NS(=O)(=O)c1cc(NC(=O)Cc2ccncc2Cl)ccc1-n1cc(Br)cn1]

According to general procedure GP5.1, 5-amino-2-(4-bromo-1H-pyrazol-1-yl)-N-(2,4-dimethoxybenzyl)benzenesulfonamide (0.20 mmol) and (3-chloropyridin-4-yl)acetic acid (0.40 mmol) were converted to the title compound (5.9 mg, 0.0125 mmol, 6% yield, 92% purity).

LC-MS (Method A): Rt=0.96 min; MS (ESIpos): m/z=470 [M+H]$^+$

Example 73

N-[4-(4-Bromo-1H-pyrazol-1-yl)-3-sulfamoylphenyl]-2-[4-(difluoromethyl)-phenyl]acetamide

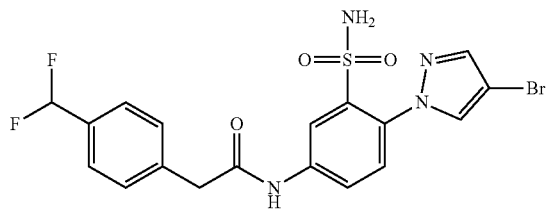 [SMILES: NS(=O)(=O)c1cc(NC(=O)Cc2ccc(C(F)F)cc2)ccc1-n1cc(Br)cn1]

According to general procedure GP5.1, 5-amino-2-(4-bromo-1H-pyrazol-1-yl)-N-(2,4-dimethoxybenzyl)benzenesulfonamide (0.20 mmol) and [4-(difluoromethyl)phenyl]acetic acid (0.40 mmol) were converted to the title compound (15.7 mg, 0.0323 mmol, 16% yield, 100% purity).

LC-MS (Method A): Rt=1.14 min; MS (ESIpos): m/z=485 [M+H]$^+$

Example 74

2-(2-Bromophenyl)-N-[4-(4-chloro-1H-pyrazol-1-yl)-3-sulfamoylphenyl]acetamide

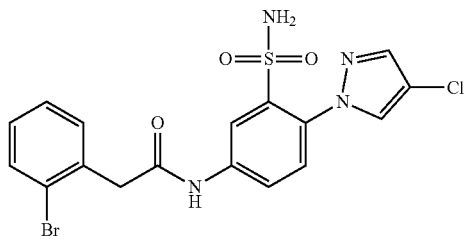 [SMILES: NS(=O)(=O)c1cc(NC(=O)Cc2ccccc2Br)ccc1-n1cc(Cl)cn1]

According to general procedure GP5.1, 5-amino-2-(4-chloro-1H-pyrazol-1-yl)-N-(2,4-dimethoxybenzyl)benzenesulfonamide (0.20 mmol) and (2-bromophenyl)acetic acid (0.40 mmol) were converted to the title compound (28.8 mg, 0.0613 mmol, 31% yield, 100% purity).

LC-MS (Method A): Rt=1.14 min; MS (ESIpos): m/z=469 [M+H]$^+$

Example 75

N-[4-(4-Chloro-1H-pyrazol-1-yl)-3-sulfamoylphenyl]-2-(2-methoxyphenyl)acetamide

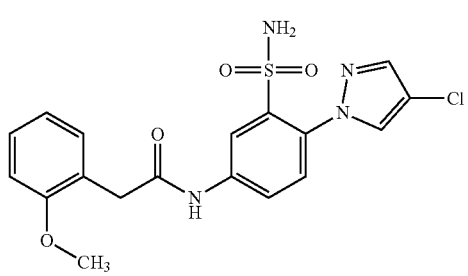 [SMILES: COc1ccccc1CC(=O)Nc1ccc(-n2cc(Cl)cn2)c(S(N)(=O)=O)c1]

According to general procedure GP5.1, 5-amino-2-(4-chloro-1H-pyrazol-1-yl)-N-(2,4-dimethoxybenzyl)benzenesulfonamide (0.20 mmol) and (2-methoxyphenyl)acetic acid (0.40 mmol) were converted to the title compound (2.7 mg, 0.0642 mmol, 3% yield, 100% purity).

LC-MS (Method A): Rt=1.09 min; MS (ESIpos): m/z=421 [M+H]$^+$

Example 76

2-(4-Chlorophenyl)-N-[4-(4-chloro-1H-pyrazol-1-yl)-3-sulfamoylphenyl]acetamide

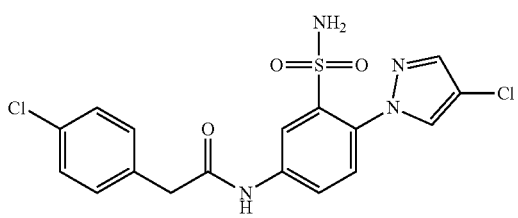 [SMILES: NS(=O)(=O)c1cc(NC(=O)Cc2ccc(Cl)cc2)ccc1-n1cc(Cl)cn1]

According to general procedure GP5.1, 5-amino-2-(4-chloro-1H-pyrazol-1-yl)-N-(2,4-dimethoxybenzyl)benzenesulfonamide (0.20 mmol) and (4-chlorophenyl)acetic acid (0.40 mmol) were converted to the title compound (5.8 mg, 0.0136 mmol, 7% yield, 100% purity).

LC-MS (Method A): Rt=1.17 min; MS (ESIpos): m/z=425 [M+H]$^+$

Example 77

2-(2-Chloro-6-fluorophenyl)-N-[4-(4-chloro-1H-pyrazol-1-yl)-3-sulfamoylphenyl]-acetamide

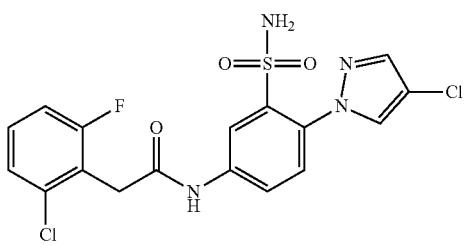 [SMILES: NS(=O)(=O)c1cc(NC(=O)Cc2c(F)cccc2Cl)ccc1-n1cc(Cl)cn1]

According to general procedure GP5.1, 5-amino-2-(4-chloro-1H-pyrazol-1-yl)-N-(2,4-dimethoxybenzyl)benzenesulfonamide (0.20 mmol) and (2-chloro-6-fluorophenyl)acetic acid (0.40 mmol) were converted to the title compound (33.9 mg, 0.0765 mmol, 38% yield, 100% purity).

LC-MS (Method A): Rt=1.14 min; MS (ESIpos): m/z=443 [M+H]$^+$

Example 78

N-[4-(4-Chloro-1H-pyrazol-1-yl)-3-sulfamoylphenyl]-2-(2-nitrophenyl)acetamide

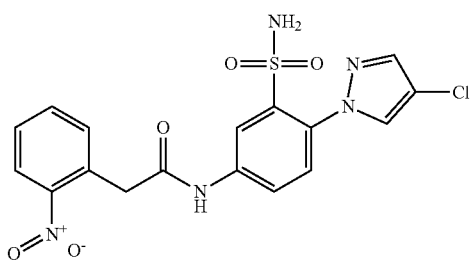

According to general procedure GP5.1, 5-amino-2-(4-chloro-1H-pyrazol-1-yl)-N-(2,4-dimethoxybenzyl)benzenesulfonamide (0.20 mmol) and (2-nitrophenyl)acetic acid (0.40 mmol) were converted to the title compound (8.3 mg, 0.0190 mmol, 10% yield, 100% purity).

LC-MS (Method A): Rt=1.07 min; MS (ESIpos): m/z=436 [M+H]$^+$

Example 79

N-[4-(4-Chloro-1H-pyrazol-1-yl)-3-sulfamoylphenyl]-2-(2,4-dichlorophenyl)acetamide

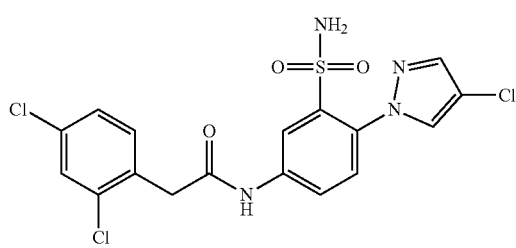 [SMILES: NS(=O)(=O)c1cc(NC(=O)Cc2ccc(Cl)cc2Cl)ccc1-n1cc(Cl)cn1]

According to general procedure GP5.1, 5-amino-2-(4-chloro-1H-pyrazol-1-yl)-N-(2,4-dimethoxybenzyl)benzenesulfonamide (0.20 mmol) and (2,4-dichlorophenyl)acetic acid (0.40 mmol) were converted to the title compound (4.2 mg, 0.00914 mmol, 5% yield, 100% purity).

LC-MS (Method A): Rt=1.23 min; MS (ESIpos): m/z=459 [M+H]$^+$

Example 80

N-[4-(4-Chloro-1H-pyrazol-1-yl)-3-sulfamoylphenyl]-2-(2,6-dichlorophenyl)acetamide

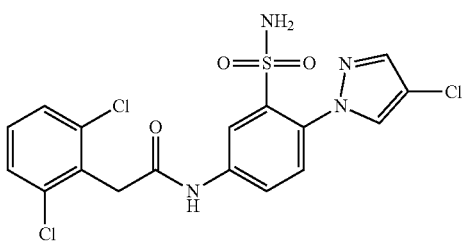 [SMILES: NS(=O)(=O)c1cc(NC(=O)Cc2c(Cl)cccc2Cl)ccc1-n1cc(Cl)cn1]

According to general procedure GP5.1, 5-amino-2-(4-chloro-1H-pyrazol-1-yl)-N-(2,4-dimethoxybenzyl)benzenesulfonamide (0.20 mmol) and (2,6-dichlorophenyl)acetic acid (0.40 mmol) were converted to the title compound (43.4 mg, 0.0944 mmol, 47% yield, 100% purity).

LC-MS (Method A): Rt=1.18 min; MS (ESIpos): m/z=459 [M+H]$^+$

Example 81

N-[4-(4-Chloro-1H-pyrazol-1-yl)-3-sulfamoylphenyl]-2-(3,4-difluorophenyl)acetamide

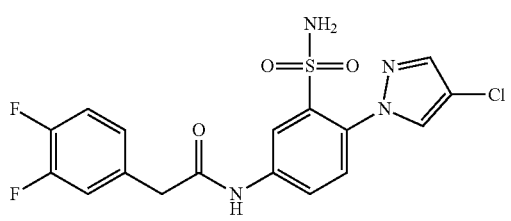 [SMILES: NS(=O)(=O)c1cc(NC(=O)Cc2ccc(F)c(F)c2)ccc1-n1cc(Cl)cn1]

According to general procedure GP5.1, 5-amino-2-(4-chloro-1H-pyrazol-1-yl)-N-(2,4-dimethoxybenzyl)benzenesulfonamide (0.20 mmol) and (3,4-difluorophenyl)acetic acid (0.40 mmol) were converted to the title compound (7.1 mg, 0.0166 mmol, 8% yield, 100% purity).

LC-MS (Method A): Rt=1.13 min; MS (ESIpos): m/z=427 [M+H]$^+$

Example 82

2-(3-Chlorophenyl)-N-[4-(4-chloro-1H-pyrazol-1-yl)-3-sulfamoylphenyl]acetamide

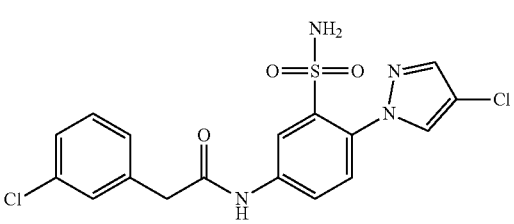 [SMILES: NS(=O)(=O)c1cc(NC(=O)Cc2cccc(Cl)c2)ccc1-n1cc(Cl)cn1]

According to general procedure GP5.1, 5-amino-2-(4-chloro-1H-pyrazol-1-yl)-N-(2,4-dimethoxybenzyl)benzenesulfonamide (0.20 mmol) and (3-chlorophenyl)acetic acid (0.40 mmol) were converted to the title compound (11.4 mg, 0.0268 mmol, 13% yield, 100% purity).

LC-MS (Method A): Rt=1.17 min, MS (ESIpos): m/z=425 [M+H]$^+$

Example 83

N-[4-(4-Chloro-1H-pyrazol-1-yl)-3-sulfamoylphenyl]-2-(3,5-difluorophenyl)acetamide

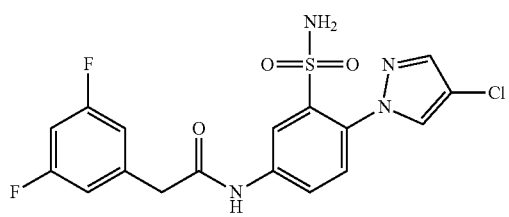

According to general procedure GP5.1, 5-amino-2-(4-chloro-1H-pyrazol-1-yl)-N-(2,4-dimethoxybenzyl)benzenesulfonamide (0.20 mmol) and (3,5-difluorophenyl)acetic acid (0.40 mmol) were converted to the title compound (6.3 mg, 0.0148 mmol, 7% yield, 100% purity).

LC-MS (Method A): Rt=1.14 min; MS (ESIpos): m/z=427 [M+H]$^+$

Example 84

N-[4-(4-Chloro-1H-pyrazol-1-yl)-3-sulfamoylphenyl]-2-(4-fluorophenyl)acetamide

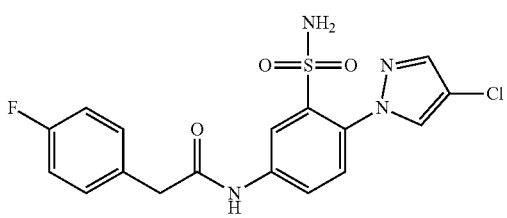 [SMILES: NS(=O)(=O)c1cc(NC(=O)Cc2ccc(F)cc2)ccc1-n1cc(Cl)cn1]

According to general procedure GP5.1, 5-amino-2-(4-chloro-1H-pyrazol-1-yl)-N-(2,4-dimethoxybenzyl)benzenesulfonamide (0.20 mmol) and (4-fluorophenyl)acetic acid (0.40 mmol) were converted to the title compound (8.2 mg, 0.0201 mmol, 10% yield, 100% purity).

LC-MS (Method A): Rt=1.10 min; MS (ESIpos): m/z=409 [M+H]$^+$

Example 85

N-[4-(4-Chloro-1H-pyrazol-1-yl)-3-sulfamoylphenyl]-2-(2-hydroxyphenyl)acetamide

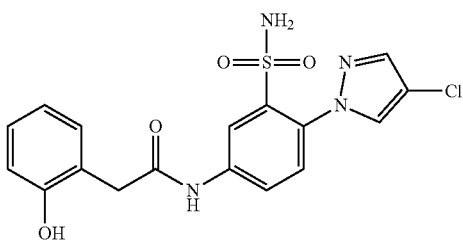 [SMILES: NS(=O)(=O)c1cc(NC(=O)Cc2ccccc2O)ccc1-n1cc(Cl)cn1]

According to general procedure GP5.1, 5-amino-2-(4-chloro-1H-pyrazol-1-yl)-N-(2,4-dimethoxybenzyl)benzenesulfonamide (0.20 mmol) and (2-hydroxyphenyl)acetic acid (0.40 mmol) were converted to the title compound (12.5 mg, 0.0307 mmol, 15% yield, 100% purity).

LC-MS (Method A): Rt=1.00 min; MS (ESIpos): m/z=407 [M+H]$^+$

Example 86

N-[4-(4-Chloro-1H-pyrazol-1-yl)-3-sulfamoylphenyl]-2-(4-hydroxyphenyl)acetamide

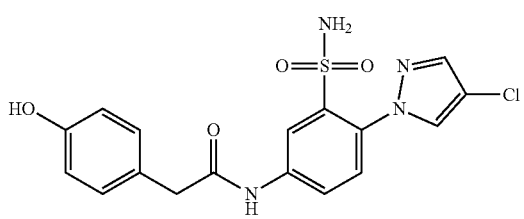 [SMILES: NS(=O)(=O)c1cc(NC(=O)Cc2ccc(O)cc2)ccc1-n1cc(Cl)cn1]

According to general procedure GP5.1, 5-amino-2-(4-chloro-1H-pyrazol-1-yl)-N-(2,4-dimethoxybenzyl)benzenesulfonamide (0.20 mmol) and (4-hydroxyphenyl)acetic acid (0.40 mmol) were converted to the title compound (5.5 mg, 0.0135 mmol, 7% yield, 100% purity).

LC-MS (Method A): Rt=0.93 min; MS (ESIpos): m/z=407 [M+H]$^+$

Example 87

N-[4-(4-Chloro-1H-pyrazol-1-yl)-3-sulfamoylphenyl]-2-(2,3-difluorophenyl)acetamide

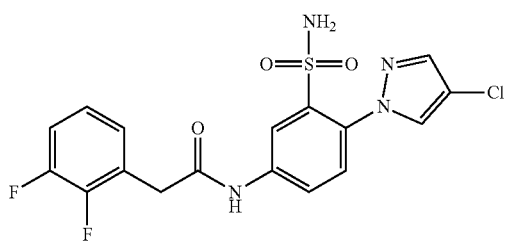 [SMILES: NS(=O)(=O)c1cc(NC(=O)Cc2cccc(F)c2F)ccc1-n1cc(Cl)cn1]

According to general procedure GP5.1, 5-amino-2-(4-chloro-1H-pyrazol-1-yl)-N-(2,4-dimethoxybenzyl)benzenesulfonamide (0.20 mmol) and (2,3-difluorophenyl)acetic acid (0.40 mmol) were converted the title compound (18.4 mg, 0.0431 mmol, 22% yield, 100% purity).

LC-MS (Method A): Rt=1.12 min; MS (ESIpos): m/z=427 [M+H]$^+$

Example 88

2-(2-Chloro-4-fluorophenyl)-N-[4-(4-chloro-1H-pyrazol-1-yl)-3-sulfamoyl-phenyl]acetamide

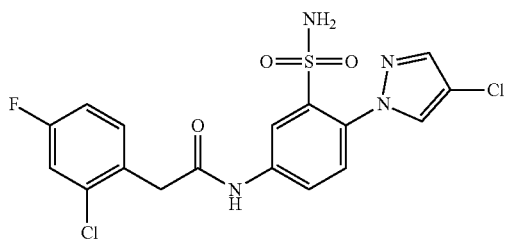 [SMILES: NS(=O)(=O)c1cc(NC(=O)Cc2ccc(F)cc2Cl)ccc1-n1cc(Cl)cn1]

According to general procedure GP5.1, 5-amino-2-(4-chloro-1H-pyrazol-1-yl)-N-(2,4-dimethoxybenzyl)benzenesulfonamide (0.20 mmol) and (2-chloro-4-fluorophenyl)acetic acid (0.40 mmol) were converted to the title compound (14.5 mg, 0.0327 mmol, 16% yield, 100% purity).

LC-MS (Method A): Rt=1.16 min; MS (ESIpos): m/z=443 [M+H]$^+$

Example 89

N-[4-(4-Chloro-1H-pyrazol-1-yl)-3-sulfamoylphenyl]-2-(2-chloropyridin-3-yl)-acetamide

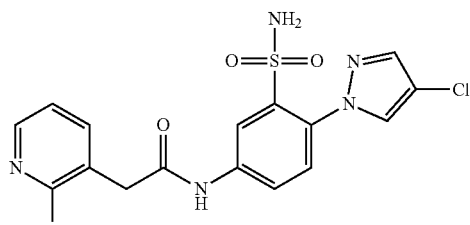

According to general procedure GP5.1, 5-amino-2-(4-chloro-1H-pyrazol-1-yl)-N-(2,4-dimethoxybenzyl)benzenesulfonamide (0.20 mmol) and (2-chloropyridin-3-yl)acetic acid (0.40 mmol) were converted to the title compound (21.3 mg, 0.0500 mmol, 25% yield, 81% purity).

LC-MS (Method A): Rt=0.96 min, MS (ESIpos): m/z=426 [M+H]$^+$

Example 90

N-[4-(4-Chloro-1H-pyrazol-1-yl)-3-sulfamoylphenyl]-2-[2-chloro-3-(trifluoromethyl)-phenyl]acetamide

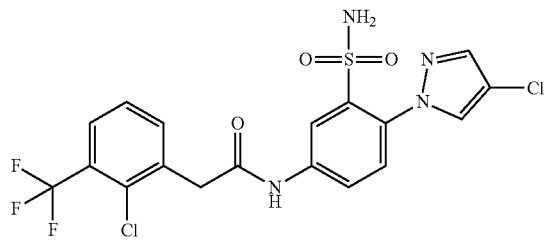 [SMILES: NS(=O)(=O)c1cc(NC(=O)Cc2cccc(C(F)(F)F)c2Cl)ccc1-n1cc(Cl)cn1]

According to general procedure GP5.1, 5-amino-2-(4-chloro-1H-pyrazol-1-yl)-N-(2,4-dimethoxybenzyl)benzenesulfonamide (0.20 mmol) and [2-chloro-3-(trifluoromethyl)phenyl]acetic acid (0.40 mmol) were converted to the title compound (30.4 mg, 0.0616 mmol, 31% yield, 100% purity).

LC-MS (Method A): Rt=1.24 min; MS (ESIpos): m/z=493 [M+H]$^+$

Example 91

N-[4-(4-Chloro-1H-pyrazol-1-yl)-3-sulfamoylphenyl]-2-[2-(difluoromethoxy)-phenyl]acetamide

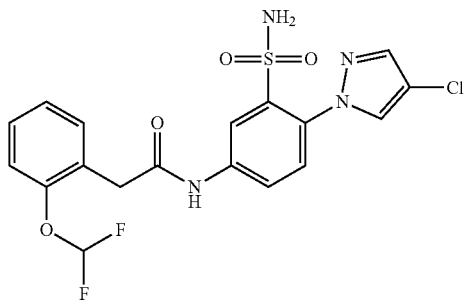 [SMILES: NS(=O)(=O)c1cc(NC(=O)Cc2ccccc2OC(F)F)ccc1-n1cc(Cl)cn1]

According to general procedure GP5.1, 5-amino-2-(4-chloro-1H-pyrazol-1-yl)-N-(2,4-dimethoxybenzyl)benzenesulfonamide (0.20 mmol) and [2-(difluoromethoxy)phenyl]acetic acid (0.40 mmol) were converted to the title compound (20.7 mg, 0.0453 mmol, 23% yield, 100% purity).

LC-MS (Method A): Rt=1.14 min; MS (ESIpos): m/z=457 [M+H]$^+$

Example 92

N-[4-(4-Chloro-1H-pyrazol-1-yl)-3-sulfamoylphenyl]-2-[2-(trifluoromethoxy)-phenyl]acetamide

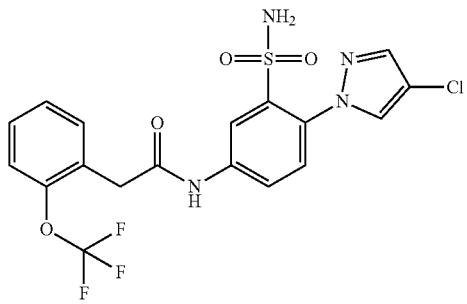 [SMILES: NS(=O)(=O)c1cc(NC(=O)Cc2ccccc2OC(F)(F)F)ccc1-n1cc(Cl)cn1]

According to general procedure GP5.1, 5-amino-2-(4-chloro-1H-pyrazol-1-yl)-N-(2,4-dimethoxybenzyl)benzenesulfonamide (0.20 mmol) and [2-(trifluoromethoxy)phenyl]acetic acid (0.40 mmol) were converted to the title compound (14.1 mg, 0.0297 mmol, 15% yield, 100% purity).

LC-MS (Method A): Rt=1.21 min; MS (ESIpos): m/z=475 [M+H]$^+$

Example 93

2-(2-Chloro-4,5-difluorophenyl)-N-[4-(4-chloro-1H-pyrazol-1-yl)-3-sulfamoylphenyl]-acetamide

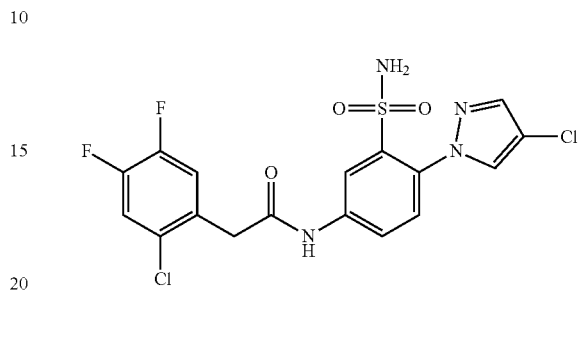

According to general procedure GP5.1, 5-amino-2-(4-chloro-1H-pyrazol-1-yl)-N-(2,4-dimethoxybenzyl)benzenesulfonamide (0.20 mmol) and (2-chloro-4,5-difluorophenyl)acetic acid (0.40 mmol) were converted to the title compound (9.8 mg, 0.0212 mmol, 11% yield, 100% purity).

LC-MS (Method A): Rt=1.19 min; MS (ESIpos): m/z=461 [M+H]$^+$

Example 94

2-(2-Chloro-4-methoxyphenyl)-N-[4-(4-chloro-1H-pyrazol-1-yl)-3-sulfamoylphenyl]-acetamide

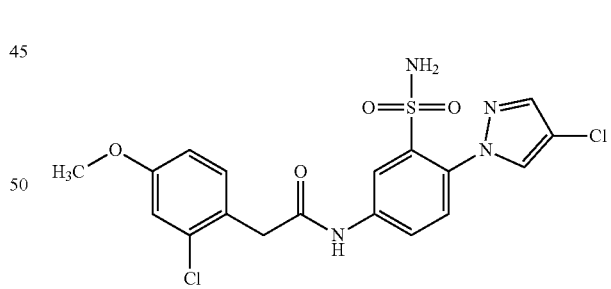

According to general procedure GP5.1, 5-amino-2-(4-chloro-1H-pyrazol-1-yl)-N-(2,4-dimethoxybenzyl)benzenesulfonamide (0.20 mmol) and (2-chloro-4-methoxyphenyl)acetic acid (0.40 mmol) were converted to the title compound (16.4 mg, 0.0360 mmol, 18% yield, 100% purity).

LC-MS (Method A): Rt=1.14 min; MS (ESIpos): m/z=455 [M+H]$^+$

Example 95

2-(2-Chloro-6-fluoro-3-methylphenyl)-N-[4-(4-chloro-1H-pyrazol-1-yl)-3-sulfamoyl-phenyl]acetamide

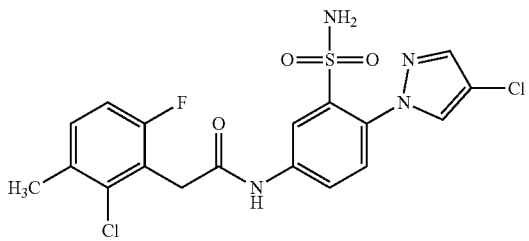 [SMILES: Cc1ccc(F)c(CC(=O)Nc2ccc(-n3cc(Cl)cn3)c(S(N)(=O)=O)c2)c1Cl]

According to general procedure GP5.1, 5-amino-2-(4-chloro-1H-pyrazol-1-yl)-N-(2,4-dimethoxybenzyl)benzenesulfonamide (0.20 mmol) and (2-chloro-6-fluoro-3-methylphenyl)acetic acid (0.40 mmol) were converted to the title compound (18.3 mg, 0.0400 mmol, 20% yield, 100% purity).

LC-MS (Method A): Rt=1.21 min; MS (ESIpos): m/z=457 [M+H]$^+$

Example 96

2-(2-Chloro-3,6-difluorophenyl)-N-[4-(4-chloro-1H-pyrazol-1-yl)-3-sulfamoylphenyl]-acetamide

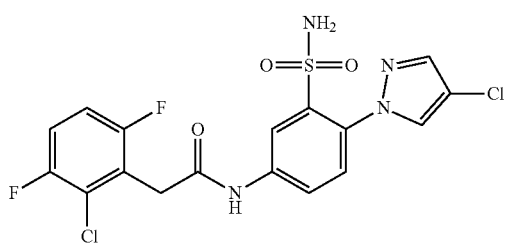 [SMILES: NS(=O)(=O)c1cc(NC(=O)Cc2c(F)ccc(F)c2Cl)ccc1-n1cc(Cl)cn1]

According to general procedure GP5.1, 5-amino-2-(4-chloro-1H-pyrazol-1-yl)-N-(2,4-dimethoxybenzyl)benzenesulfonamide (0.20 mmol) and (2-chloro-3,6-difluorophenyl)acetic acid (0.40 mmol) were converted to the title compound (20.1 mg, 0.0436 mmol, 22% yield, 100% purity).

LC-MS (Method A): Rt=1.16 min; MS (ESIpos): m/z=461 [M+H]$^+$

Example 97

2-(2-Chloro-5-methylphenyl)-N-[4-(4-chloro-1H-pyrazol-1-yl)-3-sulfamoylphenyl]-acetamide

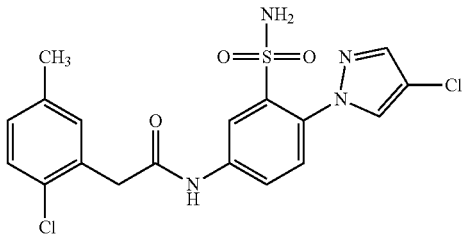 [SMILES: NS(=O)(=O)c1cc(NC(=O)Cc2cc(F)ccc2Cl)ccc1-n1cc(Cl)cn1]

According to general procedure GP5.1, 5-amino-2-(4-chloro-1H-pyrazol-1-yl)-N-(2,4-dimethoxybenzyl)benzenesulfonamide (0.20 mmol) and (2-chloro-5-methylphenyl)acetic acid (0.40 mmol) were converted to the title compound (29.6 mg, 0.0674 mmol, 34% yield, 100% purity).

LC-MS (Method A): Rt=1.20 min; MS (ESIpos): m/z=439 [M+H]$^+$

Example 98

2-(2-Chloro-5-fluorophenyl)-N-[4-(4-chloro-1H-pyrazol-1-yl)-3-sulfamoylphenyl]-acetamide

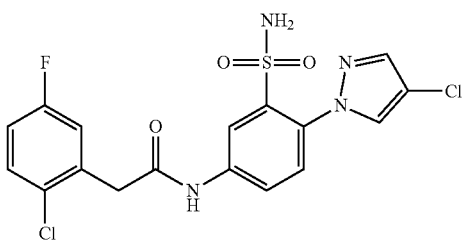 [SMILES: NS(=O)(=O)c1cc(NC(=O)Cc2cc(Cl)ccc2Cl)ccc1-n1cc(Cl)cn1]

According to general procedure GP5.1, 5-amino-2-(4-chloro-1H-pyrazol-1-yl)-N-(2,4-dimethoxybenzyl)benzenesulfonamide (0.20 mmol) and (2-chloro-5-fluorophenyl)acetic acid (0.40 mmol) were converted to the title compound (17.2 mg, 0.0388 mmol, 19% yield, 100% purity).

LC-MS (Method A): Rt=1.15 min; MS (ESIpos): m/z=443 [M+H]$^+$

Example 99

N-[4-(4-Chloro-1H-pyrazol-1-yl)-3-sulfamoylphenyl]-2-(2,5-dichlorophenyl)acetamide

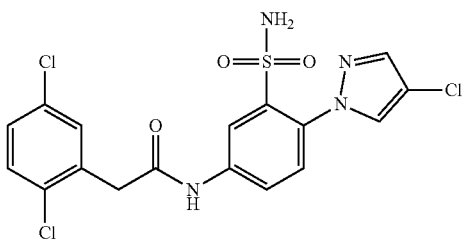

According to general procedure GP5.1, 5-amino-2-(4-chloro-1H-pyrazol-1-yl)-N-(2,4-dimethoxybenzyl)benzenesulfonamide (0.20 mmol) and (2,5-dichlorophenyl)acetic acid (0.40 mmol) were converted to the title compound (26.1 mg, 0.0568 mmol, 28% yield, 100% purity).

LC-MS (Method A): Rt=1.22 min; MS (ESIpos): m/z=459 [M+H]+

Example 100

N-[4-(4-Chloro-1H-pyrazol-1-yl)-3-sulfamoylphenyl]-2-(2-isopropylphenyl)acetamide

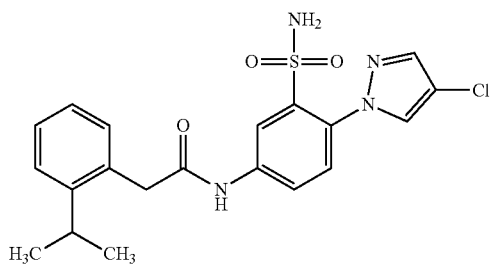 [SMILES: CC(C)c1ccccc1CC(=O)Nc1ccc(-n2cc(Cl)cn2)c(S(N)(=O)=O)c1]

According to general procedure GP5.1, 5-amino-2-(4-chloro-1H-pyrazol-1-yl)-N-(2,4-dimethoxybenzyl)benzenesulfonamide (0.20 mmol) and (2-isopropylphenyl)acetic acid (0.40 mmol) were converted to the title compound (24.2 mg, 0.0559 mmol, 28% yield, 100% purity).

LC-MS (Method A): Rt=1.25 min; MS (ESIpos): m/z=433 [M+H]+

Example 101

2-(2-Chloro-5-methoxyphenyl)-N-[4-(4-chloro-1H-pyrazol-1-yl)-3-sulfamoylphenyl]-acetamide

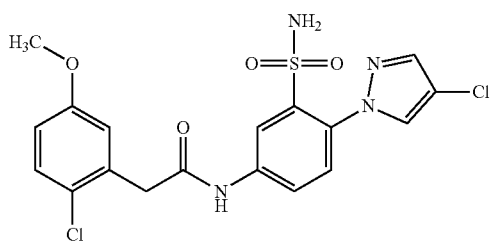 [SMILES: COc1ccc(Cl)c(CC(=O)Nc2ccc(-n3cc(Cl)cn3)c(S(N)(=O)=O)c2)c1]

According to general procedure GP5.1, 5-amino-2-(4-chloro-1H-pyrazol-1-yl)-N-(2,4-dimethoxybenzyl)benzenesulfonamide (0.20 mmol) and (2-chloro-5-methoxyphenyl)acetic acid (0.40 mmol) were converted to the title compound (8.0 mg, 0.0176 mmol, 9% yield, 100% purity).

LC-MS (Method A): Rt=1.15 min; MS (ESIpos): m/z=455 [M+H]+

Example 102

2-(2-Chloro-4,6-difluorophenyl)-N-[4-(4-chloro-1H-pyrazol-1-yl)-3-sulfamoylphenyl]-acetamide

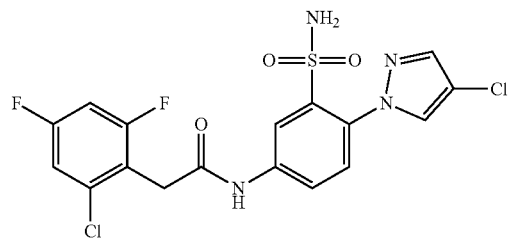 [SMILES: NS(=O)(=O)c1cc(NC(=O)Cc2c(F)cc(F)cc2Cl)ccc1-n1cc(Cl)cn1]

According to general procedure GP5.1, 5-amino-2-(4-chloro-1H-pyrazol-1-yl)-N-(2,4-dimethoxybenzyl)benzenesulfonamide (0.20 mmol) and (2-chloro-4,6-difluorophenyl)acetic acid (0.40 mmol) were converted to the title compound (25.8 mg, 0.0559 mmol, 28% yield, 92% purity).

LC-MS (Method A): Rt=1.18 min; MS (ESIpos): m/z=461 [M+H]+

Example 103

N-[4-(4-Chloro-1H-pyrazol-1-yl)-3-sulfamoylphenyl]-2-[2-chloro-6-(trifluoromethyl)-phenyl]acetamide

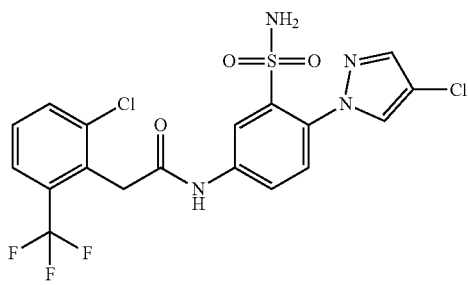 [SMILES: NS(=O)(=O)c1cc(NC(=O)Cc2c(Cl)cccc2C(F)(F)F)ccc1-n1cc(Cl)cn1]

According to general procedure GP5.1, 5-amino-2-(4-chloro-1H-pyrazol-1-yl)-N-(2,4-dimethoxybenzyl)benzenesulfonamide (0.20 mmol) and [2-chloro-6-(trifluoromethyl)phenyl]acetic acid (0.40 mmol) were converted to the title compound (26.7 mg, 0.0541 mmol, 27% yield, 100% purity).

LC-MS (Method A): Rt=1.22 min; MS (ESIpos): m/z=493 [M+H]+

Example 104

2-(5-Bromo-4-fluoro-2-methylphenyl)-N-[4-(4-chloro-1H-pyrazol-1-yl)-3-sulfamoyl-phenyl]acetamide

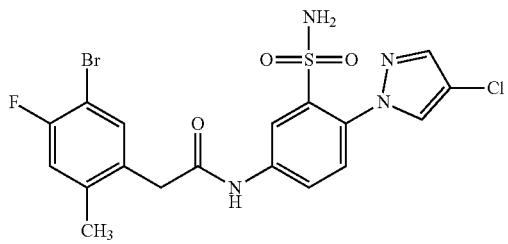 [SMILES: Cc1cc(F)c(Br)cc1CC(=O)Nc1ccc(-n2cc(Cl)cn2)c(S(N)(=O)=O)c1]

According to general procedure GP5.1, 5-amino-2-(4-chloro-1H-pyrazol-1-yl)-N-(2,4-dimethoxybenzyl)benzenesulfonamide (0.20 mmol) and (5-bromo-4-fluoro-2-methylphenyl)acetic acid (0.40 mmol) were converted to the title compound (11.2 mg, 0.0223 mmol, 11% yield, 83% purity).

LC-MS (Method A): Rt=1.24 min; MS (ESIpos): m/z=501 [M+H]$^+$

Example 105

2-(2-Chloro-6-methoxyphenyl)-N-[4-(4-chloro-1H-pyrazol-1-yl)-3-sulfamoyl-phenyl]acetamide

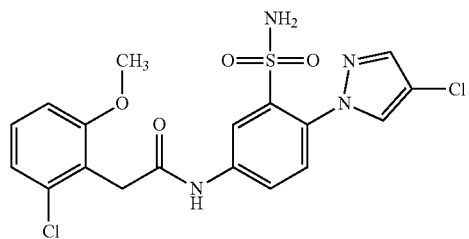 [SMILES: COc1cccc(Cl)c1CC(=O)Nc1ccc(-n2cc(Cl)cn2)c(S(N)(=O)=O)c1]

According to general procedure GP5.1, 5-amino-2-(4-chloro-1H-pyrazol-1-yl)-N-(2,4-dimethoxybenzyl)benzenesulfonamide (0.20 mmol) and (2-chloro-6-methoxyphenyl)acetic acid (0.40 mmol) were converted to the title compound (23.6 mg, 0.0518 mmol, 26% yield, 100% purity).

LC-MS (Method A): Rt=1.16 min; MS (ESIpos): m/z=455 [M+H]$^+$

Example 106

N-[4-(4-Chloro-1H-pyrazol-1-yl)-3-sulfamoylphenyl]-2-(2,6-difluorophenyl)-propanamide

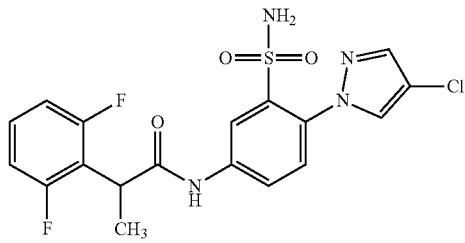 [SMILES: CC(C(=O)Nc1ccc(-n2cc(Cl)cn2)c(S(N)(=O)=O)c1)c1c(F)cccc1F]

According to general procedure GP5.1, 5-amino-2-(4-chloro-1H-pyrazol-1-yl)-N-(2,4-dimethoxybenzyl)benzenesulfonamide (0.20 mmol) and 2-(2,6-difluorophenyl)propanoic acid (0.40 mmol) were converted to the title compound (21.1 mg, 0.0479 mmol, 24% yield, 100% purity).

LC-MS (Method A): Rt=1.17 min; MS (ESIpos): m/z=441 [M+H]$^+$

Example 107

N-[4-(4-Chloro-1H-pyrazol-1-yl)-3-sulfamoylphenyl]-2-[4-(difluoromethyl)-phenyl]acetamide

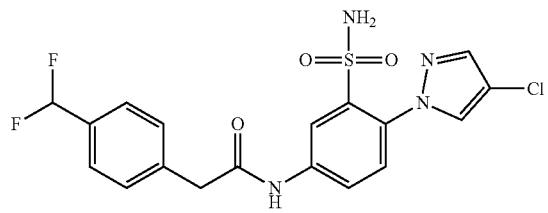 [SMILES: NS(=O)(=O)c1cc(NC(=O)Cc2ccc(C(F)F)cc2)ccc1-n1cc(Cl)cn1]

According to general procedure GP5.1, 5-amino-2-(4-chloro-1H-pyrazol-1-yl)-N-(2,4-dimethoxybenzyl)benzenesulfonamide (0.20 mmol) and [4-(difluoromethyl)phenyl]acetic acid (0.40 mmol) were converted to the title compound (20.0 mg, 0.0454 mmol, 23% yield, 100% purity).

LC-MS (Method A): Rt=1.13 min; MS (ESIpos): m/z=441 [M+H]$^+$

Example 108

2-(4-Chlorophenyl)-N-{3-sulfamoyl-4-[4-(trifluoromethyl)-1H-pyrazol-1-yl]phenyl}-acetamide

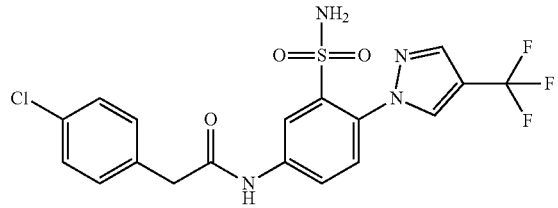 [SMILES: NS(=O)(=O)c1cc(NC(=O)Cc2ccc(Cl)cc2)ccc1-n1cc(C(F)(F)F)cn1]

According to general procedure GP5.1, 5-amino-N-(2,4-dimethoxybenzyl)-2-[4-(trifluoromethyl)-1H-pyrazol-1-yl]benzenesulfonamide (0.20 mmol) and (4-chlorophenyl)acetic acid (0.40 mmol) were converted to the title compound (18.5 mg, 0.0403 mmol, 23% yield, 100% purity).

LC-MS (Method A): Rt=1.22 min; MS (ESIpos): m/z=459 [M+H]+

Example 109

2-(2-Chlorophenyl)-N-[4-(4-chloro-1H-pyrazol-1-yl)-3-sulfamoylphenyl]-2,2-difluoroacetamide

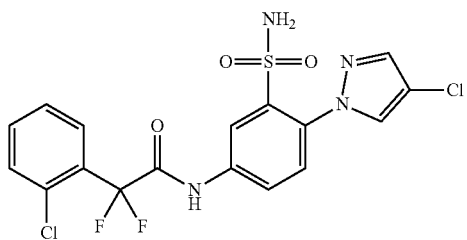 [SMILES: NS(=O)(=O)c1cc(NC(=O)C(F)(F)c2ccccc2Cl)ccc1-n1cc(Cl)cn1]

According to general procedure GP5.1, 5-amino-2-(4-chloro-1H-pyrazol-1-yl)-N-(2,4-dimethoxybenzyl)benzenesulfonamide (0.20 mmol) and (2-chlorophenyl)(difluoro)acetic acid (0.40 mmol) were converted to the title compound (3.4 mg, 0.00737 mmol, 4% yield, 81% purity).

LC-MS (Method A): Rt=1.20 min; MS (ESIpos): m/z=461 [M+H]+

Example 110

2-(2-Nitrophenyl)-N-{3-sulfamoyl-4-[4-(trifluoromethyl)-1H-pyrazol-1-yl]phenyl}-acetamide

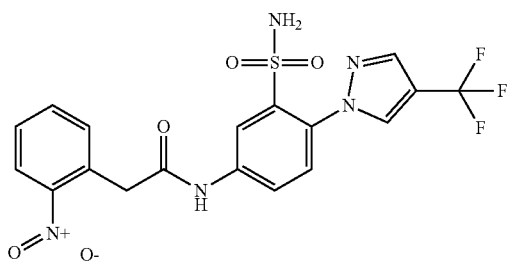

According to general procedure GP5.1, 5-amino-N-(2,4-dimethoxybenzyl)-2-[4-(trifluoromethyl)-1H-pyrazol-1-yl]benzenesulfonamide (0.20 mmol) and (2-nitrophenyl)acetic acid (0.40 mmol) were converted to the title compound (14.0 mg, 0.0298 mmol, 15% yield, 91% purity).

LC-MS (Method A): Rt=1.13 min; MS (ESIpos): m/z=470 [M+H]+

Example 111

2-(2,4-Dichlorophenyl)-N-{3-sulfamoyl-4-[4-(trifluoromethyl)-1H-pyrazol-1-yl]phenyl}-acetamide

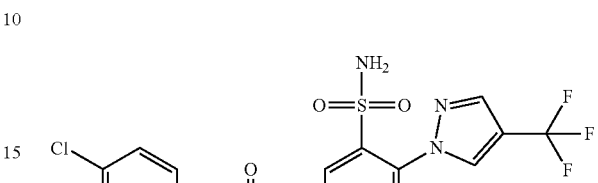

According to general procedure GP5.1, 5-amino-N-(2,4-dimethoxybenzyl)-2-[4-(trifluoromethyl)-1H-pyrazol-1-yl]benzenesulfonamide (0.20 mmol) and (2,4-dichlorophenyl)acetic acid (0.40 mmol) were converted to the title compound (16.4 mg, 0.0332 mmol, 17% yield, 100% purity).

LC-MS (Method A): Rt=1.28 min; MS (ESIpos): m/z=493 [M+H]+

Example 112

2-(2-Methoxyphenyl)-N-{3-sulfamoyl-4-[4-(trifluoromethyl)-1H-pyrazol-1-yl]phenyl}-acetamide

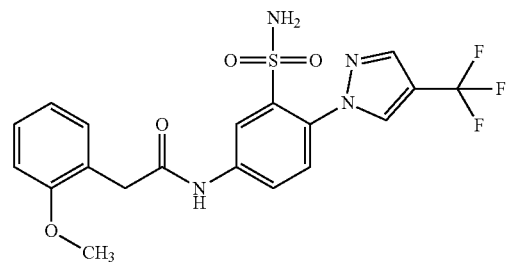 [SMILES: COc1ccccc1CC(=O)Nc1ccc(-n2cc(C(F)(F)F)cn2)c(S(N)(=O)=O)c1]

According to general procedure GP5.1, 5-amino-N-(2,4-dimethoxybenzyl)-2-[4-(trifluoromethyl)-1H-pyrazol-1-yl]benzenesulfonamide (0.20 mmol) and (2-methoxyphenyl)acetic acid (0.40 mmol) were converted to the title compound (13.8 mg, 0.0304 mmol, 15% yield, 100% purity).

LC-MS (Method A): Rt=1.15 min; MS (ESIpos): m/z=455 [M+H]+

Example 113

2-(2-Chloro-6-fluorophenyl)-N-{3-sulfamoyl-4-[4-(trifluoromethyl)-1H-pyrazol-1-yl]phenyl}acetamide

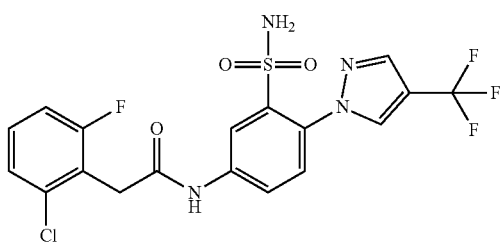 [SMILES: NS(=O)(=O)c1cc(NC(=O)Cc2c(F)cccc2Cl)ccc1-n1cc(C(F)(F)F)cn1]

According to general procedure GP5.1, 5-amino-N-(2,4-dimethoxybenzyl)-2-[4-(trifluoromethyl)-1H-pyrazol-1-yl]benzenesulfonamide (0.20 mmol) and (2-chloro-6-fluorophenyl)acetic acid (0.40 mmol) were converted to the title compound (10.0 mg, 0.0210 mmol, 10% yield, 100% purity).

LC-MS (Method A): Rt=1.20 min; MS (ESIpos): m/z=477 [M+H]$^+$

Example 114

2-(3-Fluorophenyl)-N-{3-sulfamoyl-4-[4-(trifluoromethyl)-1H-pyrazol-1-yl]phenyl}-acetamide

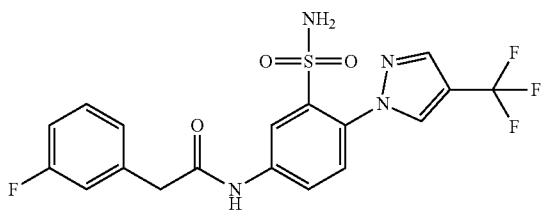

According to general procedure GP5.1, 5-amino-N-(2,4-dimethoxybenzyl)-2-[4-(trifluoromethyl)-1H-pyrazol-1-yl]benzenesulfonamide (0.20 mmol) and (3-fluorophenyl)acetic acid (0.40 mmol) were converted to the title compound (13.5 mg, 0.0305 mmol, 15% yield, 100% purity).

LC-MS (Method A): Rt=1.16 min; MS (ESIpos): m/z=443 [M+H]$^+$

Example 115

2-(3,5-Difluorophenyl)-N-{3-sulfamoyl-4-[4-(trifluoromethyl)-1H-pyrazol-1-yl]phenyl}-acetamide

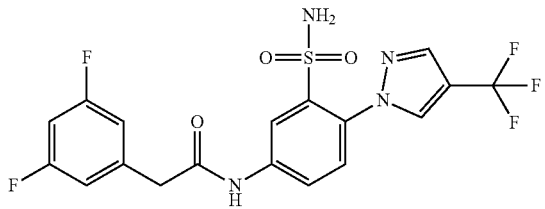 [SMILES: NS(=O)(=O)c1cc(NC(=O)Cc2cc(F)cc(F)c2)ccc1-n1cc(C(F)(F)F)cn1]

According to general procedure GP5.1, 5-amino-N-(2,4-dimethoxybenzyl)-2-[4-(trifluoromethyl)-1H-pyrazol-1-yl]benzenesulfonamide (0.20 mmol) and (3,5-difluorophenyl)acetic acid (0.40 mmol) were converted to the title compound (16.4 mg, 0.0356 mmol, 18% yield, 100% purity).

LC-MS (Method A): Rt=1.19 min; MS (ESIpos): m/z=461 [M+H]$^+$

Example 116

2-(2,6-Dichlorophenyl)-N-{3-sulfamoyl-4-[4-(trifluoromethyl)-1H-pyrazol-1-yl]phenyl}-acetamide

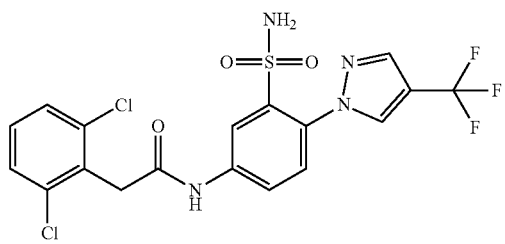 [SMILES: NS(=O)(=O)c1cc(NC(=O)Cc2c(Cl)cccc2Cl)ccc1-n1cc(C(F)(F)F)cn1]

According to general procedure GP5.1, 5-amino-N-(2,4-dimethoxybenzyl)-2-[4-(trifluoromethyl)-1H-pyrazol-1-yl]benzenesulfonamide (0.20 mmol) and (2,6-dichlorophenyl)acetic acid (0.40 mmol) were converted to the title compound (15.8 mg, 0.0320 mmol, 16% yield, 100% purity).

LC-MS (Method A): Rt=1.23 min; MS (ESIpos): m/z=493 [M+H]$^+$

Example 117

2-(2-Bromophenyl)-N-{3-sulfamoyl-4-[4-(trifluoromethyl)-1H-pyrazol-1-yl]phenyl}-acetamide

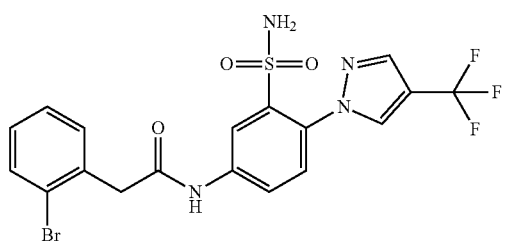

According to general procedure GP5.1, 5-amino-N-(2,4-dimethoxybenzyl)-2-[4-(trifluoromethyl)-1H-pyrazol-1-yl]benzenesulfonamide (0.20 mmol) and (2-bromophenyl)acetic acid (0.40 mmol) were converted to the title compound (7.4 mg, 0.0147 mmol, 7% yield, 100% purity).

LC-MS (Method A): Rt=1.20 min; MS (ESIpos): m/z=503 [M+H]$^+$

Example 118

2-(3,4-Difluorophenyl)-N-{3-sulfamoyl-4-[4-(trifluoromethyl)-1H-pyrazol-1-yl]phenyl}-acetamide

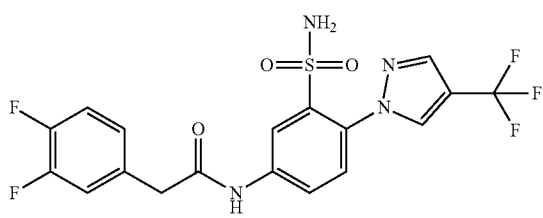 [SMILES: NS(=O)(=O)c1cc(NC(=O)Cc2ccc(F)c(F)c2)ccc1-n1cc(C(F)(F)F)cn1]

According to general procedure GP5.1, 5-amino-N-(2,4-dimethoxybenzyl)-2-[4-(trifluoromethyl)-1H-pyrazol-1-yl]benzenesulfonamide (0.20 mmol) and (3,4-difluorophenyl)acetic acid (0.40 mmol) were converted to the title compound (13.3 mg, 0.0289 mmol, 14% yield, 100% purity).

LC-MS (Method A): Rt=1.18 min; MS (ESIpos): m/z=461 [M+H]$^+$

Example 119

2-(4-Fluorophenyl)-N-{3-sulfamoyl-4-[4-(trifluoromethyl)-1H-pyrazol-1-yl]phenyl}-acetamide

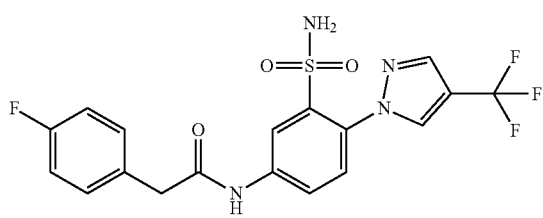 [SMILES: NS(=O)(=O)c1cc(NC(=O)Cc2ccc(F)cc2)ccc1-n1cc(C(F)(F)F)cn1]

According to general procedure GP5.1, 5-amino-N-(2,4-dimethoxybenzyl)-2-[4-(trifluoromethyl)-1H-pyrazol-1-yl]benzenesulfonamide (0.20 mmol) and (4-fluorophenyl)-acetic acid (0.40 mmol) were converted to the title compound (20.9 mg, 0.0472 mmol, 24% yield, 100% purity).

LC-MS (Method A): Rt=1.16 min; MS (ESIpos): m/z=443 [M+H]$^+$

Example 120

2-(3-Chlorophenyl)-N-{3-sulfamoyl-4-[4-(trifluoromethyl)-1H-pyrazol-1-yl]phenyl}-acetamide

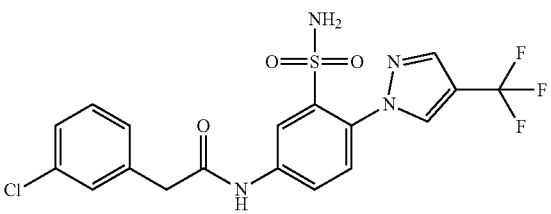 [SMILES: NS(=O)(=O)c1cc(NC(=O)Cc2cccc(Cl)c2)ccc1-n1cc(C(F)(F)F)cn1]

According to general procedure GP5.1, 5-amino-N-(2,4-dimethoxybenzyl)-2-[4-(trifluoromethyl)-1H-pyrazol-1-yl]benzenesulfonamide (0.20 mmol) and (3-chlorophenyl)-acetic acid (0.40 mmol) were converted to the title compound (12.6 mg, 0.0275 mmol, 14% yield, 100% purity).

LC-MS (Method A): Rt=1.22 min; MS (ESIpos): m/z=459 [M+H]$^+$

Example 121

2-(4-Methoxyphenyl)-N-{3-sulfamoyl-4-[4-(trifluoromethyl)-1H-pyrazol-1-yl]phenyl}-acetamide

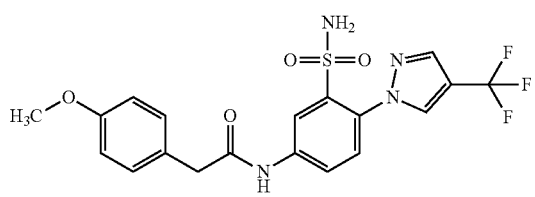 [SMILES: COc1ccc(CC(=O)Nc2ccc(-n3cc(C(F)(F)F)cn3)c(S(N)(=O)=O)c2)cc1]

According to general procedure GP5.1, 5-amino-N-(2,4-dimethoxybenzyl)-2-[4-(trifluoromethyl)-1H-pyrazol-1-yl]benzenesulfonamide (0.20 mmol) and (4-methoxy-phenyl)acetic acid (0.40 mmol) were converted to the title compound (14.3 mg, 0.0315 mmol, 16% yield, 100% purity).

LC-MS (Method A): Rt=1.13 min; MS (ESIpos): m/z=455 [M+H]$^+$

Example 122

2-(2,3-Difluorophenyl)-N-{3-sulfamoyl-4-[4-(trifluoromethyl)-1H-pyrazol-1-yl]phenyl}-acetamide

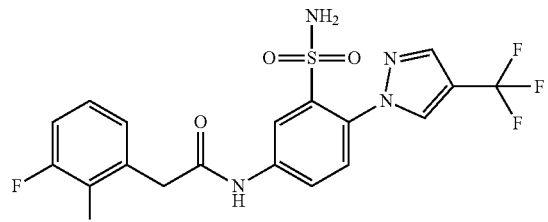

According to general procedure GP5.1, 5-amino-N-(2,4-dimethoxybenzyl)-2-[4-(trifluoromethyl)-1H-pyrazol-1-yl]benzenesulfonamide (0.20 mmol) and (2,3-difluoro-phenyl)acetic acid (0.40 mmol) were converted to the title compound (8.0 mg, 0.0174 mmol, 92% yield, 100% purity).

LC-MS (Method A): Rt=1.17 min; MS (ESIpos): m/z=461 [M+H]$^+$

Example 123

2-(2-Methylphenyl)-N-{3-sulfamoyl-4-[4-(trifluoromethyl)-1H-pyrazol-1-yl]phenyl}-acetamide

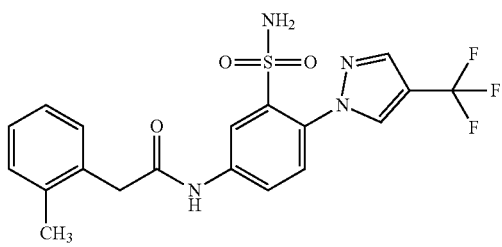 [SMILES: Cc1ccccc1CC(=O)Nc1ccc(-n2cc(C(F)(F)F)cn2)c(S(N)(=O)=O)c1]

According to general procedure GP5.1, 5-amino-N-(2,4-dimethoxybenzyl)-2-[4-(trifluoromethyl)-1H-pyrazol-1-yl]benzenesulfonamide (0.20 mmol) and (2-methylphenyl)-acetic acid (0.40 mmol) were converted to the title compound (21.4 mg, 0.0488 mmol, 24% yield, 100% purity).

LC-MS (Method A): Rt=1.19 min; MS (ESIpos): m/z=439 [M+H]$^+$

Example 124

2-(3-Methylphenyl)-N-{3-sulfamoyl-4-[4-(trifluoromethyl)-1H-pyrazol-1-yl]phenyl}-acetamide

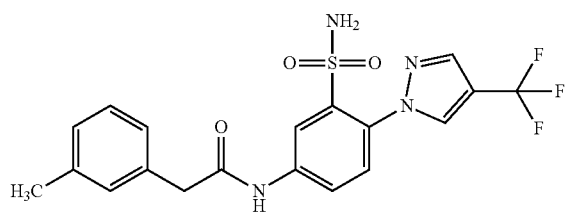 [SMILES: Cc1cccc(CC(=O)Nc2ccc(-n3cc(C(F)(F)F)cn3)c(S(N)(=O)=O)c2)c1]

According to general procedure GP5.1, 5-amino-N-(2,4-dimethoxybenzyl)-2-[4-(trifluoromethyl)-1H-pyrazol-1-yl]benzenesulfonamide (0.20 mmol) and (3-methylphenyl)-acetic acid (0.40 mmol) were converted to the title compound (15.8 mg, 0.0360 mmol, 18% yield, 100% purity).

LC-MS (Method A): Rt=1.20 min; MS (ESIpos): m/z=439 [M+H]$^+$

Example 125

2-[2-(Difluoromethoxy)phenyl]-N-{3-sulfamoyl-4-[4-(trifluoromethyl)-1H-pyrazol-1-yl]phenyl}acetamide

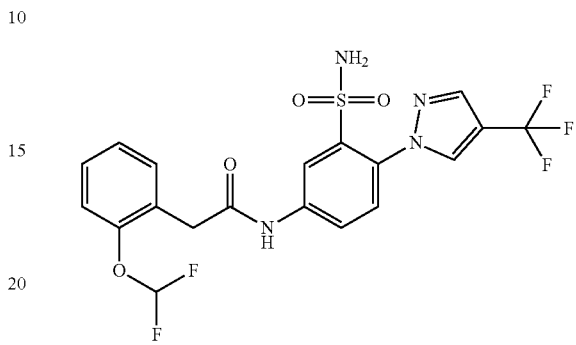

According to general procedure GP5.1, 5-amino-N-(2,4-dimethoxybenzyl)-2-[4-(trifluoromethyl)-1H-pyrazol-1-yl]benzenesulfonamide (0.20 mmol) and [2-(difluoromethoxy)phenyl]acetic acid (0.40 mmol) were converted to the title compound (5.3 mg, 0.0108 mmol, 5% yield, 100% purity).

LC-MS (Method A): Rt=1.19 min; MS (ESIpos): m/z=491 [M+H]$^+$

Example 126

2-(2-Chloropyridin-3-yl)-N-{3-sulfamoyl-4-[4-(trifluoromethyl)-1H-pyrazol-1-yl]phenyl}acetamide

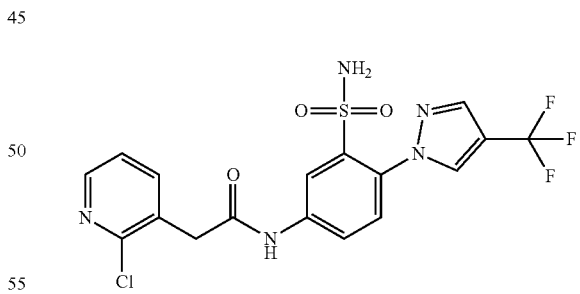

According to general procedure GP5.1, 5-amino-N-(2,4-dimethoxybenzyl)-2-[4-(trifluoromethyl)-1H-pyrazol-1-yl]benzenesulfonamide (0.20 mmol) and (2-chloropyridin-3-yl)acetic acid (0.40 mmol) were converted to the title compound (12.7 mg, 0.0276 mmol, 14% yield, 100% purity).

LC-MS (Method A): Rt=1.03 min; MS (ESIpos): m/z=460 [M+H]$^+$

Example 127

2-(2-Chloro-4-fluorophenyl)-N-{3-sulfamoyl-4-[4-(trifluoromethyl)-1H-pyrazol-1-yl]phenyl}acetamide

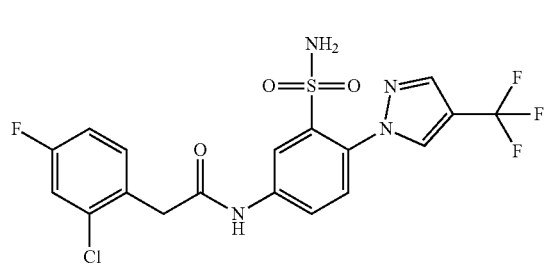 [SMILES: NS(=O)(=O)c1cc(NC(=O)Cc2ccc(F)cc2Cl)ccc1-n1cc(C(F)(F)F)cn1]

According to general procedure GP5.1, 5-amino-N-(2,4-dimethoxybenzyl)-2-[4-(trifluoromethyl)-1H-pyrazol-1-yl]benzenesulfonamide (0.20 mmol) and (2-chloro-4-fluorophenyl)acetic acid (0.40 mmol) were converted to the title compound (9.1 mg, 0.0191 mmol, 10% yield, 100% purity).

LC-MS (Method A): Rt=1.21 min; MS (ESIpos): m/z=477 [M+H]$^+$

Example 128

2-(2-Chloro-5-methylphenyl)-N-{3-sulfamoyl-4-[4-(trifluoromethyl)-1H-pyrazol-1-yl]-phenyl}acetamide

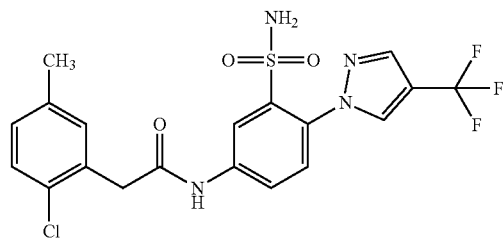

According to general procedure GP5.1, 5-amino-N-(2,4-dimethoxybenzyl)-2-[4-(trifluoromethyl)-1H-pyrazol-1-yl]benzenesulfonamide (0.20 mmol) and (2-chloro-5-methylphenyl)acetic acid (0.40 mmol) were converted to the title compound (13.7 mg, 0.0290 mmol, 14% yield, 100% purity).

LC-MS (Method A): Rt=1.25 min; MS (ESIpos): m/z=473 [M+H]$^+$

Example 129

N-{3-Sulfamoyl-4-[4-(trifluoromethyl)-1H-pyrazol-1-yl]phenyl}-2-[2-(trifluoro-methoxy)phenyl]acetamide

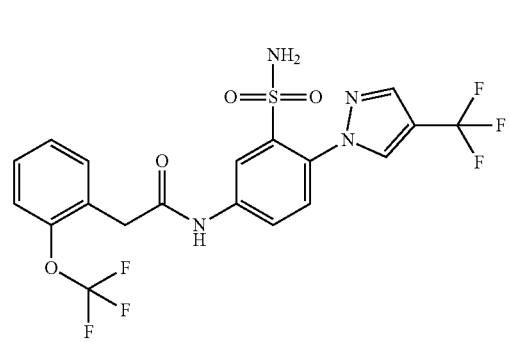 [SMILES: NS(=O)(=O)c1cc(NC(=O)Cc2ccccc2OC(F)(F)F)ccc1-n1cc(C(F)(F)F)cn1]

According to general procedure GP5.1, 5-amino-N-(2,4-dimethoxybenzyl)-2-[4-(trifluoromethyl)-1H-pyrazol-1-yl]benzenesulfonamide (0.20 mmol) and [2-(trifluoromethoxy)phenyl]acetic acid (0.40 mmol) were converted to the title compound (9.5 mg, 0.0189 mmol, 9% yield, 100% purity).

LC-MS (Method A): Rt=1.25 min; MS (ESIpos): m/z=509 [M+H]$^+$

Example 130

2-(2-Chloro-4,5-difluorophenyl)-N-{3-sulfamoyl-4-[4-(trifluoromethyl)-1H-pyrazol-1-yl]phenyl}acetamide

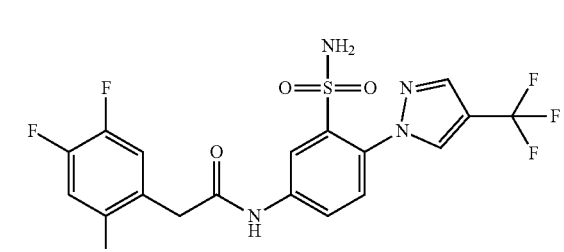

According to general procedure GP5.1, 5-amino-N-(2,4-dimethoxybenzyl)-2-[4-(trifluoromethyl)-1H-pyrazol-1-yl]benzenesulfonamide (0.20 mmol) and (2-chloro-4,5-difluorophenyl)acetic acid (0.40 mmol) were converted to the title compound (17.1 mg, 0.0346 mmol, 17% yield, 100% purity).

LC-MS (Method A): Rt=1.24 min; MS (ESIpos): m/z=495 [M+H]$^+$

Example 131

2-[2-Chloro-3-(trifluoromethyl)phenyl]-N-{3-sulfamoyl-4-[4-(trifluoromethyl)-1H-pyrazol-1-yl]phenyl}acetamide

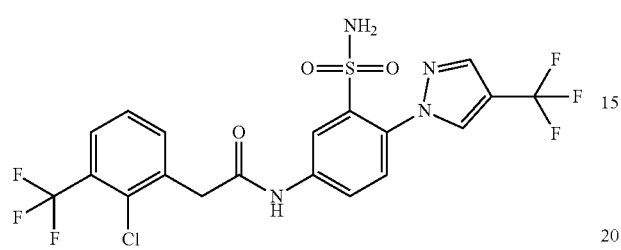

According to general procedure GP5.1, 5-amino-N-(2,4-dimethoxybenzyl)-2-[4-(trifluoromethyl)-1H-pyrazol-1-yl]benzenesulfonamide (0.20 mmol) and [2-chloro-3-(trifluoromethyl)phenyl]acetic acid (0.40 mmol) were converted the title compound (15.3 mg, 0.0290 mmol, 15% yield, 100% purity).

LC-MS (Method A): Rt=1.28 min; MS (ESIpos): m/z=527 [M+H]$^+$

Example 132

2-(2-Chloro-6-fluoro-3-methylphenyl)-N-{3-sulfamoyl-4-[4-(trifluoromethyl)-1H-pyrazol-1-yl]phenyl}acetamide

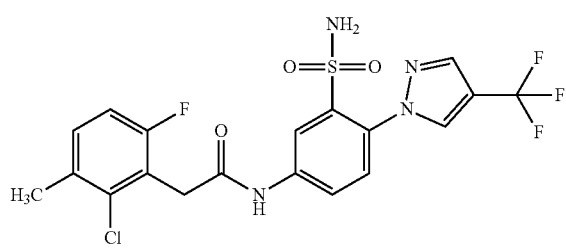 [SMILES: Cc1ccc(F)c(CC(=O)Nc2ccc(-n3cc(C(F)(F)F)cn3)c(S(N)(=O)=O)c2)c1Cl]

According to general procedure GP5.1, 5-amino-N-(2,4-dimethoxybenzyl)-2-[4-(trifluoromethyl)-1H-pyrazol-1-yl]benzenesulfonamide (0.20 mmol) and (2-chloro-6-fluoro-3-methylphenyl)acetic acid (0.40 mmol) were converted to the title compound (10.9 mg, 0.0222 mmol, 11% yield, 100% purity).

LC-MS (Method A): Rt=1.25 min; MS (ESIpos): m/z=491 [M+H]$^+$

Example 133

2-(2-Chloro-3,6-difluorophenyl)-N-{3-sulfamoyl-4-[4-(trifluoromethyl)-1H-pyrazol-1-yl]phenyl}acetamide

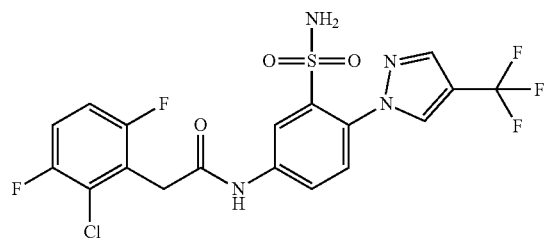 [SMILES: NS(=O)(=O)c1cc(NC(=O)Cc2c(F)ccc(F)c2Cl)ccc1-n1cc(C(F)(F)F)cn1]

According to general procedure GP5.1, 5-amino-N-(2,4-dimethoxybenzyl)-2-[4-(trifluoromethyl)-1H-pyrazol-1-yl]benzenesulfonamide (0.20 mmol) and (2-chloro-3,6-difluorophenyl)acetic acid (0.40 mmol) were converted to the title compound (16.4 mg, 0.0331 mmol, 17% yield, 100% purity).

LC-MS (Method A): Rt=1.21 min; MS (ESIpos): m/z=495 [M+H]$^+$

Example 134

2-[2-Chloro-6-(trifluoromethyl)phenyl]-N-{3-sulfamoyl-4-[4-(trifluoromethyl)-1H-pyrazol-1-yl]phenyl}acetamide

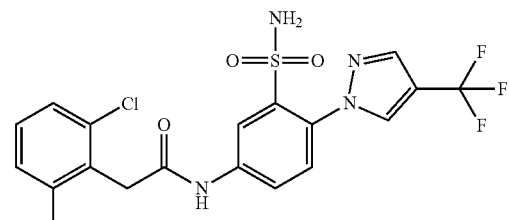

According to general procedure GP5.1, 5-amino-N-(2,4-dimethoxybenzyl)-2-[4-(trifluoromethyl)-1H-pyrazol-1-yl]benzenesulfonamide (0.20 mmol) and [2-chloro-6-(trifluoromethyl)phenyl]acetic acid (0.40 mmol) were converted to the title compound (11.2 mg, 0.0213 mmol, 11% yield, 100% purity).

LC-MS (Method A): Rt=1.26 min; MS (ESIpos): m/z=527 [M+H]$^+$

Example 135

2-(2-Chloro-4-methoxyphenyl)-N-{3-sulfamoyl-4-[4-(trifluoromethyl)-1H-pyrazol-1-yl]phenyl}acetamide

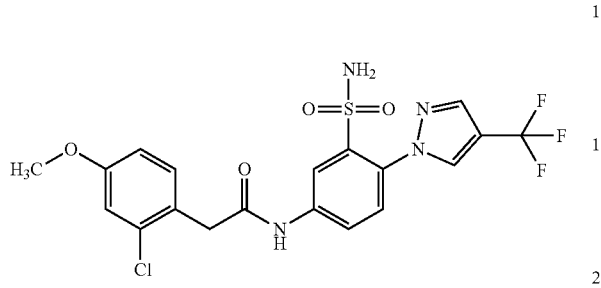

According to general procedure GP5.1, 5-amino-N-(2,4-dimethoxybenzyl)-2-[4-(trifluoromethyl)-1H-pyrazol-1-yl]benzenesulfonamide (0.20 mmol) and (2-chloro-4-methoxyphenyl)acetic acid (0.40 mmol) were converted to the title compound (17.9 mg, 0.0366 mmol, 18% yield, 100% purity).

LC-MS (Method A): Rt=1.19 min; MS (ESIpos): m/z=489 [M+H]$^+$

Example 136

2-(2,5-Dichlorophenyl)-N-{3-sulfamoyl-4-[4-(trifluoromethyl)-1H-pyrazol-1-yl]phenyl}-acetamide

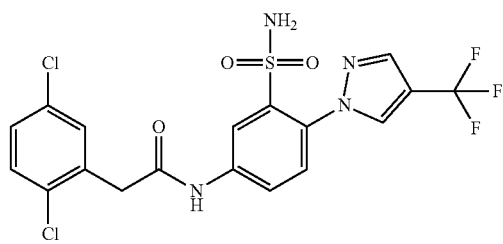

According to general procedure GP5.1, 5-amino-N-(2,4-dimethoxybenzyl)-2-[4-(trifluoromethyl)-1H-pyrazol-1-yl]benzenesulfonamide (0.20 mmol) and (2,5-dichloro-phenyl)acetic acid (0.40 mmol) were converted to the title compound (10.3 mg, 0.0209 mmol, 10% yield, 100% purity).

LC-MS (Method A): Rt=1.26 min; MS (ESIpos): m/z=493 [M+H]$^+$

Example 137

2-(2-Isopropylphenyl)-N-{3-sulfamoyl-4-[4-(trifluoromethyl)-1H-pyrazol-1-yl]phenyl}-acetamide

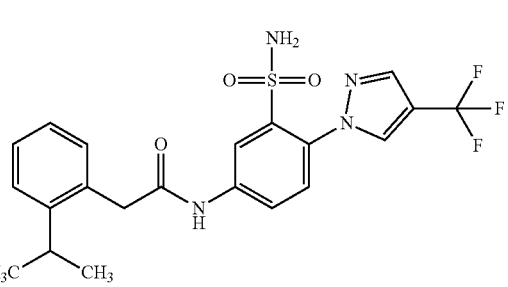

According to general procedure GP5.1, 5-amino-N-(2,4-dimethoxybenzyl)-2-[4-(trifluoromethyl)-1H-pyrazol-1-yl]benzenesulfonamide (0.20 mmol) and (2-isopropyl-phenyl)acetic acid (0.40 mmol) were converted to the title compound (19.8 mg, 0.0424 mmol, 21% yield, 100% purity).

LC-MS (Method A): Rt=1.30 min; MS (ESIpos): m/z=467 [M+H]$^+$

Example 138

2-(2-Chloro-5-methoxyphenyl)-N-{3-sulfamoyl-4-[4-(trifluoromethyl)-1H-pyrazol-1-yl]phenyl}acetamide

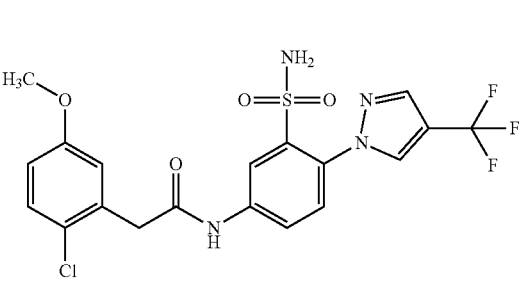 [SMILES: COc1ccc(Cl)c(CC(=O)Nc2ccc(-n3cc(C(F)(F)F)cn3)c(S(N)(=O)=O)c2)c1]

According to general procedure GP5.1, 5-amino-N-(2,4-dimethoxybenzyl)-2-[4-(trifluoromethyl)-1H-pyrazol-1-yl]benzenesulfonamide (0.20 mmol) and (2-chloro-5-methoxyphenyl)acetic acid (0.40 mmol) were converted to the title compound (6.7 mg, 0.0137 mmol, 7% yield, 100% purity).

LC-MS (Method A): Rt=1.20 min; MS (ESIpos): m/z=489 [M+H]$^+$

Example 139

2-(2-Chloro-5-fluorophenyl)-N-{3-sulfamoyl-4-[4-(trifluoromethyl)-1H-pyrazol-1-yl]phenyl}acetamide

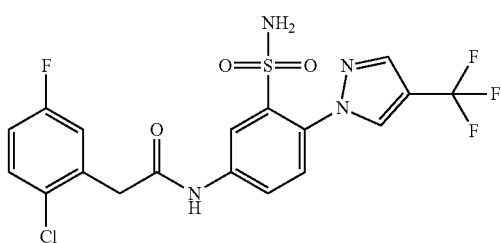 [SMILES: NS(=O)(=O)c1cc(NC(=O)Cc2cc(F)ccc2Cl)ccc1-n1cc(C(F)(F)F)cn1]

According to general procedure GP5.1, 5-amino-N-(2,4-dimethoxybenzyl)-2-[4-(trifluoromethyl)-1H-pyrazol-1-yl]benzenesulfonamide (0.20 mmol) and (2-chloro-5-fluorophenyl)acetic acid (0.40 mmol) were converted to the title compound (12.6 mg, 0.0264 mmol, 13% yield, 100% purity).

LC-MS (Method A): Rt=1.21 min; MS (ESIpos): m/z=477 [M+H]$^+$

Example 140

N-[4-(4-Fluoro-1H-pyrazol-1-yl)-3-sulfamoylphenyl]-2-[2-(trifluoromethyl)phenyl]-acetamide

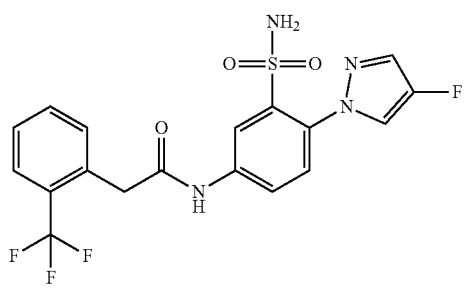 [SMILES: NS(=O)(=O)c1cc(NC(=O)Cc2ccccc2C(F)(F)F)ccc1-n1cc(F)cn1]

According to general procedure GP5.1, 5-amino-N-(2,4-dimethoxybenzyl)-2-(4-fluoro-1H-pyrazol-1-yl)benzenesulfonamide (0.20 mmol) and [2-(trifluoromethyl)phenyl]acetic acid (0.40 mmol) were converted to the title compound (11.8 mg, 0.0267 mmol, 13% yield, 92% purity).

LC-MS (Method A): Rt=1.12 min; MS (ESIpos): m/z=443 [M+H]$^+$

Example 141

2-(5-Bromo-4-fluoro-2-methylphenyl)-N-{3-sulfamoyl-4-[4-(trifluoromethyl)-1H-pyrazol-1-yl]phenyl}acetamide

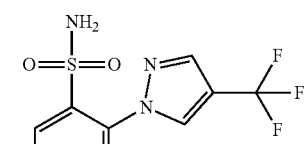

According to general procedure GP5.1, 5-amino-N-(2,4-dimethoxybenzyl)-2-[4-(trifluoromethyl)-1H-pyrazol-1-yl]benzenesulfonamide (0.20 mmol) and (5-bromo-4-fluoro-2-methylphenyl)acetic acid (0.40 mmol) were converted to the title compound (19.5 mg, 0.0364 mmol, 18% yield, 100% purity).

LC-MS (Method A): Rt=1.29 min; MS (ESIpos): m/z=535 [M+H]$^+$

Example 142

2-(2-Chloro-6-methoxyphenyl)-N-{3-sulfamoyl-4-[4-(trifluoromethyl)-1H-pyrazol-1-yl]phenyl}acetamide

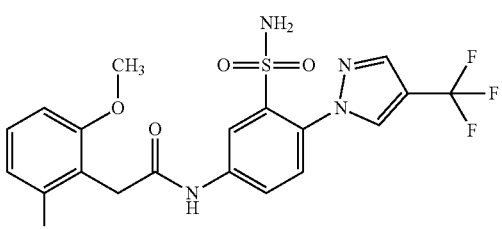

According to general procedure GP5.1, 5-amino-N-(2,4-dimethoxybenzyl)-2-[4-(trifluoromethyl)-1H-pyrazol-1-yl]benzenesulfonamide (0.20 mmol) and (2-chloro-6-methoxyphenyl)acetic acid (0.40 mmol) were converted to the title compound (23.8 mg, 0.0487 mmol, 24% yield, 100% purity).

LC-MS (Method A): Rt=1.21 min; MS (ESIpos): m/z=489 [M+H]$^+$

Example 143

2-(2-Chloro-4,6-difluorophenyl)-N-{3-sulfamoyl-4-[4-(trifluoromethyl)-1H-pyrazol-1-yl]phenyl}acetamide

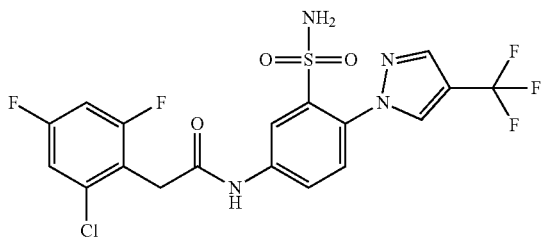 [SMILES: NS(=O)(=O)c1cc(NC(=O)Cc2c(F)cc(F)cc2Cl)ccc1-n1cc(C(F)(F)F)cn1]

According to general procedure GP5.1, 5-amino-N-(2,4-dimethoxybenzyl)-2-[4-(trifluoromethyl)-1H-pyrazol-1-yl]benzenesulfonamide (0.20 mmol) and (2-chloro-4,6-difluorophenyl)acetic acid (0.40 mmol) were converted to the title compound (7.7 mg, 0.0156 mmol, 8% yield, 91% purity).

LC-MS (Method A): Rt=1.23 min; MS (ESIpos): m/z=495 [M+H]$^+$

Example 144

2-(3-Fluorophenyl)-N-[4-(4-fluoro-1H-pyrazol-1-yl)-3-sulfamoylphenyl]acetamide

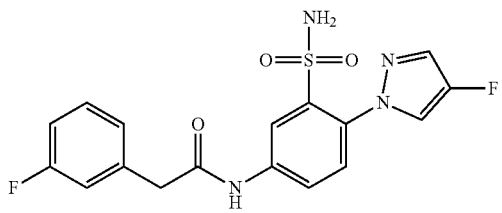 [SMILES: NS(=O)(=O)c1cc(NC(=O)Cc2cccc(F)c2)ccc1-n1cc(F)cn1]

According to general procedure GP5.1, 5-amino-N-(2,4-dimethoxybenzyl)-2-(4-fluoro-1H-pyrazol-1-yl)benzenesulfonamide (0.20 mmol) and (3-fluorophenyl)acetic acid (0.40 mmol) were converted to the title compound (12.9 mg, 0.0328 mmol, 16% yield, 100% purity).

LC-MS (Method A): Rt=1.04 min; MS (ESIpos): m/z=393 [M+H]$^+$

Example 145

2-(3,4-Difluorophenyl)-N-[4-(4-fluoro-1H-pyrazol-1-yl)-3-sulfamoylphenyl]acetamide

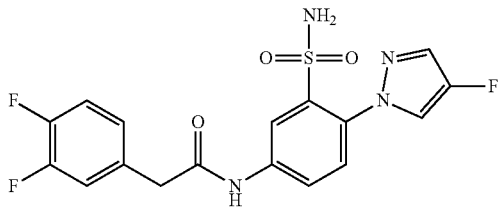 [SMILES: NS(=O)(=O)c1cc(NC(=O)Cc2ccc(F)c(F)c2)ccc1-n1cc(F)cn1]

According to general procedure GP5.1, 5-amino-N-(2,4-dimethoxybenzyl)-2-(4-fluoro-1H-pyrazol-1-yl)benzenesulfonamide (0.20 mmol) and (3,4-difluorophenyl)acetic acid (0.40 mmol) were converted to the title compound (16.0 mg, 0.0390 mmol, 19% yield, 100% purity).

LC-MS (Method A): Rt=1.07 min; MS (ESIpos): m/z=411 [M+H]$^+$

Example 146

2-(3,5-Difluorophenyl)-N-[4-(4-fluoro-1H-pyrazol-1-yl)-3-sulfamoylphenyl]acetamide

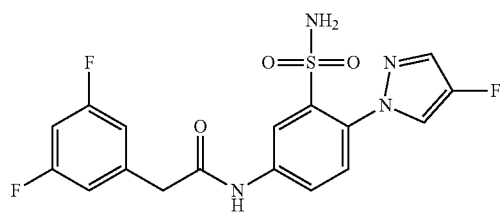 [SMILES: NS(=O)(=O)c1cc(NC(=O)Cc2cc(F)cc(F)c2)ccc1-n1cc(F)cn1]

According to general procedure GP5.1, 5-amino-N-(2,4-dimethoxybenzyl)-2-(4-fluoro-1H-pyrazol-1-yl)benzenesulfonamide (0.20 mmol) and (3,5-difluorophenyl)acetic acid (0.40 mmol) were converted to the title compound (11.4 mg, 0.0278 mmol, 14% yield, 81% purity).

LC-MS (Method A): Rt=1.08 min; MS (ESIpos): m/z=411 [M+H]$^+$

Example 147

N-[4-(4-Fluoro-1H-pyrazol-1-yl)-3-sulfamoylphenyl]-2-(2-hydroxyphenyl)acetamide

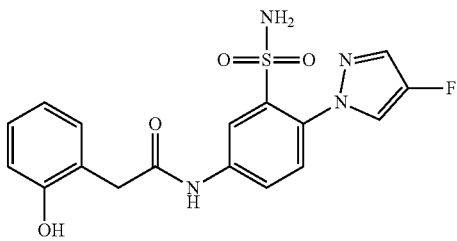

According to general procedure GP5.1, 5-amino-N-(2,4-dimethoxybenzyl)-2-(4-fluoro-1H-pyrazol-1-yl)benzenesulfonamide (0.20 mmol) and (2-hydroxyphenyl)acetic acid (0.40 mmol) were converted to the title compound (8.8 mg, 0.0225 mmol, 11% yield, 100% purity).

LC-MS (Method A): Rt=0.93 min; MS (ESIpos): m/z=391 [M+H]$^+$

Example 148

2-(3-Chlorophenyl)-N-[4-(4-fluoro-1H-pyrazol-1-yl)-3-sulfamoylphenyl]acetamide

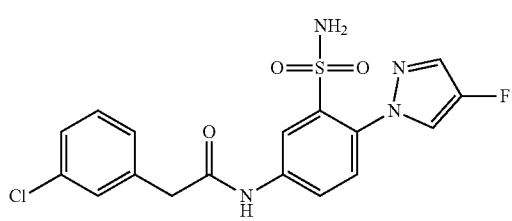 [SMILES: NS(=O)(=O)c1cc(NC(=O)Cc2cccc(Cl)c2)ccc1-n1cc(F)cn1]

According to general procedure GP5.1, 5-amino-N-(2,4-dimethoxybenzyl)-2-(4-fluoro-1H-pyrazol-1-yl)benzenesulfonamide (0.20 mmol) and (3-chlorophenyl)acetic acid (0.40 mmol) were converted to the title compound (15.2 mg, 0.0372 mmol, 19% yield, 86% purity).

LC-MS (Method A): Rt=1.11 min; MS (ESIpos): m/z=409 [M+H]$^+$

Example 149

2-(4-Fluorophenyl)-N-[4-(4-fluoro-1H-pyrazol-1-yl)-3-sulfamoylphenyl]acetamide

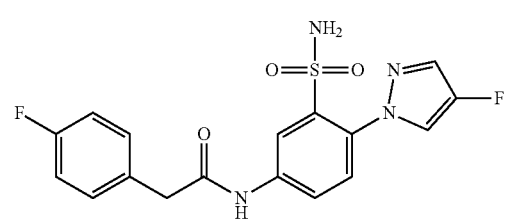 [SMILES: NS(=O)(=O)c1cc(NC(=O)Cc2ccc(F)cc2)ccc1-n1cc(F)cn1]

According to general procedure GP5.1, 5-amino-N-(2,4-dimethoxybenzyl)-2-(4-fluoro-1H-pyrazol-1-yl)benzenesulfonamide (0.20 mmol) and (4-fluorophenyl)acetic acid (0.40 mmol) were converted to the title compound (20.3 mg, 0.0517 mmol, 26% yield, 92% purity).

LC-MS (Method A): Rt=1.04 min; MS (ESIpos): m/z=393 [M+H]$^+$

Example 150

N-[4-(4-Fluoro-1H-pyrazol-1-yl)-3-sulfamoylphenyl]-2-(4-hydroxyphenyl)acetamide

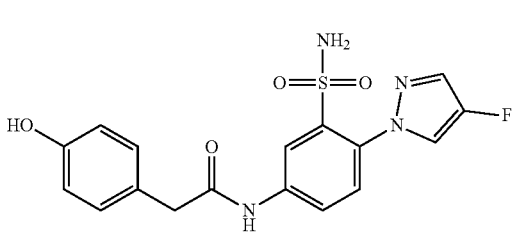 [SMILES: NS(=O)(=O)c1cc(NC(=O)Cc2ccc(O)cc2)ccc1-n1cc(F)cn1]

According to general procedure GP5.1, 5-amino-N-(2,4-dimethoxybenzyl)-2-(4-fluoro-1H-pyrazol-1-yl)benzenesulfonamide (0.20 mmol) and (4-hydroxyphenyl)acetic acid (0.40 mmol) were converted to the title compound (13.9 mg, 0.0356 mmol, 18% yield, 100% purity).

LC-MS (Method A): Rt=0.85 min; MS (ESIpos): m/z=391 [M+H]$^+$

Example 151

N-[4-(4-Fluoro-1H-pyrazol-1-yl)-3-sulfamoylphenyl]-2-(3-methylphenyl)acetamide

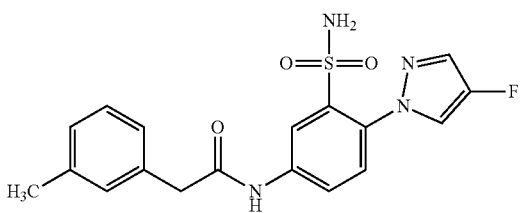 [SMILES: Cc1cccc(CC(=O)Nc2ccc(-n3cc(F)cn3)c(S(N)(=O)=O)c2)c1]

According to general procedure GP5.1, 5-amino-N-(2,4-dimethoxybenzyl)-2-(4-fluoro-1H-pyrazol-1-yl)benzenesulfonamide (0.20 mmol) and (3-methylphenyl)acetic acid (0.40 mmol) were converted to the title compound (6.1 mg, 0.0157 mmol, 8% yield, 100% purity).

LC-MS (Method A): Rt=1.09 min, MS (ESIpos): m/z=389 [M+H]$^+$

Example 152

N-[4-(4-Fluoro-1H-pyrazol-1-yl)-3-sulfamoylphenyl]-2-(4-methylphenyl)acetamide

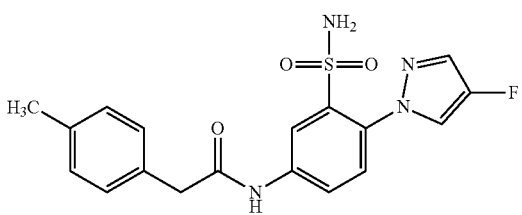 [SMILES: Cc1ccc(CC(=O)Nc2ccc(-n3cc(F)cn3)c(S(N)(=O)=O)c2)cc1]

According to general procedure GP5.1, 5-amino-N-(2,4-dimethoxybenzyl)-2-(4-fluoro-1H-pyrazol-1-yl)benzenesulfonamide (0.20 mmol) and (4-methylphenyl)acetic acid (0.40 mmol) were converted to the title compound (11.4 mg, 0.0293 mmol, 15% yield, 91% purity).

LC-MS (Method A): Rt=1.09 min; MS (ESIpos): m/z=389 [M+H]$^+$

Example 153

N-[4-(4-Fluoro-1H-pyrazol-1-yl)-3-sulfamoylphenyl]-2-(4-methoxyphenyl)acetamide

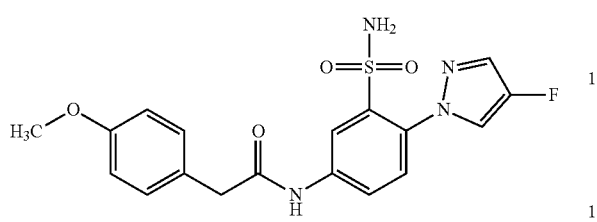

According to general procedure GP5.1, 5-amino-N-(2,4-dimethoxybenzyl)-2-(4-fluoro-1H-pyrazol-1-yl)benzenesulfonamide (0.20 mmol) and (4-methoxyphenyl)acetic acid (0.40 mmol) were converted to the title compound (21.8 mg, 0.0539 mmol, 27% yield, 100% purity).

LC-MS (Method A): Rt=1.01 min, MS (ESIpos): m/z=405 [M+H]$^+$

Example 154

N-[4-(4-Fluoro-1H-pyrazol-1-yl)-3-sulfamoylphenyl]-2-(2-methylphenyl)acetamide

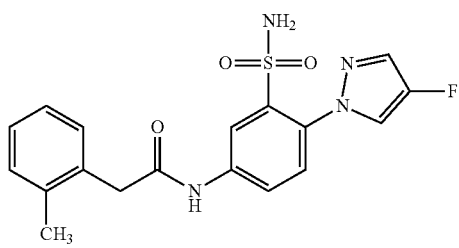 [SMILES: Cc1ccccc1CC(=O)Nc1ccc(-n2cc(F)cn2)c(S(N)(=O)=O)c1]

According to general procedure GP5.1, 5-amino-N-(2,4-dimethoxybenzyl)-2-(4-fluoro-1H-pyrazol-1-yl)benzenesulfonamide (0.20 mmol) and (2-methylphenyl)acetic acid (0.40 mmol) were converted to the title compound (18.9 mg, 0.0487 mmol, 24% yield, 100% purity).

LC-MS (Method A): Rt=1.07 min, MS (ESIpos): m/z=389 [M+H]$^+$

Example 155

2-(2,3-Difluorophenyl)-N-[4-(4-fluoro-1H-pyrazol-1-yl)-3-sulfamoylphenyl]acetamide

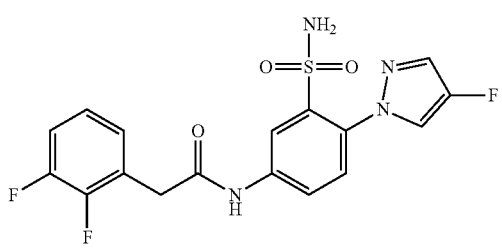 [SMILES: NS(=O)(=O)c1cc(NC(=O)Cc2cccc(F)c2F)ccc1-n1cc(F)cn1]

According to general procedure GP5.1, 5-amino-N-(2,4-dimethoxybenzyl)-2-(4-fluoro-1H-pyrazol-1-yl)benzenesulfonamide (0.20 mmol) and (2,3-difluorophenyl)acetic acid (0.40 mmol) were converted to the title compound (10.4 mg, 0.0253 mmol, 13% yield, 100% purity).

LC-MS (Method A): Rt=1.05 min; MS (ESIpos): m/z=411 [M+H]$^+$

Example 156

2-(2-Ethoxyphenyl)-N-[4-(4-fluoro-1H-pyrazol-1-yl)-3-sulfamoylphenyl]acetamide

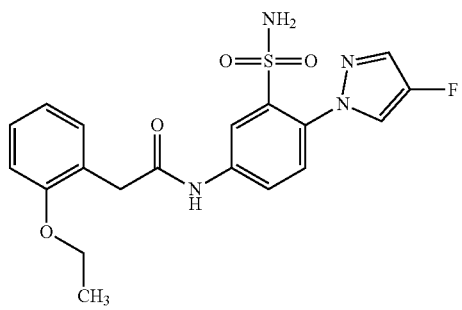 [SMILES: CCOc1ccccc1CC(=O)Nc1ccc(-n2cc(F)cn2)c(S(N)(=O)=O)c1]

According to general procedure GP5.1, 5-amino-N-(2,4-dimethoxybenzyl)-2-(4-fluoro-1H-pyrazol-1-yl)benzenesulfonamide (0.20 mmol) and (2-ethoxyphenyl)acetic acid (0.40 mmol) were converted to the title compound (20.2 mg, 0.0483 mmol, 24% yield, 92% purity).

LC-MS (Method A): Rt=1.10 min; MS (ESIpos): m/z=419 [M+H]$^+$

Example 157

2-[2-(Difluoromethoxy)phenyl]-N-[4-(4-fluoro-1H-pyrazol-1-yl)-3-sulfamoylphenyl]-acetamide

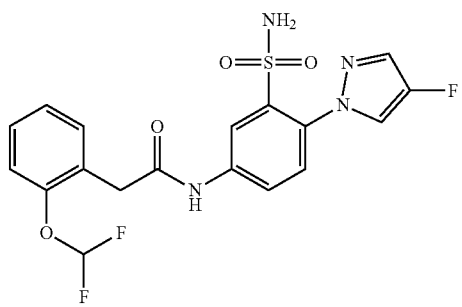 [SMILES: NS(=O)(=O)c1cc(NC(=O)Cc2ccccc2OC(F)F)ccc1-n1cc(F)cn1]

According to general procedure GP5.1, 5-amino-N-(2,4-dimethoxybenzyl)-2-(4-fluoro-1H-pyrazol-1-yl)benzenesulfonamide (0.20 mmol) and [2-(difluoromethoxy)phenyl]acetic acid (0.40 mmol) were converted to the title compound (14.9 mg, 0.0338 mmol, 17% yield, 88% purity).

LC-MS (Method A): Rt=1.08 min; MS (ESIpos): m/z=441 [M+H]$^+$

Example 158

2-(2-Chloropyridin-3-yl)-N-[4-(4-fluoro-1H-pyrazol-1-yl)-3-sulfamoylphenyl]acetamide

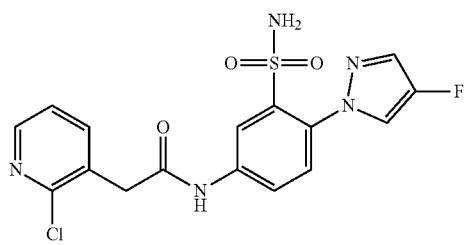 [SMILES: NS(=O)(=O)c1cc(NC(=O)Cc2cccnc2Cl)ccc1-n1cc(F)cn1]

According to general procedure GP5.1, 5-amino-N-(2,4-dimethoxybenzyl)-2-(4-fluoro-1H-pyrazol-1-yl)benzenesulfonamide (0.20 mmol) and (2-chloropyridin-3-yl)acetic acid (0.40 mmol) were converted to the title compound (7.1 mg, 0.0173 mmol, 9% yield, 100% purity).

LC-MS (Method A): Rt=0.88 min; MS (ESIpos): m/z=410 [M+H]$^+$

Example 159

2-(2-Chloro-6-fluoro-3-methylphenyl)-N-[4-(4-fluoro-1H-pyrazol-1-yl)-3-sulfamoyl-phenyl]acetamide

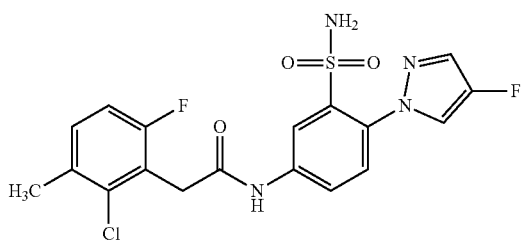 [SMILES: Cc1ccc(F)c(CC(=O)Nc2ccc(-n3cc(F)cn3)c(S(N)(=O)=O)c2)c1Cl]

According to general procedure GP5.1, 5-amino-N-(2,4-dimethoxybenzyl)-2-(4-fluoro-1H-pyrazol-1-yl)benzenesulfonamide (0.20 mmol) and (2-chloro-6-fluoro-3-methylphenyl)-acetic acid (0.40 mmol) were converted to the title compound (17.7 mg, 0.0401 mmol, 20% yield, 100% purity).

LC-MS (Method A): Rt=1.15 min; MS (ESIpos): m/z=441 [M+H]$^+$

Example 160

N-[4-(4-Fluoro-1H-pyrazol-1-yl)-3-sulfamoylphenyl]-2-[2-(trifluoromethoxy)phenyl]-acetamide

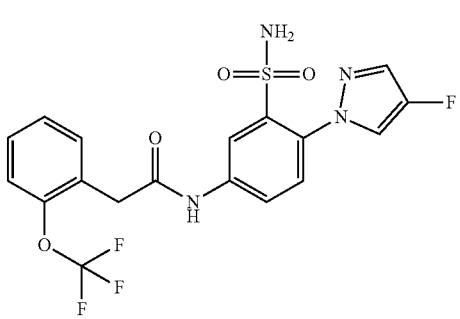

According to general procedure GP5.1, 5-amino-N-(2,4-dimethoxybenzyl)-2-(4-fluoro-1H-pyrazol-1-yl)benzenesulfonamide (0.20 mmol) and [2-(trifluoromethoxy)phenyl]acetic acid (0.40 mmol) were converted to the title compound (16.4 mg, 0.0358 mmol, 18% yield, 100% purity).

LC-MS (Method A): Rt=1.15 min; MS (ESIpos): m/z=459 [M+H]$^+$

Example 161

2-(2-Chloro-4,5-difluorophenyl)-N-[4-(4-fluoro-1H-pyrazol-1-yl)-3-sulfamoylphenyl]

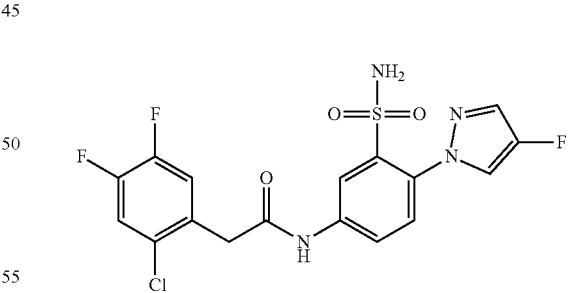

According to general procedure GP5.1, 5-amino-N-(2,4-dimethoxybenzyl)-2-(4-fluoro-1H-pyrazol-1-yl)benzenesulfonamide (0.20 mmol) and (2-chloro-4,5-difluorophenyl)acetic acid (0.40 mmol) were converted to the title compound (6.4 mg, 0.0144 mmol, 7% yield, 100% purity).

LC-MS (Method A): Rt=1.13 min; MS (ESIpos): m/z=445 [M+H]$^+$

Example 162

2-[2-Chloro-3-(trifluoromethyl)phenyl]-N-[4-(4-fluoro-1H-pyrazol-1-yl)-3-sulfamoyl-phenyl]acetamide

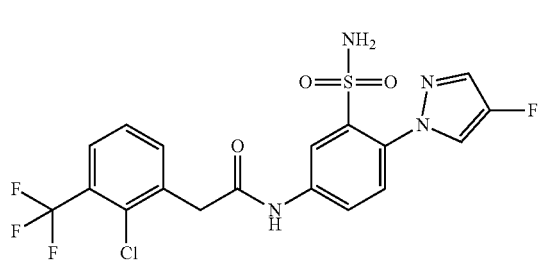 [SMILES: NS(=O)(=O)c1cc(NC(=O)Cc2cccc(C(F)(F)F)c2Cl)ccc1-n1cc(F)cn1]

According to general procedure GP5.1, 5-amino-N-(2,4-dimethoxybenzyl)-2-(4-fluoro-1H-pyrazol-1-yl)benzenesulfonamide (0.20 mmol) and [2-chloro-3-(trifluoromethyl)phenyl]acetic acid (0.40 mmol) were converted to the title compound (13.6 mg, 0.0285 mmol, 14% yield, 100% purity).

LC-MS (Method A): Rt=1.19 min; MS (ESIpos): m/z=477 [M+H]$^+$

Example 163

2-(2,5-Dichlorophenyl)-N-[4-(4-fluoro-1H-pyrazol-1-yl)-3-sulfamoylphenyl]acetamide

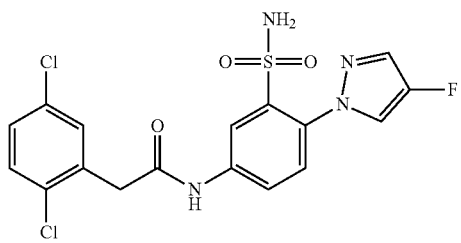

According to general procedure GP5.1, 5-amino-N-(2,4-dimethoxybenzyl)-2-(4-fluoro-1H-pyrazol-1-yl)benzenesulfonamide (0.20 mmol) and (2,5-dichlorophenyl)acetic acid (0.40 mmol) were converted to the title compound (13.8 mg, 0.0311 mmol, 16% yield, 92% purity).

LC-MS (Method A): Rt=1.16 min; MS (ESIpos): m/z=443 [M+H]$^+$

Example 164

2-(2-Chloro-3,6-difluorophenyl)-N-[4-(4-fluoro-1H-pyrazol-1-yl)-3-sulfamoylphenyl]-acetamide

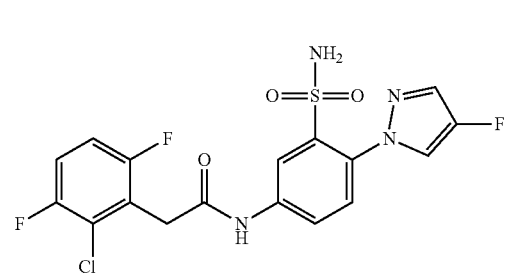 [SMILES: NS(=O)(=O)c1cc(NC(=O)Cc2c(F)ccc(F)c2Cl)ccc1-n1cc(F)cn1]

According to general procedure GP5.1, 5-amino-N-(2,4-dimethoxybenzyl)-2-(4-fluoro-1H-pyrazol-1-yl)benzenesulfonamide (0.20 mmol) and (2-chloro-3,6-difluorophenyl)acetic acid (0.40 mmol) were converted to the title compound (19.1 mg, 0.0429 mmol, 22% yield, 90% purity).

LC-MS (Method A): Rt=1.10 min; MS (ESIpos): m/z=445 [M+H]$^+$

Example 165

2-(2-Chloro-5-methylphenyl)-N-[4-(4-fluoro-1H-pyrazol-1-yl)-3-sulfamoylphenyl]-acetamide

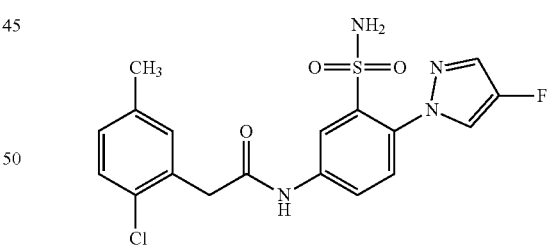

According to general procedure GP5.1, 5-amino-N-(2,4-dimethoxybenzyl)-2-(4-fluoro-1H-pyrazol-1-yl)benzenesulfonamide (0.20 mmol) and (2-chloro-5-methylphenyl) acetic acid (0.40 mmol) were converted to the title compound (20.6 mg, 0.0487 mmol, 24% yield, 100% purity).

LC-MS (Method A): Rt=1.14 min; MS (ESIpos): m/z=423 [M+H]$^+$

Example 166

2-(5-Bromo-4-fluoro-2-methylphenyl)-N-[4-(4-fluoro-1H-pyrazol-1-yl)-3-sulfamoylphenyl]acetamide

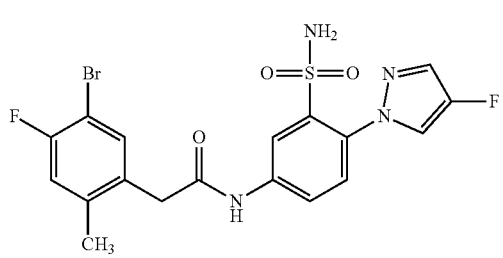 [SMILES: Cc1cc(F)c(Br)cc1CC(=O)Nc1ccc(-n2cc(F)cn2)c(S(N)(=O)=O)c1]

According to general procedure GP5.1, 5-amino-N-(2,4-dimethoxybenzyl)-2-(4-fluoro-1H-pyrazol-1-yl)benzenesulfonamide (0.20 mmol) and (5-bromo-4-fluoro-2-methylphenyl)acetic acid (0.40 mmol) were converted to the title compound (13.7 mg, 0.0282 mmol, 14% yield, 100% purity).

LC-MS (Method A): Rt=1.19 min; MS (ESIpos): m/z=485 [M+H]$^+$

Example 167

N-[4-(4-Fluoro-1H-pyrazol-1-yl)-3-sulfamoylphenyl]-2-(2-isopropylphenyl)acetamide

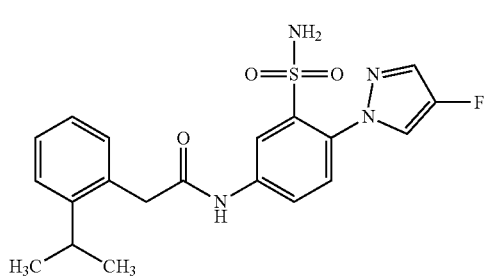 [SMILES: CC(C)c1ccccc1CC(=O)Nc1ccc(-n2cc(F)cn2)c(S(N)(=O)=O)c1]

According to general procedure GP5.1, 5-amino-N-(2,4-dimethoxybenzyl)-2-(4-fluoro-1H-pyrazol-1-yl)benzenesulfonamide (0.20 mmol) and (2-isopropylphenyl)acetic acid (0.40 mmol) were converted to the title compound (21.3 mg, 0.0511 mmol, 26% yield, 100% purity).

LC-MS (Method A): Rt=1.20 min; MS (ESIpos): m/z=417 [M+H]$^+$

Example 168

2-(2-Chloro-5-fluorophenyl)-N-[4-(4-fluoro-1H-pyrazol-1-yl)-3-sulfamoylphenyl]-acetamide

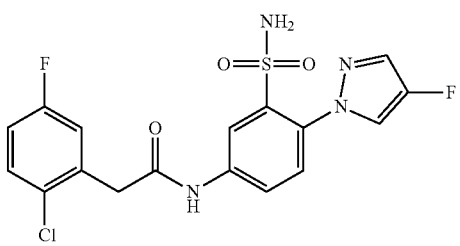 [SMILES: NS(=O)(=O)c1cc(NC(=O)Cc2cc(F)ccc2Cl)ccc1-n1cc(F)cn1]

According to general procedure GP5.1, 5-amino-N-(2,4-dimethoxybenzyl)-2-(4-fluoro-1H-pyrazol-1-yl)benzenesulfonamide (0.20 mmol) and (2-chloro-5-fluorophenyl)acetic acid (0.40 mmol) were converted to the title compound (16.7 mg, 0.0391 mmol, 20% yield, 84% purity).

LC-MS (Method A): Rt=1.09 min; MS (ESIpos): m/z=427 [M+H]$^+$

Example 169

2-[2-Chloro-6-(trifluoromethyl)phenyl]-N-[4-(4-fluoro-1H-pyrazol-1-yl)-3-sulfamoyl-phenyl]acetamide

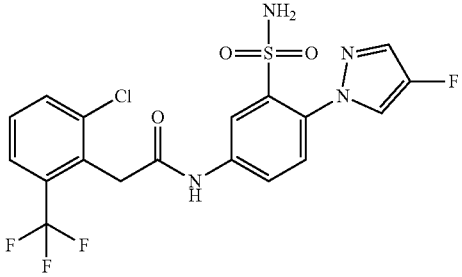

According to general procedure GP5.1, 5-amino-N-(2,4-dimethoxybenzyl)-2-(4-fluoro-1H-pyrazol-1-yl)benzenesulfonamide (0.20 mmol) and [2-chloro-6-(trifluoromethyl)phenyl]acetic acid (0.40 mmol) were converted to the title compound (10.8 mg, 0.0226 mmol, 11% yield, 100% purity).

LC-MS (Method A): Rt=1.16 min, MS (ESIpos): m/z=477 [M+H]$^+$

Example 170

N-[4-(4-Chloro-1H-pyrazol-1-yl)-3-sulfamoylphenyl]-2-(4-methoxyphenyl)acetamide

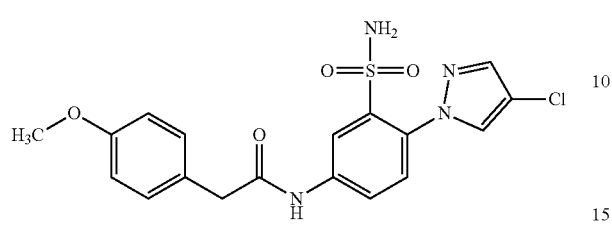

According to general procedure GP5.1, 5-amino-2-(4-chloro-1H-pyrazol-1-yl)-N-(2,4-dimethoxybenzyl)benzenesulfonamide (0.20 mmol) and (4-methoxyphenyl)acetic acid (0.40 mmol) were converted to the title compound (12.2 mg, 0.0290 mmol, 14% yield, 100% purity).

LC-MS (Method A): Rt=1.07 min; MS (ESIpos): m/z=421 [M+H]$^+$

Example 171

2-(2,6-Difluorophenyl)-N-[4-(4-fluoro-1H-pyrazol-1-yl)-3-sulfamoylphenyl]-propanamide

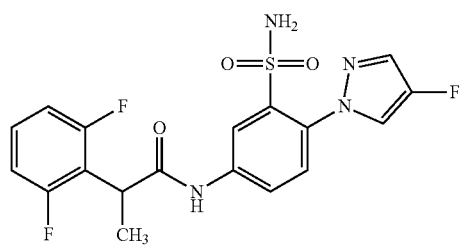 [SMILES: CC(C(=O)Nc1ccc(-n2cc(F)cn2)c(S(N)(=O)=O)c1)c1c(F)cccc1F]

According to general procedure GP5.1, 5-amino-N-(2,4-dimethoxybenzyl)-2-(4-fluoro-1H-pyrazol-1-yl)benzenesulfonamide (0.20 mmol) and (2,6-difluorophenyl)acetic acid (0.40 mmol) were converted to the title compound (12.2 mg, 0.0287 mmol, 14% yield, 100% purity).

LC-MS (Method A): Rt=1.11 min; MS (ESIpos): m/z=425 [M+H]$^+$

Example 172

N-[4-(4-Chloro-1H-pyrazol-1-yl)-3-sulfamoylphenyl]-2-(4-methylphenyl)acetamide

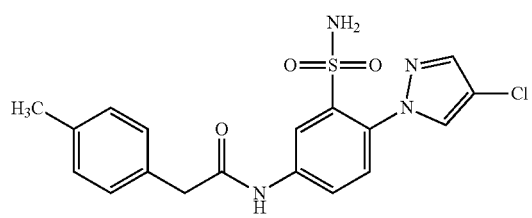 [SMILES: Cc1ccc(CC(=O)Nc2ccc(-n3cc(Cl)cn3)c(S(N)(=O)=O)c2)cc1]

According to general procedure GP5.1, 5-amino-2-(4-chloro-1H-pyrazol-1-yl)-N-(2,4-dimethoxybenzyl)benzenesulfonamide (0.20 mmol) and (4-methylphenyl)acetic acid (0.40 mmol) were converted to the title compound (8.8 mg, 0.0217 mmol, 11% yield, 100% purity).

LC-MS (Method A): Rt=1.15 min, MS (ESIpos): m/z=405 [M+H]$^+$

Example 173

N-[4-(4-Chloro-1H-pyrazol-1-yl)-3-sulfamoylphenyl]-2-(2-methylphenyl)acetamide

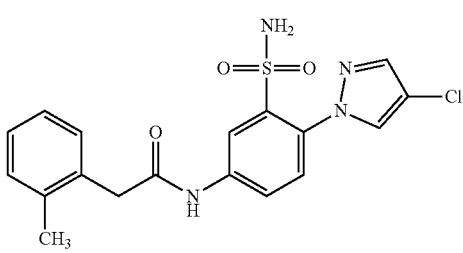 [SMILES: Cc1ccccc1CC(=O)Nc1ccc(-n2cc(Cl)cn2)c(S(N)(=O)=O)c1]

According to general procedure GP5.1, 5-amino-2-(4-chloro-1H-pyrazol-1-yl)-N-(2,4-dimethoxybenzyl)benzenesulfonamide (0.20 mmol) and (2-methylphenyl)acetic acid (0.40 mmol) were converted to the title compound (13.7 mg, 0.0338 mmol, 17% yield, 100% purity).

LC-MS (Method A): Rt=1.13 min; MS (ESIpos): m/z=405 [M+H]$^+$

Example 174

N-[4-(4-Chloro-1H-pyrazol-1-yl)-3-sulfamoylphenyl]-2-(3-methylphenyl)acetamide

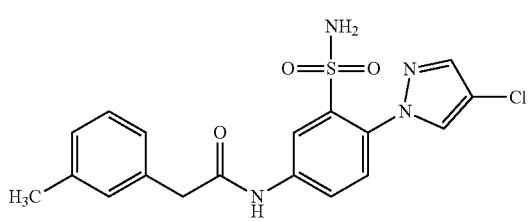 [SMILES: Cc1cccc(CC(=O)Nc2ccc(-n3cc(Cl)cn3)c(S(N)(=O)=O)c2)c1]

According to general procedure GP5.1, 5-amino-2-(4-chloro-1H-pyrazol-1-yl)-N-(2,4-dimethoxybenzyl)benzenesulfonamide (0.20 mmol) and (3-methylphenyl)acetic acid (0.40 mmol) were converted to the title compound (27.3 mg, 0.0674 mmol, 34% yield, 100% purity).

LC-MS (Method A): Rt=1.15 min; MS (ESIpos): m/z=405 [M+H]$^+$

Example 175

N-[4-(4-Chloro-1H-pyrazol-1-yl)-3-sulfamoylphenyl]-2-(2-ethoxyphenyl)acetamide

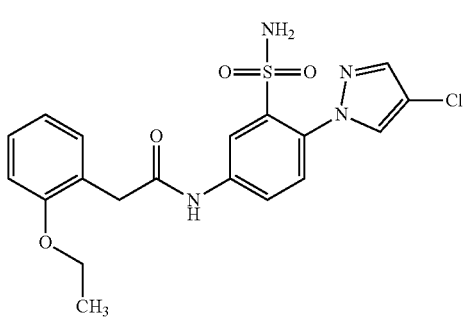

According to general procedure GP5.1, 5-amino-2-(4-chloro-1H-pyrazol-1-yl)-N-(2,4-dimethoxybenzyl)benzenesulfonamide (0.20 mmol) and (2-ethoxyphenyl)acetic acid (0.40 mmol) were converted to the title compound (28.3 mg, 0.0651 mmol, 33% yield, 100% purity).

LC-MS (Method A): Rt=1.15 min; MS (ESIpos): m/z=435 $[M+H]^+$

Example 176

2-(2-Ethoxyphenyl)-N-{3-sulfamoyl-4-[4-(trifluoromethyl)-1H-pyrazol-1-yl]phenyl}acetamide

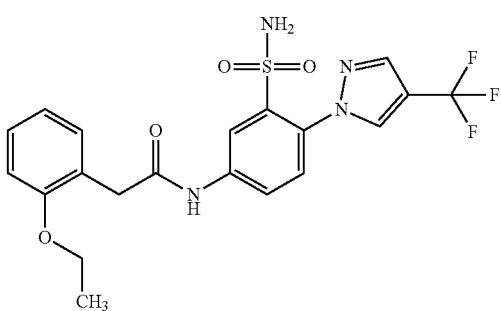 [SMILES: CCOc1ccccc1CC(=O)Nc1ccc(-n2cc(C(F)(F)F)cn2)c(S(N)(=O)=O)c1]

According to general procedure GP5.1, 5-amino-N-(2,4-dimethoxybenzyl)-2-[4-(trifluoromethyl)-1H-pyrazol-1-yl]benzenesulfonamide (0.20 mmol) and (2-ethoxyphenyl)acetic acid (0.40 mmol) were converted to the title compound (4.9 mg, 0.0105 mmol, 5% yield, 100% purity).

LC-MS (Method A): Rt=1.21 min; MS (ESIpos): m/z=469 $[M+H]^+$

Example 177

2-(2-Bromophenyl)-N-[4-(4-fluoro-1H-pyrazol-1-yl)-3-sulfamoylphenyl]acetamide

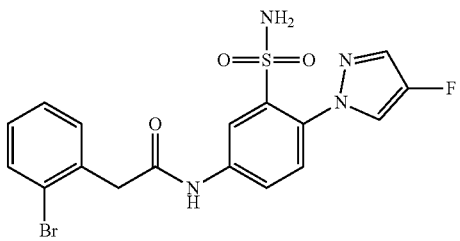 [SMILES: NS(=O)(=O)c1cc(NC(=O)Cc2ccccc2Br)ccc1-n1cc(F)cn1]

According to general procedure GP5.1, 5-amino-N-(2,4-dimethoxybenzyl)-2-(4-fluoro-1H-pyrazol-1-yl)benzenesulfonamide (0.20 mmol) and (2-bromophenyl)acetic acid (0.40 mmol) were converted to the title compound (17.9 mg, 0.0395 mmol, 20% yield, 91% purity).

LC-MS (Method A): Rt=1.09 min; MS (ESIpos): m/z=453 $[M+H]^+$

Example 178

2-(2,4-Dichlorophenyl)-N-[4-(4-fluoro-1H-pyrazol-1-yl)-3-sulfamoylphenyl]acetamide

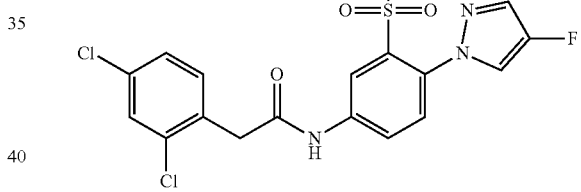

According to general procedure GP5.1, 5-amino-N-(2,4-dimethoxybenzyl)-2-(4-fluoro-1H-pyrazol-1-yl)benzenesulfonamide (0.20 mmol) and (2,4-dichlorophenyl)acetic acid (0.40 mmol) were converted to the title compound (8.3 mg, 0.0187 mmol, 9% yield, 100% purity).

LC-MS (Method A): Rt=1.18 min; MS (ESIpos): m/z=443 $[M+H]^+$

Example 179

2-(2,6-Dichlorophenyl)-N-[4-(4-fluoro-1H-pyrazol-1-yl)-3-sulfamoylphenyl]acetamide

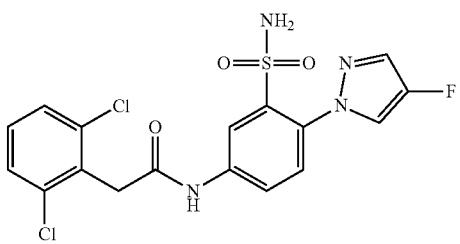 [SMILES: NS(=O)(=O)c1cc(NC(=O)Cc2c(Cl)cccc2Cl)ccc1-n1cc(F)cn1]

According to general procedure GP5.1, 5-amino-N-(2,4-dimethoxybenzyl)-2-(4-fluoro-1H-pyrazol-1-yl)benzenesulfonamide (0.20 mmol) and (2,6-dichlorophenyl)acetic acid (0.40 mmol) were converted to the title compound (20.0 mg, 0.0451 mmol, 23% yield, 100% purity).

LC-MS (Method A): Rt=1.13 min; MS (ESIpos): m/z=443 [M+H]$^+$

Example 180

N-[4-(4-Cyano-1H-pyrazol-1-yl)-3-sulfamoylphenyl]-2-(2-nitrophenyl)acetamide

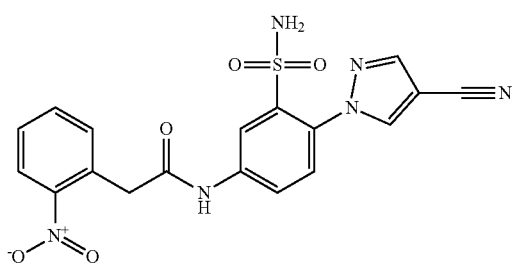

According to general procedure GP5.2, 5-amino-2-(4-cyano-1H-pyrazol-1-yl)-N-(2,4-dimethoxybenzyl)benzenesulfonamide (0.20 mmol) and (2-nitrophenyl)acetic acid (0.40 mmol) were converted to the title compound (19.0 mg, 0.0446 mmol, 22% yield, 100% purity).

LC-MS (Method A): Rt=0.95 min; MS (ESIpos): m/z=427 [M+H]$^+$

Example 181

2-(4-Chlorophenyl)-N-[4-(4-cyano-1H-pyrazol-1-yl)-3-sulfamoylphenyl]acetamide

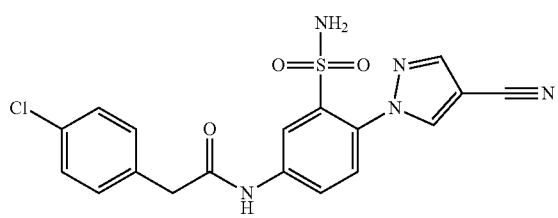 [SMILES: N#Cc1cnn(-c2ccc(NC(=O)Cc3ccc(Cl)cc3)cc2S(N)(=O)=O)c1]

According to general procedure GP5.2, 5-amino-2-(4-cyano-1H-pyrazol-1-yl)-N-(2,4-dimethoxybenzyl)benzenesulfonamide (0.20 mmol) and 4-chlorophenyl)acetic acid (0.40 mmol) were converted to the title compound (17.8 mg, 0.0428 mmol, 21% yield, 100% purity).

LC-MS (Method A): Rt=1.07 min; MS (ESIpos): m/z=416 [M+H]$^+$

Example 182

N-[4-(4-Cyano-1H-pyrazol-1-yl)-3-sulfamoylphenyl]-2-(2-methoxyphenyl)acetamide

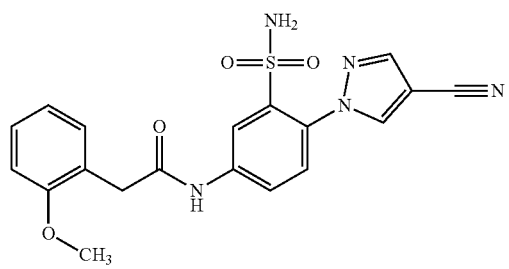 [SMILES: COc1ccccc1CC(=O)Nc1ccc(-n2cc(C#N)cn2)c(S(N)(=O)=O)c1]

According to general procedure GP5.2, 5-amino-2-(4-cyano-1H-pyrazol-1-yl)-N-(2,4-dimethoxybenzyl)benzenesulfonamide (0.20 mmol) and (2-methoxyphenyl)acetic acid (0.40 mmol) were converted to the title compound (24.1 mg, 0.0586 mmol, 29% yield, 100% purity).

LC-MS (Method A): Rt=0.99 min; MS (ESIpos): m/z=412 [M+H]$^+$

Example 183

2-(2-Chloro-6-fluorophenyl)-N-[4-(4-cyano-1H-pyrazol-1-yl)-3-sulfamoylphenyl]-acetamide

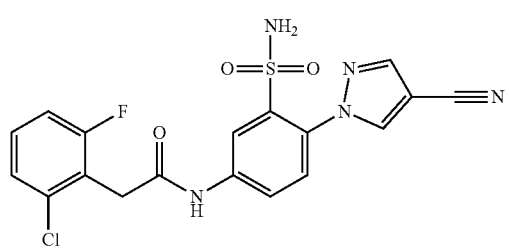

According to general procedure GP5.2, 5-amino-2-(4-cyano-1H-pyrazol-1-yl)-N-(2,4-dimethoxybenzyl)benzenesulfonamide (0.20 mmol) and (2-chloro-6-fluorophenyl)acetic acid (0.40 mmol) were converted to the title compound (37.3 mg, 0.0860 mmol, 43% yield, 100% purity).

LC-MS (Method A): Rt=1.04 min; MS (ESIpos): m/z=434 [M+H]$^+$

Example 184

N-[4-(4-Cyano-1H-pyrazol-1-yl)-3-sulfamoylphenyl]-2-[2-(trifluoromethyl)-phenyl]acetamide

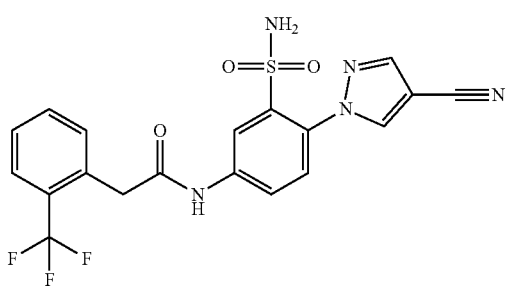 [SMILES: N#Cc1cnn(-c2ccc(NC(=O)Cc3ccccc3C(F)(F)F)cc2S(N)(=O)=O)c1]

According to general procedure GP5.2 5-amino-2-(4-cyano-1H-pyrazol-1-yl)-N-(2,4-dimethoxybenzyl)benzenesulfonamide (0.20 mmol) and [2-(trifluoromethyl)phenyl]acetic acid (0.40 mmol) were converted to the title compound (28.1 mg, 0.0625 mmol, 31% yield, 100% purity).

LC-MS (Method A): Rt=1.08 min; MS (ESIpos): m/z=450 $[M+H]^+$

Example 185

N-[4-(4-Cyano-1H-pyrazol-1-yl)-3-sulfamoylphenyl]-2-(3-fluorophenyl)acetamide

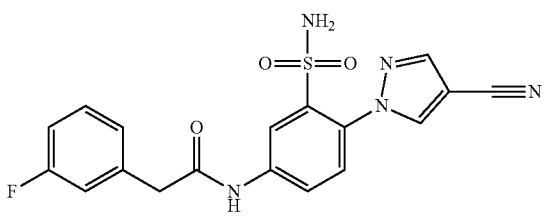 [SMILES: N#Cc1cnn(-c2ccc(NC(=O)Cc3cccc(F)c3)cc2S(N)(=O)=O)c1]

According to general procedure GP5.2, 5-amino-2-(4-cyano-1H-pyrazol-1-yl)-N-(2,4-dimethoxybenzyl)benzenesulfonamide (0.20 mmol) and (3-fluorophenyl)acetic acid (0.40 mmol) were converted to the title compound (24.7 mg, 0.0618 mmol, 31% yield, 100% purity).

LC-MS (Method A): Rt=0.99 min; MS (ESIpos): m/z=400 $[M+H]^+$

Example 186

N-[4-(4-Cyano-1H-pyrazol-1-yl)-3-sulfamoylphenyl]-2-(2,4-dichlorophenyl)acetamide

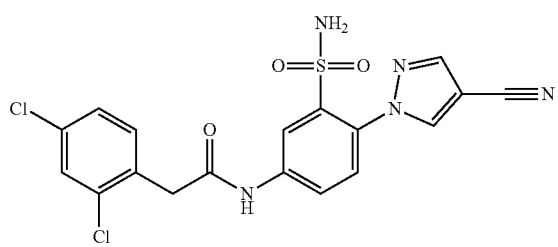 [SMILES: N#Cc1cnn(-c2ccc(NC(=O)Cc3ccc(Cl)cc3Cl)cc2S(N)(=O)=O)c1]

According to general procedure GP5.2, 5-amino-2-(4-cyano-1H-pyrazol-1-yl)-N-(2,4-dimethoxybenzyl)benzenesulfonamide (0.20 mmol) and (2,4-dichlorophenyl)acetic acid (0.40 mmol) were converted to the title compound (25.9 mg, 0.0575 mmol, 29% yield, 100% purity).

LC-MS (Method A): Rt=1.13 min; MS (ESIpos): m/z=450 $[M+H]^+$

Example 187

N-[4-(4-Cyano-1H-pyrazol-1-yl)-3-sulfamoylphenyl]-2-(2,6-dichlorophenyl)acetamide

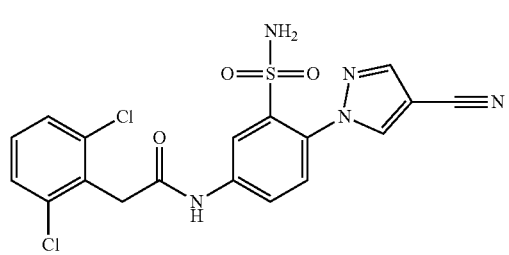 [SMILES: N#Cc1cnn(-c2ccc(NC(=O)Cc3c(Cl)cccc3Cl)cc2S(N)(=O)=O)c1]

According to general procedure GP5.2, 5-amino-2-(4-cyano-1H-pyrazol-1-yl)-N-(2,4-dimethoxybenzyl)benzenesulfonamide (0.20 mmol) and (2,6-dichlorophenyl)acetic acid (0.40 mmol) were converted to the title compound (27.8 mg, 0.0617 mmol, 31% yield, 100% purity).

LC-MS (Method A): Rt=1.08 min; MS (ESIpos): m/z=450 $[M+H]^+$

Example 188

2-(2-Bromophenyl)-N-[4-(4-cyano-1H-pyrazol-1-yl)-3-sulfamoylphenyl]acetamide

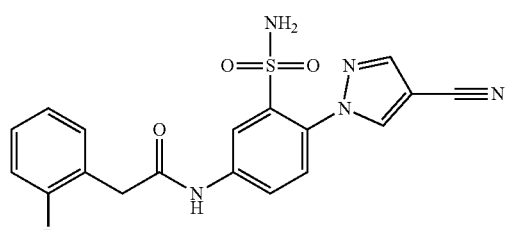

According to general procedure GP5.2, 5-amino-2-(4-cyano-1H-pyrazol-1-yl)-N-(2,4-dimethoxybenzyl)benzenesulfonamide (0.20 mmol) and (2-bromophenyl)acetic acid (0.40 mmol) were converted to the title compound (32.0 mg, 0.0695 mmol, 35% yield, 100% purity).

LC-MS (Method A): Rt=1.04 min; MS (ESIpos): m/z=460 $[M+H]^+$

Example 189

N-[4-(4-Cyano-1H-pyrazol-1-yl)-3-sulfamoylphenyl]-2-(3,4-difluorophenyl)acetamide

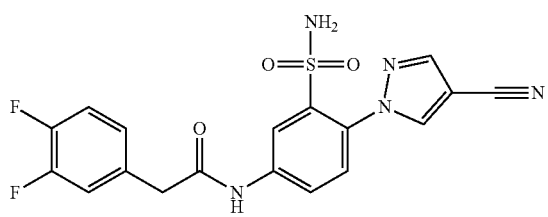 [SMILES: N#Cc1cnn(-c2ccc(NC(=O)Cc3ccc(F)c(F)c3)cc2S(N)(=O)=O)c1]

According to general procedure GP5.2, 5-amino-2-(4-cyano-1H-pyrazol-1-yl)-N-(2,4-dimethoxybenzyl)benzenesulfonamide (0.20 mmol) and (3,4-difluorophenyl)acetic (0.40 mmol) were converted the title compound (4.0 mg, 0.00958 mmol, 5% yield, 86% purity).

LC-MS (Method A): Rt=1.03 min; MS (ESIpos): m/z=418 [M+H]$^+$

Example 190

N-[4-(4-Cyano-1H-pyrazol-1-yl)-3-sulfamoylphenyl]-2-(3,5-difluorophenyl)acetamide

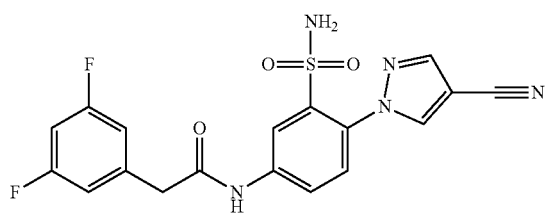

According to general procedure GP5.2, 5-amino-2-(4-cyano-1H-pyrazol-1-yl)-N-(2,4-dimethoxybenzyl)benzenesulfonamide (0.20 mmol) and (3,5-difluorophenyl)acetic acid (0.40 mmol) were converted to the title compound (6.2 mg, 0.0149 mmol, 7% yield, 100% purity).

LC-MS (Method A): Rt=1.03 min; MS (ESIpos): m/z=418 [M+H]$^+$

Example 191

2-(3-Chlorophenyl)-N-[4-(4-cyano-1H-pyrazol-1-yl)-3-sulfamoylphenyl]acetamide

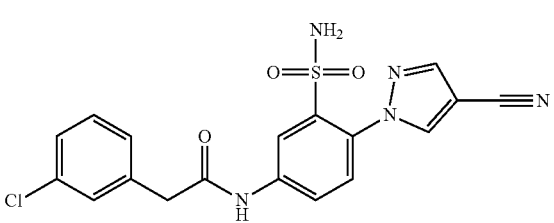 [SMILES: N#Cc1cnn(-c2ccc(NC(=O)Cc3cccc(Cl)c3)cc2S(N)(=O)=O)c1]

According to general procedure GP5.2, 5-amino-2-(4-cyano-1H-pyrazol-1-yl)-N-(2,4-dimethoxybenzyl)benzenesulfonamide (0.20 mmol) and (3-chlorophenyl)acetic acid (0.40 mmol) were converted to the title compound (28.6 mg, 0.0688 mmol, 34% yield, 100% purity).

LC-MS (Method A): Rt=1.07 min; MS (ESIpos): m/z=416 [M+H]$^+$

Example 192

N-[4-(4-Cyano-1H-pyrazol-1-yl)-3-sulfamoylphenyl]-2-(4-fluorophenyl)acetamide

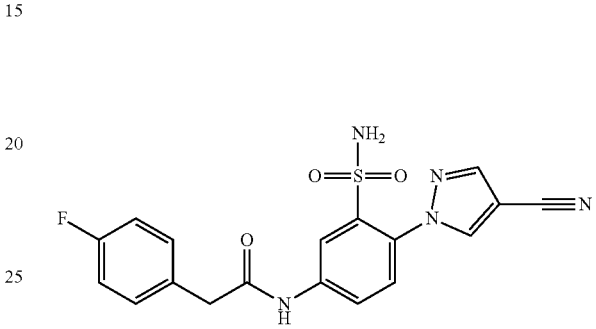

According to general procedure GP5.2 5-amino-2-(4-cyano-1H-pyrazol-1-yl)-N-(2,4-dimethoxybenzyl)benzenesulfonamide (0.20 mmol) and (4-fluorophenyl)acetic acid (0.40 mmol) were converted to the title compound (8:7 mg, 0.0218 mmol, 11% yield, 100% purity).

LC-MS (Method A): Rt=0:99 min; MS (ESIpos): m/z=400 [M+H]$^+$

Example 193

N-[4-(4-Cyano-1H-pyrazol-1-yl)-3-sulfamoylphenyl]-2-(2-hydroxyphenyl)acetamide

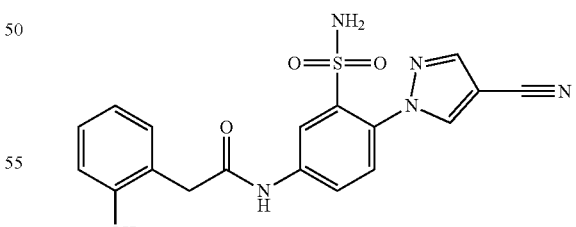

According to general procedure GP5.2, 5-amino-2-(4-cyano-1H-pyrazol-1-yl)-N-(2,4-dimethoxybenzyl)benzenesulfonamide (0.20 mmol) and (2-hydroxyphenyl)acetic acid (0.40 mmol) were converted to the title compound (18:5 mg, 0.0466 mmol, 23% yield, 100% purity).

LC-MS (Method A): Rt=0:88 min; MS (ESIpos): m/z=398 [M+H]$^+$

Example 194

N-[4-(4-Cyano-1H-pyrazol-1-yl)-3-sulfamoylphenyl]-2-(4-hydroxyphenyl)acetamide

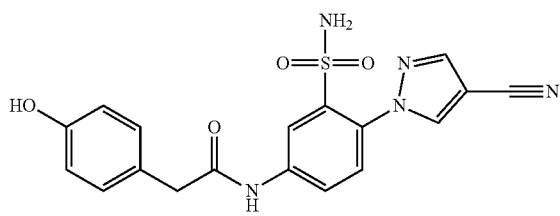 [SMILES: N#Cc1cnn(-c2ccc(NC(=O)Cc3ccc(O)cc3)cc2S(N)(=O)=O)c1]

According to general procedure GP5.2, 5-amino-2-(4-cyano-1H-pyrazol-1-yl)-N-(2,4-dimethoxybenzyl)benzenesulfonamide (0.20 mmol) and (4-hydroxyphenyl)acetic acid (0.40 mmol) were converted to the title compound (14.4 mg, 0.0362 mmol, 18% yield, 100% purity).

LC-MS (Method A): Rt=0:79 min; MS (ESIpos): m/z=398 [M+H]$^+$

Example 195

N-[4-(4-Cyano-1H-pyrazol-1-yl)-3-sulfamoylphenyl]-2-(4-methylphenyl)acetamide

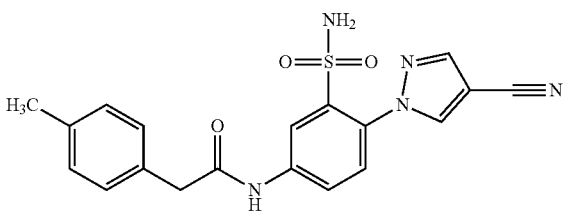 [SMILES: Cc1ccc(CC(=O)Nc2ccc(-n3cc(C#N)cn3)c(S(N)(=O)=O)c2)cc1]

According to general procedure GP5.2, 5-amino-2-(4-cyano-1H-pyrazol-1-yl)-N-(2,4-dimethoxybenzyl)benzenesulfonamide (0.20 mmol) and (4-methylphenyl)acetic acid (0.40 mmol) were converted to the title compound (27.2 mg, 0.0688 mmol, 34% yield, 100% purity).

LC-MS (Method A): Rt=1.04 min; MS (ESIpos): m/z=396 [M+H]$^+$

Example 196

N-[4-(4-Cyano-1H-pyrazol-1-yl)-3-sulfamoylphenyl]-2-(4-methoxyphenyl)acetamide

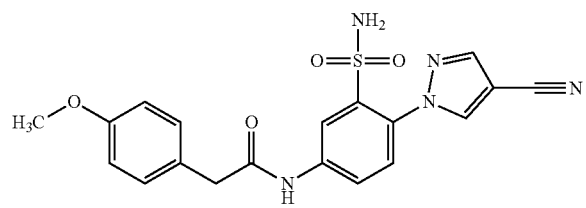 [SMILES: COc1ccc(CC(=O)Nc2ccc(-n3cc(C#N)cn3)c(S(N)(=O)=O)c2)cc1]

According to general procedure GP5.2, 5-amino-2-(4-cyano-1H-pyrazol-1-yl)-N-(2,4-dimethoxybenzyl)benzenesulfonamide (0.20 mmol) and (4-methoxyphenyl)acetic acid (0.40 mmol) were converted to the title compound (25.9 mg, 0.0629 mmol, 31% yield, 100% purity).

LC-MS (Method A): Rt=0.96 min; MS (ESIpos): m/z=412 [M+H]$^+$

Example 197

N-[4-(4-Cyano-1H-pyrazol-1-yl)-3-sulfamoylphenyl]-2-(2-methylphenyl)acetamide

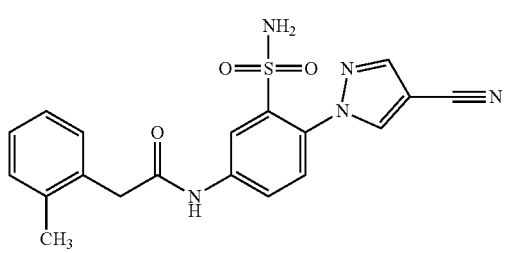 [SMILES: Cc1ccccc1CC(=O)Nc1ccc(-n2cc(C#N)cn2)c(S(N)(=O)=O)c1]

According to general procedure GP5.2, 5-amino-2-(4-cyano-1H-pyrazol-1-yl)-N-(2,4-dimethoxybenzyl)benzenesulfonamide (0.20 mmol) and (2-methylphenyl)acetic acid (0.40 mmol) were converted to the title compound (14.9 mg, 0.0377 mmol, 19% yield, 100% purity).

LC-MS (Method A): Rt=1.03 min; MS (ESIpos): m/z=396 [M+H]$^+$

Example 198

N-[4-(4-Cyano-1H-pyrazol-1-yl)-3-sulfamoylphenyl]-2-(3-methylphenyl)acetamide

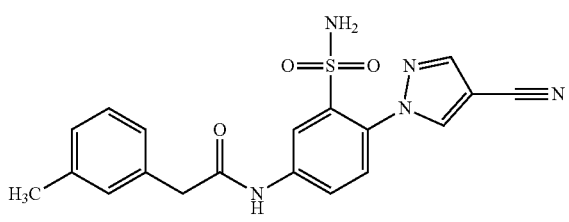 [SMILES: Cc1cccc(CC(=O)Nc2ccc(-n3cc(C#N)cn3)c(S(N)(=O)=O)c2)c1]

According to general procedure GP5.2, 5-amino-2-(4-cyano-1H-pyrazol-1-yl)-N-(2,4-dimethoxybenzyl)benzenesulfonamide (0.20 mmol) and (3-methylphenyl)acetic acid (0.40 mmol) were converted to the title compound (22.0 mg, 0.0556 mmol, 28% yield, 100% purity).

LC-MS (Method A): Rt=1.04 min; MS (ESIpos): m/z=396 [M+H]$^+$

Example 199

N-[4-(4-Cyano-1H-pyrazol-1-yl)-3-sulfamoylphenyl]-2-(2-ethoxyphenyl)acetamide

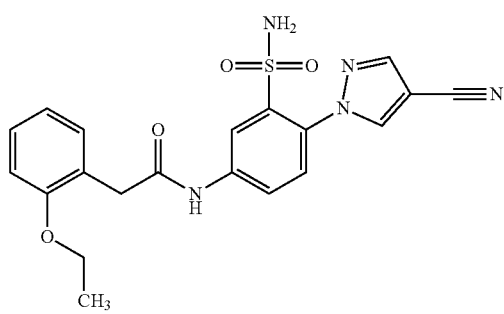 [SMILES: CCOc1ccccc1CC(=O)Nc1ccc(-n2cc(C#N)cn2)c(S(N)(=O)=O)c1]

According to general procedure GP5.2, 5-amino-2-(4-cyano-1H-pyrazol-1-yl)-N-(2,4-dimethoxybenzyl)benzenesulfonamide (0.20 mmol) and (2-ethoxyphenyl)acetic acid (0.40 mmol) were converted to the title compound (27.6 mg, 0.0649 mmol, 32% yield, 100% purity).

LC-MS (Method A): Rt=1.05 min; MS (ESIpos): m/z=426 [M+H]$^+$

Example 200

N-[4-(4-Cyano-1H-pyrazol-1-yl)-3-sulfamoylphenyl]-2-(2,3-difluorophenyl)acetamide

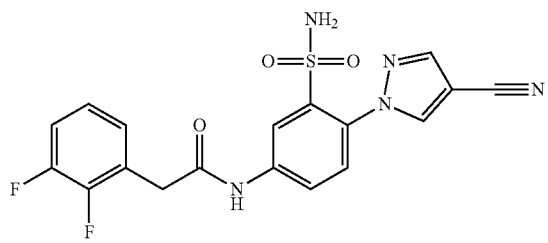 [SMILES: N#Cc1cnn(-c2ccc(NC(=O)Cc3cccc(F)c3F)cc2S(N)(=O)=O)c1]

According to general procedure GP5.2, 5-amino-2-(4-cyano-1H-pyrazol-1-yl)-N-(2,4-dimethoxybenzyl)benzenesulfonamide (0.20 mmol) and (2,3-difluorophenyl)acetic acid (0.40 mmol) were converted to the title compound (28.0 mg, 0.0671 mmol, 34% yield, 100% purity).

LC-MS (Method A): Rt=1.01 min; MS (ESIpos): m/z=418 [M+H]$^+$

Example 201

2-(2-Chloropyridin-3-yl)-N-[4-(4-cyano-1H-pyrazol-1-yl)-3-sulfamoylphenyl]-acetamide

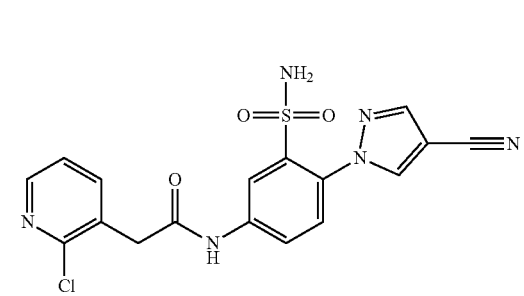 [SMILES: N#Cc1cnn(-c2ccc(NC(=O)Cc3cccnc3Cl)cc2S(N)(=O)=O)c1]

According to general procedure GP5.2, 5-amino-2-(4-cyano-1H-pyrazol-1-yl)-N-(2,4-dimethoxybenzyl)benzenesulfonamide (0.20 mmol) and (2-chloropyridin-3-yl)acetic acid (0.40 mmol) were converted to the title compound (20.7 mg, 0.0497 mmol, 25% yield, 92% purity).

LC-MS (Method A): Rt=0.83 min; MS (ESIpos): m/z=417 [M+H]$^+$

Example 202

2-(2-Chloro-4-fluorophenyl)-N-[4-(4-cyano-1H-pyrazol-1-yl)-3-sulfamoylphenyl]-acetamide

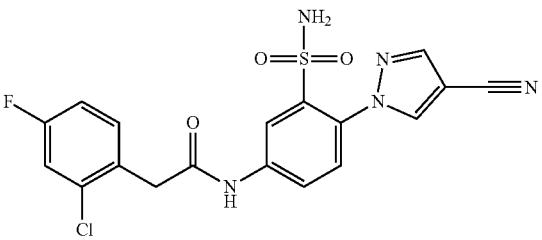 [SMILES: N#Cc1cnn(-c2ccc(NC(=O)Cc3ccc(F)cc3Cl)cc2S(N)(=O)=O)c1]

According to general procedure GP5.2, 5-amino-2-(4-cyano-1H-pyrazol-1-yl)-N-(2,4-dimethoxybenzyl)benzenesulfonamide (0.20 mmol) and (2-chloro-4-fluorophenyl)acetic acid (0.40 mmol) were converted to the title compound (23.4 mg, 0.0539 mmol, 27% yield, 100% purity).

LC-MS (Method A): Rt=1.06 min; MS (ESIpos): m/z=434 [M+H]$^+$

Example 203

N-[4-(4-Cyano-1H-pyrazol-1-yl)-3-sulfamoylphenyl]-2-[2-(difluoromethoxy)phenyl]-acetamide

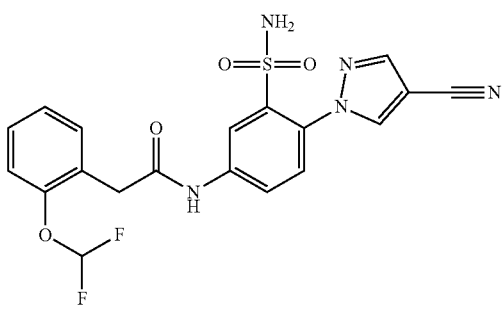 [SMILES: N#Cc1cnn(-c2ccc(NC(=O)Cc3ccccc3OC(F)F)cc2S(N)(=O)=O)c1]

According to general procedure GP5.2, 5-amino-2-(4-cyano-1H-pyrazol-1-yl)-N-(2,4-dimethoxybenzyl)benzenesulfonamide (0.20 mmol) and [2-(difluoromethoxy)phenyl] acetic acid (0.40 mmol) were converted to the title compound (28.4 mg, 0.0635 mmol, 32% yield, 100% purity).

LC-MS (Method A): Rt=1.03 min; MS (ESIpos): m/z=448 [M+H]$^+$

Example 204

N-[4-(4-Cyano-1H-pyrazol-1-yl)-3-sulfamoylphenyl]-2-[2-(trifluoromethoxy)phenyl]-acetamide

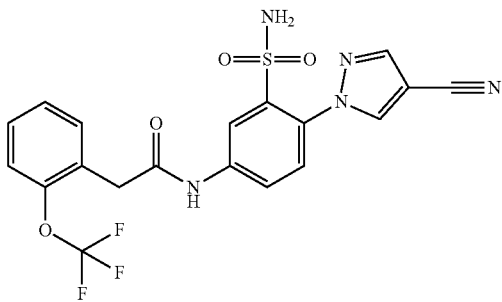 [SMILES: N#Cc1cnn(-c2ccc(NC(=O)Cc3ccccc3OC(F)(F)F)cc2S(N)(=O)=O)c1]

According to general procedure GP5.2, 5-amino-2-(4-cyano-1H-pyrazol-1-yl)-N-(2,4-dimethoxybenzyl)benzenesulfonamide (0.20 mmol) and [2-(trifluoromethoxy)phenyl] acetic acid (0.40 mmol) were converted to the title compound (25.1 mg, 0.0539 mmol, 27% yield, 100% purity).

LC-MS (Method A): Rt=1.11 min; MS (ESIpos): m/z=466 [M+H]$^+$

Example 205

2-(2-Chloro-4,5-difluorophenyl)-N-[4-(4-cyano-1H-pyrazol-1-yl)-3-sulfamoylphenyl]-acetamide

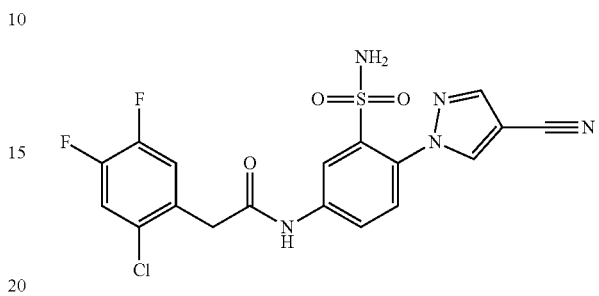

According to general procedure GP5.2, 5-amino-2-(4-cyano-1H-pyrazol-1-yl)-N-(2,4-dimethoxybenzyl)benzenesulfonamide (0.20 mmol) and (2-chloro-4,5-difluorophenyl) acetic acid (0.40 mmol) were converted the title compound (16.5 mg, 0.0365 mmol, 18% yield, 100% purity).

LC-MS (Method A): Rt=1.09 min; MS (ESIpos): m/z=452 [M+H]$^+$

Example 206

2-[2-Chloro-3-(trifluoromethyl)phenyl]-N-[4-(4-cyano-1H-pyrazol-1-yl)-3-sulfamoylphenyl]acetamide

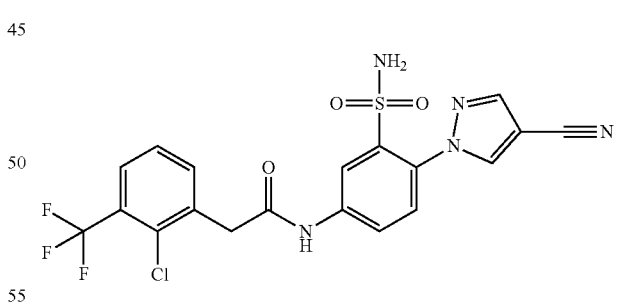

According to general procedure GP5.2, 5-amino-2-(4-cyano-1H-pyrazol-1-yl)-N-(2,4-dimethoxybenzyl)benzenesulfonamide (0.20 mmol) and [2-chloro-3-(trifluoromethyl)phenyl]acetic acid (0.40 mmol) were converted to the title compound (14.4 15 mg, 0.0298 mmol, 15% yield, 100% purity).

LC-MS (Method A): Rt=1.15 min; MS (ESIpos): m/z=484 [M+H]$^+$

Example 207

2-(2-Chloro-6-fluoro-3-methylphenyl)-N-[4-(4-cyano-1H-pyrazol-1-yl)-3-sulfamoylphenyl]acetamide

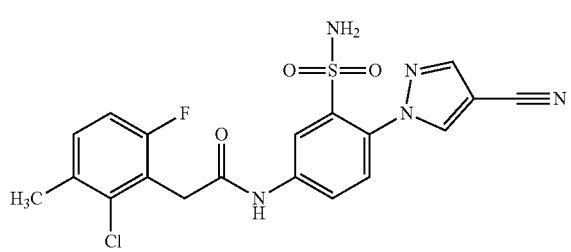 [SMILES: Cc1ccc(F)c(CC(=O)Nc2ccc(-n3cc(C#N)cn3)c(S(N)(=O)=O)c2)c1Cl]

According to general procedure GP5.2, 5-amino-2-(4-cyano-1H-pyrazol-1-yl)-N-(2,4-dimethoxybenzyl)benzenesulfonamide (0.20 mmol) and (2-chloro-6-fluoro-3-methylphenyl)acetic acid (0.40 mmol) were converted to the title compound (28.1 mg, 0.0627 mmol, 31% yield, 100% purity).

LC-MS (Method A): Rt=1.11 min; MS (ESIpos): m/z=448 [M+H]$^+$

Example 208

2-(2-Chloro-3,6-difluorophenyl)-N-[4-(4-cyano-1H-pyrazol-1-yl)-3-sulfamoylphenyl]-acetamide

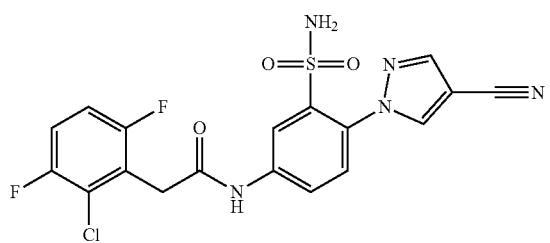 [SMILES: N#Cc1cnn(-c2ccc(NC(=O)Cc3c(F)ccc(F)c3Cl)cc2S(N)(=O)=O)c1]

According to general procedure GP5.2, 5-amino-2-(4-cyano-1H-pyrazol-1-yl)-N-(2,4-dimethoxybenzyl)benzenesulfonamide (0.20 mmol) and (2-chloro-3,6-difluorophenyl)acetic acid (0.40 mmol) were converted to the title compound (6.5 mg, 0.0144 mmol, 7% yield, 100% purity).

LC-MS (Method A): Rt=1.05 min; MS (ESIpos): m/z=452 [M+H]$^+$

Example 209

2-(2-Chloro-5-methylphenyl)-N-[4-(4-cyano-1H-pyrazol-1-yl)-3-sulfamoylphenyl]-acetamide

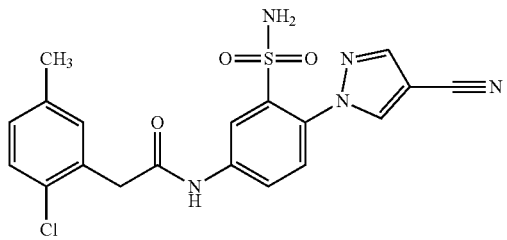 [SMILES: Cc1ccc(Cl)c(CC(=O)Nc2ccc(-n3cc(C#N)cn3)c(S(N)(=O)=O)c2)c1]

According to general procedure GP5.2, 5-amino-2-(4-cyano-1H-pyrazol-1-yl)-N-(2,4-dimethoxybenzyl)benzenesulfonamide (0.20 mmol) and (2-chloro-5-methylphenyl)acetic acid (0.40 mmol) were converted to the title compound (19.4 mg, 0.0451 mmol, 23% yield, 100% purity).

LC-MS (Method A): Rt=1.10 min; MS (ESIpos): m/z=430 [M+H]$^+$

Example 210

2-(2-Chloro-4-methoxyphenyl)-N-[4-(4-cyano-1H-pyrazol-1-yl)-3-sulfamoylphenyl]-acetamide

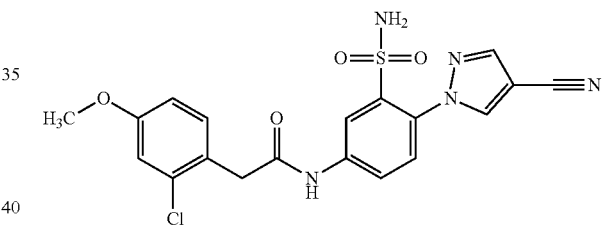

According to general procedure GP5.2, 5-amino-2-(4-cyano-1H-pyrazol-1-yl)-N-(2,4-dimethoxybenzyl)benzenesulfonamide (0.20 mmol) and (2-chloro-4-methoxyphenyl)acetic acid (0.40 mmol) were converted to the title compound (14.9 mg, 0.0334 mmol, 17% yield, 100% purity).

LC-MS (Method A): Rt=1.04 min; MS (ESIpos): m/z=446 [M+H]$^+$

Example 211

N-[4-(4-Cyano-1H-pyrazol-1-yl)-3-sulfamoylphenyl]-2-(2,5-dichlorophenyl)acetamide

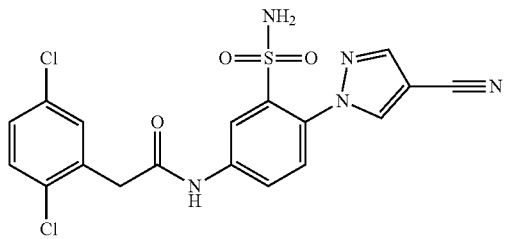 [SMILES: N#Cc1cnn(-c2ccc(NC(=O)Cc3cc(Cl)ccc3Cl)cc2S(N)(=O)=O)c1]

According to general procedure GP5.2, 5-amino-2-(4-cyano-1H-pyrazol-1-yl)-N-(2,4-dimethoxybenzyl)benzenesulfonamide (0.20 mmol) and (2,5-dichlorophenyl)acetic acid (0.40 mmol) were converted to the title compound (17.1 mg, 0.0380 mmol, 19% yield, 100% purity).

LC-MS (Method A): Rt=1.12 min; MS (ESIpos): m/z=450 [M+H]+

Example 212

2-(5-Chloro-2-methoxyphenyl)-N-[4-(4-cyano-1H-pyrazol-1-yl)-3-sulfamoylphenyl]-acetamide

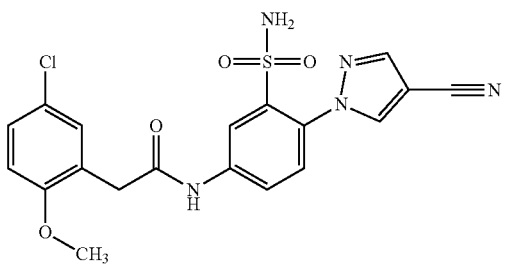

According to general procedure GP5.2, 5-amino-2-(4-cyano-1H-pyrazol-1-yl)-N-(2,4-dimethoxybenzyl)benzenesulfonamide (0.20 mmol) and (5-chloro-2-methoxyphenyl) acetic acid (0.40 mmol) were converted to the title compound (26.8 mg, 0.0601 mmol, 30% yield, 100% purity).

LC-MS (Method A): Rt=1.08 min; MS (ESIpos): m/z=446 [M+H]+

Example 213

N-[4-(4-Cyano-1H-pyrazol-1-yl)-3-sulfamoylphenyl]-2-[2-(propan-2-yl)phenyl]-acetamide

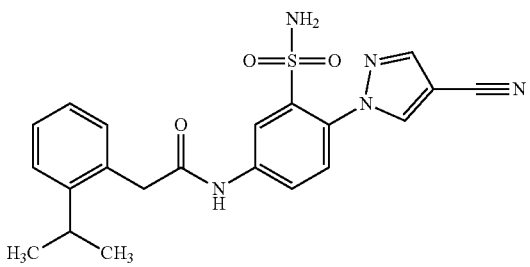 [SMILES: CC(C)c1ccccc1CC(=O)Nc1ccc(-n2cc(C#N)cn2)c(S(N)(=O)=O)c1]

According to general procedure GP5.2, 5-amino-2-(4-cyano-1H-pyrazol-1-yl)-N-(2,4-dimethoxybenzyl)benzenesulfonamide (0.20 mmol) and (2-isopropylphenyl)acetic acid (0.40 mmol) were converted to the title compound (33.3 mg, 0.0786 mmol, 39% yield, 100% purity).

LC-MS (Method A): Rt=1.15 min; MS (ESIpos): m/z=424 [M+H]+

Example 214

2-(2-Chloro-5-fluorophenyl)-N-[4-(4-cyano-1H-pyrazol-1-yl)-3-sulfamoylphenyl]-acetamide

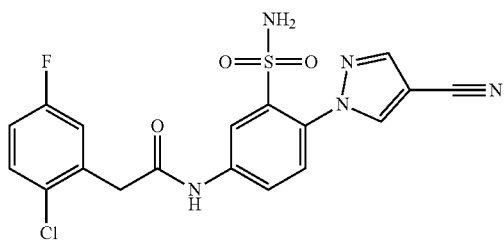 [SMILES: N#Cc1cnn(-c2ccc(NC(=O)Cc3cc(F)ccc3Cl)cc2S(N)(=O)=O)c1]

According to general procedure GP5.2, 5-amino-2-(4-cyano-1H-pyrazol-1-yl)-N-(2,4-dimethoxybenzyl)benzenesulfonamide (0.20 mmol) and (2-chloro-5-fluorophenyl)acetic acid (0.40 mmol) were converted the title compound (23.0 mg, 0.0530 mmol, 27% yield, 100% purity).

LC-MS (Method A): Rt=1.04 min, MS (ESIpos): m/z=434 [M+H]+

Example 215

2-[2-Chloro-6-(trifluoromethyl)phenyl]-N-[4-(4-cyano-1H-pyrazol-1-yl)-3-sulfamoylphenyl]acetamide

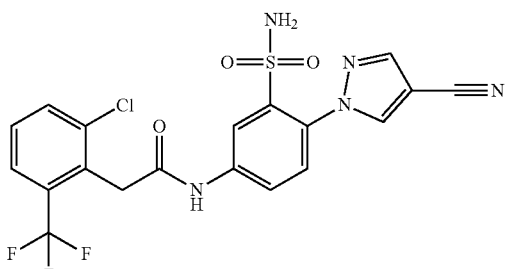

According to general procedure GP5.2, 5-amino-2-(4-cyano-1H-pyrazol-1-yl)-N-(2,4-dimethoxybenzyl)benzenesulfonamide (0.20 mmol) and [2-chloro-6-(trifluoromethyl)phenyl]acetic acid (0.40 mmol) were converted to the title compound (25.0 mg, 0.0517 mmol, 26% yield, 100% purity).

LC-MS (Method A): Rt=1.12 min; MS (ESIpos): m/z=484 [M+H]+

Example 216

2-(2-Chloro-6-methoxyphenyl)-N-[4-(4-cyano-1H-pyrazol-1-yl)-3-sulfamoyl-phenyl]acetamide

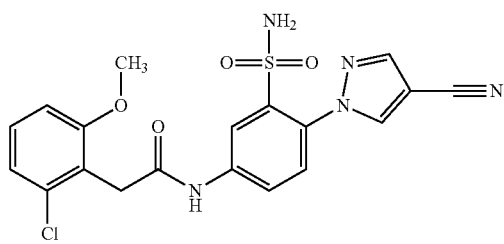 [SMILES: COc1cccc(Cl)c1CC(=O)Nc1ccc(-n2cc(C#N)cn2)c(S(N)(=O)=O)c1]

According to general procedure GP5.2, 5-amino-2-(4-cyano-1H-pyrazol-1-yl)-N-(2,4-dimethoxybenzyl)benzenesulfonamide (0.20 mmol) and (2-chloro-6-methoxyphenyl)acetic acid (0.40 mmol) were converted to the title compound (7.8 mg, 0.0175 mmol, 9% yield, 100% purity).

LC-MS (Method A): Rt=1.06 min; MS (ESIpos): m/z=446 [M+H]$^+$

Example 217

2-(2-Chloro-4,6-difluorophenyl)-N-[4-(4-cyano-1H-pyrazol-1-yl)-3-sulfamoyl-phenyl]acetamide

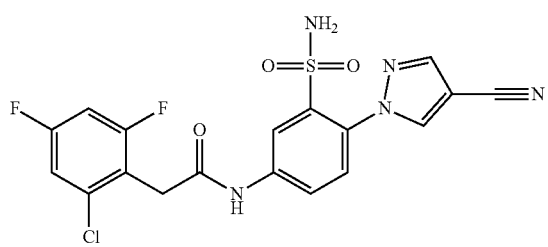 [SMILES: N#Cc1cnn(-c2ccc(NC(=O)Cc3c(F)cc(F)cc3Cl)cc2S(N)(=O)=O)c1]

According to general procedure GP5.2, 5-amino-2-(4-cyano-1H-pyrazol-1-yl)-N-(2,4-dimethoxybenzyl)benzenesulfonamide (0.20 mmol) and (2-chloro-4,6-difluorophenyl)acetic acid (0.40 mmol) were converted to the title compound (18.0 mg, 0.0398 mmol, 20% yield, 100% purity).

LC-MS (Method A): Rt=1.07 min; MS (ESIpos): m/z=452 [M+H]$^+$

Example 218

2-(3-Chloropyridin-4-yl)-N-[4-(4-cyano-1H-pyrazol*1-yl)-3-sulfamoyl-phenyl]acetamide

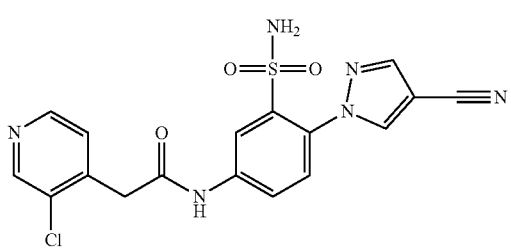 [SMILES: N#Cc1cnn(-c2ccc(NC(=O)Cc3ccncc3Cl)cc2S(N)(=O)=O)c1]

According to general procedure GP5.2, 5-amino-2-(4-cyano-1H-pyrazol-1-yl)-N-(2,4-dimethoxybenzyl)benzenesulfonamide (0.20 mmol) and (3-chloropyridin-4-yl)acetic acid (0.40 mmol) were converted to the title compound (31.2 mg, 0.0748 mmol, 37% yield, 100% purity).

LC-MS (Method A): Rt=0.81 min; MS (ESIpos): m/z=417 [M+H]$^+$

Example 219

N-[4-(4-Cyano-1H-pyrazol-1-yl)-3-sulfamoylphenyl]-2-[4-(difluoromethyl)-phenyl]acetamide

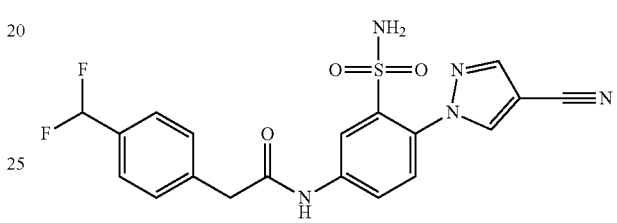

According to general procedure GP5.2, 5-amino-2-(4-cyano-1H-pyrazol-1-yl)-N-(2,4-dimethoxybenzyl)benzenesulfonamide (0.20 mmol) and [4-(difluoromethyl)phenyl]acetic acid (0.40 mmol) were converted to the title compound (21.8 mg, 0.0505 mmol, 25% yield, 100% purity).

LC-MS (Method A): Rt=1.02 min; MS (ESIpos): m/z=432 [M+H]$^+$

Example 220

2-(2-Chlorophenyl)-N-[4-(4-cyano-1H-pyrazol-1-yl)-3-sulfamoylphenyl]-2,2-difluoroacetamide

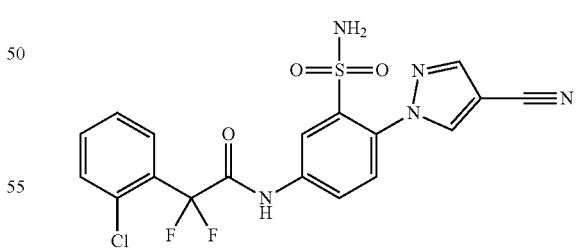

According to general procedure GP5.2, 5-amino-2-(4-cyano-1H-pyrazol-1-yl)-N-(2,4-dimethoxybenzyl)benzenesulfonamide (0.20 mmol) and (2-chlorophenyl)(difluoro)acetic acid (0.40 mmol) were converted to the title compound (10.9 mg, 0.0241 mmol, 12% yield, 100% purity).

LC-MS (Method A): Rt=1.09 min; MS (ESIpos): m/z=452 [M+H]$^+$

Example 221

2-(2-Fluorophenyl)-N-{3-sulfamoyl-4-[5-(trifluoromethyl)pyridin-3-yl]phenyl}-acetamide

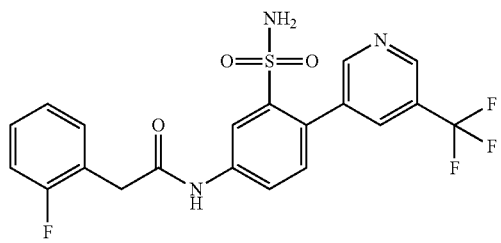 [SMILES: NS(=O)(=O)c1cc(NC(=O)Cc2ccccc2F)ccc1-c1cncc(C(F)(F)F)c1]

According to general procedure GP6, 5-amino-N-[(dimethylamino)methylene]-2-[5-(trifluoromethyl)pyridin-3-yl]benzenesulfonamide (47.0 mg, 0.126 mmol) and (2-fluorophenyl)acetic acid (29.2 mg, 0.189 mmol) were converted to the title compound and were purified by preparative HPLC (Waters XBridge C18 5μ 100×30 mm, acetonitrile/water+0.2% aqueous ammonia (32%)) (14 mg, 0.0309 mmol, 25% yield over 2 steps, 97% purity).

LC-MS (Method B): Rt=0.97 min; MS (ESIpos): m/z=454 [M+H]$^+$ $^1$H-NMR (400 MHz, DMSO-d$_6$) δ [ppm]: 3.80 (s, 2H), 7.15-7.23 (m, 2H), 7.30-7.52 (m, 5H), 7.87 (dd, 1H), 8.12-8.15 (m, 1H), 8.40 (d, 1H), 8.81 (d, 1H), 8.96 (d, 1H), 10.71 (s, 1H).

Example 222

N-{3-Sulfamoyl-4-[5-(trifluoromethyl)pyridin-3-yl]phenyl}-2-[2-(trifluoromethoxy)-phenyl]acetamide

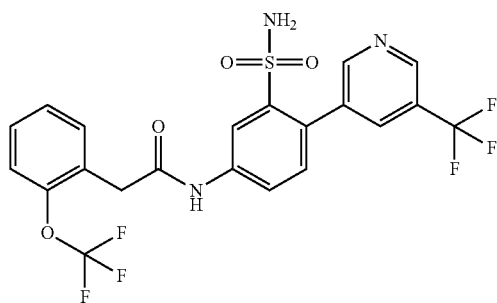 [SMILES: NS(=O)(=O)c1cc(NC(=O)Cc2ccccc2OC(F)(F)F)ccc1-c1cncc(C(F)(F)F)c1]

According to general procedure GP6, 5-amino-N-[(dimethylamino)methylene]-2-[5-(trifluoromethyl)pyridin-3-yl]benzenesulfonamide (47.0 mg, 0.126 mmol) and [2-(trifluoromethoxy)phenyl]acetic acid (41.7 mg, 0.189 mmol) were converted to the title compound and were purified by preparative HPLC (Waters XBridge C18 5μ 100×30 mm, acetonitrile/water+0.2% aqueous ammonia (32%)) (14 mg, 0.0270 mmol, 21% yield over 2 steps, 98% purity).

LC-MS (Method B): Rt=1.11 min; MS (ESIpos): m/z=520 [M+H]$^+$ $^1$H-NMR (400 MHz, DMSO-d$_6$) δ [ppm]: 3.85 (s, 2H), 7.34-7.49 (m, 6H), 7.51 (dd, 1H), 7.88 (dd, 1H), 8.12-8.15 (m, 1H), 8.37 (d, 1H), 8.82 (d, 1H), 8.96 (d, 1H), 10.72 (s, 1H).

Example 223

N-{4-[1-(Difluoromethyl)-1H-pyrazol-4-yl]-3-sulfamoylphenyl}-2-(2-methylphenyl)-acetamide

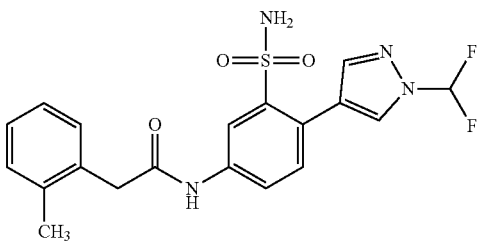

According to general procedure GP6, 5-amino-2-[1-(difluoromethyl)-1H-pyrazol-4-yl]-N-[(dimethylamino)methylene]benzenesulfonamide (47.0 mg, 0.137 mmol) and (2-methylphenyl)acetic acid (30.8 mg, 0.205 mmol) were converted to the title compound and were purified by preparative HPLC (Waters XBridge C18 5μ 100×30 mm, acetonitrile/water+0.2% aqueous ammonia (32%)) (13 mg, 0.0309 mmol, 23% yield over 2 steps, 97% purity).

LC-MS (Method B): Rt=0.93 min; MS (ESIpos): m/z=421 [M+H]$^+$ $^1$H-NMR (400 MHz, DMSO-d$_6$) δ [ppm]: 3.72 (s, 2H), 7.12-7.20 (m, 3H), 7.22-7.28 (m, 1H), 7.39 (s, 2H), 7.47 (d, 1H), 7.84 (t, 1H), 7.86 (dd, 1H), 8.01 (s, 1H), 8.34 (d, 1H), 8.42 (s, 1H), 10.57 (s, 1H).

Example 224

N-{4-[1-(Difluoromethyl)-1H-pyrazol-4-yl]-3-sulfamoylphenyl}-2-[2-(trifluoromethyl)-phenyl]acetamide

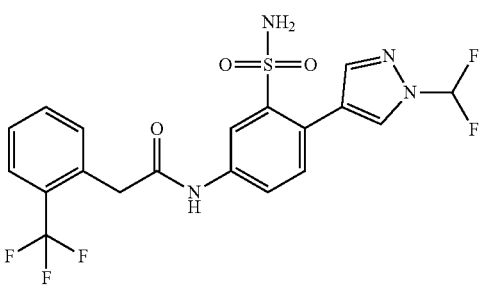

According to general procedure GP6, 5-amino-2-[1-(difluoromethyl)-1H-pyrazol-4-yl]-N-[(dimethylamino)methylene]benzenesulfonamide (47.0 mg, 0.137 mmol) and [2-(trifluoromethyl)phenyl]acetic acid (42.0 mg, 0.205 mmol) were converted to the title compound and were purified by preparative HPLC (Waters XBridge C18 5μ 100×30 mm, acetonitrile/water+0.2% aqueous ammonia (32%)) (14 mg, 0.0295 mmol, 22% yield over 2 steps, 97% purity).

LC-MS (Method B): Rt=1.00 min; MS (ESIpos): m/z=475 [M+H]$^+$ $^1$H-NMR (400 MHz, DMSO-d$_6$) δ [ppm]: 3.97 (s, 2H), 7.40 (s, 2H), 7.45-7.57 (m, 3H), 7.63-7.74 (m, 2H), 7.83 (dd, 1H), 7.84 (t, 1H), 8.01 (s, 1H), 8.34 (d, 1H), 8.42 (s, 1H), 10.62 (s, 1H).

Example 225

2-[2-(Difluoromethyl)phenyl]-N-{4-[1-(difluoromethyl)-1H-pyrazol-4-yl]-3-sulfamoylphenyl}acetamide

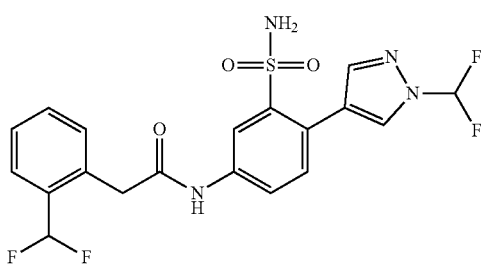 [SMILES: NS(=O)(=O)c1cc(NC(=O)Cc2ccccc2C(F)F)ccc1-c1cnn(C(F)F)c1]

According to general procedure GP6, 5-amino-2-[1-(difluoromethyl)-1H-pyrazol-4-yl]-N-[(dimethylamino)methylene]benzenesulfonamide (47.0 mg, 0.137 mmol) and [2-(difluoromethyl)phenyl]acetic acid (38.2 mg, 0.205 mmol) were converted to the title compound and were purified by preparative HPLC (Waters XBridge C18 5μ 100×30 mm, acetonitrile/water+0.2% aqueous ammonia (32%)) (14 mg, 0.0307 mmol, 22% yield over 2 steps, 99% purity).

LC-MS (Method B): Rt=0.94 min; MS (ESIpos): m/z=457 [M+H]$^+$ $^1$H-NMR (400 MHz, DMSO-d$_6$) δ [ppm]: 3.92 (s, 2H), 7.24 (t, 1H), 7.30-7.56 (m, 6H), 7.60 (d, 1H), 7.84 (dd, 1H), 7.84 (t, 1H), 8.01 (s, 1H), 8.34 (d, 1H), 8.42 (s, 1H), 10.62 (s, 1H).

Example 226

N-{4-[1-(Difluoromethyl)-1H-pyrazol-4-yl]-3-sulfamoylphenyl}-2-(2-methoxyphenyl)-acetamide

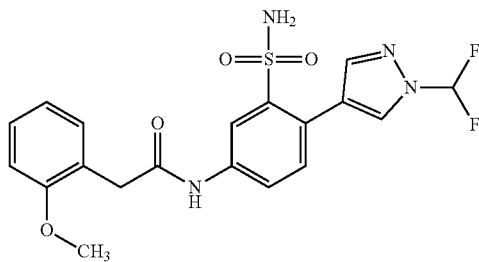 [SMILES: COc1ccccc1CC(=O)Nc1ccc(-c2cnn(C(F)F)c2)c(S(N)(=O)=O)c1]

According to general procedure GP6.1, 5-amino-2-[1-(difluoromethyl)-1H-pyrazol-4-yl]-N-[(dimethylamino)methylene]benzenesulfonamide (47.0 mg, 0.137 mmol) and (2-methoxyphenyl)acetic acid (34.1 mg, 0.205 mmol) were converted to the title compound and were purified by preparative HPLC (Waters XBridge C18 5μ 100×30 mm, acetonitrile/water+0.2% aqueous ammonia (32%)) (15 mg, 0.0344 mmol, 25% yield over 2 steps, 98% purity).

LC-MS (Method B): Rt=0.89 min; MS (ESIpos): m/z=437 [M+H]$^+$ $^1$H-NMR (400 MHz, DMSO-d$_6$) δ [ppm]: 3.67 (s, 2H), 3.77 (s, 3H), 6.91 (td, 1H), 6.98 (dd, 1H), 7.20-7.29 (m, 2H), 7.39 (s, 2H), 7.46 (d, 1H), 7.84 (t, 1H), 7.84 (dd, 1H), 8.01 (s, 1H), 8.36 (d, 1H), 8.42 (s, 1H), 10.47 (s, 1H).

Example 227

N-{4-[1-(Difluoromethyl)-1H-pyrazol-4-yl]-3-sulfamoylphenyl}-2-(4-fluorophenyl)-acetamide

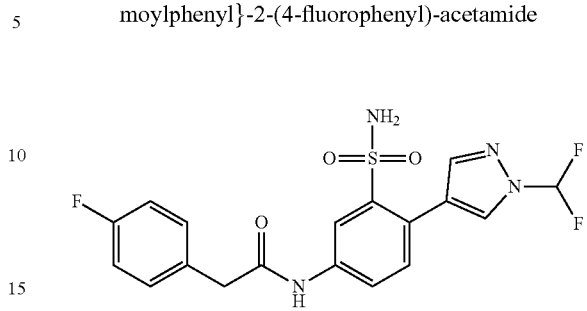

According to general procedure GP6.1, 5-amino-2-[1-(difluoromethyl)-1H-pyrazol-4-yl]-N-[(dimethylamino)methylene]benzenesulfonamide (47.0 mg, 0.137 mmol) and (4-fluorophenyl)acetic acid (31.6 mg, 0.205 mmol) were converted to the title compound and were purified by preparative HPLC (Waters XBridge C18 5μ 100×30 mm, acetonitrile/water+0.2% aqueous ammonia (32%)) (14 mg, 0.0330 mmol, 24% yield over 2 steps, 98% purity).

LC-MS (Method B): Rt=0.89 min; MS (ESIpos): m/z=425 [M+H]$^+$ $^1$H-NMR (400 MHz, DMSO-d$_6$) δ [ppm]: 3.68 (s, 2H), 7.12-7.20 (m, 2H), 7.32-7.44 (m, 4H), 7.46 (d, 1H), 7.83 (t, 1H), 7.84 (dd, 1H), 8.00 (s, 1H), 8.33 (d, 1H), 8.42 (s, 1H), 10.57 (s, 1H).

Example 228

2-(2-Chloro-5-fluorophenyl)-N-{4-[1-(difluoromethyl)-1H-pyrazol-4-yl]-3-sulfamoylphenyl}acetamide

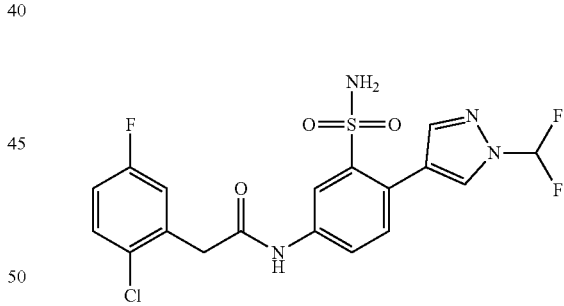

According to general procedure GP6.1, 5-amino-2-[1-(difluoromethyl)-1H-pyrazol-4-yl]-N-[(dimethylamino)methylene]benzenesulfonamide (47.0 mg, 0.137 mmol) and (2-chloro-5-fluorophenyl)acetic acid (38.7 mg, 0.205 mmol) were converted to the title compound and were purified by preparative HPLC (Waters XBridge C18 5μ 100×30 mm, acetonitrile/water+0.2% aqueous ammonia (32%)) (13 mg, 0.0283 mmol, 21% yield over 2 steps, 99% purity).

LC-MS (Method B): Rt=0.95 min; MS (ESIpos): m/z=459 [M+H]$^+$ $^1$H-NMR (400 MHz, DMSO-d$_6$) δ [ppm]: 3.90 (s, 2H), 7.20 (td, 1H), 7.37 (dd, 1H), 7.41 (s, 2H), 7.46-7.53 (m, 2H), 7.83 (dd, 1H), 7.84 (t, 1H), 8.01 (s, 1H), 8.35 (d, 1H), 8.42 (d, 1H), 10.66 (s, 1H).

Example 229

2-(2,3-Dichlorophenyl)-N-{4-[1-(difluoromethyl)-1H-pyrazol-4-yl]-3-sulfamoylphenyl}-acetamide

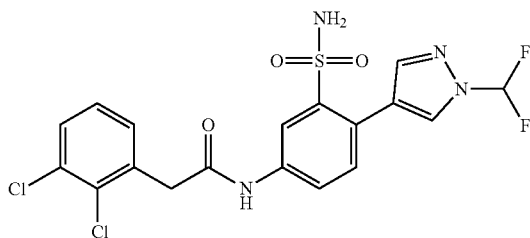 [SMILES: NS(=O)(=O)c1cc(NC(=O)Cc2cccc(Cl)c2Cl)ccc1-c1cnn(C(F)F)c1]

According to general procedure GP6.1, 5-amino-2-[1-(difluoromethyl)-1H-pyrazol-4-yl]-N-[(dimethylamino)methylene]benzenesulfonamide (47.0 mg, 0.137 mmol) and (2,3-dichlorophenyl)acetic acid (42.1 mg, 0.205 mmol) were converted to the title compound and were purified by preparative HPLC (Waters XBridge C18 5μ 100×30 mm, acetonitrile/water+0.2% aqueous ammonia (32%)) (14 mg, 0.0295 mmol, 22% yield over 2 steps, 98% purity).

LC-MS (Method B): Rt=1.02 min; MS (ESIpos): m/z=475 [M+H]$^+$ $^1$H-NMR (400 MHz, DMSO-d$_6$) δ [ppm]: 3.97 (s, 2H), 7.33-7.45 (m, 4H), 7.48 (d, 1H), 7.58 (dd, 1H), 7.83 (dd, 1H), 7.84 (t, 1H), 8.01 (s, 1H), 8.35 (d, 1H), 8.42 (d, 1H), 10.67 (s, 1H).

Example 230

2-(3-Chloropyridin-4-yl)-N-{4-[1-(difluoromethyl)-1H-pyrazol-4-yl]-3-sulfamoyl-phenyl}acetamide

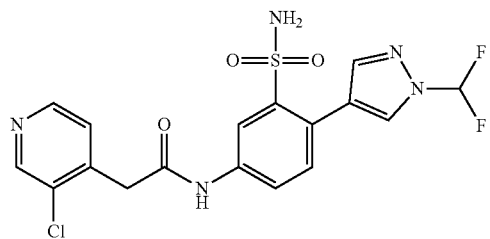 [SMILES: NS(=O)(=O)c1cc(NC(=O)Cc2ccncc2Cl)ccc1-c1cnn(C(F)F)c1]

According to general procedure GP6.1, 5-amino-2-[1-(difluoromethyl)-1H-pyrazol-4-yl]-N-[(dimethylamino)methylene]benzenesulfonamide (47.0 mg, 0.137 mmol) and (3-chloropyridin-4-yl)acetic acid (35.2 mg, 0.205 mmol) were converted to the title compound and were purified by preparative HPLC (Waters XBridge C18 5μ 100×30 mm, acetonitrile/water+0.2% aqueous ammonia (32%)) (11 mg, 0.0249 mmol, 18% yield over 2 steps, 98% purity).

LC-MS (Method B): Rt=0.72 min; MS (ESIpos): m/z=442 [M+H]$^+$ $^1$H-NMR (400 MHz, DMSO-d$_6$) δ [ppm]: 3.96 (s, 2H), 7.42 (s, 2H), 7.47-7.53 (m, 2H), 7.83 (dd, 1H), 7.84 (t, 1H), 8.01 (s, 1H), 8.34 (d, 1H), 8.43 (d, 1H), 8.50 (d, 1H), 8.62 (s, 1H), 10.73 (s, 1H).

Example 231

2-(2-Chlorophenyl)-N-[4-(3-cyclobutyl-1H-1,2,4-triazol-1-yl)-3-sulfamoylphenyl]-acetamide

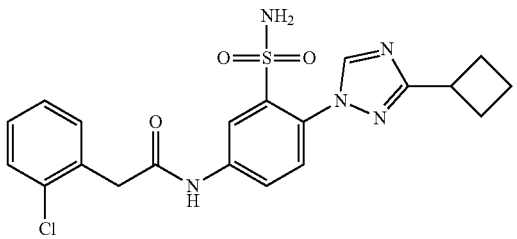 [SMILES: NS(=O)(=O)c1cc(NC(=O)Cc2ccccc2Cl)ccc1-n1cnc(C2CCC2)n1]

According to general procedures GP1.2, GP2.2, GP3.3 and GP4.1, 2-chloro-N-(2,4-dimethoxybenzyl)-5-nitrobenzenesulfonamide (350 mg, 0.904 mmol), 3-cyclobutyl-1H-1,2,4-triazole (167 mg, 1.36 mmol) and (2-chlorophenyl)acetic acid (231 mg, 1.36 mmol) were converted without purification of intermediates to the title compound and were purified at the end by preparative HPLC (Waters XBridge C18 5μ 100×30 mm, acetonitrile/water+0.1% formic acid) followed by another preparative HPLC (YMC Triart 5μ 100×30 mm, acetonitrile/water+0.2% aqueous ammonia (32%)) (8.8 mg, 0.0197 mmol, 2% yield over 4 steps, 97% purity).

LC-MS (Method A): Rt=1.03 min; MS (ESIpos): m/z=446 [M+H]$^+$ $^1$H-NMR (400 MHz, DMSO-d$_6$) δ [ppm]: 1.85-1.97 (m, 1H), 1.98-2.08 (m, 1H), 2.22-2.32 (m, 4H), 3.63 (quin, 1H), 3.91 (s, 2H), 7.29-7.36 (m, 2H), 7.38-7.50 (m, 4H), 7.59 (d, 1H), 7.96 (dd, 1H), 8.39 (d, 1H), 8.70 (s, 1H), 10.82 (s, 1H).

Example 232

N-[4-(4-Acetyl-1H-pyrazol-1-yl)-3-sulfamoylphenyl]-2-(2-chlorophenyl)acetamide

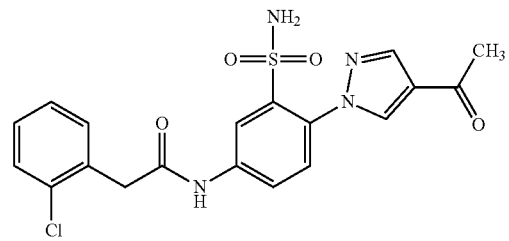 [SMILES: CC(=O)c1cnn(-c2ccc(NC(=O)Cc3ccccc3Cl)cc2S(N)(=O)=O)c1]

According to general procedures GP1.2, GP2.2, GP3.3 and GP4.1, 2-chloro-N-(2,4-dimethoxybenzyl)-5-nitrobenzenesulfonamide (350 mg, 0.904 mmol), 1-(1H-pyrazol-4-yl)ethanone (149 mg, 1.36 mmol) and (2-chlorophenyl)acetic acid (231 mg, 1.36 mmol) were converted without purification of intermediates to the title compound and were purified at the end by preparative HPLC (Waters XBridge C18 5μ 100×30 mm, acetonitrile/water+0.1% formic acid) followed by another preparative HPLC (YMC Triart 5μ 100×30 mm, acetonitrile/water+0.2% aqueous ammonia (32%)) (5.4 mg, 0.0125 mmol, 1% yield over 4 steps, 97% purity).

LC-MS (Method A): Rt=0.94 min; MS (ESIpos): m/z=433 [M+H]+

1H-NMR (400 MHz, DMSO-d6) δ [ppm]: 2.44 (s, 3H), 3.91 (s, 2H), 7.29-7.37 (m, 2H), 7.38-7.49 (m, 4H), 7.60 (d, 1H), 7.99 (dd, 1H), 8.17 (d, 1H), 8.39 (d, 1H), 8.75 (d, 1H), 10.82 (s, 1H).

Example 233

2-(2-Chlorophenyl)-N-[4-(3-isopropyl-1H-1,2,4-triazol-1-yl)-3-sulfamoylphenyl]-acetamide

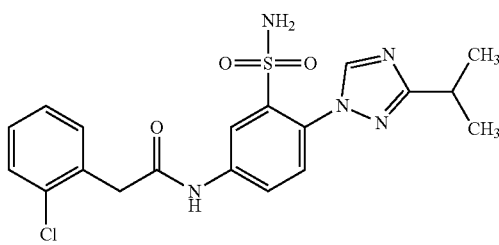

According to general procedures GP1.2, GP2.2, GP3.3 and GP4.1, 2-chloro-N-(2,4-dimethoxybenzyl)-5-nitrobenzenesulfonamide (350 mg, 0.904 mmol), 3-isopropyl-1H-1,2,4-triazole (51 mg, 1.36 mmol) and (2-chlorophenyl)acetic acid (231 mg, 1.36 mmol) were converted without purification of intermediates to the title compound and were purified at the end by preparative HPLC (Waters XBridge C18 5μ 100×30 mm, acetonitrile/water+0.1% formic acid) followed by another preparative HPLC (YMC Triart 5μ 100×30 mm, acetonitrile/water+0.2% aqueous ammonia (32%)) (16 mg, 0.0369 mmol, 4% yield over 4 steps, 96% purity).

LC-MS (Method A): Rt=1.00 min, MS (ESIpos): m/z=434 [M+H]+

1H-NMR (400 MHz, DMSO-d6) δ [ppm]: 1.28 (d, 6H), 3.05 (sept., 1H), 3.91 (s, 2H), 7.29-7.37 (m, 2H), 7.40-7.52 (m, 4H), 7.60 (d, 1H), 7.97 (dd, 1H), 8.39 (d, 1H), 8.69 (s, 1H), 10.82 (s, 1H).

Example 234

N-[4-(4-Chloro-1H-pyrazol-1-yl)-3-sulfamoylphenyl]-2-[2-(trifluoromethyl)-phenyl]acetamide

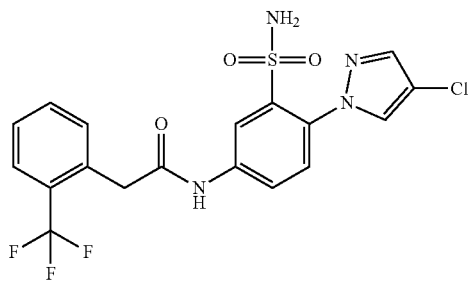 [SMILES: NS(=O)(=O)c1cc(NC(=O)Cc2ccccc2C(F)(F)F)ccc1-n1cc(Cl)cn1]

According to general procedures GP3.3 and GP4.1, 5-amino-2-(4-chloro-1H-pyrazol-1-yl)-N-(2,4-dimethoxybenzyl)benzenesulfonamide (500 mg, 1.18 mmol) and [2-(trifluoromethyl)phenyl]acetic acid (362 mg, 1.77 mmol) were converted without purification of intermediates to the title compound and were purified at the by preparative HPLC (Waters XBridge C18 5μ 100×30 mm, acetonitrile/water+0.1% formic acid) (70 mg, 0.153 mmol, 13% yield over 2 steps, 95% purity).

LC-MS (Method A): Rt=1.13 min; MS (ESIpos): m/z=459 [M+H]+

1H-NMR (400 MHz, DMSO-d6) δ [ppm]: 3.99 (s, 2H), 7.40 (s, 2H), 7.48-7.58 (m, 3H), 7.67 (t, 1H), 7.73 (d, 1H), 7.86 (s, 1H), 7.94 (dd, 1H), 8.32-8.38 (m, 2H), 10.78 (s, 1H).

Example 235

Ethyl 1-(4-{[(2-chlorophenyl)acetyl]amino}-2-sulfamoylphenyl)-1H-pyrazole-4-carboxylate

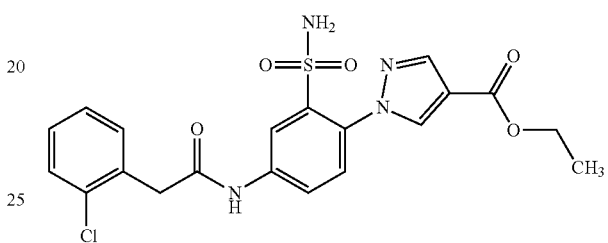

According to general procedures GP1.2, GP2.1, GP3.3 and GP4.1, 2-chloro-N-(2,4-dimethoxybenzyl)-5-nitrobenzenesulfonamide (1.00 g, 0.645 mmol), ethyl 1H-pyrazole-4-carboxylate (544 mg, 3.88 mmol) and (2-chlorophenyl)acetic acid (661 mg, 3.88 mmol) were converted without purification of intermediates to the title compound and were purified at the end by preparative HPLC (Waters XBridge C18 5μ 100×30 mm, acetonitrile/water+0.2% aqueous ammonia (32%)) followed by another preparative HPLC (YMC Triart 5p 100×30 mm, acetonitrile/water+0.2% aqueous ammonia (32%)) (22 mg, 0.0475 mmol, 7% yield over 4 steps, 98% purity).

LC-MS (Method B): Rt=0.95 min; MS (ESIpos): m/z=463 [M+H]+

1H-NMR (400 MHz, DMSO-d6) δ [ppm]: 1.29 (t, 3H), 3.91 (s, 2H), 4.26 (q, 2H), 7.30-7.36 (m, 2H), 7.40-7.49 (m, 4H), 7.59 (d, 1H), 7.96 (dd, 1H), 8.12 (d, 1H), 8.38 (d, 1H), 8.62 (d, 1H), 10.82 (s, 1H).

Example 236 Ethyl 1-(4-{[(2-fluorophenyl)acetyl]amino}-2-sulfamoylphenyl)-1H-pyrazole-4-carboxylate

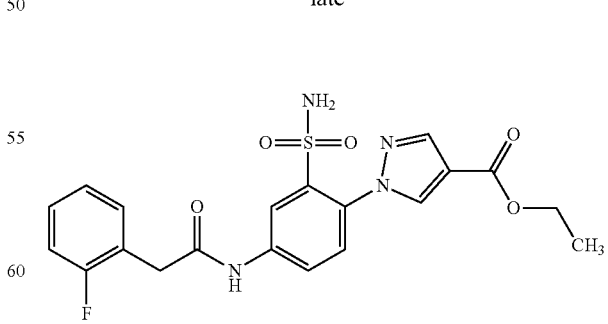

According to general procedures GP1.2, GP2.1, GP3.3 and GP4.1, 2-chloro-N-(2,4-dimethoxybenzyl)-5-nitrobenzenesulfonamide (1.00 g, 0.645 mmol), ethyl 1H-pyrazole-4-carboxylate (544 mg, 3.88 mmol) and (2-fluorophenyl)

acetic acid (596 mg, 3.88 mmol) were converted without purification of intermediates to the title compound and were purified at the end by preparative HPLC (Waters XBridge C18 5μ 100×30 mm, acetonitrile/water+0.2% aqueous ammonia (32%)) followed by another preparative HPLC (YMC Triart 5p 100×30 mm, acetonitrile/water+0.2% aqueous ammonia (32%)) (28 mg, 0.0627 mmol, 10% yield over 4 steps, 95% purity).

LC-MS (Method B): Rt=0.92 min; MS (ESIpos): m/z=447 [M+H]$^+$ $^1$H-NMR (400 MHz, DMSO-d$_6$) δ [ppm]: 1.29 (t, 3H), 3.81 (s, 2H), 4.26 (q, 2H), 7.16-7.22 (m, 2H), 7.30-7.37 (m, 1H), 7.41 (m, 3H), 7.58 (d, 1H), 7.96 (dd, 1H), 8.12 (d, 1H), 8.37 (d, 1H), 8.62 (d, 1H), 10.79 (s, 1H).

Example 237

2-(2-Fluorophenyl)-N-{4-[4-(2-hydroxypropan-2-yl)-1H-pyrazol-1-yl]-3-sulfamoyl-phenyl}acetamide

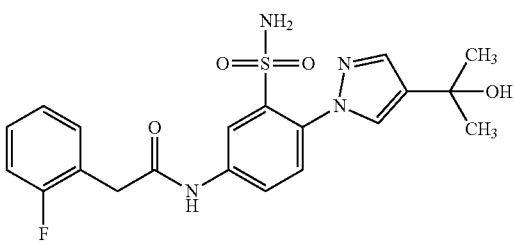 [SMILES: CC(C)(O)c1cnn(-c2ccc(NC(=O)Cc3ccccc3F)cc2S(N)(=O)=O)c1]

A solution of 1.4M methyl magnesium bromide in toluene/tetrahydrofuran (4.8 mL, 6.72 mmol) was added slowly under nitrogen atmosphere at 0° C. to a solution of ethyl 1-(4-{[(2-fluorophenyl)acetyl]amino}-2-sulfamoylphenyl)-1H-pyrazole-4-carboxylate (250 mg, 0.600 mmol) in tetrahydrofuran (10 mL). Stirring at 0° C. was continued for 2 hours, followed by stirring at room temperature overnight. It was quenched with saturated aqueous ammonium chloride solution and extracted twice with ethyl acetate. The organic phases were combined, washed with brine, dried over sodium sulfate and concentrated in vacuo.

Purification by preparative HPLC (Waters XBridge C18 5μ 100×30 mm, acetonitrile/water+0.2% aqueous ammonia (32%)) followed by another preparative HPLC (Chromatorex C-18 μm, 125×30 mm, acetonitrile/water+0.1% aqueous ammonia (32%)) led to the title compound (25 mg, 0.0578 mmol, 10%, 95% purity).

LC-MS (Method B): Rt=0.79 min; MS (ESIpos): m/z=433 [M+H]$^+$ $^1$H-NMR (400 MHz, DMSO-d$_6$) δ [ppm]: 1.45 (s, 6H), 3.79 (s, 2H), 4.98 (s, 1H), 7.15-7.23 (m, 2H), 7.30-7.37 (m, 1H), 7.41 (td, 1H), 7.50 (d, 1H), 7.48 (s, 2H), 7.71 (d, 1H), 7.94 (d, 1H), 7.97 (dd, 1H), 8.33 (d, 1H), 10.73 (s, 1H).

Example 238

2-(2-Chlorophenyl)-N-{4-[4-(2-hydroxypropan-2-yl)-1H-pyrazol-1-yl]-3-sulfamoyl-phenyl}acetamide

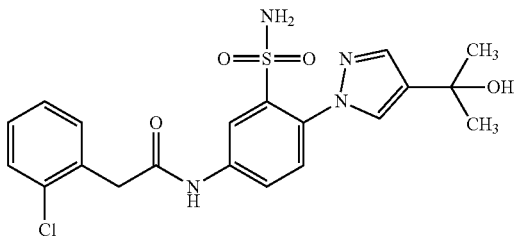

A solution of 1.4M methyl magnesium bromide in toluene/tetrahydrofuran (2.8 mL, 3.89 mmol) was added slowly under nitrogen atmosphere at 0° C. to a solution of ethyl 1-(4-{[(2-chlorophenyl)acetyl]amino}-2-sulfamoylphenyl)-1H-pyrazole-4-carboxylate (150 mg, 0.324 mmol) in tetrahydrofuran (10 mL). Stirring at 0° C. was continued for 2 hours, followed by stirring at room temperature overnight. It was quenched with saturated aqueous ammonium chloride solution and extracted twice with ethyl acetate. The organic phases were combined, washed with brine, dried over sodium sulfate and concentrated in vacuo.

Purification by preparative HPLC (Waters XBridge C18 5μ 100×30 mm, acetonitrile/water+0.2% aqueous ammonia (32%)) led to the title compound (30 mg, 0.0668 mmol, 21%, 97% purity).

LC-MS (Method B): Rt=0.85 min; MS (ESIpos): m/z=449 [M+H]$^+$ $^1$H-NMR (400 MHz, DMSO-d$_6$) δ [ppm]: 1.45 (s, 6H), 3.89 (s, 2H), 4.98 (s, 1H), 7.29-7.36 (m, 2H), 7.41-7.54 (m, 5H), 7.72 (d, 1H), 7.94 (d, 1H), 7.98 (dd, 1H), 8.34 (d, 1H), 10.75 (s, 1H).

Example 239

2-(2-Chloropyridin-3-yl)-N-{3-sulfamoyl-4-[3-(trifluoromethyl)-1H-1,2,4-triazol-1-yl]phenyl}acetamide

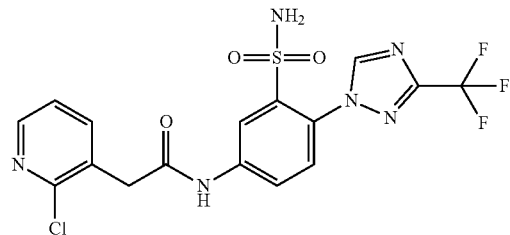 [SMILES: NS(=O)(=O)c1cc(NC(=O)Cc2cccnc2Cl)ccc1-n1cnc(C(F)(F)F)n1]

According to general procedure GP5.1, 5-amino-N-(2,4-dimethoxybenzyl)-2-[3-(trifluoromethyl)-1H-1,2,4-triazol-1-yl]benzenesulfonamide (0.20 mmol) and (2-chloropyridin-3-yl)acetic acid (0.40 mmol) were converted to the title compound (4.0 mg, 0.00868 mmol, 4% yield, 98% purity).

LC-MS (Method B): Rt=0.63 min; MS (ESIpos): m/z=461 [M+H]$^+$ $^1$H-NMR (400 MHz, DMSO-d$_6$) δ [ppm]: 3.97 (s, 2H), 7.45 (dd, 1H), 7.63-7.70 (m, 3H), 7.91 (dd, 1H), 7.95 (dd, 1H), 8.35 (dd, 1H), 8.44 (d, 1H), 9.04-9.06 (m, 1H), 10.95 (s, 1H).

Example 240

2-(2-Chlorophenyl)-N-methyl-N-{3-sulfamoyl-4-[4-(trifluoromethyl)-1H-pyrazol-1-yl]phenyl}acetamide

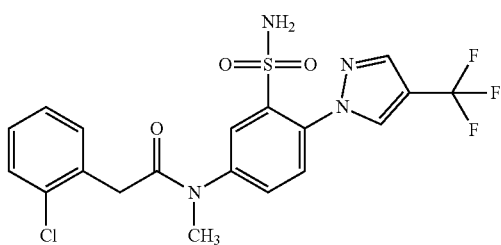 [SMILES: CN(C(=O)Cc1ccccc1Cl)c1ccc(-n2cc(C(F)(F)F)cn2)c(S(N)(=O)=O)c1]

2-(2-Chlorophenyl)-N-(3-{[(dimethylamino)methylene]sulfamoyl}-4-[4-(trifluoromethyl)-1H-pyrazol-1-yl]phenyl)acetamide (200 mg, 0.39 mmol) was dissolved in tetrahydrofuran (5 mL) and treated portionwise with sodium hydride (14.4 mg, 0.39 mmol, 65% purity). After stirring at room temperature for 10 min 2M iodomethane solution in methyl tert-butyl ether was added and stirring was continued overnight. The reaction mixture was extracted with water and ethyl acetate and the organic phase was washed with ammonium chloride and brine solutions followed by drying over sodium sulfate. Concentration in vacuo led to 2-(2-chlorophenyl)-N-(3-{[(dimethylamino)methylene]sulfamoyl}-4-[4-(trifluoromethyl)-1H-pyrazol-1-yl]phenyl)-N-methylacetamide which was redissolved in methanol (1 mL).

Aqueous ammonia (1 mL, 33%) was added and stirring was continued overnight. A second batch of aqueous ammonia (1 mL, 33%) was added and stirring was continued over the weekend. The reaction mixture was concentrated in vacuo and was purified by preparative HPLC (Chromatorex C-18 10 µm, 125×30 mm, acetonitrile/water+0.1% aqueous ammonia (32%)) to give the title compound (28 mg, 0.0592 mmol, 15% yield, 99% purity).

LC-MS (Method B): Rt=1.00 min; MS (ESIpos): m/z=473 [M+H]$^+$ $^1$H-NMR (400 MHz, DMSO-d$_6$) δ [ppm]: NMe overlapped by water signal, 3.55-3.90 (m, 2H), 7.25-7.31 (m, 2H), 7.31-7.36 (m, 1H), 7.39-7.44 (m, 1H), 7.55-7.64 (m, 2H), 7.71-7.78 (m, 1H), 7.80-7.84 (m, 1H), 8.06 (d, 1H), 8.21 (s, 1H), 8.77 (s, 1H).

Example 241 and Example 242

Tris(dibenzylideneacetone)dipalladium(0) (81.7 mg, 0.079 mmol) and di-tert-butyl(2',4',6'-triisopropyl-3,4,5,6-tetramethyl-[1,1'-biphenyl]-2-yl)phosphine (42.9 mg, 0.089 mmol) were dissolved in toluene (1.2 mL), evacuated and refilled three times with argon and heated afterwards to reflux (resulting in a brown color). In a separate flask 2-bromo-N-[(dimethylamino)methylene]-5-nitrobenzenesulfonamide (600 mg, 1.79 mmol) and 4-(trifluoromethyl)-2H-1,2,3-triazole (294 mg, 2.15 mmol) were dissolved in toluene (1.2 mL), evacuated and refilled three times with argon and added afterwards to the hot catalyst solution. Potassium phosphate (758 mg, 3.58 mmol) was added and it was stirred overnight at reflux. The reaction mixture was diluted with ethyl acetate and washed twice with brine solution, followed by drying over sodium sulfate. Concentration in vacuo gave a crude mixture of two regioisomers that was used in the next step without further purification.

The intermediate from the previous step was redissolved in methanol (9 mL), palladium on charcoal (90 mg, 10% loading) was added and it was stirred 5 h under a hydrogen atmosphere. The catalyst was removed by filtration followed by concentration in vacuo.

The crude intermediate was redissolved in DMF (10 mL). (2-Chlorophenyl)acetic acid (383 mg, 2.25 mmol), HATU (855 mg, 2.25 mmol) and N,N-diisopropylethylamine (775 mg, 5.99 mmol) were added and it was stirred overnight. The reaction mixture was concentrated in vacuo, and extracted with dichloromethane and water. The organic phase was washed with brine and dried over sodium sulfate, followed by filtration and concentration in vacuo.

The intermediate from the previous step was redissolved in methanol (5 mL) and aqueous ammonia (2.5 mL, 33%) was added, followed by stirring overnight. A second batch of aqueous ammonia (2 mL, 33%) was added and it was stirred again overnight. It was concentrated in vacuo and purified by preparative HPLC (Chromatorex C-18 10 µm, 125×30 mm, acetonitrile/water+0.1% formic acid) to give the two regioisomers 2-(2-chlorophenyl)-N-{3-sulfamoyl-4-[4-(trifluoromethyl)-2H-1,2,3-triazol-2-yl]phenyl}acetamide (17 mg, 0.0370 mmol, 2% yield, 85% purity) and 2-(2-chlorophenyl)-N-{3-sulfamoyl-4-[4-(trifluoromethyl)-1H-1,2,3-triazol-1-yl]phenyl}acetamide (11 mg, 0.0239 mmol, 1% yield, 90% purity), which could be separated under those HPLC conditions.

Example 241

2-(2-Chlorophenyl)-N-{3-sulfamoyl-4-[4-(trifluoromethyl)-2H-1,2,3-triazol-2-yl]-phenyl}acetamide

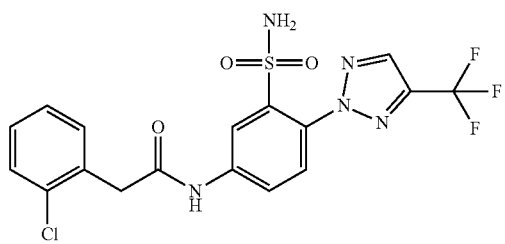 [SMILES: NS(=O)(=O)c1cc(NC(=O)Cc2ccccc2Cl)ccc1-n1ncc(C(F)(F)F)n1]

LC-MS (Method A): Rt=1.18 min; MS (ESIpos): m/z=460 [M+H]$^+$ $^1$H-NMR (400 MHz, DMSO-d$_6$) δ [ppm]: 3.93 (s, 2H), 7.30-7.48 (m, 6H), 7.75 (d, 1H), 8.00 (dd, 1H), 8.46 (d, 1H), 8.69 (s, 1H), 10.91 (s, 1H).

Example 242

2-(2-Chlorophenyl)-N-{3-sulfamoyl-4-[4-(trifluoromethyl)-1H-1,2,3-triazol-1-yl]-phenyl}acetamide

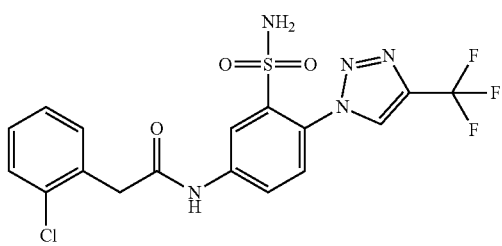

LC-MS (Method A): Rt=1.12 min; MS (ESIpos): m/z=460 [M+H]+

$^1$H-NMR (400 MHz, DMSO-d$_6$) δ [ppm]: 3.94 (s, 2H), 7.30-7.36 (m, 2H), 7.43-7.48 (m, 2H), 7.65 (s, 2H), 7.67 (d, 1H), 7.98 (dd, 1H), 8.46 (d, 1H), 9.16 (d, 1H), 10.92 (s, 1H).

Example 243

2-(2-Chloro-5-cyanophenyl)-N-{3-sulfamoyl-4-[4-(trifluoromethyl)-1H-pyrazol-1-yl]-phenyl}acetamide

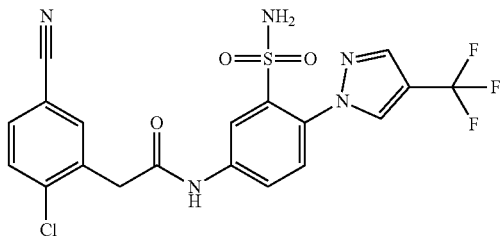 [SMILES: N#Cc1ccc(Cl)c(CC(=O)Nc2ccc(-n3cc(C(F)(F)F)cn3)c(S(N)(=O)=O)c2)c1]

2-(2-Chlorophenyl)-N-{3-sulfamoyl-4-[4-(trifluoromethyl)-1H-pyrazol-1-yl]phenyl}acetamide (50 mg, 0.11 mmol) was dissolved in trifluoroacetic acid (0.25 mL) and treated portionwise with N-iodosuccinimide (111 mg, 0.28 mmol). The reaction mixture was stirred at room temperature for 5 min, then at 65° C. for 3.5 hours. Ethyl acetate (100 mL) was added and it was washed with 10% aqueous sodium thiosulfate solution, followed by neutralization (to pH8) with aqueous sodium bicarbonate solution and another washing step with water. Then the organic phase was dried over sodium sulfate and concentrated in vacuo.

It was redissolved in DMSO (0.5 mL) in a pressure tube, copper(I) cyanide (14.6 mg, 0.16 mmol) and N,N-dimethylethylenediamine (14.4 mg, 0.16 mmol) were added and the sealed pressure tube was heated to 140° C. for two hours. The reaction mixture was purified by preparative HPLC (Chromatorex C-18 10 µm, 125×30 mm, acetonitrile/water+0.1% aqueous ammonia (32%)), followed by a second preparative HPLC (Chiralpak IA 5p 250×30 mm, ethanol/hexane+0.1 Vol-% diethylamine) and a third preparative HPLC (Chiralpak IE 5µ 250×30 mm, ethanol/hexane+0.1 Vol-% diethylamine) to give the title compound (5 mg, 0.0103 mmol, 9% yield, 98% purity).

LC-MS (Method A): Rt=1.14 min; MS (ESIpos): m/z=484 [M+H]+

$^1$H-NMR (400 MHz, chloroform-d) δ [ppm]: 3.84 (s, 2H), 7.31 (d, 1H), 7.46-7.49 (m, 2H), 7.61-7.64 (m, 1H), 7.85 (s, 1H), 7.96-7.98 (m, 1H), 8.01 (d, 1H), 8.14 (dd, 1H).

Example 244

2-(2-Chlorophenyl)-N-{3-cyano-5-sulfamoyl-4-[4-(trifluoromethyl)-1H-pyrazol-1-yl]-phenyl}acetamide

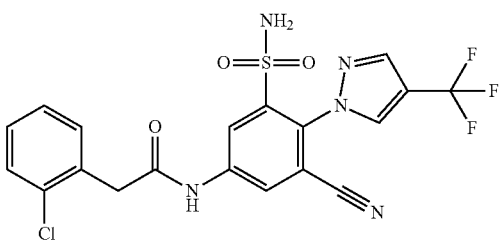 [SMILES: N#Cc1cc(NC(=O)Cc2ccccc2Cl)cc(S(N)(=O)=O)c1-n1cc(C(F)(F)F)cn1]

2-(2-Chlorophenyl)-N-(3-{[(dimethylamino)methylene]sulfamoyl}-4-[4-(trifluoromethyl)-1H-pyrazol-1-yl]phenyl)acetamide (51.4 mg, 0.10 mmol), N-cyano-4-methyl-N-phenylbenzene-sulfonamide, (54.5 mg, 0.20 mmol), tris(acetonitrile)pentamethylcyclo-pentadienylrhodium(III) hexafluoroantimonate (8.3 mg, 0.01 mmol) and silver carbonate (11.0 mg, 0.04 mmol) were added to a pressure tube, it was flushed with argon, followed by the addition of dioxane (0.5 mL). The tube was sealed and the reaction mixture stirred at 130° C. overnight. Water was added and it was extracted twice with dichloromethane. The organic phases were combined, concentrated in vacuo and purified by preparative HPLC (Chromatorex C-18 10 µm, 125×30 mm, acetonitrile/water+0.1% aqueous ammonia (32%) to give 2-(2-chlorophenyl)-N-(3-cyano-5-{[(dimethylamino)methylene]sulfamoyl}-4-[4-(trifluoromethyl)-1H-pyrazol-1-yl]phenyl)acetamide.

This intermediate was resdissolved in methanol (2 mL) and aqueous ammonia (1 mL, 25%) was added, followed by stirring at 50° C. overnight, concentrated in vacuo and purified by preparative HPLC (Waters XBridge C18 5µ 100×30 mm, acetonitrile/water+0.2% aqueous ammonia (32%)) to give the title compound (6.3 mg, 0.0130 mmol, 13% Yield, 95% purity).

LC-MS (Method B): Rt=0.81 min; MS (ESIpos): m/z=484 [M+H]+

$^1$H-NMR (400 MHz, chloroform-d) δ [ppm]: 3.92 (s, 2H), 5.81 (s, 2H), 7.31-7.36 (m, 2H), 7.38-7.42 (m, 1H), 7.45-7.50 (m, 1H), 8.00 (s, 1H), 8.02 (s, 1H), 8.09 (s, 1H), 8.12 (d, 1H), 8.66 (d, 1H).

Example 245

2-(5-Bromo-2-chlorophenyl)-N-{3-sulfamoyl-4-[4-(trifluoromethyl)-1H-pyrazol-1-yl]phenyl}acetamide

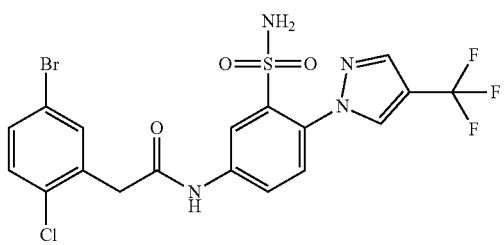

2-(2-Chlorophenyl)-N-{3-sulfamoyl-4-[4-(trifluoromethyl)-1H-pyrazol-1-yl]phenyl}acetamide (100 mg, 0.22 mmol) was dissolved in trifluoroacetic acid, N-bromosuccinimide (48.4 mg, 0.27 mmol) was added and it was stirred at 60° C. overnight. Another batch N-bromosuccinimide (19.4 mg, 0.11 mmol) was added and it was stirred again at 60° C. overnight. Water (1 mL) and saturated sodium bicarbonate solution (1 mL) were added and it was extracted with ethyl acetate three times. The combined organic phases were washed with brine, dried and concentrated in vacuo. Purification by preparative HPLC (Chromatorex C-18 10 μm, 125×30 mm, acetonitrile/water+0.1% aqueous ammonia (32%)) followed by another preparative HPLC (Chiralpak ID 5μ 250×30 mm, ethanol/hexane+0.1% trifluoroacetic acid) and another washing step with 1M HCl gave 2-(5-bromo-2-chlorophenyl)-N-{3-sulfamoyl-4-[4-(trifluoromethyl)-1H-pyrazol-1-yl]phenyl}acetamide (8.3 mg, 0.0154 mmol, 7% yield, 98% purity).

LC-MS (Method B): Rt=1.19 min; MS (ESIpos): m/z=537/539 [M+H]$^+$ $^1$H-NMR (400 MHz, DMSO-d$_6$) δ [ppm]: 3.93 (s, 2H), 7.35-7.47 (m, 3H), 7.53 (dd, 1H), 7.60 (d, 1H), 7.71 (d, 1H), 7.95 (dd, 1H), 8.17 (s, 1H), 8.38 (d, 1H), 8.74 (s, 1H), 10.86 (s, 1H).

Example 246

N-[4-(3-Chloro-1H-1,2,4-triazol-1-yl)-3-sulfamoylphenyl]-2-(2-fluorophenyl)acetamide

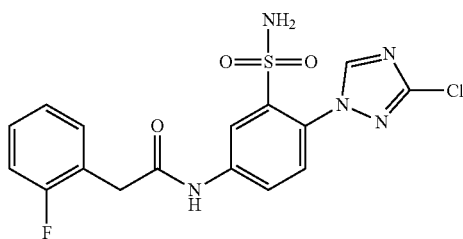 [SMILES: NS(=O)(=O)c1cc(NC(=O)Cc2ccccc2F)ccc1-n1cnc(Cl)n1]

According to general procedures GP1.2, GP2.5, GP3.3 and GP4.2, 2-chloro-N-(2,4-dimethoxybenzyl)-5-nitrobenzenesulfonamide (161 mg, 1.03 mmol), 3-chloro-1H-1,2,4-triazole (201 mg, 1.56 mmol) and (2-fluorophenyl)acetic acid (273 mg, 1.77 mmol) were converted without purification of intermediates to the title compound and were purified at the end by preparative HPLC (Chromatorex C-18 10 μm, 125×30 mm, acetonitrile/water+0.1% formic acid), followed by a second preparative HPLC (Waters XBridge C18 5μ 100×30 mm, acetonitrile/water+0.2% aqueous ammonia (32%)) and by a third preparative HPLC (YMC Triart C18 5μ 100×30 mm, acetonitrile/water+0.2% aqueous ammonia (32%)) (13 mg, 0.0317 mmol, 3% yield over 4 steps, 98% purity).

LC-MS (Method B): Rt=0.66 min; MS (ESIpos): m/z=410 [M+H]$^+$ $^1$H-NMR (600 MHz, DMSO-d$_6$) δ [ppm]: 3.82 (s, 2H), 7.15-7.23 (m, 2H), 7.30-7.44 (m, 2H), 7.54-7.66 (m, 3H), 7.94 (dd, 1H), 8.41 (d, 1H), 8.81 (s, 1H), 10.85 (s, 1H).

Example 247

2-(2-Chlorophenyl)-N-[3-cyano-4-(4-fluoro-1H-pyrazol-1-yl)-5-sulfamoyl-phenyl]acetamide

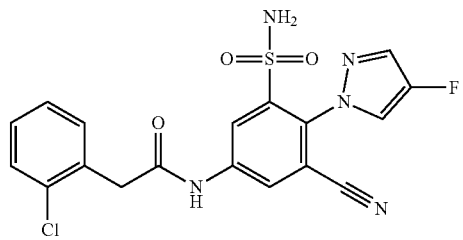 [SMILES: N#Cc1cc(NC(=O)Cc2ccccc2Cl)cc(S(N)(=O)=O)c1-n1cc(F)cn1]

2-(2-chlorophenyl)-N-[3-{[(dimethylamino)methylene]sulfamoyl}-4-(4-fluoro-1H-pyrazol-1-yl)phenyl]acetamide (51.4 mg, 0.11 mmol), N-cyano-4-methyl-N-phenylbenzene-sulfonamide, (58.7 mg, 0.22 mmol), tris(acetonitrile) pentamethylcyclopentadienyl-rhodium(III) hexafluoroantimonate (8.3 mg, 0.01 mmol) and silver carbonate (11.9 mg, 0.04 mmol) were added to a pressure tube, it was flushed with argon, followed by the addition of dioxane (0.5 mL). The tube was sealed and the reaction mixture stirred at 130° C. overnight. Water was added and it was extracted twice with dichloromethane. The organic phases were combined, concentrated in vacuo and purified by preparative HPLC to give 2-(2-chlorophenyl)-N-[3-cyano-5-{[(dimethylamino)methylene]sulfamoyl}-4-(4-fluoro-1H-pyrazol-1-yl)phenyl] acetamide.

This intermediate was resdissolved in methanol (2 mL) and aqueous ammonia (2 mL) was added, followed by stirring at 50° C. overnight. Water was added and it was extracted three times with dichloromethane. The combined organic layers were washed with brine, dried and concentrated in vacuo. Purification by preparative HPLC (Chromatorex C-18 10 μm, 125×30 mm, acetonitrile/water+0.1% aqueous ammonia (32%)), followed by another preparative HPLC (Waters XBridge C18 5μ 100×30 mm, acetonitrile/water+0.2% aqueous ammonia (32%)) gave the title compound (4.9 mg, 0.0113 mmol, 10% yield, 95% purity).

LC-MS (Method A): Rt=1.08 min; MS (ESIpos): m/z=434 [M+H]$^+$ $^1$H-NMR (400 MHz, methanol-d$_4$) δ [ppm]: 3.94 (s, 2H), 7.27-7.33 (m, 2H), 7.38-7.44 (m, 2H), 7.78 (dd, 1H), 8.05 (dd, 1H), 8.41 (d, 1H), 8.56 (d, 1H).

Example 248

2-(2-Chlorophenyl)-N-[4-(4-methyl-1H-pyrazol-1-yl)-3-sulfamoylphenyl]acetamide

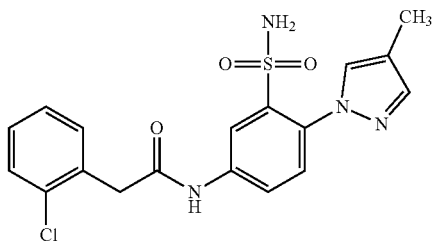 [SMILES: Cc1cnn(-c2ccc(NC(=O)Cc3ccccc3Cl)cc2S(N)(=O)=O)c1]

2-(2-Chlorophenyl)-N-{3-[(2,4-dimethoxybenzyl)sulfamoyl]-4-(4-methyl-1H-pyrazol-1-yl)-phenyl}acetamide (170 mg, 306 µmol) was dissolved in dichloromethane (8 mL) and treated with trifluoroacetic acid (142 µL, 1.84 mmol) followed by stirring at room temperature for three hours. Further trifluoroacetic acid (71 µL, 0.92 mmol) was added and stirring was continued overnight at room temperature. The mixture was concentrated in vacuo and purified by HPLC to give the title compound (26 mg, 21% yield, 99% purity).

LC-MS (Method B): Rt=1.02 min; MS (ESIpos): m/z=405 [M+H]$^+$ $^1$H-NMR (400 MHz, DMSO-d$_6$) δ [ppm] 2.10 (s, 3H), 3.90 (s, 2H), 7.33 (m, 2H), 7.45 (m, 2H), 7.48 (s, 2H), 7.49 (d, 1H), 7.60 (s, 1H), 7.87 (s, 1H), 7.96 (dd, 1H), 8.34 (d, 1H), 10.75 (s, 1H).

Example 249

2-(2-Chlorophenyl)-N-[4-(3-methoxy-1H-1,2,4-triazol-1-yl)-3-sulfamoylphenyl]-acetamide

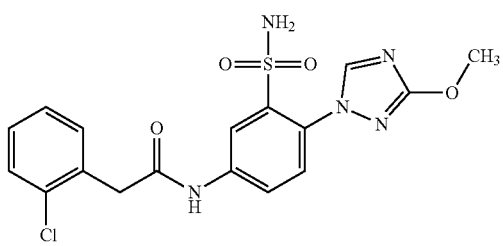

2-(2-Chlorophenyl)-N-{3-[(2,4-dimethoxybenzyl)sulfamoyl]-4-(3-methoxy-1H-1,2,4-triazol-1-yl) phenyl}acetamide (17 mg, 18 µmol, 60% purity) was dissolved in dichloromethane (0.8 mL) and treated with trifluoroacetic acid (13.7 µL, 178 µmol) followed by stirring at room temperature for six hours. Further trifluoroacetic acid (13.7 µL, 178 µmol) was added and stirring was continued overnight at room temperature. The mixture was concentrated in vacuo and purified by HPLC to give the title compound (4.3 mg, 47% yield, 82% purity).

LC-MS (Method B): Rt=0.73 min; MS (ESIpos): m/z=422 [M+H]$^+$ $^1$H-NMR (400 MHz, DMSO-d$_6$) δ [ppm] 3.26 (s, 3H), 3.90 (s, 2H), 7.25 (s, 2H), 7.32 (m, 2H), 7.45 (m, 2H), 7.49 (d, 1H), 7.95 (dd, 1H), 8.19 (s, 1H), 8.34 (d, 1H), 10.77 (s, 1H).

Example 250

2-(2-Chlorophenyl)-N-[4-(4-cyclopropyl-1H-imidazol-1-yl)-3-sulfamoylphenyl]-acetamide

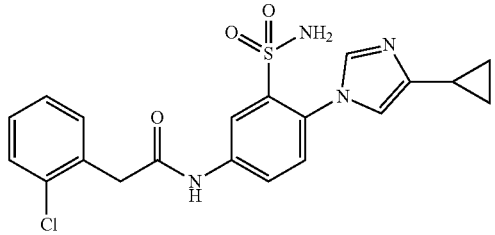 [SMILES: NS(=O)(=O)c1cc(NC(=O)Cc2ccccc2Cl)ccc1-n1cnc(C2CC2)c1]

2-(2-Chlorophenyl)-N-{4-(4-cyclopropyl-1H-imidazol-1-yl)-3-[(2,4-dimethoxybenzyl)sulfamoyl] phenyl}acetamide (35.0 mg, 60.2 µmol) was dissolved in dichloromethane (1.6 mL) and treated with trifluoroacetic acid (231 µL, 3.0 mmol) followed by stirring at room temperature for 48 hours. Further trifluoroacetic acid (13.7 µL, 178 µmol) was added and stirring was continued overnight at room temperature. The mixture was concentrated in vacuo and purified by HPLC to give the title compound (13.4 mg, 51% yield, 99% purity).

LC-MS (Method D): Rt=0.84 min; MS (ESIpos): m/z=431 [M+H]$^+$ $^1$H-NMR (400 MHz, DMSO-d$_6$) δ [ppm] 0.68 (m, 2H), 0.78 (m, 2H), 1.82 (m, 1H), 3.90 (s, 2H), 7.06 (d, 1H), 7.32 (m, 2H), 7.37 (d, 1H), 7.45 (m, 2H), 7.47 (d, 1H), 7.50 (s, 2H), 7.86 (dd, 1H), 8.38 (d, 1H), 10.75 (s, 1H).

Example 251

2-(2-Chlorophenyl)-N-[4-(4-methyl-1H-imidazol-1-yl)-3-sulfamoylphenyl]acetamide

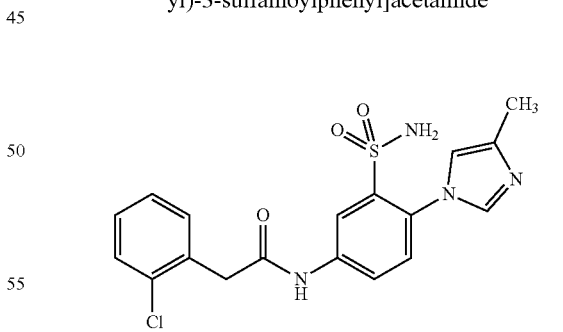

2-(2-Chlorophenyl)-N-{3-[(2,4-dimethoxybenzyl)sulfamoyl]-4-(4-methyl-1H-imidazol-1-yl)phenyl}acetamide (69.5 mg, 125 µmol) was dissolved in dichloromethane (4.0 mL) and treated with trifluoroacetic acid (480 µL, 6.3 mmol) followed by stirring at room temperature overnight. The mixture was concentrated in vacuo and purified by HPLC to give the title compound (12 mg, 22% yield, 95% purity).

LC-MS (Method B): Rt=0.74 min; MS (ESIpos): m/z=405 [M+H]$^+$

¹H-NMR (400 MHz, DMSO-d₆) δ [ppm] 2.14 (s, 3H), 3.90 (s, 2H), 7.01 (d, 1H), 7.32 (m, 2H), 7.36 (d, 1H), 7.45 (m, 2H), 7.47 (s, 2H), 7.60 (d, 1H), 7.86 (dd, 1H), 8.37 (d, 1H), 10.76 (s, 1H).

Example 252

2-(2-Chlorophenyl)-N-[4-(3-cyclopropyl-1H-pyrazol-1-yl)-3-sulfamoylphenyl]-acetamide

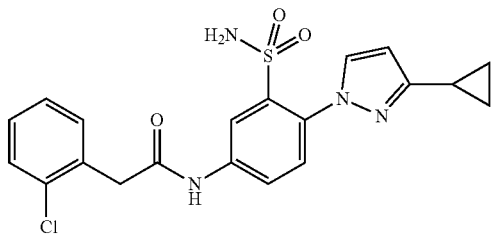 [SMILES: NS(=O)(=O)c1cc(NC(=O)Cc2ccccc2Cl)ccc1-n1ccc(C2CC2)n1]

2-(2-Chlorophenyl)-N-{4-(3-cyclopropyl-1H-pyrazol-1-yl)-3-[(2,4-dimethoxybenzyl)sulfamoyl]phenyl}acetamide (306 mg, 527 µmol) was dissolved in dichloromethane (6.8 mL) and treated with trifluoroacetic acid (410 µL, 5.3 mmol) followed by stirring at room temperature overnight. The mixture was concentrated in vacuo and purified by HPLC to give the title compound (12 mg, 5% yield, 90% purity).

LC-MS (Method A): Rt=1.13 min; MS (ESIpos): m/z=431 [M+H]⁺

¹H-NMR (400 MHz, DMSO-d₆) δ [ppm] 0.69 (m, 2H), 0.93 (m, 2H), 1.98 (m, 1H), 3.89 (s, 2H), 6.23 (d, 1H), 7.32 (m, 2H), 7.45 (m, 2H), 7.49 (d, 1H), 7.54 (s, 2H), 7.96 (dd, 1H), 7.94 (d, 1H), 8.33 (d, 1H), 10.74 (s, 1H). 36.1

Example 253

2-(2-Chlorophenyl)-N-[4-(2H-pyrazolo[3,4-b]pyridin-2-yl)-3-sulfamoylphenyl]-acetamide

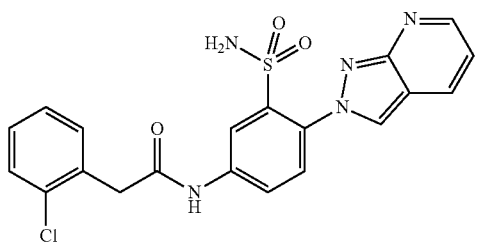 [SMILES: NS(=O)(=O)c1cc(NC(=O)Cc2ccccc2Cl)ccc1-n1cc2cccnc2n1]

2-(2-Chlorophenyl)-N-{3-[(2,4-dimethoxybenzyl)sulfamoyl]-4-(2H-pyrazolo[3,4-b]pyridin-2-yl) phenyl}acetamide (751 mg, 863 µmol, 68% purity) was dissolved in dichloromethane (11 mL) and treated with trifluoroacetic acid (2.0 mL, 26 mmol) followed by stirring at room temperature for 48 hours. Further trifluoroacetic acid (2.66 mL, 34.5 mmol) was added and stirring was continued for 1 hour at room temperature. The mixture was concentrated in vacuo and purified by HPLC to give the title compound (41 mg, 11% yield, 98% purity).

LC-MS (Method A): Rt=0.99 min; MS (ESIpos): m/z=442 [M+H]⁺

¹H-NMR (400 MHz, DMSO-d₆) δ [ppm] 3.93 (s, 2H), 7.31 (s, 2H), 7.34 (m, 1H), 7.35 (m, 2H), 7.47 (m, 2H), 7.67 (d, 1H), 8.02 (dd, 1H), 8.38 (dd, 1H), 8.45 (s, 1H), 8.45 (d, 1H), 8.56 (dd, 1H), 10.83 (s, 1H).

Example 254

2-(2-Chlorophenyl)-N-[4-(2H-pyrazolo[3,4-c]pyridin-2-yl)-3-sulfamoylphenyl]-acetamide

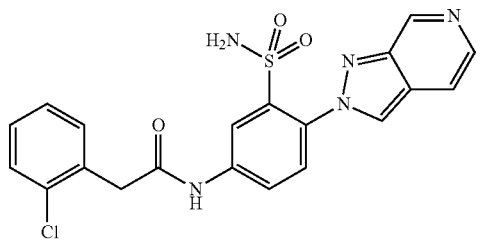 [SMILES: NS(=O)(=O)c1cc(NC(=O)Cc2ccccc2Cl)ccc1-n1cc2ccncc2n1]

2-(2-Chlorophenyl)-N-{3-[(2,4-dimethoxybenzyl)sulfamoyl]-4-(2H-pyrazolo[3,4-c]pyridin-2-yl) phenyl}acetamide (1.09 g, 1.84 mmol) was dissolved in dichloromethane (24 mL) and treated with trifluoroacetic acid (1.4 mL, 18 mmol) followed by stirring at room temperature overnight. The mixture was concentrated in vacuo and purified by HPLC to give the title compound (210 mg, 26% yield, 99% purity).

LC-MS (Method A): Rt=0.78 min; MS (ESIpos): m/z=442 [M+H]⁺

¹H-NMR (400 MHz, DMSO-d₆) δ [ppm] 3.94 (s, 2H), 7.33 (s, 2H), 7.34 (m, 2H), 7.47 (m, 2H), 7.71 (d, 1H), 7.87 (d, 1H), 8.04 (dd, 1H), 8.34 (d, 1H), 8.49 (d, 1H), 8.50 (s, 1H), 8.80 (s, 1H), 10.88 (s, 1H).

Example 255

2-(2-Chlorophenyl)-N-[4-(2H-pyrazolo[4,3-b]pyridin-2-yl)-3-sulfamoylphenyl]-acetamide

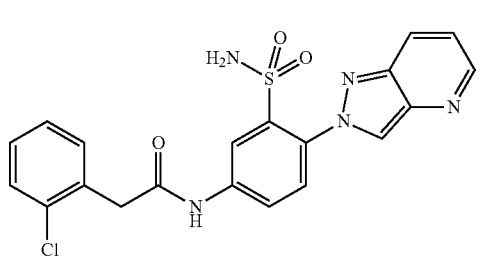 [SMILES: NS(=O)(=O)c1cc(NC(=O)Cc2ccccc2Cl)ccc1-n1cc2ncccc2n1]

2-(2-Chlorophenyl)-N-{3-[(2,4-dimethoxybenzyl)sulfamoyl]-4-(2H-pyrazolo[4,3-b]pyridin-2-yl) phenyl}acetamide (405 mg, 171 µmol, 25% purity) was dissolved in dichloromethane (2.2 mL) and treated with trifluoroacetic acid (790 µL, 10 mmol) followed by stirring at room temperature overnight. The mixture was concentrated in vacuo and purified by HPLC to give the title compound (20 mg, 25% yield, 95% purity).

LC-MS (Method A): Rt=0.97 min; MS (ESIpos): m/z=442 [M+H]⁺

¹H-NMR (400 MHz, DMSO-d₆) δ [ppm] 3.93 (s, 2H), 7.32 (s, 2H), 7.34 (m, 2H), 7.44 (dd, 1H), 7.46 (m, 2H), 7.63

(d, 1H), 7.82 (ddd, 1H), 8.03 (dd, 1H), 8.46 (d, 1H), 8.58 (d, 1H), 8.63 (dd, 1H), 10.86 (s, 1H).

Example 256

2-(2-Chlorophenyl)-N-{4-[4-(2-methoxyethyl)-1H-pyrazol-1-yl]-3-sulfamoylphenyl}-acetamide

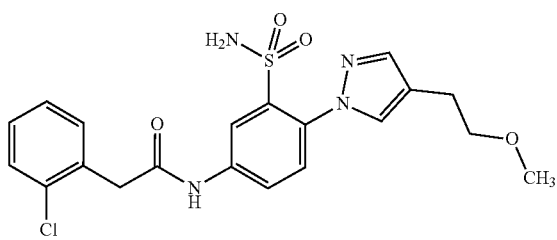 [SMILES: COCCc1cnn(-c2ccc(NC(=O)Cc3ccccc3Cl)cc2S(N)(=O)=O)c1]

2-(2-Chlorophenyl)-N-{3-[(2,4-dimethoxybenzyl)sulfamoyl]-4-[4-(2-methoxyethyl)-1H-pyrazol-1-yl]phenyl}acetamide (551 mg, 570 µmol, 62% purity) was dissolved in dichloromethane (7.3 mL) and treated with trifluoroacetic acid (2.2 mL, 28 mmol) followed by stirring at room temperature overnight. The mixture was concentrated in vacuo and purified by HPLC to give the title compound (203 mg, 74% yield, 94% purity).

LC-MS (Method A): Rt=1.02 min; MS (ESIpos): m/z=449 [M+H]$^+$ $^1$H-NMR (400 MHz, DMSO-d$_6$) δ [ppm] 2.72 (t, 2H), 3.28 (s, 3H), 3.52 (t, 2H), 3.89 (s, 2H), 7.33 (m, 2H), 7.45 (m, 2H), 7.47 (s, 2H), 7.50 (d, 1H), 7.65 (s, 1H), 7.92 (s, 1H), 7.97 (dd, 1H), 8.34 (d, 1H), 10.75 (s, 1H).

Example 257

2-(2-Chlorophenyl)-N-[4-(3-fluoro-1H-pyrazol-1-yl)-3-sulfamoylphenyl]acetamide

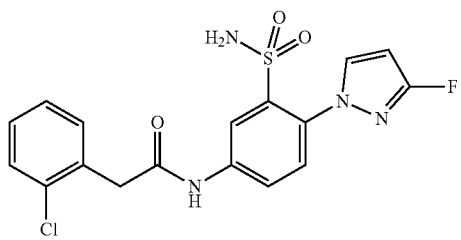 [SMILES: NS(=O)(=O)c1cc(NC(=O)Cc2ccccc2Cl)ccc1-n1ccc(F)n1]

2-(2-Chlorophenyl)-N-{3-[(2,4-dimethoxybenzyl)sulfamoyl]-4-(3-fluoro-1H-pyrazol-1-yl)-phenyl}acetamide (840 mg, 601 µmol, 40% purity) was dissolved in dichloromethane (7.7 mL) and treated with trifluoroacetic acid (2.3 mL, 30 mmol) followed by stirring at room temperature overnight. The mixture was concentrated in vacuo and purified by HPLC to give the title compound (36 mg, 14% yield, 95% purity).

LC-MS (Method B): Rt=0.93 min; MS (ESIpos): m/z=409 [M+H]$^+$ $^1$H-NMR (400 MHz, DMSO-d$_6$) δ [ppm] 3.90 (s, 2H), 6.26 (dd, 1H), 7.33 (m, 2H), 7.39 (s, 2H), 7.45 (m, 2H), 7.53 (d, 1H), 7.95 (dd, 1H), 7.98 (dd, 1H), 8.36 (d, 1H), 10.79 (s, 1H).

Example 258

2-(2-Chlorophenyl)-N-(4-{4-[(2,2-difluoroethyl)amino]-1H-pyrazol-1-yl}-3-sulfamoyl-phenyl)acetamide

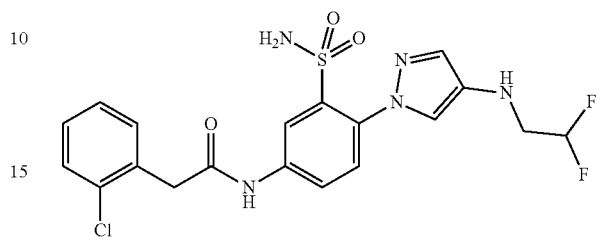

2-(2-Chlorophenyl)-N-(4-{4-[(2,2-difluoroethyl)amino]-1H-pyrazol-1-yl}-3-[(2,4-dimethoxy-benzyl)sulfamoyl]phenyl)acetamide (190 mg, 184 µmol, 60% purity) was dissolved in dichloromethane (2.4 mL) and treated with trifluoroacetic acid (710 µL, 9.2 mmol) followed by stirring at room temperature overnight. The mixture was concentrated in vacuo and purified by HPLC to give the title compound (13 mg, 14% yield, 90% purity).

LC-MS (Method A): Rt=0.97 min; MS (ESIpos): m/z=470 [M+H]$^+$ $^1$H-NMR (400 MHz, DMSO-d$_6$) δ [ppm] 3.34 (m, 2H), 3.89 (s, 2H), 5.18 (t, 1H), 6.12 (tt, 1H), 7.32 (m, 2H), 7.41 (d, 1H), 7.45 (m, 2H), 7.48 (s, 2H), 7.49 (d, 1H), 7.56 (d, 1H), 7.95 (dd, 1H), 8.32 (d, 1H), 10.71 (s, 1H).

Example 259

2-(2-Chlorophenyl)-N-{4-[4-(2,2-difluoroethyl)-1H-pyrazol-1-yl]-3-sulfamoylphenyl}-acetamide

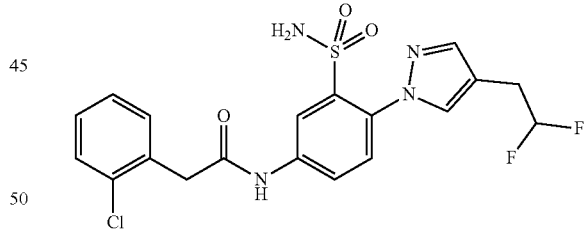

2-(2-Chlorophenyl)-N-{4-[4-(2,2-difluoroethyl)-1H-pyrazol-1-yl]-3-[(2,4-dimethoxybenzyl)sulfamoyl]phenyl}acetamide (336 mg, 222 µmol, 40% purity) was dissolved in dichloromethane (4.3 mL) and treated with trifluoroacetic acid (860 µL, 11 mmol) followed by stirring at room temperature overnight. The mixture was concentrated in vacuo and purified by HPLC to give the title compound (66 mg, 62% yield, 95% purity).

LC-MS (Method A): Rt=1.08 min; MS (ESIpos): m/z=455 [M+H]$^+$ $^1$H-NMR (400 MHz, DMSO-d$_6$) δ [ppm] 3.12 (td, 2H), 6.22 (tt, 1H), 7.33 (m, 2H), 7.45 (m, 2H), 7.45 (s, 2H), 7.50 (d, 1H), 7.70 (s, 1H), 7.97 (dd, 1H), 8.02 (s, 1H), 8.35 (d, 1H), 10.77 (s, 1H).

Example 260

2-(2-Chlorophenyl)-N-[4-(4-{[(2,2-difluoroethyl)amino]methyl}-1H-pyrazol-1-yl)-3-sulfamoylphenyl]acetamide

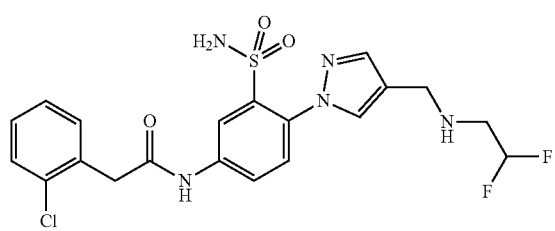 [SMILES: NS(=O)(=O)c1cc(NC(=O)Cc2ccccc2Cl)ccc1-n1cc(CNCC(F)F)cn1]

tert-butyl {[1-(4-{[(2-Chlorophenyl)acetyl]amino}-2-[(2,4-dimethoxybenzyl)sulfamoyl]phenyl)-1H-pyrazol-4-yl]methyl}(2,2-difluoroethyl)carbamate (75.0 mg, 102 μmol) was dissolved in dichloromethane (3.0 μL) and treated with trifluoroacetic acid (390 μL, 5.1 mmol) followed by stirring at room temperature overnight. The mixture was concentrated in vacuo and purified by HPLC to give the title compound (9 mg, 16% yield, 90% purity).

LC-MS (Method A): Rt=0.79 min; MS (ESIpos): m/z=484 [M+H]$^+$ $^1$H-NMR (400 MHz, DMSO-d$_6$) δ [ppm] 2.87 (td, 2H), 3.68 (s, 2H), 3.90 (s, 2H), 6.01 (tt, 1H), 7.33 (m, 2H), 7.45 (m, 2H), 7.46 (s, 2H), 7.51 (d, 1H), 7.71 (s, 1H), 7.97 (s, 1H), 7.97 (dd, 1H), 8.34 (d, 1H), 10.76 (s, 1H).

Example 261

2-(2-Chlorophenyl)-N-{3-sulfamoyl-4-[5-(trifluoromethyl)-1,2,4-oxadiazol-3-yl]phenyl}acetamide

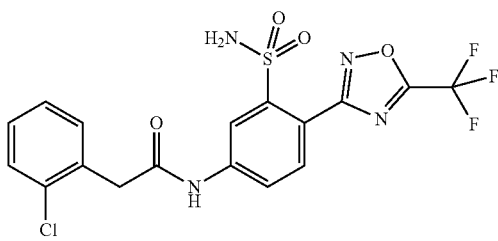 [SMILES: NS(=O)(=O)c1cc(NC(=O)Cc2ccccc2Cl)ccc1-c1noc(C(F)(F)F)n1]

2-(2-Chlorophenyl)-N-{3-[(2,4-dimethoxybenzyl)sulfamoyl]-4-[5-(trifluoromethyl)-1,2,4-oxa-diazol-3-yl]phenyl}acetamide (112 mg, 156 μmol, 85% purity) was dissolved in dichloromethane (3.0 mL) and treated with trifluoroacetic acid (600 μL, 7.8 mmol) followed by stirring at room temperature overnight. The mixture was concentrated in vacuo and purified by HPLC to give the title compound (8 mg, 10% yield, 90% purity).

LC-MS (Method A): Rt=1.19 min; MS (ESIpos): m/z=461 [M+H]$^+$ $^1$H-NMR (400 MHz, DMSO-d$_6$) δ [ppm] 3.93 (s, 2H), 7.33 (m, 2H), 7.44 (m, 2H), 7.46 (m, 2H), 7.75 (d, 1H), 8.00 (dd, 1H), 8.45 (d, 1H), 10.90 (s, 1H).

Example 262

2-(2-Fluorophenyl)-N-[4-(4-methyl-1H-pyrazol-1-yl)-3-sulfamoylphenyl]acetamide

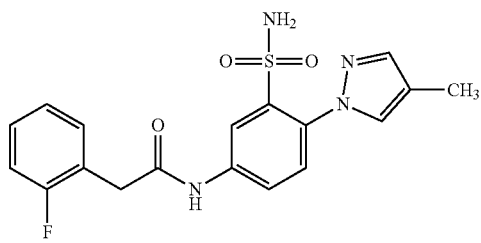 [SMILES: Cc1cnn(-c2ccc(NC(=O)Cc3ccccc3F)cc2S(N)(=O)=O)c1]

N-{3-[(2,4-Dimethoxybenzyl)sulfamoyl]-4-(4-methyl-1H-pyrazol-1-yl)phenyl}-2-(2-fluoro-phenyl)acetamide (599 mg, 65% purity, 1.003 mmol) was dissolved in dichloromethane (29 mL) and treated with trifluoroacetic acid (514 μL, 6.67 mmol) followed by stirring at room temperature overnight. Further trifluoroacetic acid (257 μL, 334 μmol) was added and stirring was continued for 2 hours at room temperature. The mixture was concentrated in vacuo and purified by HPLC to give the title compound (85 mg, 96% purity).

LC-MS (Method D): Rt=1.02 min; MS (ESIpos): m/z=389 [M+H]$^+$ $^1$H-NMR (400 MHz, DMSO-d$_6$) δ [ppm] 2.09 (s, 3H), 3.79 (s, 2H), 7.18 (m, 1H), 7.19 (m, 1H), 7.33 (m, 1H), 7.41 (ddd, 1H), 7.48 (s, 2H), 7.49 (d, 1H), 7.60 (s, 1H), 7.87 (s, 1H), 7.96 (dd, 1H), 8.33 (d, 1H), 10.73 (s, 1H).

Example 263

N-[4-(4-Cyclopropyl-1H-imidazol-1-yl)-3-sulfamoylphenyl]-2-(2-fluorophenyl)-acetamide

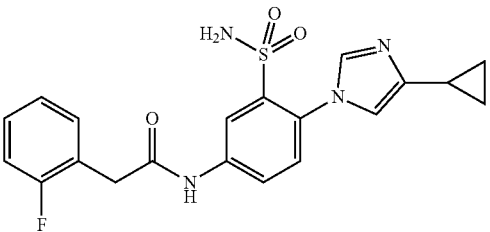 [SMILES: NS(=O)(=O)c1cc(NC(=O)Cc2ccccc2F)ccc1-n1cnc(C2CC2)c1]

N-{4-(4-Cyclopropyl-1H-imidazol-1-yl)-3-[(2,4-dimethoxybenzyl)sulfamoyl]phenyl}-2-(2-fluorophenyl)acetamide (50.0 mg, 44.3 μmol, 50% purity) was dissolved in dichloromethane (280 μL) and treated with trifluoroacetic acid (170 μL, 2.2 mmol) followed by stirring at room temperature overnight. The mixture was concentrated in vacuo and purified by HPLC to give the title compound (2.3 mg, 11% yield, 90% purity).

LC-MS (Method B): Rt=0.74 min; MS (ESIpos): m/z=415 [M+H]$^+$ $^1$H-NMR (400 MHz, DMSO-d$_6$) δ [ppm] 0.68 (m, 2H), 0.78 (m, 2H), 1.82 (m, 1H), 3.79 (s, 2H), 7.06 (d, 1H), 7.18 (m, 1H), 7.19 (m, 1H), 7.33 (m, 1H), 7.39 (s, 1H), 7.37 (d, 1H), 7.50 (s, 2H), 7.57 (d, 1H), 7.85 (dd, 1H), 8.37 (d, 1H), 10.73 (s, 1H).

Example 264

N-[4-(3-Cyclopropyl-1H-pyrazol-1-yl)-3-sulfamoylphenyl]-2-(2-fluorophenyl)-acetamide

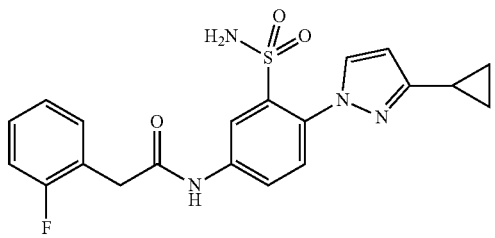 [SMILES: NS(=O)(=O)c1cc(NC(=O)Cc2ccccc2F)ccc1-n1ccc(C2CC2)n1]

N-{4-(3-Cyclopropyl-1H-pyrazol-1-yl)-3-[(2,4-dimethoxybenzyl)sulfamoyl]phenyl}-2-(2-fluorophenyl)acetamideacetamide (507 mg, 494 µmol, 55% purity) was dissolved in dichloromethane (3.2 mL) and treated with trifluoroacetic acid (230 µL, 3.0 mmol) followed by stirring at room temperature overnight. Further trifluoroacetic acid (799 µL, 10.4 mmol) was added and stirring was continued for 4 hours at room temperature. The mixture was concentrated in vacuo and purified by HPLC to give the title compound (115 mg, 53% yield, 95% purity).

LC-MS (Method A): Rt=1.09 min; MS (ESIpos): m/z=415 [M+H]$^+$ $^1$H-NMR (400 MHz, DMSO-d$_6$) δ [ppm] 0.69 (m, 2H), 0.93 (m, 2H), 1.98 (m, 1H), 3.79 (s, 2H), 6.24 (d, 1H), 7.18 (m, 1H), 7.19 (m, 1H), 7.33 (m, 1H), 7.40 (m, 1H), 7.49 (d, 1H), 7.53 (s, 2H), 7.95 (dd, 1H), 7.94 (d, 1H), 8.23 (d, 1H), 10.72 (s, 1H).

Example 265

2-(2-Fluorophenyl)-N-{4-[4-(2-methoxyethyl)-1H-pyrazol-1-yl]-3-sulfamoyl-phenyl}acetamide

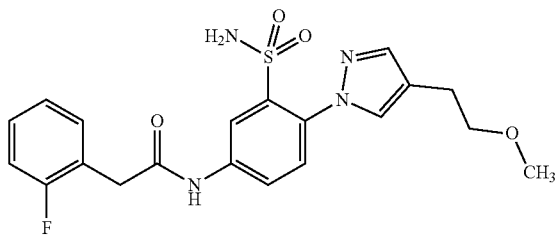 [SMILES: COCCc1cnn(-c2ccc(NC(=O)Cc3ccccc3F)cc2S(N)(=O)=O)c1]

N-{3-[(2,4-Dimethoxybenzyl)sulfamoyl]-4-[4-(2-methoxyethyl)-1H-pyrazol-1-yl]phenyl}-2-(2-fluorophenyl)acetamide (500 mg, 566 µmol, 66% purity) was dissolved in dichloromethane (7.3 mL) and treated with trifluoroacetic acid (2.2 mL, 28 mmol) followed by stirring at room temperature overnight. The mixture was concentrated in vacuo and purified by HPLC to give the title compound (197 mg, 72% yield, 90% purity).

LC-MS (Method A): Rt=1.06 min; MS (ESIpos): m/z=433 [M+H]$^+$ $^1$H-NMR (400 MHz, DMSO-d$_6$) δ [ppm] 2.72 (t, 2H), 3.28 (s, 3H), 3.52 (t, 2H), 3.79 (s, 2H), 7.18 (m, 1H), 7.19 (m, 1H), 7.33 (m, 1H), 7.40 (ddd, 1H), 7.47 (s, 2H), 7.50 (d, 1H), 7.65 (s, 1H), 7.92 (s, 1H), 7.96 (dd, 1H), 8.34 (d, 1H), 10.73 (s, 1H).

Example 266

2-(2-Chlorophenyl)-N-(2-sulfamoylbiphenyl-4-yl) acetamide

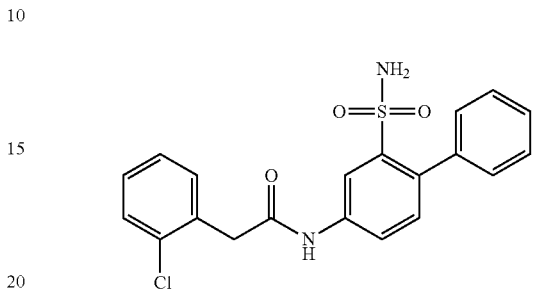

2-Chloro-N-(2,4-dimethoxybenzyl)-5-nitrobenzenesulfonamide (300 mg, 776 µmol) and phenylboronic acid (113 mg, 931 µmol) were dissolved in DMF (10 ml) followed by addition of bis(triphenylphosphine)palladium(II) dichloride (CAS 13965-03-2) (127 mg, 155 µmol) and aq. potassium carbonate (1.2 ml, 1.0 M, 1.2 mmol). The reaction was heated for 1 h at 120° C. in the microwave. Afterwards, ethyl acetate was added and washed with water. The combined organic phases were dried over Whatman filter, the solvent was removed under reduced pressure and the crude was purified by chromatography on silica gel (Biotage, hexane/ethyl acetate 1/1) to yield N-(2,4-dimethoxybenzyl)-4-nitrobiphenyl-2-sulfonamide 260 mg (99% purity, 78% yield).

LC-MS (Method A): Rt=1.33 min; MS (ESIneg): m/z=427 [M−H]$^-$ $^1$H-NMR (400 MHz, DMSO-d$_6$) δ [ppm]=3.62 (s, 3H), 3.68 (s, 3H), 3.91 (s, 2H), 6.28-6.37 (m, 2H), 6.96 (d, 1H), 7.33-7.41 (m, 2H), 7.41-7.47 (m, 3H), 7.54 (d, 1H), 7.96 (s, 1H), 8.33 (dd, 1H), 8.50 (d, 1H).

N-(2,4-dimethoxybenzyl)-4-nitrobiphenyl-2-sulfonamide (260 mg, 607 µmol) was dissolved in THF (15 ml) and palladium on charcoal (10% loading, 6.46 mg, 60.7 µmol) was added. The flask was evacuated and purged with hydrogen (1 bar) and stirring was continued at room temperature until completion of the reaction. The mixture was filtered over Celite, the solvent was removed under reduced pressure and the crude was used without further purification in the next step.

4-Amino-N-(2,4-dimethoxybenzyl)biphenyl-2-sulfonamide (90.0 mg, 226 µmol) was dissolved in DMF (4.0 ml) and (2-chlorophenyl)acetic acid (46.2 mg, 271 µmol) was added followed by the addition of N,N-diisopropylethylamine (190 µl, 1.1 mmol) and HATU (129 mg, 339 µmol). The reaction mixture was heated at 50° C. for 16 h. Afterwards, the solvent was removed under reduced pressure and the crude was used without further purification in the next step.

2-(2-Chlorophenyl)-N-{2-[(2,4-dimethoxybenzyl)sulfamoyl]biphenyl-4-yl}acetamide (490 mg, 889 µmol) was dissolved in dichloromethane (2 ml) and treated with triflic acid (2.0 ml, 26 mmol). The reaction was stirred at room temperature until completion of the reaction. The solvent was evaporated and the crude was dissolved in ethyl acetate and an aqueous solution of NaOH/NaCl (30 g/5 g in 90 g water) was added. The phases were separated and the aqueous phase was extracted with ethyl acetate. The combined organic phases were dried over Whatman filter, the solvent was removed under reduced pressure and the crude was purified by HPLC chromatography (Waters XBrigde C18 5µ 100×30 mm, acetonitrile/water+0.1% formic acid) to yield the title compound (43 mg, 97% purity, 12% yield over 3 steps).

LC-MS (Method A): Rt=1.13 min; MS (ESIpos): m/z=401 [M+H]⁺

¹H-NMR (400 MHz, DMSO-de) δ [ppm]=3.89 (s, 2H), 7.04 (s, 2H), 7.24 (d, 1H), 7.30-7.35 (m, 2H), 7.35-7.40 (m, 5H), 7.42-7.48 (m, 2H), 7.82 (dd, 1H), 8.34 (d, 1H), 10.60 (s, 1H).

Example 267

2-(2-Chlorophenyl)-N-{4-[1-(cyclopropylmethyl)-1H-pyrazol-4-yl]-3-sulfamoyl-phenyl}acetamide

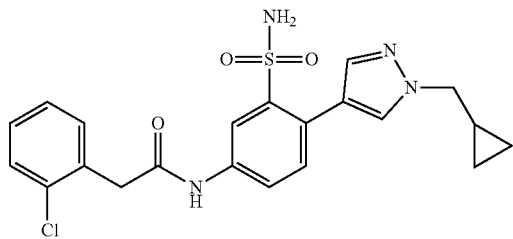 [SMILES: NS(=O)(=O)c1cc(NC(=O)Cc2ccccc2Cl)ccc1-c1cnn(CC2CC2)c1]

N-(4-Bromo-3-{[(dimethylamino)methylidene]sulfamoyl}phenyl)-2-(2-chlorophenyl)acetamide (200 mg, 436 µmol), 1-(cyclopropylmethyl)-4-(4,4,5,5-tetramethyl-1,3,2-dioxaborolan-2-yl)-1H-pyrazole (216 mg, 872 µmol), bis(triphenylphosphine)-palladium(II) dichloride (CAS 13965-03-2) (15.3 mg, 21.8 µmol), potassium fluoride (50.7 mg, 872 µmol) and triphenylphosphine (5.72 mg, 21.8 µmol) were dissolved in n-propanol (3.6 ml). Afterwards, potassium fluoride (50.7 mg, 872 µmol) and aqueous potassium carbonate (540 µl, 2.0 M, 1.1 mmol) were added and the solution was purged with argon for 5 minutes. The reaction mixture was heated for 3 h at 80° C. The crude was filtered over celite and the solvent was removed under reduced pressure. The crude was used without further purification in the next step.

2-(2-Chlorophenyl)-N-(4-[1-(cyclopropylmethyl)-1H-pyrazol-4-yl]-3-{[(dimethylamino)methylidene]sulfamoyl}phenyl)acetamide (240 mg, 480 µmol) was dissolved in methanol (4.9 ml) and 32% aq. sodium hydroxide solution (210 µl, 7.2 mmol) was added. The reaction was heated at 80° C. until completion of the reaction and the solvent was removed under reduced pressure. The crude was partitioned between dichloromethane and water, the organic phases were combined and dried over Whatman filter and the solvent was removed under reduced pressure. The crude was purified by HPLC (Waters XBrigde C18 5µ 100×30 mm, acetonitrile/water+0.2% aqueous ammonia (32%)) to yield the final compound (9.20 mg, 95% purity, 4% yield over 2 steps)

LC-MS (Method B): Rt=1.00 min; MS (ESIpos): m/z=445 [M+H]⁺

¹H-NMR (400 MHz, DMSO-d₆): δ [ppm]=0.30-0.43 (m, 2H), 0.50-0.59 (m, 2H), 1.21-1.34 (m, 1H), 3.88 (s, 2H), 3.99 (d, 2H), 7.16 (s, 2H), 7.29-7.39 (m, 2H), 7.41-7.50 (m, 3H), 7.70 (d, 1H), 7.78-7.86 (m, 1H), 8.01-8.09 (m, 1H), 8.28-8.35 (m, 1H), 10.57 (s, 1H).

Example 268

2-(2-Chlorophenyl)-N-{4-[1-(2-methoxyethyl)-1H-pyrazol-4-yl]-3-sulfamoylphenyl}-acetamide

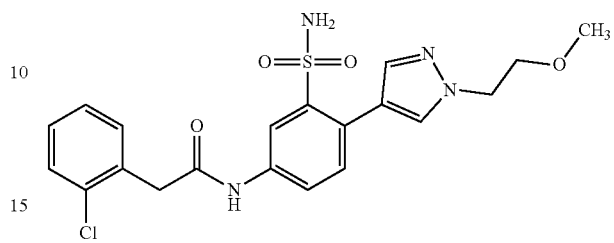

5-Amino-2-[1-(2-methoxyethyl)-1H-pyrazol-4-yl]benzenesulfonamide (190 mg, 641 µmol) was dissolved in DMF (4.5 ml) and HATU (390 mg, 1.03 mmol), N,N-diisopropylethylamine (560 µl, 3.2 mmol) and (2-chlorophenyl)acetic acid (131 mg, 769 µmol) were added. The reaction mixture was stirred for 18 h at 50° C. Afterwards, water and dichloromethane were added, the phases were separated and the combined organic phases were dried over Whatman filter. The solvents were removed under reduced pressure and the crude was purified by HPLC (Waters XBrigde C18 5µ 100×30 mm, acetonitrile/water+0.2% aqueous ammonia (32%)) (70.0 mg, 95% purity, 23% yield).

LC-MS (Method B): Rt=0.92 min; MS (ESIpos): m/z=449 [M+H]⁺

¹H-NMR (400 MHz, DMSO-d₆) δ [ppm]=3.24 (s, 3H), 3.70 (t, 2H), 3.87 (s, 2H), 4.28 (t, 2H), 7.08 (s, 2H), 7.27-7.37 (m, 2H), 7.40-7.50 (m, 3H), 7.70 (m, 1H), 7.81 (dd, 1H), 8.00 (m, 1H), 8.32 (d, 1H), 10.56 (s, 1H).

Example 269

2-(2-Chlorophenyl)-N-{4-[1-(piperidin-4-yl)-1H-pyrazol-4-yl]-3-sulfamoylphenyl}-acetamide

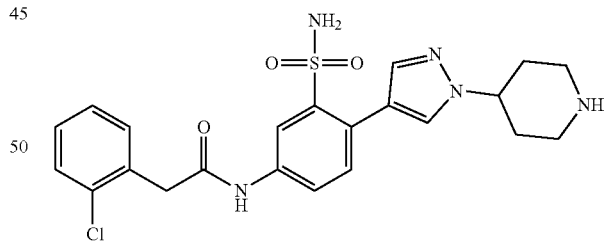

tert-Butyl 4-[4-(4-amino-2-sulfamoylphenyl)-1H-pyrazol-1-yl]piperidine-1-carboxylate (190 mg, 451 µmol) was dissolved in DMF (3.2 ml) and (2-chlorophenyl)acetic acid (92.3 mg, 541 µmol) was added, followed by the addition of N,N-diisopropylethylamine (390 µl, 2.3 mmol) and HATU (274 mg, 721 µmol). The reaction was stirred at 50° C. for 18 h. Water and dichloromethane were added. The phases were separated and the aqueous phase was washed with dichloromethane. The combined organic phases were dried over Whatman filter and the solvent was removed under reduced pressure. The crude was used in the next step without further purification.

tert-Butyl 4-[4-(4-{[(2-chlorophenyl)acetyl]amino}-2-sulfamoylphenyl)-1H-pyrazol-1-yl]piperidine-1-carboxylate (260 mg, 453 µmol) was dissolved in dichloromethane (2.7 ml) and trifluoroacetic acid (1.7 ml, 23 mmol) was added and stirring was continued at room temperature until completion of the reaction. The solvent was removed under reduced pressure and the crude co-distilled twice with toluene. The pure title compound was obtained after HPLC purification (first: Waters XBrigde C18 5µ 100×30 mm, acetonitrile/water+0.2% aqueous ammonia (32%); then Waters XBrigde C18 5µ 100×30 mm, acetonitrile/water+0.1% formic acid) (2.6 mg, 96% purity, 2% yield over 3 steps).

LC-MS (Method B): Rt=0.87 min; MS (ESIneg): m/z=472 [M–H]⁻

$^1$H-NMR (400 MHz, DMSO-d$_6$) δ [ppm]=1.87-2.03 (m, 2H), 2.04-2.13 (m, 2H), 2.73-2.86 (m, 2H), 3.15-3.23 (m, 2H), 3.88 (s, 2H), 4.25-4.38 (m, 1H), 7.21 (s, 2H), 7.25-7.38 (m, 2H), 7.41-7.50 (m, 3H), 7.74 (s, 1H), 7.82 (dd, 1H), 8.07 (s, 1H), 8.29-8.36 (m, 2H), 10.61 (s, 1H).

Example 270

2-(2-Fluorophenyl)-N-{4-[1-(piperidin-4-yl)-1H-pyrazol-4-yl]-3-sulfamoylphenyl}acetamide

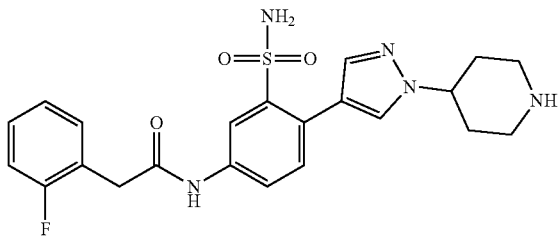 [SMILES: NS(=O)(=O)c1cc(NC(=O)Cc2ccccc2Cl)ccc1-c1cnn(C2CCNCC2)c1]

tert-Butyl 4-[4-(4-amino-2-sulfamoylphenyl)-1H-pyrazol-1-yl]piperidine-1-carboxylate (190 mg, 451 µmol) was dissolved in DMF (3.7 ml) and (2-fluorophenyl)acetic acid (83.4 mg, 541 µmol) was added, followed by the addition of N,N-diisopropylethylamine (390 µl, 2.3 mmol) and HATU (274 mg, 721 µmol). The reaction was stirred at 50° C. for 18 h. Then water and dichloromethane were added. The phases were separated and the aqueous phase was extracted with dichloromethane. The combined organic phases were dried over Whatman filter and the solvent was removed under reduced pressure. The crude was used in the next step without further purification.

tert-Butyl 4-[4-(4-{[(2-fluorophenyl)acetyl]amino}-2-sulfamoylphenyl)-1H-pyrazol-1-yl]piperidine-1-carboxylate (250 mg, 448 µmol) was dissolved in dichloromethane (2.6 ml) and trifluoroacetic acid (1.7 ml, 22 mmol) was added and stirring was continued at room temperature until completion of the reaction. The solvent was removed under reduced pressure and the crude was co-distilled with toluene twice. The pure title compound was obtained after HPLC (Waters XBrigde C18 5µ 100×30 mm, acetonitrile/water+0.2% aqueous ammonia (32%)) (13.6 mg, 90% purity, 12% yield over 3 steps).

LC-MS (Method B): Rt=0.81 min; MS (ESIneg): m/z=456 [M–H]⁻

$^1$H-NMR (400 MHz, DMSO-d$_6$): δ [ppm]=1.74-1.96 (m, 2H), 1.96-2.09 (m, 2H), 2.63-2.75 (m, 2H), 3.06-3.17 (m, 2H), 3.77 (s, 2H), 4.17-4.32 (m, 1H), 7.13-7.23 (m, 4H), 7.26-7.48 (m, 3H), 7.72 (s, 1H), 7.81 (dd, 1H), 8.05 (s, 1H), 8.31 (d, 1H), 10.55 (s, 1H), 10.51-10.61 (m, 1H).

Example 271

N-{4-[1-(Azetidin-3-yl)-1H-pyrazol-4-yl]-3-sulfamoylphenyl}-2-(2-chlorophenyl)-acetamide

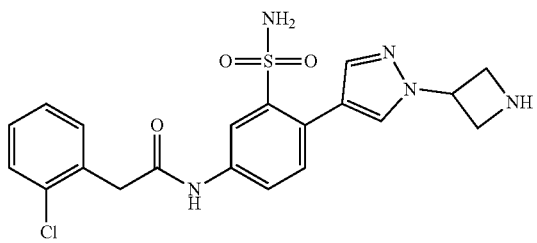 [SMILES: NS(=O)(=O)c1cc(NC(=O)Cc2ccccc2Cl)ccc1-c1cnn(C2CNC2)c1]

2-Chloro-N-[(dimethylamino)methylidene]-5-nitrobenzenesulfonamide (170 mg, 583 µmol) and tert-butyl 3-[4-(4,4,5,5-tetramethyl-1,3,2-dioxaborolan-2-yl)-1H-pyrazol-1-yl]azetidine-1-carboxylate (305 mg, 874 µmol) were dissolved in n-propanol (7.8 ml) and bis(triphenylphosphine)palladium(II) dichloride (CAS 13965-03-2) (20.5 mg, 29.1 µmol), triphenylphosphine (7.64 mg, 29.1 µmol) and aq. potassium carbonate (730 µl, 2.0 M, 1.5 mmol) were added. The solution was purged with argon for 5 minutes and the reaction was heated at 80° C. for 16 h. Afterwards the mixture was filtered over Celite, the solvent was removed under reduced pressure and the crude was co-distilled with THE and used without further purification in the next step. tert-Butyl 3-[4-(4-nitro-2-sulfamoylphenyl)-1H-pyrazol-1-yl]azetidine-1-carboxylate (250 mg, 590 µmol) was dissolved in THE (59 ml)/methanol (50 ml) and the flask was flushed with nitrogen. Palladium on charcoal (10% loading, 64.1 mg, 602 µmol) was added and the flask was evacuated and subsequently flushed with hydrogen (1 bar). Stirring was continued at room temperature for 4 h. The reaction mixture was filtered over Celite and the solvent was removed under reduced pressure. The crude was used without further purification in the next step.

tert-Butyl 3-[4-(4-amino-2-sulfamoylphenyl)-1H-pyrazol-1-yl]azetidine-1-carboxylate (230 mg, 585 µmol) was dissolved in DMF (4.1 ml) and (2-chlorophenyl)acetic acid (120 mg, 701 µmol) was added followed by the addition of N,N-diisopropylethylamine (510 µl, 2.9 mmol) and HATU (356 mg, 935 µmol). The reaction was stirred at 50° C. for 18 h. Then water and dichloromethane were added. The phases were separated and the aqueous phase was extracted with dichloromethane. The combined organic phases were dried over Whatman filter and the solvent was removed under reduced pressure. The crude was used in the next step without further purification.

tert-Butyl 3-[4-(4-{[(2-chlorophenyl)acetyl]amino}-2-sulfamoylphenyl)-1H-pyrazol-1-yl]azetidine-1-carboxylate (150 mg, 275 µmol) was dissolved in dichloromethane (1.6 ml) and trifluoroacetic acid (1.1 ml, 14 mmol) was added and stirring was continued at room temperature until completion of the reaction. Dichloromethane and water were added. The phases were separated and the aqueous phase was extracted with dichloromethane. The combined organic phases were dried over Whatman filter and the solvent was removed under reduced pressure. The crude was co-distilled with toluene and the pure product was obtained after purification by HPLC (Waters XBrigde C18 5μ 100×30 mm, methanol/water+0.2% aqueous ammonia (32%) then Waters XBrigde C18 5μ 100×30 mm, acetonitrile/water+0.1% formic acid) (4.90 mg, 90% purity, 4% yield over 3 steps).

LC-MS (Method 1): Rt=1.05 min; MS (ESIneg): m/z=444 [M−H]⁻

$^1$H-NMR (400 MHz, DMSO-d$_6$) δ [ppm]=3.87 (s, 2H), 3.94-4.04 (m, 2H), 4.07-4.18 (m, 2H), 5.23-5.35 (m, 1H), 7.09-7.28 (m, 2H), 7.29-7.35 (m, 2H), 7.41-7.48 (m, 3H), 7.76-7.88 (m, 2H), 8.12 (s, 1H), 8.28-8.38 (m, 2H), 10.61 (s, 1H).

Example 272

2-(3-Chlorophenyl)-N-(2-sulfamoylbiphenyl-4-yl)acetamide

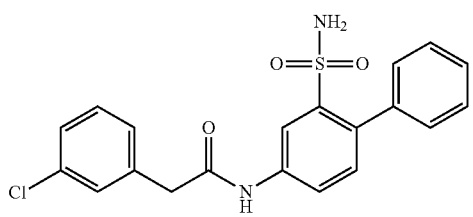 [SMILES: NS(=O)(=O)c1cc(NC(=O)Cc2cccc(Cl)c2)ccc1-c1ccccc1]

4-Amino-N-(2,4-dimethoxybenzyl)biphenyl-2-sulfonamide (75.0 mg, 188 μmol) was dissolved in DMF (1.5 ml) and (3-chlorophenyl)acetic acid (38.5 mg, 226 μmol) was added followed by the addition of N,N-diisopropylethylamine (160 μl, 940 μmol) and HATU (107 mg, 282 μmol). The reaction was stirred at 60° C. for 2 h. The solvent was removed under reduced pressure and the crude was used without further purification.

2-(3-Chlorophenyl)-N-{2-[(2,4-dimethoxybenzyl)sulfamoyl]biphenyl-4-yl}acetamide (340 mg, 617 μmol) was dissolved in dichloromethane (1.9 ml) and trifluoroacetic acid (1.9 ml, 24 mmol) was added and stirring was continued at room temperature until completion of the reaction. The solvent was removed under reduced pressure and the crude was dissolved in ethyl acetate and washed with an aqueous solution of sodium hydroxide/sodium chloride (30 g/5 g in 90 g water). The phases were separated and the aqueous phase was extracted with ethyl acetate. The combined organic phases were dried over Whatman filter and the solvent was removed under reduced pressure. The crude was purified by HPLC (Waters XBrigde C18 5μ 100×30 mm, acetonitrile/water+0.1% formic acid) to yield the title compound (41.7 mg, 98% purity, 17% yield over 2 steps).

LC-MS (Method A): Rt=1.16 min; MS (ESIneg): m/z=399 [M−H]⁻

$^1$H-NMR (400 MHz, DMSO-de) δ [ppm]=3.73 (s, 2H), 7.07 (s, 2H), 7.24 (d, 1H), 7.29-7.40 (m, 8H), 7.43 (s, 1H), 7.80-7.86 (m, 1H), 8.31 (d, 1H), 10.57 (s, 1H).

Example 273

2-(2-Chlorophenyl)-N-[4-(3-methyl-1H-pyrazol-1-yl)-3-sulfamoylphenyl]acetamide

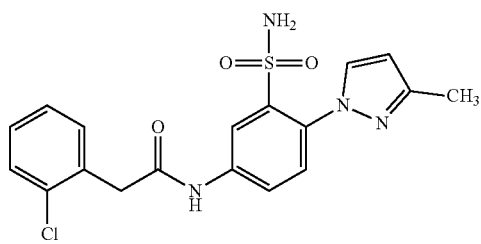 [SMILES: Cc1ccn(-c2ccc(NC(=O)Cc3ccccc3Cl)cc2S(N)(=O)=O)n1]

2-Chloro-N-(2,4-dimethoxybenzyl)-5-nitrobenzenesulfonamide (500 mg, 1.29 mmol), 3-methyl-1H-pyrazole (159 mg, 1.94 mmol) and potassium carbonate (536 mg, 3.88 mmol) were dissolved in acetonitrile (15 ml) and the reaction was stirred at 100° C. overnight. The solvent was removed under reduced pressure and water and dichloromethane were added. The phases were separated and the aqueous phase was extracted with dichloromethane. The combined organic phases were dried over Whatman filter and the solvent was removed under reduced pressure. The crude was used in the next step without further purification.

N-(2,4-Dimethoxybenzyl)-2-(3-methyl-1H-pyrazol-1-yl)-5-nitrobenzenesulfonamide (500 mg, 1.16 mmol) was dissolved in ethyl acetate/ethanol (1/1, 40 ml) and the flask was flushed with nitrogen. Palladium on charcoal (10% loading, 123 mg, 116 μmol) was added and the flask was evacuated and subsequently flushed with hydrogen (1 bar). Stirring was continued at room temperature for 18 h. The reaction mixture was filtered over Celite and the solvent was removed under reduced pressure. The crude was used without further purification in the next step.

5-Amino-N-(2,4-dimethoxybenzyl)-2-(3-methyl-1H-pyrazol-1-yl)benzenesulfonamide (410 mg, 1.02 mmol) was dissolved in DMF (30 ml) and (2-chlorophenyl)acetic acid (209 mg, 1.22 mmol) was added followed by the addition of N,N-diisopropylethylamine (890 μl, 5.1 mmol) and HATU (799 mg, 2.04 mmol). The reaction was stirred at 50° C. for 3 h. The solvent was removed under reduced pressure and ethyl acetate and water were added. The phases were separated and the aqueous phase was extracted with ethyl acetate. The combined organic phases were dried over Whatman filter and the solvent was removed under reduced pressure. The crude was purified by chromatography on silica gel (Biotage, hexane/ethyl acetate) to yield 80 mg (14% yield over 3 steps).

2-(2-Chlorophenyl)-N-{3-[(2,4-dimethoxybenzyl)sulfamoyl]-4-(3-methyl-1H-pyrazol-1-yl)phenyl}acetamide (80.0 mg, 144 μmol) was dissolved in dichloromethane (2.0 ml) and trifluoroacetic acid (1.5 ml, 19 mmol) was added and stirring was continued at room temperature until completion of the reaction. The solvent was removed under reduced pressure and the pure title compound was obtained after purification by HPLC (Waters XBrigde C18 5μ 100×30 mm, acetonitrile/water+0.2% aqueous ammonia (32%)) (9.00 mg, 95% purity, 15% yield).

LC-MS (Method B): Rt=0.98 min; MS (ESIneg): m/z=403 [M−H]⁻

¹H-NMR (400 MHz, DMSO-d₆) δ [ppm]=2.27 (s, 3H), 3.90 (s, 2H), 6.31 (d, 1H), 7.27-7.37 (m, 2H), 7.43-7.50 (m, 2H), 7.52 (s, 2H), 7.86-8.08 (m, 2H), 8.35 (d, 1H), 10.75 (s, 1H).

Example 274

2-(2-Chlorophenyl)-N-[4-(6-chloropyridin-3-yl)-3-sulfamoylphenyl]acetamide

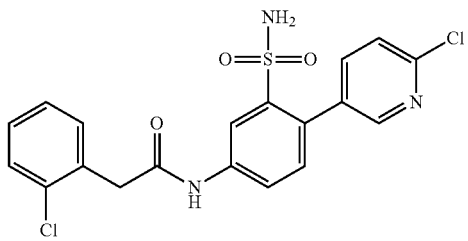 [SMILES: NS(=O)(=O)c1cc(NC(=O)Cc2ccccc2Cl)ccc1-c1ccc(Cl)nc1]

2-Bromo-N-[(dimethylamino)methylidene]-5-nitrobenzenesulfonamide (632 mg, 1.88 mmol) and 2-chloro-5-(4,4,5,5-tetramethyl-1,3,2-dioxaborolan-2-yl)pyridine (450 mg, 1.88 mmol) were dissolved in n-propanol (35 ml) and bis(triphenylphosphine)palladium(II) dichloride (CAS 13965-03-2) (66.1 mg, 93.9 µmol) and triphenylphosphine (24.6 mg, 93.9 µmol) were added. The solution was purged with argon for 5 minutes and aq. potassium carbonate (5.6 ml, 1.0 M, 5.6 mmol) was added. The reaction was heated at 100° C. for 3 h. Afterwards the mixture was filtered over Celite, the solvent was removed and ethyl acetate and water were added. The phases were separated and the aqueous phase was extracted with ethyl acetate. The combined organic phases were dried over Whatman filter and the solvent was removed under reduced pressure. The crude was used in the next step without further purification.

2-(6-Chloropyridin-3-yl)-N-[(dimethylamino)methylidene]-5-nitrobenzenesulfonamide (660 mg, 1.79 mmol) was dissolved in THF (50 ml) and the flask was flushed with nitrogen. Platinum on charcoal (5% loading, 698 mg, 179 µmol) was added and the flask was evacuated and subsequently flushed with hydrogen (1 bar). Stirring was continued at room temperature for 2 h. Platinum on charcoal (698 mg, 179 µmol) was added again and stirring was continued for 2 h. The reaction mixture was filtered over Celite and the solvent was removed under reduced pressure. The crude was used without further purification in the next step.

5-Amino-2-(6-chloropyridin-3-yl)-N-[(dimethylamino)methylidene]benzenesulfonamide (630 mg, 1.86 mmol) was dissolved in DMF (25 ml) and (2-chlorophenyl)acetic acid (381 mg, 2.23 mmol) was added followed by the addition of N,N-diisopropylethylamine (1.6 ml, 9.3 mmol) and HATU (1.41 g, 372 mmol). The reaction was stirred at 50° C. for 16 h. Water and ethyl acetate were added. The phases were separated and the aqueous phase was extracted with ethyl acete. The combined organic phases were dried over Whatman filter and the solvent was removed under reduced pressure. The crude was purified by chromatography on silica gel (Biotage, 2% gradient of ethanol in dichloromethane) to yield 100 mg (11% yield over 3 steps).

LC-MS (Method B): Rt=1.15 min; MS (ESIneg): m/z=489 [M−H]⁻

2-(2-Chlorophenyl)-N-[4-(6-chloropyridin-3-yl)-3-{[(dimethylamino)methylidene]-sulfamoyl}phenyl]acetamide (100 mg, 204 µmol) was dissolved in methanol (30 ml) and treated with 25% aqueous ammonia solution (30 ml) at room temperature until completion of the reaction. The solvent was removed under reduced pressure and the crude was purified by HPLC (Chromatorex C-18 10 µm, 125×30 mm, acetonitrile/water+0.2% aqueous ammonia (32%)) to yield the title compound (4.90 mg, 95% purity, 5% yield).

LC-MS (Method B): Rt=1.01 min; MS (ESIneg): m/z=434 [M−H]⁻

¹H-NMR (400 MHz, DMSO-d₆) δ [ppm]=3.90 (s, 2H), 7.26-7.36 (m, 3H), 7.39 (s, 2H), 7.43-7.50 (m, 2H), 7.53 (d, 1H), 7.84 (ddd, 2H), 8.36 (dd, 2H), 10.70 (s, 1H).

Example 275

2-(2-Chlorophenyl)-N-[4-(3,5-dimethyl-1,2-oxazol-4-yl)-3-sulfamoylphenyl]acetamide

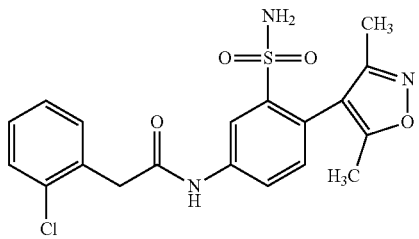 [SMILES: Cc1noc(C)c1-c1ccc(NC(=O)Cc2ccccc2Cl)cc1S(N)(=O)=O]

2-Bromo-N-[(dimethylamino)methylidene]-5-nitrobenzenesulfonamide (400 mg, 1.19 mmol) and (3,5-dimethyl-1,2-oxazol-4-yl)boronic acid (335 mg, 2.38 mmol) were dissolved in n-propanol (110 ml) and bis(triphenylphosphine)palladium(II) dichloride (CAS 13965-03-2) (41.9 mg, 59.5 µmol), triphenylphosphine (21.6 mg, 59.5 µmol) and aq. potassium carbonate (1.8 ml, 2.0 M, 3.6 mmol) were added. The reaction was stirred at 120° C. for 1 h in the microwave. Afterwards the mixture was filtered over Celite, the solvent was removed under reduced pressure and the crude was co-distilled with methanol and used without further purification in the next step.

2-(3,5-Dimethyl-1,2-oxazol-4-yl)-5-nitrobenzenesulfonamide (450 mg, 1.51 mmol) was dissolved in methanol (69 ml) and the flask was flushed with nitrogen. Palladium on charcoal (10% loading, 164 mg, 1.54 mmol) was added and the flask was evacuated and subsequently flushed with hydrogen (1 bar). Stirring was continued at room temperature for 4 h. The reaction mixture was filtered over Celite and the solvent was removed under reduced pressure. The crude was co-distilled with THF and used without further purification in the next step.

5-Amino-2-(3,5-dimethyl-1,2-oxazol-4-yl)benzenesulfonamide (200 mg, 748 µmol) was dissolved in DMF (5.3 ml) and (2-chlorophenyl)acetic acid (153 mg, 898 µmol) was added followed by the addition of N,N-diisopropylethylamine (620 µl, 3.7 mmol) and HATU (455 mg, 1.20 mmol). The reaction was stirred at 50° C. for 4 h, then water and dichloromethane were added. The phases were separated and the aqueous phase was extracted with dichloromethane. The combined organic phases were dried over Whatman filter and the solvent was removed under reduced pressure. The pure product was obtained after HPLC purification (Waters XBrigde C18 5µ 100×30 mm, methanol/water+0.2% aqueous ammonia (32%)) (28.4 mg, 95% purity, 9% yield over 3 steps).

LC-MS (Method J): Rt=0.99 min; MS (ESIneg): m/z=418 [M−H]⁻

¹H-NMR (500 MHz, DMSO-d₆) δ [ppm]=1.94 (s, 3H), 2.12 (s, 3H), 3.89 (s, 2H), 7.22 (d, 1H), 7.29-7.38 (m, 4H), 7.42-7.48 (m, 2H), 7.85 (dd, 1H), 8.34 (d, 1H), 10.67 (s, 1H).

Example 276

2-(2-Chlorophenyl)-N-(4-{1-[(3-methyloxetan-3-yl)methyl]-1H-pyrazol-4-yl}-3-sulfamoylphenyl)acetamide

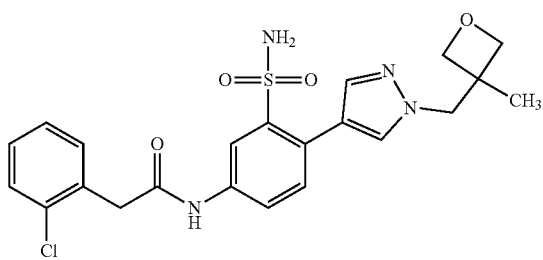

N-(4-Bromo-3-{[(dimethylamino)methylidene]sulfamoyl}phenyl)-2-(2-chlorophenyl)acetamide (225 mg, 490 μmol) and 1-[(3-methyloxetan-3-yl)methyl]-4-(4,4,5,5-tetramethyl-1,3,2-dioxaborolan-2-yl)-1H-pyrazole (273 mg, 981 μmol) were dissolved in n-propanol (9.0 ml) and bis(triphenylphosphine)palladium(II) dichloride (CAS 13965-03-2) (17.3 mg, 24.5 μmol), triphenylphosphine (6.43 mg, 24.5 μmol) and potassium fluoride (6.55 mg, 113 μmol) were added. The solution was purged with argon for 5 minutes and aq. potassium carbonate (610 μl, 2.0 M, 1.2 mmol) was added. The reaction was heated at 100° C. for 1 h in the microwave. Afterwards the mixture was filtered over Celite, the solvent was removed under reduced pressure and the crude was used without further purification in the next step.

2-(2-Chlorophenyl)-N-(3-{[(dimethylamino)methylidene]sulfamoyl}-4-{1-[(3-methyloxetan-3-yl)methyl]-1H-pyrazol-4-yl}phenyl)acetamide (270 mg, 509 μmol) was dissolved in methanol (5.2 ml) and treated with 32% aqueous sodium hydroxide (300 μl) at 50° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Chromatorex C-18 10 μm, 125×30 mm, acetonitrile/water+0.1% formic acid) to yield the title compound (20.8 mg, 95% purity, 8% yield over 2 steps).

LC-MS (Method A): Rt=0.99 min; MS (ESIneg): m/z=473 [M−H]⁻

¹H-NMR (400 MHz, DMSO-d₆) δ [ppm]=1.17 (s, 3H), 3.88 (s, 2H), 4.25 (d, 2H), 4.36 (s, 2H), 4.61 (d, 2H), 7.13 (s, 2H), 7.26-7.39 (m, 2H), 7.39-7.50 (m, 3H), 7.69-7.71 (m, 1H), 7.82 (dd, 1H), 8.03 (s, 1H), 8.33 (d, 1H), 10.58 (s, 1H).

Example 277

2-(2-Chloro-4-fluorophenyl)-N-{4-[1-(2-methoxyethyl)-1H-pyrazol-4-yl]-3-sulfamoylphenyl}acetamide

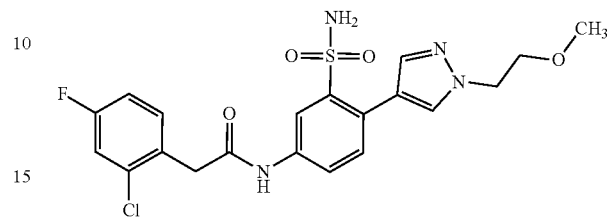

N-(4-Bromo-3-{[(dimethylamino)methylidene]sulfamoyl}phenyl)-2-(2-chloro-4-fluoro-phenyl)acetamide (250 mg, 524 μmol) and 1-(2-methoxyethyl)-4-(4,4,5,5-tetramethyl-1,3,2-dioxaborolan-2-yl)-1H-pyrazole (264 mg, 1.05 mmol) were dissolved in n-propanol (9.6 ml) and bis(triphenylphosphine)palladium(II) dichloride (CAS 13965-03-2) (18.5 mg, 26.2 μmol) and triphenylphosphine (6.88 mg, 26.2 μmol) were added. The solution was purged with argon for 5 minutes and aq. potassium carbonate (660 μl, 2.0 M, 1.3 mmol) was added. The reaction was heated at 120° C. for 1 h (5 bar/25 W). Afterwards the mixture was filtered over Celite, the solvent was removed under reduced pressure and the crude was purified by HPLC (Waters XBrigde C18 5μ 100×30 mm, acetonitrile/water+0.2% aqueous ammonia (32%)) to yield the title compound (37.8 mg, 95% purity, 15% yield).

LC-MS (Method B): Rt=0.93 min; MS (ESIneg): m/z=465 [M−H]⁻

¹H-NMR (400 MHz, DMSO-d₆) δ [ppm]=3.25 (s, 3H), 3.71 (t, 2H), 3.87 (s, 2H), 4.28 (t, 2H), 7.09 (s, 2H), 7.23 (td, 1H), 7.43-7.52 (m, 3H), 7.71 (s, 1H), 7.81 (dd, 1H), 8.01 (s, 1H), 8.32 (d, 1H), 10.57 (s, 1H).

Example 278

2-(2-Chloro-4-fluorophenyl)-N-[4-(1-cyclopropyl-1H-pyrazol-4-yl)-3-sulfamoyl-phenyl]acetamide

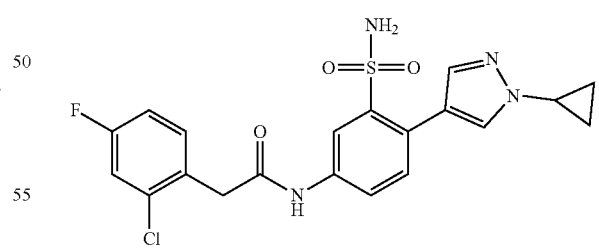

N-(4-Bromo-3-{[(dimethylamino)methylidene]sulfamoyl}phenyl)-2-(2-chloro-4-fluoro-phenyl)acetamide (250 mg, 524 μmol) and 1-cyclopropyl-4-(4,4,5,5-tetramethyl-1,3,2-dioxaborolan-2-yl)-1H-pyrazole (246 mg, 1.05 mmol) were dissolved in n-propanol (9.6 ml) and bis(triphenylphosphine)palladium(II) dichloride (CAS 13965-03-2) (18.5 mg, 26.2 μmol) and triphenylphosphine (6.88 mg, 26.2 μmol) were added. The solution was purged with argon for 5 minutes and aq. potassium carbonate (660 μl, 2.0 M, 1.3 mmol) was added. The reaction was heated at 120° C. for 1 h in the microwave (2 bar/25 W). Afterwards the mixture was filtered over Celite, the solvent was removed under reduced pressure and the crude was dissolved in methanol (5 ml) and treated with 32% aqueous sodium hydroxide (0.2 ml) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Waters XBrigde C18 5µ 100×30 mm, acetonitrile/water+ 0.2% aqueous ammonia (32%)) to yield the title compound (38.2 mg, 95% purity, 15% yield over 2 steps).

LC-MS (Method B): Rt=0.98 min; MS (ESIneg): m/z=447 [M−H]⁻

$^1$H-NMR (400 MHz, DMSO-d$_6$) δ [ppm]=0.94-1.01 (m, 2H), 1.05-1.11 (m, 2H), 3.74 (tt, 1H), 3.87 (s, 2H), 7.17-7.25 (m, 3H), 7.41-7.52 (m, 3H), 7.67 (s, 1H), 7.80 (dd, 1H), 8.04 (s, 1H), 8.31 (d, 1H), 10.57 (s, 1H).

Example 279

2-(2-Chlorophenyl)-N-(3-sulfamoyl-4-{1-[2-(trifluoromethoxy)ethyl]-1H-pyrazol-4-yl}phenyl)acetamide

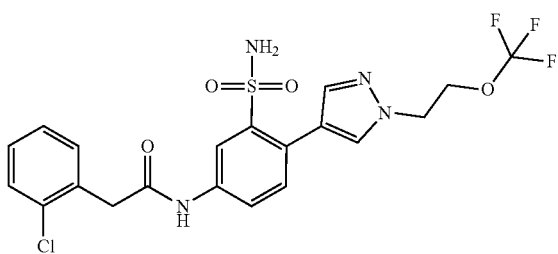

N-(4-Bromo-3-{[(dimethylamino)methylidene]sulfamoyl}phenyl)-2-(2-chlorophenyl)-acetamide (250 mg, 545 µmol) and 4-(4,4,5,5-tetramethyl-1,3,2-dioxaborolan-2-yl)-1-[2-(trifluoromethoxy)ethyl]-1H-pyrazole (334 mg, 1.09 mmol) were dissolved in n-propanol (10 ml) and bis(triphenylphosphine)palladium(II) dichloride (CAS 13965-03-2) (19.2 mg, 27.2 µmol) and triphenylphosphine (7.15 mg, 27.2 µmol) were added. The solution was purged with argon for 5 minutes and aq. potassium carbonate (680 µl, 2.0 M, 1.4 mmol) was added. The reaction was heated at 80° C. for 18 h. Afterwards the mixture was filtered over Celite, the solvent was removed under reduced pressure and the crude was used without further purification in the next step.

2-(2-Chlorophenyl)-N-(3-{[(dimethylamino)methylidene]sulfamoyl}-4-{1-[2-(trifluoro-methoxy)ethyl]-1H-pyrazol-4-yl}phenyl)acetamide (250 mg, 448 µmol) was dissolved in methanol (4.6 ml) and treated with 32% aqueous sodium hydroxide (0.2 ml) at room temperature until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Waters XBrigde C18 5µ 100×30 mm, acetonitrile/water+0.2% aqueous ammonia (32%)) to yield the title compound (1.60 mg, 95% purity, 1% yield over 2 steps).

LC-MS (Method B): Rt=1.06 min; MS (ESIneg): m/z=501 [M−H]⁻

$^1$H-NMR (400 MHz, DMSO-d$_6$) δ [ppm]=3.88 (s, 2H), 4.48 (s, 4H), 7.14 (s, 2H), 7.28-7.37 (m, 2H), 7.41-7.49 (m, 3H), 7.76 (s, 1H), 7.82 (dd, 1H), 8.07 (s, 1H), 8.33 (d, 1H), 10.59 (s, 1H).

Example 280

2-(2-Chlorophenyl)-N-[4-(1-cyclobutyl-1H-pyrazol-4-yl)-3-sulfamoylphenyl]acetamide

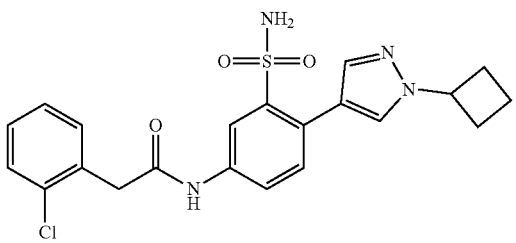 [SMILES: NS(=O)(=O)c1cc(NC(=O)Cc2ccccc2Cl)ccc1-c1cnn(C2CCC2)c1]

N-(4-Bromo-3-{[(dimethylamino)methylidene]sulfamoyl}phenyl)-2-(2-chlorophenyl)-acetamide (225 mg, 490 µmol) and (1-cyclobutyl-1H-pyrazol-4-yl)boronic acid (163 mg, 981 µmol) were dissolved in n-propanol (9.0 ml) and bis(triphenylphosphine)palladium(II) dichloride (CAS 13965-03-2) (17.3 mg, 24.5 µmol), triphenylphosphine (6.43 mg, 24.5 µmol) and potassium fluoride (6.55 mg, 113 µmol) were added. The solution was purged with argon for 5 minutes and aq. potassium carbonate (610 µl, 2.0 M, 1.2 mmol) was added. The reaction was heated at 100° C. for 1 h in the microwave. Afterwards the mixture was filtered over Celite, the solvent was removed under reduced pressure and the crude was used without further purification in the next step.

2-(2-Chlorophenyl)-N-[4-(1-cyclobutyl-1H-pyrazol-4-yl)-3-{[(dimethylamino)methylidene]-sulfamoyl}phenyl]acetamide (250 mg, 500 µmol) was dissolved in methanol (5.1 ml) and treated with 32% aqueous sodium hydroxide (0.2 ml) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Chromatorex C-18 10 µm, 125×30 mm, acetonitrile/water+ 0.1% formic acid) to yield the title compound (71.8 mg, 95% purity, 31% yield over 2 steps).

LC-MS (Method A): Rt=1.10 min; MS (ESIneg): m/z=443 [M−H]⁻.

$^1$H-NMR (400 MHz, DMSO-d$_6$) δ [ppm]=1.74-1.84 (m, 2H), 2.35-2.44 (m, 2H), 3.88 (s, 2H), 4.85 (quin, 1H), 7.22 (s, 2H), 7.29-7.36 (m, 2H), 7.42-7.48 (m, 3H), 7.74 (s, 1H), 7.81 (dd, 1H), 8.05 (s, 1H), 8.32 (d, 1H), 10.58 (s, 1H).

Example 281

2-(2-Chlorophenyl)-N-(4-{1-[2-(pyrrolidin-1-yl)ethyl]-1H-pyrazol-4-yl}-3-sulfamoyl-phenyl)acetamide

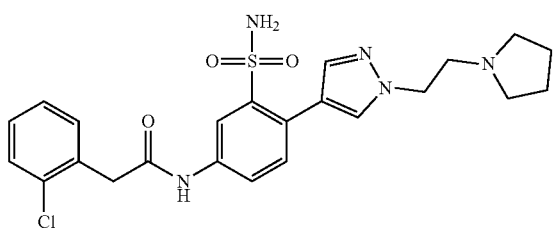 [SMILES: NS(=O)(=O)c1cc(NC(=O)Cc2ccccc2Cl)ccc1-c1cnn(CCN2CCCC2)c1]

N-(4-Bromo-3-{[(dimethylamino)methylidene]sulfamoyl}phenyl)-2-(2-chlorophenyl)acetamide (90.0 mg, 196 µmol) and 1-[2-(pyrrolidin-1-yl)ethyl]-4-(4,4,5,5-tetramethyl-1,3,2-dioxaborolan-2-yl)-1H-pyrazole (114 mg, 392 µmol) were dissolved in n-propanol (3.6 ml) and bis(triphenylphosphine)palladium(II) dichloride (CAS 13965-03-2) (6.90 mg, 9.81 µmol), triphenylphosphine (2.57 mg, 9.81 µmol) and potassium fluoride (2.62 mg, 45.1 µmol) were added. The solution was purged with argon for 5 minutes and aq. potassium carbonate (250 µl, 2.0 M, 490 µmol) was added. The reaction was heated at 100° C. for 1 h in the microwave. Afterwards the mixture was filtered over Celite, the solvent was removed under reduced pressure and the crude was used without further purification in the next step.

2-(2-Chlorophenyl)-N-(3-{[(dimethylamino)methylidene]sulfamoyl}-4-{1-[2-(pyrrolidin-1-yl)ethyl]-1H-pyrazol-4-yl}phenyl)acetamide (110 mg, 203 µmol) was dissolved in methanol (2.1 ml) and treated with 32% aqueous sodium hydroxide (80 µl) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Chromatorex C-18 10 µm, 125×30 mm, acetonitrile/water+0.1% formic acid) to yield the title compound (4.00 mg, 95% purity, 4% yield).

LC-MS (Method A): Rt=0.81 min; MS (ESIneg): m/z=486 [M−H]⁻

¹H-NMR (400 MHz, DMSO-d₆) δ [ppm]=1.69 (s, 4H), 2.79 (t, 2H), 3.88 (s, 2H), 4.25 (t, 2H), 6.94 (s, 2H), 7.28-7.37 (m, 2H), 7.41-7.50 (m, 3H), 7.66 (s, 1H), 7.84 (dd, 1H), 8.05 (s, 1H), 8.32 (d, 1H), 10.58 (s, 1H).

Example 282

2-(2-Chlorophenyl)-N-[4-(5-cyanopyridin-3-yl)-3-sulfamoylphenyl]acetamide

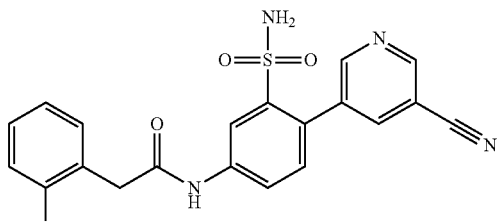

N-(4-Bromo-3-{[(dimethylamino)methylidene]sulfamoyl}phenyl)-2-(2-chlorophenyl)acetamide (250 mg, 545 µmol) and 5-(4,4,5,5-tetramethyl-1,3,2-dioxaborolan-2-yl)pyridine-3-carbonitrile (125 mg, 545 µmol) were dissolved in n-propanol (10 ml) and bis(triphenylphosphine)palladium(II) dichloride (CAS 13965-03-2) (19.2 mg, 27.2 µmol) and triphenylphosphine (7.15 mg, 27.2 µmol) were added. The solution was purged with argon for 5 minutes and aq. potassium carbonate (1.6 ml, 1.0 M, 1.6 mmol) was added. The reaction was heated at 100° C. for 1 h. Afterwards the mixture was filtered over Celite, the solvent was removed under reduced pressure and ethyl acetate and water were added. The phases were separated and the aqueous phase was extracted with ethyl acetate. The combined organic phases were dried over Whatman filter and the solvent was removed under reduced pressure. The crude was used in the next step without further purification. 2-(2-Chlorophenyl)-N-[4-(5-cyanopyridin-3-yl)-3-{[(dimethylamino)methylidene] sulfamoyl}-phenyl]acetamide (270 mg, 560 µmol) was dissolved in methanol (25 ml) and treated with 25% aqueous ammonia solution (25 ml) at room temperature until completion of the reaction. The solvent was removed under reduced pressure and the crude was purified by two HPLC runs (first Waters XBrigde C18 5µ 100×30 mm, acetonitrile/water+0.2% aqueous ammonia (32%) then Chromatorex C-18 10 µm, 125×30 mm, acetonitrile/water+0.1% formic acid) to yield the final product (10.4 mg, 98% purity, 4% yield over 2 steps).

LC-MS (Method B): Rt=0.90 min; MS (ESIneg): m/z=425 [M−H]⁻

¹H-NMR (400 MHz, DMSO-d₆) δ [ppm]=3.91 (s, 2H), 7.30-7.39 (m, 3H), 7.41-7.53 (m, 4H), 7.89 (dd, 1H), 8.27 (t, 1H), 8.39 (d, 1H), 8.79 (d, 1H), 9.02 (d, 1H), 10.74 (s, 1H).

Example 283

2-(2-Chlorophenyl)-N-(4-{1-[oxetan-2-ylmethyl]-1H-pyrazol-4-yl}-3-sulfamoylphenyl)-acetamide

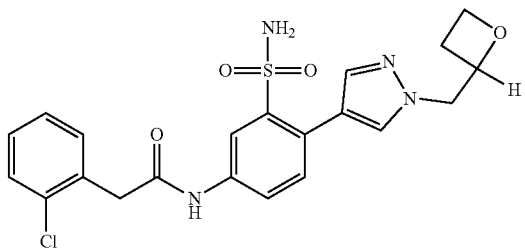

N-(4-Bromo-3-{[(dimethylamino)methylidene]sulfamoyl}phenyl)-2-(2-chlorophenyl)acetamide (250 mg, 545 µmol) and 1-[oxetan-2-ylmethyl]-4-(4,4,5,5-tetramethyl-1,3,2-dioxaborolan-2-yl)-1H-pyrazole (288 mg, 1.09 mmol) were dissolved in n-propanol (10 ml) and bis(triphenylphosphine)palladium(II) dichloride (CAS 13965-03-2) (19.2 mg, 27.2 µmol), triphenylphosphine (7.15 mg, 27.2 µmol) and potassium fluoride (7.28 mg, 125 µmol) were added. The solution was purged with argon for 5 minutes and aq. potassium carbonate (680 µl, 2.0 M, 1.4 mmol) was added. The reaction was heated at 100° C. for 1 h in the microwave. Afterwards the mixture was filtered over Celite, the solvent was removed under reduced pressure and the crude was purified by HPLC (Waters XBrigde C18 5µ 100×30 mm, acetonitrile/water+0.2% aqueous ammonia (32%)) to yield the final product (16.7 mg, 95% purity, 6% yield over 2 steps).

LC-MS (Method B): Rt=0.88 min; MS (ESIneg): m/z=459 [M−H]−

$^1$H-NMR (400 MHz, DMSO-$d_6$) δ [ppm]=2.34-2.46 (m, 1H), 2.60-2.70 (m, 1H), 3.88 (s, 2H), 4.29-4.51 (m, 4H), 4.98-5.05 (m, 1H), 7.14 (s, 2H), 7.28-7.38 (m, 2H), 7.41-7.50 (m, 3H), 7.73 (d, 1H), 7.82 (dd, 1H), 8.05 (s, 1H), 8.33 (d, 1H), 10.58 (s, 1H).

Example 284

2-(2-Chlorophenyl)-N-{3-sulfamoyl-4-[2-(2,2,2-trifluoroethoxy)pyrimidin-5-yl]phenyl}-acetamide

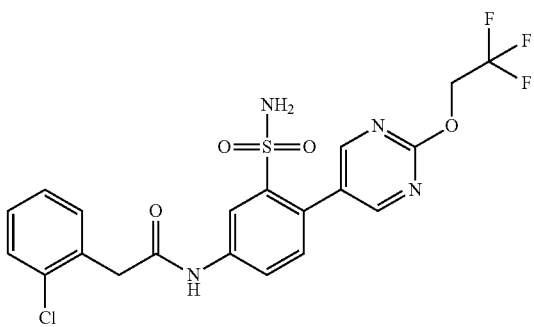 [SMILES: NS(=O)(=O)c1cc(NC(=O)Cc2ccccc2Cl)ccc1-c1cnc(OCC(F)(F)F)nc1]

N-(4-Bromo-3-{[(dimethylamino)methylidene]sulfamoyl}phenyl)-2-(2-chlorophenyl)-acetamide (210 mg, 458 µmol) and 5-(4,4,5,5-tetramethyl-1,3,2-dioxaborolan-2-yl)-2-(2,2,2-trifluoroethoxy)pyrimidine (251 mg, 824 µmol) were dissolved in n-propanol (6.2 ml) and bis(triphenylphosphine)palladium(II) dichloride (CAS 13965-03-2) (16.1 mg, 22.9 µmol), triphenylphosphine (6.00 mg, 22.9 µmol), potassium fluoride (53.2 mg, 915 µmol) and aq. potassium carbonate (690 µl, 2.0 M, 1.4 mmol) were added. The solution was purged with argon for 5 minutes and the reaction was heated at 80° C. for 1 h. Afterwards the mixture was filtered over Celite, the solvent was removed under reduced pressure and the crude was used without further purification in the next step.

2-(2-Chlorophenyl)-N-(3-{[(dimethylamino)methylidene]sulfamoyl}-4-[2-(2,2,2-trifluoro-ethoxy)pyrimidin-5-yl]phenyl)acetamide (250 mg, 450 µmol) was dissolved in methanol (4.6 ml) and treated with 25% aqueous ammonia solution (4.6 ml) at room temperature for 18 h. Afterwards, 32% aqueous sodium hydroxide (50 µl) was added and stirring was continued until completion of the reaction. The solvent was removed under reduced pressure and the crude was purified by HPLC (twice, Chromatorex C-18 10 µm, 125×30 mm, acetonitrile/water+0.2% aqueous ammonia (32%)) to yield the title compound (2.50 mg, 95% purity, 1% yield over 2 steps).

LC-MS (Method B): Rt=1.05 min; MS (ESIneg): m/z=499 [M−H]−

$^1$H-NMR (400 MHz, DMSO-$d_6$) δ [ppm]=3.91 (s, 2H), 5.09 (q, 2H), 7.30-7.48 (m, 7H), 7.89 (dd, 1H), 8.39 (d, 1H), 8.61 (s, 2H), 10.71 (s, 1H).

Example 285

2-(2-Chlorophenyl)-N-[4-(2-methoxypyrimidin-5-yl)-3-sulfamoylphenyl]acetamide

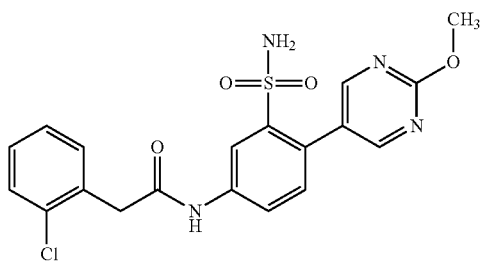 [SMILES: COc1ncc(-c2ccc(NC(=O)Cc3ccccc3Cl)cc2S(N)(=O)=O)cn1]

The title compound was isolated as a side product in the deprotection of 2-(2-chlorophenyl)-N-{3-sulfamoyl-4-[2-(2,2,2-trifluoroethoxy)pyrimidin-5-yl]phenyl}acetamide (56.8 mg, 95% purity, 28% yield).

LC-MS (Method B): Rt=0.85 min; MS (ESIneg): m/z=431 [M−H]−

$^1$H-NMR (400 MHz, DMSO-$d_6$) δ [ppm]=3.90 (s, 2H), 3.97 (s, 3H), 7.28-7.41 (m, 5H), 7.41-7.51 (m, 2H), 7.87 (dd, 1H), 8.38 (d, 1H), 8.53 (s, 2H), 10.70 (s, 1H).

Example 286

2-(2-Chlorophenyl)-N-(4-{1-[2-(propan-2-yloxy)ethyl]-1H-pyrazol-4-yl}-3-sulfamoylphenyl)acetamide

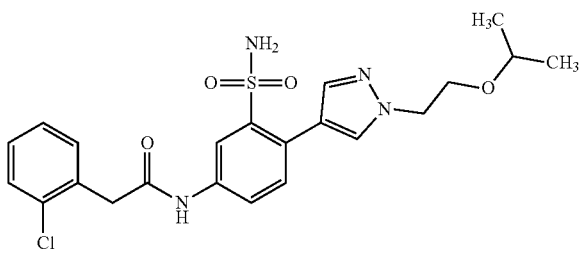 [SMILES: CC(C)OCCn1cc(-c2ccc(NC(=O)Cc3ccccc3Cl)cc2S(N)(=O)=O)cn1]

N-(4-Bromo-3-{[(dimethylamino)methylidene]sulfamoyl}phenyl)-2-(2-chlorophenyl) acetamide hydrochloride (1:1) (200 mg, 404 µmol), 1-[2-(propan-2-yloxy)ethyl]-4-(4,4,5,5-tetramethyl-1,3,2-dioxaborolan-2-yl)-1H-pyrazole (226 mg, 808 µmol) and potassium fluoride (51.6 mg, 888 µmol) were dissolved in dry and degassed DMF (8.0 ml) and the solution was purged again with argon for 5 minutes followed by addition of bis(tri-tert-butylphosphine)palladium(0) (CAS 53199-31-8) (10.3 mg, 20.2 µmol). The reaction was heated for 18 h at 100° C. Afterwards the mixture was filtered over Celite, the solvent was removed under reduced pressure and the crude was used without further purification in the next step.

2-(2-Chlorophenyl)-N-(3-{[(dimethylamino)methylidene]sulfamoyl}-4-{1-[2-(propan-2-yloxy)ethyl]-1H-pyrazol-4-yl}phenyl)acetamide (230 mg, 432 µmol) was dissolved in methanol (4.4 ml) and treated with 32% aqueous sodium hydroxide (170 µl) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Chromatorex C-18 10 µm, 125×30 mm, acetonitrile/water+0.2% aqueous ammonia (32%) then acetonitrile/water+0.1% formic acid) to yield the title compound (11.8 mg, 95% purity, 5% yield over 2 steps).

LC-MS (Method A): Rt=1.11 min; MS (ESIneg): m/z=475 [M−H]−

$^1$H-NMR (400 MHz, DMSO-$d_6$) δ [ppm]=1.05 (d, 6H), 3.54 (spt, 1H), 3.73 (t, 2H), 3.88 (s, 2H), 4.24 (t, 2H), 7.07 (s, 2H), 7.29-7.36 (m, 2H), 7.42-7.48 (m, 3H), 7.70 (d, 1H), 7.82 (dd, 1H), 8.03 (s, 1H), 8.33 (d, 1H), 10.57 (s, 1H).

Example 287

2-(2-Chlorophenyl)-N-{4-[1-(3-hydroxy-3-methylbutyl)-1H-pyrazol-4-yl]-3-sulfamoylphenyl}acetamide

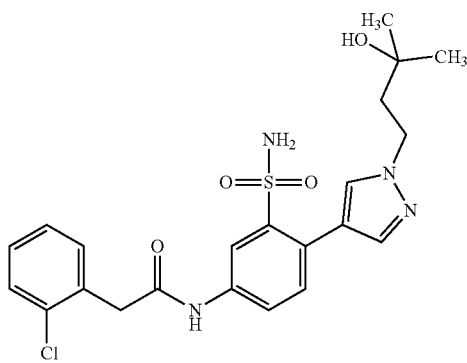 [SMILES: CC(C)(O)CCn1cc(-c2ccc(NC(=O)Cc3ccccc3Cl)cc2S(N)(=O)=O)cn1]

N-(4-Bromo-3-{[(dimethylamino)methylidene]sulfamoyl}phenyl)-2-(2-chlorophenyl)-acetamide hydrochloride (1:1) (250 mg, 505 µmol), 2-methyl-4-[4-(4,4,5,5-tetramethyl-1,3,2-dioxaborolan-2-yl)-1H-pyrazol-1-yl]butan-2-ol (283 mg, 1.01 mmol) and potassium fluoride (64.5 mg, 1.11 mmol) were dissolved in dry and degassed DMF (14 ml) and the solution was purged again with argon for 5 minutes followed by addition of bis(tri-tert-butylphosphine)palladium(0) (CAS 53199-31-8) (12.9 mg, 25.2 µmol). The reaction was heated for 18 h at 100° C. Afterwards the mixture was filtered over Celite, the solvent was removed under reduced pressure and the crude was used without further purification in the next step.

2-(2-Chlorophenyl)-N-(3-{[(dimethylamino)methylidene]sulfamoyl}-4-[1-(3-hydroxy-3-methylbutyl)-1H-pyrazol-4-yl]phenyl)acetamide (250 mg, 470 µmol) was dissolved in methanol (4.8 ml) and treated with 32% aqueous sodium hydroxide (180 µl) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Chromatorex C-18 10 µm, 125×30 mm, acetonitrile/water+0.2% aqueous ammonia (32%)) to yield the title compound (31.3 mg, 95% purity, 14% yield over 2 steps).

LC-MS (Method B): Rt=0.92 min; MS (ESIneg): m/z=475 [M−H]−

$^1$H-NMR (400 MHz, DMSO-$d_6$): δ [ppm]=1.15 (s, 6H), 1.88-1.99 (m, 2H), 3.88 (s, 2H), 4.16-4.23 (m, 2H), 4.48 (s, 1H), 7.15 (s, 2H), 7.29-7.37 (m, 2H), 7.41-7.49 (m, 3H), 7.66-7.70 (m, 1H), 7.81 (dd, 1H), 8.01 (s, 1H), 8.31 (d, 1H), 10.57 (s, 1H).

Example 288

2-(2-Chlorophenyl)-N-{4-[5-(2-hydroxypropan-2-yl)-1-methyl-1H-pyrazol-3-yl]-3-sulfamoylphenyl}acetamide

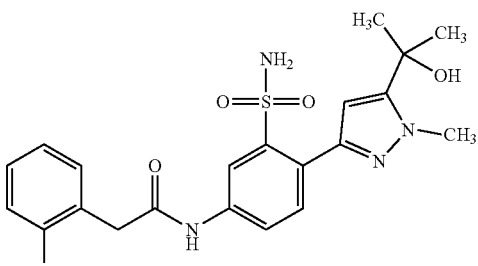

N-(4-Bromo-3-{[(dimethylamino)methylidene]sulfamoyl}phenyl)-2-(2-chlorophenyl)-acetamide hydrochloride (1:1) (500 mg, 1.01 mmol) and methyl 1-methyl-3-(4,4,5,5-tetramethyl-1,3,2-dioxaborolan-2-yl)-1H-pyrazole-5-carboxylate (537 mg, 2.02 mmol) were dissolved in n-propanol (19 ml) and bis(triphenylphosphine)palladium (II) dichloride (CAS 13965-03-2) (35.5 mg, 50.5 µmol), triphenylphosphine (13.2 mg, 50.5 µmol) and potassium fluoride (13.5 mg, 232 µmol) were added. The solution was purged with argon for 5 minutes and aq. potassium carbonate (1.3 ml, 2.0 M, 2.5 mmol) was added. The reaction was heated at 100° C. for 1 h. Afterwards the mixture was filtered over Celite, the solvent was removed under reduced pressure and the crude was purified by chromatography on silica gel (Biotage, hexane/ethyl acetate) (260 mg, 47% yield).

LC-MS (Method B): Rt=1.10 min; MS (ESIneg): m/z=516 [M−H]−

Propyl 3-(4-{[(2-chlorophenyl)acetyl]amino}-2-{[(dimethylamino)methylidene] sulfamoyl}-phenyl)-1-methyl-1H-pyrazole-5-carboxylate (250 mg, 458 µmol) was dissolved in dry THF (8.3 ml) and methylmagnesium bromide in THF (14 ml, 1.0 M, 14 mmol) was added. The reaction was stirred for 18 h at 22° C., then saturated aqueous ammonium chloride solution and ethyl acetate were added. The phases were separated and the aqueous phase was extracted with ethyl acetate. The combined organic phases were dried over Whatman filter and the solvent was removed under reduced pressure. The crude was used in the next step without further purification.

2-(2-Chlorophenyl)-N-(3-{[(dimethylamino)methylidene]sulfamoyl}-4-[5-(2-hydroxypropan-2-yl)-1-methyl- 1H-pyrazol-3-yl]phenyl)acetamide (250 mg, 483 µmol) was dissolved in methanol (5.0 ml) and treated with 32% aqueous sodium hydroxide (0.6 ml) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Chromatorex C-18 10 µm, 125×30 mm, acetonitrile/water+0.2% aqueous ammonia (32%)) to yield the final product (10.1 mg, 95% purity, 4% yield over 2 steps).

LC-MS (Method B): Rt=1.02 min; MS (ESIneg): m/z=461 [M–H]⁻

¹H-NMR (400 MHz, DMSO-$d_6$): δ [ppm]=1.55 (s, 6H), 3.88 (s, 2H), 4.02 (s, 3H), 5.45 (s, 1H), 6.45 (s, 1H), 7.28-7.38 (m, 2H), 7.41-7.49 (m, 2H), 7.49-7.78 (m, 3H), 7.93 (dd, 1H), 8.28 (d, 1H), 10.64 (s, 1H).

Example 289

2-(2-Chlorophenyl)-N-{4-[5-(difluoromethoxy)pyridin-3-yl]-3-sulfamoylphenyl}acetamide

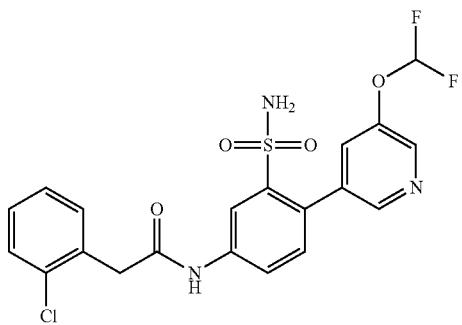 [SMILES: NS(=O)(=O)c1cc(NC(=O)Cc2ccccc2Cl)ccc1-c1cncc(OC(F)F)c1]

N-(4-Bromo-3-{[(dimethylamino)methylidene]sulfamoyl}phenyl)-2-(2-chlorophenyl)-acetamide hydrochloride (1:1) (250 mg, 505 µmol) and potassium [5-(difluoro-methoxy)pyridin-3-yl](trifluoro)borate (380 mg, 1.51 mmol) were dissolved in n-propanol (9.3 ml) and bis(triphenylphosphine)palladium(II) dichloride (CAS 13965-03-2) (17.8 mg, 25.2 µmol), triphenylphosphine (6.62 mg, 25.2 µmol) and potassium fluoride (7.33 mg, 126 µmol) were added. The solution was purged with argon for 5 minutes and aq. potassium carbonate (760 µl, 2.0 M, 1.5 mmol) was added. The reaction was heated at 100° C. for 2 h in the microwave. Afterwards the mixture was filtered over Celite, the solvent was removed under reduced pressure and the crude was used without further purification in the next step.

2-(2-Chlorophenyl)-N-(4-[5-(difluoromethoxy)pyridin-3-yl]-3-{[(dimethylamino)-methylidene]sulfamoyl}phenyl) acetamide (250 mg, 478 µmol) was dissolved in methanol (4.9 ml) and treated with 32% aqueous sodium hydroxide (0.6 ml) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Chromatorex C-18 10 µm, 125×30 mm, acetonitrile/water+ 0.1% formic acid) to yield the title compound (39.1 mg, 95% purity, 17% yield over 2 steps).

LC-MS (Method A): Rt=1.09 min; MS (ESIneg): m/z=466 [M–H]⁻

¹H-NMR (400 MHz, DMSO-$d_6$) δ [ppm]=3.91 (s, 2H), 7.15-7.54 (m, 8H), 7.65 (t, 1H), 7.88 (dd, 1H), 8.39-8.49 (m, 3H), 10.71 (s, 1H).

Example 290

N-[4-(2-Chloro-5-methoxypyridin-3-yl)-3-sulfamoylphenyl]-2-(2-chlorophenyl)acetamide

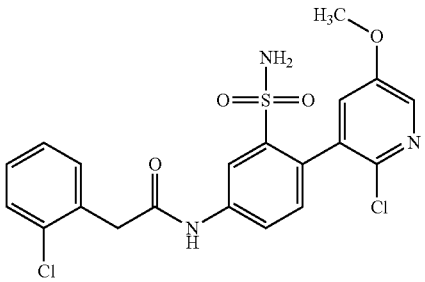 [SMILES: COc1cnc(Cl)c(-c2ccc(NC(=O)Cc3ccccc3Cl)cc2S(N)(=O)=O)c1]

DMF was dried over molecular sieves and purged with argon. Then N-(4-bromo-3-{[(dimethylamino)methylidene]sulfamoyl}phenyl)-2-(2-chlorophenyl)acetamide hydrochloride (1:1) (250 mg, 505 µmol), (2-chloro-5-methoxypyridin-3-yl)boronic acid (189 mg, 1.01 mmol) and potassium fluoride (64.5 mg, 1.11 mmol) were dissolved in dry and degassed DMF (14 ml) and the solution was purged again with argon for 5 minutes followed by addition of CataXCium A Pre Cat (18.4 mg, 25.2 µmol). The reaction was heated for 18 h at 100° C. Afterwards the mixture was filtered over Celite, the solvent was removed under reduced pressure and the crude was used without further purification in the next step.

N-[4-(2-Chloro-5-methoxypyridin-3-yl)-3-{[(dimethylamino)methylidene]sulfamoyl}phenyl]-2-(2-chlorophenyl)acetamide (350 mg, 25% purity, 168 µmol) was dissolved in methanol (1.7 ml) and treated with 32% aqueous sodium hydroxide (0.2 ml) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Chromatorex C-18 10 µm, 125×30 mm, acetonitrile/water+ 0.1% formic acid) to yield the title compound (25.5 mg, 90% purity, 29% yield over 2 steps).

LC-MS (Method A): Rt=1.08 min; MS (ESIneg): m/z=464 [M–H]⁻

¹H-NMR (400 MHz, DMSO-$d_6$) δ [ppm]=3.84 (s, 3H), 3.90 (s, 2H), 7.27 (d, 1H), 7.31-7.38 (m, 5H), 7.43-7.50 (m, 2H), 7.85 (dd, 1H), 8.12 (d, 1H), 8.35 (d, 1H), 10.70 (s, 1H).

Example 291

2-(2-Chlorophenyl)-N-{4-[1-(2-hydroxyethyl)-1H-pyrazol-4-yl]-3-sulfamoylphenyl}acetamide

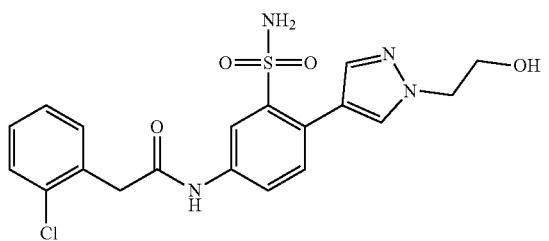 [SMILES: NS(=O)(=O)c1cc(NC(=O)Cc2ccccc2Cl)ccc1-c1cnn(CCO)c1]

DMF was dried over molecular sieves and purged with argon. Then N-(4-bromo-3-{[(dimethylamino)methylidene]sulfamoyl}phenyl)-2-(2-chlorophenyl)acetamide hydrochloride (1:1) (250 mg, 505 µmol), 2-[4-(4,4,5,5-tetramethyl-1,3,2-dioxaborolan-2-yl)-1H-pyrazol-1-yl]ethanol (240 mg, 1.01 mmol) and potassium fluoride (65.0 mg, 1.1 mmol) were dissolved in dry and degassed DMF (6.6 ml) and the solution was purged again with argon for 5 minutes followed by addition of bis(tri-tert-butylphosphine)palladium(0) (CAS 53199-31-8) (12.9 mg, 25.2 µmol). The reaction was heated for 4 h at 100° C. Afterwards the mixture was filtered over Celite, the solvent was removed under reduced pressure and the crude was used without further purification in the next step.

2-(2-Chlorophenyl)-N-(3-{[(dimethylamino)methylidene]sulfamoyl}-4-[1-(2-hydroxyethyl)-1H-pyrazol-4-yl]phenyl)acetamide (250 mg, 510 µmol) was dissolved in methanol (5.2 ml) and treated with 32% aqueous sodium hydroxide (0.2 ml) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Chromatorex C-18 10 µm, 125×30 mm, acetonitrile/water+0.1% formic acid) to yield the title compound (28.1 mg, 90% purity, 11% yield over 2 steps). The second fraction was crystallized additionally from diethylether (47.1 mg, 95% purity, 20% yield over 2 steps).

LC-MS (Method A): Rt=0.89 min; MS (ESIneg): m/z=433 [M–H]$^-$ $^1$H-NMR (400 MHz, DMSO-d$_6$) δ [ppm]=3.75 (q, 2H), 3.88 (s, 2H), 4.16 (t, 2H), 4.94 (t, 1H), 7.04 (s, 2H), 7.29-7.36 (m, 2H), 7.42-7.48 (m, 3H), 7.71 (s, 1H), 7.83 (dd, 1H), 8.01 (s, 1H), 8.32 (d, 1H), 10.57 (s, 1H).

Example 292

N-[4-(5-tert-Butyl-1H-pyrazol-3-yl)-3-sulfamoylphenyl]-2-(2-chlorophenyl)acetamide

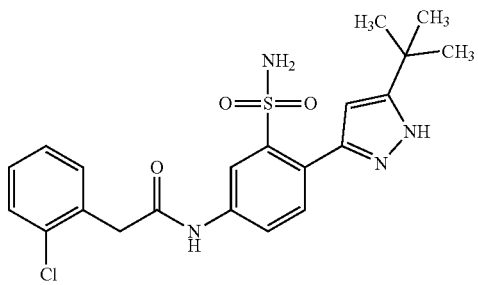 [SMILES: CC(C)(C)c1cc(-c2ccc(NC(=O)Cc3ccccc3Cl)cc2S(N)(=O)=O)n[nH]1]

DMF was dried over molecular sieves and purged with argon. Then N-(4-bromo-3-{[(dimethylamino)methylidene]sulfamoyl}phenyl)-2-(2-chlorophenyl)acetamide hydrochloride (1:1) (250 mg, 505 µmol), potassium (3-(tert-butyl)-1H-pyrazol-5-yl)trifluoroborate (232 mg, 1.01 mmol) and potassium fluoride (65.0 mg, 1.1 mmol) were dissolved in dry and degassed DMF (14 ml) and the solution was purged again with argon for 5 minutes followed by addition of bis(tri-tert-butylphosphine)palladium(0) (CAS 53199-31-8) (12.9 mg, 25.2 µmol). The reaction was heated for 18 h at 100° C. Afterwards the mixture was filtered over silica gel and washed with ethyl acetate. After removing the solvent the reaction was repeated. After filtration over Celite, the solvent was removed under reduced pressure and the crude was used without further purification in the next step.

N-[4-(5-tert-Butyl-1H-pyrazol-3-yl)-3-{[(dimethylamino)methylidene]sulfamoyl}phenyl]-2-(2-chlorophenyl)acetamide (270 mg, 30% purity, 161 µmol) was dissolved in methanol (1.7 ml) and treated with 32% aqueous sodium hydroxide (63 µl) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Chromatorex C-18 10 µm, 125×30 mm, acetonitrile/water+0.2% aqueous ammonia (32%)) to yield the title compound (10.1 mg, 90% purity, 12% yield over 2 steps).

LC-MS (Method B): Rt=1.15 min; MS (ESIneg): m/z=445 [M–H]$^-$ $^1$H-NMR (400 MHz, DMSO-d$_6$) δ [ppm]=1.33 (s, 9H), 3.88 (s, 2H), 6.38 (s, 1H), 7.30-7.36 (m, 2H), 7.42-7.49 (m, 2H), 7.64 (d, 1H), 7.86-7.97 (m, 3H), 8.30 (d, 1H), 10.64 (s, 1H), 12.89 (s, 1H).

Example 293

N-[4-(1-Benzyl-1H-pyrazol-4-yl)-3-sulfamoylphenyl]-2-(2-chlorophenyl)acetamide

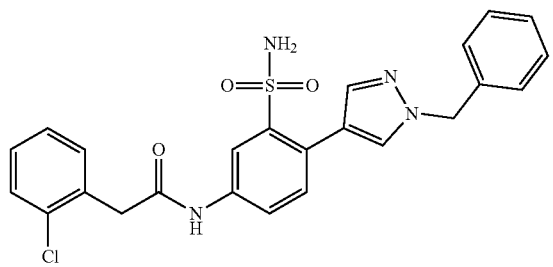 [SMILES: NS(=O)(=O)c1cc(NC(=O)Cc2ccccc2Cl)ccc1-c1cnn(Cc2ccccc2)c1]

N-(4-Bromo-3-{[(dimethylamino)methylidene]sulfamoyl}phenyl)-2-(2-chlorophenyl)-acetamide (200 mg, 436 µmol) and 1-benzyl-4-(4,4,5,5-tetramethyl-1,3,2-dioxaborolan-2-yl)-1H-pyrazole (248 mg, 872 µmol) were dissolved in n-propanol (8.0 ml) and bis(triphenylphosphine)palladium(II) dichloride (CAS 13965-03-2) (15.3 mg, 21.8 µmol) and triphenylphosphine (5.72 mg, 21.8 µmol) were added. The solution was purged with argon for 5 minutes and aq. potassium carbonate (540 µl, 2.0 M, 1.1 mmol) was added. The reaction was heated at 80° C. for 2 h. Afterwards the mixture was filtered over Celite, the solvent was removed under reduced pressure and the crude was used without further purification in the next step.

N-[4-(1-Benzyl-1H-pyrazol-4-yl)-3-{[(dimethylamino)methylidene]sulfamoyl}phenyl]-2-(2-chlorophenyl)acetamide (250 mg, 466 µmol) was dissolved in methanol (4.8 ml) and treated with 32% aqueous sodium hydroxide (0.6 ml) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Waters XBrigde C18 5µ 100×30 mm, methanol/water+0.2% aqueous ammonia (32%)) to yield the title compound (5.50 mg, 80% purity, 2% yield over 2 steps).

LC-MS (Method J): Rt=1.29 min; MS (ESIneg): m/z=479 [M−H]⁻

¹H-NMR (400 MHz, DMSO-d₆): δ [ppm]=3.88 (s, 2H), 5.36 (s, 2H), 7.22-7.37 (m, 8H), 7.42-7.46 (m, 3H), 7.73 (s, 1H), 7.81 (dd, 1H), 8.12 (s, 1H), 8.33 (d, 1H), 8.45 (s, 1H), 10.60 (s, 1H).

Example 294

2-(2-Chlorophenyl)-N-[4-(6-methylpyridazin-4-yl)-3-sulfamoylphenyl]acetamide

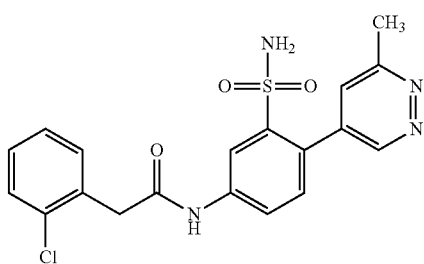 [SMILES: Cc1cc(-c2ccc(NC(=O)Cc3ccccc3Cl)cc2S(N)(=O)=O)cnn1]

2-Bromo-N-[(dimethylamino)methylidene]-5-nitrobenzenesulfonamide (400 mg, 1.19 mmol) and 3-methyl-5-(4,4,5,5-tetramethyl-1,3,2-dioxaborolan-2-yl)pyridazine (524 mg, 2.38 mmol) were dissolved in n-propanol (110 ml) and bis(triphenylphosphine)palladium(II) dichloride (CAS 13965-03-2) (41.9 mg, 59.5 µmol), triphenylphosphine (21.6 mg, 59.5 µmol) and aq. potassium carbonate (1.8 ml, 2.0 M, 3.6 mmol) were added. The reaction was heated at 120° C. for 1 h in the microwave (4 bar/40 W). Afterwards the mixture was filtered over Celite, the solvent was removed under reduced pressure and the crude was co-distilled with THF and used without further purification in the next step.

2-(6-Methylpyridazin-4-yl)-5-nitrobenzenesulfonamide (400 mg, 1.36 mmol) was dissolved in THF (140 ml)/methanol (50 ml) and the flask was flushed with nitrogen. Palladium on charcoal (148 mg, 1.39 mmol) was added and the flask was evacuated and subsequently flushed with hydrogen (1 bar). Stirring was continued at room temperature for 4 h. The reaction mixture was filtered over Celite and the solvent was removed under reduced pressure. The crude was used without further purification in the next step.

5-Amino-2-(6-methylpyridazin-4-yl)benzenesulfonamide (200 mg, 757 µmol) was dissolved in DMF (5.3 ml) and (2-chlorophenyl)acetic acid (155 mg, 908 µmol) was added followed by the addition of N,N-diisopropylethylamine (630 µl, 3.8 mmol) and HATU (460 mg, 1.21 mmol). The reaction was stirred at 50° C. for 18 h. Then water and dichloromethane were added. The phases were separated and the aqueous phase was extracted with dichloromethane. The combined organic phases were dried over Whatman filter and the solvent was removed under reduced pressure. The crude was purified twice by HPLC (first Waters XBrigde C18 5µ 100×30 mm, acetonitrile/water+0.1% formic acid then Chromatorex C-18 10 µm, 125×30 mm, acetonitrile/water+0.1% formic acid) to yield the title compound (2.20 mg, 95% purity, 1% yield over 3 steps).

LC-MS (Method B): Rt=0.78 min; MS (ESIneg): m/z=415 [M−H]⁻

¹H-NMR (400 MHz, DMSO-d₆) δ [ppm]=2.66 (s, 3H), 3.91 (s, 2H), 7.30-7.37 (m, 3H), 7.43-7.55 (m, 5H), 7.89 (dd, 1H), 8.40 (d, 1H), 9.05 (d, 1H), 10.75 (s, 1H).

Example 295

2-(2-Chlorophenyl)-N-{3-sulfamoyl-4-[6-(trifluoromethyl)pyridin-2-yl]phenyl}acetamide

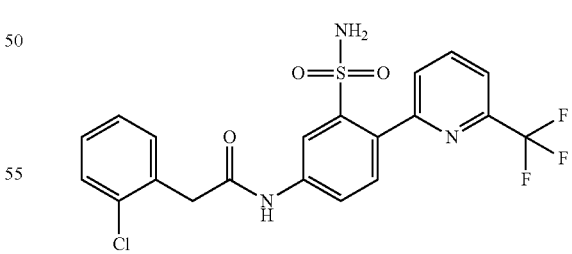

N-(4-Bromo-3-{[(dimethylamino)methylidene]sulfamoyl}phenyl)-2-(2-chlorophenyl)-acetamide (150 mg, 327 µmol), 4,4,4',4',5,5,5',5'-octamethyl-2,2'-bi-1,3,2-dioxaborolane (208 mg, 817 µmol) and CataXCium A Pre Cat (11.9 mg, 16.3 µmol) were dissolved in dry methanol (20.0 ml) under argon atmosphere followed by the addition of N,N-diisopropylethylamine (140 µl, 820 µmol). The reaction was heated for 2 h at 50° C. After cooling to room temperature, potassium fluoride (38.0 mg, 654 µmol) and 2-bromo-6-(trifluoromethyl)pyridine (148 mg, 654 µmol) were added. The solution was purged with argon for 5 minutes and bis(tri-tert-butylphosphine)palladium(0) (CAS 53199-31-8) (8.35 mg, 16.3 µmol) was added. The reaction was heated at 80° C. for 2 h. Afterwards the mixture was filtered over Celite, the solvent was removed under reduced pressure and the crude was used without further purification in the next step.

2-(2-Chlorophenyl)-N-(3-{[(dimethylamino)methylidene]sulfamoyl}-4-[6-(trifluoromethyl)-pyridin-2-yl]phenyl)acetamide (56.0 mg, 107 µmol) was dissolved in methanol (25 ml) and treated with 32% aqueous sodium hydroxide (1.6 ml) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Chromatorex C-18 10 µm, 125×30 mm, acetonitrile/water+ 0.2% aqueous ammonia (32%)) to yield the title compound (5.50 mg, 95% purity, 10% yield over 2 steps).

LC-MS (Method B): Rt=1.16 min; MS (ESIneg): m/z=468 [M−H]$^-$ $^1$H-NMR (400 MHz, DMSO-d$_6$) δ [ppm]=3.92 (s, 2H), 7.07 (br s, 2H), 7.30-7.37 (m, 2H), 7.43-7.50 (m, 2H), 7.57 (d, 1H), 7.92-8.04 (m, 3H), 8.18-8.24 (m, 1H), 8.37 (d, 1H), 10.76 (s, 1H).

Example 296

N-{4-[1-(Difluoromethyl)-1H-pyrazol-4-yl]-3-sulfamoylphenyl}-2-(2-fluorophenyl)acetamide

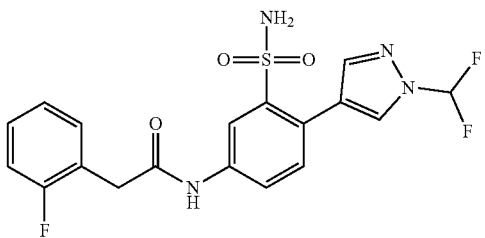 [SMILES: NS(=O)(=O)c1cc(NC(=O)Cc2ccccc2F)ccc1-c1cnn(C(F)F)c1]

N-(4-Bromo-3-{[(dimethylamino)methylidene]sulfamoyl}phenyl)-2-(2-fluorophenyl)-acetamide (250 mg, 565 µmol) and 1-(difluoromethyl)-4-(4,4,5,5-tetramethyl-1,3,2-dioxaborolan-2-yl)-1H-pyrazole (276 mg, 1.13 mmol) were dissolved in n-propanol (10 ml) and bis(triphenylphosphine)palladium(II) dichloride (CAS 13965-03-2) (19.9 mg, 28.3 µmol), triphenylphosphine (7.41 mg, 28.3 µmol) and potassium fluoride (7.55 mg, 130 µmol) were added. The solution was purged with argon for 5 minutes and aq. potassium carbonate (710 µl, 2.0 M, 1.4 mmol) was added. The reaction was heated at 100° C. for 1 h in the microwave. Afterwards the mixture was filtered over Celite, the solvent was removed under reduced pressure and the crude was used without further purification in the next step.

N-(4-[1-(Difluoromethyl)-1H-pyrazol-4-yl]-3-{[(dimethylamino)methylidene]sulfamoyl}phenyl)-2-(2-fluorophenyl)acetamide (280 mg, 584 µmol) was dissolved in methanol (2.4 ml) and treated with 32% aqueous sodium hydroxide (0.2 ml) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Chromatorex C-18 10 µm, 125×30 mm, acetonitrile/water+ 0.1% formic acid) to yield the title compound (21.8 mg, 96% purity, 8% yield over 2 steps).

LC-MS (Method A): Rt=1.00 min; MS (ESIpos): m/z=425 [M+H]$^+$ $^1$H-NMR (500 MHz, DMSO-d$_6$) δ [ppm]=3.77 (s, 2H), 7.14-7.20 (m, 2H), 7.30-7.34 (m, 1H), 7.37-7.42 (m, 3H), 7.46 (d, 1H), 7.66-7.96 (m, 2H), 8.00 (s, 1H), 8.34 (d, 1H), 8.41 (s, 1H), 10.61 (s, 1H).

Example 297

2-(2-Chlorophenyl)-N-{6-[1-(difluoromethyl)-1H-pyrazol-4-yl]-5-sulfamoylpyridin-3-yl}acetamide

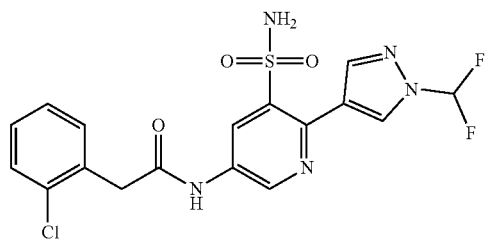 [SMILES: NS(=O)(=O)c1cc(NC(=O)Cc2ccccc2Cl)cnc1-c1cnn(C(F)F)c1]

5-Amino-2-[1-(difluoromethyl)-1H-pyrazol-4-yl]-N-[(dimethylamino)methylidene]pyridine-3-sulfonamide (750 mg, 2.18 mmol) was dissolved in DMF (43 ml) and (2-chlorophenyl)acetic acid (372 mg, 2.18 mmol) was added followed by the addition of N,N-diisopropylethylamine (1.9 ml, 11 mmol) and HATU (994 mg, 2.61 mmol). The reaction was stirred at 50° C. for 1 h. The solvent was removed under reduced pressure and water and ethyl acetate were added. The phases were separated and the aqueous phase was extracted with ethyl acetate. The combined organic phases were dried over Whatman filter and the solvent was removed under reduced pressure. The crude was purified by HPLC (Chromatorex C-18 10 µm, 125×30 mm, acetonitrile/water+ 0.2% aqueous ammonia (32%)) to yield 160 mg (15% yield over 4 steps).

LC-MS (Method B): Rt=1.00 min; MS (ESIneg): m/z=495 [M−H]$^-$ 2-(2-Chlorophenyl)-N-(6-[1-(difluoromethyl)-1H-pyrazol-4-yl]-5-{[(dimethylamino)-methylidene] sulfamoyl}pyridin-3-yl)acetamide (160 mg, 322 µmol) was dissolved in methanol (10 ml) and treated with 25% aqueous ammonia solution (10 ml) at room temperature until completion of the reaction. The solvent was removed under reduced pressure and the crude was purified by HPLC (twice, Chromatorex C-18 10 µm, 125×30 mm, acetonitrile/water+0.2% aqueous ammonia (32%)) to yield the title compound (18.9 mg, 92% purity, 13% yield).

LC-MS (Method B): Rt=0.71 min; MS (ESIneg): m/z=440 [M−H]$^-$ $^1$H-NMR (400 MHz, DMSO-d$_6$) δ [ppm]=3.94 (s, 2H), 7.30-7.38 (m, 2H), 7.43-7.52 (m, 2H), 7.71-8.08 (m, 3H), 8.29 (s, 1H), 8.70 (s, 1H), 8.78 (d, 1H), 8.93 (d, 1H), 10.88 (s, 1H).

Example 298

N-[4-(6-Chloro-5-methylpyridin-3-yl)-3-sulfamoylphenyl]-2-(2-chlorophenyl)acetamide

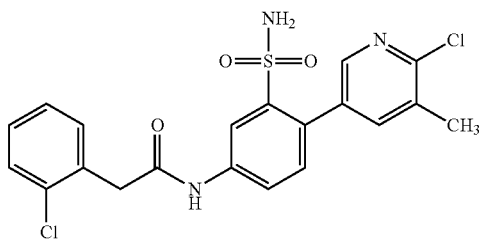 [SMILES: Cc1cc(-c2ccc(NC(=O)Cc3ccccc3Cl)cc2S(N)(=O)=O)cnc1Cl]

DMF was dried over molecular sieves and purged with argon. Then N-(4-bromo-3-{[(dimethylamino)methylidene]sulfamoyl}phenyl)-2-(2-chlorophenyl)acetamide hydrochloride (1:1) (300 mg, 606 µmol), (6-chloro-5-methylpyridin-3-yl)boronic acid (208 mg, 1.21 mmol) and potassium fluoride (77.4 mg, 1.33 mmol) were dissolved in dry and degassed DMF (9.3 ml) and the solution was purged again with argon for 5 minutes followed by addition of bis(tri-tert-butylphosphine)palladium(0) (CAS 53199-31-8) (15.5 mg, 30.3 µmol). The reaction was heated for 1 h at 100° C. Afterwards the mixture was filtered over Celite, the solvent was removed under reduced pressure and the crude was subjected again to the reaction conditions. Afterwards, the mixture was filtered over Celite, the solvent was removed under reduced pressure and was used without further purification in the next step. N-[4-(6-Chloro-5-methylpyridin-3-yl)-3-{[(dimethylamino)methylidene]sulfamoyl}phenyl]-2-(2-chlorophenyl)acetamide (250 mg, 495 µmol) was dissolved in methanol (2.0 ml) and treated with 25% aqueous ammonia solution (10 ml) at room temperature for 18 h. Afterwards, 32% aqueous sodium hydroxide (0.2 ml) was added and the reaction was heated at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Chromatorex C-18 10 µm, 125×30 mm, acetonitrile/water+0.2% aqueous ammonia (32%)) and by chromatography on silica gel (Biotage, 35% ethyl acetate in hexane) and the pure title compound was obtained after recrystallized from dichloromethane/diethyl ether (6.30 mg, 90% purity, 3% yield over 2 steps).

LC-MS (Method B): Rt=1.05 min; MS (ESIneg): m/z=448 [M−H]−

$^1$H-NMR (400 MHz, DMSO-d$_6$) δ [ppm]=2.36 (s, 3H), 3.90 (s, 2H), 7.29-7.39 (m, 5H), 7.42-7.50 (m, 2H), 7.76 (d, 1H), 7.86 (dd, 1H), 8.19 (d, 1H), 8.38 (d, 1H), 10.70 (s, 1H).

Example 299

2-(2-Chlorophenyl)-N-{4-[2-(cyclopropylamino)pyrimidin-5-yl]-3-sulfamoylphenyl}acetamide

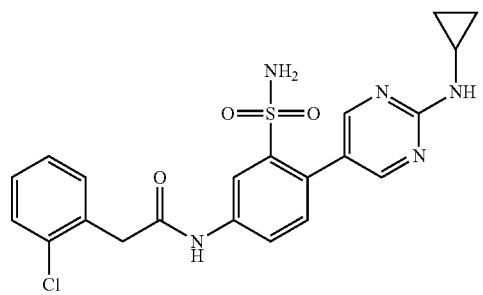 [SMILES: NS(=O)(=O)c1cc(NC(=O)Cc2ccccc2Cl)ccc1-c1cnc(NC2CC2)nc1]

DMF was dried over molecular sieves and purged with argon. Then N-(4-bromo-3-{[(dimethylamino)methylidene]sulfamoyl}phenyl)-2-(2-chlorophenyl)acetamide hydrochloride (1:1) (250 mg, 505 µmol), N-cyclopropyl-5-(4,4,5,5-tetramethyl-1,3,2-dioxaborolan-2-yl)pyrimidin-2-amine (264 mg, 1.01 mmol) and potassium fluoride (64.5 mg, 1.11 mmol) were dissolved in dry and degassed DMF (7.7 ml) and the solution was purged again with argon for 5 minutes followed by addition of bis(tri-tert-butylphosphine)palladium(0) (CAS 53199-31-8) (12.9 mg, 25.2 µmol) and the solution was purged again with argon. The reaction was heated for 2 h at 100° C. Afterwards the mixture was filtered over Celite, the solvent was removed under reduced pressure and the crude was used without further purification in the next step.

2-(2-Chlorophenyl)-N-(4-[2-(cyclopropylamino)pyrimidin-5-yl]-3-{[(dimethylamino)-methylidene]sulfamoyl}phenyl)acetamide (250 mg, 487 µmol) was dissolved in methanol (2.0 ml) and treated with 25% aqueous ammonia solution (10 ml) at room temperature for 4 h. Afterwards, 32% aqueous sodium hydroxide (0.2 ml) was added and stirring was continued until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Chromatorex C-18 10 µm, 125×30 mm, acetonitrile/water+0.2% aqueous ammonia (32%)) to yield the title compound (34.0 mg, 95% purity, 14% yield over 2 steps)

LC-MS (Method B): Rt=0.91 min; MS (ESIneg): m/z=456 [M−H]−

$^1$H-NMR (400 MHz, DMSO-de) δ [ppm]=0.48-0.53 (m, 2H), 0.65-0.71 (m, 2H), 2.73 (tq, 1H), 3.89 (s, 2H), 7.28-7.39 (m, 5H), 7.43-7.49 (m, 3H), 7.84 (dd, 1H), 8.26 (s, 2H), 8.36 (d, 1H), 10.65 (s, 1H).

Example 300

2-(2-Chlorophenyl)-N-{3-sulfamoyl-4-[1-(tetrahydrofuran-3-yl)-1H-pyrazol-4-yl]phenyl}acetamide

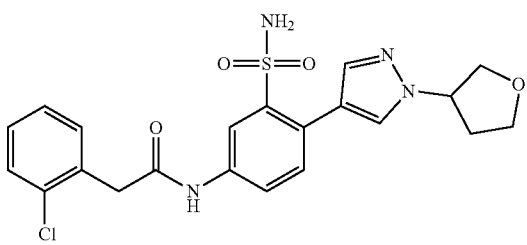 [SMILES: NS(=O)(=O)c1cc(NC(=O)Cc2ccccc2Cl)ccc1-c1cnn(C2CCOC2)c1]

DMF was dried over molecular sieves and purged with argon. Then N-(4-bromo-3-{[(dimethylamino)methylidene]sulfamoyl}phenyl)-2-(2-chlorophenyl)acetamide (250 mg, 545 µmol), 1-(tetrahydrofuran-3-yl)-4-(4,4,5,5-tetramethyl-1,3,2-dioxaborolan-2-yl)-1H-pyrazole (288 mg, 1.09 mmol) and potassium fluoride (69.6 mg, 1.20 mmol) were dissolved in dry and degassed DMF (7.7 ml) and the solution was purged again with argon for 5 minutes followed by addition of bis(tri-tert-butylphosphine)palladium(0) (CAS 53199-31-8) (13.9 mg, 27.2 µmol). The reaction was purged again for 1 minute with argon and heated for 18 h at 100° C. Afterwards the mixture was filtered over Celite, the solvent was removed under reduced pressure and the crude was subjected again to the reaction conditions. After filtration and removal of the solvent, the crude was used without further purification in the next step.

2-(2-Chlorophenyl)-N-(3-{[(dimethylamino)methylidene]sulfamoyl}-4-[1-(tetrahydrofuran-3-yl)-1H-pyrazol-4-yl]phenyl)acetamide (300 mg, 20% purity, 116 µmol) was dissolved in methanol (0.5 ml) and treated with 32% aqueous sodium hydroxide (45 µl) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Chromatorex C-18 10 µm, 125×30 mm, acetonitrile/water+0.2% aqueous ammonia (32%)) and the pure title compound was obtained after crystallization from dichloromethane/diethyl ether (4.70 mg, 95% purity, 8% yield over 2 steps).

LC-MS (Method A): Rt=0.98 min; MS (ESIneg): m/z=459 [M−H]⁻

¹H-NMR (400 MHz, DMSO-d₆): δ [ppm]=2.36-2.42 (m, 1H), 3.76-3.91 (m, 4H), 3.92-4.04 (m, 3H), 4.99-5.11 (m, 1H), 7.18 (s, 2H), 7.30-7.34 (m, 2H), 7.43-7.48 (m, 3H), 7.74 (s, 1H), 7.82 (dd, 1H), 8.06 (d, 1H), 8.32 (d, 1H), 10.58 (s, 1H).

Example 301

2-(2-Chlorophenyl)-N-{4-[2-(methylamino)pyrimidin-5-yl]-3-sulfamoylphenyl}acetamide

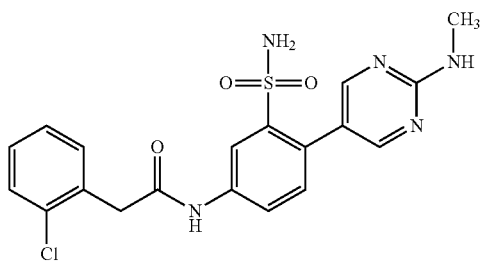 [SMILES: CNc1ncc(-c2ccc(NC(=O)Cc3ccccc3Cl)cc2S(N)(=O)=O)cn1]

N-(4-Bromo-3-{[(dimethylamino)methylidene]sulfamoyl}phenyl)-2-(2-chlorophenyl)-acetamide (250 mg, 545 µmol) and N-methyl-5-(4,4,5,5-tetramethyl-1,3,2-dioxaborolan-2-yl)pyrimidin-2-amine (256 mg, 1.1 mmol) were dissolved in n-propanol (8.1 ml) and bis(triphenylphosphine)palladium(II) dichloride (CAS 13965-03-2) (19.2 mg, 27.2 µmol), triphenylphosphine (5.4 µl, 27 µmol), potassium fluoride (7.91 mg, 136 µmol) and aqueous potassium phosphate (540 µl, 2.0 M, 1.1 mmol) were added. The solution was purged with argon for 5 minutes and the reaction was heated at 100° C. for 1 h in the microwave. Afterwards the mixture was filtered over Celite, the solvent was removed under reduced pressure and the crude was used without further purification in the next step.

2-(2-Chlorophenyl)-N-(3-{[(dimethylamino)methylidene]sulfamoyl}-4-[2-(methylamino)-pyrimidin-5-yl]phenyl)acetamide (300 mg, 616 µmol) was dissolved in methanol (2.5 ml) and treated with 32% aqueous sodium hydroxide (240 µl) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by chromatography on silica gel (Biotage, ethyl acetate), the solid was triturated in diethyl ether/ethyl acetate and the filtrate subsequently subjected to HPLC purification (Chromatorex C-18 10 µm, 125×30 mm, acetonitrile/water+0.2% aqueous ammonia (32%)) to yield the title compound (36.0 mg, 95% purity, 13% yield over 2 steps).

LC-MS (Method B): Rt=0.84 min; MS (ESIneg): m/z=430 [M−H]⁻

¹H-NMR (400 MHz, DMSO-d₆) δ [ppm]=2.84 (d, 3H), 3.89 (s, 2H), 7.18 (q, 1H), 7.26-7.38 (m, 5H), 7.43-7.49 (m, 2H), 7.83 (dd, 1H), 8.24 (s, 2H), 8.35 (d, 1H), 10.64 (s, 1H).

Example 302

2-(2-Chlorophenyl)-N-[6-(1-methyl-1H-pyrazol-4-yl)-5-sulfamoylpyridin-3-yl]acetamide

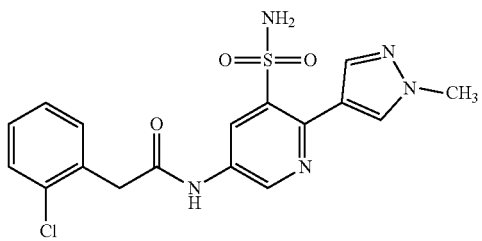 [SMILES: Cn1cc(-c2ncc(NC(=O)Cc3ccccc3Cl)cc2S(N)(=O)=O)cn1]

5-Amino-N-[(dimethylamino)methylidene]-2-(1-methyl-1H-pyrazol-4-yl)pyridine-3-sulfonamide (500 mg, 1.62 mmol) was dissolved in DMF (15 ml) and (2-chlorophenyl) acetic acid (277 mg, 1.62 mmol) was added followed by the addition of N,N-diisopropylethylamine (1.4 ml, 8.1 mmol) and HATU (925 mg, 2.43 mmol). The reaction was stirred at room temperature for 3 h. The solvent was removed under reduced pressure and water and ethyl acetate were added. The phases were separated and the aqueous phase was washed with ethyl acetate. The combined organic phases were dried over Whatman filter and the solvent was removed under reduced pressure. The crude was purified by chromatography on silica gel (Biotage, 2% gradient of ethanol in dichloromethane) to yield 120.0 mg (16% yield over 3 steps).

LC-MS (Method B): Rt=0.93 min; MS (ESIneg): m/z=459 [M−H]⁻

2-(2-Chlorophenyl)-N-[5-{[(dimethylamino)methylidene]sulfamoyl}-6-(1-methyl-1H-pyrazol-4-yl)pyridin-3-yl]acetamide (120 mg, 260 µmol) was dissolved in methanol (20 ml) and treated with 25% aqueous ammonia solution (20 ml) at room temperature until completion of the reaction. The solvent was removed under reduced pressure and the crude was purified by HPLC (Chromatorex C-18 10 µm, 125×30 mm, acetonitrile/water+0.2% aqueous ammonia (32%)) to yield the title compound (2.60 mg, 97% purity, 2% yield).

LC-MS (Method B): Rt=0.65 min; MS (ESIneg): m/z=404 [M−H]⁻

$^1$H-NMR (400 MHz, DMSO-$d_6$) δ [ppm]=3.81-3.98 (m, 5H), 7.26-7.37 (m, 2H), 7.42-7.51 (m, 2H), 7.65 (s, 2H), 7.99 (d, 1H), 8.26 (s, 1H), 8.71 (d, 1H), 8.88 (d, 1H), 10.77 (s, 1H).

Example 303

2-(2-Chlorophenyl)-N-{4-[1-(2,2-difluoroethyl)-1H-pyrazol-4-yl]-3-sulfamoylphenyl}acetamide

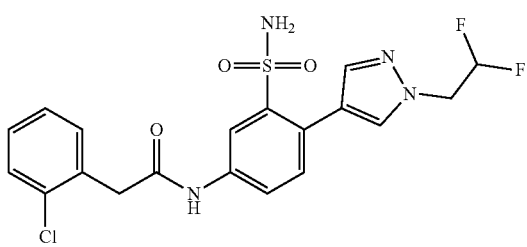 [SMILES: NS(=O)(=O)c1cc(NC(=O)Cc2ccccc2Cl)ccc1-c1cnn(CC(F)F)c1]

DMF was dried over molecular sieves and purged with argon. Then N-(4-bromo-3-{[(dimethylamino)methylidene]sulfamoyl}phenyl)-2-(2-chlorophenyl)acetamide (250 mg, 545 µmol), 1-(2,2-difluoroethyl)-4-(4,4,5,5-tetramethyl-1,3,2-dioxaborolan-2-yl)-1H-pyrazole (281 mg, 1.09 mmol) and potassium fluoride (69.6 mg, 1.20 mmol) were dissolved in dry and degassed DMF (8.3 ml) and the solution was purged again with argon for 5 minutes followed by addition of bis(tri-tert-butylphosphine)palladium(0) (CAS 53199-31-8) (13.9 mg, 27.2 µmol). The reaction was heated for 1 h at 100° C. Afterwards the mixture was filtered over Celite, the solvent was removed under reduced pressure and the crude was dissolved in dry DMF (8.0 ml). 1-(2,2-Difluoroethyl)-4-(4,4,5,5-tetramethyl-1,3,2-dioxaborolan-2-yl)-1H-pyrazole (281 mg, 1.09 mmol), bis(triphenylphosphine)palladium(II) dichloride (CAS 13965-03-2) (19.2 mg, 27.2 µmol) and aqueous potassium phosphate solution (540 µl, 2.0 M, 1.1 mmol) were added. The reaction was heated at 100° C. for 1 h in the microwave. Afterwards the mixture was filtered over Celite, the solvent was removed under reduced pressure and the crude was purified by chromatography on silica gel (Biotage, hexane/ethyl acetate) to yield 100 mg (36% yield).

LC-MS (Method B): Rt=1.07 min; MS (ESIneg): m/z=508 [M−H]⁻

2-(2-Chlorophenyl)-N-(4-[1-(2,2-difluoroethyl)-1H-pyrazol-4-yl]-3-{[(dimethylamino)-methylidene]sulfamoyl}phenyl)acetamide (100 mg, 196 µmol) was dissolved in methanol (0.8 ml) and treated with 32% aqueous sodium hydroxide (280 µl) at room temperature over night. 32% Aqueous sodium hydroxide (280 µl) was added and the reaction heated at 50° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Chromatorex C-18 10 µm, 125×30 mm, acetonitrile/water+0.2% aqueous ammonia (32%)) to yield the title compound (9.20 mg, 95% purity, 10% yield).

LC-MS (Method A): Rt=1.02 min; MS (ESIneg): m/z=453 [M−H]⁻

$^1$H-NMR (400 MHz, DMSO-$d_6$) δ [ppm]=3.88 (s, 2H), 4.65 (td, 2H), 6.19-6.59 (m, 1H), 7.19 (s, 2H), 7.29-7.36 (m, 2H), 7.42-7.48 (m, 3H), 7.78 (s, 1H), 7.83 (dd, 1H), 8.08 (s, 1H), 8.33 (d, 1H), 10.59 (s, 1H).

Example 304

N-{3-Sulfamoyl-4-[5-(trifluoromethyl)pyridin-3-yl]phenyl}-2-[2-(trifluoromethyl)phenyl]acetamide

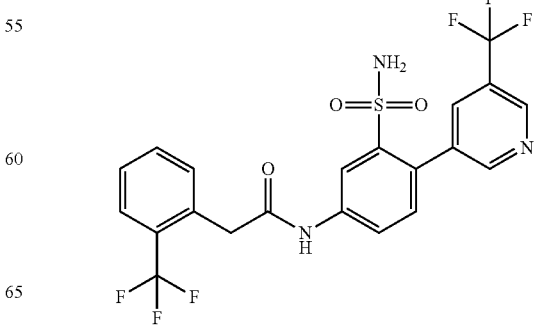

5-Amino-N-[(dimethylamino)methylidene]-2-[5-(trifluoromethyl)pyridin-3-yl]benzenesulfonamide (185 mg, 497 µmol) was dissolved in DMF (3.5 ml) and [2-(trifluoromethyl)phenyl]acetic acid (122 mg, 596 µmol) was added followed by the addition of N,N-diisopropylethylamine (410 µl, 2.5 mmol) and HATU (302 mg, 795 µmol). The reaction was stirred at 50° C. for 2 h. Water and dichloromethane were added. The phases were separated and the aqueous phase was washed with dichloromethane. The combined organic phases were dried over Whatman filter and the solvent was removed under reduced pressure. The crude was purified by chromatography on silica gel (Biotage, hexane/ethyl acetate) to yield 200 mg (41% purity, 72% yield over 2 steps).

LC-MS (Method B): Rt=1.21 min; MS (ESIneg): m/z=557 [M–H]⁻

N-(3-{[(Dimethylamino)methylidene]sulfamoyl}-4-[5-(trifluoromethyl)pyridin-3-yl]phenyl)-2-[2-(trifluoromethyl)phenyl]acetamide (200 mg, 358 µmol) was dissolved in methanol (1.5 ml) and treated with 25% aqueous ammonia solution (0.5 ml) at room temperature over night. Then 32% aqueous sodium hydroxide (0.2 ml) was added and stirring was continued at 50° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by chromatography on silica gel (Biotage, 40% ethyl acetate in hexane) and subsequently by HPLC (Chromatorex C-18 µm, 125×30 mm, acetonitrile/water+0.2% aqueous ammonia (32%)) to yield the title compound (10.0 mg, 95% purity, 5% yield).

LC-MS (Method A): Rt=1.18 min; MS (ESIneg): m/z=502 [M–H]⁻

¹H-NMR (500 MHz, DMSO-d6): Shift [ppm]=4.00 (s, 2H), 7.28-7.45 (m, 2H), 7.48-7.59 (m, 2H), 7.65-7.70 (m, 1H), 7.73 (d, 1H), 7.87 (dd, 1H), 8.08-8.23 (m, 1H), 8.31 (s, 1H), 8.38 (d, 1H), 8.82 (d, 1H), 8.95 (d, 1H), 10.70 (s, 1H).

Example 305

2-(2-Chlorophenyl)-N-[3-sulfamoyl-5'-(trifluoromethyl)-2,3'-bipyridin-5-yl]acetamide

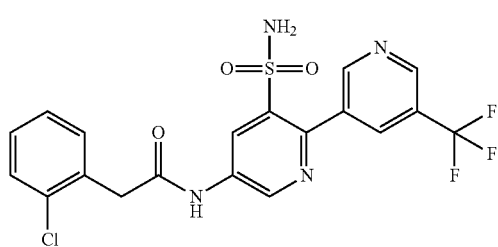

5-Amino-N-[(dimethylamino)methylidene]-5'-(trifluoromethyl)-2,3'-bipyridine-3-sulfonamide (250 mg, 670 µmol) was dissolved in DMF (10 ml) and (2-chlorophenyl)acetic acid (126 mg, 737 µmol) was added followed by the addition of N,N-diisopropylethylamine (580 µl, 3.3 mmol) and HATU (306 mg, 804 µmol). The reaction was stirred at 50° C. for 3 h. Then same amount of acid was added and stirring was continued for 2 h. The solvent was removed under reduced pressure and ethyl acetate and water were added. The phases were separated and the aqueous phase was washed with ethyl acetate. The combined organic phases were dried over Whatman filter and the solvent was removed under reduced pressure. The crude was purified by HPLC (Chromatorex C-18 10 µm, 125×30 mm, acetonitrile/water+0.1% aqueous ammonia (32%)) to yield 160 mg (45% yield over 3 steps).

LC-MS (Method B): Rt=1.13 min; MS (ESIneg): m/z=524 [M–H]⁻

2-(2-Chlorophenyl)-N-[3-{[(dimethylamino)methylidene]sulfamoyl}-5'-(trifluoromethyl)-2,3'-bipyridin-5-yl] acetamide (160 mg, 304 µmol) was dissolved in methanol (20 ml) and treated with 25% aqueous ammonia solution (20 ml) at room temperature until completion of the reaction. The solvent was removed under reduced pressure and the crude was purified by HPLC (Chromatorex C-18 10 µm, 125×30 mm, acetonitrile/water+0.2% aqueous ammonia (32%)) to yield the title compound (11.6 mg, 99% purity, 8% yield).

LC-MS (Method B): Rt=0.81 min; MS (ESIneg): m/z=469 [M–H]⁻

¹H-NMR (400 MHz, DMSO-d₆) δ [ppm]=3.96 (s, 2H), 7.29-7.40 (m, 2H), 7.43-7.52 (m, 2H), 7.77 (s, 2H), 8.28-8.35 (m, 1H), 8.86 (d, 1H), 8.99 (d, 1H), 9.02 (dd, 2H), 10.99 (s, 1H).

Example 306

2-(2-Chlorophenyl)-N-{3-sulfamoyl-4-[2-(trifluoromethyl)pyrimidin-5-yl]phenyl}acetamide

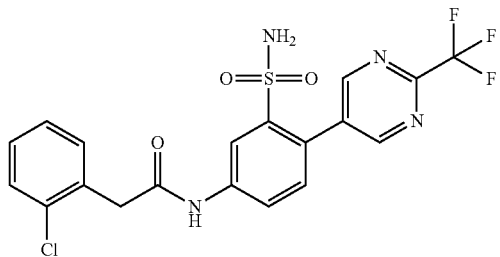 [SMILES: NS(=O)(=O)c1cc(NC(=O)Cc2ccccc2Cl)ccc1-c1cnc(C(F)(F)F)nc1]

To the solution containing the boronic ester intermediate 2-(2-chlorophenyl)-N-[3-{[(dimethylamino)methylidene]sulfamoyl}-4-(4,4,5,5-tetramethyl-1,3,2-dioxaborolan-2-yl)phenyl]acetamide (250 mg, 494 µmol), 5-bromo-2-(trifluoromethyl)pyrimidine (224 mg, 988 µmol) and potassium fluoride (57.4 mg, 988 µmol) were added under argon atmosphere. The solution was purged with argon for 5 minutes and bis(triphenylphosphine)palladium(II) dichloride (CAS 13965-03-2) (12.6 mg, 24.7 µmol) was added. The solution was purged again with argon and the reaction was heated at 80° C. for 1 h. Afterwards the mixture was filtered over Celite, the solvent was removed under reduced pressure and the crude was used without further purification in the next step.

2-(2-Chlorophenyl)-N-(3-{[(dimethylamino)methylidene]sulfamoyl}-4-[2-(trifluoromethyl)pyrimidin-5-yl]phenyl)acetamide (300 mg, 570 µmol) was dissolved in methanol (2.3 ml) and treated with aqueous ammonia solution (810 µl, 7.0 M, 5.7 mmol) at room temperature. Afterwards, 32% aqueous sodium hydroxide solution (200 µl) was added and stirring was continued until completion of the reaction. The solvent was removed under reduced pressure and the crude was purified by HPLC (Chromatorex C-18 10

µm, 125×30 mm, acetonitrile/water+0.2% aqueous ammonia (32%)) to yield the title compound (19.1 mg, 95% purity, 7% yield over 3 steps).

LC-MS (Method B): Rt=0.98 min; MS (ESIneg): m/z=469 [M−H]⁻

¹H-NMR (400 MHz, DMSO-d₆): δ [ppm]=3.92 (s, 2H), 7.24-7.40 (m, 3H), 7.41-7.55 (m, 4H), 7.93 (dd, 1H), 8.42 (d, 1H), 9.03 (s, 2H), 10.77 (s, 1H).

Example 307

2-(2-Chlorophenyl)-N-{3-sulfamoyl-4-[5-(trifluoromethoxy)pyridin-3-yl]phenyl}acetamide

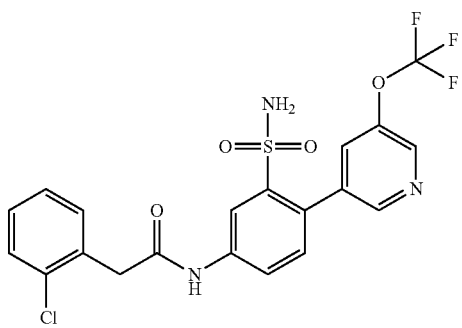 [SMILES: NS(=O)(=O)c1cc(NC(=O)Cc2ccccc2Cl)ccc1-c1cncc(OC(F)(F)F)c1]

To the solution containing the boronic ester intermediate 2-(2-chlorophenyl)-N-[3-{[(dimethylamino)methylidene] sulfamoyl}-4-(4,4,5,5-tetramethyl-1,3,2-dioxaborolan-2-yl) phenyl]acetamide (100 mg, 197 µmol), 3-bromo-5-(trifluoromethoxy)pyridine (95.7 mg, 395 µmol) and potassium fluoride (23.0 mg, 395 µmol) were added under argon atmosphere. The solution was purged with argon for 5 minutes and bis(triphenylphosphine)palladium(II) dichloride (CAS 13965-03-2) (5.05 mg, 9.88 µmol) was added. The solution was purged again with argon and the reaction was heated at 80° C. for 1 h. Afterwards the mixture was filtered over Celite, the solvent was removed under reduced pressure and the crude was purified by chromatography on silica gel (Biotage, hexane /ethyl acetate) to yield 81.3 mg (76% yield).

LC-MS (Method B): Rt=1.21 min; MS (ESIneg): m/z=539 [M−H]⁻

2-(2-Chlorophenyl)-N-(3-{[(dimethylamino)methylidene]sulfamoyl}-4-[5-(trifluoromethoxy)-pyridin-3-yl] phenyl)acetamide (190 mg, 351 µmol) was dissolved in methanol (1.4 ml) and treated with aqueous ammonia solution (500 µl, 7.0 M, 3.5 mmol) at room temperature.

After 18 h, 32% aqueous sodium hydroxide solution (200 µl) was added and stirring was continued until completion of the reaction. The solvent was removed under reduced pressure and the crude was purified by HPLC (Chromatorex C-18 10 µm, 125×30 mm, acetonitrile/water+0.2% aqueous ammonia (32%)) to yield the title compound (27.3 mg, 95% purity, 15% yield over 3 steps).

LC-MS (Method B): Rt=1.11 min; MS (ESIneg): m/z=484 [M−H]⁻

¹H-NMR (400 MHz, DMSO-d₆) δ [ppm]=3.91 (s, 2H), 7.29-7.41 (m, 3H), 7.43-7.53 (m, 4H), 7.80-7.97 (m, 2H), 8.40 (d, 1H), 8.58 (d, 1H), 8.67 (d, 1H), 10.73 (s, 1H).

Example 308

2-(2-Chlorophenyl)-N-[4-(2-cyclopropylpyrimidin-5-yl)-3-sulfamoylphenyl]acetamide

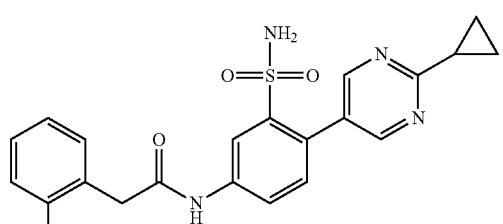

To the solution containing the boronic ester intermediate 2-(2-chlorophenyl)-N-[3-{[(dimethylamino)methylidene] sulfamoyl}-4-(4,4,5,5-tetramethyl-1,3,2-dioxaborolan-2-yl) phenyl]acetamide (100 mg, 198 µmol), 5-bromo-2-cyclopropylpyrimidine (78.7 mg, 395 µmol) and potassium fluoride (23.0 mg, 395 µmol) were added under argon atmosphere.

The solution was purged with argon for 5 minutes and bis(triphenylphosphine)palladium(II) dichloride (CAS 13965-03-2) (5.05 mg, 9.88 µmol) was added. The solution was purged again with argon and the reaction was heated at 80° C. for 1 h. Afterwards the mixture was filtered over Celite, the solvent was removed under reduced pressure and the crude was purified by chromatography on silica gel (Biotage, hexane/ethyl acetate) to yield 50.0 mg (51% yield).

LC-MS (Method B): Rt=1.15 min; MS (ESIneg): m/z=496 [M−H]⁻

2-(2-Chlorophenyl)-N-[4-(2-cyclopropylpyrimidin-5-yl)-3-{[(dimethylamino)methylidene]-sulfamoyl}phenyl]acetamide (50.0 mg, 100 µmol) was dissolved in methanol (0.4 ml) and treated with aqueous ammonia solution (140 µl, 7.0 M, 3.5 mmol) at room temperature.

After 18 h, 32% aqueous sodium hydroxide solution (200 µl) was added and stirring was continued until completion of the reaction. The solvent was removed under reduced pressure and the crude was purified by HPLC (Chromatorex C-18 10 µm, 125×30 mm, acetonitrile/water+0.2% aqueous ammonia (32%)) to yield the title compound (6.30 mg, 95% purity, 13% yield).

LC-MS (Method B): Rt=0.95 min; MS (ESIneg): m/z=441 [M−H]⁻

¹H-NMR (400 MHz, DMSO-d₆) δ [ppm]=0.93-1.17 (m, 4H), 2.11-2.28 (m, 1H), 3.90 (s, 2H), 7.19-7.40 (m, 3H), 7.42-7.59 (m, 4H), 7.87 (dd, 1H), 8.39 (d, 1H), 8.57 (s, 2H), 10.70 (s, 1H).

Example 309

2-(2-Chlorophenyl)-N-[4-(2-ethoxypyrimidin-5-yl)-3-sulfamoylphenyl]acetamide

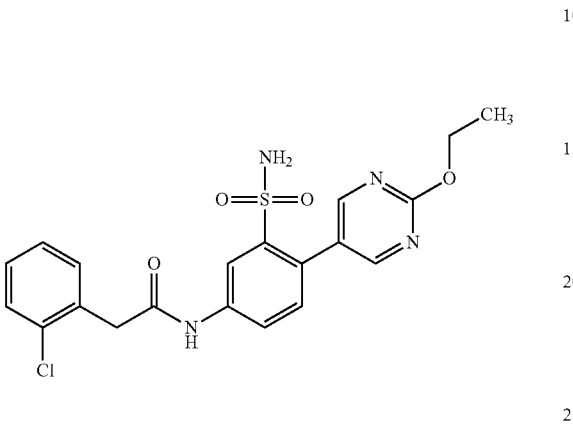

To the solution containing the boronic ester intermediate 2-(2-chlorophenyl)-N-[3-{[(dimethylamino)methylidene]sulfamoyl}-4-(4,4,5,5-tetramethyl-1,3,2-dioxaborolan-2-yl)phenyl]acetamide (100 mg, 198 µmol), 5-bromo-2-ethoxypyrimidine (80.3 mg, 395 µmol) and potassium fluoride (23.0 mg, 395 µmol) were added under argon atmosphere. The solution was purged with argon for 5 minutes and bis(triphenylphosphine)palladium(II) dichloride (CAS 13965-03-2) (5.05 mg, 9.88 µmol) was added. The solution was purged again with argon and the reaction was heated at 80° C. for 1 h. Afterwards the mixture was filtered over Celite, the solvent was removed under reduced pressure and the crude was purified by chromatography on silica gel (Biotage, hexane/ethyl acetate) to yield 50.0 mg (50% yield).

LC-MS (Method B): Rt=1.15 min; MS (ESIneg): m/z=500 [M−H]⁻

2-(2-Chlorophenyl)-N-[3-{[(dimethylamino)methylidene]sulfamoyl}-4-(2-ethoxypyrimidin-5-yl)phenyl]acetamide (50.0 mg, 99.6 µmol) was dissolved in methanol (0.4 ml) and treated with aqueous ammonia solution (140 µl, 7.0 M, 3.5 mmol) at room temperature. After 18 h, 32% aqueous sodium hydroxide solution (200 µl) was added and stirring was continued until completion of the reaction. The solvent was removed under reduced pressure and the crude was purified by HPLC (Chromatorex C-18 10 µm, 125×30 mm, acetonitrile/water+0.2% aqueous ammonia (32%)) to yield the title compound (1.00 mg, 95% purity, 2% yield).

LC-MS (Method B): Rt=0.96 min; MS (ESIneg): m/z=445 [M−H]⁻

¹H-NMR (400 MHz, DMSO-d₆) δ [ppm]=1.37 (t, 3H), 3.90 (s, 2H), 4.40 (q, 2H), 7.09-7.63 (m, 7H), 7.87 (dd, 1H), 8.36 (s, 1H), 8.53 (s, 2H), 10.68 (s, 1H).

Example 310

2-(2-Chlorophenyl)-N-{4-[2-(propan-2-ylamino)pyrimidin-5-yl]-3-sulfamoylphenyl}acetamide

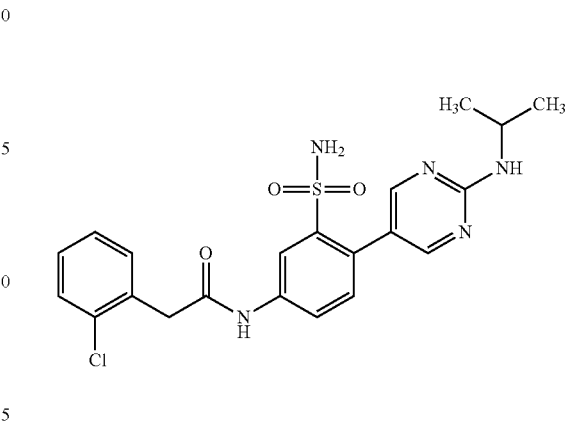

To the solution containing the boronic ester intermediate 2-(2-chlorophenyl)-N-[3-{[(dimethylamino)methylidene]sulfamoyl}-4-(4,4,5,5-tetramethyl-1,3,2-dioxaborolan-2-yl)phenyl]acetamide (100 mg, 198 µmol), 5-bromo-N-(propan-2-yl)pyrimidin-2-amine (85.4 mg, 395 µmol) and potassium fluoride (23.0 mg, 395 µmol) were added under argon atmosphere. The solution was purged with argon for 5 minutes and bis(triphenylphosphine)palladium(II) dichloride (CAS 13965-03-2) (5.05 mg, 9.88 µmol) was added. The solution was purged again with argon and the reaction was heated at 80° C. for 1 h. Afterwards the mixture was filtered over Celite, the solvent was removed under reduced pressure and the crude was purified by chromatography on silica gel (Biotage, hexane/ethyl acetate) to yield 50.0 mg (49% yield).

LC-MS (Method B): Rt=1.17 min; MS (ESIneg): m/z=513 [M−H]⁻

2-(2-Chlorophenyl)-N-(3-{[(dimethylamino)methylidene]sulfamoyl}-4-[2-(propan-2-yl-amino)pyrimidin-5-yl]phenyl)acetamide (50.0 mg, 97.1 µmol) was dissolved in methanol (0.4 ml) and treated with aqueous ammonia solution (140 µl, 7.0 M, 3.5 mmol) at room temperature. After 18 h, 32% aqueous sodium hydroxide solution (200 µl) was added and stirring was continued until completion of the reaction. The solvent was removed under reduced pressure and the crude was purified by HPLC (Chromatorex C-18 10 µm, 125×30 mm, acetonitrile/water+0.2% aqueous ammonia (32%)) to yield the title compound (2.70 mg, 95% purity, 6% yield).

LC-MS (Method B): Rt=1.03 min; MS (ESIneg): m/z=458 [M−H]⁻

¹H-NMR (400 MHz, DMSO-d₆) δ [ppm]=1.18 (d, 6H), 3.89 (s, 2H), 4.07 (spt, 1H), 7.10 (d, 1H), 7.29 (d, 1H), 7.31-7.39 (m, 4H), 7.42-7.50 (m, 2H), 7.83 (dd, 1H), 8.23 (s, 2H), 8.35 (d, 1H), 10.63 (s, 1H).

Example 311

2-(2-Chlorophenyl)-N-{4-[2-(propan-2-yloxy)pyrimidin-5-yl]-3-sulfamoylphenyl}acetamide

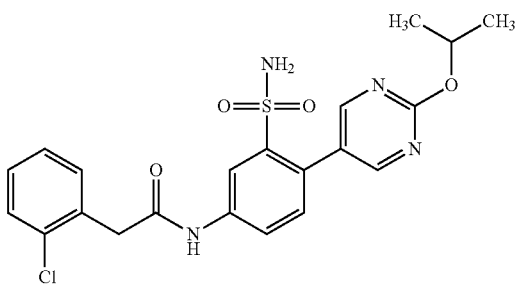 [SMILES: CC(C)Oc1ncc(-c2ccc(NC(=O)Cc3ccccc3Cl)cc2S(N)(=O)=O)cn1]

To the solution containing the boronic ester intermediate 2-(2-chlorophenyl)-N-[3-{[(dimethylamino)methylidene]sulfamoyl}-4-(4,4,5,5-tetramethyl-1,3,2-dioxaborolan-2-yl)phenyl]acetamide (100 mg, 198 µmol), 5-bromo-2-(propan-2-yloxy)pyrimidine (94.6 mg, 436 µmol) and potassium fluoride (25.3 mg, 436 µmol) were added under argon atmosphere. The solution was purged with argon for 5 minutes and palladium-tri-tert-butylphosphane (1:2) (5.57 mg, 10.9 µmol) was added. The solution was purged again with argon and the reaction was heated at 80° C. for 1 h. Afterwards the mixture was filtered over Celite, the solvent was removed under reduced pressure and the crude was used without further purification in the next step.

LC-MS (Method B): $R_t$=1.16 min; MS (ESIpos): m/z=516 [M+H]$^+$ 2-(2-Chlorophenyl)-N-(3-{[(dimethylamino)methylidene]sulfamoyl}-4-[2-(propan-2-yloxy)-pyrimidin-5-yl]phenyl)acetamide (150 mg, 291 µmol) was dissolved in methanol (1.1 ml) and treated with 32% aqueous sodium hydroxide solution (140 µl) at 50° C. for 4 h. The solvent was removed under reduced pressure and the crude was purified by HPLC (Chromatorex C-18 10 µm, 125×30 mm, acetonitrile/water+0.2% aqueous ammonia (32%)) to yield the title compound (23.7 mg, 95% purity, 17% yield over 2 steps).

LC-MS (Method B): Rt=1.02 min; MS (ESIneg): m/z=459 [M−H]$^+$ $^1$H-NMR (400 MHz, DMSO-d$_6$) δ [ppm]=1.35 (d, 6H), 3.89 (s, 2H), 5.24 (quin, 1H), 6.99-7.67 (m, 7H), 7.85-8.04 (m, 1H), 8.36 (d, 1H), 8.51 (s, 2H), 10.68 (s, 1H).

Example 312

2-(2-Chlorophenyl)-N-{4-[2-(ethylamino)pyrimidin-5-yl]-3-sulfamoylphenyl}-acetamide

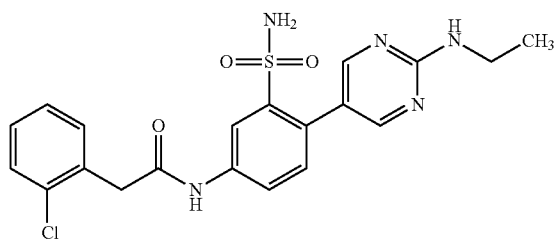 [SMILES: CCNc1ncc(-c2ccc(NC(=O)Cc3ccccc3Cl)cc2S(N)(=O)=O)cn1]

To the solution containing the boronic ester intermediate 2-(2-chlorophenyl)-N-[3-{[(dimethylamino)methylidene]sulfamoyl}-4-(4,4,5,5-tetramethyl-1,3,2-dioxaborolan-2-yl)phenyl]acetamide (100 mg, 198 µmol), 5-bromo-N-ethylpyrimidin-2-amine (88.1 mg, 436 µmol) and potassium fluoride (25.3 mg, 436 µmol) were added under argon atmosphere. The solution was purged with argon for 5 minutes and bis(tri-tert-butylphosphine)palladium(0) (CAS 53199-31-8) (5.57 mg, 10.9 µmol) was added. The solution was purged again with argon and the reaction was heated at 80° C. for 1 h. Afterwards the mixture was filtered over Celite, the solvent was removed under reduced pressure and the crude was used without further purification in the next step.

LC-MS (Method B): $R_t$=1.05 min; MS (ESIpos): m/z=501 [M+H]$^+$ 2-(2-Chlorophenyl)-N-(3-{[(dimethylamino)methylidene]sulfamoyl}-4-[2-(ethylamino)-pyrimidin-5-yl]phenyl)acetamide (150 mg, 299 µmol) was dissolved in methanol (1.2 ml) and treated with 32% aqueous sodium hydroxide solution (140 µl) at 50° C. until completion of the reaction. The solvent was removed under reduced pressure and the crude was purified by HPLC (Chromatorex C-18 10 µm, 125×30 mm, acetonitrile/water+0.2% aqueous ammonia (32%)) to yield the final product 25.1 mg (95% purity, 18% yield over 2 steps).

LC-MS (Method B): Rt=0.95 min; MS (ESIpos): m/z=446 [M+H]$^+$ $^1$H-NMR (400 MHz, DMSO-d$_6$) δ [ppm]=1.15 (t, 3H), 3.89 (s, 2H), 7.14-7.41 (m, 6H), 7.42-7.56 (m, 2H), 7.83 (dd, 1H), 8.23 (s, 2H), 8.35 (d, 1H), 10.64 (s, 1H).

Example 313

2-(2-Chlorophenyl)-N-[4-(2-methylpyrimidin-5-yl)-3-sulfamoylphenyl]acetamide

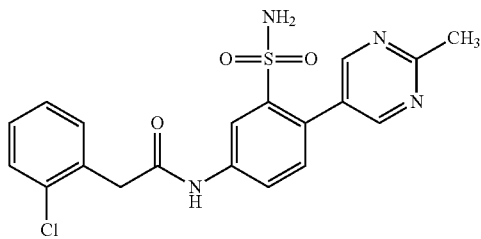 [SMILES: Cc1ncc(-c2ccc(NC(=O)Cc3ccccc3Cl)cc2S(N)(=O)=O)cn1]

To the solution containing the boronic ester intermediate 2-(2-chlorophenyl)-N-[3-{[(dimethylamino)methylidene]sulfamoyl}-4-(4,4,5,5-tetramethyl-1,3,2-dioxaborolan-2-yl)phenyl]acetamide (100 mg, 198 µmol), 5-bromo-2-methylpyrimidine (75.4 mg, 436 µmol) and potassium fluoride (25.3 mg, 436 µmol) were added under argon atmosphere. The solution was purged with argon for 5 minutes and bis(tri-tert-butylphosphine)palladium(0) (CAS 53199-31-8) (5.57 mg, 10.9 µmol) was added. The solution was purged again with argon and the reaction was heated at 80° C. for 1 h. Afterwards the mixture was filtered over Celite, the solvent was removed under reduced pressure and the crude was used without further purification in the next step.

LC-MS (Method B): R, =0.98 min; MS (ESIpos): m/z=472 [M+H]$^+$ 2-(2-Chlorophenyl)-N-[3-{[(dimethylamino)methylidene]sulfamoyl}-4-(2-methylpyrimidin-5-yl)phenyl]acetamide (150 mg, 318 µmol) was dissolved in methanol (1.3 ml) and treated with 32% aqueous sodium hydroxide solution (200 µl) at 80° C. until completion of the reaction. The solvent was removed under reduced pressure and the crude was purified by HPLC (Chromatorex C-18 10 μm, 125×30 mm, acetonitrile/water+0.2% aqueous ammonia (32%), then Waters XBrigde C18 5μ 100×30 mm, acetonitrile/water+0.1% formic acid) to yield the title compound (10.0 mg, 93% purity, 7% yield over 2 steps).

LC-MS (Method A): R$_t$=1.12 min; MS (ESIpos): m/z=417 [M+H]$^+$ $^1$H-NMR (400 MHz, DMSO-d$_6$): δ [ppm]=2.67 (s, 3H), 3.91 (s, 2H), 7.28-7.38 (m, 3H), 7.41-7.58 (m, 4H), 7.88 (dd, 1H), 8.40 (d, 1H), 8.63 (s, 2H), 10.71 (s, 1H).

Example 314

2-(2-Chlorophenyl)-N-{4-[2-(propylamino)pyrimidin-5-yl]-3-sulfamoylphenyl}-acetamide

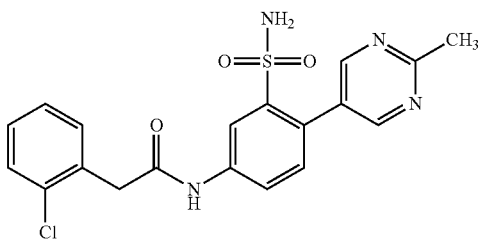 [SMILES: Cc1ncc(-c2ccc(NC(=O)Cc3ccccc3Cl)cc2S(N)(=O)=O)cn1]

To the solution containing the boronic ester intermediate 2-(2-chlorophenyl)-N-[3-{[(dimethylamino)methylidene]sulfamoyl}-4-(4,4,5,5-tetramethyl-1,3,2-dioxaborolan-2-yl)phenyl]acetamide (150 mg, 297 μmol), 5-bromo-N-propylpyrimidin-2-amine (141 mg, 654 μmol) and potassium fluoride (38.0 mg, 654 μmol) were added under argon atmosphere. The solution was purged with argon for 5 minutes and bis(tri-tert-butylphosphine)palladium(0) (CAS 53199-31-8) (8.35 mg, 16.3 μmol) was added. The solution was purged again with argon and the reaction was heated at 80° C. for 2 h. Afterwards the mixture was filtered over Celite, the solvent was removed under reduced pressure and the crude was purified by chromatography on silica gel (Biotage, hexane/ethyl acetate) to yield 90.0 mg (53% yield).

LC-MS (Method B): Rt=1.12 min; MS (ESIpos): m/z=515 [M+H+]2-(2-Chlorophenyl)-N-(3-{[(dimethylamino)methylidene]sulfamoyl}-4-[2-(propylamino)-pyrimidin-5-yl]phenyl)acetamide (90.0 mg, 175 μmol) was dissolved in methanol (1.8 ml) and treated with 32% aqueous sodium hydroxide solution (200 μl) at room temperature until completion of the reaction. The solvent was removed under reduced pressure and the crude was purified by HPLC (Chromatorex C-18 10 μm, 125×30 mm, acetonitrile/water+0.2% aqueous ammonia (32%)) to yield the title compound (30.3 mg, 95% purity, 36% yield).

LC-MS (Method B): R$_t$=1.01 min; MS (ESIpos): m/z=460 [M+H*]

$^1$H-NMR (400 MHz, DMSO-d$_6$) δ [ppm]=0.91 (t, 3H), 1.56 (sxt, 2H), 3.23-3.29 (m, 2H), 3.89 (s, 2H), 7.21-7.37 (m, 6H), 7.42-7.52 (m, 2H), 7.83 (dd, 1H), 8.23 (s, 1H), 8.35 (d, 1H), 10.64 (s, 1H).

Example 315

2-(2-Chlorophenyl)-N-(3-sulfamoyl-4-{2-[(2,2,2-trifluoroethyl)amino]pyrimidin-5-yl}phenyl)acetamide

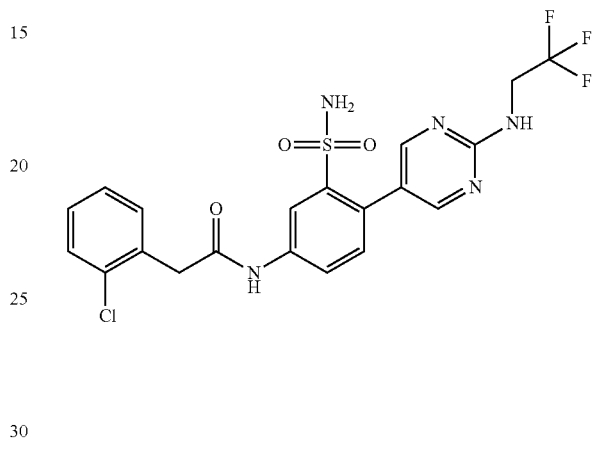

To the solution containing the boronic ester intermediate 2-(2-chlorophenyl)-N-[3-{[(dimethylamino)methylidene]sulfamoyl}-4-(4,4,5,5-tetramethyl-1,3,2-dioxaborolan-2-yl)phenyl]acetamide (150 mg, 297 μmol), 5-bromo-N-(2,2,2-trifluoroethyl)pyrimidin-2-amine (167 mg, 654 μmol) and potassium fluoride (38.0 mg, 654 μmol) were added under argon atmosphere. The solution was purged with argon for 5 minutes and bis(tri-tert-butylphosphine)palladium(0) (CAS 53199-31-8) (8.35 mg, 16.3 μmol) was added. The solution was purged again with argon and the reaction was heated at 80° C. for 2 h. Afterwards the mixture was filtered over Celite, the solvent was removed under reduced pressure and the crude was purified by chromatography on silica gel (Biotage, hexane/ethyl acetate) to yield 150 mg (80% purity, 66% yield).

LC-MS (Method B): R$_t$=1.14 min; MS (ESIpos): m/z=555 [M+H*]2-(2-Chlorophenyl)-N-(3-{[(dimethylamino)methylidene]sulfamoyl}-4-{2-[(2,2,2-trifluoroethyl)amino]pyrimidin-5-yl}phenyl)acetamide (150 mg, 80% purity, 216 μmol) was dissolved in methanol (2.2 ml) and treated with 32% aqueous sodium hydroxide solution (200 μl) at room temperature until completion of the reaction. The solvent was removed under reduced pressure and the crude was purified by HPLC (Chromatorex C-18 10 μm, 125×30 mm, acetonitrile/water+0.2% aqueous ammonia (32%)) to yield the title compound (41.3 mg, 95% purity, 36% yield).

LC-MS (Method B): R$_t$=0.99 min; MS (ESIpos): m/z=500 [M+H*]

$^1$H-NMR (400 MHz, DMSO-d$_6$) δ [ppm]=3.90 (s, 2H), 4.12-4.25 (m, 2H), 7.29-7.35 (m, 3H), 7.39 (s, 2H), 7.43-7.49 (m, 2H), 7.81-7.92 (m, 2H), 8.32 (s, 2H), 8.36 (d, 1H), 10.66 (s, 1H).

Example 316

2-(2-Chlorophenyl)-N-{4-[2-(cyclobutyloxy)pyrimidin-5-yl]-3-sulfamoylphenyl}acetamide

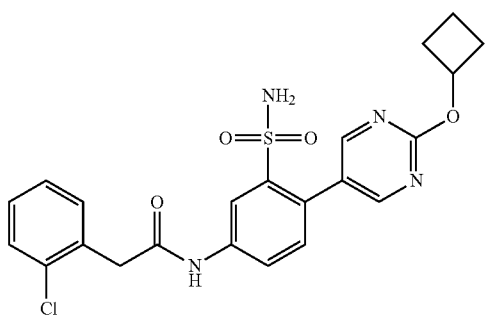 [SMILES: NS(=O)(=O)c1cc(NC(=O)Cc2ccccc2Cl)ccc1-c1cnc(OC2CCC2)nc1]

To the solution containing the boronic ester intermediate 2-(2-chlorophenyl)-N-[3-{[(dimethylamino)methylidene]sulfamoyl}-4-(4,4,5,5-tetramethyl-1,3,2-dioxaborolan-2-yl)phenyl]acetamide (150 mg, 297 µmol), 5-bromo-2-(cyclobutyloxy)pyrimidine (150 mg, 654 µmol) and potassium fluoride (38.0 mg, 654 µmol) were added under argon atmosphere. The solution was purged with argon for 5 minutes and bis(tri-tert-butylphosphine)palladium(0) (CAS 53199-31-8) (8.35 mg, 16.3 µmol) was added. The solution was purged again with argon and the reaction was heated at 80° C. for 2 h. Afterwards the mixture was filtered over Celite, the solvent was removed under reduced pressure and the crude was purified by chromatography on silica gel (Biotage, hexane/ethyl acetate) to yield 110 mg (64% yield).

LC-MS (Method B): $R_t$=1.20 min; MS (ESIpos): m/z=528 [M+H*]2-(2-Chlorophenyl)-N-(4-[2-(cyclobutyloxy)pyrimidin-5-yl]-3-{[(dimethylamino)methylidene]sulfamoyl}phenyl)acetamide (110 mg, 208 µmol) was dissolved in methanol (2.3 ml) and treated with 32% aqueous sodium hydroxide solution (200 µl) at room temperature until completion of the reaction. The solvent was removed under reduced pressure and the crude was purified by HPLC (Chromatorex C-18 10 µm, 125×30 mm, acetonitrile/water+0.2% aqueous ammonia (32%)) to yield the title compound (10.6 mg, 95% purity, 10% yield).

LC-MS (Method B): $R_t$=1.07 min; MS (ESIpos): m/z=473 [M+H*]

$^1$H-NMR (400 MHz, DMSO-d$_6$) δ [ppm]=1.59-1.71 (m, 1H), 1.81 (q, 1H), 2.06-2.24 (m, 2H), 2.39-2.47 (m, 2H), 3.89 (s, 2H), 5.08-5.26 (m, 1H), 7.26-7.40 (m, 5H), 7.42-7.52 (m, 2H), 7.86 (dd, 1H), 8.37 (d, 1H), 8.50 (s, 2H), 10.69 (s, 1H).

Example 317

N-[4-(2-Chloro-4-methylpyrimidin-5-yl)-3-sulfamoylphenyl]-2-(2-chlorophenyl)acetamide

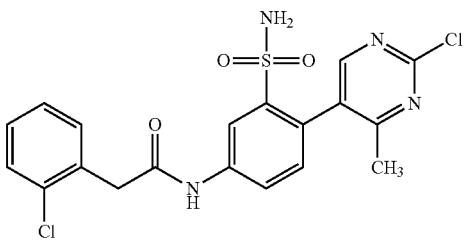 [SMILES: Cc1nc(Cl)ncc1-c1ccc(NC(=O)Cc2ccccc2Cl)cc1S(N)(=O)=O]

To the solution containing the boronic ester intermediate 2-(2-chlorophenyl)-N-[3-{[(dimethylamino)methylidene]sulfamoyl}-4-(4,4,5,5-tetramethyl-1,3,2-dioxaborolan-2-yl)phenyl]acetamide (400 mg, 792 µmol), 5-bromo-2-chloro-4-methylpyrimidine (362 mg, 1.74 mmol) and potassium fluoride (101 mg, 1.74 mmol) were added under argon atmosphere. The solution was purged with argon for 5 minutes and bis(tri-tert-butylphosphine)palladium(0) (CAS 53199-31-8) (22.3 mg, 43.6 µmol) was added. The solution was purged again with argon and the reaction was heated at 80° C. for 2 h. Afterwards the mixture was filtered over Celite, the solvent was removed under reduced pressure and the crude was purified by chromatography on silica gel (Biotage, hexane/ethyl acetate) to yield 124 mg (28% yield).

LC-MS (Method B): $R_t$=1.12 min; MS (ESIneg): m/z=504 [M–H*]N-[4-(2-Chloro-4-methylpyrimidin-5-yl)-3-{[(dimethylamino)methylidene]sulfamoyl}phenyl]-2-(2-chlorophenyl)acetamide (124 mg, 245 µmol) was dissolved in methanol (2.5 ml) and treated with 32% aqueous sodium hydroxide solution (200 µl) at room temperature until completion of the reaction. The solvent was removed under reduced pressure and the crude was purified by HPLC (Chromatorex C-18 10 µm, 125×30 mm, acetonitrile/water+0.2% aqueous ammonia (32%) then Waters XBrigde C18 5µ 100×30 mm, acetonitrile/water+0.1% formic acid) to yield the title compound (2.60 mg, 95% purity, 2% yield).

LC-MS (Method A): $R_t$=1.04 min; MS (ESIpos): m/z=451 [M+H*]

$^1$H-NMR (400 MHz, DMSO-d$_6$) δ [ppm]=2.20 (s, 3H), 3.91 (s, 2H), 7.27-7.39 (m, 3H), 7.41-7.56 (m, 4H), 7.89 (dd, 1H), 8.31-8.45 (m, 2H), 10.73 (s, 1H).

Example 318

2-(2-Chlorophenyl)-N-{3-sulfamoyl-4-[4-(trifluoromethyl)pyridin-2-yl]phenyl}acetamide

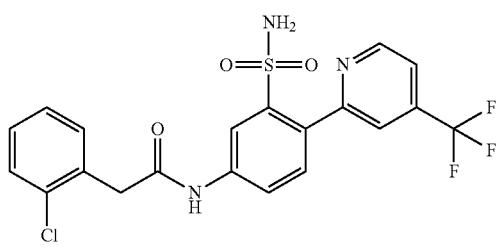 [SMILES: NS(=O)(=O)c1cc(NC(=O)Cc2ccccc2Cl)ccc1-c1cc(C(F)(F)F)ccn1]

To the solution containing the boronic ester intermediate 2-(2-chlorophenyl)-N-[3-{[(dimethylamino)methylidene]sulfamoyl}-4-(4,4,5,5-tetramethyl-1,3,2-dioxaborolan-2-yl)phenyl]acetamide (300 mg, 594 µmol), 2-bromo-4-(trifluoromethyl)pyridine (296 mg, 1.31 mmol) and potassium fluoride (76.0 mg, 1.31 mmol) were added under argon atmosphere. The solution was purged with argon for 5 minutes and bis(tri-tert-butylphosphine)palladium(0) (CAS 53199-31-8) (16.7 mg, 32.7 µmol) was added. The solution was purged again with argon and the reaction was heated at 80° C. for 3 h. Afterwards the mixture was filtered over Celite, the solvent was removed under reduced pressure and the crude was purified by chromatography on silica gel (Biotage, hexane/ethyl acetate) to yield 150 mg (44% yield).

LC-MS (Method B): $R_t$=1.17 min; MS (ESIpos): m/z=525 [M+H]$^+$2-(2-Chlorophenyl)-N-(3-{[(dimethylamino)methylidene]sulfamoyl}-4-[4-(trifluoromethyl)-pyridin-2-yl]phenyl)acetamide (50.0 mg, 95.2 µmol) was dissolved in methanol (1.2 ml) and treated with 32% aqueous sodium hydroxide solution (200 µl) at 80° C. until completion of the reaction. The solvent was removed under reduced pressure and the crude was purified by HPLC (Chromatorex C-18 10 µm, 125×30 mm, acetonitrile/water+0.2% aqueous ammonia (32%)) to yield the title compound (9.90 mg, 95% purity, 21% yield).

LC-MS (Method B): $R_t$=1.17 min; MS (ESIpos): m/z=470 [M+H]$^+$ $^1$H-NMR (400 MHz, DMSO-d$_6$) δ [ppm]=3.91 (s, 2H), 6.90-7.22 (s, 1H), 7.25-7.42 (m, 3H), 7.44-7.53 (m, 2H), 7.61 (d, 1H), 7.78 (d, 1H), 7.97 (dd, 1H), 8.10 (s, 1H), 8.35 (s, 1H), 8.93 (d, 1H), 10.73 (s, 1H).

Example 319

2-(2-Chlorophenyl)-N-[4-(5-chloropyridin-2-yl)-3-sulfamoylphenyl]acetamide

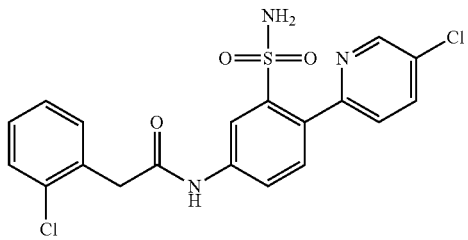 [SMILES: NS(=O)(=O)c1cc(NC(=O)Cc2ccccc2Cl)ccc1-c1ccc(Cl)cn1]

To the solution containing the boronic ester intermediate 2-(2-chlorophenyl)-N-[3-{[(dimethylamino)methylidene]sulfamoyl}-4-(4,4,5,5-tetramethyl-1,3,2-dioxaborolan-2-yl)phenyl]acetamide (300 mg, 594 µmol), 2-bromo-5-chloropyridine (252 mg, 1.31 mmol) and potassium fluoride (76.0 mg, 1.31 mmol) were added under argon atmosphere. The solution was purged with argon for 5 minutes and bis(tri-tert-butylphosphine)palladium(0) (CAS 53199-31-8) (16.7 mg, 32.7 µmol) was added. The solution was purged again with argon and the reaction was heated at 80° C. for 3 h. Afterwards the mixture was filtered over Celite, the solvent was removed under reduced pressure and the crude was purified by chromatography on silica gel (Biotage, hexane/ethyl acetate) to yield 100 mg (31% yield).

LC-MS (Method B): $R_t$=1.11 min; MS (ESIneg): m/z=489 [M−H]$^+$2-(2-Chlorophenyl)-N-[4-(5-chloropyridin-2-yl)-3-{[(dimethylamino)methylidene]sulfamoyl}-phenyl]acetamide (68.8 mg, 140 µmol) was dissolved in methanol (0.6 ml) and treated with 32% aqueous sodium hydroxide solution (200 µl) at room temperature for 1 h followed by stirring at 80° C. until completion of the reaction. The solvent was removed under reduced pressure and the crude was purified by HPLC (Chromatorex C-18 10 µm, 125×30 mm, acetonitrile/water+0.2% aqueous ammonia (32%) then Waters XBrigde C18 5µ 100×30 mm, acetonitrile/water+0.2% aqueous ammonia (32%)) to yield the title compound (7.20 mg, 93% purity, 11% yield).

LC-MS (Method B): $R_t$=1.13 min; MS (ESIneg): m/z=434 [M−H]$^+$ $^1$H-NMR (400 MHz, DMSO-d$_6$) δ [ppm]=3.91 (s, 2H), 7.26-7.38 (m, 2H), 7.39-7.51 (m, 4H), 7.56 (d, 1H), 7.65 (d, 1H), 7.98 (dd, 1H), 8.03-8.15 (m, 1H), 8.36 (d, 1H), 8.73 (d, 1H), 10.74 (s, 1H).

Example 320

2-(2-Chlorophenyl)-N-[4-(1,2-dimethyl-1H-imidazol-4-yl)-3-sulfamoylphenyl]acetamide

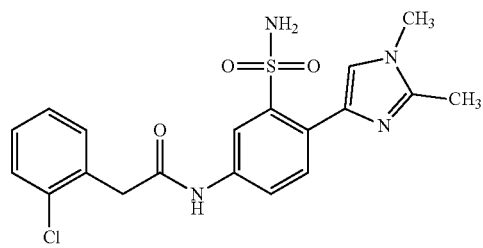 [SMILES: Cc1nc(-c2ccc(NC(=O)Cc3ccccc3Cl)cc2S(N)(=O)=O)cn1C]

To the solution containing the boronic ester intermediate 2-(2-chlorophenyl)-N-[3-{[(dimethylamino)methylidene]sulfamoyl}-4-(4,4,5,5-tetramethyl-1,3,2-dioxaborolan-2-yl)phenyl]acetamide (100 mg, 198 µmol), 4-bromo-1,2-dimethyl-1H-imidazole (76.3 mg, 436 µmol) and potassium fluoride (25.3 mg, 436 µmol) were added under argon atmosphere. The solution was purged with argon for 5 minutes and bis(triphenylphosphine)palladium(II) dichloride (CAS 13965-03-2) (7.67 mg, 10.9 µmol) was added. The solution was purged again with argon and the reaction was heated at 80° C. for 2 h. Afterwards the mixture was filtered over Celite, the solvent was removed under reduced pressure and the crude was purified by chromatography on silica gel (Biotage, hexane/ethyl acetate) to yield 11.6 mg (11% yield).

LC-MS (Method A): $R_t$=0.8 min; MS (ESInes): m/z=472 [M−H]$^+$ 2-(2-Chlorophenyl)-N-[3-{[(dimethylamino)methylidene]sulfamoyl}-4-(1,2-dimethyl-1H-imidazol-4-yl)phenyl]acetamide (11.6 mg, 24.5 µmol) was dissolved in ammonia in methanol (1.2 ml, 7M, 10 eq) and stirred at room temperature over night. Afterwards the solvent was removed under reduced pressure and the crude was purified by HPLC chromatography (Chromatorex C-18 10 µm, 125×30 mm, acetonitrile/water+0.2% aqueous ammonia (32%)) to yield the title compound (1.80 mg, 95% purity, 17% yield).

LC-MS (Method B): $R_t$=0.99 min; MS (ESIpos): m/z=419 [M+H]$^+$ $^1$H-NMR (400 MHz, DMSO-d$_6$) δ [ppm]=2.34 (s, 3H), 3.61 (s, 3H), 3.87 (s, 2H), 7.27-7.36 (m, 2H), 7.38 (s, 1H), 7.40-7.55 (m, 3H), 7.87 (dd, 1H), 8.23 (d, 1H), 8.31 (s, 2H), 10.57 (s, 1H).

Example 321

N-{6-[1-(Difluoromethyl)-1H-pyrazol-4-yl]-5-sulfamoylpyridin-3-yl}-2-(2-fluorophenyl)acetamide

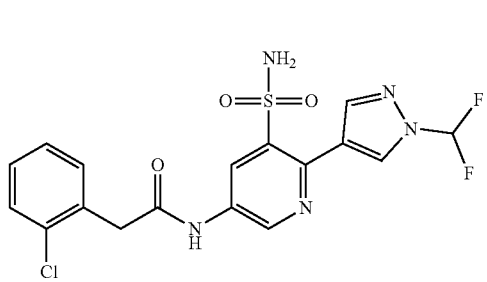 [SMILES: NS(=O)(=O)c1cc(NC(=O)Cc2ccccc2Cl)cnc1-c1cnn(C(F)F)c1]

5-Amino-2-[1-(difluoromethyl)-1H-pyrazol-4-yl]-N-[(dimethylamino)methylidene]pyridine-3-sulfonamide (400 mg, 1.16 mmol) was dissolved in DMF (10 ml) and (2-fluorophenyl)acetic acid (179 mg, 1.16 mmol) was added followed by the addition of N,N-diisopropylethylamine (1.0 ml, 5.8 mmol) and HATU (530 mg, 1.39 mmol). The reaction was stirred at room temperature for 2 h. The solvent was removed under reduced pressure and ethyl acetate and water were added. The phases were separated and the aqueous phase was washed with ethyl acetate. The combined organic phases were dried over Whatman filter and the solvent was removed under reduced pressure. The crude was purified by HPLC (Chromatorex C-18 10 µm, 125×30 mm, acetonitrile/water+0.2% aqueous ammonia (32%)) to yield 30.0 mg (5% yield).

LC-MS (Method B): $R_t$ =0.99 min; MS (ESIpos): m/z=481 [M+H]$^+$

N-(6-[1-(Difluoromethyl)-1H-pyrazol-4-yl]-5-{[(dimethylamino)methylidene]sulfamoyl}-pyridin-3-yl)-2-(2-fluorophenyl)acetamide (30.0 mg, 62.4 µmol) was dissolved in ammonia in methanol (10 ml, 7 M) and stirred at room temperature. Afterwards the solvent was removed under reduced pressure and the crude was purified by HPLC (Chromatorex C-18 µm, 125×30 mm, acetonitrile/water+0.2% aqueous ammonia (32%)) to yield the title compound (10.1 mg, 99% purity, 38% yield).

LC-MS (Method B): $R_t$=0.66 min; MS (ESIpos): m/z=426 [M+H]$^+$ $^1$H-NMR (400 MHz, DMSO-d$_6$) δ [ppm]=3.83 (s, 2H), 7.15-7.24 (m, 2H), 7.31-7.38 (m, 1H), 7.42 (td, 1H), 7.71-8.07 (m, 3H), 8.29 (s, 1H), 8.70 (s, 1H), 8.78 (d, 1H), 8.93 (d, 1H), 10.86 (s, 1H).

Example 322

2-(2-Chlorophenyl)-N-{4-[5-(pyrrolidin-1-yl)pyridin-3-yl]-3-sulfamoylphenyl}acetamide

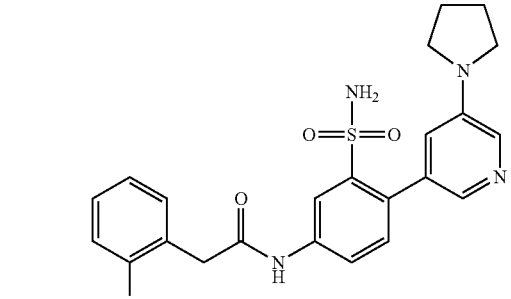

N-(4-Bromo-3-{[(dimethylamino)methylidene]sulfamoyl}phenyl)-2-(2-chlorophenyl)-acetamide (250 mg, 545 µmol) and [5-(pyrrolidin-1-yl)pyridin-3-yl]boronic acid (209 mg, 1.09 mmol) were dissolved in n-propanol (8.1 ml) and bis(triphenylphosphine)palladium(II) dichloride (CAS 13965-03-2) (19.2 mg, 27.2 µmol), triphenylphosphine (7.16 mg, 27 µmol) and potassium fluoride (7.91 mg, 136 µmol) were added. The solution was purged with argon for 5 minutes and aqueous potassium phosphate (540 µl, 2.0 M, 1.1 mmol) was added. The reaction was heated at 100° C. for 3 h in the microwave. Afterwards the mixture was filtered over Celite, the solvent was removed under reduced pressure and the crude was used without further purification in the next step.

LC-MS (Method B): $R_t$=1.16 min; MS (ESIpos): m/z=526 [M+H]$^+$ 2-(2-Chlorophenyl)-N-(3-{[(dimethylamino)methylidene]sulfamoyl}-4-[5-(pyrrolidin-1-yl)-pyridin-3-yl]phenyl)acetamide (190 mg, 361 µmol) was dissolved in methanol (1.5 ml) and treated with 32% aqueous sodium hydroxide solution (200 µl, 3.6 mmol) for 1 h at room temperature followed by stirring at 80° C. until completion of the reaction. The solvent was removed under reduced pressure and the crude was purified by HPLC (Chromatorex C-18 µm, 125×30 mm, acetonitrile/water+0.2% aqueous ammonia (32%)) to yield the title compound (79.1 mg, 95% purity, 44% yield over 2 steps).

LC-MS (Method B): $R_t$=1.08 min; MS (ESIpos): m/z=417 [M+H]$^+$ $^1$H-NMR (400 MHz, DMSO-d$_6$): δ [ppm]=1.87-2.06 (m, 4H), 3.22-3.30 (m, 4H), 3.90 (s, 2H), 6.86-6.97 (m, 1H), 7.20 (s, 2H), 7.27-7.40 (m, 3H), 7.43-7.52 (m, 2H), 7.80 (d, 1H), 7.83 (dd, 1H), 7.90 (d, 1H), 8.37 (d, 1H), 10.65 (s, 1H).

Example 323

2-(2-Chlorophenyl)-N-[4-(1-cyclopropyl-1H-pyrazol-4-yl)-3-sulfamoylphenyl]-2-hydroxyethanamide

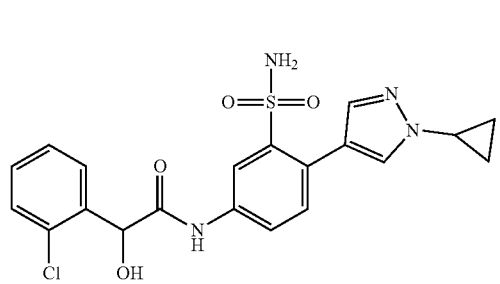 [SMILES: NS(=O)(=O)c1cc(NC(=O)C(O)c2ccccc2Cl)ccc1-c1cnn(C2CC2)c1]

N-(4-Bromo-3-{[(dimethylamino)methylidene]sulfamoyl}phenyl)-2-(2-chlorophenyl)-acetamide (1.45 g, 3.16 mmol), 1-cyclopropyl-4-(4,4,5,5-tetramethyl-1,3,2-dioxaborolan-2-yl)-1H-pyrazole (740 mg, 3.16 mmol), bis(triphenylphosphine)palladium(II) dichloride (CAS 13965-03-2) (111 mg, 158 μmol) and triphenylphosphine (41.5 mg, 158 μmol) were dissolved in n-propanol (40 ml) and the solution was purged with argon for 5 minutes. Afterwards, aqueous potassium carbonate solution (9.5 ml, 1.0 M, 9.5 mmol) was added and the reaction mixture was stirred for 1 h at 80° C. Afterwards, the solvent was removed under reduced pressure and ethyl acetate and water were added. The phases were separated and the aqueous phase was washed with ethyl acetate three times. The combined organic layers were dried over Whatman filter and the solvent was removed under reduced pressure. The crude was purified by chromatography on silica gel (Biotage Isolera, gradient hexane/ethyl acetate) to yield 310 mg (20% yield).

This intermediate amide (310 mg, 638 μmol) was dissolved in methanol (30 ml) and treated with 25% aqueous ammonia solution (30 ml). The reaction was stirred at room temperature for 16 h. The solvent was removed under reduced pressure and the crude was purified by HPLC (Chromatorex C-18 10 μm, 125×30 mm, acetonitrile/water+0.1% formic acid) to yield the title compound (43.3 mg, 99% purity, 15% yield).

LC-MS (Method B): Rt=0.88 min; MS (ESIpos): m/z=447 [M+H]$^+$ $^1$H-NMR (400 MHz, DMSO-d$_6$) δ [ppm]=0.98 (dd, 2H), 1.04-1.14 (m, 2H), 3.67-3.80 (m, 1H), 5.51 (d, 1H), 6.69 (d, 1H), 7.18 (s, 2H), 7.30-7.49 (m, 4H), 7.58 (s, 1H), 7.68 (d, 1H), 7.87 (d, 1H), 8.05 (s, 1H), 8.51 (s, 1H), 10.42 (s, 1H).

Example 324

2-(2-Chlorophenyl)-N-{4-[1-(difluoromethyl)-1H-pyrazol-4-yl]-3-sulfamoylphenyl}-2-hydroxyethanamide

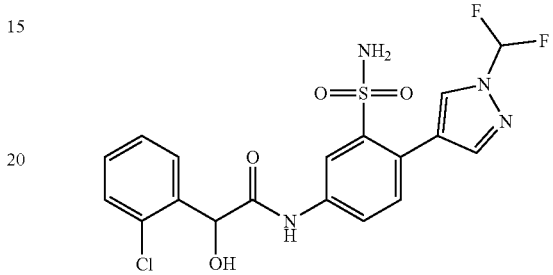

This compound was isolated as a side product formed during the Suzuki reaction (observed when potassium carbonate as base was used): N-(4-Bromo-3-{[(dimethylamino)methylidene]sulfamoyl}phenyl)-2-(2-chlorophenyl)-acetamide (1.10 g, 2.40 mmol), 1-(difluoromethyl)-4-(4,4,5,5-tetramethyl-1,3,2-dioxaborolan-2-yl)-1H-pyrazole (585 mg, 2.40 mmol), bis(triphenylphosphine)palladium(II) dichloride (CAS 13965-03-2) (84.4 mg, 120 μmol) and triphenylphosphine (31.4 mg, 120 μmol) were dissolved in n-propanol (40 ml) and the solution was purged with argon for 5 minutes. Afterwards, aqueous potassium carbonate (7.2 ml, 1.0 M, 7.2 mmol) was added and the reaction mixture was stirred for 1 h at 100° C. Afterwards, the solvent was removed under reduced pressure and ethyl acetate and water were added. The phases were separated and the aqueous phase was washed with ethyl acetate three times. The combined organic layers were dried over Whatman filter and the solvent was removed under reduced pressure. The crude was purified by chromatography on silica gel (Biotage Isolera, gradient hexane/ethyl acetate) to yield 460 mg (39% yield).

This intermediate amide (460 mg, 928 μmol) was dissolved in methanol (40 ml) and treated with 25% aqueous ammonia solution (40 ml). The reaction was stirred at room temperature for 16 h. The solvent was removed under reduced pressure and the crude was purified by HPLC (Chromatorex C-18 10 μm, 125×30 mm, acetonitrile/water+0.1% formic acid) to yield the title compound (4.7 mg, 95% purity, 1% yield).

LC-MS (Method B): Rt=0.86 min; MS (ESIpos): m/z=457 [M+H]$^+$ $^1$H-NMR (400 MHz, DMSO-d$_6$) δ [ppm]=5.52 (d, 1H), 6.72 (d, 1H), 7.30-7.44 (m, 4H), 7.44-7.53 (m, 2H), 7.60 (dd, 1H), 7.67-8.06 (m, 3H), 8.44 (s, 1H), 8.56 (d, 1H), 10.50 (s, 1H).

Example 325

2-(2-Chlorophenyl)-N-[4-(5-chloropyridin-3-yl)-3-sulfamoylphenyl]acetamide

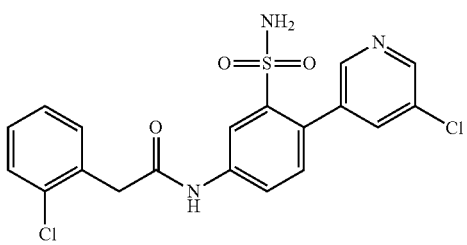 [SMILES: NS(=O)(=O)c1cc(NC(=O)Cc2ccccc2Cl)ccc1-c1cncc(Cl)c1]

2-Chloro-N-(2,4-dimethoxybenzyl)-5-nitrobenzenesulfonamide (1.00 g, 2.59 mmol) and (5-chloropyridin-3-yl)boronic acid (814 mg, 5.17 mmol) were dissolved in DMF (10 ml) followed by addition of bis(triphenylphosphine)palladium(II) dichloride (CAS 13965-03-2) (273 mg, 388 µmol) and aq. potassium carbonate (6.2 ml, 1.0 M, 6.2 mmol). The reaction was heated for 1 h at 120° C. in the microwave. The reaction mixture was filtered over Celite, the solvent was removed under reduced pressure and the crude was purified by chromatography on silica gel (Biotage, hexane/ethyl acetate 1/1) to yield 700 mg (58% yield).

LC-MS (Method A): Rt=1.20 min; MS (ESIpos): m/z=396 [M+H]$^+$

Iron (421 mg, 7.54 mmol) and ammonium acetate (404 mg, 7.54 mmol) were suspended in water (20 ml). 2-(5-Chloropyridin-3-yl)-N-(2,4-dimethoxybenzyl)-5-nitrobenzenesulfonamide (700 mg, 1.51 mmol) was dissolved in THF/methanol (10 ml/10 ml) and added to the aqueous suspension. The reaction mixture was heated for 2 h at 80° C. and after completion of the reaction was filtered over Celite. The solvent was removed under reduced pressure and the crude was dissolved in ethyl acetate and water. The phases were separated and the aqueous phase was washed with ethyl acetate. The combined organic phases were dried over Whatman filter and the solvent was removed under reduced pressure. The crude was used in the next step without further purification.

5-Amino-2-(5-chloropyridin-3-yl)-N-(2,4-dimethoxybenzyl)benzenesulfonamide (690 mg, 1.59 mmol) was dissolved in dichloromethane (9.4 ml) and the solution was cooled to 0° C. (2-chlorophenyl)acetyl chloride (110 µl, 800 µmol) and triethylamine (1.3 ml, 9.5 mmol) were added and stirring was continued for 4 h at 0° C. (2-Chlorophenyl)acetyl chloride (110 µl, 800 µmol) was added and stirring was continued at room temperature for 18 h. Afterwards, water was added and the phases were separated. The combined organic phases were dried over Whatman filter and the solvent was removed under reduced pressure. The crude was purified via column chromatography on silica gel (Biotage, 10% gradient of ethyl acetate in hexane) to yield 179 mg (19% yield).

LC-MS (Method B): Rt=1.32 min; MS (ESIpos): m/z=586 [M+H]$^+$ 2-(2-Chlorophenyl)-N-{4-(5-chloropyridin-3-yl)-3-[(2,4-dimethoxybenzyl)sulfamoyl]-phenyl}acetamide (179 mg, 305 µmol) was dissolved in dichloromethane (3.9 ml) and trifluoroacetic acid (3.9 ml, 50 mmol) was added and stirring was continued at room temperature until completion of the reaction. The solvent was removed under reduced pressure and the crude was dissolved in ethyl acetate and washed with water. The phases were separated and the aqueous phase was extracted with ethyl acetate. The combined organic phases were dried over Whatman filter and the solvent was removed under reduced pressure. The crude was purified by HPLC chromatography (Chromatorex C-18 10 µm, 125×30 mm, acetonitrile/water+0.2% aqueous ammonia (32%)) to yield the title compound (12.0 mg, 95% purity, 9% yield).

LC-MS (Method A): Rt=1.07 min; MS (ESIpos): m/z=436 [M+H]$^+$ $^1$H-NMR (400 MHz, DMSO-d$_6$) δ [ppm]=3.90 (s, 2H), 7.27-7.38 (m, 3H), 7.41 (s, 2H), 7.43-7.48 (m, 2H), 7.82-7.94 (m, 2H), 8.38 (d, 1H), 8.48 (d, 1H), 8.61 (d, 1H), 10.70 (s, 1H).

Example 326

2-(2-Chlorophenyl)-N-{4-[1-(difluoromethyl)-1H-pyrazol-4-yl]-3-sulfamoylphenyl}acetamide

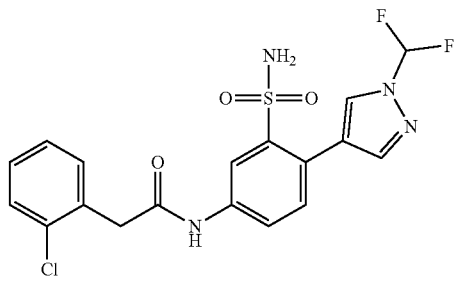 [SMILES: NS(=O)(=O)c1cc(NC(=O)Cc2ccccc2Cl)ccc1-c1cnn(C(F)F)c1]

N-(4-Bromo-3-{[(dimethylamino)methylidene]sulfamoyl}phenyl)-2-(2-chlorophenyl)acetamide (1.50 g, 3.27 mmol), 1-(difluoromethyl)-4-(4,4,5,5-tetramethyl-1,3,2-dioxaborolan-2-yl)-1H-pyrazole (958 mg, 3.92 mmol) and potassium fluoride (418 mg, 7.19 mmol) were dissolved in DMF (36 ml). The mixture was purged with argon for 5 minutes, followed by addition of bis(tri-tert-butylphosphine)palladium(0) (CAS 53199-31-8) (83.5 mg, 163 µmol). The reaction was heated for 1 h at 100° C., filtered over a glass fibre filter and the procedure was repeated. Afterwards, the solvent was removed under reduced pressure and ethyl acetate and water were added. The phases were separated and the aqueous phase was washed with ethyl acetate. The combined organic phases were dried over Whatman filter and the solvent was removed under reduced pressure. The crude was used in the next step without further purification (2.78 g).

2-(2-Chlorophenyl)-N-(4-[1-(difluoromethyl)-1H-pyrazol-4-yl]-3-{[(dimethylamino)-methylidene]sulfamoyl}phenyl)acetamide (2.78 g, 5.61 mmol) was dissolved in methanol (90 ml) and treated with 25% aqueous ammonia solution (90 ml) at room temperature until completion of the reaction. The solvent was removed under reduced pressure and the crude was purified by chromatography on silica gel (Biotage, 8% ethanol in dichloromethane) and subsequently by HPLC (Chromatorex C-18 10 µm, 125×30 mm, acetonitrile/water+0.2% aqueous ammonia (32%)) to yield the title compound (1.09 g, 99% purity, 34% over 2 steps).

LC-MS (Method B): Rt=0.94 min; MS (ESIpos): m/z=441 [M+H]$^+$ $^1$H-NMR (400 MHz, DMSO-d$_6$) δ [ppm]=3.89 (s, 2H), 7.31-7.35 (m, 2H), 7.41 (s, 2H), 7.43-7.50 (m, 3H), 7.69-8.00 (m, 2H), 8.02 (m, 1H), 8.36 (d, 1H), 8.43 (m, 1H), 10.65 (s, 1H).

Example 327

2-(2-Chlorophenyl)-N-[4-(5-fluoropyridin-3-yl)-3-sulfamoylphenyl]acetamide

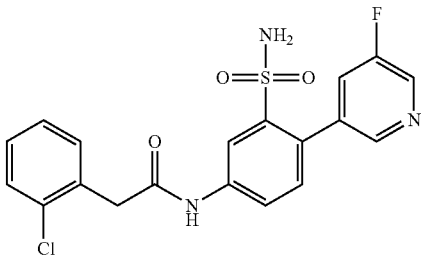 [SMILES: NS(=O)(=O)c1cc(NC(=O)Cc2ccccc2Cl)ccc1-c1cncc(F)c1]

2-Bromo-N-[(dimethylamino)methylidene]-5-nitrobenzenesulfonamide (400 mg, 1.19 mmol) and (5-fluoropyridin-3-yl)boronic acid (335 mg, 2.38 mmol) were dissolved in n-propanol (110 ml, 1.5 mol) and bis(triphenylphosphine)palladium(II) dichloride (CAS 13965-03-2) (41.9 mg, 59.5 µmol), triphenylphosphine (21.6 mg, 59.5 µmol) and aq. potassium carbonate solution (1.8 ml, 2.0 M, 3.6 mmol) were added. The reaction was heated at 120° C. for 1 h (4 bar/40 W). The reaction mixture was filtered over Celite and the solvent was removed under reduced pressure The crude was co-distilled with THF and used without further purification in the next step.

2-(5-Fluoropyridin-3-yl)-5-nitrobenzenesulfonamide (400 mg, 1.35 mmol) was dissolved in methanol (37 ml) and the flask was flushed with nitrogen. Platinum on charcoal (5% loading, 71.4 mg, 366 µmol) was added and the flask was evacuated and subsequently flushed with hydrogen (1 bar). Stirring was continued at room temperature until completion of the reaction. The reaction mixture was filtered over Celite and the solvent was removed under reduced pressure. The crude was used without further purification in the next step (400 mg). 5-Amino-2-(5-fluoropyridin-3-yl)benzenesulfonamide (200 mg, 748 µmol) was dissolved in DMF (5.3 ml) and (2-chlorophenyl)acetic acid (153 mg, 898 µmol) was added followed by the addition of N,N-diisopropylethylamine (620 µl, 3.7 mmol) and HATU (455 mg, 1.20 mmol). The reaction was stirred for 18 h at 50° C. Afterwards, dichloromethane and water were added and the passes were separated. The aqueous phase was washed with dichloromethane and the combined organic phases were dried over Whatman filter and the solvent was removed under reduced pressure. The crude was purified by HPLC (Waters XBrigde C18 5µ 100×30 mm, acetonitrile/water+0.2% aqueous ammonia (32%) then Waters XBrigde C18 5µ 100×30 mm, acetonitrile/water+0.1% formic acid) to yield the title compound (4.70 mg, 95% purity, 1% yield over 3 steps).

LC-MS (Method B): Rt=0.93 min; MS (ESIpos): m/z=420 [M+H]$^+$ $^1$H-NMR (400 MHz, DMSO-d$_6$) δ [ppm]=3.90 (s, 2H), 7.31-7.37 (m, 3H), 7.40 (s, 2H), 7.42-7.48 (m, 2H), 7.68-7.75 (m, 1H), 7.87 (dd, 1H), 8.34-8.44 (m, 2H), 8.57 (d, 1H), 10.71 (s, 1H).

Example 328

2-(2-Chlorophenyl)-N-{4-[1-(2-methylpropyl)-1H-pyrazol-4-yl]-3-sulfamoylphenyl}acetamide

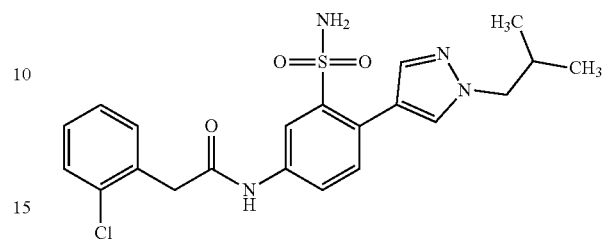

N-(4-Bromo-3-{[(dimethylamino)methylidene]sulfamoyl}phenyl)-2-(2-chlorophenyl)acetamide (200 mg, 436 µmol) and 1-(2-methylpropyl)-4-(4,4,5,5-tetramethyl-1,3,2-dioxaborolan-2-yl)-1H-pyrazole (220 µl, 870 µmol) were dissolved in n-propanol (5.9 ml) and bis(triphenylphosphine)palladium(II) dichloride (CAS 13965-03-2) (15.3 mg, 21.8 µmol), triphenylphosphine (5.72 mg, 21.8 µmol) and aq. potassium carbonate solution (540 µl, 2.0 M, 1.1 mmol) were added. The reaction was purged with argon for 5 minutes and afterwards heated at 800C for 3 h. Then, the mixture was filtered over Celite and the solvent was removed under reduced pressure.

The crude was dissolved in methanol (51 ml) and treated with 32% aqueous sodium hydroxide (100 ml) at 40° C. until completion of the reaction. The reaction mixture was neutralized by addition of 2N HCl. The solvent was removed under reduced pressure and dichloromethane and water were added. The phases were separated and the aqueous phase was washed with dichloromethane. The combined organic phases were dried over Whatman filter and the solvent was removed under reduced pressure. The crude was purified by HPLC (Chromatorex C-18 10 µm, 125×30 mm, acetonitrile/water+0.2% aqueous ammonia (32%)) to yield the title compound (10.9 mg, 98% purity, 5% yield over 3 steps).

LC-MS (Method B): Rt=1.09 min; MS (ESIneg): m/z=445 [M−H]$^-$ $^1$H-NMR (400 MHz, DMSO-de) δ [ppm]=0.86 (d, 6H), 2.01-2.22 (m, 1H), 3.87 (s, 2H), 3.92 (d, 2H), 7.16 (s, 2H), 7.27-7.38 (m, 2H), 7.38-7.51 (m, 3H), 7.64-7.73 (m, 1H), 7.78-7.83 (m, 1H), 7.95-8.00 (m, 1H), 8.31 (d, 1H), 10.57 (s, 1H).

Example 329

2-(2-Chlorophenyl)-N-[4-(1-cyclopentyl-1H-pyrazol-4-yl)-3-sulfamoylphenyl]acetamide

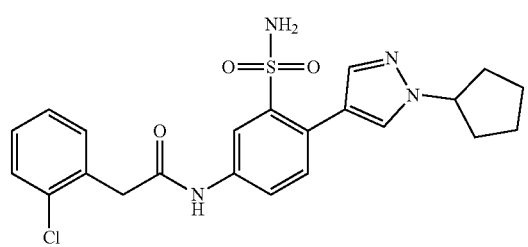 [SMILES: NS(=O)(=O)c1cc(NC(=O)Cc2ccccc2Cl)ccc1-c1cnn(C2CCCC2)c1]

N-(4-Bromo-3-{[(dimethylamino)methylidene]sulfamoyl}phenyl)-2-(2-chlorophenyl)acetamide (200 mg, 436 µmol) and 1-cyclopentyl-4-(4,4,5,5-tetramethyl-1,3,2-dioxaborolan-2-yl)-1H-pyrazole (229 mg, 872 µmol) were dissolved in n-propanol (5.9 ml) and bis(triphenylphosphine)palladium(II) dichloride (CAS 13965-03-2) (15.3 mg, 21.8 µmol), triphenylphosphine (5.72 mg, 21.8 µmol) and aq. potassium carbonate solution (540 µl, 2M, 1.1 mmol) were added. The reaction mixture was purged with argon for 5 minutes and subsequently stirred for 2 h at 80° C. Afterwards the mixture was filtered over Celite, the solvent was removed under reduced pressure and the crude was used without further purification in the next step (250 mg).

2-(2-Chlorophenyl)-N-[4-(1-cyclopentyl-1H-pyrazol-4-yl)-3-{[(dimethylamino)methylidene]-sulfamoyl}phenyl]acetamide (250 mg, 486 µmol) was dissolved in methanol (5.0 ml) and treated with 32% aqueous sodium hydroxide solution (300 µl) at 65° C. until completion of the reaction. Dichloromethane and water were added and the phases were separated. The combined organic phases were dried over Whatman filter and the solvent was removed under reduced pressure and the crude was purified by HPLC (Waters XBrigde C18 5µ 100×30 mm, acetonitrile/water+0.2% aqueous ammonia (32%) then Chromatorex C-18 µm, 125×30 mm, acetonitrile/water+0.2% aqueous ammonia (32%)) to yield the title compound (7.80 mg, 98% purity, 3% yield).

LC-MS (Method B): Rt=1.12 min; MS (ESIpos): m/z=459 [M+H]$^+$ $^1$H-NMR (400 MHz, DMSO-d$_6$) δ [ppm]=1.56-1.71 (m, 2H), 1.74-1.89 (m, 2H), 1.90-2.03 (m, 2H), 2.03-2.17 (m, 2H), 3.87 (s, 2H), 4.63-4.77 (m, 1H), 7.17 (s, 2H), 7.27-7.36 (m, 2H), 7.39-7.50 (m, 3H), 7.70 (s, 1H), 7.77-7.85 (m, 1H), 8.03 (s, 1H), 8.31 (d, 1H), 10.56 (s, 1H).

Example 330

2-(2-Chlorophenyl)-N-[2'-fluoro-3'-(propan-2-yloxy)-2-sulfamoylbiphenyl-4-yl]-acetamide

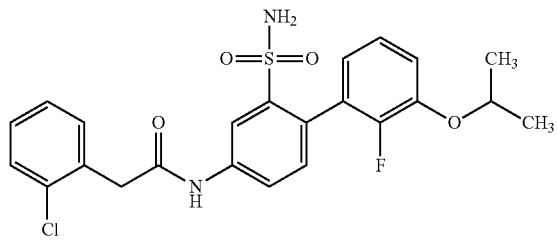 [SMILES: CC(C)Oc1cccc(-c2ccc(NC(=O)Cc3ccccc3Cl)cc2S(N)(=O)=O)c1F]

N-(4-Bromo-3-{[(dimethylamino)methylidene]sulfamoyl}phenyl)-2-(2-chlorophenyl)-acetamide (250 mg, 545 µmol) and [2-fluoro-3-(propan-2-yloxy)phenyl]boronic acid (108 mg, 545 µmol) were dissolved in n-propanol (10 ml) and bis(triphenylphosphine)palladium(II) dichloride (CAS 13965-03-2) (19.2 mg, 27.2 µmol) and triphenylphosphine (7.15 mg, 27.2 µmol) were added. The reaction mixture was purged with argon for 5 minutes and aq. potassium carbonate solution (1.6 ml, 1.0 M, 1.6 mmol) was added. The reaction was heated at 100° C. for 2 h. Afterwards the mixture was filtered over Celite, the solvent was removed under reduced pressure and the crude was used without further purification in the next step (630 mg).

2-(2-Chlorophenyl)-N-[2-{[(dimethylamino)methylidene]sulfamoyl}-2'-fluoro-3'-(propan-2-yloxy)biphenyl-4-yl]acetamide (630 mg, 1.18 mmol) was dissolved in methanol (25 ml) and treated with 33% aqueous ammonia solution (25 ml) at room temperature until completion of the reaction. The solvent was removed under reduced pressure and the crude was purified by HPLC (Chromatorex C-18 10 µm, 125×30 mm, acetonitrile/water+0.2% aqueous ammonia (32%)) to yield the final product (37.6 mg, 95% purity, 6% yield over 2 steps).

LC-MS (Method B): Rt=1.24 min; MS (ESIpos): m/z=477 [M+H]$^+$ $^1$H-NMR (400 MHz, DMSO-d$_6$): δ [ppm]=1.24-1.34 (m, 6H), 3.89 (s, 2H), 4.54-4.66 (m, 1H), 6.77-6.90 (m, 1H), 7.00-7.11 (m, 1H), 7.17 (m, 3H), 7.22-7.39 (m, 3H), 7.43-7.52 (m, 2H), 7.81 (dd, 1H), 8.34 (d, 1H), 10.65 (s, 1H).

Example 331

2-(2-Chlorophenyl)-N-{3-sulfamoyl-4-[5-(trifluoromethyl)pyridin-3-yl]phenyl}-acetamide

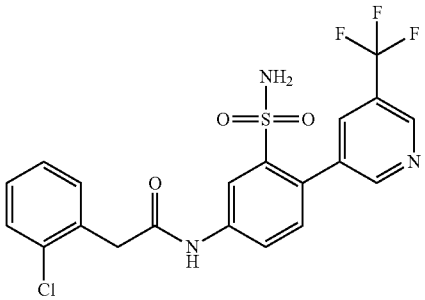 [SMILES: NS(=O)(=O)c1cc(NC(=O)Cc2ccccc2Cl)ccc1-c1cncc(C(F)(F)F)c1]

N-(4-Bromo-3-{[(dimethylamino)methylidene]sulfamoyl}phenyl)-2-(2-chlorophenyl)acetamide (500 mg, 1.09 mmol) and [5-(trifluoromethyl)pyridin-3-yl]boronic acid (520 mg, 2.72 mmol) were dissolved in n-propanol (15 ml) and bis(triphenylphosphine)palladium(II) dichloride (CAS 13965-03-2) (38.4 mg, 54.5 µmol), triphenylphosphine (14.3 mg, 54.5 µmol), potassium fluoride (23.1 mg, 270 µmol) and aq. potassium carbonate solution (1.4 ml, 2.0 M, 2.7 mmol) were added. The reaction was heated at 100° C. for 1 h in the microwave (1 bar/15 W). Afterwards the mixture was filtered over Celite, the solvent was removed under reduced pressure and the crude was co-distilled with THF and used without further purification in the next step.

2-(2-Chlorophenyl)-N-(3-{[(dimethylamino)methylidene]sulfamoyl}-4-[5-(trifluoromethyl)-pyridin-3-yl]phenyl)acetamide (1.50 g, 2.86 mmol) was dissolved in methanol (29 ml) and treated with 32% aqueous sodium hydroxide (1.6 ml) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by chromatography on silica gel (Biotage, 40% ethyl acetate in hexane) and subsequently by HPLC (Chromatorex C-18 10 µm, 125×30 mm, acetonitrile/water+0.1% formic acid) to yield the title compound (562 mg, 95% purity, 40% yield over 2 steps).

LC-MS (Method A): Rt=1.13 min; MS (ESIneg): m/z=468 [M−H]$^-$

¹H-NMR (400 MHz, DMSO-d₆) δ [ppm]=3.91 (s, 2H), 7.28-7.37 (m, 2H), 7.39 (d, 1H), 7.42-7.51 (m, 4H), 7.88 (dd, 1H), 8.10-8.16 (m, 1H), 8.40 (d, 1H), 8.81 (d, 1H), 8.96 (d, 1H), 10.73 (s, 1H).

Example 332

N-[4-(6-Chloro-5-methoxypyridin-3-yl)-3-sulfamoylphenyl]-2-(2-chlorophenyl)-acetamide

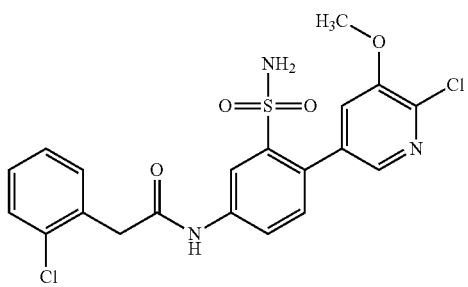 [SMILES: COc1cc(-c2ccc(NC(=O)Cc3ccccc3Cl)cc2S(N)(=O)=O)cnc1Cl]

N-(4-Bromo-3-{[(dimethylamino)methylidene]sulfamoyl}phenyl)-2-(2-chlorophenyl)-acetamide hydrochloride (1:1) (250 mg, 50% purity, 252 µmol) and 2-chloro-3-methoxy-5-(4,4,5,5-tetramethyl-1,3,2-dioxaborolan-2-yl)pyridine (81.6 mg, 303 µmol) were dissolved in DMF (7 ml) and potassium fluoride (32.3 mg, 555 µmol) was added. The solution was purged with argon for 5 minutes and bis(tri-tert-butylphosphine)palladium(0) (CAS 53199-31-8) (6.45 mg, 12.6 µmol) was added. The solution was purged again with argon for 1 minute and then was heated at 100° C. for 18 h. Afterwards the mixture was filtered over Celite, the solvent was removed under reduced pressure and the crude was co-distilled with THF and used without further purification in the next step (270 mg).

LC-MS (Method B): Rt=1.12 min; MS (ESIpos): m/z=521 [M+H]⁺

N-[4-(6-Chloro-5-methoxypyridin-3-yl)-3-{[(dimethylamino)methylidene]sulfamoyl}phenyl]-2-(2-chlorophenyl)acetamide (270 mg, 259 µmol) was dissolved in methanol (2.7 ml) and treated with 32% aqueous sodium hydroxide (100 µl, 850 µmol) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Chromatorex C-18 10 µm, 125×30 mm, acetonitrile/water+0.2% aqueous ammonia (32%)) to yield the title compound (24.2 mg, 95% purity, 19% yield over 2 steps).

LC-MS (Method B): Rt=1.02 min; MS (ESIpos): m/z=466 [M+H]⁺

¹H-NMR (400 MHz, DMSO-d6): Shift [ppm]=3.86-3.91 (m, 5H), 7.28-7.39 (m, 5H), 7.41-7.47 (m, 2H), 7.54 (d, 1H), 7.86 (dd, 1H), 7.91 (d, 1H), 8.37 (d, 1H), 10.68 (s, 1H).

Example 333

2-(2-Chloro-6-fluorophenyl)-N-[4-(1-cyclopropyl-1H-pyrazol-4-yl)-3-sulfamoylphenyl]acetamide

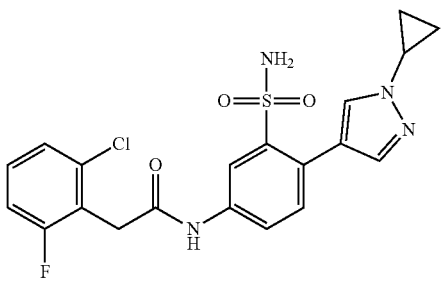 [SMILES: NS(=O)(=O)c1cc(NC(=O)Cc2c(F)cccc2Cl)ccc1-c1cnn(C2CC2)c1]

5-Amino-2-(1-cyclopropyl-1H-pyrazol-4-yl)-N-[(dimethylamino)methylidene]benzenesulfonamide (200 mg, 600 µmol) was dissolved in DMF (10 ml) and (2-chloro-6-fluorophenyl)acetic acid (136 mg, 720 µmol) was added followed by the addition of N,N-diisopropylethylamine (520 µl, 3.0 mmol) and HATU (456 mg, 1.20 mmol). The reaction was heated at 50° C. for 16 h. Afterwards, the solvent was removed under reduced pressure and ethyl acetate and water were added. The phases were separated and the aqueous phase was washed with ethyl acetate. The combined organic phases were dried over Whatman filter and the solvent was removed under reduced pressure. The crude was used in the next step without further purification (750 mg).

2-(2-Chloro-6-fluorophenyl)-N-[4-(1-cyclopropyl-1H-pyrazol-4-yl)-3-{[(dimethylamino)-methylidene]sulfamoyl}phenyl]acetamide (302 mg, 600 µmol) was dissolved in methanol (5.0 ml) and treated with 25% aqueous ammonia solution (10 ml) at room temperature until completion of the reaction. The solvent was removed under reduced pressure and the crude was purified by HPLC (Waters XBrigde C18 5µ 100×30 mm, acetonitrile/water+0.2% aqueous ammonia (32%)) to yield the title compound (21.5 mg, 94% purity, 8% yield over 5 steps).

LC-MS (Method A): Rt=1.03 min; MS (ESIneg): m/z=447 [M−H]⁻

¹H-NMR (400 MHz, DMSO-d₆) δ [ppm]=0.91-1.00 (m, 2H), 1.04-1.12 (m, 2H), 3.66-3.79 (m, 1H), 3.92 (d, 2H), 7.13-7.33 (m, 3H), 7.33-7.46 (m, 3H), 7.63-7.71 (m, 1H), 7.74-7.81 (m, 1H), 8.00-8.08 (m, 1H), 8.31 (d, 1H), 10.66 (s, 1H).

Example 334

2-(2-Chloro-3-fluorophenyl)-N-[4-(1-methyl-1H-pyrazol-4-yl)-3-sulfamoylphenyl]-acetamide

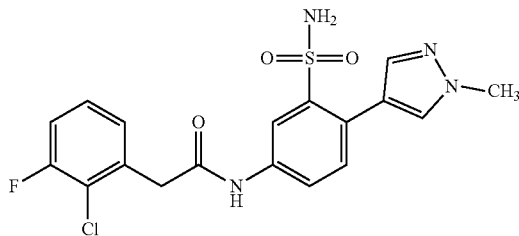 [SMILES: Cn1cc(-c2ccc(NC(=O)Cc3cccc(F)c3Cl)cc2S(N)(=O)=O)cn1]

5-Amino-2-(1-methyl-1H-pyrazol-4-yl)benzenesulfonamide (200 mg, 793 μmol) was dissolved in DMF (6.6 ml) and (2-chloro-3-fluorophenyl)acetic acid (179 mg, 951 μmol) was added followed by the addition of N,N-diisopropylethylamine (690 μl, 4.0 mmol) and HATU (482 mg, 1.27 mmol). The reaction was stirred at 50° C. for 18 h. Afterwards, water and dichloromethane were added. The phases were separated and the aqueous phase was washed with dichloromethane. The combined organic phases were dried over Whatman filter and the solvent was removed under reduced pressure. The crude was purified by HPLC (Waters XBrigde C18 5μ 100×30 mm, acetonitrile/water+0.2% aqueous ammonia (32%)) to yield the title compound (111 mg, 95% purity, 32% yield over 4 steps).

LC-MS (Method B): Rt=0.90 min; MS (ESIneg): m/z=421 [M−H]−

$^1$H-NMR (400 MHz, DMSO-$d_6$) δ [ppm]=3.86 (s, 3H), 3.93 (s, 2H), 7.17 (s, 2H), 7.27-7.45 (m, 4H), 7.64-7.68 (m, 1H), 7.77-7.83 (m, 1H), 7.94-7.98 (m, 1H), 8.31 (d, 1H), 10.60 (s, 1H).

Example 335

N-[4-(1-tert-Butyl-1H-pyrazol-4-yl)-3-sulfamoylphenyl]-2-(2-chlorophenyl)acetamide

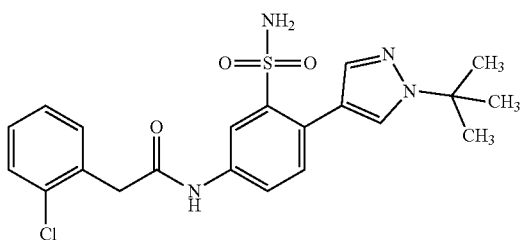 [SMILES: CC(C)(C)n1cc(-c2ccc(NC(=O)Cc3ccccc3Cl)cc2S(N)(=O)=O)cn1]

5-Amino-2-(1-tert-butyl-1H-pyrazol-4-yl)benzenesulfonamide (125 mg, 425 μmol) was dissolved in DMF (3.0 ml) and (2-chlorophenyl)acetic acid (86.9 mg, 510 μmol) was added followed by the addition of N,N-diisopropylethylamine (370 μl, 2.1 mmol) and HATU (258 mg, 679 μmol). The reaction was stirred for 18 h at 50° C. Water and dichloromethane were added and the phases were separated. The aqueous phase was washed with dichloromethane. The combined organic phases were dried over Whatman filter and the solvent was removed under reduced pressure. The crude was purified by HPLC (Waters XBrigde C18 5μ 100×30 mm, acetonitrile/water+0.2% aqueous ammonia (32%) then Waters XBrigde C18 5μ 100×30 mm, methanol/water+0.1% formic acid) to yield the title compound (5.60 mg, 80% purity, 2% yield over 4 steps).

LC-MS (Method B): Rt=1.07 min; MS (ESIneg): m/z=445 [M−H]−

$^1$H-NMR (400 MHz, DMSO-$d_6$) δ [ppm]=1.54 (s, 9H), 3.87 (s, 2H), 7.15 (s, 2H), 7.30-7.39 (m, 2H), 7.39-7.52 (m, 3H), 7.74 (d, 1H), 7.78-7.86 (m, 1H), 8.10 (d, 1H), 8.31 (d, 1H), 10.56 (s, 1H).

Example 336

2-(2-Chlorophenyl)-N-{4-[2-(propan-2-yloxy)pyridin-3-yl]-3-sulfamoylphenyl}acetamide

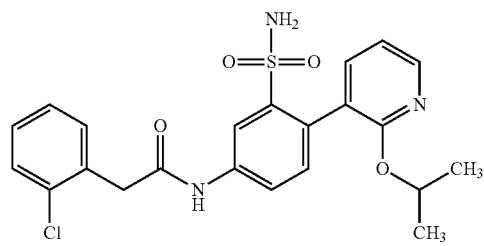 [SMILES: CC(C)Oc1ncccc1-c1ccc(NC(=O)Cc2ccccc2Cl)cc1S(N)(=O)=O]

N-(4-Bromo-3-{[(dimethylamino)methylidene]sulfamoyl}phenyl)-2-(2-chlorophenyl)-acetamide (200 mg, 436 μmol) and [2-(propan-2-yloxy)pyridin-3-yl]boronic acid (78.9 mg, 436 μmol) were dissolved in n-propanol (10 ml) and bis(triphenylphosphine)palladium(II) dichloride (CAS 13965-03-2) (15.3 mg, 21.8 μmol), triphenylphosphine (5.72 mg, 21.8 μmol) were added. The mixture was purged with nitrogen for 5 minutes and aq. potassium carbonate solution (1.3 ml, 1.0 M, 1.3 mmol) was added. The reaction was heated at 100° C. for 1 h. Afterwards the mixture was filtered over Celite, the solvent was removed under reduced pressure and the crude was used without further purification in the next step (590 mg).

2-(2-Chlorophenyl)-N-(3-{[(dimethylamino)methylidene]sulfamoyl}-4-[2-(propan-2-yloxy)-pyridin-3-yl]phenyl)acetamide (590 mg, 1.15 mmol) was dissolved in methanol (51 ml) and treated with 25% aqueous ammonia solution (51 ml) at room temperature until completion of the reaction. The solvent was removed under reduced pressure and the crude was purified by HPLC (Waters XBrigde C18 5μ 100×30 mm, acetonitrile/water+0.2% aqueous ammonia (32%)) to yield the title compound (19.5 mg, 96% purity, 4% yield over 2 steps).

LC-MS (Method B): Rt=1.15 min; MS (ESIneg): m/z=458 [M−H]−

$^1$H-NMR (400 MHz, DMSO-$d_6$) δ [ppm]=1.15 (d, 6H), 3.89 (s, 2H), 5.15-5.28 (m, 1H), 6.86-6.99 (m, 1H), 7.12 (s, 2H), 7.19 (d, 1H), 7.29-7.38 (m, 2H), 7.45-7.57 (m, 3H), 7.75-7.85 (m, 1H), 8.07-8.14 (m, 1H), 8.30 (d, 1H), 10.61 (s, 1H).

Example 337

2-(2-Chloro-3-fluorophenyl)-N-[4-(1-cyclopropyl-1H-pyrazol-4-yl)-3-sulfamoylphenyl]acetamide

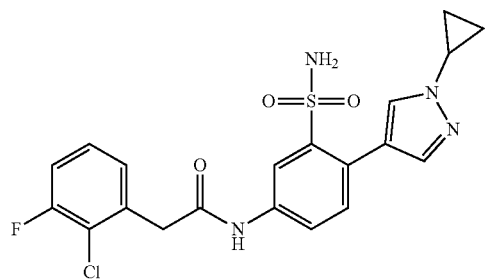 [SMILES: NS(=O)(=O)c1cc(NC(=O)Cc2cccc(F)c2Cl)ccc1-c1cnn(C2CC2)c1]

5-Amino-2-(1-cyclopropyl-1H-pyrazol-4-yl)-N-[(dimethylamino)methylidene]benzenesulfonamide (200 mg, 600 µmol) was dissolved in DMF (10 ml) and (2-chloro-3-fluorophenyl)acetic acid (136 mg, 720 µmol) was added followed by the addition of N,N-diisopropylethylamine (520 µl, 3.0 mmol) and HATU (456 mg, 1.20 mmol). The reaction was stirred at 50° C. for 16 h. Afterwards, ethyl acetate and water were added. The phases were separated and the aqueous phase was washed with ethyl acetate. The combined organic phases were dried over Whatman filter and the solvent was removed under reduced pressure. The crude was used in the next step without further purification (810 mg).

2-(2-Chloro-3-fluorophenyl)-N-[4-(1-cyclopropyl-1H-pyrazol-4-yl)-3-{[(dimethylamino)-methylidene]sulfamoyl}phenyl]acetamide (302 mg, 600 µmol) was dissolved in methanol (5 ml) and treated with 25% aqueous ammonia solution (5 ml) at room temperature for 16 h then same amount of ammonia solution was added and stirring was continued until completion of the reaction. The solvent was removed under reduced pressure and the crude was purified by HPLC (Chromatorex C-18 10 µm, 125×30 mm, acetonitrile/water+0.2% aqueous ammonia (32%) then Waters XBrigde C18 5µ 100×30 mm, acetonitrile/water+0.2% aqueous ammonia (32%)) to yield the title compound (19.7 mg, 98% purity, 7% yield over 2 steps).

LC-MS (Method B): Rt=1.06 min; MS (ESIneg): m/z=502 [M–H]⁻

¹H-NMR (400 MHz, DMSO-d₆) δ [ppm]=0.90-1.00 (m, 2H), 1.03-1.14 (m, 2H), 3.68-3.81 (m, 1H), 3.93 (s, 2H), 7.20 (s, 2H), 7.28-7.49 (m, 4H), 7.67 (s, 1H), 7.74-7.83 (m, 1H), 8.03 (s, 1H), 8.30 (d, 1H), 10.61 (s, 1H).

Example 338

2-(2-Fluorophenyl)-N-[4-(pyridin-3-yl)-3-sulfamoylphenyl]acetamide

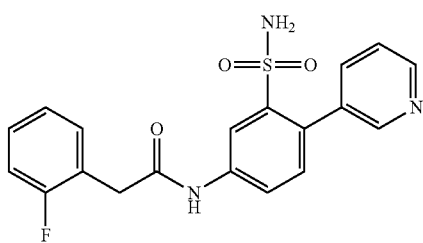 [SMILES: NS(=O)(=O)c1cc(NC(=O)Cc2ccccc2F)ccc1-c1cccnc1]

2-Chloro-N-(2,4-dimethoxybenzyl)-5-nitrobenzenesulfonamide (1.00 g, 2.59 mmol) and pyridin-3-ylboronic acid (477 mg, 3.88 mmol) were dissolved in DMF (8.0 ml) followed by addition of aq. potassium carbonate solution (4.1 ml, 1.0 M, 4.1 mmol). The reaction was purged with argon for 5 minutes and bis(triphenylphosphine)palladium (II) dichloride (CAS 13965-03-2) (273 mg, 388 µmol) was added subsequently. The reaction was heated for 1 h at 120° C. in the microwave. Afterwards the mixture was filtered over Celite, the solvent was removed under reduced pressure and ethyl acetate and water were added. The phases were separated and the aqueous phase was washed with ethyl acetate. The combined organic phases were dried over Whatman filter and the solvent was removed under reduced pressure. The crude was purified by chromatography on silica gel (Biotage, ethyl acetate/hexane) to yield 390 mg (35% yield).

N-(2,4-Dimethoxybenzyl)-5-nitro-2-(pyridin-3-yl)benzenesulfonamide (390 mg, 908 µmol) was dissolved in THF (20 ml) and the flask was flushed with nitrogen. Palladium on charcoal (10% loading, 966 mg, 908 µmol) was added and the flask was evacuated and subsequently flushed with hydrogen (1 bar). Stirring was continued at room temperature for 2 h. Afterwards, same amount of palladium on charcoal was added and stirring was continued until completion of the reaction. The reaction mixture was filtered over Celite and the solvent was removed under reduced pressure. The crude was used without further purification in the next step (490 mg).

5-Amino-N-(2,4-dimethoxybenzyl)-2-(pyridin-3-yl)benzenesulfonamide (245 mg, 613 µmol) was dissolved in DMF (5.0 ml) and (2-fluorophenyl)acetic acid (113 mg, 736 µmol) was added followed by the addition of N,N-diisopropylethylamine (530 µl, 3.1 mmol) and HATU (303 mg, 797 µmol). The reaction was stirred at 50° C. for 16 h. Ethyl acetate and water were added. The phases were separated and the aqueous phase was washed with ethyl acetate. The combined organic phases were dried over Whatman filter and the solvent was removed under reduced pressure. The crude was used in the next step without further purification (490 mg).

N-{3-[(2,4-Dimethoxybenzyl)sulfamoyl]-4-(pyridin-3-yl)phenyl}-2-(2-fluorophenyl)acetamide (328 mg, 613 µmol) was dissolved in dichloromethane (2.0 ml) and trifluoroacetic acid (2.0 ml, 26 mmol) was added and stirring was continued at room temperature until completion of the reaction. The reaction mixture was added to a saturated aqueous sodium bicarbonate solution. Dichloromethane was added and the phases were separated. The aqueous phase was washed with dichloromethane. The combined organic phases were dried over Whatman filter and the solvent was removed under reduced pressure. The crude was purified by HPLC (Chromatorex C-18 10 µm, 125×30 mm, acetonitrile/water+0.1% formic acid) to yield the title compound (49.2 mg, 97% purity, 21% yield over 4 steps).

LC-MS (Method A): Rt=0.75 min; MS (ESIneg): m/z=384 [M–H]⁻

¹H-NMR (400 MHz, DMSO-d₆) δ [ppm]=3.79 (s, 2H), 7.15-7.22 (m, 2H), 7.28-7.37 (m, 4H), 7.38-7.44 (m, 2H), 7.73-7.80 (m, 1H), 7.82-7.87 (m, 1H), 8.37 (d, 1H), 8.49-8.58 (m, 2H), 10.65 (s, 1H).

Example 339

2-(2-Chloro-6-fluorophenyl)-N-[4-(1-methyl-1H-pyrazol-4-yl)-3-sulfamoylphenyl]-acetamide

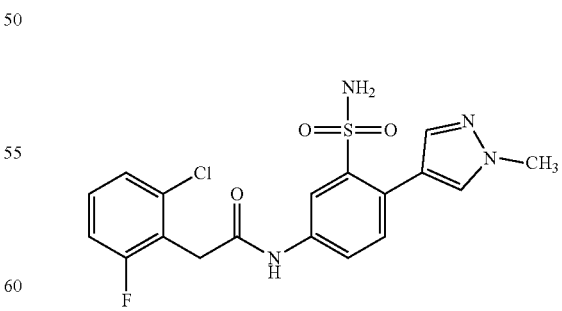

5-Amino-2-(1-methyl-1H-pyrazol-4-yl)benzenesulfonamide (200 mg, 793 µmol) was dissolved in DMF (6.6 ml) and (2-chloro-6-fluorophenyl)acetic acid (179 mg, 951 µmol) was added followed by the addition of N,N-diisopropylethylamine (690 µl, 4.0 mmol) and HATU (482 mg, 1.27 mmol). The reaction was stirred at 50° C. for 18 h. Water and dichloromethane were added and the phases were separated. The aqueous phase was washed with dichloromethane. The combined organic phases were dried over Whatman filter and the solvent was removed under reduced pressure. The crude was purified by HPLC (Waters XBrigde C18 5μ 100×30 mm, acetonitrile/water+0.2% aqueous ammonia (32%)) to yield the title compound (67.6 mg, 95% purity, 19% yield over 2 steps).

LC-MS (Method B): Rt=0.89 min; MS (ESIneg): m/z=421 [M−H]⁻

$^{1}$H-NMR (400 MHz, DMSO-d$_6$) δ [ppm]=3.86 (s, 3H), 3.92 (d, 2H), 7.18 (s, 2H), 7.22-7.29 (m, 1H), 7.33-7.45 (m, 3H), 7.62-7.69 (m, 1H), 7.75-7.79 (m, 1H), 7.94-7.98 (m, 1H), 8.31 (d, 1H), 10.65 (s, 1H).

Example 340

2-(2-Chlorophenyl)-N-[3'-fluoro-5'-(2-hydroxypropan-2-yl)-2-sulfamoylbiphenyl-4-yl]acetamide

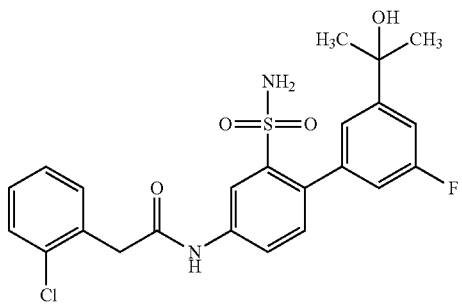 [SMILES: CC(C)(O)c1cc(F)cc(-c2ccc(NC(=O)Cc3ccccc3Cl)cc2S(N)(=O)=O)c1]

2-Chloro-5-nitrobenzenesulfonamide (330 mg, 1.39 mmol) and [3-fluoro-5-(2-hydroxypropan-2-yl)phenyl]boronic acid (552 mg, 2.79 mmol) were dissolved in n-propanol (130 ml) and bis(triphenylphosphine)palladium(II) dichloride (CAS 13965-03-2) (49.1 mg, 69.7 μmol), triphenylphosphine (18.3 mg, 69.7 μmol) and aq. potassium carbonate solution (2.1 ml, 2.0 M, 4.2 mmol) were added. The reaction was purged with argon for 5 minutes and subsequently heated at 120° C. for 2 h in the microwave (4 bar/40 W). Afterwards the mixture was filtered over Celite, the solvent was removed under reduced pressure and the crude was co-distilled with THF and used without further purification in the next step (550 mg).

3'-Fluoro-5'-(2-hydroxypropan-2-yl)-4-nitrobiphenyl-2-sulfonamide (330 mg, 931 μmol) was dissolved in THF (93 ml) and the flask was flushed with nitrogen. Platinum on charcoal (5% loading, 185 mg, 950 μmol) was added and the flask was evacuated and subsequently flushed with hydrogen (1 bar). Stirring was continued at room temperature for 1 h. Afterwards, the flask was evacuated and purged with hydrogen three times and stirring was continued until completion of the reaction. The reaction mixture was filtered over Celite and the solvent was removed under reduced pressure. The crude was used without further purification in the next step (350 mg).

4-Amino-3'-fluoro-5'-(2-hydroxypropan-2-yl)biphenyl-2-sulfonamide (175 mg, 539 μmol) was dissolved in DMF (3.8 ml) and (2-chlorophenyl)acetic acid (110 mg, 647 μmol) was added followed by the addition of N,N-diisopropylethylamine (470 μl, 2.7 mmol) and HATU (328 mg, 863 μmol). The reaction was stirred at 50° C. for 18 h. Afterwards water and dichloromethane were added. The phases were separated and the aqueous phase was washed with dichloromethane. The combined organic phases were dried over Whatman filter and the solvent was removed under reduced pressure. The crude was purified by HPLC (twice Waters XBrigde C18 5μ 100×30 mm, methanol/water+0.2% aqueous ammonia (32%)) to yield the title compound (10.0 mg, 98% purity, 4% yield over 3 steps).

LC-MS (Method J): Rt=1.28 min; MS (ESIneg): m/z=475 [M−H]⁻

$^{1}$H-NMR (400 MHz, DMSO-d$_6$) δ [ppm]=1.43 (s, 6H), 3.89 (s, 2H), 5.15 (s, 1H), 6.99-7.08 (m, 1H), 7.12-7.22 (s, 2H), 7.22-7.40 (m, 5H), 7.42-7.50 (m, 2H), 7.76-7.90 (m, 1H), 8.35 (d, 1H), 10.65 (s, 1H).

Example 341

2-(2-Chlorophenyl)-N-[4-(5-methoxypyridin-3-yl)-3-sulfamoylphenyl]acetamide

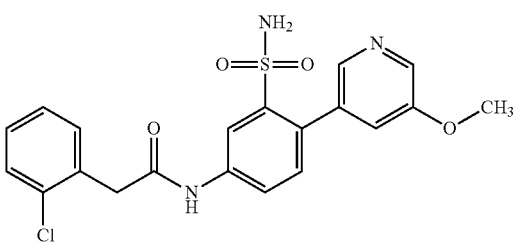 [SMILES: COc1cncc(-c2ccc(NC(=O)Cc3ccccc3Cl)cc2S(N)(=O)=O)c1]

N-(4-Bromo-3-{[(dimethylamino)methylidene]sulfamoyl}phenyl)-2-(2-chlorophenyl)acetamide (250 mg, 545 μmol) and 3-methoxy-5-(4,4,5,5-tetramethyl-1,3,2-dioxaborolan-2-yl)pyridine (192 mg, 817 μmol) were dissolved in n-propanol (10 ml) and bis(triphenylphosphine) palladium(II) dichloride (CAS 13965-03-2) (19.2 mg, 27.2 μmol) and triphenylphosphine (7.15 mg, 27.2 μmol) were added and the solution was purged with argon for 5 minutes. Afterwards aq. potassium carbonate solution (1.6 ml, 1.0 M, 1.6 mmol) was added and the reaction was stirred for 2 h at 100° C. The mixture was filtered over Celite, the solvent was removed under reduced pressure and the crude was purified by chromatography on silica gel (Biotage, 5% ethanol in dichloromethane) to yield 60 mg (23% yield).

LC-MS (Method B): Rt=1.05 min; MS (ESIneg): m/z=485 [M−H]⁻

2-(2-Chlorophenyl)-N-[3-{[(dimethylamino)methylidene]sulfamoyl}-4-(5-methoxypyridin-3-yl)phenyl]acetamide (60.0 mg, 123 μmol) was dissolved in methanol (10 ml) and treated with 25% aqueous ammonia solution (10 ml) at room temperature until completion of the reaction. The solvent was removed under reduced pressure and the crude was purified by HPLC (Waters XBrigde C18 5μ 100×30 mm, acetonitrile/water+0.2% aqueous ammonia (32%)) to yield the title compound (4.2 mg, 90% purity, 8% yield over 2 steps).

LC-MS (Method B): Rt=0.92 min; MS (ESIneg): m/z=430 [M−H]⁻

$^{1}$H-NMR (400 MHz, CD$_3$OD) δ [ppm]=3.91 (s, 3H), 3.94 (s, 2H), 7.31 (d, 3H), 7.38-7.49 (m, 2H), 7.52-7.60 (m, 1H), 7.82-7.92 (m, 1H), 8.12-8.35 (m, 2H), 8.41-8.53 (m, 1H).

Example 342

2-(2-Chlorophenyl)-N-[3'-(2-hydroxypropan-2-yl)-2-sulfamoylbiphenyl-4-yl]acetamide

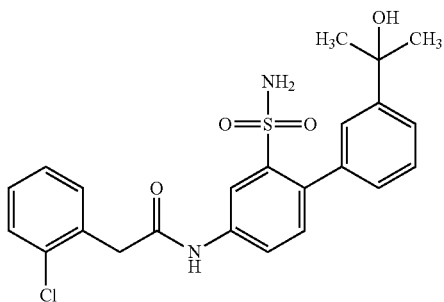 [SMILES: CC(C)(O)c1cccc(-c2ccc(NC(=O)Cc3ccccc3Cl)cc2S(N)(=O)=O)c1]

N-(4-Bromo-3-{[(dimethylamino)methylidene]sulfamoyl}phenyl)-2-(2-chlorophenyl)-acetamide (200 mg, 436 µmol) and [3-(2-hydroxypropan-2-yl)phenyl]boronic acid (157 mg, 872 µmol) were dissolved in n-propanol (12 ml) and bis(triphenylphosphine)palladium(II) dichloride (CAS 13965-03-2) (15.3 mg, 21.8 µmol), triphenylphosphine (7.90 mg, 21.8 µmol) and potassium fluoride (50.7 mg, 872 µmol) were added. The solution was purged for 5 minutes with argon and aq. potassium carbonate solution (650 µl, 2.0 M, 1.3 mmol) was added. The reaction was heated at 80° C. for 2 h. Afterwards the mixture was filtered over Celite, the solvent was removed under reduced pressure and the crude was used without further purification in the next step (250 mg).

2-(2-Chlorophenyl)-N-[2-{[(dimethylamino)methylidene]sulfamoyl}-3'-(2-hydroxypropan-2-yl)biphenyl-4-yl]acetamide (250 mg, 486 µmol) was dissolved in methanol (1.8 ml) and treated with 32% aqueous sodium hydroxide (140 µl) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC ((Waters XBrigde C18 5µ 100×30 mm, acetonitrile/water+ 0.2% aqueous ammonia (32%) then Chromatorex C-18 10 µm, 125×30 mm, acetonitrile/water+0.2% aqueous ammonia (32%)) to yield the title compound (7.70 mg, 95% purity, 3% yield over 2 steps).

LC-MS (Method B): Rt=1.02 min; MS (ESIneg): m/z=457 [M−H]⁻

¹H-NMR (400 MHz, DMSO-d₆) δ [ppm]=1.43 (s, 6H), 3.89 (s, 2H), 5.01 (s, 1H), 6.94 (s, 2H), 7.18-7.40 (m, 5H), 7.42-7.52 (m, 4H), 7.82 (dd, 1H), 8.34 (d, 1H), 10.62 (s, 1H).

Example 343

2-(2-Fluorophenyl)-N-{4-[1-(propan-2-yl)-1H-pyrazol-4-yl]-3-sulfamoylphenyl}-acetamide

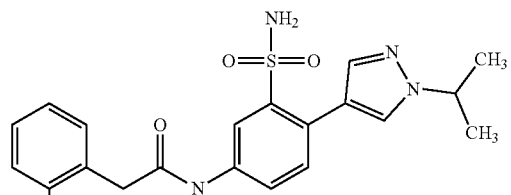

N-(4-Bromo-3-{[(dimethylamino)methylidene]sulfamoyl}phenyl)-2-(2-fluorophenyl)acetamide (250 mg, 565 µmol) and 1-(propan-2-yl)-4-(4,4,5,5-tetramethyl-1,3,2-dioxaborolan-2-yl)-1H-pyrazole (267 mg, 1.13 mmol) were dissolved in n-propanol (10 ml) and bis(triphenylphosphine)palladium(II) dichloride (CAS 13965-03-2) (19.9 mg, 28.3 µmol), triphenylphosphine (7.41 mg, 28.3 µmol) and potassium fluoride (7.55 mg, 130 µmol) were added. The solution was purged with argon for 5 minutes and aq. potassium carbonate solution (710 µl, 2.0 M, 1.4 mmol) was added. The reaction was heated at 120° C. for 1 h in the microwave (4 bar/25 W). Afterwards the mixture was filtered over Celite, the solvent was removed under reduced pressure and the crude was used without further purification in the next step (270 mg).

N-(3-{[(Dimethylamino)methylidene]sulfamoyl}-4-[1-(propan-2-yl)-1H-pyrazol-4-yl]phenyl)-2-(2-fluorophenyl)acetamide (250 mg, 530 µmol) was dissolved in methanol (15 ml) and treated with 32% aqueous sodium hydroxide (470 µl) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Chromatorex C-18 10 µm, 125×30 mm, acetonitrile/water+ 0.1% formic acid) to yield the title compound (47.5 mg, 95% purity, 20% yield over 2 steps).

LC-MS (Method A): Rt=1.00 min; MS (ESIneg): m/z=415 [M−H]⁻

¹H-NMR (400 MHz, DMSO-d₆) δ [ppm]=1.44 (d, 6H), 3.76 (s, 2H), 4.43-4.56 (m, 1H), 7.09-7.24 (m, 4H), 7.27-7.51 (m, 3H), 7.67-7.74 (m, 1H), 7.77-7.85 (m, 1H), 8.02-8.05 (m, 1H), 8.30 (d, 1H), 10.55 (s, 1H).

Example 344

N-[4-(1-Cyclopropyl-1H-pyrazol-4-yl)-3-sulfamoylphenyl]-2-(2-fluorophenyl)-acetamide

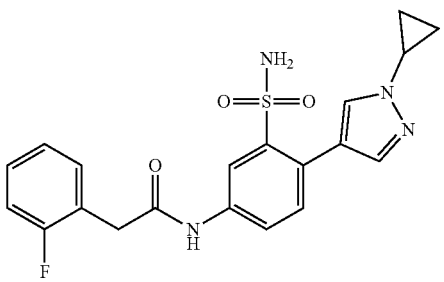 [SMILES: NS(=O)(=O)c1cc(NC(=O)Cc2ccccc2F)ccc1-c1cnn(C2CC2)c1]

5-Amino-2-(1-cyclopropyl-1H-pyrazol-4-yl)-N-[(dimethylamino)methylidene]benzenesulfonamide (200 mg, 600 µmol) was dissolved in DMF (10 ml) and (2-fluorophenyl)acetic acid (111 mg, 720 µmol) was added followed by the addition of N,N-diisopropylethylamine (520 µl, 3.0 mmol) and HATU (456 mg, 1.20 mmol). The reaction was stirred at 50° C. for 16 h, the solvent was removed under reduced pressure and ethyl acetate and water were added. The phases were separated and the aqueous phase was washed with ethyl acetate. The combined organic phases were dried over Whatman filter and the solvent was removed under reduced pressure. The crude was used in the next step without further purification.

N-[4-(1-Cyclopropyl-1H-pyrazol-4-yl)-3-{[(dimethylamino)methylidene]sulfamoyl}phenyl]-2-(2-fluorophenyl)acetamide (282 mg, 600 µmol) was dissolved in methanol (5 ml) and treated with 25% aqueous ammonia solution (5+5 ml) at room temperature until completion of the reaction. The solvent was removed under reduced pressure and the crude was purified by HPLC (Waters XBrigde C18 5µ 100×30 mm, acetonitrile/water+0.2% aqueous ammonia (32%)) to yield the title compound (27.2 mg, 98% purity, 11% yield over 2 steps).

LC-MS (Method B): Rt=0.91 min; MS (ESIneg): m/z=413 [M−H]⁻

¹H-NMR (400 MHz, DMSO-$d_6$) δ [ppm]=0.91-1.01 (m, 2H), 1.04-1.13 (m, 2H), 3.67-3.82 (m, 3H), 7.13-7.26 (m, 4H), 7.28-7.37 (m, 1H), 7.37-7.47 (m, 2H), 7.67 (d, 1H), 7.80 (dd, 1H), 7.98-8.07 (m, 1H), 8.30 (d, 1H), 10.55 (s, 1H).

Example 345

2-(2-Chlorophenyl)-N-{3-sulfamoyl-4-[1-(tetrahydro-2H-pyran-2-yl)-1H-pyrazol-4-yl]phenyl}acetamide

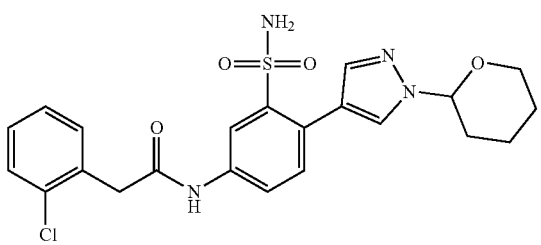 [SMILES: NS(=O)(=O)c1cc(NC(=O)Cc2ccccc2Cl)ccc1-c1cnn(C2CCCCO2)c1]

5-Amino-N-[(dimethylamino)methylidene]-2-[1-(tetrahydro-2H-pyran-2-yl)-1H-pyrazol-4-yl]benzenesulfonamide (3.40 g, 9.01 mmol) was dissolved in DMF (63 ml) and (2-chlorophenyl)acetic acid (1.84 g, 10.8 mmol) was added followed by the addition of N,N-diisopropylethylamine (7.8 ml, 45 mmol) and HATU (5.48 g, 14.4 mmol). The reaction was stirred at 50° C. for 18 h. The solvent was removed under reduced pressure and dichloromethane and water were added. The phases were separated and the aqueous phase was extracted with dichloromethane. The combined organic phases were dried over Whatman filter and the solvent was removed under reduced pressure. The crude was purified by chromatography on ammonia coated silica gel (10% gradient of ethyl acetate in hexane) to yield 2.1 g (50% purity, 43% yield).

LC-MS (Method A): Rt=1.12 min; MS (ESIneg): m/z=528 [M−H]⁻

2-(2-Chlorophenyl)-N-(3-{[(dimethylamino)methylidene]sulfamoyl}-4-[1-(tetrahydro-2H-pyran-2-yl)-1H-pyrazol-4-yl]phenyl)acetamide (350 mg, 660 µmol) was dissolved in methanol (15 ml) and treated with 32% aqueous sodium hydroxide (190 µl) at 80° C. until completion of the reaction. Aq. HCl (100 µl, 6.0 M) was added to adjust the pH to 7. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Waters XBrigde C18 5µ 100×30 mm, acetonitrile/water+0.2% aqueous ammonia (32%)) to yield the title compound (31 mg, 80% purity, 8% yield over 3 steps).

LC-MS (Method B): Rt=1.02 min; MS (ESIneg): m/z=473 [M−H]⁻

¹H-NMR (400 MHz, DMSO-$d_6$) δ [ppm]=1.45-1.61 (m, 2H), 1.61-1.74 (m, 1H), 1.88-2.01 (m, 2H), 2.02-2.17 (m, 1H), 3.60-3.71 (m, 1H), 3.81-3.98 (m, 3H), 5.42 (dd, 1H), 7.24 (s, 2H), 7.30-7.36 (m, 2H), 7.42-7.48 (m, 3H), 7.77 (s, 1H), 7.81 (dd, 1H), 8.14 (s, 1H), 8.32 (d, 1H), 10.59 (s, 1H).

Example 346

N-[4-(1-tert-Butyl-1H-pyrazol-4-yl)-3-sulfamoylphenyl]-2-(2-fluorophenyl)acetamide

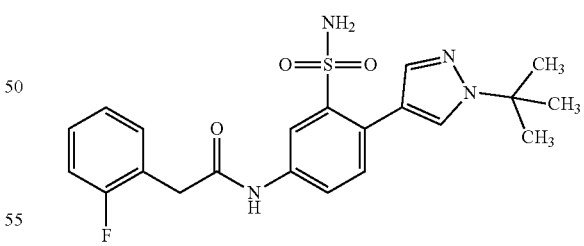

5-Amino-2-(1-tert-butyl-1H-pyrazol-4-yl)benzenesulfonamide (125 mg, 425 µmol) was dissolved in DMF (3.5 ml) and (2-fluorophenyl)acetic acid (78.5 mg, 510 µmol) was added followed by the addition of N,N-diisopropylethylamine (370 µl, 2.1 mmol) and HATU (258 mg, 679 µmol). The reaction was stirred at 50° C. for 18 h and water and dichloromethane were added. The phases were separated and the aqueous phase was extracted with dichloromethane. The combined organic phases were dried over Whatman filter and the solvent was removed under reduced pressure.

The crude was purified by HPLC (Waters XBrigde C18 5μ 100×30 mm, acetonitrile/water+0.2% aqueous ammonia (32%) then Waters XBrigde C18 5μ 100×30 mm, methanol/water+0.1% formic acid) to yield the title compound (12.8 mg, 96% purity, 7% yield over 2 steps).

LC-MS (Method B): Rt=1.03 min; MS (ESIneg): m/z=429 [M−H]⁻

$^1$H-NMR (400 MHz, DMSO-d$_6$) δ [ppm]=1.54 (s, 9H), 3.77 (s, 2H), 7.11-7.22 (m, 4H), 7.29-7.37 (m, 1H), 7.37-7.43 (m, 1H), 7.46 (d, 1H), 7.74 (s, 1H), 7.78-7.85 (m, 1H), 8.10 (s, 1H), 8.31 (d, 1H), 10.55 (s, 1H).

Example 347

N-[3'-Fluoro-5'-(2-hydroxypropan-2-yl)-2-sulfamoylbiphenyl-4-yl]-2-(2-fluorophenyl)acetamide

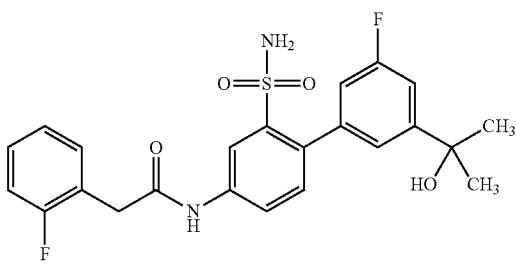 [SMILES: CC(C)(O)c1cc(F)cc(-c2ccc(NC(=O)Cc3ccccc3F)cc2S(N)(=O)=O)c1]

N-(4-Bromo-3-{[(dimethylamino)methylidene]sulfamoyl}phenyl)-2-(2-fluorophenyl)acetamide (500 mg, 1.13 mmol) and [3-(ethoxycarbonyl)-5-fluorophenyl]boronic acid (479 mg, 2.26 mmol) were dissolved in n-propanol (21 ml) and bis(triphenylphosphine)palladium(II) dichloride (CAS 13965-03-2) (39.8 mg, 56.5 μmol), triphenylphosphine (14.8 mg, 56.5 μmol) and potassium fluoride (15.1 mg, 260 μmol) were added. The solution was purged with argon and aq. potassium carbonate solution (1.4 ml, 2.0 M, 2.8 mmol) was added. The reaction was heated at 100° C. for 1 h in the microwave. Afterwards the mixture was filtered over Celite, the solvent was removed under reduced pressure and the crude was purified by chromatography on silica gel (Biotage, ethyl acetate/hexane) to yield 220 mg (37% yield).

LC-MS (Method B): Rt=1.28 min; MS (ESIneg): m/z=528 [M−H]⁻

Ethyl 2'-{[(dimethylamino)methylidene]sulfamoyl}-5-fluoro-4'-{[(2-fluorophenyl)acetyl]amino}biphenyl-3-carboxylate (220 mg, 415 μmol) was dissolved in dry THF (7.6 ml) and methyl magnesium bromide solution in THF (12 ml, 1.0 M, 12 mmol) was added and stirring was continued for 18 h at room temperature. Then ethyl acetate was added followed by saturated aqueous ammonium chloride solution. The precipitate was filtered off, the phases were separated and the organic phase was concentrated under reduced pressure. The crude was used without further purification in the next step (430 mg).

N-[2-{[(Dimethylamino)methylidene]sulfamoyl}-3'-fluoro-5'-(2-hydroxypropan-2-yl)biphenyl-4-yl]-2-(2-fluorophenyl)acetamide (250 mg, 485 μmol) was dissolved in methanol (1.8 ml) and treated with 32% aqueous sodium hydroxide (430 μl) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Chromatorex C-18 10 μm, 125×30 mm, acetonitrile/water+0.2% aqueous ammonia (32%)) to yield the title compound (50.2 mg, 95% purity, 21% yield over 2 steps).

LC-MS (Method B): Rt=1.01 min; MS (ESIneg): m/z=459 [M−H]⁻

$^1$H-NMR (400 MHz, DMSO-de) δ [ppm]=1.43 (s, 6H), 3.79 (s, 2H), 5.15 (s, 1H), 6.98-7.10 (m, 1H), 7.15-7.37 (m, 8H), 7.38-7.45 (m, 1H), 7.76-7.86 (m, 1H), 8.35 (d, 1H), 10.63 (s, 1H).

Example 348

N-[4-(1-Cyclopentyl-1H-pyrazol-4-yl)-3-sulfamoylphenyl]-2-(2-fluorophenyl)-acetamide

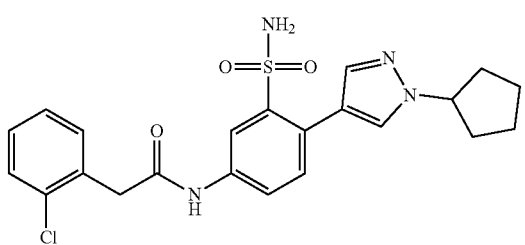 [SMILES: NS(=O)(=O)c1cc(NC(=O)Cc2ccccc2Cl)ccc1-c1cnn(C2CCCC2)c1]

5-Amino-2-(1-cyclopentyl-1H-pyrazol-4-yl)benzenesulfonamide (290 mg, 947 μmol) was dissolved in DMF (7.8 ml) and (2-fluorophenyl)acetic acid (175 mg, 1.14 mmol) was added followed by the addition of N,N-diisopropylethylamine (820 μl, 4.7 mmol) and HATU (576 mg, 1.51 mmol). The reaction was stirred at 50° C. for 16 h. Water and dichloromethane were added. The phases were separated and the aqueous phase was extracted with dichloromethane. The combined organic phases were dried over Whatman filter and the solvent was removed under reduced pressure. The crude was dissolved in methanol (2 ml) and treated with 32% aqueous sodium hydroxide (210 μl) at 80° C. for 2 h. The pH was adjusted to 7 by addition of aq. 6N HCl. Afterwards, the solvent was removed under reduced pressure, the crude was dissolved in dichloromethane and washed with water. The phases were separated and the combined organic phases were dried over Whatman filter and the solvent was removed under reduced pressure. The crude was purified by HPLC (Waters XBrigde C18 5μ 100×30 mm, methanol/water+0.2% aqueous ammonia (32%)) to yield the title compound (37.1 mg, 95% purity, 8% yield over 3 steps).

LC-MS (Method J): Rt=1.26 min; MS (ESIneg): m/z=441 [M−H]⁻

$^1$H-NMR (400 MHz, DMSO-de) δ [ppm]=1.57-1.73 (m, 2H), 1.73-1.89 (m, 2H), 1.89-2.03 (m, 2H), 2.03-2.15 (m, 2H), 3.76 (s, 2H), 4.63-4.79 (m, 1H), 7.13-7.25 (m, 4H), 7.28-7.49 (m, 3H), 7.71 (d, 1H), 7.76-7.85 (m, 1H), 8.03 (d, 1H), 8.30 (d, 1H), 10.55 (s, 1H).

Example 349

2-(2-Chlorophenyl)-N-[4-(1-cyclopropyl-1H-pyrazol-4-yl)-3-sulfamoylphenyl]acetamide

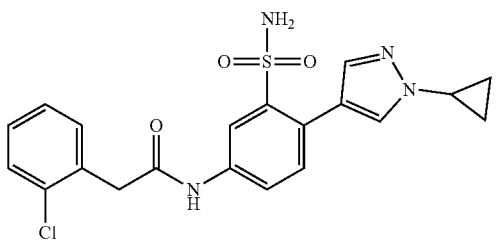 [SMILES: NS(=O)(=O)c1cc(NC(=O)Cc2ccccc2Cl)ccc1-c1cnn(C2CC2)c1]

N-(4-Bromo-3-{[(dimethylamino)methylidene]sulfamoyl}phenyl)-2-(2-chlorophenyl)acetamide (500 mg, 1.09 mmol), 1-cyclopropyl-4-(4,4,5,5-tetramethyl-1,3,2-dioxaborolan-2-yl)-1H-pyrazole (510 mg, 2.18 mmol) and potassium fluoride (139 mg, 2.4 mmol) were dissolved in dry and degassed DMF (30 ml) and the solution was purged again with argon for 5 minutes followed by addition of bis(tri-tert-butylphosphine)palladium(0) (CAS 53199-31-8) (28 mg, 54 µmol). The reaction was heated for 2 h at 100° C. Afterwards the mixture was filtered over Celite, the solvent was removed under reduced pressure and the crude was used without further purification in the next step.

2-(2-Chlorophenyl)-N-[4-(1-cyclopropyl-1H-pyrazol-4-yl)-3-{[(dimethylamino)methylidene]-sulfamoyl}phenyl]acetamide (560 mg, 1.15 mmol) was dissolved in methanol (54 ml) and treated with 32% aqueous sodium hydroxide (560 µl) at 80° C. until completion of the reaction. The solvent was removed under reduced pressure and purified by chromatography on silica gel (Biotage, ethyl acetate/hexane) and subsequently by HPLC (Waters XBrigde C18 5µ 100×30 mm, acetonitrile/water+0.2% aqueous ammonia (32%)) to yield the title compound (192 mg, 95% purity, 37% yield over 2 steps).

LC-MS (Method B): Rt=0.96 min; MS (ESIneg): m/z=429 [M−H]⁻

$^1$H-NMR (400 MHz, DMSO-de) δ [ppm]=0.94-1.01 (m, 2H), 1.05-1.10 (m, 2H), 3.67-3.80 (m, 1H), 3.88 (s, 2H), 7.19 (s, 2H), 7.30-7.35 (m, 2H), 7.40-7.48 (m, 3H), 7.67 (d, 1H), 7.81 (dd, 1H), 8.04 (s, 1H), 8.31 (d, 1H), 10.57 (s, 1H).

Example 350

2-(2-Chloro-6-fluorophenyl)-N-{4-[1-(2-methoxyethyl)-1H-pyrazol-4-yl]-3-sulfamoylphenyl}acetamide

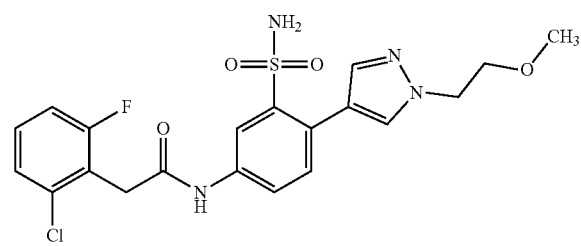 [SMILES: COCCn1cc(-c2ccc(NC(=O)Cc3c(F)cccc3Cl)cc2S(N)(=O)=O)cn1]

5-Amino-2-[1-(2-methoxyethyl)-1H-pyrazol-4-yl]benzenesulfonamide (190 mg, 641 µmol) was dissolved in DMF (5.3 ml) and (2-chloro-6-fluorophenyl)acetic acid (145 mg, 769 µmol) was added followed by the addition of N,N-diisopropylethylamine (560 µl, 3.2 mmol) and HATU (390 mg, 1.03 mmol). The reaction was stirred at 50° C. for 16 h. Water and dichloromethane were added. The phases were separated and the aqueous phase was extracted with dichloromethane. The combined organic phases were dried over Whatman filter and the solvent was removed under reduced pressure. The crude was purified by HPLC (Waters XBrigde C18 5µ 100×30 mm, acetonitrile/water+0.2% aqueous ammonia (32%) then Waters XBrigde C18 5µ 100×30 mm, methanol/water+0.1% formic acid) to yield the title compound (53.8 mg, 99% purity, 18% yield over 3 steps).

LC-MS (Method 1): Rt=1.17 min; MS (ESIneg): m/z=465 [M−H]⁻

$^1$H-NMR (400 MHz, DMSO-d$_6$) δ [ppm]=3.24 (s, 3H), 3.70 (t, 2H), 3.92 (d, 2H), 4.28 (t, 2H), 7.10 (s, 2H), 7.22-7.32 (m, 1H), 7.32-7.50 (m, 3H), 7.69-7.72 (m, 1H), 7.78 (dd, 1H), 8.00-8.02 (m, 1H), 8.32 (d, 1H), 10.66 (s, 1H).

Example 351

2-(2-Chlorophenyl)-N-[4-(1,3-dimethyl-1H-pyrazol-5-yl)-3-sulfamoylphenyl]acetamide

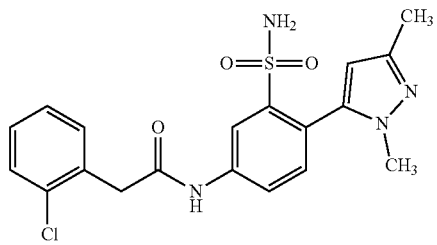 [SMILES: Cc1cc(-c2ccc(NC(=O)Cc3ccccc3Cl)cc2S(N)(=O)=O)n(C)n1]

5-Amino-2-(1,3-dimethyl-1H-pyrazol-5-yl)benzenesulfonamide (200 mg, 751 µmol) was dissolved in DMF (5.3 ml) and (2-chlorophenyl)acetic acid (154 mg, 901 µmol) was added followed by the addition of N,N-diisopropylethylamine (620 µl, 3.8 mmol) and HATU (457 mg, 1.20 mmol). The reaction was stirred at 50° C. for 5 h. Water and dichloromethane were added and the phases were separated and the aqueous phase was extracted with dichloromethane. The combined organic phases were dried over Whatman filter and the solvent was removed under reduced pressure. The crude was purified by chromatography on ammonia coated silica gel (Biotage, hexane/ethyl acetate) and then subjected to HPLC purification (Waters XBrigde C18 5µ 100×30 mm, acetonitrile/water+0.2% aqueous ammonia (32%)) to yield the title compound (12.6 mg, 95% purity, 4% yield over 3 steps).

LC-MS (Method B): Rt=0.87 min; MS (ESIneg): m/z=417 [M−H]⁻

$^1$H-NMR (400 MHz, DMSO-de) δ [ppm]=2.16 (s, 3H), 3.41 (s, 3H), 3.89 (s, 2H), 6.07 (s, 1H), 7.08 (s, 2H), 7.26-7.39 (m, 3H), 7.41-7.51 (m, 2H), 7.86 (dd, 1H), 8.36 (d, 1H), 10.72 (s, 1H).

Example 352

2-(2-Chlorophenyl)-N-(4'-chloro-2-sulfamoylbiphenyl-4-yl)acetamide

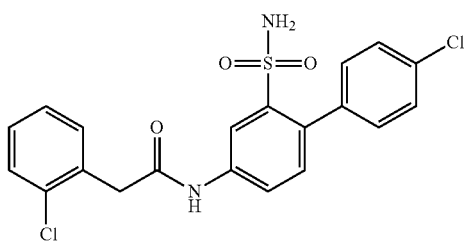

2-Chloro-N-(2,4-dimethoxybenzyl)-5-nitrobenzenesulfonamide (400 mg, 1.03 mmol) and (4-chlorophenyl)boronic acid (243 mg, 1.55 mmol) were dissolved in DMF (50 ml) followed by addition of bis(triphenylphosphine)palladium (II) dichloride (CAS 13965-03-2) (109 mg, 155 µmol) and aq. potassium carbonate solution (2.5 ml, 1.0 M, 2.5 mmol). The reaction was heated for 1 h at 120° C. in the microwave (2 bar, 50 W). Afterwards the mixture was filtered over Celite, the solvent was removed under reduced pressure and the crude was purified by chromatography on silica gel (Biotage, ethyl acetate/hexane) to yield 467 mg (82% purity, 97% yield).

LC-MS (Method B): Rt=1.39 min; MS (ESIneg): m/z=461 [M−H]−

4'-Chloro-N-(2,4-dimethoxybenzyl)-4-nitrobiphenyl-2-sulfonamide (467 mg, 1.01 mmol) was dissolved in dioxane (4.8 ml) and tin(II) chloride dihydrate (1.14 g, 5.04 mmol) was added. The reaction was stirred for 2 h at 70° C. Afterwards the mixture was filtered over silica gel, the solvent was removed under reduced pressure and the crude was suspended in dichloromethane and filtered again. The solvent was removed under reduced pressure and the crude was used without further purification in the next step (230 mg).

4-Amino-4'-chloro-N-(2,4-dimethoxybenzyl)biphenyl-2-sulfonamide (110 mg, 254 µmol) was dissolved in DMF (1.8 ml) and (2-chlorophenyl)acetic acid (52.0 mg, 305 µmol) was added followed by the addition of N,N-diisopropylethylamine (210 µl, 1.3 mmol) and HATU (155 mg, 407 µmol). The reaction was stirred at 50° C. for 4 h and water and dichloromethane were added. The phases were separated and the aqueous phase was extracted with dichloromethane. The combined organic phases were dried over Whatman filter and the solvent was removed under reduced pressure. The crude was used in the next step without further purification (150 mg).

N-{4'-Chloro-2-[(2,4-dimethoxybenzyl)sulfamoyl]biphenyl-4-yl}-2-(2-chlorophenyl)acetamide (150 mg, 256 µmol) was dissolved in dichloromethane (1.5 ml) and trifluoroacetic acid (990 µl, 13 mmol) was added and stirring was continued at room temperature until completion of the reaction. The solvent was removed under reduced pressure and the crude co-distilled with toluene. The crude was purified by HPLC (Waters XBrigde C18 5µ 100×30 mm, acetonitrile/water+0.2% aqueous ammonia (32%)) to yield the title compound (29.8 mg, 95% purity, 25% yield over 3 steps).

LC-MS (Method B): Rt=1.20 min; MS (ESIneg): m/z=432 [M−H]−

1H-NMR (400 MHz, DMSO-d6) δ [ppm]=3.89 (s, 2H), 7.17-7.27 (m, 3H), 7.30-7.39 (m, 4H), 7.40-7.48 (m, 4H), 7.82 (dd, 1H), 8.35 (d, 1H), 10.63 (s, 1H).

Example 353

2-(2-Chlorophenyl)-N-{4-[1-methyl-3-(trifluoromethyl)-1H-pyrazol-5-yl]-3-sulfamoylphenyl}acetamide

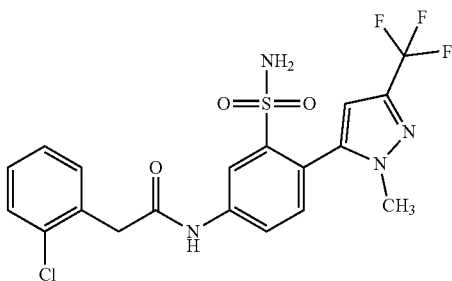

5-Amino-2-[1-methyl-3-(trifluoromethyl)-1H-pyrazol-5-yl]benzenesulfonamide (300 mg, 937 µmol) was dissolved in DMF (6.6 ml) and (2-chlorophenyl)acetic acid (192 mg, 1.12 mmol) was added followed by the addition of N,N-diisopropylethylamine (820 µl, 4.7 mmol) and HATU (570 mg, 1.50 mmol). The reaction was stirred at 50° C. for 18 h. Water and dichloromethane were added. The phases were separated and the aqueous phase was extracted with dichloromethane. The combined organic phases were dried over Whatman filter and the solvent was removed under reduced pressure. The crude was purified by HPLC (Waters XBrigde C18 5µ 100×30 mm, methanol/water+0.2% aqueous ammonia (32%) then acetonitrile/water+0.1% formic acid) to yield the title compound (28.2 mg, 99% purity, 6% yield over 3 steps).

LC-MS (Method A): Rt=1.14 min; MS (ESIneg): m/z=471 [M−H]−

1H-NMR (400 MHz, DMSO-d6) δ [ppm]=3.59 (s, 3H), 3.91 (s, 2H), 6.72 (s, 1H), 7.31-7.35 (m, 2H), 7.38-7.48 (m, 5H), 7.85-7.93 (m, 1H), 8.40 (d, 1H), 10.79 (s, 1H).

Example 354

2-(2-Chlorophenyl)-N-[4-(pyridin-3-yl)-3-sulfamoylphenyl]acetamide

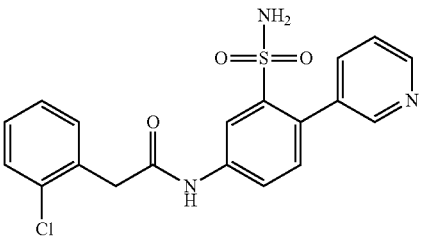 [SMILES: NS(=O)(=O)c1cc(NC(=O)Cc2ccccc2Cl)ccc1-c1cccnc1]

N-{4-bromo-3-[(2,4-dimethoxybenzyl)sulfamoyl]phenyl}-2-(2-chlorophenyl)acetamide (250 mg, 451 µmol) and pyridin-3-ylboronic acid (83.2 mg, 677 µmol) were dissolved in DMF (10 ml) followed by addition of aq. potassium carbonate solution (1.1 ml, 1.0 M, 1.1 mmol). The solution was purged with argon for 5 minutes and bis(triphenylphosphine)palladium(II) dichloride (CAS 13965-03-2) (47.7 mg, 67.7 µmol) was added. The reaction was heated for 30 minutes at 120° C. in the microwave. Afterwards the mixture was filtered over Celite, the solvent was removed under reduced pressure and ethyl acetate and water were added. The phases were separated and the aqueous phase was extracted with ethyl acetate. The combined organic phases were dried over Whatman filter and the solvent was removed under reduced pressure. The crude was used in the next step without further purification (740 mg).

2-(2-Chlorophenyl)-N-{3-[(2,4-dimethoxybenzyl)sulfamoyl]-4-(pyridin-3-yl)phenyl}acetamide (347 mg, 628 µmol) was dissolved in dichloromethane (5.0 ml) and trifluoroacetic acid (5.0 ml, 65 mmol) was added. Stirring was continued at room temperature until completion of the reaction. The solvent was removed under reduced pressure and ethyl acetate and water were added. The phases were separated and the aqueous phase was extracted with ethyl acetate. The combined organic phases were dried over Whatman filter and the solvent was removed under reduced pressure. The crude was purified by HPLC (Chromatorex C-18 10 µm, 125×30 mm, acetonitrile/water+0.2% aqueous ammonia (32%)) to yield the title compound (49.6 mg, 95% purity, 19% yield over 2 steps).

LC-MS (Method B): Rt=0.85 min; MS (ESIneg): m/z=400 [M−H]⁻

¹H-NMR (400 MHz, DMSO-d₆) δ [ppm]=3.90 (s, 2H), 7.27-7.36 (m, 5H), 7.38-7.42 (m, 1H), 7.44-7.46 (m, 2H), 7.73-7.81 (m, 1H), 7.81-7.89 (m, 1H), 8.38 (d, 1H), 8.49-8.59 (m, 2H), 10.66 (s, 1H).

Example 355

2-(2-Chlorophenyl)-N-{4-[1-methyl-3-(trifluoromethyl)-1H-pyrazol-4-yl]-3-sulfamoylphenyl}acetamide

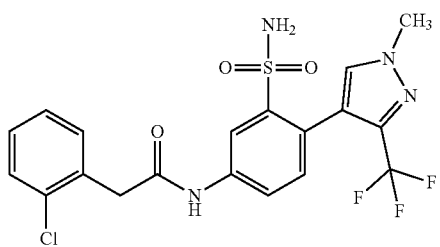 [SMILES: Cn1cc(-c2ccc(NC(=O)Cc3ccccc3Cl)cc2S(N)(=O)=O)c(C(F)(F)F)n1]

N-(4-Bromo-3-{[(dimethylamino)methylidene]sulfamoyl}phenyl)-2-(2-chlorophenyl)acetamide (200 mg, 436 µmol) and [1-methyl-3-(trifluoromethyl)-1H-pyrazol-4-yl]boronic acid (169 mg, 872 µmol) were dissolved in n-propanol (8.0 ml) and bis(triphenylphosphine)palladium (II) dichloride (CAS 13965-03-2) (15.3 mg, 21.8 µmol) and triphenylphosphine (5.72 mg, 21.8 µmol) were added. The solution was purged with argon for 5 minutes and aq. potassium carbonate solution (540 µl, 2.0 M, 1.1 mmol) was added. The reaction was heated at 80° C. for 2 h. Afterwards the mixture was filtered over Celite, the solvent was removed under reduced pressure and the crude was used without further purification in the next step (250 mg).

2-(2-Chlorophenyl)-N-(3-{[(dimethylamino)methylidene]sulfamoyl}-4-[1-methyl-3-(trifluoromethyl)-1H-pyrazol-4-yl]phenyl)acetamide (250 mg, 474 µmol) was dissolved in methanol (4.9 ml) and treated with 32% aqueous sodium hydroxide (130 µl) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Waters XBrigde C18 5µ 100×30 mm, acetonitrile/water+0.2% aqueous ammonia (32%)) to yield the title compound t (3.60 mg, 98% purity, 2% yield over 2 steps).

LC-MS (Method B): Rt=1.20 min; MS (ESIneg): m/z=471 [M−H]⁻

¹H-NMR (400 MHz, DMSO-d₆) δ [ppm]=3.88 (s, 2H), 3.93 (s, 3H), 7.14-7.29 (m, 3H), 7.29-7.39 (m, 2H), 7.41-7.53 (m, 2H), 7.80 (dd, 1H), 7.84-7.89 (m, 1H), 8.32 (d, 1H), 10.65 (s, 1H).

Example 356

2-(2-Chlorophenyl)-N-(3'-chloro-2-sulfamoylbiphenyl-4-yl)acetamide

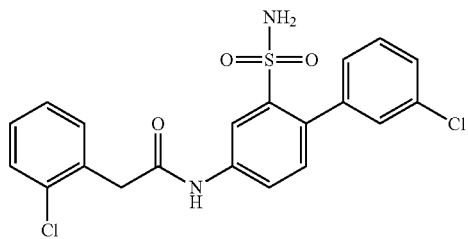 [SMILES: NS(=O)(=O)c1cc(NC(=O)Cc2ccccc2Cl)ccc1-c1cccc(Cl)c1]

2-Chloro-N-(2,4-dimethoxybenzyl)-5-nitrobenzenesulfonamide (400 mg, 1.03 mmol) and (3-chlorophenyl)boronic acid (243 mg, 1.55 mmol) were dissolved in DMF (20 ml) followed by addition of bis(triphenylphosphine)palladium (II) dichloride (CAS 13965-03-2) (109 mg, 155 µmol) and aq. potassium carbonate solution (2.5 ml, 1.0 M, 2.5 mmol). The reaction was heated for 1 h at 120° C. in the microwave (2 bar, 50 W). Afterwards the mixture was filtered over Celite, the solvent was removed under reduced pressure and the crude was purified by chromatography on silica gel (Biotage, ethyl acetate/hexane) to yield 702 mg.

LC-MS (Method A): Rt=1.39 min; MS (ESIneg): m/z=461 [M−H]⁻

3'-Chloro-N-(2,4-dimethoxybenzyl)-4-nitrobiphenyl-2-sulfonamide (470 mg, 1.02 mmol) was dissolved in dioxane (4.9 ml) and tin(II)chloride dihydrate (1.15 g, 5.08 mmol) was added. The reaction was stirred for 2 h at 70° C. Afterwards the mixture was filtered over silica gel, the solvent was removed under reduced pressure and the crude was suspended in dichloromethane and filtered again. The solvent was removed under reduced pressure and the crude was used without further purification in the next step (652 mg).

4-Amino-3'-chloro-N-(2,4-dimethoxybenzyl)biphenyl-2-sulfonamide (200 mg, 60% purity, 277 µmol) was dissolved in DMF (2.0 ml) and (2-chlorophenyl)acetic acid (56.7 mg, 333 µmol) was added followed by the addition of N,N-diisopropylethylamine (230 µl, 1.4 mmol) and HATU (169 mg, 443 µmol). The reaction was stirred at 50° C. for 4 h. Water and dichloromethane were added. The phases were separated and the aqueous phase was extracted with dichloromethane. The combined organic phases were dried over Whatman filter and the solvent was removed under reduced pressure. The crude was used in the next step without further purification (170 mg).

N-{3'-Chloro-2-[(2,4-dimethoxybenzyl)sulfamoyl]biphenyl-4-yl}-2-(2-chlorophenyl)-acetamide (170 mg, 290 µmol) was dissolved in dichloromethane (1.5 ml) and trifluoroacetic acid (1.1 ml) was added and stirring was continued at room temperature until completion of the reaction. The solvent was removed under reduced pressure and the crude was co-distilled with toluene. The crude was purified by HPLC (Waters XBrigde C18 5µ 100×30 mm, acetonitrile/water+0.2% aqueous ammonia (32%)) to yield the title compound (22.6 mg, 95% purity, 17% yield over 4 steps).

LC-MS (Method B): Rt=1.15 min; MS (ESIneg): m/z=433 [M–H]⁻

¹H-NMR (400 MHz, DMSO-d₆) δ [ppm]=3.90 (s, 2H), 7.22-7.29 (m, 3H), 7.31-7.35 (m, 3H), 7.38-7.42 (m, 3H), 7.43-7.48 (m, 2H), 7.82 (dd, 1H), 8.35 (d, 1H), 10.65 (s, 1H).

Example 357

2-(2-Chlorophenyl)-N-(4-{1-[(2,2-dichlorocyclopropyl)methyl]-1H-pyrazol-4-yl}-3-sulfamoylphenyl)acetamide

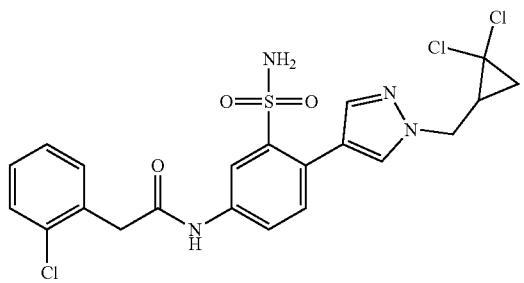 [SMILES: NS(=O)(=O)c1cc(NC(=O)Cc2ccccc2Cl)ccc1-c1cnn(CC2CC2(Cl)Cl)c1]

2-(2-Chlorophenyl)-N-[3-{[(dimethylamino)methylidene]sulfamoyl}-4-(1H-pyrazol-4-yl)phenyl]acetamide (200 mg, 448 µmol) was dissolved in DMF (3 ml) and cesium carbonate (292 mg, 897 µmol), potassium iodide (74.5 mg, 448 µmol) and 2-(bromomethyl)-1,1-dichlorocyclopropane (101 mg, 493 µmol) were added. The reaction was stirred for 18 h at 100° C. Same amount of reagents were added and stirring was continued for 24 h at 100° C. Then water and ethyl acetate were added. The phases were separated and the aqueous phase was extracted with ethyl acetate. The combined organic phases were dried over Whatman filter and the solvent was removed under reduced pressure. The crude was used in the next step without further purification.

2-(2-Chlorophenyl)-N-(4-{1-[(2,2-dichlorocyclopropyl)methyl]-1H-pyrazol-4-yl}-3-{[(dimethylamino)methylidene]sulfamoyl}phenyl)acetamide (302 mg, 531 µmol) was dissolved in methanol (4.4 ml) and treated with 25% aqueous ammonia solution (4.4 ml) at room temperature. After 16 h, 32% aqueous sodium hydroxide solution (200 µl) was added and stirring was continued until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Waters XBrigde C18 5µ 100×30 mm, acetonitrile/water+0.2% aqueous ammonia (32%)) to yield the title compound (6.80 mg, 95% purity, 2% yield over 3 steps).

LC-MS (Method B): Rt=1.11 min; MS (ESIneg): m/z=511 [M–H]⁻

¹H-NMR (400 MHz, DMSO-d₆) δ [ppm]=1.57-1.71 (m, 1H), 1.81-1.90 (m, 1H), 2.26-2.35 (m, 1H), 3.87 (s, 2H), 4.33 (m, 2H), 7.14 (s, 2H), 7.27-7.40 (m, 2H), 7.40-7.53 (m, 3H), 7.76 (s, 1H), 7.80-7.86 (m, 1H), 8.11 (s, 1H), 8.30-8.39 (m, 1H), 10.59 (s, 1H).

Example 358

2-(2-Chlorophenyl)-N-[4-(1,3-dimethyl-1H-pyrazol-4-yl)-3-sulfamoylphenyl]acetamide

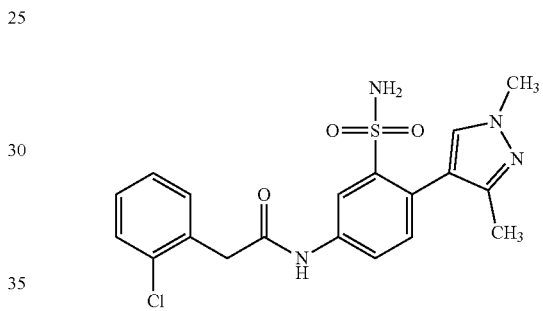

5-Amino-2-(1,3-dimethyl-1H-pyrazol-4-yl)benzenesulfonamide (250 mg, 939 µmol) was dissolved in DMF (6.6 ml) and (2-chlorophenyl)acetic acid (192 mg, 1.13 mmol) was added followed by the addition of N,N-diisopropylethylamine (820 µl, 4.7 mmol) and HATU (571 mg, 1.50 mmol). The reaction was stirred at 50° C. for 18 h. Water and dichloromethane were added. The phases were separated and the aqueous phase was extracted with dichloromethane. The combined organic phases were dried over Whatman filter and the solvent was removed under reduced pressure. The crude was dissolved in methanol (4 ml) and 32% aqueous sodium hydroxide solution (210 µl) was added. The reaction was stirred at 80° C. for 2 h. Afterwards, the reaction was neutralized with 6N HCl and water and dichloromethane were added. The phases were separated, the organic phase was dried over Whatman filter and the solvent was removed under reduced pressure. The crude was purified by HPLC (Waters XBrigde C18 5µ 100×30 mm, acetonitrile/water+0.2% aqueous ammonia (32%) then Chromatorex C-18 10 µm, 125×30 mm, acetonitrile/water+0.2% aqueous ammonia (32%)) to yield the final compound (19.6 mg, 90% purity, 4% yield over 3 steps).

LC-MS (Method B): Rt=0.94 min; MS (ESIneg): m/z=417 [M–H]⁻

¹H-NMR (400 MHz, DMSO-d₆) δ [ppm]=1.99 (s, 3H), 3.77 (s, 3H), 3.87 (s, 2H), 6.91 (s, 2H), 7.23 (d, 1H), 7.27-7.38 (m, 2H), 7.38-7.52 (m, 2H), 7.59 (s, 1H), 7.77-7.88 (m, 1H), 8.30 (d, 1H), 10.58 (s, 1H).

Example 359

2-(2-Chlorophenyl)-N-{4-[1-(propan-2-yl)-1H-pyrazol-4-yl]-3-sulfamoylphenyl}-acetamide

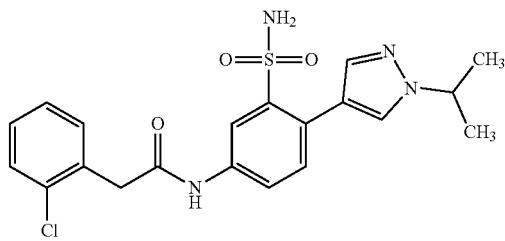 [SMILES: CC(C)n1cc(-c2ccc(NC(=O)Cc3ccccc3Cl)cc2S(N)(=O)=O)cn1]

2-Chloro-5-nitrobenzenesulfonamide (500 mg, 2.11 mmol) and 1-(propan-2-yl)-4-(4,4,5,5-tetramethyl-1,3,2-dioxaborolan-2-yl)-1H-pyrazole (998 mg, 4.23 mmol) were dissolved in n-propanol (28 ml) and bis(triphenylphosphine) palladium(II) dichloride (CAS 13965-03-2) (74.4 mg, 106 µmol), triphenylphosphine (27.7 mg, 106 µmol) and aq. potassium carbonate solution (3.2 ml, 2.0 M, 6.3 mmol) were added. The solution was purged with argon for 5 minutes and the reaction was heated for 1 h at 120° C. in the microwave (4 bar/40 W). Afterwards the mixture was filtered over Celite, the solvent was removed under reduced pressure and the crude was co-distilled with methanol and used without further purification in the next step (700 mg).

5-Nitro-2-[1-(propan-2-yl)-1H-pyrazol-4-yl]benzenesulfonamide (700 mg, 2.26 mmol) was dissolved in THF (230 ml) and methanol (50 ml) and the flask was flushed with nitrogen. Palladium on charcoal (10% loading, 245 mg, 2.30 mmol) was added and the flask was evacuated and subsequently flushed with hydrogen (1 bar). Stirring was continued at room temperature for 16 h. The reaction mixture was filtered over Celite and the solvent was removed under reduced pressure. The crude was used without further purification in the next step (600 mg).

5-Amino-2-[1-(propan-2-yl)-1H-pyrazol-4-yl]benzenesulfonamide (300 mg, 1.07 mmol) was dissolved in DMF (7.5 ml) and (2-chlorophenyl)acetic acid (219 mg, 1.28 mmol) was added followed by the addition of N,N-diisopropylethylamine (880 µl, 5.4 mmol) and HATU (651 mg, 1.71 mmol). The reaction was stirred at 50° C. for 18 h. Water and dichloromethane were added. The phases were separated and the aqueous phase was extracted with dichloromethane. The combined organic phases were dried over Whatman filter and the solvent was removed under reduced pressure. The crude was purified by HPLC (Waters XBrigde C18 5µ 100×30 mm, methanol/water+0.1% formic acid) to yield the title compound (66.6 mg, 95% purity, 14% yield over 3 steps).

LC-MS (Method 1): Rt=1.27 min; MS (ESIneg): m/z=431 [M−H]−

$^1$H-NMR (400 MHz, DMSO-d$_6$) δ [ppm]=1.45 (d, 6H), 3.88 (s, 2H), 4.45-4.58 (m, 1H), 7.16 (s, 2H), 7.27-7.40 (m, 2H), 7.41-7.49 (m, 3H), 7.72 (s, 1H), 7.78-7.89 (m, 1H), 8.04 (s, 1H), 8.32 (d, 1H), 10.57 (s, 1H).

Example 360

2-(2-Chlorophenyl)-N-[4-(1-methyl-1H-pyrazol-4-yl)-3-sulfamoylphenyl]acetamide

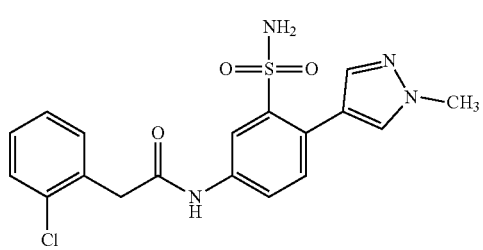

N-(4-Bromo-3-{[(dimethylamino)methylidene]sulfamoyl}phenyl)-2-(2-chlorophenyl)acetamide (900 mg, 1.96 mmol) and 1-methyl-4-(4,4,5,5-tetramethyl-1,3,2-dioxaborolan-2-yl)-1H-pyrazole (490 mg, 2.35 mmol) were dissolved in DMF (25 ml) followed by addition of potassium fluoride (251 mg, 4.32 mmol). The solution was purged with argon for 5 minutes and bis(tri-tert-butylphosphine)palladium(0) (CAS 53199-31-8) (50.1 mg, 98.1 µmol) was added. The reaction was heated for 1 h at 100° C. The mixture was filtered via a glass fiber filter and the solvent was removed under reduced pressure. The crude was subjected once more to the reaction procedure described above. Afterwards, the solvent was removed under reduced pressure and ethyl acetate and water were added. The phases were separated and the aqueous phase was extracted with ethyl acetate. The combined organic phases were dried over Whatman filter and the solvent was removed under reduced pressure. The crude was used in the next step without further purification (2.39 g).

2-(2-Chlorophenyl)-N-[3-{[(dimethylamino)methylidene]sulfamoyl}-4-(1-methyl-1H-pyrazol-4-yl)phenyl]acetamide (2.39 g, 5.20 mmol) was dissolved in methanol (80 ml) and treated with 25% aqueous ammonia solution (80 ml) at room temperature. UPLC indicated incomplete reaction, 25% aqueous ammonia solution (80 ml) was added and stirring was continued until completion of the reaction. The solvent was removed under reduced pressure and the crude was purified by chromatography on silica gel (Biotage, 10% ethanol in dichloromethane) followed by HPLC (Waters XBrigde C18 5µ 100×30 mm, acetonitrile/water+0.2% aqueous ammonia (32%)) to yield the title compound (327 mg, 98% purity, 15% yield over 2 steps).

LC-MS (Method B): Rt=0.86 min; MS (ESIneg): m/z=403 [M−H]−

$^1$H-NMR (400 MHz, DMSO-d$_6$) δ [ppm]=3.78-3.96 (m, 5H), 7.17 (s, 2H), 7.28-7.37 (m, 2H), 7.38-7.52 (m, 3H), 7.66 (d, 1H), 7.82 (dd, 1H), 7.96 (s, 1H), 8.32 (d, 1H), 10.57 (s, 1H).

Example 361

2-(2-Chlorophenyl)-N-{4-[1-(2-hydroxy-3,3-dimethylbutyl)-1H-pyrazol-4-yl]-3-sulfamoylphenyl}acetamide

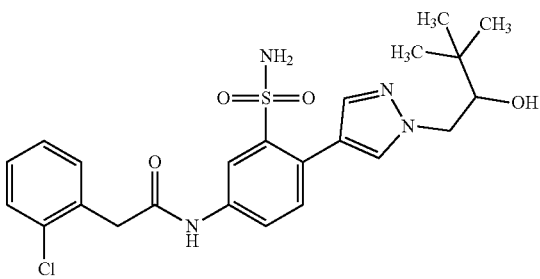 [SMILES: CC(C)(C)C(O)Cn1cc(-c2ccc(NC(=O)Cc3ccccc3Cl)cc2S(N)(=O)=O)cn1]

2-(2-Chlorophenyl)-N-[3-{[(dimethylamino)methylidene]sulfamoyl}-4-(1H-pyrazol-4-yl)phenyl]acetamide (250 mg, 561 µmol) was dissolved in DMF (10 ml) and 2-tert-butyloxirane (1.68 g, 16.8 mmol) and cesium carbonate (365 mg, 1.12 mmol) were added. The reaction was heated at 130° C. for 30 minutes in the microwave. The solvent was removed under reduced pressure and the crude was used without further purification in the next step (306 mg).

2-(2-Chlorophenyl)-N-(3-{[(dimethylamino)methylidene]sulfamoyl}-4-{1-[2-hydroxy-3,3-dimethylbutyl]-1H-pyrazol-4-yl}phenyl)acetamide (306 mg, 560 µmol) was dissolved in methanol (5.8 ml) and treated with 32% aqueous sodium hydroxide (480 µl) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Waters XBrigde C18 5µ 100×30 mm, acetonitrile/water+0.2% aqueous ammonia (32%)) to yield the title compound (8.80 mg, 95% purity, 3% yield over 2 steps).

LC-MS (Method B): Rt=1.28 min; MS (ESIneg): m/z=489 [M−H]$^-$ $^1$H-NMR (400 MHz, DMSO-d$_6$) δ [ppm]=0.93 (s, 9H), 3.37-3.51 (m, 1H), 3.85-3.93 (m, 3H), 4.26 (dd, 1H), 4.91 (d, 1H), 6.99 (s, 2H), 7.29-7.36 (m, 2H), 7.41-7.49 (m, 3H), 7.70 (s, 1H), 7.84 (dd, 1H), 8.02 (s, 1H), 8.31 (d, 1H), 10.58 (s, 1H).

Example 362

2-(2-Fluorophenyl)-N-[4-(5-fluoropyridin-3-yl)-3-sulfamoylphenyl]acetamide

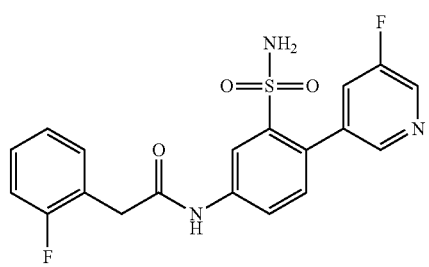 [SMILES: NS(=O)(=O)c1cc(NC(=O)Cc2ccccc2F)ccc1-c1cncc(F)c1]

N-(4-Bromo-3-{[(dimethylamino)methylidene]sulfamoyl}phenyl)-2-(2-fluorophenyl)-acetamide (750 mg, 1.70 mmol) and (5-fluoropyridin-3-yl)boronic acid (478 mg, 3.39 mmol) were dissolved in n-propanol (15 ml) and bis(triphenylphosphine)palladium(II) dichloride (CAS 13965-03-2) (59.7 mg, 84.8 µmol) and triphenylphosphine (22.2 mg, 84.8 µmol) were added. The solution was purged with argon for 5 minutes and aq. potassium carbonate solution (2.1 ml, 2.0 M, 4.2 mmol) was added. The reaction was heated at 100° C. for 1 h. Afterwards the mixture was filtered over Celite, the solvent was removed under reduced pressure and ethyl acetate and water were added. The phases were separated and the aqueous phase was extracted with ethyl acetate. The combined organic phases were dried over Whatman filter and the solvent was removed under reduced pressure. The crude was used in the next step without further purification (970 mg).

N-[3-{[(Dimethylamino)methylidene]sulfamoyl}-4-(5-fluoropyridin-3-yl)phenyl]-2-(2-fluorophenyl)acetamide (970 mg, 2.12 mmol) was dissolved in methanol (50 ml) and treated with 25% aqueous ammonia solution (50 ml) at room temperature for 4 h. UPLC indicated incomplete reaction, and 25% aqueous ammonia solution (50 ml) was added again. Stirring was continued at room temperature until completion of the reaction. The solvent was removed under reduced pressure and the crude was purified by HPLC (Chromatorex C-18 µm, 125×30 mm, acetonitrile/water+0.2% aqueous ammonia (32%)) to yield the title compound (126 mg, 99% purity, 15% yield over 2 steps).

LC-MS (Method B): Rt=0.83 min; MS (ESIneg): m/z=402 [M−H]$^-$ $^1$H-NMR (400 MHz, DMSO-d$_6$) δ [ppm]=3.80 (s, 2H), 7.14-7.24 (m, 2H), 7.30-7.47 (m, 5H), 7.68-7.75 (m, 1H), 7.87 (dd, 1H), 8.33-8.44 (m, 2H), 8.57 (d, 1H), 10.69 (s, 1H).

Example 363

2-(2-Chlorophenyl)-N-[4-(5-methyl-1-phenyl-1H-pyrazol-4-yl)-3-sulfamoylphenyl]-acetamide

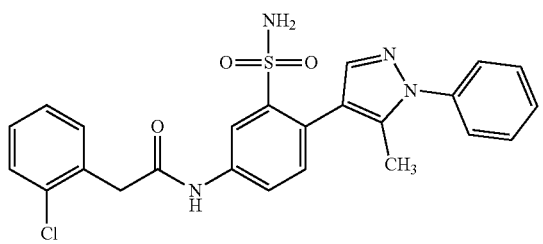 [SMILES: Cc1c(-c2ccc(NC(=O)Cc3ccccc3Cl)cc2S(N)(=O)=O)cnn1-c1ccccc1]

2-Chloro-N-[(dimethylamino)methylidene]-5-nitrobenzenesulfonamide (170 mg, 583 µmol) and 5-methyl-1-phenyl-4-(4,4,5,5-tetramethyl-1,3,2-dioxaborolan-2-yl)-1H-pyrazole (248 mg, 874 µmol) were dissolved in n-propanol (7.8 ml) and bis(triphenylphosphine)palladium(II) dichloride (CAS 13965-03-2) (20.5 mg, 29.1 µmol), triphenylphosphine (7.64 mg, 29.1 µmol) and aq. potassium carbonate solution (730 µl, 2.0 M, 1.5 mmol) were added. The reaction was heated at 80° C. for 16 h. Afterwards the mixture was filtered over Celite, the solvent was removed under reduced pressure and the crude was co-distilled with THF and used without further purification in the next step (210 mg). The protecting group was partially removed under the reaction conditions. The mixture was subjected to the next steps.

2-(5-Methyl-1-phenyl-1H-pyrazol-4-yl)-5-nitrobenzenesulfonamide (210 mg, 586 µmol) was dissolved in methanol (30 ml) and THF (59 ml) and the flask was flushed with nitrogen. Palladium on charcoal (10% loading, 63.6 mg, 598 µmol) was added and the flask was evacuated and subsequently flushed with hydrogen (1 bar). Stirring was continued at room temperature for 16 h. The reaction mixture was filtered over Celite and the solvent was removed under reduced pressure. The crude was used without further purification in the next step (190 mg).

5-Amino-2-(5-methyl-1-phenyl-1H-pyrazol-4-yl)benzenesulfonamide (190 mg, 579 µmol) was dissolved in DMF (4.1 ml) and (2-chlorophenyl)acetic acid (118 mg, 694 µmol) was added followed by the addition of N,N-diisopropylethylamine (500 µl, 2.9 mmol) and HATU (352 mg, 926 µmol). The reaction was stirred at 50° C. for 16 h. Water and dichloromethane were added. The phases were separated and the aqueous phase was extracted with dichloromethane. The combined organic phases were dried over Whatman filter and the solvent was removed under reduced pressure. The crude was dissolved in methanol (5 ml) and treated with 32% aqueous sodium hydroxide (130 µl) at 45° C. until the deprotection was complete. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Waters XBrigde C18 5µ 100×30 mm, acetonitrile/water+0.2% aqueous ammonia (32%)) then Waters XBrigde C18 5µ 100×30 mm, acetonitrile/water+0.1% formic acid) to yield the title compound (10.0 mg, 95% purity, 3% yield over 3 steps).

LC-MS (Method A): Rt=1.35 min; MS (ESIneg): m/z=479 [M−H]⁻

$^1$H-NMR (400 MHz, DMSO-$d_6$) δ [ppm]=2.16 (s, 3H), 3.89 (s, 2H), 7.05 (s, 2H), 7.27-7.37 (m, 3H), 7.40-7.49 (m, 3H), 7.51-7.62 (m, 4H), 7.65 (s, 1H), 7.84-7.93 (m, 1H), 8.35 (d, 1H), 10.63 (s, 1H).

Example 364

4'-{[(2-Chlorophenyl)acetyl]amino}-N-[2-(dimethylamino)ethyl]-2'-sulfamoylbiphenyl-3-carboxamide

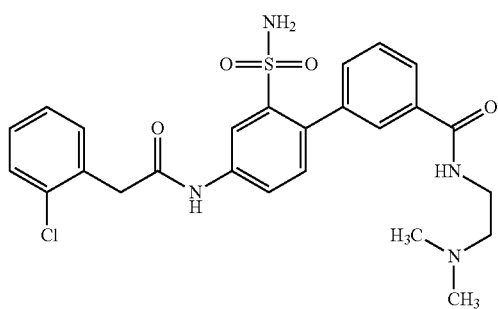 [SMILES: CN(C)CCNC(=O)c1cccc(-c2ccc(NC(=O)Cc3ccccc3Cl)cc2S(N)(=O)=O)c1]

N-(4-Bromo-3-{[(dimethylamino)methylidene]sulfamoyl}phenyl)-2-(2-chlorophenyl)-acetamide (300 mg, 654 µmol) and N-[2-(dimethylamino)ethyl]-3-(4,4,5,5-tetramethyl-1,3,2-dioxaborolan-2-yl)benzamide (229 mg, 719 µmol) were dissolved in n-propanol (13 ml) and bis(triphenylphosphine)palladium(II) dichloride (CAS 13965-03-2) (23.0 mg, 32.7 µmol) and triphenylphosphine (8.58 mg, 32.7 µmol) were added. The solution was purged with argon for 5 minutes and aq. potassium carbonate solution (2.0 ml, 1.0 M, 2.0 mmol) was added.

The reaction was heated at 100° C. for 2 h. Afterwards the mixture was filtered over Celite, the solvent was removed under reduced pressure and the crude was partitioned between ethyl acetate and water. The phases were separated and the aqueous phase was extracted with ethyl acetate. The combined organic phases were dried over Whatman filter and the solvent was removed under reduced pressure. The crude was used in the next step without further purification (350 mg).

4'-{[(2-Chlorophenyl)acetyl]amino}-N-[2-(dimethylamino)ethyl]-2'-{[(dimethylamino)-methylidene]sulfamoyl}biphenyl-3-carboxamide (350 mg, 614 µmol) was dissolved in methanol (40 ml) and treated with 25% aqueous ammonia solution (40 ml) at room temperature until completion of the reaction. The solvent was removed under reduced pressure and the crude was purified by HPLC (Chromatorex C-18 10 µm, 125×30 mm, acetonitrile/water+0.2% aqueous ammonia (32%)) to yield the title compound (19.5 mg, 96% purity, 6% yield over 2 steps).

LC-MS (Method B): Rt=0.95 min; MS (ESIneg): m/z=513 [M−H]⁻

$^1$H-NMR (600 MHz, DMSO-$d_6$) δ [ppm]=2.20 (s, 6H), 2.44 (t, 2H), 3.34-3.40 (m, 2H), 3.90 (s, 2H), 7.17 (s, 2H), 7.28 (d, 1H), 7.30-7.36 (m, 2H), 7.42-7.49 (m, 3H), 7.51-7.58 (m, 1H), 7.76-7.86 (m, 3H), 8.16 (s, 1H), 8.31-8.44 (m, 2H), 10.63 (s, 1H).

Example 365

2-(2-Chlorophenyl)-N-[4-(pyrazolo[1,5-a]pyrimidin-3-yl)-3-sulfamoylphenyl]acetamide

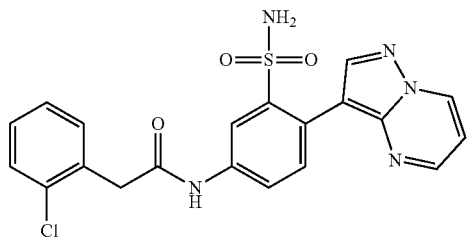 [SMILES: NS(=O)(=O)c1cc(NC(=O)Cc2ccccc2Cl)ccc1-c1cnn2cccnc12]

2-Bromo-N-[(dimethylamino)methylidene]-5-nitrobenzenesulfonamide (229 mg, 680 µmol) and 3-(4,4,5,5-tetramethyl-1,3,2-dioxaborolan-2-yl)pyrazolo[1,5-a]pyrimidine (250 mg, 1.02 mmol) were dissolved in n-propanol (9.1 ml) and bis(triphenylphosphine)palladium(II) dichloride (CAS 13965-03-2) (23.9 mg, 34.0 µmol), triphenylphosphine (8.92 mg, 34.0 µmol) and aq. potassium carbonate solution (850 µl, 2.0 M, 1.7 mmol) were added. The solution was purged with argon for 5 minutes and the reaction was heated at 80° C. for 4 h. Afterwards the mixture was filtered over Celite, the solvent was removed under reduced pressure and the crude was partitioned between dichloromethane and water. The phases were separated and the aqueous phase was extracted with dichloromethane. The combined organic phases were dried over Whatman filter and the solvent was removed under reduced pressure. The crude was co-distilled with THF and used in the next step without further purification (260 mg).

N-[(Dimethylamino)methylidene]-5-nitro-2-(pyrazolo[1,5-a]pyrimidin-3-yl)benzenesulfonamide (260 mg, 694 µmol) was dissolved in methanol (30 ml) and THF (70 ml) and the flask was flushed with nitrogen. Palladium on charcoal (10% loading, 75.4 mg, 708 µmol) was added and the flask was evacuated and subsequently flushed with hydrogen (1 bar). Stirring was continued at room temperature for 16 h. The reaction mixture was filtered over Celite and the solvent was removed under reduced pressure. The crude was used without further purification in the next step.

5-Amino-N-[(dimethylamino)methylidene]-2-(pyrazolo[1,5-a]pyrimidin-3-yl)benzenesulfonamide (330 mg, 958 µmol) was dissolved in DMF (6.7 ml) and (2-chlorophenyl)acetic acid (196 mg, 1.15 mmol) was added followed by the addition of N,N-diisopropylethylamine (830µ, 4.8 mmol) and HATU (583 mg, 1.53 mmol). The reaction was stirred at 50° C. for 16 h. Water and dichloromethane were added. The phases were separated and the aqueous phase was extracted with dichloromethane. The combined organic phases were dried over Whatman filter and the solvent was removed under reduced pressure. The crude was used in the next step without further purification (480 mg).

2-(2-Chlorophenyl)-N-[3-{[(dimethylamino)methylidene]sulfamoyl}-4-(pyrazolo[1,5-a]-pyrimidin-3-yl)phenyl]acetamide (450 mg, 905 µmol) was dissolved in methanol (10 ml) and treated with 32% aqueous sodium hydroxide (100 µl) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Waters XBrigde C18 5µ 100×30 mm, acetonitrile/water+0.2% aqueous ammonia (32%)) to yield the title compound (9.60 mg, 95% purity, 2% yield over 4 steps).

LC-MS (Method B): Rt=0.90 min; MS (ESIneg): m/z=440 [M−H]⁻

$^1$H-NMR (400 MHz, DMSO-d$_6$) δ [ppm]=3.90 (s, 2H), 7.05-7.13 (m, 1H), 7.23 (s, 2H), 7.29-7.38 (m, 2H), 7.43-7.50 (m, 2H), 7.57 (d, 1H), 7.83-7.91 (m, 1H), 8.40 (d, 1H), 8.44 (s, 1H), 8.51-8.61 (m, 1H), 9.11-9.21 (m, 1H), 10.64 (s, 1H).

Example 366

2-(2-Chlorophenyl)-N-{4-[5-(pyrrolidin-1-ylcarbonyl)pyridin-3-yl]-3-sulfamoylphenyl}acetamide

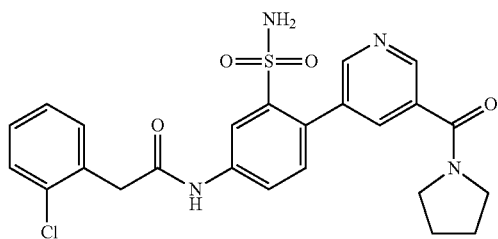 [SMILES: NS(=O)(=O)c1cc(NC(=O)Cc2ccccc2Cl)ccc1-c1cncc(C(=O)N2CCCC2)c1]

N-(4-Bromo-3-{[(dimethylamino)methylidene]sulfamoyl}phenyl)-2-(2-chlorophenyl)acetamide (250 mg, 545 µmol) and pyrrolidin-1-yl[5-(4,4,5,5-tetramethyl-1,3,2-dioxaborolan-2-yl)pyridin-3-yl]methanone (165 mg, 545 µmol) were dissolved in DMF (10 ml) and bis(triphenylphosphine)palladium(II) dichloride (CAS 13965-03-2) (19.2 mg, 27.2 µmol), triphenylphosphine (7.15 mg, 27.2 µmol) were added. The solution was purged with argon for 5 minutes and aq. potassium carbonate solution (1.6 ml, 1.0 M, 1.6 mmol) was added. The reaction was heated at 100° C. for 1 h. Afterwards the mixture was filtered over Celite, the solvent was removed under reduced pressure and ethyl acetate and water were added. The phases were separated and the aqueous phase was washed with ethyl acetate. The combined organic phases were dried over Whatman filter and the solvent was removed under reduced pressure. The crude was used in the next step without further purification (280 mg).

2-(2-Chlorophenyl)-N-(3-{[(dimethylamino)methylidene]sulfamoyl}-4-[5-(pyrrolidin-1-ylcarbonyl)pyridin-3-yl]phenyl)acetamide (280 mg, 505 µmol) was dissolved in methanol (25 ml) and treated with 25% aqueous ammonia solution (25 ml) at room temperature until completion of the reaction. The solvent was removed under reduced pressure and the crude was purified by HPLC (Chromatorex C-18 10 µm, 125×30 mm, acetonitrile/water+0.2% aqueous ammonia (32%)) to yield the title compound (67.3 mg, 97% purity, 26% yield over 2 steps).

LC-MS (Method B): Rt=0.89 min; MS (ESIneg): m/z=497 [M−H]⁻

$^1$H-NMR (400 MHz, DMSO-d$_6$) δ [ppm]=1.73-1.99 (m, 4H), 3.43-3.52 (m, 4H), 3.91 (s, 2H), 7.29-7.37 (m, 3H), 7.38-7.43 (m, 2H), 7.43-7.49 (m, 2H), 7.82-7.89 (m, 2H), 8.40 (d, 1H), 8.58 (d, 1H), 8.68 (d, 1H), 10.71 (s, 1H).

Example 367

2-(2-Chlorophenyl)-N-[4-(1H-pyrazol-4-yl)-3-sulfamoylphenyl]acetamide

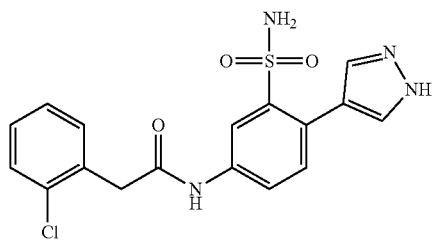 [SMILES: NS(=O)(=O)c1cc(NC(=O)Cc2ccccc2Cl)ccc1-c1cn[nH]c1]

2-(2-Chlorophenyl)-N-{3-sulfamoyl-4-[1-(tetrahydro-2H-pyran-2-yl)-1H-pyrazol-4-yl]phenyl}acetamide (197 mg, 414 µmol) was dissolved in dichloromethane (5 ml) and trifluoroacetic acid (950 µl, 12 mmol) was added and stirring was continued at room temperature until completion of the reaction. Water and dichloromethane were added. The phases were separated and the aqueous phase was extracted with dichloromethane. The combined organic phases were dried over Whatman filter and the solvent was removed under reduced pressure. The crude was purified by HPLC (Waters XBrigde C18 5µ 100×30 mm, acetonitrile/water+0.1% formic acid) to yield the title compound (30.9 mg, 95% purity, 18% yield).

LC-MS (Method A): Rt=0.89 min; MS (ESIneg): m/z=389 [M−H]⁻

$^1$H-NMR (400 MHz, DMSO-de) δ [ppm]=3.88 (s, 2H), 7.15 (s, 2H), 7.29-7.37 (m, 2H), 7.42-7.48 (m, 3H), 7.70-7.91 (m, 2H), 7.91-8.11 (m, 1H), 8.33 (d, 1H), 10.57 (s, 1H), 12.92 (s, 1H).

Example 368

2-(2-Fluorophenyl)-N-{4-[1-methyl-3-(trifluoromethyl)-1H-pyrazol-5-yl]-3-sulfamoylphenyl}acetamide

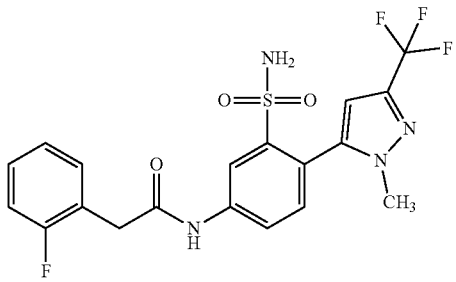 [SMILES: Cn1nc(C(F)(F)F)cc1-c1ccc(NC(=O)Cc2ccccc2F)cc1S(N)(=O)=O]

2-Chloro-N-[(dimethylamino)methylidene]-5-nitrobenzenesulfonamide (550 mg, 1.89 mmol) and 1-methyl-5-(4,4,5,5-tetramethyl-1,3,2-dioxaborolan-2-yl)-3-(trifluoromethyl)-1H-pyrazole (1.04 g, 3.77 mmol) were dissolved in n-propanol (25 ml) and bis(triphenylphosphine)palladium (II) dichloride (CAS 13965-03-2) (66.4 mg, 94.3 μmol), triphenylphosphine (24.7 mg, 94.3 μmol) and aq. potassium carbonate solution (2.4 ml, 2.0 M, 4.7 mmol) were added. The solution was purged with argon for 5 minutes and the reaction was heated at 80° C. for 16 h. Afterwards the mixture was filtered over Celite, the solvent was removed under reduced pressure and the crude was co-distilled with THE and used without further purification in the next step (660 mg).

2-[1-Methyl-3-(trifluoromethyl)-1H-pyrazol-5-yl]-5-nitrobenzenesulfonamide (660 mg, 1.88 mmol) was dissolved in methanol (30 ml) and THE (30 ml) and the flask was flushed with nitrogen. Platinum on charcoal (5% loading, 375 mg, 1.92 mmol) was added and the flask was evacuated and subsequently flushed with hydrogen (1 bar). Stirring was continued at room temperature for 4 h. The reaction mixture was filtered over Celite and the solvent was removed under reduced pressure. The crude was used without further purification in the next step (600 mg). Partial deprotection was observed under the reaction conditions, the mixture was taken to the next steps.

5-Amino-2-[1-methyl-3-(trifluoromethyl)-1H-pyrazol-5-yl]benzenesulfonamide (300 mg, 937 μmol) was dissolved in DMF (7.8 ml) and (2-fluorophenyl)acetic acid (173 mg, 1.12 mmol) was added followed by the addition of N,N-diisopropylethylamine (820 μl, 4.7 mmol) and HATU (570 mg, 1.50 mmol). The reaction was stirred at 50° C. for 18 h. Water and dichloromethane were added. The phases were separated and the aqueous phase was extracted with dichloromethane. The combined organic phases were dried over Whatman filter and the solvent was removed under reduced pressure.

The crude was dissolved in methanol (20 ml) and treated with 32% aqueous sodium hydroxide (1.6 ml) at 80° C. for 2 h. The reaction was neutralized and the solvent was removed under reduced pressure. The residue was dissolved in dichloromethane and washed with water. The phases were separated and the combined organic phases were dried over Whatman filter and the solvent was removed under reduced pressure. The crude was purified by HPLC (Waters XBrigde C18 5μ 100×30 mm, acetonitrile/water+0.2% aqueous ammonia (32%) then Waters XBrigde C18 5μ 100×30 mm, acetonitrile/water+0.1% formic acid) to yield the title compound (10.2 mg, 95% purity, 2% yield over 3 steps).

LC-MS (Method A): Rt=1.10 min; MS (ESIneg): m/z=455 [M−H]⁻

$^1$H-NMR (400 MHz, DMSO-d$_6$): δ [ppm]=3.58 (s, 3H), 3.80 (s, 2H), 6.72 (s, 1H), 7.14-7.25 (m, 2H), 7.29-7.48 (m, 5H), 7.84-7.93 (m, 1H), 8.40 (d, 1H), 10.77 (s, 1H).

Example 369

2-(2-Fluorophenyl)-N-{4-[1-(2-methoxyethyl)-1H-pyrazol-4-yl]-3-sulfamoylphenyl}acetamide

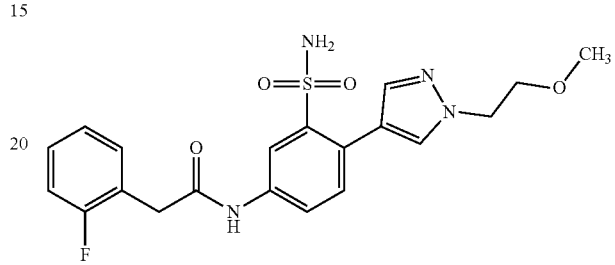

5-Amino-2-[1-(2-methoxyethyl)-1H-pyrazol-4-yl]benzenesulfonamide (190 mg, 641 μmol) was dissolved in DMF (5.3 ml) and (2-fluorophenyl)acetic acid (119 mg, 769 μmol) was added followed by the addition of N,N-diisopropylethylamine (560 μl, 3.2 mmol) and HATU (390 mg, 1.03 mmol). The reaction was stirred at 50° C. for 16 h, then water and dichloromethane were added. The phases were separated and the aqueous phase was extracted with dichloromethane. The combined organic phases were dried over Whatman filter and the solvent was removed under reduced pressure. The crude was purified by HPLC (Waters XBrigde C18 5μ 100×30 mm, acetonitrile/water+0.2% aqueous ammonia (32%)) to yield the title compound (66.4 mg, 95% purity, 23% yield).

LC-MS (Method B): Rt=0.96 min; MS (ESIneg): m/z=529 [M−H]⁻

$^1$H-NMR (400 MHz, DMSO-d$_6$) δ [ppm]=3.24 (s, 3H), 3.70 (t, 2H), 3.77 (s, 2H), 4.28 (t, 2H), 7.09 (s, 2H), 7.14-7.25 (m, 2H), 7.29-7.48 (m, 3H), 7.70 (s, 1H), 7.81 (dd, 1H), 8.01 (s, 1H), 8.31 (d, 1H), 10.55 (s, 1H).

Example 370

2-(2-Chlorophenyl)-N-{4-[1-(2-hydroxy-2-methylpropyl)-1H-pyrazol-4-yl]-3-sulfamoylphenyl}acetamide

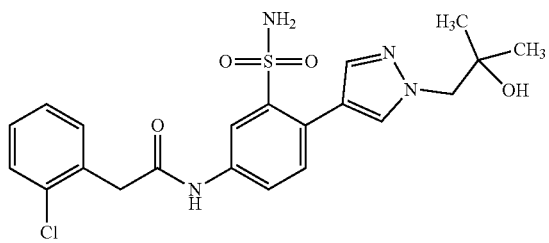 [SMILES: CC(C)(O)Cn1cc(-c2ccc(NC(=O)Cc3ccccc3Cl)cc2S(N)(=O)=O)cn1]

2-(2-Chlorophenyl)-N-[3-{[(dimethylamino)methylidene]sulfamoyl}-4-(1H-pyrazol-4-yl)-phenyl]acetamide (180 mg, 404 μmol) was dissolved in DMF (4 ml), 2,2-dimethyloxirane (1.3 ml, 14 mmol) and cesium carbonate (263 mg, 807 μmol) were added and the reaction was heated for 30 minutes at 130° C. in the microwave (2 bar/35 W). Afterwards the mixture was filtered, the solvent was removed under reduced pressure and the crude was used without further purification in the next step (250 mg).

2-(2-Chlorophenyl)-N-(3-{[(dimethylamino)methylidene]sulfamoyl}-4-[1-(2-hydroxy-2-methylpropyl)-1H-pyrazol-4-yl]phenyl)acetamide (250 mg, 483 μmol) was dissolved in methanol (5.0 ml) and treated with 32% aqueous sodium hydroxide (270 μl) at 80° C. until completion of the reaction. The solvent was removed under reduced pressure, the crude was dissolved in dichloromethane and washed with water. The phases were separated and the combined organic phases were dried over Whatman filter and the solvent was removed under reduced pressure. The crude was purified by HPLC (Waters XBrigde C18 5μ 100×30 mm, acetonitrile/water+0.2% aqueous ammonia (32%) then Chromatorex C-18 μm, 125×30 mm, acetonitrile/water+0.2% aqueous ammonia (32%)) to yield the title compound (2.60 mg, 95% purity, 1% yield over 2 steps).

LC-MS (Method B): Rt=0.88 min; MS (ESIneg): m/z=461 [M−H]⁻

$^1$H-NMR (400 MHz, DMSO-$d_6$) δ [ppm]=1.09 (s, 6H), 3.88 (s, 2H), 4.04 (s, 2H), 4.77 (s, 1H), 7.04 (s, 2H), 7.29-7.37 (m, 2H), 7.41-7.50 (m, 3H), 7.67 (s, 1H), 7.83 (dd, 1H), 8.02 (s, 1H), 8.32 (d, 1H), 10.57 (s, 1H).

Example 371

2-(5-Chloro-2-fluorophenyl)-N-[4-(1-cyclopropyl-1H-pyrazol-4-yl)-3-sulfamoylphenyl]acetamide

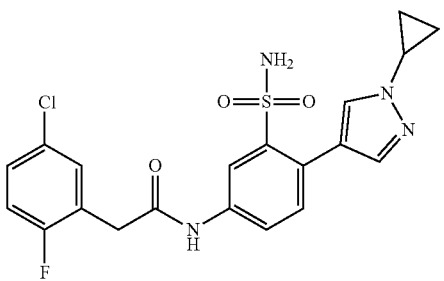 [SMILES: NS(=O)(=O)c1cc(NC(=O)Cc2cc(Cl)ccc2F)ccc1-c1cnn(C2CC2)c1]

5-Amino-2-(1-cyclopropyl-1H-pyrazol-4-yl)-N-[(dimethylamino)methylidene]benzenesulfonamide (200 mg, 600 μmol) was dissolved in DMF (10 ml) and (5-chloro-2-fluorophenyl)acetic acid (136 mg, 720 μmol) was added followed by the addition of N,N-diisopropylethylamine (520 μl, 3.0 mmol) and HATU (456 mg, 1.20 mmol). The reaction was stirred at 50° C. for 16 h. Water and ethyl acetate were added. The phases were separated and the aqueous phase was extracted with ethyl acetate. The combined organic phases were dried over Whatman filter and the solvent was removed under reduced pressure. The crude was used in the next step without further purification. 2-(5-Chloro-2-fluorophenyl)-N-[4-(1-cyclopropyl-1H-pyrazol-4-yl)-3-{[(dimethylamino)methylidene]sulfamoyl}phenyl]acetamide (302 mg, 600 μmol) was dissolved in methanol (5.0 ml) and treated with 25% aqueous ammonia solution (5.0 ml) at room temperature. After 16 h, the same amount of ammonia was added and stirring was continued until completion of the reaction. The solvent was removed under reduced pressure and the crude was purified by HPLC (Waters XBrigde C18 5μ 100×30 mm, acetonitrile/water+0.2% aqueous ammonia (32%)) to yield the title compound (27.6 mg, 96% purity, 10% yield over steps).

LC-MS (Method B): Rt=0.99 min; MS (ESIneg): m/z=447 [M−H]⁻

$^1$H-NMR (600 MHz, CD$_3$OD) δ [ppm]=1.03-1.08 (m, 2H), 1.13-1.19 (m, 2H), 3.66-3.73 (m, 1H), 7.12 (t, 1H), 7.29-7.36 (m, 1H), 7.37-7.45 (m, 2H), 7.69 (s, 1H), 7.80 (dd, 1H), 7.97 (s, 1H), 8.37 (d, 1H).

Example 372

2-(2-Chlorophenyl)-N-[4-(6-methylpyridin-3-yl)-3-sulfamoylphenyl]acetamide

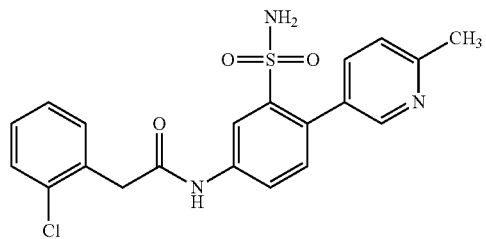 [SMILES: Cc1ccc(-c2ccc(NC(=O)Cc3ccccc3Cl)cc2S(N)(=O)=O)cn1]

2-Bromo-N-[(dimethylamino)methylidene]-5-nitrobenzenesulfonamide (200 mg, 595 μmol) and 2-methyl-5-(4,4,5,5-tetramethyl-1,3,2-dioxaborolan-2-yl)pyridine (261 mg, 1.19 mmol) were dissolved in n-propanol (55 ml) and bis(triphenylphosphine)palladium(II) dichloride (CAS 13965-03-2) (20.9 mg, 29.7 μmol), triphenylphosphine (10.8 mg, 29.7 μmol) and aq. potassium carbonate solution (890 μl, 2.0 M, 1.8 mmol) were added. The solution was purged with argon for 5 minutes and heated at 120° C. for 1 h in the microwave. Afterwards the mixture was filtered over Celite, the solvent was removed under reduced pressure and the crude was co-distilled with THF and used without further purification in the next step. Deprotection was observed under the reaction conditions and the free sulfonamide was taken to the next steps.

2-(6-Methylpyridin-3-yl)-5-nitrobenzenesulfonamide (450 mg, 1.53 mmol) was dissolved in methanol (70 ml) and the flask was flushed with nitrogen. Palladium on charcoal (10% loading, 167 mg, 1.56 mmol) was added and the flask was evacuated and subsequently flushed with hydrogen (1 bar). Stirring was continued at room temperature for 4 h. The reaction mixture was filtered over Celite and the solvent was removed under reduced pressure. The crude was co-distilled with THF and used without further purification in the next step (400 mg).

5-Amino-2-(6-methylpyridin-3-yl)benzenesulfonamide (200 mg, 760 μmol) was dissolved in DMF (5.3 ml) and (2-chlorophenyl)acetic acid (155 mg, 911 μmol) was added followed by the addition of N,N-diisopropylethylamine (630 μl, 3.8 mmol) and HATU (462 mg, 1.22 mmol). The reaction was stirred at 50° C. for 16 h. Water and dichloromethane were added. The phases were separated and the aqueous phase was extracted with dichloromethane. The combined organic phases were dried over Whatman filter and the solvent was removed under reduced pressure. The crude was purified by HPLC (Waters XBrigde C18 5μ 100×30 mm, acetonitrile/water+0.2% aqueous ammonia (32%)) to yield the title compound (33.3 mg, 95% purity, 10% yield over 3 steps).

LC-MS (Method B): Rt=0.94 min; MS (ESIneg): m/z=414 [M−H]⁻

¹H-NMR (400 MHz, DMSO-d₆) δ [ppm]=1.11 (s, 3H), 3.89 (s, 2H), 7.20-7.39 (m, 6H), 7.42-7.52 (m, 2H), 7.62-7.70 (m, 1H), 7.78-7.89 (m, 1H), 8.31-8.44 (m, 2H), 10.66 (s, 1H).

Example 373

2-(2-Chlorophenyl)-N-{4-[1-(oxetan-3-yl)-1H-pyrazol-4-yl]-3-sulfamoylphenyl}-acetamide

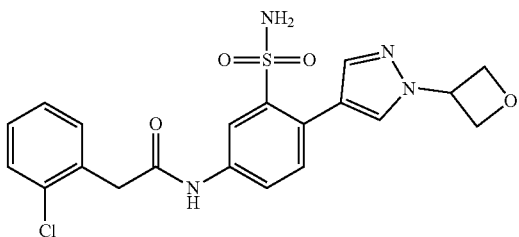 [SMILES: NS(=O)(=O)c1cc(NC(=O)Cc2ccccc2Cl)ccc1-c1cnn(C2COC2)c1]

2-Bromo-5-nitrobenzenesulfonamide (100 mg, 356 µmol) and 1-(oxetan-3-yl)-4-(4,4,5,5-tetramethyl-1,3,2-dioxaborolan-2-yl)-1H-pyrazole (107 mg, 427 µmol) were dissolved in n-propanol (4.8 ml) and bis(triphenylphosphine)palladium (II) dichloride (CAS 13965-03-2) (12.5 mg, 17.8 µmol), triphenylphosphine (4.67 mg, 17.8 µmol) and aq. potassium carbonate solution (530 µl, 2.0 M, 1.1 mmol) were added. The solution was purged with argon for 5 minutes and the reaction was heated at 120° C. for 1 h in the microwave (4 bar/40 W). Afterwards the mixture was filtered over Celite, the solvent was removed under reduced pressure and the crude was co-distilled with methanol and used without further purification in the next step (120 mg).

5-Nitro-2-[1-(oxetan-3-yl)-1H-pyrazol-4-yl]benzenesulfonamide (120 mg, 370 µmol) was dissolved in THF (37 ml) and the flask was flushed with nitrogen. Palladium on charcoal (10% loading, 40.2 mg, 377 µmol) was added and the flask was evacuated and subsequently flushed with hydrogen (1 bar). Stirring was continued at room temperature for 4 h. The reaction mixture was filtered over Celite and the solvent was removed under reduced pressure. The crude was used without further purification in the next step (110 mg). 5-Amino-2-[1-(oxetan-3-yl)-1H-pyrazol-4-yl]benzenesulfonamide (110 mg, 374 µmol) was dissolved in DMF (2.6 ml) and (2-chlorophenyl)acetic acid (76.5 mg, 448 µmol) was added followed by the addition of N,N-diisopropylethylamine (330 µl, 1.9 mmol) and HATU (227 mg, 598 µmol). The reaction was stirred at 50° C. for 18 h. Water and dichloromethane were added. The phases were separated and the aqueous phase was extracted with dichloromethane. The combined organic phases were dried over Whatman filter and the solvent was removed under reduced pressure. The crude was purified by HPLC (Waters XBrigde C18 5µ 100×30 mm, methanol/water+0.2% aqueous ammonia (32%)) to yield the title compound (38.6 mg, 95% purity, 22% yield over 3 steps).

LC-MS (Method J): Rt=1.09 min; MS (ESIneg): m/z=445 [M−H]⁻

¹H-NMR (400 MHz, DMSO-d₆) δ [ppm]=3.88 (s, 2H), 4.86-5.00 (m, 4H), 5.54-5.68 (m, 1H), 7.19 (s, 2H), 7.29-7.37 (m, 2H), 7.40-7.51 (m, 3H), 7.78-7.86 (m, 2H), 8.11 (s, 1H), 8.27-8.35 (m, 1H), 10.58 (s, 1H).

Example 374

2-(2-Fluorophenyl)-N-[4-(1-methyl-1H-pyrazol-4-yl)-3-sulfamoylphenyl]acetamide

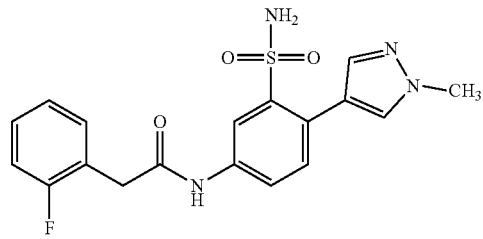

5-Amino-2-(1-methyl-1H-pyrazol-4-yl)benzenesulfonamide (200 mg, 793 µmol) was dissolved in DMF (6.6 ml) and (2-fluorophenyl)acetic acid (147 mg, 951 µmol) was added followed by the addition of N,N-diisopropylethylamine (350 µl, 4.0 mmol) and HATU (482 mg, 1.27 mmol). The reaction was stirred at 50° C. for 18 h. Water and dichloromethane were added. The phases were separated and the aqueous phase was extracted with ethyl acetate. The combined organic phases were dried over Whatman filter and the solvent was removed under reduced pressure. The crude was purified by HPLC (Waters XBrigde C18 5µ 100×30 mm, acetonitrile/water+0.1% formic acid) to yield the title compound (75.6 mg, 95% purity, 23% yield).

LC-MS (Method A): Rt=0.90 min; MS (ESIneg): m/z=387 [M−H]⁻

¹H-NMR (400 MHz, DMSO-d₆) δ [ppm]=3.76 (s, 2H), 3.86 (s, 3H), 7.12-7.27 (m, 4H), 7.30-7.44 (m, 3H), 7.66 (d, 1H), 7.77-7.86 (m, 1H), 7.95 (s, 1H), 8.30 (d, 1H), 10.55 (s, 1H).

Example 375

N-[4-(1,3-Dimethyl-1H-pyrazol-4-yl)-3-sulfamoylphenyl]-2-(2-fluorophenyl)acetamide

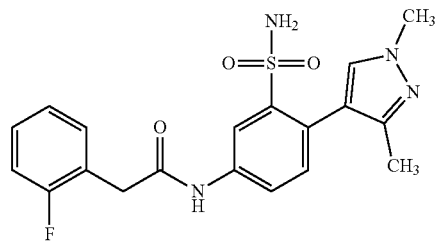 [SMILES: Cc1nn(C)cc1-c1ccc(NC(=O)Cc2ccccc2F)cc1S(N)(=O)=O]

A mixture of (dimethylamino)methylene protected/unprotected starting material was used: 5-Amino-2-(1,3-dimethyl-1H-pyrazol-4-yl)benzenesulfonamide (250 mg, 939 µmol) was dissolved in DMF (7.8 ml) and (2-fluorophenyl)acetic acid (174 mg, 1.13 mmol) was added followed by the addition of N,N-diisopropylethylamine (820 µl, 4.7 mmol) and HATU (571 mg, 1.50 mmol). The reaction was stirred at 50° C. for 18 h. Dichloromethane and water were added. The phases were separated and the aqueous phase was extracted with dichloromethane. The combined organic phases were dried over Whatman filter and the solvent was removed under reduced pressure. The residue was redissolved in methanol (10 ml) and treated with 32% aqueous sodium hydroxide (0.2 ml) at 80° C. for 2 h. The reaction mixture was neutralized and water and dichloromethane were added. The phases were separated and the combined organic phases were dried over Whatman filter and the solvent was removed under reduced pressure. The crude was purified by (Waters XBrigde C18 5μ 100×30 mm, acetonitrile/water+0.2% aqueous ammonia (32%)) to yield the title compound (28.0 mg, 90% purity, 7% yield).

LC-MS (Method B): Rt=0.94 min; MS (ESIneg): m/z=456 [M−H]⁻

$^1$H-NMR (400 MHz, DMSO-d$_6$) δ [ppm]=1.99 (s, 3H), 3.77 (s, 5H), 6.91 (s, 2H), 7.14-7.25 (m, 3H), 7.29-7.46 (m, 2H), 7.59 (s, 1H), 7.77-7.85 (m, 1H), 8.29 (d, 1H), 10.56 (s, 1H).

Example 376

N-[4-(5-Cyclopropyl-1,3,4-oxadiazol-2-yl)-3-sulfamoylphenyl]-2-(2-fluorophenyl)-acetamide

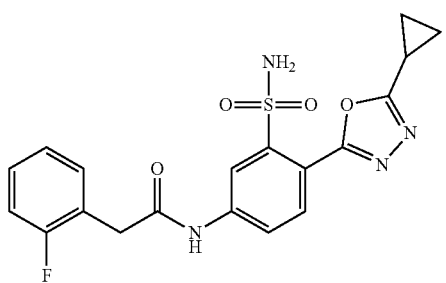

5-Amino-2-(5-cyclopropyl-1,3,4-oxadiazol-2-yl)-N-[(dimethylamino)methylidene]-benzenesulfonamide (100 mg, 298 μmol) was dissolved in DMF (5.0 ml) and (2-fluorophenyl)acetic acid (55.2 mg, 358 μmol) was added followed by the addition of N,N-diisopropylethylamine (260 μl, 1.5 mmol) and HATU (227 mg, 596 μmol). The reaction was stirred at room temperature for 2 h. Afterwards, the solvent was removed under reduced pressure and ethyl acetate and water were added. The phases were separated and the aqueous phase was extracted with ethyl acetate. The combined organic phases were dried over Whatman filter and the solvent was removed under reduced pressure. The crude was used without further purification in the next step (290 mg).

LC-MS (Method A): Rt=1.00 min; MS (ESIpos): m/z=472 [M+H]⁺

N-[4-(5-Cyclopropyl-1,3,4-oxadiazol-2-yl)-3-{[(dimethylamino)methylidene]sulfamoyl}-phenyl]-2-(2-fluorophenyl)acetamide (290 mg, 615 μmol) was dissolved in methanol (50 ml) and treated with concentrated ammonia solution (10 ml) at room temperature for 2 h. The solvent was removed under reduced pressure and the pure title compound was obtained after HPLC purification (Chromatorex C-18 10 μm, 125×30 mm, acetonitrile/water+0.2% aqueous ammonia (32%)) (56.8 mg, 98% purity, 22% yield over 2 steps).

LC-MS (Method A): Rt=1.02 min; MS (ESIpos): m/z=417 [M+H]⁺

$^1$H-NMR (400 MHz, DMSO-d$_6$) δ [ppm]=1.07-1.22 (m, 4H), 2.34 (tt, 1H), 3.82 (s, 2H), 7.15-7.24 (m, 2H), 7.30-7.38 (m, 1H), 7.41 (td, 1H), 7.62 (s, 2H), 7.88 (d, 1H), 7.99 (dd, 1H), 8.43 (d, 1H), 10.88 (s, 1H).

Example 377

2-(2-Chlorophenyl)-N-[4-(5-cyclopropyl-1,3,4-oxadiazol-2-yl)-3-sulfamoylphenyl]-acetamide

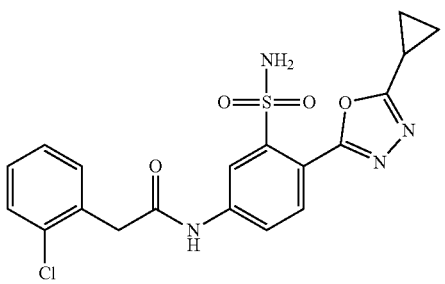 [SMILES: NS(=O)(=O)c1cc(NC(=O)Cc2ccccc2F)ccc1-c1nnc(C2CC2)o1]

5-Amino-2-(5-cyclopropyl-1,3,4-oxadiazol-2-yl)-N-[(dimethylamino)methylidene]benzenesulfonamide (100 mg, 298 μmol) was dissolved in DMF (5.0 ml) and (2-chlorophenyl)acetic acid (61.0 mg, 358 μmol) was added followed by the addition of N,N-diisopropylethylamine (260 μl, 1.5 mmol) and HATU (227 mg, 596 μmol). The reaction was stirred at room temperature for 2 h. Afterwards, 0.5 eq of all reagents was added and stirring was continued for 16 h at room temperature. Afterwards, the solvent was removed under reduced pressure and ethyl acetate and water were added. The phases were separated and the aqueous phase was extracted with ethyl acetate. The combined organic phases were dried over Whatman filter and the solvent was removed under reduced pressure. The crude was used without further purification in the next step (340 mg).

LC-MS (Method A): Rt=1.05 min; MS (ESIpos): m/z=488 [M+H]⁺

2-(2-Chlorophenyl)-N-[4-(5-cyclopropyl-1,3,4-oxadiazol-2-yl)-3-{[(dimethylamino)-methylidene]sulfamoyl}phenyl]acetamide (340 mg, 697 μmol) was dissolved in methanol (10 ml) and treated with concentrated ammonia solution (10 ml) at room temperature for 2 h. The solvent was removed under reduced pressure and the pure product was obtained after HPLC purification (Chromatorex C-18 10 μm, 125×30 mm, acetonitrile/water+0.1% formic acid) (56.6 mg, 93% purity, 17% yield over 2 steps).

LC-MS (Method A): Rt=1.06 min; MS (ESIpos): m/z=433 [M+H]⁺

$^1$H-NMR (400 MHz, DMSO-d$_6$) δ [ppm]=1.06-1.22 (m, 4H), 2.28-2.39 (m, 1H), 3.93 (s, 2H), 7.29-7.38 (m, 2H), 7.42-7.50 (m, 2H), 7.62 (s, 2H), 7.88 (d, 1H), 7.99 (dd, 1H), 8.44 (d, 1H), 10.90 (s, 1H).

Example 378

N-{4-[4-(Difluoromethyl)-1H-pyrazol-1-yl]-3-sulfamoylphenyl}-2-(2-fluorophenyl)acetamide

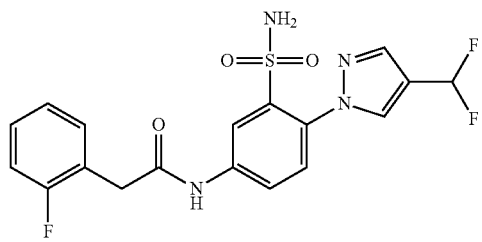 [SMILES: NS(=O)(=O)c1cc(NC(=O)Cc2ccccc2F)ccc1-n1cc(C(F)F)cn1]

According to general procedures GP2.3 and GP6.1 2-[4-(difluoromethyl)-1H-pyrazol-1-yl]-N-[(dimethylamino)methylene]-5-nitrobenzenesulfonamide (250 mg, 0.670 mmol), and (2-fluorophenyl)acetic acid (154 mg, 1.00 mmol) were converted without purification of intermediates to the title compound and were purified at the end by preparative HPLC (Waters XBridge C18 5μ 100×30 mm, acetonitrile/water+0.1% formic acid).

LC-MS (Method A): Rt=1.02 min, MS (ESIpos): m/z=425 [M+H]$^+$ $^1$H-NMR (400 MHz, DMSO-d$_6$) δ [ppm]: 3.80 (s, 2H), 7.11 (t, 1H), 7.15-7.23 (m, 2H), 7.30-7.47 (m, 4H), 7.56 (d, 1H), 7.97 (dd, 1H), 7.99 (d, 1H), 8.37 (d, 1H), 8.41-8.44 (m, 1H), 10.79 (s, 1H).

Example 379

2-(2-Chlorophenyl)-N-{4-[4-(difluoromethyl)-1H-pyrazol-1-yl]-3-sulfamoylphenyl}acetamide

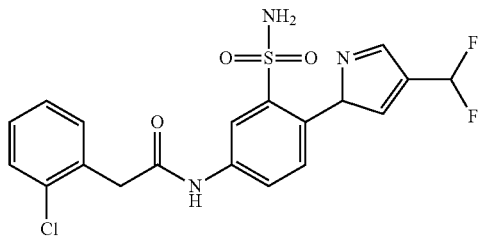 [SMILES: NS(=O)(=O)c1cc(NC(=O)Cc2ccccc2Cl)ccc1C1C=C(C(F)F)C=N1]

According to general procedures GP2.3 and GP6.1 2-[4-(difluoromethyl)-1H-pyrazol-1-yl]-N-[(dimethylamino)methylene]-5-nitrobenzenesulfonamide (250 mg, 0.670 mmol), and (2-chlorophenyl)acetic acid (154 mg, 1.00 mmol) were converted without purification of intermediates to the title compound and were purified at the end by preparative HPLC (Waters XBridge C18 5μ 100×30 mm, acetonitrile/water+0.1% formic acid).

LC-MS (Method A): Rt=1.05 min, MS (ESIpos): m/z=441 [M+H]$^+$ $^1$H-NMR (400 MHz, DMSO-d$_6$) δ [ppm]: 3.91 (s, 2H), 7.12 (t, 1H), 7.29-7.37 (m, 2H), 7.39-7.49 (m, 4H), 7.56 (d, 1H), 7.97 (dd, 1H), 7.99 (s, 1H), 8.38 (d, 1H), 8.41-8.44 (m, 1H), 10.81 (s, 1H).

Example 380

2-(2-Chlorophenyl)-N-{5-sulfamoyl-6-[4-(trifluoromethyl)-1H-pyrazol-1-yl]pyridin-3-yl}acetamide

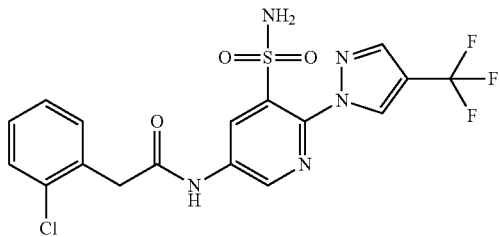 [SMILES: NS(=O)(=O)c1cc(NC(=O)Cc2ccccc2Cl)cnc1-n1cc(C(F)(F)F)cn1]

5-Amino-N-[(dimethylamino)methylidene]-2-[4-(trifluoromethyl)-1H-pyrazol-1-yl]pyridine-3-sulfonamide (250 mg, 690 μmol) and (2-chlorophenyl)acetic acid (177 mg, 1.03 mmol) were dissolved in DMF (10 ml) and N,N-diisopropylethylamine (600 μl, 3.4 mmol) and 2,4,6-tripropyl-1,3,5,2,4,6-trioxatriphosphinane 2,4,6-trioxide (310 μl, 1.0 mmol) were added successively. The reaction was stirred at room temperature over night. Afterwards, the solvent was removed under reduced pressure and ethyl acetate and water were added. The phases were separated and the organic phase was dried over Whatman filter. The solvent was removed under reduced pressure and the crude was used without further purification in the next step (400 mg).

2-(2-Chlorophenyl)-N-(5-{[(dimethylamino)methylidene]sulfamoyl}-6-[4-(trifluoromethyl)-1H-pyrazol-1-yl]pyridin-3-yl)acetamide (400 mg, 777 μmol) was dissolved in methanol (37 ml) and treated with 40% aqueous sodium hydroxide solution (24 μl, 1.9 mmol) for 1 h at 50° C. Afterwards, the solvent was removed under reduced pressure and the crude was purified by HPLC chromatography (Chromatorex C-18 10 μm, 125×30 mm, acetonitrile/water+0.2% aqueous ammonia (32%)) to yield 3.8 mg of the title compound (95% purity, 1% yield over 2 steps).

LC-MS (Method B): Rt=0.93 min; MS (ESIpos): m/z=460 [M+H]$^+$ $^1$H-NMR (400 MHz, DMSO-d$_6$) δ [ppm]=3.95 (s, 2H), 7.29-7.39 (m, 2H), 7.43-7.52 (m, 2H), 7.61 (s, 2H), 8.24 (s, 1H), 8.86 (d, 1H), 8.91 (d, 1H), 8.97 (d, 1H), 11.06 (s, 1H).

Example 381

2-(2-Fluorophenyl)-N-{5-sulfamoyl-6-[4-(trifluoromethyl)-1H-pyrazol-1-yl]pyridin-3-yl}acetamide

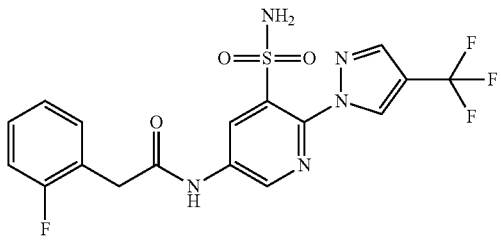 [SMILES: NS(=O)(=O)c1cc(NC(=O)Cc2ccccc2F)cnc1-n1cc(C(F)(F)F)cn1]

The title compound was obtained analoguous to Example 380 starting from 5-amino-N-[(dimethylamino)methylidene]-2-[4-(trifluoromethyl)-1H-pyrazol-1-yl]pyridine-3-sulfonamide (250 mg, 690 μmol) in 2 steps after HPLC purification (Chromatorex C-18 10 μm, 125×30 mm, acetonitrile/water+0.2% aqueous ammonia (32%)) (12.8 mg, 90% purity, 4% yield).

LC-MS (Method B): Rt=0.90 min; MS (ESIpos): m/z=444 [M+H]$^+$ $^1$H-NMR (400 MHz, DMSO-d6) δ [ppm]=3.85 (s, 2H), 7.13-7.26 (m, 2H), 7.29-7.47 (m, 2H), 7.61 (s, 2H), 8.23 (s, 1H), 8.86 (d, 1H), 8.91 (d, 1H), 8.97 (s, 1H), 11.04 (s, 1H).

Example 382

N-[6-(4-Cyano-1H-pyrazol-1-yl)-5-sulfamoylpyridin-3-yl]-2-(2-fluorophenyl)acetamide

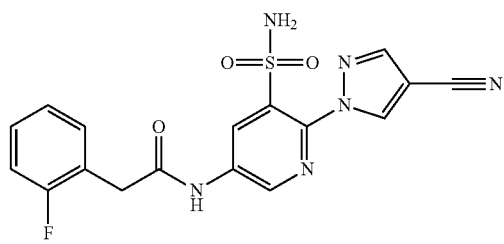

According to general procedure GP6.1, crude 5-amino-2-(4-cyano-1H-pyrazol-1-yl)-N-[(dimethylamino)methylene]pyridine-3-sulfonamide (200 mg) and (2-fluorophenyl)acetic acid (145 mg, 0.94 mmol) were converted without purification of intermediates to the title compound and were purified at the end by preparative HPLC (Chromatorex C-18 10 μm, 125×30 mm, acetonitrile/water+0.1% formic acid) (13 mg, 0.0325 mmol, 2% yield over 5 steps, 99% purity).

LC-MS (Method A): Rt=0.96 min, MS (ESIpos): m/z=401 [M+H]$^+$ $^1$H-NMR (400 MHz, DMSO-d$_6$) δ [ppm]: 3.85 (s, 2H), 7.16-7.23 (m, 2H), 7.30-7.38 (m, 1H), 7.42 (td, 1H), 7.63 (s, 2H), 8.35 (d, 1H), 8.87 (d, 1H), 8.89 (d, 1H), 9.10 (d, 1H), 11.06 (s, 1H).

Example 383

2-(2-Chlorophenyl)-N-[6-(4-cyano-1H-pyrazol-1-yl)-5-sulfamoylpyridin-3-yl]acetamide

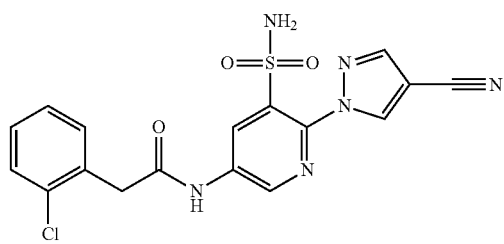 [SMILES: N#Cc1cnn(-c2ncc(NC(=O)Cc3ccccc3Cl)cc2S(N)(=O)=O)c1]

According to general procedure GP6.1, crude 5-amino-2-(4-cyano-1H-pyrazol-1-yl)-N-[(dimethylamino)methylene]pyridine-3-sulfonamide (55 mg) and (2-chlorophenyl)acetic acid (41 mg, 0.26 mmol) were converted without purification of intermediates to the title compound. The title compound precipitated during the reaction and was obtained by filtration, no further purification was necessary (20.5 mg, 0.0492 mmol, 9% yield over 5 steps, 97% purity).

LC-MS (Method A): Rt=1.01 min, MS (ESIpos): m/z=417 [M+H]$^+$ $^1$H-NMR (400 MHz, DMSO-d$_6$) δ [ppm]: 3.95 (s, 2H), 7.30-7.37 (m, 2H), 7.43-7.50 (m, 2H), 7.63 (s, 2H), 8.36 (d, 1H), 8.87 (d, 1H), 8.90 (d, 1H), 9.10 (d, 1H), 11.08 (s, 1H).

Example 384

2-(2-Fluorophenyl)-N-[6-(4-fluoro-1H-pyrazol-1-yl)-5-sulfamoylpyridin-3-yl]acetamide

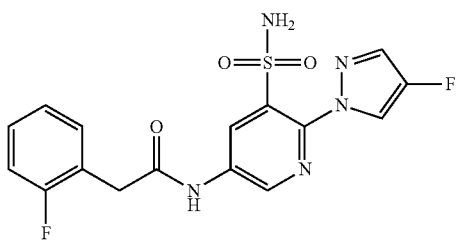

According to general procedure GP6.1, crude 5-amino-N-[(dimethylamino)methylene]-2-(4-fluoro-1H-pyrazol-1-yl)pyridine-3-sulfonamide (150 mg) and (2-fluorophenyl)acetic acid (111 mg, 0.72 mmol) were converted without purification of intermediates to the title compound and were purified at the end by preparative HPLC (Waters XBridge C18 5μ 100×30 mm, acetonitrile/water+0.1% formic acid) (24 mg, 0.061 mmol, 8% yield over 5 steps, 97% purity).

LC-MS (Method A): Rt=0.98 min, MS (ESIpos): m/z=394 [M+H]$^+$ $^1$H-NMR (400 MHz, DMSO-d6) δ[ppm]: 3.94 (s, 2H), 7.30-7.37 (m, 2H), 7.44-7.49 (m, 2H), 7.60 (s, 2H), 7.93 (dd, 1H), 8.50 (dd, 1H), 8.83 (d, 1H), 8.88 (d, 1H), 10.99 (s, 1H).

Example 385

2-(2-Chlorophenyl)-N-[6-(4-fluoro-1H-pyrazol-1-yl)-5-sulfamoylpyridin-3-yl]acetamide

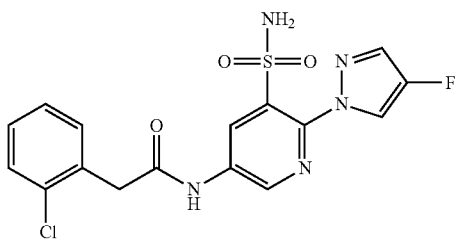 [SMILES: NS(=O)(=O)c1cc(NC(=O)Cc2ccccc2Cl)cnc1-n1cc(F)cn1]

According to general procedure GP6.1, crude 5-amino-N-[(dimethylamino)methylene]-2-(4-fluoro-1H-pyrazol-1-yl)pyridine-3-sulfonamide (150 mg) and (2-chlorophenyl)acetic acid (123 mg, 0.72 mmol) were converted without purification of intermediates to the title compound and were purified at the end by preparative HPLC (Waters XBridge C18 5μ 100×30 mm, acetonitrile/water+0.1% formic acid) (25 mg, 0.061 mmol, 8% yield over 5 steps, 98% purity).

LC-MS (Method A): Rt=1.03 min, MS (ESIpos): m/z=410 [M+H]$^+$ $^1$H-NMR (400 MHz, DMSO-d$_6$) δ [ppm]: 3.84 (s, 2H), 7.16-7.23 (m, 2H), 7.31-7.38 (m, 1H), 7.42 (td, 1H), 7.60 (s, 2H), 7.93 (dd, 1H), 8.50 (dd, 1H), 8.83 (d, 1H), 8.88 (d, 1H), 10.97 (s, 1H).

Example 386

N-[6-(4-Bromo-1H-pyrazol-1-yl)-5-sulfamoylpyridin-3-yl]-2-(2-fluorophenyl)acetamide

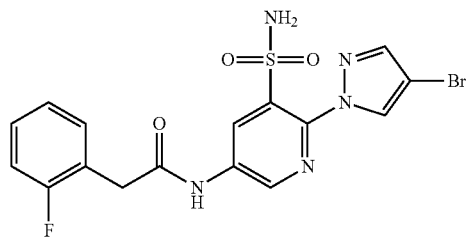 [SMILES: NS(=O)(=O)c1cc(NC(=O)Cc2ccccc2F)cnc1-n1cc(Br)cn1]

According to general procedure GP6.1, crude 5-amino-2-(4-bromo-1H-pyrazol-1-yl)-N-[(dimethylamino)methylene]pyridine-3-sulfonamide (84 mg) and (2-fluorophenyl)acetic acid (50.5 mg, 0.33 mmol) were converted without purification of intermediates to the title compound. The desired product precipitated during the reaction and was obtained by filtration, no further purification was necessary (14 mg, 0.0308 mmol, 12% yield over 5 steps, 97% purity).

LC-MS (Method A): Rt=1.10 min, MS (ESIpos): m/z=454/456 [M+H]$^+$ $^1$H-NMR (400 MHz, DMSO-d$_6$) δ [ppm]: 3.84 (s, 2H), 7.16-7.23 (m, 2H), 7.31-7.38 (m, 1H), 7.42 (td, 1H), 7.59-7.65 (m, 2H), 7.94 (d, 1H), 8.58 (d, 1H), 8.83 (d, 1H), 8.88 (d, 1H), 10.99 (s, 1H).

Example 387

2-(2-Chlorophenyl)-N-[6-(4-chloro-1H-pyrazol-1-yl)-5-sulfamoylpyridin-3-yl]acetamide

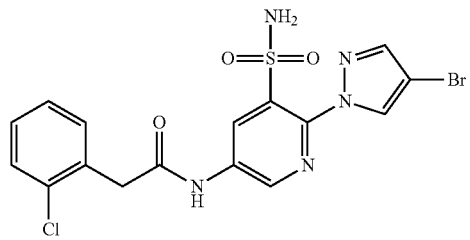 [SMILES: NS(=O)(=O)c1cc(NC(=O)Cc2ccccc2Cl)cnc1-n1cc(Br)cn1]

According to general procedure GP6.1, crude 5-amino-2-(4-chloro-1H-pyrazol-1-yl)-N-[(dimethylamino)methylene]pyridine-3-sulfonamide (100 mg) and (2-chlorophenyl)acetic acid (77.8 mg, 0.46 mmol) were converted without purification of intermediates to 2 the title compound. The title compound precipitated during the reaction and was obtained by filtration, no further purification was necessary (38 mg, 0.0891 mmol, 27% yield over 5 steps, 99% purity).

LC-MS (Method A): Rt=1.13 min, MS (ESIpos): m/z=426 [M+H]$^+$ $^1$H-NMR (400 MHz, DMSO-d$_6$) δ [ppm]: 3.94 (s, 2H), 7.30-7.37 (m, 2H), 7.43-7.49 (m, 2H), 7.60 (s, 2H), 7.94 (d, 1H), 8.58 (d, 1H), 8.84 (d, 1H), 8.89 (d, 1H), 11.01 (s, 1H).

Example 388

N-[6-(4-Chloro-1H-pyrazol-1-yl)-5-sulfamoylpyridin-3-yl]-2-(2-fluorophenyl)acetamide

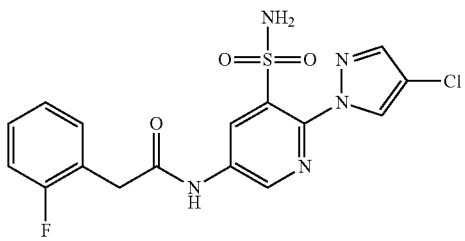 [SMILES: NS(=O)(=O)c1cc(NC(=O)Cc2ccccc2F)cnc1-n1cc(Cl)cn1]

According to general procedure GP6.1, crude 5-amino-2-(4-chloro-1H-pyrazol-1-yl)-N-[(dimethylamino)methylene]pyridine-3-sulfonamide (100 mg) and (2-fluorophenyl)acetic acid (70 mg, 0.46 mmol) were converted without purification of intermediates to the title compound. The title compound precipitated during the reaction and was obtained by filtration, no further purification was necessary (8 mg, 0.0195 mmol, 6% yield over 5 steps, 99% purity).

LC-MS (Method A): Rt=1.08 min, MS (ESIpos): m/z=410 [M+H]$^+$ $^1$H-NMR (400 MHz, DMSO-d$_6$) δ [ppm]: 3.84 (s, 2H), 7.16-7.24 (m, 2H), 7.31-7.38 (m, 1H), 7.42 (td, 1H), 7.60 (s, 2H), 7.94 (d, 1H), 8.58 (d, 1H), 8.83 (d, 1H), 8.88 (d, 1H), 10.99 (s, 1H).

Example 389

N-[6-(4-Bromo-1H-pyrazol-1-yl)-5-sulfamoylpyridin-3-yl]-2-(2-chlorophenyl)-acetamide

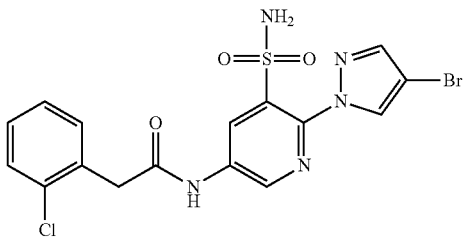 [SMILES: NS(=O)(=O)c1cc(NC(=O)Cc2ccccc2Cl)cnc1-n1cc(Br)cn1]

According to general procedure GP6.1, crude 5-amino-2-(4-bromo-1H-pyrazol-1-yl)-N-[(dimethylamino)methylene]pyridine-3-sulfonamide (84 mg) and (2-chlorophenyl)acetic acid (55.9 mg, 0.33 mmol) were converted without purification of intermediates to the title compound. The title compound precipitated during the reaction and was obtained by filtration, no further purification was necessary (20 mg, 0.0425 mmol, 17% yield over 5 steps, 98% purity).

LC-MS (Method A): Rt=1.14 min, MS (ESIpos): m/z=470/472 [M+H]$^+$ $^1$H-NMR (400 MHz, DMSO-d$_6$) δ [ppm]: 3.94 (s, 2H), 7.31-7.36 (m, 2H), 7.43-7.49 (m, 2H), 7.60 (s, 2H), 7.94 (d, 1H), 8.57 (d, 1H), 8.83 (d, 1H), 8.87 (d, 1H), 11.02 (s, 1H).

Example 390

2-(2-Fluorophenyl)-N-{3-sulfamoyl-4-[5-(trifluoromethyl)-1,3,4-oxadiazol-2-yl]phenyl}acetamide

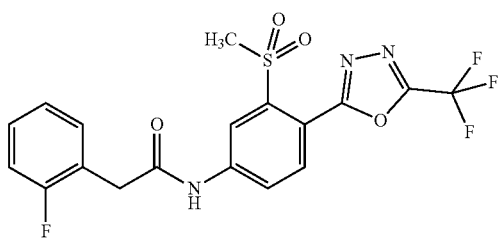 [SMILES: CS(=O)(=O)c1cc(NC(=O)Cc2ccccc2F)ccc1-c1nnc(C(F)(F)F)o1]

2-(2-Fluorophenyl)-N-{3-[(2,4-dimethoxybenzyl)sulfamoyl]-4-[5-(trifluoromethyl)-1,3,4-oxa-diazol-2-yl]phenyl}acetamide (268 mg, 451 μmol) was dissolved in dichloromethane (7.3 mL) and treated with trifluoroacetic acid (1.7 mL, 23 mmol) followed by stirring at room temperature overnight. The mixture was concentrated in vacuo and purified by HPLC to give the title compound (25 mg, 12% yield, 99% purity).

LC-MS (Method A): Rt=0.93 min

MS (ESIpos): m/z=445 (M+H)+

$^1$H-NMR (600 MHz, DMSO-$d_6$) δ [ppm] 3.85 (s, 2H), 7.19 (m, 2H), 7.34 (m, 1H), 7.41 (m, 1H), 7.91 (dd, 1H), 8.06 (d, 1H), 8.29 (d, 1H), 11.00 (s, 1H).

Example 391

2-(2-Chlorophenyl)-N-{3-sulfamoyl-4-[5-(trifluoromethyl)-1,3,4-oxadiazol-2-yl]phenyl}acetamide

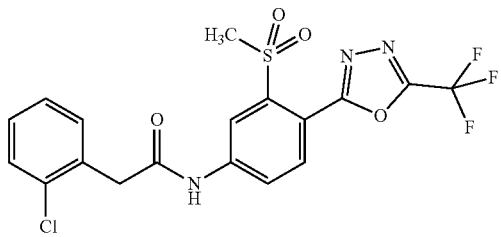 [SMILES: CS(=O)(=O)c1cc(NC(=O)Cc2ccccc2Cl)ccc1-c1nnc(C(F)(F)F)o1]

2-(2-Chlorophenyl)-N-{3-[(2,4-dimethoxybenzyl)sulfamoyl]-4-[5-(trifluoromethyl)-1,3,4-oxa-diazol-2-yl]phenyl}acetamide (276 mg, 451 μmol) was dissolved in dichloromethane (7.3 mL) and treated with trifluoroacetic acid (1.7 mL, 23 mmol) followed by stirring at room temperature overnight. The mixture was concentrated in vacuo and purified by HPLC to give the title compound (23 mg, 11% yield, 95% purity).

LC-MS (Method A): Rt=0.97 min

MS (ESIpos): m/z=461 (M+H)+

$^1$H-NMR (400 MHz, DMSO-$d_6$) δ [ppm] 3.95 (s, 2H), 7.33 (m, 2H), 7.46 (m, 2H), 7.90 (dd, 1H), 8.06 (d, 1H), 8.28 (d, 1H), 11.01 (s, 1H).

Example 392

2-(2-Chlorophenyl)-N-{4-[3-(pyridin-3-yl)-1H-1,2,4-triazol-1-yl]-3-sulfamoylphenyl}acetamide

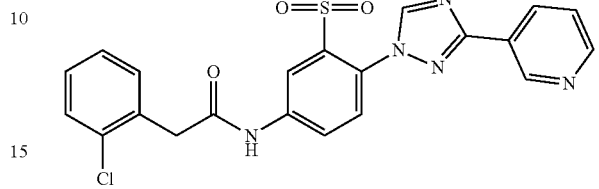

According to general procedures GP1.2, GP2.4, GP3.2 and GP4.2, 2-chloro-N-(2,4-dimethoxybenzyl)-5-nitrobenzenesulfonamide (500 mg, 1.29 mmol), 3-(1H-1,2,4-triazol-3-yl)pyridine (283 mg, 1.94 mmol) and (2-chlorophenyl)acetic acid (197 mg, 1.15 mmol) were converted without purification of intermediates to the title compound and were purified at the end by preparative HPLC (Waters XBridge C18 5μ 100×30 mm, acetonitrile/water+0.1% formic acid) followed by another preparative HPLC (Waters XBridge C18 5μ 100×30 mm, methanol/water+0.1% trifluoroacetic acid) (10 mg, 0.0213 mmol, 2% yield over 4 steps, 96% purity).

LC-MS (Method A): Rt=0.90 min; MS (ESIpos): m/z=469 [M+H]+

$^1$H-NMR (400 MHz, DMSO-$d_6$) δ [ppm]: 3.94 (s, 2H), 7.31-7.39 (m, 2H), 7.44-7.50 (m, 2H), 7.55 (s, 2H), 7.61 (dd, 1H), 7.69 (d, 1H), 8.00 (dd, 1H), 8.46 (d, 1H), 8.48 (dt, 1H), 8.71 (dd, 1H), 8.93 (s, 1H), 9.28 (d, 1H), 10.88 (s, 1H).

Example 393

2-(2-Fluorophenyl)-N-[4-(1H-pyrazol-1-yl)-3-sulfamoylphenyl]acetamide

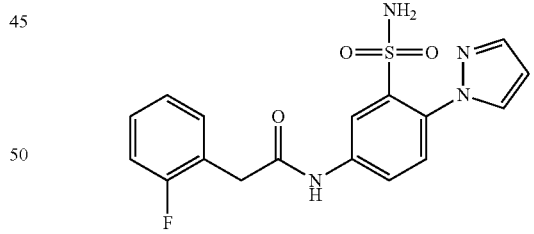

According to general procedures GP1.2, GP2.4, GP3.2 and GP4.3, 2-chloro-N-(2,4-dimethoxybenzyl)-5-nitrobenzenesulfonamide (250 mg, 0.65 mmol), 1H-pyrazole (66 mg, 0.97 mmol) and (2-fluorophenyl)acetic acid (120 mg, 0.78 mmol) were converted without purification of intermediates to the title compound and were purified at the end by preparative HPLC (Waters XBridge C18 5μ 100×30 mm, acetonitrile/water+0.1% formic acid) (11 mg, 0.294 mmol, 5% yield over 4 steps, 95% purity).

LC-MS (Method A): Rt=0.91 min; MS (ESIpos): m/z=375 [M+H]+

$^1$H-NMR (400 MHz, DMSO-$d_6$) δ [ppm]: 3.80 (s, 2H), 6.51 (t, 1H), 7.15-7.23 (m, 2H), 7.30-7.37 (m, 1H), 7.41 (td, 1H), 7.46 (s, 2H), 7.53 (d, 1H), 7.78 (dd, 1H), 7.97 (dd, 1H), 8.10 (dd, 1H), 8.36 (d, 1H), 10.75 (s, 1H).

Example 394

N-[4-(4-tert-Butyl-1H-pyrazol-1-yl)-3-sulfamoylphenyl]-2-(2-chlorophenyl)acetamide

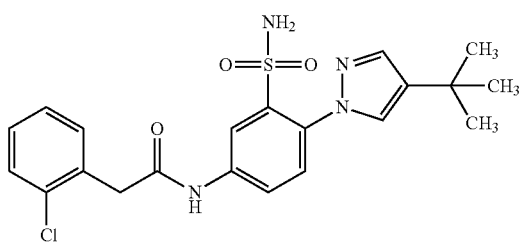 [SMILES: CC(C)(C)c1cnn(-c2ccc(NC(=O)Cc3ccccc3Cl)cc2S(N)(=O)=O)c1]

According to general procedures GP1.2, GP2.1, GP3.3 and GP4.1, 2-chloro-N-(2,4-dimethoxybenzyl)-5-nitrobenzenesulfonamide (500 mg, 1.29 mmol), 4-tert-butyl-1H-pyrazole (241 mg, 1.94 mmol) and (2-chlorophenyl)acetic acid (330 mg, 1.94 mmol) were converted without purification of intermediates to the title compound and were purified at the end twice by preparative HPLC (Waters XBridge C18 5μ 100×30 mm, acetonitrile/water+0.1% formic acid) (28 mg, 0.0626 mmol, 3% yield over 4 steps, 97% purity).

LC-MS (Method A): Rt=1.26 min; MS (ESIpos): m/z=447 [M+H]$^+$ $^1$H-NMR (400 MHz, DMSO-d$_6$) δ [ppm]: 1.27 (s, 9H), 3.89 (s, 2H), 7.29-7.36 (m, 2H), 7.42-7.48 (m, 2H), 7.50 (s, 2H), 5.52 (d, 1H), 7.72 (d, 1H), 7.94 (d, 1H), 7.97 (dd, 1H), 8.33 (d, 1H), 10.74 (s, 1H).

Example 395 and Example 396

According to general procedures GP1.2, GP2.1, GP3.3 and GP4.1, 2-chloro-N-(2,4-dimethoxybenzyl)-5-nitrobenzenesulfonamide (500 mg, 1.29 mmol), 2H-indazole (229 mg, 1.94 mmol) and (2-chlorophenyl)acetic acid (321 mg, 1.88 mmol) were converted without purification of intermediates to the two title compounds and were purified and separated at the end by preparative HPLC (Waters XBridge C18 5μ 100×30 mm, acetonitrile/water+0.1% formic acid), followed by preparative HPLC (Waters XBridge C18 5μ 100×30 mm, acetonitrile/water+0.2% aqueous ammonia (32%)).

Example 395

2-(2-Chlorophenyl)-N-[4-(1H-indazol-1-yl)-3-sulfamoylphenyl]acetamide

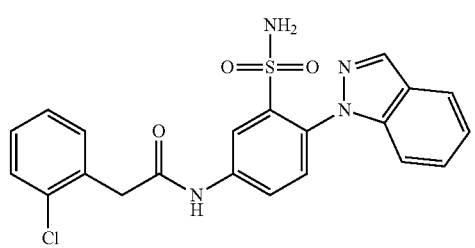

58 mg, 0.132 mmol, 10% yield over 4 steps, 99% purity

LC-MS (Method B): Rt=1.33 min; MS (ESIpos): m/z=441 [M+H]$^+$ $^1$H-NMR (400 MHz, DMSO-d$_6$) δ [ppm]: 3.93 (s, 2H), 7.26 (ddd, 1H), 7.29-7.40 (m, 5H), 7.41-7.49 (m, 3H), 7.64 (d, 1H), 7.89 (dt, 1H), 8.05 (dd, 1H), 8.40 (d, 1H), 8.46 (d, 1H), 10.84 (s, 1H).

Example 396

2-(2-Chlorophenyl)-N-[4-(2H-indazol-2-yl)-3-sulfamoylphenyl]acetamide

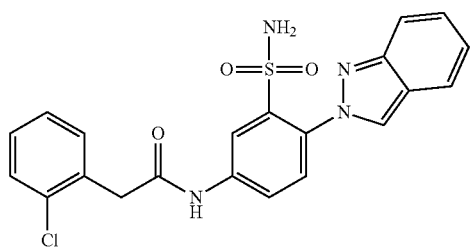 [SMILES: NS(=O)(=O)c1cc(NC(=O)Cc2ccccc2Cl)ccc1-n1cc2ccccc2n1]

14 mg, 0.0318 mmol, 2% yield over 4 steps, 99% purity

LC-MS (Method B): Rt=1.27 min; MS (ESIpos): m/z=441 [M+H]$^+$ $^1$H-NMR (400 MHz, DMSO-d$_6$) δ [ppm]: 3.93 (s, 2H), 7.14 (ddd, 1H), 7.30-7.39 (m, 3H), 7.44-7.50 (m, 2H), 7.64 (br s, 2H), 7.70 (d, 1H), 7.74 (dd, 1H), 7.78-7.82 (m, 1H), 8.04 (dd, 1H), 8.44 (d, 1H), 8.71 (d, 1H), 10.86 (s, 1H).

Example 397 and Example 398

According to general procedures GP1.2, GP2.1, GP3.3 and GP4.1, 2-chloro-N-(2,4-dimethoxybenzyl)-5-nitrobenzenesulfonamide (500 mg, 1.29 mmol), 2H-indazole (229 mg, 1.94 mmol) and (2-fluorophenyl)acetic acid (290 mg, 1.88 mmol) were converted without purification of intermediates to the two title compounds and were purified and separated at the end by preparative HPLC (Waters XBridge C18 5μ 100×30 mm, acetonitrile/water+0.1% formic acid), followed by preparative HPLC (Waters XBridge C18 5μ 100×30 mm, acetonitrile/water+0.2% aqueous ammonia (32%)).

Example 397

2-(2-Fluorophenyl)-N-[4-(2H-indazol-2-yl)-3-sulfamoylphenyl]acetamide

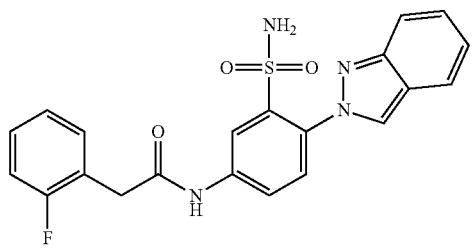 [SMILES: NS(=O)(=O)c1cc(NC(=O)Cc2ccccc2F)ccc1-n1cc2ccccc2n1]

15 mg, 0.0353 mmol, 3% yield over 4 steps, 99% purity
LC-MS (Method B): Rt=1.21 min; MS (ESIpos): m/z=425 [M+H]+

$^1$H-NMR (400 MHz, DMSO-d$_6$) δ [ppm]: 3.83 (s, 2H), 7.11-7.24 (m, 3H), 7.31-7.38 (m, 2H), 7.43 (td, 1H), 7.63 (br s, 2H), 7.70 (d, 1H), 7.74 (dd, 1H), 7.78-7.82 (m, 1H), 8.03 (dd, 1H), 8.43 (d, 1H), 8.72 (d, 1H), 10.85 (s, 1H).

Example 398

2-(2-Fluorophenyl)-N-[4-(1H-indazol-1-yl)-3-sulfamoylphenyl]acetamide

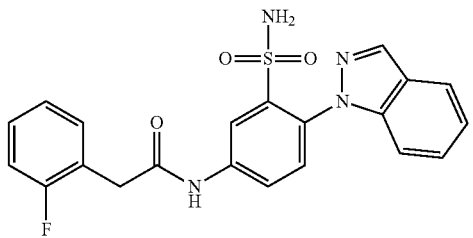

70 mg, 0.0165 mmol, 13% yield over 4 steps, 99% purity
LC-MS (Method B): Rt=1.27 min; MS (ESIpos): m/z=425 [M+H]+

$^1$H-NMR (400 MHz, DMSO-d$_6$) δ [ppm]: 3.83 (s, 2H), 7.17-7.23 (m, 2H), 7.26 (t, 1H), 7.29-7.39 (m, 4H), 7.41-7.47 (m, 2H), 7.64 (d, 1H), 7.89 (d, 1H), 8.05 (dd, 1H), 8.40 (s, 1H), 8.46 (d, 1H), 10.84 (s, 1H).

Example 399

1-(4-{[(2-Chlorophenyl)acetyl]amino}-2-sulfamoylphenyl)-N,N-dimethyl-1H-pyrazole-4-carboxamide

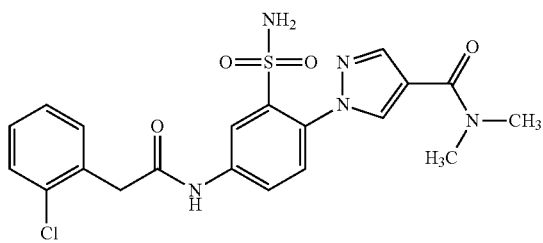 [SMILES: CN(C)C(=O)c1cnn(-c2ccc(NC(=O)Cc3ccccc3Cl)cc2S(N)(=O)=O)c1]

According to general procedures GP1.2, GP2.1, GP3.3 and GP4.1, 2-chloro-N-(2,4-dimethoxybenzyl)-5-nitrobenzenesulfonamide (500 mg, 1.29 mmol), N,N-dimethyl-1H-pyrazole-4-carboxamide (270 mg, 1.94 mmol) and (2-chlorophenyl)acetic acid (330 mg, 1.94 mmol) were converted without purification of intermediates to the title compound and were purified at the end twice by preparative HPLC (Waters XBridge C18 5μ 100×30 mm, acetonitrile/water+0.1% formic acid) (35 mg, 0.0758 mmol, 6% yield over 4 steps, 97% purity).

LC-MS (Method A): Rt=0.91 min; MS (ESIpos): m/z=462 [M+H]+

$^1$H-NMR (400 MHz, DMSO-d$_6$) δ [ppm]: 2.97 (br s, 3H), 3.18 (br s, 3H), 3.91 (s, 2H), 7.30-7.37 (m, 2H), 7.38-7.48 (m, 4H), 7.60 (d, 1H), 7.97 (dd, 1H), 8.00 (d, 1H), 8.38 (d, 1H), 8.42 (d, 1H), 10.80 (s, 1H).

Example 400

N-[1-(4-{[(2-Chlorophenyl)acetyl]amino}-2-sulfamoylphenyl)-1H-pyrazol-4-yl]cyclopropanecarboxamide

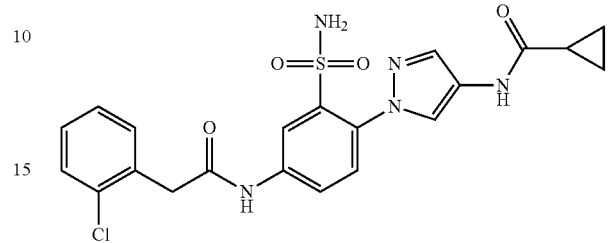

According to general procedures GP1.2, GP2.1, GP3.3 and GP4.1, 2-chloro-N-(2,4-dimethoxybenzyl)-5-nitrobenzenesulfonamide (500 mg, 1.29 mmol), N-(1H-pyrazol-4-yl)cyclopropanecarboxamide (293 mg, 1.94 mmol) and (2-chlorophenyl)acetic acid (330 20 mg, 1.94 mmol) were converted without purification of intermediates to the title compound and were purified at the end twice by preparative HPLC (Waters XBridge C18 5μ 100×30 mm, acetonitrile/water+0.1% formic acid) (44 mg, 0.0928 mmol, 7% yield over 4 steps, 97% purity).

LC-MS (Method A): Rt=0.98 min; MS (ESIpos): m/z=474 [M+H]+

$^1$H-NMR (400 MHz, DMSO-d$_6$) δ [ppm]: 0.76-0.82 (m, 4H), 1.72 (quin, 1H), 3.90 (s, 2H), 7.29-7.36 (m, 2H), 7.39-7.48 (m, 4H), 7.52 (d, 1H), 7.77 (d, 1H), 7.95 (dd, 1H), 8.14 (s, 1H), 8.35 (d, 1H), 10.40 (s, 1H), 10.75 (s, 1H).

Example 401

2-(2-Chlorophenyl)-N-{4-[4-(pyrazin-2-yl)-1H-pyrazol-1-yl]-3-sulfamoylphenyl}acetamide

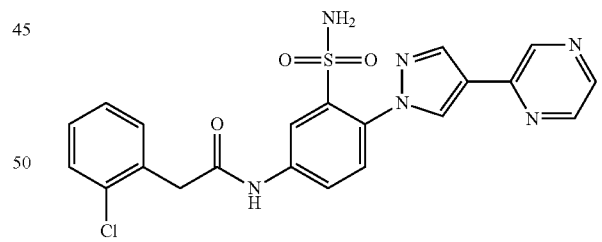

According to general procedures GP1.2, GP2.1, GP3.3 and GP4.1, 2-chloro-N-(2,4-dimethoxybenzyl)-5-nitrobenzenesulfonamide (500 mg, 1.29 mmol), 2-(1H-pyrazol-4-yl)pyrazine (283 mg, 1.94 mmol) and (2-chlorophenyl)acetic acid (330 mg, 1.94 mmol) were converted without purification of intermediates to the title compound and were purified at the end by preparative HPLC (Waters XBridge C18 5μ 100×30 mm, acetonitrile/water+0.1% formic acid) (41 mg, 0.0874 mmol, 7% yield over 4 steps, 97% purity).

LC-MS (Method A): Rt=0.98 min; MS (ESIpos): m/z=469 [M+H]+

$^1$H-NMR (400 MHz, DMSO-de) δ [ppm]: 3.92 (s, 2H), 7.30-7.37 (m, 2H), 7.43-7.50 (m, 4H), 7.65 (d, 1H), 8.01 (dd, 1H), 8.40 (d, 1H), 8.43 (d, 1H), 8.49 (d, 1H), 8.62 (dd, 1H), 8.81 (d, 1H), 9.11 (d, 1H), 10.82 (s, 1H).

Example 402

2-(2-Chlorophenyl)-N-{4-[4-(pyridin-2-yl)-1H-pyrazol-1-yl]-3-sulfamoylphenyl}acetamide

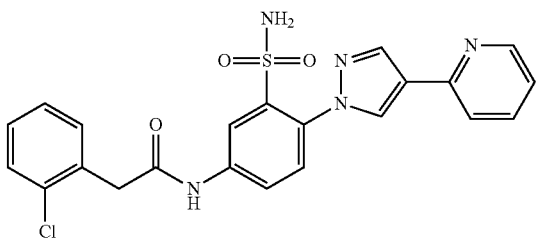

According to general procedures GP1.2, GP2.1, GP3.3 and GP4.1, 2-chloro-N-(2,4-dimethoxybenzyl)-5-nitrobenzenesulfonamide (500 mg, 1.29 mmol), 2-(1H-pyrazol-4-yl)pyridine (281 mg, 1.94 mmol) and (2-chlorophenyl)acetic acid (330 mg, 1.94 mmol) were converted without purification of intermediates to the title compound and were purified at the end twice by preparative HPLC (Waters XBridge C18 5µ 100×30 mm, acetonitrile/water+0.1% formic acid) (54 mg, 0.115 mmol, 9% yield over 4 steps, 97% purity).

LC-MS (Method A): Rt=0.91 min; MS (ESIpos): m/z=468 [M+H]$^+$ $^1$H-NMR (400 MHz, DMSO-d$_6$) δ [ppm]: 3.91 (s, 2H), 7.24 (ddd, 1H), 7.30-7.37 (m, 2H), 7.42-7.51 (m, 4H), 7.64 (d, 1H), 7.76-7.85 (m, 2H), 8.00 (dd, 1H), 8.34 (d, 1H), 8.39 (d, 1H), 8.57 (ddd, 1H), 8.67 (d, 1H), 10.80 (s, 1H).

Example 403

2-(2-Chlorophenyl)-N-{4-[4-(pyridin-3-yl)-1H-pyrazol-1-yl]-3-sulfamoylphenyl}acetamide

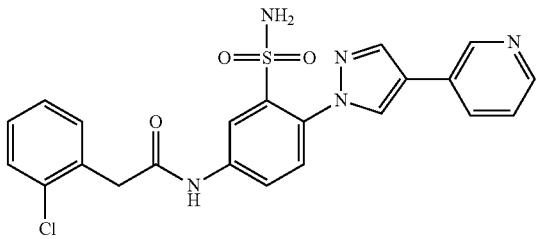 [SMILES: NS(=O)(=O)c1cc(NC(=O)Cc2ccccc2Cl)ccc1-n1cc(-c2cnccn2)cn1]

According to general procedures GP1.2, GP2.1, GP3.3 and GP4.1, 2-chloro-N-(2,4-dimethoxybenzyl)-5-nitrobenzenesulfonamide (500 mg, 1.29 mmol), 3-(1H-pyrazol-4-yl)pyridine (281 mg, 1.94 mmol) and (2-chlorophenyl)acetic acid (330 mg, 1.94 mmol) were converted without purification of intermediates to the title compound and were purified at the end twice by preparative HPLC (Waters XBridge C18 5µ 100×30 mm, acetonitrile/water 15+0.1% formic acid) (20 mg, 0.0427 mmol, 3% yield over 4 steps, 97% purity).

LC-MS (Method A): Rt=0.92 min; MS (ESIpos): m/z=468 [M+H]$^+$ $^1$H-NMR (400 MHz, DMSO-d$_6$) δ [ppm]: 3.92 (s, 2H), 7.30-7.37 (m, 2H), 7.40-7.52 (m, 5H), 7.63 (d, 1H), 8.01 (dd, 1H), 8.09 (dt, 1H), 8.35 (s, 1H), 8.39 (d, 1H), 8.45 (dd, 1H), 8.70 (s, 1H), 8.97 (d, 1H), 10.81 (s, 1H).

Example 404

2-(2-Chlorophenyl)-N-{4-[4-(pyrimidin-4-yl)-1H-pyrazol-1-yl]-3-sulfamoylphenyl}acetamide

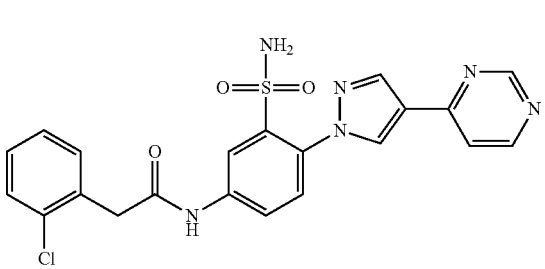 [SMILES: NS(=O)(=O)c1cc(NC(=O)Cc2ccccc2Cl)ccc1-n1cc(-c2ccncn2)cn1]

According to general procedures GP1.2, GP2.4, GP3.2 and GP4.2, 2-chloro-N-(2,4-dimethoxybenzyl)-5-nitrobenzenesulfonamide (250 mg, 0.65 mmol), 4-(1H-pyrazol-4-yl)pyrimidine (142 mg, 0.97 mmol) and (2-chlorophenyl)acetic acid (162 mg, 0.95 mmol) were converted without purification of intermediates to the title compound and were purified at the end by preparative HPLC (Waters XBridge C18 5µ 100×30 mm, acetonitrile/water+0.1% formic acid) followed by preparative HPLC (Waters XBridge C18 5µ 100×30 mm, methanol/water+0.1% formic acid) (6.1 mg, 0.0130 mmol, 2% yield over 4 steps, 95% purity).

LC-MS (Method 1): Rt=1.21 min; MS (ESIpos): m/z=469 [M+H]$^+$ $^1$H-NMR (400 MHz, DMSO-d$_6$) δ [ppm]: 3.92 (s, 2H), 7.28-7.39 (m, 2H), 7.43-7.52 (m, 4H), 7.64 (d, 1H), 7.87 (dd, 1H), 8.00 (dd, 1H), 8.40 (d, 1H), 8.46 (s, 1H), 8.77 (d, 1H), 8.87 (s, 1H), 9.12 (d, 1H), 10.83 (s, 1H).

Example 405

2-(2-Fluorophenyl)-N-{4-[4-(pyrimidin-4-yl)-1H-pyrazol-1-yl]-3-sulfamoylphenyl}acetamide

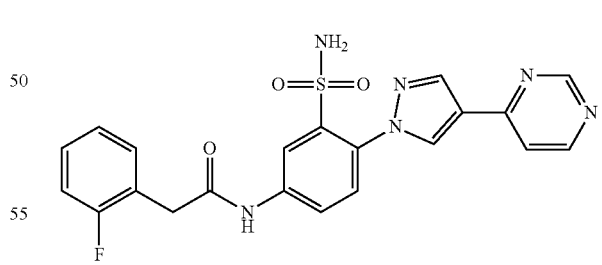

According to general procedures GP1.2, GP2.4, GP3.2 and GP4.2, 2-chloro-N-(2,4-dimethoxybenzyl)-5-nitrobenzenesulfonamide (250 mg, 0.65 mmol), 4-(1H-pyrazol-4-yl)pyrimidine (142 mg, 0.97 mmol) and (2-fluorophenyl)acetic acid (146 mg, 0.95 mmol) were converted without purification of intermediates to the title compound and were purified at the end by preparative HPLC (Waters XBridge C18 5µ 100×30 mm, acetonitrile/water+0.1% formic acid) followed by preparative HPLC (Waters XBridge C18 5µ

100×30 mm, methanol/water+0.1% formic acid) (7.3 mg, 0.0161 mmol, 2% yield over 4 steps, 95% purity).

LC-MS (Method 1): Rt=1.16 min; MS (ESIpos): m/z=453 [M+H]⁺

¹H-NMR (400 MHz, DMSO-d₆) δ [ppm]: 3.81 (s, 2H), 6.50-8.00 (very broad peak in the baseline, 2H), 7.15-7.24 (m, 2H), 7.29-7.37 (m, 1H), 7.42 (td, 1H), 7.64 (d, 1H), 7.87 (dd, 1H), 8.00 (dd, 1H), 8.40 (d, 1H), 8.46 (s, 1H), 8.77 (d, 1H), 8.87 (s, 1H), 9.12 (d, 1H), 10.85 (s, 1H).

Example 406 and 407

According to general procedures GP2.4 and GP6.3, a regioisomeric mixture of N-[(dimethylamino)methylene]-5-nitro-2-[4-(trifluoromethyl)-2H-1,2,3-triazol-2-yl]benzenesulfonamide and N-[(dimethylamino)methylene]-5-nitro-2-[4-(trifluoromethyl)-1H-1,2,3-triazol-1-yl] benzenesulfonamide (159 mg, 0.404 mmol) and (4-methoxyphenyl)acetic acid (99.8 mg, 0.60 mmol) were converted without purification of intermediates to the title compounds which were purified and separated by preparative HPLC (Chromatorex C-18 10 µm, 125×30 mm, acetonitrile/water+0.1% aqueous ammonia (32%)).

Example 406

2-(4-Methoxyphenyl)-N-{3-sulfamoyl-4-[4-(trifluoromethyl)-2H-1,2,3-triazol-2-yl]phenyl}acetamide

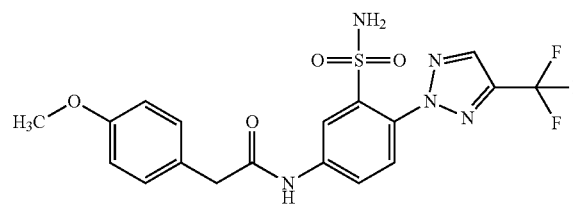

17 mg, 0.0373 mmol, 9% yield over 3 steps, 97% purity
LC-MS (Method B): Rt=0.99 min; MS (ESIneg): m/z=454 [M-H]⁻

¹H-NMR (400 MHz, DMSO-d₆) δ [ppm]: 3.64 (s, 2H), 3.73 (s, 3H), 6.90 (d, 2H), 7.27 (d, 2H), 7.39 (br s, 2H), 7.73 (d, 1H), 8.01 (dd, 1H), 8.42 (d, 1H), 8.69 (s, 1H), 10.78 (s, 1H).

Example 407

2-(4-Methoxyphenyl)-N-{3-sulfamoyl-4-[4-(trifluoromethyl)-1H-1,2,3-triazol-1-yl]phenyl}acetamide

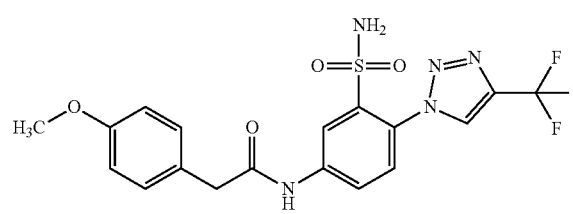

48 mg, 0.105 mmol, 26% yield over 3 steps, 97% purity
LC-MS (Method B): Rt=0.81 min; MS (ESIneg): m/z=454 [M-H]⁻

¹H-NMR (400 MHz, DMSO-d₆) δ [ppm]: 3.65 (s, 2H), 3.73 (s, 3H), 6.91 (d, 2H), 7.27 (d, 2H), 7.33 (br s, 2H), 7.65 (d, 1H), 7.99 (dd, 1H), 8.43 (d, 1H), 9.16 (d, 1H), 10.79 (s, 1H).

Example 408 and 409

According to general procedures GP2.4 and GP6.3, a regioisomeric mixture of N-[(dimethylamino)methylene]-5-nitro-2-[4-(trifluoromethyl)-2H-1,2,3-triazol-2-yl]benzenesulfonamide and N-[(dimethylamino)methylene]-5-nitro-2-[4-(trifluoromethyl)-1H-1,2,3-triazol-1-yl] benzenesulfonamide (159 mg, 0.404 mmol) and (4-methylphenyl)acetic acid (90.1 mg, 0.60 mmol) were converted without purification of intermediates to the title compounds which were purified and separated by preparative HPLC (Chromatorex C-18 10 µm, 125×30 mm, acetonitrile/water+0.1% aqueous ammonia (32%)).

Example 408

2-(4-Methylphenyl)-N-{3-sulfamoyl-4-[4-(trifluoromethyl)-2H-1,2,3-triazol-2-yl]phenyl}acetamide

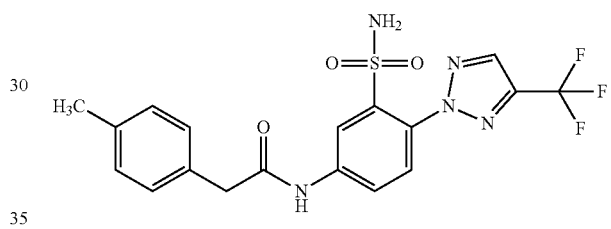

12.4 mg, 0.0282 mmol, 7% yield over 3 steps, 98% purity, after additional purification by another preparative HPLC (Waters XBridge C18 5µ 100×30 mm, acetonitrile/water+0.1% formic acid)

LC-MS (Method A): Rt=1.19 min; MS (ESIneg): m/z=438 [M-H]⁻

¹H-NMR (400 MHz, DMSO-d₆) δ [ppm]: 2.28 (s, 3H), 3.67 (s, 2H), 7.15 (d, 2H), 7.24 (d, 2H), 7.44 (s, 2H), 7.73 (d, 1H), 8.01 (dd 1H), 8.42 (d, 1H), 8.69 (s, 1H), 10.80 (s, 1H).

Example 409

2-(4-Methylphenyl)-N-{3-sulfamoyl-4-[4-(trifluoromethyl)-1H-1,2,3-triazol-1-yl]phenyl}acetamide

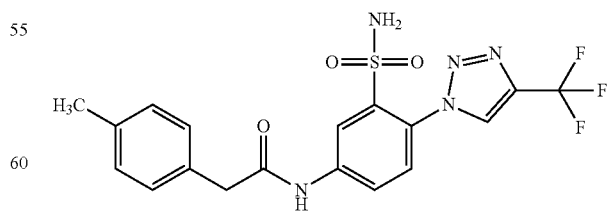

22.3 mg, 0.0507 mmol, 13% yield over 3 steps, 98% purity
LC-MS (Method B): Rt=0.98 min; MS (ESIneg): m/z=438 [M-H]⁻

¹H-NMR (400 MHz, DMSO-d₆) δ [ppm]: 2.28 (s, 3H), 3.67 (s, 2H), 7.15 (d, 2H), 7.24 (d, 2H), 7.62 (br s, 2H), 7.65 (d, 1H), 7.99 (dd, 1H), 8.43 (d, 1H), 9.16 (d, 1H), 10.80 (s, 1H).

Example 410

2-[4-(Difluoromethyl)phenyl]-N-{3-sulfamoyl-4-[4-(trifluoromethyl)-2H-1,2,3-triazol-2-yl]phenyl}acetamide

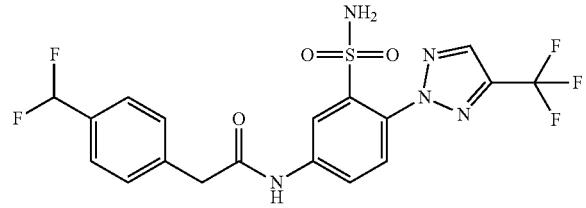 [SMILES: NS(=O)(=O)c1cc(NC(=O)Cc2ccc(C(F)F)cc2)ccc1-n1ncc(C(F)(F)F)n1]

According to general procedures GP2.4 and GP6.4, N-[(dimethylamino)methylene]-5-nitro-2-[4-(trifluoromethyl)-2H-1,2,3-triazol-2-yl]benzenesulfonamide (48 mg, 0.123 mmol), and [4-(difluoromethyl)phenyl]acetic acid (36.5 mg, 0.20 mmol) were converted without purification of intermediates to the title compound which precipitated after the last step out of the reaction mixture (15 mg, 0.0316 mmol, 26% yield over 3 steps, 95% purity).

LC-MS (Method A): Rt=1.16 min; MS (ESIneg): m/z=474 [M−H]⁻

¹H-NMR (400 MHz, DMSO-d₆) δ [ppm]: 3.81 (s, 2H), 7.02 (t, 1H), 7.45 (s, 2H), 7.49 (d, 2H), 7.55 (d, 2H), 7.74 (d, 1H), 8.01 (dd, 1H), 8.43 (d, 1H), 8.69 (d, 1H), 10.88 (s, 1H).

Example 411

2-[4-(Difluoromethyl)phenyl]-N-{3-sulfamoyl-4-[4-(trifluoromethyl)-1H-1,2,3-triazol-1-yl]phenyl}acetamide

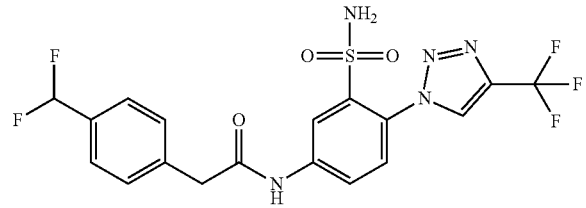

According to general procedures GP2.4 and GP6.4, N-[(dimethylamino)methylene]-5-nitro-2-[4-(trifluoromethyl)-1H-1,2,3-triazol-1-yl]benzenesulfonamide (45 mg, 0.115 mmol), and [4-(difluoromethyl)phenyl]acetic acid (40 mg, 0.22 mmol) were converted without purification of intermediates to the title compound and were purified at the end by preparative HPLC (Chromatorex C-18 10 μm, 125×30 mm, acetonitrile/water+0.1% aqueous ammonia (32%)) (16 mg, 0.0337 mmol, 29% yield over 3 steps, 98% purity).

LC-MS (Method B): Rt=0.88 min; MS (ESIpos): m/z=476 [M+H]⁺

¹H-NMR (400 MHz, DMSO-d₆) δ [ppm]: 3.82 (s, 2H), 7.03 (t, 1H), 7.37-7.60 (m, 6H), 7.67 (d, 1H), 7.99 (dd, 1H), 8.43 (d, 1H), 9.16 (d, 1H), 10.89 (s, 1H).

Example 412

2-(2-Fluorophenyl)-N-{3-sulfamoyl-4-[4-(trifluoromethyl)-2H-1,2,3-triazol-2-yl]phenyl}acetamide

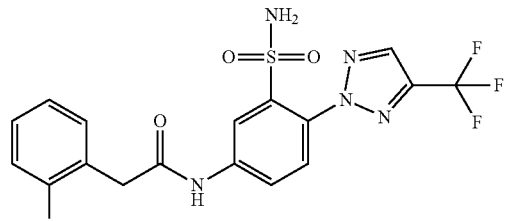

According to general procedures GP2.4 and GP6.4, N-[(dimethylamino)methylene]-5-nitro-2-[4-(trifluoromethyl)-2H-1,2,3-triazol-2-yl]benzenesulfonamide (48 mg, 0.123 mmol), and (2-fluorophenyl)acetic acid (30.2 mg, 0.20 mmol) were converted without purification of intermediates to the title compound and were purified at the end by preparative HPLC (Chromatorex C-18 10 μm, 125×30 mm, acetonitrile/water+0.1% formic acid) (3 mg, 0.00677 mmol, 6% yield over 3 steps, 97% purity).

LC-MS (Method A): Rt=1.13 min; MS (ESIneg): m/z=442 [M−H]⁻

¹H-NMR (400 MHz, DMSO-d₆) δ [ppm]: 3.83 (s, 2H), 7.15-7.23 (m, 2H), 7.30-7.51 (m, 4H), 7.75 (d, 1H), 8.00 (dd, 1H), 8.45 (d, 1H), 8.70 (d, 1H), 10.90 (s, 1H).

Example 413

2-(2-Fluorophenyl)-N-{3-sulfamoyl-4-[4-(trifluoromethyl)-1H-1,2,3-triazol-1-yl]phenyl}acetamide

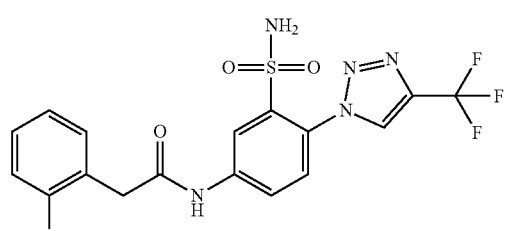

According to general procedures GP2.4 and GP6.4, N-[(dimethylamino)methylene]-5-nitro-2-[4-(trifluoromethyl)-1H-1,2,3-triazol-1-yl]benzenesulfonamide (45 mg, 0.115 mmol), and (2-fluorophenyl)acetic acid (33.2 mg, 0.22 mmol) were converted without purification of intermediates to the title compound and were purified at the end by preparative HPLC (Chromatorex C-18 10 μm, 125×30 mm, acetonitrile/water+0.1% aqueous ammonia (32%)) (21 mg, 0.0474 mmol, 41% yield over 3 steps, 98% purity).

LC-MS (Method B): Rt=0.82 min; MS (ESIpos): m/z=444 [M+H]⁺

¹H-NMR (400 MHz, DMSO-d₆) δ [ppm]: 3.83 (s, 2H), 7.15-7.23 (m, 2H), 7.31-7.38 (m, 1H), 7.42 (td, 1H), 7.57 (br s, 2H), 7.67 (d, 1H), 7.97 (dd, 1H), 8.46 (d, 1H), 9.17 (d, 1H), 10.90 (s, 1H).

Example 414

2-[2-Chloro-4-(trifluoromethyl)phenyl]-N-{3-sulfamoyl-4-[4-(trifluoromethyl)-2H-1,2,3-triazol-2-yl]phenyl}acetamide

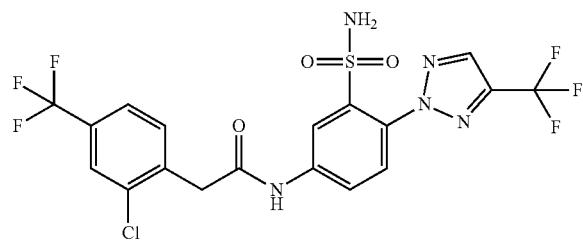 [SMILES: NS(=O)(=O)c1cc(NC(=O)Cc2ccc(C(F)(F)F)cc2Cl)ccc1-n1ncc(C(F)(F)F)n1]

According to general procedures GP2.4 and GP6.4, N-[(dimethylamino)methylene]-5-nitro-2-[4-(trifluoromethyl)-2H-1,2,3-triazol-2-yl]benzenesulfonamide (48 mg, 0.123 mmol), and [2-chloro-4-(trifluoromethyl)phenyl]acetic acid (46.7 mg, 0.20 mmol) were converted without purification of intermediates to the title compound and were purified at the end by preparative HPLC (Chromatorex C-18 10 μm, 125×30 mm, acetonitrile/water+0.1% formic acid) (5 mg, 0.00947 mmol, 5% yield over 3 steps, 97% purity).

LC-MS (Method A): Rt=1.29 min; MS (ESIneg): m/z=526 [M−H]⁻

$^1$H-NMR (400 MHz, DMSO-$d_6$) δ [ppm]: 4.06 (s, 2H), 7.46 (br s, 2H), 7.68-7.78 (m, 3H), 7.89 (s, 1H), 7.99 (dd, 1H), 8.44 (d, 1H), 8.70 (s, 1H), 10.99 (s, 1H).

Example 415

2-[2-Chloro-4-(trifluoromethyl)phenyl]-N-{3-sulfamoyl-4-[4-(trifluoromethyl)-1H-1,2,3-triazol-1-yl]phenyl}acetamide

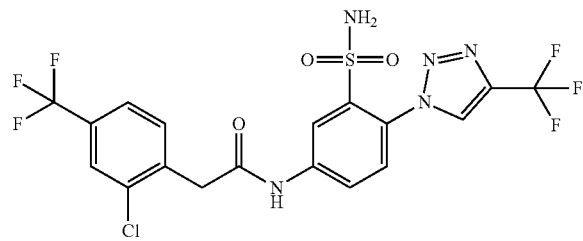 [SMILES: NS(=O)(=O)c1cc(NC(=O)Cc2ccc(C(F)(F)F)cc2Cl)ccc1-n1cc(C(F)(F)F)nn1]

According to general procedures GP2.4 and GP6.4, N-[(dimethylamino)methylene]-5-nitro-2-[4-(trifluoromethyl)-1H-1,2,3-triazol-1-yl]benzenesulfonamide (45 mg, 0.115 mmol), and [2-chloro-4-(trifluoromethyl)phenyl]acetic acid (51.4 mg, 0.22 mmol) were converted without purification of intermediates to the title compound and were purified at the end by preparative HPLC (Chromatorex C-18 10 μm, 125×30 mm, acetonitrile/water+0.1% aqueous ammonia (32%)) (17 mg, 0.0322 mmol, 28% yield over 3 steps, 97% purity).

LC-MS (Method B): Rt=1.04 min; MS (ESIpos): m/z=528 [M+H]⁺

$^1$H-NMR (400 MHz, DMSO-$d_6$) δ [ppm]: 4.06 (s, 2H), 7.57 (br s, 2H), 7.65-7.77 (m, 3H), 7.90 (s, 1H), 7.97 (dd, 1H), 8.45 (d, 1H), 9.17 (s, 1H), 10.99 (s, 1H).

Example 416

2-(2,4-Dichlorophenyl)-N-{3-sulfamoyl-4-[4-(trifluoromethyl)-2H-1,2,3-triazol-2-yl]phenyl}acetamide

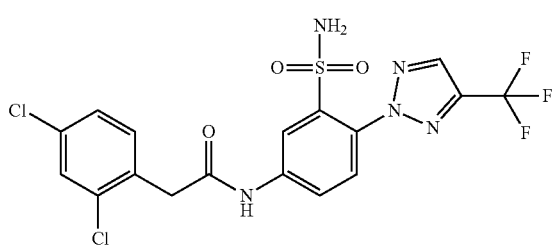 [SMILES: NS(=O)(=O)c1cc(NC(=O)Cc2ccc(Cl)cc2Cl)ccc1-n1ncc(C(F)(F)F)n1]

According to general procedures GP2.4 and GP6.4, N-[(dimethylamino)methylene]-5-nitro-2-[4-(trifluoromethyl)-2H-1,2,3-triazol-2-yl]benzenesulfonamide (48 mg, 0.123 mmol), and (2,4-dichlorophenyl)acetic acid (40.2 mg, 0.20 mmol) were converted without purification of intermediates to the title compound which precipitated after the last step out of the reaction mixture (26 mg, 0.0526 mmol, 43% yield over 3 steps, 97% purity).

LC-MS (Method A): Rt=1.26 min; MS (ESIneg): m/z=492 [M−H]⁻

$^1$H-NMR (400 MHz, DMSO-$d_6$) δ [ppm]: 3.94 (s, 2H), 7.41-7.52 (m, 4H), 7.64 (d, 1H), 7.75 (d, 1H), 7.99 (dd, 1H), 8.44 (d, 1H), 8.70 (s, 1H), 10.92 (s, 1H).

Example 417

2-(2,4-Dichlorophenyl)-N-{3-sulfamoyl-4-[4-(trifluoromethyl)-1H-1,2,3-triazol-1-yl]phenyl}acetamide

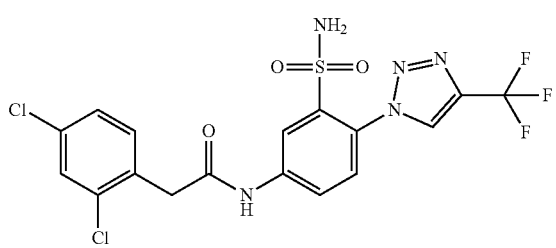

According to general procedures GP2.4 and GP6.4, N-[(dimethylamino)methylene]-5-nitro-2-[4-(trifluoromethyl)-1H-1,2,3-triazol-1-yl]benzenesulfonamide (45 mg, 0.115 mmol), and (2,4-dichlorophenyl)acetic acid (44.1 mg, 0.22 mmol) were converted without purification of intermediates to the title compound and were purified at the end by preparative HPLC (Chromatorex C-18 10 μm, 125×30 mm, acetonitrile/water+0.1% aqueous ammonia (32%)) (17 mg, 0.0344 mmol, 30% yield over 3 steps, 97% purity).

LC-MS (Method B): Rt=0.98 min; MS (ESIpos): m/z=494 [M+H]⁺

$^1$H-NMR (400 MHz, DMSO-$d_6$) δ [ppm]: 3.94 (s, 2H), 7.44 (dd, 1H), 7.50 (dd, 1H), 7.53-7.71 (m, 4H), 7.97 (dd, 1H), 8.45 (d, 1H), 9.17 (d, 1H), 10.93 (s, 1H).

Example 418

2-(2-Chlorophenyl)-N-[3-sulfamoyl-4-(1,3-thiazol-5-yl)phenyl]acetamide

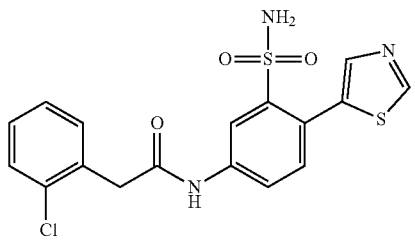 [SMILES: NS(=O)(=O)c1cc(NC(=O)Cc2ccccc2Cl)ccc1-c1cncs1]

According to general procedure GP8.1, N-(4-bromo-3-{[(dimethylamino)methylene]sulfamoyl}phenyl)-2-(2-chlorophenyl)acetamide (150 mg, 0.33 mmol) and 5-bromo-1,3-thiazole (97.3 mg, 0.59 mmol) were converted to the title compound and were purified by preparative HPLC (Chromatorex C-18 10 μm, 125×30 mm, acetonitrile/water+0.1% formic acid), followed by another preparative HPLC (Waters XBridge C18 5μ 100×30 mm, methanol/water+0.1% formic acid) (5.9 mg, 0.0145 mmol, 4% yield, 90% purity).

LC-MS (Method I): Rt=1.22 min; MS (ESIpos): m/z=408 [M+H]$^+$ $^1$H-NMR (400 MHz, DMSO-d$_6$) δ [ppm]: 3.90 (s, 2H), 7.29-7.36 (m, 2H), 7.38 (s, 2H), 7.42-7.49 (m, 3H), 7.85 (dd, 1H), 7.94 (s, 1H), 8.40 (d, 1H), 9.13 (s, 1H), 10.72 (s, 1H).

Example 419

2-(2-Chlorophenyl)-N-[3-sulfamoyl-4-(1,2-thiazol-3-yl)phenyl]acetamide

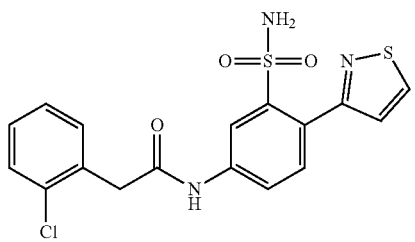 [SMILES: NS(=O)(=O)c1cc(NC(=O)Cc2ccccc2Cl)ccc1-c1ccsn1]

According to general procedure GP8.2, N-(4-bromo-3-{[(dimethylamino)methylene]sulfamoyl}phenyl)-2-(2-chlorophenyl)acetamide (300 mg, 0.65 mmol) and 3-bromo-1,2-thiazole (195 mg, 1.19 mmol) were converted to the title compound and were purified by preparative HPLC (Chromatorex C-18 10 μm, 125×30 mm, acetonitrile/water+0.1% aqueous ammonia (32%)), followed by another preparative HPLC (Waters XBridge C18 5μ 100×30 mm, methanol/water+0.2% aqueous ammonia (32%)) (2.9 mg, 0.00711 mmol, 1% yield, 95% purity).

LC-MS (Method J): Rt=1.19 min; MS (ESIpos): m/z=408 [M+H]$^+$ $^1$H-NMR (400 MHz, DMSO-d$_6$) δ [ppm]: 3.90 (s, 2H), 7.29-7.36 (m, 2H), 7.40-7.50 (m, 4H), 7.60-7.67 (m, 2H), 7.96 (dd, 1H), 8.36 (d, 1H), 9.15 (d, 1H), 10.74 (s, 1H).

Example 420

2-(2-Chlorophenyl)-N-[4-(2-methyl-1,3-thiazol-4-yl)-3-sulfamoylphenyl]acetamide

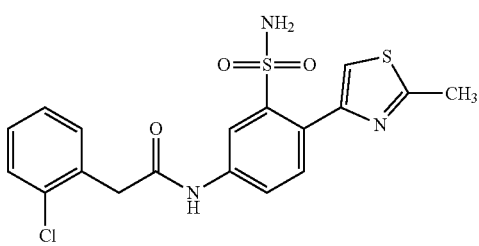 [SMILES: Cc1nc(-c2ccc(NC(=O)Cc3ccccc3Cl)cc2S(N)(=O)=O)cs1]

According to general procedure GP8.2, N-(4-bromo-3-{[(dimethylamino)methylene]-sulfamoyl}phenyl)-2-(2-chlorophenyl)acetamide (300 mg, 0.65 mmol) and 4-bromo-2-methyl-1,3-thiazole (211 mg, 1.19 mmol) were converted to the title compound and were purified by preparative HPLC (Waters XBridge C18 5μ 100×30 mm, acetonitrile/water+0.1% formic acid) (19 mg, 0.0450 mmol, 7% yield, 97% purity).

LC-MS (Method A): Rt=1.06 min; MS (ESIpos): m/z=422 [M+H]$^+$ $^1$H-NMR (400 MHz, DMSO-de) δ [ppm]: 2.73 (s, 3H), 3.89 (s, 2H), 7.30-7.35 (m, 2H), 7.42-7.48 (m, 2H), 7.59-7.63 (m, 3H), 7.71 (s, 1H), 7.93 (dd, 1H), 8.32 (d, 1H), 10.69 (s, 1H).

Example 421

2-(2-Chlorophenyl)-N-[4-(2-methoxy-1,3-thiazol-4-yl)-3-sulfamoylphenyl]acetamide

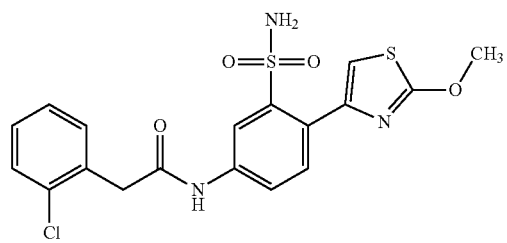 [SMILES: COc1nc(-c2ccc(NC(=O)Cc3ccccc3Cl)cc2S(N)(=O)=O)cs1]

According to general procedure GP8.2, N-(4-bromo-3-{[(dimethylamino)methylene]-sulfamoyl}phenyl)-2-(2-chlorophenyl)acetamide (300 mg, 0.65 mmol) and 4-bromo-2-methoxy-1,3-thiazole (230 mg, 1.19 mmol) were converted to the title compound and were purified by preparative HPLC (Waters XBridge C18 5μ 100×30 mm, acetonitrile/water+0.1% formic acid) (25 mg, 0.057 mmol, 9% yield, 97% purity).

LC-MS (Method A): Rt=1.08 min; MS (ESIpos): m/z=438 [M+H]$^+$ $^1$H-NMR (500 MHz, DMSO-d$_6$) δ [ppm]: 3.89 (s, 2H), 4.05 (s, 3H), 7.25 (s, 1H), 7.30-7.35 (m, 2H), 7.42-7.47 (i, 2H), 7.49 (s, 2H), 7.61 (d, 1H), 7.92 (dd, 1H), 8.31 (d, 1H), 10.69 (s, 1H).

Example 422

2-(2-Chlorophenyl)-N-[4-(2-methoxy-1,3-thiazol-5-yl)-3-sulfamoylphenyl]acetamide

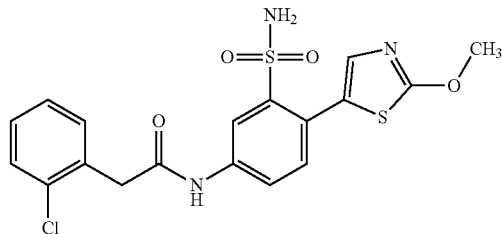 [SMILES: COc1ncc(-c2ccc(NC(=O)Cc3ccccc3Cl)cc2S(N)(=O)=O)s1]

According to general procedure GP8.2, N-(4-bromo-3-{[(dimethylamino)methylene]-sulfamoyl}phenyl)-2-(2-chlorophenyl)acetamide (300 mg, 0.65 mmol) and 5-bromo-2-methoxy-1,3-thiazole (230 mg, 1.19 mmol) were converted to the title compound and were purified by preparative HPLC (Waters XBridge C18 5μ 100×30 mm, acetonitrile/water+0.1% formic acid), followed by another preparative HPLC (Waters XBridge C18 5μ 100×30 mm, acetonitrile/water+0.2% aqueous ammonia (32%)) (23 mg, 0.0525 mmol, 8% yield, 98% purity).

LC-MS (Method B): Rt=0.97 min; MS (ESIpos): m/z=438 [M+H]$^+$ $^1$H-NMR (400 MHz, DMSO-d$_6$) δ [ppm]: 3.89 (s, 2H), 4.04 (s, 3H), 7.22 (s, 1H), 7.29-7.35 (m, 2H), 7.37 (s, 2H), 7.41-7.47 (m, 3H), 7.83 (dd, 1H), 8.36 (d, 1H), 10.69 (s, 1H).

Example 423

2-(2-Chlorophenyl)-N-[4-(2-methyl-1,3-thiazol-5-yl)-3-sulfamoylphenyl]acetamide

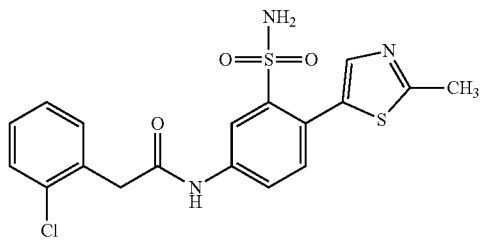 [SMILES: Cc1ncc(-c2ccc(NC(=O)Cc3ccccc3Cl)cc2S(N)(=O)=O)s1]

According to general procedure GP8.2, N-(4-bromo-3-{[(dimethylamino)methylene]-sulfamoyl}phenyl)-2-(2-chlorophenyl)acetamide (300 mg, 0.65 mmol) and 5-bromo-2-methyl-1,3-thiazole (211 mg, 1.19 mmol) were converted to the title compound and were purified twice by preparative HPLC (Waters XBridge C18 5μ 100×30 mm, acetonitrile/water+0.1% formic acid) (20 mg, 0.0474 mmol, 7% yield, 97% purity).

LC-MS (Method A): Rt=0.99 min; MS (ESIpos): m/z=422 [M+H]$^+$ $^1$H-NMR (400 MHz, DMSO-d$_6$) δ [ppm]: 2.67 (s, 3H), 3.89 (s, 2H), 7.28-7.38 (m, 4H), 7.39-7.48 (m, 3H), 7.65 (s, 1H), 7.83 (dd, 1H), 8.37 (d, 1H), 10.70 (s, 1H).

Example 424

2-(2-Chlorophenyl)-N-[4-(3-methyl-1,2-thiazol-5-yl)-3-sulfamoylphenyl]acetamide

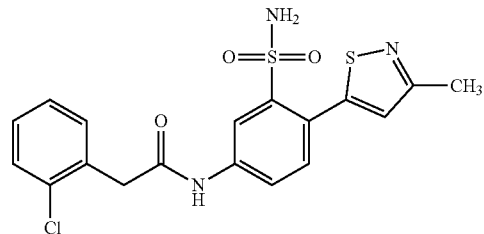 [SMILES: Cc1cc(-c2ccc(NC(=O)Cc3ccccc3Cl)cc2S(N)(=O)=O)sn1]

According to general procedure GP8.2, N-(4-bromo-3-{[(dimethylamino)methylene]-sulfamoyl}phenyl)-2-(2-chlorophenyl)acetamide (300 mg, 0.65 mmol) and 5-bromo-3-methyl-1,2-thiazole (211 mg, 1.19 mmol) were converted to the title compound and were purified by preparative HPLC (Waters XBridge C18 5μ 100×30 mm, acetonitrile/water+0.1% formic acid), followed by another by preparative HPLC (Waters XBridge C18 5μ 100×30 mm, methanol/water+0.2% aqueous ammonia (32%)) (32 mg, 0.0758 mmol, 12% yield, 97% purity).

LC-MS (Method J): Rt=1.22 min; MS (ESIpos): m/z=422 [M+H]$^+$ $^1$H-NMR (400 MHz, DMSO-d$_6$) δ [ppm]: 2.45 (s, 3H), 3.90 (s, 2H), 7.28-7.36 (m, 3H), 7.39-7.50 (m, 5H), 7.87 (dd, 1H), 8.40 (d, 1H), 10.75 (s, 1H).

Example 425

2-(2-Chlorophenyl)-N-[4-(4-methyl-1,3-thiazol-2-yl)-3-sulfamoylphenyl]acetamide

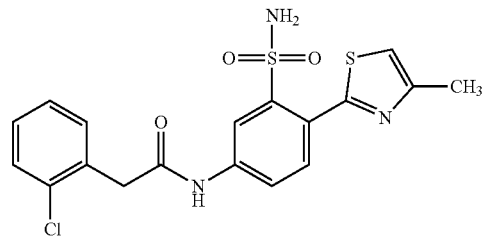 [SMILES: Cc1csc(-c2ccc(NC(=O)Cc3ccccc3Cl)cc2S(N)(=O)=O)n1]

According to general procedure GP8.2, N-(4-bromo-3-{[(dimethylamino)methylene]-sulfamoyl}phenyl)-2-(2-chlorophenyl)acetamide (300 mg, 0.65 mmol) and 2-bromo-4-methyl-1,3-thiazole (211 mg, 1.19 mmol) were converted to the title compound and were purified by preparative HPLC (Waters XBridge C18 5μ 100×30 mm, acetonitrile/water+0.1% formic acid) (35 mg, 0.0830 mmol, 13% yield, 98% purity).

LC-MS (Method A): Rt=1.10 min; MS (ESIpos): m/z=422 [M+H]$^+$ $^1$H-NMR (400 MHz, DMSO-d$_6$) δ [ppm]: 2.43 (d, 3H), 3.90 (s, 2H), 7.28-7.37 (m, 2H), 7.41-7.49 (m, 3H), 7.72-7.78 (m, 3H), 7.99 (dd, 1H), 8.38 (d, 1H), 10.81 (s, 1H).

Example 426

2-(2-Chlorophenyl)-N-[3-sulfamoyl-4-(1,2-thiazol-4-yl)phenyl]acetamide

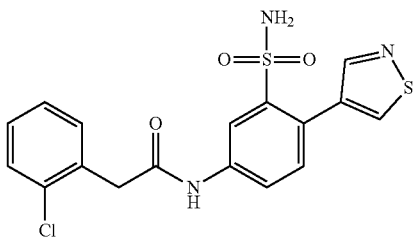 [SMILES: NS(=O)(=O)c1cc(NC(=O)Cc2ccccc2Cl)ccc1-c1cnsc1]

According to general procedure GP8.2, N-(4-bromo-3-{[(dimethylamino)methylene]-sulfamoyl}phenyl)-2-(2-chlorophenyl)acetamide (300 mg, 0.65 mmol) and 4-bromo-1,2-thiazole (195 mg, 1.19 mmol) were converted to the title compound and were purified by preparative HPLC (Waters XBridge C18 5μ 100×30 mm, acetonitrile/water+0.1% formic acid), followed by another preparative HPLC (Waters XBridge C18 5μ 100×30 mm, acetonitrile/water+0.2% aqueous ammonia (32%)) (9 mg, 0.0221 mmol, 3% yield, 95% purity).

LC-MS (Method B): Rt=0.86 min; MS (ESIpos): m/z=408 [M+H]$^+$ $^1$H-NMR (400 MHz, DMSO-d$_6$) δ [ppm]: 3.90 (s, 2H), 7.30-7.35 (m, 2H), 7.37 (s, 2H), 7.40 (d, 1H), 7.42-7.48 (m, 2H), 7.85 (dd, 1H), 8.38 (d, 1H), 8.63 (s, 1H), 9.04 (s, 1H), 10.68 (s, 1H).

Example 427

2-(2-Chlorophenyl)-N-[3-sulfamoyl-4-(1,3-thiazol-2-yl)phenyl]acetamide

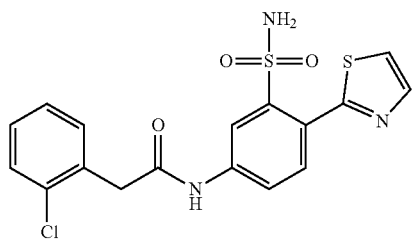 [SMILES: NS(=O)(=O)c1cc(NC(=O)Cc2ccccc2Cl)ccc1-c1nccs1]

According to general procedure GP8.2, N-(4-bromo-3-{[(dimethylamino)methylene]-sulfamoyl}phenyl)-2-(2-chlorophenyl)acetamide (300 mg, 0.65 mmol) and 2-bromo-1,3-thiazole (195 mg, 1.19 mmol) were converted to the title compound and were purified by preparative HPLC (Waters XBridge C18 5μ 100×30 mm, acetonitrile/water+0.1% formic acid), followed by another preparative HPLC (Waters XBridge C18 5μ 100×30 mm, acetonitrile/water+0.2% aqueous ammonia (32%)) (6 mg, 0.0147 mmol, 2% yield, 95% purity).

LC-MS (Method B): Rt=1.01 min; MS (ESIpos): m/z=408 [M+H]$^+$ $^1$H-NMR (400 MHz, DMSO-d$_6$) δ [ppm]: 3.91 (s, 2H), 7.29-7.37 (m, 2H), 7.42-7.49 (m, 2H), 7.73 (s, 2H), 7.77 (d, 1H), 7.91 (d, 1H), 7.98-8.03 (m, 2H), 8.40 (d, 1H), 10.82 (s, 1H).

Example 428

2-(2-Chlorophenyl)-N-[4-(4-cyano-1,3-thiazol-2-yl)-3-sulfamoylphenyl]acetamide

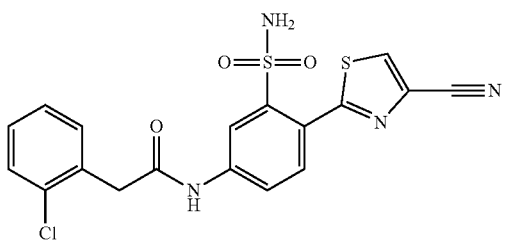 [SMILES: N#Cc1csc(-c2ccc(NC(=O)Cc3ccccc3Cl)cc2S(N)(=O)=O)n1]

According to general procedure GP8.2, N-(4-bromo-3-{[(dimethylamino)methylene]-sulfamoyl}phenyl)-2-(2-chlorophenyl)acetamide (300 mg, 0.65 mmol) and 2-bromo-1,3-thiazole-4-carbonitrile (224 mg, 1.19 mmol) were converted to the title compound and were purified twice by preparative HPLC (Waters XBridge C18 5μ 100×30 mm, acetonitrile/water+0.1% formic acid) (5 mg, 0.0116 mmol, 2% yield, 95% purity).

LC-MS (Method B): Rt=0.95 min; MS (ESIpos): m/z=433 [M+H]$^+$ $^1$H-NMR (400 MHz, DMSO-d$_6$) δ [ppm]: 3.92 (s, 2H), 7.30-7.36 (m, 2H), 7.43-7.53 (m, 4H), 7.75 (d, 1H), 7.98 (dd, 1H), 8.42 (d, 1H), 9.01 (s, 1H), 10.87 (s, 1H).

Example 429

2-(2-Chlorophenyl)-N-{4-[2-(difluoromethyl)-1,3-thiazol-5-yl]-3-sulfamoylphenyl}acetamide

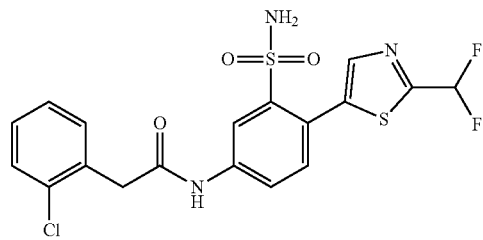 [SMILES: NS(=O)(=O)c1cc(NC(=O)Cc2ccccc2Cl)ccc1-c1cnc(C(F)F)s1]

According to general procedure GP8.2, N-(4-bromo-3-{[(dimethylamino)methylene]-sulfamoyl}phenyl)-2-(2-chlorophenyl)acetamide (300 mg, 0.65 mmol) and 5-bromo-2-(difluoromethyl)-1,3-thiazole (254 mg, 1.19 mmol) were converted to the title compound and were purified twice by preparative HPLC (Chromatorex C-18 10 μm, 125×30 mm, acetonitrile/water+0.1% formic acid) (11 mg, 0.0240 mmol, 4% yield, 85% purity).

LC-MS (Method A): Rt=1.11 min; MS (ESIpos): m/z=458 [M+H]$^+$ $^1$H-NMR (400 MHz, DMSO-d$_6$) δ [ppm]: 3.90 (s, 2H), 7.30-7.35 (m, 2H), 7.38 (tr, 1H), 7.42-7.48 (m, 2H), 7.49-7.55 (m, 3H), 7.88 (dd, 1H), 8.00 (s, 1H), 8.42 (d, 1H), 10.77 (s, 1H).

Example 430

2-(2-Chlorophenyl)-N-[4-(2-cyclopropyl-1,3-thiazol-5-yl)-3-sulfamoylphenyl]acetamide

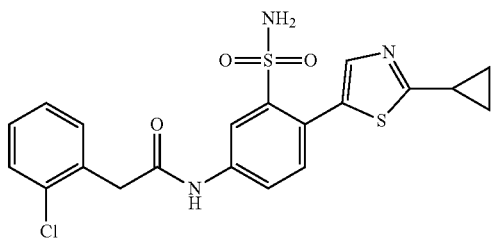 [SMILES: NS(=O)(=O)c1cc(NC(=O)Cc2ccccc2Cl)ccc1-c1cnc(C2CC2)s1]

According to general procedure GP8.2, N-(4-bromo-3-{[(dimethylamino)methylene]-sulfamoyl}phenyl)-2-(2-chlorophenyl)acetamide (300 mg, 0.65 mmol) and 5-bromo-2-cyclopropyl-1,3-thiazole (242 mg, 1.19 mmol) were converted to the title compound and were purified by preparative HPLC (Waters XBridge C18 5μ 100×30 mm, acetonitrile/water+0.1% formic acid) (26 mg, 0.0580 mmol, 9% yield, 95% purity).

LC-MS (Method A): Rt=1.06 min; MS (ESIpos): m/z=448 [M+H]$^+$ $^1$H-NMR (400 MHz, DMSO-d$_6$) δ [ppm]: 0.97-1.02 (m, 2H), 1.09-1.15 (m, 2H), 2.39 (tt, 1H), 3.89 (s, 2H), 7.30-7.34 (m, 2H), 7.37 (s, 2H), 7.40-7.47 (m, 3H), 7.60 (s, 1H), 7.82 (dd, 1H), 8.37 (d, 1H), 10.69 (s, 1H).

Example 431

2-(2-Chlorophenyl)-N-[4-(2-cyclopropyl-1,3-thiazol-4-yl)-3-sulfamoylphenyl]acetamide

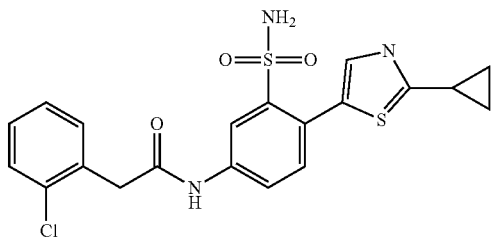

According to general procedure GP8.2, N-(4-bromo-3-{[(dimethylamino)methylene]-sulfamoyl}phenyl)-2-(2-chlorophenyl)acetamide (300 mg, 0.65 mmol) and 4-bromo-2-cyclopropyl-1,3-thiazole (242 mg, 1.19 mmol) were converted to the title compound and were purified by preparative HPLC (Waters XBridge C18 5μ 100×30 mm, acetonitrile/water+0.1% formic acid) (12 mg, 0.0268 mmol, 4% yield, 95% purity).

LC-MS (Method A): Rt=1.14 min; MS (ESIpos): m/z=448 [M+H]$^+$ $^1$H-NMR (400 MHz, DMSO-d$_6$) δ [ppm]: 0.95-0.99 (m, 2H), 1.16-1.21 (m, 2H), 1H overlapped by solvent signal, 3.89 (s, 2H), 7.29-7.36 (m, 2H), 7.42-7.49 (m, 2H), 7.54-7.64 (m, 4H), 7.93 (dd, 1H), 8.30 (d, 1H), 10.69 (s, 1H).

Example 432

2-(2-Chlorophenyl)-N-[4-(4-methyl-1,3-oxazol-2-yl)-3-sulfamoylphenyl]acetamide

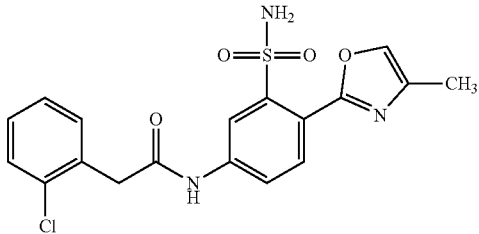 [SMILES: Cc1coc(-c2ccc(NC(=O)Cc3ccccc3Cl)cc2S(N)(=O)=O)n1]

According to general procedure GP8.2, N-(4-bromo-3-{[(dimethylamino)methylene]-sulfamoyl}phenyl)-2-(2-chlorophenyl)acetamide (300 mg, 0.65 mmol) and 4-bromo-2-methyl-1,3-oxazole hydrochloride (235 mg, 1.19 mmol) were converted to the title compound and were purified twice by preparative HPLC (Chromatorex C-18 10 μm, 125×30 mm, acetonitrile/water+0.1% formic acid) (1 mg, 0.00246 mmol, 1% yield, 80% purity).

LC-MS (Method A): Rt=1.09 min; MS (ESIpos): m/z=406 [M+H]$^+$ $^1$H-NMR (400 MHz, DMSO-d$_6$) δ [ppm]: 2.18 (d, 3H), 3.90 (s, 2H), 7.29-7.36 (m, 2H), 7.41-7.49 (m, 2H), 7.87 (s, 2H), 7.91 (d, 1H), 7.96-8.03 (m, 2H), 8.39 (d, 1H), 10.83 (s, 1H).

Example 433

2-(2-Chlorophenyl)-N-{3-sulfamoyl-4-[2-(trifluoromethyl)-1,3-thiazol-4-yl]phenyl}acetamide

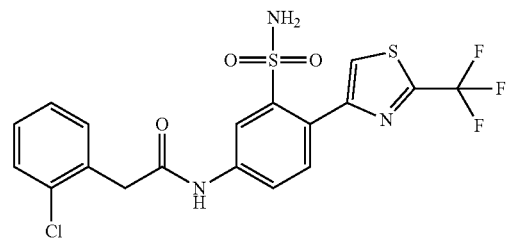 [SMILES: NS(=O)(=O)c1cc(NC(=O)Cc2ccccc2Cl)ccc1-c1csc(C(F)(F)F)n1]

According to general procedure GP8.2, N-(4-bromo-3-{[(dimethylamino)methylene]-sulfamoyl}phenyl)-2-(2-chlorophenyl)acetamide (300 mg, 0.65 mmol) and 4-bromo-2-(trifluoromethyl)-1,3-thiazole (275 mg, 1.19 mmol) were converted to the title compound and were purified by preparative HPLC (Chromatorex C-18 10 μm, 125×30 mm, acetonitrile/water+0.1% formic acid), followed by another preparative HPLC (Waters XBridge C18 5μ 100×30 mm, acetonitrile/water+0.2% aqueous ammonia (32%)) (9 mg, 0.0189 mmol, 3% yield, 85% purity).

LC-MS (Method B): Rt=1.14 min; MS (ESIneg): m/z=474 [M−H]$^-$ $^1$H-NMR (400 MHz, DMSO-d$_6$) δ [ppm]: 3.91 (s, 2H), 7.28-7.38 (m, 4H), 7.42-7.49 (m, 2H), 7.67 (d, 1H), 7.95 (dd, 1H), 8.35 (s, 1H), 8.39 (d, 1H), 10.76 (s, 1H).

Example 434

2-(2-Chlorophenyl)-N-{3-sulfamoyl-4-[4-(trifluoromethyl)-1,3-thiazol-2-yl]phenyl}acetamide

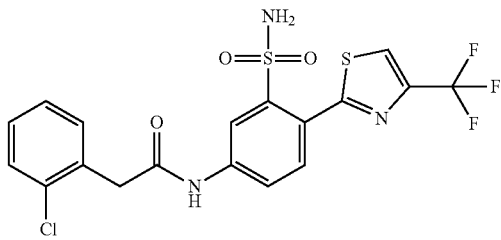 [SMILES: NS(=O)(=O)c1cc(NC(=O)Cc2ccccc2Cl)ccc1-c1nc(C(F)(F)F)cs1]

According to general procedure GP8.2, N-(4-bromo-3-{[(dimethylamino)methylene]-sulfamoyl}phenyl)-2-(2-chlorophenyl)acetamide (300 mg, 0.65 mmol) and 2-bromo-4-(trifluoromethyl)-1,3-thiazole (275 mg, 1.19 mmol) were converted to the title compound and were purified by preparative HPLC (Chromatorex C-18 10 μm, 125×30 mm, acetonitrile/water+0.1% formic acid), followed by another preparative HPLC (Waters XBridge C18 5μ 100×30 mm, acetonitrile/water+0.1% formic acid) (5 mg, 0.0105 mmol, 2% yield, 97% purity).

LC-MS (Method A): Rt=1.18 min; MS (ESIpos): m/z=476 [M+H]+

$^1$H-NMR (400 MHz, DMSO-$d_6$) δ [ppm]: 3.92 (s, 2H), 7.28-7.37 (m, 2H), 7.41-7.51 (m, 4H), 7.80 (d, 1H), 8.00 (dd, 1H), 8.43 (d, 1H), 8.69 (d, 1H), 10.87 (s, 1H).

Example 435

2-(2-Chlorophenyl)-N-{4-[2-(2-hydroxypropan-2-yl)-1,3-thiazol-5-yl]-3-sulfamoylphenyl}acetamide

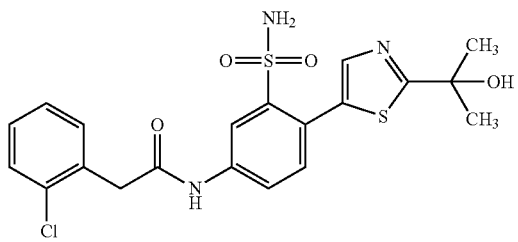 [SMILES: CC(C)(O)c1ncc(-c2ccc(NC(=O)Cc3ccccc3Cl)cc2S(N)(=O)=O)s1]

According to general procedure GP8.2, N-(4-bromo-3-{[(dimethylamino)methylene]-sulfamoyl}phenyl)-2-(2-chlorophenyl)acetamide (300 mg, 0.65 mmol) and 2-(5-bromo-1,3-thiazol-2-yl)propan-2-ol (263 mg, 1.19 mmol) were converted to the title compound and were purified by preparative HPLC (Waters XBridge C18 5μ 100×30 mm, acetonitrile/water+0.1% formic acid) (25 mg, 0.0537 mmol, 8% yield, 99% purity).

LC-MS (Method A): Rt=0.95 min; MS (ESIpos): m/z=466 [M+H]+

$^1$H-NMR (400 MHz, DMSO-$d_6$) δ [ppm]: 1.54 (s, 6H), 3.89 (s, 2H), 5.99 (s, 1H), 7.28-7.40 (m, 4H), 7.41-7.48 (m, 3H), 7.70 (s, 1H), 7.83 (dd, 1H), 8.38 (d, 1H), 10.70 (s, 1H).

Example 436

2-(2-Chlorophenyl)-N-{4-[2-(2-hydroxypropan-2-yl)-1,3-thiazol-4-yl]-3-sulfamoylphenyl}acetamide

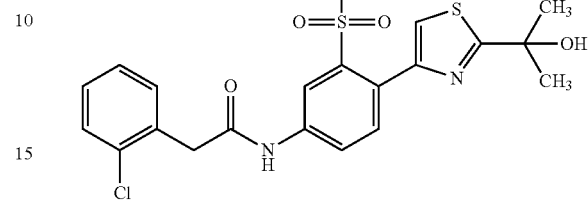

According to general procedure GP8.2, N-(4-bromo-3-{[(dimethylamino)methylene]-sulfamoyl}phenyl)-2-(2-chlorophenyl)acetamide (300 mg, 0.65 mmol) and 2-(4-bromo-1,3-thiazol-2-yl)propan-2-ol (263 mg, 1.19 mmol) were converted to the title compound and were purified by preparative HPLC (Waters XBridge C18 5μ 100×30 mm, acetonitrile/water+0.1% formic acid) (42 mg, 0.0901 mmol, 14% yield, 97% purity).

LC-MS (Method A): Rt=1.01 min; MS (ESIpos): m/z=466 [M+H]+

$^1$H-NMR (400 MHz, DMSO-$d_6$) δ [ppm]: 1.53 (s, 6H), 3.89 (s, 2H), 6.15 (s, 1H), 7.29-7.36 (m, 2H), 7.41-7.48 (m, 2H), 7.59-7.66 (m, 3H), 7.74 (s, 1H), 7.95 (dd, 1H), 8.31 (d, 1H), 10.69 (s, 1H).

Example 437

2-(2-Chlorophenyl)-N-[3-sulfamoyl-4-(1,3-thiazol-4-yl)phenyl]acetamide

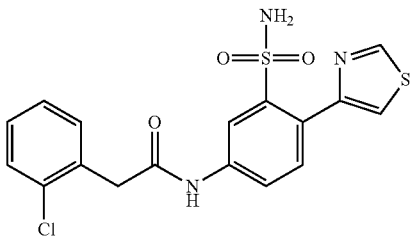 [SMILES: NS(=O)(=O)c1cc(NC(=O)Cc2ccccc2Cl)ccc1-c1cscn1]

According to general procedure GP8.2, N-(4-bromo-3-{[(dimethylamino)methylene]-sulfamoyl}phenyl)-2-(2-chlorophenyl)acetamide (600 mg, 1.31 mmol) and 4-bromo-1,3-thiazole (389 mg, 2.37 mmol) were converted to the title compound and were purified by preparative HPLC (Chromatorex C-18 10 μm, 125×30 mm, acetonitrile/water+0.1% formic acid), followed by another preparative HPLC (Waters XBridge C18 5μ 100×30 mm, acetonitrile/water+0.1% formic acid) (3 mg, 0.00735 mmol, 1% yield, 97% purity).

LC-MS (Method A): Rt=1.02 min; MS (ESIpos): m/z=408 [M+H]+

$^1$H-NMR (400 MHz, DMSO-$d_6$) δ [ppm]: 3.89 (s, 2H), 7.29-7.36 (m, 2H), 7.41-7.49 (m, 2H), 7.54-7.65 (m, 3H), 7.92-7.97 (m, 2H), 8.34 (d, 1H), 9.25 (d, 1H), 10.70 (s, 1H).

Example 438

2-(2-Chlorophenyl)-N-[4-(5-cyclopropyl-1,2-oxazol-3-yl)-3-sulfamoylphenyl]acetamide

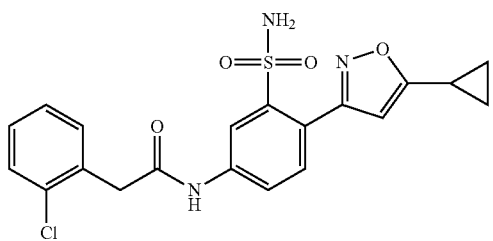 [SMILES: NS(=O)(=O)c1cc(NC(=O)Cc2ccccc2Cl)ccc1-c1cc(C2CC2)on1]

According to general procedure GP8.2, N-(4-bromo-3-{[(dimethylamino)methylene]-sulfamoyl}phenyl)-2-(2-chlorophenyl)acetamide (300 mg, 0.65 mmol) and 3-bromo-5-cyclopropyl-1,2-oxazole (223 mg, 1.19 mmol) were converted to the title compound and were purified by preparative HPLC (Waters XBridge C18 5μ 100×30 mm, acetonitrile/water+0.1% formic acid) (12 mg, 0.0427 mmol, 7% yield, 97% purity).

LC-MS (Method A): Rt=1.07 min; MS (ESIpos): m/z=432 [M+H]+

¹H-NMR (400 MHz, DMSO-d₆) δ [ppm]: 0.79-0.85 (m, 2H), 1.00-1.07 (m, 2H), 2.00-2.07 (m, 1H), 3.90 (s, 2H), 6.60 (s, 1H), 7.28-7.36 (m, 2H), 7.40-7.50 (m, 4H), 7.67 (d, 1H), 7.92 (dd, 1H), 8.40 (d, 1H), 10.80 (s, 1H).

Example 439

2-(2-Chlorophenyl)-N-[4-(2-cyclopropyl-1,3-oxazol-5-yl)-3-sulfamoylphenyl]acetamide

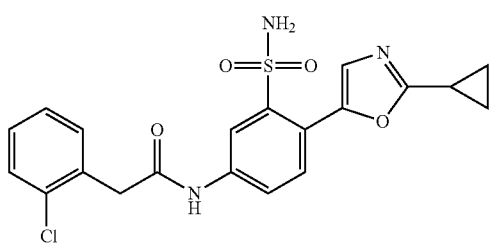 [SMILES: NS(=O)(=O)c1cc(NC(=O)Cc2ccccc2Cl)ccc1-c1cnc(C2CC2)o1]

According to general procedure GP8.2, N-(4-bromo-3-{[(dimethylamino)methylene]-sulfamoyl}phenyl)-2-(2-chlorophenyl)acetamide (300 mg, 0.65 mmol) and 5-bromo-2-cyclopropyl-1,3-oxazole (223 mg, 1.19 mmol) were converted to the title compound and were purified purified by preparative HPLC (Waters XBridge C18 5μ 100×30 mm, acetonitrile/water+0.1% formic acid), followed by another preparative HPLC (Waters XBridge C18 5μ 100×30 mm, methanol/water+0.1% formic acid) (12 mg, 0.0427 mmol, 7% yield, 97% purity).

LC-MS (Method 1): Rt=1.31 min; MS (ESIpos): m/z=432 [M+H]+

¹H-NMR (400 MHz, DMSO-d₆) δ [ppm]: 0.98-1.10 (m, 4H), 2.13-2.21 (m, 1H), 3.89 (s, 2H), 7.28-7.36 (m, 2H), 7.39-7.48 (m, 5H), 7.68 (d, 1H), 7.89 (dd, 1H), 8.37 (d, 1H), 10.71 (s, 1H).

Example 440

2-(2-Chlorophenyl)-N-(4-{4-[(3,3-difluoroazetidin-1-yl)carbonyl]-1H-pyrazol-1-yl}-3-sulfamoylphenyl)acetamide

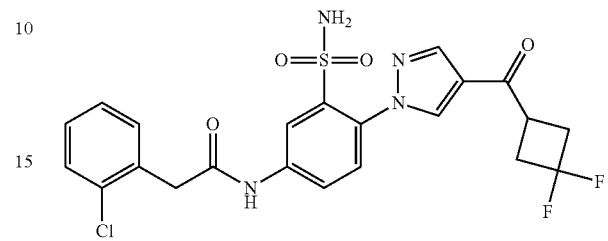

According to general procedures GP7.1, methyl 1-(4-{[(2-chlorophenyl)acetyl]amino}-2-sulfamoylphenyl)-1H-pyrazole-4-carboxylate (100 mg, 0.22 mmol) and 3,3-difluoroazetidine (51.8 mg, 0.56 mmol) were converted to the title compound and were purified by preparative HPLC (Waters XBridge C18 5μ 100×30 mm, acetonitrile/water+0.1% formic acid) (31 mg, 0.0608 mmol, 28% yield, 97% purity).

LC-MS (Method A): Rt=0.97 min; MS (ESIpos): m/z=510 [M+H]+

¹H-NMR (400 MHz, DMSO-d₆) δ [ppm]: 3.91 (s, 2H), 4.35-4.56 (m, 2H), 4.74-5.00 (m, 2H), 7.30-7.37 (m, 2H), 7.38-7.49 (m, 4H), 7.59 (d, 1H), 7.98 (dd, 1H), 8.07 (s, 1H), 8.39 (d, 1H), 8.50 (s, 1H), 10.82 (s, 1H).

Example 441

N-{4-[4-(Azetidin-1-ylcarbonyl)-1H-pyrazol-1-yl]-3-sulfamoylphenyl}-2-(2-chlorophenyl)acetamide

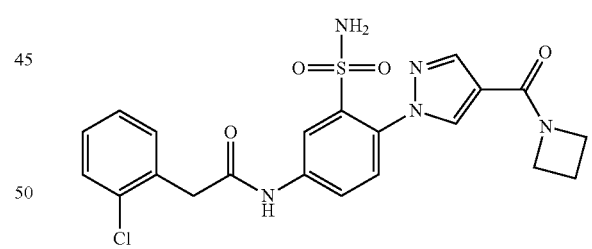

According to general procedures GP7.1, methyl 1-(4-{[(2-chlorophenyl)acetyl]amino}-2-sulfamoylphenyl)-1H-pyrazole-4-carboxylate (100 mg, 0.22 mmol) and azetidine (31.8 mg, 0.56 mmol) were converted to the title compound and were purified by preparative HPLC (Waters XBridge C18 5μ 100×30 mm, acetonitrile/water+0.1% formic acid) (17 mg, 0.0359 mmol, 16% yield, 98% purity).

LC-MS (Method A): Rt=0.90 min; MS (ESIpos): m/z=474 [M+H]+

¹H-NMR (400 MHz, DMSO-d₆) δ [ppm]: 2.24-2.32 (m, 2H), 3.91 (s, 2H), 4.00 (br t, 2H), 4.39 (br. t, 2H), 7.30-7.36 (m, 2H), 7.40-7.48 (m, 4H), 7.58 (d, 1H), 7.97 (dd, 1H), 8.01 (d, 1H), 8.38 (d, 1H), 8.41 (d, 1H), 10.80 (s, 1H).

Example 442

2-(2-Chlorophenyl)-N-{4-[4-(pyrrolidin-1-ylcarbonyl)-1H-pyrazol-1-yl]-3-sulfamoylphenyl}acetamide

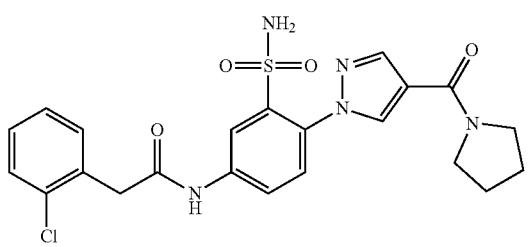 [SMILES: NS(=O)(=O)c1cc(NC(=O)Cc2ccccc2Cl)ccc1-n1cc(C(=O)N2CCCC2)cn1]

According to general procedures GP7.1, methyl 1-(4-{[(2-chlorophenyl)acetyl]amino}-2-sulfamoylphenyl)-1H-pyrazole-4-carboxylate (100 mg, 0.22 mmol) and pyrrolidine (39.6 mg, 0.56 mmol) were converted to the title compound and were purified by preparative HPLC (Waters XBridge C18 5μ 100×30 mm, acetonitrile/water+0.1% formic acid) (21 mg, 0.0430 mmol, 20% yield, 98% purity).

LC-MS (Method A): Rt=0.95 min; MS (ESIpos): m/z=488 [M+H]$^+$ $^1$H-NMR (400 MHz, DMSO-d$_6$) δ [ppm]: 1.79-1.88 (m, 2H), 1.89-1.97 (m, 2H), 3.46 (t, 2H), 3.68 (t, 2H), 3.91 (s, 2H), 7.29-7.37 (m, 2H), 7.40-7.49 (m, 4H), 7.60 (d, 1H), 7.97 (dd, 1H), 8.06 (d, 1H), 8.38 (d, 1H), 8.46 (d, 1H), 10.80 (s, 1H).

Example 443

2-(2-Chlorophenyl)-N-(4-{4-[(3,3-difluoropyrrolidin-1-yl)carbonyl]-1H-pyrazol-1-yl}-3-sulfamoylphenyl)acetamide

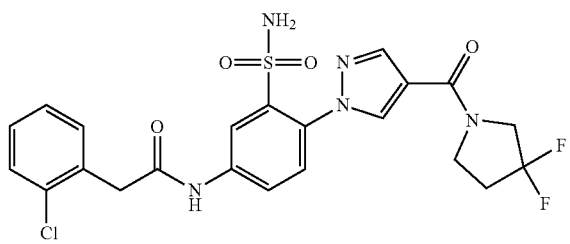 [SMILES: NS(=O)(=O)c1cc(NC(=O)Cc2ccccc2Cl)ccc1-n1cc(C(=O)N2CCC(F)(F)C2)cn1]

According to general procedures GP7.1, methyl 1-(4-{[(2-chlorophenyl)acetyl]amino}-2-sulfamoylphenyl)-1H-pyrazole-4-carboxylate (100 mg, 0.22 mmol) and 3,3-difluoropyrrolidine (59.7 mg, 0.56 mmol) were converted to the title compound and were purified by preparative HPLC (Waters XBridge C18 5μ 100×30 mm, acetonitrile/water+0.1% formic acid) (31 mg, 0.0592 mmol, 27% yield, 95% purity).

LC-MS (Method A): Rt=0.99 min; MS (ESIpos): m/z=524 [M+H]$^+$ $^1$H-NMR (400 MHz, DMSO-d$_6$) δ [ppm]: 3.70 (br t, 1H), 3.88 (br t, 1H), 3.91 (s, 2H), 3.97 (br t, 1H), 4.19 (br t, 1H), 7.29-7.36 (m, 2H), 7.40-7.49 (m, 4H), 7.62 (br t, 1H), 7.98 (dd, 1H), 8.10 (s, 1H), 8.38 (d, 1H), 8.53 (br d, 1H), 10.81 (s, 1H), 2H probably overlapped by water signal Example

444 2-(4-Chlorophenyl)-N-{3-sulfamoyl-4-[5-(trifluoromethyl)pyridin-3-yl]phenyl}acetamide

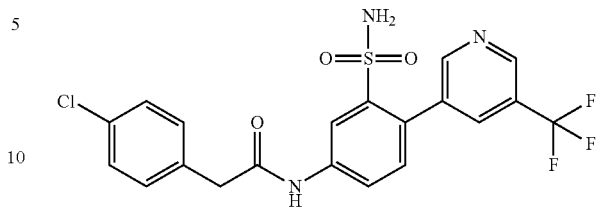

According to general procedure GP6.2, 5-amino-N-[(dimethylamino)methylene]-2-[5-(trifluoromethyl)pyridin-3-yl]benzenesulfonamide (0.20 mmol) and (4-chlorophenyl)acetic acid were converted to the title compound (12.9 mg, 0.0275 mmol, 14% yield, 100% purity).

LC-MS (Method A): Rt=1.15 min; MS (ESIpos): m/z=470 [M+H]$^+$

Example 445

2-(2-Chloro-6-fluorophenyl)-N-{3-sulfamoyl-4-[5-(trifluoromethyl)pyridin-3-yl]phenyl}acetamide

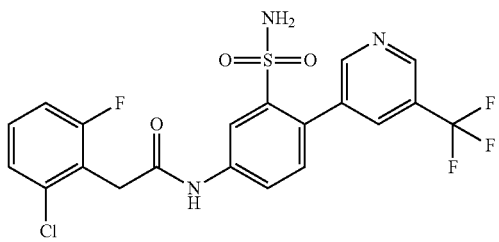 [SMILES: NS(=O)(=O)c1cc(NC(=O)Cc2c(F)cccc2Cl)ccc1-c1cncc(C(F)(F)F)c1]

According to general procedure GP6.2, 5-amino-N-[(dimethylamino)methylene]-2-[5-(trifluoromethyl)pyridin-3-yl]benzenesulfonamide (0.20 mmol) and (2-chloro-6-fluorophenyl)acetic acid were converted to the title compound (18.0 mg, 0.0369 mmol, 18% yield, 100% purity).

LC-MS (Method A): Rt=1.13 min; MS (ESIpos): m/z=488 [M+H]$^+$

Example 446

N-{3-Sulfamoyl-4-[5-(trifluoromethyl)pyridin-3-yl]phenyl}-2-[4-(trifluoromethyl)phenyl]acetamide

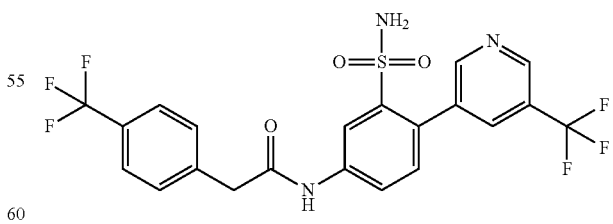

According to general procedure GP6.2, 5-amino-N-[(dimethylamino)methylene]-2-[5-(trifluoromethyl)pyridin-3-yl]benzenesulfonamide (0.20 mmol) and [4-(trifluoromethyl)phenyl]acetic acid were converted to the title compound (10.6 mg, 0.0211 mmol, 11% yield, 100% purity).

LC-MS (Method A): Rt=1.20 min; MS (ESIpos): m/z=504 [M+H]+

Example 447

2-(3-Fluorophenyl)-N-{3-sulfamoyl-4-[5-(trifluoromethyl)pyridin-3-yl]phenyl}acetamide

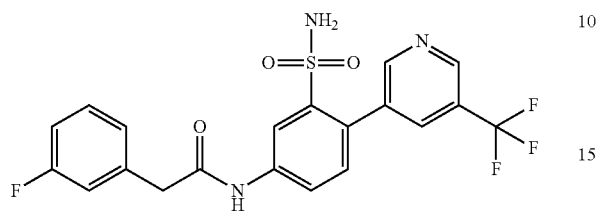

According to general procedure GP6.2, 5-amino-N-[(dimethylamino)methylene]-2-[5-(trifluoromethyl)pyridin-3-yl]benzenesulfonamide (0.20 mmol) and (3-fluorophenyl)acetic acid were converted to the title compound (20.7 mg, 0.0457 mmol, 23% yield, 100% purity).

LC-MS (Method A): Rt=1.09 min; MS (ESIpos): m/z=454 [M+H]+

Example 448

2-(2,4-Dichlorophenyl)-N-{3-sulfamoyl-4-[5-(trifluoromethyl)pyridin-3-yl]phenyl}acetamide

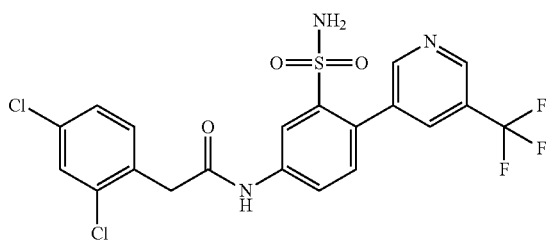 [SMILES: NS(=O)(=O)c1cc(NC(=O)Cc2ccc(Cl)cc2Cl)ccc1-c1cncc(C(F)(F)F)c1]

According to general procedure GP6.2, 5-amino-N-[(dimethylamino)methylene]-2-[5-(trifluoromethyl)pyridin-3-yl]benzenesulfonamide (0.20 mmol) and (2,4-dichlorophenyl)acetic acid were converted to the title compound (15.0 mg, 0.0297 mmol, 15% yield, 100% purity).

LC-MS (Method A): Rt=1.22 min; MS (ESIpos): m/z=504 [M+H]+

Example 449

2-(2-Bromophenyl)-N-{3-sulfamoyl-4-[5-(trifluoromethyl)pyridin-3-yl]phenyl}acetamide

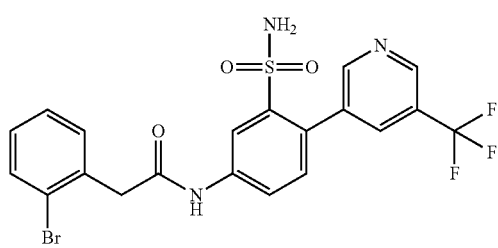 [SMILES: NS(=O)(=O)c1cc(NC(=O)Cc2ccccc2Br)ccc1-c1cncc(C(F)(F)F)c1]

According to general procedure GP6.2, 5-amino-N-[(dimethylamino)methylene]-2-[5-(trifluoromethyl)pyridin-3-yl]benzenesulfonamide (0.20 mmol) and (2-bromophenyl)acetic acid were converted to the title compound (12.9 mg, 0.0251 mmol, 13% yield, 100% purity).

LC-MS (Method A): Rt=1.13 min; MS (ESIpos): m/z=514 [M+H]+

Example 450

2-(2,4-Difluorophenyl)-N-{3-sulfamoyl-4-[5-(trifluoromethyl)pyridin-3-yl]phenyl}acetamide

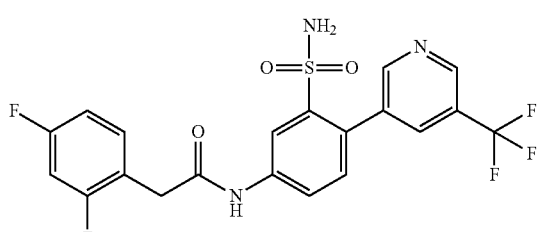

According to general procedure GP6.2, 5-amino-N-[(dimethylamino)methylene]-2-[5-(trifluoromethyl)pyridin-3-yl]benzenesulfonamide (0.20 mmol) and (2,4-difluorophenyl)acetic acid were converted to the title compound (13.9 mg, 0.0295 mmol, 15% yield, 100% purity).

LC-MS (Method A): Rt=1.10 min; MS (ESIpos): m/z=472 [M+H]+

Example 451

2-(3,4-Difluorophenyl)-N-{3-sulfamoyl-4-[5-(trifluoromethyl)pyridin-3-yl]phenyl}acetamide

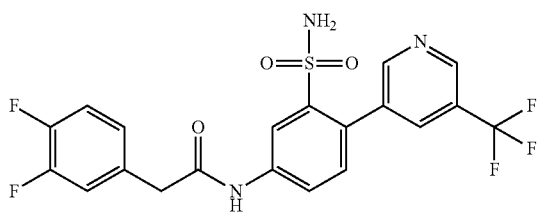

According to general procedure GP6.2, 5-amino-N-[(dimethylamino)methylene]-2-[5-(trifluoromethyl)pyridin-3-yl]benzenesulfonamide (0.20 mmol) and (3,4-difluorophenyl)acetic acid were converted to the title compound (20.3 mg, 0.0431 mmol, 22% yield, 100% purity).

LC-MS (Method A): Rt=1.12 min; MS (ESIpos): m/z=472 [M+H]+

Example 452

2-(3,5-Difluorophenyl)-N-{3-sulfamoyl-4-[5-(trifluoromethyl)pyridin-3-yl]phenyl}acetamide

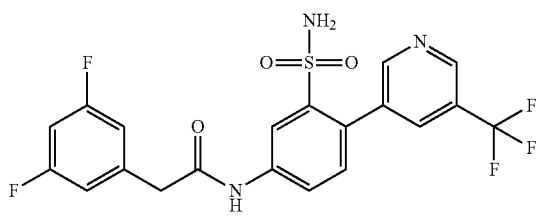 [SMILES: NS(=O)(=O)c1cc(NC(=O)Cc2cc(F)cc(F)c2)ccc1-c1cncc(C(F)(F)F)c1]

According to general procedure GP6.2, 5-amino-N-[(dimethylamino)methylene]-2-[5-(trifluoromethyl)pyridin-3-yl]benzenesulfonamide (0.20 mmol) and (3,4-difluorophenyl)acetic acid were converted to the title compound (20.3 mg, 0.0431 mmol, 22% yield, 100% purity).

LC-MS (Method A): Rt=1.12 min; MS (ESIpos): m/z=472 [M+H]$^+$

Example 453

2-(3-Chlorophenyl)-N-{3-sulfamoyl-4-[5-(trifluoromethyl)pyridin-3-yl]phenyl}acetamide

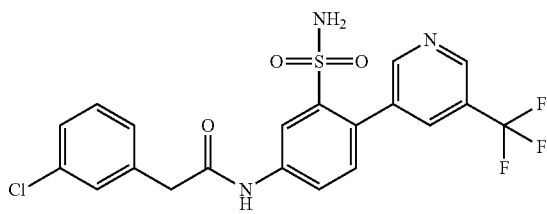 [SMILES: NS(=O)(=O)c1cc(NC(=O)Cc2cccc(Cl)c2)ccc1-c1cncc(C(F)(F)F)c1]

According to general procedure GP6.2, 5-amino-N-[(dimethylamino)methylene]-2-[5-(trifluoromethyl)pyridin-3-yl]benzenesulfonamide (0.20 mmol) and (3-chlorophenyl)acetic acid were converted to the title compound (7.0 mg, 0.0149 mmol, 7% yield, 78% purity).

LC-MS (Method A): Rt=1.15 min; MS (ESIpos): m/z=470 [M+H]$^+$

Example 454

2-(4-Methylphenyl)-N-{3-sulfamoyl-4-[5-(trifluoromethyl)pyridin-3-yl]phenyl}acetamide

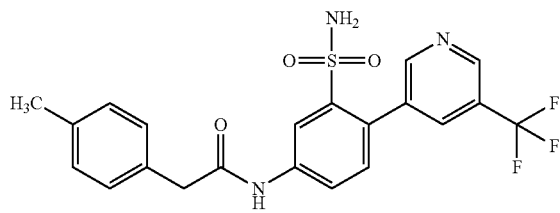 [SMILES: Cc1ccc(CC(=O)Nc2ccc(-c3cncc(C(F)(F)F)c3)c(S(N)(=O)=O)c2)cc1]

According to general procedure GP6.2, 5-amino-N-[(dimethylamino)methylene]-2-[5-(trifluoromethyl)pyridin-3-yl]benzenesulfonamide (0.20 mmol) and (4-methylphenyl)acetic acid were converted to the title compound (13.2 mg, 0.0294 mmol, 15% yield, 100% purity).

LC-MS (Method A): Rt=1.13 min; MS (ESIpos): m/z=450 [M+H]$^+$

Example 455

2-(4-Methoxyphenyl)-N-{3-sulfamoyl-4-[5-(trifluoromethyl)pyridin-3-yl]phenyl}acetamide

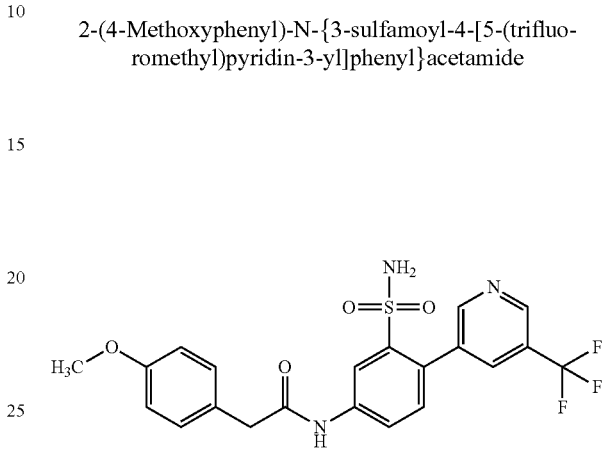

According to general procedure GP6.2, 5-amino-N-[(dimethylamino)methylene]-2-[5-(trifluoromethyl)pyridin-3-yl]benzenesulfonamide (0.20 mmol) and (4-methoxyphenyl)acetic acid were converted to the title compound (17.9 mg, 0.0385 mmol, 19% yield, 100% purity).

LC-MS (Method A): Rt=1.06 min; MS (ESIpos): m/z=466 [M+H]$^+$

Example 456

2-(2-Fluoro-4-methylphenyl)-N-{3-sulfamoyl-4-[5-(trifluoromethyl)pyridin-3-yl]phenyl}acetamide

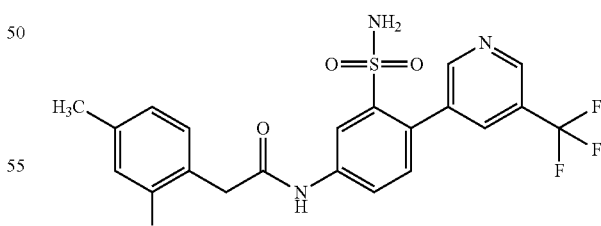

According to general procedure GP6.2, 5-amino-N-[(dimethylamino)methylene]-2-[5-(trifluoromethyl)pyridin-3-yl]benzenesulfonamide (0.20 mmol) and (2-fluoro-4-methylphenyl)acetic acid were converted to the title compound (21.6 mg, 0.0462 mmol, 23% yield, 100% purity).

LC-MS (Method A): Rt=1.14 min; MS (ESIpos): m/z=468 [M+H]$^+$

Example 457

2-(2-Fluoro-4-methoxyphenyl)-N-{3-sulfamoyl-4-[5-(trifluoromethyl)pyridin-3-yl]phenyl}acetamide

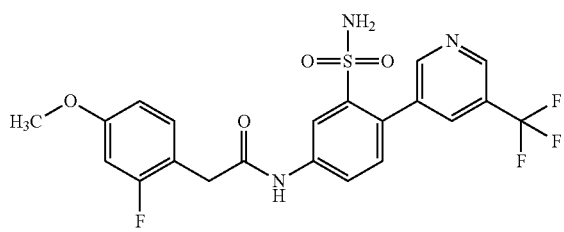 [SMILES: COc1ccc(CC(=O)Nc2ccc(-c3cncc(C(F)(F)F)c3)c(S(N)(=O)=O)c2)c(F)c1]

According to general procedure GP6.2, 5-amino-N-[(dimethylamino)methylene]-2-[5-(trifluoromethyl)pyridin-3-yl]benzenesulfonamide (0.20 mmol) and (2-fluoro-4-methoxyphenyl)acetic acid were converted to the title compound (23.5 mg, 0.0486 mmol, 24% yield, 100% purity).

LC-MS (Method A): Rt=1.09 min; MS (ESIpos): m/z=484 [M+H]$^+$

Example 458

2-[4-(Difluoromethyl)phenyl]-N-{3-sulfamoyl-4-[5-(trifluoromethyl)pyridin-3-yl]phenyl}acetamide

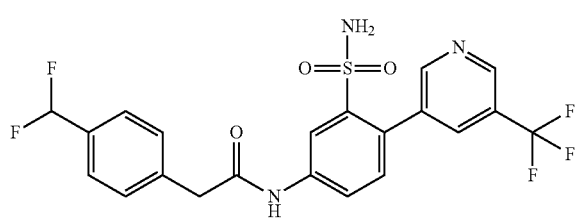 [SMILES: NS(=O)(=O)c1cc(NC(=O)Cc2ccc(C(F)F)cc2)ccc1-c1cncc(C(F)(F)F)c1]

According to general procedure GP6.2, 5-amino-N-[(dimethylamino)methylene]-2-[5-(trifluoromethyl)pyridin-3-yl]benzenesulfonamide (0.20 mmol) and [4-(difluoromethyl)phenyl]acetic acid were converted to the title compound (17.1 mg, 0.0352 mmol, 18% yield, 100% purity).

LC-MS (Method A): Rt=1.11 min; MS (ESIpos): m/z=486 [M+H]$^+$

Example 459

2-(4-Chlorophenyl)-N-[4-(6-chloropyridin-3-yl)-3-sulfamoylphenyl]acetamide

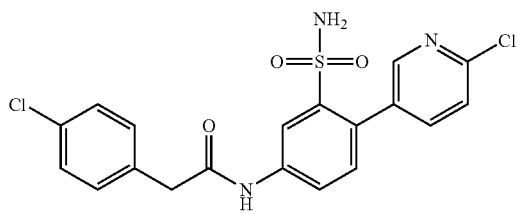 [SMILES: NS(=O)(=O)c1cc(NC(=O)Cc2ccc(Cl)cc2)ccc1-c1ccc(Cl)nc1]

According to general procedure GP6.2, 5-amino-2-(6-chloropyridin-3-yl)-N-[(dimethylamino)methylene]benzenesulfonamide (0.21 mmol) and (4-chlorophenyl)acetic acid were converted to the title compound (14.0 mg, 0.0321 mmol, 15% yield, 81% purity).

LC-MS (Method A): Rt=1.11 min; MS (ESIpos): m/z=436 [M+H]$^+$

Example 460

N-[4-(6-Chloropyridin-3-yl)-3-sulfamoylphenyl]-2-(2-fluorophenyl)acetamide

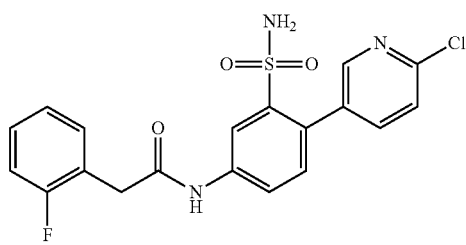 [SMILES: NS(=O)(=O)c1cc(NC(=O)Cc2ccccc2F)ccc1-c1ccc(Cl)nc1]

According to general procedure GP6.2, 5-amino-2-(6-chloropyridin-3-yl)-N-[(dimethylamino)methylene]benzenesulfonamide (0.21 mmol) and (2-fluorophenyl)acetic acid were converted to the title compound (15.0 mg, 0.0357 mmol, 17% yield, 91% purity).

LC-MS (Method A): Rt=1.02 min; MS (ESIpos): m/z=420 [M+H]$^+$

Example 461

2-(2-Chloro-6-fluorophenyl)-N-[4-(6-chloropyridin-3-yl)-3-sulfamoylphenyl]acetamide

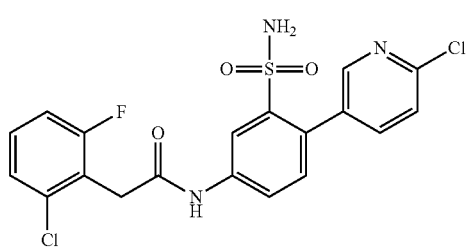

According to general procedure GP6.2, 5-amino-2-(6-chloropyridin-3-yl)-N-[(dimethylamino)methylene]benzenesulfonamide (0.21 mmol) and (2-chloro-6-fluorophenyl)acetic acid were converted to the title compound (10.3 mg, 0.0223 mmol, 11% yield, 100% purity).

LC-MS (Method A): Rt=1.08 min; MS (ESIpos): m/z=454 [M+H]$^+$

Example 462

N-[4-(6-Chloropyridin-3-yl)-3-sulfamoylphenyl]-2-[4-(trifluoromethyl)phenyl]acetamide

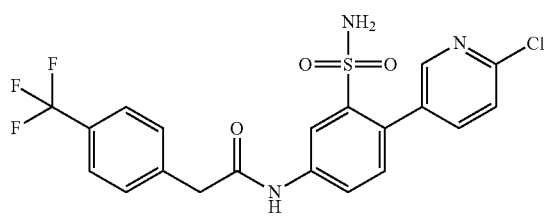 [SMILES: NS(=O)(=O)c1cc(NC(=O)Cc2ccc(C(F)(F)F)cc2)ccc1-c1ccc(Cl)nc1]

According to general procedure GP6.2, 5-amino-2-(6-chloropyridin-3-yl)-N-[(dimethylamino)methylene]benzenesulfonamide (0.21 mmol) and [4-(trifluoromethyl)phenyl]acetic acid were converted to the title compound (12.6 mg, 0.0268 mmol, 13% yield, 100% purity).

LC-MS (Method A): Rt=1.16 min; MS (ESIpos): m/z=470 [M+H]$^+$

Example 463

N-[4-(6-Chloropyridin-3-yl)-3-sulfamoylphenyl]-2-[2-(trifluoromethyl)phenyl]acetamide

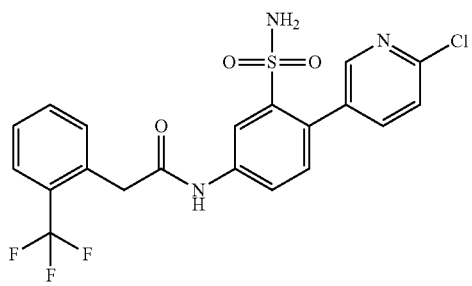 [SMILES: NS(=O)(=O)c1cc(NC(=O)Cc2ccccc2C(F)(F)F)ccc1-c1ccc(Cl)nc1]

According to general procedure GP6.2, 5-amino-2-(6-chloropyridin-3-yl)-N-[(dimethylamino)methylene]benzenesulfonamide (0.21 mmol) and [2-(trifluoromethyl)phenyl]acetic acid were converted to the title compound (20.0 mg, 0.0426 mmol, 20% yield, 76% purity).

LC-MS (Method A): Rt=1.12 min; MS (ESIpos): m/z=470 [M+H]$^+$

Example 464

N-[4-(6-Chloropyridin-3-yl)-3-sulfamoylphenyl]-2-(3-fluorophenyl)acetamide

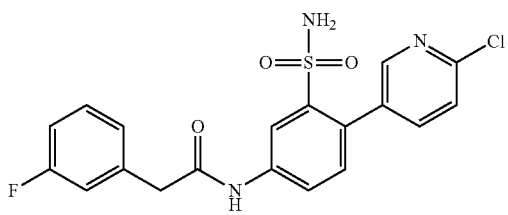 [SMILES: NS(=O)(=O)c1cc(NC(=O)Cc2cccc(F)c2)ccc1-c1ccc(Cl)nc1]

According to general procedure GP6.2, 5-amino-2-(6-chloropyridin-3-yl)-N-[(dimethylamino)methylene]benzenesulfonamide (0.21 mmol) and (3-fluorophenyl)acetic acid were converted to the title compound (13.1 mg, 0.0312 mmol, 15% yield, 100% purity).

LC-MS (Method A): Rt=1.04 min; MS (ESIpos): m/z=420 [M+H]$^+$

Example 465

N-[4-(6-Chloropyridin-3-yl)-3-sulfamoylphenyl]-2-(2,4-dichlorophenyl)acetamide

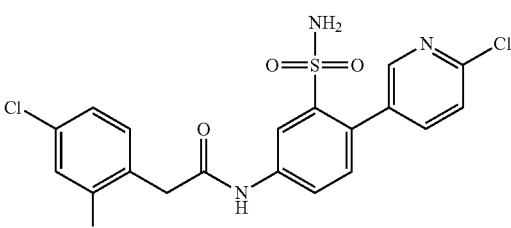

According to general procedure GP6.2, 5-amino-2-(6-chloropyridin-3-yl)-N-[(dimethylamino)methylene]benzenesulfonamide (0.21 mmol) and (2,4-dichlorophenyl)acetic acid were converted to the title compound (13.0 mg, 0.0276 mmol, 13% yield, 100% purity).

LC-MS (Method A): Rt=1.17 min; MS (ESIpos): m/z=470 [M+H]$^+$

Example 466

N-[4-(6-Chloropyridin-3-yl)-3-sulfamoylphenyl]-2-(2,4-difluorophenyl)acetamide

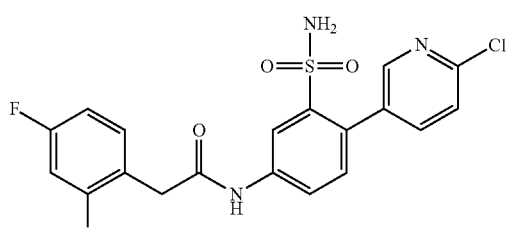

According to general procedure GP6.2, 5-amino-2-(6-chloropyridin-3-yl)-N-[(dimethylamino)methylene]benzenesulfonamide (0.21 mmol) and (2,4-difluorophenyl)acetic acid were converted to the title compound (13.0 mg, 0.0297 mmol, 14% yield, 82% purity).

LC-MS (Method A): Rt=1.05 min; MS (ESIpos): m/z=438 [M+H]$^+$

Example 467

2-(2-Bromophenyl)-N-[4-(6-chloropyridin-3-yl)-3-sulfamoylphenyl]acetamide

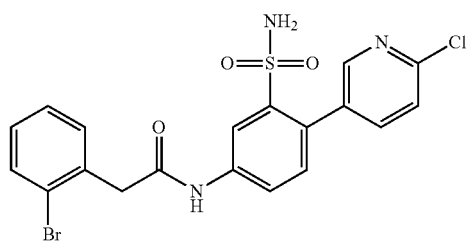

According to general procedure GP6.2, 5-amino-2-(6-chloropyridin-3-yl)-N-[(dimethylamino)methylene]benzenesulfonamide (0.21 mmol) and (2-bromophenyl)acetic acid were converted to the title compound (18.8 mg, 0.0391 mmol, 19% yield, 100% purity).

LC-MS (Method A): Rt=1.08 min; MS (ESIpos): m/z=480 [M+H]$^+$

Example 468

N-[4-(6-Chloropyridin-3-yl)-3-sulfamoylphenyl]-2-(3,4-difluorophenyl)acetamide

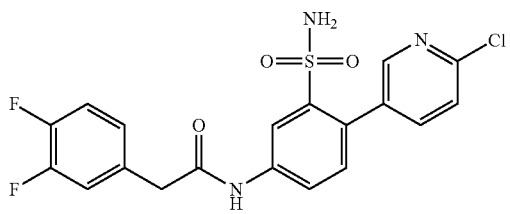 [SMILES: NS(=O)(=O)c1cc(NC(=O)Cc2ccc(F)c(F)c2)ccc1-c1ccc(Cl)nc1]

According to general procedure GP6.2, 5-amino-2-(6-chloropyridin-3-yl)-N-[(dimethylamino)methylene]benzenesulfonamide (0.21 mmol) and (3,4-difluorophenyl)acetic acid were converted to the title compound (13.9 mg, 0.0317 mmol, 15% yield, 100% purity).

LC-MS (Method A): Rt=1.07 min; MS (ESIpos): m/z=438 [M+H]$^+$

Example 469

N-[4-(6-Chloropyridin-3-yl)-3-sulfamoylphenyl]-2-(4-methylphenyl)acetamide

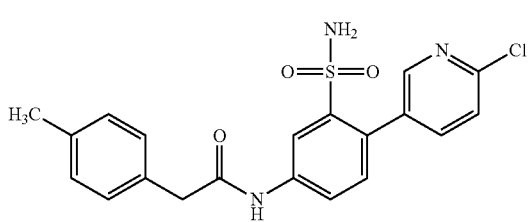 [SMILES: Cc1ccc(CC(=O)Nc2ccc(-c3ccc(Cl)nc3)c(S(N)(=O)=O)c2)cc1]

According to general procedure GP6.2, 5-amino-2-(6-chloropyridin-3-yl)-N-[(dimethylamino)methylene]benzenesulfonamide (0.21 mmol) and (4-methylphenyl)acetic acid were converted to the title compound (9.4 mg, 0.0226 mmol, 11% yield, 100% purity).

LC-MS (Method A): Rt=1.08 min; MS (ESIpos): m/z=416 [M+H]$^+$

Example 470

N-[4-(6-Chloropyridin-3-yl)-3-sulfamoylphenyl]-2-(4-methoxyphenyl)acetamide

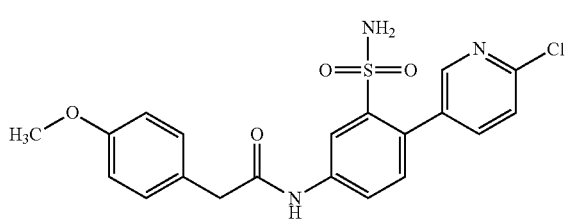 [SMILES: COc1ccc(CC(=O)Nc2ccc(-c3ccc(Cl)nc3)c(S(N)(=O)=O)c2)cc1]

According to general procedure GP6.2, 5-amino-2-(6-chloropyridin-3-yl)-N-[(dimethylamino)methylene]benzenesulfonamide (0.21 mmol) and (4-methoxyphenyl)acetic acid were converted to the title compound (18.8 mg, 0.0435 mmol, 21% yield, 92% purity).

LC-MS (Method A): Rt=1.01 min; MS (ESIpos): m/z=432 [M+H]$^+$

Example 471

N-[4-(6-Chloropyridin-3-yl)-3-sulfamoylphenyl]-2-(2-fluoro-4-methylphenyl)acetamide

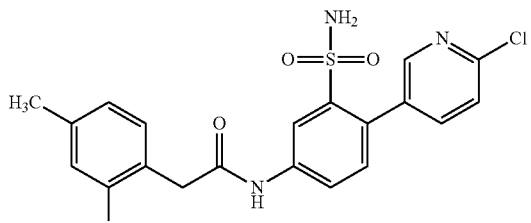

According to general procedure GP6.2, 5-amino-2-(6-chloropyridin-3-yl)-N-[(dimethylamino)methylene]benzenesulfonamide (0.21 mmol) and (2-fluoro-4-methylphenyl)acetic acid were converted to the title compound (21.2 mg, 0.0489 mmol, 23% yield, 85% purity).

LC-MS (Method A): Rt=1.09 min; MS (ESIpos): m/z=434 [M+H]$^+$

Example 472

N-[4-(6-Chloropyridin-3-yl)-3-sulfamoylphenyl]-2-(2-fluoro-4-methoxyphenyl)acetamide

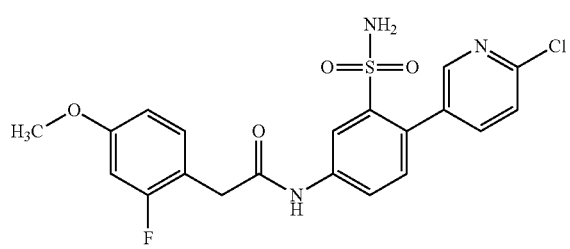 [SMILES: COc1ccc(CC(=O)Nc2ccc(-c3ccc(Cl)nc3)c(S(N)(=O)=O)c2)c(F)c1]

According to general procedure GP6.2, 5-amino-2-(6-chloropyridin-3-yl)-N-[(dimethylamino)methylene]benzenesulfonamide (0.21 mmol) and (2-fluoro-4-methoxyphenyl)acetic acid were converted to the title compound (15.3 mg, 0.0340 mmol, 16% yield, 100% purity).

LC-MS (Method A): Rt=1.04 min; MS (ESIpos): m/z=450 [M+H]$^+$

Example 473

N-[4-(6-Chloropyridin-3-yl)-3-sulfamoylphenyl]-2-[4-(difluoromethyl)phenyl]acetamide

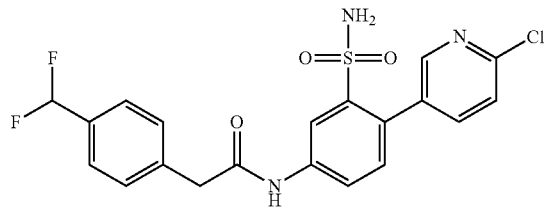 [SMILES: NS(=O)(=O)c1cc(NC(=O)Cc2ccc(C(F)F)cc2)ccc1-c1ccc(Cl)nc1]

According to general procedure GP6.2, 5-amino-2-(6-chloropyridin-3-yl)-N-[(dimethylamino)methylene]benzenesulfonamide (0.21 mmol) and [4-(difluoromethyl)phenyl]acetic acid were converted to the title compound (12.6 mg, 0.0279 mmol, 13% yield, 100% purity).

LC-MS (Method A): Rt=1.06 min; MS (ESIpos): m/z=452 [M+H]$^+$

Example 474

N-[4-(6-Chloropyridin-3-yl)-3-sulfamoylphenyl]-2-[2-chloro-4-(trifluoromethyl)phenyl]acetamide

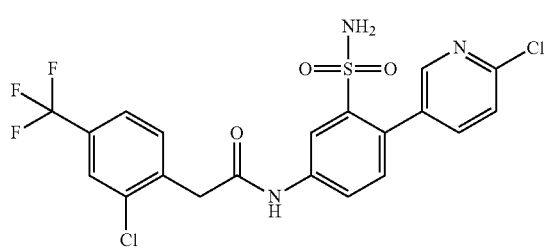 [SMILES: NS(=O)(=O)c1cc(NC(=O)Cc2ccc(C(F)(F)F)cc2Cl)ccc1-c1ccc(Cl)nc1]

According to general procedure GP6.2, 5-amino-2-(6-chloropyridin-3-yl)-N-[(dimethylamino)methylene]benzenesulfonamide (0.21 mmol) and [2-chloro-4-(trifluoromethyl)phenyl]acetic acid were converted to the title compound (13.7 mg, 0.0272 mmol, 13% yield, 100% purity).

LC-MS (Method A): Rt=1.21 min; MS (ESIpos): m/z=504 [M+H]$^+$

Example 475

2-(2,4-Dichlorophenyl)-N-[4-(5-fluoropyridin-3-yl)-3-sulfamoylphenyl]acetamide

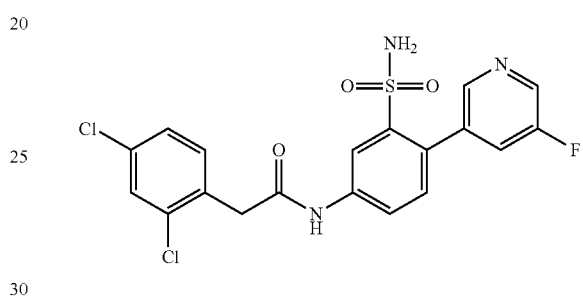

According to general procedure GP6.2, 5-amino-N-[(dimethylamino)methylene]-2-(5-fluoropyridin-3-yl)benzenesulfonamide (0.25 mmol) and (2,4-dichlorophenyl)acetic acid were converted to the title compound (16.0 mg, 0.0352 mmol, 14% yield, 100% purity).

LC-MS (Method A): Rt=1.11 min; MS (ESIpos): m/z=454 [M+H]$^+$

Example 476

2-(2-Fluoro-4-methylphenyl)-N-[4-(5-fluoropyridin-3-yl)-3-sulfamoylphenyl]acetamide

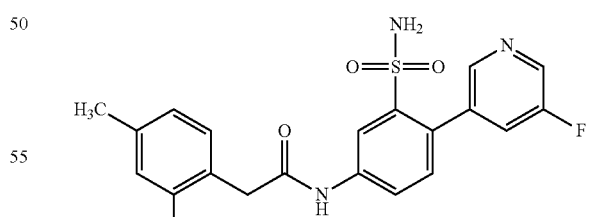

According to general procedure GP6.2, 5-amino-N-[(dimethylamino)methylene]-2-(5-fluoropyridin-3-yl)benzenesulfonamide (0.25 mmol) and (2-fluoro-4-methylphenyl)acetic acid were converted to the title compound (42.2 mg, 0.101 mmol, 40% yield, 73% purity).

LC-MS (Method A): Rt=1.03 min; MS (ESIpos): m/z=418 [M+H]$^+$

Example 477

2-[4-(Difluoromethyl)phenyl]-N-[4-(5-fluoropyridin-3-yl)-3-sulfamoylphenyl]acetamide

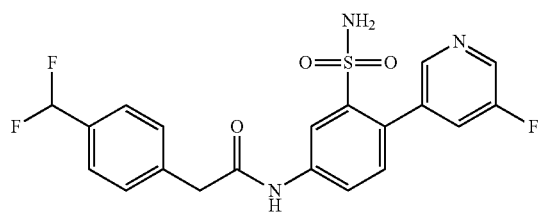 [SMILES: NS(=O)(=O)c1cc(NC(=O)Cc2ccc(C(F)F)cc2)ccc1-c1cncc(F)c1]

According to general procedure GP6.2, 5-amino-N-[(dimethylamino)methylene]-2-(5-fluoropyridin-3-yl)benzenesulfonamide (0.25 mmol) and [4-(difluoromethyl)phenyl]acetic acid were converted to the title compound (27.5 mg, 0.0632 mmol, 25% yield, 78% purity).

LC-MS (Method A): Rt=1.00 min; MS (ESIpos): m/z=436 [M+H]$^+$

Example 478

2-(2-Chlorophenyl)-N-[4-(4-cyclopropyl-1H-pyrazol-1-yl)-3-sulfamoylphenyl]acetamide

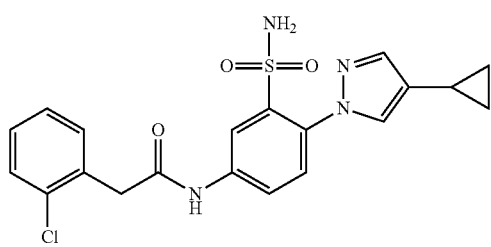 [SMILES: NS(=O)(=O)c1cc(NC(=O)Cc2ccccc2Cl)ccc1-n1cc(C2CC2)cn1]

According to general procedures GP1.2, GP2.1, GP3.3 and GP4.1, 2-chloro-N-(2,4-dimethoxybenzyl)-5-nitrobenzenesulfonamide (500 mg, 1.29 mmol), 4-cyclopropyl-1H-pyrazole (210 mg, 1.94 mmol) and (2-chlorophenyl)acetic acid (330 mg, 1.94 mmol) were converted without purification of intermediates to the title compound and were purified at the end twice by preparative HPLC (Waters XBridge C18 5μ 100×30 mm, acetonitrile/water+0.1% formic acid) (1 mg, 0.00232 mmol, 2% yield over 4 steps, 97% purity).

LC-MS (Method A): Rt=1.27 min; MS (ESIpos): m/z=431 [M+H]$^+$ $^1$H-NMR (400 MHz, DMSO-d$_6$) δ [ppm]: 0.55-0.61 (m, 2H), 0.84-0.90 (m, 2H), 1.73-1.81 (m, 1H), 3.89 (s, 2H), 7.29-7.37 (m, 2H), 7.42-7.51 (m, 5H), 7.58 (s, 1H), 7.88 (s, 1H), 7.96 (dd, 1H), 8.33 (d, 1H), 10.74 (s, 1H).

Example 479 and Example 480

According to general procedures GP1.2, GP2.1, GP3.3 and GP4.1, 2-chloro-N-(2,4-dimethoxybenzyl)-5-nitrobenzenesulfonamide (500 mg, 1.29 mmol), 4,6-difluoro-2H-benzotriazole (300 mg, 1.94 mmol) and (2-fluorophenyl)acetic acid (267 mg, 1.74 mmol) were converted without purification of intermediates to the title compounds which were purified and separated at the end by preparative HPLC (Chromatorex C-18 10 μm, 125×30 mm, acetonitrile/water+0.1% formic acid), followed by another preparative HPLC (Phenomenex Kinetex C18 EVO 5μ 100×30 mmk, acetonitrile/water+0.2% aqueous ammonia (32%)).

Example 479

N-[4-(4,6-Difluoro-2H-benzotriazol-2-yl)-3-sulfamoylphenyl]-2-(2-fluorophenyl)acetamide

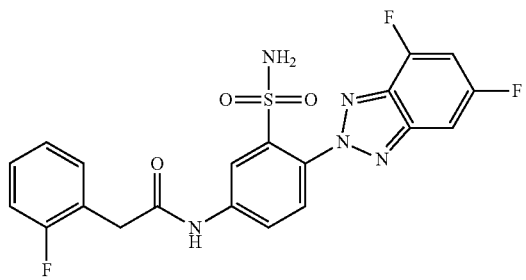

11 mg, 0.0238 mmol, 2% yield over 4 steps, 95% purity
LC-MS (Method J): Rt=1.32 min; MS (ESIpos): m/z=460 [M−H]$^-$ $^1$H-NMR (400 MHz, DMSO-d$_6$) δ [ppm]: 3.84 (s, 2H), 7.16-7.24 (m, 2H), 7.31-7.38 (m, 1H), 7.43 (td, 1H), 7.52-7.61 (m, 3H), 7.81 (dd, 1H), 7.87 (d, 1H), 8.05 (dd, 1H), 8.50 (d, 1H), 10.93 (s, 1H).

Example 480

N-[4-(4,6-Difluoro-1H-benzotriazol-1-yl)-3-sulfamoylphenyl]-2-(2-fluorophenyl)acetamide

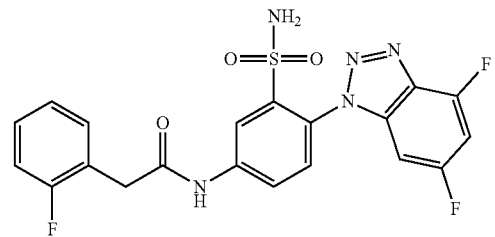

6.1 mg, 0.0132 mmol, 1% yield over 4 steps, 95% purity
LC-MS (Method J): Rt=1.22 min; MS (ESIpos): m/z=460 [M−H]$^-$ $^1$H-NMR (400 MHz, DMSO-d$_6$) δ [ppm]: 3.85 (s, 2H), 7.15-7.24 (m, 3H), 7.31-7.39 (m, 1H), 7.40-7.48 (m, 2H), 7.50 (s, 2H), 7.66 (d, 1H), 8.02 (dd, 1H), 8.52 (d, 1H), 10.93 (s, 1H).

Example 481 and Example 482

According to general procedures GP1.2, GP2.1, GP3.3 and GP4.1, 2-chloro-N-(2,4-dimethoxybenzyl)-5-nitrobenzenesulfonamide (500 mg, 1.29 mmol), 4,6-difluoro-2H-benzotriazole (300 mg, 1.94 mmol) and (2-chlorophenyl)acetic acid (296 mg, 1.74 mmol) were converted without purification of intermediates to the title compounds which were purified and separated at the end by preparative HPLC (Chromatorex C-18 10 μm, 125×30 mm, acetonitrile/water+0.1% formic acid), followed by another preparative HPLC (Phenomenex Kinetex C18 EVO 5μ 100×30 mmk, acetonitrile/water+0.2% aqueous ammonia (32%)).

Example 481

2-(2-Chlorophenyl)-N-[4-(4,6-difluoro-1H-benzotriazol-1-yl)-3-sulfamoylphenyl]acetamide

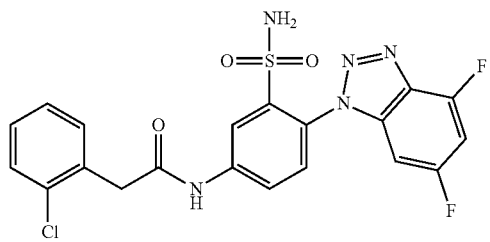 [SMILES: NS(=O)(=O)c1cc(NC(=O)Cc2ccccc2F)ccc1-n1nnc2c(F)cc(F)cc21]

10.6 mg, 0.0222 mmol, 2% yield over 4 steps, 95% purity

LC-MS (Method J): Rt=1.28 min; MS (ESIpos): m/z=476 [M−H]⁻

¹H-NMR (400 MHz, DMSO-$d_6$) δ [ppm]: 3.95 (s, 2H), 7.19 (dd, 1H), 7.30-7.38 (m, 2H), 7.41-7.54 (m, 5H), 7.66 (d, 1H), 8.02 (dd, 1H), 8.53 (d, 1H), 10.95 (s, 1H).

Example 482

2-(2-Chlorophenyl)-N-[4-(4,6-difluoro-2H-benzotriazol-2-yl)-3-sulfamoylphenyl]acetamide

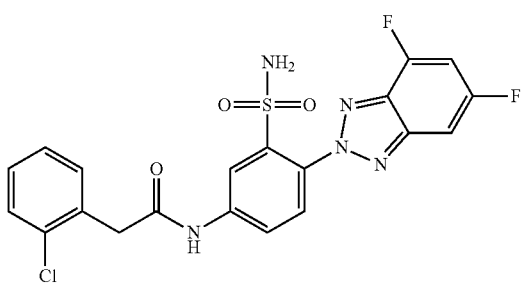 [SMILES: NS(=O)(=O)c1cc(NC(=O)Cc2ccccc2Cl)ccc1-n1nc2cc(F)cc(F)c2n1]

13.1 mg, 0.0274 mmol, 2% yield over 4 steps, 95% purity

LC-MS (Method J): Rt=1.36 min; MS (ESIpos): m/z=476 [M−H]⁻

¹H-NMR (600 MHz, DMSO-$d_6$) δ [ppm]: 3.95 (s, 2H), 7.31-7.37 (m, 2H), 7.45-7.49 (m, 2H), 7.52-7.60 (m, 3H), 7.82 (dd, 1H), 7.88 (d, 1H), 8.06 (dd, 1H), 8.51 (d, 1H), 10.97 (s, 1H).

Example 483

2-(2-Chlorophenyl)-N-{3-sulfamoyl-4-[2-(trifluoromethyl)-1,3-thiazol-5-yl]phenyl}acetamide

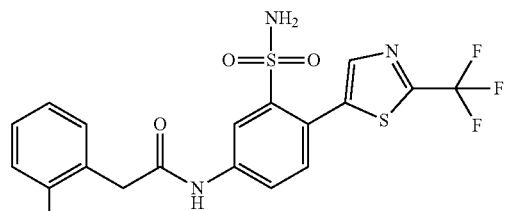

According to general procedure GP8.2, N-(4-bromo-3-{[(dimethylamino)methylene]-sulfamoyl}phenyl)-2-(2-chlorophenyl)acetamide (300 mg, 0.65 mmol) and 5-bromo-2-(trifluoromethyl)-1,3-thiazole (275 mg, 1.19 mmol) were converted to the title compound and were purified by preparative HPLC (Waters XBridge C18 5μ 100×30 mm, acetonitrile/water+0.1% formic acid) (11 mg, 0.0462 mmol, 7% yield, 97% purity).

LC-MS (Method A): Rt=1.16 min; MS (ESIpos): m/z=476 [M+H]⁺

¹H-NMR (400 MHz, DMSO-$d_6$) δ [ppm]: 3.91 (s, 2H), 7.29-7.36 (m, 2H), 7.41-7.48 (m, 2H), 7.53-7.58 (m, 3H), 7.90 (dd, 1H), 8.13 (d, 1H), 8.42 (d, 1H), 10.80 (s, 1H).

Example 484, Example 485, Example 486, Example 487 and Example 488

To a mixture of 2-(2-chlorophenyl)-N-[4-(4-cyano-1H-pyrazol-1-yl)-3-sulfamoyl-phenyl]acetamide (200 mg, 0.48 mmol), sodium trifluoromethanesulfonate (600 mg, 3.85 mmol) and copper (II) triflate (35 mg; 0.10 mmol), under argon, was added acetonitrile (2 mL). To the resulting mixture, at vigorous stirring, was added dropwise tert-butylhydroperoxide (70 wt. % in water, 0.53 mL, 3.85 mmol) over 30 min by a syringe pump. After stirring for additional 15 h the reaction mixture was filtered. The resulting filtrate was concentrated in vacuo to ca. 1 mL and was purified by HPLC to give and to separate the title compounds.

Example 484

2-(2-Chlorophenyl)-N-[4-(4-cyano-1H-pyrazol-1-yl)-5-sulfamoyl-2-(trifluoromethyl)phenyl]acetamide

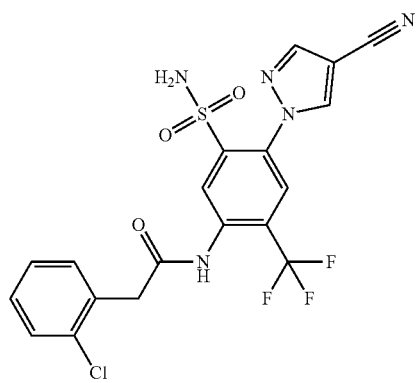 [SMILES: N#Cc1cnn(-c2cc(C(F)(F)F)c(NC(=O)Cc3ccccc3Cl)cc2S(N)(=O)=O)c1]

0.9 mg, 1% yield, 85% purity

LC-MS (Method M): Rt=2.63 min; MS (ESIpos): m/z=484 [M+H]$^+$ $^1$H-NMR (600 MHz, CD$_3$CN) δ [ppm] 3.99 (s, 2H), 6.33 (s, 2H), 7.35 (m, 2H), 7.45 (m, 1H), 7.48 (m, 1H), 7.87 (s, 1H), 8.14 (d, 1H), 8.22 (bs, 1H), 8.45 (d, 1H), 8.76 (s, 1H).

Example 485

2-[2-Chloro-5-(trifluoromethyl)phenyl]-N-[4-(4-cyano-1H-pyrazol-1-yl)-3-sulfamoylphenyl]acetamide

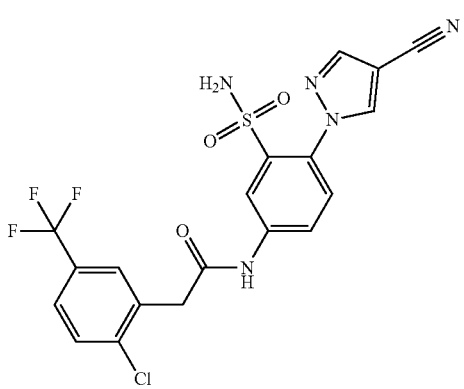 [SMILES: N#Cc1cnn(-c2ccc(NC(=O)Cc3cc(C(F)(F)F)ccc3Cl)cc2S(N)(=O)=O)c1]

6.5 mg, 2% yield, 85% purity

LC-MS (Method M): Rt=2.64 min; MS (ESIpos): m/z=484 [M+H]$^+$ $^1$H-NMR (600 MHz, CD$_3$CN) δ [ppm] 3.99 (s, 2H), 6.33 (s, 2H), 7.35 (m, 2H), 7.45 (m, 1H), 7.48 (m, 1H), 7.87 (s, 1H), 8.14 (d, 1H), 8.22 (bs, 1H), 8.45 (d, 1H), 8.76 (s, 1H).

Example 486

2-[2-Chloro-5-(trifluoromethyl)phenyl]-N-[4-(4-cyano-1H-pyrazol-1-yl)-5-sulfamoyl-2-(trifluoromethyl)phenyl]acetamide

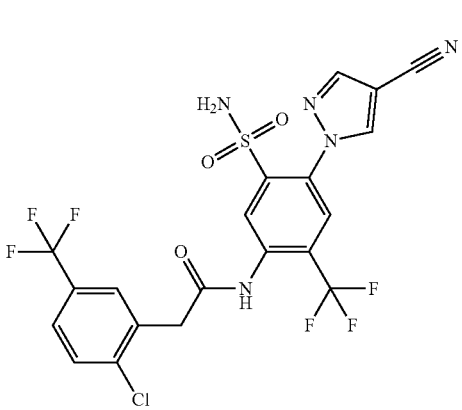 [SMILES: N#Cc1cnn(-c2cc(C(F)(F)F)c(NC(=O)Cc3cc(C(F)(F)F)ccc3Cl)cc2S(N)(=O)=O)c1]

5.0 mg, 2% yield, 90% purity

LC-MS (Method M): Rt=2.93 min; MS (ESIpos): m/z=552 [M+H]$^+$ $^1$H-NMR (600 MHz, CD$_3$CN) δ [ppm] 4.07 (s, 2H), 6.34 (s, 2H), 7.66 (m, 2H), 7.78 (m, 1H), 7.89 (s, 1H), 8.15 (d, 1H), 8.39 (s, 1H), 8.46 (d, 1H), 8.67 (s, 1H).

Example 487

2-(2-Chlorophenyl)-N-[4-(4-cyano-1H-pyrazol-1-yl)-3-sulfamoyl-2-(trifluoromethyl)phenyl]acetamide

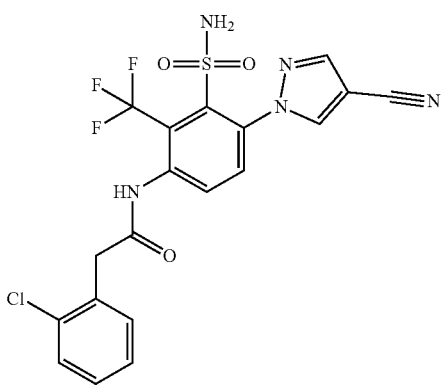 [SMILES: N#Cc1cnn(-c2ccc(NC(=O)Cc3ccccc3Cl)c(C(F)(F)F)c2S(N)(=O)=O)c1]

0.7 mg, 1% yield, 90% purity

LC-MS (Method M): Rt=2.33 min; MS (ESIpos): m/z=484 [M+H]$^+$ $^1$H-NMR (600 MHz, CD$_3$CN) δ [ppm] 3.94 (s, 2H), 6.08 (s, 2H), 7.34 (m, 2H), 7.43 (m, 1H), 7.47 (m, 1H), 7.73 (d, 1H), 8.02 (d, 1H), 8.13 (d, 1H), 8.37 (s, 1H), 8.47 (d, 1H).

Example 488

2-[2-Chloro-3-(trifluoromethyl)phenyl]-N-[4-(4-cyano-1H-pyrazol-1-yl)-5-sulfamoyl-2-(trifluoromethyl)phenyl]acetamide

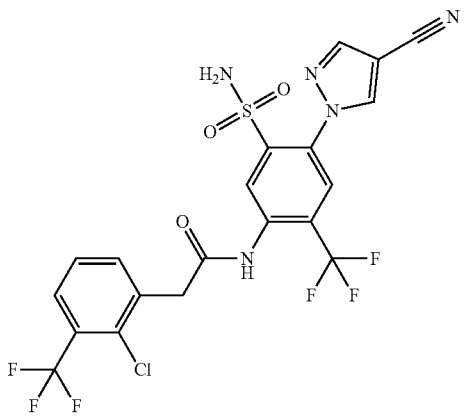 [SMILES: N#Cc1cnn(-c2cc(C(F)(F)F)c(NC(=O)Cc3cccc(C(F)(F)F)c3Cl)cc2S(N)(=O)=O)c1]

5.3 mg, 2% yield, 90% purity

LC-MS (Method M): Rt=2.89 min; MS (ESIpos): m/z=552 [M+H]$^+$ $^1$H-NMR (600 MHz, CD$_3$CN) δ [ppm] 4.13 (s, 2H), 6.37 (s, 2H), 7.54 (t, 1H), 7.74 (d, 1H), 7.81 (d, 1H), 7.92 (s, 1H), 8.18 (s, 1H), 8.40 (s, 1H), 8.49 (s, 1H), 8.71 (s, 1H).

Example 489, Example 490 and Example 491

To a mixture of 2-(2-chlorophenyl)-N-(4-[1-(difluoromethyl)-1H-pyrazol-4-yl]-3-{[(dimethylamino)methylene]sulfamoyl}phenyl)acetamide (150 mg, 0.30 mmol), sodium trifluoromethanesulfonate (378 mg, 2.42 mmol) and copper(II) triflate (22 mg; 0.06 mmol), under argon, was added acetonitrile (1.5 mL). To the resulting mixture, at vigorous stirring, was added dropwise tert-butylhydroperoxide (70 wt. % in H$_2$O, 0.33 mL, 2.42 mmol) over 30 min by a syringe pump. After stirring for additional 15 h the reaction mixture was filtered. The resulting filtrate was concentrated in vacuo to ca. 1 mL and purified by HPLC to give following intermediates: 2-(2-chlorophenyl)-N-{4-[1-(difluoromethyl)-1H-pyrazol-4-yl]-3-{[(dimethylamino)methylene]sulfamoyl}-2-(trifluoromethyl)phenyl}acetamide (5.4 mg, 3.0% yield, 95% purity), 2-[2-chloro-3-(trifluoromethyl)phenyl]-N-(4-[1-(difluoromethyl)-1H-pyrazol-4-yl]-3-{[(dimethylamino)methylene]sulfamoyl}phenyl)acetamide (6.1 mg, 3.2% yield, 90% purity), 2-(2-chlorophenyl)-N-{4-[1-(difluoromethyl)-1H-pyrazol-4-yl]-5-{[(dimethylamino)methylene]sulfamoyl}-2-(trifluoromethyl)phenyl}acetamide (5.0 mg, 2.8% yield, 95% purity) and 2-(2-chlorophenyl)-N-(4-[1-(difluoromethyl)-5-(trifluoromethyl)-1H-pyrazol-4-yl]-3-{[(dimethylamino)methylene]sulfamoyl}phenyl)acetamide (2.3 mg, 1.2% yield, 90% purity).

These intermediates were separately redissolved in methanol (0.5 mL) and aqueous ammonia (0.5 mL) was added, followed by stirring at room temperature for 2 days. Water was added and the resulting mixture was extracted three times with dichloromethane. The combined organic layers were washed with brine, dried and concentrated in vacuo to give the title compounds.

Example 489

2-(2-Chlorophenyl)-N-{4-[1-(difluoromethyl)-1H-pyrazol-4-yl]-3-sulfamoyl-2-(trifluoromethyl)phenyl}acetamide

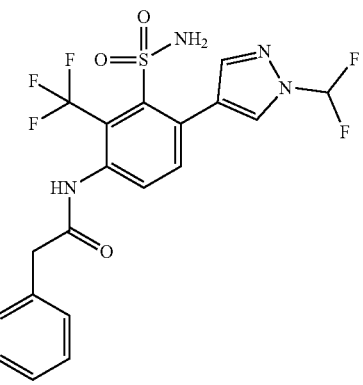

4.3 mg, 3% yield, 95% purity

LC-MS (Method M): Rt=2.64 min; MS (ESIpos): m/z=509 [M+H]$^+$ $^1$H-NMR (600 MHz, CD$_3$CN) δ [ppm] 3.92 (s, 2H), 5.57 (s, 2H), 7.33 (m, 2H), 7.42 (t, 1H), 7.43 (m, 1H), 7.46 (m, 1H), 7.60 (d, 1H), 7.82 (d, 1H), 7.92 (s, 1H), 8.20 (s, 1H), 8.25 (s, 1H).

Example 490

2-[2-Chloro-3-(trifluoromethyl)phenyl]-N-{4-[1-(difluoromethyl)-1H-pyrazol-4-yl]-3-sulfamoylphenyl}acetamide

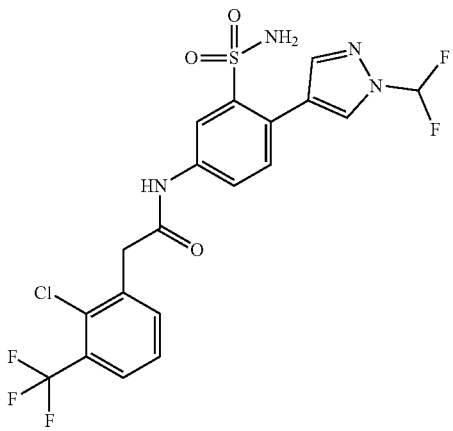 [SMILES: NS(=O)(=O)c1cc(NC(=O)Cc2cccc(C(F)(F)F)c2Cl)ccc1-c1cnn(C(F)F)c1]

5.0 mg, 3% yield, 90% purity

LC-MS (Method M): Rt=2.82 min; MS (ESIpos): m/z=509 [M+H]$^+$ $^1$H-NMR (600 MHz, CD$_3$CN) δ [ppm] 3.99 (s, 2H), 5.50 (bs, 2H), 7.40 (t, 1H), 7.42 (d, 1H), 7.49 (dd, 1H), 7.68 (dd, 1H), 7.75 (dd, 1H), 7.79 (dd, 1H), 7.89 (s, 1H), 8.22 (d, 1H), 8.38 (d, 1H), 8.88 (s, 1H).

Example 491

2-(2-Chlorophenyl)-N-{4-[1-(difluoromethyl)-1H-pyrazol-4-yl]-5-sulfamoyl-2-(trifluoromethyl)phenyl}acetamide

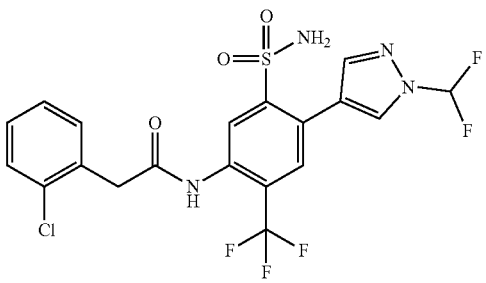 [SMILES: NS(=O)(=O)c1cc(NC(=O)Cc2ccccc2Cl)c(C(F)(F)F)cc1-c1cnn(C(F)F)c1]

4.6 mg, 3% yield, 90% purity
LC-MS (Method M): Rt=2.92 min; MS (ESIpos): m/z=509 [M+H]$^+$
$^1$H-NMR (600 MHz, CD$_3$CN) δ [ppm] 3.95 (s, 2H), 5.65 (s, 2H), 7.35 (m, 2H), 7.41 (t, 1H), 7.45 (m, 1H), 7.48 (m, 1H), 7.76 (s, 1H), 7.94 (s, 1H), 8.12 (s, 1H), 8.28 (s, 1H), 8.62 (s, 1H).

Example 492

2-(2-Chlorophenyl)-N-{4-[1-(difluoromethyl)-5-(trifluoromethyl)-1H-pyrazol-4-yl]-3-sulfamoylphenyl}acetamide

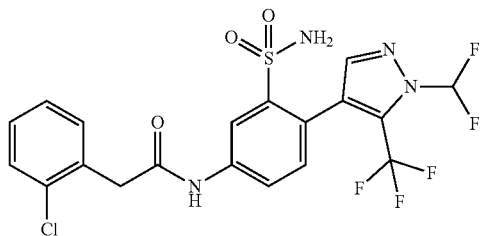 [SMILES: NS(=O)(=O)c1cc(NC(=O)Cc2ccccc2Cl)ccc1-c1cnn(C(F)F)c1C(F)(F)F]

2.4 mg, 1% yield, 80% purity
LC-MS (Method M): Rt=2.87 min; MS (ESIpos): m/z=509 [M+H]$^+$
$^1$H-NMR (600 MHz, CD$_3$CN) δ [ppm] 3.92 (s, 2H), 5.50 (bs, 2H), 7.35 (m, 3H), 7.45 (m, 1H), 7.47 (m, 1H), 7.59 (t, 1H), 7.81 (dd, 1H), 7.82 (s, 1H), 8.43 (d, 1H), 8.90 (s, 1H).

Example 493 and Example 494

In a pressure tube to a mixture of 2-(2-chlorophenyl)-N-(4-[1-(difluoromethyl)-1H-pyrazol-4-yl]-3-{[(dimethylamino)methylene]sulfamoyl}phenyl)acetamide (200 mg, 0.40 mmol) and 1-chloromethyl-4-fluoro-1,4-diazoniabicyclo[2.2.2]octane bis(tetrafluoroborate) (286 mg, 0.81 mmol) was added, under argon, acetonitrile (2 mL). The resulting mixture was vigorously stirred at 80° C. for 15 h, then concentrated in vacuo and purified by HPLC to give following intermediates: 2-(2-chlorophenyl)-N-(4-[1-(difluoromethyl)-1H-pyrazol-4-yl]-3-{[(dimethylamino)methylene]sulfamoyl}-2-fluorophenyl)acetamide (18.5 mg, 8.5% yield, 95% purity) and 2-(2-chlorophenyl)-N-(4-[1-(difluoromethyl)-1H-pyrazol-4-yl]-5-{[(dimethylamino)methylene]sulfamoyl}-2-fluorophenyl)acetamide (4.9 mg, 2.0% yield, 85% purity).

These intermediates were separately redissolved in methanol (0.5 mL) and aqueous ammonia (0.5 mL) was added, followed by stirring at room temperature for 2 days. Water was added and the resulting mixture was extracted three times with dichloromethane. The combined organic layers were washed with brine, dried and concentrated in vacuo to give the title compounds.

Example 493

2-(2-Chlorophenyl)-N-{4-[1-(difluoromethyl)-1H-pyrazol-4-yl]-2-fluoro-3-sulfamoylphenyl}acetamide

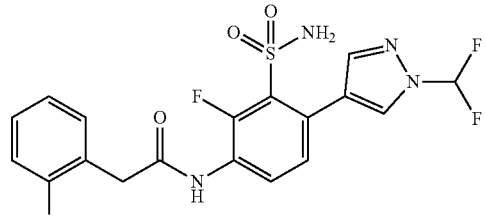

16.1 mg, 8% yield, 95% purity
LC-MS (Method M): Rt=2.41 min; MS (ESIpos): m/z=459 [M+H]$^+$
$^1$H-NMR (600 MHz, CD$_3$CN) δ [ppm] 3.95 (s, 2H), 5.95 (bs, 2H), 7.16 (dd, 1H), 7.33 (m, 2H), 7.38 (t, 1H), 7.42 (m, 1H), 7.46 (m, 1H), 7.76 (s, 1H), 8.04 (s, 1H), 8.25 (t, 1H), 8.47 (s, 1H).

Example 494

2-(2-Chlorophenyl)-N-{4-[1-(difluoromethyl)-1H-pyrazol-4-yl]-2-fluoro-5-sulfamoylphenyl}acetamide

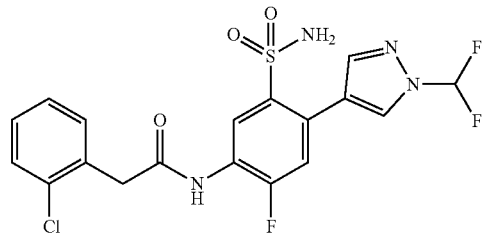 [SMILES: NS(=O)(=O)c1cc(NC(=O)Cc2ccccc2Cl)c(F)cc1-c1cnn(C(F)F)c1]

4.1 mg, 2% yield, 85% purity
LC-MS (Method M): Rt=2.56 min; MS (ESIpos): m/z=459 [M+H]$^+$
$^1$H-NMR (600 MHz, CD$_3$CN) δ [ppm] 3.95 (s, 2H), 5.62 (bs, 2H), 7.32 (m, 3H), 7.41 (t, 1H), 7.42 (m, 1H), 7.46 (m, 1H), 7.91 (s, 1H), 8.26 (s, 1H), 8.53 (s, 1H), 8.90 (d, 1H).

Example 495

2-(2-Chlorophenyl)-N-{4-[2-(dimethylamino)-1,3-thiazol-4-yl]-3-sulfamoylphenyl}acetamide

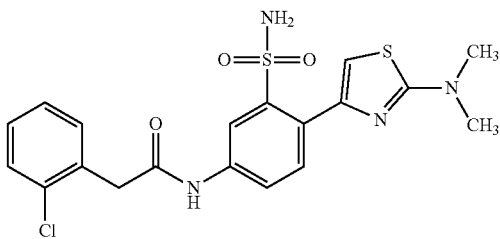 [SMILES: CN(C)c1nc(-c2ccc(NC(=O)Cc3ccccc3Cl)cc2S(N)(=O)=O)cs1]

According to general procedure GP8.2, N-(4-bromo-3-{[(dimethylamino)methylene]-sulfamoyl}phenyl)-2-(2-chlorophenyl)acetamide (300 mg, 0.65 mmol) and 4-bromo-N,N-dimethyl-1,3-thiazol-2-amine (123 mg, 0.59 mmol) were converted to the title compound and were purified by preparative HPLC (Chromatorex C-18 10 µm, 125×30 mm, acetonitrile/water+0.1% formic acid) (30 mg, 0.0665 mmol, 10% yield, 97% purity).

LC-MS (Method A): Rt=1.13 min; MS (ESIpos): m/z=452 [M+H]$^+$ $^1$H-NMR (400 MHz, DMSO-d$_6$) δ [ppm]: 3.06 (s, 6H), 3.88 (s, 2H), 6.91 (s, 1H), 7.29-7.35 (m, 2H), 7.42-7.48 (m, 2H), 7.56 (d, 1H), 7.83 (s, 2H), 7.90 (dd, 1H), 8.27 (d, 1H), 10.65 (s, 1H).

Example 496

2-(2-Chlorophenyl)-N-[3-sulfamoyl-4-(1,2-thiazol-5-yl)phenyl]acetamide

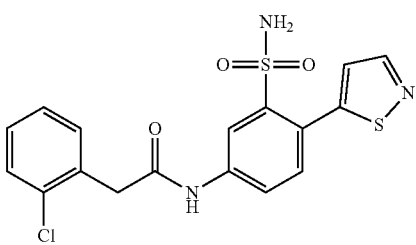 [SMILES: NS(=O)(=O)c1cc(NC(=O)Cc2ccccc2Cl)ccc1-c1ccns1]

According to general procedure GP8.2, N-(4-bromo-3-{[(dimethylamino)methylene]-sulfamoyl}phenyl)-2-(2-chlorophenyl)acetamide (300 mg, 0.65 mmol) and 5-bromo-1,2-thiazole (195 mg, 1.19 mmol) were converted to the title compound and were purified by preparative HPLC (Waters XBridge C18 5µ 100×30 mm, acetonitrile/water+0.1% formic acid), followed by another preparative HPLC (Waters Phenomenex Kinetex EVO C18 5µ 100×30 mm, acetonitrile/water+0.1% formic acid) (6.5 mg, 0.0159 mmol, 2% yield, 97% purity).

LC-MS (Method 1): Rt=1.25 min; MS (ESIpos): m/z=408 [M+H]$^+$ $^1$H-NMR (400 MHz, DMSO-d$_6$) δ [ppm]: 3.90 (s, 2H), 7.29-7.35 (m, 2H), 7.41-7.52 (m, 5H), 7.56 (d, 1H), 7.88 (dd, 1H), 8.42 (d, 1H), 8.54 (d, 1H), 10.76 (s, 1H).

Example 497

1-(4-{[(2-Chlorophenyl)acetyl]amino}-2-sulfamoylphenyl)-N-cyclopropyl-N-methyl-1H-pyrazole-4-carboxamide

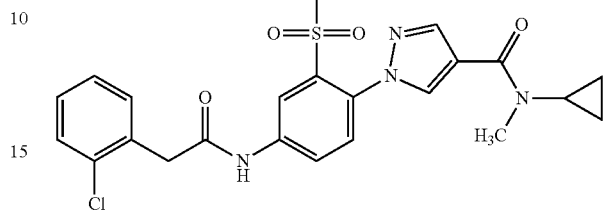

According to general procedure GP7.1, methyl 1-(4-{[(2-chlorophenyl)acetyl]amino}-2-sulfamoylphenyl)-1H-pyrazole-4-carboxylate (100 mg, 0.22 mmol) and N-methylcyclopropanamine (39.6 mg, 0.56 mmol) in THF (only 0.25 mL) were converted to the title compound and were purified by preparative HPLC (Chromatorex C-18 10 µm, 125×30 mm, acetonitrile/water+0.1% formic acid), followed by another preparative HPLC (Waters XBridge C18 5µ 100×30 mm, acetonitrile/water+0.1% formic acid) (2.4 mg, 0.00492 mmol, 2% yield, 97% purity).

LC-MS (Method A): Rt=0.99 min; MS (ESIpos): m/z=488 [M+H]$^+$ $^1$H-NMR (400 MHz, DMSO-d$_6$) δ [ppm]: 0.58-0.64 (m, 2H), 0.80-0.87 (m, 2H), 2.97 (s, 3H), 3.03-3.11 (m, 1H), 3.91 (s, 2H), 7.29-7.37 (m, 2H), 7.37-7.49 (m, 4H), 7.58 (d, 1H), 7.98 (dd, 1H), 8.07 (s, 1H), 8.38 (d, 1H), 8.50 (s, 1H), 10.81 (s, 1H).

Example 498

2-(2-Chlorophenyl)-2-hydroxy-N-{3-sulfamoyl-4-[4-(trifluoromethyl)-1H-pyrazol-1-yl]phenyl}ethanamide

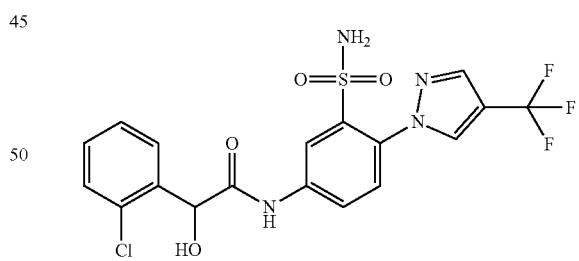

2-(2-Chlorophenyl)-N-{3-sulfamoyl-4-[4-(trifluoromethyl)-1H-pyrazol-1-yl]phenyl}acetamide (160 mg, 0.35 mmol), was dissolved in ethylene glycol (1.2 ml) in a crimp sealable microwave vessel (5 ml) and copper (II) trifluoroacetate hydrate (151 mg, 0.52 mmol) was added, the vessel sealed with a septum and the flask heated at 150° C. for 12 hours. Dichloromethane (30 ml) and water (20 ml) were added, the layers separated, the aqueous layer extracted with dichloromethane (2×30 ml), the organic layers combined, dried over sodium sulfate and the solvent removed under reduced pressure. The crude reaction mixture was purified by preparative HPLC (Waters XBridge C18 5µ 100×30 mm, acetonitrile/water+0.1% formic acid) followed by a second preparative HPLC (Waters XBridge C18 5μ 100×30 mm, acetonitrile/water+0.2% ammonia solution (32%)) yielding the title compound (1.5 mg, 0.003 mmol, 1% yield, 98% purity).

LC-MS (Method B): Rt=0.98 min; MS (ESIpos): m/z=474 [M+H]$^+$ $^1$H NMR (400 MHz, DMSO-d6) δ ppm 5.53 (d, 1H) 6.77 (br s, 1H) 7.29-7.49 (m, 5H) 7.55-7.66 (m, 2H) 8.07 (dd, 1H) 8.18 (s, 1H) 8.61 (d, 1H) 8.73 (s, 1H) 10.72 (s, 1H)

Example 499

2-(2-Chlorophenyl)-N-{3-chloro-5-sulfamoyl-4-[4-(trifluoromethyl)-1H-pyrazol-1-yl]phenyl}acetamide

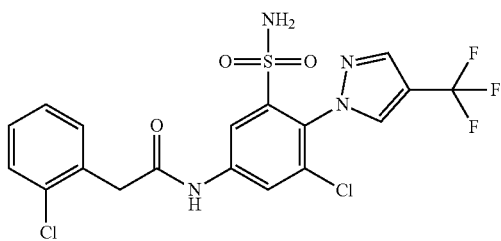 [SMILES: NS(=O)(=O)c1cc(NC(=O)Cc2ccccc2Cl)cc(Cl)c1-n1cc(C(F)(F)F)cn1]

2-(2-Chlorophenyl)-N-(3-{[(dimethylamino)methylene]sulfamoyl}-4-[4-(trifluoromethyl)-1H-pyrazol-1-yl]phenyl) acetamide (135 mg, 0.26 mmol), was dissolved in dichloroethane (1 ml) in a crimp sealable microwave vessel (5 ml) and copper (II) trifluoroacetate hydrate (91 mg, 0.32 mmol) was added, the vessel sealed with a septum and the flask heated at 130° C. for 24 hours. Methanol (3 ml) and aqueous ammonia (25%, 1 ml) were added and the flask heated at 50° C. for 36 hours. Dichloromethane (30 ml) and water (20 ml) were added, the layers separated, and the aqueous layer extracted with dichloromethane (2×30 ml), the organic layers combined, dried over sodium sulfate and the solvent removed under reduced pressure. The resulting mixture was purified by preparative HPLC (Waters XBridge C18 5μ 100×30 mm, acetonitrile/water+0.1% formic acid) yielding the title compound (5 mg, 0.01 mmol, 4% yield over 2 steps, 81% purity).

LC-MS (Method A): Rt=1.26 min; MS (ESIpos): m/z=493 [M+H]$^+$ $^1$H-NMR (400 MHz, DMSO-d$_6$) δ [ppm]: 3.94 (s, 2H), 7.26-7.33 (m, 2H), 7.37-7.45 (m, 2H), 8.06 (d, 1H), 8.25 (d, 1H), 8.29 (d, 1H), 8.35 (s, 1H).

Example 500

2-(2-Chlorophenyl)-N-[4-(4-cyano-3-hydroxy-1H-pyrazol-1-yl)-3-sulfamoylphenyl]acetamide

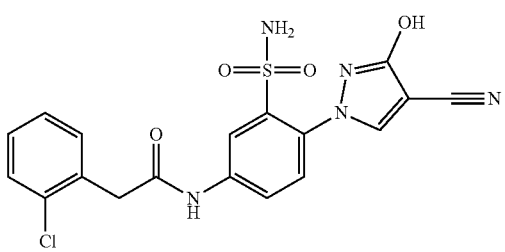 [SMILES: N#Cc1cn(-c2ccc(NC(=O)Cc3ccccc3Cl)cc2S(N)(=O)=O)nc1O]

2-(2-Chlorophenyl)-N-[4-(4-cyano-1H-pyrazol-1-yl)-3{[(dimethylamino)methylene]sulfamoyl}phenyl]acetamide (200 mg, 0.425 mmol), was placed in a crimp sealable microwave vessel (5 ml) and, the vessel crimped shut and flushed with argon for 5 minutes. A solution of (1,5-cyclooctadiene)(methoxy)iridium(1) dimer (14 mg, 0.021 mmol), 4,4'-di-tert-butyl-2,2'-dipyridyl (11.4 mg, 0,042 mmol) and bis(pinacolato)diboron (129.4 mg, 0.51 mmol) in THE (0.42 ml) that had been stirred under argon for 1 hour at 80° C. was added under an atmosphere of argon. The vessel was then heated at 80° C. for 24 hours, following which the solvent was removed under reduced pressure. Potassium hydroxide (72 mg, 1.27 mmol) water (2 ml) and dimethylformamide (2 ml) were added and hydrogen peroxide (30% solution in water, 0.13 ml, 1.27 mmol) was added dropwise. The mixture was stirred for 1 hour at RT after which aqueous ammonia (4 ml) was added and the mixture stirred at RT overnight. An additional volume of aqueous ammonia (6 ml) was added and the mixture stirred for a further 48 hours at RT. Dichloromethane (30 ml) and water (20 ml) were added, the layers separated, and the aqueous layer extracted with dichloromethane (2×30 ml) and ethyl acetate (30 ml), the organic layers combined, dried over sodium sulfate and the solvent removed under reduced pressure. The solid was first purified by flash chromatography (MeOH:DCM 2:98 to 20:80) followed by purification with preparative HPLC (Waters XBridge C18 5μ 100×30 mm, acetonitrile/water+0.1% formic acid) yielding the title compound (5.5 mg, 0.01 mmol, 3% yield over 3 steps, 95% purity).

LC-MS (Method A): Rt=1.84 min; MS (ESIpos): m/z=431 [M+H]$^+$ $^1$H-NMR (400 MHz, DMSO-d$_6$) δ [ppm]: 3.90 (s, 2H) 7.28-7.36 (m, 2H) 7.41-7.48 (m, 2H) 7.50 (br s, 2H) 7.55 (d, 1H) 7.95 (dd, 1H) 8.34 (d, 1H) 8.54 (s, 1H) 10.79 (s, 1H) 11.35-12.45 (br s, 1H)

Example 501

2-(2-Chlorophenyl)-N-[4-(1H-pyrazolo[4,3-c]pyridin-1-yl)-3-sulfamoylphenyl]acetamide

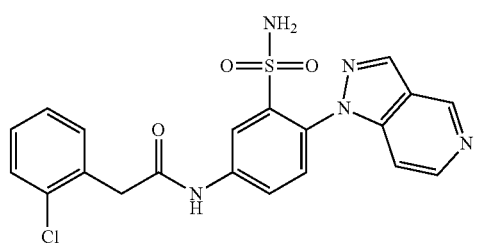 [SMILES: NS(=O)(=O)c1cc(NC(=O)Cc2ccccc2Cl)ccc1-n1ncc2cnccc21]

According to general procedures GP1.2, GP2.4, GP3.2 and GP4.3, 2-chloro-N-(2,4-dimethoxybenzyl)-5-nitrobenzenesulfonamide (500 mg, 1.29 mmol), 1H-pyrazolo[4,3-c]pyridine (231 mg, 1.94 mmol) and (2-chlorophenyl)acetic acid (352 mg, 2.07 mmol) were converted to the title compound without purification of intermediates to the title compound and were purified at the end by preparative HPLC (Chromatorex C-18 10 μm, 125×30 mm, acetonitrile/water+0.1% formic acid), followed by another preparative HPLC (Waters XBridge C18 5μ 100×30 mm, acetonitrile/water+0.1% formic acid) (4.4 mg, 0.0100 mmol, 1% yield over 4 steps, 99% purity).

LC-MS (Method A): Rt=0.72 min; MS (ESIpos): m/z=442 [M+H]⁺

$^1$H-NMR (400 MHz, DMSO-$d_6$) δ [ppm]: 3.93 (s, 2H), 7.26-7.38 (m, 5H), 7.44-7.49 (m, 2H), 7.63 (d, 1H), 8.03 (dd, 1H), 8.40 (d, 1H), 8.47 (d, 1H), 8.58 (d, 1H), 9.21 (d, 1H), 10.87 (s, 1H).

Example 502

2-(2-Chlorophenyl)-N-[4-(4,5-dimethyl-1,3-thiazol-2-yl)-3-sulfamoylphenyl]acetamide

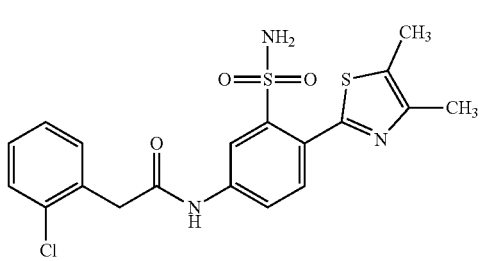 [SMILES: Cc1nc(-c2ccc(NC(=O)Cc3ccccc3Cl)cc2S(N)(=O)=O)sc1C]

According to general procedure GP8.2, N-(4-bromo-3-{[(dimethylamino)methylene]-sulfamoyl}phenyl)-2-(2-chlorophenyl)acetamide (300 mg, 0.65 mmol) and 2-bromo-4,5-dimethyl-1,3-thiazole (114 mg, 0.59 mmol) were converted to the title compound and were purified by preparative HPLC (Waters XBridge C18 5µ 100×30 mm, acetonitrile/water+0.2% aqueous ammonia (32%)) (2.5 mg, 0.00573 mmol, 1% yield, 99% purity).

LC-MS (Method B): Rt=1.19 min; MS (ESIpos): m/z=436 [M+H]⁺

$^1$H-NMR (400 MHz, DMSO-$d_6$) δ [ppm]: 2.32 (s, 3H), 2.41 (s, 3H), 3.90 (s, 2H), 7.28-7.36 (m, 2H), 7.41-7.49 (m, 2H), 7.68 (d, 1H), 7.75 (s, 2H), 7.97 (dd, 1H), 8.36 (d, 1H), 10.79 (s, 1H).

Example 503

2-(2-Chlorophenyl)-N-[4-(2,4-dimethyl-1,3-thiazol-5-yl)-3-sulfamoylphenyl]acetamide

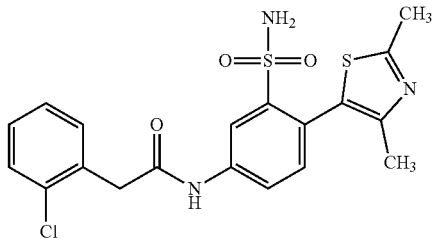 [SMILES: Cc1nc(C)c(-c2ccc(NC(=O)Cc3ccccc3Cl)cc2S(N)(=O)=O)s1]

According to general procedure GP8.2, N-(4-bromo-3-{[(dimethylamino)methylene]-sulfamoyl}phenyl)-2-(2-chlorophenyl)acetamide (300 mg, 0.65 mmol) and 5-bromo-2,4-dimethyl-1,3-thiazole (114 mg, 0.59 mmol) were converted to the title compound and were purified by preparative HPLC (Waters XBridge C18 5µ 100×30 mm, acetonitrile/water+0.1% formic acid), followed by another preparative HPLC (Laomatic XBridge C18 5µ 100×30 mm, acetonitrile/water+0.2% aqueous ammonia (32%)) (2.4 mg, 0.00551 mmol, 1% yield, 99% purity).

LC-MS (Method B): Rt=0.94 min; MS (ESIpos): m/z=436 [M+H]⁺

$^1$H-NMR (400 MHz, DMSO-$d_6$) δ [ppm]: 2.03 (s, 3H), 2.60 (s, 3H), 3.89 (s, 2H), 7.25 (s, 2H), 7.28-7.37 (m, 3H), 7.41-7.48 (m, 2H), 7.83 (dd, 1H), 8.35 (d, 1H), 10.69 (s, 1H).

Example 504

2-(2-Chlorophenyl)-N-[4-(4-methyl-1,3-thiazol-5-yl)-3-sulfamoylphenyl]acetamide

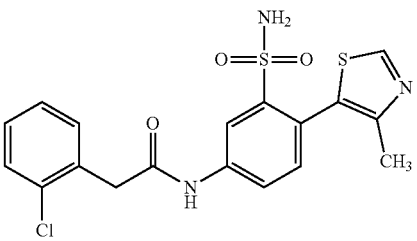 [SMILES: Cc1ncsc1-c1ccc(NC(=O)Cc2ccccc2Cl)cc1S(N)(=O)=O]

According to general procedure GP8.2, N-(4-bromo-3-{[(dimethylamino)methylene]-sulfamoyl}phenyl)-2-(2-chlorophenyl)acetamide (300 mg, 0.65 mmol) and 5-bromo-4-methyl-1,3-thiazole (106 mg, 0.59 mmol) were converted to the title compound and were purified by preparative HPLC (Waters XBridge C18 5µ 100×30 mm, acetonitrile/water+0.1% formic acid), followed by another preparative HPLC (Laomatic XBridge C18 5µ 100×30 mm, acetonitrile/water+0.2% aqueous ammonia (32%)) (3.7 mg, 0.00877 mmol, 1% yield, 97% purity).

LC-MS (Method B): Rt=0.90 min; MS (ESIpos): m/z=422 [M+H]⁺

$^1$H-NMR (400 MHz, DMSO-$d_6$) δ [ppm]: 2.13 (s, 3H), 3.90 (s, 2H), 7.25-7.37 (m, 5H), 7.42-7.48 (m, 2H), 7.84 (dd, 1H), 8.37 (d, 1H), 9.01 (s, 1H), 10.71 (s, 1H).

Example 505

N-{4-(4-Amino-1H-pyrazol-1-yl)-3-[(2,4-dimethoxybenzyl)sulfamoyl]phenyl}-2-(2-chlorophenyl)acetamide

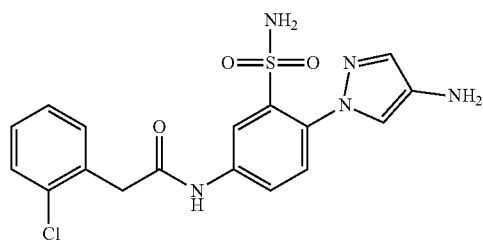 [SMILES: Nc1cnn(-c2ccc(NC(=O)Cc3ccccc3Cl)cc2S(N)(=O)=O)c1]

N-{4-(4-Amino-1H-pyrazol-1-yl)-3-[(2,4-dimethoxybenzyl)sulfamoyl]phenyl}-2-(2-chloro-phenyl)acetamide (403 mg, 435 µmol, 60% purity) was dissolved in dichloromethane (5.6 mL) and treated with trifluoroacetic acid (1.7 mL, 22 mmol) followed by stirring at room temperature overnight. The mixture was concentrated in vacuo and purified by HPLC to give the title compound (28 mg, 16% yield, 100% purity).

LC-MS (Method A): Rt=0.74 min; MS (ESIpos): m/z=406 (M+H)+

$^1$H-NMR (400 MHz, DMSO-d$_6$) δ [ppm] 3.88 (s, 2H), 4.14 (s, 2H), 7.30 (d, 1H), 7.32 (m, 2H), 7.35 (d, 1H), 7.44 (m, 2H), 7.45 (d, 1H), 7.48 (s, 2H), 7.94 (dd, 1H), 8.32 (d, 1H), 10.70 (s, 1H).

Example 506

N-[1-(4-{[(2-Chlorophenyl)acetyl]amino}-2-sulfamoylphenyl)-1H-pyrazol-4-yl]-2,2-difluoroacetamide

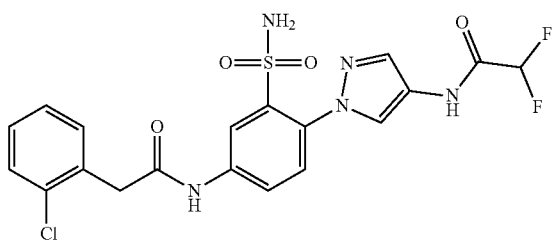 [SMILES: NS(=O)(=O)c1cc(NC(=O)Cc2ccccc2Cl)ccc1-n1cc(NC(=O)C(F)F)cn1]

N-[1-(4-{[(2-Chlorophenyl)acetyl]amino}-2-[(2,4-dimethoxybenzyl)sulfamoyl]phenyl)-1H-pyrazol-4-yl]-2,2-difluoroacetamide (231 mg, 182 μmol, 50% purity) was dissolved in dichloromethane (3.6 mL) and treated with trifluoroacetic acid (0.7 mL, 9.1 mmol) followed by stirring at room temperature overnight. The mixture was concentrated in vacuo and purified by HPLC to give the title compound (8.6 mg, 10% yield, 99% purity).

LC-MS (Method A): Rt=0.98 min; MS (ESIpos): m/z=484 (M+H)+

$^1$H-NMR (400 MHz, DMSO-d$_6$) δ [ppm] 3.90 (s, 2H), 6.44 (t, 1H), 7.33 (m, 2H), 7.41 (s, 2H), 7.45 (m, 2H), 7.55 (d, 1H), 7.91 (s, 1H), 7.96 (dd, 1H), 8.27 (s, 1H), 8.37 (d, 1H), 10.79 (s, 1H), 11.13 (s, 1H).

Example 507

N-[1-(4-{[(2-Chlorophenyl)acetyl]amino}-2-sulfamoylphenyl)-1H-pyrazol-4-yl]-3,3,3-trifluoropropanamide

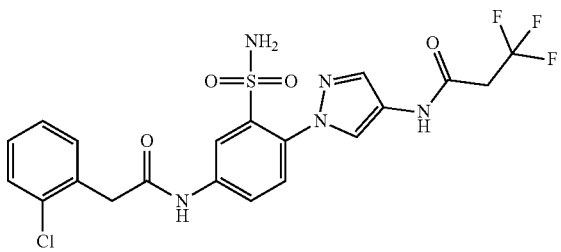 [SMILES: NS(=O)(=O)c1cc(NC(=O)Cc2ccccc2Cl)ccc1-n1cc(NC(=O)CC(F)(F)F)cn1]

N-[1-(4-{[(2-Chlorophenyl)acetyl]amino}-2-[(2,4-dimethoxybenzyl)sulfamoyl]phenyl)-1H-pyrazol-4-yl]-3,3,3-trifluoropropanamide (285 mg, 214 μmol, 50% purity) was dissolved in dichloromethane (2.8 mL) and treated with trifluoroacetic acid (0.8 mL, 10.7 mmol) followed by stirring at room temperature for 195 min. The mixture was concentrated in vacuo and purified by flash chromatography to give the title compound (14.9 mg, 13% yield, 95% purity).

LC-MS (Method A): Rt=1.03 min; MS (ESIpos): m/z=516 (M+H)+

$^1$H-NMR (400 MHz, DMSO-d$_6$) δ [ppm] 3.44 (q, 2H), 3.90 (s, 2H), 7.33 (m, 2H), 7.42 (s, 2H), 7.45 (m, 2H), 7.55 (d, 1H), 7.83 (d, 1H), 7.96 (dd, 1H), 8.21 (d, 1H), 8.36 (d, 1H), 10.59 (s, 1H), 10.77 (s, 1H).

Example 508 (racemic), Example 509 (Enantiomer A) and Example 510 (Enantiomer B)

Example 508

N-[1-(4-{[(2-Chlorophenyl)acetyl]amino}-2-sulfamoylphenyl)-1H-pyrazol-4-yl]-3,3,3-trifluoro-2-methylpropanamide

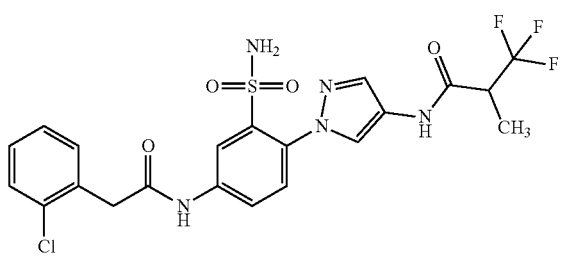 [SMILES: CC(C(=O)Nc1cnn(-c2ccc(NC(=O)Cc3ccccc3Cl)cc2S(N)(=O)=O)c1)C(F)(F)F]

(±)-N-[1-(4-{[(2-Chlorophenyl)acetyl]amino}-2-[(2,4-dimethoxybenzyl)sulfamoyl]phenyl)-1H-pyrazol-4-yl]-3,3,3-trifluoro-2-methylpropanamide (298 mg, 350 μmol, 80% purity) was dissolved in dichloromethane (7 mL) and treated with trifluoroacetic acid (1.3 mL, 17.5 mmol) followed by stirring at room temperature for 4 h. The mixture was concentrated in vacuo and purified by HPLC to give the title compound (55 mg, 30% yield, 100% purity).

LC-MS (Method A): Rt=1.08 min; MS (ESIpos): m/z=530 (M+H)+

$^1$H-NMR (400 MHz, DMSO-d$_6$) δ [ppm] 1.35 (d, 3H), 3.47 (m, 1H), 3.90 (s, 2H), 7.33 (m, 2H), 7.42 (s, 2H), 7.45 (m, 2H), 7.55 (d, 1H), 7.84 (d, 1H), 7.95 (dd, 1H), 8.22 (d, 1H), 8.36 (d, 1H), 10.63 (s, 1H), 10.77 (s, 1H).

51 mg of the racemic compound were separated into the enantiomers by chiral phase HPLC (Instrument: Sepiatec: Prep SFC100; Column: Chiralpak IA 5 μm 250×30 mm; Eluent A: CO$_2$, Eluent B: methanol; isocratic: 21% B; flow 100.0 mL/min; temperature: 40° C.; BPR: 150 bar; MWD @ 254 nm) yielding the following two isomers:

Example 509

N-[1-(4-{[(2-Chlorophenyl)acetyl]amino}-2-sulfamoylphenyl)-1H-pyrazol-4-yl]-3,3,3-trifluoro-2-methylpropanamide (Enantiomer A)

20 mg, 96% purity
LC (Method N): Rt=2.56 min

Example 510

N-[1-(4-{[(2-Chlorophenyl)acetyl]amino}-2-sulfamoylphenyl)-1H-pyrazol-4-yl]-3,3,3-trifluoro-2-methylpropanamide (Enantiomer B)

20 mg, 99% purity
LC (Method N): Rt=3.62 min

Example 511 (Cis Racemic), Example 512 (Trans Enantiomer A) and Example 513 (Trans Enantiomer B)

Example 511

2-(2-Chlorophenyl)-N-(4-{4-[(cis)-2,5-dimethylpyrrolidin-1-yl]-1H-pyrazol-1-yl}-3-sulfamoylphenyl)acetamide

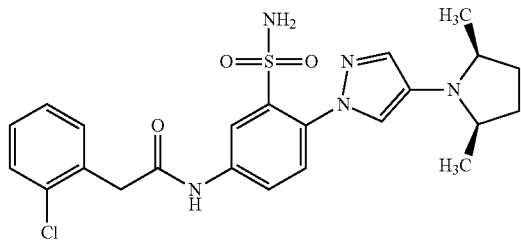 [SMILES: C[C@@H]1CC[C@H](C)N1c1cnn(-c2ccc(NC(=O)Cc3ccccc3Cl)cc2S(N)(=O)=O)c1]

2-(2-Chlorophenyl)-N-(3-[(2,4-dimethoxybenzyl)sulfamoyl]-4-{4-(2,5-dimethyl-pyrrolidin-1-yl)-1H-pyrazol-1-yl}phenyl)acetamide (mixture of stereoisomers) (531 mg, 575 μmol, 80% purity) was dissolved in dichloromethane (7.4 mL) and treated with trifluoroacetic acid (2.2 mL, 28.8 mmol) followed by stirring at room temperature for 5 h. The mixture was concentrated in vacuo and purified by HPLC to give the title compound (23.5 mg, 8% yield, 97% purity) as the meso-isomer.

LC-MS (Method A): Rt=0.93 min; MS (ESIpos): m/z=488 (M+H)+

$^1$H-NMR (400 MHz, DMSO-d$_6$) δ [ppm] 1.57 (m, 2H), 1.98 (m, 2H), 1.19 (d, 6H), 3.30 (m, 2H), 3.89 (s, 2H), 7.33 (m, 2H), 7.45 (m, 2H), 7.46 (d, 1H), 7.52 (m, 2H), 7.54 (d, 1H), 7.54 (d, 1H), 7.95 (dd, 1H), 8.33 (d, 1H), 10.72 (s, 1H).

As another fraction, the racemic trans-isomer 2-(2-chlorophenyl)-N-(4-{4-[(trans)-2,5-dimethylpyrrolidin-1-yl]-1H-pyrazol-1-yl}-3-sulfamoylphenyl)acetamide was isolated (85.6 mg, 21%, 70% purity).

LC-MS (Method A): Rt=1.02 min; MS (ESIpos): m/z=488 (M+H)$^+$ $^1$H-NMR (400 MHz, DMSO-d$_6$) δ [ppm] 1.52 (m, 2H), 2.15 (m, 2H), 1.01 (d, 6H), 3.64 (m, 2H), 3.89 (s, 2H), 7.33 (m, 2H), 7.40 (d, 1H), 7.44 (d, 1H), 7.45 (m, 2H), 7.49 (m, 2H), 7.53 (d, 1H), 7.95 (dd, 1H), 8.33 (d, 1H), 10.72 (s, 1H).

80 mg of the racemic compound were separated into the enantiomers by chiral phase HPLC (Instrument: Labomatic HD5000, Labocord-5000; Gilson GX-241, Labcol Vario 4000; Column: YMC Cellulose SC 5μ 250×30 mm; Eluent A: hexane+0.1 Vol-% diethylamine (99%), Eluent B: ethanol; gradient: 20-50% B in 20 min; flow 40.0 mL/min; UV @ 254 nm) yielding the following two isomers:

Example 512

2-(2-Chlorophenyl)-N-(4-{4-[(trans)-2,5-dimethylpyrrolidin-1-yl]-1H-pyrazol-1-yl}-3-sulfamoylphenyl)acetamide (Enantiomer A)

22.3 mg, 100% purity
LC (Method O): Rt=4.35 min

Example 513

2-(2-Chlorophenyl)-N-(4-{4-[(trans)-2,5-dimethylpyrrolidin-1-yl]-1H-pyrazol-1-yl}-3-sulfamoylphenyl)acetamide (Enantiomer B)

21 mg, 99% purity
LC (Method O): Rt=5.32 min

Example 514

N-(4-{4-[(2,2-Difluoroethyl)amino]-1H-pyrazol-1-yl}-3-sulfamoylphenyl)-2-(2-fluorophenyl)acetamide

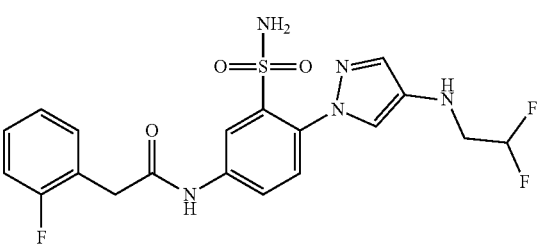 [SMILES: NS(=O)(=O)c1cc(NC(=O)Cc2ccccc2F)ccc1-n1cc(NCC(F)F)cn1]

N-(4-{4-[(2,2-Difluoroethyl)amino]-1H-pyrazol-1-yl}-3-[(2,4-dimethoxybenzyl)sulfamoyl]-phenyl)-2-(2-fluorophenyl)acetamide (420 mg, 417 μmol, 60% purity) was dissolved in dichloromethane (5.4 mL) and treated with trifluoroacetic acid 1.6 mL, 20.9 mmol) followed by stirring at room temperature overnight. The mixture was concentrated in vacuo and purified by HPLC to give the title compound (13.8 mg, 7% yield, 95% purity).

LC-MS (Method A): Rt=0.99 min; MS (ESIpos): m/z=454 [M+H]$^+$ $^1$H-NMR (400 MHz, DMSO-d$_6$) δ [ppm] 3.33 (m, 2H), 3.78 (s, 2H), 5.18 (t, 1H), 6.12 (tt, 1H), 7.19 (m, 2H), 7.33 (m, 1H), 7.40 (m, 1H), 7.41 (d, 1H), 7.47 (s, 2H), 7.49 (d, 1H), 7.56 (d, 1H), 7.95 (dd, 1H), 8.32 (d, 1H), 10.74 (s, 1H).

Example 515

2-(2-Chlorophenyl)-N-(3-sulfamoyl-4-{4-[(2,2,2-trifluoroethyl)amino]-1H-pyrazol-1-yl}phenyl)acetamide

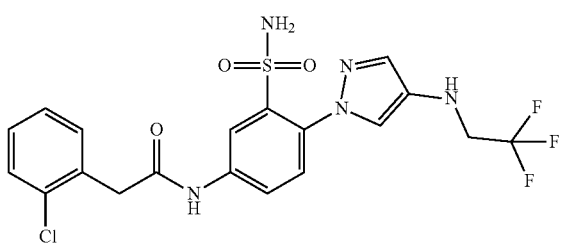 [SMILES: NS(=O)(=O)c1cc(NC(=O)Cc2ccccc2Cl)ccc1-n1cc(NCC(F)(F)F)cn1]

2-(2-Chlorophenyl)-N-(3-[(2,4-dimethoxybenzyl)sulfamoyl]-4-{4-[(2,2,2-trifluoroethyl)amino]-1H-pyrazol-1-yl}phenyl)acetamide (528 mg, 455 μmol, 55% purity) was dissolved in dichloromethane (5.9 mL) and treated with trifluoroacetic acid 1.8 mL, 22.8 mmol) followed by stirring at room temperature overnight. The mixture was concentrated in vacuo and purified by HPLC to give the title compound (30 mg, 13% yield, 99% purity).

LC-MS (Method A): Rt=1.09 min; MS (ESIpos): m/z=488 [M+H]$^+$ $^1$H-NMR (400 MHz, DMSO-d$_6$) δ [ppm] 3.74 (dq, 2H), 3.89 (s, 2H), 5.51 (t, 1H), 7.32 (m, 2H), 7.43 (d, 1H), 7.46 (s, 2H), 7.46 (d, 1H), 7.46 (m, 2H), 7.58 (d, 1H), 7.95 (dd, 1H), 8.32 (d, 1H), 10.72 (s, 1H).

Example 516

2-(2-Chlorophenyl)-N-[4-(4-isopropyl-1H-pyrazol-1-yl)-3-sulfamoylphenyl]acetamide

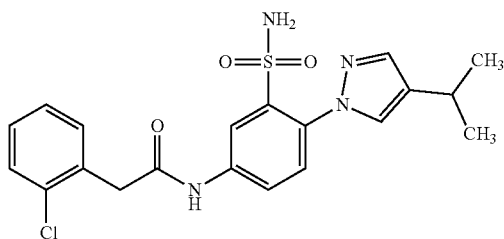

2-(2-Chlorophenyl)-N-{3-[(2,4-dimethoxybenzyl)sulfamoyl]-4-(4-isopropyl-1H-pyrazol-1-yl)-phenyl}acetamide (410 mg, 457 μmol, 65% purity) was dissolved in dichloromethane (5.9 mL) and treated with trifluoroacetic acid 1.8 mL, 22.9 mmol) followed by stirring at room temperature overnight. The mixture was concentrated in vacuo and purified by HPLC to give the title compound (44 mg, 22% yield, 100% purity).

LC-MS (Method A): Rt=1.21 min; MS (ESIpos): m/z=433 [M+H]$^+$ $^1$H-NMR (400 MHz, DMSO-d$_6$) δ [ppm] 1.22 (d, 6H), 2.86 (sept, 1H), 3.89 (s, 2H), 7.33 (m, 2H), 7.45 (m, 2H), 7.50 (s, 2H), 7.51 (d, 1H), 7.68 (s, 1H), 7.91 (s, 1H), 7.97 (dd, 1H), 8.33 (d, 1H), 10.74 (s, 1H).

Example 517

2-(2-Fluorophenyl)-N-[4-(4-isopropyl-1H-pyrazol-1-yl)-3-sulfamoylphenyl]acetamide

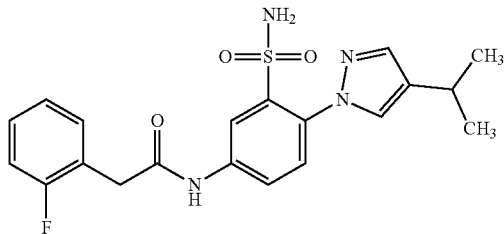 [SMILES: CC(C)c1cnn(-c2ccc(NC(=O)Cc3ccccc3F)cc2S(N)(=O)=O)c1]

N-{3-[(2,4-Dimethoxybenzyl)sulfamoyl]-4-(4-isopropyl-1H-pyrazol-1-yl)phenyl}-2-(2-fluoro-phenyl)acetamide (407 mg, 467 μmol, 65% purity) was dissolved in dichloromethane (6.0 mL) and treated with trifluoroacetic acid 1.8 mL, 23.3 mmol) followed by stirring at room temperature overnight. The mixture was concentrated in vacuo and purified by HPLC to give the title compound (70 mg, 34% yield, 95% purity).

LC-MS (Method A): Rt=1.17 min; MS (ESIpos): m/z=417 [M+H]$^+$ $^1$H-NMR (400 MHz, DMSO-d$_6$) δ [ppm] 1.22 (d, 6H), 2.86 (sept, 1H), 3.79 (s, 2H), 7.18 (m, 1H), 7.20 (m, 1H), 7.38 (m, 1H), 7.41 (m, 1H), 7.50 (s, 2H), 7.51 (d, 1H), 7.68 (s, 1H), 7.91 (s, 1H), 7.97 (dd, 1H), 8.33 (d, 1H), 10.72 (s, 1H).

Example 518

2-(2-Chlorophenyl)-N-{3-sulfamoyl-4-[4-(2,2,2-trifluoroethyl)-1H-pyrazol-1-yl]phenyl}acetamide

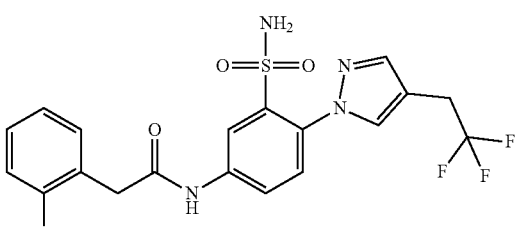

2-(2-Chlorophenyl)-N-{3-[(2,4-dimethoxybenzyl)sulfamoyl]-4-[4-(2,2,2-trifluoroethyl)-1H-pyrazol-1-yl]phenyl}acetamide (219 mg, 300 μmol, 85% purity) was dissolved in dichloromethane (6.0 mL) and treated with trifluoroacetic acid (1.2 mL, 15.0 mmol) followed by stirring at room temperature overnight. The mixture was concentrated in vacuo and purified by HPLC to give the title compound (56 mg, 39% yield, 100% purity).

LC-MS (Method A): Rt=1.13 min; MS (ESIpos): m/z=473 [M+H]$^+$ $^1$H-NMR (400 MHz, DMSO-d$_6$) δ [ppm] 3.60 (q, 2H), 3.90 (s, 2H), 7.33 (m, 2H), 7.43 (s, 2H), 7.45 (m, 2H), 7.52 (d, 1H), 7.75 (s, 1H), 7.97 (dd, 1H), 8.10 (s, 1H), 8.36 (d, 1H), 10.78 (s, 1H).

Example 519

2-(2-Fluorophenyl)-N-{3-sulfamoyl-4-[4-(2,2,2-trifluoroethyl)-1H-pyrazol-1-yl]phenyl}acetamide

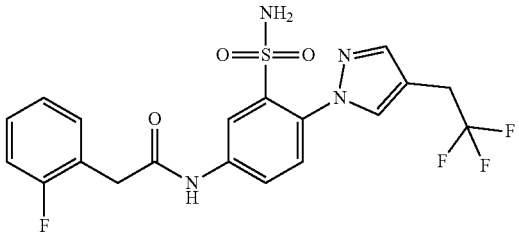 [SMILES: NS(=O)(=O)c1cc(NC(=O)Cc2ccccc2F)ccc1-n1cc(CC(F)(F)F)cn1]

N-{3-[(2,4-Dimethoxybenzyl)sulfamoyl]-4-[4-(2,2,2-trifluoroethyl)-1H-pyrazol-1-yl]phenyl}-2-(2-fluorophenyl)acetamide (136 mg, 190 μmol, 85% purity) was dissolved in dichloromethane (3.8 mL) and treated with trifluoroacetic acid (0.7 mL, 9.50 mmol) followed by stirring at room temperature overnight. The mixture was concentrated in vacuo and purified by HPLC to give the title compound (22 mg, 24% yield, 95% purity).

LC-MS (Method A): Rt=1.09 min; MS (ESIpos): m/z=457 [M+H]⁺

¹H-NMR (400 MHz, DMSO-d₆) δ [ppm] 3.60 (q, 2H), 3.80 (s, 2H), 7.19 (m, 2H), 7.33 (m, 1H), 7.41 (m, 1H), 7.43 (s, 2H), 7.52 (d, 1H), 7.75 (s, 1H), 7.97 (dd, 1H), 8.10 (s, 1H), 8.36 (d, 1H), 10.76 (s, 1H).

Example 520

2-(2-Chlorophenyl)-N-[4-(5-cyclopropyl-1,2,4-oxadiazol-3-yl)-3-sulfamoylphenyl]acetamide

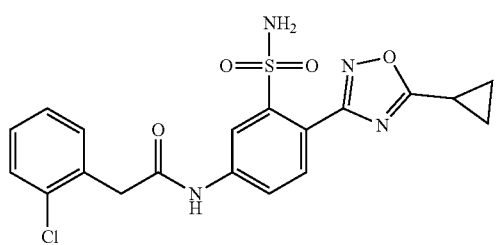 [SMILES: NS(=O)(=O)c1cc(NC(=O)Cc2ccccc2Cl)ccc1-c1noc(C2CC2)n1]

2-(2-Chlorophenyl)-N-{4-(5-cyclopropyl-1,2,4-oxadiazol-3-yl)-3-[(2,4-dimethoxybenzyl)sulfamoyl]phenyl}acetamide (135 mg, 220 µmol, 95% purity) was dissolved in dichloromethane (4.4 mL) and treated with trifluoroacetic acid (847 µL, 11.0 mmol) followed by stirring at room temperature overnight. The mixture was concentrated in vacuo and purified by HPLC to give the title compound (13 mg, 14% yield, 100% purity).

LC-MS (Method A): Rt=1.11 min; MS (ESIpos): m/z=433 [M+H]⁺

¹H-NMR (400 MHz, DMSO-d₆) δ [ppm] 1.18 (m, 2H), 1.32 (m, 2H), 2.46 (m, 1H), 3.91 (s, 2H), 7.33 (m, 2H), 7.35 (s, 2H), 7.46 (m, 2H), 7.75 (d, 1H), 7.98 (dd, 1H), 8.40 (d, 1H), 10.85 (s, 1H).

Example 521

2-(2-Chlorophenyl)-N-{3-sulfamoyl-4-[3-(trifluoromethyl)-1,2,4-oxadiazol-5-yl]phenyl}acetamide

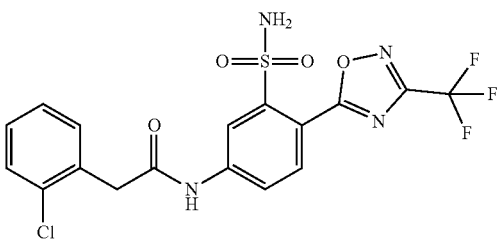 [SMILES: NS(=O)(=O)c1cc(NC(=O)Cc2ccccc2Cl)ccc1-c1nc(C(F)(F)F)no1]

2-(2-Chlorophenyl)-N-{3-[(2,4-dimethoxybenzyl)sulfamoyl]-4-[3-(trifluoromethyl)-1,2,4-oxa-diazol-5-yl]phenyl}acetamide (355 mg, 380 µmol, 65% purity) was dissolved in dichloromethane (4.9 mL) and treated with trifluoroacetic acid (1.46 mL, 19.0 mmol) followed by stirring at room temperature overnight. The mixture was concentrated in vacuo and purified by HPLC to give the title compound (13 mg, 7% yield, 90% purity).

LC-MS (Method A): Rt=1.20 min; MS (ESIpos): m/z=461 [M+H]⁺

¹H-NMR (400 MHz, DMSO-d₆) δ [ppm] 3.94 (s, 2H), 7.33 (m, 2H), 7.46 (m, 2H), 7.72 (s, 2H), 7.95 (d, 1H), 8.00 (dd, 1H), 8.50 (d, 1H), 11.01 (s, 1H).

Example 522

2-(2-Chlorophenyl)-N-{4-[5-(difluoromethyl)-1,3,4-oxadiazol-2-yl]-3-sulfamoylphenyl}acetamide

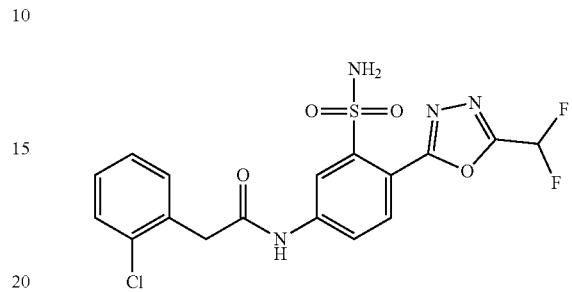

2-(2-Chlorophenyl)-N-{4-[5-(difluoromethyl)-1,3,4-oxadiazol-2-yl]-3-[(2,4-dimethoxybenzyl)sulfamoyl]phenyl}acetamide (498 mg, 495 µmol, 60% purity) was dissolved in dichloromethane (6.4 mL) and treated with trifluoroacetic acid (1.91 mL, 24.8 mmol) followed by stirring at room temperature overnight. The mixture was concentrated in vacuo and purified by flash chromatography to give the title compound (15 mg, 6% yield, 90% purity).

LC-MS (Method A): Rt=1.08 min; MS (ESIpos): m/z=443 [M+H]⁺

¹H-NMR (400 MHz, DMSO-d₆) δ [ppm] 3.93 (s, 2H), 7.33 (m, 2H), 7.46 (m, 2H), 7.55 (t, 1H), 7.64 (s, 2H), 7.89 (d, 1H), 8.00 (dd, 1H), 8.47 (d, 1H), 10.95 (s, 1H).

Example 523

N-{4-[5-(Difluoromethyl)-1,3,4-oxadiazol-2-yl]-3-sulfamoylphenyl}-2-(2-fluorophenyl)acetamide

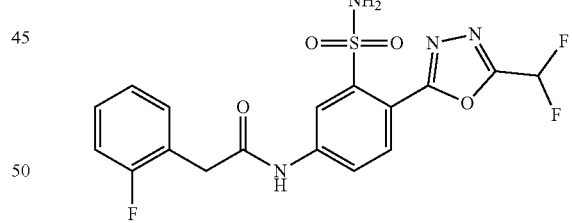

N-{4-[5-(Difluoromethyl)-1,3,4-oxadiazol-2-yl]-3-[(2,4-dimethoxybenzyl)sulfamoyl]phenyl}-2-(2-fluorophenyl)acetamide (466 mg, 297 µmol, 37% purity) was dissolved in dichloromethane (3.8 mL) and treated with trifluoroacetic acid (1.14 mL, 14.9 mmol) followed by stirring at room temperature overnight. The mixture was concentrated in vacuo and purified by flash chromatography to give the title compound (30 mg, 21% yield, 90% purity).

LC-MS (Method A): Rt=1.01 min; MS (ESIpos): m/z=427 [M+H]⁺

¹H-NMR (400 MHz, DMSO-d₆) δ [ppm] 3.83 (s, 2H), 7.19 (m, 1H), 7.20 (m, 1H), 7.34 (m, 1H), 7.41 (m, 1H), 7.55 (t, 1H), 7.64 (s, 2H), 7.88 (d, 1H), 8.00 (dd, 1H), 8.46 (d, 1H), 10.93 (s, 1H).

Example 524

2-(2-Chlorophenyl)-N-[4-(5-methyl-1,3,4-oxadiazol-2-yl)-3-sulfamoylphenyl]acetamide

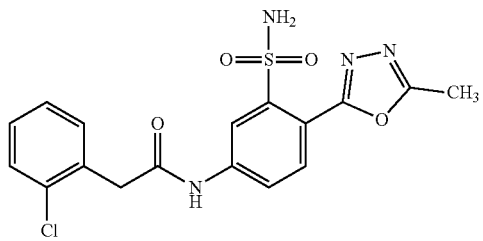 [SMILES: Cc1nnc(-c2ccc(NC(=O)Cc3ccccc3Cl)cc2S(N)(=O)=O)o1]

2-(2-Chlorophenyl)-N-{3-[(2,4-dimethoxybenzyl)sulfamoyl]-4-(5-methyl-1,3,4-oxadiazol-2-yl)phenyl}acetamide (260 mg, 313 µmol, 60% purity) was dissolved in dichloromethane (6.4 mL) and treated with trifluoroacetic acid (1.21 mL, 15.7 mmol) followed by stirring at room temperature overnight. The mixture was concentrated in vacuo and purified by flash chromatography to give the title compound (51 mg, 39% yield, 96% purity).

LC-MS (Method A): Rt=0.96 min; MS (ESIpos): m/z=407 [M+H]$^+$ $^1$H-NMR (400 MHz, DMSO-d$_6$) δ [ppm] 2.59 (s, 3H), 3.92 (s, 2H), 7.33 (m, 2H), 7.45 (m, 2H), 7.62 (s, 2H), 7.85 (d, 1H), 8.01 (dd, 1H), 8.43 (d, 1H), 10.91 (s, 1H).

Example 525

2-(2-Fluorophenyl)-N-[4-(5-methyl-1,3,4-oxadiazol-2-yl)-3-sulfamoylphenyl]acetamide

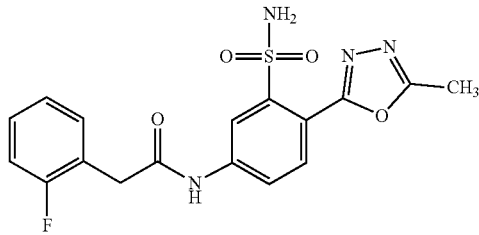 [SMILES: Cc1nnc(-c2ccc(NC(=O)Cc3ccccc3F)cc2S(N)(=O)=O)o1]

N-{3-[(2,4-Dimethoxybenzyl)sulfamoyl]-4-(5-methyl-1,3,4-oxadiazol-2-yl)phenyl}-2-(2-fluorophenyl)acetamide (427 mg, 476 µmol, 60% purity) was dissolved in dichloromethane (6.1 mL) and treated with trifluoroacetic acid (1.83 mL, 23.8 mmol) followed by stirring at room temperature overnight. The mixture was concentrated in vacuo and purified by flash chromatography to give the title compound (105 mg, 51% yield, 95% purity).

LC-MS (Method A): Rt=0.93 min; MS (ESIpos): m/z=391 [M+H]$^+$ $^1$H-NMR (400 MHz, DMSO-d$_6$) δ [ppm] 2.59 (s, 3H), 3.82 (s, 2H), 7.18 (m, 1H), 7.19 (m, 1H), 7.34 (m, 1H), 7.41 (m, 1H), 7.61 (s, 2H), 7.85 (d, 1H), 8.01 (dd, 1H), 8.43 (d, 1H), 10.89 (s, 1H).

Example 526

N-[4-(5-Methyl-1,3,4-oxadiazol-2-yl)-3-sulfamoylphenyl]-2-(4-methylphenyl)acetamide

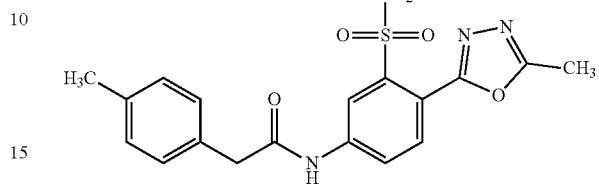

N-{3-[(2,4-Dimethoxybenzyl)sulfamoyl]-4-(5-methyl-1,3,4-oxadiazol-2-yl)phenyl}-2-(4-methylphenyl)acetamide (351 mg, 476 µmol, 72% purity) was dissolved in dichloromethane (6.1 mL) and treated with trifluoroacetic acid (1.83 mL, 23.8 mmol) followed by stirring at room temperature overnight. The mixture was concentrated in vacuo and purified by HPLC to give the title compound (21 mg, 11% yield, 95% purity).

LC-MS (Method B): Rt=0.85 min; MS (ESIpos): m/z=387 [M+H]$^+$ $^1$H-NMR (400 MHz, DMSO-d$_6$) δ [ppm] 2.28 (s, 3H), 2.58 (s, 3H), 3.65 (s, 2H), 7.14 (d, 2H), 7.23 (d, 2H), 7.60 (s, 2H), 7.84 (d, 1H), 8.02 (dd, 1H), 8.40 (d, 1H), 10.78 (s, 1H).

Example 527

2-(2-Chlorophenyl)-N-[4-(1H-pyrrol-3-yl)-3-sulfamoylphenyl]acetamide

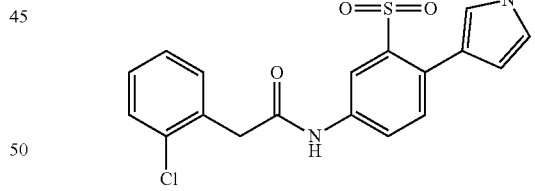

C1H tert-Butyl 3-(4-{[(2-chlorophenyl)acetyl]amino}-2-{[(dimethylamino)methylene]sulfamoyl}-phenyl)-1H-pyrrole-1-carboxylate (50 mg, 92 µmol) was dissolved in methanol (2 ml) and treated with 30% aqueous ammonia solution (2 ml) at room temperature for 3 days. The solvent was removed under reduced pressure and the crude was purified by HPLC to yield 22 mg (94% purity, 58% yield).

LC-MS (Method A): Rt=0.97 min; MS (ESIpos): m/z=390 [M+H]$^+$ $^1$H-NMR (400 MHz, DMSO-d$_6$) δ [ppm]: 3.86 (s, 2H), 6.36 (ddd, 1H), 6.56 (s, 2H), 6.83 (ddd, 1H), 7.13 (ddd, 1H), 7.32 (m, 2H), 7.40 (d, 2H), 7.44 (m, 2H), 7.79 (d, 1H), 8.27 (d, 1H), 10.50 (s, 1H), 11.04 (s, 1H).

Example 528

2-(2-Chlorophenyl)-N-{4-[5-(difluoroacetyl)-1H-pyrrol-3-yl]-3-sulfamoylphenyl}acetamide

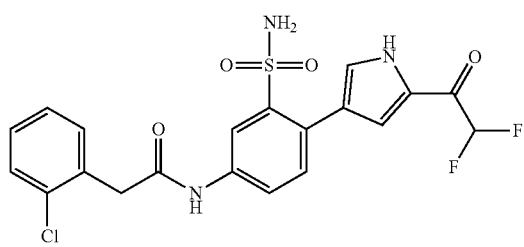 [SMILES: NS(=O)(=O)c1cc(NC(=O)Cc2ccccc2Cl)ccc1-c1c[nH]c(C(=O)C(F)F)c1]

2-(2-Chlorophenyl)-N-[3-{[(dimethylamino)methylene]sulfamoyl}-4-(1H-pyrrol-3-yl)phenyl]-acetamide (67 mg, 136 µmol, 90% purity) was dissolved in dichloromethane (6 mL) and treated with difluoroacetyl chloride (93 mg, 813 mmol) and N,N-diisopropylethylamine (242 µL, 1.35 mmol) followed by stirring at room temperature overnight. Saturated aqueous sodium hydrogen carbonate solution was added to the reaction mixture, and it was extracted with dichloromethane. The combined organic phases were washed with brine, dried over a Whatman filter, and concentrated under reduced pressure yielding crude 2-(2-chlorophenyl)-N-(4-[1-(difluoroacetyl)-1H-pyrrol-3-yl]-3-{[(dimethylamino)methylene]sulfamoyl}phenyl)acetamide (57 mg) that was used without further purification.

The crude acylation product (57 mg) was dissolved in methanol (1 mL) and THF (1 mL) and treated with 25% aqueous ammonia solution (2 ml) at 50° C. for 3 h. The solvent was removed under reduced pressure and the crude was purified by HPLC to yield 7 mg (95% purity, 13% yield) of the title compound.

LC-MS (Method B): Rt=0.95 min; MS (ESIpos): m/z=468 (M+H)$^+$ $^1$H-NMR (400 MHz, DMSO-d$_6$) δ [ppm]: 3.88 (s, 2H), 6.85 (t, 1H), 7.22 (s, 2H), 7.32 (m, 2H), 7.43 (d, 1H), 7.43 (s, 1H), 7.45 (m, 2H), 7.64 (s, 1H), 7.83 (dd, 1H), 8.32 (d, 1H), 10.60 (s, 1H), 12.53 (s, 1H).

Example 529

2-(2-Chlorophenyl)-N-[4-(1-methyl-1H-pyrrol-3-yl)-3-sulfamoylphenyl]acetamide

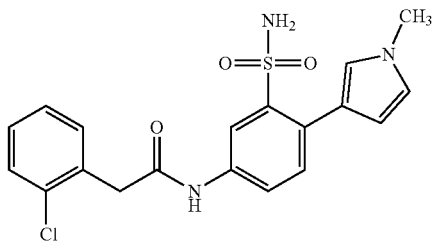 [SMILES: Cn1ccc(-c2ccc(NC(=O)Cc3ccccc3Cl)cc2S(N)(=O)=O)c1]

2-(2-Chlorophenyl)-N-[3-{[(dimethylamino)methylene]sulfamoyl}-4-(1-methyl-1H-pyrrol-3-yl)phenyl]acetamide (105 mg, 229 µmol) was dissolved in methanol (0.8 mL) and treated with 30% aqueous ammonia solution (4.5 ml) at room temperature for 2 days. The solvent was removed under reduced pressure and the crude was purified by HPLC to yield 30 mg (95% purity, 31% yield).

LC-MS (Method A): Rt=1.07 min; MS (ESIpos): m/z=404 [M+H]$^+$ $^1$H-NMR (400 MHz, DMSO-d$_6$) δ [ppm]: 3.65 (s, 3H), 3.86 (s, 2H), 6.31 (dd, 1H), 6.70 (s, 2H), 6.76 (dd, 1H), 7.08 (dd, 1H), 7.32 (m, 2H), 7.38 (d, 1H), 7.44 (m, 2H), 7.78 (dd, 1H), 8.26 (d, 1H), 10.50 (s, 1H).

Example 530

2-(2-Chlorophenyl)-N-[4-(5-cyano-1-methyl-1H-pyrrol-2-yl)-3-sulfamoylphenyl]acetamide

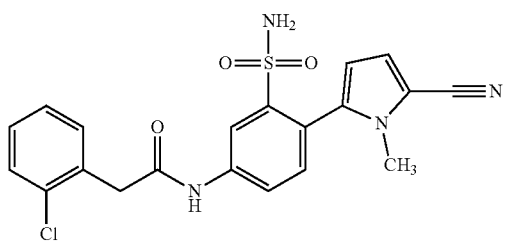 [SMILES: Cn1c(C#N)ccc1-c1ccc(NC(=O)Cc2ccccc2Cl)cc1S(N)(=O)=O]

2-(2-Chlorophenyl)-N-[4-(5-cyano-1-methyl-1H-pyrrol-2-yl)-3-{[(dimethylamino)methylene]-sulfamoyl}phenyl]acetamide (93 mg, 192 µmol) was dissolved in methanol (0.8 mL) and THF (0.9 mL) and treated with 30% aqueous ammonia solution (2 ml) at 50° C. overnight.

The solvent was removed under reduced pressure and the crude was purified by HPLC to yield 43 mg (99% purity, 51% yield).

LC-MS (Method A): Rt=1.07 min; MS (ESIpos): m/z=429 [M+H]$^+$ $^1$H-NMR (400 MHz, DMSO-d$_6$) δ [ppm]: 3.37 (s, 3H), 3.90 (s, 2H), 6.21 (d, 1H), 7.16 (s, 2H), 6.97 (d, 1H), 7.33 (m, 2H), 7.35 (d, 1H), 7.45 (m, 2H), 7.87 (dd, 1H), 8.37 (d, 1H), 10.74 (s, 1H).

Examples 531, Example 532, Example 533 and Example 534

To a mixture of 2-(2-chlorophenyl)-N-(3-{[(dimethylamino)methylene]sulfamoyl}-4-[4-(trifluoromethyl)-1H-pyrazol-1-yl]phenyl)acetamide (200 mg, 0.39 mmol), sodium trifluoromethanesulfonate (486 mg, 3.11 mmol) and copper (II) triflate (28 mg; 0.08 mmol), under argon, was added acetonitrile (4 mL). To the resulting mixture, at vigorous stirring, was added dropwise tert-butylhydroperoxide (70 wt. % in H$_2$O, 0.42 mL, 3.11 mmol) over 30 min by a syringe pump. After stirring for additional 15 h additional amounts of sodium trifluoromethanesulfonate (486 mg, 3.11 mmol) and tert-butylhydroperoxide (70 wt. % in H$_2$O, 0.42 mL, 3.11 mmol) were added. The reaction mixture was stirred for 12 h, and then filtered. The resulting filtrate was concentrated in vacuo to ca. 1 mL and purified by HPLC to give following intermediates: 2-(2-chlorophenyl)-N-(3-{[(dimethylamino)methylene]sulfamoyl}-2-(trifluoromethyl)-4-[4-(trifluoromethyl)-1H-pyrazol-1-yl]phenyl)acetamide (3.1 mg, 1.1% yield, 80% purity), 2-(2-chlorophenyl)-N-(5-{[(dimethylamino)methylene]sulfamoyl}-2-(trifluoromethyl)-4-[4-(trifluoromethyl)-1H-pyrazol-1-yl]phenyl)acetamide (5.5 mg, 1.8% yield, 75% purity), 2-[2-chloro-3-(trifluoromethyl)phenyl]-N-(5-{[(dimethylamino)methylene]sulfamoyl}-2-(trifluoromethyl)-4-

[4-(trifluoromethyl)-1H-pyrazol-1-yl]phenyl)acetamide (5.0 mg, 1.5% yield, 75% purity), 2-[2-chloro-5-(trifluoromethyl)phenyl]-N-(5-{[(dimethylamino)methylene]sulfamoyl}-2-(trifluoromethyl)-4-[4-(trifluoromethyl)-1H-pyrazol-1-yl]phenyl)acetamide (3.9 mg, 1.3% yield, 85% purity).

The corresponding intermediates were redissolved in methanol (0.5 mL) and aqueous ammonia (0.5 mL) was added, followed by stirring at room temperature for 2 days. Water was added and the resulting mixture was extracted three times with dichloromethane. The combined organic layers were washed with brine, dried, concentrated in vacuo, and selected residues further purified by HPLC to give the title compounds.

Example 531

2-(2-Chlorophenyl)-N-{3-sulfamoyl-2-(trifluoromethyl)-4-[4-(trifluoromethyl)-1H-pyrazol-1-yl]phenyl}acetamide

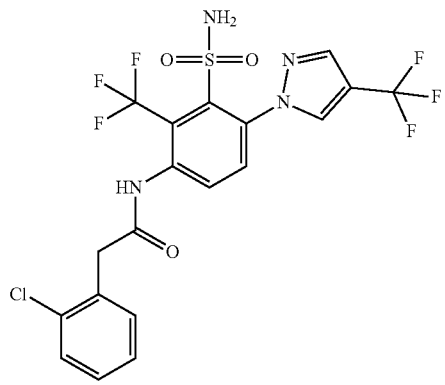 [SMILES: NS(=O)(=O)c1c(-n2cc(C(F)(F)F)cn2)ccc(NC(=O)Cc2ccccc2Cl)c1C(F)(F)F]

2.8 mg, 1.1% yield, 80% purity
LC-MS (Method K): Rt=2.93 min; MS (ESIpos): m/z=527 [M+H]$^+$
$^1$H-NMR (600 MHz, CD3CN) δ [ppm] 3.94 (s, 2H), 6.10 (s, 2H), 7.34 (m, 2H), 7.43 (m, 1H), 7.47 (m, 1H), 7.75 (d, 1H), 8.01 (d, 1H), 8.06 (s, 1H), 8.35 (s, 1H), 8.38 (s, 1H).

Example 532

2-(2-Chlorophenyl)-N-{5-sulfamoyl-2-(trifluoromethyl)-4-[4-(trifluoromethyl)-1H-pyrazol-1-yl]phenyl}acetamide

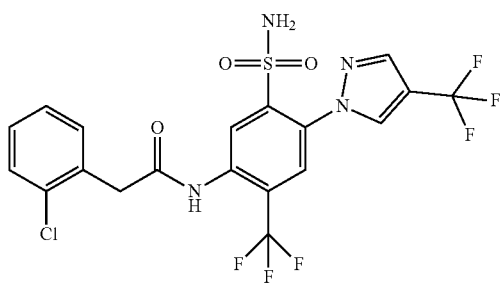 [SMILES: NS(=O)(=O)c1cc(NC(=O)Cc2ccccc2Cl)c(C(F)(F)F)cc1-n1cc(C(F)(F)F)cn1]

0.6 mg, 0.2% yield, 75% purity
LC-MS (Method K): Rt=3.22 min; MS (ESIpos): m/z=527 [M+H]$^+$
$^1$H-NMR (600 MHz, CD$_3$CN) δ [ppm] 3.99 (s, 2H), 6.39 (s, 2H), 7.36 (m, 2H), 7.46 (m, 1H), 7.48 (m, 1H), 7.90 (s, 1H), 8.07 (s, 1H), 8.20 (s, 1H), 8.35 (s, 1H), 8.78 (s, 1H).

Example 533

2-[2-Chloro-3-(trifluoromethyl)phenyl]-N-{5-sulfamoyl-2-(trifluoromethyl)-4-[4-(trifluoromethyl)-1H-pyrazol-1-yl]phenyl}acetamide

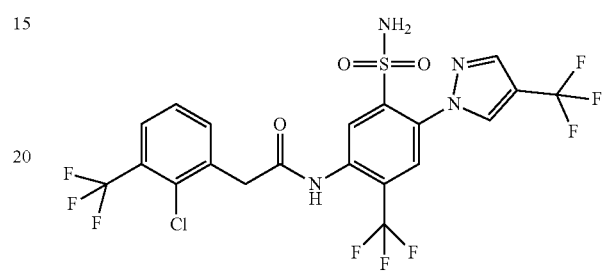

1.5 mg, 0.6% yield, 95% purity
LC-MS (Method K): Rt=3.42 min; MS (ESIpos): m/z=595 [M+H]$^+$
$^1$H-NMR (600 MHz, CD$_3$CN) δ [ppm] 4.10 (s, 2H), 6.40 (s, 2H), 7.52 (t, 1H), 7.71 (d, 1H), 7.78 (d, 1H), 7.92 (s, 1H), 8.08 (s, 1H), 8.34 (s, 1H), 8.36 (s, 1H), 8.68 (s, 1H).

Example 534

2-[2-Chloro-5-(trifluoromethyl)phenyl]-N-{5-sulfamoyl-2-(trifluoromethyl)-4-[4-(trifluoromethyl)-1H-pyrazol-1-yl]phenyl}acetamide

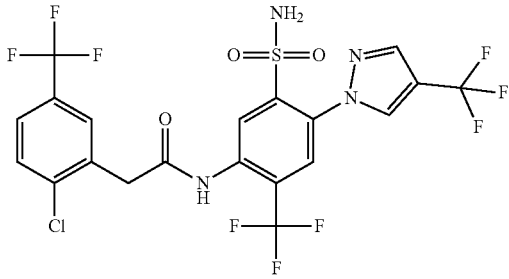 [SMILES: NS(=O)(=O)c1cc(NC(=O)Cc2cc(C(F)(F)F)ccc2Cl)c(C(F)(F)F)cc1-n1cc(C(F)(F)F)cn1]

1.4 mg, 0.6% yield, 99% purity
LC-MS (Method K): Rt=3.45 min; MS (ESIpos): m/z=595 [M+H]$^+$
$^1$H-NMR (600 MHz, CD$_3$CN) δ [ppm] 4.07 (s, 2H), 6.41 (s, 2H), 7.65 (m, 2H), 7.78 (d, 1H), 7.92 (s, 1H), 8.08 (s, 1H), 8.37 (s, 1H), 8.38 (s, 1H), 8.66 (s, 1H).

Examples 535, Example 536, Example 537 and Example 538 To a mixture of 2-(2-chlorophenyl)-N-[4-(4-fluoro-1H-pyrazol-1-yl)-3-sulfamoylphenyl]acetamide (200 mg, 0.49 mmol), sodium trifluoromethanesulfonate (611 mg, 3.91 mmol) and copper (II) triflate (35 mg; 0.10 mmol), under argon, was added acetonitrile (6 mL). To the resulting mixture, at vigorous stirring, was added dropwise tert-butylhydroperoxide (70 wt. % in H$_2$O, 0.54 mL, 3.91 mmol) over 30 min by a syringe pump. After stirring for additional Example 535

2-[2-Chloro-6-(trifluoromethyl)phenyl]-N-[4-(4-fluoro-1H-pyrazol-1-yl)-5-sulfamoyl-2-(trifluoromethyl)phenyl]acetamide

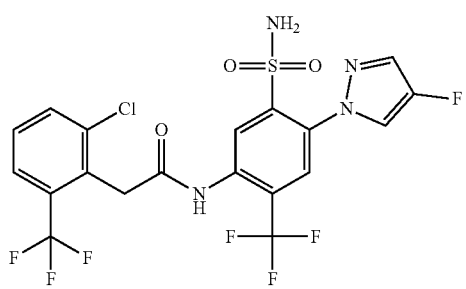 [SMILES: NS(=O)(=O)c1cc(NC(=O)Cc2c(Cl)cccc2C(F)(F)F)c(C(F)(F)F)cc1-n1cc(F)cn1]

3.0 mg, 0.8% yield, 70% purity

LC-MS (Method K): Rt=3.10 min; MS (ESIpos): m/z=545 [M+H]$^+$ $^1$H-NMR (600 MHz, CD$_3$CN) δ [ppm] 4.22 (s, 2H), 6.45 (s, 2H), 7.51 (t, 1H), 7.75 (m, 3H), 7.83 (s, 1H), 7.94 (d, 1H), 8.35 (s, 1H), 8.55 (s, 1H).

Example 536

2-[2-Chloro-3-(trifluoromethyl)phenyl]-N-[4-(4-fluoro-1H-pyrazol-1-yl)-5-sulfamoyl-2-(trifluoromethyl)phenyl]acetamide

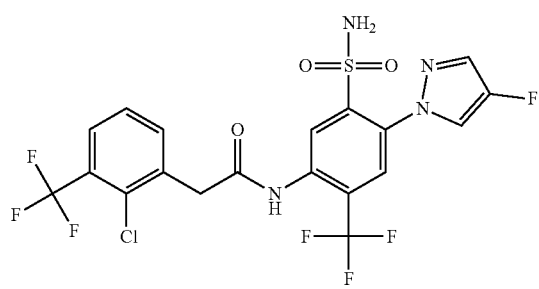 [SMILES: NS(=O)(=O)c1cc(NC(=O)Cc2cccc(C(F)(F)F)c2Cl)c(C(F)(F)F)cc1-n1cc(F)cn1]

5.4 mg, 1.8% yield, 90% purity

LC-MS (Method K): Rt=3.14 min; MS (ESIpos): m/z=545 [M+H]$^+$ $^1$H-NMR (600 MHz, CD$_3$CN) δ [ppm] 4.08 (s, 2H), 6.46 (s, 2H), 7.51 (t, 1H), 7.71 (d, 1H), 7.74 (d, 1H), 7.78 (d, 1H), 7.82 (s, 1H), 7.94 (d, 1H), 8.31 (s, 1H), 8.63 (s, 1H).

Example 537

2-[2-Chloro-5-(trifluoromethyl)phenyl]-N-[4-(4-fluoro-1H-pyrazol-1-yl)-5-sulfamoyl-2-(trifluoromethyl)phenyl]acetamide

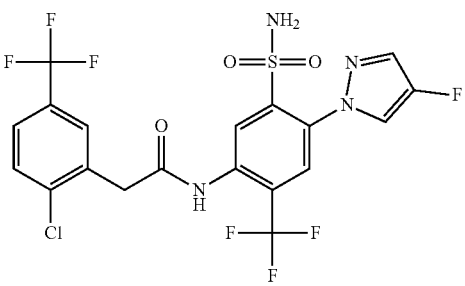 [SMILES: NS(=O)(=O)c1cc(NC(=O)Cc2cc(C(F)(F)F)ccc2Cl)c(C(F)(F)F)cc1-n1cc(F)cn1]

6.5 mg, 1.7% yield, 70% purity

LC-MS (Method K): Rt=3.19 min; MS (ESIpos): m/z=545 [M+H]$^+$ $^1$H-NMR (600 MHz, CD$_3$CN) δ [ppm] 4.06 (s, 2H), 6.46 (s, 2H), 7.65 (m, 2H), 7.74 (d, 1H), 7.78 (d, 1H), 7.82 (s, 1H), 7.95 (d, 1H), 8.33 (s, 1H), 8.61 (s, 1H).

Example 538

2-[2-Chloro-4-(trifluoromethyl)phenyl]-N-[4-(4-fluoro-1H-pyrazol-1-yl)-5-sulfamoyl-2-(trifluoromethyl)phenyl]acetamide

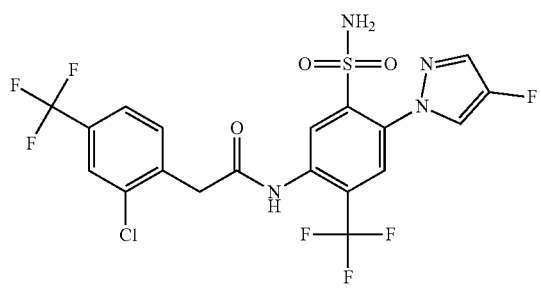 [SMILES: NS(=O)(=O)c1cc(NC(=O)Cc2ccc(C(F)(F)F)cc2Cl)c(C(F)(F)F)cc1-n1cc(F)cn1]

3.2 mg, 0.9% yield, 75% purity

LC-MS (Method K): Rt=3.23 min; MS (ESIpos): m/z=545 [M+H]$^+$ $^1$H-NMR (600 MHz, CD$_3$CN) δ [ppm] 4.06 (s, 2H), 6.46 (s, 2H), 7.64 (m, 2H), 7.74 (d, 1H), 7.81 (s, 1H), 7.83 (s, 1H), 7.95 (d, 1H), 8.33 (s, 1H), 8.61 (s, 1H).

Example 539

N-[4-(3-tert-Butyl-4-cyano-1H-pyrazol-1-yl)-3-sulfamoylphenyl]-2-(2-chlorophenyl)acetamide

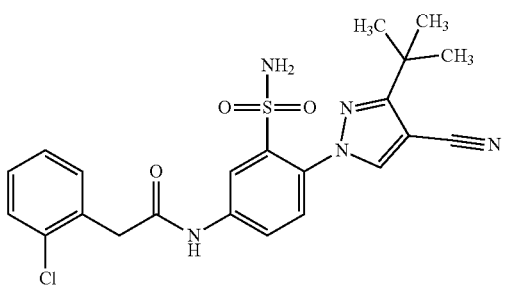 [SMILES: CC(C)(C)c1nn(-c2ccc(NC(=O)Cc3ccccc3Cl)cc2S(N)(=O)=O)cc1C#N]

According to general procedures GP1.2, GP2.2, GP3.2 and GP4.2, 2-chloro-N-(2,4-dimethoxybenzyl)-5-nitrobenzenesulfonamide (1.00 g, 2.59 mmol), 3-tert-butyl-1H-pyrazole-4-carbonitrile (579 mg, 3.88 mmol) and (2-chlorophenyl)acetic acid (661 mg, 3.88 mmol) were converted without purification of intermediates to the title compound and were purified at the end by preparative HPLC (Chromatorex C-18 10 μm, 125×30 mm, acetonitrile/water+0.1% formic acid) (303 mg, 0.642 mmol, 25% yield over 4 steps, 98% purity).

LC-MS (Method A): Rt=1.23 min; MS (ESIpos): m/z=472 [M+H]$^+$ $^1$H-NMR (400 MHz, DMSO-d$_6$) δ [ppm]: 1.39 (s, 9H), 3.91 (s, 2H), 7.30-7.36 (m, 2H), 7.39-7.48 (m, 4H), 7.61 (d, 1H), 7.98 (dd, 1H), 8.38 (d, 1H), 8.84 (s, 1H), 10.84 (s, 1H).

Example 540

N-[4-(3-Bromo-4-cyano-1H-pyrazol-1-yl)-3-sulfamoylphenyl]-2-(2-chlorophenyl)acetamide

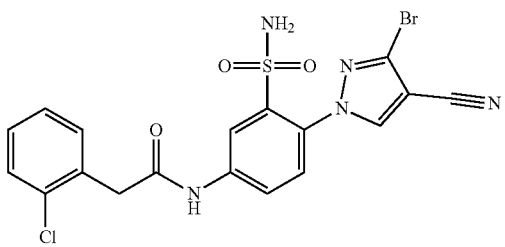 [SMILES: N#Cc1cn(-c2ccc(NC(=O)Cc3ccccc3Cl)cc2S(N)(=O)=O)nc1Br]

According to general procedures GP1.2, GP2.2, GP3.2 and GP4.2, 2-chloro-N-(2,4-dimethoxybenzyl)-5-nitrobenzenesulfonamide (1.00 g, 2.59 mmol), 3-bromo-1H-pyrazole-4-carbonitrile (667 mg, 3.88 mmol) and (2-chlorophenyl)acetic acid (480 mg, 2.81 mmol) were converted without purification of intermediates to the title compound and were purified at the end by preparative HPLC (Chromatorex C-18 10 μm, 125×30 mm, acetonitrile/water+0.1% formic acid) (92 mg, 0.186 mmol, 7% yield over 4 steps, 97% purity).

LC-MS (Method A): Rt=1.15 min; MS (ESIpos): m/z=494/496 [M+H]$^+$ $^1$H-NMR (400 MHz, DMSO-d$_6$) δ [ppm]: 3.92 (s, 2H), 7.30-7.36 (m, 2H), 7.42-7.48 (m, 2H), 7.55 (s, 2H), 7.60 (d, 1H), 7.94 (dd, 1H), 8.40 (d, 1H), 8.56 (s, 1H), 10.87 (s, 1H).

Example 541

2-(2-Chlorophenyl)-N-{4-[4-chloro-3-(trifluoromethyl)-1H-pyrazol-1-yl]-3-sulfamoylphenyl}acetamide

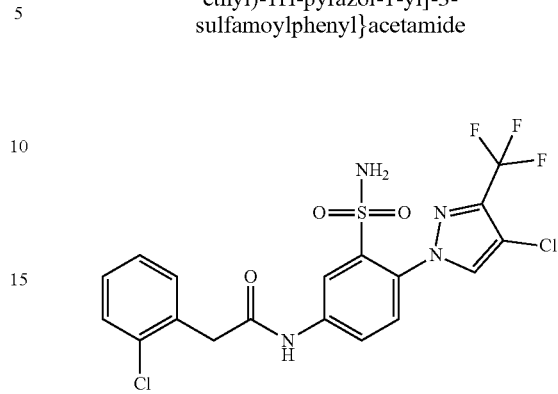

According to general procedures GP1.2, GP2.2, GP3.2 and GP4.2, 2-chloro-N-(2,4-dimethoxybenzyl)-5-nitrobenzenesulfonamide (500 mg, 1.29 mmol), 4-chloro-3-(trifluoromethyl)-1H-pyrazole (331 mg, 1.94 mmol) and (2-chlorophenyl)acetic acid (293 mg, 1.72 mmol) were converted without purification of intermediates to the title compound and were purified at the end by preparative HPLC (Waters XBridge C18 5μ 100×30 mm, acetonitrile/water+0.1% formic acid) (90 mg, 0.182 mmol, 14% yield over 4 steps, 90% purity).

LC-MS (Method A): Rt=1.26 min; MS (ESIpos): m/z=493 [M+H]$^+$ $^1$H-NMR (400 MHz, DMSO-d$_6$) δ [ppm]: 3.92 (s, 2H), 7.30-7.37 (m, 2H), 7.42-7.49 (m, 2H), 7.53 (s, 2H), 7.62 (d, 1H), 7.95 (dd, 1H), 8.41 (d, 1H), 8.55 (d, 1H), 10.86 (s, 1H).

Example 542

2-(2-Chlorophenyl)-N-[4-(3,4-dimethyl-1H-pyrazol-1-yl)-3-sulfamoylphenyl]acetamide

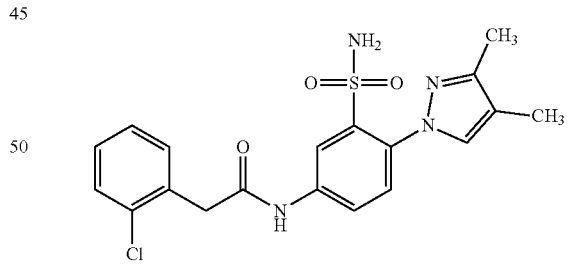

According to general procedures GP1.2, GP2.2, GP3.2 and GP4.2, 2-chloro-N-(2,4-dimethoxybenzyl)-5-nitrobenzenesulfonamide (500 mg, 1.29 mmol), 3,4-dimethyl-1H-pyrazole (186 mg, 1.94 mmol) and (2-chlorophenyl)acetic acid (216 mg, 1.27 mmol) were converted without purification of intermediates to the title compound and were purified at the end by preparative HPLC (Waters XBridge C18 5μ 100×30 mm, acetonitrile/water+0.1% formic acid) (27 mg, 0.0645 mmol, 5% yield over 4 steps, 90% purity).

LC-MS (Method A): Rt=1.13 min; MS (ESIpos): m/z=419 [M+H]$^+$

¹H-NMR (400 MHz, DMSO-d₆) δ [ppm]: 2.01 (d, 3H), 2.17 (s, 3H), 3.89 (s, 2H), 7.29-7.36 (m, 2H), 7.41-7.49 (m, 3H), 7.56 (s, 2H), 7.78 (s, 1H), 7.94 (dd, 1H), 8.32 (d, 1H), 10.72 (s, 1H).

Example 543

N-[4-(4-Chloro-3,5-dimethyl-1H-pyrazol-1-yl)-3-sulfamoylphenyl]-2-(2-chlorophenyl)acetamide

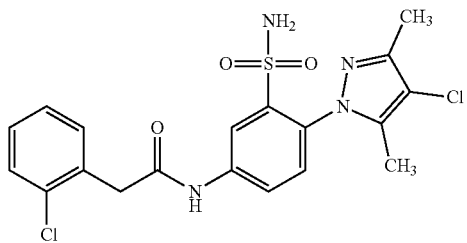 [SMILES: Cc1nn(-c2ccc(NC(=O)Cc3ccccc3Cl)cc2S(N)(=O)=O)c(C)c1Cl]

According to general procedures GP1.2, GP2.2, GP3.2 and GP4.2, 2-chloro-N-(2,4-dimethoxybenzyl)-5-nitrobenzenesulfonamide (500 mg, 1.29 mmol), 4-chloro-3,5-dimethyl-1H-pyrazole (253 mg, 1.94 mmol) and (2-chlorophenyl)acetic acid (291 mg, 1.71 mmol) were converted without purification of intermediates to the title compound and were purified at the end by preparative HPLC (Waters XBridge C18 5µ 100×30 mm, acetonitrile/water+0.1% formic acid) (52 mg, 0.115 mmol, 9% yield over 4 steps, 98% purity).

LC-MS (Method A): Rt=1.21 min; MS (ESIpos): m/z=453 [M+H]⁺

¹H-NMR (400 MHz, DMSO-d₆) δ [ppm]: 2.02 (s, 3H), 2.19 (s, 3H), 3.91 (s, 2H), 7.15 (s, 2H), 7.30-7.37 (m, 2H), 7.42-7.52 (m, 3H), 7.96 (dd, 1H), 8.37 (d, 1H), 10.82 (s, 1H).

Example 544

2-(2-Chlorophenyl)-N-[4-(1H-pyrazol-1-yl)-3-sulfamoylphenyl]acetamide

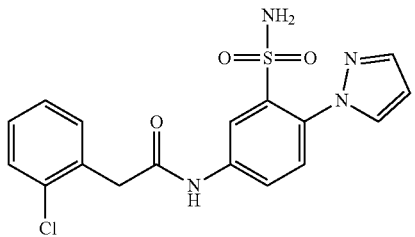 [SMILES: NS(=O)(=O)c1cc(NC(=O)Cc2ccccc2Cl)ccc1-n1cccn1]

According to general procedures GP1.2, GP2.4, GP3.2 and GP4.3, 2-chloro-N-(2,4-dimethoxybenzyl)-5-nitrobenzenesulfonamide (500 mg, 1.29 mmol), 1H-pyrazole (132 mg, 1.94 mmol) and (2-chlorophenyl)acetic acid (339 mg, 1.99 mmol) were converted without purification of intermediates to the title compound and were purified at the end by preparative HPLC (Waters XBridge C18 5µ 100×30 mm, acetonitrile/water+0.1% formic acid), followed by two further preparative HPLCs (Waters XBridge C18 5µ 100×30 mm, acetonitrile/water+0.2% aqueous ammonia (32%)) (25 mg, 0.640 mmol, 5% yield over 4 steps, 97% purity).

LC-MS (Method A): Rt=1.01 min; MS (ESIpos): m/z=391 [M+H]⁺

¹H-NMR (400 MHz, DMSO-d₆) δ [ppm]: 3.90 (s, 2H), 6.51 (dd, 1H), 7.29-7.36 (m, 2H), 7.40-7.50 (m, 4H), 7.53 (d, 1H), 7.78 (d, 1H), 7.98 (dd, 1H), 8.09 (dd, 1H), 8.36 (d, 1H), 10.77 (s, 1H).

Example 545

2-(2-Chlorophenyl)-N-[4-(3-cyano-5-methyl-1H-pyrazol-1-yl)-3-sulfamoylphenyl]acetamide

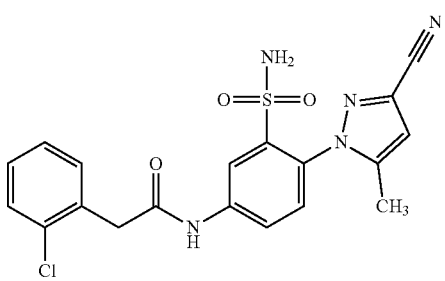 [SMILES: Cc1cc(C#N)nn1-c1ccc(NC(=O)Cc2ccccc2Cl)cc1S(N)(=O)=O]

According to general procedures GP1.2, GP2.2, GP3.2 and GP4.2, 2-chloro-N-(2,4-dimethoxybenzyl)-5-nitrobenzenesulfonamide (500 mg, 1.29 mmol), 5-methyl-1H-pyrazole-3-carbonitrile (208 mg, 1.94 mmol) and (2-chlorophenyl)acetic acid (292 mg, 1.71 mmol) were converted without purification of intermediates to the title compound and were purified at the end by preparative HPLC (Waters XBridge C18 5µ 100×30 mm, acetonitrile/water+0.1% formic acid), followed by another preparative HPLC (Waters YMC C18 5µ 100×50 mm, acetonitrile/water+0.2% aqueous ammonia (32%)) (110 mg, 0.256 mmol, 20% yield over 4 steps, 90% purity).

LC-MS (Method B): Rt=0.94 min; MS (ESIneg): m/z=428 [M−H]⁻

¹H-NMR (400 MHz, DMSO-d₆) δ [ppm]: 2.09 (s, 3H), 3.93 (s, 2H), 6.92 (s, 1H), 7.31-7.36 (m, 2H), 7.39 (br s, 2H), 7.44-7.49 (m, 2H), 7.52 (d, 1H), 7.96 (dd, 1H), 8.42 (d, 1H), 10.89 (s, 1H).

Example 546

2-(2-Chlorophenyl)-N-[4-(3-hydroxy-5-methyl-1H-pyrazol-1-yl)-3-sulfamoylphenyl]acetamide

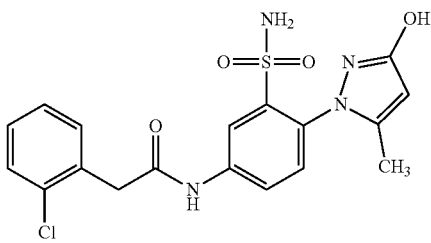 [SMILES: Cc1cc(O)nn1-c1ccc(NC(=O)Cc2ccccc2Cl)cc1S(N)(=O)=O]

According to general procedures GP1.2, GP2.2, GP3.2 and GP4.2, 2-chloro-N-(2,4-dimethoxybenzyl)-5-nitrobenzenesulfonamide (500 mg, 1.29 mmol), 5-methyl-1H-pyrazol-3-ol (190 mg, 1.94 mmol) and (2-chlorophenyl)acetic acid (229 mg, 1.34 mmol) were converted without purification of intermediates to the title compound and were purified at the end by preparative HPLC (Waters XBridge C18 5μ 100×30 mm, acetonitrile/water+0.1% formic acid), followed by another preparative HPLC (Waters XBridge C18 5μ 100×30 mm, acetonitrile/water+0.2% aqueous ammonia (32%)) (16.1 mg, 0.0383 mmol, 3% yield over 4 steps, 98% purity).

LC-MS (Method B): Rt=0.61 min; MS (ESIpos): m/z=421 [M+H]+

$^1$H-NMR (400 MHz, DMSO-$d_6$) δ [ppm]: 2.01 (s, 3H), 3.89 (s, 2H), 5.55 (s, 1H), 7.30-7.36 (m, 4H), 7.43-7.48 (m, 3H), 7.95 (dd, 1H), 8.32 (d, 1H), 10.00 (s, 1H), 10.76 (s, 1H).

Examples 547 and Example 548

According to general procedures GP1.2, GP2.2, GP3.2 and GP4.2, 2-chloro-N-(2,4-dimethoxybenzyl)-5-nitrobenzenesulfonamide (500 mg, 1.29 mmol), 5-methyl-1H-pyrazole-4-carbonitrile (208 mg, 1.94 mmol) and (2-chlorophenyl)acetic acid (291 mg, 1.71 mmol) were converted without purification of intermediates to the title compounds and were purified and separated at the end by preparative HPLC (Waters XBridge C18 5μ 100×30 mm, acetonitrile/water+ 0.1% formic acid), followed by another preparative HPLC (Sepiatec Prep SFC100; Chiralpak IA 5 μm 250×30 mm; Eluent A: C02, Eluent B: Ethanol+0.2 Vol-% wässriger Ammoniak (32%)).

Example 547

2-(2-Chlorophenyl)-N-[4-(4-cyano-5-methyl-1H-pyrazol-1-yl)-3-sulfamoylphenyl]acetamide

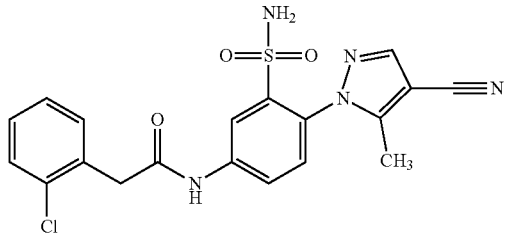 [SMILES: Cc1c(C#N)cnn1-c1ccc(NC(=O)Cc2ccccc2Cl)cc1S(N)(=O)=O]

45 mg, 0.105 mmol, 8% yield over 4 steps, 98% purity

LC-MS (Method A): Rt=1.05 min; MS (ESIpos): m/z=430 [M+H]+

LC-MS (Method L): Rt=1.69 min $^1$H-NMR (400 MHz, DMSO-$d_6$) δ [ppm]: 2.20 (s, 3H), 3.91 (s, 2H), 7.21-7.37 (m, 4H), 7.41-7.49 (m, 2H), 7.54 (d, 1H), 7.94 (dd, 1H), 8.15 (s, 1H), 8.41 (d, 1H), 10.88 (s, 1H).

Example 548

2-(2-Chlorophenyl)-N-[4-(4-cyano-3-methyl-1H-pyrazol-1-yl)-3-sulfamoylphenyl]acetamide

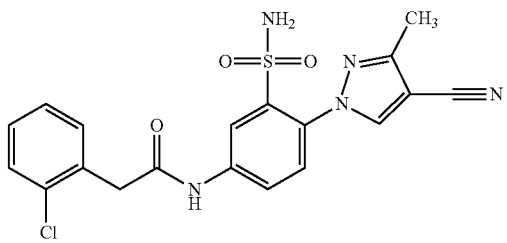 [SMILES: Cc1nn(-c2ccc(NC(=O)Cc3ccccc3Cl)cc2S(N)(=O)=O)cc1C#N]

95 mg, 0.221 mmol, 16% yield over 4 steps, 98% purity

LC-MS (Method A): Rt=1.05 min; MS (ESIpos): m/z=430 [M+H]+

LC-MS (Method L): Rt=2.81 min $^1$H-NMR (400 MHz, DMSO-$d_6$) δ [ppm]: 2.37 (s, 3H), 3.90 (s, 2H), 7.29-7.36 (m, 2H), 7.37-7.50 (m, 4H), 7.55 (d, 1H), 7.93 (dd, 1H), 8.38 (d, 1H), 8.72 (s, 1H), 10.83 (s, 1H).

Example 549

2-(2-Chlorophenyl)-N-{4-[4-(morpholin-4-yl)-1,3-thiazol-2-yl]-3-sulfamoylphenyl}acetamide

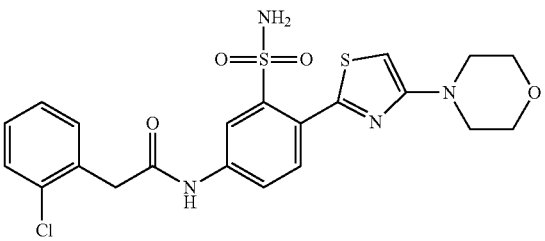 [SMILES: NS(=O)(=O)c1cc(NC(=O)Cc2ccccc2Cl)ccc1-c1nc(N2CCOCC2)cs1]

According to general procedure GP8.2, N-(4-bromo-3-{[(dimethylamino)methylene]-sulfamoyl}phenyl)-2-(2-chlorophenyl)acetamide (300 mg, 0.65 mmol) and 4-(2-bromo-1,3-thiazol-4-yl)morpholine (148 mg, 0.59 mmol) were converted to the title compound and were purified by preparative HPLC (Waters XBridge C18 5μ 100×30 mm, acetonitrile/water+0.1% formic acid) (16 mg, 0.0325 mmol, 5% yield, 97% purity).

LC-MS (Method A): Rt=1.09 min; MS (ESIpos): m/z=493 [M+H]+

$^1$H-NMR (400 MHz, DMSO-$d_6$) δ [ppm]: 3.34-3.40 (m, 4H), 3.71-3.77 (m, 4H), 3.88 (s, 2H), 7.05 (s, 1H), 7.29-7.36 (m, 2H), 7.41-7.48 (m, 2H), 7.57 (d, 1H), 7.62 (s, 2H), 7.90 (dd, 1H), 8.28 (d, 1H), 10.66 (s, 1H).

Example 550

2-(2-Chlorophenyl)-N-{4-[5-(morpholin-4-yl)-1,3-thiazol-2-yl]-3-sulfamoylphenyl}acetamide

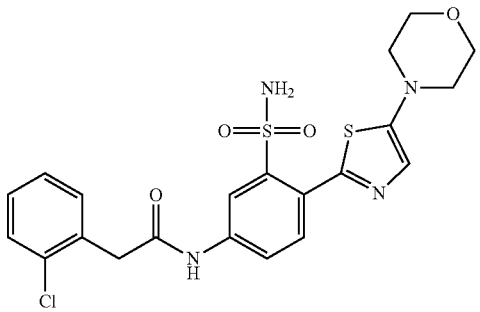 [SMILES: NS(=O)(=O)c1cc(NC(=O)Cc2ccccc2Cl)ccc1-c1ncc(N2CCOCC2)s1]

According to general procedure GP8.2, N-(4-bromo-3-{[(dimethylamino)methylene]-sulfamoyl}phenyl)-2-(2-chlorophenyl)acetamide (300 mg, 0.65 mmol) and 4-(2-bromo-1,3-thiazol-5-yl)morpholine (148 mg, 0.59 mmol) were converted to the title compound and were purified twice by preparative HPLC (Waters XBridge C18 5μ 100×30 mm, acetonitrile/water+0.1% formic acid) (23 mg, 0.0467 mmol, 8% yield, 97% purity).

LC-MS (Method A): Rt=0.99 min; MS (ESIpos): m/z=493 [M+H]+

$^{1}$H-NMR (400 MHz, DMSO-d$_6$) δ [ppm]: 3.37-3.42 (m, 4H), 3.69-3.76 (m, 4H), 3.88 (s, 2H), 7.27-7.35 (m, 5H), 7.38-7.47 (m, 3H), 7.81 (dd, 1H), 8.34 (d, 1H), 10.65 (s, 1H).

Example 551

2-(2-Chlorophenyl)-N-[4-(5-methyl-1,3-thiazol-2-yl)-3-sulfamoylphenyl]acetamide

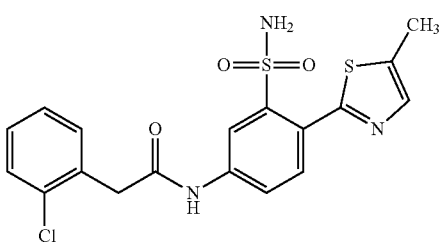 [SMILES: Cc1cnc(-c2ccc(NC(=O)Cc3ccccc3Cl)cc2S(N)(=O)=O)s1]

According to general procedure GP8.2, N-(4-bromo-3-{[(dimethylamino)methylene]-sulfamoyl}phenyl)-2-(2-chlorophenyl)acetamide (300 mg, 0.65 mmol) and 2-bromo-5-methyl-1,3-thiazole (211 mg, 1.19 mmol) were converted to the title compound and were purified by preparative HPLC (Waters XBridge C18 5μ 100×30 mm, acetonitrile/water+0.1% formic acid), followed by another preparative HPLC (Waters Phenomenex Kinetex EVO C18 5μ 100×30 mm, acetonitrile/water+0.1% formic acid) (2.1 mg, 0.00498 mmol, 1% yield, 98% purity).

LC-MS (Method A): Rt=1.14 min; MS (ESIpos): m/z=422 [M+H]+

$^{1}$H-NMR (400 MHz, DMSO-d$_6$) δ [ppm]: methyl signal overlapped by solvent signal, 3.90 (s, 2H), 7.29-7.36 (m, 2H), 7.42-7.48 (m, 2H), 7.65-7.74 (m, 4H), 7.98 (dd, 1H), 8.38 (d, 1H), 10.80 (s, 1H).

Example 552

2-(2-Chlorophenyl)-N-[4-(pyridin-4-yl)-3-sulfamoylphenyl]acetamide

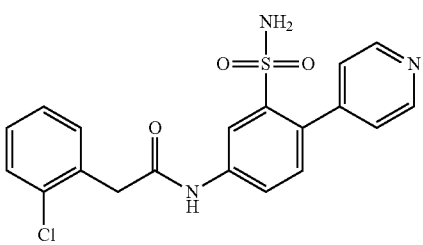 [SMILES: NS(=O)(=O)c1cc(NC(=O)Cc2ccccc2Cl)ccc1-c1ccncc1]

N-(4-Bromo-3-{[(dimethylamino)methylidene]sulfamoyl}phenyl)-2-(2-chlorophenyl)-acetamide (500 mg, 1.09 mmol), pyridin-4-ylboronic acid (268 mg, 2.18 mmol), bis(triphenylphosphine)-palladium(II) dichloride (CAS 13965-03-2) (38.4 mg, 54.5 μmol) and triphenylphosphine (14.3 mg, 54.5 μmol) were dissolved in n-propanol (10 ml). After purging with argon for 5 minutes, aqueous potassium carbonate (2.7 ml, 1.0 M, 2.7 mmol) was added and the solution was purged again with argon for 5 minutes. The reaction mixture was heated for 1 h at 100° C. Same amount of reagents were added and the reaction was heated for 1 h at 100° C. Afterwards, the crude was filtered over celite and the solvent was removed under reduced pressure. The crude was used without further purification in the next step.

Crude 2-(2-chlorophenyl)-N-[3-{[(dimethylamino)methylidene]sulfamoyl}-4-(pyridin-4-yl)phenyl]acetamide from the previous step (530 mg, 1.16 mmol) was dissolved in methanol (50 ml) and aqueous ammonia (50 ml) was added. The reaction was stirred at room temperature until completion of the reaction and the solvent was removed under reduced pressure. The crude was purified by HPLC (Chromatorex C-18 10 μm, 125×30 mm, acetonitrile/water+0.1% aqueous ammonia (32%)). Traces of triphenylphosphine oxide were removed after a second HPLC run to yield the title compound (79.3 mg, 90% purity, 15% yield over 2 steps)

LC-MS (Method A): Rt=0.80 min; MS (ESIpos): m/z=402 [M+H]+

$^{1}$H-NMR (400 MHz, DMSO-d$_6$) δ [ppm]: 3.91 (s, 2H), 7.26-7.37 (m, 4H), 7.37-7.41 (m, 3H), 7.44-7.49 (m, 2H), 7.86 (dd, 1H), 8.38 (d, 1H), 8.55-8.61 (m, 2H), 10.70 (s, 1H).

Example 553

1-(4-{[(2-Chlorophenyl)acetyl]amino}-2-sulfamoylphenyl)-1H-pyrazole-4-carboxamide

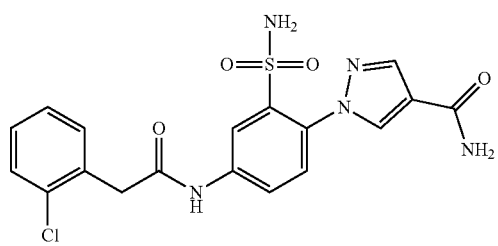 [SMILES: NC(=O)c1cnn(-c2ccc(NC(=O)Cc3ccccc3Cl)cc2S(N)(=O)=O)c1]

2-(2-Chlorophenyl)-N-[4-(4-cyano-1H-pyrazol-1-yl)-3{[(dimethylamino)methylene]sulfamoyl}phenyl]acetamide (200 mg, 0.425 mmol), was placed in a crimp sealable microwave vessel (5 ml) and, the vessel was crimped shut and flushed with argon for 5 minutes. A solution of (1,5-cyclooctadiene)(methoxy)iridium(1) dimer (14 mg, 0.021 mmol), 4,4'-di-tert-butyl-2,2'-dipyridyl (11.4 mg, 0.042 mmol) and bis(pinacolato)diboron (129.4 mg, 0.51 mmol) in THF (0.42 ml) that had been stirred under argon for 1 hour at 80° C. was added under an atmosphere of argon. The vessel was then heated at 80° C. for 24 hours, following which the solvent was removed under reduced pressure. Potassium hydroxide (72 mg, 1.27 mmol), water (2 mL) and dimethylformamide (2 ml) were added and hydrogen peroxide (30% solution in water, 0.13 mL, 1.27 mmol) was added dropwise. The mixture was stirred for 1 hour at room temperature after which aqueous ammonia (4 mL) was added and the mixture stirred at room temperature overnight. An additional volume of aqueous ammonia (6 mL) was added and the mixture stirred for a further 48 hours at room temperature. Dichloromethane (30 mL) and water (20 mL) were added, the layers were separated, and the aqueous layer extracted with dichloromethane (2×30 mL) and ethyl acetate (30 mL), the organic layers were combined, dried over sodium sulfate and the solvent was removed under reduced pressure. The solid was first purified by flash chromatography (MeOH:DCM 2/98 to 20/80) followed by purification with preparative HPLC (Waters XBridge C18 5µ 100×30 mm, acetonitrile/water+0.1% formic acid) yielding a white solid (9.7 mg, 0.01 mmol, 5% yield over 3 steps, 92% purity).

LC-MS (Method A): Rt=0.84 min; MS (ESIpos): m/z=434 [M+H]$^+$ $^1$H NMR (400 MHz, DMSO-d6) δ ppm 3.91 (s, 2H) 7.19 (br s, 1H) 7.27-7.37 (m, 2H) 7.38-7.51 (m, 4H) 7.57 (d, 1H) 7.70 (br s, 1H) 7.97 (dd, 1H) 8.10 (s, 1H) 8.37 (d, 1H) 8.44 (s, 1H) 10.81 (s, 1H).

Example 554, Example 555, Example 556 and Example 557

2-(2-Chlorophenyl)-N-[4-(4-cyano-1H-pyrazol-1-yl)-3-sulfamoylphenyl]acetamide (500 mg, 1.2 mmol), was dissolved in acetonitrile (4 mL) and ferrocene (224 mg, 1.2 mmol) was added along with trifluoroacetic acid (308 µl, 2.4 mmol). The mixture was stirred at room temperature and hydrogen peroxide (30% aqueous, 491 µl, 4.81 mmol) was added over 15 minutes using a syringe pump. The mixture was stirred for 1 hour at room temperature following which aqueous sodium thiosulfate (saturated solution, 2 mL) was added and the mixture stirred for a further 5 minutes. Brine (50 mL) was then added and the aqueous layer was extracted with dichloromethane (3×70 mL), the organic layers combined, a peroxide test performed on the organic layer (negative result), the organic phase was passed through a water repellant filter and the solvent removed under reduced pressure. The resulting solid was purified by flash chromatography (MeOH/DCM 2/98 to 20/80 to 100/0), followed by preparative HPLC (Waters XBridge C18 5µ 100×30 mm, acetonitrile/water+0.1% formic acid) yielding the four separated title compounds as white solids.

Example 554

2-(2-Chloro-3-hydroxyphenyl)-N-[4-(4-cyano-1H-pyrazol-1-yl)-3-sulfamoylphenyl]acetamide

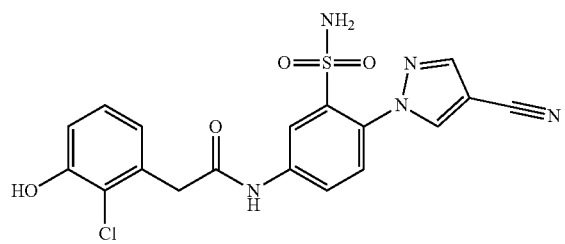 [SMILES: N#Cc1cnn(-c2ccc(NC(=O)Cc3cccc(O)c3Cl)cc2S(N)(=O)=O)c1]

19.2 mg, 0.04 mmol, 4% yield, 95% purity.
LC-MS (Method A): Rt=0.82 min; MS (ESIpos): m/z=432 [M+H]$^+$
$^1$H-NMR (400 MHz, DMSO-d$_6$) δ [ppm]: 3.85 (s, 2H) 6.85 (dd, 1H) 6.90 (dd, 1H) 7.05-7.14 (m, 1H) 7.44 (br s, 2H) 7.58 (d, 1H) 7.97 (dd, 1H) 8.31 (s, 1H) 8.39 (d, 1H) 8.86 (s, 1H) 10.13 (br s, 1H) 10.80 (s, 1H).

Example 555

2-(2-Chloro-4-hydroxyphenyl)-N-[4-(4-cyano-1H-pyrazol-1-yl)-3-sulfamoylphenyl]acetamide

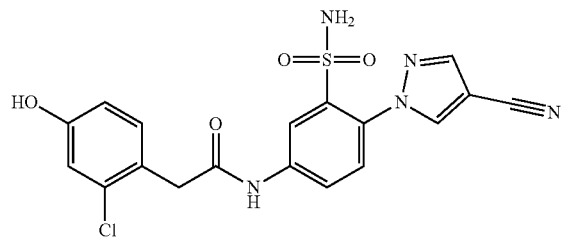 [SMILES: N#Cc1cnn(-c2ccc(NC(=O)Cc3ccc(O)cc3Cl)cc2S(N)(=O)=O)c1]

20 mg, 0.04 mmol, 4% yield, 95% purity.
LC-MS (Method A): Rt=0.84 min; MS (ESIpos): m/z=432 [M+H]$^+$
$^1$H-NMR (400 MHz, DMSO-d$_6$) δ [ppm]: 3.76 (s, 2H) 6.72 (dd, 1H) 6.83 (d, 1H) 7.22 (d, 1H) 7.44 (br s, 2H) 7.57 (d, 1H) 7.96 (dd, 1H) 8.31 (s, 1H) 8.39 (d, 1H) 8.86 (s, 1H) 9.84 (br s, 1H) 10.75 (s, 1H).

Example 556

2-(2-Chloro-5-hydroxyphenyl)-N-[4-(4-cyano-1H-pyrazol-1-yl)-3-sulfamoylphenyl]acetamide

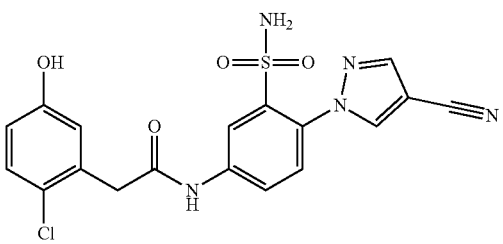 [SMILES: N#Cc1cnn(-c2ccc(NC(=O)Cc3cc(O)ccc3Cl)cc2S(N)(=O)=O)c1]

17.4 mg, 0.04 mmol, 4% yield, 95% purity.
LC-MS (Method A): Rt=0.87 min; MS (ESIpos): m/z=432 [M+H]+
1H-NMR (400 MHz, DMSO-d6) δ [ppm]: 3.79 (s, 2H) 6.70 (dd, 1H) 6.84 (d, 1H) 7.21 (d, 1H) 7.45 (br s, 2H) 7.58 (d, 1H) 7.98 (dd, 1H) 8.29-8.32 (m, 1H) 8.40 (d, 1H) 8.86 (s, 1H) 9.67 (s, 1H) 10.81 (s, 1H).

Example 557

2-(2-Chloro-6-hydroxyphenyl)-N-[4-(4-cyano-1H-pyrazol-1-yl)-3-sulfamoylphenyl]acetamide

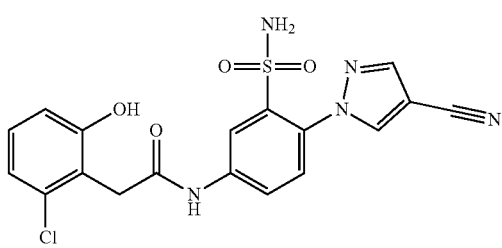 [SMILES: N#Cc1cnn(-c2ccc(NC(=O)Cc3c(O)cccc3Cl)cc2S(N)(=O)=O)c1]

19.4 mg, 0.04 mmol, 4% yield, 95% purity.
LC-MS (Method A): Rt=0.93 min; MS (ESIpos): m/z=432 [M+H]+
1H-NMR (400 MHz, DMSO-d6) δ [ppm]: 3.86 (s, 2H) 6.81 (d, 1H) 6.90 (dd, 1H) 7.07-7.14 (m, 1H) 7.44 (s, 2H) 7.56 (d, 1H) 7.94 (dd, 1H) 8.30 (s, 1H) 8.41 (d, 1H) 8.85 (s, 1H) 10.02 (s, 1H) 10.74 (s, 1H).

Example 558

2-(2-Chlorophenyl)-N-[4-(4-cyano-1H-pyrazol-1-yl)-3-sulfamoylphenyl]-2-hydroxyacetamide

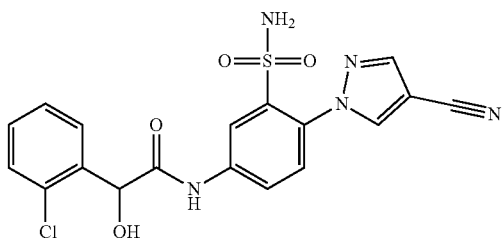 [SMILES: N#Cc1cnn(-c2ccc(NC(=O)C(O)c3ccccc3Cl)cc2S(N)(=O)=O)c1]

A 100-mL Erlenmeyer flask containing sterile growth medium (20 mL) was inoculated with a DMSO cryo culture (0.2 mL) of *Streptomyces antibioticus* (NRRL 3238). A growth medium consisting of D-(+)-glucose monohydrate (10 g/L), yeast extract (1 g/L), beef extract (1 g/L), tryptase (2 g/L), was adjusted to pH 7.2 with sodium hydroxide solution (16% in water) and sterilized at 121° C. for 20 minutes. After inoculation, the growth flask was shaken on a rotation shaker (165 rpm) at 27° C. for 72 hours. A 2 L Erlenmeyer flask containing the same sterile growth medium (1000 mL, prepared under the same conditions) was inoculated with the preculture (5 mL). Then, the flask was shaken on a rotation shaker (165 rpm) at 27° C. for 72 hours.

A 10-L fermenter was filled with the same growth medium (8.3 L) and adjusted to pH 7.2. Silicon oil (0.5 mL) and Synperonic (0.5 mL) were added, and it was sterilized at 121° C. for 40 minutes. The culture of the 2 L Erlenmeyer flask was added to the fermenter under sterile conditions. The fermenter was operated under gauge pressure (0.7 bar), aerated with air (3 L min-1) and stirred (300 rpm) at 27° C. After 8 hours, Example 39 (250 mg, 0.601 mmol), dissolved in DMF (20 mL), was added and the fermentation was continued for 123.5 hours. The culture broth was extracted with methyl isobutyl ketone (20 L) for 19.5 hours and again with methyl isobutyl ketone (10 L) for 14.3 hours. The two organic phases were combined and concentrated to dryness under reduced pressure. The residue was treated with a methanol/water mix. This solution was extracted three times with n-hexane (50 mL). The methanol/water layer was concentrated to dryness. The crude product was absorbed on isolute and chromatographed first by a Biotage Isolera, then by preparative HPLC (Waters XBridge C18 5μ 100×30 mm; eluent A: water+0.1% vol. formic acid (99%), eluent B: acetonitrile; gradient: 0.00-0.50 min 10% B (40>70 mL/min), 0.51-5.50 min 21-41% B (70 mL/min), room temperature) affording the title compound.

25.3 mg, 0.0586 mmol, 10% yield, 99% purity.
Optical rotation: $[\alpha]_D^{20}$=−15°+/−0.2° (c=1, DMSO)
MS (ESIpos): m/z=432 [M+H]+
1H-NMR (400 MHz, DMSO-d6) δ [ppm]: 5.53 (d, 1H), 6.79 (d, 1H), 7.34-7.40 (m, 2H), 7.43 (br s, 2H), 7.47 (dd, 1H), 7.57-7.62 (m, 2H), 8.08 (dd, 1H), 8.31 (s, 1H), 8.62 (d, 1H), 8.87 (s, 1H), 10.74 (s, 1H).

Biological Assays

The following assays can be used to illustrate the commercial utility of the compounds according to the present invention.

Examples were tested in selected biological assays one or more times. When tested more than once, data are reported as either average (avg) values or as median values, wherein
the average value, also referred to as the arithmetic mean value, represents the sum of the obtained values divided by the number of values obtained, and
the median value represents the middle number of the group of obtained values when ranked in ascending or descending order. If the number of values in the data set is odd, the median is the middle value. If the number of values in the data set is even, the median is the arithmetic mean of the two middle values.

When no meaningful calculation of average values or median values is possible due to the existence of measurement values falling outside the detection range of the assay (indicated by < or > in the tables below) all individual measurement values are indicated. Examples were synthesized one or more times. When synthesized more than once, data from biological assays represent average values or median values calculated utilizing data sets obtained from testing of one or more synthetic batch.

In Vitro Studies
Human P2X4 HEK Cell FLIPR Assay

HEK293 cells stably expressing human P2X4 were plated in poly-D-lysine-coated 384-well plates at a seeding density of 30000 cells/well and incubated overnight. P2X4 function was assessed by measuring intracellular calcium changes using the calcium-chelating dye Fluo8-AM (Molecular Devices) on a fluorescent imaging plate reader (FLEX/FLIPR station; Molecular Devices). On the day of the assay, the medium was removed and the cells were incubated for 30 min at 37° C. and 5% $CO_2$ in 30 μL of dye buffer (Hank's balanced salt solution, 10 mM HEPES, 1.8 mM $CaCl_2$, 1 mM $MgCl_2$, 2 mM probenecid, 5 mM D-glucose monohydrate, 5 μM Fluo8-AM, pH=7.4). Compounds diluted in probenecid buffer (Hank's balanced salt solution, 10 mM HEPES, 1.8 mM $CaCl_2$, 1 mM $MgCl_2$, 2 mM probenecid, 5 mM D-glucose monohydrate, pH=7.4) were added in a volume of 10 µL and allowed to incubate for 30 min at room temperature. The final assay DMSO concentration was 0.5%. The agonist, Bz-ATP (Tocris), was added in a volume of 10 µL at a concentration representing the $EC_{80}$ value. The $EC_{80}$ value of Bz-ATP was determined each assay day prior to compound profiling. The fluorescence was measured for an interval of 120 sec at 2 sec intervals. The excitation and emission wavelengths used to monitor fluorescence were 470-495 nm and 515-575 nm, respectively. The data was analyzed based on the increase in peak relative fluorescence units (RFU) compared to the basal fluorescence and the data was normalized to the agonist control. The compounds were tested in triplicates per plate and mean values were plotted in Excel XLFit to determine $IC_{50}$ values, percentage of maximal inhibition and the Hill coefficients.

| Example Number | Human P2X4 HEK Cells (FLIPR Assay) avg $IC_{50}$ [nM] | Human P2X4 HEK Cells (FLIPR Assay) avg Efficacy [%] |
|---|---|---|
| 2 | 19384 | 50 |
| 3 | 942 | 76 |
| 4 | 259 | 83 |
| 5 | 249 | 91 |
| 6 | 1069 | 84 |
| 7 | 3081 | 73 |
| 8 | 2555 | 79 |
| 9 | 7 | 83 |
| 10 | 7 | 81 |
| 11 | >25000 | 31 |
| 12 | >25000 | 34 |
| 13 | 514 | 100 |
| 14 | >25000 | 26 |
| 15 | 379 | 99 |
| 16 | 262 | 89 |
| 17 | 288 | 89 |
| 18 | 4700 | 66 |
| 19 | 47 | 71 |
| 20 | 140 | 67 |
| 21 | 170 | 67 |
| 22 | 224 | 76 |
| 23 | 1176 | 89 |
| 24 | 45 | 92 |
| 25 | 26 | 93 |
| 26 | 27 | 85 |
| 27 | 70 | 74 |
| 28 | 31 | 90 |
| 29 | 113 | 75 |
| 30 | 222 | 87 |
| 31 | 112 | 81 |
| 32 | 139 | 93 |
| 33 | 31 | 79 |
| 34 | 448 | 79 |
| 35 | 224 | 90 |
| 36 | 667 | 81 |
| 37 | 848 | 81 |
| 38 | 329 | 87 |
| 39 | 32 | 96 |
| 40 | 1236 | 90 |
| 41 | 357 | 70 |
| 42 | 24 | 71 |
| 43 | 210 | 87 |
| 44 | 378 | 97 |
| 45 | 75 | 74 |
| 46 | 916 | 87 |
| 47 | 472 | 66 |
| 48 | 297 | 82 |
| 49 | 135 | 94 |
| 50 | 149 | 88 |
| 51 | 134 | 94 |
| 52 | 154 | 82 |
| 53 | 169 | 52 |
| 54 | 557 | 75 |
| 55 | 1403 | 74 |
| 56 | 121 | 70 |
| 57 | 141 | 71 |
| 58 | 73 | 54 |
| 59 | 4650 | 73 |
| 60 | 917 | 80 |
| 61 | 400 | 79 |
| 62 | 249 | 94 |
| 63 | 130 | 87 |
| 64 | 104 | 83 |
| 65 | 355 | 62 |
| 66 | 86 | 90 |
| 67 | 1510 | 98 |
| 68 | 128 | 75 |
| 69 | 210 | 80 |
| 70 | 118 | 85 |
| 71 | 132 | 80 |
| 72 | 576 | 96 |
| 73 | 168 | 52 |
| 74 | 49 | 84 |
| 75 | 213 | 87 |
| 76 | >25000 | 34 |
| 77 | 71 | 82 |
| 78 | 517 | 97 |
| 79 | 2035 | 78 |
| 80 | 79 | 96 |
| 81 | >25000 | 40 |
| 82 | >25000 | 36 |
| 83 | >25000 | 36 |
| 84 | >25000 | 29 |
| 85 | 42 | 92 |
| 86 | 353 | 97 |
| 87 | 342 | 82 |
| 88 | 80 | 87 |
| 89 | 2315 | 83 |
| 90 | 774 | 85 |
| 91 | 169 | 94 |
| 92 | 143 | 92 |
| 93 | 74 | 73 |
| 94 | 413 | 72 |
| 95 | 54 | 87 |
| 96 | 233 | 83 |
| 97 | 201 | 103 |
| 98 | 124 | 77 |
| 99 | 499 | 87 |
| 100 | 319 | 86 |
| 101 | 202 | 83 |
| 102 | 99 | 80 |
| 103 | 174 | 103 |
| 104 | 2231 | 95 |
| 105 | 108 | 101 |
| 106 | 4633 | 92 |
| 107 | >25000 | 44 |
| 108 | >25000 | 35 |
| 109 | 655 | 86 |
| 110 | 267 | 51 |
| 111 | 373 | 58 |
| 112 | 263 | 62 |
| 113 | 133 | 86 |
| 114 | 367 | 69 |
| 115 | 802 | 57 |
| 116 | 155 | 75 |
| 117 | 102 | 66 |
| 118 | 347 | 53 |
| 119 | 270 | 55 |
| 120 | >25000 | 31 |
| 121 | 292 | 70 |
| 122 | 266 | 88 |
| 123 | 109 | 79 |
| 124 | 166 | 62 |
| 125 | 292 | 86 |
| 126 | 1906 | 92 |
| 127 | 209 | 85 |
| 128 | 107 | 91 |
| 129 | 157 | 89 |
| 130 | 284 | 71 |

| Example Number | Human P2X4 HEK Cells (FLIPR Assay) avg IC$_{50}$ [nM] | Human P2X4 HEK Cells (FLIPR Assay) avg Efficacy [%] |
|---|---|---|
| 131 | 155 | 58 |
| 132 | 80 | 62 |
| 133 | 107 | 82 |
| 134 | 147 | 89 |
| 135 | 73 | 90 |
| 136 | 211 | 84 |
| 137 | 1168 | 89 |
| 138 | 238 | 100 |
| 139 | 107 | 100 |
| 140 | 77 | 92 |
| 141 | 638 | 96 |
| 142 | 116 | 78 |
| 143 | 247 | 84 |
| 144 | 292 | 62 |
| 145 | >25000 | 49 |
| 146 | 364 | 66 |
| 147 | 80 | 100 |
| 148 | 132 | 63 |
| 149 | 211 | 56 |
| 150 | 433 | 80 |
| 151 | 81 | 83 |
| 152 | 105 | 79 |
| 153 | 182 | 74 |
| 154 | 30 | 84 |
| 155 | 108 | 86 |
| 156 | 243 | 94 |
| 157 | 153 | 90 |
| 158 | 2598 | 89 |
| 159 | 12 | 82 |
| 160 | 58 | 89 |
| 161 | >25000 | 43 |
| 162 | 19 | 92 |
| 163 | 93 | 89 |
| 164 | 27 | 83 |
| 165 | 42 | 93 |
| 166 | 1519 | 78 |
| 167 | 64 | 94 |
| 168 | 70 | 75 |
| 169 | 85 | 86 |
| 170 | 126 | 70 |
| 171 | 2238 | 90 |
| 172 | 48 | 58 |
| 173 | 28 | 80 |
| 174 | 45 | 79 |
| 175 | 226 | 88 |
| 176 | 268 | 71 |
| 177 | 35 | 83 |
| 178 | 40 | 70 |
| 179 | 35 | 89 |
| 180 | 319 | 77 |
| 181 | 179 | 59 |
| 182 | 161 | 89 |
| 183 | 39 | 96 |
| 184 | 67 | 96 |
| 185 | 248 | 71 |
| 186 | 40 | 78 |
| 187 | 33 | 84 |
| 188 | 31 | 89 |
| 189 | 199 | 60 |
| 190 | 540 | 58 |
| 191 | 180 | 76 |
| 192 | 575 | 69 |
| 193 | 427 | 84 |
| 194 | 325 | 84 |
| 195 | 86 | 68 |
| 196 | 164 | 75 |
| 197 | 86 | 87 |
| 198 | 136 | 94 |
| 199 | 299 | 85 |
| 200 | 131 | 90 |
| 201 | 4326 | 83 |
| 202 | 48 | 90 |
| 203 | 99 | 86 |
| 204 | 72 | 86 |
| 205 | 73 | 89 |
| 206 | 29 | 98 |
| 207 | 12 | 98 |
| 208 | 33 | 91 |
| 209 | 37 | 91 |
| 210 | 116 | 76 |
| 211 | 75 | 94 |
| 212 | 149 | 86 |
| 213 | 47 | 93 |
| 214 | 36 | 86 |
| 215 | 38 | 95 |
| 216 | 96 | 101 |
| 217 | 51 | 84 |
| 218 | 957 | 92 |
| 219 | 250 | 65 |
| 220 | 276 | 108 |
| 221 | 40 | 63 |
| 222 | 92 | 83 |
| 223 | 26 | 87 |
| 224 | 28 | 94 |
| 225 | 70 | 91 |
| 226 | 111 | 104 |
| 227 | 404 | 95 |
| 228 | 37 | 92 |
| 229 | 16 | 94 |
| 230 | 351 | 90 |
| 231 | 51 | 81 |
| 232 | 81 | 89 |
| 233 | 93 | 80 |
| 234 | 93 | 96 |
| 235 | >25000 | 35 |
| 236 | 36 | 54 |
| 237 | 1885 | 72 |
| 238 | 682 | 76 |
| 239 | 2592 | 81 |
| 240 | 3438 | 93 |
| 241 | 48 | 92 |
| 242 | 37 | 86 |
| 243 | 496 | 87 |
| 244 | 141 | 73 |
| 245 | 474 | 88 |
| 246 | 252 | 100 |
| 247 | 69 | 64 |
| 248 | 84 | 74 |
| 249 | 8463 | 72 |
| 250 | 193 | 82 |
| 251 | 21 | 96 |
| 252 | 808 | 88 |
| 253 | 257 | 85 |
| 254 | 41 | 102 |
| 255 | 25 | 81 |
| 256 | 130 | 83 |
| 257 | 51 | 81 |
| 258 | 30 | 97 |
| 259 | 50 | 91 |
| 260 | 398 | 100 |
| 261 | 111 | 81 |
| 262 | 235 | 92 |
| 263 | 337 | 96 |
| 264 | 4067 | 76 |
| 265 | 352 | 84 |
| 266 | 7 | 94 |
| 267 | 2 | 98 |
| 268 | 5 | 103 |
| 269 | 1043 | 81 |
| 270 | >25000 | 51 |
| 271 | 1146 | 82 |
| 272 | 507 | 90 |
| 273 | 35 | 60 |
| 274 | 19 | 97 |
| 275 | 507 | 82 |
| 276 | 195 | 96 |
| 277 | 186 | 90 |
| 278 | 93 | 102 |
| 279 | 61 | 96 |
| 280 | 60 | 101 |

| Example Number | Human P2X4 HEK Cells (FLIPR Assay) avg IC$_{50}$ [nM] | Human P2X4 HEK Cells (FLIPR Assay) avg Efficacy [%] |
|---|---|---|
| 281 | 481 | 76 |
| 282 | 56 | 80 |
| 283 | 60 | 94 |
| 284 | 54 | 94 |
| 285 | 246 | 97 |
| 286 | 6 | 87 |
| 287 | 31 | 78 |
| 288 | 275 | 68 |
| 289 | 6 | 89 |
| 290 | 36 | 81 |
| 291 | 100 | 95 |
| 292 | 58 | 87 |
| 293 | 76 | 75 |
| 294 | 174 | 75 |
| 295 | >25000 | 9 |
| 296 | 136 | 87 |
| 297 | 32 | 87 |
| 298 | 108 | 104 |
| 299 | 203 | 88 |
| 300 | 27 | 100 |
| 301 | 10 | 74 |
| 302 | 56 | 97 |
| 303 | 97 | 91 |
| 304 | 73 | 65 |
| 305 | 21 | 49 |
| 306 | 278 | 80 |
| 307 | 115 | 62 |
| 308 | 64 | 91 |
| 309 | 317 | 93 |
| 310 | 86 | 59 |
| 311 | 285 | 104 |
| 312 | 37 | 69 |
| 313 | 713 | 82 |
| 314 | 27 | 83 |
| 315 | 34 | 81 |
| 316 | 362 | 86 |
| 317 | 1206 | 68 |
| 318 | >25000 | 43 |
| 319 | 7277 | 73 |
| 320 | >25000 | 51 |
| 321 | 87 | 84 |
| 322 | 186 | 81 |
| 323 | 2584 | 81 |
| 324 | 3050 | 59 |
| 325 | 9 | 94 |
| 326 | 17 | 95 |
| 327 | 11 | 94 |
| 328 | 12 | 94 |
| 329 | 13 | 100 |
| 330 | 14 | 101 |
| 331 | 25 | 66 |
| 332 | 326 | 89 |
| 333 | 15 | 101 |
| 334 | 18 | 98 |
| 335 | 20 | 98 |
| 336 | 28 | 109 |
| 337 | 30 | 96 |
| 338 | 32 | 91 |
| 339 | 33 | 92 |
| 340 | 34 | 89 |
| 341 | 41 | 86 |
| 342 | 41 | 101 |
| 343 | 42 | 101 |
| 344 | 44 | 102 |
| 345 | 46 | 93 |
| 346 | 46 | 105 |
| 347 | 85 | 89 |
| 348 | 47 | 96 |
| 349 | 37 | 99 |
| 350 | 49 | 87 |
| 351 | 51 | 88 |
| 352 | 54 | 91 |
| 353 | 57 | 87 |
| 354 | 60 | 92 |
| 355 | 62 | 76 |
| 356 | 63 | 96 |
| 357 | 71 | 87 |
| 358 | 74 | 88 |
| 359 | 77 | 84 |
| 360 | 132 | 93 |
| 361 | 97 | 83 |
| 362 | 102 | 78 |
| 363 | 108 | 110 |
| 364 | 715 | 77 |
| 365 | 113 | 89 |
| 366 | 128 | 97 |
| 367 | 131 | 83 |
| 368 | 133 | 100 |
| 369 | 141 | 110 |
| 370 | 143 | 76 |
| 371 | 152 | 99 |
| 372 | 166 | 83 |
| 373 | 167 | 89 |
| 374 | 386 | 82 |
| 375 | 660 | 79 |
| 376 | 9 | 98 |
| 377 | 27 | 80 |
| 378 | 89 | 84 |
| 379 | 29 | 87 |
| 380 | 299 | 69 |
| 381 | 1241 | 77 |
| 382 | 315 | 87 |
| 383 | 45 | 93 |
| 384 | 524 | 81 |
| 385 | 47 | 72 |
| 386 | 76 | 64 |
| 387 | 34 | 73 |
| 388 | 196 | 68 |
| 389 | 22 | 77 |
| 390 | 1698 | 91 |
| 391 | 186 | 98 |
| 392 | 9659 | 64 |
| 393 | 134:16400; >25000; >25000 | 49 |
| 394 | 740 | 86 |
| 395 | 73 | 86 |
| 396 | 9580; >25000; >25000; >25000; >25000 | 44 |
| 397 | >25000 | 43 |
| 398 | 207 | 57 |
| 399 | 84 | 92 |
| 400 | 87 | 88 |
| 401 | 23 | 82 |
| 402 | 41 | 85 |
| 403 | 16 | 88 |
| 404 | 175 | 73 |
| 405 | 5665 | 65 |
| 406 | 6839 | 64 |
| 407 | 429 | 86 |
| 408 | 2645 | 74 |
| 409 | 445 | 85 |
| 410 | 5450 | 69 |
| 411 | 84 | 90 |
| 412 | 1595 | 68 |
| 413 | 74 | 89 |
| 414 | >25000 | 20 |
| 415 | 200 | 69 |
| 416 | 8300; 17800; >25000; >25000 | 51 |
| 417 | 51 | 68 |
| 418 | 15 | 91 |
| 419 | 274 | 89 |
| 420 | 69 | 75 |
| 421 | 680 | 86 |
| 422 | 46 | 90 |
| 423 | 53 | 86 |
| 424 | 29 | 88 |
| 425 | 50 | 74 |
| 426 | 24 | 86 |
| 427 | 72 | 65 |

| Example Number | Human P2X4 HEK Cells (FLIPR Assay) avg IC$_{50}$ [nM] | Human P2X4 HEK Cells (FLIPR Assay) avg Efficacy [%] |
|---|---|---|
| 428 | 27 | 57 |
| 429 | 108 | 91 |
| 430 | 86 | 87 |
| 431 | 2880 | 83 |
| 432 | 597 | 92 |
| 433 | >25000 | 28 |
| 434 | 17800; >25000 | 50 |
| 435 | 588 | 77 |
| 436 | 12527 | 56 |
| 437 | 39 | 53 |
| 438 | 18 | 75 |
| 439 | 4 | 94 |
| 440 | 112 | 96 |
| 441 | 185 | 91 |
| 442 | 181 | 89 |
| 443 | 122 | 84 |
| 444 | 635 | 77 |
| 445 | 60 | 71 |
| 446 | 621 | 76 |
| 447 | 1022 | 68 |
| 448 | 472 | 63 |
| 449 | 135 | 73 |
| 450 | 148 | 72 |
| 451 | 244 | 86 |
| 452 | 76 | 65 |
| 453 | 74 | 77 |
| 454 | 1442 | 58 |
| 455 | 5 | 74 |
| 456 | 18 | 59 |
| 457 | 558 | 70 |
| 458 | 1075 | 85 |
| 459 | 1340 | 88 |
| 460 | 646 | 84 |
| 461 | 137 | 93 |
| 462 | 929 | 89 |
| 463 | 18 | 99 |
| 464 | 648 | 92 |
| 465 | 26 | 92 |
| 466 | 363 | 91 |
| 467 | 9 | 93 |
| 468 | 278 | 97 |
| 469 | 453 | 90 |
| 470 | 483 | 93 |
| 471 | 269 | 92 |
| 472 | 197 | 97 |
| 473 | 530 | 93 |
| 474 | 323 | 93 |
| 475 | 64 | 88 |
| 476 | 58 | 89 |
| 477 | 259 | 91 |
| 478 | 47 | 82 |
| 479 | 145 | 79 |
| 480 | 125 | 105 |
| 481 | 50 | 103 |
| 482 | 2341 | 73 |
| 483 | 71 | 86 |
| 484 | 401 | 63 |
| 485 | 128 | 100 |
| 486 | 7343 | 71 |
| 487 | >25000 | 45 |
| 488 | 2330 | 78 |
| 489 | 2055 | 83 |
| 490 | 91 | 95 |
| 491 | 9092 | 67 |
| 492 | 531 | 92 |
| 493 | 228 | 90 |
| 494 | 205 | 94 |
| 495 | 128 | 75 |
| 496 | 22 | 87 |
| 497 | 54 | 97 |
| 498 | 18200; >25000 | 50 |
| 499 | 347 | 69 |
| 500 | >25000 | 40 |
| 501 | 3 | 92 |
| 502 | 13785 | 49 |
| 503 | 47 | 102 |
| 504 | 33 | 98 |
| 505 | 131 | 93 |
| 506 | 391 | 91 |
| 507 | 180 | 86 |
| 508 | 172 | 63 |
| 509 | 326 | 71 |
| 510 | 439 | 73 |
| 511 | 343 | 60 |
| 512 | 4253 | 76 |
| 513 | 893 | 94 |
| 514 | 106 | 102 |
| 515 | 45 | 101 |
| 516 | 96 | 68 |
| 517 | 187 | 74 |
| 518 | 36 | 80 |
| 519 | 105 | 82 |
| 520 | 43 | 76 |
| 521 | 6900; 17200; >25000; >25000; >25000 | 52 |
| 522 | 71 | 87 |
| 523 | 149 | 89 |
| 524 | 322 | 87 |
| 525 | 5170 | 72 |
| 526 | 331 | 51 |
| 527 | 125 | 86 |
| 528 | 42 | 95 |
| 529 | 72 | 92 |
| 530 | 33 | 112 |
| 531 | 2317 | 84 |
| 532 | 11500; 12900; 17000 | 60 |
| 533 | >25000 | 26 |
| 534 | >25000 | 17 |
| 535 | 3839 | 91 |
| 536 | 12400; 16800 | 67 |
| 537 | 3618 | 95 |
| 538 | 3908 | 83 |
| 539 | 127 | 103 |
| 540 | 1 | 79 |
| 541 | >25000 | 50 |
| 542 | 20 | 97 |
| 543 | 267 | 98 |
| 544 | 1 | 85 |
| 545 | 19 | 100 |
| 546 | 97 | 75 |
| 547 | 60 | 94 |
| 548 | 5 | 94 |
| 549 | 8 | 85 |
| 550 | 1 | 87 |
| 552 | 1 | 88 |
| 553 | 5 | 82 |
| 554 | 383 | 83 |
| 555 | 22 | 94 |
| 556 | 65 | 94 |
| 557 | 11 | 89 |
| 558 | 1377 | 75 |

FLIPR Methods for h/m/rP2X4 1321N1 Astrocytoma Cells

1321N1 Astrocytoma cells stably expressing human P2X4 or rat P2X4 or mouse P2X4 were plated in Collagen I TC-treated microplate at a seeding density of 10000 cells/well and incubated overnight. P2X4 function was assessed by measuring intracellular calcium changes using the calcium-chelating dye Fluo8-AM (Molecular Devices) on a fluorescent imaging plate reader (FLEX/FLIPR station; Molecular Devices). On the day of the assay, the medium was removed and the cells were incubated for 30 min at 370C and 5% $CO_2$ in 30 μL of dye buffer (Hank's balanced salt solution, 10 mM HEPES, 1.8 mM CaCl2, 1 mM $MgCl_2$, 2 mM probenecid, 5 mM D-glucose monohydrate, 5 μM Fluo8-AM, pH=7.4). Compounds diluted in probenecid buffer (Hank's balanced salt solution, 10 mM HEPES, 1.8 mM CaCl$_2$, 1 mM MgCl$_2$, 2 mM probenecid, 5 mM D-glucose monohydrate, pH=7.4) were added in a volume of 10 µL and allowed to incubate for 30 min at room temperature. The final assay DMSO concentration was 0.25%. The agonist, Mg-ATP (Sigma), was added in a volume of 10 µL at a concentration representing the EC$_{80}$ value. EC$_{80}$ was determined to be 0.5 µM for human and mouse P2X4 and 5 µM for rat P2X4. The fluorescence was measured for an interval of 120 sec at 2 sec intervals. The excitation and emission wavelengths used to monitor fluorescence were 470-495 nm and 515-575 nm, respectively. The data was analyzed based on the increase in peak relative fluorescence units (RFU) compared to the basal fluorescence and the data was normalized to the agonist control. The compounds were tested in triplicates per plate and mean values were plotted in Excel XLFit to determine IC50 values, percentage of maximal inhibition and the Hill coefficients.

| Example Number | Human P2X41321N1 Astrocytoma Cells (FLIPR Assay) avg IC$_{50}$ [nM] | Human P2X4 1321N1 Astrocytoma Cells (FLIPR Assay) avg Efficacy [%] |
|---|---|---|
| 19 | 57 nM | 60% |
| 39 | 64 nM | 83% |
| 326 | 46 nM | 80% |

| Example Number | Mouse P2X4 1321N1 Astrocytoma Cells (FLIPR Assay) avg IC$_{50}$ [nM] | Mouse P2X4 1321N1 Astrocytoma Cells (FLIPR Assay) avg Efficacy [%] |
|---|---|---|
| 19 | 43 nM | 69% |
| 39 | 37 nM | 87% |
| 326 | 26 nM | 87% |

| Example Number | Rat P2X41321N1 Astrocytoma Cells (FLIPR Assay) avg IC$_{50}$ [nM] | Rat P2X4 1321N1 Astrocytoma Cells (FLIPR Assay) avg Efficacy [%] |
|---|---|---|
| 19 | 71 nM | 57% |
| 39 | 308 nM | 87% |
| 326 | 325 nM | 99% |

Human P2X4 HEK Cell Elektophysiology Assay
Electrophysiology Assay A

HEK293 cells stably expressing human P2X4 were seeded in T75 cell culturing flasks at a density of 7*106 cells and incubated overnight. P2X4 function was assayed using the automated patch clamp platform PatchLiner (Nanion) in single hole mode. Composition of extracellular buffer was (in mM) NaCl 145, KCl 4, HEPES 10, CaCl$_2$ 1, MgCl$_2$ 0.5, D-glucose monohydrate 10, pH=7.4. The intracellular buffer contained (in mM): CsF 135, EGTA 1, HEPES 10, NaCl 10, pH 7.2. On the day of the assay, cells were harvested using Accumax (Sigma) and were resuspended in extracellular buffer. The ligand agonist, adenosine 5'-trisphosphate (ATP, 5 µM) was added in a volume of 5 µL, directly washed off by extracellular buffer (40 µL). The cells were voltage clamped at −80 mV and ligand was applied every 5 min. for 20 min. Over this period the agonist response was stable and compounds were measured in single concentration per well mode. Compounds diluted in extracellular buffer (final assay DMSO concentration 0.3%) were added in a volume of 40 µL and allowed to incubate for 8 min at room temperature. The data was analyzed based on the decrease in peak current amplitude and normalized to the agonist control. Mean values were plotted in Excel XLFit to determine IC$_{50}$ values, percentage of maximal inhibition and the Hill coefficients.

| Example Number | Human P2X4 HEK Cells (PatchLiner Electrophysiology) avg IC$_{50}$ [nM] |
|---|---|
| 19 | 111 |
| 39 | 138 |
| 326 | 57 |
| 380 | 320 |

Electrophysiology Assay B

Cell culture conditions: HEK-293 mito-Photina pcDNA3 (neo-)/pPURO N/pcDNA3_P2RX4, clone 2a/4 (HEK-293 mito-Photina/hP2RX4) cells were cultured in EMEM Minimum Essential Medium Eagle with Earl's salts Balanced Salt Solution (BioWhittaker cat. BE12-125F) supplemented with 5 mL of 200 mM Ultraglutaminel (BioWhittaker cat. BE17-605E/U1), 5 mL of 100× Penicillin/Streptomycin (BioWhittaker cat. DE17-602E; final concentration 1%), 4 mL of 50 mg/mL G418 (Sigma cat. G8168-100 mL; final concentration 400 µg/mL), 10 µL of 10 mg/mL Puromicin (InvivoGen cat. ant-pr-1; final concentration 0.2 µg/mL) and 50 mL of Fetal Bovine Serum (Sigma cat. F7524; final concentration 10%).

Experimental protocol: HEK-293 cell lines are seeded 72 or 96 hours before experiment, at a concentration of 5 or 2.5 million cells, respectively onto a T225 flask. Just before the experiments cells are washed twice with D-PBS w/o Ca2+/Mg2+(Euroclone cat. ECB4004L) and detached from the flask with trypsin-EDTA (Sigma, cat. T4174 diluted 1/10). Cells are then re-suspended in the suspension solution: 25 mL EX-CELL ACF CHO medium (Sigma, cat. C5467); 0.625 mL HEPES (BioWhittaker, cat. BE17-737E); 0.25 mL of 100× Penicillin/Streptomycin (BioWhittaker, cat. DE17-602E), 0.1 mL of Soybean Trypsin Inhibitor 10 mg/mL (Sigma, cat. T6522) and placed on the QPatch 16X.

Compound preparation and storage: Compound stock solutions (10 mM; 100% DMSO; stored at −20° C.) were used. Fresh solutions from stock (1 or 3 mM, 100% DMSO) were prepared just before the experiments (0.1% final DMSO concentration).

DMSO solution was obtained from SIGMA (cat. # D-5879) and stored at room temperature.

Patch clamp analysis with QPatch16X (FIG. 1): Standard whole-cell voltage clamp experiments are performed at room temperature using the multihole technology.

For the voltage clamp experiments on hP2X4, data are sampled at 2 KHz. After establishment of the seal and the passage in the whole cell configuration, the cells are held at −90 mV and the hP2X4 current is evoked by the agonist in the absence (vehicle period, i.e. 0.1% DMSO) or in the presence of the compound under investigation at increasing concentrations; see the application protocol in FIG. 1.

Output: the maximum inward current induced by the agonist (ATP 5 microM).

The intracellular solution contained (mM) 135 CsF, 10 NaCl, 1 EGTA, 10 HEPES (pH 7.2 with CsOH) whereas the extracellular solution (mM) 145 NaCl, 4 KCl, 0.5 MgCl2, 1 CaCl$_2$), HEPES, 10 Glucose (pH 7.4 with NaOH).

For data collection, the Sophion software was used and the analysis was performed off-line using Excel and GraphPad Prism.

When possible, i.e. when the % of inhibition with the highest concentration tested was more than 50%, the dose-response curves data were fitted with the following equation:

$$Y=100/(1+10\hat{}((LogIC50-X)*HillSlope))$$

[X is log of concentration; Y is normalized response (100% down to 0%, decreasing as X increases); $LogIC_{50}$ same log units as X; HillSlope is unitless slope factor or hill slope]

| Example Number | Human P2X4 HEK Cells (QPatch Electrophysiology) avg $IC_{50}$ [nM] | Number of Exp. |
|---|---|---|
| 19 | 278 | 4 |
| 20 | 195 | 4 |
| 25 | 222 | 5 |
| 26 | 222 | 5 |
| 321 | 227 | 4 |
| 326 | 51 | 6 |
| 331 | 155 | 5 |
| 349 | 117 | 3 |
| 360 | 205 | 3 |
| 380 | 157 | 4 |
| 381 | 2583 | 3 |

Ex Vivo Studies
Human Monocyte P2X4 Assay

The principle of the assay is to measure calcium influx through endogenous P2X4 channels into primary human monocytes, following activation by 2',3'-O-(4-benzoyl-benzoyl)-ATP (Bz-ATP). Intracellular calcium concentration changes were measured with a Flipr® (Molecular Devices) device using a calcium sensitive dye (Fluo-8). In primary monocytes P2X4 is located at the lysosome membrane, therefore exocytosis has to be triggered to expose P2X4 at the cellular membrane.

Human peripheral blood mononuclear cells (PBMCs) from anticoagulated blood (blood cells, BC) were isolated via density gradient centrifugation. Whole blood was diluted 1:3 with PBS. Samples of 30 mL were layered carefully on top of 15 mL Biocoll (BIOCHROM) in 50 mL centrifuge tubes (Falcon). Tubes were centrifuged at 914×g for 25 min at RT without brake. The PBMC layer was removed with a 10 mL pipette and transferred into tubes with ice-cold PBS in a total volume of 50 mL. Cells were washed twice by pelleting at 300×g at 4° C., for 10 min and for 5 min respectively. PBMCs were re-suspended in 10 mL medium (X-vivo, Biozym Scientific) and counted in a Neubauer chamber.

Monocytes were isolated by negative selection using the Monocyte isolation kit II from Miltenyi (#130-091-153) according to the instructions. Isolation should be done fast and cells and solutions should be kept on ice at any time. PBMCs in batches of 10 exp8 cells were pelleted (300×g, 10 min) and re-suspended with 300 μL MACS buffer in a 50 mL Falcon tube. FcR Blocking reagent (100 μl) and Biotin-Ab (100 μl) were added, mixed and incubated on ice for 10 min. MACS buffer (300 μL) and anti-Biotin Micro-beads (100 μL) were added, mixed and incubated on ice for 15 min. Cells were washed by pelleting (300×g for 10 min) and re-suspended in 500 μL MACS buffer. For each batch one separation column was placed in the MACS separator and rinsed with 3 mL MACS buffer. The cell suspension was added to the column, followed by 3×3 mL MACS buffer for washing, and the eluent containing the monocytes was collected. Cells were pelleted (300×g for 10 min), re-suspended in X-vivo medium and counted. Monocytes were seeded into fibronectin-coated micro-plates (384-well, black, flat transparent bottom; Corning #3848) at a density of 30,000 cells/well in 50 μL, and cultivated over night (37° C., 5% $CO_2$).

Test substances were dissolved in 100% DMSO at a stock concentration of 10 mM and stored at −20° C. in aliquots. Serial dilutions (2×) were prepared in DMSO and diluted 500× with assay buffer to generate the antagonist plate. In the Flipr measurement, 10 μL per well were transferred (4× dilution) and a final top concentrations of 5 μM and 0.05% DMSO were obtained in the assay. Agonist BzATP was stored at 10 mM in aliquots and diluted to an intermediate concentration of 15 μM to generate the agonist plate. In the Flipr measurement, 10 μL per well were transferred (5× dilution) so that a final assay concentration of 3 μM was obtained.

For the experiment, the medium of the cell plate was discarded manually and 70 μL/well loading buffer was added and incubated for 1 h (37° C., 5% $CO_2$). Loading buffer contained HBSS (w/o calcium/magnesium), 10 mM Hepes pH 7.4, 5 μM Fluo-8 (AM) (Tebu-bio) and 50 mM methylamine (Sigma) to trigger exocytosis. Loading buffer was discarded manually and 30 μL/well low-calcium assay buffer (5 mM KCl, 145 mM NaCl, 0.5 mM $CaCl_2$, 13 mM glucose, 10 mM Hepes pH 7.4) was added. The antagonist plate was transferred (10 μL/well) and after 15 min at RT the agonist plate (10 μL/well) was transferred.

Agonist addition was recorded for 240 seconds after a 10 second baseline. For analysis, a baseline correction was applied, and the maximum of the curve was extracted. Data were normalized towards 0% inhibition (signal at 3 μM BzATP) and 100% inhibition (absence of BzATP stimulation) and fitted with a four-parameter sigmoidal inhibition curve using Prism GraphPad to obtain $IC_{50}$ values.

| Example Number | Human P2X4 Monocytes (FLIPR Assay) $IC_{50}$ (Efficacy) for different donors |
|---|---|
| 19 | 59 nM (57%), 21 nM (74%), 76 nM (48%), 59 nM (46%), 45 nM (93%) |
| 24 | 141 nM (79%), 34 nM (77%), 91 nM (88%) |
| 25 | 27 nM (87%), 5 nM (82%), 127 nM (70%), 87 nM (70%), 118 nM (70%), 59 nM (53%), 63 nM (68%), 39 nM (111 %) |
| 26 | 290 nM (71%), 182 nM (88%) |
| 28 | 78 nM (64%), 164 nM (90%) |
| 39 | 105 nM (88%), 32 nM (81%), 71 nM (78%) |
| 170 | 303 nM (60%), 183 nM (69%), 110 nM (54%) |
| 321 | 158 nM (49%), 94 nM (49%), 157 nM (60%), 537 nM (60%), 173 nM (34%), 331 nM (46%), 39 nM (95%) |
| 326 | 407 nM (86%), 167 nM (89%), 149 nM (82%), 45 nM (91%), 49 nM (70%) |
| 380 | 263 nM (70%), 251 nM (70%), 434 nM (70%), 93 nM (43%), 50 nM (32%), 207 nM (107%) |
| 387 | 122 nM (35%), 104 nM (51%) |

Human Whole Blood P2X4 Assay

In this assay, ex vivo, the blood of healthy female volunteers is first sensitized with lipopolysacharide (LPS) and then stimulated with ATP to trigger the release of Interleukin 1beta (IL-1β). In this system, the efficacy of P2X4 antagonists on the production of IL-1R in whole blood was tested. The cells were first treated with 100 ng/ml LPS for 2 h and then stimulated with 3 mM ATP and treated in triplicates with examples 19, 28, 39, 321, 326 and 380 at different concentrations. After 1 h incubation, supernatant was taken and following centrifugation IL-1β in the supernatant was assayed using standard ELISA kits. The assay was performed with blood from three different donors (see Figures (1), 2a(2), 2a(3), 2b(1), 2b(2) and 2b(3)).

Figures (1)-2a(3) and 2b(1)-(3) as nonbinding explanatory example of compounds according to the invention represents the effect of the compounds according to examples 19, 28, 39, 321, 326 and 380 on the generation of IL-1β in human whole blood after ATP stimulation following priming of the cells with lipopolysaccharide for two hours and indicated treatment. Data show the absolute amount of IL-1β in pg/ml in the supernatant of blood from three donors on the y-axis and control treatments and treatments with different concentrations of examples are indicated on the x-axis. For each bar the average of three technical replicates and SD are shown. The data show inhibition of IL-1β release by several but not all of the tested examples.

In Vivo Studies

CFA Inflammation Model in Mice with Pain Behaviour Read Out

Wild type female C57BL/6 mice (Taconic) received intraplantar injection of complete Freund's adjuvant (CFA) (30 μL, 1 mg/mL, Sigma) into the left hind paw under isoflurane anesthesia. Animals were administered orally with example 326 (0.3, 1, and 3 mg/kg, n=10/group) on day 2 post-CFA injection. Spontaneous pain-related behavior in freely moving animals was assessed using the automated dynamic weight bearing device (DWB, Bioseb, France) one hour after compound treatment according to published and validated protocols (Robinson et al., 2012; Tetreault et al., 2011; Gruen et al. 2014). For behavioral testing, the animal was placed inside a Plexiglas chamber in which the exerted pressure on the floor was measured. The animals were allowed to move freely within the apparatus for 5 min and subsequently pain behavior is recorded for a test period of another 5 min. The relative weight distribution is calculated by determining the ratio of the weight put on naïve (contralateral) vs. that put on the intraplantar CFA treated (ipsilateral) paws.

Figure 3:
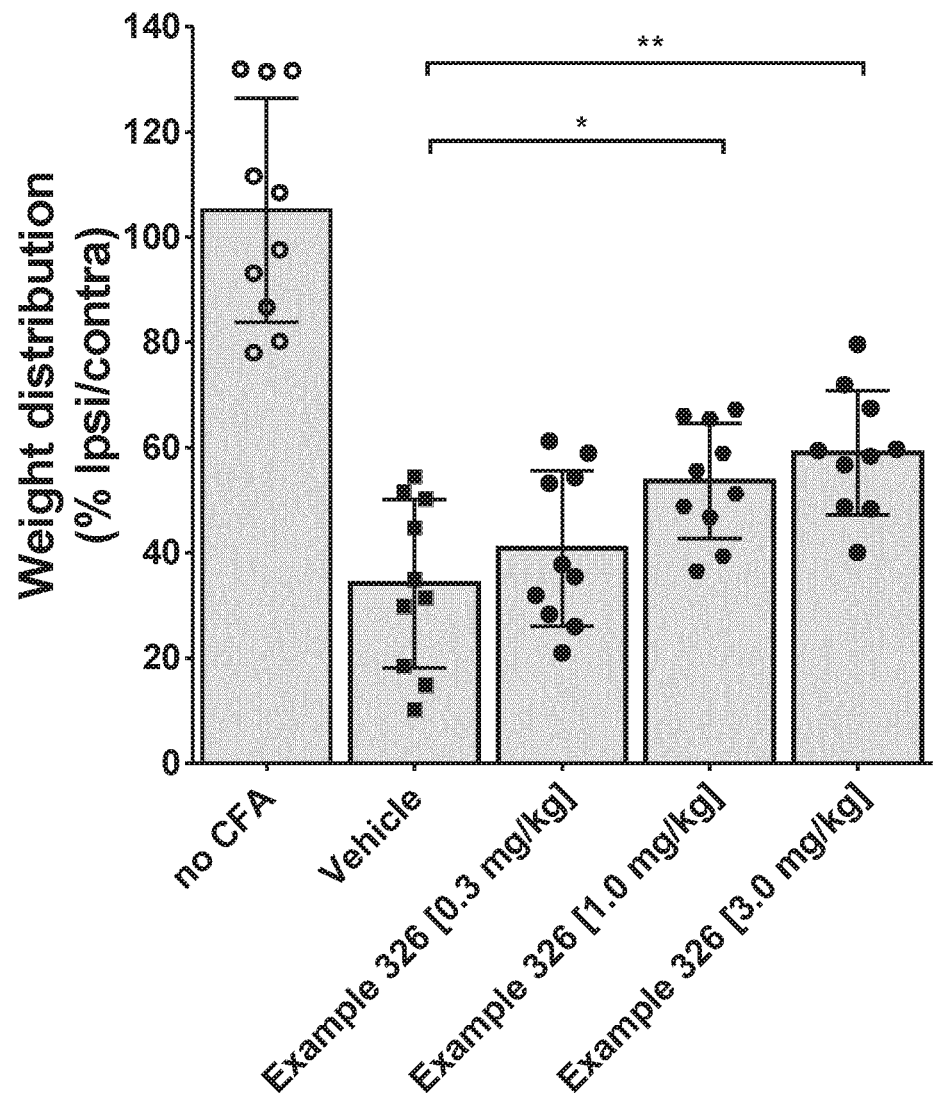
FIG. 3 depicts the ratio of weight distribution (contralateral vs ipsilateral) of mice orally treated with the compound of example 326 or vehicle 1 following injection of complete Freund's adjuvant (CFA) in a mouse CFA inflammation model.

FIG. 3 as nonbinding explanatory example of compounds according to the invention represents the ratio of weight distribution in percent (y-axis) of mice orally treated with example 326 or vehicle 1 hour prior to weight distribution measurement. Each symbol represents the relative weight distribution for one mouse. Statistical analysis was performed with one-way analysis of variance, followed by Dunnet's multiple comparison test against the vehicle control group using the GraphPad PRISM software, *p<0.05, **p<0.01. Example 326 significantly reduced pain behavior.

CFA-Induced Mechanical Hyperalgesia Model in Rat

Male Sprague Dawley rats were used. Mechanical hyperalgesia was induced by injecting pL of Complete Freund's Adjuvant (CFA) into the plantar surface of the left hind paw. Mechanical hyperalgesia was measured using the Pressure Application Measurement apparatus (Ugo Basile, Gemonio, Italy). Briefly, a linearly increasing pressure was applied to an area of approximately 50 mm² of the plantar side of the hind paw, until a behavioural response (paw withdrawal) was observed or until the pressure reached 1000 gf. The pressure at which the behavioural response occurred was recorded as the Paw Withdrawal Threshold (PWT). Both CFA-injected and contralateral PWTs were determined for each rat, in each treatment group and at each time point of the studies. Rats received 3 oral doses of test compound at approximately 12 hours interval starting 1 hour prior to CFA injection. Mechanical hyperalgesia testing was performed 2 hours before CFA injection and 2 hours after the last dosing (FIGS. 4a and 4b).

Figure 4A:
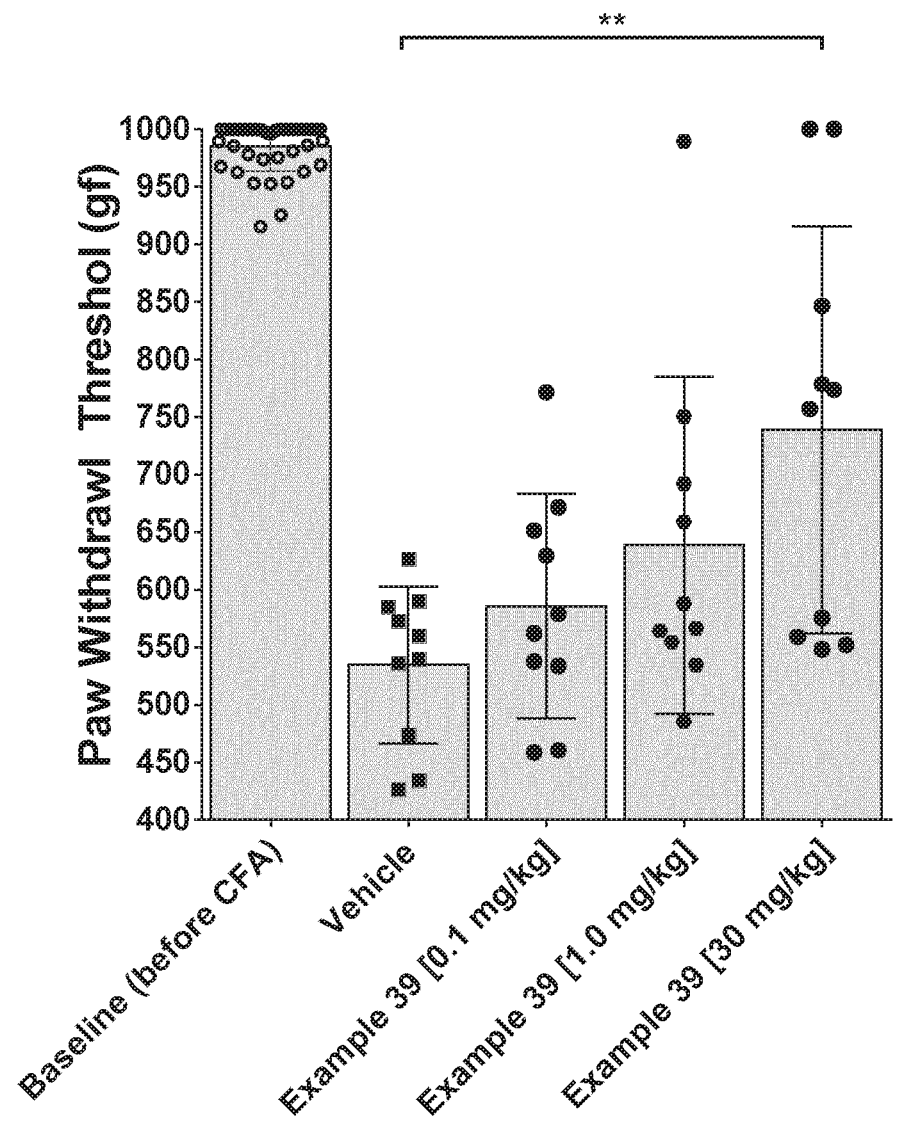
FIGS. 4a and 4b depict result of Paw Withdrawal Threshold measurements for a CFA-induced mechanical hyperalgesia model in rats, before CFA injection and after treatment with compounds according to Example 39 (FIG. 4a) and Example 326 (FIG. 4b) as compared to a vehicle control.
Figure 4B:
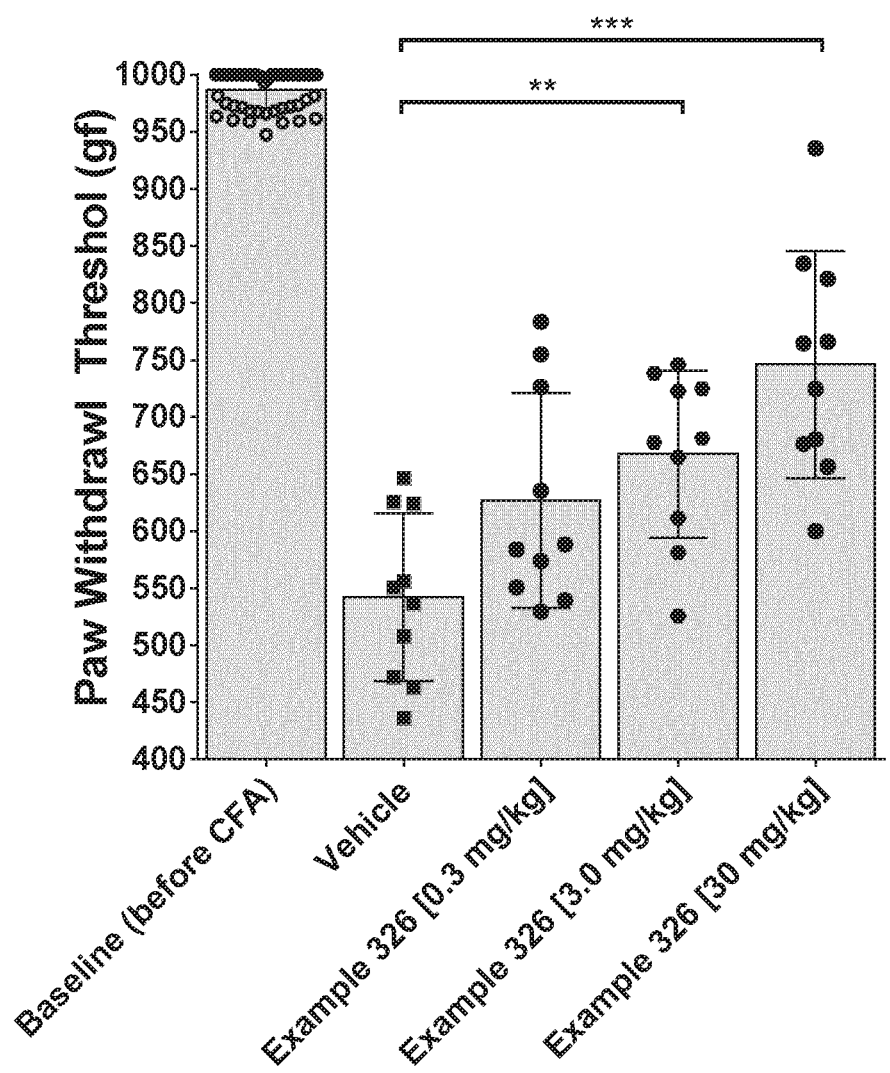

FIGS. 4a and 4b as nonbinding explanatory examples of compounds according to the invention represent Paw Withdrawal Threshold in gramm (y-axis) of the ipsilateral paw of all tested animals before CFA treatment and 26 h after CFA treatment and vehicle or Example 39 (FIG. 4a) or 326 (FIG. 4b) treatment. Statistical analysis was performed with one-way analysis of variance, followed by Dunnett's multiple comparison test against vehicle control groups using the GraphPad PRISM software, *p<0.05, p<0.01 *p<0.001. Examples 39 and 326 significantly increased PWT compared to vehicle treated animals.

The invention claimed is:

1. A method for treatment of a disease, comprising administering to a patient in need thereof a pharmaceutically effective amount of a compound of formula (I):

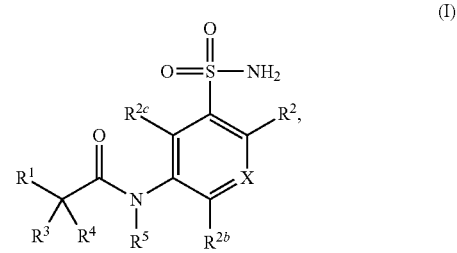

wherein:
X is C—R$^{2a}$ or N;
R$^1$ is a group:

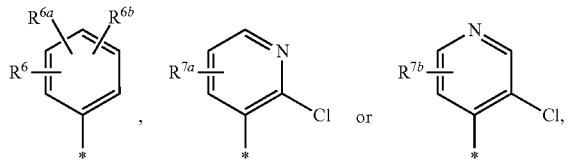

wherein * indicates the point of attachment of said group to the rest of the molecule;
R$^2$ is phenyl or heteroaryl,
wherein said phenyl or heteroaryl is optionally independently substituted one to three times with R$^{11}$, or independently substituted one time with R$^{11a}$ and optionally one to two times with R$^{11}$, or substituted with two adjacent substituents R$^{11}$ which together represent a methylendioxy group to form a 5-membered ring;
R$^{2a}$ is hydrogen, cyano, nitro, halogen, C$_1$-C$_2$-alkyl, or C$_1$-C$_2$-haloalkyl;
R$^{2b}$ is hydrogen, halogen, C$_1$-C$_2$-alkyl, or C$_1$-C$_2$-haloalkyl;
R$^{2c}$ is hydrogen, halogen, C$_1$-C$_2$-alkyl, or C$_1$-C$_2$-haloalkyl,
wherein not less than one of R$^{2a}$, R$^{2b}$ and R$^{2c}$ is hydrogen;
R$^3$ is hydrogen or fluoro;
R$^4$ is hydrogen, fluoro, methyl, or OH;
R$^5$ is hydrogen or C$_1$-C$_3$-alkyl;
R$^6$ is halogen, cyano, nitro, OH, C$_1$-C$_4$-alkyl, C$_1$-C$_4$-haloalkyl, C$_1$-C$_4$-alkoxy, C$_1$-C$_4$-haloalkoxy, or F$_3$CS—;
R$^{6a}$ and R$^{6b}$ are the same or different, wherein
R$^{6a}$ is independently hydrogen, halogen, hydroxy, nitro, cyano, C$_1$-C$_4$-alkyl, C$_3$-C$_6$-cycloalkyl, C$_1$-C$_4$-haloalkyl, C$_1$-C$_4$-alkoxy, C$_1$-C$_4$-haloalkoxy, HO—(C$_2$-C$_4$- alkoxy)-, ($C_1$-$C_4$-alkoxy)-($C_2$-$C_4$-alkoxy)-, $R^9R^{10}N$—, $R^8$—C(O)—NH—, $R^8$—C(O)—, $R^8$—O—C(O)—, $R^9R^{10}N$—C(O)—, or ($C_1$-$C_4$-alkyl)-$SO_2$—;

$R^{6b}$ is independently hydrogen, halogen, hydroxy, nitro, cyano, $C_1$-$C_4$-alkyl, $C_3$-$C_6$-cycloalkyl, $C_1$-$C_4$-haloalkyl, $C_1$-$C_4$-haloalkoxy, HO—($C_2$-$C_4$-alkoxy)-, ($C_1$-$C_4$-alkoxy)-($C_2$-$C_4$-alkoxy)-, $R^9R^{10}N$—, $R^8$—C(O)—NH—, $R^8$—C(O)—, $R^8$—O—C(O)—, $R^9R^{10}N$—C(O)— or ($C_1$-$C_4$-alkyl)-$SO_2$—; or $R^{6a}$ and $R^{6b}$ adjacent to each other together represent a group selected from —O—$CH_2$—$CH_2$—, —O—$CH_2$—O— or —O—$CH_2$—$CH_2$—O—;

$R^{7a}$ and $R^{7b}$ are the same or different and are independently hydrogen, hydroxy, halogen, $C_1$-$C_4$-alkyl, or $C_1$-$C_4$-haloalkyl;

each $R^8$ is independently $C_1$-$C_6$-alkyl, $C_1$-$C_4$-alkoxy-$C_1$-$C_4$-alkyl, $C_3$-$C_6$-cycloalkyl, or $C_1$-$C_4$-haloalkyl;

$R^9$ and $R^{10}$ are independently hydrogen, $C_1$-$C_4$-alkyl, $C_3$-$C_6$-cycloalkyl, $C_1$-$C_4$-haloalkyl, or $(CH_3)_2N$—$C_1$-$C_4$-alkyl, or $R^9$ and $R^{10}$ together with the nitrogen atom to which they are attached form a 4- to 6-membered nitrogen containing heterocyclic ring, said ring optionally containing one additional heteroatom selected from the group consisting of O, S, NH, and $NR^a$, wherein $R^a$ is a $C_1$-$C_6$-alkyl or $C_1$-$C_6$-haloalkyl group and wherein said $C_1$-$C_6$-alkyl or $C_1$-$C_6$-haloalkyl group is optionally substituted, one to three times, independently from each other, with halogen or $C_1$-$C_4$-alkyl;

each $R^{11}$ is independently halogen, hydroxy, nitro, cyano, $C_1$-$C_4$-alkyl, $C_2$-$C_4$-alkenyl, $C_1$-$C_4$-haloalkyl, $C_1$-$C_6$-hydroxyalkyl, $C_1$-$C_4$-alkoxy, $C_1$-$C_4$-haloalkoxy, ($C_1$-$C_4$-alkoxy)-($C_1$-$C_4$-alkyl)-, ($C_1$-$C_4$-haloalkoxy)-($C_1$-$C_4$-alkyl)-, $R^9R^{10}N$—($C_1$-$C_4$-alkyl)-, $R^9R^{10}N$—, $R^8$—C(O)—NH—, $R^8$—C(O)—, $R^8$—O—C(O)—, $R^9R^{10}N$—C(O)—, ($C_1$-$C_4$-alkyl)-S—, or ($C_1$-$C_4$-alkyl)-$SO_2$—;

$R^{11a}$ is a group $C_3$-$C_6$-cycloalkyl, morpholino,

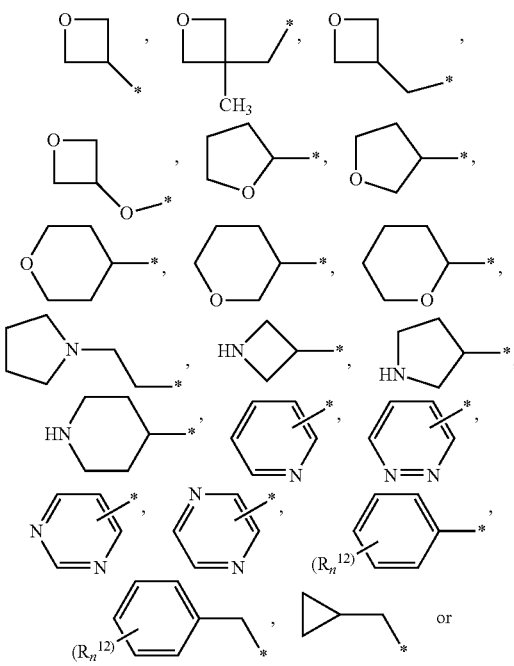

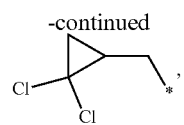

wherein * indicates the point of attachment of said group to the rest of the molecule;

each $R^{12}$ is independently halogen, hydroxy, nitro, cyano, $C_1$-$C_4$-alkyl, $C_2$-$C_4$-alkenyl, $C_1$-$C_4$-haloalkyl, $C_1$-$C_4$-hydroxyalkyl, $C_1$-$C_4$-alkoxy, $C_1$-$C_4$-haloalkoxy, ($C_1$-$C_4$-alkoxy)-($C_2$-$C_4$-alkyl)-, ($C_1$-$C_4$-haloalkoxy)-($C_2$-$C_4$-alkyl)-, $R^9R^{10}N$—, $R^8$—C(O)—NH—, $R^8$—C(O)—, $R^8$—O—C(O)—, $R^9R^{10}N$—C(O)—, or ($C_1$-$C_4$-alkyl)-$SO_2$—; and n is 0, 1, 2 or 3, or a stereoisomer, a tautomer, an N oxide, a hydrate, a solvate, or a pharmaceutically acceptable salt thereof, or a mixture of the same, wherein said disease is a genitourinary, gastrointestinal, proliferative or pain-related disease, condition or disorder; cancer; fibrotic disease, lung fibrosis; heart fibrosis; kidney fibrosis; fibrosis of other organs; gynaecological disease; dysmenorrhea; dyspareunia; endometriosis; adenomyosis; endometriosis-associated pain; endometriosis-associated symptoms; dysuria; dyschezia; pelvic hypersensitivity; urethritis; prostatitis; prostatodynia; cystitis; idiopathic bladder hypersensitivity; gastrointestinal disorder; irritable bowel syndrome (IBS); inflammatory bowel disease (IBD); biliary colic; other biliary disorders; renal colic; diarrhea-dominant IBS; gastroesophageal reflux, gastrointestinal distension; Crohn's disease; Parkinson's disease; Alzheimer's disease; myocardial infarction; atherosclerosis; lipid disorder; functional bowel disorder; arthritis; osteoarthritis; rheumatoid arthritis; pain-associated disease or syndrome; acute, chronic, inflammatory and neuropathic pain; inflammatory pain; low back pain; surgical pain; visceral pain; dental pain; premenstrual pain; pain associated with fibrotic diseases; central pain; pain due to burning mouth syndrome; pain due to burns; pain due to migraine; cluster headaches; hyperalgesia; allodynia; pain due to traumatic nerve-injury; pain due to post-traumatic injuries; fractures; sport injuries; pain due to trigeminal neuralgia; pain associated with small fiber neuropathy; pain associated with diabetic neuropathy; chronic lower back pain; phantom limb pain; pelvic pain syndrome; chronic pelvic pain; neuroma pain; complex regional pain syndrome; pain associated with gastrointestinal distension; chronic arthritic pain and related neuralgias; pain associated with cancer; pain associated with chemotherapy; HIV and HIV treatment-induced neuropathy; pruritus; impaired wound healing; disease of the skeleton; or ankylosing spondylitis.

2. The method of claim 1, wherein said disease is a gynaecological disease, dysmenorrhea, dyspareunia, endometriosis, adenomyosis, endometriosis-associated pain, other endometriosis-associated symptoms, dysuria, or dyschezia.

3. The method of claim 1, wherein said disease is lung fibrosis, liver fibrosis, pruritus, osteoarthritis, or burning mouth syndrome.

4. A method for treatment of a disease, comprising administering to a patient in need thereof a pharmaceutically effective amount of a compound, or a stereoisomer, a tautomer, an N oxide, a hydrate, a solvate, or a pharmaceutically acceptable salt thereof, or a mixture of the same,
wherein the compound is selected from the group consisting of:

2-(2-Chlorophenyl)-N-[4-(2-oxopyridin-1(2H)-yl)-3-sulfamoylphenyl]acetamide;
N-[4-(4-Chloro-2-oxopyridin-1(2H)-yl)-3-sulfamoylphenyl]-2-(2-chlorophenyl)acetamide;
2-(2-Chlorophenyl)-N-[4-(3, 5-dichloro-2-oxopyridin-1 (2H)-yl)-3-sulfamoylphenyl]acetamide;
N-[4-(3-Chloro-2-oxopyridin-1(2H)-yl)-3-sulfamoylphenyl]-2-(2-chlorophenyl)acetamide;
2-(2-Chlorophenyl)-N-[4-(3-methyl-1H-1,2,4-triazol-1-yl)-3-sulfamoylphenyl]acetamide;
2-(2-Chlorophenyl)-N-[4-(5-methyl-1H-1,2,4-triazol-1-yl)-3-sulfamoylphenyl]acetamide;
2-(2-Chlorophenyl)-N-{3-sulfamoyl-4-[3-(trifluoromethyl)-1H-1,2,4-triazol-1-yl]phenyl}acetamide;
2-(2-Chlorophenyl)-N-{4-[5-methyl-3-(trifluoromethyl)-1H-1,2,4-triazol-1-yl]-3-sulfamoylphenyl}acetamide;
2-(2-Chlorophenyl)-N-[4-(1H-imidazol-1-yl)-3-sulfamoylphenyl]acetamide;
2-(2-Chlorophenyl)-N-{3-sulfamoyl-4-[4-(trifluoromethyl)-1H-imidazol-1-yl]phenyl}acetamide;
2-(2-Chlorophenyl)-N-{3-sulfamoyl-4-[3-(trifluoromethyl)-1H-pyrazol-1-yl]phenyl}acetamide;
2-(2-Chlorophenyl)-N-{4-[3-(difluoromethyl)-1H-pyrazol-1-yl]-3-sulfamoylphenyl}acetamide;
2-(2-Chlorophenyl)-N-{4-[5-cyclopropyl-3-(difluoromethyl)-1H-pyrazol-1-yl]-3-sulfamoylphenyl}acetamide;
2-(2-Chlorophenyl)-N-{4-[4-methyl-3-(trifluoromethyl)-1H-pyrazol-1-yl]-3-sulfamoylphenyl}acetamide;
2-(2-Chlorophenyl)-N-{4-[5-methyl-3-(trifluoromethyl)-1H-pyrazol-1-yl]-3-sulfamoylphenyl}acetamide;
2-(2-Chlorophenyl)-N-[3-sulfamoyl-4-(1H-1,2,4-triazol-1-yl)phenyl]acetamide;
2-(2-Chlorophenyl)-N-{4-[3-(difluoromethyl)-1H-1,2,4-triazol-1-yl]-3-sulfamoylphenyl}acetamide;
N-{4-[3-(Difluoromethyl)-1H-1,2,4-triazol-1-yl]-3-sulfamoylphenyl}-2-(2-fluorophenyl)acetamide;
2-(2-Chlorophenyl)-N-{3-sulfamoyl-4-[4-(trifluoromethyl)-1H-pyrazol-1-yl]phenyl}acetamide;
2-(2-Fluorophenyl)-N-{3-sulfamoyl-4-[4-(trifluoromethyl)-1H-pyrazol-1-yl]phenyl}acetamide;
2-[2-(Difluoromethyl)phenyl]-N-{3-sulfamoyl-4-[4-(trifluoromethyl)-1H-pyrazol-1-yl]phenyl}acetamide;
N-{3-Sulfamoyl-4-[4-(trifluoromethyl)-1H-pyrazol-1-yl]phenyl}-2-[2-(trifluoromethyl)phenyl]acetamide;
N-[4-(3-tert-Butyl-1H-1,2,4-triazol-1-yl)-3-sulfamoylphenyl]-2-(2-chlorophenyl)acetamide;
2-(2-Chlorophenyl)-N-[4-(3-chloro-1H-1,2,4-triazol-1-yl)-3-sulfamoylphenyl]acetamide;
2-(2-Chlorophenyl)-N-[4-(4-chloro-1H-pyrazol-1-yl)-3-sulfamoylphenyl]acetamide;
2-(2-Chlorophenyl)-N-[4-(4-fluoro-1H-pyrazol-1-yl)-3-sulfamoylphenyl]acetamide;
2-(2-Chlorophenyl)-N-[4-(4-isopropoxy-1H-pyrazol-1-yl)-3-sulfamoylphenyl]acetamide;
N-[4-(4-Bromo-1H-pyrazol-1-yl)-3-sulfamoylphenyl]-2-(2-chlorophenyl)acetamide;
2-(2-Chlorophenyl)-N-[4-(3-isobutyl-1H-1,2,4-triazol-1-yl)-3-sulfamoylphenyl]acetamide;
2-(2-Chlorophenyl)-N-{4-[4-(methylsulfanyl)-1H-pyrazol-1-yl]-3-sulfamoylphenyl}acetamide;
2-(2-Chlorophenyl)-N-[4-(4-methoxy-1H-pyrazol-1-yl)-3-sulfamoylphenyl]acetamide;
N-[4-(1H-Benzimidazol-1-yl)-3-sulfamoylphenyl]-2-(2-chlorophenyl)acetamide;
N-[4-(4-Chloro-1H-imidazol-1-yl)-3-sulfamoylphenyl]-2-(2-chlorophenyl)acetamide;
2-(2-Chlorophenyl)-N-{4-[3-(dimethylamino)-1H-1,2,4-triazol-1-yl]-3-sulfamoylphenyl}acetamide;
2-(2-Chlorophenyl)-N-[4-(3-ethyl-1H-1,2,4-triazol-1-yl)-3-sulfamoylphenyl]acetamide;
(2-Chlorophenyl)-N-[4-(3-cyclopropyl-1H-1,2,4-triazol-1-yl)-3-sulfamoylphenyl]acetamide;
2-(2-Chlorophenyl)-N-[4-(5-cyclopropyl-1H-1,2,4-triazol-1-yl)-3-sulfamoylphenyl]acetamide;
2-(2-Chlorophenyl)-N-{4-[3-(methoxymethyl)-1H-1,2,4-triazol-1-yl]-3-sulfamoylphenyl}acetamide;
2-(2-Chlorophenyl)-N-[4-(4-cyano-1H-pyrazol-1-yl)-3-sulfamoylphenyl]acetamide;
N-[4-(4-tert-Butyl-1H-imidazol-1-yl)-3-sulfamoylphenyl]-2-(2-chlorophenyl)acetamide;
2-(2-Chlorophenyl)-N-[4-(3-cyano-1H-1,2,4-triazol-1-yl)-3-sulfamoylphenyl]acetamide;
N-[4-(4-Bromo-1H-imidazol-1-yl)-3-sulfamoylphenyl]-2-(2-chlorophenyl)acetamide;
2-(2-Chlorophenyl)-N-[4-(3H-imidazo[4,5-b]pyridin-3-yl)-3-sulfamoylphenyl]acetamide;
2-(2-Chlorophenyl)-N-[4-(1H-imidazo[4,5-b]pyridin-1-yl)-3-sulfamoylphenyl]acetamide;
2-(2-Chlorophenyl)-N-[4-(1H-imidazo[4,5-c]pyridin-1-yl)-3-sulfamoylphenyl]acetamide;
2-(2-Chlorophenyl)-N-[4-(3H-imidazo[4,5-c]pyridin-3-yl)-3-sulfamoylphenyl]acetamide;
2-(2-Chlorophenyl)-N-[4-(2,4-dimethyl-1H-imidazol-1-yl)-3-sulfamoylphenyl]acetamide;
2-(2-Fluorophenyl)-N-[4-(4-fluoro-1H-pyrazol-1-yl)-3-sulfamoylphenyl]acetamide;
N-[4-(4-Chloro-1H-pyrazol-1-yl)-3-sulfamoylphenyl]-2-[2-(difluoromethyl)phenyl]acetamide;
N-[4-(4-Chloro-1H-pyrazol-1-yl)-3-sulfamoylphenyl]-2-(2-fluorophenyl)acetamide;
2-[2-(Difluoromethyl)phenyl]-N-[4-(4-fluoro-1H-pyrazol-1-yl)-3-sulfamoylphenyl]acetamide;
N-[4-(4-Cyano-1H-pyrazol-1-yl)-3-sulfamoylphenyl]-2-(2-fluorophenyl)acetamide;
2-(2-Methoxyphenyl)-N-{3-sulfamoyl-4-[3-(trifluoromethyl)-1H-1,2,4-triazol-1-yl]phenyl}acetamide;
2-(2-Fluorophenyl)-N-{3-sulfamoyl-4-[3-(trifluoromethyl)-1H-1,2,4-triazol-1-yl]phenyl}acetamide;
2-(3-Fluorophenyl)-N-{3-sulfamoyl-4-[3-(trifluoromethyl)-1H-1,2,4-triazol-1-yl]phenyl}acetamide;
2-(2-Chloro-4-fluorophenyl)-N-{3-sulfamoyl-4-[3-(trifluoromethyl)-1H-1,2,4-triazol-1-yl]phenyl}acetamide;
2-[2-(Difluoromethoxy)phenyl]-N-{3-sulfamoyl-4-[3-(trifluoromethyl)-1H-1,2,4-triazol-1-yl]phenyl}acetamide;
2-(2-Chloro-5-fluorophenyl)-N-{3-sulfamoyl-4-[3-(trifluoromethyl)-1H-1,2,4-triazol-1-yl]phenyl}acetamide;
2-(3-Chloropyridin-4-yl)-N-{3-sulfamoyl-4-[3-(trifluoromethyl)-1H-1,2,4-triazol-1-yl]phenyl}acetamide;
2-[4-(Difluoromethyl)phenyl]-N-{3-sulfamoyl-4-[3-(trifluoromethyl)-1H-1,2,4-triazol-1-yl]phenyl}acetamide;
2-(2-Chlorophenyl)-2,2-difluoro-N-{3-sulfamoyl-4-[3-(trifluoromethyl)-1H-1,2,4-triazol-1-yl]phenyl}acetamide;
N-[4-(4-Bromo-1H-pyrazol-1-yl)-3-sulfamoylphenyl]-2-(2-chlorophenyl)-2,2-difluoroacetamide;
N-[4-(4-Bromo-1H-pyrazol-1-yl)-3-sulfamoylphenyl]-2-(2-fluorophenyl)acetamide;

N-[4-(4-Bromo-1H-pyrazol-1-yl)-3-sulfamoylphenyl]-2-[2-(trifluoromethyl)phenyl]acetamide;
N-[4-(4-Bromo-1H-pyrazol-1-yl)-3-sulfamoylphenyl]-2-(3-fluorophenyl)acetamide;
N-[4-(4-Bromo-1H-pyrazol-1-yl)-3-sulfamoylphenyl]-2-(2-methylphenyl)acetamide;
N-[4-(4-Bromo-1H-pyrazol-1-yl)-3-sulfamoylphenyl]-2-(2-chloropyridin-3-yl)acetamide;
N-[4-(4-Bromo-1H-pyrazol-1-yl)-3-sulfamoylphenyl]-2-(2-chloro-4-fluorophenyl)acetamide;
N-[4-(4-Bromo-1H-pyrazol-1-yl)-3-sulfamoylphenyl]-2-[2-(difluoromethoxy)phenyl]acetamide;
N-[4-(4-Bromo-1H-pyrazol-1-yl)-3-sulfamoylphenyl]-2-[2-(trifluoromethoxy)phenyl]acetamide;
N-[4-(4-Bromo-1H-pyrazol-1-yl)-3-sulfamoylphenyl]-2-(2-chloro-4,5-difluorophenyl)acetamide;
N-[4-(4-Bromo-1H-pyrazol-1-yl)-3-sulfamoylphenyl]-2-(3-chloropyridin-4-yl)acetamide;
N-[4-(4-Bromo-1H-pyrazol-1-yl)-3-sulfamoylphenyl]-2-[4-(difluoromethyl)phenyl]acetamide;
2-(2-Bromophenyl)-N-[4-(4-chloro-1H-pyrazol-1-yl)-3-sulfamoylphenyl]acetamide;
N-[4-(4-Chloro-1H-pyrazol-1-yl)-3-sulfamoylphenyl]-2-(2-methoxyphenyl)acetamide;
2-(4-Chlorophenyl)-N-[4-(4-chloro-1H-pyrazol-1-yl)-3-sulfamoylphenyl]acetamide;
2-(2-Chloro-6-fluorophenyl)-N-[4-(4-chloro-1H-pyrazol-1-yl)-3-sulfamoylphenyl]acetamide;
N-[4-(4-Chloro-1H-pyrazol-1-yl)-3-sulfamoylphenyl]-2-(2-nitrophenyl)acetamide;
N-[4-(4-Chloro-1H-pyrazol-1-yl)-3-sulfamoylphenyl]-2-(2,4-dichlorophenyl)acetamide;
N-[4-(4-Chloro-1H-pyrazol-1-yl)-3-sulfamoylphenyl]-2-(2,6-dichlorophenyl)acetamide;
N-[4-(4-Chloro-1H-pyrazol-1-yl)-3-sulfamoylphenyl]-2-(3,4-difluorophenyl)acetamide;
2-(3-Chlorophenyl)-N-[4-(4-chloro-1H-pyrazol-1-yl)-3-sulfamoylphenyl]acetamide;
N-[4-(4-Chloro-1H-pyrazol-1-yl)-3-sulfamoylphenyl]-2-(3, 5-difluorophenyl)acetamide;
N-[4-(4-Chloro-1H-pyrazol-1-yl)-3-sulfamoylphenyl]-2-(4-fluorophenyl)acetamide;
N-[4-(4-Chloro-1H-pyrazol-1-yl)-3-sulfamoylphenyl]-2-(2-hydroxyphenyl)acetamide;
N-[4-(4-Chloro-1H-pyrazol-1-yl)-3-sulfamoylphenyl]-2-(4-hydroxyphenyl)acetamide;
N-[4-(4-Chloro-1H-pyrazol-1-yl)-3-sulfamoylphenyl]-2-(2,3-difluorophenyl)acetamide;
2-(2-Chloro-4-fluorophenyl)-N-[4-(4-chloro-1H-pyrazol-1-yl)-3-sulfamoylphenyl]acetamide;
N-[4-(4-Chloro-1H-pyrazol-1-yl)-3-sulfamoylphenyl]-2-(2-chloropyridin-3-yl)acetamide;
N-[4-(4-Chloro-1H-pyrazol-1-yl)-3-sulfamoylphenyl]-2-[2-chloro-3-(trifluoromethyl)phenyl]acetamide;
N-[4-(4-Chloro-1H-pyrazol-1-yl)-3-sulfamoylphenyl]-2-[2-(difluoromethoxy)phenyl]acetamide;
N-[4-(4-Chloro-1H-pyrazol-1-yl)-3-sulfamoylphenyl]-2-[2-(trifluoromethoxy)phenyl]acetamide;
2-(2-Chloro-4,5-difluorophenyl)-N-[4-(4-chloro-1H-pyrazol-1-yl)-3-sulfamoylphenyl]acetamide;
2-(2-Chloro-4-methoxyphenyl)-N-[4-(4-chloro-1H-pyrazol-1-yl)-3-sulfamoylphenyl]acetamide;
2-(2-Chloro-6-fluoro-3-methylphenyl)-N-[4-(4-chloro-1H-pyrazol-1-yl)-3-sulfamoylphenyl]acetamide;
2-(2-Chloro-3,6-difluorophenyl)-N-[4-(4-chloro-1H-pyrazol-1-yl)-3-sulfamoylphenyl]acetamide;
2-(2-Chloro-5-methylphenyl)-N-[4-(4-chloro-1H-pyrazol-1-yl)-3-sulfamoylphenyl]acetamide;
2-(2-Chloro-5-fluorophenyl)-N-[4-(4-chloro-1H-pyrazol-1-yl)-3-sulfamoylphenyl]acetamide;
N-[4-(4-Chloro-1H-pyrazol-1-yl)-3-sulfamoylphenyl]-2-(2,5-dichlorophenyl)acetamide;
N-[4-(4-Chloro-1H-pyrazol-1-yl)-3-sulfamoylphenyl]-2-(2-isopropylphenyl)acetamide;
2-(2-Chloro-5-methoxyphenyl)-N-[4-(4-chloro-1H-pyrazol-1-yl)-3-sulfamoylphenyl]acetamide;
2-(2-Chloro-4,6-difluorophenyl)-N-[4-(4-chloro-1H-pyrazol-1-yl)-3-sulfamoylphenyl]acetamide;
N-[4-(4-Chloro-1H-pyrazol-1-yl)-3-sulfamoylphenyl]-2-[2-chloro-6-(trifluoromethyl)phenyl]acetamide;
2-(5-Bromo-4-fluoro-2-methylphenyl)-N-[4-(4-chloro-1H-pyrazol-1-yl)-3-sulfamoylphenyl]acetamide;
2-(2-Chloro-6-methoxyphenyl)-N-[4-(4-chloro-1H-pyrazol-1-yl)-3-sulfamoylphenyl]acetamide;
N-[4-(4-Chloro-1H-pyrazol-1-yl)-3-sulfamoylphenyl]-2-(2,6-difluorophenyl)propanamide;
N-[4-(4-Chloro-1H-pyrazol-1-yl)-3-sulfamoylphenyl]-2-[4-(difluoromethyl)phenyl]acetamide;
2-(2-Chlorophenyl)-N-{3-sulfamoyl-4-[4-(trifluoromethyl)-1H-pyrazol-1-yl]phenyl}acetamide;
2-(2-Chlorophenyl)-N-[4-(4-chloro-1H-pyrazol-1-yl)-3-sulfamoylphenyl]-2,2-difluoroacetamide;
2-(2-Nitrophenyl)-N-{3-sulfamoyl-4-[4-(trifluoromethyl)-1H-pyrazol-1-yl]phenyl}acetamide;
2-(2,4-Dichlorophenyl)-N-{3-sulfamoyl-4-[4-(trifluoromethyl)-1H-pyrazol-1-yl]phenyl}acetamide;
2-(2-Methoxyphenyl)-N-{3-sulfamoyl-4-[4-(trifluoromethyl)-1H-pyrazol-1-yl]phenyl}acetamide;
2-(2-Chloro-6-fluorophenyl)-N-{3-sulfamoyl-4-[4-(trifluoromethyl)-1H-pyrazol-1-yl]phenyl}acetamide;
2-(3-Fluorophenyl)-N-{3-sulfamoyl-4-[4-(trifluoromethyl)-1H-pyrazol-1-yl]phenyl}acetamide;
2-(3, 5-Difluorophenyl)-N-{3-sulfamoyl-4-[4-(trifluoromethyl)-1H-pyrazol-1-yl]phenyl}acetamide;
2-(2,6-Dichlorophenyl)-N-{3-sulfamoyl-4-[4-(trifluoromethyl)-1H-pyrazol-1-yl]phenyl}acetamide;
2-(2-Bromophenyl)-N-{3-sulfamoyl-4-[4-(trifluoromethyl)-1H-pyrazol-1-yl]phenyl}acetamide;
2-(3,4-Difluorophenyl)-N-{3-sulfamoyl-4-[4-(trifluoromethyl)-1H-pyrazol-1-yl]phenyl}acetamide;
2-(4-Fluorophenyl)-N-{3-sulfamoyl-4-[4-(trifluoromethyl)-1H-pyrazol-1-yl]phenyl}acetamide;
2-(3-Chlorophenyl)-N-{3-sulfamoyl-4-[4-(trifluoromethyl)-1H-pyrazol-1-yl]phenyl}acetamide;
2-(4-Methoxyphenyl)-N-{3-sulfamoyl-4-[4-(trifluoromethyl)-1H-pyrazol-1-yl]phenyl}acetamide;
2-(2,3-Difluorophenyl)-N-{3-sulfamoyl-4-[4-(trifluoromethyl)-1H-pyrazol-1-yl]phenyl}acetamide;
2-(2-Methylphenyl)-N-{3-sulfamoyl-4-[4-(trifluoromethyl)-1H-pyrazol-1-yl]phenyl}acetamide;
2-(3-Methylphenyl)-N-{3-sulfamoyl-4-[4-(trifluoromethyl)-1H-pyrazol-1-yl]phenyl}acetamide;
2-[2-(Difluoromethoxy)phenyl]-N-{3-sulfamoyl-4-[4-(trifluoromethyl)-1H-pyrazol-1-yl]phenyl}acetamide;
2-(2-Chloropyridin-3-yl)-N-{3-sulfamoyl-4-[4-(trifluoromethyl)-1H-pyrazol-1-yl]phenyl}acetamide;
2-(2-Chloro-4-fluorophenyl)-N-{3-sulfamoyl-4-[4-(trifluoromethyl)-1H-pyrazol-1-yl]phenyl}acetamide;
2-(2-Chloro-5-methylphenyl)-N-{3-sulfamoyl-4-[4-(trifluoromethyl)-1H-pyrazol-1-yl]phenyl}acetamide;
N-{3-Sulfamoyl-4-[4-(trifluoromethyl)-1H-pyrazol-1-yl]phenyl}-2-[2-(trifluoromethoxy)phenyl]acetamide;

2-(2-Chloro-4,5-difluorophenyl)-N-{3-sulfamoyl-4-[4-(trifluoromethyl)-1H-pyrazol-1-yl]phenyl}acetamide;
2-[2-Chloro-3-(trifluoromethyl)phenyl]-N-{3-sulfamoyl-4-[4-(trifluoromethyl)-1H-pyrazol-1-yl]phenyl}acetamide;
2-(2-Chloro-6-fluoro-3-methylphenyl)-N-{3-sulfamoyl-4-[4-(trifluoromethyl)-1H-pyrazol-1-yl]phenyl}acetamide;
2-(2-Chloro-3,6-difluorophenyl)-N-{3-sulfamoyl-4-[4-(trifluoromethyl)-1H-pyrazol-1-yl]phenyl}acetamide;
2-[2-Chloro-6-(trifluoromethyl)phenyl]-N-{3-sulfamoyl-4-[4-(trifluoromethyl)-1H-pyrazol-1-yl]phenyl}acetamide;
2-(2-Chloro-4-methoxyphenyl)-N-{3-sulfamoyl-4-[4-(trifluoromethyl)-1H-pyrazol-1-yl]phenyl}acetamide;
2-(2,5-Dichlorophenyl)-N-{3-sulfamoyl-4-[4-(trifluoromethyl)-1H-pyrazol-1-yl]phenyl}acetamide;
2-(2-Isopropylphenyl)-N-{3-sulfamoyl-4-[4-(trifluoromethyl)-1H-pyrazol-1-yl]phenyl}acetamide;
2-(2-Chloro-5-methoxyphenyl)-N-{3-sulfamoyl-4-[4-(trifluoromethyl)-1H-pyrazol-1-yl]phenyl}acetamide;
2-(2-Chloro-5-fluorophenyl)-N-{3-sulfamoyl-4-[4-(trifluoromethyl)-1H-pyrazol-1-yl]phenyl}acetamide;
N-[4-(4-Fluoro-1H-pyrazol-1-yl)-3-sulfamoylphenyl]-2-[2-(trifluoromethyl)phenyl]acetamide;
2-(5-Bromo-4-fluoro-2-methylphenyl)-N-{3-sulfamoyl-4-[4-(trifluoromethyl)-1H-pyrazol-1-yl]phenyl}acetamide;
2-(2-Chloro-6-methoxyphenyl)-N-{3-sulfamoyl-4-[4-(trifluoromethyl)-1H-pyrazol-1-yl]phenyl}acetamide;
2-(2-Chloro-4,6-difluorophenyl)-N-{3-sulfamoyl-4-[4-(trifluoromethyl)-1H-pyrazol-1-yl]phenyl}acetamide;
2-(3-Fluorophenyl)-N-[4-(4-fluoro-1H-pyrazol-1-yl)-3-sulfamoylphenyl]acetamide;
2-(3,4-Difluorophenyl)-N-[4-(4-fluoro-1H-pyrazol-1-yl)-3-sulfamoylphenyl]acetamide;
2-(3,5-Difluorophenyl)-N-[4-(4-fluoro-1H-pyrazol-1-yl)-3-sulfamoylphenyl]acetamide;
N-[4-(4-Fluoro-1H-pyrazol-1-yl)-3-sulfamoylphenyl]-2-(2-hydroxyphenyl)acetamide;
2-(3-Chlorophenyl)-N-[4-(4-fluoro-1H-pyrazol-1-yl)-3-sulfamoylphenyl]acetamide;
2-(4-Fluorophenyl)-N-[4-(4-fluoro-1H-pyrazol-1-yl)-3-sulfamoylphenyl]acetamide;
N-[4-(4-Fluoro-1H-pyrazol-1-yl)-3-sulfamoylphenyl]-2-(4-hydroxyphenyl)acetamide;
N-[4-(4-Fluoro-1H-pyrazol-1-yl)-3-sulfamoylphenyl]-2-(3-methylphenyl)acetamide;
N-[4-(4-Fluoro-1H-pyrazol-1-yl)-3-sulfamoylphenyl]-2-(4-methylphenyl)acetamide;
N-[4-(4-Fluoro-1H-pyrazol-1-yl)-3-sulfamoylphenyl]-2-(4-methoxyphenyl)acetamide;
N-[4-(4-Fluoro-1H-pyrazol-1-yl)-3-sulfamoylphenyl]-2-(2-methylphenyl)acetamide;
2-(2,3-Difluorophenyl)-N-[4-(4-fluoro-1H-pyrazol-1-yl)-3-sulfamoylphenyl]acetamide;
2-(2-Ethoxyphenyl)-N-[4-(4-fluoro-1H-pyrazol-1-yl)-3-sulfamoylphenyl]acetamide;
2-[2-(Difluoromethoxy)phenyl]-N-[4-(4-fluoro-1H-pyrazol-1-yl)-3-sulfamoylphenyl]acetamide;
2-(2-Chloropyridin-3-yl)-N-[4-(4-fluoro-1H-pyrazol-1-yl)-3-sulfamoylphenyl]acetamide;
2-(2-Chloro-6-fluoro-3-methylphenyl)-N-[4-(4-fluoro-1H-pyrazol-1-yl)-3-sulfamoylphenyl]acetamide;
N-[4-(4-Fluoro-1H-pyrazol-1-yl)-3-sulfamoylphenyl]-2-[2-(trifluoromethoxy)phenyl]acetamide;
2-(2-Chloro-4,5-difluorophenyl)-N-[4-(4-fluoro-1H-pyrazol-1-yl)-3-sulfamoylphenyl]acetamide;
2-[2-Chloro-3-(trifluoromethyl)phenyl]-N-[4-(4-fluoro-1H-pyrazol-1-yl)-3-sulfamoylphenyl]acetamide;
2-(2,5-dichlorophenyl)-N-[4-(4-fluoro-1H-pyrazol-1-yl)-3-sulfamoylphenyl]acetamide;
2-(2-Chloro-3,6-difluorophenyl)-N-[4-(4-fluoro-1H-pyrazol-1-yl)-3-sulfamoylphenyl]acetamide;
2-(2-Chloro-5-methylphenyl)-N-[4-(4-fluoro-1H-pyrazol-1-yl)-3-sulfamoylphenyl]acetamide;
2-(5-Bromo-4-fluoro-2-methylphenyl)-N-[4-(4-fluoro-1H-pyrazol-1-yl)-3-sulfamoylphenyl]acetamide;
N-[4-(4-Fluoro-1H-pyrazol-1-yl)-3-sulfamoylphenyl]-2-(2-isopropylphenyl)acetamide;
2-(2-Chloro-5-fluorophenyl)-N-[4-(4-fluoro-1H-pyrazol-1-yl)-3-sulfamoylphenyl]acetamide;
2-[2-Chloro-6-(trifluoromethyl)phenyl]-N-[4-(4-fluoro-1H-pyrazol-1-yl)-3-sulfamoylphenyl]acetamide;
N-[4-(4-Chloro-1H-pyrazol-1-yl)-3-sulfamoylphenyl]-2-(4-methoxyphenyl)acetamide;
2-(2,6-Difluorophenyl)-N-[4-(4-fluoro-1H-pyrazol-1-yl)-3-sulfamoylphenyl]propanamide;
N-[4-(4-Chloro-1H-pyrazol-1-yl)-3-sulfamoylphenyl]-2-(4-methylphenyl)acetamide;
N-[4-(4-Chloro-1H-pyrazol-1-yl)-3-sulfamoylphenyl]-2-(2-methylphenyl)acetamide;
N-[4-(4-Chloro-1H-pyrazol-1-yl)-3-sulfamoylphenyl]-2-(3-methylphenyl)acetamide;
N-[4-(4-Chloro-1H-pyrazol-1-yl)-3-sulfamoylphenyl]-2-(2-ethoxyphenyl)acetamide;
2-(2-Ethoxyphenyl)-N-{3-sulfamoyl-4-[4-(trifluoromethyl)-1H-pyrazol-1-yl]phenyl}acetamide;
2-(2-Bromophenyl)-N-[4-(4-fluoro-1H-pyrazol-1-yl)-3-sulfamoylphenyl]acetamide;
2-(2,4-Dichlorophenyl)-N-[4-(4-fluoro-1H-pyrazol-1-yl)-3-sulfamoylphenyl]acetamide;
2-(2,6-Dichlorophenyl)-N-[4-(4-fluoro-1H-pyrazol-1-yl)-3-sulfamoylphenyl]acetamide;
N-[4-(4-Cyano-1H-pyrazol-1-yl)-3-sulfamoylphenyl]-2-(2-nitrophenyl)acetamide;
2-(4-Chlorophenyl)-N-[4-(4-cyano-1H-pyrazol-1-yl)-3-sulfamoylphenyl]acetamide;
N-[4-(4-Cyano-1H-pyrazol-1-yl)-3-sulfamoylphenyl]-2-(2-methoxyphenyl)acetamide;
2-(2-Chloro-6-fluorophenyl)-N-[4-(4-cyano-1H-pyrazol-1-yl)-3-sulfamoylphenyl]acetamide;
N-[4-(4-Cyano-1H-pyrazol-1-yl)-3-sulfamoylphenyl]-2-[2-(trifluoromethyl)phenyl]acetamide;
N-[4-(4-Cyano-1H-pyrazol-1-yl)-3-sulfamoylphenyl]-2-(3-fluorophenyl)acetamide;
N-[4-(4-Cyano-1H-pyrazol-1-yl)-3-sulfamoylphenyl]-2-(2,4-dichlorophenyl)acetamide;
N-[4-(4-Cyano-1H-pyrazol-1-yl)-3-sulfamoylphenyl]-2-(2,6-dichlorophenyl)acetamide;
2-(2-Bromophenyl)-N-[4-(4-cyano-1H-pyrazol-1-yl)-3-sulfamoylphenyl]acetamide;
N-[4-(4-Cyano-1H-pyrazol-1-yl)-3-sulfamoylphenyl]-2-(3,4-difluorophenyl)acetamide;
N-[4-(4-Cyano-1H-pyrazol-1-yl)-3-sulfamoylphenyl]-2-(3,5-difluorophenyl)acetamide;
2-(3-Chlorophenyl)-N-[4-(4-cyano-1H-pyrazol-1-yl)-3-sulfamoylphenyl]acetamide;
N-[4-(4-Cyano-1H-pyrazol-1-yl)-3-sulfamoylphenyl]-2-(4-fluorophenyl)acetamide;
N-[4-(4-Cyano-1H-pyrazol-1-yl)-3-sulfamoylphenyl]-2-(2-hydroxyphenyl)acetamide;

N-[4-(4-Cyano-1H-pyrazol-1-yl)-3-sulfamoylphenyl]-2-(4-hydroxyphenyl)acetamide;
N-[4-(4-Cyano-1H-pyrazol-1-yl)-3-sulfamoylphenyl]-2-(4-methylphenyl)acetamide;
N-[4-(4-Cyano-1H-pyrazol-1-yl)-3-sulfamoylphenyl]-2-(4-methoxyphenyl)acetamide;
N-[4-(4-Cyano-1H-pyrazol-1-yl)-3-sulfamoylphenyl]-2-(2-methylphenyl)acetamide;
N-[4-(4-Cyano-1H-pyrazol-1-yl)-3-sulfamoylphenyl]-2-(3-methylphenyl)acetamide;
N-[4-(4-Cyano-1H-pyrazol-1-yl)-3-sulfamoylphenyl]-2-(2-ethoxyphenyl)acetamide;
N-[4-(4-Cyano-1H-pyrazol-1-yl)-3-sulfamoylphenyl]-2-(2,3-difluorophenyl)acetamide;
2-(2-Chloropyridin-3-yl)-N-[4-(4-cyano-1H-pyrazol-1-yl)-3-sulfamoylphenyl]acetamide;
2-(2-Chloro-4-fluorophenyl)-N-[4-(4-cyano-1H-pyrazol-1-yl)-3-sulfamoylphenyl]acetamide;
N-[4-(4-Cyano-1H-pyrazol-1-yl)-3-sulfamoylphenyl]-2-[2-(difluoromethoxy)phenyl]acetamide;
N-[4-(4-Cyano-1H-pyrazol-1-yl)-3-sulfamoylphenyl]-2-[2-(trifluoromethoxy)phenyl]acetamide;
2-(2-Chloro-4,5-difluorophenyl)-N-[4-(4-cyano-1H-pyrazol-1-yl)-3-sulfamoylphenyl]acetamide;
2-[2-Chloro-3-(trifluoromethyl)phenyl]-N-[4-(4-cyano-1H-pyrazol-1-yl)-3-sulfamoylphenyl]acetamide;
2-(2-chloro-6-fluoro-3-methylphenyl)-N-[4-(4-cyano-1H-pyrazol-1-yl)-3-sulfamoylphenyl]acetamide;
2-(2-Chloro-3,6-difluorophenyl)-N-[4-(4-cyano-1H-pyrazol-1-yl)-3-sulfamoylphenyl]acetamide;
2-(2-Chloro-5-methylphenyl)-N-[4-(4-cyano-1H-pyrazol-1-yl)-3-sulfamoylphenyl]acetamide;
2-(2-Chloro-4-methoxyphenyl)-N-[4-(4-cyano-1H-pyrazol-1-yl)-3-sulfamoylphenyl]acetamide;
N-[4-(4-Cyano-1H-pyrazol-1-yl)-3-sulfamoylphenyl]-2-(2,5-dichlorophenyl)acetamide;
2-(5-Chloro-2-methoxyphenyl)-N-[4-(4-cyano-1H-pyrazol-1-yl)-3-sulfamoylphenyl]acetamide;
N-[4-(4-Cyano-1H-pyrazol-1-yl)-3-sulfamoylphenyl]-2-[2-(propan-2-yl)phenyl]acetamide;
2-(2-Chloro-5-fluorophenyl)-N-[4-(4-cyano-1H-pyrazol-1-yl)-3-sulfamoylphenyl]acetamide;
2-[2-Chloro-6-(trifluoromethyl)phenyl]-N-[4-(4-cyano-1H-pyrazol-1-yl)-3-sulfamoylphenyl]acetamide;
2-(2-Chloro-6-methoxyphenyl)-N-[4-(4-cyano-1H-pyrazol-1-yl)-3-sulfamoylphenyl]acetamide;
2-(2-Chloro-4,6-difluorophenyl)-N-[4-(4-cyano-1H-pyrazol-1-yl)-3-sulfamoylphenyl]acetamide;
2-(3-Chloropyridin-4-yl)-N-[4-(4-cyano-1H-pyrazol-1-yl)-3-sulfamoylphenyl]acetamide;
N-[4-(4-Cyano-1H-pyrazol-1-yl)-3-sulfamoylphenyl]-2-[4-(difluoromethyl)phenyl]acetamide;
2-(2-Chlorophenyl)-N-[4-(4-cyano-1H-pyrazol-1-yl)-3-sulfamoylphenyl]-2,2-difluoroacetamide;
2-(2-Fluorophenyl)-N-{3-sulfamoyl-4-[5-(trifluoromethyl)pyridin-3-yl]phenyl}acetamide;
N-{3-Sulfamoyl-4-[5-(trifluoromethyl)pyridin-3-yl]phenyl}-2-[2-(trifluoromethoxy)phenyl]acetamide;
N-{4-[1-(Difluoromethyl)-1H-pyrazol-4-yl]-3-sulfamoylphenyl}-2-(2-methylphenyl)acetamide;
N-{4-[1-(Difluoromethyl)-1H-pyrazol-4-yl]-3-sulfamoylphenyl}-2-[2-(trifluoromethyl)phenyl]acetamide;
2-[2-(Difluoromethyl)phenyl]-N-{4-[1-(difluoromethyl)-1H-pyrazol-4-yl]-3-sulfamoylphenyl}acetamide;
N-{4-[1-(Difluoromethyl)-1H-pyrazol-4-yl]-3-sulfamoylphenyl}-2-(2-methoxyphenyl)acetamide;
N-{4-[1-(Difluoromethyl)-1H-pyrazol-4-yl]-3-sulfamoylphenyl}-2-(4-fluorophenyl)acetamide;
2-(2-Chloro-5-fluorophenyl)-N-{4-[1-(difluoromethyl)-1H-pyrazol-4-yl]-3-sulfamoylphenyl}acetamide;
2-(2,3-Dichlorophenyl)-N-{4-[1-(difluoromethyl)-1H-pyrazol-4-yl]-3-sulfamoylphenyl}acetamide;
2-(3-Chloropyridin-4-yl)-N-{4-[1-(difluoromethyl)-1H-pyrazol-4-yl]-3-sulfamoylphenyl}acetamide;
2-(2-Chlorophenyl)-N-[4-(3-cyclobutyl-1H-1,2,4-triazol-1-yl)-3-sulfamoylphenyl]acetamide;
N-[4-(4-Acetyl-1H-pyrazol-1-yl)-3-sulfamoylphenyl]-2-(2-chlorophenyl)acetamide 2-(2-Chlorophenyl)-N-[4-(3-isopropyl-1H-1,2,4-triazol-1-yl)-3-sulfamoylphenyl]acetamide;
N-[4-(4-Chloro-1H-pyrazol-1-yl)-3-sulfamoylphenyl]-2-[2-(trifluoromethyl)phenyl]acetamide;
Ethyl 1-(4-{[(2-chlorophenyl)acetyl]amino}-2-sulfamoylphenyl)-1H-pyrazole-4-carboxylate;
Ethyl 1-(4-{[(2-fluorophenyl)acetyl]amino}-2-sulfamoylphenyl)-1H-pyrazole-4-carboxylate;
2-(2-Fluorophenyl)-N-{4-[4-(2-hydroxypropan-2-yl)-1H-pyrazol-1-yl]-3-sulfamoylphenyl}acetamide;
2-(2-Chlorophenyl)-N-{4-[4-(2-hydroxypropan-2-yl)-1H-pyrazol-1-yl]-3-sulfamoylphenyl}acetamide;
2-(2-Chloropyridin-3-yl)-N-{3-sulfamoyl-4-[3-(trifluoromethyl)-1H-1,2,4-triazol-1-yl]phenyl}acetamide;
2-(2-Chlorophenyl)-N-methyl-N-{3-sulfamoyl-4-[4-(trifluoromethyl)-1H-pyrazol-1-yl]phenyl}acetamide;
2-(2-Chlorophenyl)-N-{3-sulfamoyl-4-[4-(trifluoromethyl)-2H-1,2,3-triazol-2-yl]phenyl}acetamide;
2-(2-Chlorophenyl)-N-{3-sulfamoyl-4-[4-(trifluoromethyl)-1H-1,2,3-triazol-1-yl]phenyl}acetamide;
2-(2-Chloro-5-cyanophenyl)-N-{3-sulfamoyl-4-[4-(trifluoromethyl)-1H-pyrazol-1-yl]phenyl}acetamide;
2-(2-Chlorophenyl)-N-{3-cyano-5-sulfamoyl-4-[4-(trifluoromethyl)-1H-pyrazol-1-yl]phenyl}acetamide;
2-(5-Bromo-2-chlorophenyl)-N-{3-sulfamoyl-4-[4-(trifluoromethyl)-1H-pyrazol-1-yl]phenyl}acetamide;
N-[4-(3-Chloro-1H-1,2,4-triazol-1-yl)-3-sulfamoylphenyl]-2-(2-fluorophenyl)acetamide;
2-(2-Chlorophenyl)-N-[3-cyano-4-(4-fluoro-1H-pyrazol-1-yl)-5-sulfamoylphenyl]acetamide;
2-(2-Chlorophenyl)-N-[4-(4-methyl-1H-pyrazol-1-yl)-3-sulfamoylphenyl]acetamide;
2-(2-Chlorophenyl)-N-[4-(3-methoxy-1H-1,2,4-triazol-1-yl)-3-sulfamoylphenyl]acetamide;
2-(2-Chlorophenyl)-N-[4-(4-cyclopropyl-1H-imidazol-1-yl)-3-sulfamoylphenyl]acetamide;
2-(2-Chlorophenyl)-N-[4-(4-methyl-1H-imidazol-1-yl)-3-sulfamoylphenyl]acetamide;
2-(2-Chlorophenyl)-N-[4-(3-cyclopropyl-1H-pyrazol-1-yl)-3-sulfamoylphenyl]acetamide;
2-(2-Chlorophenyl)-N-[4-(2H-pyrazolo[3,4-b]pyridin-2-yl)-3-sulfamoylphenyl]acetamide;
2-(2-Chlorophenyl)-N-[4-(2H-pyrazolo[3,4-c]pyridin-2-yl)-3-sulfamoylphenyl]acetamide;
2-(2-Chlorophenyl)-N-[4-(2H-pyrazolo[4,3-b]pyridin-2-yl)-3-sulfamoylphenyl]acetamide;
2-(2-Chlorophenyl)-N-{4-[4-(2-methoxyethyl)-1H-pyrazol-1-yl]-3-sulfamoylphenyl}acetamide;
2-(2-Chlorophenyl)-N-[4-(3-fluoro-1H-pyrazol-1-yl)-3-sulfamoylphenyl]acetamide;
2-(2-Chlorophenyl)-N-(4-{4-[(2,2-difluoroethyl)amino]-1H-pyrazol-1-yl}-3-sulfamoylphenyl)acetamide;
2-(2-Chlorophenyl)-N-{4-[4-(2,2-difluoroethyl)-1H-pyrazol-1-yl]-3-sulfamoylphenyl}acetamide;

2-(2-Chlorophenyl)-N-[4-(4-{[(2,2-difluoroethyl)amino]methyl}-1H-pyrazol-1-yl)-3-sulfamoylphenyl]acetamide;
2-(2-Chlorophenyl)-N-{3-sulfamoyl-4-[5-(trifluoromethyl)-1,2,4-oxadiazol-3-yl]phenyl}acetamide;
2-(2-Fluorophenyl)-N-[4-(4-methyl-1H-pyrazol-1-yl)-3-sulfamoylphenyl]acetamide;
N-[4-(4-Cyclopropyl-1H-imidazol-1-yl)-3-sulfamoylphenyl]-2-(2-fluorophenyl)acetamide;
N-[4-(3-Cyclopropyl-1H-pyrazol-1-yl)-3-sulfamoylphenyl]-2-(2-fluorophenyl)acetamide;
2-(2-Fluorophenyl)-N-{4-[4-(2-methoxyethyl)-1H-pyrazol-1-yl]-3-sulfamoylphenyl}acetamide;
2-(2-Chlorophenyl)-N-(2-sulfamoylbiphenyl-4-yl)acetamide;
2-(2-Chlorophenyl)-N-{4-[1-(cyclopropylmethyl)-1H-pyrazol-4-yl]-3-sulfamoylphenyl}acetamide;
2-(2-Chlorophenyl)-N-{4-[1-(2-methoxyethyl)-1H-pyrazol-4-yl]-3-sulfamoylphenyl}acetamide;
2-(2-Chlorophenyl)-N-{4-[1-(piperidin-4-yl)-1H-pyrazol-4-yl]-3-sulfamoylphenyl}acetamide;
2-(2-Fluorophenyl)-N-{4-[1-(piperidin-4-yl)-1H-pyrazol-4-yl]-3-sulfamoylphenyl} acetamide;
N-{4-[1-(Azetidin-3-yl)-1H-pyrazol-4-yl]-3-sulfamoylphenyl}-2-(2-chlorophenyl) acetamide;
2-(3-Chlorophenyl)-N-(2-sulfamoylbiphenyl-4-yl)acetamide;
2-(2-Chlorophenyl)-N-[4-(3-methyl-1H-pyrazol-1-yl)-3-sulfamoylphenyl]acetamide;
2-(2-Chlorophenyl)-N-[4-(6-chloropyridin-3-yl)-3-sulfamoylphenyl]acetamide;
2-(2-Chlorophenyl)-N-[4-(3, 5-dimethyl-1,2-oxazol-4-yl)-3-sulfamoylphenyl]acetamide;
2-(2-Chlorophenyl)-N-(4-{1-[(3-methyloxetan-3-yl)methyl]-1H-pyrazol-4-yl}-3-sulfamoylphenyl)acetamide;
2-(2-Chloro-4-fluorophenyl)-N-{4-[1-(2-methoxyethyl)-1H-pyrazol-4-yl]-3-sulfamoylphenyl}acetamide;
2-(2-Chloro-4-fluorophenyl)-N-[4-(1-cyclopropyl-1H-pyrazol-4-yl)-3-sulfamoylphenyl]acetamide;
2-(2-Chlorophenyl)-N-(3-sulfamoyl-4-{1-[2-(trifluoromethoxy)ethyl]-1H-pyrazol-4-yl}phenyl)acetamide;
2-(2-Chlorophenyl)-N-[4-(1-cyclobutyl-1H-pyrazol-4-yl)-3-sulfamoylphenyl]acetamide;
2-(2-Chlorophenyl)-N-(4-{1-[2-(pyrrolidin-1-yl)ethyl]-1H-pyrazol-4-yl}-3-sulfamoylphenyl)acetamide;
2-(2-Chlorophenyl)-N-[4-(5-cyanopyridin-3-yl)-3-sulfamoylphenyl]acetamide;
2-(2-Chlorophenyl)-N-(4-{1-[oxetan-2-ylmethyl]-1H-pyrazol-4-yl}-3-sulfamoylphenyl)acetamide;
2-(2-Chlorophenyl)-N-{3-sulfamoyl-4-[2-(2,2,2-trifluoroethoxy)pyrimidin-5-yl]phenyl}acetamide;
2-(2-Chlorophenyl)-N-[4-(2-methoxypyrimidin-5-yl)-3-sulfamoylphenyl]acetamide;
2-(2-Chlorophenyl)-N-(4-{1-[2-(propan-2-yloxy)ethyl]-1H-pyrazol-4-yl}-3-sulfamoylphenyl)acetamide;
2-(2-Chlorophenyl)-N-{4-[1-(3-hydroxy-3-methylbutyl)-1H-pyrazol-4-yl]-3-sulfamoylphenyl}acetamide;
2-(2-Chlorophenyl)-N-{4-[5-(2-hydroxypropan-2-yl)-1-methyl-1H-pyrazol-3-yl]-3-sulfamoylphenyl}acetamide;
2-(2-Chlorophenyl)-N-{4-[5-(difluoromethoxy)pyridin-3-yl]-3-sulfamoylphenyl}acetamide;
N-[4-(2-Chloro-5-methoxypyridin-3-yl)-3-sulfamoylphenyl]-2-(2-chlorophenyl)acetamide;
2-(2-Chlorophenyl)-N-{4-[1-(2-hydroxyethyl)-1H-pyrazol-4-yl]-3-sulfamoylphenyl}acetamide;
N-[4-(5-tert-Butyl-1H-pyrazol-3-yl)-3-sulfamoylphenyl]-2-(2-chlorophenyl)acetamide;
N-[4-(1-Benzyl-1H-pyrazol-4-yl)-3-sulfamoylphenyl]-2-(2-chlorophenyl)acetamide;
2-(2-Chlorophenyl)-N-[4-(6-methylpyridazin-4-yl)-3-sulfamoylphenyl]acetamide;
2-(2-Chlorophenyl)-N-{3-sulfamoyl-4-[6-(trifluoromethyl)pyridin-2-yl]phenyl}acetamide;
N-{4-[1-(Difluoromethyl)-1H-pyrazol-4-yl]-3-sulfamoylphenyl}-2-(2-fluorophenyl)acetamide;
2-(2-Chlorophenyl)-N-{6-[1-(difluoromethyl)-1H-pyrazol-4-yl]-5-sulfamoylpyridin-3-yl}acetamide;
N-[4-(6-Chloro-5-methylpyridin-3-yl)-3-sulfamoylphenyl]-2-(2-chlorophenyl)acetamide;
2-(2-Chlorophenyl)-N-{4-[2-(cyclopropylamino)pyrimidin-5-yl]-3-sulfamoylphenyl}acetamide;
2-(2-Chlorophenyl)-N-{3-sulfamoyl-4-[1-(tetrahydrofuran-3-yl)-1H-pyrazol-4-yl]phenyl}acetamide;
2-(2-Chlorophenyl)-N-{4-[2-(methylamino)pyrimidin-5-yl]-3-sulfamoylphenyl}acetamide;
2-(2-Chlorophenyl)-N-[6-(1-methyl-1H-pyrazol-4-yl)-5-sulfamoylpyridin-3-yl]acetamide;
2-(2-Chlorophenyl)-N-{4-[1-(2,2-difluoroethyl)-1H-pyrazol-4-yl]-3-sulfamoylphenyl}acetamide;
N-{3-Sulfamoyl-4-[5-(trifluoromethyl)pyridin-3-yl]phenyl}-2-[2-(trifluoromethyl)phenyl]acetamide;
2-(2-Chlorophenyl)-N-[3-sulfamoyl-5'-(trifluoromethyl)-2,3'-bipyridin-5-yl]acetamide;
2-(2-Chlorophenyl)-N-{3-sulfamoyl-4-[2-(trifluoromethyl)pyrimidin-5-yl]phenyl}acetamide;
2-(2-Chlorophenyl)-N-{3-sulfamoyl-4-[5-(trifluoromethoxy)pyridin-3-yl]phenyl}acetamide;
2-(2-Chlorophenyl)-N-[4-(2-cyclopropylpyrimidin-5-yl)-3-sulfamoylphenyl]acetamide;
2-(2-Chlorophenyl)-N-[4-(2-ethoxypyrimidin-5-yl)-3-sulfamoylphenyl]acetamide;
2-(2-Chlorophenyl)-N-{4-[2-(propan-2-ylamino)pyrimidin-5-yl]-3-sulfamoylphenyl}acetamide;
2-(2-Chlorophenyl)-N-{4-[2-(propan-2-yloxy)pyrimidin-5-yl]-3-sulfamoylphenyl}acetamide;
2-(2-Chlorophenyl)-N-{4-[2-(ethylamino)pyrimidin-5-yl]-3-sulfamoylphenyl}acetamide;
2-(2-Chlorophenyl)-N-[4-(2-methylpyrimidin-5-yl)-3-sulfamoylphenyl]acetamide;
2-(2-Chlorophenyl)-N-{4-[2-(propylamino)pyrimidin-5-yl]-3-sulfamoylphenyl}acetamide;
2-(2-Chlorophenyl)-N-(3-sulfamoyl-4-{2-[(2,2,2-trifluoroethyl)amino]pyrimidin-5-yl}phenyl)acetamide;
2-(2-Chlorophenyl)-N-{4-[2-(cyclobutyloxy)pyrimidin-5-yl]-3-sulfamoylphenyl}acetamide;
N-[4-(2-Chloro-4-methylpyrimidin-5-yl)-3-sulfamoylphenyl]-2-(2-chlorophenyl)acetamide;
2-(2-Chlorophenyl)-N-{3-sulfamoyl-4-[4-(trifluoromethyl)pyridin-2-yl]phenyl}acetamide;
2-(2-Chlorophenyl)-N-[4-(5-chloropyridin-2-yl)-3-sulfamoylphenyl]acetamide;
2-(2-Chlorophenyl)-N-[4-(1,2-dimethyl-1H-imidazol-4-yl)-3-sulfamoylphenyl]acetamide;
N-{6-[1-(Difluoromethyl)-1H-pyrazol-4-yl]-5-sulfamoylpyridin-3-yl}-2-(2-fluorophenyl)acetamide;
2-(2-Chlorophenyl)-N-{4-[5-(pyrrolidin-1-yl)pyridin-3-yl]-3-sulfamoylphenyl}acetamide;
2-(2-Chlorophenyl)-N-[4-(1-cyclopropyl-1H-pyrazol-4-yl)-3-sulfamoylphenyl]-2-hydroxyethanamide;
2-(2-Chlorophenyl)-N-{4-[1-(difluoromethyl)-1H-pyrazol-4-yl]-3-sulfamoylphenyl}-2-hydroxyethanamide;

2-(2-Chlorophenyl)-N-[4-(5-chloropyridin-3-yl)-3-sulfamoylphenyl]acetamide;
2-(2-Chlorophenyl)-N-{4-[1-(difluoromethyl)-1H-pyrazol-4-yl]-3-sulfamoylphenyl}acetamide;
2-(2-Chlorophenyl)-N-[4-(5-fluoropyridin-3-yl)-3-sulfamoylphenyl]acetamide;
2-(2-Chlorophenyl)-N-{4-[1-(2-methylpropyl)-1H-pyrazol-4-yl]-3-sulfamoylphenyl}acetamide;
2-(2-Chlorophenyl)-N-[4-(1-cyclopentyl-1H-pyrazol-4-yl)-3-sulfamoylphenyl]acetamide;
2-(2-Chlorophenyl)-N-[2'-fluoro-3'-(propan-2-yloxy)-2-sulfamoylbiphenyl-4-yl]acetamide;
2-(2-Chlorophenyl)-N-{3-sulfamoyl-4-[5-(trifluoromethyl)pyridin-3-yl]phenyl}acetamide;
N-[4-(6-chloro-5-methoxypyridin-3-yl)-3-sulfamoylphenyl]-2-(2-chlorophenyl)acetamide;
2-(2-Chloro-6-fluorophenyl)-N-[4-(1-cyclopropyl-1H-pyrazol-4-yl)-3-sulfamoylphenyl]acetamide;
2-(2-Chloro-3-fluorophenyl)-N-[4-(1-methyl-1H-pyrazol-4-yl)-3-sulfamoylphenyl]acetamide;
N-[4-(1-tert-butyl-1H-pyrazol-4-yl)-3-sulfamoylphenyl]-2-(2-chlorophenyl)acetamide;
2-(2-Chlorophenyl)-N-{4-[2-(propan-2-yloxy)pyridin-3-yl]-3-sulfamoylphenyl}acetamide;
2-(2-Chloro-3-fluorophenyl)-N-[4-(1-cyclopropyl-1H-pyrazol-4-yl)-3-sulfamoylphenyl]acetamide;
2-(2-Fluorophenyl)-N-[4-(pyridin-3-yl)-3-sulfamoylphenyl]acetamide;
2-(2-Chloro-6-fluorophenyl)-N-[4-(1-methyl-1H-pyrazol-4-yl)-3-sulfamoylphenyl]acetamide;
2-(2-Chlorophenyl)-N-[3'-fluoro-5'-(2-hydroxypropan-2-yl)-2-sulfamoylbiphenyl-4-yl]acetamide;
2-(2-Chlorophenyl)-N-[4-(5-methoxypyridin-3-yl)-3-sulfamoylphenyl]acetamide;
2-(2-Chlorophenyl)-N-[3'-(2-hydroxypropan-2-yl)-2-sulfamoylbiphenyl-4-yl]acetamide;
2-(2-Fluorophenyl)-N-{4-[1-(propan-2-yl)-1H-pyrazol-4-yl]-3-sulfamoylphenyl}acetamide;
N-[4-(1-Cyclopropyl-1H-pyrazol-4-yl)-3-sulfamoylphenyl]-2-(2-fluorophenyl)acetamide;
2-(2-Chlorophenyl)-N-{3-sulfamoyl-4-[1-(tetrahydro-2H-pyran-2-yl)-1H-pyrazol-4-yl]phenyl}acetamide;
N-[4-(1-tert-Butyl-1H-pyrazol-4-yl)-3-sulfamoylphenyl]-2-(2-fluorophenyl)acetamide;
N-[3'-Fluoro-5'-(2-hydroxypropan-2-yl)-2-sulfamoylbiphenyl-4-yl]-2-(2-fluorophenyl)acetamide;
N-[4-(1-Cyclopentyl-1H-pyrazol-4-yl)-3-sulfamoylphenyl]-2-(2-fluorophenyl)acetamide;
2-(2-Chlorophenyl)-N-[4-(1-cyclopropyl-1H-pyrazol-4-yl)-3-sulfamoylphenyl]acetamide;
2-(2-Chloro-6-fluorophenyl)-N-{4-[1-(2-methoxyethyl)-1H-pyrazol-4-yl]-3-sulfamoylphenyl}acetamide;
2-(2-Chlorophenyl)-N-[4-(1,3-dimethyl-1H-pyrazol-5-yl)-3-sulfamoylphenyl]acetamide;
2-(2-Chlorophenyl)-N-(4'-chloro-2-sulfamoylbiphenyl-4-yl)acetamide;
2-(2-Chlorophenyl)-N-{4-[1-methyl-3-(trifluoromethyl)-1H-pyrazol-5-yl]-3-sulfamoylphenyl}acetamide;
2-(2-Chlorophenyl)-N-[4-(pyridin-3-yl)-3-sulfamoylphenyl]acetamide;
2-(2-Chlorophenyl)-N-{4-[1-methyl-3-(trifluoromethyl)-1H-pyrazol-4-yl]-3-sulfamoylphenyl}acetamide;
2-(2-Chlorophenyl)-N-(3'-chloro-2-sulfamoylbiphenyl-4-yl)acetamide;
2-(2-Chlorophenyl)-N-(4-{1-[(2,2-dichlorocyclopropyl)methyl]-1H-pyrazol-4-yl}-3-sulfamoylphenyl)acetamide;
2-(2-Chlorophenyl)-N-[4-(1,3-dimethyl-1H-pyrazol-4-yl)-3-sulfamoylphenyl]acetamide;
2-(2-Chlorophenyl)-N-{4-[1-(propan-2-yl)-1H-pyrazol-4-yl]-3-sulfamoylphenyl}acetamide;
2-(2-Chlorophenyl)-N-[4-(1-methyl-1H-pyrazol-4-yl)-3-sulfamoylphenyl]acetamide;
2-(2-Chlorophenyl)-N-{4-[1-(2-hydroxy-3,3-dimethylbutyl)-1H-pyrazol-4-yl]-3-sulfamoylphenyl}acetamide;
2-(2-Fluorophenyl)-N-[4-(5-fluoropyridin-3-yl)-3-sulfamoylphenyl]acetamide;
2-(2-Chlorophenyl)-N-[4-(5-methyl-1-phenyl-1H-pyrazol-4-yl)-3-sulfamoylphenyl]acetamide;
4'-{[(2-Chlorophenyl)acetyl]amino}-N-[2-(dimethylamino)ethyl]-2'-sulfamoylbiphenyl-3-carboxamide;
2-(2-Chlorophenyl)-N-[4-(pyrazolo[1,5-a]pyrimidin-3-yl)-3-sulfamoylphenyl]acetamide;
2-(2-Chlorophenyl)-N-{4-[5-(pyrrolidin-1-ylcarbonyl)pyridin-3-yl]-3-sulfamoylphenyl}acetamide;
2-(2-Chlorophenyl)-N-[4-(1H-pyrazol-4-yl)-3-sulfamoylphenyl]acetamide;
2-(2-Fluorophenyl)-N-{4-[1-methyl-3-(trifluoromethyl)-1H-pyrazol-5-yl]-3-sulfamoylphenyl}acetamide;
2-(2-Fluorophenyl)-N-{4-[1-(2-methoxyethyl)-1H-pyrazol-4-yl]-3-sulfamoylphenyl}acetamide;
2-(2-Chlorophenyl)-N-{4-[1-(2-hydroxy-2-methylpropyl)-1H-pyrazol-4-yl]-3-sulfamoylphenyl}acetamide;
2-(5-Chloro-2-fluorophenyl)-N-[4-(1-cyclopropyl-1H-pyrazol-4-yl)-3-sulfamoylphenyl]acetamide;
2-(2-Chlorophenyl)-N-[4-(6-methylpyridin-3-yl)-3-sulfamoylphenyl]acetamide;
2-(2-Chlorophenyl)-N-{4-[1-(oxetan-3-yl)-1H-pyrazol-4-yl]-3-sulfamoylphenyl}acetamide;
2-(2-Fluorophenyl)-N-[4-(1-methyl-1H-pyrazol-4-yl)-3-sulfamoylphenyl]acetamide;
N-[4-(1,3-dimethyl-1H-pyrazol-4-yl)-3-sulfamoylphenyl]-2-(2-fluorophenyl)acetamide;
N-[4-(5-cyclopropyl-1,3,4-oxadiazol-2-yl)-3-sulfamoylphenyl]-2-(2-fluorophenyl)acetamide;
2-(2-Chlorophenyl)-N-[4-(5-cyclopropyl-1,3,4-oxadiazol-2-yl)-3-sulfamoylphenyl]acetamide;
N-{4-[4-(Difluoromethyl)-1H-pyrazol-1-yl]-3-sulfamoylphenyl}-2-(2-fluorophenyl)acetamide;
2-(2-Chlorophenyl)-N-{4-[4-(difluoromethyl)-1H-pyrazol-1-yl]-3-sulfamoylphenyl}acetamide;
2-(2-Chlorophenyl)-N-{5-sulfamoyl-6-[4-(trifluoromethyl)-1H-pyrazol-1-yl]pyridin-3-yl}acetamide;
2-(2-Fluorophenyl)-N-{5-sulfamoyl-6-[4-(trifluoromethyl)-1H-pyrazol-1-yl]pyridin-3-yl}acetamide;
N-[6-(4-Cyano-1H-pyrazol-1-yl)-5-sulfamoylpyridin-3-yl]-2-(2-fluorophenyl)acetamide;
2-(2-Chlorophenyl)-N-[6-(4-cyano-1H-pyrazol-1-yl)-5-sulfamoylpyridin-3-yl]acetamide;
2-(2-Fluorophenyl)-N-[6-(4-fluoro-1H-pyrazol-1-yl)-5-sulfamoylpyridin-3-yl]acetamide;
2-(2-chlorophenyl)-N-[6-(4-fluoro-1H-pyrazol-1-yl)-5-sulfamoylpyridin-3-yl]acetamide;
N-[6-(4-Bromo-1H-pyrazol-1-yl)-5-sulfamoylpyridin-3-yl]-2-(2-fluorophenyl)acetamide;
2-(2-Chlorophenyl)-N-[6-(4-chloro-1H-pyrazol-1-yl)-5-sulfamoylpyridin-3-yl]acetamide;
N-[6-(4-Chloro-1H-pyrazol-1-yl)-5-sulfamoylpyridin-3-yl]-2-(2-fluorophenyl)acetamide;
N-[6-(4-Bromo-1H-pyrazol-1-yl)-5-sulfamoylpyridin-3-yl]-2-(2-chlorophenyl)acetamide;
2-(2-Fluorophenyl)-N-{3-sulfamoyl-4-[5-(trifluoromethyl)-1,3,4-oxadiazol-2-yl]phenyl}acetamide;

2-(2-Chlorophenyl)-N-{3-sulfamoyl-4-[5-(trifluoromethyl)-1,3,4-oxadiazol-2-yl]phenyl}acetamide;
2-(2-Chlorophenyl)-N-{4-[3-(pyridin-3-yl)-1H-1,2,4-triazol-1-yl]-3-sulfamoylphenyl}acetamide;
2-(2-Fluorophenyl)-N-[4-(1H-pyrazol-1-yl)-3-sulfamoylphenyl]acetamide;
N-[4-(4-tert-Butyl-1H-pyrazol-1-yl)-3-sulfamoylphenyl]-2-(2-chlorophenyl)acetamide;
2-(2-Chlorophenyl)-N-[4-(1H-indazol-1-yl)-3-sulfamoylphenyl]acetamide;
2-(2-Chlorophenyl)-N-[4-(2H-indazol-2-yl)-3-sulfamoylphenyl]acetamide;
2-(2-Fluorophenyl)-N-[4-(2H-indazol-2-yl)-3-sulfamoylphenyl]acetamide;
2-(2-Fluorophenyl)-N-[4-(1H-indazol-1-yl)-3-sulfamoylphenyl]acetamide;
1-(4-{[(2-Chlorophenyl)acetyl]amino}-2-sulfamoylphenyl)-N,N-dimethyl-1H-pyrazole-4-carboxamide;
N-[1-(4-{[(2-Chlorophenyl)acetyl]amino}-2-sulfamoylphenyl)-1H-pyrazol-4-yl]cyclopropanecarboxamide;
2-(2-Chlorophenyl)-N-{4-[4-(pyrazin-2-yl)-1H-pyrazol-1-yl]-3-sulfamoylphenyl}acetamide;
2-(2-Chlorophenyl)-N-{4-[4-(pyridin-2-yl)-1H-pyrazol-1-yl]-3-sulfamoylphenyl}acetamide;
2-(2-Chlorophenyl)-N-{4-[4-(pyridin-3-yl)-1H-pyrazol-1-yl]-3-sulfamoylphenyl}acetamide;
2-(2-Chlorophenyl)-N-{4-[4-(pyrimidin-4-yl)-1H-pyrazol-1-yl]-3-sulfamoylphenyl}acetamide;
2-(2-Fluorophenyl)-N-{4-[4-(pyrimidin-4-yl)-1H-pyrazol-1-yl]-3-sulfamoylphenyl}acetamide;
2-(4-Methoxyphenyl)-N-{3-sulfamoyl-4-[4-(trifluoromethyl)-2H-1,2,3-triazol-2-yl]phenyl}acetamide;
2-(4-Methoxyphenyl)-N-{3-sulfamoyl-4-[4-(trifluoromethyl)-1H-1,2,3-triazol-1-yl]phenyl}acetamide;
2-(4-Methylphenyl)-N-{3-sulfamoyl-4-[4-(trifluoromethyl)-2H-1,2,3-triazol-2-yl]phenyl}acetamide;
2-(4-Methylphenyl)-N-{3-sulfamoyl-4-[4-(trifluoromethyl)-1H-1,2,3-triazol-1-yl]phenyl}acetamide;
2-[4-(Difluoromethyl)phenyl]-N-{3-sulfamoyl-4-[4-(trifluoromethyl)-2H-1,2,3-triazol-2-yl]phenyl}acetamide;
2-[4-(Difluoromethyl)phenyl]-N-{3-sulfamoyl-4-[4-(trifluoromethyl)-1H-1,2,3-triazol-1-yl]phenyl}acetamide;
2-(2-Fluorophenyl)-N-{3-sulfamoyl-4-[4-(trifluoromethyl)-2H-1,2,3-triazol-2-yl]phenyl}acetamide;
2-(2-Fluorophenyl)-N-{3-sulfamoyl-4-[4-(trifluoromethyl)-1H-1,2,3-triazol-1-yl]phenyl}acetamide;
2-[2-Chloro-4-(trifluoromethyl)phenyl]-N-{3-sulfamoyl-4-[4-(trifluoromethyl)-2H-1,2,3-triazol-2-yl]phenyl}acetamide;
2-[2-Chloro-4-(trifluoromethyl)phenyl]-N-{3-sulfamoyl-4-[4-(trifluoromethyl)-1H-1,2,3-triazol-1-yl]phenyl}acetamide;
2-(2,4-Dichlorophenyl)-N-{3-sulfamoyl-4-[4-(trifluoromethyl)-2H-1,2,3-triazol-2-yl]phenyl}acetamide;
2-(2,4-Dichlorophenyl)-N-{3-sulfamoyl-4-[4-(trifluoromethyl)-1H-1,2,3-triazol-1-yl]phenyl}acetamide;
2-(2-Chlorophenyl)-N-[3-sulfamoyl-4-(1,3-thiazol-5-yl)phenyl]acetamide;
2-(2-Chlorophenyl)-N-[3-sulfamoyl-4-(1,2-thiazol-3-yl)phenyl]acetamide;
2-(2-Chlorophenyl)-N-[4-(2-methyl-1,3-thiazol-4-yl)-3-sulfamoylphenyl]acetamide;
2-(2-Chlorophenyl)-N-[4-(2-methoxy-1,3-thiazol-4-yl)-3-sulfamoylphenyl]acetamide;
2-(2-Chlorophenyl)-N-[4-(2-methoxy-1,3-thiazol-5-yl)-3-sulfamoylphenyl]acetamide;
2-(2-Chlorophenyl)-N-[4-(2-methyl-1,3-thiazol-5-yl)-3-sulfamoylphenyl]acetamide;
2-(2-Chlorophenyl)-N-[4-(3-methyl-1,2-thiazol-5-yl)-3-sulfamoylphenyl]acetamide;
2-(2-Chlorophenyl)-N-[4-(4-methyl-1,3-thiazol-2-yl)-3-sulfamoylphenyl]acetamide;
2-(2-Chlorophenyl)-N-[3-sulfamoyl-4-(1,2-thiazol-4-yl)phenyl]acetamide;
2-(2-Chlorophenyl)-N-[3-sulfamoyl-4-(1,3-thiazol-2-yl)phenyl]acetamide;
2-(2-Chlorophenyl)-N-[4-(4-cyano-1,3-thiazol-2-yl)-3-sulfamoylphenyl]acetamide;
2-(2-Chlorophenyl)-N-{4-[2-(difluoromethyl)-1,3-thiazol-5-yl]-3-sulfamoylphenyl}acetamide;
2-(2-Chlorophenyl)-N-[4-(2-cyclopropyl-1,3-thiazol-5-yl)-3-sulfamoylphenyl]acetamide;
2-(2-Chlorophenyl)-N-[4-(2-cyclopropyl-1,3-thiazol-4-yl)-3-sulfamoylphenyl]acetamide;
2-(2-Chlorophenyl)-N-[4-(4-methyl-1,3-oxazol-2-yl)-3-sulfamoylphenyl]acetamide;
2-(2-Chlorophenyl)-N-{3-sulfamoyl-4-[2-(trifluoromethyl)-1,3-thiazol-4-yl]phenyl}acetamide;
2-(2-Chlorophenyl)-N-{3-sulfamoyl-4-[4-(trifluoromethyl)-1,3-thiazol-2-yl]phenyl}acetamide;
2-(2-Chlorophenyl)-N-{4-[2-(2-hydroxypropan-2-yl)-1,3-thiazol-5-yl]-3-sulfamoylphenyl}acetamide;
2-(2-Chlorophenyl)-N-{4-[2-(2-hydroxypropan-2-yl)-1,3-thiazol-4-yl]-3-sulfamoylphenyl}acetamide;
2-(2-Chlorophenyl)-N-[3-sulfamoyl-4-(1,3-thiazol-4-yl)phenyl]acetamide;
2-(2-Chlorophenyl)-N-[4-(5-cyclopropyl-1,2-oxazol-3-yl)-3-sulfamoylphenyl]acetamide;
2-(2-Chlorophenyl)-N-[4-(2-cyclopropyl-1,3-oxazol-5-yl)-3-sulfamoylphenyl]acetamide;
2-(2-Chlorophenyl)-N-(4-{4-[(3,3-difluoroazetidin-1-yl)carbonyl]-1H-pyrazol-1-yl}-3-sulfamoylphenyl)acetamide;
N-{4-[4-(Azetidin-1-ylcarbonyl)-1H-pyrazol-1-yl]-3-sulfamoylphenyl}-2-(2-chlorophenyl)acetamide;
2-(2-Chlorophenyl)-N-{4-[4-(pyrrolidin-1-ylcarbonyl)-1H-pyrazol-1-yl]-3-sulfamoylphenyl}acetamide;
2-(2-Chlorophenyl)-N-(4-{4-[(3,3-difluoropyrrolidin-1-yl)carbonyl]-1H-pyrazol-1-yl}-3-sulfamoylphenyl)acetamide;
2-(4-Chlorophenyl)-N-{3-sulfamoyl-4-[5-(trifluoromethyl)pyridin-3-yl]phenyl}acetamide;
2-(2-Chloro-6-fluorophenyl)-N-{3-sulfamoyl-4-[5-(trifluoromethyl)pyridin-3-yl]phenyl}acetamide;
N-{3-Sulfamoyl-4-[5-(trifluoromethyl)pyridin-3-yl]phenyl}-2-[4-(trifluoromethyl)phenyl]acetamide;
2-(3-Fluorophenyl)-N-{3-sulfamoyl-4-[5-(trifluoromethyl)pyridin-3-yl]phenyl}acetamide;
2-(2,4-Dichlorophenyl)-N-{3-sulfamoyl-4-[5-(trifluoromethyl)pyridin-3-yl]phenyl}acetamide;
2-(2-Bromophenyl)-N-{3-sulfamoyl-4-[5-(trifluoromethyl)pyridin-3-yl]phenyl}acetamide;
2-(2,4-Difluorophenyl)-N-{3-sulfamoyl-4-[5-(trifluoromethyl)pyridin-3-yl]phenyl}acetamide;
2-(3,4-Difluorophenyl)-N-{3-sulfamoyl-4-[5-(trifluoromethyl)pyridin-3-yl]phenyl}acetamide;
2-(3,5-Difluorophenyl)-N-{3-sulfamoyl-4-[5-(trifluoromethyl)pyridin-3-yl]phenyl}acetamide;
2-(3-Chlorophenyl)-N-{3-sulfamoyl-4-[5-(trifluoromethyl)pyridin-3-yl]phenyl}acetamide;
2-(4-Methylphenyl)-N-{3-sulfamoyl-4-[5-(trifluoromethyl)pyridin-3-yl]phenyl}acetamide;

2-(4-Methoxyphenyl)-N-{3-sulfamoyl-4-[5-(trifluoromethyl)pyridin-3-yl]phenyl}acetamide;
2-(2-Fluoro-4-methylphenyl)-N-{3-sulfamoyl-4-[5-(trifluoromethyl)pyridin-3-yl]phenyl}acetamide;
2-(2-Fluoro-4-methoxyphenyl)-N-{3-sulfamoyl-4-[5-(trifluoromethyl)pyridin-3-yl]phenyl}acetamide;
2-[4-(Difluoromethyl)phenyl]-N-{3-sulfamoyl-4-[5-(trifluoromethyl)pyridin-3-yl]phenyl}acetamide;
2-(4-Chlorophenyl)-N-[4-(6-chloropyridin-3-yl)-3-sulfamoylphenyl]acetamide;
N-[4-(6-Chloropyridin-3-yl)-3-sulfamoylphenyl]-2-(2-fluorophenyl)acetamide;
2-(2-Chloro-6-fluorophenyl)-N-[4-(6-chloropyridin-3-yl)-3-sulfamoylphenyl]acetamide;
N-[4-(6-Chloropyridin-3-yl)-3-sulfamoylphenyl]-2-[4-(trifluoromethyl)phenyl]acetamide;
N-[4-(6-Chloropyridin-3-yl)-3-sulfamoylphenyl]-2-[2-(trifluoromethyl)phenyl]acetamide;
N-[4-(6-Chloropyridin-3-yl)-3-sulfamoylphenyl]-2-(3-fluorophenyl)acetamide;
N-[4-(6-Chloropyridin-3-yl)-3-sulfamoylphenyl]-2-(2,4-dichlorophenyl)acetamide;
N-[4-(6-Chloropyridin-3-yl)-3-sulfamoylphenyl]-2-(2,4-difluorophenyl)acetamide;
2-(2-Bromophenyl)-N-[4-(6-chloropyridin-3-yl)-3-sulfamoylphenyl]acetamide;
N-[4-(6-Chloropyridin-3-yl)-3-sulfamoylphenyl]-2-(3,4-difluorophenyl)acetamide;
N-[4-(6-Chloropyridin-3-yl)-3-sulfamoylphenyl]-2-(4-methylphenyl)acetamide;
N-[4-(6-Chloropyridin-3-yl)-3-sulfamoylphenyl]-2-(4-methoxyphenyl)acetamide;
N-[4-(6-Chloropyridin-3-yl)-3-sulfamoylphenyl]-2-(2-fluoro-4-methylphenyl)acetamide;
N-[4-(6-Chloropyridin-3-yl)-3-sulfamoylphenyl]-2-(2-fluoro-4-methoxyphenyl)acetamide;
N-[4-(6-Chloropyridin-3-yl)-3-sulfamoylphenyl]-2-[4-(difluoromethyl)phenyl]acetamide;
N-[4-(6-Chloropyridin-3-yl)-3-sulfamoylphenyl]-2-[2-chloro-4-(trifluoromethyl)phenyl]acetamide;
2-(2,4-Dichlorophenyl)-N-[4-(5-fluoropyridin-3-yl)-3-sulfamoylphenyl]acetamide;
2-(2-Fluoro-4-methylphenyl)-N-[4-(5-fluoropyridin-3-yl)-3-sulfamoylphenyl]acetamide;
2-[4-(Difluoromethyl)phenyl]-N-[4-(5-fluoropyridin-3-yl)-3-sulfamoylphenyl]acetamide;
2-(2-Chlorophenyl)-N-[4-(4-cyclopropyl-1H-pyrazol-1-yl)-3-sulfamoylphenyl]acetamide;
N-[4-(4,6-Difluoro-2H-benzotriazol-2-yl)-3-sulfamoylphenyl]-2-(2-fluorophenyl)acetamide;
N-[4-(4,6-Difluoro-1H-benzotriazol-1-yl)-3-sulfamoylphenyl]-2-(2-fluorophenyl)acetamide;
2-(2-Chlorophenyl)-N-[4-(4,6-difluoro-1H-benzotriazol-1-yl)-3-sulfamoylphenyl]acetamide;
2-(2-Chlorophenyl)-N-[4-(4,6-difluoro-2H-benzotriazol-2-yl)-3-sulfamoylphenyl]acetamide;
2-(2-Chlorophenyl)-N-{3-sulfamoyl-4-[2-(trifluoromethyl)-1,3-thiazol-5-yl]phenyl}acetamide;
2-(2-Chlorophenyl)-N-[4-(4-cyano-1H-pyrazol-1-yl)-5-sulfamoyl-2-(trifluoromethyl)phenyl]acetamide;
2-[2-Chloro-5-(trifluoromethyl)phenyl]-N-[4-(4-cyano-1H-pyrazol-1-yl)-3-sulfamoylphenyl]acetamide;
2-[2-Chloro-5-(trifluoromethyl)phenyl]-N-[4-(4-cyano-1H-pyrazol-1-yl)-5-sulfamoyl-2-(trifluoromethyl)phenyl]acetamide;
2-(2-Chlorophenyl)-N-[4-(4-cyano-1H-pyrazol-1-yl)-3-sulfamoyl-2-(trifluoromethyl)phenyl]acetamide;
2-[2-Chloro-3-(trifluoromethyl)phenyl]-N-[4-(4-cyano-1H-pyrazol-1-yl)-5-sulfamoyl-2-(trifluoromethyl)phenyl]acetamide;
2-(2-Chlorophenyl)-N-{4-[1-(difluoromethyl)-1H-pyrazol-4-yl]-3-sulfamoyl-2-(trifluoromethyl)phenyl}acetamide;
2-[2-Chloro-3-(trifluoromethyl)phenyl]-N-{4-[1-(difluoromethyl)-1H-pyrazol-4-yl]-3-sulfamoylphenyl}acetamide;
2-(2-Chlorophenyl)-N-{4-[1-(difluoromethyl)-1H-pyrazol-4-yl]-5-sulfamoyl-2-(trifluoromethyl)phenyl}acetamide;
2-(2-Chlorophenyl)-N-{4-[1-(difluoromethyl)-5-(trifluoromethyl)-1H-pyrazol-4-yl]-3-sulfamoylphenyl}acetamide;
2-(2-Chlorophenyl)-N-{4-[1-(difluoromethyl)-1H-pyrazol-4-yl]-2-fluoro-3-sulfamoylphenyl}acetamide;
2-(2-Chlorophenyl)-N-{4-[1-(difluoromethyl)-1H-pyrazol-4-yl]-2-fluoro-5-sulfamoylphenyl}acetamide;
2-(2-Chlorophenyl)-N-{4-[2-(dimethylamino)-1,3-thiazol-4-yl]-3-sulfamoylphenyl}acetamide;
2-(2-Chlorophenyl)-N-[3-sulfamoyl-4-(1,2-thiazol-5-yl)phenyl]acetamide;
1-(4-{[(2-Chlorophenyl)acetyl]amino}-2-sulfamoylphenyl)-N-cyclopropyl-N-methyl-1H-pyrazole-4-carboxamide;
2-(2-Chlorophenyl)-2-hydroxy-N-{3-sulfamoyl-4-[4-(trifluoromethyl)-1H-pyrazol-1-yl]phenyl}ethanamide;
2-(2-Chlorophenyl)-N-{3-chloro-5-sulfamoyl-4-[4-(trifluoromethyl)-1H-pyrazol-1-yl]phenyl}acetamide;
2-(2-Chlorophenyl)-N-[4-(4-cyano-3-hydroxy-1H-pyrazol-1-yl)-3-sulfamoylphenyl]acetamide;
2-(2-Chlorophenyl)-N-[4-(1H-pyrazolo[4,3-c]pyridin-1-yl)-3-sulfamoylphenyl]acetamide;
2-(2-Chlorophenyl)-N-[4-(4,5-dimethyl-1,3-thiazol-2-yl)-3-sulfamoylphenyl]acetamide;
2-(2-Chlorophenyl)-N-[4-(2,4-dimethyl-1,3-thiazol-5-yl)-3-sulfamoylphenyl]acetamide;
2-(2-Chlorophenyl)-N-[4-(4-methyl-1,3-thiazol-5-yl)-3-sulfamoylphenyl]acetamide;
N-{4-(4-Amino-1H-pyrazol-1-yl)-3-[(2,4-dimethoxybenzyl)sulfamoyl]phenyl}-2-(2-chlorophenyl)acetamide;
N-[1-(4-{[(2-Chlorophenyl)acetyl]amino}-2-sulfamoylphenyl)-1H-pyrazol-4-yl]-2,2-difluoroacetamide;
N-[1-(4-{[(2-Chlorophenyl)acetyl]amino}-2-sulfamoylphenyl)-1H-pyrazol-4-yl]-3,3,3-trifluoropropanamide;
N-[1-(4-{[(2-Chlorophenyl)acetyl]amino}-2-sulfamoylphenyl)-1H-pyrazol-4-yl]-3,3,3-trifluoro-2-methylpropanamide (racemic);
N-[1-(4-{[(2-Chlorophenyl)acetyl]amino}-2-sulfamoylphenyl)-1H-pyrazol-4-yl]-3,3,3-trifluoro-2-methylpropanamide (Enantiomer A);
N-[1-(4-{[(2-Chlorophenyl)acetyl]amino}-2-sulfamoylphenyl)-1H-pyrazol-4-yl]-3,3,3-trifluoro-2-methylpropanamide (Enantiomer B);
2-(2-Chlorophenyl)-N-(4-{4-[(cis-2,5-dimethylpyrrolidin-1-yl]-1H-pyrazol-1-yl}-3-sulfamoylphenyl)acetamide;
2-(2-Chlorophenyl)-N-(4-{4-[(trans-2,5-dimethylpyrrolidin-1-yl]-1H-pyrazol-1-yl}-3-sulfamoylphenyl)acetamide (Enantiomer A);
2-(2-Chlorophenyl)-N-(4-{4-[(trans-2,5-dimethylpyrrolidin-1-yl]-1H-pyrazol-1-yl}-3-sulfamoylphenyl)acetamide (Enantiomer B);
N-(4-{4-[(2,2-Difluoroethyl)amino]-1H-pyrazol-1-yl}-3-sulfamoylphenyl)-2-(2-fluorophenyl)acetamide;

2-(2-Chlorophenyl)-N-(3-sulfamoyl-4-{4-[(2,2,2-trifluoroethyl)amino]-1H-pyrazol-1-yl}phenyl)acetamide;
2-(2-Chlorophenyl)-N-[4-(4-isopropyl-1H-pyrazol-1-yl)-3-sulfamoylphenyl]acetamide;
2-(2-Fluorophenyl)-N-[4-(4-isopropyl-1H-pyrazol-1-yl)-3-sulfamoylphenyl]acetamide;
2-(2-Chlorophenyl)-N-{3-sulfamoyl-4-[4-(2,2,2-trifluoroethyl)-1H-pyrazol-1-yl]phenyl}acetamide;
2-(2-Fluorophenyl)-N-{3-sulfamoyl-4-[4-(2,2,2-trifluoroethyl)-1H-pyrazol-1-yl]phenyl}acetamide;
2-(2-Chlorophenyl)-N-[4-(5-cyclopropyl-1,2,4-oxadiazol-3-yl)-3-sulfamoylphenyl]acetamide;
2-(2-Chlorophenyl)-N-{3-sulfamoyl-4-[3-(trifluoromethyl)-1,2,4-oxadiazol-5-yl]phenyl}acetamide;
2-(2-Chlorophenyl)-N-{4-[5-(difluoromethyl)-1,3,4-oxadiazol-2-yl]-3-sulfamoylphenyl}acetamide;
N-{4-[5-(Difluoromethyl)-1,3,4-oxadiazol-2-yl]-3-sulfamoylphenyl}-2-(2-fluorophenyl)acetamide;
2-(2-Chlorophenyl)-N-[4-(5-methyl-1,3,4-oxadiazol-2-yl)-3-sulfamoylphenyl]acetamide;
2-(2-Fluorophenyl)-N-[4-(5-methyl-1,3,4-oxadiazol-2-yl)-3-sulfamoylphenyl]acetamide;
N-[4-(5-Methyl-1,3,4-oxadiazol-2-yl)-3-sulfamoylphenyl]-2-(4-methylphenyl)acetamide;
2-(2-Chlorophenyl)-N-[4-(1H-pyrrol-3-yl)-3-sulfamoylphenyl]acetamide;
2-(2-Chlorophenyl)-N-{4-[5-(difluoroacetyl)-1H-pyrrol-3-yl]-3-sulfamoylphenyl}acetamide;
2-(2-Chlorophenyl)-N-[4-(1-methyl-1H-pyrrol-3-yl)-3-sulfamoylphenyl]acetamide;
2-(2-Chlorophenyl)-N-[4-(5-cyano-1-methyl-1H-pyrrol-2-yl)-3-sulfamoylphenyl]acetamide;
2-(2-Chlorophenyl)-N-{3-sulfamoyl-2-(trifluoromethyl)-4-[4-(trifluoromethyl)-1H-pyrazol-1-yl]phenyl}acetamide;
2-(2-Chlorophenyl)-N-{5-sulfamoyl-2-(trifluoromethyl)-4-[4-(trifluoromethyl)-1H-pyrazol-1-yl]phenyl}acetamide;
2-[2-Chloro-3-(trifluoromethyl)phenyl]-N-{5-sulfamoyl-2-(trifluoromethyl)-4-[4-(trifluoromethyl)-1H-pyrazol-1-yl]phenyl}acetamide;
2-[2-Chloro-5-(trifluoromethyl)phenyl]-N-{5-sulfamoyl-2-(trifluoromethyl)-4-[4-(trifluoromethyl)-1H-pyrazol-1-yl]phenyl}acetamide;
2-[2-Chloro-6-(trifluoromethyl)phenyl]-N-[4-(4-fluoro-1H-pyrazol-1-yl)-5-sulfamoyl-2-(trifluoromethyl)phenyl]acetamide;
2-[2-Chloro-3-(trifluoromethyl)phenyl]-N-[4-(4-fluoro-1H-pyrazol-1-yl)-5-sulfamoyl-2-(trifluoromethyl)phenyl]acetamide;
2-[2-Chloro-5-(trifluoromethyl)phenyl]-N-[4-(4-fluoro-1H-pyrazol-1-yl)-5-sulfamoyl-2-(trifluoromethyl)phenyl]acetamide;
2-[2-Chloro-4-(trifluoromethyl)phenyl]-N-[4-(4-fluoro-1H-pyrazol-1-yl)-5-sulfamoyl-2-(trifluoromethyl)phenyl]acetamide;
N-[4-(3-tert-Butyl-4-cyano-1H-pyrazol-1-yl)-3-sulfamoylphenyl]-2-(2-chlorophenyl)acetamide;
N-[4-(3-Bromo-4-cyano-1H-pyrazol-1-yl)-3-sulfamoylphenyl]-2-(2-chlorophenyl)acetamide;
2-(2-Chlorophenyl)-N-{4-[4-chloro-3-(trifluoromethyl)-1H-pyrazol-1-yl]-3-sulfamoylphenyl}acetamide;
2-(2-Chlorophenyl)-N-[4-(3,4-dimethyl-1H-pyrazol-1-yl)-3-sulfamoylphenyl]acetamide;
N-[4-(4-Chloro-3, 5-dimethyl-1H-pyrazol-1-yl)-3-sulfamoylphenyl]-2-(2-chlorophenyl)acetamide;
2-(2-Chlorophenyl)-N-[4-(1H-pyrazol-1-yl)-3-sulfamoylphenyl]acetamide;
2-(2-Chlorophenyl)-N-[4-(3-cyano-5-methyl-1H-pyrazol-1-yl)-3-sulfamoylphenyl]acetamide;
2-(2-Chlorophenyl)-N-[4-(3-hydroxy-5-methyl-1H-pyrazol-1-yl)-3-sulfamoylphenyl]acetamide;
2-(2-Chlorophenyl)-N-[4-(4-cyano-5-methyl-1H-pyrazol-1-yl)-3-sulfamoylphenyl]acetamide;
2-(2-Chlorophenyl)-N-[4-(4-cyano-3-methyl-1H-pyrazol-1-yl)-3-sulfamoylphenyl]acetamide;
2-(2-Chlorophenyl)-N-{4-[4-(morpholin-4-yl)-1,3-thiazol-2-yl]-3-sulfamoylphenyl}acetamide;
2-(2-Chlorophenyl)-N-{4-[5-(morpholin-4-yl)-1,3-thiazol-2-yl]-3-sulfamoylphenyl}acetamide;
2-(2-Chlorophenyl)-N-[4-(5-methyl-1,3-thiazol-2-yl)-3-sulfamoylphenyl]acetamide;
2-(2-Chlorophenyl)-N-[4-(pyridin-4-yl)-3-sulfamoylphenyl]acetamide;
1-(4-{[(2-Chlorophenyl)acetyl]amino}-2-sulfamoylphenyl)-1H-pyrazole-4-carboxamide;
2-(2-Chloro-3-hydroxyphenyl)-N-[4-(4-cyano-1H-pyrazol-1-yl)-3-sulfamoylphenyl]acetamide;
2-(2-Chloro-4-hydroxyphenyl)-N-[4-(4-cyano-1H-pyrazol-1-yl)-3-sulfamoylphenyl]acetamide;
2-(2-Chloro-5-hydroxyphenyl)-N-[4-(4-cyano-1H-pyrazol-1-yl)-3-sulfamoylphenyl]acetamide;
2-(2-Chloro-6-hydroxyphenyl)-N-[4-(4-cyano-1H-pyrazol-1-yl)-3-sulfamoylphenyl]acetamide, and
2-(2-Chlorophenyl)-N-[4-(4-cyano-1H-pyrazol-1-yl)-3-sulfamoylphenyl]-2-hydroxyacetamide,
wherein said disease is a genitourinary, gastrointestinal, proliferative or pain-related disease, condition or disorder; cancer; fibrotic disease; lung fibrosis; heart fibrosis; kidney fibrosis; fibrosis of other organs; gynaecological disease; dysmenorrhea; dyspareunia; endometriosis; adenomyosis; endometriosis-associated pain; endometriosis-associated symptoms; dysuria; dyschezia; pelvic hypersensitivity; urethritis; prostatitis; prostatodynia; cystitis; idiopathic bladder hypersensitivity; gastrointestinal disorder; irritable bowel syndrome (IBS); inflammatory bowel disease (IBD); biliary colic; other biliary disorders; renal colic; diarrhea-dominant IBS; gastroesophageal reflux, gastrointestinal distension; Crohn's disease; Parkinson's disease; Alzheimer's disease; myocardial infarction; atherosclerosis; lipid disorder; functional bowel disorder; arthritis; osteoarthritis; rheumatoid arthritis; pain-associated disease or syndrome; acute, chronic, inflammatory and neuropathic pain; inflammatory pain; low back pain; surgical pain; visceral pain; dental pain; premenstrual pain; endometriosis-associated pain, pain associated with fibrotic diseases; central pain; pain due to burning mouth syndrome; pain due to burns; pain due to migraine; cluster headaches; hyperalgesia; allodynia; pain due to traumatic nerve-injury; pain due to post-traumatic injuries; including fractures; sport injuries; pain due to trigeminal neuralgia; pain associated with small fiber neuropathy; pain associated with diabetic neuropathy; chronic lower back pain; phantom limb pain; pelvic pain syndrome; chronic pelvic pain; neuroma pain; complex regional pain syndrome; pain associated with gastrointestinal distension; chronic arthritic pain and related neuralgias; pain associated with cancer; pain associated with chemotherapy; HIV and HIV treatment-induced neuropathy; pruritus; impaired wound healing; disease of the skeleton; or ankylosing spondylitis.

5. The method of claim 4, wherein said disease is a gynaecological disease, dysmenorrhea, dyspareunia, endometriosis, adenomyosis, endometriosis-associated pain, other endometriosis-associated symptoms, dysuria, or dyschezia.

6. The method of claim 4, wherein said disease is lung fibrosis, liver fibrosis, pruritus, osteoarthritis, or burning mouth syndrome.

7. A method for treatment of a disease, comprising administering to a patient in need thereof a pharmaceutically effective amount of a compound, or a stereoisomer, a tautomer, an N oxide, a hydrate, a solvate, or a pharmaceutically acceptable salt thereof, or a mixture of the same,
wherein the compound is 2-(2-Chlorophenyl)-N-[4-(4-cyano-1H-pyrazol-1-yl)-3-sulfamoylphenyl]acetamide,
wherein said disease is a genitourinary, gastrointestinal, proliferative or pain-related disease, condition or disorder; cancer; fibrotic disease; lung fibrosis; heart fibrosis; kidney fibrosis; fibrosis of other organs; gynaecological disease; dysmenorrhea; dyspareunia; endometriosis; adenomyosis; endometriosis-associated pain; endometriosis-associated symptoms; dysuria; dyschezia; pelvic hypersensitivity; urethritis; prostatitis; prostatodynia; cystitis; idiopathic bladder hypersensitivity; gastrointestinal disorder; irritable bowel syndrome (IBS); inflammatory bowel disease (IBD); biliary colic; other biliary disorders; renal colic; diarrhea-dominant IBS; gastroesophageal reflux, gastrointestinal distension; Crohn's disease; Parkinson's disease; Alzheimer's disease; myocardial infarction; atherosclerosis; lipid disorder; functional bowel disorder; arthritis; osteoarthritis; rheumatoid arthritis; pain-associated disease or syndrome; acute, chronic, inflammatory and neuropathic pain; inflammatory pain; low back pain; surgical pain; visceral pain; dental pain; premenstrual pain; endometriosis-associated pain, pain associated with fibrotic diseases; central pain; pain due to burning mouth syndrome; pain due to burns; pain due to migraine; cluster headaches; hyperalgesia; allodynia; pain due to traumatic nerve-injury; pain due to post-traumatic injuries; including fractures; sport injuries; pain due to trigeminal neuralgia; pain associated with small fiber neuropathy; pain associated with diabetic neuropathy; chronic lower back pain; phantom limb pain; pelvic pain syndrome; chronic pelvic pain; neuroma pain; complex regional pain syndrome; pain associated with gastrointestinal distension; chronic arthritic pain and related neuralgias; pain associated with cancer; pain associated with chemotherapy; HIV and HIV treatment-induced neuropathy; pruritus; impaired wound healing; disease of the skeleton; or ankylosing spondylitis.

8. The method of claim 7, wherein said disease is a gynaecological disease, dysmenorrhea, dyspareunia, endometriosis, adenomyosis, endometriosis-associated pain, other endometriosis-associated symptoms, dysuria, or dyschezia.

9. The method of claim 7, wherein said disease is lung fibrosis, liver fibrosis, pruritus, osteoarthritis, or burning mouth syndrome.

* * * * *